US012091426B2

(12) United States Patent
Buell et al.

(10) Patent No.: US 12,091,426 B2
(45) Date of Patent: Sep. 17, 2024

(54) BIFUNCTIONAL DEGRADERS OF HEMATOPOIETIC PROGENITOR KINASE AND THERAPEUTIC USES THEREOF

(71) Applicants: Nurix Therapeutics, Inc., San Francisco, CA (US); Gilead Sciences, Inc., Foster City, CA (US)

(72) Inventors: John Buell, San Francisco, CA (US); Frederick Cohen, San Francisco, CA (US); Ryan Pemberton, San Francisco, CA (US); Hunter P. Shunatona, San Francisco, CA (US); Lan Wang, San Francisco, CA (US); Mark Edward Zak, San Francisco, CA (US)

(73) Assignees: Nurix Therapeutics, Inc., San Francisco, CA (US); Gilead Sciences, Inc., Foster City, CA (US)

( * ) Notice: Subject to any disclaimer, the term of this patent is extended or adjusted under 35 U.S.C. 154(b) by 22 days.

(21) Appl. No.: 18/054,118

(22) Filed: Nov. 9, 2022

(65) Prior Publication Data

US 2024/0018162 A1 Jan. 18, 2024

Related U.S. Application Data

(60) Provisional application No. 63/263,875, filed on Nov. 10, 2021.

(51) Int. Cl.
*C07D 519/00* (2006.01)

(52) U.S. Cl.
CPC .................................. *C07D 519/00* (2013.01)

(58) Field of Classification Search
CPC C07D 519/00; A61K 31/513; A61K 31/4745; A61P 35/00; A61P 37/02
See application file for complete search history.

(56) References Cited

U.S. PATENT DOCUMENTS

| | | | | |
|---|---|---|---|---|
| 11,739,101 | B2 * | 8/2023 | Shunatona | A61P 35/00 514/278 |
| 2015/0038488 | A1 | 2/2015 | Currie et al. | |
| 2019/0151295 | A1 | 5/2019 | Crew et al. | |
| 2019/0192668 | A1 | 6/2019 | Mainolfi et al. | |
| 2021/0355140 | A1 | 11/2021 | Shunatona et al. | |

FOREIGN PATENT DOCUMENTS

| | | | |
|---|---|---|---|
| WO | 2019/099926 | A1 | 5/2019 |
| WO | 2020/023851 | A1 | 1/2020 |
| WO | 2020/038415 | A1 | 2/2020 |
| WO | 2020/092528 | A1 | 5/2020 |
| WO | 2020/092621 | A1 | 5/2020 |
| WO | 2020/227325 | A1 | 11/2020 |
| WO | 2021/168197 | A1 | 8/2021 |
| WO | 2021/226262 | A1 | 11/2021 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*
International Search Report and Written Opinion, dated Jul. 20, 2021, for International Application No. PCT/US2021/030928. (12 pages).
International Search Report and Written Opinion, mailed Apr. 19, 2023, for International Application No. PCT/US2022/049426. (12 pages).

* cited by examiner

*Primary Examiner* — Deepak R Rao
(74) *Attorney, Agent, or Firm* — Seed IP Law Group LLP

(57) ABSTRACT

The present disclosure provides bifunctional compounds as HPK1 degraders via ubiquitin proteasome pathway, and method for treating diseases modulated by HPK1.

29 Claims, No Drawings

BIFUNCTIONAL DEGRADERS OF HEMATOPOIETIC PROGENITOR KINASE AND THERAPEUTIC USES THEREOF

CROSS-REFERENCE TO RELATED APPLICATIONS

This application claims the benefit of priority to U.S. Provisional Application No. 63/263,875, filed Nov. 10, 2021, which application is hereby incorporated by reference in its entirety.

BACKGROUND

Technical Field

The present invention provides novel bifunctional compounds for proteolytically degrading Hematopoietic progenitor kinase (HPK1) and methods for treating diseases modulated by HPK1.

Description of the Related Art

Immuno-oncology utilizes inhibitor antibodies against the immune checkpoint receptors CTLA4, PD-1 and PD-L1. Targeted disruption of these checkpoint pathways releases the immune cell from key regulatory pathways, allowing for a boost in the immune response against cancer cells. Current therapies utilizing these antibodies are highlighted by both significant and durable response to many different cancers but also by low overall response rates (<25%). Improvement in these response rates could benefit from a combination of checkpoint blockade with other immune activating agents or cell based therapies.

Hematopoietic progenitor kinase 1, a STE20 ser/thr kinase from the germinal center family of kinases, regulates the function of diverse immune populations including T cells, B cells, and dendritic cells (Hu et al., Gens Dev, 1996; Alzabin et al., J Immunol 2009). In T cells, HPK1 serves as a negative regulator of T cell receptor (TCR) signaling (Liou et al., Immunity 2000; Sauer et al., JBC 2001) by phosphorylating SLP76 on serine 376, which induces the association of SLP76 with 14-3-3 proteins, and leads to the disassociation of the signaling complex (Di Bartolo et al., JEM 2007). Further supporting the role of HPK1 as a negative regulator of TCR signaling, murine HPK1 deficient T cells or HPK1 kinase inactive mutant T cells have enhanced ERK 1/2 activation and effector cytokine secretion upon TCR activation compared to their wild-type counterparts (Shui et al., Nat Immunol 2007; Hernandez et al., Cell Reports 2018).

Thus, HPK1 may be targeted for degradation, thereby providing therapeutic opportunities in enhancing anti-tumor immunity and increasing the response to checkpoint receptor blockade.

BRIEF SUMMARY

Provided herein are bifunctional compounds represented by Formula (I):

Formula (I)

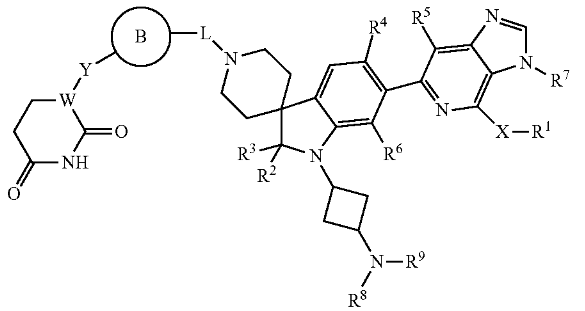

or a pharmaceutically acceptable salt thereof, wherein:

$R^1$ is i) phenyl optionally substituted with 1-3 groups independently selected from halogen, $C_{1-3}$ alkyl, —C(O)N($R^{11}$)$_2$, —CN, —OH, and $C_{1-3}$ alkoxy, ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy; or v) $C_{1-6}$ alkyl optionally substituted with 1-3 groups independently selected from halogen, $C_{1-3}$ alkyl, —C(O)N($R^{11}$)$_2$, —CN, —OH, and $C_{1-3}$ alkoxy, $R^2$ and $R^3$ are each H, or $R^2$ and $R^3$ together form =O;

$R^4$, $R^5$, $R^6$, and $R^{10}$ are each independently H, halogen, $C_{1-3}$ alkyl, or $C_{1-3}$ alkoxy;

$R^7$ is H or $C_{1-6}$ alkyl optionally substituted with 1-3 groups independently selected from —OH, halogen, $C_{1-3}$ alkoxy, and $C_{3-7}$ monocyclic cycloalkyl;

$R^8$ and $R^9$ are independently i) H, ii) $C_{3-7}$ monocyclic cycloalkyl optionally substituted with 1-3 groups independently selected from —OH, halogen, $C_{1-3}$ alkyl, and $C_{1-3}$ alkoxy, iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, iv) $C_{1-6}$ alkyl optionally substituted with 1-6 groups independently selected from a) —CN, b) —OH, c) halogen, d) $C_{1-3}$ alkoxy,
e) $C_{3-7}$ monocyclic cycloalkyl optionally substituted with 1-3 groups independently selected from —OH, halogen, $C_{1-3}$ alkyl, and $C_{1-3}$ alkoxy, and
f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or $R^8$ and $R^9$, together with the nitrogen to which they are attached, form 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{12}$;

each $R^{11}$ is independently
i) H,
ii) $C_{1-6}$ alkyl optionally substituted with 1-6 groups independently selected from —CN, —OH, halogen, $C_{1-3}$ alkoxy, and $C_{3-7}$ monocyclic cycloalkyl,
iii) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or
iv) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy;

each $R^{12}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) $—C(O)N(R^{13})_2$, wherein each $R^{13}$ is independently H or $C_{1-6}$ alkyl;

X is $—N(R^{11})—$ or —O—, wherein $R^{11}$, together with $R^1$ and the nitrogen atom to which they are connected, may form a 4-12 membered heterocylcle optionally substituted with 1-3 $R^b$.

L is $-L_1-L_2-L_3-L_4-L_5-L_6-$, each $L_1$, $L_2$, $L_3$, $L_4$, $L_5$ and $L_6$ being independently:
i) $C_{3-12}$ cycloalkyl optionally substituted with 1-3 $R^b$;
ii) $C_{6-12}$ aryl optionally substituted with 1-3 $R^b$;
iii) 4-12 membered heterocyclyl optionally substituted with 1-3 $R^b$;
iv) 5-12 membered heteroaryl optionally substituted with 1-3 $R^b$;
v) direct bond;
vi) $C_{1-12}$ alkylene chain optionally substituted with 1-3 $R^d$;
vii) $C_{2-12}$ alkenylene chain optionally substituted with 1-3 $R^d$;
viii) $C_{2-12}$ alkynylene chain optionally substituted with 1 to 3 $R^d$;
ix) —C(O)—, —C(O)O—, —O—, $—N(R^c)—$, —S—, —C(S)—, —C(S)—O—, $—S(O)_2—$, —S(O)═N—, $—S(O)_2NH—$, $—C(O)—N(R^c)—$, —C═N—, $—O—C(O)—N(R^c)—$, —O—C(O)—O—, $—(CH_2)_m—C(O)—$, or $—NH—(CH_2)_m—C(O)—$, wherein m is 0, 1, 2 or 3;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or $—OR^c$;

each $R^b$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, $—O—R^c$, $—C(O)—R^c$, $—C(O)O—R^c$, $—C(O)—N(R^c)(R^c)$, $—N(R^c)(R^c)$, $—N(R^c)C(O)—R^c$, $—N(R^c)C(O)O—R^c$, $—N(R^c)C(O)N(R^c)(R^c)$, $—N(R^c)S(O)_2(R^c)$, $—NR^cS(O)_2N(R^c)(R^c)$, $—N(R^c)S(O)_2O(R^c)$, $—OC(O)R^c$, $—OC(O)—N(R^c)(R^c)$, $—Si(R^c)_3$, $—S—R^c$, $—S(O)R^c$, $—S(O)(NH)R^c$, $—S(O)_2R^c$ or $—S(O)_2N(R^c)(R^c)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or $—O—C_{1-6}$ alkyl optionally substituted with 1 to 3 fluoro;

W is $—C(R^g)—$ or —N—;

Y is direct bond, $C_{1-4}$ alkylene chain, —C(O)—, —C(O)O—, —O—, $—N(R^g)—$, —S—, —C(S)—, —C(S)—O—, —O—C(O)O—, $—C(O)—N(R^g)—$, or $—O—C(O)—N(R^g)—$;

B ring is $C_{6-12}$ aryl, 5-12 membered heteroaryl, or 4-12 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, $—O—R^g$, $—C(O)—R^g$, $—C(O)O—R^g$, $—C(O)—N(R^g)(R^g)$, $—N(R^g)(R^g)$, $—N(R^g)C(O)—R^g$, $—N(R^9)C(O)O—R^9$, $—N(R^9)C(O)N(R^9)(R^9)$, $—N(R^g)S(O)_2(R^g)$, $—NR^gS(O)_2N(R^g)(R^g)$, $—N(R^g)S(O)_2O(R^g)$, $—OC(O)R^9$, $—OC(O)—N(R^9)(R^g)$, $—Si(R^g)_3$, $—S—R^9$, $—S(O)R^g$, $—S(O)(NH)R^g$, $—S(O)_2R^g$ or $—S(O)_2N(R^g)(R^g)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or $—O—C_{1-6}$ alkyl optionally substituted with 1 to 3 fluoro.

Also provided herein are bifunctional compounds represented by Formula (I):

Formula (I)

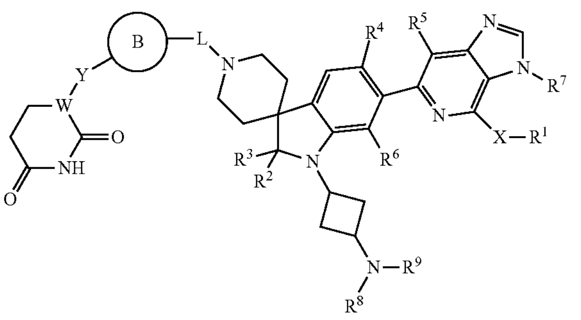

or a pharmaceutically acceptable salt thereof, wherein:

$R^1$ is i) phenyl optionally substituted with 1-3 groups independently selected from halogen, $C_{1-3}$ alkyl, —$C(O)N(R^{11})_2$, —CN, —OH, and $C_{1-3}$ alkoxy, ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, or iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy;

$R^2$ and $R^3$ are each H, or $R^2$ and $R^3$ together form =O;

$R^4$, $R^5$, $R^6$, and $R^{10}$ are each independently H, halogen, $C_{1-3}$ alkyl, or $C_{1-3}$ alkoxy;

$R^7$ is H or $C_{1-6}$ alkyl optionally substituted with 1-3 groups independently selected from —OH, halogen, $C_{1-3}$ alkoxy, and $C_{3-7}$ monocyclic cycloalkyl;

$R^8$ and $R^9$ are independently i) H, ii) $C_{3-7}$ monocyclic cycloalkyl optionally substituted with 1-3 groups independently selected from —OH, halogen, $C_{1-3}$ alkyl, and $C_{1-3}$ alkoxy, iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, iv) $C_{1-6}$ alkyl optionally substituted with 1-6 groups independently selected from a) —CN, b) —OH, c) halogen, d) $C_{1-3}$ alkoxy, e) $C_{3-7}$ monocyclic cycloalkyl optionally substituted with 1-3 groups independently selected from —OH, halogen, $C_{1-3}$ alkyl, and $C_{1-3}$ alkoxy, and f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or $R^8$ and $R^9$, together with the nitrogen to which they are attached, form 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{12}$;

each $R^{11}$ is independently i) H, ii) $C_{1-6}$ alkyl optionally substituted with 1-6 groups independently selected from —CN, —OH, halogen, $C_{1-3}$ alkoxy, and $C_{3-7}$ monocyclic cycloalkyl, iii) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or iv) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy;

each $R^{12}$ is independently i) —CN, ii) a halogen, iii) —OH, iv) $C_{1-6}$ alkoxy optionally substituted with 1-3 groups independently selected from —OH, halogen, $C_{1-3}$ alkoxy, and $C_{3-7}$ monocyclic cycloalkyl, v) $C_{1-6}$ alkyl optionally substituted with 1-3 groups independently selected from —OH, halogen, $C_{1-3}$ alkoxy, and $C_{3-7}$ monocyclic cycloalkyl, vi) —COOH, or vii) —$C(O)N(R^{13})_2$, wherein each $R^{13}$ is independently H or $C_{1-6}$ alkyl;

X is —$N(R^{11})$— or —O—;

L is -$L_1$-$L_2$-$L_3$-$L_4$-$L_5$-, each $L_1$, $L_2$, $L_3$, $L_4$ and $L_5$ being independently:

i) $C_{3-12}$ cycloalkyl optionally substituted with 1-3 $R^b$;

ii) $C_{6-12}$ aryl optionally substituted with 1-3 $R^b$;

iii) 4-12 membered heterocyclyl optionally substituted with 1-3 $R^b$;

iv) 5-12 membered heteroaryl optionally substituted with 1-3 $R^b$;

v) direct bond;

vi) $C_{1-12}$ alkylene chain optionally substituted with 1-3 $R^d$;

vii) $C_{2-12}$ alkenylene chain optionally substituted with 1-3 $R^d$;

viii) $C_{2-12}$ alkynylene chain optionally substituted with 1 to 3 $R^d$;

ix) —C(O)—, —C(O)O—, —O—, —$N(R^c)$—, —$(CH_2)_m$—C(O)—, —S—, —C(S)—, —C(S)—O—, —$S(O)_2$—, —S(O)=N—, —$S(O)_2NH$—, —C(O)—$N(R^c)$—, —C=N—, —O—C(O)—N ($R^c$)—, —O—C(O)—O—, or —NH—$(CH_2)_m$—C(O)—, wherein m is 0, 1, 2 or 3;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —$OR^c$;

each $R^b$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)$S(O)_2$($R^c$), —NR'$S(O)_2$N($R^c$)($R^c$), —N($R^c$)$S(O)_2$O($R^c$), —OC(O)$R^c$, —OC(O)—N($R^c$)($R^c$), —Si$(R^c)_3$, —S—$R^c$, —S(O)$R^c$, —S(O)(NH)$R^c$, —$S(O)_2R^c$ or —$S(O)_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

Y is direct bond, $C_{1-4}$ alkylene chain, —C(O)—, —C(O)O—, —O—, —N($R^g$)—, —S—, —C(S)—, —C(S)—O—, —O—C(O)O—, —C(O)—N($R^g$)—, or —O—C(O)—N($R^g$)—;

B ring is $C_{6-12}$ aryl, 5-12 membered heteroaryl, or 4-12 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—R, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)$S(O)_2$($R^g$), —$NR^g$$S(O)_2$N($R^g$)($R^g$), —N($R^g$)$S(O)_2$O($R^g$), —OC(O)$R^g$, —OC(O)—N($R^g$)($R^g$), —Si$(R^g)_3$, —S—$R^g$, —S(O)$R^g$, —S(O)(NH)$R^g$, —$S(O)_2R^g$ or —$S(O)_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In some embodiments, $R^1$ is not

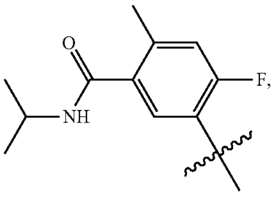 [SMILES: *c1cc(C(=O)NC(C)C)c(C)cc1F]

In some embodiments, when $R^1$ is

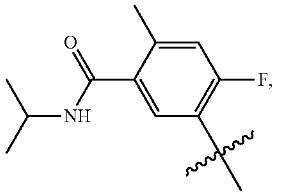 [SMILES: *c1cc(C(=O)NC(C)C)c(C)cc1F]

the

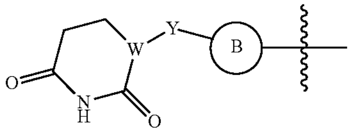

moiety is not

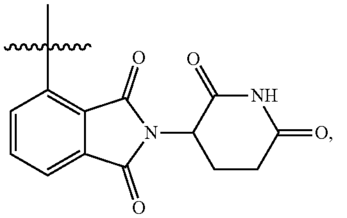

or

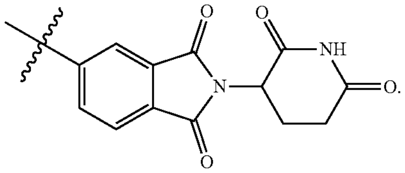

In some embodiments, $R^2$ and $R^3$ together form =O and the compound has a structure of Formula (Ia):

Formula (Ia)

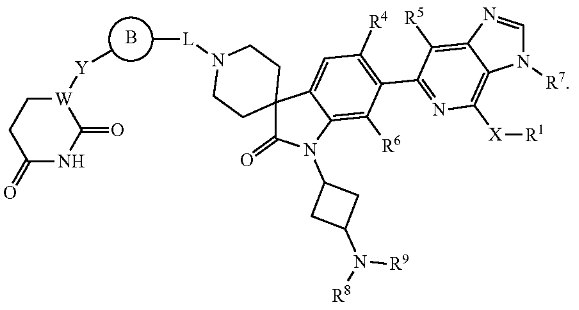

In some embodiments, $R^8$ and $R^9$, together with the nitrogen to which they are attached, form piperidinyl, and the compound has a structure of Formula (Ib):

Formula (Ib)

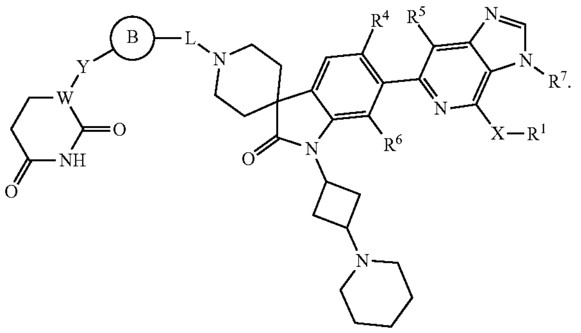

In some embodiments, X is —NH—, and the compound has a structure of Formula (Ic):

Formula (Ic)

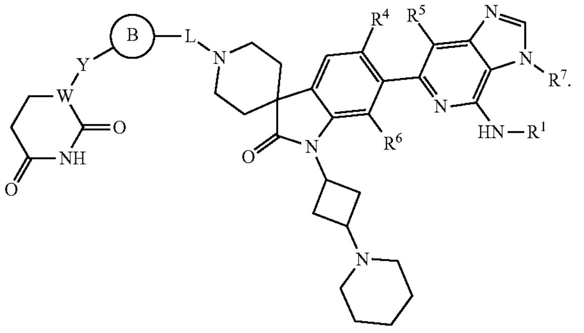

In other embodiments, X is —O—, and the compound has a structure of Formula (Id):

Formula (Id)

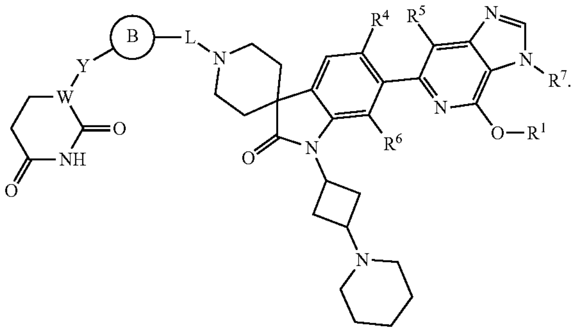

In further embodiments, X is —NH—, and the compound has a structure of Formula (Ie):

Formula (Ie)

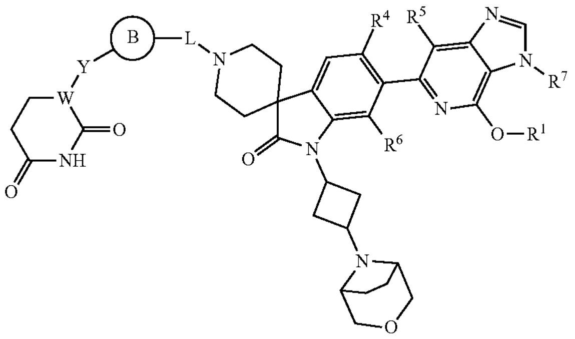

In further embodiments, X is —NH—, and the compound has a structure of Formula (If):

Formula (If)

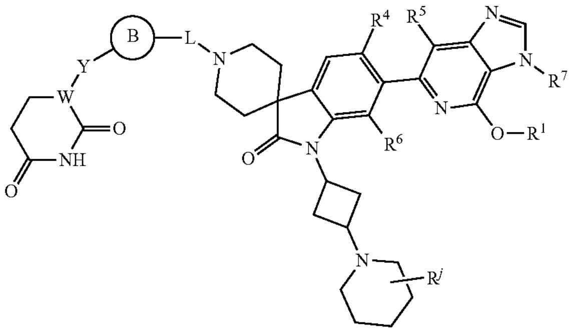

In certain other embodiments, $R^8$ and $R^9$ are each $C_{1-3}$ alkyl.

In some embodiments, $R^1$ is phenyl optionally substituted with halo, pyridinyl optionally substituted with halo, $C_{3-6}$ cycloalkyl, or 4-6 member heterocyclyl.

In some embodiments, $R^1$ is 2-fluorophenyl, 3-fluoropyrini-4-yl, cyclopropyl or oxan-4-yl.

In some embodiments, each $L_1$, $L_2$, $L_3$, $L_4$ and $L_5$ is independently:

i)

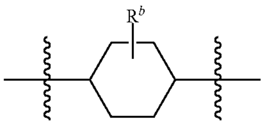

;

ii)

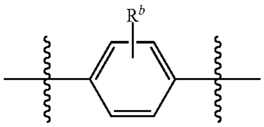

;

iii)

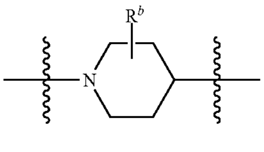

,

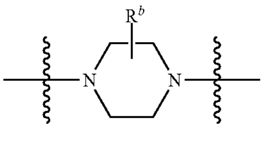

,

-continued

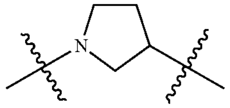
,
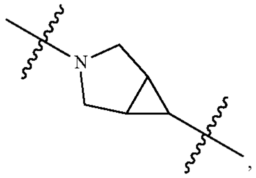
,

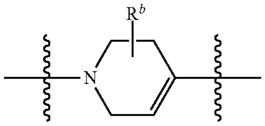
;

iv)

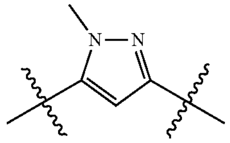
, or
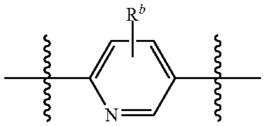
;

Also provided herein is a pharmaceutical composition comprising a compound of Formula (I), or any one of the substructures or specific compounds of Examples 1-146, or a pharmaceutically acceptable salt thereof, and a pharmaceutically acceptable excipient or carrier.

Further embodiments provide methods for treating a disease or disorder associated with increased hematopoietic progenitor kinase 1 (HPK1) activity, for increasing T-cell activation, for treating cancer, for inhibiting the growth or proliferation of cancer cells, for treating or preventing a hepatitis B virus (HBV) infection, or for treating or preventing a human immunodeficiency virus (HIV) infection, the method comprising administering to a subject in need thereof a therapeutically effective amount of a compound of Formula (I), or any one of the substructures or compounds of Examples 1-303.

DETAILED DESCRIPTION

Specific degradation of HPK1 could be accomplished by using heterobifunctional small molecules to recruit HPK1 to a ubiquitin ligase and thus promoting ubiquitylation and proteasomal degradation of HPK1. Thus, provided herein are bifunctional compounds, each comprising an HPK1 binder, which is covalently conjugated via a linker moiety (L) to a ligase harness moiety (LHM) for targeting ubiquitin ligase. Preferably, the LHM targets cereblon (CRBN) proteins, which are substrate recognition subunits of two ubiquitously expressed and biologically important Cullin RING E3 ubiquitin ligase complexes. See, e.g., WO 2019/099926, WO 2020/023851, and U.S. Published Application No. 2019/0192668.

One embodiment provides a bifunctional compound of Formula (I):

Formula (I)

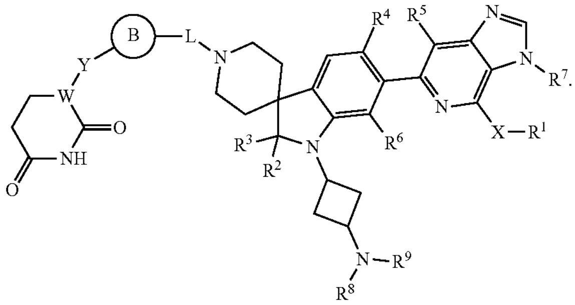

or a pharmaceutically acceptable salt thereof, wherein:

$R^1$ is
- i) phenyl optionally substituted with 1-3 groups independently selected from halogen, $C_{1-3}$ alkyl, —C(O)N($R^{11}$)$_2$, —CN, —OH, and $C_{1-3}$ alkoxy,
- ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
- iii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
- iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy;

$R^2$ and $R^3$ are each H, or $R^2$ and $R^3$ together form ═O;

$R^4$, $R^5$, $R^6$, and $R^{10}$ are each independently H, halogen, $C_{1-3}$ alkyl, or $C_{1-3}$ alkoxy;

$R^7$ is H or $C_{1-6}$ alkyl optionally substituted with 1-3 groups independently selected from —OH, halogen, $C_{1-3}$ alkoxy, and $C_{3-7}$ monocyclic cycloalkyl;

$R^8$ and $R^9$ are independently
- i) H,
- ii) $C_{3-7}$ monocyclic cycloalkyl optionally substituted with 1-3 groups independently selected from —OH, halogen, $C_{1-3}$ alkyl, and $C_{1-3}$ alkoxy,
- iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
- iv) $C_{1-6}$ alkyl optionally substituted with 1-6 groups independently selected from
  - a) —CN,
  - b) —OH,
  - c) halogen,
  - d) $C_{1-3}$ alkoxy,
  - e) $C_{3-7}$ monocyclic cycloalkyl optionally substituted with 1-3 groups independently selected from —OH, halogen, $C_{1-3}$ alkyl, and $C_{1-3}$ alkoxy, and f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or $R^8$ and $R^9$, together with the nitrogen to which they are attached, form 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{12}$;

each $R^{11}$ is independently i) H, ii) $C_{1-6}$ alkyl optionally substituted with 1-6 groups independently selected from —CN, —OH, halogen, $C_{1-3}$ alkoxy, and $C_{3-7}$ monocyclic cycloalkyl, iii) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or iv) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy, each $R^{12}$ is independently i) —CN, ii) a halogen, iii) —OH, iv) $C_{1-6}$ alkoxy optionally substituted with 1-3 groups independently selected from —OH, halogen, $C_{1-3}$ alkoxy, and $C_{3-7}$ monocyclic cycloalkyl, v) $C_{1-6}$ alkyl optionally substituted with 1-3 groups independently selected from —OH, halogen, $C_{1-3}$ alkoxy, and $C_{3-7}$ monocyclic cycloalkyl, vi) —COOH, or vii) —C(O)N($R^{13}$)$_2$, wherein each $R^{13}$ is independently H or $C_{1-6}$ alkyl;

X is —N($R^{11}$)— or —O—;

L is -$L_1$-$L_2$-$L_3$-$L_4$-$L_5$-, each $L_1$, $L_2$, $L_3$, $L_4$ and $L_5$ being independently:

i) $C_{3-12}$ cycloalkyl optionally substituted with 1-3 $R^b$, ii) $C_{6-12}$ aryl optionally substituted with 1-3 $R^b$, iii) 4-12 membered heterocyclyl optionally substituted with 1-3 $R^b$, iv) 5-12 membered heteroaryl optionally substituted with 1-3 $R^b$, v) direct bond, vi) $C_{1-12}$ alkylene chain optionally substituted with 1-3 $R^d$, vii) $C_{2-12}$ alkenylene chain optionally substituted with 1-3 $R^d$, viii) $C_{2-12}$ alkynylene chain optionally substituted with 1 to 3 $R^d$, or ix) —C(O)—, —C(O)O—, —O—, —N($R^c$)—, —$(CH_2)_m$—C(O)—, —S—, —C(S)—, —C(S)—O—, —S(O)$_2$—, —S(O)═N—, —S(O)$_2$NH—, —C(O)—N($R^c$)—, —C═N—, —O—C(O)—N($R^c$)—, —O—C(O)—O—, or —NH—$(CH_2)_m$—C(O)—, wherein m is 0, 1, 2 or 3;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$;

each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —NR'S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$;

each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

Y is direct bond, $C_{1-4}$ alkylene chain, —C(O)—, —C(O)O—, —O—, —N($R^g$)—, —S—C(S)—, —C(S)—O—, —O—C(O)O—, —C(O)—N($R^g$)—, or —O—C(O)—N($R^g$)—;

B ring is $C_{6-12}$ aryl, 5-12 membered heteroaryl, or 4-12 membered heterocyclyl, each being optionally substituted with 1 to 3 $R^j$;

each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—R, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^1$;

$R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

In more specific embodiments, the compound of Formula (I) may be represent by one or more of the following substructures, wherein the variables are as defined herein:

Formula (Ia)
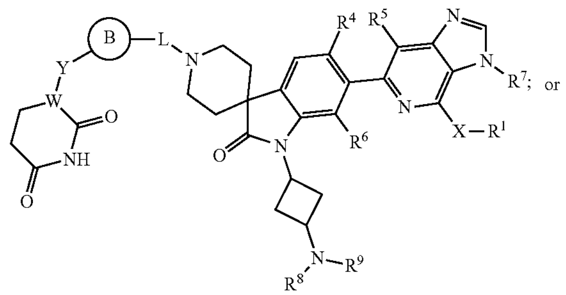
or
Formula (Ib)
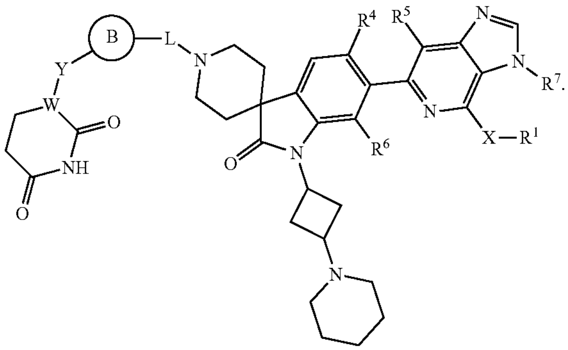
Formula (Ic)
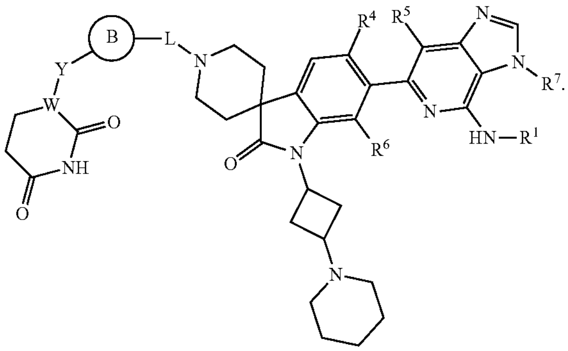
Formula (Id)
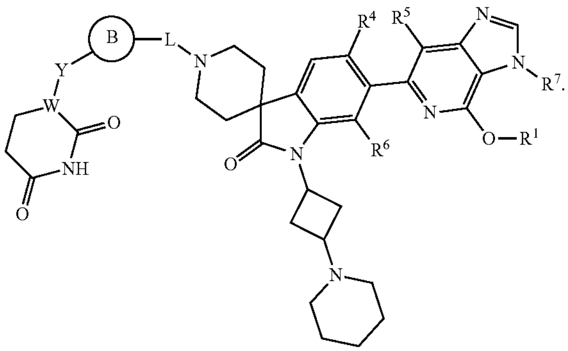
In certain embodiments, $R^1$ is not
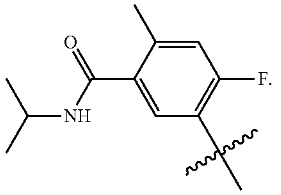 [SMILES: *c1cc(C(=O)NC(C)C)c(C)cc1F]
In some embodiments, when $R^1$ is
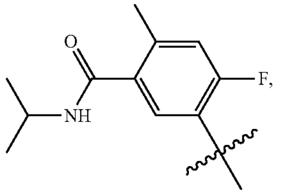
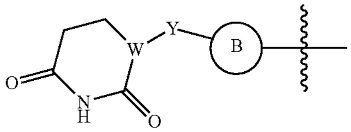
is not
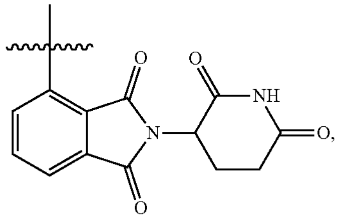
or
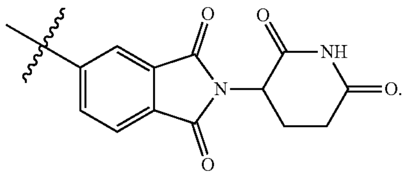
In some embodiments, a compound of Formula (I) is not any of the compounds disclosed in PCT/US2021/030928.
HPK1 Binders
Formula (A) depicts the HPK1 Binder moiety of the bifunctional compound of Formula (I):

Formula (A)

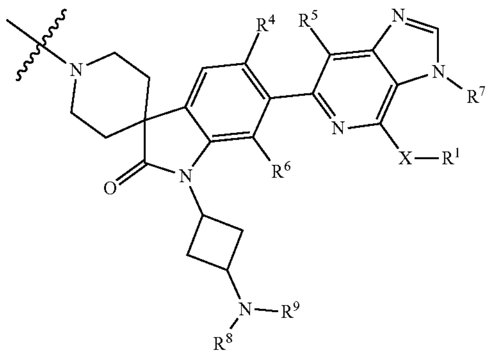

wherein, $R^1$-$R^9$ and X are defined above, and the wavy line depicts the coupling site to the linker moiety (L).

In some embodiments, X is —NH—, and Formula (A) is represented by Formula (A1):

Formula (A1)

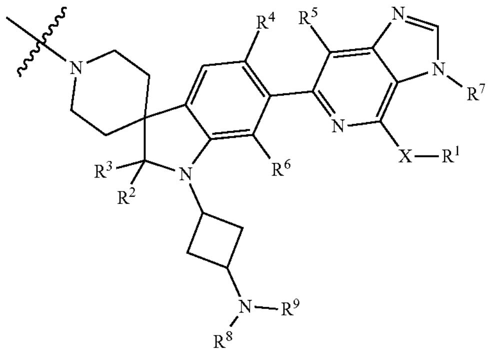

In more specific embodiments, $R^2$ and $R^3$ form oxo, $R^8$ and $R^9$, together with the nitrogen to which they are attached, form piperidinyl, and the HPK1 Binder moiety has a structure of Formula (A2):

Formula (A2)

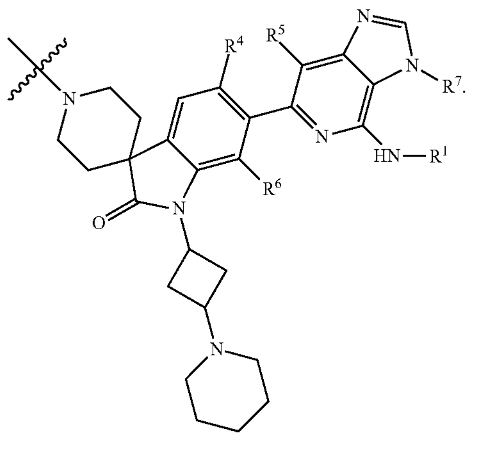

In yet more specific embodiments, a compound of Formula (A2) may have one of the following diastereomeric structures:

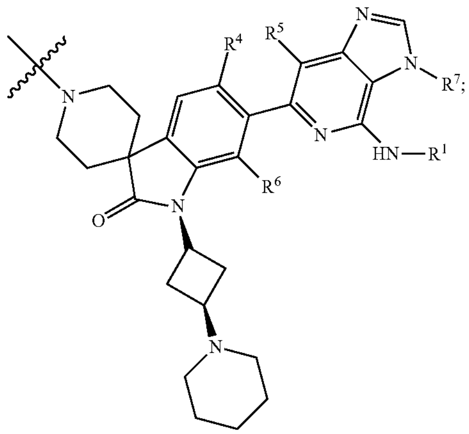

or

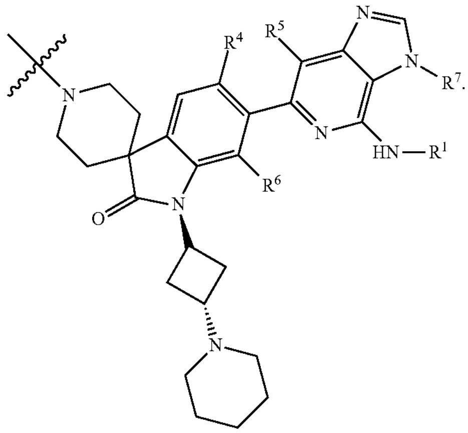

In other more specific embodiments, $R^8$ and $R^9$ are each $C_{1-3}$ alkyl.

In yet other more specific embodiments, X is —O—.

In various embodiments, $R^1$ is phenyl optionally substituted with halo, pyridinyl optionally substituted with halo, $C_{3-6}$ cycloalkyl, or 4-6 member heterocyclyl.

In more specific embodiments, $R^1$ is 2-fluorophenyl, 3-fluoropyrini-4-yl, cyclopropyl or oxan-4-yl.

In other more specific embodiments, $R^1$ is

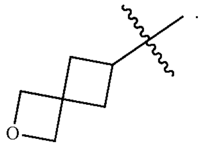 [SMILES: *C1CC2(COC2)C1]

In other more embodiments, $R^1$ is $C_{3-6}$ cycloalkyl optionally substituted with halo or CN. In more specific embodiments, $R^1$ is cyclobutyl optionally substituted with halo or CN. In even more specific embodiments, $R^1$ is

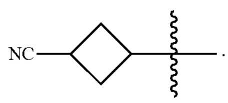 [SMILES: *C1CC(C#N)C1]

In other embodiments, $R^1$ is $C_{1-6}$ alkyl. In more specific embodiments, $R^1$ is isopropyl.

In yet other embodiments, X is —N($R^{11}$)—, and $R^{11}$ and $R^1$, together with the nitrogen atom to which they are connected, may form a 4-12 membered heterocylcle optionally substituted halo or CN, and the HPK1 binder moiety is represented by Formula (A3):

Formula (A3)

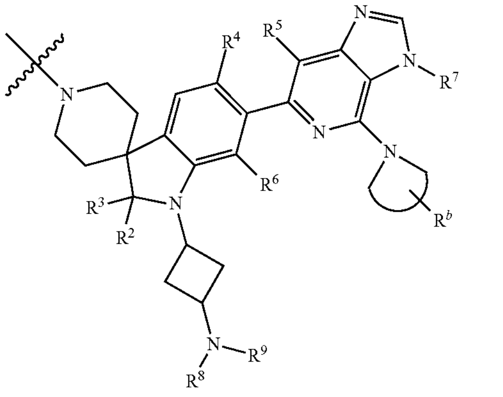

In more specific embodiments, Formula (A3) has the following structures:

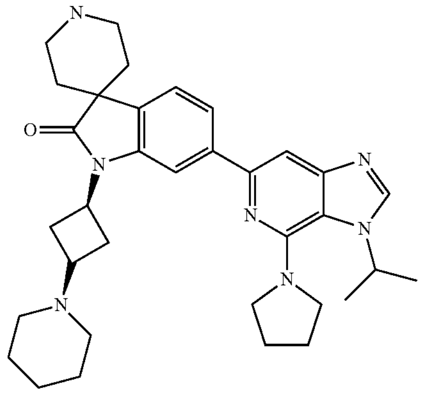

or

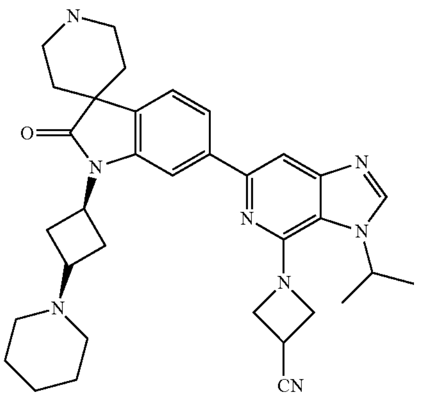

.

In more specific embodiments of Formula (A1), wherein $R^2$ and $R^3$ form oxo, $R^8$ and $R^9$, together with the nitrogen to which they are attached, form one of the following heterocycle rings:

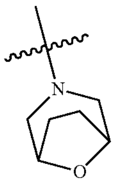

,

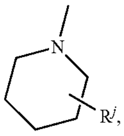

,

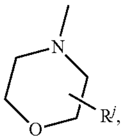

,

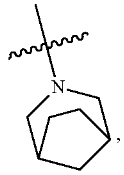

,

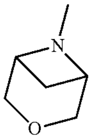

,

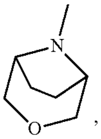

, wherein R is H or halo.

In more specific embodiments, the HPK1 Binder moiety has one of the following structures:

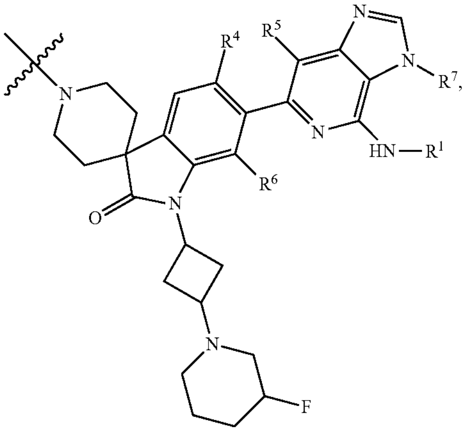

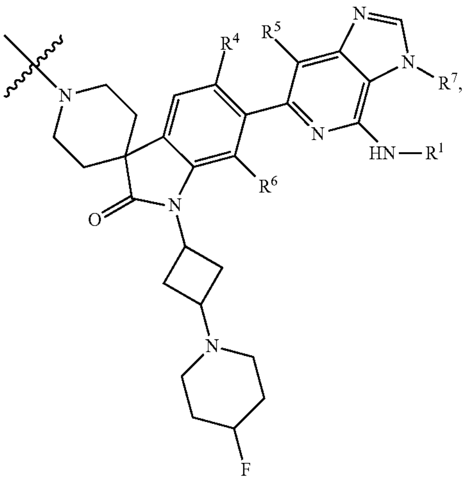

-continued

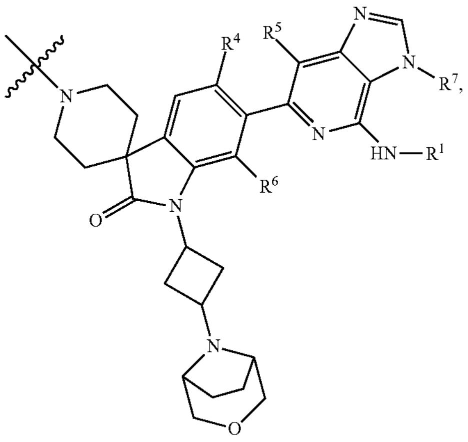

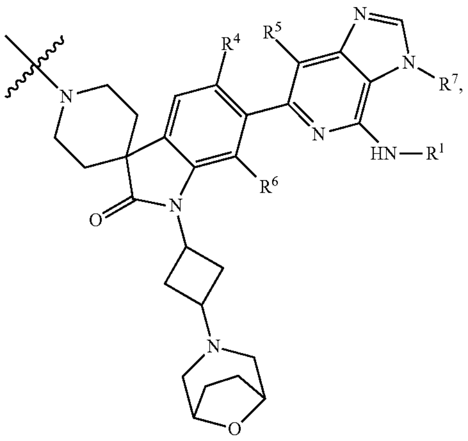

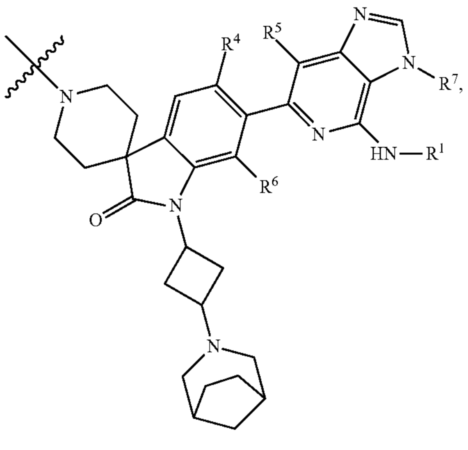

-continued

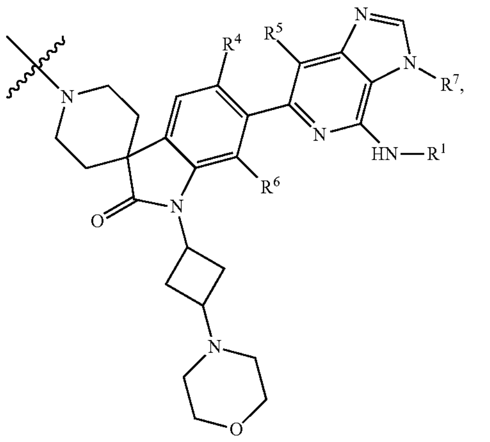

or

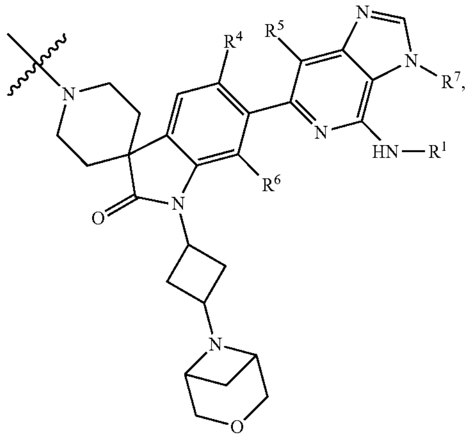

wherein, $R^1$ is phenyl optionally substituted with halo, pyridinyl optionally substituted with halo, $C_{3-6}$ cycloalkyl, or 4-6 member heterocyclyl; and $R^4$, $R^5$, $R^6$ and $R^7$ are independently H or $C_{1-3}$alkyl.

In more specific embodiments, $R^1$ is cyclopropyl, $R^4$, $R^5$, and $R^6$ are hydrogen, and $R^7$ is cyclopropyl.

Ligase Harness Moieties (LHM)

The LHM moiety of the bifunctional compound of Formula (I) targets CRBN of E3 ligases. Once harnessed by the bifunctional compounds, the E3 ligases are capable of inducing ubiquitination and subsequent proteasomal degradation of HPK1.

The LHM moiety of Formula (I) typically comprises a glutarimide or uracil moiety coupled to a ring structure, as represented by Formula (B):

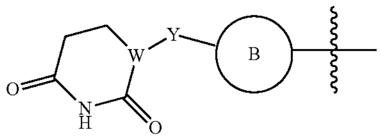

wherein W, Y and B are as defined herein.

In certain embodiments, W is —CH—, Y is direct bond; and B ring is

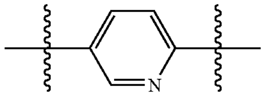, 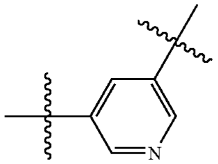,

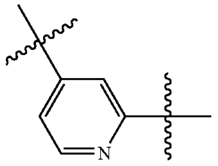, 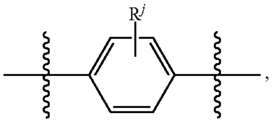,

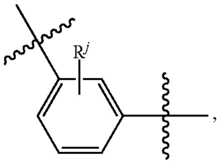, 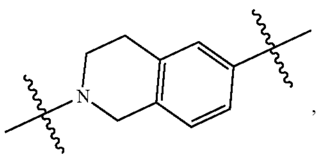,

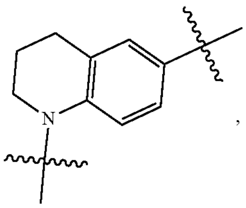, 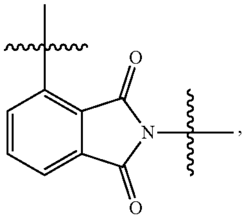,

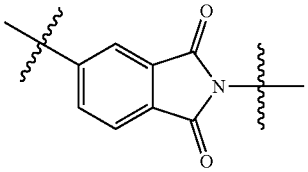, 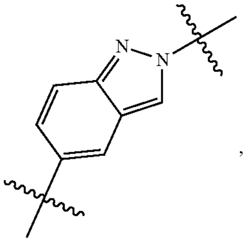,

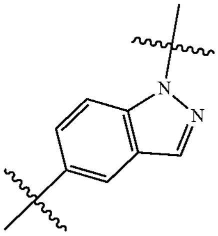, 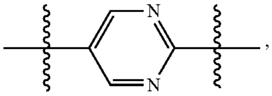, or

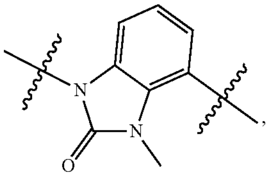, wherein $R^j$ is H or $C_{1-3}$alkyl.

In other embodiment, when W is —CH—, Y is direct bond; and B ring is

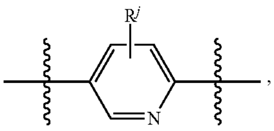, 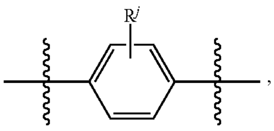,

-continued

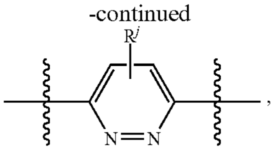, wherein $R^j$ is H, $C_{1-3}$alkyl or halo.

In more specific embodiments, when W is —CH—, Y is direct bond; and B ring is

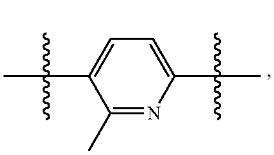, 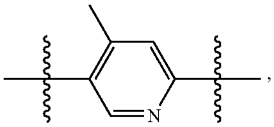,

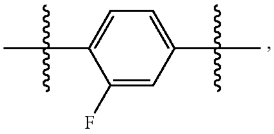, 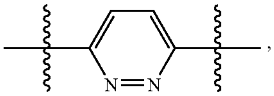, wherein $R^j$ is H, $C_{1-3}$alkyl or halo.

In other embodiments, W is —N—, Y is direct bond; and B ring is

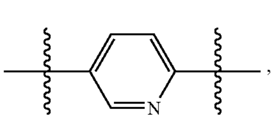, 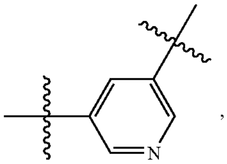,

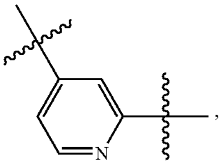, 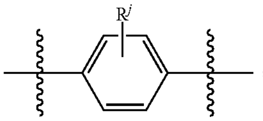,

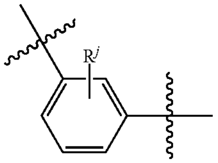, or

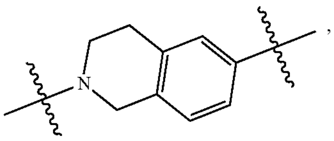, wherein $R^j$ is H or $C_{1-3}$alkyl.

In yet other embodiments W is —CH—, Y is —NHC(O)—, and B ring is

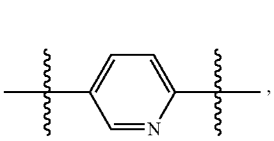, 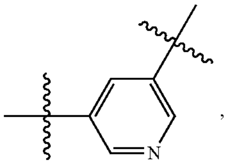,

-continued

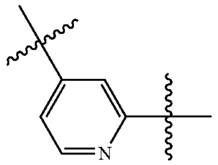,
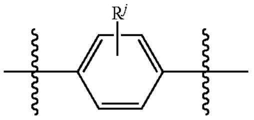, or
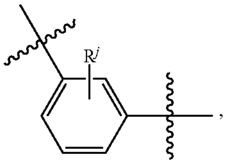, wherein $R^j$ is H or $C_{1-3}$alkyl.

Linker

Each bifunctional compound of Formula (I) comprises a Linker (L), which is a bivalent moiety that couples the HPK1 Binder moiety to the LHM. The structure (e.g., length or rigidity) of the linker moiety may impact the efficiency or selectivity of the degradation process. The Linker comprises a continuous sequence of covalent bonds between the respective attachment points to the HPK1 Binder moiety and the LHM, inclusive of the bond indicated by a wavy line of Formulae (A) and (B) and their respective substructures.

Typically, the linker moiety comprises multiple bivalent segments (i.e., $L_1$, $L_2$, $L_3$, $L_4$ and $L_5$), which collectively contribute to the overall length and rigidity of the Linker, in addition to providing the respective attachment points to the HPK1 Binder moiety and the LHM. In various embodiments, the linker segments $L_1$, $L_2$, $L_3$, $L_4$ and $L_5$ are each independently:

i) $C_{3-12}$ cycloalkyl optionally substituted with 1-3 $R^b$;
ii) $C_{6-12}$ aryl optionally substituted with 1-3 $R^b$;
iii) 4-12 membered heterocyclyl optionally substituted with 1-3 $R^b$;
iv) 5-12 membered heteroaryl optionally substituted with 1-3 $R^b$;
v) direct bond;
vi) $C_{1-12}$ alkylene chain optionally substituted with 1-3 $R^d$;
vii) $C_{2-12}$ alkenylene chain optionally substituted with 1-3 $R^d$;
viii) $C_{2-12}$ alkynylene chain optionally substituted with 1 to 3 $R^d$;
ix) —C(O)—, —C(O)O—, —O—, —N($R^c$)—, —$(CH_2)_m$—C(O)—, —S—, —C(S)—, —C(S)—O—, —$S(O)_2$—, —S(O)═N—, —$S(O)_2$NH—, —C(O)—N($R^c$)—, —C═N—, —O—C(O)—N($R^c$)—, —O—C(O)—O—, or —NH—$(CH_2)_m$—C(O)—, wherein m is 0, 1, 2 or 3;

wherein $R^d$, $R^c$ and $R^d$ are as defined herein.

It is to be understood that, unless otherwise specified and provided that the valence is satisfied, the bivalent moieties described herein (e.g., $L^1$ or $L^2$) are not limited to the direction in which they are expressed. For instance, for a given $L^1$, e.g., —C(O)—NH—, the manner in which it is connected to the remainder of the molecule may be either direction: i.e., —C(O)—NH— or —NH—C(O)—, provided that the connection does not violate valence rules.

One or more linker segments may be direct bonds. To illustrate, in a sequence of linker segments represented by -$L_2$-$L_3$-$L_4$-, when $L_3$ is a direct bond, it is effectively absent because $L_2$ and $L_4$ are attached directly to each other.

In another embodiment, the Linker has one or more rings, which tend to increase the linker rigidity. A combination of chain bonds and ring(s) may be used to tune the relative orientations of the bifunctional groups or the distance therebetween.

In more specific embodiments, each $L_1$, $L_2$, $L_3$, $L_4$ and $L_5$ is independently:

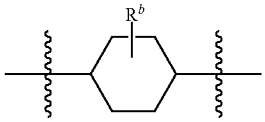;
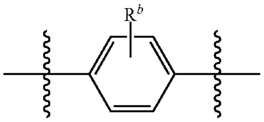;
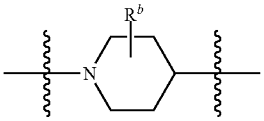,
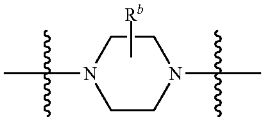,
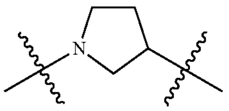,
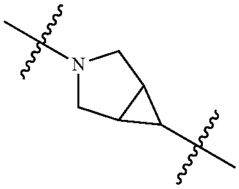,
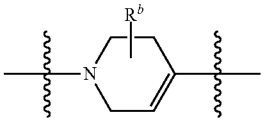;
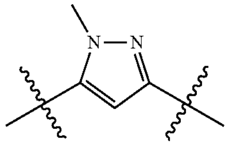, or
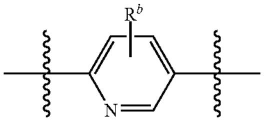;

v) direct bond;
vi) $C_{1-3}$ alkylene chain; or
vii) —C(O)—, —O—, —C(O)—N($R^c$)—, —$(CH_2)_m$—C(O)—, or —NH—$(CH_2)_m$—C(O)—, wherein m is 0, 1, 2 or 3;

wherein $R^b$ is H or $C_{1-3}$ alkyl, $R^c$ is H or $C_{1-3}$ alkyl.

In more specific embodiments, L is connected to the B ring by $L_1$, and wherein $L_1$ is direct bond, —C(O)—, —N($R^c$)— (wherein $R^c$ is H or methyl), —O—, —$CH_2$—, or —NH—$CH_2$—C(O)—.

In further embodiments, when L is connected to the B ring by $L_1$, -$L_2$-$L_3$-$L_4$-$L_5$- has one of the following structures, or a stereoisomer thereof:

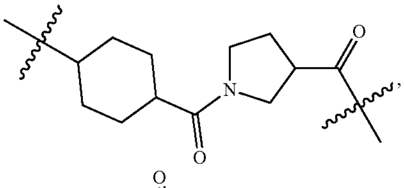,
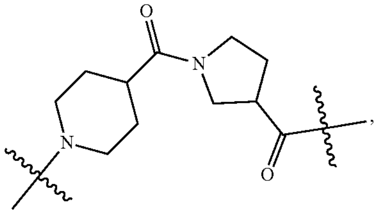,

-continued
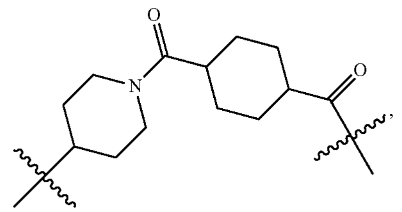
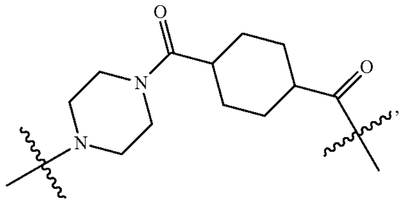
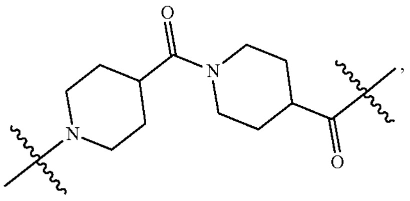
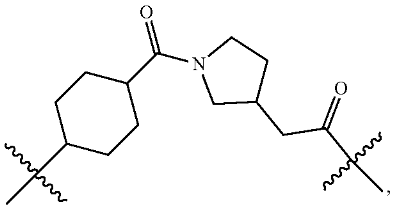
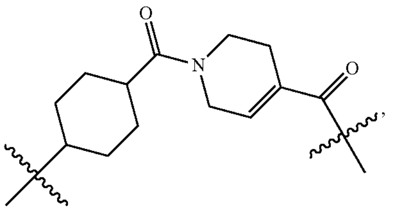
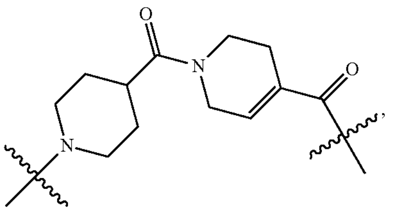
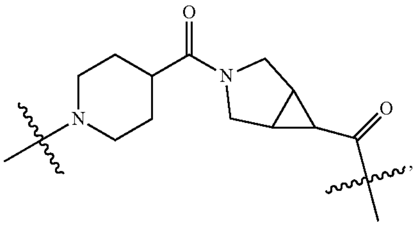
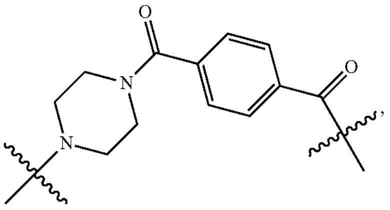
-continued
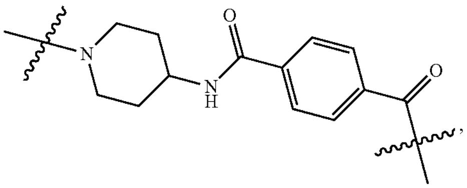
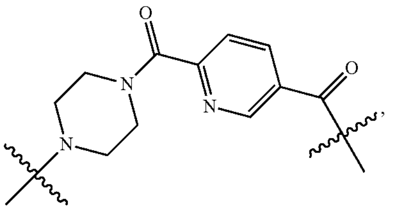
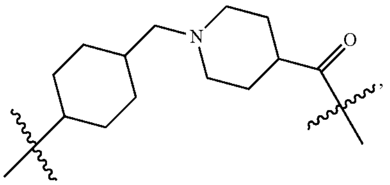
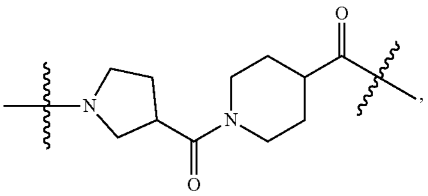
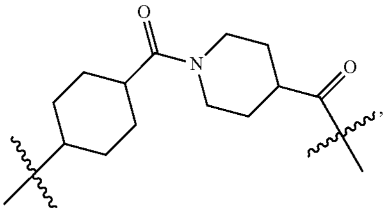
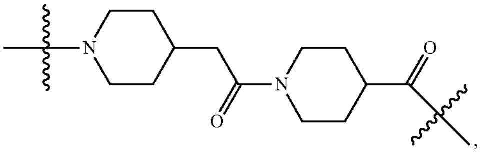
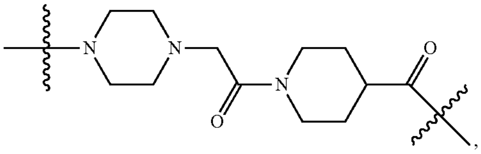
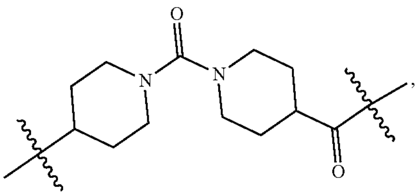
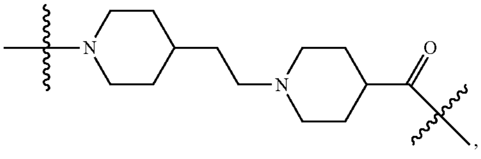

-continued
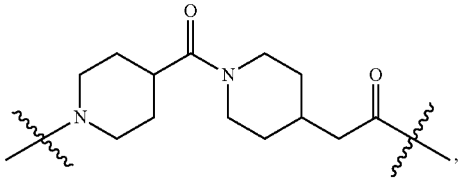
,
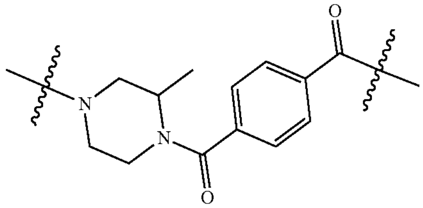
,
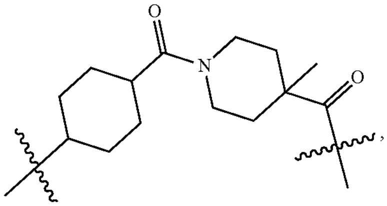
,
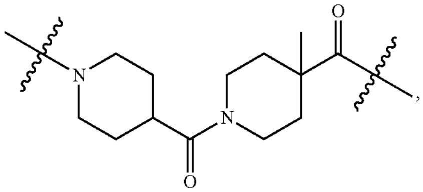
,
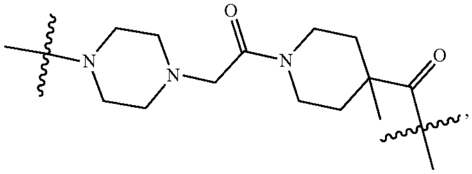
,
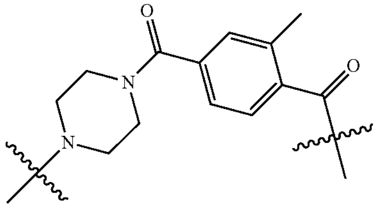
,
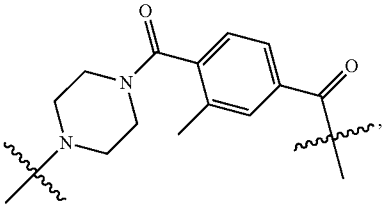
,
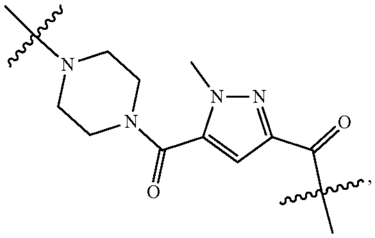
,
-continued
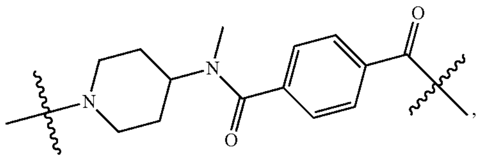
,
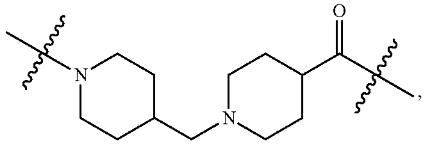
, or
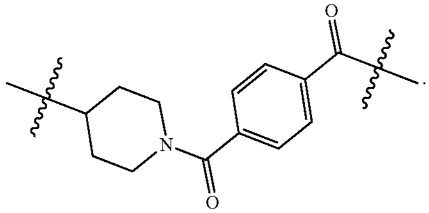
.
In other embodiments, the Linker may have specific stereochemistry configuration at one or more stereocenters. Thus, in more specific embodiments, L has one of the following structures:
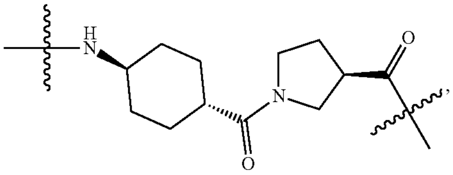
,
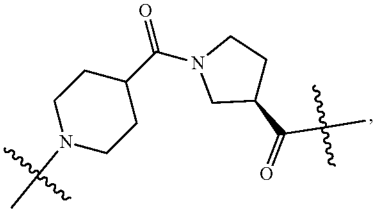
,
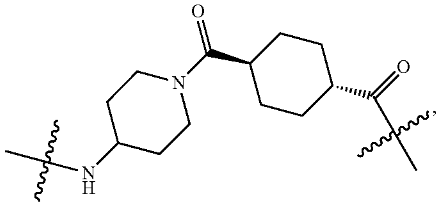
,
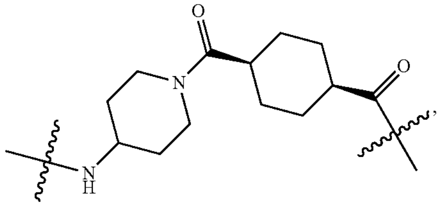
,
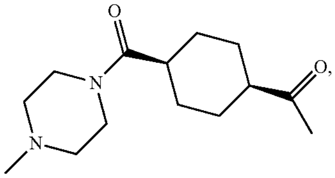

-continued
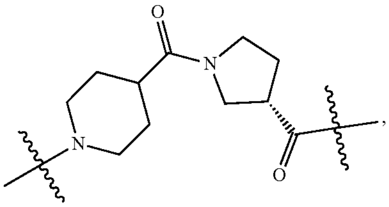
,
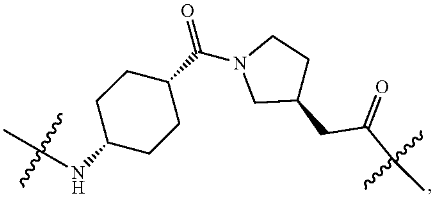
,
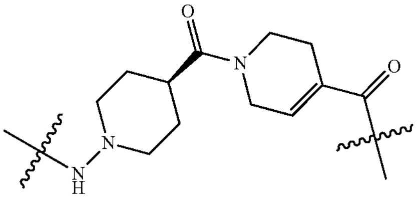
,
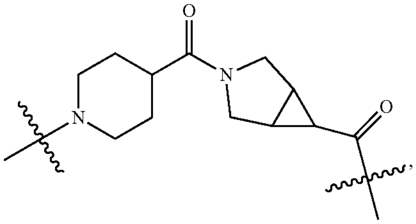
,
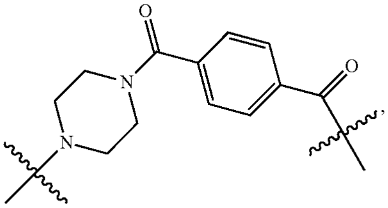
,
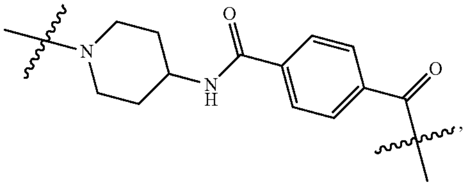
,
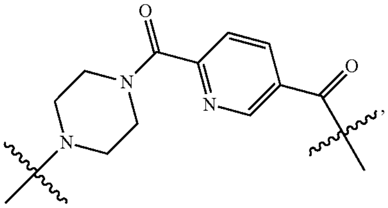
,
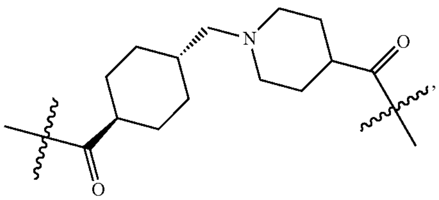
,
-continued
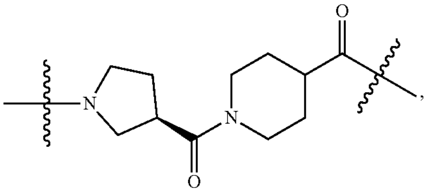
,
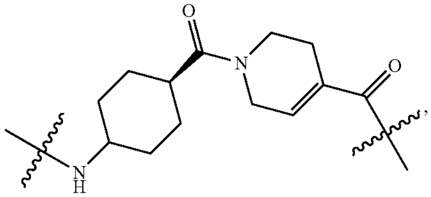
,
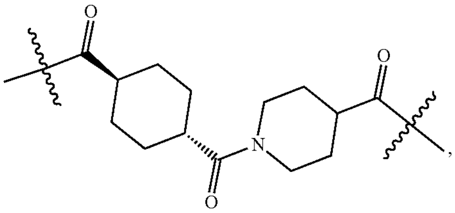
,
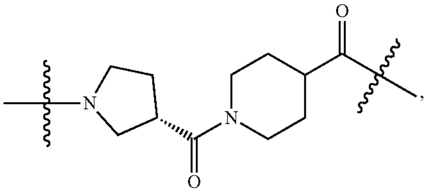
,
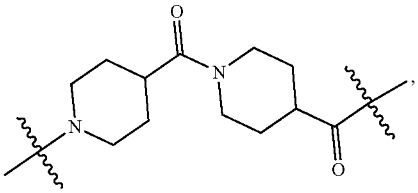
,
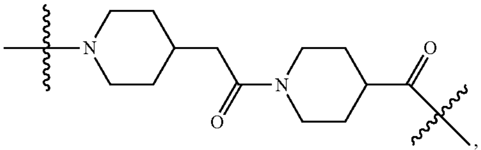
,
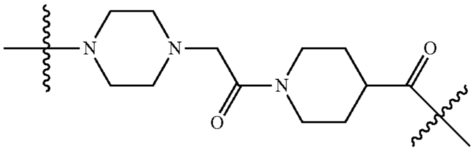
,
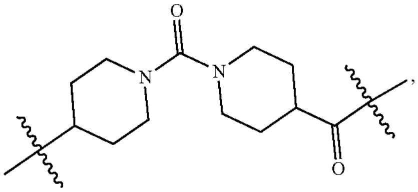
,
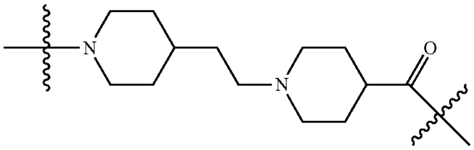
, -continued
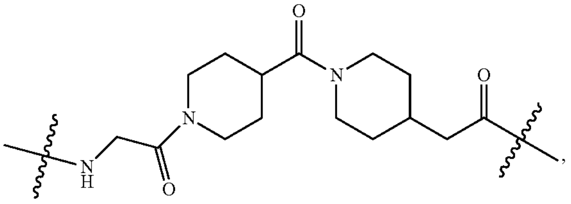
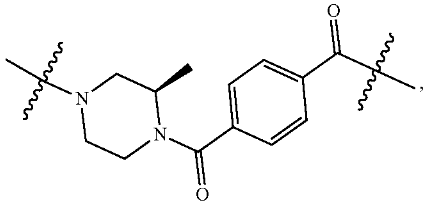
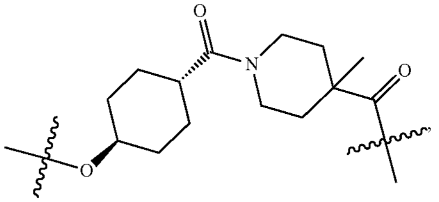
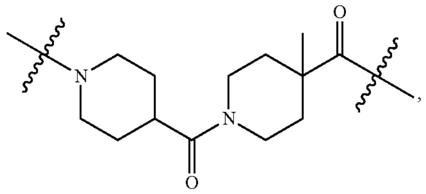
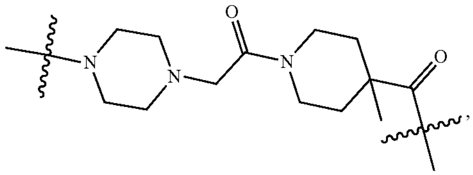
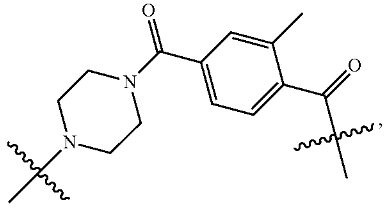
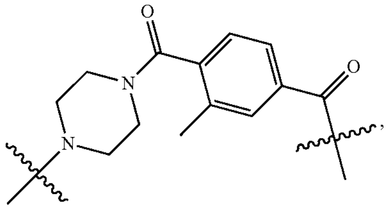
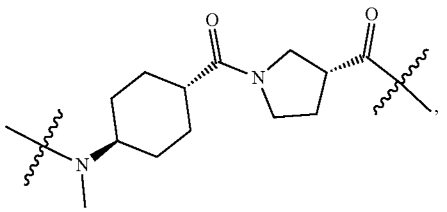
-continued
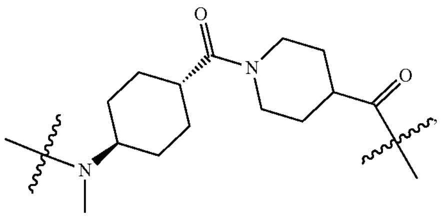
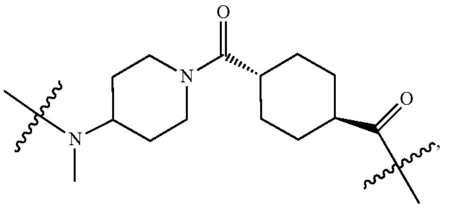
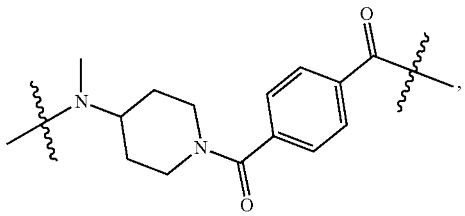
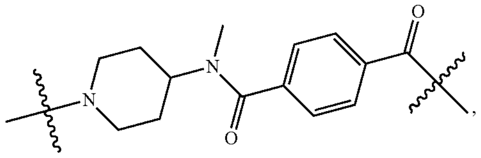
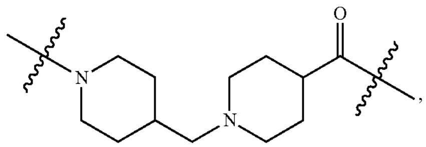
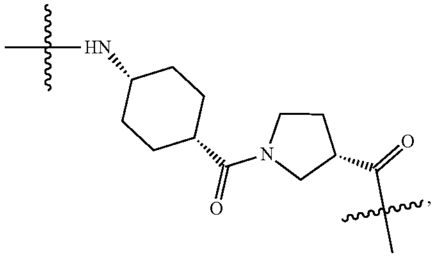
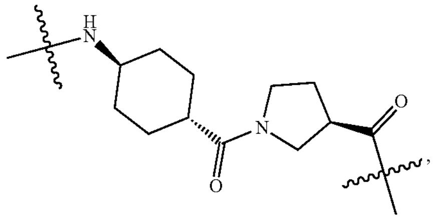
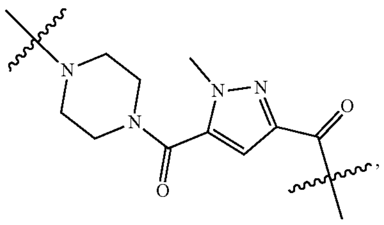

-continued
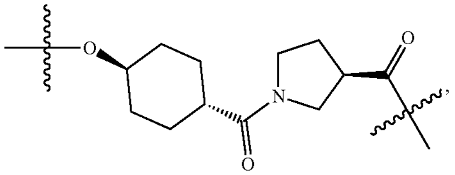,
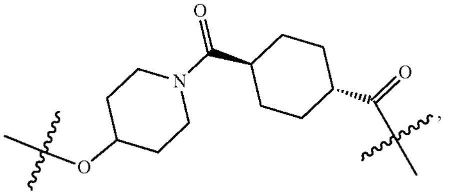,
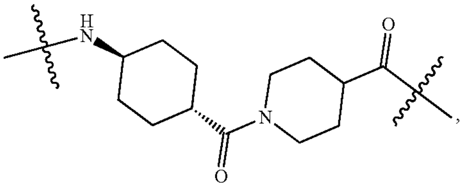,
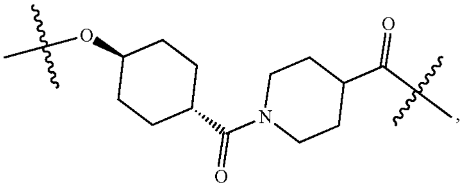,
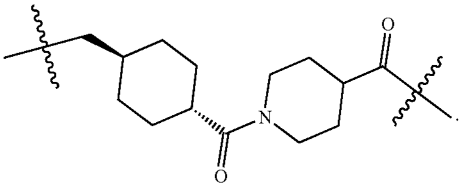.
In other more specific embodiments, L is $-L_1-L_2-L_3-L_4-L_5-$ and each $L_1$, $L_2$, $L_3$, $L_4$ and $L_5$ is independently:
i)
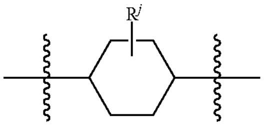 or 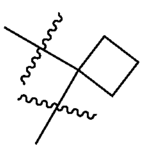,
ii)
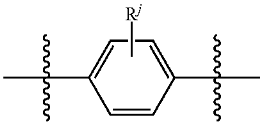 or 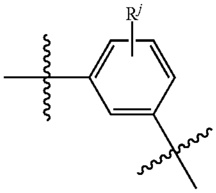
iii)
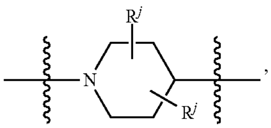, 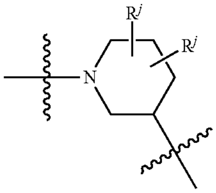,
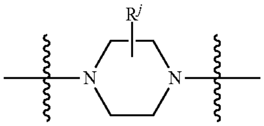, 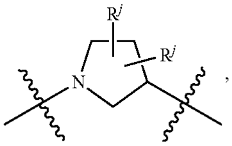, or
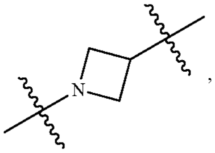,
iv)
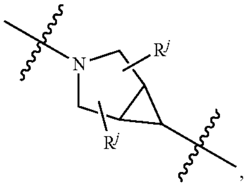, 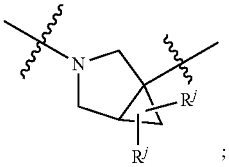;
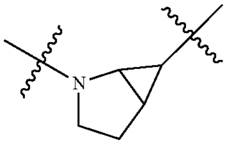 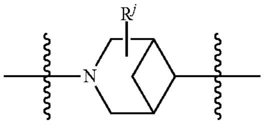,
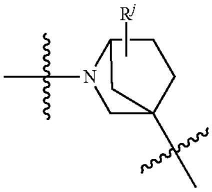, 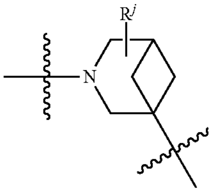,
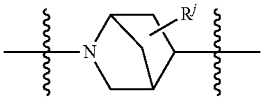, 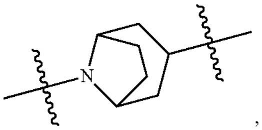,
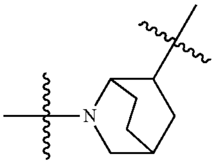, or 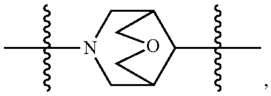, v)

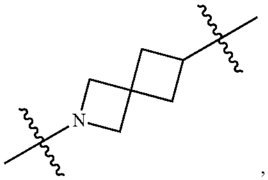
,
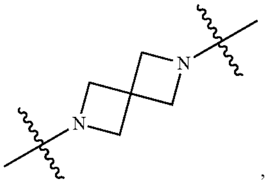
,
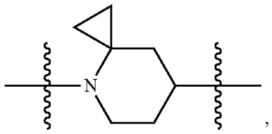
,
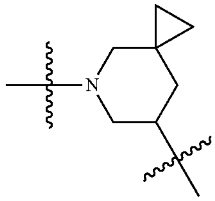
,
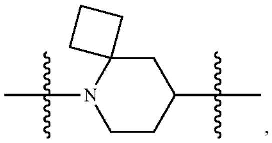
,
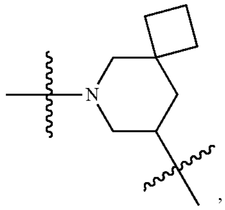
,
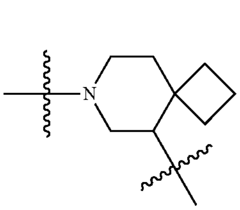
,
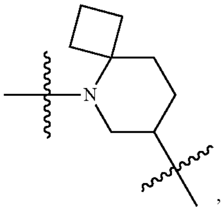
,
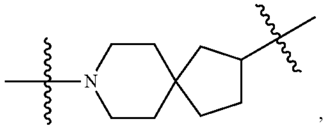
,
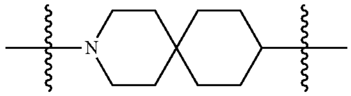
, or
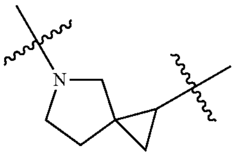
;

vi) direct bond;

vii) $C_{1-3}$ alkylene chain optionally substituted with 1-3 $R^d$;

viii) $C_{2-12}$ alkynylene chain optionally substituted with 1 to 3 $R^d$; or ix) —$S(O)_2$—, —$N(R^c)$—, —C(O)—, —O—, —C(O)—$N(R^c)$—, —$(CH_2)_m$—C(O)—, or —NH—$(CH_2)_m$—C(O)—, wherein m is 0, 1, 2 or 3, wherein each $R^j$ is independently H, halo, hydroxy, $C_{1-3}$ alkoxy, CN, $C_{1-6}$alkyl, or haloalkyl;

$R^d$ is halo or $C_{1-3}$alkyl; and $R^c$ is H or $C_{1-3}$ alkyl.

In more specific embodiments, each $L_1$, $L_2$, $L_3$, $L_4$ and $L_5$ is the same or different and independently:

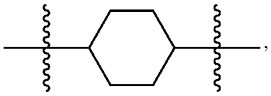
,
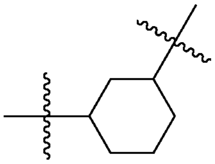
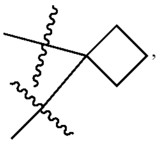
,
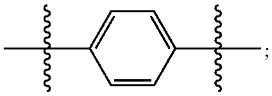
;
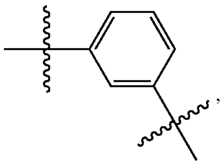
,
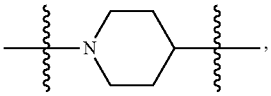
,
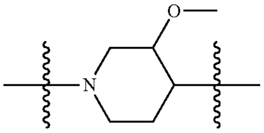
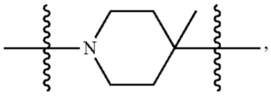
,
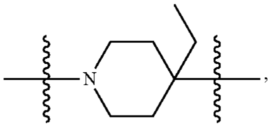
,
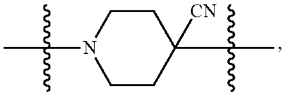
,
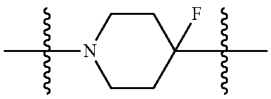
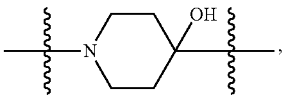
,
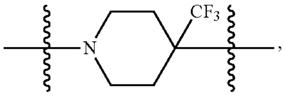
,
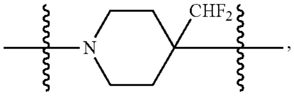
,
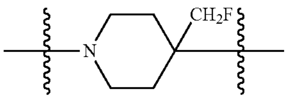
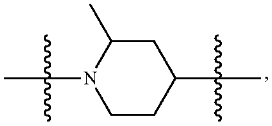
,
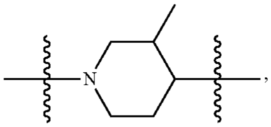
,
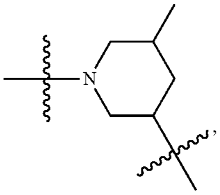
,
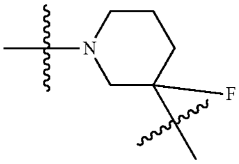
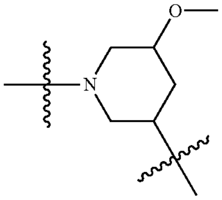

-continued
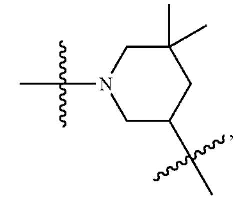,
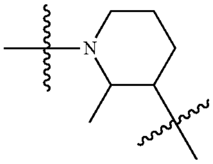
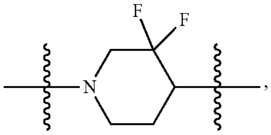,
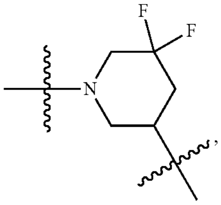,
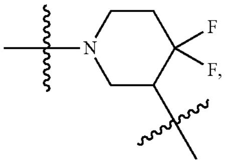
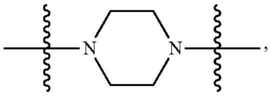,
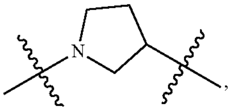,
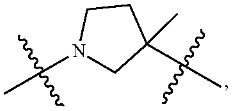,
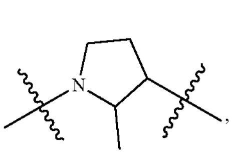,
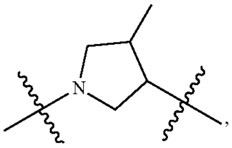,
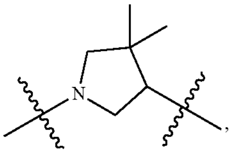,
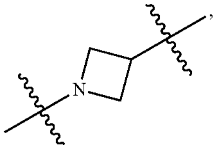,
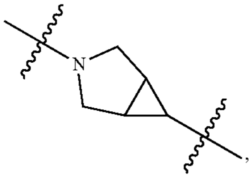,
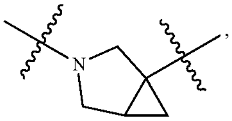,
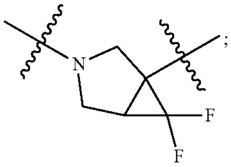;
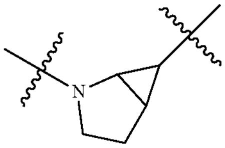
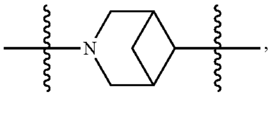,
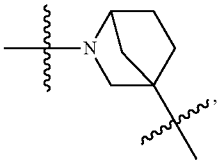,
-continued
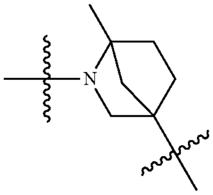
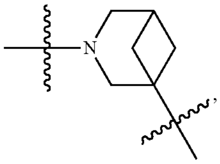,
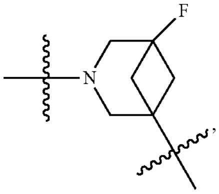,
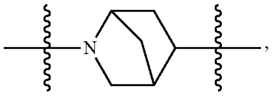,
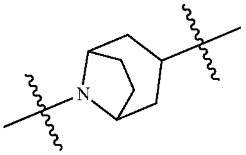,
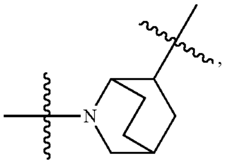,
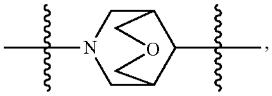,
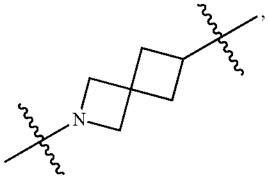,
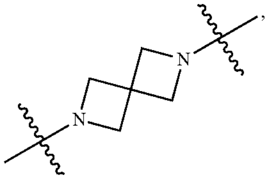,
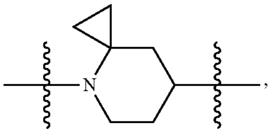,
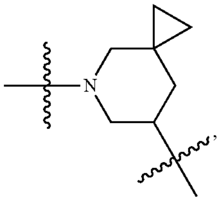,
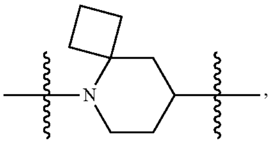,
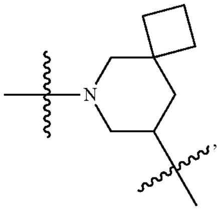, -continued
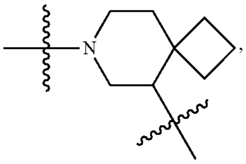,
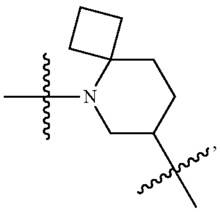,
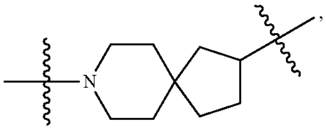,
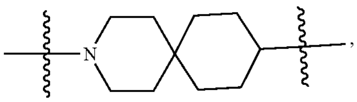, or
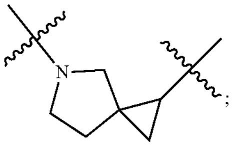;
ii) direct bond;
iii) —$(CH_2)$—, —$CH(CH_3)$—, —$C(CH_3)_2$—,
iv) —C≡C—; or
v) —$S(O)_2$—, —$N(CH_3)$—, —C(O)—, —O—, —C(O)—$N(CH_3)$—, —$(CH_2)$—C(O)—, or —NH—$(CH_2)_m$ C(O)—, wherein m is 0, 1, 2 or 3,
In more specific embodiments, L has one of the following structures, or a stereoisomer thereof:
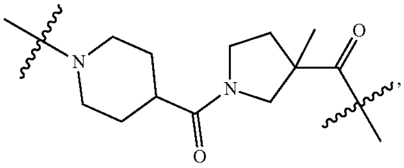,
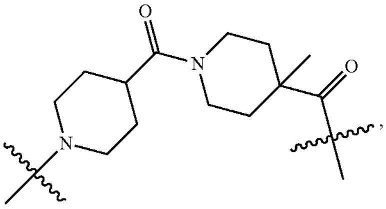,
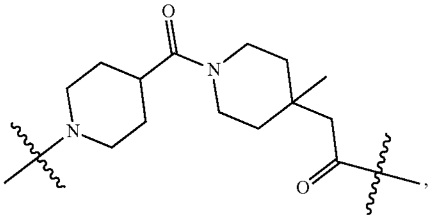,
-continued
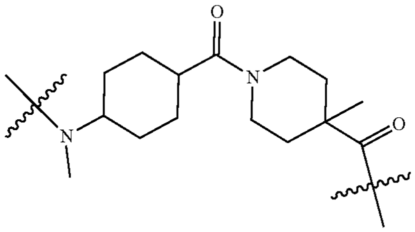
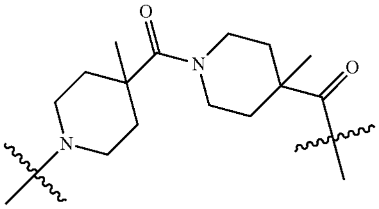
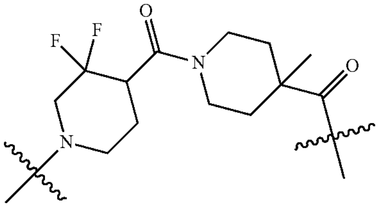
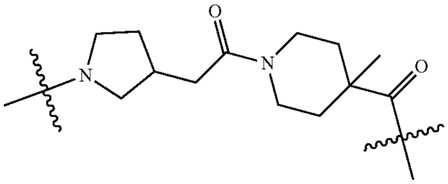
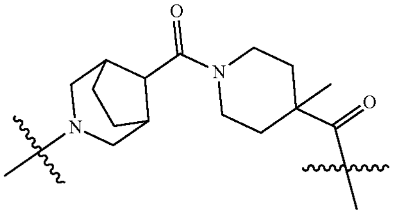
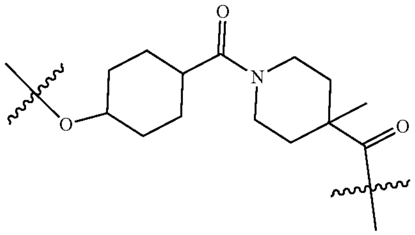
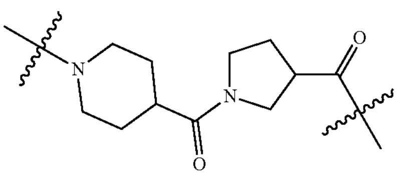
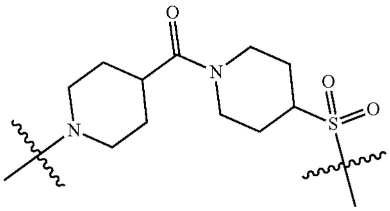

-continued
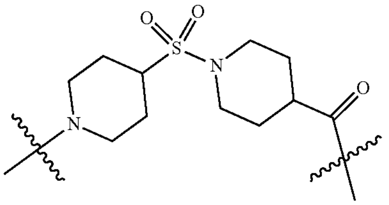
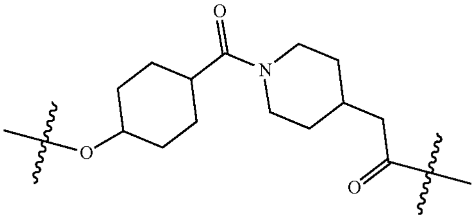
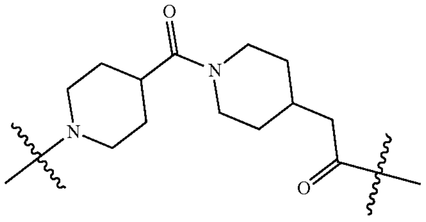
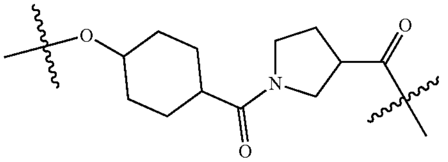
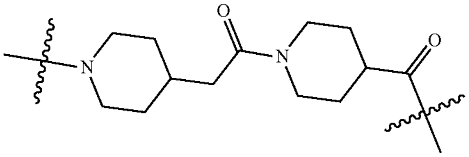
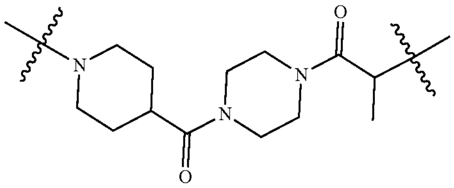
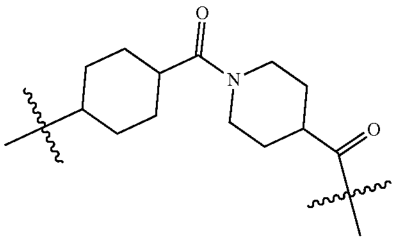
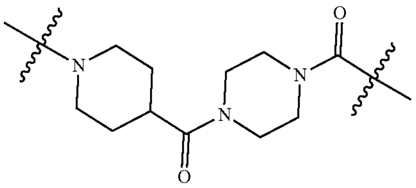
-continued
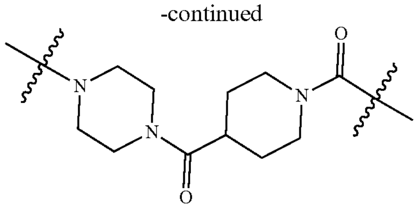
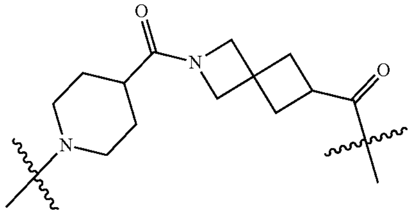
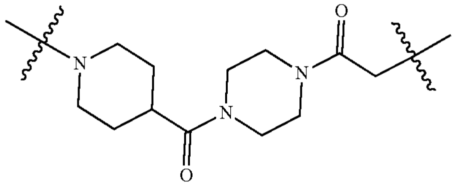
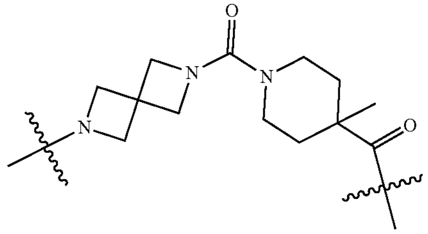
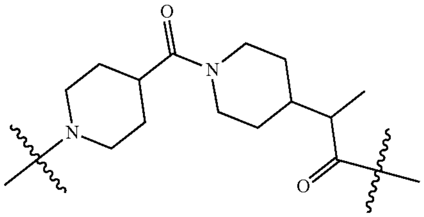
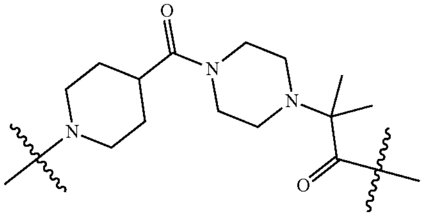
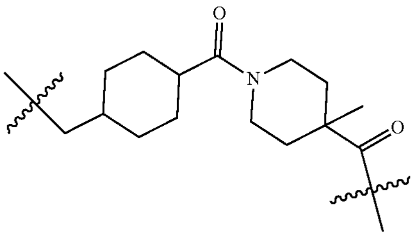
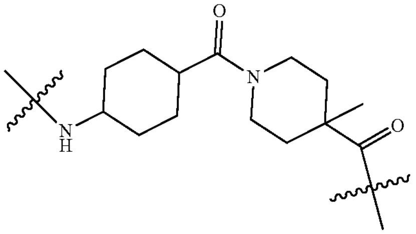

-continued
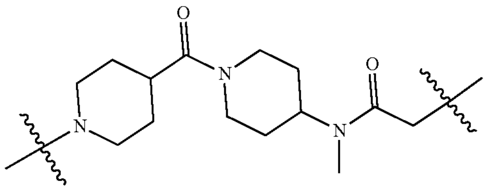
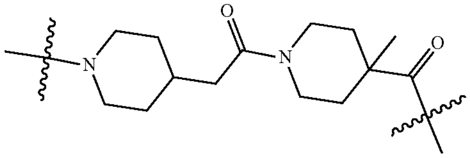
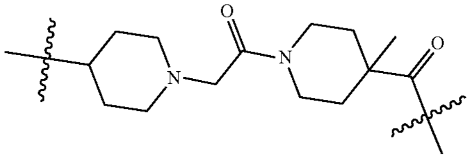
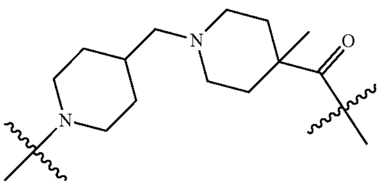
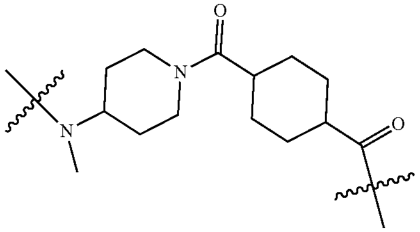
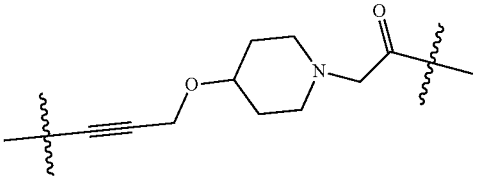
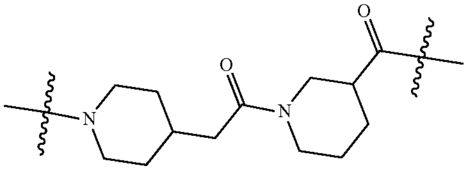
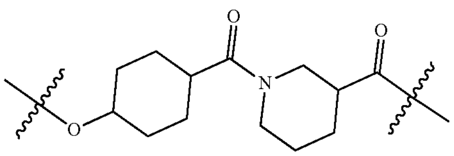
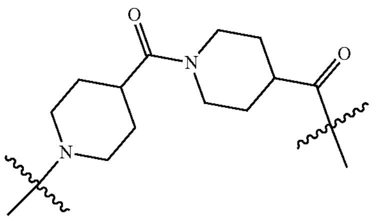
-continued
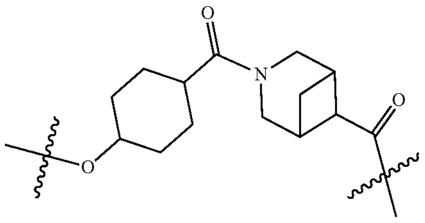
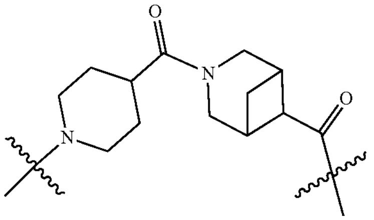
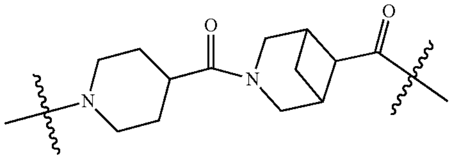
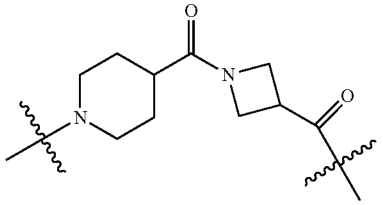
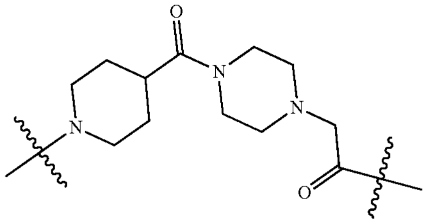
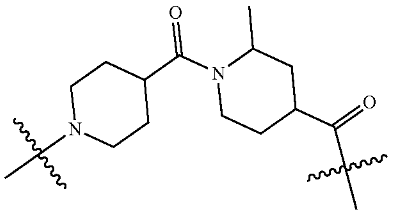
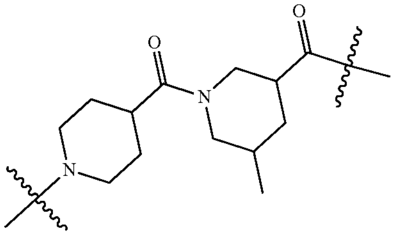
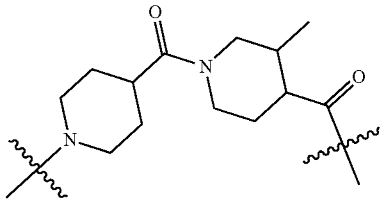

-continued
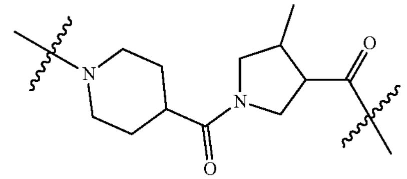
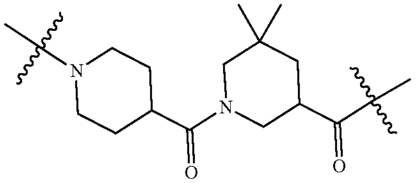
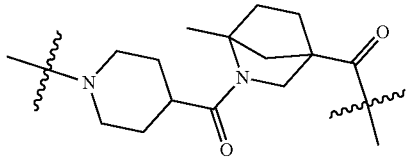
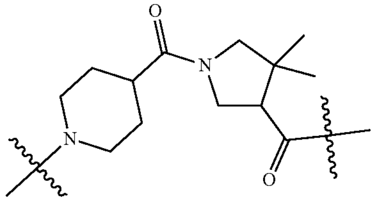
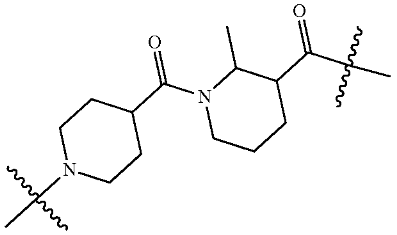
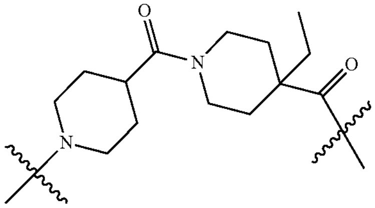
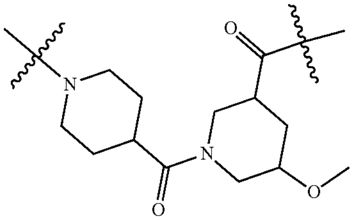
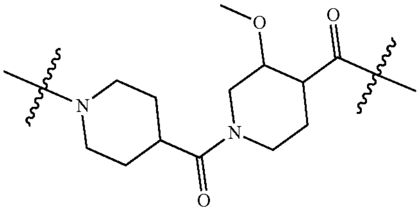
-continued
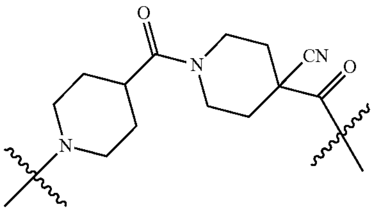
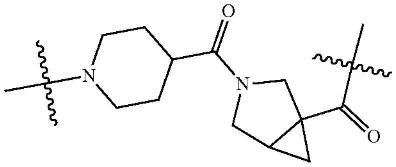
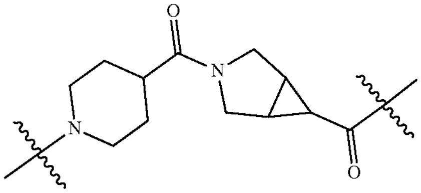
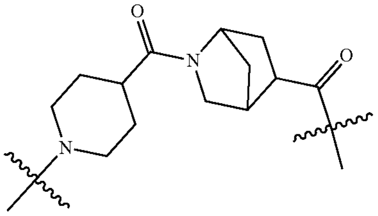
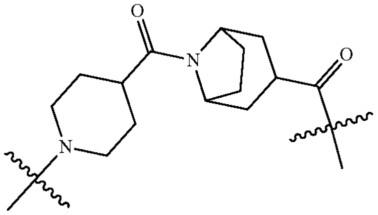
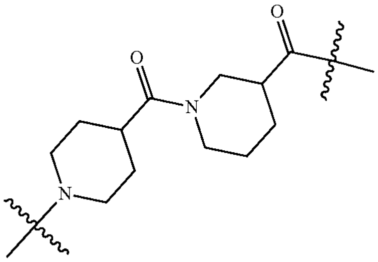
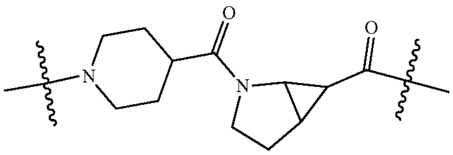
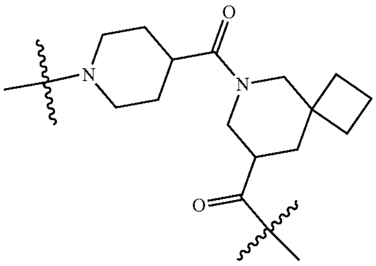

-continued
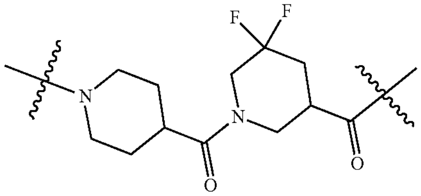
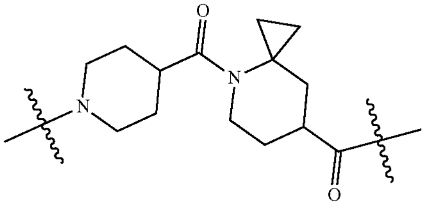
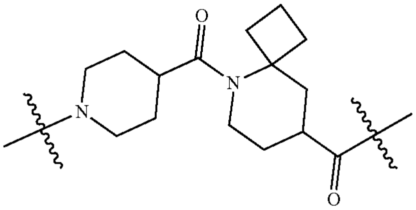
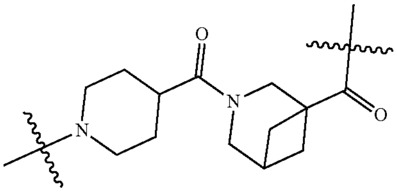
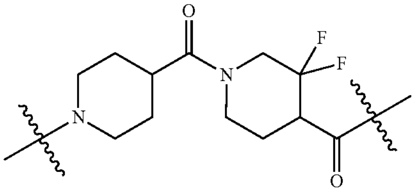
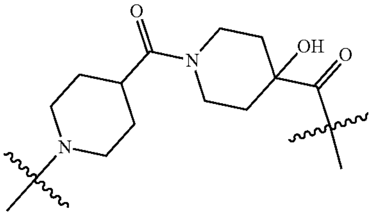
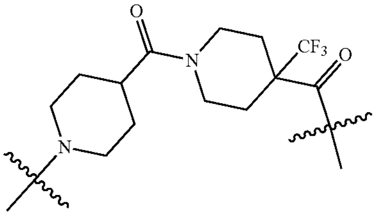
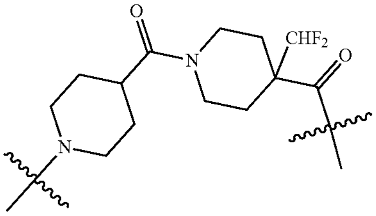
-continued
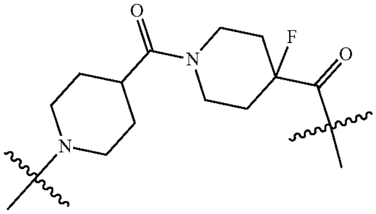
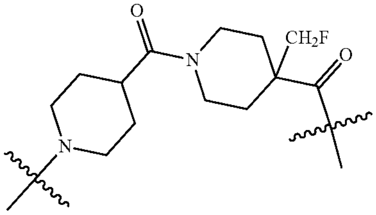
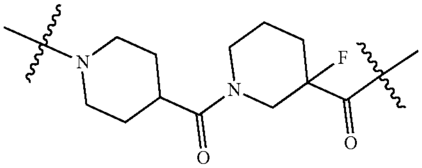
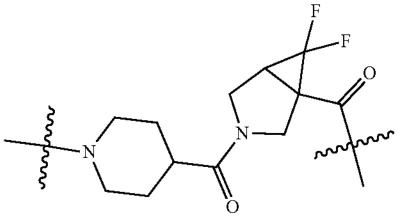
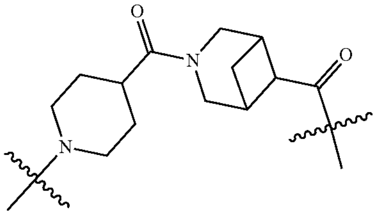
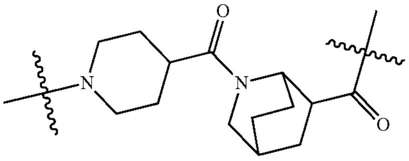
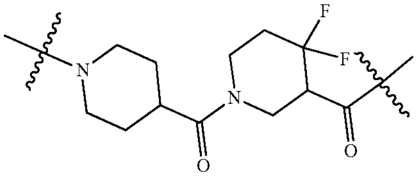
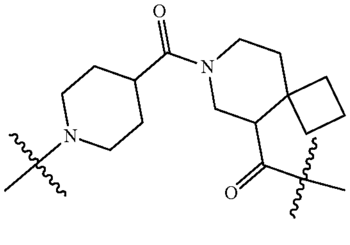

-continued

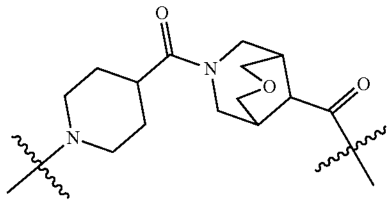

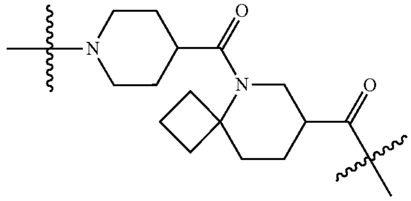

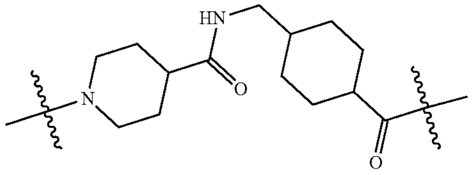

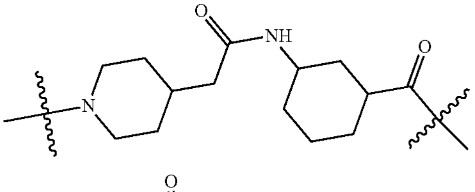

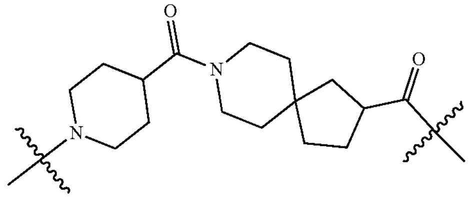

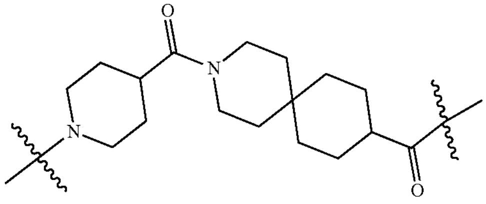

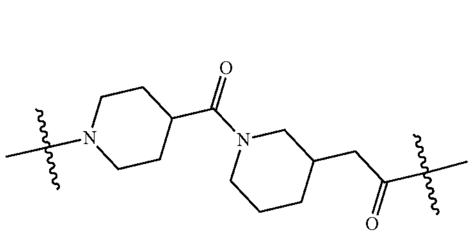

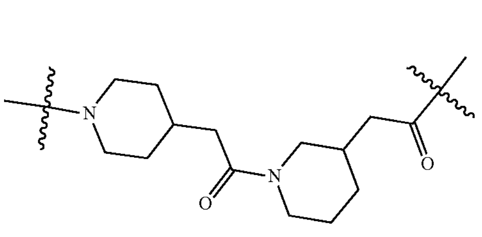

-continued

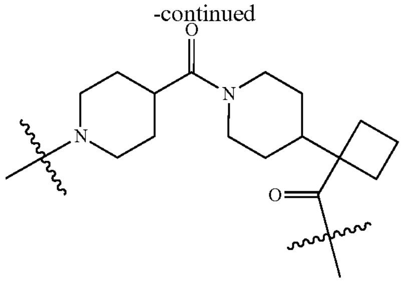

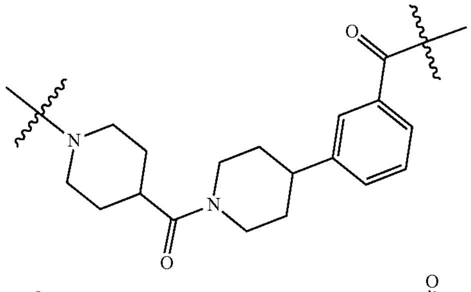

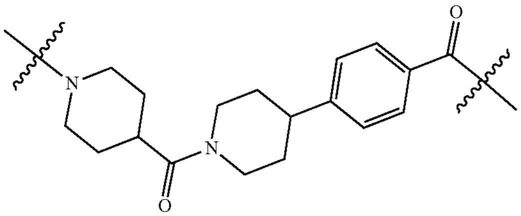

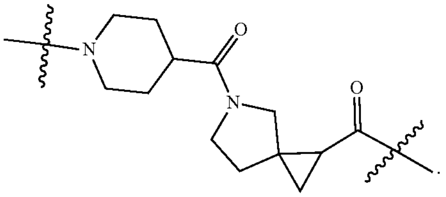

In a further specific embodiment, L is $-L_1-L_2-L_3-L_4-L_5-L_6-$ and has the following structure:

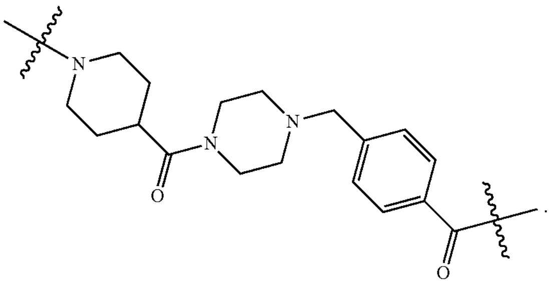 [SMILES: *C(=O)c1ccc(CN2CCN(C(=O)C3CCN(*)CC3)CC2)cc1]

Construction of Compounds of Formula (I)

The synthesis or construction of the compounds of Formula (I) can be carried out in multiple steps, typically involving separately preparing building blocks of the HPK1 binder and the LHM moiety, followed by joining the respective building blocks through covalent bond formation. Generally speaking, either or both building blocks may be prepared with one or more linker precursors. A linker precursor comprises one or more linker segments ($L_s$) and has a terminal reactive group for further coupling. The two building blocks can be finally coupled (via formation of a further linker segment) to afford a compound of Formula (I).

The following schemes demonstrate the general approaches of preparing building blocks. Specific examples (Examples 1-303) were synthesized and characterized by their respective physiochemical properties according to the general schemes described herein.

General Schemes

Step 1—Preparation of a Compound of Formula (3)

Compounds of formula (3) can be made by combining compounds (1) and (2). Compounds (1) and (2) are commercially available or can be made by methods known in the art. Compounds (1) and (2) can be mixed in a suitable solvent such as THF. After stirring at a temperature between 0° C. and 100° C. for between 10 min and 24 h or until

REACTION SCHEME A

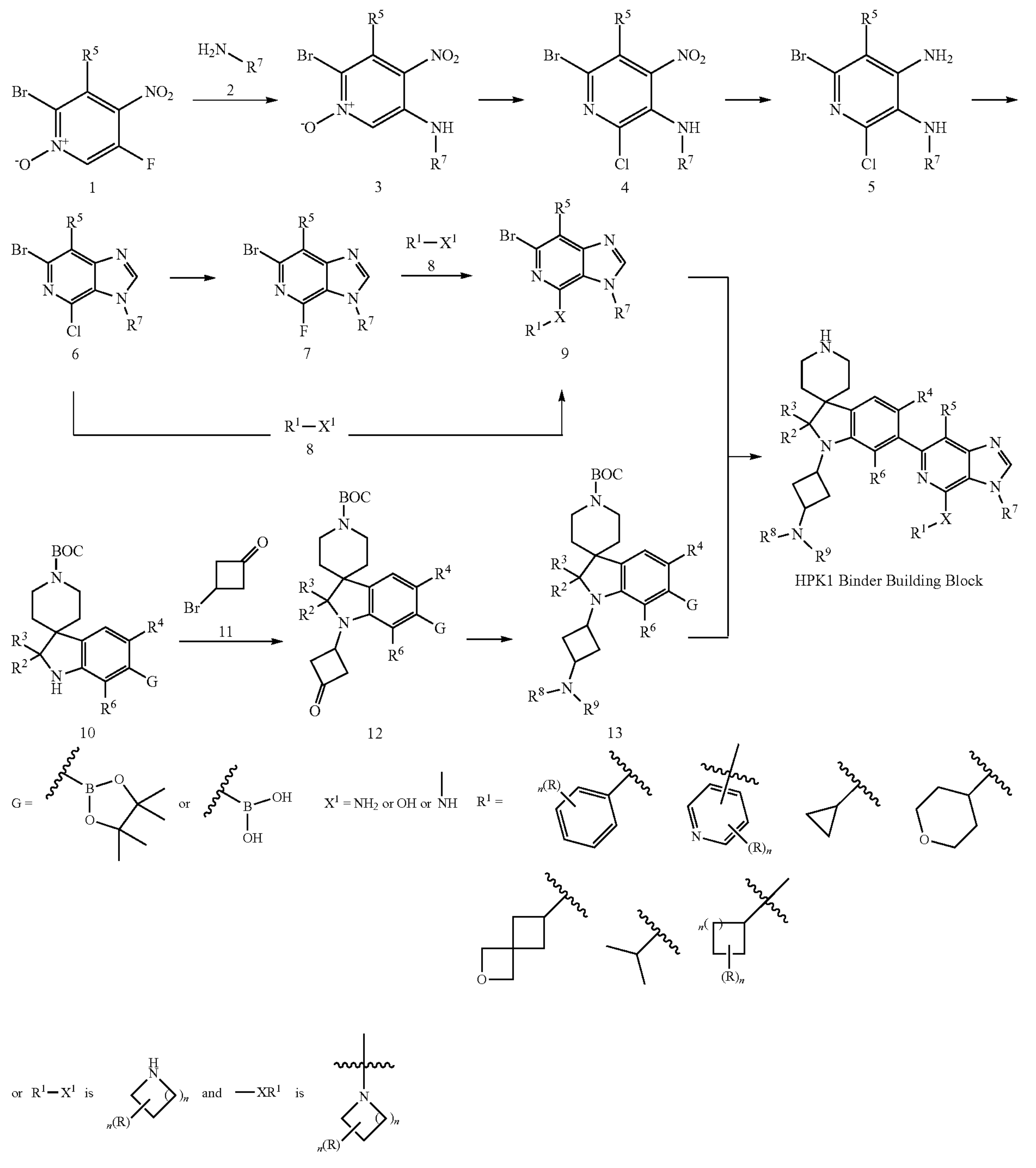

n is 0-3, R is halogen, $C_{1-3}$ alkyl, —C(O)N($R^{11}$)$_2$, —CN, —OH, and $C_{1-3}$ alkoxy reaction is complete, the reaction is allowed to cool to room temperature. The compound of formula (3) can be obtained by filtration or precipitation.

Step 2—Preparation of a Compound of Formula (4)

Compounds of formula (4) may be prepared by chlorination of the compounds of formula (3) by methods known in the art. A compound of formula (3) may be mixed with $POCl_3$ in a suitable solvent such as toluene. After stirring at a temperature between 0° C. and 100° C. for between 10 min and 24 h or until reaction is complete, the reaction is allowed to cool to room temperature. The solvent can then be removed under reduced pressure. To extract the compound of formula (4), an organic solvent such as ethyl acetate may be added, followed by washing with water and brine. The organic phase can be concentrated to obtain the compound of formula (4). The compound of formula (4) may be purified by any suitable methods known in the art such as chromatography on silica gel, trituration, precipitation, or crystallization.

Step 3—Preparation of a Compound of Formula (5)

Compounds of formula (5) may be prepared by reduction of the compounds of formula (4) by methods known in the art. A compound of formula (4) can be mixed with Zinc dust and ammonium chloride in suitable solvent such as THF, MeOH, or water, or a mixture of solvents such as THF, MeOH, and water. After stirring at a temperature between 0° C. and 100° C. for between 1 h and 24 h or until reaction is complete, the reaction is allowed to cool to room temperature and filtered through a celite bed. To extract the compound of formula (5), an organic solvent such as ethyl acetate may be added, followed by washing with water and brine. The organic phase can be concentrated to obtain the compound of formula (5). The compound of formula (5) may be purified by any suitable methods known in the art such as chromatography on silica gel, trituration, precipitation, or crystallization.

Step 4—Preparation of a Compound of Formula (6)

Compounds of formula (6) may be prepared by cyclization of the compounds of formula (5) by methods known in the art. A compound of formula (5) can be mixed with trimethyl orthoformate and formic acid. After stirring at a temperature between 0° C. and 100° C. for between 1 h and 24 h or until reaction is complete, the remaining solvent is removed via distillation. To extract the compound of formula (6), an organic solvent such as dichloromethane may be added, followed by washing with water and brine. The organic phase can be concentrated to obtain the compound of formula (6). The compound of formula (6) may be purified by any suitable methods known in the art such as chromatography on silica gel, trituration, precipitation, crystallization, or washing with organic solvent such as ether including but not limited to methyl t-butyl ether.

Step 5—Preparation of a Compound of Formula (7)

Compounds of formula (7) may be prepared by fluorination of the compounds of formula (6) by methods known in the art. A compound of formula (6) can be mixed with cesium fluoride in a solvent such DMF. After stirring at a temperature between room temperature and 110° C. for between 1 h and 24 h or until reaction is complete, the reaction is cooled to between 0° C. and room temperature by adding ice water or by adding the reaction mixture to ice water. To extract the compound of formula (7), an organic solvent such as ethyl acetate may be added, followed by washing with water and brine. The organic phase can be concentrated to obtain the compound of formula (7). The compound of formula (7) may be purified by any suitable methods known in the art such as chromatography on silica gel, trituration, precipitation, or crystallization.

Step 6—Preparation of a Compound of Formula (9)

Compounds of formula (9) can be made by combining compounds of formulae (6) and (8) or combining compounds of formulae (7) and (8) by methods known in the art. Compounds of formula (8) are commercially available or can be made by methods known in the art. A compound of formula (8) can be mixed with either compounds of formula (6) or (7) in the presence of a base such as sodium hydride in a suitable solvent such as NMP or DMA. After stirring at a temperature between room temperature and 100° C. for between 1 h and 24 h or until reaction is complete, the reaction can be added to water and treated with acid such as 10% citric acid. The compound of formula (9) may be obtained by filtration or precipitation.

Step 7—Preparation of a Compound of Formula (12)

Compounds of formula (12) can be made by combining compounds of formulae (10) and (11) by methods known in the art. Compounds of formulae (10) and (11) are commercially available or can be made by methods known in the art. Compounds of formulae (10) and (11) can be mixed in the presence of a base such as potassium carbonate in a suitable solvent such as DMF. After stirring at a temperature between room temperature and 50° C. for between 1 h and 24 h or until reaction is complete, the reaction is cooled to room temperature. To extract the compound of formula (12), an organic solvent such as ethyl acetate may be added, followed by washing with water and brine. The organic phase can be concentrated to obtain the compound of formula (12). The compound of formula (12) may be purified by any suitable methods known in the art such as chromatography on silica gel, trituration, precipitation, or crystallization.

Step 8—Preparation of a Compound of Formula (13)

Compounds of formula (13) may be prepared by reductive amination of the compounds of formula (12) by methods known in the art. Compounds of formula (12) and amines, that are commercially available or synthesized by methods known in the art, can be mixed with a reducing agent such as sodium triacetoxy borohydride or sodium cyanoborohydride in the presence of acid, such as acetic acid, or Lewis acid, such as zinc chloride, in a suitable solvent such as dichloroethane or methanol. After stirring at a temperature between 0° C. and room temperature for between 1 h and 24 h or until reaction is complete, the reaction may be added to aqueous solution such as saturated aqueous sodium bicarbonate solution. To extract the compound of formula (13), an organic solvent such as methylene chloride may be added, followed by washing with water and brine. The compound of formula (13) may be purified by any suitable methods known in the art such as chromatography on silica gel, trituration, precipitation, or crystallization.

Step 9—Preparation of HPK1 Binder Building Block

An HPK1 Binder building block can be made by combining the compounds of formula (9) and compounds of formula (13) by methods known in the art. Compounds of formulae (9) and (13) can be mixed in the presence of a catalyst such as tetrakis(triphenylphosphine)palladium and a base such as cesium carbonate, sodium carbonate, or potassium phosphate tribasic in a suitable solvent such as a mixture of dimethoxyethane and water, or a mixture of DMAc and water. After stirring at a temperature between 50° C. and 150° C. for between 1 and 24 hours, the reaction is allowed to cool to room temperature. The crude product may be filtered and concentrated under reduced pressure. To extract the compound, an organic solvent such as methylene chloride may be added, followed by washing with water and brine. The organic phase can be concentrated, and the resulting product may be purified by any suitable methods known in the art such as chromatography on silica gel, reverse phase chromatography, trituration, precipitation, or crystallization. The resulting HPK1 Binder building block may be further chemically elaborated, for example, as shown in Reaction Scheme C.

REACTION SCHEME B1

PYRIDINE/PYRIMIDINE

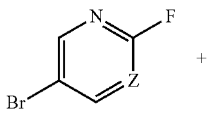

14 or

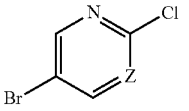

14'

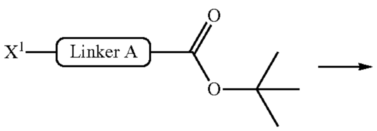

15

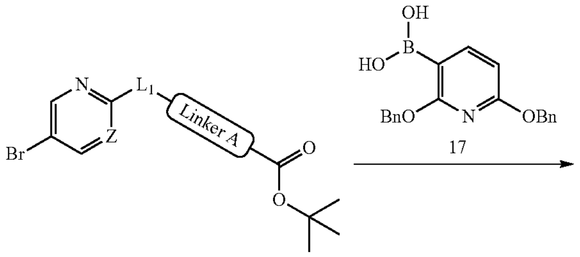

17

16

-continued

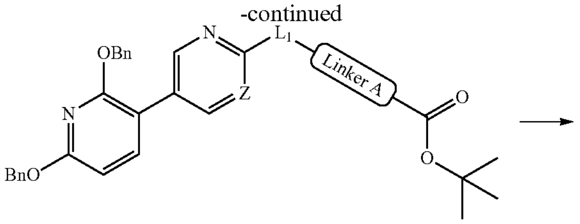

18

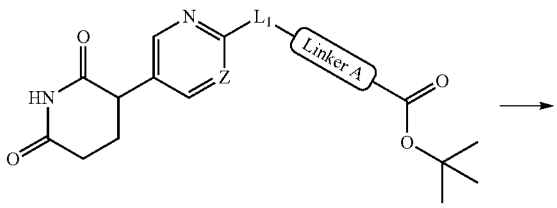

19

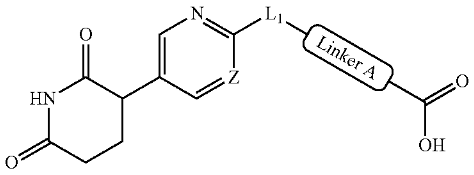

20

Z = CH or N $X^1$ = NH, $NH_2$ or OH, and $L_1$ = N, NH or O

Step 1—Preparation of a Compound of Formula (16)

Compounds of formula (16) can be made by combining compounds of formulae (14) (or 14') and (15). Compounds of formulae (14) (or 14') and (15) are commercially available or can be made by methods known in the art. Compounds of formulae (14) (or 14') and (15) can be mixed in a suitable solvent such as DMA with a suitable base such as sodium hydride. After stirring at a temperature between 0° C. and 100° C. for between 10 min and 24 h or until reaction is complete, the reaction is allowed to cool to room temperature. The compounds of formula (16) can be obtained by filtration or precipitation followed by purification by any suitable methods known in the art such as chromatography on silica gel, reverse phase chromatography, trituration, precipitation, or crystallization.

Step 2—Preparation of a Compound of Formula (18)

Compounds of formula (18) can be made by combining the compounds of formula (16) and compound (17) by methods known in the art. Compounds of formulae (16) and compound (17) can be mixed in the presence of a catalyst such as Pd(dppf)$Cl_2$-DCM and a base such as cesium carbonate, sodium carbonate, or potassium phosphate tribasic in a suitable solvent such as a mixture of dioxane and water. After stirring at a temperature of 100° C. for between 1 and 3 hours, the reaction is allowed to cool to room temperature. The crude product may be filtered and concentrated under reduced pressure. To extract the compound, an organic solvent such as methylene chloride may be added, followed by washing with water and brine. The organic phase can be concentrated to obtain compounds of formula (18), which may be purified by any suitable methods known in the art such as chromatography on silica gel, reverse phase chromatography, trituration, precipitation, or crystallization.

Step 3—Preparation of a Compound of Formula (19)

Compounds of formula (19) can be made by methods known in the art. Compounds of formula (18) can be dissolved in a 1:1 mixture of MeOH and THF, adding a catalyst such as Pd/C, and stirring under hydrogen atmosphere for between 2 and 24 hours. The reaction can be filtered through celite and concentrated to obtain the compounds of formula (19) which can be purified by any suitable methods known in the art such as chromatography on silica gel, reverse phase chromatography, trituration, precipitation, or crystallization.

Step 4—Preparation of a Compound of Formula (20)

Compounds of formula (20) can be made by methods known in the art. Compounds of formula (19) can be dissolved in a suitable solvent such as DCM and treated with an acid such as TFA, stirring at room temperature for between 2 and 24 hours. The crude reaction can be concentrated to obtain the compounds of formula (20) as a salt, which can be purified by any suitable methods known in the art such as chromatography on silica gel, reverse phase chromatography, trituration, precipitation, or crystallization.

REACTION SCHEME B2

AMINO PHENYL

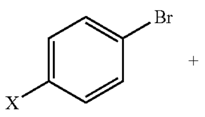

21
X = Br or I

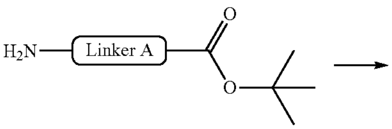

22

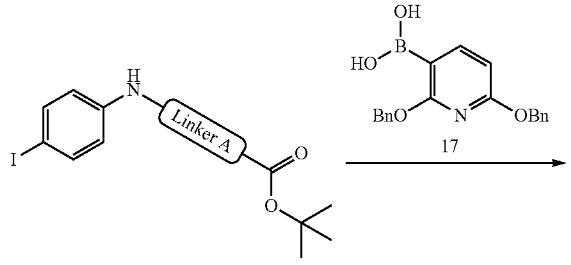

17

23

-continued

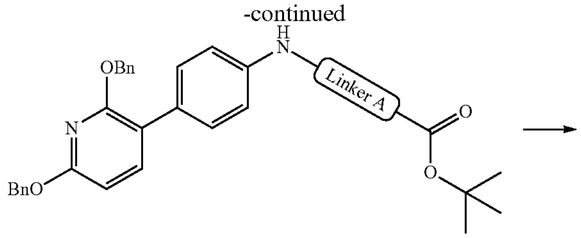

24

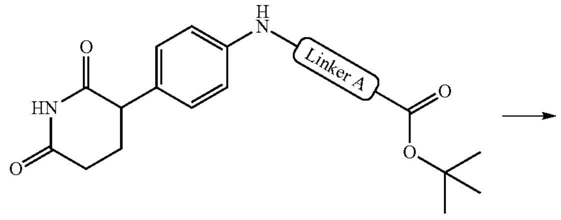

25

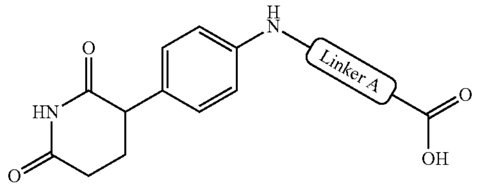

26

Step 1—Preparation of a Compound of Formula (23)

Compounds of formula (23) can be made by combining compounds of formulae (21) and (22). Compounds of formulae (21) and (22) are commercially available or can be made by methods known in the art. Compounds of formulae (21) and (22) can be combined with a suitable catalyst such as XantPhos Pd G3, and a base such as $CsCO_3$ in a suitable solvent such as dioxane. After stirring at a temperature of about 100° C. for between 10 min and 24 h or until reaction is complete, the reaction is allowed to cool to room temperature. The reaction can be filtered through celite and concentrated to obtain the compounds of formula (23) which can be purified by any suitable methods known in the art such as chromatography on silica gel, reverse phase chromatography, trituration, precipitation, or crystallization.

Step 2—Preparation of a Compound of Formula (24)

Compounds of formula (24) can be made by combining the compounds of formula (23) and compound (17) by methods known in the art. Compounds of formulae (23) and compound (17) can be mixed in the presence of a catalyst such as $Pd(dppf)Cl_2$-DCM and a base such as cesium carbonate, sodium carbonate, or potassium phosphate tribasic in a suitable solvent such as a mixture of dioxane and water. After stirring at a temperature of 100° C. for between 1 and 3 hours, the reaction is allowed to cool to room temperature. The crude product may be filtered and concentrated under reduced pressure. To extract the compound, an organic solvent such as methylene chloride may be added, followed by washing with water and brine. Compounds of formula (24) may be obtained by any suitable methods known in the art such as chromatography on silica gel, reverse phase chromatography, trituration, precipitation, or crystallization.

Step 3—Preparation of a Compound of Formula (25)

Compounds of formula (25) can be made by methods known in the art. Compounds of formula (24) can be dissolved in a 1:1 mixture of MeOH and THF, adding a catalyst such as Pd/C, and stirring under hydrogen atmosphere for between 2 and 24 hours. The reaction can be filtered through celite and concentrated to obtain the compounds of formula (25) which can be purified by any suitable methods known in the art such as chromatography on silica gel, reverse phase chromatography, trituration, precipitation, or crystallization.

Step 4—Preparation of a Compound of Formula (26)

Compounds of formula (26) can be made by methods known in the art. Compounds of formula (25) can be dissolved in a suitable solvent such as DCM and treated with an acid such as TFA, stirring at room temperature for between 2 and 24 hours. The crude reaction can be concentrated to obtain the compounds of formula (26) as salts, which can be purified by any suitable methods known in the art such as chromatography on silica gel, reverse phase chromatography, trituration, precipitation, or crystallization.

REACTION SCHEME B3

PHENYL ETHER

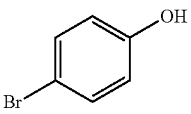

+

28

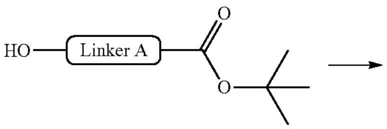

29

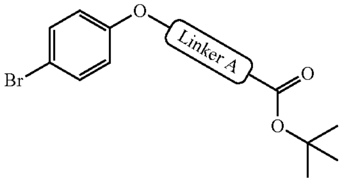

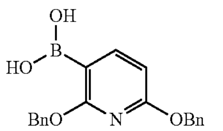

17

30

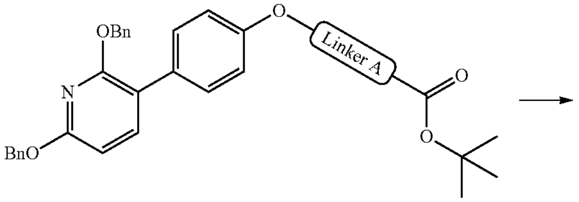

31

-continued

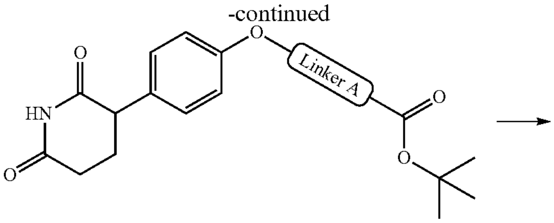

32

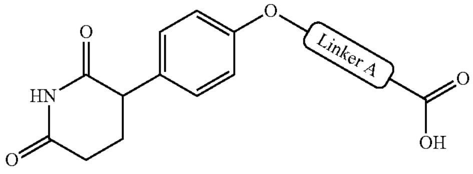

33

Step 1—Preparation of a Compound of Formula (30)

The compounds of formula (30) can be made by combining compounds of formulae (28) and (29). Compounds of formulae (28) and (29) are commercially available or can be made by Mitsunobu coupling methods known in the art. Compounds of formulae (28) and (29) can be combined with suitable reagents such as DIAD and triphenylphosphine, and a base such as TEA in a suitable solvent such as THF at 0° C. After stirring at room temperature for between 10 min and 24 h or until reaction is complete, the reaction is allowed to cool to room temperature. The crude reaction can be purified by any suitable methods known in the art such as chromatography on silica gel, reverse phase chromatography, trituration, precipitation, or crystallization to obtain compounds of formula (30).

Step 2—Preparation of a Compound of Formula (31)

Compounds of formula (31) can be made by combining the compounds of formula (30) and compound (17) by methods known in the art. Compounds of formulae (30) and compound (17) can be mixed in the presence of a catalyst such as Pd(dppf)$Cl_2$-DCM and a base such as cesium carbonate, sodium carbonate, or potassium phosphate tribasic in a suitable solvent such as a mixture of dioxane and water. After stirring at a temperature of 100° C. for between 1 and 3 hours, the reaction is allowed to cool to room temperature. The crude product may be filtered and concentrated under reduced pressure. To extract the compound, an organic solvent such as methylene chloride may be added, followed by washing with water and brine. The organic phase can be concentrated, and the resulting product may be purified by any suitable methods known in the art such as chromatography on silica gel, reverse phase chromatography, trituration, precipitation, or crystallization to obtain compounds of formula (31).

Step 3—Preparation of a Compound of Formula (32)

Compounds of formula (32) can be made by methods known in the art. Compounds of formula (31) can be dissolved in a 1:1 mixture of MeOH and THF, adding a catalyst such as Pd/C, and stirring under hydrogen atmosphere for between 2 and 24 hours. The reaction can be filtered through celite and concentrated to obtain the compounds of formula (32) which can be purified by any suitable methods known in the art such as chromatography on silica gel, reverse phase chromatography, trituration, precipitation, or crystallization.

Step 4—Preparation of a Compound of Formula (33)

Compounds of formula (33) can be made by methods known in the art. Compound of formula (32) can be dissolved in a suitable solvent such as DCM and treated with an acid such as TFA, stirring at room temperature for between 2 and 24 hours. The crude reaction can be concentrated to obtain the compound of formula (33) as a salt, which can be purified by any suitable methods known in the art such as chromatography on silica gel, reverse phase chromatography, trituration, precipitation, or crystallization.

REACTION SCHEME B4

DIHYDROURACIL

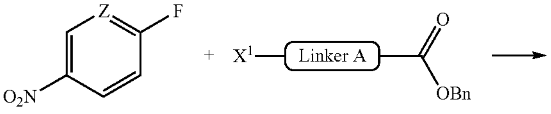

34 35

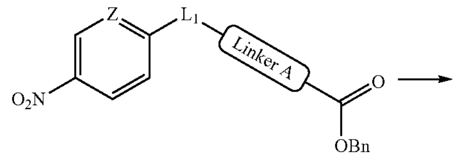

36

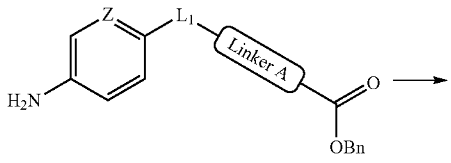

37

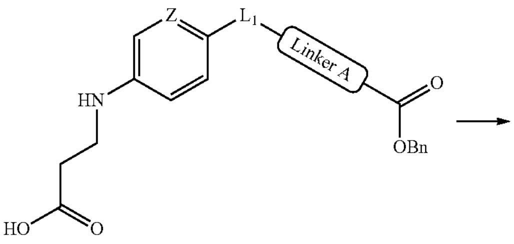

38

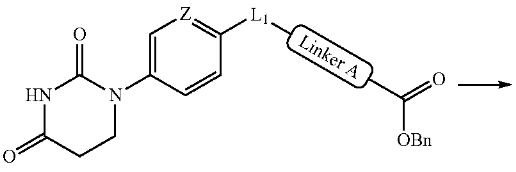

39

-continued

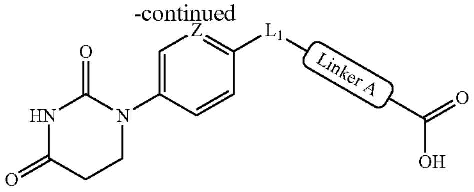

40

Z = N or CH $X^1$ = NH, $NH_2$ or OH, and $L_1$ = N, NH or O

Step 1—Preparation of a Compound of Formula (36)

The compounds of formula (36) can be made by combining compounds of formulae (34) and (35), which are commercially available or can be made by coupling methods known in the art. Compounds of formulae (34) and (35) can be mixed in a suitable solvent such as DMF with a suitable base such as cesium carbonate. After stirring at a temperature of about 90° C. for between 10 min and 24 h or until reaction is complete, the reaction is allowed to cool to room temperature. To extract the compound, an organic solvent such as methylene chloride may be added, followed by washing with water and brine. The organic phase can be concentrated, and the resulting product may be purified by any suitable methods known in the art such as chromatography on silica gel, reverse phase chromatography, trituration, precipitation, or crystallization.

Step 2—Preparation of a Compound of Formula (37)

The compounds of formula (37) can be made by methods of reduction known in the art. Compounds of formula (36) can be combined with Fe dust, acetic acid, and water in a suitable solvent such as EtOH. After stirring at about 50° C. for between 2 h and 4 h, the crude reaction can be filtered to obtain compounds of formula (37) which may be purified by any suitable methods known in the art such as chromatography on silica gel, reverse phase chromatography, trituration, precipitation, or crystallization to afford compounds of formula (37).

Step 3—Preparation of a Compound of Formula (38)

The compounds of formula (38) can be obtained by methods known in the art. Compounds of formula (37) can be combined with acrylic acid in a suitable solvent such as dioxane and stirred at 90° C. for between 2 h and 24 h. The crude reaction can be purified by any suitable methods known in the art such as chromatography on silica gel, reverse phase chromatography, trituration, precipitation, or crystallization to afford compounds of formula (38).

Step 4—Preparation of a Compound of Formula (39)

The compounds of formula (39) can be obtained by methods known in the art. Compounds of formula (38) can be combined with urea and acetic acid and stirred at about 90° C. for between 12 h and 48 h. To extract the compound, an organic solvent such as methylene chloride may be added, followed by washing with water and brine. The organic phase can be concentrated, and the resulting product may be purified by any suitable methods known in the art such as chromatography on silica gel, reverse phase chromatography, trituration, precipitation, or crystallization to obtain compounds of formula (39).

Step 5—Preparation of a Compound of Formula (40)

Compounds of formula (40) can be made by methods known in the art. Compounds of formula (39) can be dissolved in an anhydrous solvents such as THF, adding a catalyst such as Pd/C, and stirring under hydrogen atmosphere for between 2 and 24 hours. The reaction can be filtered through celite and concentrated to obtain the compounds of formula (40) which can be purified by any suitable methods known in the art such as chromatography on silica gel, reverse phase chromatography, trituration, precipitation, or crystallization.

Step 1—Preparation of Compounds of Formula (43)

Compounds of formula (43) can be made by combining compounds of formulae (41) and (42) using methods known in the art. Compounds of formulae (41) and (42) can be combined with a coupling reagent such as BOP and a base such as DIEA in an appropriate solvent such as DMF. After stirring at room temperature for between 2 and 24 hours, compounds of formula (43) can be purified by any suitable methods known in the art such as chromatography on silica gel, reverse phase chromatography, trituration, precipitation, or crystallization.

Step 2—Preparation of Compounds of Formula (44)

Compounds of formula (44) can be made using methods known in the art. Compounds of formula (43) can be

REACTION SCHEME B5

SECOND LINKER RING AMIDE COUPLING

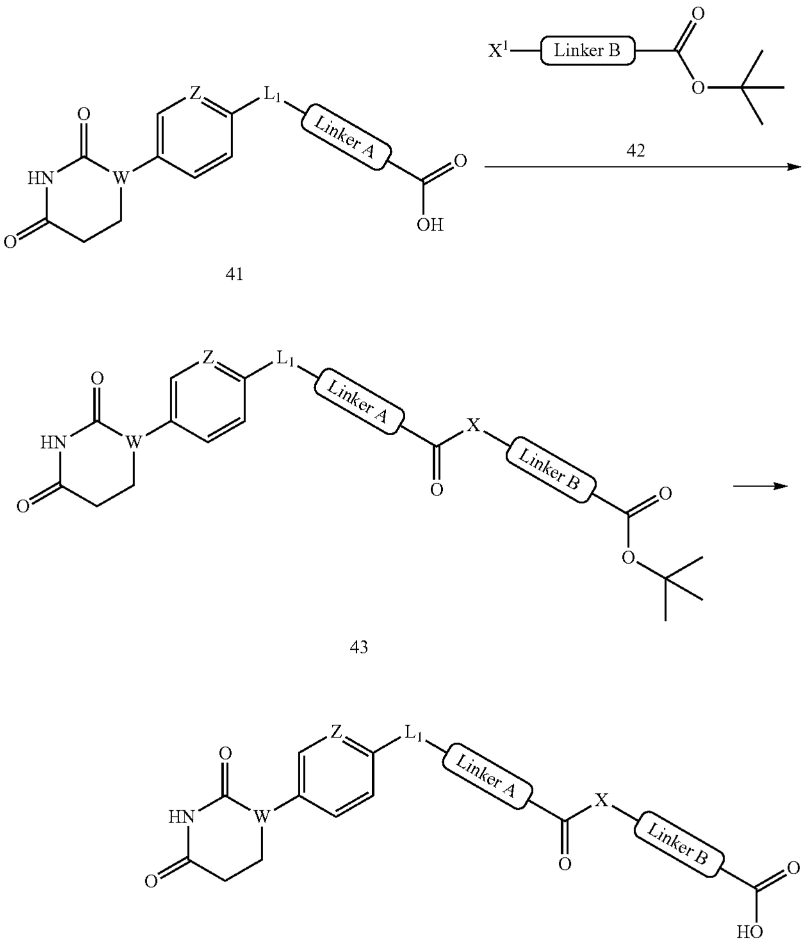

41

42

43

44

Z = N or CH
W = N or CH
X = N, NH or O
$X^1$ = NH, $NH_2$ or OH, $L_1$ = N, NH or O dissolved in a solvent such as DCM and treated with an appropriate acid such as TFA. After stirring at room temperature for between 2 and 24 hours the reaction can be concentrated to give compounds of the formula (44) as a salt, which can be purified by any suitable methods known in the art such as chromatography on silica gel, reverse phase chromatography, trituration, precipitation, or crystallization.

Step 2—Preparation of Compounds of Formula (48)

Compounds of formula (48) can be made using methods known in the art. Compounds of formula (47) can be dissolved in a solvent such as DCM and treated with an appropriate acid such as TFA. After stirring at room temperature for between 2 and 24 hours the reaction can be

REACTION SCHEME B6

SECOND LINKER RING REDUCTIVE AMINATION

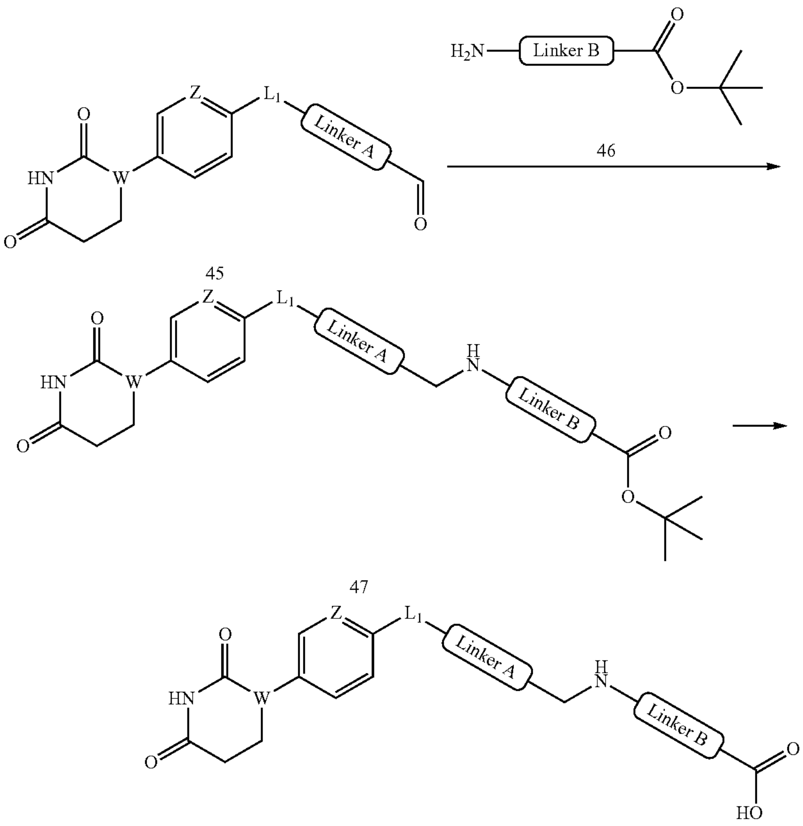

45, 46, 47, 48

Z = N or CH
W = N or CH
$L_1$ = N, NH or O

Step 1—Preparation of Compounds of Formula (47)

Compounds of formula (47) can be made by combining compounds of formulae (45) and (46) using methods known in the art. Compounds of formulae (45) and (46) can be combined with $NaCNBH_3$ and acetic acid in an appropriate solvent such as MeOH. After stirring at room temperature for between 2 and 24 hours, the crude reaction can be diluted in brine and extracted with a solvent such as DCM. Compounds of formula (47) can be purified by any suitable methods known in the art such as chromatography on silica gel, reverse phase chromatography, trituration, precipitation, or crystallization.

concentrated to give compounds of the formula (48) as a salt, which can be purified by any suitable methods known in the art such as chromatography on silica gel, reverse phase chromatography, trituration, precipitation, or crystallization.

REACTION SCHEME B7

ADDITIONAL AMINO PHENYL GROUPS

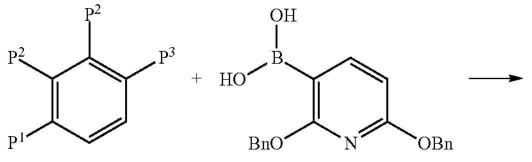

50 17

-continued

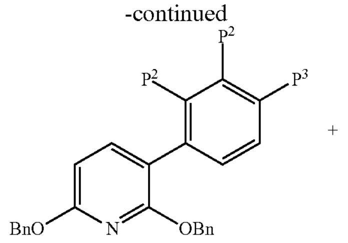

51

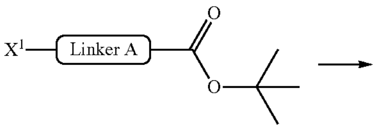

52

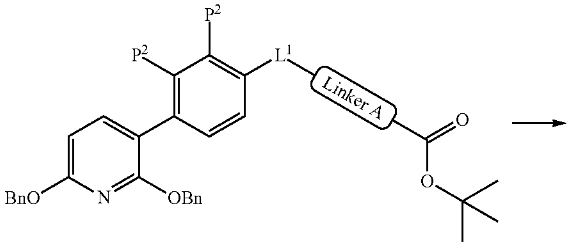

53

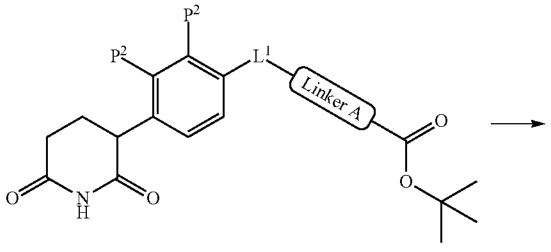

54

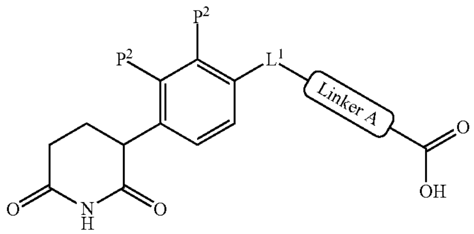

55

$P^1$ = I or Br, and $P^2$ = H or F or Methyl, and $P^3$ = Br or Cl, and $X^1$ = NH or $NH_2$, and $L_1$ = N or NH Compounds of formula (55) can be made by methods known in the art. For example, compounds of formula (51) may be produced using standard Suzuki-Miyaura conditions to couple compounds of formulae (50) and (17) in the presence of a base such as aqueous potassium carbonate and a catalyst such as Pd(dppf)$Cl_2$ in a suitable solvent such as dioxane, and typically with thermal heating or microwave irradiation. Compounds of formula (53) can be made using typical Buchwald-Hartwig amination conditions to couple compounds of formulae (51) and (52) in the presence of a base such as cesium carbonate and a catalyst such as 1,3-bis[2,6-bis(pentan-3-yl)phenyl]-2H-imidazole; 3-chloropyridine; palladium chloride in a suitable solvent such as dioxane, and typically with thermal heating or microwave irradiation. Compounds of formula (54) may be accessed by subjecting compounds of formula (53) to hydrogenolysis/hydrogenation conditions such as stirring under one or more atmospheres of hydrogen gas in the presence of a catalyst such as palladium on carbon in suitable solvents such as a mixture of THF and isopropyl alcohol. Compounds of formula (55) may be made by treating compounds of formula (54) with an acid such as TFA in a suitable solvent such as HFIP. Compounds of formula (55) and the precursors thereof may be isolated and purified by suitable methods known in the art such as partitioning reaction mixtures between an aqueous phase and an organic solvent, followed by isolation of the desired product by filtration or concentration of the relevant layer. Crude products may be purified by techniques such as chromatography on silica gel, reverse phase chromatography, trituration, precipitation, or crystallization.

REACTION SCHEME B8

ADDITIONAL PYRIDINES

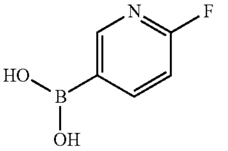

56

+

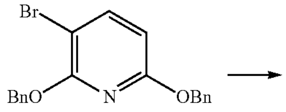

57

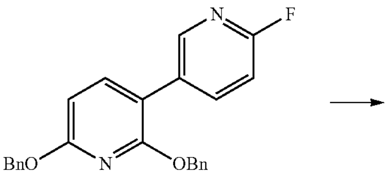

58

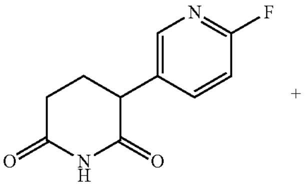

59

+

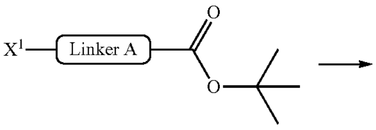

60

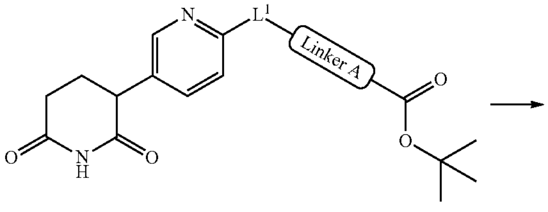

61

-continued

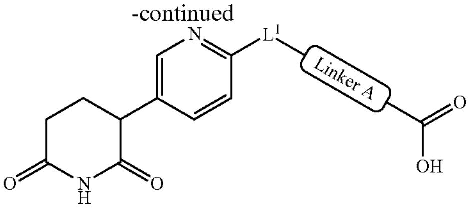

62

$X^1$ = NH or $NH_2$, and $L_1$ = N or NH

Compounds of formula (62) can be made by methods known in the art. For example, compounds of formula (58) may be produced using standard Suzuki-Miyaura conditions to couple compounds of formulae (56) and (57) in the presence of a base such as aqueous potassium phosphate and a catalyst such as $Pd(dppf)Cl_2$ in a suitable solvent such as dioxane, and typically with thermal heating or microwave irradiation. Compounds of formula (59) may be accessed by subjecting compounds of formula (58) to hydrogenolysis/hydrogenation conditions such as stirring under one or more atmospheres of hydrogen gas in the presence of catalysts such as palladium on carbon and $Pd(OH)_2$ in a suitable solvent such as THF. Compounds of formula (61) may be produced under SNAr conditions by heating a mixture of compounds of formula (59) and (60) in a suitable solvent such as DMSO in the presence of a base such as DIPEA. Compounds of formula (62) may be made by treating compounds of formula (61) with an acid such as HCl in a suitable solvent such as a DCM/dioxane mixture. Compounds of formula (62) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B9

ADDITIONAL PYRIDINES

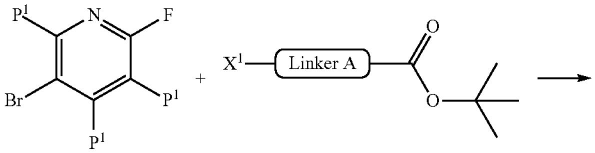

63 64

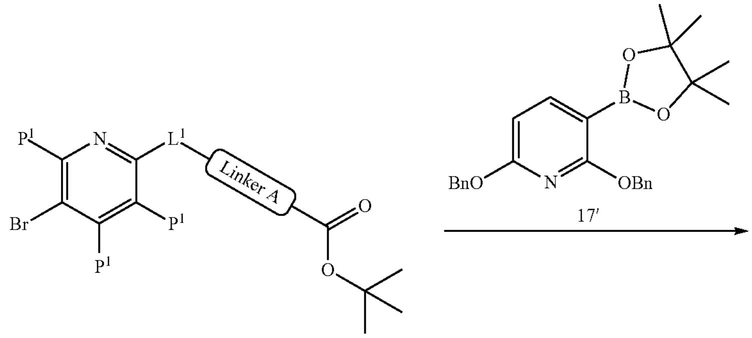

65

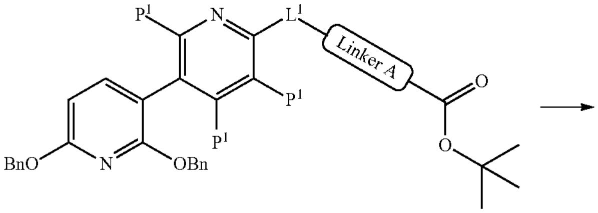

66

-continued

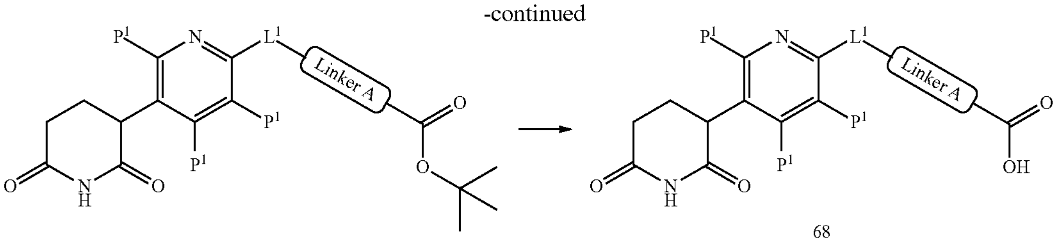

67

68

$P^1$ = H or Methyl, and $X^1$ = NH or $NH_2$, and $L_1$ = N or NH

Compounds of formula (68) can be made by methods known in the art. For example, compounds of formula (65) may be produced under SNAr conditions by heating a mixture of compounds of formula (63) and (64) in a suitable solvent such as DMSO in the presence of a base such as DIPEA. Compounds of formula (66) can be accessed by standard Suzuki-Miyaura conditions to couple compounds of formulae (65) and (17') in the presence of a base such as aqueous cesium carbonate and a catalyst such as Pd(dppf) $Cl_2$-DCMin a suitable solvent such as dioxane, and typically with thermal heating or microwave irradiation. Compounds of formula (67) may be accessed by subjecting compounds of formula (66) to hydrogenolysis/hydrogenation conditions such as stirring under one or more atmospheres of hydrogen gas in the presence of a catalyst such as palladium on carbon in a suitable solvent such as a mixture of THF and EtOH. Compounds of formula (68) may be made by treating compounds of formula (67) with an acid such as HCl in a suitable solvent such as a DCM/dioxane mixture. Compounds of formula (68) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B10

ADDITIONAL PYRIDINES

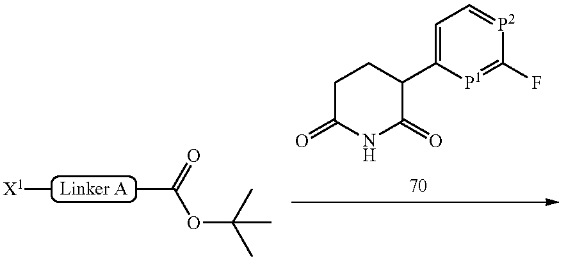

70

69

-continued

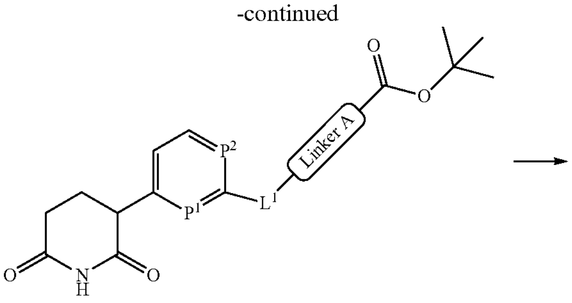

71

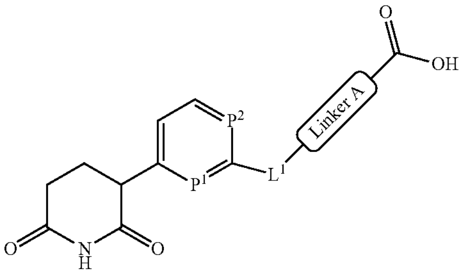

72

$P^1$ = CH and $P^2$ = N, or $P^1$ = N and $P^2$ = CH, and $X^1$ = NH or $NH_2$, and $L_1$ = N or NH Compounds of formula (72) can be made by methods known in the art. For example, compounds of formula (71) may be produced under SNAr conditions by heating a mixture of compounds of formula (69) and (70) in a suitable solvent such as DMSO in the presence of a base such as DIPEA. Compounds of formula (72) may be made by treating compounds of formula (71) with an acid such as HCl in a suitable solvent such as a DCM/dioxane mixture. Compounds of formula (72) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B11
ADDITIONAL PYRIDINES
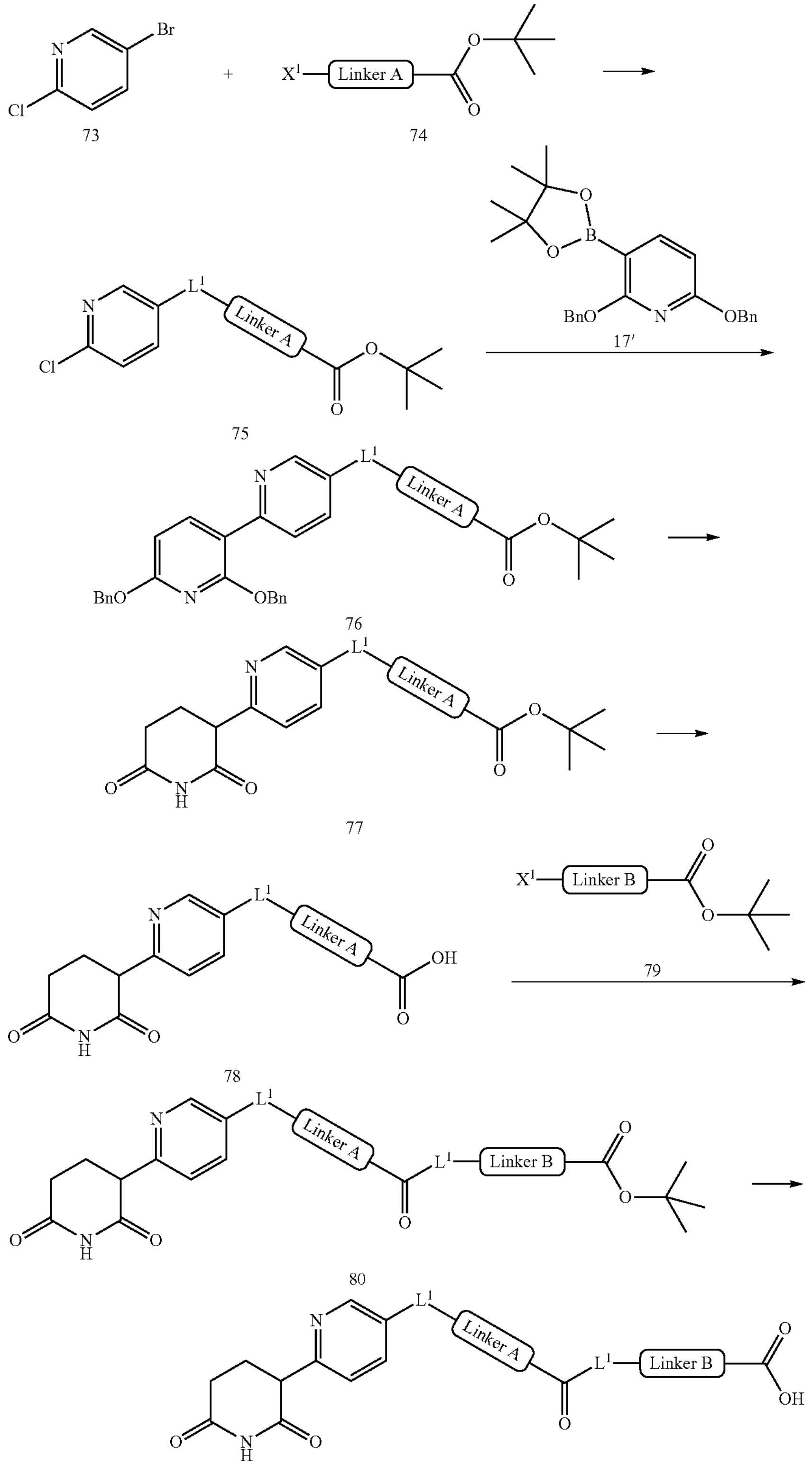
73 74 75 76 77 78 80 81
$X^1$ = NH or $NH_2$, and $L_1$ = N or NH Compounds of formula (81) can be made by methods known in the art. For example, compounds of formula (75) may be accessed by typical Buchwald-Hartwig amination conditions to couple compounds of formulae (73) and (74) in the presence of a base such as sodium tert-butoxide, a ligand such as XantPhos and a catalyst such as $Pd_2(dba)_3$ in a suitable solvent such as dioxane, and typically with thermal heating or microwave irradiation. Compounds of formula (76) may be produced by standard Suzuki-Miyaura conditions to couple compounds of formulae (75) and (17') in the presence of a base such as potassium carbonate and a catalyst such as $Pd(PPh_3)_4$ in a suitable solvent such as a THF/water mixture, and typically with thermal heating or microwave irradiation. Compounds of formula (77) may be accessed by subjecting compounds of formula (76) to hydrogenolysis/hydrogenation conditions such as stirring under one or more atmospheres of hydrogen gas in the presence of a catalyst such as palladium on carbon in a suitable solvent such as THF. Compounds of formula (78) may be made by treating compounds of formula (77) with an acid such as HCl in a suitable solvent such as dioxane. Compounds of formula (80) may be produced by coupling compounds of formulae (78) and (79) under standard amide bond forming conditions such as BOP in the presence of a base such as DIPEA in a suitable solvent such as DMF. Compounds of formula (81) may be made by treating compounds of formula (80) with an acid such as TFA in a suitable solvent such as HFIP. Compounds of formula (81) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B12
UREAS

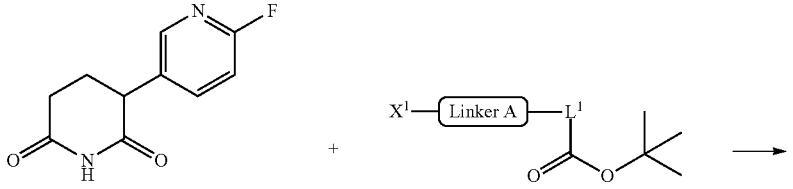

59 82

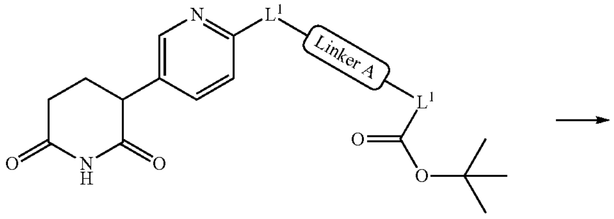

83

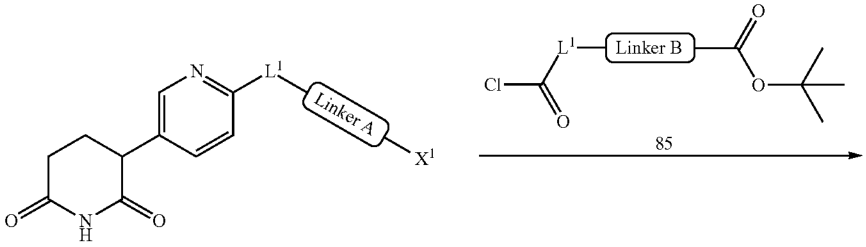

85

84

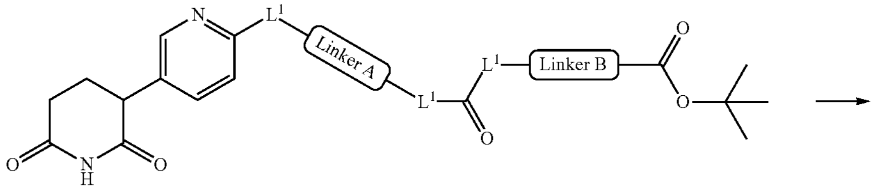

86

-continued

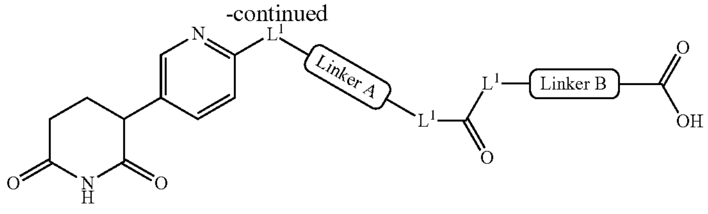

87

$X^1$ = NH or $NH_2$, and $L_1$ = N or NH

Compounds of formula (87) can be made by methods known in the art. For example, compounds of formula (83) may be produced under SNAr conditions by heating a mixture of compounds of formula (59) and (82) in a suitable solvent such as DMSO in the presence of a base such as triethylamine. Compounds of formula (84) may be made by treating compounds of formula (83) with an acid such as TFA in a suitable solvent such as a DCM. Compounds of formula (86) may be produced by reacting compounds of formula (84) with compounds of formula (85) in the presence of a catalyst and base such as pyridine and a solvent such as DCM, typically with heating. Compounds of formula (87) may be made by treating compounds of formula (86) with an acid such as TFA in a suitable solvent such as a DCM. Compounds of formula (87) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B13
SULFONAMIDES

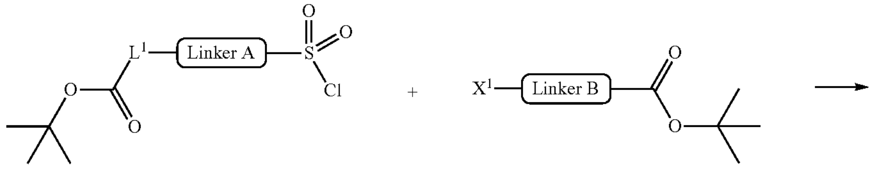

88 89

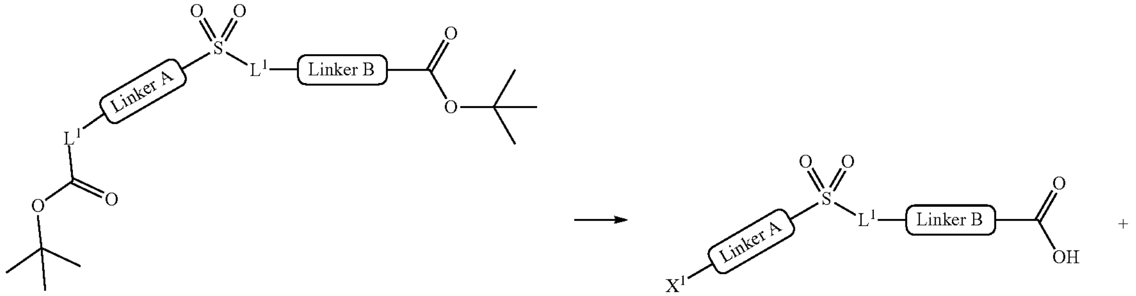

90 91

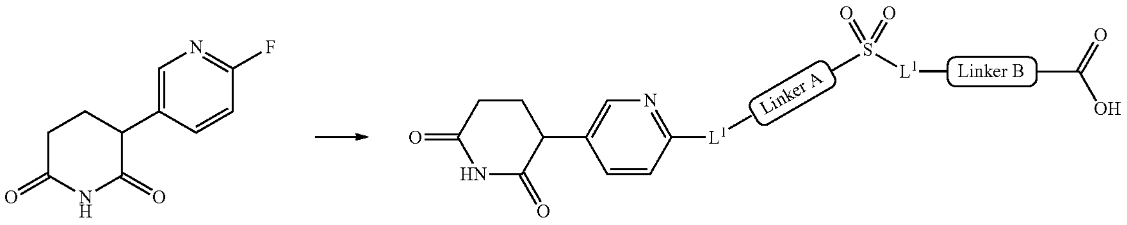

59 92

$X^1$ = NH or $NH_2$, and $L_1$ = N or NH

Compounds of formula (92) can be made by methods known in the art. For example, compounds of formula (90) may be produced by reacting compounds of formula (88) with compounds of formula (89) in the presence of a base such as DIPEA in a suitable solvent such as DCM. Compounds of formula (91) may be made by treating compounds of formula (90) with an acid such as TFA in a suitable solvent such as a DCM. Compounds of formula (92) may be produced under SNAr conditions by heating a mixture of compounds of formula (59) and (91) in a suitable solvent such as DMSO in the presence of a base such as DIPEA. Compounds of formula (92) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B14
ADDITIONAL PHENYL DIHYDROURACYLS

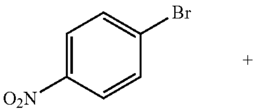

93

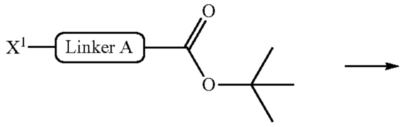

94

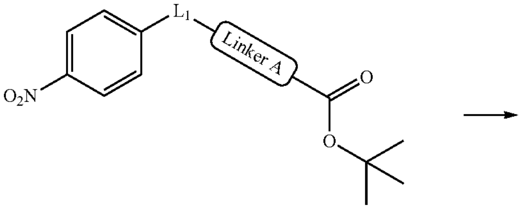

95

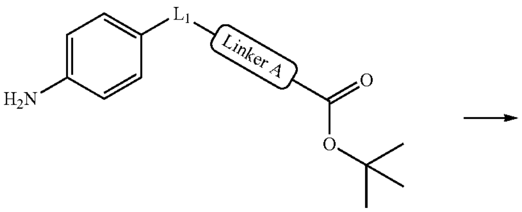

96

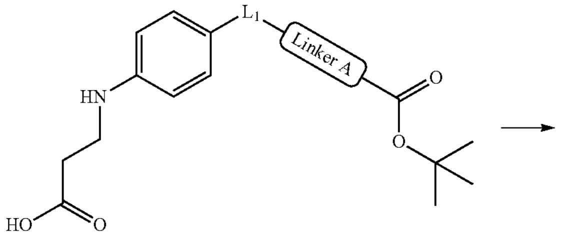

97

-continued

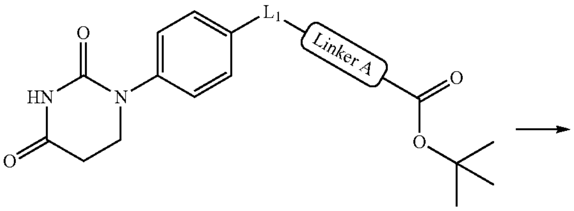

98

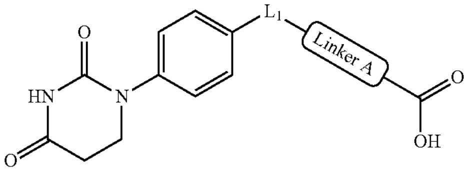

99

$X^1$ = NH or $NH_2$, and $L_1$ = N or NH

Compounds of formula (99) can be made by methods known in the art. For example, compounds of formula (95) can be made using typical Buchwald-Hartwig amination conditions to couple compounds of formulae (93) and (94) in the presence of a base such as cesium carbonate and a catalyst such as 1,3-bis[2,6-bis(pentan-3-yl)phenyl]-2H-imidazole; 3-chloropyridine; palladium chloride in a suitable solvent such as dioxane, and typically with thermal heating or microwave irradiation. Compounds of formula (96) can be produced by subjecting compounds of formula (95) to reduction conditions such as zinc powder and aqueous ammonium chloride solution in a suitable solvent such as THF. Compounds of formula (97) can be accessed by treating compounds of formula (96) with acrylic acid in an appropriate solvent such as toluene, typically with heating. Compounds of formula (98) can be obtained by treating compounds of formula (97) with urea in refluxing acetic acid. Compounds of formula (99) can be made by treating compounds of formula (98) with an acid such as TFA in a suitable solvent such as a HFIP. Compounds of formula (99) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME B15
ADDITIONAL PYRIDYL DIHYDROURACYLS

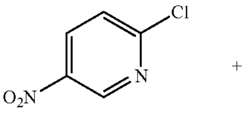

100

-continued

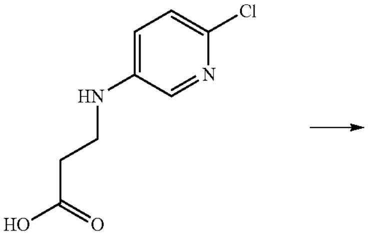

101

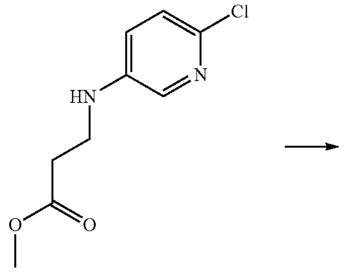

102

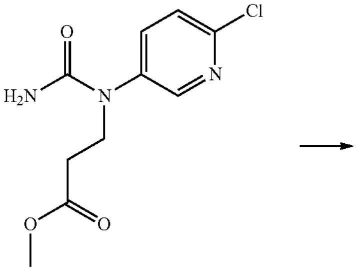

103

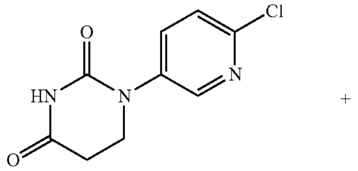

104

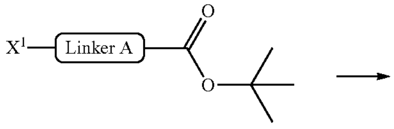

105

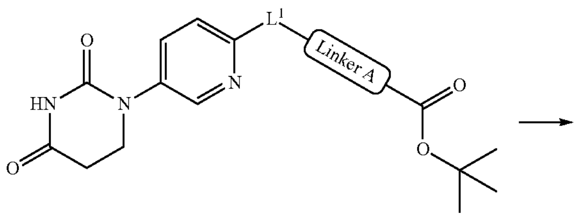

106

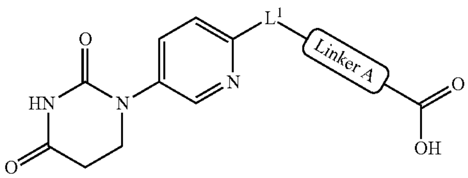

107

$X^1$ = NH or $NH_2$, and $L_1$ = N or NH

Compounds of formula (107) can be made by methods known in the art. For example, compounds of formula (101) can be accessed by treating compounds of formula (100) with acrylic acid in an appropriate solvent such as toluene, typically with heating. Compounds of formula (102) can be obtained by treating compounds of formula (101) with $SOCl_2$ in methanol as solvent. Compounds of formula (103) can be produced by treating compounds of formula (102) with potassium cyanate in an appropriate solvent such as an acetic acid/DCM mixture. Compounds of formula (104) can be obtained by treating compounds of formula (103) with a base such as potassium silanolate in an appropriate solvent such as THF. Compounds of formula (106) can be made using typical Buchwald-Hartwig amination conditions to couple compounds of formulae (104) and (105) in the presence of a base such as cesium carbonate and a catalyst such as 1,3-bis[2,6-bis(pentan-3-yl)phenyl]-2H-imidazole; 3-chloropyridine; palladium chloride in a suitable solvent such as dioxane, and typically with thermal heating or microwave irradiation. Compounds of formula (107) can be made by treating compounds of formula (106) with an acid such as HCl in a suitable solvent such as a dioxane. Compounds of formula (107) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME C1
FINAL COMPOUNDS

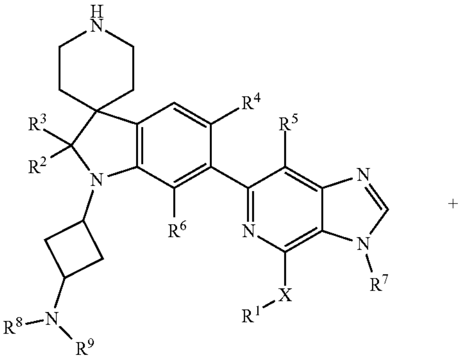

HPK1 Binder Building Block
Prepared according to Scheme A

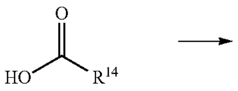

Carboxylic acids
Prepared according
to Schemes B

-continued

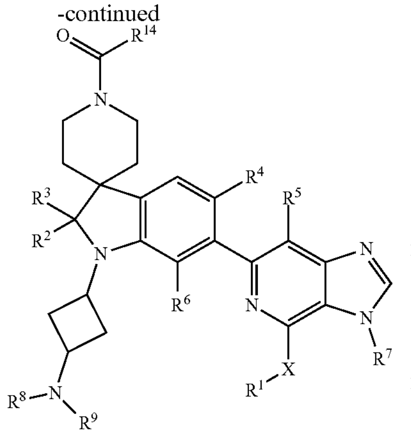

49

HPK1 Binder building blocks prepared according to Reaction Scheme A typically have at least one reactive site, such as an amine moiety or a carboxyl moiety, that can be further coupled to the moieties described in Schemes B. In one specific example (Structures shown in Reaction Scheme C1), the free piperidine NH group of the HPK1 Binder building block (Prepared according to Reaction Scheme A) can be coupled with the carboxylic acids prepared according to Reaction Schemes B under conditions known in the art to produce compounds of formula 49. For example, the HPK1 Binder Building Block Amine can be combined with carboxylic acids in the presence of a reagent such as BOP, EDCI, or HATU in a solvent such as DMF, with optional inclusion of an additive such as HOBT, and sometimes in the presence of a base such as DIPEA. The reaction mixtures are typically stirred at room temperature for between 15 minutes and 48 hours, then the products are isolated by purification methods such as flash chromatography or preparative HPLC. In certain instances the purification method is preceded by an optional workup comprising dilution with an organic solvent such as EtOAc or DCM, washing with water or aqueous solutions of sodium chloride, sodium bicarbonate or hydrogen chloride, drying over sodium sulfate, filtering, and concentrating.

REACTION SCHEME C2
FINAL COMPOUNDS, MODULAR APPROACH
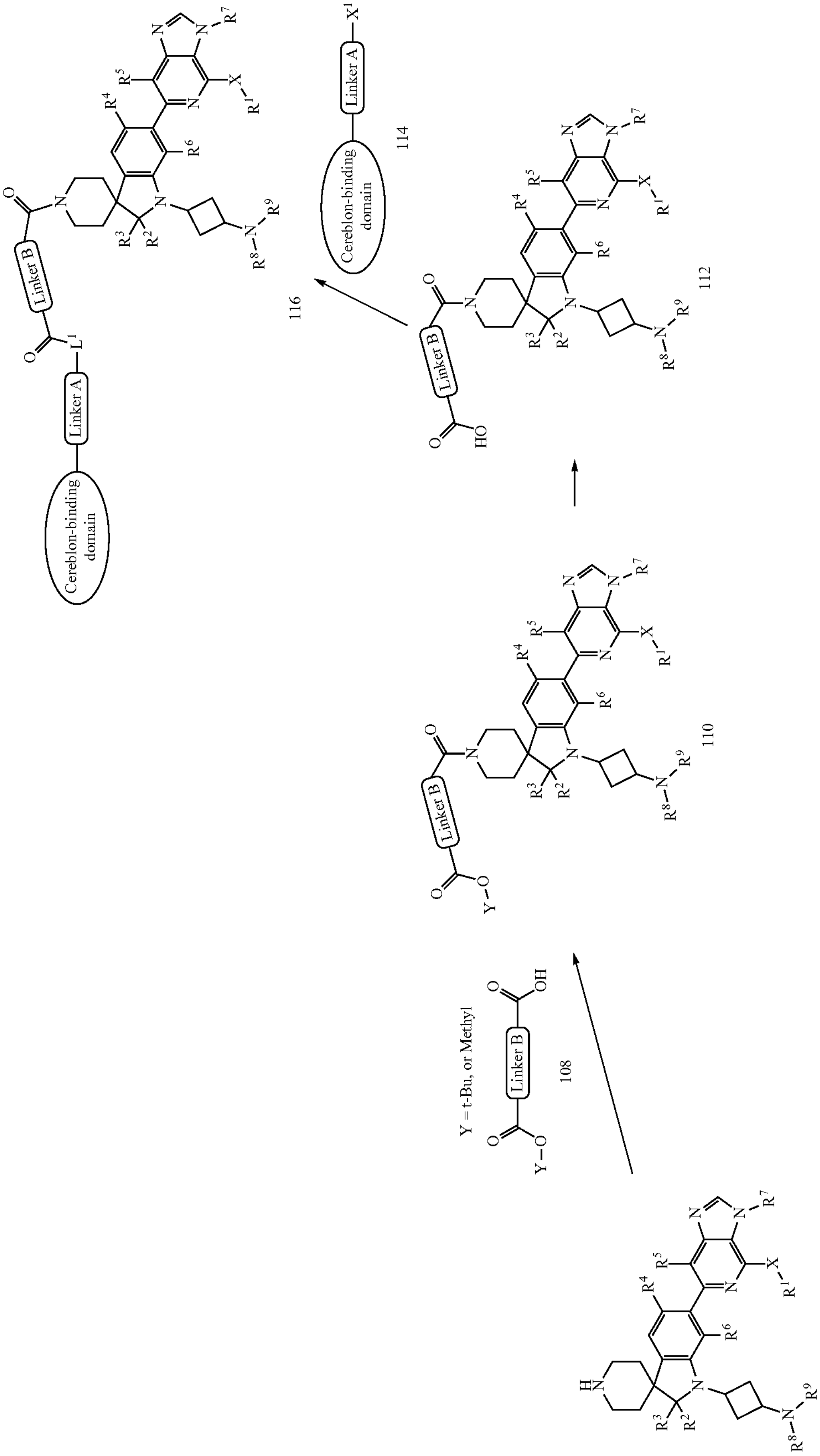
108
110
112
114
116
HPK1 Binder Building Blocks -continued
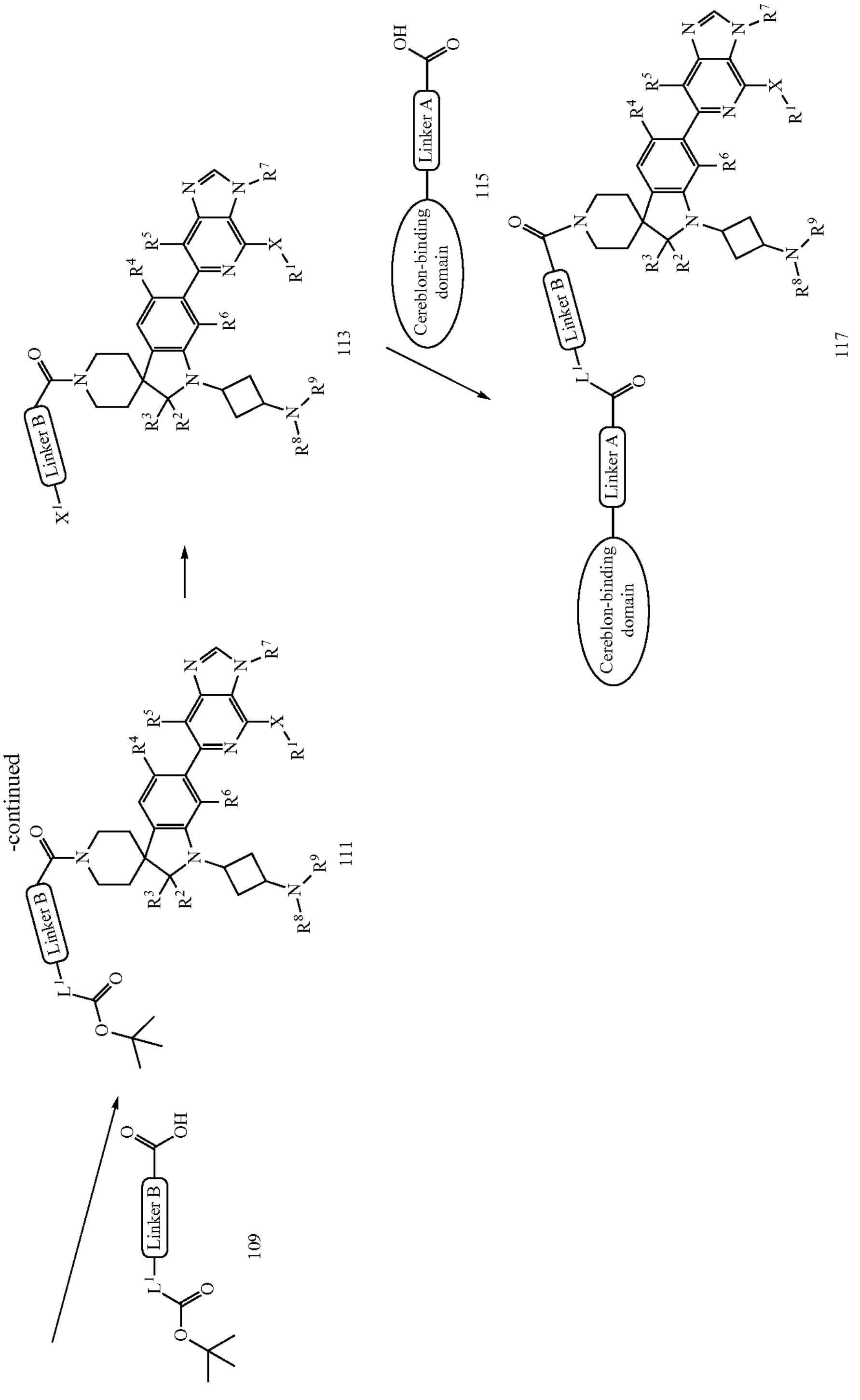
109
111
113
115
117
$X^1$ = NH or $NH_2$, and $L_1$ = N or NH A modular approach to final compound assembly is also possible using methods known in the art. For example, the HPK1 Binder Building Blocks can be coupled with compounds of formulae (108) and (109) under standard amide bond forming conditions such as HATU in the presence of a base such as DIPEA in an appropriate solvent such as DMF to provide compounds of formulae (110) and (111). Compounds of formula (110) can be produced by treating compounds of formula (108) with either acidic hydrolysis conditions (when Y=t-Bu) such as TFA in a suitable solvent such as DCM, or basic conditions (when Y=methyl) such as LiOH in a suitable solvent such as a water/THF mixture. Final compounds are made by coupling compounds of formulae (113) with (115) to afford compounds of formula (117) or by coupling of compounds of formulae (112) with (114) to afford compounds of formula (116) under standing amide bond forming conditions such as HATU in the presence of a base such as DIPEA in a suitable solvent such as DMF. Compounds of formulae (116) and (117) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME C3
ALKYLATED FINAL COMPOUNDS
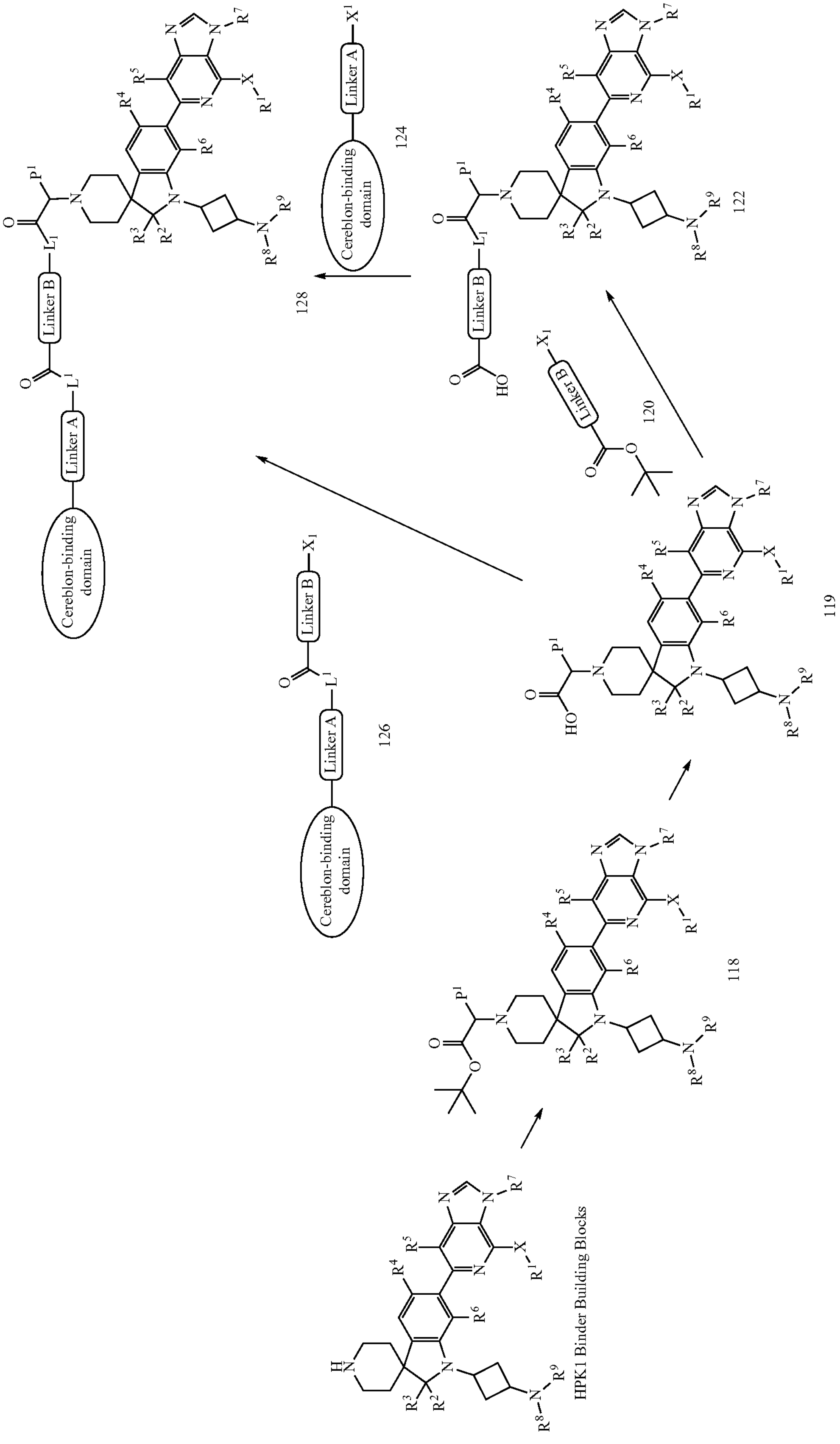
HPK1 Binder Building Blocks
118
119
120
122
124
126
128

-continued
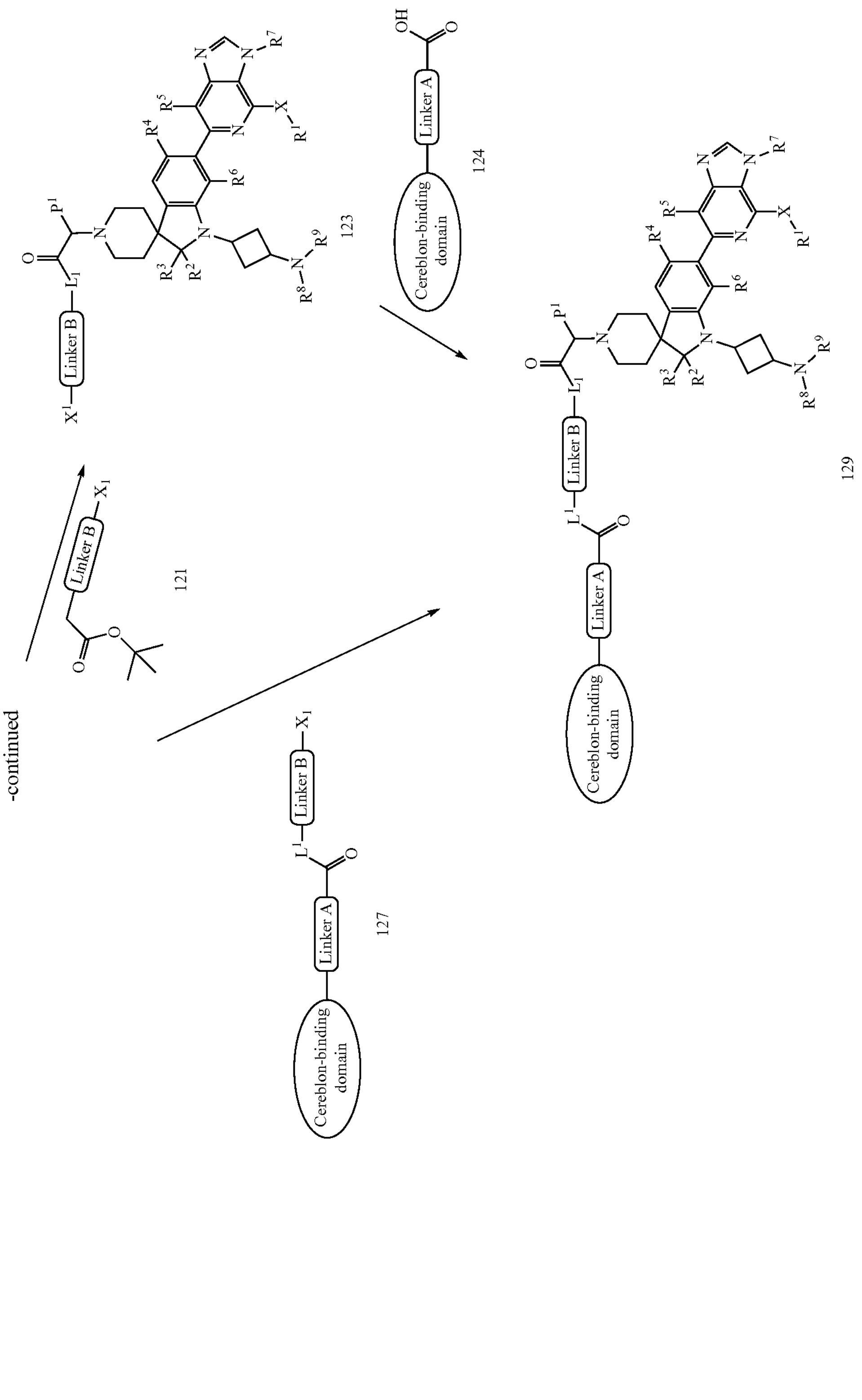
121
123
124
127
129
$X^1$ = NH or $NH_2$, and $L_1$ = N or NH, and $P^1$ = H or Methyl Compounds of formulae (128) and (129) can be made using methods known in the art. For example, the HPK1 Binder Building Blocks can be alkylated with either tert-butyl bromoacetate or tert-butyl 2-bromopropanoate in the presence of a base such as triethylamine and a suitable solvent such as DCM to give compounds of formula (118). Compounds of formula (119) can be produced by treating compounds of formula (118) with an acid such as HCl in an appropriate solvent such as a mixture of dioxane and glacial acetic acid. Compounds of formulae (122) and (123) can be accessed by first coupling compounds of formula (119) with compounds of formulae (120) and (121) under standard amide bond forming conditions such as BOP in the presence of a base such as DIPEA and a suitable solvent such as DMF, followed by treatment with an acid such as TFA in a suitable solvent such as DCM. Compounds of formulae (128) and (129) can be made by coupling compounds of formulae (123) and (125), or compounds of formulae (122) and (124) under standard amide bond forming conditions such as BOP in the presence of a base such as DIPEA in a suitable solvent such as DMF. Alternatively, compounds of formula (119) can be converted directly to compounds of formulae (128) and (129) by coupling to compounds of formulae (126) or (127) under standard amide bond forming conditions such as BOP in the presence of a base such as DIPEA and a suitable solvent such as DMF. Compounds of formulae (128) and (129) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME C4
UREA-CONTAINING FINAL COMPOUNDS
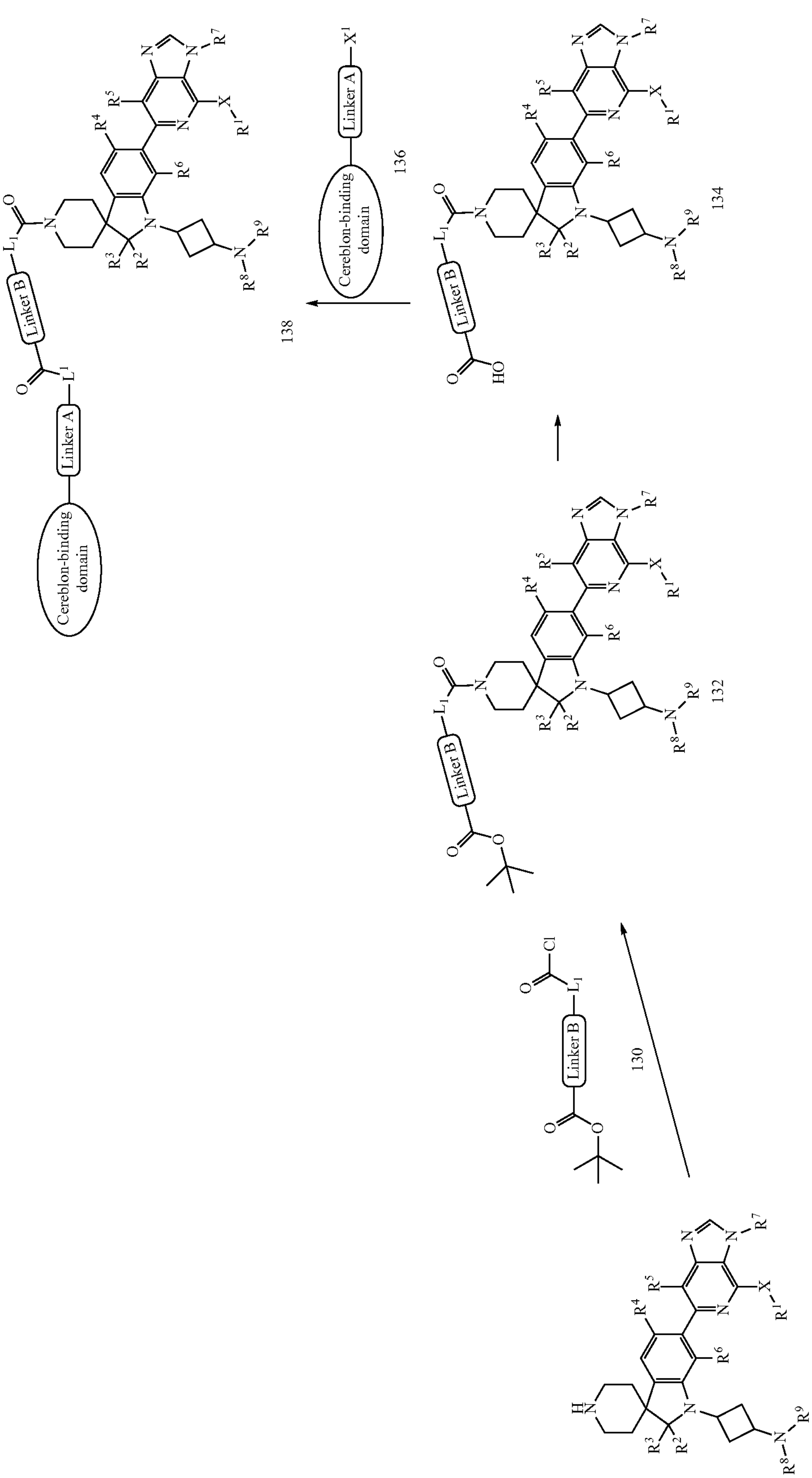
HPK1 Binder Building Blocks
130 132 134 136 138

-continued
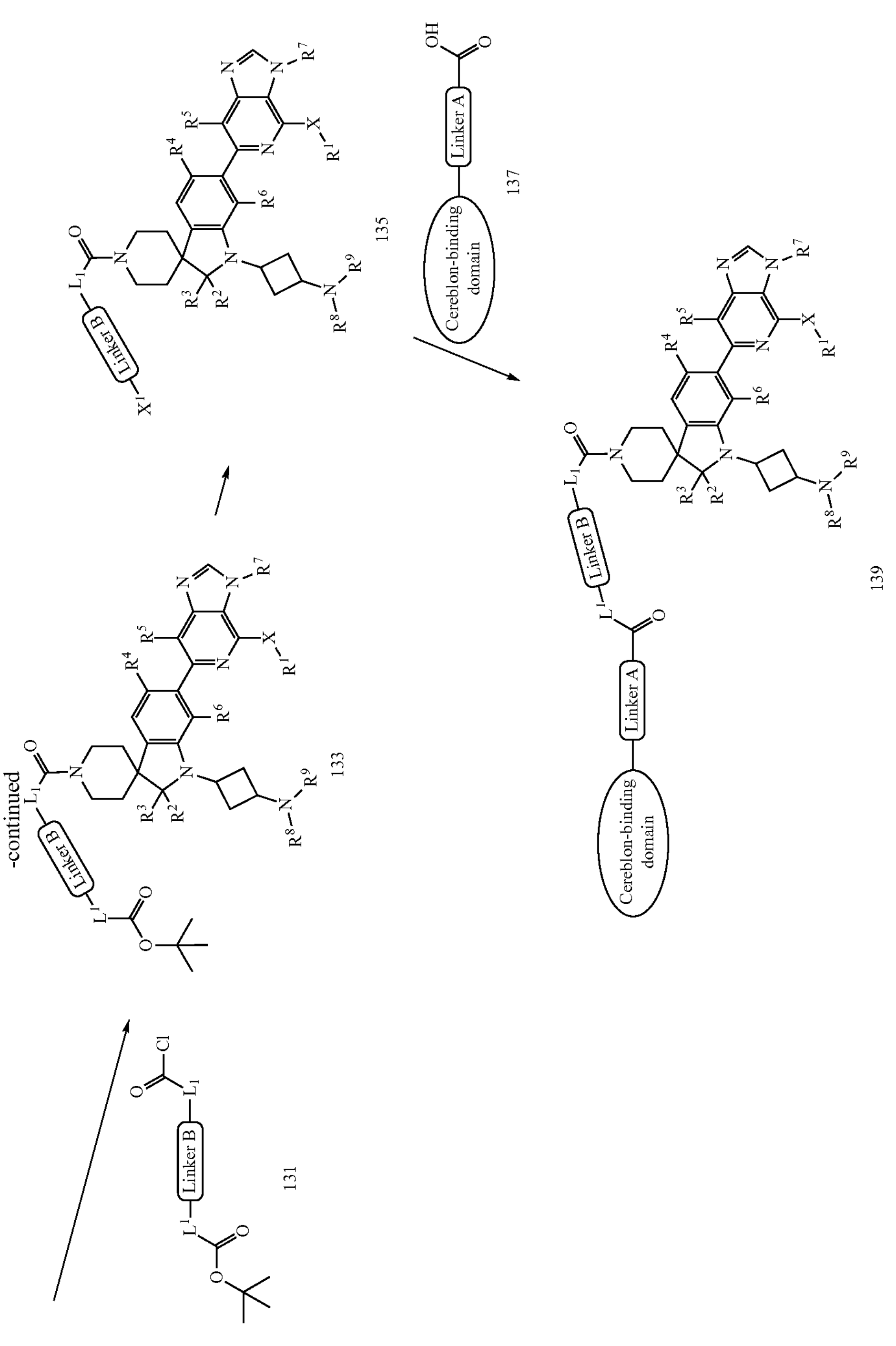
131
133
135
137
139
$X^1$ = NH or $NH_2$, and $L_1$ = N or NH Compounds of formulae (138) and (139) can be made using methods known in the art. For example, the HPK1 Binder Building Blocks can be treated with compounds of formulae (130) and (131) in the presence of a base such as triethylamine in a suitable solvent such as DCM, typically with heating. Compounds of formulae (134) and (135) can be produced by treating compounds of formula (132) and (133) with an acid such as TFA in a suitable solvent such as DCM. Compounds of formulae (138) and (139) can be accessed by coupling compounds of formulae (134) with (136) and (135) with (137) under standard amide bond forming conditions such as BOP in the presence of a base such as DIPEA and a suitable solvent such as DMF. Compounds of formulae (138) and (139) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME C5
SULFONAMIDE-CONTAINING FINAL COMPOUNDS
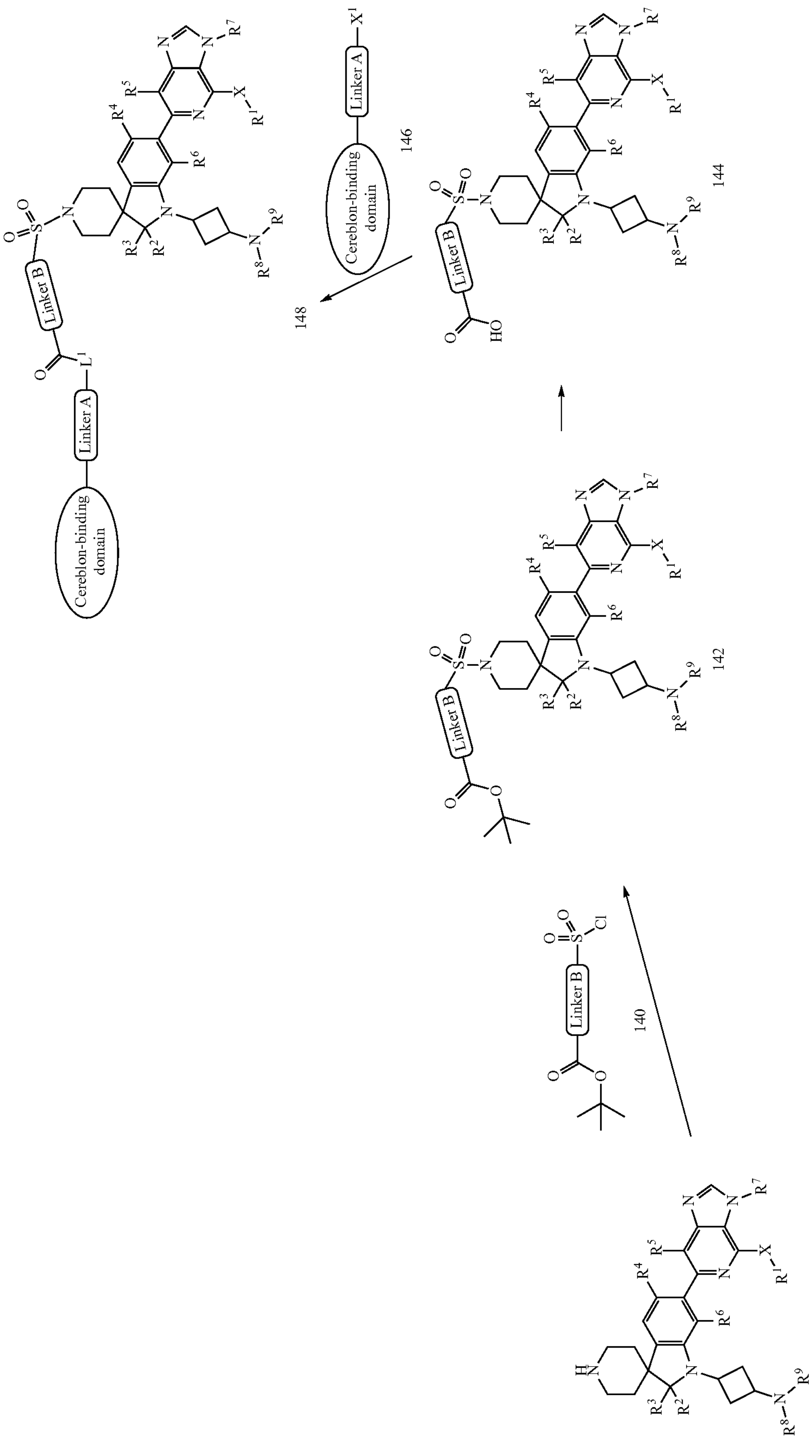
HPK1 Binder Building Blocks
140
142
144
146
148

-continued
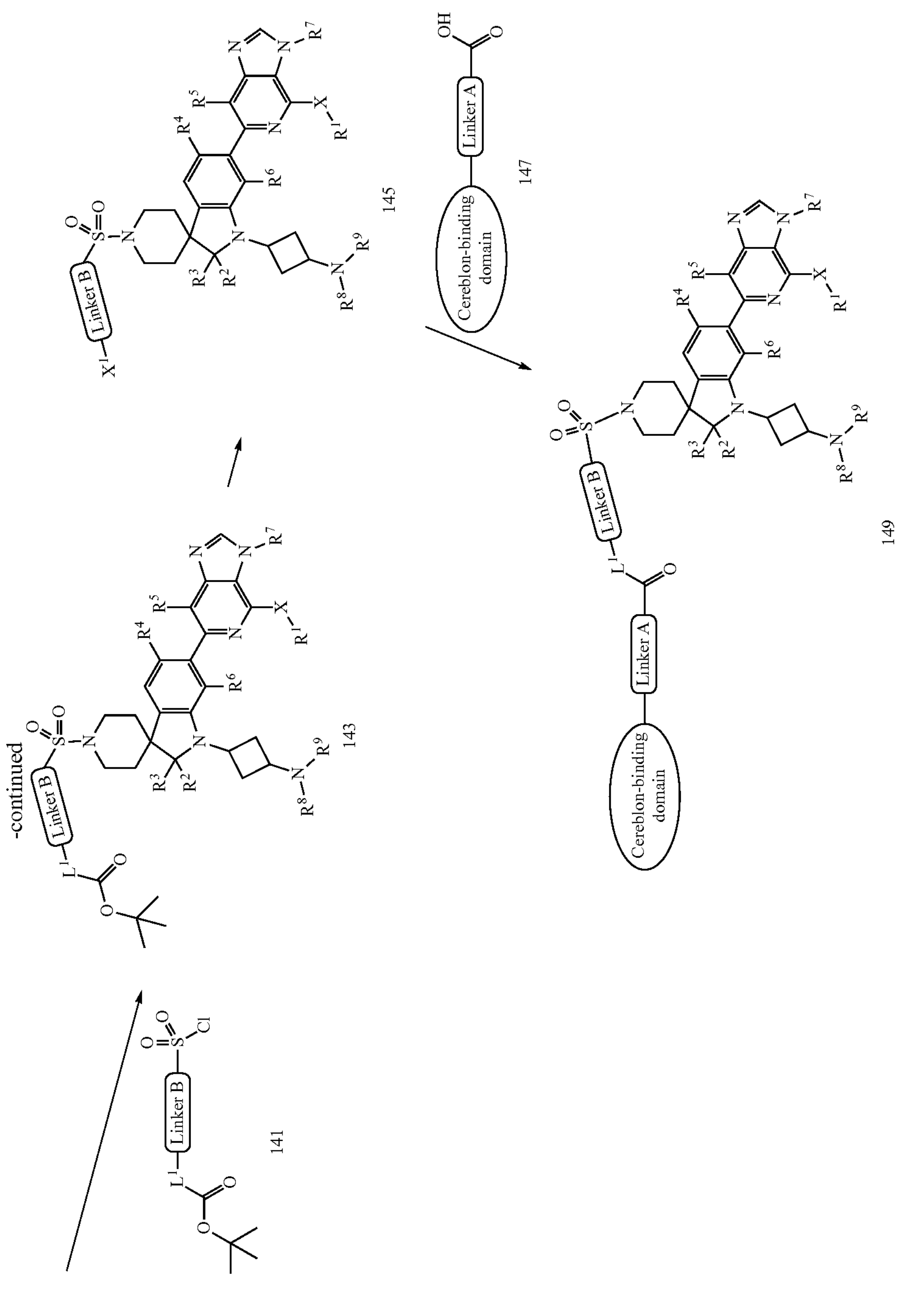
141
143
145
147
149
$X^1$ = NH or $NH_2$, and $L_1$ = N or NH Compounds of formulae (148) and (149) can be made using methods known in the art. For example, the HPK1 Binder Building Blocks can be treated with compounds of formulae (140) and (141) in the presence of a base such as DIPEA in a suitable solvent such as DMF. Compounds of formulae (144) and (145) can be produced by treating compounds of formula (142) and (143) with an acid such as HCl in a suitable solvent such as a mixture of DCM/dioxane. Compounds of formulae (148) and (149) can be accessed by coupling compounds of formulae (144) with (146) and (145) with (147) under standard amide bond forming conditions such as BOP in the presence of a base such as DIPEA and a suitable solvent such as DMF. Compounds of formulae (148) and (149) and the precursors thereof may be isolated and purified by suitable methods known in the art such as partitioning reaction mixtures between an aqueous phase and an organic solvent, followed by isolation of the desired product by filtration or concentration of the relevant layer. Crude products may be further purified by techniques such as chromatography on silica gel, reverse phase chromatography, trituration, precipitation, or crystallization.

REACTION SCHEME AA
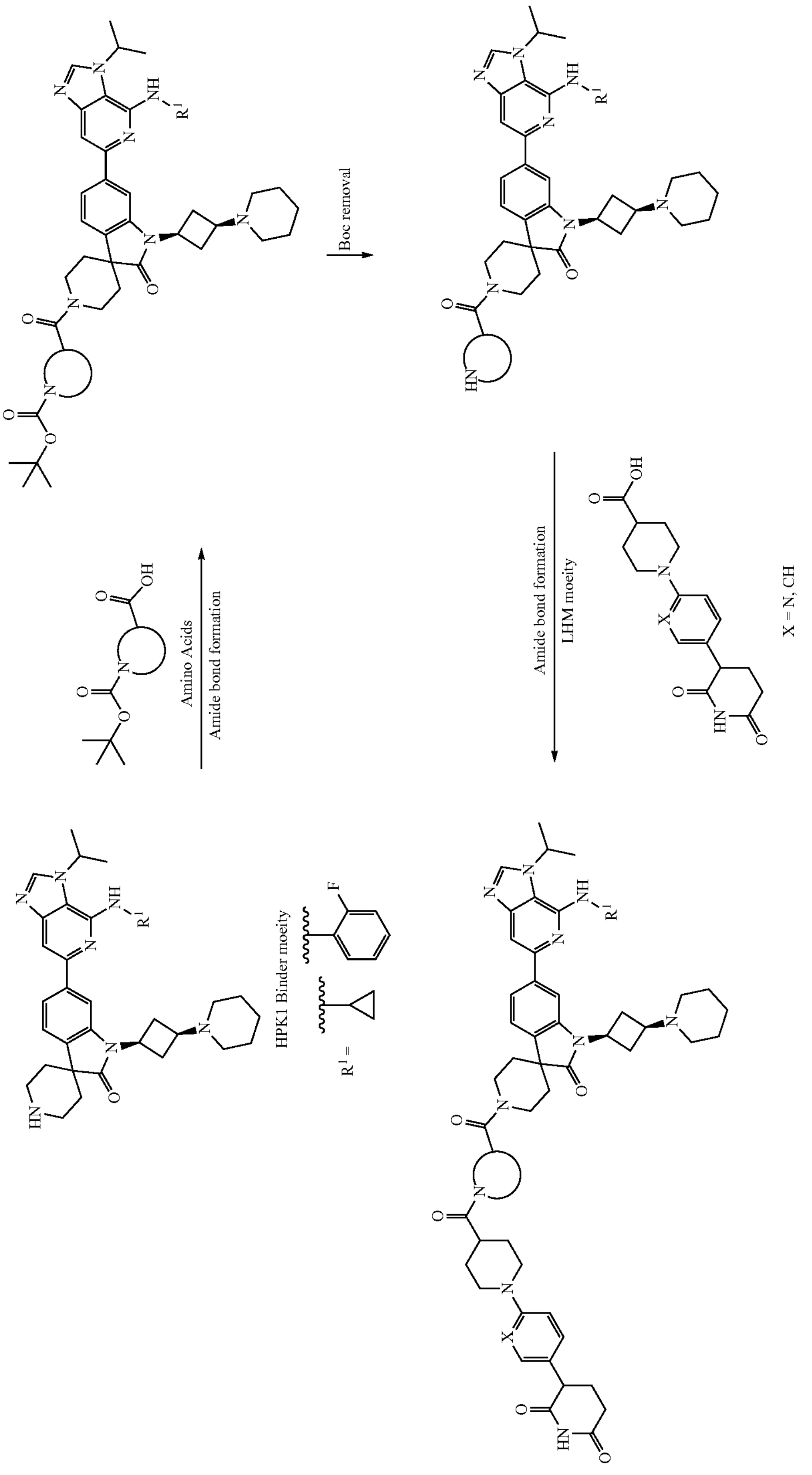

Step 1. Amide Bond Formation Between a HPK1 Binder Moiety a Boc-Amino Acid

Barcoded Boc-amino acid stocks in NMP (0.1M, eq=10 umol) were retrieved from the Hamilton Storage Q20 unit and placed onto the deck of a 1.3 m Hamilton Robotics Vantage system. The HPK1 binder moieties were dissolved in NMP (0.1M) in V-bottom 20 mL vials and placed into vial racks onto the deck of a 1.3 m Vantage. Transfers of 100 μL from the Boc-amino acid stocks into corresponding wells of 96 deep well plates were performed, followed by addition of each DIEA (0.2M, 2 eq), DIC (0.1M, 1 eq) and HOBT (0.1M, 1 eq). The plates were shaken for 10 minutes at 600 rpm for activation. Transfers of 100 uL from the HPK1 binder stocks into corresponding wells of the previous 96 deep well plates were performed, then the plates were sealed and shaken overnight at 600 rpm for amide bond formation.

Step 2. Deprotection

The crudes obtained from Step 1 were dried under vacuum in a Genevac HT12 instrument with heating at 40° C. for 6 hours, followed by addition of 500 μL of 50% TFA/DCM mixture in each well. The plates were shaken for 60 minutes at 600 rpm after which they were dried under vacuum in a Genevac HT12 instrument with heating at 40° C. overnight. DMF was added to each well (300 μL) and the evaporation was repeated for 6 hours to help remove residual TFA from the crude mixtures.

Step 3. Final Amide Bond with a LHM Moiety

The crude mixtures from the previous step were dissolved in 200 uL of 7% DIEA in NMP and then placed back onto the deck of a 1.3 m Vantage system. LHM moieties were dissolved with 20% DIEA in NMP (0.14M) in V-bottom 20 mL vials and placed into vial racks onto the deck of a 1.3 m Vantage system. Transfers of DIC (0.4M, 1 eq) and HOBT (0.4M, 1 eq) mixtures into the V-bottom 20 mL vials were performed and then the vial rack was shaken for 10 minutes at 600 rpm for activation. Transfers of 120 μL from the resulting activation mixtures into corresponding wells were performed, then the plates were sealed and shaken overnight at 600 rpm for amide bond formation. Crude mixtures were submitted as-is to reverse-phase HPLC purification.

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain containing no unsaturation. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkylene" or "alkylene chain" refers to a unbranched or branched divalent hydrocarbon chain, linking the rest of the molecule to a radical group, containing no unsaturation and having from 1 to 20 carbon atoms, or more typically 1 to 12 carbon atoms ($C_{1-12}$ alkylene), or 1 to 8 carbon atoms ($C_{1-8}$ alkylene), or 1 to 3 carbon atoms ($C_{1-3}$ alkylene) e.g., methylene, ethylene, propylene, n-butylene, and the like. The alkylene chain may be attached to the rest of the molecule and to the radical group through one carbon within the chain or through any two carbons within the chain.

"Alkenyl" refers to an alkyl group containing at least one carbon-carbon double bond and having from 2 to 20 carbon atoms (i.e., $C_{2-20}$ alkenyl), or more typically 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkenylene" and "alkenylene chain" refer to a unbranched or branched divalent hydrocarbon chain linking the rest of the molecule to a radical group, containing at least one double bond and having from 2 to 20 carbon atoms, or more typically 2 to 12 carbon atoms, or 2 to 8 carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkynyl" refers to an alkyl group containing at least one carbon-carbon triple bond and having from 2 to 20 carbon atoms (i.e., $C_{2-20}$ alkynyl), or more typically 2 to 12 carbon atoms (i.e., $C_{2-12}$ alkynyl), or more typically 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkynylene" and "alkynylene chain" refer to a unbranched or branched divalent hydrocarbon chain linking the rest of the molecule to a radical group, containing at least one triple bond and having from 2 to 20 carbon atoms, or more typically 2 to 12 carbon atoms, or 2 to 8 carbon atoms. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group —$NR^yR^y$ wherein each $R^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 15 carbon ring atoms (i.e., $C_{6-15}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group —O—C(O)$NR^yR^z$ and an "N-carbamoyl" group which refers to the group —$NR^y$C(O)$OR^z$, wherein $R^y$ and $R^z$ are independently selected from the group consisting of hydrogen, alkyl, aryl, haloalkyl, or heteroaryl; each of which may be optionally substituted.

"Carboxyl" or "carboxylic acid" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 15 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, and bicyclo[2.2.2]octan-1-yl. Cycloalkyl may be attached to the remainder of a molecule by a single ring atom (e.g., as a substituent) or by two ring atoms (e.g., as a linker).

"Ethylene glycol unit" refers to a bivalent monomer having the structure of —$CH_2CH_2O$—, which may be repeated and extended into a longer chain. A linker segment may have up to 12 ethylene glycol units, or more typically up to 6 ethylene glycol units.

"Propylene glycol unit" refers to a bivalent monomer having the structure of —$CH(CH_3)$—$CH_2O$—, which may be repeated and extended into a longer chain. A linker segment may have up to 12 propylene glycol units, or more typically up to 6 propylene glycol units.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatoms such as N, O, S, and the likes. The term "heteroalkyl" includes unbranched or branched saturated chain having carbon and heteroatoms. By way of example, 1, 2 or 3 carbon atoms may be independently replaced with the same or different heteroatoms. Heteroatomic groups include, but are not limited to, —N(R)—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a 5-15 membered, or more typically, 5-12 membered aromatic group having a single ring, multiple rings, or multiple fused rings, with 1-3 ring heteroatoms independently selected from nitrogen, oxygen, and sulfur. As used herein, heteroaryl includes 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl (which has no heteroatom) or heterocyclyl (which has at least one non-aromatic ring). Heteroaryl may be attached to the remainder of a molecule by a single ring atom (e.g., as a substituent) or by two ring atoms (e.g., as a linker).

"Heterocyclyl" refers to a 3-15 membered, or more typically, 5-12 membered, saturated or unsaturated cyclic alkyl group, with 1-3 ring heteroatoms independently selected from nitrogen, oxygen and sulfur. The term "heterocyclyl" includes heterocycloalkenyl groups (i.e., the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 3 to 15 ring atoms (e.g., 3-15 membered heterocyclyl, 3-12 membered heterocyclyl, 4 to 10 membered heterocyclyl, 4-8 membered heterocyclyl or 4-6 membered heterocyclyl; having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, heterocyclyl may include a bridged structure (i.e., "bridged heterocyclyl), in which a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group. Heteroaryl may be attached to the remainder of a molecule by a single ring atom (e.g., as a substituent) or by two ring atoms (e.g., as a linker).

"Fused" refers to a ring which is joint to an adjacent ring and share two adjacent ring atoms that form a covalent bond.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group $—NO_2$.

"Imino" refers to a group that contains a C═N double bond, such as C═N—$R^y$, or ═N—C(O)$R^y$, wherein $R^y$ is selected from the group consisting of hydrogen, alkyl, aryl, cyano, haloalkyl, or heteroaryl; each of which may be optionally substituted. Imino may be a linker segment by attaching to the remainder molecule at the carbon and nitrogen respectively.

"Sulfonyl" refers to the group $—S(O)_2R$, where R is a substituent, or a defined group.

"Alkylsulfonyl" refers to the group $—S(O)_2R$, where R is a substituent, or a defined group.

"Alkylsulfinyl" refers to the group —S(O)R, where R is a substituent, or a defined group.

"Thiocyanate"—SCN.

"Thiol" refers to the group —SR, where R is a substituent, or a defined group.

"Thioxo" or "thione" refer to the group (═S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some compounds of Formula (I) may exist as a "stereoisomer" or a mixture of stereoisomers. Stereoisomer refers to a compound made up of the same atoms bonded by the same bonds but having different three-dimensional structures, which are not interchangeable. The compounds of the disclosure, or their pharmaceutically acceptable salts may contain one or more asymmetric centers and may thus give rise to enantiomers (two stereoisomers whose molecules are non-superimposable mirror images of one another), diastereomers, and other stereoisomeric forms that may be defined, in terms of absolute stereochemistry, as (R)- or (S)-. The present disclosure is meant to include all such possible isomers, as well as their racemic mixture (i.e., equal amounts of (R) and (S) enantiomers) and optically pure forms. Optically active (+) and (−), (R)- and (S)-isomers may be prepared using chiral synthons or chiral reagents, or resolved using conventional techniques, such as HPLC or SFC using a chiral column.

The disclosure also includes "deuterated analogues" of compounds of Formula (I) in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula (I) when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula (I).

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, or solvates of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical uses.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Targeted HPK1 Degradation

The compounds of the present disclosure are demonstrated by cell-based profiling to degrade HPK1.

HiBiT HPK1 Jurkat cell lines were used to evaluate the total protein levels of HPK1 in a robust human cellular high throughput format. The level of HPK1 remaining following treatment with HPK1 CTMs is reported as $D_{max}$ (maximum degradation) achieved at 24 hours when compared to vehicle treated controls. As further described in the Biological Example, the results indicate that HPK1 CTMs are able to degrade HPK1. These decreases were not a result of cytotoxicity measured by a parallel viability assessment (CTG). See also Table 1 and Table 2.

Pharmaceutical Composition and Use of the Bifunctional Compounds of Formula (I)

The bifunctional compounds of Formula (I) are demonstrated to degrade HPK1 and are therefore useful for treating disease indications or disorders involving the function of HPK1, such as signaling or scaffolding.

Various embodiments provide pharmaceutical compositions of a compound of Formula (I), or any one of the substructures or specific compounds of Examples 1-303, and a pharmaceutically acceptable carrier.

Further embodiments provide methods for treating a disease or disorder associated with increased hematopoietic progenitor kinase 1 (HPK1) activity, for increasing T-cell activation, for treating cancer, for inhibiting the growth or proliferation of cancer cells, for treating or preventing a hepatitis B virus (HBV) infection, or for treating or preventing a human immunodeficiency virus (HIV) infection, the method comprising administering to a subject in need thereof a therapeutically effective amount of a compound of Formula (I), any one of the substructures or compounds of Examples 1-303.

In more specific embodiments, cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer.

In some embodiments, a compound of Formula (I), or any one of the substructures or a compound of Examples 1-303 may be administered with a therapeutically effective amount of one or more additional therapeutic agents, or a pharmaceutically acceptable salt thereof.

In further embodiments, the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C—X—C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In more specific embodiments, the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino)pyrimidin-4-yl]benzamide, XL147, BKM120, GDC-0941, BAY80-6946, PX-866, CH5132799, XL756, BEZ235, and GDC-0980, wortmannin, LY294002, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4(3H)-one, (S)-4-amino-6-((1-(5-chloro-4-oxo-3-phenyl-3,4-dihydroquinazolin-2-yl)ethyl)amino)pyrimidine-5- carbonitrile, and ipilimumab, or a pharmaceutically acceptable salt of any of the foregoing, or any combinations thereof.

In more specific embodiments, the one or more additional therapeutic agents is selected from the group consisting of idelalisib, tirabrutinib, momelotinib, and entospletinib, or a pharmaceutically acceptable salt of any of the foregoing, or any combinations thereof.

In further embodiments, the one or more additional therapeutic agents is selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In more specific embodiments, the one or more additional therapeutic agents is selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1 (Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In more specific embodiments, the one or more additional therapeutic agents is selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In more specific embodiments, the one or more additional therapeutic agents is selected from the group consisting of tenofovir alafenamide, tenofovir alafenamide fumarate, and tenofovir alafenamide hemifumarate, or a pharmaceutically acceptable salt of any of the foregoing, or any combinations thereof.

In further embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In more specific embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir, tenofovir alafenamide, tenofovir alafenamide fumarate or tenofovir alafenamide hemifumarate, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir or a pharmaceutically acceptable salt thereof, tenofovir disoproxil, tenofovir disoproxil hemifumarate or tenofovir disoproxil fumarate, or a pharmaceutically acceptable salt of any of the foregoing, or any combinations thereof.

Synthetic Procedures

Representative LCMS Methods

Method 1: ACN-Water-0.1% FA-5% B-1.5 mL-3 min(90-900)+-0.1 cm

Instrument: Shimadzu LCMS-2020

Column: SPD-M20A

Solvent A: water/0.1% FA

Solvent B: ACN/0.1% FA

Flow rate: 1.5000 mL/min

Method 2: ACN-Water-5 mM $NH_4HCO_3$-10% B-1.5-2.0 min(90-900)+-0.1 cm

Instrument: Shimadzu LCMS-2020

Column: HALO

Solvent A: Water/5 mM $NH_4HCO_3$

Solvent B: Acetonitrile

Flow rate: 1.2000 mL/min

Method 3: ACN-Water-0.05% TFA-5% B-1.5-2.0MIN(90-900).lcm

Instrument: Shimadzu LCMS-2020

Column: SPD-M20A

Solvent A: Water/0.05% TFA

Solvent B: Acetonitrile/0.05% TFA

Flow rate: 1.5000 mL/min

Method 4: LCMS2-036-20-80-95-6-1-25-UV-BCM

Instrument: Dionex UHPLC Ultimate 3000 with DAD detector/Thermo Scientific ISQ EC—Mass Spectrometer Column: Kinetex® 2.6 µm XB-C18 (4.6×50 mm), 110A, column no. 00B-4496-E0, internal column no. 036

Solvent A: 0.1% v/v water solution of formic acid

Solvent B: 0.1% v/v acetonitrile solution of formic acid

| Time [min] | Mobile phase A [%] | Mobile phase B [%] | Flow [mL/min] |
|---|---|---|---|
| 0.00 | 80 | 20 | 1.0 |
| 3.35 | 20 | 80 | 1.0 |
| 3.75 | 20 | 80 | 1.0 |
| 3.90 | 5 | 95 | 1.0 |
| 4.75 | 5 | 95 | 1.0 |
| 5.00 | 80 | 20 | 1.0 |
| 6.00 | 80 | 20 | 1.0 |

Flow rate: 1.0 [mL/min]

Run time: 6.0 [min]

Method 5: LCMS-019-5-80-80-7-1-25-UV-Rot

Instrument: Dionex UHPLC Ultimate 3000 with DAD detector/Thermo Scientific MSQ Plus Column: Kinetex® 2.6 µm XB-C18 (4.6×50 mm), 110A, column no. OOB-4496-E0, internal column no. 019

Solvent A: 0.1% v/v water solution of trifluoroacetic acid

Solvent B: 0.1% v/v acetonitrile solution of trifluoroacetic acid

Gradient

| Time [min] | Mobile phase C [%] | Mobile phase D [%] | Flow [mL/min] |
|---|---|---|---|
| 0.0 | 95 | 5 | 1.0 |
| 1.0 | 95 | 5 | 1.0 |
| 4.75 | 20 | 80 | 1.0 |
| 5.25 | 20 | 80 | 1.0 |
| 6.0 | 95 | 5 | 1.0 |
| 7.0 | 95 | 5 | 1.0 |

Flow rate: 1.0 [mL/min]

Run time: 7.0 [min]

Representative HPLC Purification Methods:

Method 1: 0-50% Buffer B (ACN+0.1% TFA)

Instrument: DYNAMAX

Column: Higgins analytical, C18, 30×100 mm column

Solvent A: Water+0.1% TFA (which is called Buffer A)

Solvent B: ACN+0.1% TFA (which is called Buffer B)

Gradient: 0-50% Buffer B (ACN+0.1% TFA)

Flow rate: 40 mL/min

Run time: 30 min

Method 2: 20210423-Prep2-60800420-PKU01-087 C18 Prep

Instrument: Shimadzu Model: CMB-20A, Detector: SPD-M20A IVDD, Pump: LC-20AP, Fraction collector: FRC-10A Column: Gemini NX-C18, phenomenex: 00G-4454-P0-AX, Serial number:

H19-002285, 250×21.20 mm, 5 µm/110 Å, Equipped with Pre-Column:

SecurityGuard™ PREP Cartridge Gemini NX-C18, Phenomenex; catalog number:

AJ0-8370

Solvent A: 0.1% v/v water solution of formic acid

Solvent B: 0.1% v/v acetonitrile solution of formic acid

Gradient

| Time | Mobile phase B [%] |
|---|---|
| 0.01 | 2 |
| 6.00 | 15 |
| 10.00 | 15 |
| 10.20 | 95 |
| 13.00 | 95 |
| 13.20 | 2 |
| 15.00 | 2 |

Flow rate: 30 [mL/min]

Run time: 15 [min]

Intermediate 1

(3R)-1-((1R,4R)-4-((4-(2,6-dioxopiperidin-3-yl)pyridin-2-yl)amino)cyclohexane-1-carbonyl)pyrrolidine-3-carboxylic acid

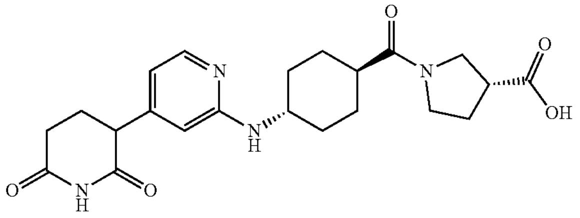 [SMILES: O=C1CCC(c2ccnc(N[C@H]3CC[C@H](C(=O)N4CC[C@@H](C(=O)O)C4)CC3)c2)C(=O)N1]

Step-1: methyl (3R)-1-[(1r,4r)-4-{[4-(2,6-dioxopiperidin-3-yl)pyridin-2-yl]amino}cyclohexanecarbonyl]pyrrolidine-3-carboxylate

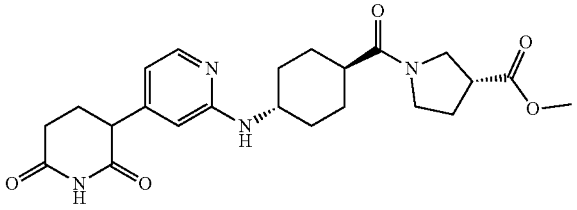 [SMILES: COC(=O)[C@@H]1CCN(C(=O)[C@H]2CC[C@H](Nc3cc(C4CCC(=O)NC4=O)ccn3)CC2)C1]

A mixture of (1r,4r)-4-{[4-(2,6-dioxopiperidin-3-yl)pyridin-2-yl]amino}cyclohexane-1-carboxylic acid (300 mg, 0.905 mmol) and HATU (516 mg, 1.357 mmol) in DMF (5 mL) was stirred for 0.5 h at room temperature, then methyl (3R)-pyrrolidine-3-carboxylate (116 mg, 0.905 mmol) and DIEA (702 mg, 5.430 mmol) were added The resulting mixture was stirred for 1 h at room temperature. The residue was purified by reverse phase flash chromatography [ACN and $H_2O$ mobile phase] to provide 130 mg (32.45%) of the title compound as an orange solid. LCMS: ($C_{23}H_{30}N_4O_5$) desired mass=442.2; found: m/z=443.1 $[M+H]^+$.

Step-2: (3R)-1-((1r,4R)-4-((4-(2,6-dioxopiperidin-3-yl)pyridin-2-yl)amino)cyclohexane-1-carbonyl)pyrrolidine-3-carboxylic acid

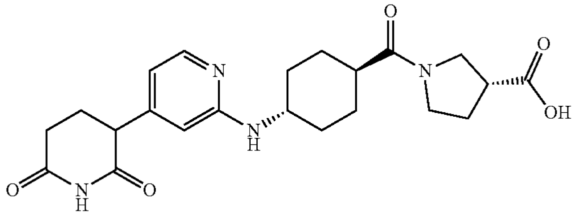 [SMILES: O=C1CCC(c2ccnc(N[C@H]3CC[C@H](C(=O)N4CC[C@@H](C(=O)O)C4)CC3)c2)C(=O)N1]

A mixture of methyl (3R)-1-[(1r,4r)-4-{[4-(2,6-dioxopiperidin-3-yl)pyridin-2-yl]amino}cyclohexanecarbonyl]pyrrolidine-3-carboxylate (80 mg, 0.181 mmo) and HCl (3 mL, 12M) was stirred for 12 h at room temperature, then concentrated under reduced pressure. The residue was purified by reverse phase flash chromatography [ACN and $H_2O$ mobile phase] to provide 29 mg (37.44%) of the title compound as a white solid. LCMS: ($C_{22}H_{28}N_4O_5$) desired mass=428.2; found: m/z=429.2 $[M+H]^+$.

Intermediate 2

(3R)-1-((1R,4R)-4-((4-(2,6-dioxopiperidin-3-yl)phenyl)amino)cyclohexane-1-carbonyl)pyrrolidine-3-carboxylic acid

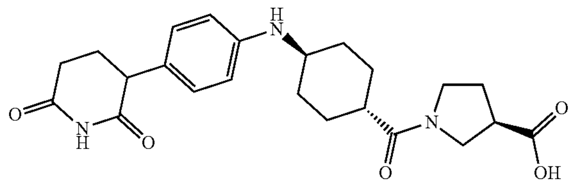 [SMILES: O=C1CCC(c2ccc(N[C@H]3CC[C@H](C(=O)N4CC[C@@H](C(=O)O)C4)CC3)cc2)C(=O)N1]

The title compound was synthesized by methods similar to those used for 1-((1R,4r)-4-((4-((RS)-2,6-dioxopiperidin-3-yl)phenyl)amino)cyclohexane-1-carbonyl)piperidine-4-carboxylic acid (Intermediate 31), and coupling dibromobenzene with methyl (R)-pyrrolidine-3-carboxylate hydrochloride in the first step.

Intermediate 3

(3R)-1-((1R,4R)-4-((5-(2,6-dioxopiperidin-3-yl)pyridin-2-yl)amino)cyclohexane-1-carbonyl)pyrrolidine-3-carboxylic acid

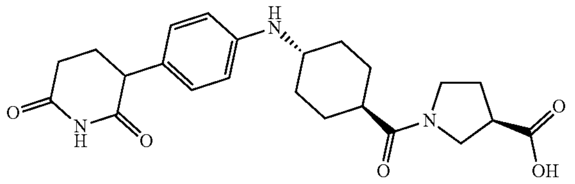 [SMILES: O=C1CCC(c2ccc(N[C@H]3CC[C@H](C(=O)N4CC[C@@H](C(=O)O)C4)CC3)cc2)C(=O)N1]

Step 1: tert-butyl (1r,4r)-4-((5-bromopyridin-2-yl)amino)cyclohexane-1-carboxylate

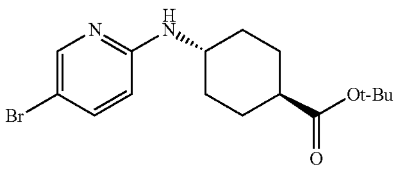 [SMILES: CC(C)(C)OC(=O)[C@H]1CC[C@H](Nc2ccc(Br)cn2)CC1]

To a solution of 5-bromo-fluoropyridine (1.8 g, 10.18 mmol) and tert-butyl (1r,4r)-4-aminocyclohexane-1-carboxylate (507 mg, 2.54 mmol) in anhydrous DMSO (12.7 mL) was added potassium carbonate (1.1 g, 10.18 mmol) and DIPEA (1.8 mL, 10.18 mmol) at room temperature. The reaction mixture was stirred for 2 h at 130° C., and then the reaction mixture was quenched with water (20 mL) and extracted with ethyl acetate (3×10 mL). The combined organic layers were dried over anhydrous sodium sulfate and concentrated under reduced pressure. The residue was used as-is for the next step (yellow oil, 612 mg). LCMS: [$C_{16}$H23Br$N_2O_2$], desired mass=354.0, found: m/z=355.2 $[M+H]^+$.

Step 2: tert-butyl (1r,4r)-4-((2',6'-bis(benzyloxy)-[3,3'-bipyridin]-6-yl)amino)cyclohexane-1-carboxylate

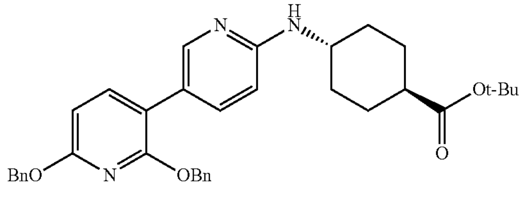 [SMILES: CC(C)(C)OC(=O)[C@H]1CC[C@H](Nc2ccc(-c3ccc(OCc4ccccc4)nc3OCc3ccccc3)cn2)CC1]

To a solution of tert-butyl (1r,4r)-4-((5-bromopyridin-2-yl)amino)cyclohexane-1-carboxylate (674 mg, 1.90 mmol) and 2,6-bis(benzyloxy)pyridin-3-ylboronic acid (639 mg, 1.90 mmol) in 1,4-dioxane (2.38 mL) was added a 1N aqueous solution of cesium carbonate (4.74 mL, 4.74 mmol). The mixture was degassed with argon gas for 10 min, then Pd(dppf)$Cl_2$·DCM (314 mg, 0.38 mmol) was added and the vial was sealed. The reaction mixture was stirred for 0.5 h at 100° C. under microwave radiation, and then the reaction mixture was quenched with water (10 mL) and extracted with ethyl acetate (3×10 mL). The combined organic layers were dried over anhydrous sodium sulfate and concentrated under reduced pressure. The residue was purified by HPLC to provide 772 mg (72% yield) of the title compound as a white solid. LCMS: [$C_{35}H_{39}N_3O_4$], desired mass=565.2, found: m/z=566.5 $[M+H]^+$.

Step 3: tert-butyl (1r,4r)-4-((5-(2,6-dioxopiperidin-3-yl)pyridin-2-yl)amino)cyclohexane-1-carboxylate

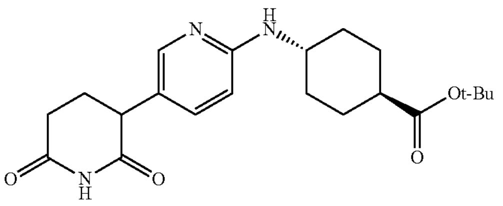 [SMILES: CC(C)(C)OC(=O)[C@H]1CC[C@H](Nc2ccc(C3CCC(=O)NC3=O)cn2)CC1]

To a solution of tert-butyl (1r,4r)-4-((2',6'-bis(benzyloxy)-[3,3'-bipyridin]-6-yl)amino)cyclohexane-1-carboxylate (376 mg, 0.66 mmol) in a mixture of THF (3.4 mL) and isopropanol (3.4 mL) was added Pd/C (71 mg, 0.06 mmol). The reaction mixture was stirred for 36 h at room temperature under $H_2$ gas and then the mixture was diluted with ethyl acetate (30 mL) and filtered through Celite. The filtrate was then concentrated under reduced pressure. The residue was used as-is for the next step. (Yellow oil, 104 mg). LCMS: [$C_{21}H_{29}N_3O_4$], desired mass=387.2, found: m/z=388.2 $[M+H]^+$.

Step 4: (1r,4r)-4-((5-(2,6-dioxopiperidin-3-yl)pyridin-2-yl)amino)cyclohexane-1-carboxylic acid

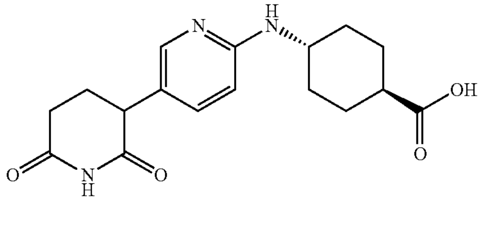 [SMILES: O=C1CCC(c2ccc(N[C@H]3CC[C@H](C(=O)O)CC3)nc2)C(=O)N1]

The title compound was obtained via TFA-mediated deprotection conditions similar to those described for 1-(5-(2,6-dioxopiperidin-3-yl)pyridin-2-yl)piperidine-4-carboxylic acid. The crude product was used as-is for the next step. (Orange oil, 305 mg). LCMS: [$C_{17}H_{21}N_3O_4$], desired mass=331.1, found: m/z=332.4 $[M+H]^+$.

Step 5: tert-butyl (3R)-1-((1r,4R)-4-((5-(2,6-dioxopiperidin-3-yl)pyridin-2-yl)amino)cyclohexane-1-carbonyl)pyrrolidine-3-carboxylate

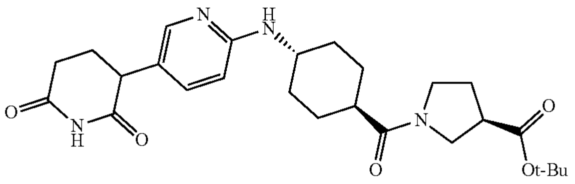 [SMILES: CC(C)(C)OC(=O)[C@@H]1CCN(C(=O)[C@H]2CC[C@H](Nc3ccc(C4CCC(=O)NC4=O)cn3)CC2)C1]

The title compound was synthesized using similar methods to tert-butyl (3R)-1-(1-(5-(2,6-dioxopiperidin-3-yl)pyridin-2-yl)piperidine-4-carbonyl)pyrrolidine-3-carboxylate using BOP coupling. The crude product was purified by silica gel chromatography using a mobile phase of 0-5% MeOH in DCM to provide 86 mg (54% yield) of the title compound as a pale-yellow oil. LCMS: [$C_{26}H_{36}N_4O_5$], desired mass=484.2, found: m/z=485.4 $[M+H]^+$.

Step 6: (3R)-1-((1r,4R)-4-((5-(2,6-dioxopiperidin-3-yl)pyridin-2-yl)amino)cyclohexane-1-carbonyl)pyrrolidine-3-carboxylic acid

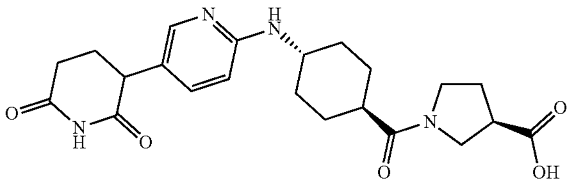 [SMILES: O=C1CCC(c2ccc(N[C@H]3CC[C@H](C(=O)N4CC[C@@H](C(=O)O)C4)CC3)nc2)C(=O)N1]

The title compound was obtained via TFA-mediated deprotection conditions similar to those described for 1-(5-(2,6-dioxopiperidin-3-yl)pyridin-2-yl)piperidine-4-carboxylic acid. The crude product was used as-is for the next step. (Pale yellow oil, 53 mg). LCMS: [$C_{22}H_{28}N_4O_5$], desired mass=[428.2.1], found: m/z=[429.3] $[M+H]^+$.

Intermediate 4

(3R)-1-((1R,4R)-4-((6-((2,6-dioxopiperidin-3-yl)carbamoyl)pyridin-3-yl)amino)cyclohexane-1-carbonyl)pyrrolidine-3-carboxylic acid

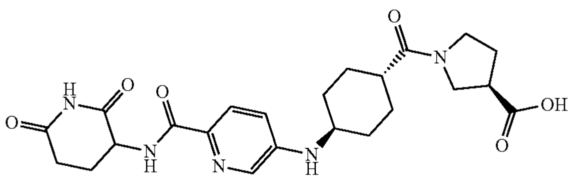 [SMILES: O=C1CCC(NC(=O)c2ccc(N[C@H]3CC[C@H](C(=O)N4CC[C@@H](C(=O)O)C4)CC3)cn2)C(=O)N1]

Step 1: methyl 5-(((1r,4r)-4-(tert-butoxycarbonyl)cyclohexyl)amino)picolinate

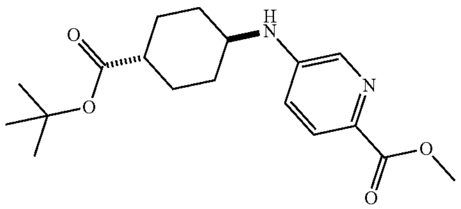 [SMILES: COC(=O)c1ccc(N[C@H]2CC[C@H](C(=O)OC(C)(C)C)CC2)cn1]

To a solution of tert-butyl (1r,4r)-4-aminocyclohexane-1-carboxylate (385 mg, 1.9 mmol) and DIPEA (0.68 mL, 0.5 g, 3.87 mmol) in DMSO (2 mL) was added methyl 5-fluoropicolinate (300 mg, 1.9 mmol). The reaction mixture was stirred at 120° C. for 16 hours. At this time LCMS showed all starting material had been consumed. The reaction mixture was cooled to room temperature and water was added. This crude mixture was purified by reverse phase FC (5-50% MeCN/H2O +0.1% TFA) to afford the title compound (200 mg, 31% yield). LCMS: [$C_{18}H_{26}N_2O_4$], desired mass=334.4, found: m/z=335.4 $[M+H]^+$.

Step 2: 5-(((1r,4r)-4-(tert-butoxycarbonyl)cyclohexyl)amino)picolinic acid

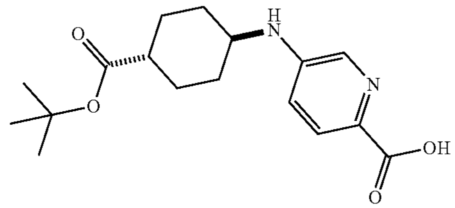 [SMILES: CC(C)(C)OC(=O)[C@H]1CC[C@H](Nc2ccc(C(=O)O)nc2)CC1]

Methyl 5-(((1r,4r)-4-(tert-butoxycarbonyl)cyclohexyl)amino)picolinate (200 mg, 0.6 mmol) was dissolved in THF (5 mL) at rt. To this solution was added 1M lithium hydroxide solution (3 mL, 3 mmol) and the resulting mixture was stirred vigorously overnight. LCMS at this point showed consumption of all starting material, and the reaction mixture was concentrated to dryness to provide the title compound as a lithium salt (80 mg, 41% yield). LCMS: [$C_{17}H_{24}N_2O_4$], desired mass=320.4, found: m/z=321.4 $[M+H]^+$.

Step 3: tert-butyl (1r,4r)-4-((6-((2,6-dioxopiperidin-3-yl)carbamoyl)pyridin-3-yl)amino)cyclohexane-1-carboxylate

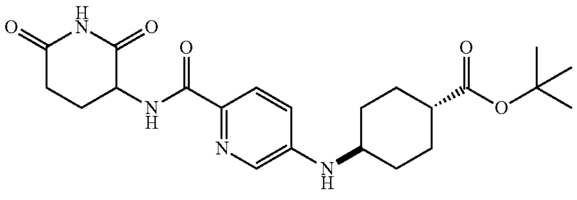 [SMILES: CC(C)(C)OC(=O)[C@H]1CC[C@H](Nc2ccc(C(=O)NC3CCC(=O)NC3=O)nc2)CC1]

To a solution of methyl 5-(((1r,4r)-4-(tert-butoxycarbonyl)cyclohexyl)amino)picolinic acid (80 mg, 0.25 mmol) in DMF (1 mL) was added HATU (190 mg, 0.49 mmol) and DIPEA (0.22 mL, 0.16 g, 1.25 mmol). 3-aminopiperidine-2,6-dione (62 mg, 0.37 mmol) was added last and the reaction mixture was stirred at room temperature for 30 minutes. The reaction mixture was diluted with DMF, and purified by reverse phase FC (5-50% MeCN/H2O +0.1% TFA) to afford the title compound (100 mg, 93% yield). LCMS: [$C_{22}H_{30}N_4O_5$], desired mass=430.5, found: m/z=431.5 $[M+H]^+$.

Step 4: (1r,4r)-4-((6-((2,6-dioxopiperidin-3-yl)carbamoyl)pyridin-3-yl)amino)cyclohexane-1-carboxylic acid

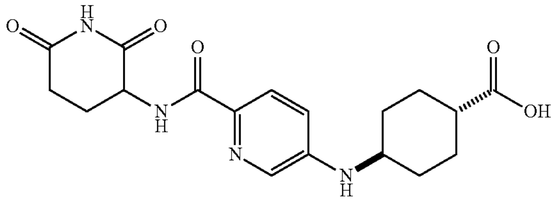

tert-Butyl (1r,4r)-4-((6-((2,6-dioxopiperidin-3-yl)carbamoyl)pyridin-3-yl)amino)cyclohexane-1-carboxylate (100 mg, 0.23 mmol) was treated with 5% TFA in HFIP (1.9 mL, 1.3 mmol). The reaction mixture was stirred for 16 hrs before being concentrated to dryness. The resulting product was then used without further purification to afford the title compound (80 mg, 92% yield). LCMS: [$C_{18}H_{22}N_4O_5$], desired mass=374.5, found: m/z=375.4 $[M+H]^+$.

Step 5: tert-butyl (3R)-1-((1r,4R)-4-((6-((2,6-dioxopiperidin-3-yl)carbamoyl)pyridin-3-yl)amino)cyclohexane-1-carbonyl)pyrrolidine-3-carboxylate

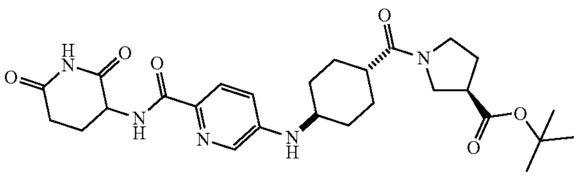 [SMILES: CC(C)(C)OC(=O)[C@@H]1CCN(C(=O)[C@H]2CC[C@H](Nc3ccc(C(=O)NC4CCC(=O)NC4=O)nc3)CC2)C1]

To a solution of (1r,4r)-4-((6-((2,6-dioxopiperidin-3-yl)carbamoyl)pyridin-3-yl)amino)cyclohexane-1-carboxylic acid (80 mg, 0.21 mmol)) was added HATU (162 mg, 0.42 mmol) and DIPEA (0.23 mL, 0.17 g, 1.3 mmol). tert-butyl (R)-pyrrolidine-3-carboxylate (55 mg, 0.32 mmol) was added last and the reaction mixture was stirred at room temperature for 30 minutes. The reaction mixture was diluted with DMF, and purified by reverse phase FC (5-50% MeCN/H2O +0.1% TFA) to afford the title compound (110 mg, 97% yield). LCMS: [$C_{27}H37N_5O_6$], desired mass=527.6, found: m/z=528.5 $[M+H]^+$.

Step 6: tert-butyl (3R)-1-((1r,4R)-4-((6-((2,6-dioxopiperidin-3-yl)carbamoyl)pyridin-3-yl)amino)cyclohexane-1-carbonyl)pyrrolidine-3-carboxylate

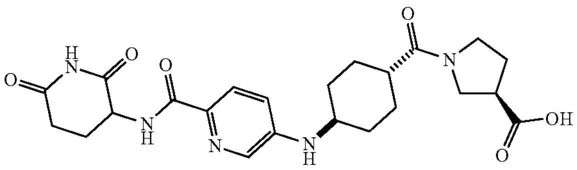 [SMILES: O=C1CCC(NC(=O)c2ccc(N[C@H]3CC[C@H](C(=O)N4CC[C@@H](C(=O)O)C4)CC3)cn2)C(=O)N1]

Prepared by similar procedures as step 4 using tert-butyl (3R)-1-((1r,4R)-4-((6-((2,6-dioxopiperidin-3-yl)carbamoyl)pyridin-3-yl)amino)cyclohexane-1-carbonyl)pyrrolidine-3-carboxylate (110 mg, 0.21 mmol) as starting material. The crude mixture was purified by reverse phase FC (5-50% MeCN/H2O) to afford the title compound (96 mg, 97% yield). LCMS: [$C_{23}H_{29}N_5O_6$], desired mass=471.5, found: m/z=472.4 [M+H]$^+$.

Intermediate 5

(3R)-1-((1R,4R)-4-((6-(2,6-dioxopiperidin-3-yl)pyridin-2-yl)amino)cyclohexane-1-carbonyl)pyrrolidine-3-carboxylic acid

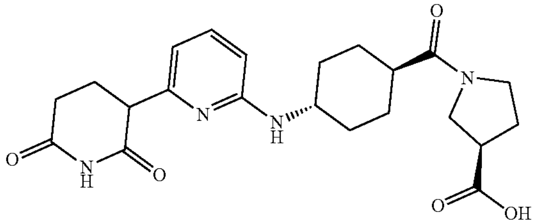 [SMILES: O=C1CCC(c2cccc(N[C@H]3CC[C@H](C(=O)N4CC[C@@H](C(=O)O)C4)CC3)n2)C(=O)N1]

Step 1: tert-butyl (3R)-1-((1r,4R)-4-((6-(2,6-dioxopiperidin-3-yl)pyridin-2-yl)amino)cyclohexane-1-carbonyl)pyrrolidine-3-carboxylate

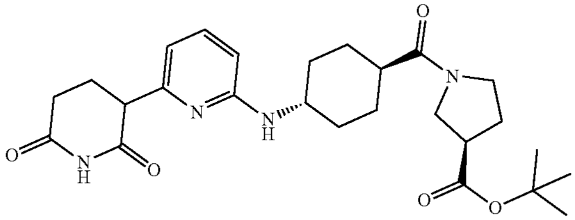 [SMILES: CC(C)(C)OC(=O)[C@@H]1CCN(C(=O)[C@H]2CC[C@H](Nc3cccc(C4CCC(=O)NC4=O)n3)CC2)C1]

To a solution of (1r,4r)-4-((6-(2,6-dioxopiperidin-3-yl)pyridin-2-yl)amino)cyclohexane-1-carboxylic acid (50 mg, 0.15 mmol) in DMF (1 mL) was added BOP (100 mg, 0.23 mmol) and DIPEA (0.13 mL, 96 mg, 0.74 mmol). tert-Butyl (R)-pyrrolidine-3-carboxylate (39 mg, 0.23 mmol) was added last and the reaction mixture was stirred at room temperature for 1 h. The reaction mixture was diluted with DMF and purified by reverse phase FC (5-50% MeCN/H2O +0.1% TFA) to afford the title compound (60 mg, 82% yield). LCMS: [$C_{26}H_{36}N_4O_5$], desired mass=484.6, found: m/z=485.6 [M+H]$^+$.

Step 2: (3R)-1-((1r,4R)-4-((6-(2,6-dioxopiperidin-3-yl)pyridin-2-yl)amino)cyclohexane-1-carbonyl)pyrrolidine-3-carboxylic acid

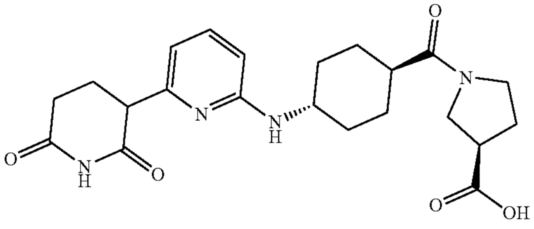 [SMILES: O=C1CCC(c2cccc(N[C@H]3CC[C@H](C(=O)N4CC[C@@H](C(=O)O)C4)CC3)n2)C(=O)N1]

tert-Butyl (3R)-1-((1r,4R)-4-((6-(2,6-dioxopiperidin-3-yl)pyridin-2-yl)amino)cyclohexane-1-carbonyl)pyrrolidine-3-carboxylate (60 mg, 0.12 mmol) was treated with 5% TFA in HFIP (1.9 mL, 1.3 mmol). The reaction mixture was stirred for 16 hr. before being concentrated to dryness. The resulting product was then used without further purification (unless otherwise noted) to afford the title compound (50 mg, 94% yield). LCMS: [$C_{22}H_{28}N_4O_5$], desired mass=428.5, found: m/z=429.3 [M+H]$^+$.

Intermediate 6

(3R)-1-[(1R,4R)-4-{[2-(2,6-dioxopiperidin-3-yl)-1,3-dioxo-2,3-dihydro-1H-isoindol-4-yl]amino}cyclohexanecarbonyl]pyrrolidine-3-carboxylic acid

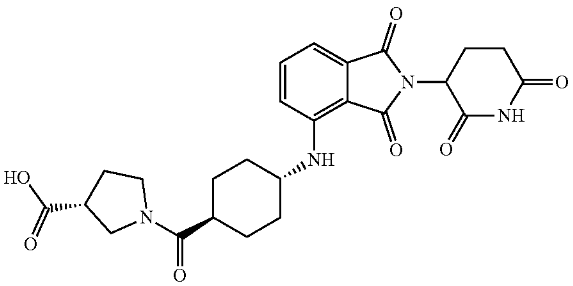 [SMILES: O=C1CCC(N2C(=O)c3cccc(N[C@H]4CC[C@H](C(=O)N5CC[C@@H](C(=O)O)C5)CC4)c3C2=O)C(=O)N1]

The title compound (1.060 g, 71% yield, yellow solid) was synthesized using similar methods to intermediate 17, and substituting benzyl 2-[(3R)-pyrrolidin-3-yl]acetate hydrochloride for benzyl (3R)-pyrrolidine-3-carboxylate hydrochloride. LCMS: $C_{25}H_{28}N_4O_7$, desired mass=496.5, found: m/z=497.1 [M+H]$^+$.

Intermediate 7

(3R)-1-((1R,4R)-4-((5-(2,6-dioxopiperidin-3-yl)pyridin-3-yl)amino)cyclohexane-1-carbonyl)pyrrolidine-3-carboxylic acid

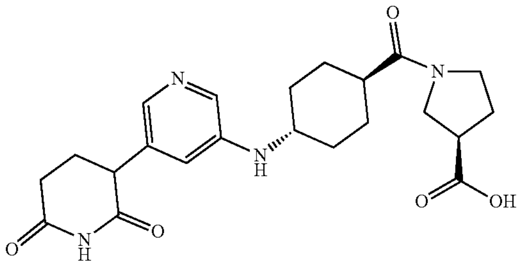 [SMILES: O=C1CCC(c2cncc(N[C@H]3CC[C@H](C(=O)N4CC[C@@H](C(=O)O)C4)CC3)c2)C(=O)N1]

Step 1: (3R)-1-((1r,4R)-4-((5-(2,6-dioxopiperidin-3-yl)pyridin-3-yl)amino)cyclohexane-1-carbonyl)pyrrolidine-3-carboxylic acid

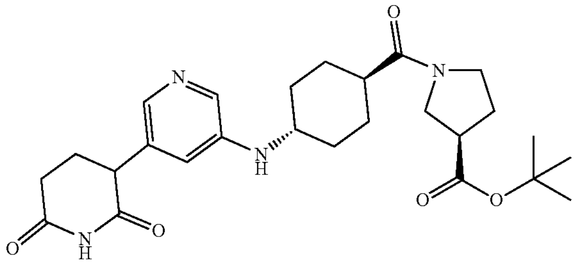 [SMILES: CC(C)(C)OC(=O)[C@@H]1CCN(C(=O)[C@H]2CC[C@H](Nc3cncc(C4CCC(=O)NC4=O)c3)CC2)C1]

Prepared by similar procedures as Intermediate 5 (step 1) using (1r,4r)-4-((5-(2,6-dioxopiperidin-3-yl)pyridin-3-yl)amino)cyclohexane-1-carboxylic acid (60 mg, 0.18 mmol) and tert-butyl (R)-pyrrolidine-3-carboxylate (26 mg, 0.18 mmol) as starting materials. The title compound (TFA salt) was isolated as an off-white solid (70 mg, 80% yield). LCMS: [$C_{26}H_{36}N_4O_5$], desired mass=484.5, found: m/z=485.5 $[M+H]^+$.

Step 2: (3R)-1-((1r,4R)-4-((5-(2,6-dioxopiperidin-3-yl)pyridin-3-yl)amino)cyclohexane-1-carbonyl)pyrrolidine-3-carboxylic acid

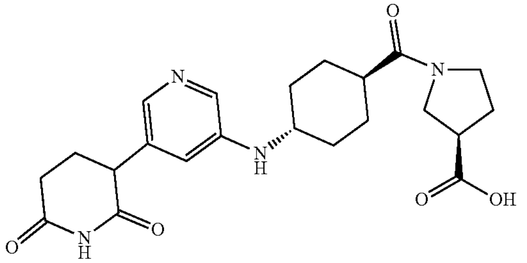 [SMILES: O=C1CCC(c2cncc(N[C@H]3CC[C@H](C(=O)N4CC[C@@H](C(=O)O)C4)CC3)c2)C(=O)N1]

Prepared by similar procedures as Intermediate 5 (step 2) using tert-butyl (3R)-1-((1r,4R)-4-((5-(2,6-dioxopiperidin-3-yl)pyridin-3-yl)amino)cyclohexane-1-carbonyl)pyrrolidine-3-carboxylate (70 mg, 0.14 mmmol) as the starting material. The title compound (TFA salt) was isolated as an off-white solid (50 mg, 84% yield). LCMS: [$C_{22}H_{28}N_4O_5$], desired mass=428.5, found: m/z=429.3 $[M+H]^+$.

Intermediate 8

(3R)-1-((1R,4R)-4-(4-(2,6-dioxopiperidin-3-yl)phenoxy)cyclohexane-1-carbonyl)pyrrolidine-3-carboxylic acid

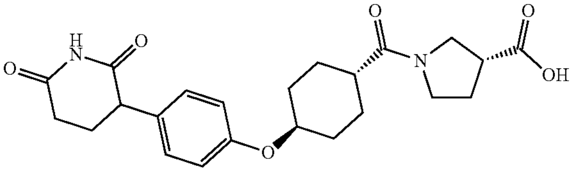 [SMILES: O=C1CCC(c2ccc(O[C@H]3CC[C@H](C(=O)N4CC[C@@H](C(=O)O)C4)CC3)cc2)C(=O)N1]

Step 1: benzyl (3R)-1-[(1r,4r)-4-[4-(2,6-dioxopiperidin-3-yl)phenoxy]cyclohexanecarbonyl]pyrrolidine-3-carboxylate

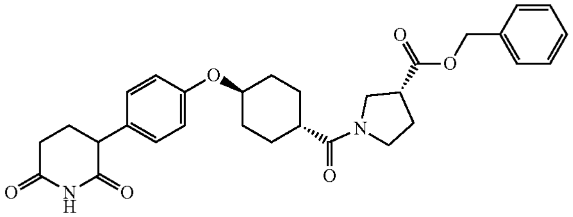 [SMILES: O=C1CCC(c2ccc(O[C@H]3CC[C@H](C(=O)N4CC[C@@H](C(=O)OCc5ccccc5)C4)CC3)cc2)C(=O)N1]

To a solution of (1r,4r)-4-(4-(2,6-dioxopiperidin-3-yl)phenoxy)cyclohexane-1-carboxylic acid (intermediate 52) (0.49 g, 1.479 mmol) in DMF (2.5 mL) were added HATU (0.675 g, 1.775 mmol) and DIPEA (0.5 mL, 2.96 mmol) and it was stirred for 0.5 h at room temperature. Then was added benzyl (3R)-1-(chlorohydrogenio)pyrrolidine-3-carboxylate (0.429 g, 1.775 mmol) and DIPEA (0.5 mL, 2.96 mmol) in DMF (2.5 mL) at room temperature. The reaction mixture was stirred overnight at room temperature, and then diluted ten-fold with water and extracted 3 times with DCM. The combined organic layers were washed with sat. aq. $NaHCO_3$, brine, dried over Na2SO4, and concentrated in vacuo. The residue was purified by silica gel chromatography using a mobile phase of DCM and MeOH (from 0 to 3% of MeOH) to provide 0.362 g (46% yield) of the title compound as an orange solid. LCMS: $C_{30}H_{34}N_2O_6$, desired mass=518.6, found: m/z=519.2 $[M+H]^+$.

Step 2: (3R)-1-((1r,4R)-4-(4-(2,6-dioxopiperidin-3-yl)phenoxy)cyclohexane-1-carbonyl)pyrrolidine-3-carboxylic acid

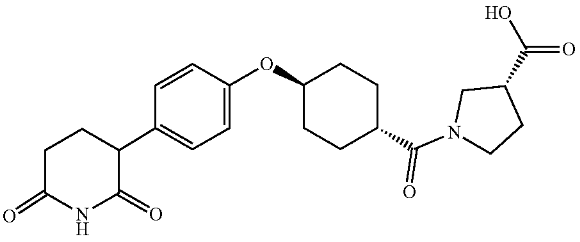 [SMILES: O=C1CCC(c2ccc(O[C@H]3CC[C@H](C(=O)N4CC[C@@H](C(=O)O)C4)CC3)cc2)C(=O)N1]

To a solution of benzyl (3R)-1-[(1r,4r)-4-[4-(2,6-dioxopiperidin-3-yl)phenoxy]cyclohexanecarbonyl] pyrrolidine-3-carboxylate (0.31 g, 0.598 mmol) in anh. DCM (12.0 mL) was added HBr solution in AcOH (19.0 mL, 7.77 mmol) at room temperature. The reaction mixture was stirred overnight at room temperature. The solvent was concentrated in vacuo. The residue was precipitated with diethyl ether and filtered to provide 102 mg (40% yield) of the title compound as a beige solid. LCMS: $C_{23}H_{28}N_2O_6$, desired mass=428.5, found: m/z=429.0 $[M+H]^+$.

Intermediate 9

(1R,4R)-4-((5-(2,6-dioxopiperidin-3-yl)pyridin-2-yl)oxy)cyclohexane-1-carboxylic acid

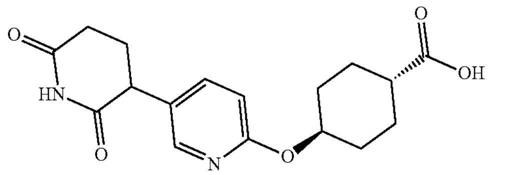 [SMILES: O=C1CCC(c2ccc(O[C@H]3CC[C@H](C(=O)O)CC3)nc2)C(=O)N1]

Step 1: (1r,4r)-4-[(5-bromopyridin-2-yl)oxy]cyclohexane-1-carboxylate 5-bromo-2-fluoropyridine (12.2 g, 69.4 mmol) and (1r,4r)-4-hydroxycyclohexane-1-carboxylic acid (10.0 g, 69.4 mmol) were dissolved in DMA (150.0 mL) and stirred at room temperature. sodium hydride (5.55 g, 138 mmol, 60.0%) was added and the reaction mixture was stirred at 100° C. for 10 hours. The product was isolated by flash column chromatography to give the title compound (10.0 g, 48.0% yield).

Step 2: (1r,4r)-4-((2',6'-bis(benzoyloxy)-[3,3'-bipyridin]-6-yl)oxy)cyclohexane-1-carboxylic acid (1r,4r)-4-[(5-bromopyridin-2-yl)oxy]cyclohexane-1-carboxylate (3.96 g, 13.2 mmol), 2,6-bis(benzyloxy)pyridin-3-ylboronic acid (5.00 g, 12.0 mmol), Pd(dppf)Cl2-DCM (877 mg, 1.20 mmol), $K_2CO_3$ (2.48 g, 18.0 mmol), and dioxane (50.0 mL) were combined in a sealed vial. The vial was purged with nitrogen gas and stirred for 12 hours at 100° C. The reaction mixture was poured over brine, extracted with ethyl acetate, filtered then concentrated on to silica. The product was isolated by flash column chromatography to afford the title compound (4.00 g, 65.4% yield).

Step 3: (1r,4r)-4-((5-(2,6-dioxopiperidin-3-yl)pyridin-2-yl)oxy)cyclohexane-1-carboxylic acid (1r,4r)-4-((2',6'-bis(benzoyloxy)-[3,3'-bipyridin]-6-yl)oxy)cyclohexane-1-carboxylic acid (4.00 g, 7.83 mmol) was dissolved in THF (60.0 mL). Pd/C (500 mg, 10.0% purity) was added and the reaction mixture was stirred under an atmosphere of hydrogen for 12 hours. After filtration and concentration the crude residue was triturated with ethyl acetate (15.0 mL) to afford the title compound (2.60 g, 79.9% yield). LCMS: $C_{17}H_{20}N_2O_5$ desired mass=332.36, found: m/z=333.1 $[M+H]^+$.

Intermediate 10

(R)-1-((1R,4R)-4-((5-(2,4-dioxotetrahydropyrimidin-1(2H)-yl)pyridin-2-yl)oxy)cyclohexane-1-carbonyl)pyrrolidine-3-carboxylic acid

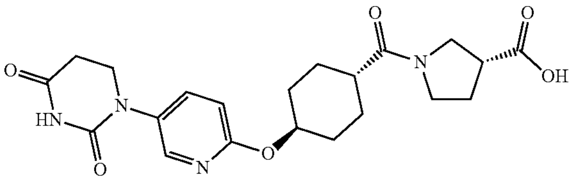 [SMILES: O=C1CCN(c2ccc(O[C@H]3CC[C@H](C(=O)N4CC[C@@H](C(=O)O)C4)CC3)nc2)C(=O)N1]

Step 1: benzyl (3R)-1-[(1r,4r)-4-{[5-(2,4-dioxo-1,3-diazinan-1-yl)pyridin-2-yl]oxy}cyclohexanecarbonyl]pyrrolidine-3-carboxylate

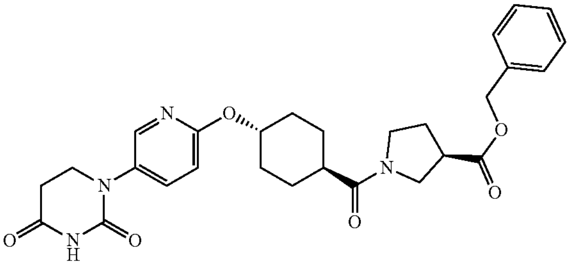 [SMILES: O=C1CCN(c2ccc(O[C@H]3CC[C@H](C(=O)N4CC[C@@H](C(=O)OCc5ccccc5)C4)CC3)nc2)C(=O)N1]

To a solution of (1r,4r)-4-((5-(2,4-dioxotetrahydropyrimidin-1(2H)-yl)pyridin-2-yl)oxy)cyclohexane-1-carboxylic acid (Intermediate 53) (0.29 g, 0.87 mmol) in anhydrous DMF (8.0 mL) were added HATU (0.31 g, 1.31 mmol) and DIPEA (0.23 mL, 1.31 mmol) at 25° C. and stirred for 0.5 h at 25° C. Then a solution of benzyl (3R)-pyrrolidine-3-carboxylate hydrochloride (0.25 g, 1.04 mmol) in anhydrous DMF (8.0 mL) was added and the reaction mixture was stirred for 16 h at 25° C. The solvents were evaporated to dryness and the residue was purified by silica gel chromatography using a mobile phase of DCM and IPA to provide 0.182 g (40% yield) of the title compound. LCMS: $C_{28}H_{32}N_4O_6$, desired mass=520.2, found: m/z=521.1 $[M+H]^+$.

Step 2: (R)-1-((1r,4R)-4-((5-(2,4-dioxotetrahydropyrimidin-1(2H)-yl)pyridin-2-yl)oxy)cyclohexane-1-carbonyl)pyrrolidine-3-carboxylic acid

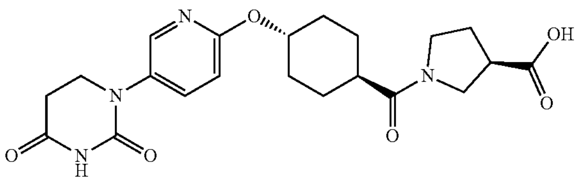 [SMILES: O=C1CCN(c2ccc(O[C@H]3CC[C@H](C(=O)N4CC[C@@H](C(=O)O)C4)CC3)nc2)C(=O)N1]

To a solution of benzyl (3R)-1-[(1r,4r)-4-{[5-(2,4-dioxo-1,3-diazinan-1-yl)pyridin-2-yl]oxy}cyclohexanecarbonyl]pyrrolidine-3-carboxylate (0.15 g, 0.288 mmol) in anh. THF (38.5 mL) was added Pd/C (0.015 g, 0.015 mmol) at 25° C. The reaction mixture was stirred under $H_2$ (1 atm) overnight at 25° C. The mixture was filtrated through a Celite cake and evaporated to dryness to provide 86 mg (70% yield) of the title compound as an off-white solid. LCMS: $C_{21}H_{26}N_4O_6$, desired mass=430.2, found: m/z=431.2 $[M+H]^+$.

Intermediate 11

(3R)-1-(1-(5-(2,6-dioxopiperidin-3-yl)pyridin-2-yl)piperidine-4-carbonyl)pyrrolidine-3-carboxylic acid

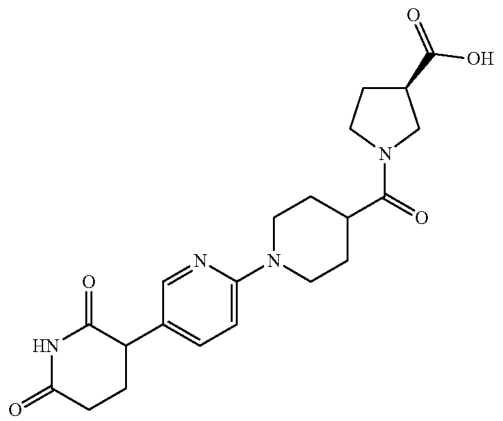 [SMILES: O=C1CCC(c2ccc(N3CCC(C(=O)N4CC[C@@H](C(=O)O)C4)CC3)nc2)C(=O)N1]

Step 1: tert-butyl 1-(5-(2,6-dioxopiperidin-3-yl)pyridin-2-yl)piperidine-4-carboxylate

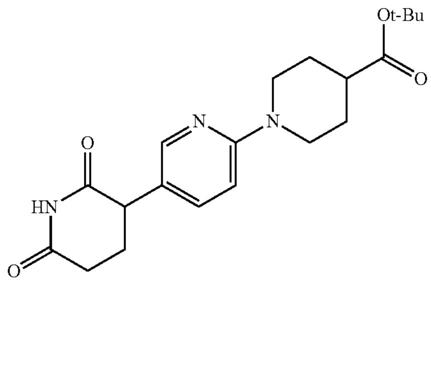 [SMILES: CC(C)(C)OC(=O)C1CCN(c2ccc(C3CCC(=O)NC3=O)cn2)CC1]

To a solution of 3-(6-fluoropyridin-3-yl) piperidine-2,6-dione (200 mg, 0.96 mmol) and tert-butylpiperidine-4-carboxylate (267 mg, 1.44 mmol) in DMSO (0.6 mL) was added DIPEA (0.5 mL, 2.88 mmol) at room temperature. The reaction mixture was stirred for 16 h at 120° C., then was diluted with ethyl acetate (10 mL) and washed with water (3×5 mL). The organic layer was dried with anhydrous sodium sulfate and concentrated under reduced pressure. The residue was purified by silica gel chromatography using a mobile phase of 0-5% MeOH in DCM to provide 232 mg (65% yield) of the title compound as an orange solid. LCMS: $[C_{20}H_{27}N_3O_4]$, desired mass=373.2, found: m/z=374.1 $[M+H]^+$.

Step 2: 1-(5-(2,6-dioxopiperidin-3-yl)pyridin-2-yl)piperidine-4-carboxylic acid

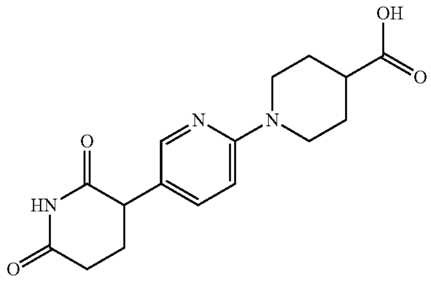 [SMILES: O=C1CCC(c2ccc(N3CCC(C(=O)O)CC3)nc2)C(=O)N1]

To a solution of tert-butyl 1-(5-(2,6-dioxopiperidin-3-yl)pyridin-2-yl)piperidine-4-carboxylate (196 mg, 0.52 mmol) in HFIP (5.2 mL) was added TFA (0.26 mL, 3.37 mmol) at room temperature. The reaction mixture was stirred for 16 h at room temperature and then was concentrated under reduced pressure, then resuspended and re-concentrated with diethyl ether (3×5 mL). The residue (yellow oil, 388 mg) was used as-is for the next step. LCMS: $[C_{16}H_{19}N_3O_4]$, desired mass=317.1, found: m/z=318.1 $[M+H]^+$.

Step 3: tert-butyl (3R)-1-(1-(5-(2,6-dioxopiperidin-3-yl)pyridin-2-yl)piperidine-4-carbonyl)pyrrolidine-3-carboxylate

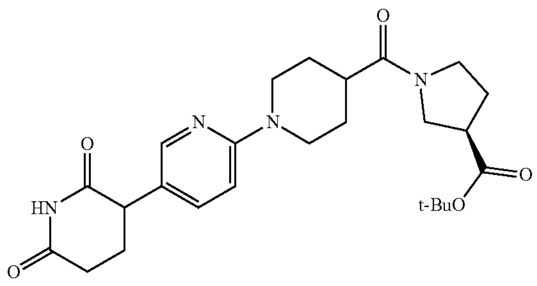 [SMILES: CC(C)(C)OC(=O)[C@@H]1CCN(C(=O)C2CCN(c3ccc(C4CCC(=O)NC4=O)cn3)CC2)C1]

To a solution of 1-(5-(2,6-dioxopiperidin-3-yl)pyridin-2-yl)piperidine-4-carboxylic acid (266 mg, 1.53 mmol) in anhydrous DMF (10.2 mL) was added BOP (678 mg, 1.53 mmol) and, after stirring for 10 min at room temperature, DIPEA (0.89 mL, 5.09 mmol) was added. The reaction mixture was stirred for 16 h at room temperature, and then the reaction mixture was quenched with water (100 mL) and extracted with ethyl acetate (3×20 mL). The combined organic layers were dried over anhydrous sodium sulfate and concentrated under reduced pressure. The residue was purified by silica gel chromatography using a mobile phase of 0-5% MeOH in DCM to provide 272 mg (48% yield) of the title compound as an off-white solid. LCMS: [$C_{25}H_{34}N_4O_5$], desired mass=470.2, found: m/z=471.4 [M+H]$^+$.

Step 4: (3R)-1-(1-(5-(2,6-dioxopiperidin-3-yl)pyridin-2-yl)piperidine-4-carbonyl)pyrrolidine-3-carboxylic acid

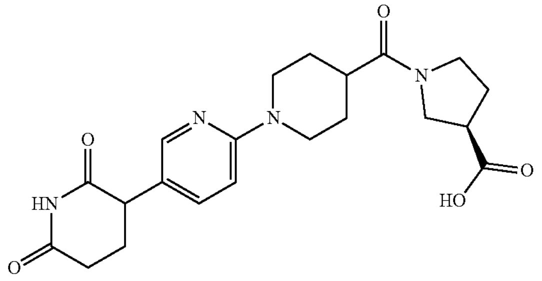 [SMILES: O=C1CCC(c2ccc(N3CCC(C(=O)N4CC[C@@H](C(=O)O)C4)CC3)nc2)C(=O)N1]

The title compound was produced by TFA deprotection of tert-butyl (3R)-1-(1-(5-(2,6-dioxopiperidin-3-yl)pyridin-2-yl)piperidine-4-carbonyl)pyrrolidine-3-carboxylate, similar to the method used in step 2. The crude product was used as-is for the next step. (Off-white solid, 305 mg). LCMS: [$C_{21}H_{26}N_4O_5$], desired mass=414.1, found: m/z=415.3 [M+H]$^+$.

Intermediate 12

(1R,4R)-4-(4-((5-(2,6-dioxopiperidin-3-yl)pyridin-2-yl)amino)piperidine-1-carbonyl)cyclohexane-1-carboxylic acid

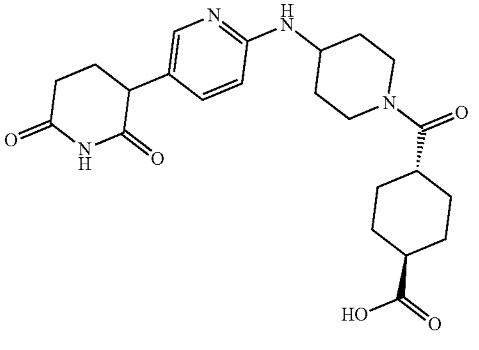 [SMILES: O=C1CCC(c2ccc(NC3CCN(C(=O)[C@H]4CC[C@H](C(=O)O)CC4)CC3)nc2)C(=O)N1]

Step 1: tert-butyl 4-((5-(2,6-dioxopiperidin-3-yl)pyridin-2-yl)amino)piperidine-1-carboxylate

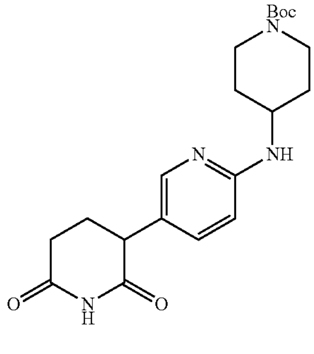 [SMILES: CC(C)(C)OC(=O)N1CCC(Nc2ccc(C3CCC(=O)NC3=O)cn2)CC1]

To a solution of 3-(6-Fluoro-3-pyridyl)-2,6-piperidinedione (250 mg, 1.20 mmol) in DMSO was added tert-butyl 4-aminopiperidine-1-carboxylate (289 mg, 1.44 mmol), and N,N-diisopropylethylamine (0.85 mL, 4.87 mmol). The reaction mixture was allowed to stir at 120° C. for 108 h, then was worked up with water (50 mL) and EtOAc (3×50 mL). The combined organic layers were dried over $Na_2SO_4$ and concentrated. The crude was purified by silica gel column chromatography using (DCM/MeOH, 0-20%) to afford the title compound (white solid, 49 mg, 0.126 mmol, 11% yield). LCMS: [$C_{20}H_{28}N_4O_4$], desired mass=388.2, found: m/z=389.3 [M+H]$^+$.

Step: 2: 3-[6-(4-Piperidylamino)-3-pyridyl]-2,6-piperidinedione

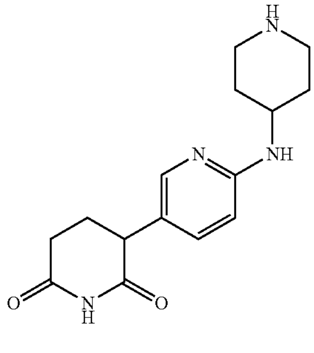 [SMILES: O=C1CCC(c2ccc(NC3CCNCC3)nc2)C(=O)N1]

A solution of tert-butyl 4-((5-(2,6-dioxopiperidin-3-yl)pyridin-2-yl)amino)piperidine-1-carboxylate (49 mg, 0.126 mmol) in 4 N HCl in dioxane (0.8 mL, 3.2 mmol) was stirred at room temperature for 1 hr. The reaction mixture was concentrated to dryness and evaporated with ether three times to afford the title compound (white solid, 38 mg) which was used as is for the next step. LCMS: [$C_{15}H_{20}N_4O_2$], desired mass=288.1, found: m/z=288.8 [M+H]$^+$.

Step 3: methyl (1r,4r)-4-(4-((5-(2,6-dioxopiperidin-3-yl)pyridin-2-yl)amino)piperidine-1-carbonyl)cyclohexane-1-carboxylate

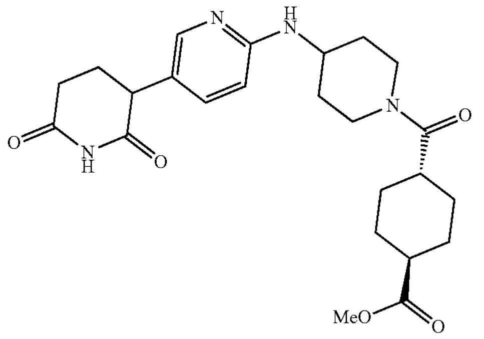 [SMILES: COC(=O)[C@H]1CC[C@H](C(=O)N2CCC(Nc3ccc(C4CCC(=O)NC4=O)cn3)CC2)CC1]

The title compound was synthesized using similar methods to intermediate 11, using BOP coupling. Afforded a white powder (46 mg, 0.1008 mmol, 76% yield) as a free base. LCMS: [$C_{24}H_{32}N_4O_5$], desired mass=456.5, found: m/z=457.4 $[M+H]^+$.

Step 4: (1r,4r)-4-(4-((5-(2,6-dioxopiperidin-3-yl)pyridin-2-yl)amino)piperidine-1-carbonyl)cyclohexane-1-carboxylic acid

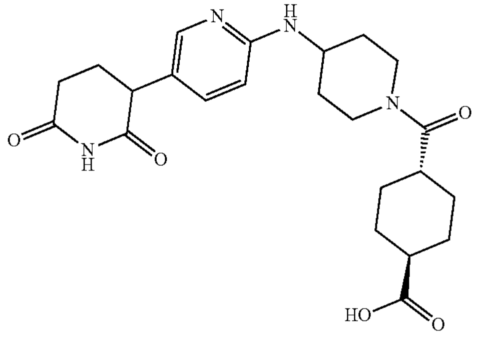 [SMILES: O=C1CCC(c2ccc(NC3CCN(C(=O)[C@H]4CC[C@H](C(=O)O)CC4)CC3)nc2)C(=O)N1]

A solution of methyl (1r,4r)-4-(4-((5-(2,6-dioxopiperidin-3-yl)pyridin-2-yl)amino)piperidine-1-carbonyl)cyclohexane-1-carboxylate (46 mg, 0.1008 mmol) in TFA (1.0 mL) and $H_2O$ (0.5 mL) and stirred at 70° C. for 6.5 h. The reaction the mixture was concentrated to afford the title compound (viscous oil, 69 mg) which was used as is for the next step. LCMS: [$C_{23}H_{30}N_4O_5$], desired Mass=442.2, found: m/z=443.4 $[M+H]^+$.

Intermediate 13

3-(6-(piperidin-4-yloxy)pyridin-3-yl)piperidine-2,6-dione

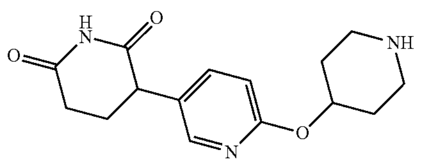 [SMILES: O=C1CCC(c2ccc(OC3CCNCC3)nc2)C(=O)N1]

Step 1: tert-butyl 4-[(5-bromopyridin-2-yl)oxy]piperidine-1-carboxylate 5-bromo-2-fluoropyridine (0.58 mL, 1.00 g, 5.68 mmol) and tert-butyl 4-hydroxypiperidine-1-carboxylate (1.14 g, 5.68 mmol) were dissolved in NMP (5.00 mL) and stirred at room temperature. sodium hydride (0.27 g, 11.36 mmol) was added and the reaction mixture was heated to 60° C. for 2 hours. The product was isolated by flash column chromatography to give the title compound (0.75 g, 37.0% yield).

Step 2: tert-butyl 4-{[2',6'-bis(benzyloxy)-[3,3'-bipyridin]-6-yl]oxy}piperidine-1-carboxylate tert-butyl 4-[(5-bromopyridin-2-yl)oxy]piperidine-1-carboxylate (750.00 mg, 2.10 mmol), Pd(dppf)Cl2-DCM (342.8 mg, 0.42 mmol), cesium carbonate 1N solution (5.25 mL, 5.25 mmol), 2,6-bis(benzyloxy)pyridin-3-ylboronic acid (703.6 mg, 2.10 mmol), and dioxane (5.00 mL) were combined in a sealed vial. The vial was purged with nitrogen gas and stirred for 60 minutes at 100° C. The reaction mixture was poured over brine, extracted with ethyl acetate, filtered then concentrated on to silica. The product was isolated by flash column chromatography to afford the title compound (1.05 g, 88% yield).

Step 3: 3-(6-(piperidin-4-yloxy)pyridin-3-yl)piperidine-2,6-dione tert-butyl 4-{[2',6'-bis(benzyloxy)-[3,3'-bipyridin]-6-yl]oxy}piperidine-1-carboxylate (1.05 g, mmol) was dissolved in MeOH (20.00 mL). Palladium on carbon 10% (0.20 g, 0.18 mmol) was added and the reaction mixture was stirred under a hydrogen balloon for 12 hours. The reaction mixture was filtered through celite and concentrated. This material was dissolved in DCM (10.00 mL), treated with 4M HCl in dioxane (3.0 mL), and stirred at room temperature overnight. The reaction mixture was concentrated to afford the title compound as an off white crystalline solid as the HCl salt (0.425 g, 84% yield). LCMS: $C_{15}H_{19}N_3O_3$ desired mass: 289.3, found: m/z=290.2 $[M+H]^+$.

Intermediate 14

(1S,4S)-4-(4-{[5-(2,6-dioxopiperidin-3-yl)pyridin-2-yl]amino}piperidine-1-carbonyl)cyclohexane-1-carboxylic acid

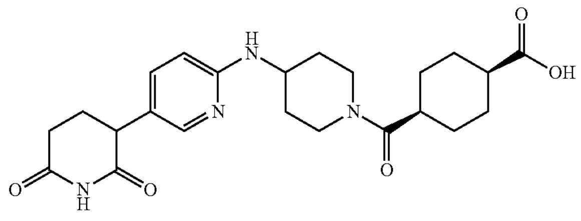 [SMILES: O=C1CCC(c2ccc(NC3CCN(C(=O)[C@H]4CC[C@@H](C(=O)O)CC4)CC3)nc2)C(=O)N1]

The title compound 16 was synthesized using similar methods to intermediate 12, and substituting (1r,4r)-4-(methoxycarbonyl)-cyclohexane-1-carboxylic acid for (1s,4s)-4-(methoxycarbonyl)cyclohexane-1-carboxylic acid. The final step was carried out as follows. To a solution of tert-butyl (1s,4s)-4-(4-{[5-(2,6-dioxopiperidin-3-yl)pyridin-2-yl]amino}piperidine-1-carbonyl)cyclohexane-1-carboxylate (157 mg, 0.32 mmol) in acetic acid (2.50 mL) was added 4M HCl in dioxane (1.26 mL, 5.04 mmol) at 25° C. The reaction mixture was stirred for 2 h at 25° C., and then solvents were evaporated to dryness under reduced pressure. The crude compound was triturated with $Et_2O$ (2×15 mL), heptane (30 mL), and dried under reduced pressure. Then the residue was dissolved in water (10 mL), frozen, and freeze-dried overnight. The residue was purified by prep-HPLC (method 20210423-prep2-60800420-PKU01-087 C18 prep) to provide 105 mg (75%) of the title compound as a white solid. LCMS: $C_{23}H_{30}N_4O_5$, desired mass=442.5, found: m/z=443.3 $[M+H]^+$.

Intermediate 15

(1R,4R)-4-(4-(2-(2,6-dioxopiperidin-3-yl)-1,3-dioxoisoindolin-5-yl)piperazine-1-carbonyl)cyclohexane-1-carboxylic acid

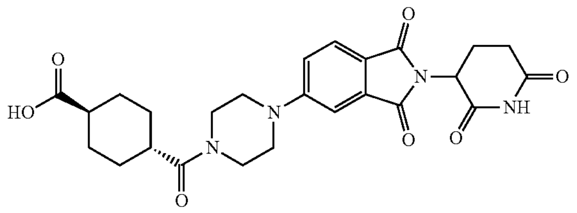 [SMILES: O=C1CCC(N2C(=O)c3ccc(N4CCN(C(=O)[C@H]5CC[C@H](C(=O)O)CC5)CC4)cc3C2=O)C(=O)N1]

Step-1: (1r,4r)-4-[(benzyloxy)carbonyl]cyclohexane-1-carboxylic acid

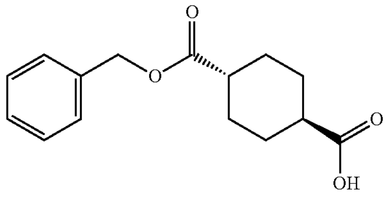 [SMILES: O=C(O)[C@H]1CC[C@H](C(=O)OCc2ccccc2)CC1]

To a mixture of (1r,4r)-cyclohexane-1,4-dicarboxylic acid (10 g, 58.079 mmol) and $K_2CO_3$ (24.0 g, 174.2 mmol) in DMF (50 mL) was added BnBr (9.93 g, 58.0 mmol) at room temperature. The resulting mixture was stirred at 80° C. overnight under nitrogen atmosphere. The resulting mixture was allowed to cool to room temperature. The mixture was poured into ice water. The solids were collected by filtration. The solids were washed with $H_2O$/MeOH (1/1) to provided 8 g (crude) of the title compound as a white solid.

Step-2: tert-butyl 4-[(1r,4r)-4-[(benzyloxy)carbonyl]cyclohexanecarbonyl]piperazine-1-carboxylate

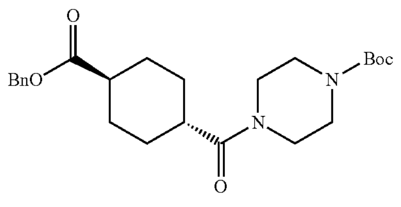 [SMILES: CC(C)(C)OC(=O)N1CCN(C(=O)[C@H]2CC[C@H](C(=O)OCc3ccccc3)CC2)CC1]

To a mixture of (1r,4r)-4-[(benzyloxy)carbonyl]cyclohexane-1-carboxylic acid (5 g, 19.084 mmol) and tert-butyl piperazine-1-carboxylate (3.54 g, 19.084 mmol) in DMF (10 mL) was added TEA (11.56 g, 114.5 mmol) at room temperature under nitrogen atmosphere. The resulting mixture was stirred at room temperature for 15 min. To the above mixture was added $T_3P$ (12.13 g, 38.168 mmol) at 0° C. The resulting mixture was stirred at room temperature overnight. The resulting mixture was purified by reverse phase flash chromatography of [$CH_3CN$ and $H_2O$] to provide 1.5 g (16.63%) of the title compound as a white solid. LCMS: ($C_{24}H_{34}N_2O_5$) desired mass=431.3; found: m/z=431.2 $[M+H]^+$.

Step-3: benzyl (1r,4r)-4-(piperazine-1-carbonyl)cyclohexane-1-carboxylate

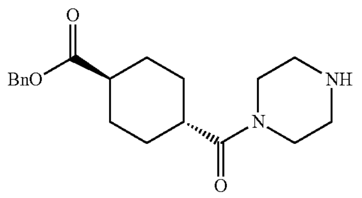 [SMILES: O=C(OCc1ccccc1)[C@H]1CC[C@H](C(=O)N2CCNCC2)CC1]

A mixture of tert-butyl 4-[(1r,4r)-4-[(benzyloxy)carbonyl]cyclohexanecarbonyl]piperazine-1-carboxylate (2 g, 4.646 mmol) in HCl/dioxane (20 mL, 4N) was stirred at room temperature for 2 h. The resulting mixture was concentrated under reduced pressure to provide 1.5 g (crude) of the title compound as a white solid. LCMS: ($C_{19}H_{26}N_2O_3$) desired mass=330.2; found: m/z=331.4 $[M+H]^+$.

Step-4: benzyl (1r,4r)-4-[4-[2-(2,6-dioxopiperidin-3-yl)-1,3-dioxoisoindol-5-yl]piperazine-1-carbonyl]cyclohexane-1-carboxylate

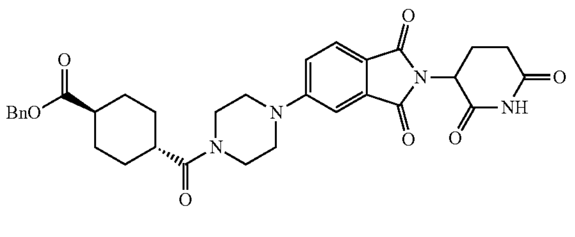 [SMILES: O=C1CCC(N2C(=O)c3ccc(N4CCN(C(=O)[C@H]5CC[C@H](C(=O)OCc6ccccc6)CC5)CC4)cc3C2=O)C(=O)N1]

To a mixture of benzyl (1r,4r)-4-(piperazine-1-carbonyl)cyclohexane-1-carboxylate (1.5 g, 4.540 mmol) and 2-(2,6-dioxopiperidin-3-yl)-5-fluoroisoindole-1,3-dione (1.25 g, 4.540 mmol) in DMSO (10 mL) was added DIEA (1.76 g, 13.619 mmol, 3 equiv) at room temperature. The resulting mixture was stirred at 80° C. overnight. The resulting mixture was purified by reverse phase flash chromatography of [$CH_3CN$ and $H_2O$] to provide 600 mg (21.47%) of the title compound as a yellow solid. LCMS: ($C_{32}H_{34}N_4O_7$) desired mass=586.2; found: m/z=587.4 $[M+H]^+$.

Step-5: (1r,4r)-4-[4-[2-(2,6-dioxopiperidin-3-yl)-1,3-dioxoisoindol-5-yl]piperazine-1-carbonyl]cyclohexane-1-carboxylic acid

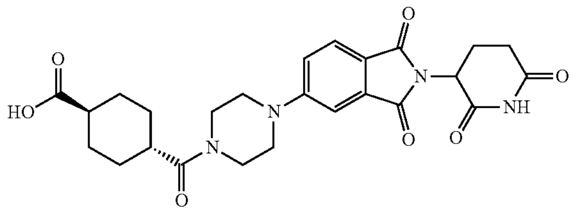 [SMILES: O=C1CCC(N2C(=O)c3ccc(N4CCN(C(=O)[C@H]5CC[C@H](C(=O)O)CC5)CC4)cc3C2=O)C(=O)N1]

To a mixture of benzyl (1r,4r)-4-[4-[2-(2,6-dioxopiperidin-3-yl)-1,3-dioxoisoindol-5-yl]piperazine-1-carbonyl]cyclohexane-1-carboxylate (600 mg, 1.023 mmol) in THF (10 mL) was added Pd/C (300 mg) at room temperature. The resulting mixture was stirred at room temperature for 3 h under hydrogen atmosphere.

The solids were filtered out. The filtrate was concentrated under reduced pressure. The residue was purified by reverse phase flash chromatography of [$CH_3CN$ and $H_2O$] to provide 392.8 mg (75.90%) of the title compound as a yellow solid. LCMS (Method 1): ($C_{25}H_{28}N_4O_7$) desired mass=496.2; found: m/z=497.1 $[M+H]^+$.

Intermediate 16

(3S)-1-(1-(5-(2,6-dioxopiperidin-3-yl)pyridin-2-yl)piperidine-4-carbonyl)pyrrolidine-3-carboxylic acid

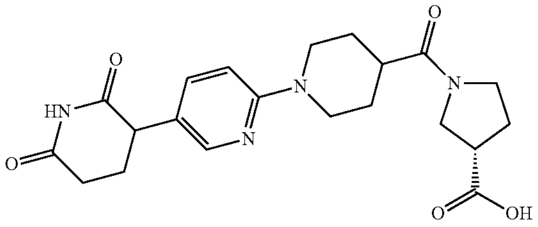 [SMILES: O=C1CCC(c2ccc(N3CCC(C(=O)N4CC[C@H](C(=O)O)C4)CC3)nc2)C(=O)N1]

Step 1: tert-butyl (3S)-1-(1-(5-(2,6-dioxopiperidin-3-yl)pyridin-2-yl)piperidine-4-carbonyl)pyrrolidine-3-carboxylate

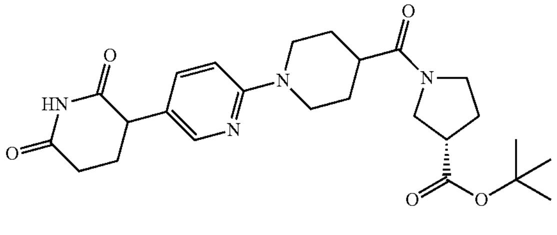 [SMILES: CC(C)(C)OC(=O)[C@H]1CCN(C(=O)C2CCN(c3ccc(C4CCC(=O)NC4=O)cn3)CC2)C1]

Prepared by similar procedures as Intermediate 5 (step 1) using 1-(5-(2,6-dioxopiperidin-3-yl)pyridin-2-yl)piperidine-4-carboxylic acid (60 mg, 0.19 mmol) and tert-butyl (S)-pyrrolidine-3-carboxylate (32 mg, 0.19 mmol) as starting materials. The title compound (TFA salt) was isolated as an off-white solid (80 mg, 90% yield). LCMS: [$C_{25}H_{34}N_4O_5$], desired mass=470.6, found: m/z=471.5 $[M+H]^+$.

Step 2: (3S)-1-(1-(5-(2,6-dioxopiperidin-3-yl)pyridin-2-yl)piperidine-4-carbonyl)pyrrolidine-3-carboxylic acid

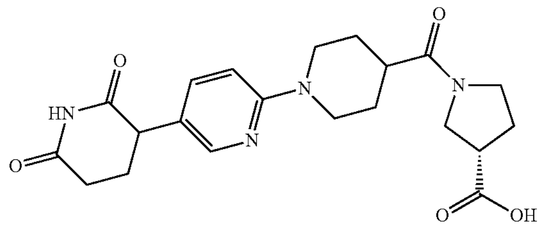 [SMILES: O=C1CCC(c2ccc(N3CCC(C(=O)N4CC[C@H](C(=O)O)C4)CC3)nc2)C(=O)N1]

Prepared by similar procedures as Intermediate 5 (step 2) using tert-butyl (3S)-1-(1-(5-(2,6-dioxopiperidin-3-yl)pyridin-2-yl)piperidine-4-carbonyl)pyrrolidine-3-carboxylate (80 mg, 0.17 mmol) as the starting material. The title compound (TFA salt) was isolated as an off-white solid (68 mg, 96% yield). LCMS: [$C_{21}H_{26}N_4O_5$], desired mass=414.5, found: m/z=415.4 $[M+H]^+$.

Intermediate 17

2-((3R)-1-((1R,4R)-4-((2-(2,6-dioxopiperidin-3-yl)-1,3-dioxoisoindolin-4-yl)amino)cyclohexane-1-carbonyl)pyrrolidin-3-yl)acetic acid

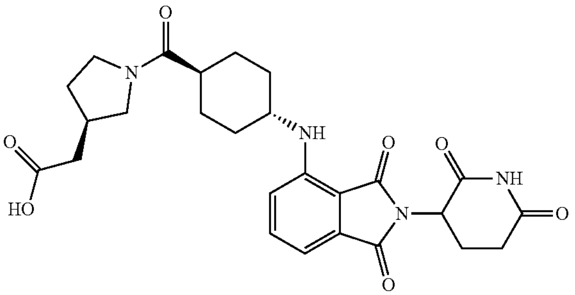 [SMILES: O=C(O)C[C@H]1CCN(C(=O)[C@H]2CC[C@H](Nc3cccc4c3C(=O)N(C3CCC(=O)NC3=O)C4=O)CC2)C1]

Step 1: (1r,4r)-4-((2-(2,6-dioxopiperidin-3-yl)-1,3-dioxoisoindolin-4-yl)amino)cyclohexane-1-carboxylic acid

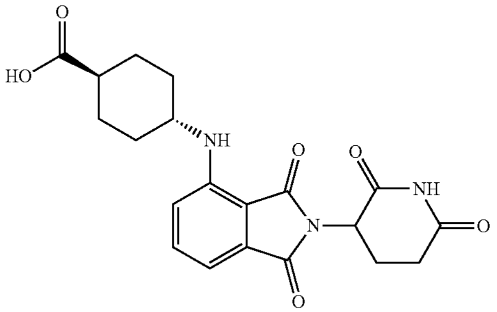 [SMILES: O=C1CCC(N2C(=O)c3cccc(N[C@H]4CC[C@H](C(=O)O)CC4)c3C2=O)C(=O)N1]

To a solution of (1r,4r)-4-aminocyclohexane-1-carboxylic acid (0.74 g, 5.17 mmol), 2-(2,6-dioxopiperidin-3-yl)-4-fluoro-2,3-dihydro-1H-isoindole-1,3-dione (0.740 g, 5.17 mmol) in anhydrous DMSO (25.0 mL) was added 2-(2,6-dioxopiperidin-3-yl)-4-fluoro-2,3-dihydro-1H-isoindole-1,3-dione (1.43 g, 5.17 mmol) and potassium fluoride (1.20 g, 20.67 mmol) at 25° C. The reaction mixture was stirred for 24 h at 120° C., and then the mixture was poured into 250 mL $H_2O$ and extracted with EtOAc (5×50 mL). The combined organic extracts were additionally washed with 50 mL brine, dried with $Na_2SO_4$, and evaporated under reduced pressure. The residue was purified by silica gel chromatography using a mobile phase of DCM and MeOH to provide 1500 mg (73% yield) of the title compound as a yellow solid. LCMS: $C_{20}H_{21}N_3O_6$, desired mass=399.1, found: m/z=400.4 $[M+H]^+$.

Step 2: tert-butyl (3R)-3-[2-(benzyloxy)-2-oxoethyl]pyrrolidine-1-carboxylate

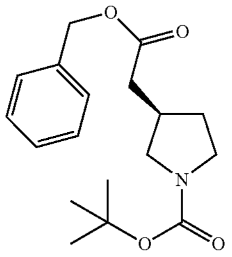 [SMILES: CC(C)(C)OC(=O)N1CC[C@H](CC(=O)OCc2ccccc2)C1]

To a solution of 2-[(3R)-1-[(tert-butoxy)carbonyl]pyrrolidin-3-yl]acetic acid (500 mg, 2.18 mmol) in anhydrous DMF (10 mL) was added $Cs_2CO_3$ (852 mg, 2.62 mmol). The reaction mixture was placed in an ice bath and stirred for 1 h at 0° C., then benzyl bromide (410 mg, 2.4 mmol) was added dropwise at 0° C. The reaction mixture was stirred for 12 h at 25° C., and then the mixture was poured into 150 mL of brine and extracted with EtOAc (5×50 mL). The combined organic layers were washed with 50 mL of brine, dried with $MgSO_4$, and concentrated under reduced pressure to provide 695 mg (100% yield) of the title compound as a yellow oil that was used as-is for the next step.

Step 3: benzyl 2-[(3R)-pyrrolidin-3-yl]acetate hydrochloride

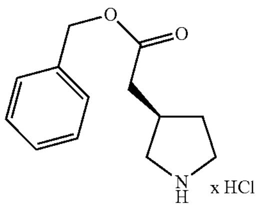 [SMILES: O=C(C[C@H]1CCNC1)OCc1ccccc1]

To a solution of tert-butyl (3R)-3-[2-(benzyloxy)-2-oxoethyl]pyrrolidine-1-carboxylate (695 mg, 2.18 mmol) in anhydrous DCM (30 mL) was added 2M HCl (6.51 g, 17.4 mmol) at 0° C. The reaction mixture was stirred for 12 h at 25° C., and then the solvents were evaporated to dryness under reduced pressure. The crude compound was washed with $Et_2O$ (2×10 mL) and dried in vacuo to provide 550 mg (99% yield) of the title compound as a white amorphous solid that was used as-is for the next step. LCMS: $C_{13}H_{17}NO_2$, desired mass=219.1, found: m/z=220.5 $[M+H]^+$.

Step 4: benzyl 2-((3R)-1-((1r,4R)-4-((2-(2,6-dioxopiperidin-3-yl)-1,3-dioxoisoindolin-4-yl)amino)cyclohexane-1-carbonyl)pyrrolidin-3-yl)acetate

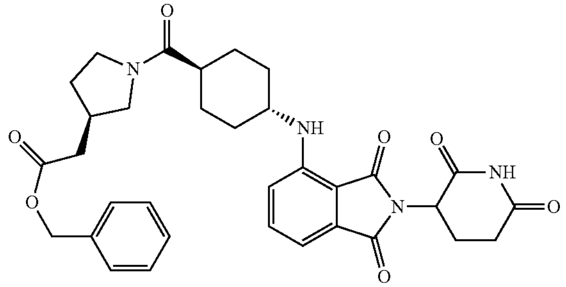 [SMILES: O=C1CCC(N2C(=O)c3cccc(N[C@H]4CC[C@H](C(=O)N5CC[C@H](CC(=O)OCc6ccccc6)C5)CC4)c3C2=O)C(=O)N1]

To a solution of benzyl 2-[(3R)-pyrrolidin-3-yl]acetate hydrochloride (550 mg, 2.15 mmol) in anhydrous DMF (50 mL) was added (1r,4r)-4-((2-(2,6-dioxopiperidin-3-yl)-1,3-dioxoisoindolin-4-yl)amino)cyclohexane-1-carboxylic acid (859 mg, 2.15 mmol), HATU (1.23 g, 0.47 mmol) and DIPEA (834 mg, 6.45 mmol) at 25° C. The reaction mixture was stirred for 48 h at 25° C., and then the mixture was poured into 800 mL of brine, followed by extraction with DCM (4×50 mL). The organic extracts were dried with $MgSO_4$ and evaporated under reduced pressure. The residue was purified by silica gel chromatography using a mobile phase of hexane and EtOAc to provide 1959 mg (82% yield) of the title compound as a yellow solid. LCMS: $C_{33}H_{36}N_4O_7$, desired mass=600.3, found: m/z=601.8 $[M+H]^+$.

Step 5: 2-[(3R)-1-[(1r,4r)-4-{[2-(2,6-dioxopiperidin-3-yl)-1,3-dioxo-2,3-dihydro-1H-isoindol-4-yl]amino}cyclohexanecarbonyl]pyrrolidin-3-yl]acetic acid

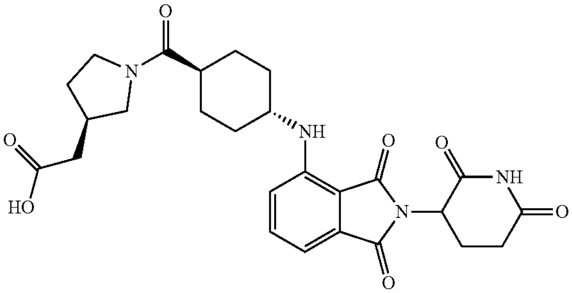 [SMILES: O=C(O)C[C@H]1CCN(C(=O)[C@H]2CC[C@H](Nc3cccc4c3C(=O)N(C3CCC(=O)NC3=O)C4=O)CC2)C1]

To a solution of benzyl 2-((3R)-1-((1r,4R)-4-((2-(2,6-dioxopiperidin-3-yl)-1,3-dioxoisoindolin-4-yl)amino)cyclohexane-1-carbonyl)pyrrolidin-3-yl)acetate (1.06 g, 1.76 mmol) in anhydrous THF (25 mL) was added 10% wt $Pd(OH)_2/C$ (25 mg, 0.176 mmol) at 25° C. The reaction mixture was stirred for 12 h at 25° C., followed by the addition of a $2^{nd}$ portion of 10% wt $Pd(OH)_2/C$ (25 mg, 0.176 mmol) at 25° C. The reaction mixture was stirred for another 12 h at 25° C. and then filtered through Celite and evaporated to dryness. The residue was purified by precipitation from a THF/$Et_2O$ mixture to provide 524 mg (58% yield) of the title compound as a yellow solid. LCMS: $C_{26}H_{30}N_4O_7$, desired mass=510.2, found: m/z=511.2 $[M+H]^+$.

Intermediate 18

1-(2-(2,6-dioxopiperidin-3-yl)-1,3-dioxoisoindolin-5-yl)piperidine-4-carboxylic acid

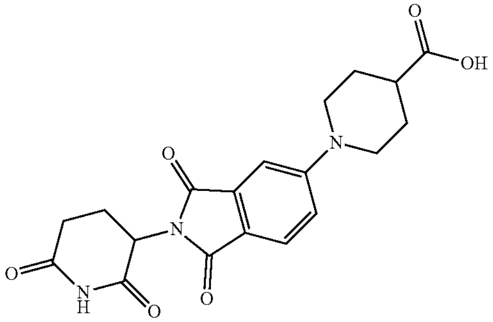 [SMILES: O=C1CCC(N2C(=O)c3ccc(N4CCC(C(=O)O)CC4)cc3C2=O)C(=O)N1]

2-(2,6-dioxopiperidin-3-yl)-5-fluoroisoindoline-1,3-dione (2.0 g, 5.2 mmol) and tert-butyl piperidine-4-carboxylate (1.34 g, 7.24 mmol) were dissolved in DMSO (5.00 mL) and N,N-diisopropylethylamine (1.00 mL, 0.74 g, 5.74 mmol) and the reaction mixture was irradiated at 125° C. for 3 hours. The reaction mixture was poured over brine and extracted with ethyl acetate. The organic layer was dried over anhydrous sodium sulfate, filtered, then evaporated to dryness. The resulting material was dissolved in DCM (50 mL), treated with TFA (20.0 mL) and stirred for 12 hours. The product was isolated by reverse phase flash column, eluting with DCM and MeOH to provide 1.45 g of the title compound as an off-white solid.

Intermediate 19

4-{4-[4-(2,6-dioxopiperidin-3-yl)phenyl]piperazine-1-carbonyl}benzoic acid

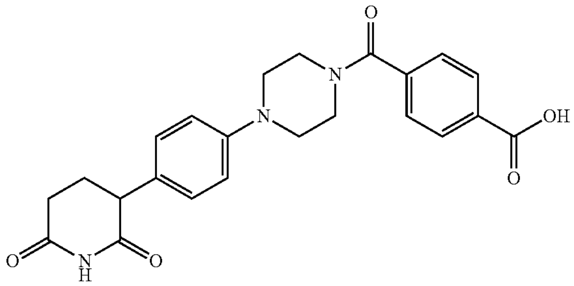 [SMILES: O=C1CCC(c2ccc(N3CCN(C(=O)c4ccc(C(=O)O)cc4)CC3)cc2)C(=O)N1]

Step-1: tert-butyl 4-[4-(4-bromophenyl)piperazine-1-carbonyl]benzoate

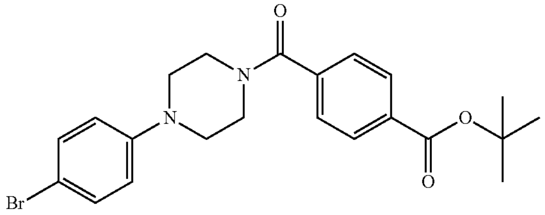 [SMILES: CC(C)(C)OC(=O)c1ccc(C(=O)N2CCN(c3ccc(Br)cc3)CC2)cc1]

To a mixture of 4-(tert-butoxycarbonyl)benzoic acid (1 g, 4.478 mmol) in DMF (8 mL) was added HATU (1.28 g, 3.358 mmol) in portions at room temperature. The resulting mixture was stirred at room temperature for 30 min. To the above mixture was added 1-(4-bromophenyl)piperazine (540 mg, 2.239 mmol) and DIEA (0.87 g, 6.717 mmol). The resulting mixture was stirred overnight at room temperature. The resulting mixture was extracted with EtOAc. The combined organic layers were washed with water, and dried over anhydrous $Na_2SO_4$. After filtration, the filtrate was concentrated under reduced pressure. The residue was purified by silica gel column chromatography [PE and EA] to provide 1 g (90.24%) of the title compound as a white solid. LCMS: ($C_{22}H_{25}BrN_2O_3$) desired mass=444.1; found: m/z=445.2 $[M+H]^+$.

Step-2: tert-butyl 4-(4-{4-[2,6-bis(benzyloxy)pyridin-3-yl]phenyl}piperazine-1-carbonyl}benzoate

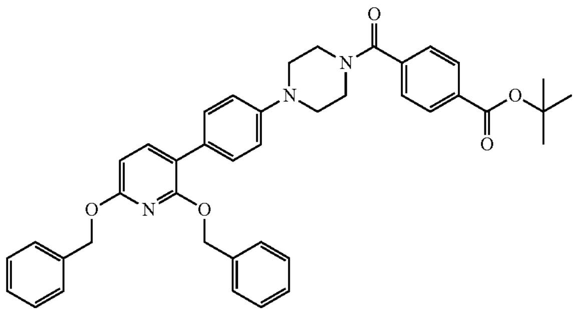 [SMILES: CC(C)(C)OC(=O)c1ccc(C(=O)N2CCN(c3ccc(-c4ccc(OCc5ccccc5)nc4OCc4ccccc4)cc3)CC2)cc1]

To a mixture of tert-butyl 4-[4-(4-bromophenyl)piperazine-1-carbonyl]benzoate (960 mg, 2.156 mmol) in THF (10 mL) was added 2,6-bis(benzyloxy)pyridin-3-ylboronic acid (1083 mg, 3.234 mmol), $K_2CO_3$ (595 mg, 4.312 mmol) in $H_2O$ (2 mL) and $Pd(PPh_3)_4$ (249 mg, 0.216 mmol) at room temperature. The reaction mixture was irradiated with microwave radiation at 110° C. for 40 min. The resulting mixture was concentrated under reduced pressure. The residue was purified by silica gel column chromatography [PE and EA] to provide 1 g (67.20%) of the title compound as a white solid. LCMS: ($C_{41}H_{41}N_3O_5$) desired mass=655.3; found: m/z=656.4 $[M+H]^+$.

Step-3: tert-butyl 4-{4-[4-(2,6-dioxopiperidin-3-yl) phenyl]piperidine-1-carbonyl}benzoate

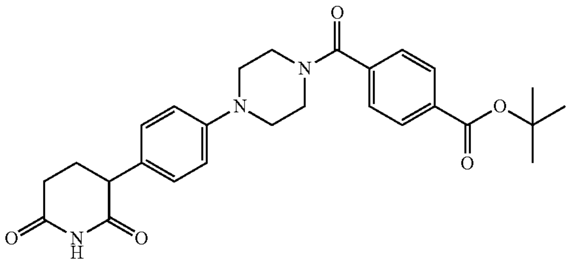 [SMILES: CC(C)(C)OC(=O)c1ccc(C(=O)N2CCN(c3ccc(C4CCC(=O)NC4=O)cc3)CC2)cc1]

Procedures similar to those in step 5 of Intermediate 15 were followed using tert-butyl 4-(4-{4-[2,6-bis(benzyloxy) pyridin-3-yl]phenyl}piperazine-1-carbonyl)benzoate (600 mg, 0.915 mmol), EtOH (6 mL), THF (6 mL) and Pd/C (449 mg). The residue was purified by silica gel column chromatography of [PE and EA] to provide 450 mg (82.56%) of the title compound as a white solid. LCMS: ($C_{27}H_{31}N_3O_5$) desired mass=477.2; found: m/z=478.2 $[M+H]^+$.

Step-4: 4-{4-[4-(2,6-dioxopiperidin-3-yl)phenyl] piperazine-1-carbonyl}benzoic acid

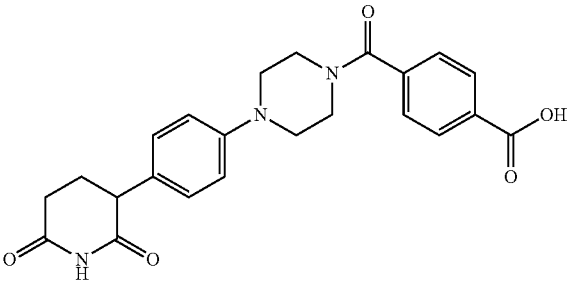 [SMILES: O=C1CCC(c2ccc(N3CCN(C(=O)c4ccc(C(=O)O)cc4)CC3)cc2)C(=O)N1]

Procedures similar to those in step 3 of Intermediate 15 were followed using tert-butyl 4-{4-[4-(2,6-dioxopiperidin-3-yl)phenyl]piperidine-1-carbonyl}benzoate (450 mg, 0.944 mmol) and HCl/dioxane (15 mL, 4M). The residue was purified by silica gel column chromatography of [ACN and $H_2O$] to provide 46.5 mg (12.91%) of the title compound as a green solid. LCMS (Method 2): ($C_{23}H_{23}N_3O_5$) desired mass=421.2; found: m/z=422.1 $[M+H]^+$.

Intermediate 20

4-(4-[2-(2,6-dioxopiperidin-3-yl)]-1,3-dioxoisoindol-5-yl]piperazine-1-carbonyl)benzoic acid

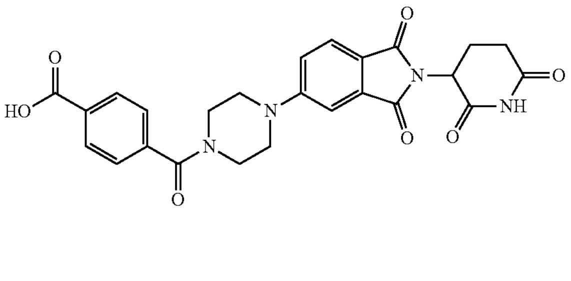 [SMILES: O=C1CCC(N2C(=O)c3ccc(N4CCN(C(=O)c5ccc(C(=O)O)cc5)CC4)cc3C2=O)C(=O)N1]

Step-1: 2-(2,6-dioxopiperidin-3-yl)-5-(piperazin-1-yl)isoindole-1,3-dione

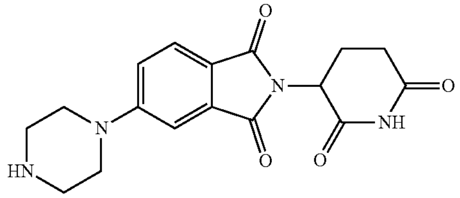 [SMILES: O=C1CCC(N2C(=O)c3ccc(N4CCNCC4)cc3C2=O)C(=O)N1]

Procedures similar to those in step 4 of Intermediate 15 were followed using 2-(2,6-dioxopiperidin-3-yl)-5-fluoroisoindole-1,3-dione (1 g, 3.620 mmol), piperazine (0.47 g, 5.430 mmol), ACN (10 mL) and DIEA (1.4 g, 10.861 mmol). The crude residue was purified by reverse phase flash chromatography, mobile phase of [$CH_3CN$ and $H_2O$] to provide 250 mg (16.94%) of the title compound as a yellow solid. LCMS: ($C_{17}H_{18}N_4O_4$) desired mass=342.1; found: m/z=343.1 $[M+H]^+$.

Step-2: tert-butyl 4-[4-[2-(2,6-dioxopiperidin-3-yl)-1,3-dioxoisoindol-5-yl]piperazine-1-carbonyl]benzoate

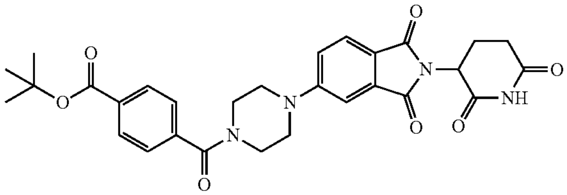 [SMILES: CC(C)(C)OC(=O)c1ccc(C(=O)N2CCN(c3ccc4c(c3)C(=O)N(C3CCC(=O)NC3=O)C4=O)CC2)cc1]

To a mixture of 4-(tert-butoxycarbonyl)benzoic acid (324.58 mg, 1.460 mmol) in DCM (10 mL) and DMF (0.1 mL) were added Oxalyl chloride (0.12 mL, 0.980 mmol) at 0° C. under $N_2$. The resulting mixture was stirred for 1 h at 0° C. under $N_2$. The acid chloride solution was added to a mixture of 2-(2,6-dioxopiperidin-3-yl)-5-(piperazin-1-yl) isoindole-1,3-dione (500 mg, 1.460 mmol) and $Na_2CO_3$ (464 mg, 4.381 mmol) in NMP (8 mL) at 0° C. The resulting mixture was stirred for 2 h at room temperature under $N_2$. The resulting mixture was quenched with water and purified by reverse phase flash chromatography, mobile phase of [$CH_3CN$ and $H_2O$] to provide 550 mg (66.83%) of the title compound as a yellow solid. LCMS: ($C_{29}H_{30}N_4O_7$) desired mass=546.2; found: m/z=547.2 $[M+H]^+$.

Step-3: 4-(4-[2-[2,6-dioxopiperidin-3-yl]-1,3-dioxoisoindol-5-yl]piperazine-1-carbonyl)benzoic acid

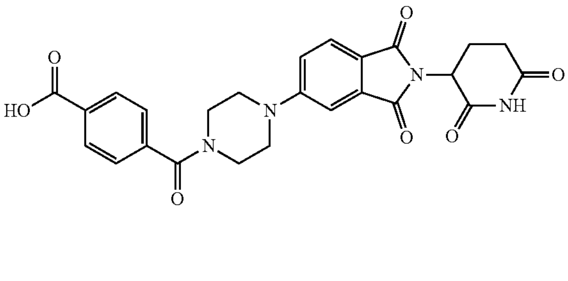 [SMILES: O=C1CCC(N2C(=O)c3ccc(N4CCN(C(=O)c5ccc(C(=O)O)cc5)CC4)cc3C2=O)C(=O)N1]

Procedures similar to those in step 3 of Intermediate 15 were followed using tert-butyl 4-[4-[2-(2,6-dioxopiperidin-3-yl)-1,3-dioxoisoindol-5-yl]piperazine-1-carbonyl]benzoate (530 mg, 0.970 mmol) and HCl/1,4-dioxane (35 mL, 4M). The residue was purified by reverse phase flash chromatography, mobile phase of [$CH_3CN$ and $H_2O$] to provide 227 mg (47.64%) of the title compound as a yellow solid. LCMS (Method 3): ($C_{25}H_{22}N_4O_7$) desired mass=490.2; found: m/z=491.2 $[M+H]^+$.

Intermediate 21

4-(4-(2-(2,6-dioxopiperidin-3-yl)-1,3-dioxoisoindolin-5-yl)piperazine-1-carbonyl)benzoic acid

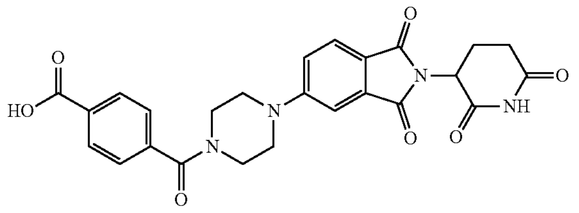 [SMILES: O=C1CCC(N2C(=O)c3ccc(N4CCN(C(=O)c5ccc(C(=O)O)cc5)CC4)cc3C2=O)C(=O)N1]

Step-1: 2-(2,6-dioxopiperidin-3-yl)-5-(piperazin-1-yl)isoindole-1,3-dione

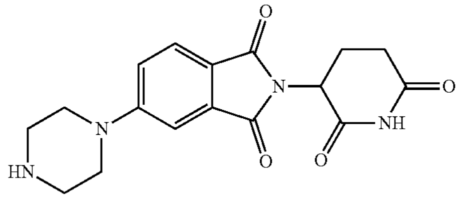 [SMILES: O=C1CCC(N2C(=O)c3ccc(N4CCNCC4)cc3C2=O)C(=O)N1]

To a mixture of 2-(2,6-dioxopiperidin-3-yl)-5-fluoroisoindole-1,3-dione (1 g, 3.620 mmol) and piperazine (0.47 g, 5.430 mmol) in ACN (10 mL) was added DIEA (1.4 g, 10.861 mmol). The resulting mixture was stirred at 80° C. overnight. The resulting mixture was purified by reverse phase flash chromatography [$CH_3CN$ and $H_2O$ mobile phase] to yield 250 mg (16.94%) of the title compound as a yellow solid. LCMS: ($C_{17}H_{18}N_4O_4$) desired mass=342.1; found: m/z=343.1 $[M+H]^+$.

Step-2: tert-butyl 4-[4-[2-(2,6-dioxopiperidin-3-yl)-1,3-dioxoisoindol-5-yl]piperazine-1-carbonyl]benzoate

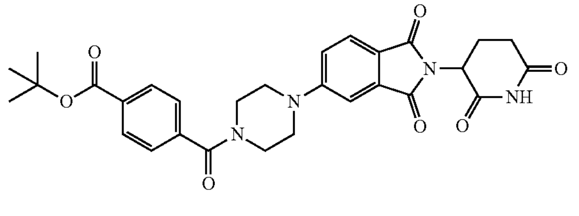 [SMILES: CC(C)(C)OC(=O)c1ccc(C(=O)N2CCN(c3ccc4c(c3)C(=O)N(C3CCC(=O)NC3=O)C4=O)CC2)cc1]

To a mixture of 4-(tert-butoxycarbonyl)benzoic acid (324.58 mg, 1.460 mmol) in DCM (10 mL) was added DMF (0.1 mL) and oxalyl chloride (0.73 mL, 1.460 mmol, 2 mol/L) at 0° C. under $N_2$. The resulting mixture was stirred for 1 h at 0° C. under $N_2$. To a mixture of 2-(2,6-dioxopiperidin-3-yl)-5-(piperazin-1-yl)isoindole-1,3-dione (500 mg, 1.460 mmol, 1 equiv) in NMP (8 mL) was added $Na_2CO_3$ (464 mg, 4.381 mmol, 3 equiv) and the above mixture at 0° C. under $N_2$. The resulting mixture was stirred for 2 h at room temperature under $N_2$, then washed with water and concentrated under vacuum. The residue was purified by reverse phase flash chromatography [$CH_3CN$ and $H_2O$ mobile phase] to yield 550 mg (66.83%) of the title compound as a yellow solid. LCMS: ($C_{29}H_{30}N_4O_7$) desired mass=546.2; found: m/z=547.2 $[M+H]^+$.

Step-3: 4-(4-(2-(2,6-dioxopiperidin-3-yl)-1,3-dioxoisoindolin-5-yl)piperazine-1-carbonyl)benzoic acid

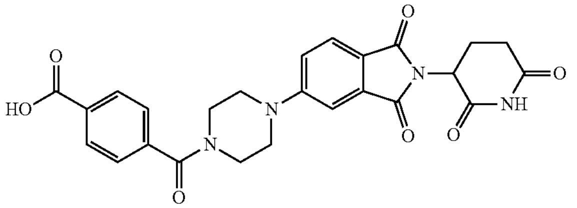 [SMILES: O=C1CCC(N2C(=O)c3ccc(N4CCN(C(=O)c5ccc(C(=O)O)cc5)CC4)cc3C2=O)C(=O)N1]

A mixture of tert-butyl 4-[4-[2-(2,6-dioxopiperidin-3-yl)-1,3-dioxoisoindol-5-yl]piperazine-1-carbonyl]benzoate (530 mg, 0.970 mmol, 1 equiv) in HCl/1,4-dioxane (35 mL, 4M) was stirred for 2 h at room temperature. The resulting mixture was concentrated under vacuum. The residue was purified by reverse phase flash chromatography [$CH_3CN$ and $H_2O$ mobile phase] to yield 227 mg (47.64%) of the title compound as a yellow solid. LCMS: ($C_{25}H_{22}N_4O_7$) desired mass=490.2; found: m/z=491.2 $[M+H]^+$.

Intermediate 22

4-({1-[2-(2,6-dioxopiperidin-3-yl)-1,3-dioxo-2,3-dihydro-1H-isoindol-5-yl]piperidin-4-yl}carbamoyl)benzoic acid

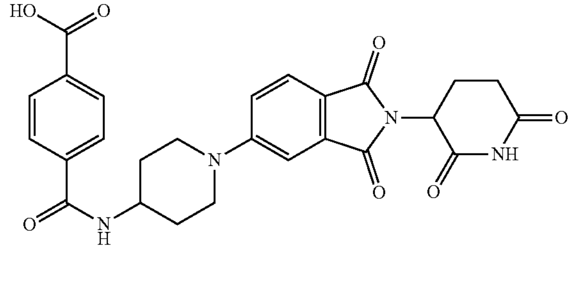 [SMILES: O=C1CCC(N2C(=O)c3ccc(N4CCC(NC(=O)c5ccc(C(=O)O)cc5)CC4)cc3C2=O)C(=O)N1]

Step 1: benzyl 4-{4-[(tert-butoxy)carbonyl]benzamido}piperidine-1-carboxylate

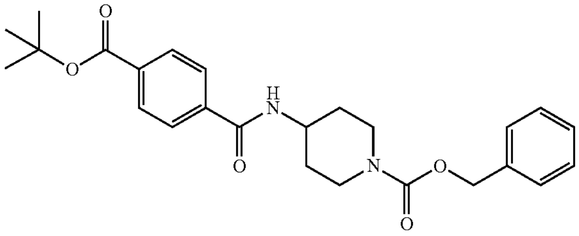 [SMILES: CC(C)(C)OC(=O)c1ccc(C(=O)NC2CCN(C(=O)OCc3ccccc3)CC2)cc1]

To a solution of 4-[(tert-butoxy)carbonyl]benzoic acid (484 mg, 2.07 mmol), and HATU (870 mg, 2.17 mmol) in anhydrous DMF (20.7 mL) was added DIPEA (0.401 g, 3.10 mmol) at 25° C. The reaction mixture was stirred for 0.5 h at 25° C. and then benzyl 4-aminopiperidine-1-carboxylate (613 mg, 2.49 mmol) in DMF (20.7 mL) was added and the reaction mixture was stirred for 16 h at 25° C. The reaction mixture was evaporated, dissolved in EtOAc, and washed successively with 5% of citric acid aq. solution, sat. $NaHCO_3$ solution and brine. The organic layers were dried with $Na_2SO_4$ and concentrated under reduced pressure. The crude residue was purified by silica gel column chromatography using a mobile phase of EtOAc to provide 685 mg (75% yield) of the title compound. LCMS: $C_{25}H_{30}N_2O_5$, desired mass=438.2, found: m/z=439.5 $[M+H]^+$.

Step 2: tert-butyl 4-[(piperidin-4-yl)carbamoyl]benzoate

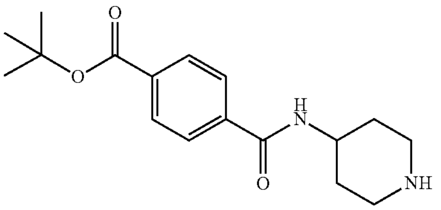 [SMILES: CC(C)(C)OC(=O)c1ccc(C(=O)NC2CCNCC2)cc1]

To a solution of benzyl 4-{4-[(tert-butoxy)carbonyl]benzamido}piperidine-1-carboxylate (680 mg, 1.55 mmol) in EtOH (38.8 mL) was added $Pd(OH)_2/C$ 10% wt (221 mg, 0.16 mmol) and the reaction mixture was stirred under $H_2$ (1 atm) for 24 h at 25° C. The reaction mixture was filtered through a Celite pad, washed with MeOH, and concentrated under reduced pressure to provide 550 mg (99% yield) of the title compound. LCMS: $C_{17}H_{24}N_2O_3$, desired mass=304.2, found: m/z=305.4 $[M+H]^+$.

Step 3: tert-butyl 4-({1-[2-(2,6-dioxopiperidin-3-yl)-1,3-dioxo-2,3-dihydro-1H-isoindol-5-yl]piperidin-4-yl}carbamoyl)benzoate

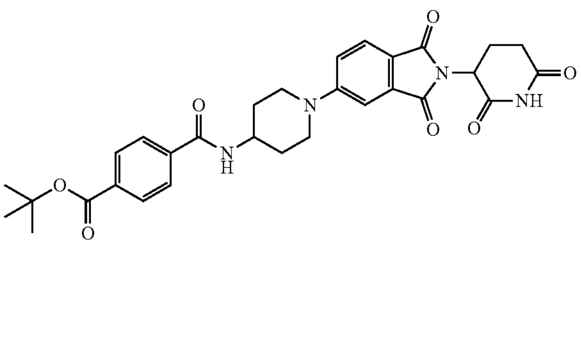 [SMILES: CC(C)(C)OC(=O)c1ccc(C(=O)NC2CCN(c3ccc4c(c3)C(=O)N(C3CCC(=O)NC3=O)C4=O)CC2)cc1]

To a solution of 2-(2,6-dioxopiperidin-3-yl)-5-fluoro-2,3-dihydro-1H-isoindole-1,3-dione (357 mg, 1.29 mmol) in DMSO (2.58 mL) were added tert-butyl 4-[(piperidin-4-yl)carbamoyl]benzoate (0.555 g, 1.55 mmol) and DIPEA (670 mg, 5.17 mmol) at 25° C. The reaction mixture was stirred for 24 h at 90° C. The reaction mixture was concentrated under reduced pressure and purified by silica gel column chromatography using a mobile phase of Hexane and EtOAc to provide 450 mg (58% yield) of the title compound. LCMS: $C_{30}H_{32}N_4O_7$, desired mass=560.2, found: m/z=561.6 $[M+H]^+$.

Step 4: 4-({1-[2-(2,6-dioxopiperidin-3-yl)-1,3-dioxo-2,3-dihydro-1H-isoindol-5-yl]piperidin-4-yl}carbamoyl)benzoic acid

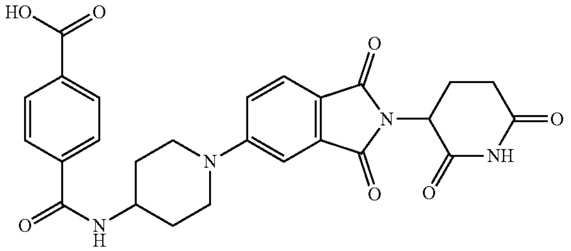 [SMILES: O=C1CCC(N2C(=O)c3ccc(N4CCC(NC(=O)c5ccc(C(=O)O)cc5)CC4)cc3C2=O)C(=O)N1]

Tert-butyl 4-({1-[2-(2,6-dioxopiperidin-3-yl)-1,3-dioxo-2,3-dihydro-1H-isoindol-5-yl]piperidin-4-yl}carbamoyl)benzoate (463 mg, 0.77 mmol) was suspended in HFIP (12.8 g, 75.99 mmol) and heated in microwave reactor for 2 h at 150° C. Then HFIP was evaporated under reduced pressure and the solid residue was triturated with $Et_2O$ to provide 216 mg (54% yield) of the title compound. LCMS: $C_{26}H_{24}N_4O_7$, desired mass=504.2, found: m/z=505.2 $[M+H]^+$.

Intermediate 23

6-{4-[2-(2,6-dioxopiperidin-3-yl)-1,3-dioxo-2,3-dihydro-1H-isoindol-5-yl]piperazine-1-carbonyl}pyridine-3-carboxylic acid

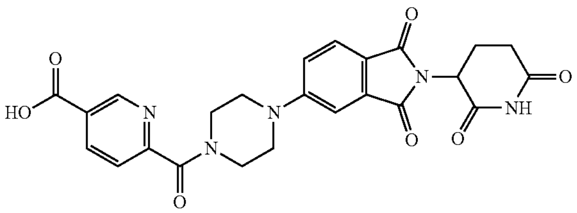 [SMILES: O=C1CCC(N2C(=O)c3ccc(N4CCN(C(=O)c5ccc(C(=O)O)cn5)CC4)cc3C2=O)C(=O)N1]

The title compound (60 mg, 43% yield) was synthesized using similar methods to Intermediate 22, and substituting 4-[(tert-butoxy)carbonyl]benzoic acid for 5-[(tert-butoxy)carbonyl]pyridine-2-carboxylic acid and benzyl 4-aminopiperidine-1-carboxylate for benzyl 1-piperazinecarboxylate. LCMS: $C_{24}H_{21}N_5O_7$, desired mass=491.1, found: m/z=492.3 $[M+H]^+$.

Intermediate 24

(1R,4R)-4-(6-(2,6-dioxopiperidin-3-yl)-1,2,3,4-tetrahydroisoquinoline-2-carbonyl)cyclohexane-1-carbaldehyde

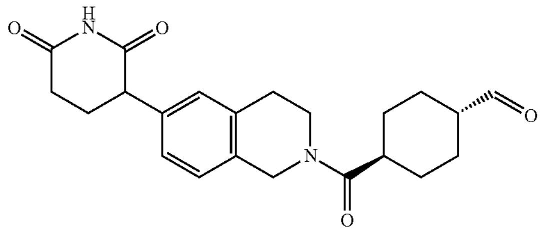 [SMILES: O=C[C@H]1CC[C@H](C(=O)N2CCc3cc(C4CCC(=O)NC4=O)ccc3C2)CC1]

Step 1: -butyl 6-(2,6-bis(benzyloxy)pyridin-3-yl)-3,4-dihydroisoquinoline-2(1H)-carboxylate To a 40 mL vial was added tert-butyl 6-bromo-3,4-dihydro-1H-isoquinoline-2-carboxylate (1000.00 mg, 3.20 mmol), 2,6-bis(benzyloxy)-3-(4,4,5,5-tetramethyl-1,3,2-dioxaborolan-2-yl)pyridine (1470.31 mg, 3.52 mmol), tripotassium phosphate (2.04 g, 9.61 mmol), Pd(dppf)$Cl_2$·DCM (0.26 g, 0.32 mmol), dioxane (7.00 mL), and water (2.50 mL). The reaction mixture was degassed with nitrogen for 15 min, then stirred at 90° C. for 16 h. The reaction mixture was then diluted with water and EtOAc, then filtered through celite. The product was extracted with EtOAc (3×), dried over $MgSO_4$, then concentrated. The resulting residue was purified by FC (80 g silica, 0-25% EtOAc/hexanes) to yield the title compound as a colorless oil (1.48 g, 88% yield). LCMS: [$C_{33}H_{34}N_2O_4$], desired mass=522.3, found: m/z=523.3 $[M+H]^+$.

Step 2: tert-butyl 6-(2,6-dioxopiperidin-3-yl)-3,4-dihydroisoquinoline-2(1H)-carboxylate To a 40 mL vial was added tert-butyl 6-[2,6-bis(benzyloxy)pyridin-3-yl]-3,4-dihydro-1H-isoquinoline-2-carboxylate (1480.00 mg, 2.83 mmol), Pd/C (700.00 mg), THF (10.00 mL), and EtOH (10.00 mL). The reaction mixture was sparged with hydrogen for 5 min, then the reaction mixture was stirred under hydrogen atmosphere (balloon) for 16 h. The reaction mixture was filtered through celite, then concentrated. The resulting residue was purified by FC (40 g silica, 0-10% MeOH/DCM) to yield the title compound as a white solid (852 mg, 87% yield). LCMS: [$C_{19}H_{24}N_2O_4$], desired mass=344.2, found: m/z=345.2 $[M+H]^+$.

Step 3: 3-(1,2,3,4-tetrahydroisoquinolin-6-yl)piperidine-2,6-dione

To a 40 mL vial was added tert-butyl 6-[(3RS)-2,6-dioxopiperidin-3-yl]-3,4-dihydro-1H-isoquinoline-2-carboxylate (852.00 mg, 2.47 mmol) and DCM (2.00 mL). To the reaction mixture was added 4 M hydrogen chloride in dioxane (6.18 mL, 0.90 g, 24.74 mmol) in a dropwise fashion. After 1 h, the reaction mixture was concentrated to yield the title compound as a white solid (707 mg, quantitative yield). LCMS: [$C_{14}H_{16}N_2O_2$] desired mass=244.1, found: m/z=245.0 $[M+H]^+$.

Step 4: 3-(2-((1r,4r)-4-(hydroxymethyl)cyclohexane-1-carbonyl)-1,2,3,4-tetrahydroisoquinolin-6-yl)piperidine-2,6-dione To a 1 dram vial was added 3-(1,2,3,4-tetrahydroisoquinolin-6-yl)piperidine-2,6-dione hydrochloride (10.00 mg, 0.04 mmol), (1r,4r)-4-(hydroxymethyl)cyclohexane-1-carboxylic acid (5.63 mg, 0.04 mmol), N,N-diisopropylethylamine (0.06 mL, 0.05 g, 0.36 mmol), and DMF (0.25 mL). To the reaction mixture was added [(dimethylamino)({[1,2,3]triazolo[4,5-b]pyridin-3-yloxy})methylidene]dimethylazanium; hexafluoro-lambda5-phosphanuide (13.54 mg, 0.04 mmol) in DMF (0.25 mL). After 3 h, the reaction mixture was quenched with $NaHCO_3$ (aq). The product was extracted with 10% MeOH/DCM (3×), dried over $MgSO_4$, then concentrated. The resulting residue was used in the next step without further purification. LCMS: [$C_{22}H_{28}N_2O_4$] desired mass=384.2, found: m/z=385.3 $[M+H]^+$.

Step 5: (1r,4r)-4-(6-(2,6-dioxopiperidin-3-yl)-1,2,3,4-tetrahydroisoquinoline-2-carbonyl)cyclohexane-1-carbaldehyde To a 1 dram vial was added (3RS)-3-{2-[(1r,4r)-4-(hydroxymethyl)cyclohexanecarbonyl]-3,4-dihydro-1H-isoquinolin-6-yl}piperidine-2,6-dione (13.70 mg, 0.04 mmol), IBX polystyrene (1.2 mmol/g, 0.09 g, 3 equiv), DMSO (0.10 mL), and DCM (0.50 mL). The reaction mixture was stirred for 16 h. The reaction mixture was filtered with DCM and concentrated. The resulting residue was used in the subsequent step without further purification. LCMS: [$C_{22}H_{26}N_2O_4$] desired mass=382.2, found: m/z=383.3 $[M+H]^+$.

Intermediate 25

(3R)-1-(5-(2,6-dioxopiperidin-3-yl)pyridin-2-yl)pyrrolidine-3-carboxylic acid

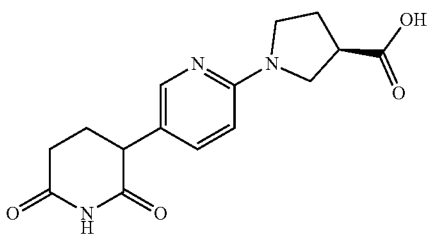 [SMILES: O=C1CCC(c2ccc(N3CC[C@@H](C(=O)O)C3)nc2)C(=O)N1]

3-(6-fluoropyridin-3-yl)piperidine-2,6-dione (100.00 mg, 0.48 mmol), (3R)-pyrrolidine-3-carboxylic acid (110.60 mg, 0.96 mmol), N,N-diisopropylethylamine (0.34 mL, 248.32 mg, 1.92 mmol), and DMSO (1.00 mL) were combined in a microwave vial and irradiated at 140° C. for 2 hours. The product was isolated by reverse phase flash column chromatography to afford the title compound (42 mg, 29% yield).

Intermediate 26

1-((1R,4R)-4-(6-(2,6-dioxopiperidin-3-yl)-1,2,3,4-tetrahydroisoquinoline-2-carbonyl)cyclohexane-1-carbonyl)piperidine-4-carboxylic acid

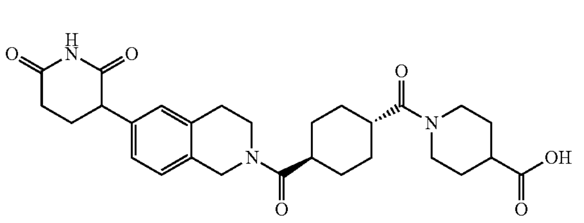 [SMILES: O=C1CCC(c2ccc3c(c2)CCN(C(=O)[C@H]2CC[C@H](C(=O)N4CCC(C(=O)O)CC4)CC2)C3)C(=O)N1]

Step 1: (1r,4r)-4-(6-(2,6-dioxopiperidin-3-yl)-1,2,3,4-tetrahydroisoquinoline-2-carbonyl)cyclohexane-1-carboxylic acid

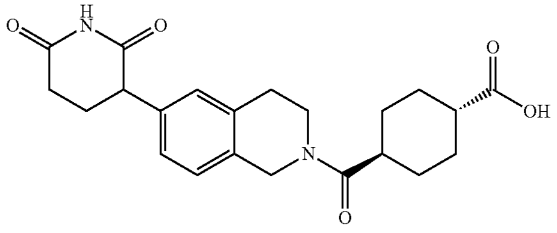 [SMILES: O=C1CCC(c2ccc3c(c2)CCN(C(=O)[C@H]2CC[C@H](C(=O)O)CC2)C3)C(=O)N1]

To a suspension of methyl (1r,4r)-4-(6-(2,6-dioxopiperidin-3-yl)-1,2,3,4-tetrahydroisoquinoline-2-carbonyl)cyclohexane-1-carboxylate (180 mg, 0.44 mmol) in water (1.8 mL) was added TFA (3.6 mL, 47.0 mmol) at room temperature. The reaction mixture was stirred for 6.5 h at 70° C., and then it was concentrated under high vacuum. The residue was used as-is for the next step (Yellow oil, 173 mg). LCMS: [$C_{22}H_{26}N_2O_5$], desired mass=398.4, found: m/z=399.1 $[M+H]^+$.

Step 2: tert-butyl 1-((1r,4r)-4-(6-(2,6-dioxopiperidin-3-yl)-1,2,3,4-tetrahydroisoquinoline-2-carbonyl)cyclohexane-1-carbonyl)piperidine-4-carboxylate

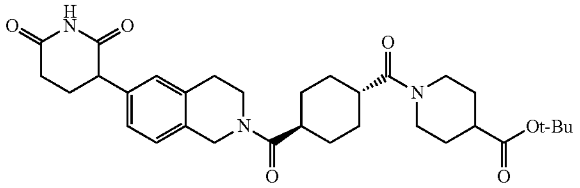 [SMILES: CC(C)(C)OC(=O)C1CCN(C(=O)[C@H]2CC[C@H](C(=O)N3CCc4cc(C5CCC(=O)NC5=O)ccc4C3)CC2)CC1]

The title compound was synthesized using similar methods to tert-butyl (3R)-1-(1-(5-(2,6-dioxopiperidin-3-yl)pyridin-2-yl)piperidine-4-carbonyl)pyrrolidine-3-carboxylate using BOP coupling. The crude product was used as-is in the next step (Pale yellow oil, 96 mg). LCMS: [$C_{32}H_{43}N_3O_6$], desired mass=565.3, found: m/z=566.7 $[M+H]^+$.

Step 3: 1-((1r,4r)-4-(6-(2,6-dioxopiperidin-3-yl)-1,2,3,4-tetrahydroisoquinoline-2-carbonyl)cyclohexane-1-carbonyl)piperidine-4-carboxylic acid

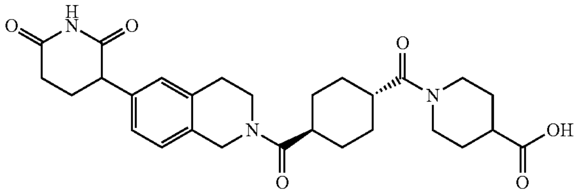 [SMILES: O=C1CCC(c2ccc3c(c2)CCN(C(=O)[C@H]2CC[C@H](C(=O)N4CCC(C(=O)O)CC4)CC2)C3)C(=O)N1]

The title compound was synthesized via TFA-mediated deprotection conditions similar to those described for 1-(5-(2,6-dioxopiperidin-3-yl)pyridin-2-yl)piperidine-4-carboxylic acid. The crude product was used as-is for the next step. (Pale yellow oil, 126 mg). LCMS: [$C_{28}H_{35}N_3O_6$], desired mass=509.2, found: m/z=510.4 $[M+H]^+$.

Intermediate 27

(1R,4R)-4-(6-(2,4-dioxotetrahydropyrimidin-1(2H)-yl)-1,2,3,4-tetrahydroisoquinoline-2-carbonyl)cyclohexane-1-carboxylic acid

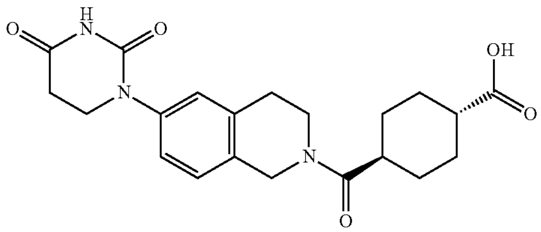 [SMILES: O=C1CCN(c2ccc3c(c2)CCN(C(=O)[C@H]2CC[C@H](C(=O)O)CC2)C3)C(=O)N1]

Step 1: 3-((2-(tert-butoxycarbonyl)-1,2,3,4-tetrahydroisoquinolin-6-yl)amino)propanoic acid To a 20 mL vial was added tert-butyl 6-amino-3,4-dihydro-1H-isoquinoline-2-carboxylate (1000.00 mg, 4.03 mmol), acrylic acid (0.28 mL, 290.20 mg, 4.03 mmol), and toluene (7.00 mL). The reaction mixture was stirred at 80° C. for 16 h, then concentrated. The resulting crude product was used in the subsequent step without further purification. LCMS: [$C_{17}H_{24}N_2O_4$], desired mass=320.2, found: m/z=321.2 $[M+H]^+$.

Step 2: 1-(1,2,3,4-tetrahydroisoquinolin-6-yl)dihydropyrimidine-2,4(1H,3H)-dione To a 40 mL vial was added 3-{[2-(tert-butoxycarbonyl)-3,4-dihydro-1H-isoquinolin-6-yl]amino}propanoic acid (1291.17 mg, 4.03 mmol), urea (0.48 g, 8.06 mmol), and acetic acid (2.00 mL). The reaction mixture was stirred at 120° C. for 16 h. To the crude reaction mixture was added TFA (1 mL). The reaction mixture was stirred for 1 h, then purified by reverse phase FC (415 g C18 silica, 0-20% MeCN/water) to yield the title compound as an off-white solid (126 mg, 10% yield). LCMS: [$C_{13}H_{15}N_3O_2$] desired mass=245.1, found: m/z=246.1 $[M+H]^+$.

Step 3: Synthesis of methyl (1r,4r)-4-(6-(2,4-dioxotetrahydropyrimidin-1(2H)-yl)-1,2,3,4-tetrahydroisoquinoline-2-carbonyl)cyclohexane-1-carboxylate To a 1 dram vial was added 1-(1,2,3,4-tetrahydroisoquinolin-6-yl)-1,3-diazinane-2,4-dione; trifluoroacetic acid (25.00 mg, 0.07 mmol), (1r,4r)-4-(methoxycarbonyl)cyclohexane-1-carboxylic acid (14.25 mg, 0.08 mmol), N,N-diisopropylethylamine (0.12 mL, 0.09 g, 0.70 mmol), and DMF (0.3 mL). To the reaction mixture was added [(dimethylamino)({[1,2,3]triazolo[4,5-b]pyridine-3-yloxy})methylidene]dimethylazanium; hexafluoro-lambda5-phosphanuide (29.10 mg, 0.08 mmol) in DMF (0.3 mL). The reaction mixture was stirred for 1 h, then quenched with $NaHCO_3$ (aq). The product was extracted with DCM, dried over $MgSO_4$, then concentrated. The resulting residue was purified by reverse phase chromatography (4 g silica, 0-10% MeOH/DCM). m/z=359.2 impurity coelutes with product. The product was further purified by reverse phase FC (30 g C18 silica, 0-60% MeCN/water +0.1% TFA) to yield the title compound as a white solid (16 mg, 57% yield). LCMS [$C_{22}H_{27}N_3O_5$], desired mass=413.2, found: m/z=414.3 $[M+H]^+$.

Step 4: Synthesis of (1r,4r)-4-(6-(2,4-dioxotetrahydropyrimidin-1(2H)-yl)-1,2,3,4-tetrahydroisoquinoline-2-carbonyl)cyclohexane-1-carboxylic acid To a 2 dram vial was added methyl (1r,4r)-4-[6-(2,4-dioxo-1,3-diazinan-1-yl)-3,4-dihydro-1H-isoquinoline-2-carbonyl]cyclohexane-1-carboxylate (16.00 mg, 0.04 mmol), water (0.20 mL), and TFA (0.20 mL). The reaction mixture was stirred for 1 h at 70° C., then stirred at 80° C. for an additional 2 h. The reaction mixture was concentrated and used without further purification. LCMS [$C_{21}H_{25}N_3O_5$], desired mass=399.2, found: m/z=400.3 $[M+H]^+$.

Intermediate 28

(1R,4R)-4-(7-(2,6-dioxopiperidin-3-yl)-1,2,3,4-tetrahydroisoquinoline-2-carbonyl)cyclohexane-1-carboxylic acid

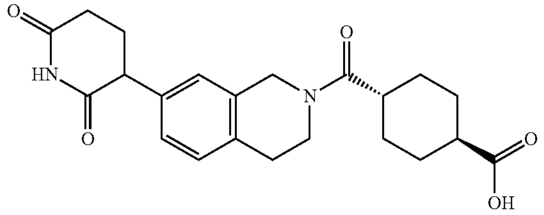 [SMILES: O=C1CCC(c2ccc3c(c2)CN(C(=O)[C@H]2CC[C@H](C(=O)O)CC2)CC3)C(=O)N1]

Step 1: 3-(1,2,3,4-tetrahydroisoquinolin-7-yl)piperidine-2,6-dione

The title compound was prepared using procedures similar to Intermediate 24, and using tert-butyl 7-bromo-3,4-dihydroisoquinoline-2(1H)-carboxylate as starting material. LCMS: [$C_{14}H_{16}N_2O_2$], desired mass=244.1, found: m/z=245.3 $[M+H]^+$.

Step 2: (1r,4r)-4-(7-(2,6-dioxopiperidin-3-yl)-1,2,3,4-tetrahydroisoquinoline-2-carbonyl)cyclohexane-1-carboxylic acid The title compound was prepared using procedures similar to Intermediate 27, and using 3-(1,2,3,4-tetrahydroisoquinolin-7-yl)piperidine-2,6-dione as starting material.

Intermediate 29

(1R,4R)-4-(6-(2,6-dioxopiperidin-3-yl)-1,2,3,4-tetrahydroquinoline-1-carbonyl)cyclohexane-1-carboxylic acid

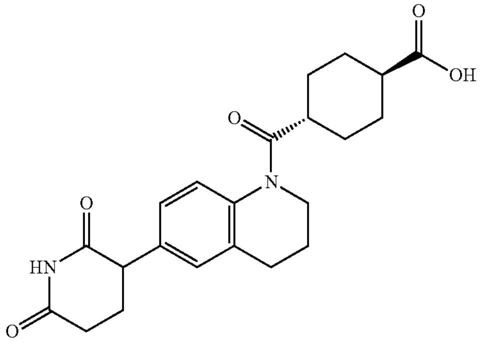 [SMILES: O=C1CCC(c2ccc3c(c2)CCCN3C(=O)[C@H]2CC[C@H](C(=O)O)CC2)C(=O)N1]

Step 1: 3-(1,2,3,4-tetrahydroquinolin-6-yl)piperidine-2,6-dione

The title compound was prepared using similar procedures to Intermediate 24, and using tert-butyl 6-bromo-3,4-dihydroquinoline-1(2H)-carboxylate as starting material. LCMS: [$C_{14}H_{16}N_2O_2$], desired mass=244.1, found: m/z=245.4 $[M+H]^+$.

Step 2: (1R,4r)-4-(6-((RS)-2,6-dioxopiperidin-3-yl)-1,2,3,4-tetrahydroquinoline-1-carbonyl)cyclohexane-1-carboxylic acid The title compound was prepared using procedures similar to Intermediate 27, and using (RS)-3-(1,2,3,4-tetrahydroquinolin-6-yl)piperidine-2,6-dione as starting material.

Intermediate 30

1-((1R,4R)-4-((4-(2,6-dioxopiperidin-3-yl)pyridin-2-yl)amino)cyclohexane-1-carbonyl)piperidine-4-carboxylic acid

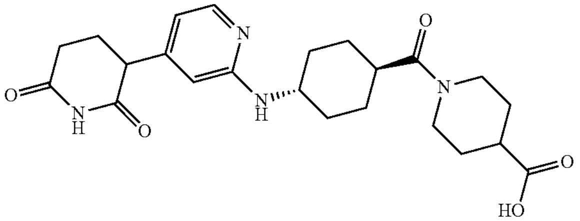 [SMILES: O=C1CCC(c2ccnc(N[C@H]3CC[C@H](C(=O)N4CCC(C(=O)O)CC4)CC3)c2)C(=O)N1]

Step 1: tert-butyl 1-((1r,4r)-4-((4-(2,6-dioxopiperidin-3-yl)pyridin-2-yl)amino)cyclohexane-1-carbonyl)piperidine-4-carboxylate

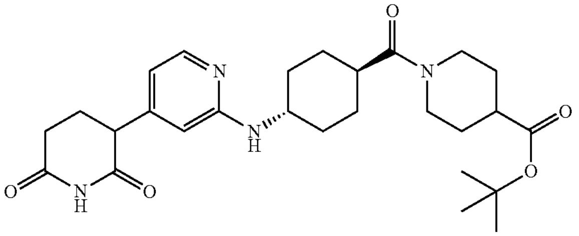 [SMILES: CC(C)(C)OC(=O)C1CCN(C(=O)[C@H]2CC[C@H](Nc3cc(C4CCC(=O)NC4=O)ccn3)CC2)CC1]

Prepared by similar procedures as Intermediate 5 (step 1) using (1r,4r)-4-((4-(2,6-dioxopiperidin-3-yl)pyridin-2-yl) amino)cyclohexane-1-carboxylic acid (75 mg, 0.226 mmmol) and tert-butyl piperidine-4-carboxylate (63 mg, 0.34 mmol) as starting materials. The title compound (TFA salt) was isolated as an off-white solid (100 mg, 89% yield). LCMS: [$C_{27}H_{38}N_4O_5$], desired mass=499.6, found: m/z=471.5 $[M+H]^+$.

Step 2: 1-((1r,4r)-4-((4-(2,6-dioxopiperidin-3-yl) pyridin-2-yl)amino)cyclohexane-1-carbonyl)piperidine-4-carboxylic acid

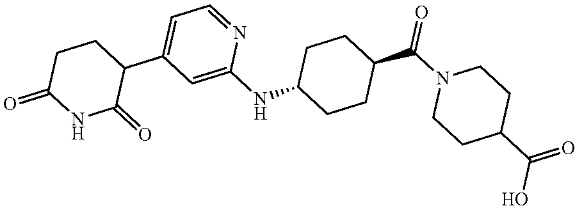 [SMILES: O=C1CCC(c2ccnc(N[C@H]3CC[C@H](C(=O)N4CCC(C(=O)O)CC4)CC3)c2)C(=O)N1]

Prepared by similar procedures as Intermediate 5 (step 2) using tert-butyl 1-((1r,4r)-4-((4-(2,6-dioxopiperidin-3-yl) pyridin-2-yl)amino)cyclohexane-1-carbonyl)piperidine-4-carboxylate (100 mg, 0.2 mmol) as the starting material. The title compound (TFA salt) was isolated as an off-white solid (64 mg, 72% yield). LCMS: [$C_{23}H_{30}N_4O_5$], desired mass=442.5, found: m/z=443.4 $[M+H]^+$.

Intermediate 31

1-((1R,4R)-4-((4-((RS)-2,6-dioxopiperidin-3-yl) phenyl)amino)cyclohexane-1-carbonyl)piperidine-4-carboxylic acid

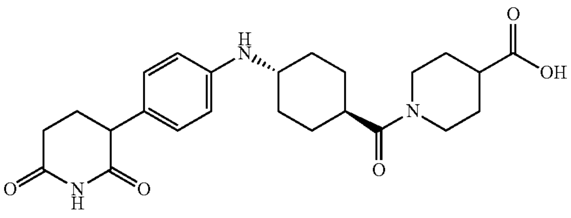 [SMILES: O=C1CCC(c2ccc(N[C@H]3CC[C@H](C(=O)N4CCC(C(=O)O)CC4)CC3)cc2)C(=O)N1]

Step 1: (1r,4r)-4-[(4-bromophenyl)amino]cyclohexane-1-carboxylic acid

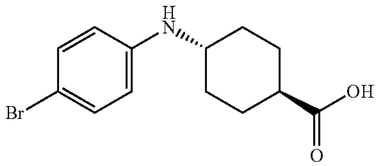 [SMILES: O=C(O)[C@H]1CC[C@H](Nc2ccc(Br)cc2)CC1]

To a mixture of methyl (1r,4r)-4-aminocyclohexane-1-carboxylate hydrochloride (5 g, 25.817 mmol) in toluene (30 mL) was added dibromobenzene (12.18 g, 51.631 mmol), $Pd_2(dba)_3$ (2.36 g, 2.577 mmol), BINAP (3.22 g, 5.171 mmol) and t-BuONa (4.96 g, 51.610 mmol). The resulting mixture was stirred at for 2 h 100° C. under nitrogen atmosphere. The resulting mixture was concentrated under reduced pressure and the residue diluted with water (100 mL). The aqueous layer was washed with EtOAc. The aqueous layer was acidified to pH 4 with HCl (3M) and extracted with EtOAc. The organic mixture was concentrated under reduced pressure to provide 1.3 g (crude) of the title compound as a brown solid. LCMS: ($C_{13}H_{16}BrNO_2$) desired mass=297.0; found: m/z=297.8 $[M+H]^+$.

Step 2: tert-butyl 1-[(1r,4r)-4-[(4-bromophenyl) amino]cyclohexanecarbonyl]piperidine-4-carboxylate

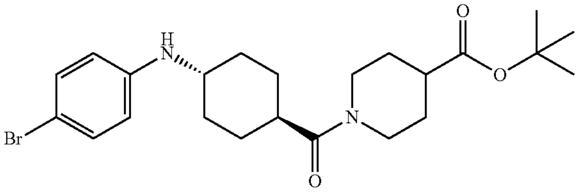 [SMILES: CC(C)(C)OC(=O)C1CCN(C(=O)[C@H]2CC[C@H](Nc3ccc(Br)cc3)CC2)CC1]

To a mixture of (1r,4r)-4-[(4-bromophenyl)amino]cyclohexane-1-carboxylic acid (1.3 g, 4.360 mmol) in DMF (15 mL) was added tert-butyl piperidine-4-carboxylate (0.81 g, 4.360 mmol) and TEA (2.65 g, 26.160 mmol). The resulting mixture was stirred for 30 min at room temperature under nitrogen atmosphere. To the above mixture was added $T_3P$ (2.77 g, 8.720 mmol) at 0° C. The resulting mixture was stirred for 1 h at room temperature. The resulting mixture was extracted with EtOAc. The combined organic layers were washed with water, dried over anhydrous $Na_2SO_4$. After filtration, the filtrate was concentrated under reduced pressure to provide 1.24 g (crude) of the title compound as a brown solid. The residue was used directly for the next step. LCMS: ($C_{23}H_{33}BrN_2O_3$) desired mass=464.2; found: m/z=465.2 $[M+H]^+$.

Step 3: tert-butyl 1-[(1r,4r)-4-({4-[2,6-bis(benzyloxy)pyridin-3-yl]phenyl}amino)cyclohexanecarbonyl]piperidine-4-carboxylate

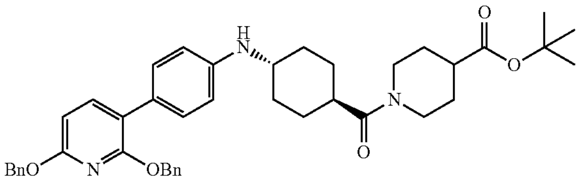 [SMILES: CC(C)(C)OC(=O)C1CCN(C(=O)[C@H]2CC[C@H](Nc3ccc(-c4ccc(OCc5ccccc5)nc4OCc4ccccc4)cc3)CC2)CC1]

To a mixture of tert-butyl 1-[(1r,4r)-4-[(4-bromophenyl)amino]cyclohexanecarbonyl]piperidine-4-carboxylate (1 g, 2.149 mmol) in $H_2O$ (2 mL) and dioxane (10 mL) was added 2,6-bis(benzyloxy)-3-(4,4,5,5-tetramethyl-1,3,2-dioxaborolan-2-yl)pyridine (0.90 g, 2.149 mmol), Pd(dppf) $Cl_2 \cdot CH_2Cl_2$ (0.35 g, 0.430 mmol), and $K_2CO_3$ (0.89 g, 6.447 mmo). The resulting mixture was stirred overnight at 100° C. under nitrogen atmosphere. The resulting mixture was concentrated under reduced pressure. The residue was purified by silica gel column chromatography [PE and EA mobile phase] to provide 420 mg (26.03%) of the title compound as a yellow solid. LCMS: ($C_{42}H_{49}N_3O_5$) desired mass=675.4; found: m/z=676.2 $[M+H]^+$ Step 4: tert-butyl 1-[(1r,4r)-4-{[4-(2,6-dioxopiperidin-3-yl)phenyl]amino}cyclohexanecarbonyl]piperidine-4-carboxylate

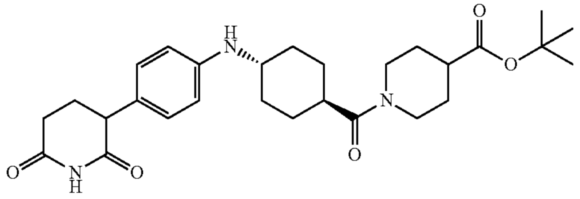 [SMILES: CC(C)(C)OC(=O)C1CCN(C(=O)[C@H]2CC[C@H](Nc3ccc(C4CCC(=O)NC4=O)cc3)CC2)CC1]

To a mixture of tert-butyl 1-[(1r,4r)-4-({4-[2,6-bis(benzyloxy)pyridin-3-yl]phenyl}amino)cyclohexanecarbonyl]piperidine-4-carboxylate (200 mg, 0.296 mmol) in THF (20 mL) was added Pd/C (400 mg). The resulting mixture was stirred for 5 h at room temperature under hydrogen atmosphere. The resulting mixture was filtered, and the filter cake was washed with THF. The filtrate was concentrated under reduced pressure. The residue was purified by silica gel column chromatography [PE and EA mobile phase] to provide 100 mg (64.51%) of the title compound as a white solid. LCMS: ($C_{28}H_{39}N_3O_5$) desired mass=497.3; found: m/z=498.3 $[M+H]^+$.

Step 5: 1-((1R,4r)-4-((4-((RS)-2,6-dioxopiperidin-3-yl)phenyl)amino)cyclohexane-1-carbonyl)piperidine-4-carboxylic acid

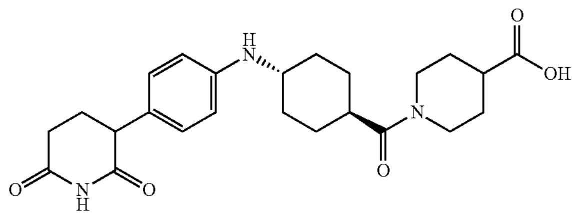 [SMILES: O=C1CCC(c2ccc(N[C@H]3CC[C@H](C(=O)N4CCC(C(=O)O)CC4)CC3)cc2)C(=O)N1]

A similar procedure to Intermediate 21 (step 3) was used with tert-butyl 1-[(1r,4r)-4-{[4-(2,6-dioxopiperidin-3-yl)phenyl]amino}cyclohexanecarbonyl]piperidine-4-carboxylate (120 mg, 0.241 mmol) and HCl in 1,4-dioxane (10 mL, 4M). The residue was purified by reverse phase flash chromatography [ACN and $H_2O$ mobile phase] to yield provide 93 mg (84.73%) of the title compound as a white solid. LCMS: ($C_{24}H_{31}N_3O_5$) desired mass=441.2; found: m/z=442.2 $[M+H]^+$.

Intermediate 32

1-[(1R,4R)-4-{[2-(2,6-dioxopiperidin-3-yl)-1,3-dioxo-2,3-dihydro-1H-isoindol-4-yl]amino}cyclohexanecarbonyl]piperidine-4-carboxylic acid

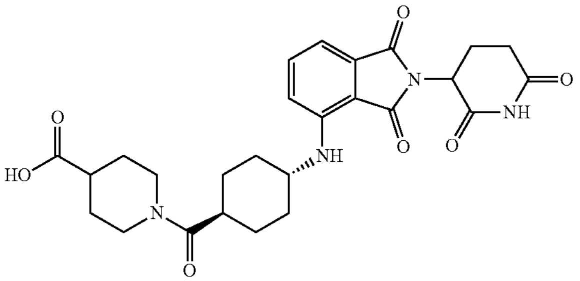 [SMILES: O=C1CCC(N2C(=O)c3cccc(N[C@H]4CC[C@H](C(=O)N5CCC(C(=O)O)CC5)CC4)c3C2=O)C(=O)N1]

The title compound (289 mg, 81% yield, yellow solid) was synthesized using similar methods to Intermediate 17 and substituting benzyl 2-[(3R)-pyrrolidin-3-yl]acetate hydrochloride for tert-butyl piperidine-4-carboxylate hydrochloride. LCMS: $C_{30}H_{30}N_4O_7$, desired mass=566.7, found: m/z=567.8 $[M+H]^+$.

Intermediate 33

1-((1R,4R)-4-((5-(2,6-dioxopiperidin-3-yl)pyridin-3-yl)amino)cyclohexane-1-carbonyl)piperidine-4-carboxylic acid

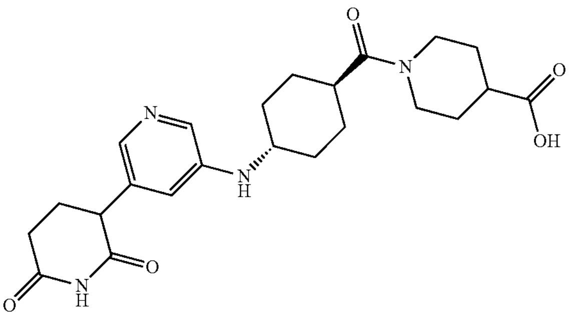 [SMILES: O=C1CCC(c2cncc(N[C@H]3CC[C@H](C(=O)N4CCC(C(=O)O)CC4)CC3)c2)C(=O)N1]

Step 1: tert-butyl 1-((1r,4r)-4-((4-(2,6-dioxopiperidin-3-yl)pyridin-2-yl)amino)cyclohexane-1-carbonyl)piperidine-4-carboxylate

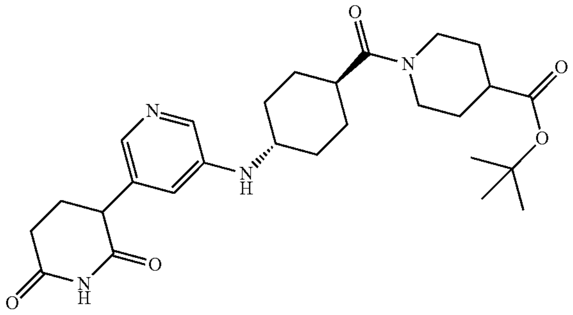 [SMILES: CC(C)(C)OC(=O)C1CCN(C(=O)[C@H]2CC[C@H](Nc3cncc(C4CCC(=O)NC4=O)c3)CC2)CC1]

Prepared by similar procedures as Intermediate 5 (step 1) using (1r,4r)-4-((4-(2,6-dioxopiperidin-3-yl)pyridin-2-yl)amino)cyclohexane-1-carboxylic acid (60 mg, 0.18 mmmol) and tert-butyl piperidine-4-carboxylate (44 mg, 0.24 mmol) as starting materials. The title compound (TFA salt) was isolated as an off-white solid (80 mg, 889% yield). LCMS: $[C_{27}H_{38}N_4O_5]$, desired mass=498.6, found: m/z=499.7 $[M+H]^+$.

Step 2: 1-((1r,4r)-4-((5-(2,6-dioxopiperidin-3-yl)pyridin-3-yl)amino)cyclohexane-1-carbonyl)piperidine-4-carboxylic acid

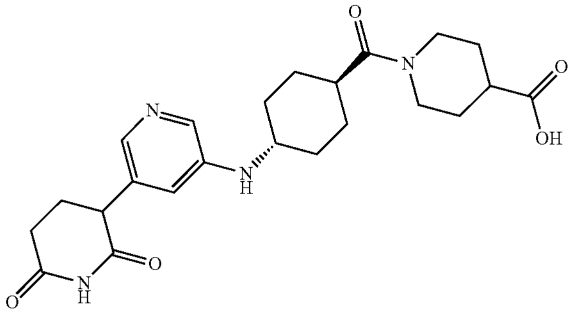 [SMILES: O=C1CCC(c2cncc(N[C@H]3CC[C@H](C(=O)N4CCC(C(=O)O)CC4)CC3)c2)C(=O)N1]

Prepared by similar procedures as Intermediate 5 (step 2) using tert-butyl 1-((1r,4r)-4-((4-(2,6-dioxopiperidin-3-yl)pyridin-2-yl)amino)cyclohexane-1-carbonyl)piperidine-4-carboxylate (80 mg, 0.16 mmol) as the starting material. The title compound (TFA salt) was isolated as an off-white solid (60 mg, 85% yield). LCMS: $[C_{23}H_{30}N_4O_5]$, desired mass=442.5, found: m/z=443.4 $[M+H]^+$.

Intermediate 34

1-((1R,4R)-4-(4-(2,6-dioxopiperidin-3-yl)phenoxy)cyclohexane-1-carbonyl)piperidine-4-carboxylic acid

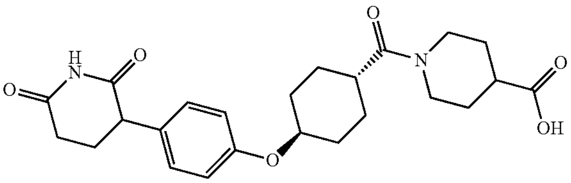 [SMILES: O=C1CCC(c2ccc(O[C@H]3CC[C@H](C(=O)N4CCC(C(=O)O)CC4)CC3)cc2)C(=O)N1]

Step 1: tert-butyl 1-[(1r,4r)-4-[4-(2,6-dioxopiperidin-3-yl)phenoxy]cyclohexanecarbonyl]piperidine-4-carboxylate

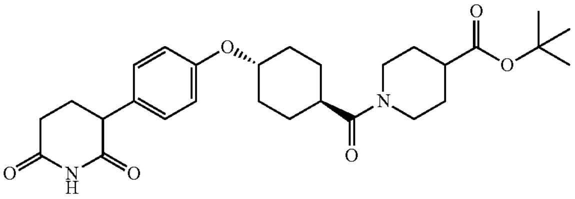 [SMILES: CC(C)(C)OC(=O)C1CCN(C(=O)[C@H]2CC[C@H](Oc3ccc(C4CCC(=O)NC4=O)cc3)CC2)CC1]

To a solution of (1r,4r)-4-(4-(2,6-dioxopiperidin-3-yl)phenoxy)cyclohexane-1-carboxylic acid (Intermediate 52) (0.504 g, 1.48 mmol) in DMF (2.5 mL) were added HATU (0.675 g, 1.78 mmol) and N,N-diisopropylethylamine (0.5 mL, 2.96 mmol). The reaction mixture was stirred for 0.5 h at room temperature, followed by addition of 4-piperidinecarboxylic acid t-butyl ester hydrochloride salt (0.328 g, 1.48 mmol) and DIPEA (0.5 mL, 2.96 mmol) in DMF (2.5 mL) at room temperature. The reaction mixture was stirred overnight at room temperature, and then was diluted ten-fold with water and extracted 3 times with DCM. The combined organic layers were washed with saturated aq $NaHCO_3$, brine, dried over $Na_2SO_4$, and concentrated in vacuo. The residue was purified by silica gel chromatography using a mobile phase of hexane and EtOAc to provide 0.62 g (75% yield) of the title compound as a yellow solid. LCMS: $C_{28}H_{38}N_2O_6$, desired mass=498.6, found: m/z=499.2 $[M+H]^+$.

Step 2: 1-[(1r,4r)-4-[4-(2,6-dioxopiperidin-3-yl)phenoxy]cyclohexanecarbonyl]piperidine-4-carboxylic acid

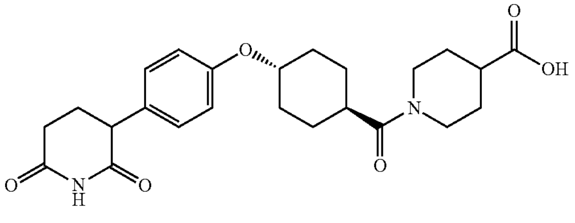 [SMILES: O=C1CCC(c2ccc(O[C@H]3CC[C@H](C(=O)N4CCC(C(=O)O)CC4)CC3)cc2)C(=O)N1]

To a solution of tert-butyl 1-[(1r,4r)-4-[4-(2,6-dioxopiperidin-3-yl)phenoxy]cyclohexanecarbonyl]piperidine-4-carboxylate (0.57 g, 1.14 mmol) in anh. DCM (11.4 mL) was added 4 M HCl in dioxane (11.4 mL, 45.7 mmol) at room temperature. The reaction mixture was stirred overnight at room temperature, and then the solvent was removed in vacuo. The residue was purified by prep-HPLC to provide 0.13 g (26% yield) of the title compound as a white powder. LCMS: $C_{24}H_{30}N_2O_6$, desired mass=442.512, found: m/z=442.98 $[M+H]^+$.

Intermediate 35

(1R,4R)-4-((5-(2,6-dioxopiperidin-3-yl)-2H-indazol-2-yl)methyl)cyclohexane-1-carboxylic acid

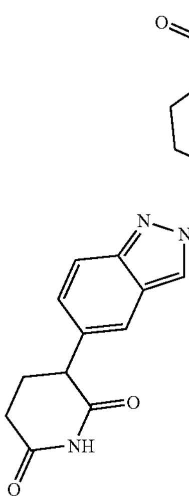

Step 1: 5-(2,6-bis(benzyloxy)pyridin-3-yl)-1H-indazole

To a 100 mL flask was added 5-bromo-1H-indazole (2.00 g, 10.2 mmol, 1.00 eq), 2,6-bis(benzyloxy)-3-(4,4,5,5-tetramethyl-1,3,2-dioxaborolan-2-yl)pyridine (4.45 g, 10.6 mmol, 1.05 eq), dioxane (20.0 mL), $H_2O$ (4.00 mL), $K_2CO_3$ (2.81 g, 20.3 mmol, 2.00 eq), and $Pd(dppf)Cl_2 \cdot CH_2Cl_2$ (829 mg, 1.02 mmol, 0.10 eq). The reaction mixture was stirred at 100° C. for 16 h. The reaction mixture was then concentrated under reduced pressure, and the resulting residue was purified by column chromatography ($SiO_2$, petroleum ether/Ethyl acetate=20/1 to 3/1, Petroleum ether/Ethyl acetate=2/1, $R_f$=0.55) to yield the title compound as a yellow solid (3.10 g, 74%). LCMS: $[C_{26}H_{21}N_3O_2]$, desired mass=407.2, found: m/z=408.1 $[M+H]^+$.

Step 2: methyl (1r,4r)-4-((5-(2,6-bis(benzyloxy)pyridin-3-yl)-2H-indazol-2-yl)methyl)cyclohexane-1-carboxylate To a 100 mL flask was added methyl (1r,4r)-4-(((methylsulfonyl)oxy)methyl)cyclohexane-1-carboxylate (3.10 g, 7.49 mmol, 1.00 eq), $K_2CO_3$ (3.10 g, 22.4 mmol, 3.00 eq), DMF (30.0 mL). To the reaction mixture was added 5-(2,6-bis(benzyloxy)pyridin-3-yl)-1H-indazole (3.75 g, 15.0 mmol, 2.00 eq). The reaction mixture was stirred at 70° C. for 16 h then filtered. The resulting filtrate was purified by prep-HPLC (column: YMC Triart C18 250*80 mm*7 um; mobile phase: [water ($NH_4HCO_3$)-ACN]; B %: 75%-95%, 22 mins) to yield the title compound (1.20 g, 28%). LCMS: $[C_{35}H_{35}N_3O_4]$, desired mass=561.3, found: m/z=562.2 $[M+H]^+$.

Step 3: (1r,4r)-4-((5-(2,6-bis(benzyloxy)pyridin-3-yl)-2H-indazol-2-yl)methyl)cyclohexane-1-carboxylic acid To a 100 mL flask was added (1r,4r)-4-((5-(2,6-bis(benzyloxy)pyridin-3-yl)-2H-indazol-2-yl)methyl)cyclohexane-1-carboxylate (1.20 g, 2.12 mmol, 99.3% purity, 1.00 eq), THF (12.0 mL), MeOH (12.0 mL), $H_2O$ (12.0 mL), $LiOH \cdot H_2O$ (178 mg, 4.24 mmol, 2.00 eq). The reaction mixture was stirred at 25° C. for 16 h, then concentrated. The resulting residue was dissolved in water (20 mL), and the pH was adjusted to 2~3 with 1.0 N HCl (5.00 mL). The resulting precipitate was filtered and washed with water (3×10 mL). The filter cake was dried under reduced pressure to yield the title compound as a white solid (0.90 g, 78%). LCMS: $[C_{34}H_{33}N_3O_4]$, desired mass=547.3, found: m/z=548.2 $[M+H]^+$.

Step 4: (1r,4r)-4-((5-(2,6-dioxopiperidin-3-yl)-2H-indazol-2-yl)methyl)cyclohexane-1-carboxylic acid To a 100 mL flask was added (1r,4r)-4-((5-(2,6-bis(benzyloxy)pyridin-3-yl)-2H-indazol-2-yl)methyl)cyclohexane-1-carboxylic acid (0.90 g, 1.63 mmol, 1.00 eq), Pd/C (225 mg, 10.0% purity), $Pd(OH)_2$ (225 mg, 20.0% purity), EtOH (22.5 mL), and THF (22.5 mL). The reaction mixture was stirred under $H_2$ atmosphere (15 psi) for 4 h. The reaction mixture was filtered through celite, and the resulting filtrate was concentrated under reduced pressure. The resulting residue was purified by prep-HPLC (column: YMC Triart C18 250*50 mm*7 um; mobile phase: [water (HCl)-ACN]; B %: 22%-52%, 10 mins) to yield the title compound as a red-brown solid (0.37 g, 59%). LCMS: $[C_{20}H_{23}N_3O_4]$, desired mass=369.2, found: m/z=370.1 $[M+H]^+$. $^1H$ NMR (400 MHz, DMSO-$d_6$) δ 10.8 (s, 1H), 8.31 (s, 1H), 7.56 (d, J=8.8 Hz, 1H), 7.51 (s, 1H), 7.11-7.09 (m, 1H), 4.26 (d, J=7.2 Hz, 2H), 3.93-3.89 (m, 1H), 2.72-2.55 (m, 1H), 2.53-2.52 (m, 1H), 2.40-2.30 (m, 1H), 2.13-2.08 (m, 2H), 1.89-1.87 (m, 3H), 1.56-1.54 (m, 2H), 1.27-1.23 (m, 2H), 1.07-1.06 (m, 2H).

Intermediate 36

(1R,4R)-4-((5-(2,6-dioxopiperidin-3-yl)-1H-indazol-1-yl)methyl)cyclohexane-1-carboxylic acid

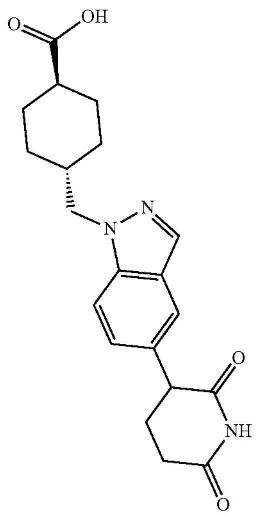 [SMILES: O=C1CCC(c2ccc3c(cnn3C[C@H]3CC[C@H](C(=O)O)CC3)c2)C(=O)N1]

The title compound was prepared using procedures similar to Intermediate 35, using methyl (1r,4r)-4-((5-(2,6-bis(benzyloxy)pyridin-3-yl)-1H-indazol-1-yl)methyl)cyclohexane-1-carboxylate. LCMS: [$C_{20}H_{23}N_3O_4$], desired mass=369.2, found: m/z=370.1 $[M+H]^+$. $^1H$ NMR (400 MHz, DMSO-$d_6$) δ 8.00 (s, 1H), 7.62 (d, J=8.8 Hz, 1H), 7.57 (s, 1H), 7.23 (d, J=8.4 Hz, 1H), 4.23 (d, J=7.2 Hz, 2H), 3.97-3.93 (m, 1H), 2.69-2.54 (m, 1H), 2.53-2.52 (m, 1H), 2.40-2.30 (m, 1H), 2.06-2.04 (m, 2H), 1.85-1.82 (m, 3H), 1.54-1.52 (m, 2H), 1.21-1.15 (m, 2H), 1.06-1.03 (m, 2H).

Intermediate 37

(3S)-1-(5-(2,6-dioxopiperidin-3-yl)pyridin-2-yl)pyrrolidine-3-carboxylic acid

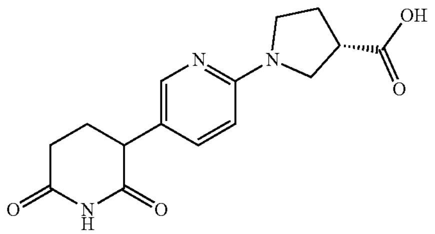 [SMILES: O=C1CCC(c2ccc(N3CC[C@H](C(=O)O)C3)nc2)C(=O)N1]

3-(6-fluoropyridin-3-yl)piperidine-2,6-dione (100.00 mg, 0.48 mmol), (3S)-1-(5-(2,6-dioxopiperidin-3-yl)pyridin-2-yl)pyrrolidine-3-carboxylic acid (110.60 mg, 0.96 mmol), N,N-diisopropylethylamine (0.34 mL, 248.32 mg, 1.92 mmol), and DMSO (1.00 mL) were combined in a microwave vial and irradiated at 140° C. for 2 hours. The product was isolated by reverse phase flash column chromatography to afford the title compound (57 mg, 31% yield).

Intermediate 38

1-(1-(4-(2,6-dioxopiperidin-3-yl)phenyl)piperidine-4-carbonyl)piperidine-4-carboxylic acid

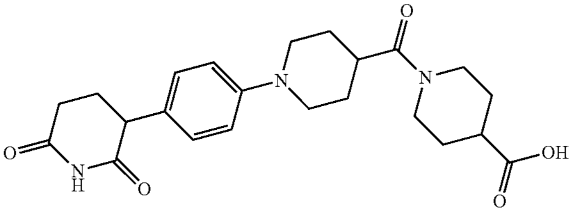 [SMILES: O=C1CCC(c2ccc(N3CCC(C(=O)N4CCC(C(=O)O)CC4)CC3)cc2)C(=O)N1]

Step 1: tert-butyl 1-(1-(4-(2,6-dioxopiperidin-3-yl)phenyl)piperidine-4-carbonyl)piperidine-4-carboxylate

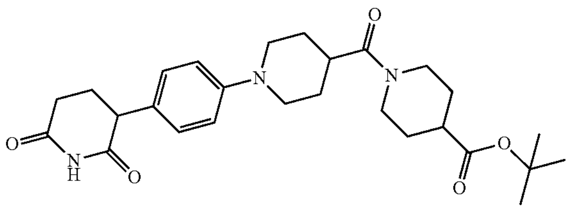 [SMILES: CC(C)(C)OC(=O)C1CCN(C(=O)C2CCN(c3ccc(C4CCC(=O)NC4=O)cc3)CC2)CC1]

The title compound was synthesized using similar methods to Intermediate 11, using BOP coupling. Afforded a white powder (112 mg, 0.231 mmol) as a free base. LCMS: [$C_{27}H_{37}N_3O_5$], desired mass=483.2, found: m/z=485.5 $[M+H]^+$.

Step: 2: 1-(1-(4-(2,6-dioxopiperidin-3-yl)phenyl)piperidine-4-carbonyl)piperidine-4-carboxylic acid

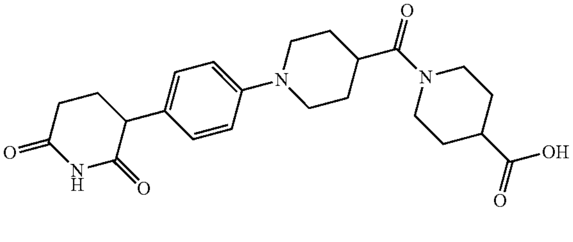 [SMILES: O=C1CCC(c2ccc(N3CCC(C(=O)N4CCC(C(=O)O)CC4)CC3)cc2)C(=O)N1]

The title compound was synthesized using similar methods to Intermediate 11 using TFA. LCMS: [$C_{23}H_{29}N_3O_5$], desired mass=427.2, found: m/z=429.2 $[M+H]^+$.

Intermediate 39

1-(1-(4-(2,4-dioxotetrahydropyrimidin-1(2H)-yl)phenyl)piperidine-4-carbonyl)piperidine-4-carboxylic acid

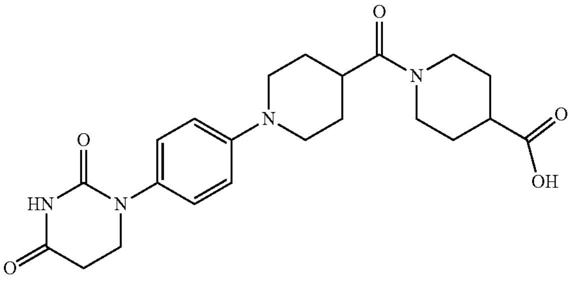

Step 1: tert-butyl 1-(1-(4-(2,4-dioxotetrahydropyrimidin-1(2H)-yl)phenyl)piperidine-4-carbonyl)piperidine-4-carboxylate

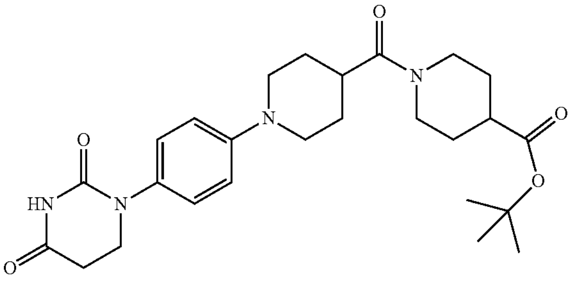

Prepared by similar procedures as Intermediate 5 (step 1) using 1-(4-(2,4-dioxotetrahydropyrimidin-1(2H)-yl)phenyl)piperidine-4-carboxylic acid (80 mg, 0.25 mmmol) and tert-butyl piperidine-4-carboxylate (47 mg, 0.25 mmol) as starting materials. The title compound (TFA salt) was isolated as an off-white solid (90 mg, 74% yield). LCMS: [$C_{26}H_{36}N_4O_5$], desired mass=484.6, found: m/z=485.5 $[M+H]^+$.

Step 2: 1-(1-(4-(2,4-dioxotetrahydropyrimidin-1(2H)-yl)phenyl)piperidine-4-carbonyl)piperidine-4-carboxylic acid

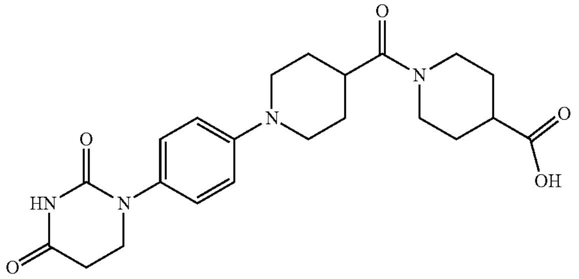 [SMILES: O=C1CCN(c2ccc(N3CCC(C(=O)N4CCC(C(=O)O)CC4)CC3)cc2)C(=O)N1]

Prepared by similar procedures as Intermediate 5 (step 2) using 1-(4-(2,4-dioxotetrahydropyrimidin-1(2H)-yl)phenyl)piperidine-4-carboxylic acid (90 mg, 0.16 mmol) as the starting material. The title compound (TFA salt) was isolated as an off-white solid (60 mg, 75% yield). LCMS: [$C_{22}H_{28}N_4O_5$], desired mass=428.5, found: m/z=429.4 $[M+H]^+$.

Intermediate 40

1-(1-{5-[2,6-dioxopiperidin-3-yl]pyridin-2-yl}piperidine-4-carbonyl)piperidine-4-carboxylic acid

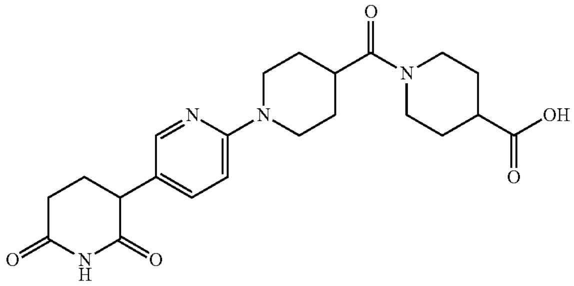 [SMILES: O=C1CCC(c2ccc(N3CCC(C(=O)N4CCC(C(=O)O)CC4)CC3)nc2)C(=O)N1]

Step-1: tert-butyl 1-{1-[5-(2,6-dioxopiperidin-3-yl)pyridin-2-yl]piperidine-4-carbonyl}piperidine-4-carboxylate

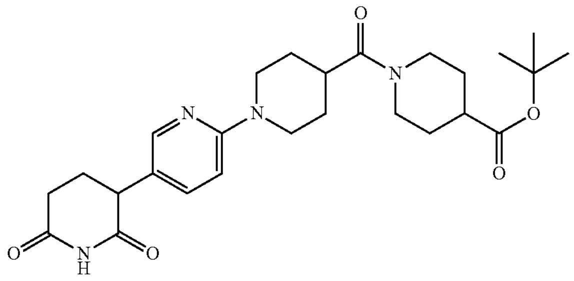 [SMILES: CC(C)(C)OC(=O)C1CCN(C(=O)C2CCN(c3ccc(C4CCC(=O)NC4=O)cn3)CC2)CC1]

To a mixture of 1-[5-(2,6-dioxopiperidin-3-yl)pyridin-2-yl]piperidine-4-carboxylic acid (70 mg, 0.221 mmol, 1 equiv) in DMF (4 mL) was added tert-butyl piperidine-4-carboxylate (40 mg, 0.221 mmol) at room temperature. The resulting mixture was stirred at room temperature for 30 min. To the above mixture was added were added DIEA (142 mg, 1.105 mmol) and BOP (126 mg, 0.287 mmol). The resulting mixture was stirred at room temperature for 2 h. The resulting mixture was purified by reverse phase flash chromatography of [$CH_3CN$ and $H_2O$] to provide 75 mg (66.66%) of the title compound as a light brown solid. LCMS: ($C_{26}H_{36}N_4O_5$) desired mass=484.3; found: m/z=485.2 $[M+H]^+$.

Step 2: 1-(1-{5-[2,6-dioxopiperidin-3-yl]pyridin-2-yl}piperidine-4-carbonyl)piperidine-4-carboxylic acid

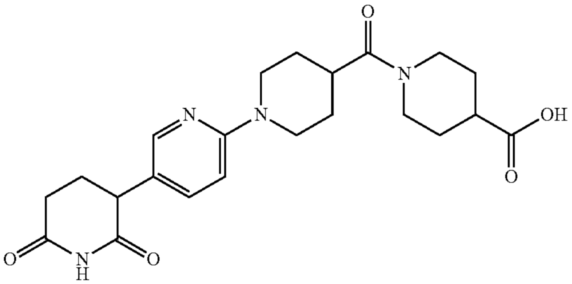 [SMILES: O=C1CCC(c2ccc(N3CCC(C(=O)N4CCC(C(=O)O)CC4)CC3)nc2)C(=O)N1]

Procedures similar to those in step 3 of Intermediate 15 were followed using tert-butyl 1-{1-[5-(2,6-dioxopiperidin-3-yl)pyridin-2-yl]piperidine-4-carbonyl}piperidine-4-carboxylate (75 mg, 0.155 mmol) and HCl/dioxane (3 mL, 4M). The residue was purified by reverse phase flash chromatography of [$CH_3CN$ and $H_2O$] to provide 53.8 mg (75.37%) of the title compound as a light yellow solid. LCMS (Method 4): ($C_{22}H_{28}N_4O_5$) desired mass=428.2; found: m/z=429.2 $[M+H]^+$.

Intermediate 41

1-(1-(5-(2,4-dioxotetrahydropyrimidin-1(2H)-yl)pyridin-2-yl)piperidine-4-carbonyl)piperidine-4-carboxylic acid

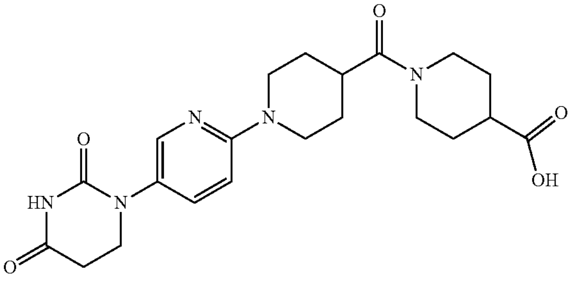

Step 1: tert-butyl 1-(1-(5-(2,4-dioxotetrahydropyrimidin-1(2H)-yl)pyridin-2-yl)piperidine-4-carbonyl)piperidine-4-carboxylate

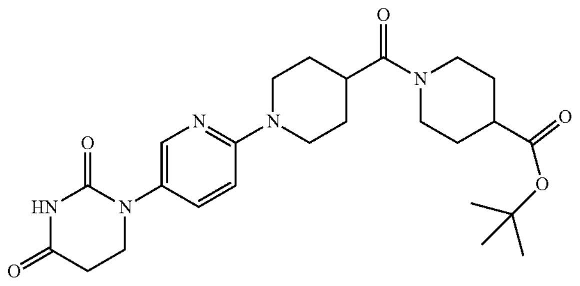 [SMILES: CC(C)(C)OC(=O)C1CCN(C(=O)C2CCN(c3ccc(N4CCC(=O)NC4=O)cn3)CC2)CC1]

Prepared by similar procedures as Intermediate 5 (step 1) using 1-(5-(2,4-dioxotetrahydropyrimidin-1(2H)-yl)pyridin-2-yl)piperidine-4-carboxylic acid ((150 mg, 0.47 mmol) and tert-butyl piperidine-4-carboxylate (87 mg, 0.47 mmol) as starting materials. The title compound (TFA salt) was isolated as an off-white solid (100 mg, 44% yield). LCMS: [$C_{25}H_{35}N_5O_5$], desired mass=485.6, found: m/z=486.3 $[M+H]^+$.

Step 2: 1-(1-(5-(2,4-dioxotetrahydropyrimidin-1(2H)-yl)pyridin-2-yl)piperidine-4-carbonyl)piperidine-4-carboxylic acid

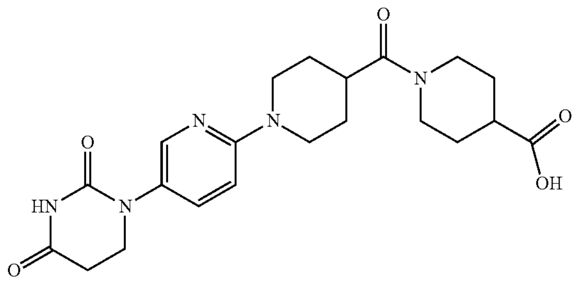 [SMILES: O=C1CCN(c2ccc(N3CCC(C(=O)N4CCC(C(=O)O)CC4)CC3)nc2)C(=O)N1]

Prepared by similar procedures as Intermediate 5 (step 2) using tert-butyl 1-(1-(5-(2,4-dioxotetrahydropyrimidin-1(2H)-yl)pyridin-2-yl)piperidine-4-carbonyl)piperidine-4-carboxylate (100 mg, 0.21 mmol) as starting materials. The title compound (TFA salt) was isolated as an off-white solid (54 mg, 61% yield). LCMS: [$C_{21}H_{27}N_5O_5$], desired mass=429.4, found: m/z=430.3 $[M+H]^+$.

Intermediate 42

1-(6-(2,6-dioxopiperidin-3-yl)pyridin-3-yl)piperidine-4-carboxylic acid

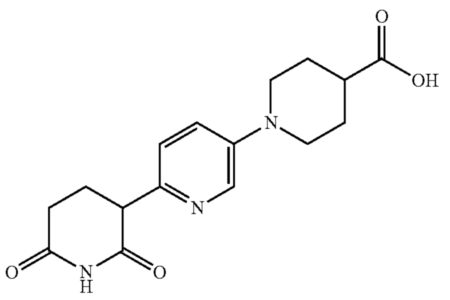 [SMILES: O=C1CCC(c2ccc(N3CCC(C(=O)O)CC3)cn2)C(=O)N1]

Step 1: tert-butyl 1-(6-chloropyridin-3-yl)piperidine-4-carboxylate

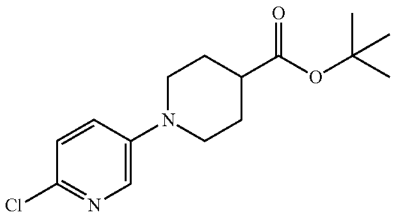 [SMILES: CC(C)(C)OC(=O)C1CCN(c2ccc(Cl)nc2)CC1]

To a mixture of 5-bromo-2-chloropyridine (40 g, 207.857 mmol) and tert-butyl piperidine-4-carboxylate (50.06 g, 270.214 mmol) in dioxane (30 mL) was added XantPhos (24.05 g, 41.571 mmol), $Pd_2(dba)_3$ (19.03 g, 20.786 mmol) and t-BuONa (59.93 g, 623.571 mmol) at 0° C. under nitrogen atmosphere. The resulting mixture was stirred for 2 h at 100° C. under nitrogen atmosphere. The resulting mixture was concentrated under reduced pressure. The residue was purified by silica gel chromatography [PE and EA mobile phase] to provide 14.7 g (21.54%) of the title compound as a yellow solid. LCMS: ($C_{15}H_{21}ClN_2O_2$) desired mass=296.1; found: m/z=297.1$[M+H]^+$.

Step 2: tert-butyl 1-[2',6'-bis(benzyloxy)-[2,3'-bipyridin]-5-yl]piperidine-4-carboxylate

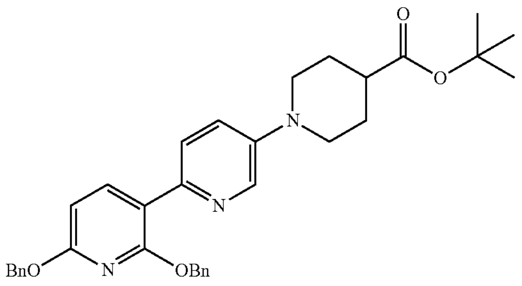 [SMILES: CC(C)(C)OC(=O)C1CCN(c2ccc(-c3ccc(OCc4ccccc4)nc3OCc3ccccc3)nc2)CC1]

To a mixture of tert-butyl 1-(6-chloropyridin-3-yl)piperidine-4-carboxylate (14.5 g, 48.854 mmol) and 2,6-bis(benzyloxy)-3-(4,4,5,5-tetramethyl-1,3,2-dioxaborolan-2-yl)pyridine (50.97 g, 122.135 mmol) in THF (30 mL) and $H_2O$ (10 mL) was added $Pd(PPh_3)_4$ (5.65 g, 4.885 mmol) and $K_2CO_3$ (13.50 g, 97.708 mmol) at room temperature under nitrogen atmosphere. The resulting mixture was stirred overnight at 110° C. under nitrogen atmosphere. The resulting mixture was concentrated under reduced pressure. The residue was purified by silica gel chromatography [PE and EA mobile phase] to provide 3.4 g (11.35%) of the title compound as a yellow solid. LCMS: ($C_{34}H_{37}N_3O_4$) desired mass=551.3; found: m/z=552.2 $[M+H]^+$.

Step 3: tert-butyl 1-[6-(2,6-dioxopiperidin-3-yl)pyridin-3-yl]piperidine-4-carboxylate

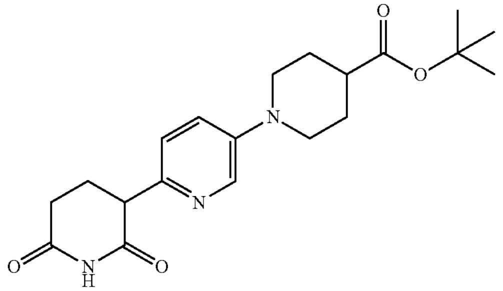 [SMILES: CC(C)(C)OC(=O)C1CCN(c2ccc(C3CCC(=O)NC3=O)nc2)CC1]

To a mixture of tert-butyl 1-[2',6'-bis(benzyloxy)-[2,3'-bipyridin]-5-yl]piperidine-4-carboxylate (3.2 g, 5.800 mmol) in THF (10 mL) was added Pd/C (6.4 g). The resulting mixture was stirred overnight at room temperature under hydrogen atmosphere. The resulting mixture was filtered, the filter cake was washed with THF. The filtrate was concentrated under reduced pressure to provide 860 mg (crude) of the title compound as a white crude solid. LCMS: ($C_{20}H_{27}N_3O_4$) desired mass=373.2; found: m/z=374.2 $[M+H]^+$.

Step 4: 1-(6-(2,6-dioxopiperidin-3-yl)pyridin-3-yl)piperidine-4-carboxylic acid

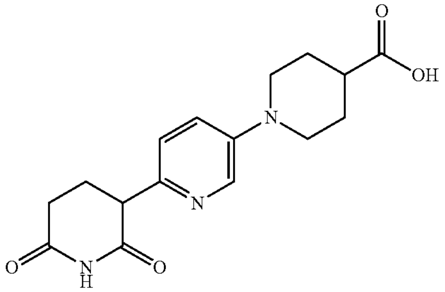 [SMILES: O=C1CCC(c2ccc(N3CCC(C(=O)O)CC3)cn2)C(=O)N1]

A procedure similar to Intermediate 21 (step 3) was used with tert-butyl 1-[6-(2,6-dioxopiperidin-3-yl)pyridin-3-yl]piperidine-4-carboxylate (860 mg, 2.303 mmol) and HCl/1,4-dioxane (5 mL, 4M). The residue was purified by reverse phase flash chromatography [ACN and $H_2O$ mobile phase] to yield 496 mg (63.60%) of the title compound as a brown solid. LCMS: ($C_{16}H_{19}N_3O_4$) desired mass=317.1; found: m/z=317.9 $[M+H]^+$.

Intermediate 43

1-(1-(6-(2,6-dioxopiperidin-3-yl)pyridin-3-yl)piperidine-4-carbonyl)piperidine-4-carboxylic acid

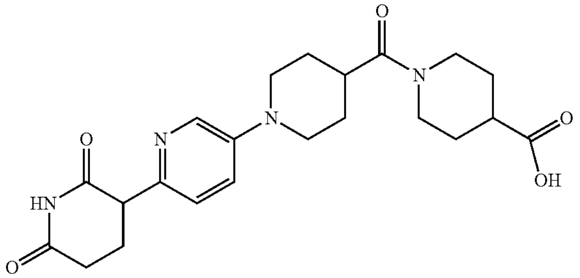 [SMILES: O=C1CCC(c2ccc(N3CCC(C(=O)N4CCC(C(=O)O)CC4)CC3)cn2)C(=O)N1]

Step 1: tert-butyl 1-(1-(6-(2,6-dioxopiperidin-3-yl)pyridin-3-yl)piperidine-4-carbonyl)piperidine-4-carboxylate

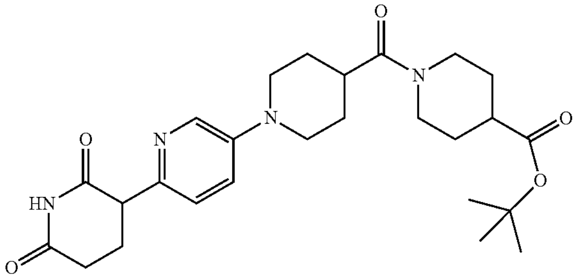 [SMILES: CC(C)(C)OC(=O)C1CCN(C(=O)C2CCN(c3ccc(C4CCC(=O)NC4=O)nc3)CC2)CC1]

Prepared by similar procedures as Intermediate 5 (step 1) using 1-(6-(2,6-dioxopiperidin-3-yl)pyridin-3-yl)piperidine-4-carboxylic acid (120 mg, 0.38 mmmol) and tert-butyl piperidine-4-carboxylate (70 mg, 0.38 mmol) as starting materials. The title compound (TFA salt) was isolated as an off-white solid (80 mg, 44% yield). LCMS: $[C_{26}H_{36}N_4O_5]$, desired mass=484.5, found: m/z=485.3 $[M+H]^+$.

Step 2: 1-(1-(6-(2,6-dioxopiperidin-3-yl)pyridin-3-yl)piperidine-4-carbonyl)piperidine-4-carboxylic acid

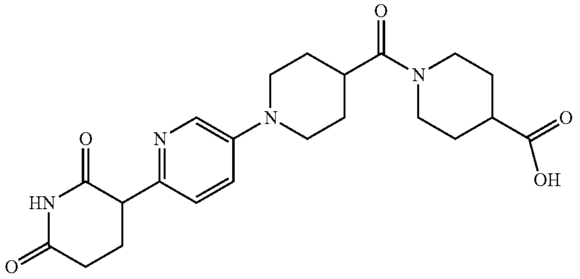 [SMILES: O=C1CCC(c2ccc(N3CCC(C(=O)N4CCC(C(=O)O)CC4)CC3)cn2)C(=O)N1]

Prepared by similar procedures as Intermediate 5 (step 2) using tert-butyl 1-(1-(6-(2,6-dioxopiperidin-3-yl)pyridin-3-yl)piperidine-4-carbonyl)piperidine-4-carboxylate (85 mg, 0.18 mmol) as the starting material. The title compound (TFA salt) was isolated as an off-white solid (60 mg, 80% yield). LCMS: $[C_{22}H_{28}N_4O_5]$, desired mass=428.5, found: m/z=429.3 $[M+H]^+$.

Intermediate 44

1-(1-(2-(2,6-dioxopiperidin-3-yl)-1,3-dioxoisoindolin-5-yl)piperidine-4-carbonyl)piperidine-4-carboxylic acid

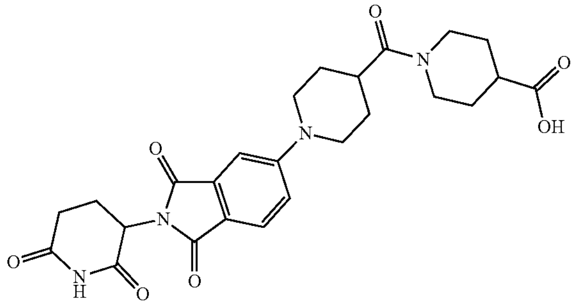 [SMILES: O=C1CCC(N2C(=O)c3ccc(N4CCC(C(=O)N5CCC(C(=O)O)CC5)CC4)cc3C2=O)C(=O)N1]

BOP mediated coupling of 1-(2-(2,6-dioxopiperidin-3-yl)-1,3-dioxoisoindolin-5-yl)piperidine-4-carboxylic acid (10 mg, 0.03 mmol, Intermediate 18) and tert-butyl piperidine-4-carboxylate (4.9 mg, 0.03 mmol) using conditions similar to those used for tert-butyl (3R)-1-(1-(5-(2,6-dioxopiperidin-3-yl)pyridin-2-yl)piperidine-4-carbonyl)pyrrolidine-3-carboxylate (Intermediate 11, step 3), followed by concentration and treatment with HCl (4N in dioxane, 1 mL) overnight, and then concentration and purification by reverse phase column chromatography (mobile phase of ACN and $H_2O$) afforded the title compound as an off-white solid (11 mg, 78% yield).

Intermediate 45

1-(1-(6-(2,6-dioxopiperidin-3-yl)pyridin-3-yl)piperidine-4-carbonyl)piperidine-4-carboxylic acid

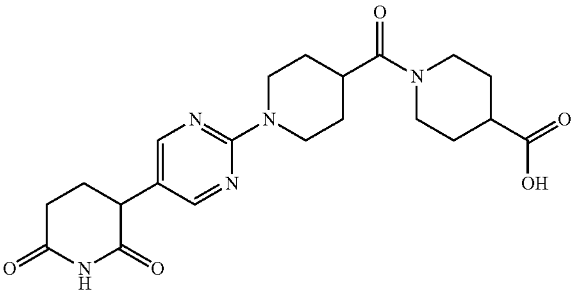 [SMILES: O=C1CCC(c2cnc(N3CCC(C(=O)N4CCC(C(=O)O)CC4)CC3)nc2)C(=O)N1]

Step 1: Synthesis tert-butyl 1-(1-(5-(2,6-dioxopiperidin-3-yl)pyrimidin-2-yl)piperidine-4-carbonyl) piperidine-4-carboxylate

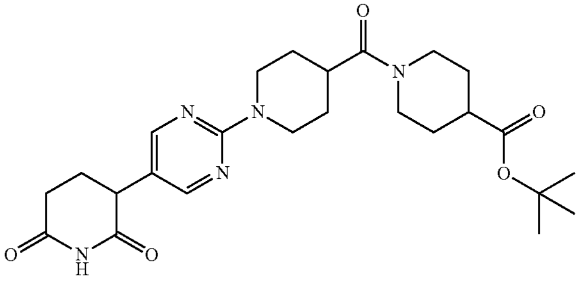 [SMILES: CC(C)(C)OC(=O)C1CCN(C(=O)C2CCN(c3ncc(C4CCC(=O)NC4=O)cn3)CC2)CC1]

Prepared by similar procedures as Intermediate 5 (step 1) using 1-(5-(2,6-dioxopiperidin-3-yl)pyrimidin-2-yl)piperidine-4-carboxylic acid (150 mg, 0.41 mmmol) and tert-butyl piperidine-4-carboxylate (131 mg, 0.71 mmol) as starting materials. The title compound (TFA salt) was isolated as an off-white solid (160 mg, 70% yield). LCMS: [$C_{25}H_{35}N_5O_5$], desired mass=484.5, found: m/z=485.3 $[M+H]^+$.

Step 2: 1-(1-(5-(2,6-dioxo-112-piperidin-3-yl)pyrimidin-2-yl)piperidine-4-carbonyl)piperidine-4-carboxylic acid

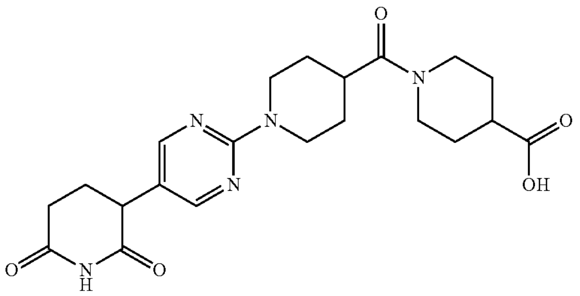 [SMILES: O=C1CCC(c2cnc(N3CCC(C(=O)N4CCC(C(=O)O)CC4)CC3)nc2)C(=O)N1]

Prepared by similar procedures as Intermediate 5 (step 2) using tert-butyl 1-(1-(5-(2,6-dioxopiperidin-3-yl)pyrimidin-2-yl)piperidine-4-carbonyl)piperidine-4-carboxylate (160 mg, 0.33 mmol) as the starting material. The title compound (TFA salt) was isolated as an off-white solid (140 mg, 79% yield). LCMS: [$C_{21}H_{27}N_5O_5$], desired mass=429.4, found: m/z=430.2 $[M+H]^+$.

Intermediate 46

1-(2-(1-(5-(2,6-dioxopiperidin-3-yl)pyridin-2-yl) piperidin-4-yl)acetyl)piperidine-4-carboxylic acid

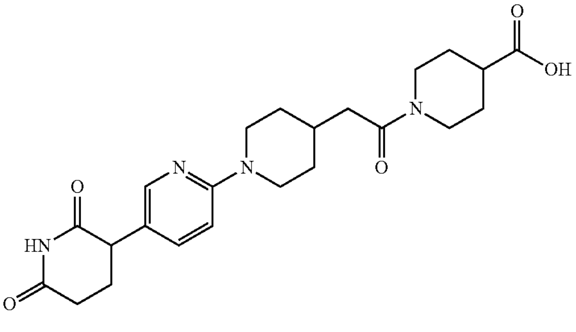 [SMILES: O=C1CCC(c2ccc(N3CCC(CC(=O)N4CCC(C(=O)O)CC4)CC3)nc2)C(=O)N1]

Step 1: tert-butyl 1-(2-(1-(5-(2,6-dioxopiperidin-3-yl)pyridin-2-yl)piperidin-4-yl)acetyl)piperidine-4-carboxylate

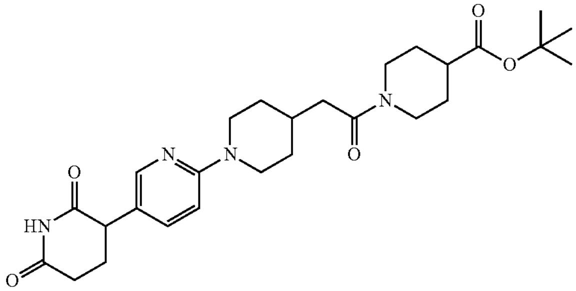

The title compound was synthesized using similar methods to intermediate 11, using BOP coupling. Afforded a white solid (320 mg, 0.642 mmol) as a free base. LCMS: [$C_{27}H_{35}N_4O_5$], exact mass=498.2, found: m/z=498.5 $[M+H]^+$.

Step 2: 1-(2-(1-(5-(2,6-dioxopiperidin-3-yl)pyridin-2-yl)piperidin-4-yl)acetyl)piperidine-4-carboxylic acid

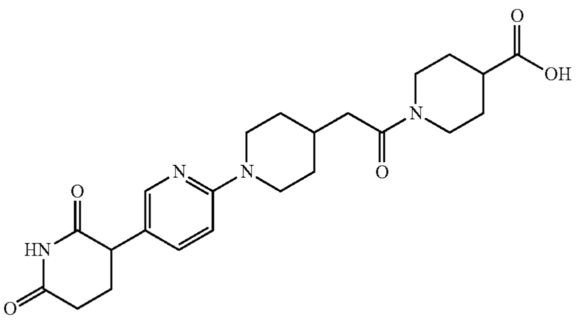 [SMILES: O=C1CCC(c2ccc(N3CCN(CC(=O)N4CCC(C(=O)O)CC4)CC3)nc2)C(=O)N1]

The title compound was synthesized using similar methods to intermediate 11 using TFA. Afforded a white solid (250 mg, 0.564 mmol) as a free base. LCMS: [$C_{23}H_{30}N_4O_5$], desired mass=442.2, found: m/z=443.3 $[M+H]^+$.

Intermediate 47

1-(2-(4-(5-(2,6-dioxopiperidin-3-yl)pyridin-2-yl)piperazin-1-yl)acetyl)piperidine-4-carboxylic acid

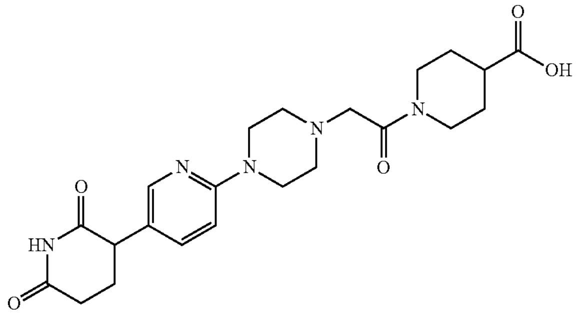

Step 1: tert-butyl 2-(4-(5-(2,6-dioxopiperidin-3-yl)pyridin-2-yl)piperazin-1-yl)acetate

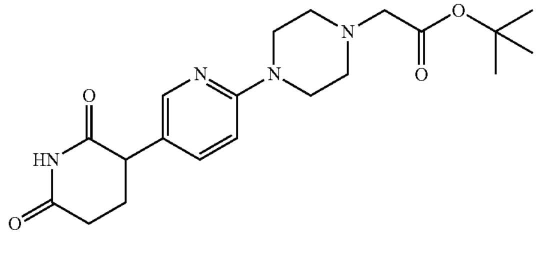 [SMILES: CC(C)(C)OC(=O)CN1CCN(c2ccc(C3CCC(=O)NC3=O)cn2)CC1]

To a solution tert-butyl 2-(piperazin-1-yl)acetate (285 mg, 1.44 mmol) and DIPEA (0.67 mL, 0.5 g, 3.84 mmol) in DMSO (1 mL) was added 3-(6-fluoropyridin-3-yl)piperidine-2,6-dione (200 mg, 0.96 mmol). The reaction mixture was stirred at 120° C. for 16 hours. At this time LCMS showed starting material had been consumed. The reaction mixture was cooled to room temperature and water was added. This crude mixture was purified by reverse phase FC (5-50% MeCN/H2O +0.1% TFA) to afford the title compound (TFA salt) as an off-white solid (330 mg, 88% yield). LCMS: [$C_{20}H_{28}N_4O_4$], desired mass=388.5, found: m/z=389.2 $[M+H]^+$.

Step 2: 2-(4-(5-(2,6-dioxopiperidin-3-yl)pyridin-2-yl)piperazin-1-yl)acetic acid

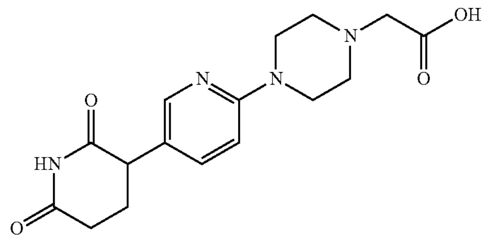 [SMILES: O=C(O)CN1CCN(c2ccc(C3CCC(=O)NC3=O)cn2)CC1]

Prepared by similar procedures as Intermediate 5 (step 2) tert-butyl 2-(4-(5-(2,6-dioxopiperidin-3-yl)pyridin-2-yl)piperazin-1-yl)acetate (330 mg, 0.85 mmol as the starting material. The title compound (TFA salt) was isolated as an off-white solid (260 mg, 92% yield). LCMS: [$C_{16}H_{20}N_4O_4$], desired mass=332.4, found: m/z=333.2 $[M+H]^+$.

Step 3: tert-butyl 1-(2-(4-(5-(2,6-dioxopiperidin-3-yl)pyridin-2-yl)piperazin-1-yl)acetyl)piperidine-4-carboxylate

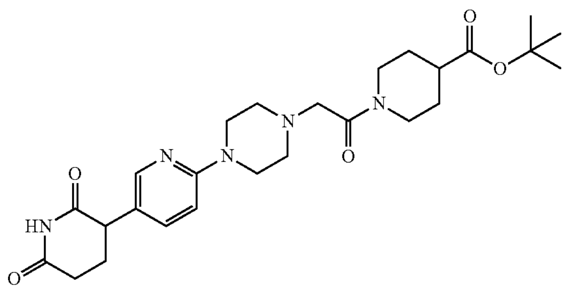 [SMILES: CC(C)(C)OC(=O)C1CCN(C(=O)CN2CCN(c3ccc(C4CCC(=O)NC4=O)cn3)CC2)CC1]

Prepared by similar procedures as Intermediate 5 (step 1) using 2-(4-(5-(2,6-dioxopiperidin-3-yl)pyridin-2-yl)piperazin-1-yl)acetic acid (300 mg, 0.9 mmol) and tert-butyl piperidine-4-carboxylate (334 mg, 1.8 mmol) as starting materials. The title compound (TFA salt) was isolated as an off-white solid (80 mg, 17% yield). LCMS: [$C_{26}H_{37}N_5O_5$], desired mass=499.6, found: m/z=500.3 $[M+H]^+$.

Step 4: 1-(2-(4-(5-(2,6-dioxopiperidin-3-yl)pyridin-2-yl)piperazin-1-yl)acetyl)piperidine-4-carboxylic acid

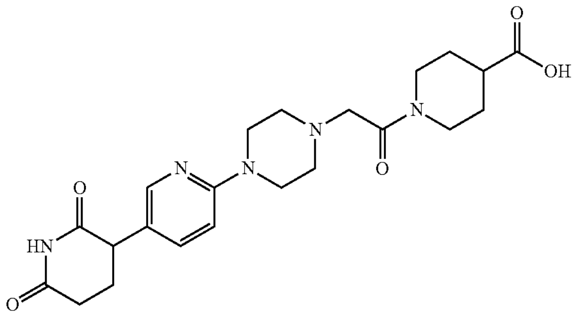 [SMILES: O=C1CCC(c2ccc(N3CCN(CC(=O)N4CCC(C(=O)O)CC4)CC3)nc2)C(=O)N1]

Prepared by similar procedures as Intermediate 5 (step 2) using tert-butyl 1-(2-(4-(5-(2,6-dioxopiperidin-3-yl)pyridin-2-yl)piperazin-1-yl)acetyl)piperidine-4-carboxylate: (80 mg, 0.16 mmol as the starting material. The title compound (TFA salt) was isolated as an off-white solid (65 mg, 91% yield). LCMS: $C_{22}H_{29}N_5O_5$ desired mass 443.5, found m/z=444.3 $[M+H]^+$.

Intermediate 48

1-(4-{5-[2,6-dioxopiperidin-3-yl]pyridin-2-yl}piperidine-1-carbonyl)piperidine-4-carboxylic acid

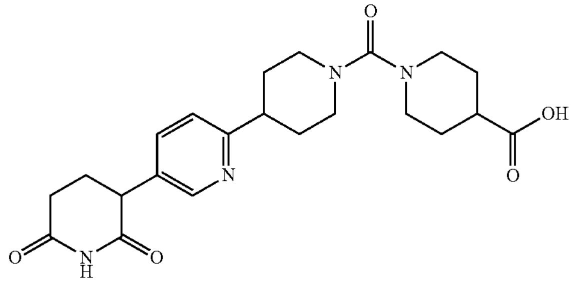 [SMILES: O=C1CCC(c2ccc(C3CCN(C(=O)N4CCC(C(=O)O)CC4)CC3)nc2)C(=O)N1]

Step-1: 5-[2,6-bis(benzyloxy)pyridin-3-yl]-1',2',3',6'-tetrahydro-2,4'-bipyridine

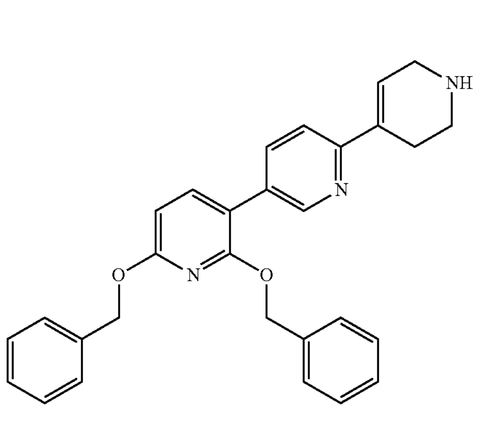 [SMILES: C1=C(c2ccc(-c3ccc(OCc4ccccc4)nc3OCc3ccccc3)cn2)CCNC1]

Procedures similar to those in step 3 of Intermediate 15 were followed using tert-butyl 5-[2,6-bis(benzyloxy)pyridin-3-yl]-3',6'-dihydro-2'H-[2,4'-bipyridine]-1'-carboxylate (500 mg, 0.910 mmol) and HCl/dioxane (10 mL, 4M). The reaction mixture was concentrated to provide 400 mg (crude) of the title compound as a light yellow solid. LCMS: ($C_{29}H_{27}N_3O_2$) desired mass=449.2; found: m/z=450.2 $[M+H]^+$.

Step-2: tert-butyl 1-{5-[2,6-bis(benzyloxy)pyridin-3-yl]-3',6'-dihydro-2'H-[2,4'-bipyridine]-'-carbonyl}piperidine-4-carboxylate

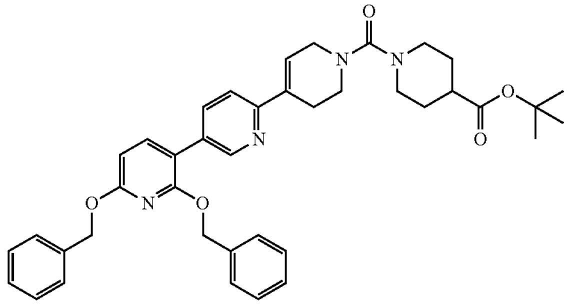 [SMILES: CC(C)(C)OC(=O)C1CCN(C(=O)N2CC=C(c3ccc(-c4ccc(OCc5ccccc5)nc4OCc4ccccc4)cn3)CC2)CC1]

To a mixture of tert-butyl piperidine-4-carboxylate hydrochloride (222 mg, 1.001 mmol) and DIEA (389 mg, 3.003 mmol) in DCM (20 mL) was added triphosgene (149 mg, 0.500 mmol). The reaction mixture was stirred for 15 min at 0° C. under nitrogen atmosphere followed by the addition of 5-[2,6-bis(benzyloxy)pyridin-3-yl]-1',2',3',6'-tetrahydro-2,4'-bipyridine (450 mg, 1.001 mmol) dropwise at 0° C. The resulting mixture was stirred overnight at 50° C. under nitrogen atmosphere. The resulting mixture was concentrated under reduced pressure. The residue was purified by silica gel chromatography using a mobile phase of [PE and EA] to provide 220 mg (29.93%) of the title compound as a yellow oil. LCMS: ($C_{40}H_{44}N_4O_5$) desired mass=660.3; found: m/z=661.3 $[M+H]^+$.

Step-3: tert-butyl 1-{4-[5-(2,6-dioxopiperidin-3-yl)pyridin-2-yl]piperidine-1-carbonyl}piperidine-4-carboxylate

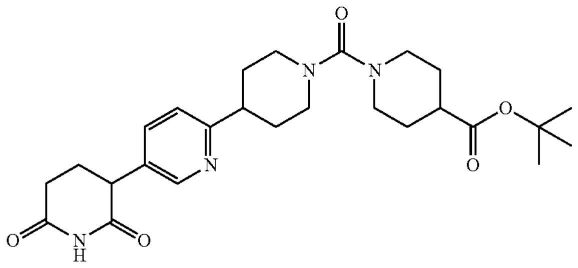 [SMILES: CC(C)(C)OC(=O)C1CCN(C(=O)N2CCC(c3ccc(C4CCC(=O)NC4=O)cn3)CC2)CC1]

Procedures similar to those in step 5 of Intermediate 15 were followed using tert-butyl 1-{5-[2,6-bis(benzyloxy)pyridin-3-yl]-3',6'-dihydro-2'H-[2,4'-bipyridine]-1'-carbonyl}piperidine-4-carboxylate (220 mg, 0.333 mmol) in EtOH (20 mL) and Pd/C (330 mg). This resulted in 100 mg (crude) of the title compound as a white solid. LCMS: ($C_{26}H_{36}N_4O_5$) desired mass=484.3; found: m/z=485.2 $[M+H]^+$.

Step-4: 1-(4-{5-[2,6-dioxopiperidin-3-yl]pyridin-2-yl}piperidine-1-carbonyl)piperidine-4-carboxylic acid

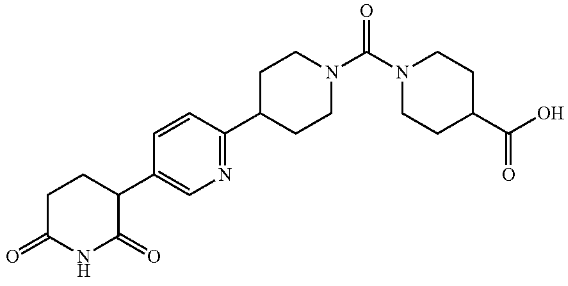 [SMILES: O=C1CCC(c2ccc(C3CCN(C(=O)N4CCC(C(=O)O)CC4)CC3)nc2)C(=O)N1]

Procedures similar to those in step 3 of Intermediate 15 were followed using tert-butyl 1-{4-[5-(2,6-dioxopiperidin-3-yl)pyridin-2-yl]piperidine-1-carbonyl}piperidine-4-carboxylate (90 mg, 0.186 mmol) in HCl/dioxane (10 mL, 4M). The residue was purified by reverse phase flash chromatography of [ACN and $H_2O$] to provide 31.4 mg (37.68%) of the title compound as a brown solid. LCMS (Method 5): ($C_{22}H_{28}N_4O_5$) desired mass=428.2; found: m/z=429.3 $[M+H]^+$.

Intermediate 49

2-(1-(5-(2,6-dioxopiperidin-3-yl)pyridin-2-yl)piperidin-4-yl)acetaldehyde

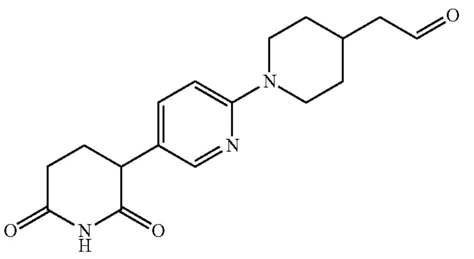 [SMILES: O=CCC1CCN(c2ccc(C3CCC(=O)NC3=O)cn2)CC1]

Step 1: 3-(6-(4-(2-hydroxyethyl)piperidin-1-yl)pyridin-3-yl)piperidine-2,6-dione To a 40 mL vial was added 3-(6-fluoropyridin-3-yl) piperidine-2,6-dione (1500.00 mg, 7.20 mmol), 4-piperidineethanol (977.44 mg, 7.57 mmol), N,N-diisopropylethylamine (5.03 mL, 3.72 g, 28.82 mmol), and DMSO (10.00 mL). Stirred at 130 C for 16 h. The reaction mixture was concentrated and the resulting residue was purified by reverse phase column chromatography (415 g C18 silica, 5-50% MeCN/H2O +0.1% TFA) to yield the title compound as an amorphous solid (2.10 g, 92%). LCMS: $[C_{17}H_{23}N_3O_3]$, desired mass=317.2, found: 318.2 $[M+H]^+$.

Step 2: 2-(1-(5-(2,6-dioxopiperidin-3-yl)pyridin-2-yl)piperidin-4-yl)acetaldehyde To a 40 mL vial was added 3-{6-[4-(2-hydroxyethyl) piperidin-1-yl]pyridin-3-yl}piperidine-2,6-dione; trifluoroacetic acid (1600.00 mg, 3.71 mmol) and DCM (30.00 mL).

The reaction mixture was cooled to 0° C., then 1,1-bis (acetyloxy)-3-oxo-1lambda5,2-benziodaoxol-1-yl acetate (1.73 g, 4.08 mmol) was added in one portion. After 10 min, the ice bath was removed, and the reaction mixture was stirred warming to RT for 1 h. 3 mL TEA was added to the reaction mixture, and the crude reaction mixture was adsorbed onto silica, then purified by column chromatography (80 g silica, 20-100% EtOAc+1% TEA/DCM) to yield the title compound as a white solid (278 mg, 47%). LCMS: $[C_{17}H_{21}N_3O_3]$, desired mass=315.2, found: m/z=316.2 $[M+H]^+$.

Intermediate 50

2-(1-(1-((2-(2,6-dioxopiperidin-3-yl)-1,3-dioxoisoindolin-4-yl)glycyl)piperidine-4-carbonyl)piperidin-4-yl)acetic acid

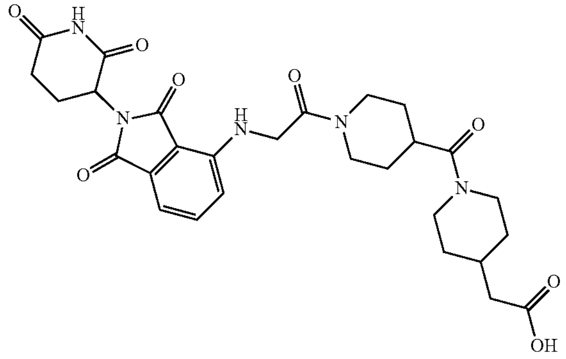 [SMILES: O=C(O)CC1CCN(C(=O)C2CCN(C(=O)CNc3cccc4c3C(=O)N(C3CCC(=O)NC3=O)C4=O)CC2)CC1]

Step 1: benzyl 1-((2-(2,6-dioxopiperidin-3-yl)-1,3-dioxoisoindolin-4-yl)glycyl)piperidine-4-carboxylate BOP mediated coupling of (2-(2,6-dioxopiperidin-3-yl)-1,3-dioxoisoindolin-4-yl)glycine (175 mg, 0.39 mmol) and benzyl piperidine-4-carboxylate (86 mg, 0.39 mmol) using conditions similar to those used for tert-butyl (3R)-1-(1-(5-(2,6-dioxopiperidin-3-yl)pyridin-2-yl)piperidine-4-carbonyl)pyrrolidine-3-carboxylate (intermediate 11, step 3) afforded the title compound as an off-white solid (212 mg, 96% yield).

Step 2: 1-((2-(2,6-dioxopiperidin-3-yl)-1,3-dioxoisoindolin-4-yl)glycyl)piperidine-4-carboxylic acid Benzyl 1-((2-(2,6-dioxopiperidin-3-yl)-1,3-dioxoisoindolin-4-yl)glycyl)piperidine-4-carboxylate (200 mg, 0.38 mmol) was diluted in a 1:1 mixture of EtOAc and EtOH (2 mL each). Pd/C (15 mg) was added, and the reaction mixture was stirred under an atmosphere of hydrogen for hours. The reaction mixture was purged with $N_2$ gas for 5 minutes, then filtered through a celite pad, washing with EtOAc, DCM, and MeOH. The filtrate was concentrated under vacuum and the residue was purified with reverse phase column chromatography (ACN and water mobile phase) to afford the title compound as a yellow solid (120 mg, 72% yield).

Step 3: 2-(1-(1-((2-(2,6-dioxopiperidin-3-yl)-1,3-dioxoisoindolin-4-yl)glycyl)piperidine-4-carbonyl) piperidin-4-yl)acetic acid BOP mediated coupling of 1-((2-(2,6-dioxopiperidin-3-yl)-1,3-dioxoisoindolin-4-yl)glycyl)piperidine-4-carboxylic acid (44 mg, 0.10 mmol) and tert-butyl 2-(piperidin-4-yl) acetate (21.8 mg, 0.11 mmol) using conditions similar to those used for tert-butyl (3R)-1-(1-(5-(2,6-dioxopiperidin-3-yl)pyridin-2-yl)piperidine-4-carbonyl)pyrrolidine-3-carboxylate (intermediate 11, step 3), followed by concentration and treatment with HCl (4N in dioxane, 1 mL) overnight, and then concentration and purification by reverse phase column chromatography (mobile phase of ACN and $H_2O$) afforded the title compound as an off-white solid (25 mg, 44% yield).

Intermediate 51

3-(6-((R)-3-methylpiperazin-1-yl)pyridin-3-yl)piperidine-2,6-dione

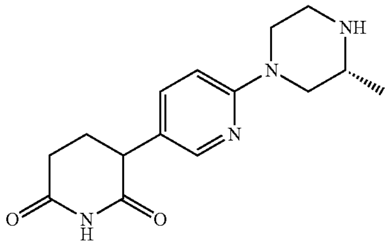 [SMILES: C[C@@H]1CN(c2ccc(C3CCC(=O)NC3=O)cn2)CCN1]

To a 20 mL microwave vial was added 3-(6-fluoropyridin-3-yl)piperidine-2,6-dione (500.0 mg, 2.40 mmol), tert-butyl (2R)-2-methylpiperazine-1-carboxylate (577.2 mg, 2.88 mmol), N,N-diisopropylethylamine (1.68 mL, 1.24 g, 9.61 mmol), and DMSO (5.00 mL). The reaction mixture was stirred at 180° C. for 6 hours then concentrated. The crude material was dissolved in DCM (10.0 mL), treated with 4M HCl in dioxane (3.0 mL), and stirred at room temperature for 4 hours. The crude mixture was purified by reverse phase flash column chromatography to afford the title compound as a white solid (131.0 mg, 19% yield).

Intermediate 52

(1R,4R)-4-(4-(2,6-dioxopiperidin-3-yl)phenoxy) cyclohexane-1-carboxylic acid

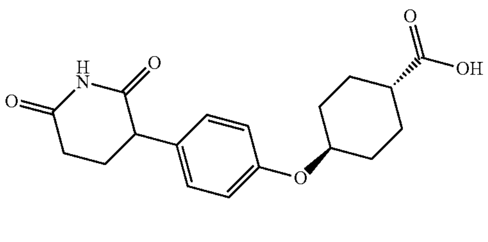 [SMILES: O=C1CCC(c2ccc(O[C@H]3CC[C@H](C(=O)O)CC3)cc2)C(=O)N1]

Step 1: benzyl (1s,4s)-4-hydroxycyclohexane-1-carboxylate

To a solution of cis-4-hydroxycyclohexanecarboxylic acid (2.0 g, 13.9 mmol) in anh. DMF (23.1 mL) was added $K_2CO_3$ (3.8 g, 27.6 mmol) at room temperature. Then benzyl chloride (2.1 mL, 18.2 mmol) was added dropwise at 55° C. The reaction mixture was stirred for 12 h at 55° C., and then water (150 mL) was poured into the reaction mixture which was extracted with DCM (4×150 mL). The combined organic layers were washed with a saturated aq. solution of $NaHCO_3$ (100 mL) and brine, then dried with $Na_2SO_4$ and the solvent was evaporated in vacuo. The resulting 3.14 g (97% yield) of the title compound as a white powder was used as-is for the next step. LCMS: $C_{14}H_{18}O_3$, desired mass=234.3, found: m/z=235.7 $[M+H]^+$.

Step 2: benzyl (1r,4r)-4-(4-bromophenoxy)cyclohexane-1-carboxylate

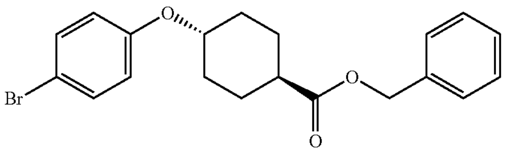 [SMILES: O=C(OCc1ccccc1)[C@H]1CC[C@H](Oc2ccc(Br)cc2)CC1]

To a solution of 4-bromophenol (7.45 g, 42.2 mmol) in anh. THF (63.0 mL) was added benzyl (1s,4s)-4-hydroxycyclohexane-1-carboxylate (11.9 g, 50.6 mmol), triethylamine (7.06 mL, 50.6 mmol), and triphenylphosphine (22.1 g, 84.4 mmol) at room temperature. Then was added diisopropyl azodicarboxylate (16.6 mL, 84.4 mmol) slowly at 0° C. under argon atmosphere and the reaction mixture was stirred overnight at room temperature. Then the solvent was removed under reduced pressure. The residue was purified by silica gel chromatography using a mobile phase of hexane/DCM (100 to 30% of hexane) to provide 6.94 g (42% yield) of the title compound as a yellow oil.

Step 3: benzyl (1r,4r)-4-{4-[2,6-bis(benzyloxy)pyridin-3-yl]phenoxy}cyclohexane-1-carboxylate

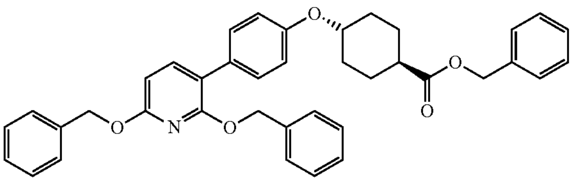

To a solution of 2,6-bis(benzyloxy)-3-(4,4,5,5-tetramethyl-1,3,2-dioxaborolan-2-yl)pyridine (1.69 g, 3.85 mmol) in degassed anhydrous DMF (11.0 mL) was added benzyl (1r,4r)-4-(4-bromophenoxy)cyclohexane-1-carboxylate (1.50 g, 3.85 mmol), [1,1'-bis(diphenylphosphino)ferrocene] dichloropalladium(II) (0.154 g, 0.193 mmol) and potassium carbonate (1.60 g, 11.6 mmol) at room temperature. The reaction mixture was stirred overnight at 85° C., and then the mixture was diluted 10-fold with water and extracted 3 times with DCM. The combined organic layers were washed with brine, dried over $Na_2SO_4$, and concentrated in vacuo. The residue was purified by silica gel chromatography using a mobile phase of hexane/DCM (0 to 70% DCM) to provide 1.53 g (66% yield) of the title compound as a brown oil. LCMS: $C_{39}H_{37}NO_5$, desired mass=599.73, found: m/z=600.20 $[M+H]^+$.

Step 4: (1r,4r)-4-(4-(2,6-dioxopiperidin-3-yl)phenoxy)cyclohexane-1-carboxylic acid

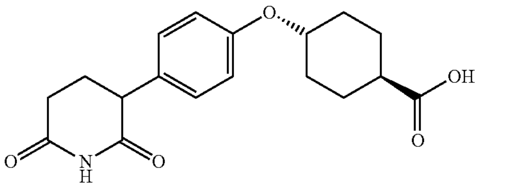

To a solution of benzyl (1r,4r)-4-{4-[2,6-bis(benzyloxy)pyridin-3-yl]phenoxy}cyclohexane-1-carboxylate (0.511 g, 0.852 mmol) in degassed tetrahydrofuran (50.1 mL) was added palladium on carbon 60-65% wet (0.154 g, 1.45 mmol) at room temperature under $H_2$ (1 atm). The reaction mixture was stirred overnight at room temperature under $H_2$ (1 atm), and then the mixture was filtered. The filtrate was concentrated under reduced pressure to provide 0.253 g (87% yield) of the title compound as a white solid. LCMS: $C_{18}H_{21}NO_5$, desired mass=331.37, found: m/z=332.05 $[M+H]^+$.

Intermediate 53

(1R,4R)-4-((5-(2,4-dioxotetrahydropyrimidin-1(2H)-yl)pyridin-2-yl)oxy)cyclohexane-1-carboxylic acid

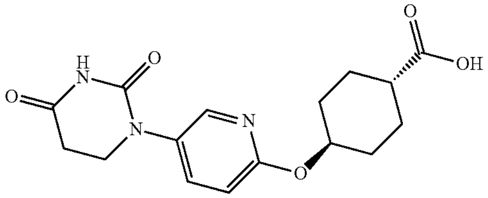 [SMILES: O=C1CCN(c2ccc(O[C@H]3CC[C@H](C(=O)O)CC3)nc2)C(=O)N1]

Step 1: benzyl (1r,4r)-4-hydroxycyclohexane-1-carboxylate

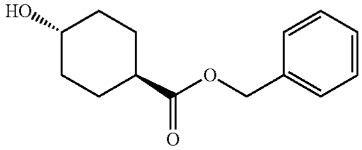 [SMILES: O=C(OCc1ccccc1)[C@H]1CC[C@H](O)CC1]

To a solution of trans-4-hydroxycyclohexanecarboxylic acid (7.9 g, 54.79 mmol) in anh. DMF (55 mL) was added $K_2CO_3$ (15.08 g, 109.15 mmol) at 25° C. and the reaction mixture was heated to 55° C. Then benzyl chloride (8.25 mL, 71.73 mmol) was added dropwise to the mixture, and the reaction mixture was stirred at 55° C. for 16 h. The reaction mixture was quenched with water (150 mL) and extracted with DCM (4×100 mL). The combined organic layers were washed with sat. aq. solution of $NaHCO_3$ (100 mL) and brine (150 mL), dried over $Na_2SO_4$ and evaporated to dryness to provide 12.7 g (99% yield) of the title compound.

Step 2: benzyl (1r,4r)-4-[(5-nitropyridin-2-yl)oxy]cyclohexane-1-carboxylate

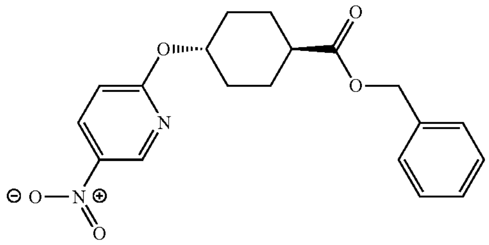 [SMILES: O=C(OCc1ccccc1)[C@H]1CC[C@H](Oc2ccc([N+](=O)[O-])cn2)CC1]

To a solution of 2-fluoro-5-nitropyridine (2.86 g, 28.38 mmol) in anh. DMF (59.0 mL) in a pressure vessel at 25° C. was added benzyl (1r,4r)-4-hydroxycyclohexane-1-carboxylate (6.65 g, 28.38 mmol) and the reaction mixture was stirred at 90° C. overnight. Another portion of 2-fluoro-5-nitropyridine (1.43 g, 14.19 mmol) was added and the reaction mixture was left stirring overnight at 90° C. The reaction mixture was then evaporated to dryness and residue was purified by silica gel chromatography using a mobile phase of hexane and EtOAc to provide 3.24 g (32% yield) of the title compound.

Step 3: benzyl (1r,4r)-4-[(5-aminopyridin-2-yl)oxy]cyclohexane-1-carboxylate

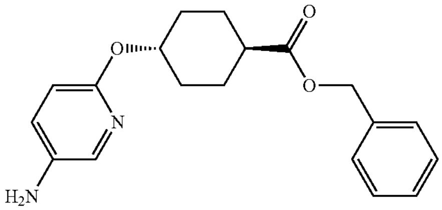 [SMILES: Nc1ccc(O[C@H]2CC[C@H](C(=O)OCc3ccccc3)CC2)nc1]

To a solution of benzyl (1r,4r)-4-[(5-nitropyridin-2-yl)oxy]cyclohexane-1-carboxylate (3.93 g, 11.2 mmol) in a mixture of EtOH (16.8 mL), Acetic acid (16.4 mL), and water (8.42 mL) was added Fe dust (0.94 g, 16.84 mmol) at 25° C. and the reaction mixture was stirred at 50° C. for 2 h. The reaction mixture was filtered and the filtrate was concentrated to dryness under reduced pressure. The remaining water solution was neutralized with $NaHCO_3$ to pH=7 and extracted with EtOAc (4×100 mL). The combined organic extracts were evaporated to dryness under reduced pressure to provide 3.44 g (94% yield) of the title compound. LCMS: $C_{19}H_{22}N_2O_3$, desired mass=326.2, found: m/z=327.8 $[M+H^+]$.

Step 4: 3-[(6-{[(1r,4r)-4-[(benzyloxy)carbonyl]cyclohexyl]oxy}pyridin-3-yl)amino]propanoic acid

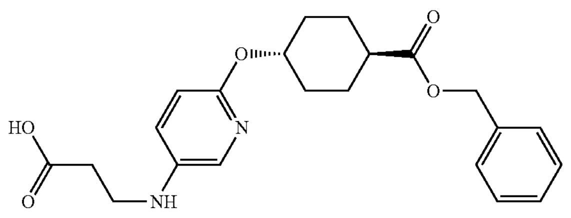 [SMILES: O=C(O)CCNc1ccc(O[C@H]2CC[C@H](C(=O)OCc3ccccc3)CC2)nc1]

To a solution of benzyl (1r,4r)-4-[(5-aminopyridin-2-yl)oxy]cyclohexane-1-carboxylate (3.94 g, 12.07 mmol) in anh. dioxane (40 mL) was added acrylic acid (0.9 mL, 12.07 mmol) at 25° C. and the reaction mixture was stirred at 90° C. for 16 h. Then another portion of acrylic acid (0.45 mL, 6.03 mmol) was added and the reaction mixture was left stirring at 90° C. for 48 h. More acrylic acid (0.22 mL, 3.01 mmol) was added and the reaction mixture was stirred at 90° C. for 16 h to achieve full consumption of starting material. The reaction mixture was evaporated to dryness under reduced pressure to provide 4.8 g (60% yield) of the title compound which was used as-if for the next step. LCMS: $C_{22}H_{26}N_2O_5$, desired mass=398.2, found: m/z=399.1 $[M+H]^+$.

Step 5: benzyl (1r,4r)-4-{[5-(2,4-dioxo-1,3-diazinan-1-yl)pyridin-2-yl]oxy}cyclohexane-1-carboxylate

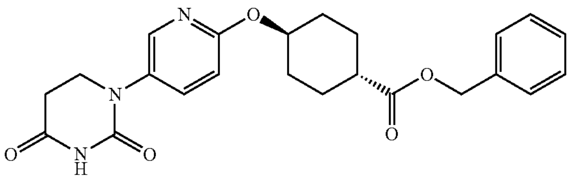 [SMILES: O=C1CCN(c2ccc(O[C@H]3CC[C@H](C(=O)OCc4ccccc4)CC3)nc2)C(=O)N1]

To a solution of 3-[(6-{[(1r,4r)-4-[(benzyloxy)carbonyl]cyclohexyl]oxy}pyridin-3-yl)amino]propanoic acid (4.8 g, 12.05 mmol) in acetic acid (48.0 mL) was added urea (1.45 g, 24.09 mmol) at 25° C. and the reaction mixture was stirred at 90° C. for 72 h. Then the reaction mixture was concentrated to dryness under reduced pressure and the residue was purified by silica gel chromatography using a mobile phase of DCM and MeOH, then hexane and EtOAc, and finally, DCM and IPA to provide 1.12 g (22% yield) of the title compound. LCMS: $C_{23}H_{25}N_3O_5$, desired mass=423.2, found: m/z=424.5 $[M+H]^+$.

Step 6: (1r,4r)-4-((5-(2,4-dioxotetrahydropyrimidin-1(2H)-yl)pyridin-2-yl)oxy)cyclohexane-1-carboxylic acid

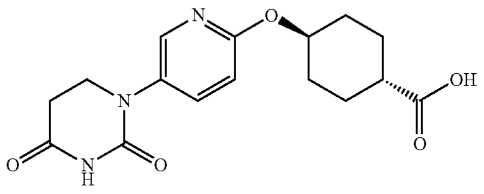 [SMILES: O=C1CCN(c2ccc(O[C@H]3CC[C@H](C(=O)O)CC3)nc2)C(=O)N1]

To a solution of benzyl (1r,4r)-4-{[5-(2,4-dioxo-1,3-diazinan-1-yl)pyridin-2-yl]oxy}cyclohexane-1-carboxylate (1.12 g, 0.273 mmol) in anh. THF (38.5 mL) was added Pd/C (0.05 g, 0.043 mmol) at 25° C. The reaction mixture was stirred under $H_2$ (1 atm) overnight at 25° C. The mixture was filtered through a Celite cake and evaporated to dryness to provide 0.8 g (89% yield) of the title compound as an off-white solid. LCMS: $C_{23}H_{25}N_3O_5$, desired mass=333.1, found: m/z=334.2 $[M+H]^+$.

Intermediate 54

1-(1-(4-(2,6-dioxopiperidin-3-yl)phenyl)piperidine-4-carbonyl)-4-methylpiperidine-4-carboxylic acid

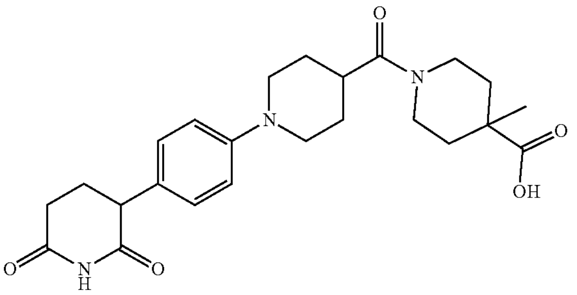 [SMILES: CC1(C(=O)O)CCN(C(=O)C2CCN(c3ccc(C4CCC(=O)NC4=O)cc3)CC2)CC1]

Step 1: tert-butyl 1-(1-(4-(2,6-dioxopiperidin-3-yl)phenyl)piperidine-4-carbonyl)-4-methylpiperidine-4-carboxylate

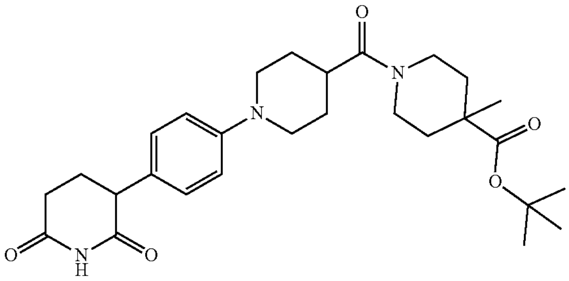 [SMILES: CC(C)(C)OC(=O)C1(C)CCN(C(=O)C2CCN(c3ccc(C4CCC(=O)NC4=O)cc3)CC2)CC1]

Prepared by similar procedures as Intermediate 5 (step 1) using 1-(4-(2,6-dioxopiperidin-3-yl)phenyl)piperidine-4-carboxylic acid (40 mg, 0.13 mmol) and tert-butyl 4-methylpiperidine-4-carboxylate (25 mg, 0.13 mmol) as starting materials. The title compound (TFA salt) was isolated as an off-white solid (50 mg, 79% yield). LCMS: $[C_{28}H_{39}N_3O_5]$, desired mass=497.6, found: m/z=498.4 $[M+H]^+$.

Step 2: 1-(1-(4-(2,6-dioxopiperidin-3-yl)phenyl)piperidine-4-carbonyl)-4-methylpiperidine-4-carboxylic acid

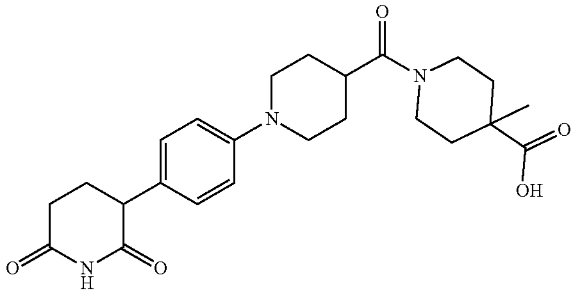 [SMILES: CC1(C(=O)O)CCN(C(=O)C2CCN(c3ccc(C4CCC(=O)NC4=O)cc3)CC2)CC1]

Prepared by similar procedures as Intermediate 5 (step 2) using tert-butyl 1-(1-(4-(2,6-dioxopiperidin-3-yl)phenyl)piperidine-4-carbonyl)-4-methylpiperidine-4-carboxylate (50 mg, 0.10 mmol) as the starting material. The title compound (TFA salt) was isolated as an off-white solid (45 mg, 100% yield). LCMS: [$C_{24}H_{31}N_3O_5$], desired mass=441.5, found: m/z=442.3 $[M+H]^+$.

Intermediate 55

1-(1-(5-(2,6-dioxopiperidin-3-yl)pyridin-2-yl)piperidine-4-carbonyl)-4-methylpiperidine-4-carboxylic acid

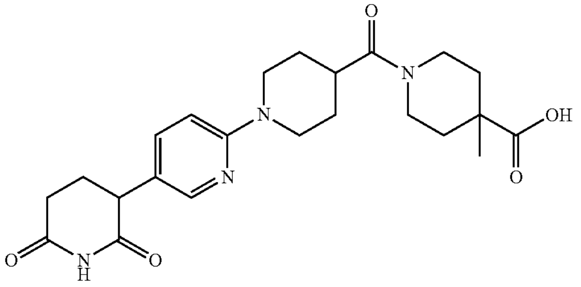 [SMILES: CC1(C(=O)O)CCN(C(=O)C2CCN(c3ccc(C4CCC(=O)NC4=O)cn3)CC2)CC1]

Step 1: tert-butyl 1-[5-(2,6-dioxopiperidin-3-yl)pyridin-2-yl]piperidine-4-carboxylate

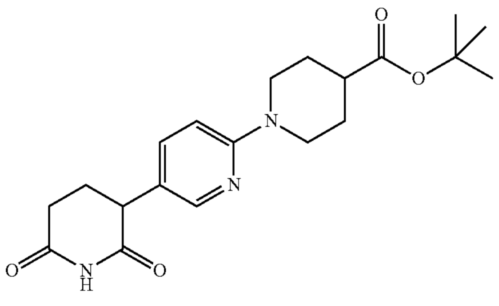 [SMILES: CC(C)(C)OC(=O)C1CCN(c2ccc(C3CCC(=O)NC3=O)cn2)CC1]

To a solution of the 3-(6-fluoropyridin-3-yl)piperidine-2,6-dione (1.0 g, 4.80 mmol) in N-methyl-2-pyrrolidone (9.6 mL) were added tert-butyl piperidine-4-carboxylate (2.403 g, 12.97 mmol) and DIPEA (2.48 g, 19.22 mmol) at 25° C. The reaction mixture was stirred at 120° C. for 72 h and then poured into 100 mL of water and extracted with DCM (4×60 mL). The combined organic layers were washed with water (100 mL), dried under $Na_2SO_4$ and evaporated under reduced pressure. The crude compound was purified by silica gel column chromatography using a mobile phase of DCM and MeOH to provide 2.45 g (56% yield) of the title compound. LCMS: $C_{20}H_{27}N_3O_4$, desired mass=373.2, found: m/z=374.5 $[M+H]^+$.

Step 2: 1-[5-(2,6-dioxopiperidin-3-yl)pyridin-2-yl]piperidine-4-carboxylic acid hydrochloride

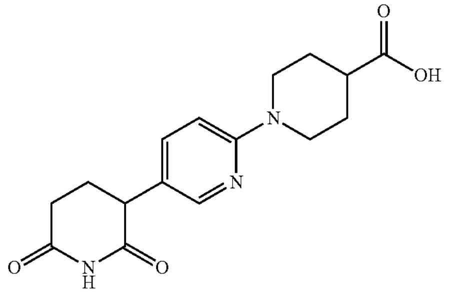 [SMILES: O=C1CCC(c2ccc(N3CCC(C(=O)O)CC3)nc2)C(=O)N1]

To solution of 1-[5-(2,6-dioxopiperidin-3-yl)pyridin-2-yl]piperidine-4-carboxylate (0.678 g, 1.815 mmol) dissolved in anhydrous DCM (7.26 mL) was added 4M HCl in dioxane (7.26 mL, 29.05 mmol) at 0° C. The reaction mixture was stirred at 25° C. for 24 h and then evaporated to dryness under reduced pressure. The residue was triturated with $Et_2O$ to provide 559 mg (86% yield) of the title compound. LCMS: $C_{20}H_{27}N_3O_4$, desired mass=317.1, found: m/z=318.23 $[M+H]^+$.

Step 3: tert-butyl 1-{1-[5-(2,6-dioxopiperidin-3-yl)pyridin-2-yl]piperidine-4-carbonyl}-4-methylpiperidine-4-carboxylate

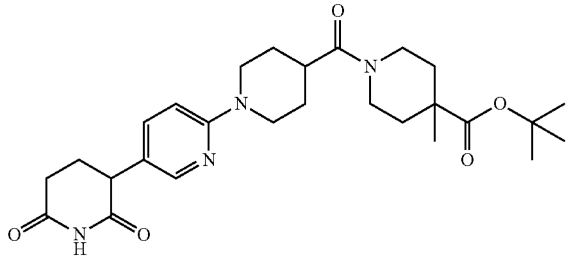 [SMILES: CC(C)(C)OC(=O)C1(C)CCN(C(=O)C2CCN(c3ccc(C4CCC(=O)NC4=O)cn3)CC2)CC1]

To a solution of 1-[5-(2,6-dioxopiperidin-3-yl)pyridin-2-yl]piperidine-4-carboxylic acid hydrochloride (0.989 g, 2.77 mmol) in anhydrous DMF (5.53 mL) were added HATU (0.989 g, 2.77 mmol) and DIPEA (2.41 mL, 13.84 mmol) at 25° C. The reaction mixture was stirred at 25° C. for 24 h and then quenched with water. The resulting solid was filtered off, dried under reduced pressure and purified by silica gel column chromatography using a mobile phase of DCM and MeOH to provide 0.33 g (67% yield) of the title compound. LCMS: $C_{27}H_{38}N_4O_5$, desired mass=498.3, found: m/z=499.7 $[M+H]^+$.

Step 4: 1-(1-(5-(2,6-dioxopiperidin-3-yl)pyridin-2-yl)piperidine-4-carbonyl)-4-methylpiperidine-4-carboxylic acid

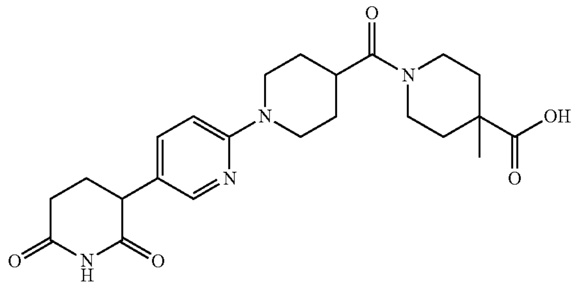 [SMILES: CC1(C(=O)O)CCN(C(=O)C2CCN(c3ccc(C4CCC(=O)NC4=O)cn3)CC2)CC1]

To solution of 1-{1-[5-(2,6-dioxopiperidin-3-yl)pyridin-2-yl]piperidine-4-carbonyl}-4-methylpiperidine-4-carboxylate (0.330 g, 0.66 mmol) in anhydrous DCM (2.6 mL) was added 4M HCl in dioxane (2.6 mL, 10.56 mmol) at 0° C. The reaction mixture was stirred at 25° C. for 24 h and then evaporated to dryness under reduced pressure. The residue was triturated with $Et_2O$ to provide 281 mg (90% yield) of the title compound (HCl salt). LCMS: $C_{23}H_{30}N_4O_5$, desired mass=442.2, found: m/z=443.2 $[M+H]^+$.

Intermediate 56

1-(1-(5-(2,4-dioxotetrahydropyrimidin-1(2H)-yl)pyridin-2-yl)piperidine-4-carbonyl)-4-methylpiperidine-4-carboxylic acid

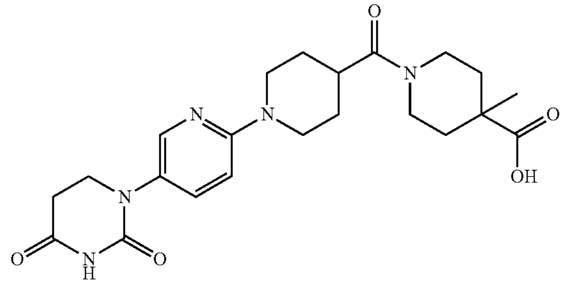 [SMILES: CC1(C(=O)O)CCN(C(=O)C2CCN(c3ccc(N4CCC(=O)NC4=O)cn3)CC2)CC1]

Step 1: Synthesis tert-butyl 1-(1-(5-(2,4-dioxotetrahydropyrimidin-1(2H)-yl)pyridin-2-yl)piperidine-4-carbonyl)-4-methylpiperidine-4-carboxylate

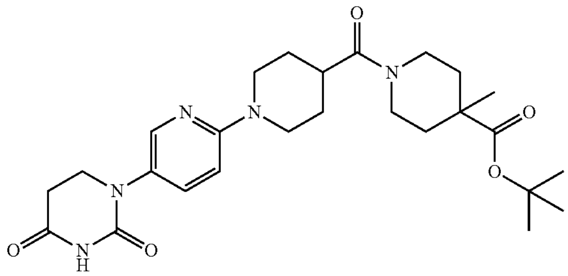 [SMILES: CC(C)(C)OC(=O)C1(C)CCN(C(=O)C2CCN(c3ccc(N4CCC(=O)NC4=O)cn3)CC2)CC1]

Prepared by similar procedures as Intermediate 5 (step 1) using 1-(5-(2,4-dioxotetrahydropyrimidin-1(2H)-yl)pyridin-2-yl)piperidine-4-carboxylic acid (30 mg, 0.094 mmol) and tert-butyl 4-methylpiperidine-4-carboxylate (28 mg, 0.14 mmol) as starting materials. The title compound (TFA salt) was isolated as an off-white solid (35 mg, 74% yield). LCMS: $[C_{26}H_{37}N_5O_5]$, desired mass=499.6, found: m/z=500.4 $[M+H]^+$.

Step 2: 1-(1-(5-(2,4-dioxotetrahydropyrimidin-1(2H)-yl)pyridin-2-yl)piperidine-4-carbonyl)-4-methylpiperidine-4-carboxylic acid

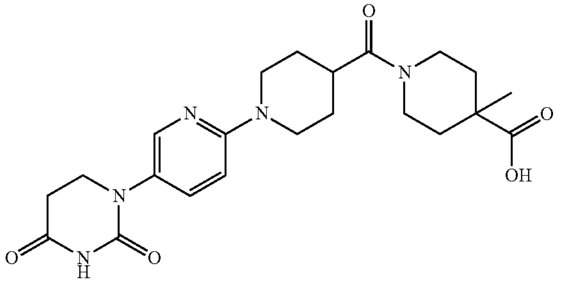 [SMILES: CC1(C(=O)O)CCN(C(=O)C2CCN(c3ccc(N4CCC(=O)NC4=O)cn3)CC2)CC1]

Prepared by similar procedures as Intermediate 5 (step 2) using tert-butyl 1-(1-(5-(2,4-dioxotetrahydropyrimidin-1(2H)-yl)pyridin-2-yl)piperidine-4-carbonyl)-4-methylpiperidine-4-carboxylate (35 mg, 0.07 mmol) as the starting material. The title compound (TFA salt) was isolated as an off-white solid (30 mg, 100% yield). LCMS: $[C_{22}H_{29}N_5O_5]$, desired mass=443.5, found: m/z=444.3 $[M+H]^+$.

Intermediate 57

1-(1-(6-(2,6-dioxopiperidin-3-yl)pyridin-3-yl)piperidine-4-carbonyl)-4-methylpiperidine-4-carboxylic acid

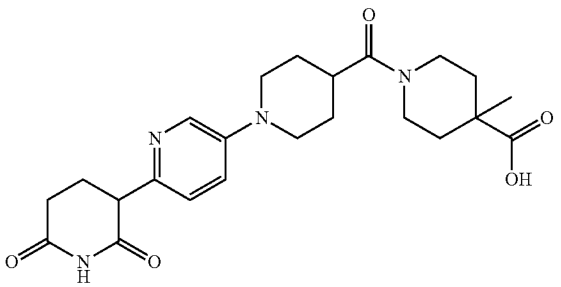 [SMILES: CC1(C(=O)O)CCN(C(=O)C2CCN(c3ccc(C4CCC(=O)NC4=O)nc3)CC2)CC1]

Step 1: Synthesis tert-butyl 1-(1-(6-(2,6-dioxopiperidin-3-yl)pyridin-3-yl)piperidine-4-carbonyl)-4-methylpiperidine-4-carboxylate

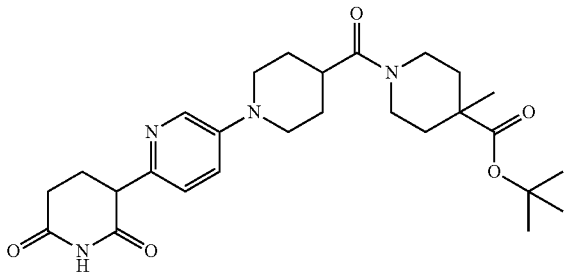 [SMILES: CC(C)(C)OC(=O)C1(C)CCN(C(=O)C2CCN(c3ccc(C4CCC(=O)NC4=O)nc3)CC2)CC1]

Prepared by similar procedures as Intermediate 5 (step 1) using 1-(6-(2,6-dioxopiperidin-3-yl)pyridin-3-yl)piperidine-4-carboxylic acid (40 mg, 0.13 mmmol) and tert-butyl 4-methylpiperidine-4-carboxylate (25 mg, 0.13 mmol) as starting materials. The title compound (TFA salt) was isolated as an off-white solid (50 mg, 79% yield). LCMS: [$C_{27}H_{38}N_4O_5$], desired mass=498.6, found: m/z=499.4 $[M+H]^+$.

Step 2: 1-(1-(6-(2,6-dioxopiperidin-3-yl)pyridin-3-yl)piperidine-4-carbonyl)-4-methylpiperidine-4-carboxylic acid

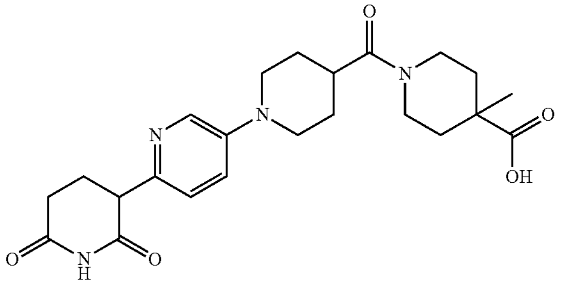 [SMILES: CC1(C(=O)O)CCN(C(=O)C2CCN(c3ccc(C4CCC(=O)NC4=O)nc3)CC2)CC1]

Prepared by similar procedures as Intermediate 5 (step 2) tert-butyl 1-(1-(6-(2,6-dioxopiperidin-3-yl)pyridin-3-yl)piperidine-4-carbonyl)-4-methylpiperidine-4-carboxylate (50 mg, 0.10 mmol) as the starting material. The title compound (TFA salt) was isolated as an off-white solid (42 mg, 95% yield). LCMS: [$C_{23}H_{30}N_4O_5$], desired mass=442.5, found: m/z=443.3 $[M+H]^+$.

Intermediate 58

Methyl 1-{1-[(tert-butoxy)carbonyl]piperidine-4-carbonyl}-4-methylpiperidine-4-carboxylate

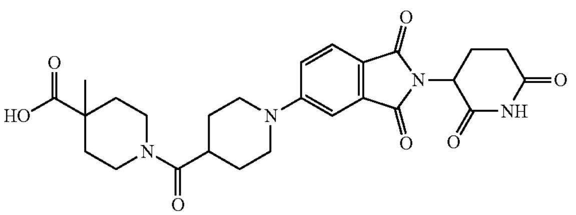 [SMILES: CC1(C(=O)O)CCN(C(=O)C2CCN(c3ccc4c(c3)C(=O)N(C3CCC(=O)NC3=O)C4=O)CC2)CC1]

Step 1: methyl 1-{1-[(tert-butoxy)carbonyl]piperidine-4-carbonyl}-4-methylpiperidine-4-carboxylate

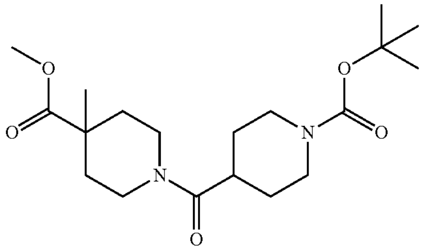 [SMILES: COC(=O)C1(C)CCN(C(=O)C2CCN(C(=O)OC(C)(C)C)CC2)CC1]

To a solution of 1-[(tert-butoxy)carbonyl]piperidine-4-carboxylic acid (592 mg, 2.58 mmol) in anhydrous DMF (52 mL) were added HATU (1472 mg, 3.87 mmol) and DIPEA (1.80 mL, 10.33 mmol) at 25° C. The reaction mixture was stirred for 20 min at 25° C. Then methyl 4-methylpiperidine-4-carboxylate hydrochloride (500 mg, 2.58 mmol) was added at 25° C. The reaction mixture was stirred for 16 h at 25° C. and then poured into 450 mL of brine, extracted with EtOAc (4×50 mL). The combined organic layers were dried with $Na_2SO_4$ and concentrated under reduced pressure. The residue was purified by silica gel chromatography using a mobile phase of DCM and MeOH to provide 828 mg (83% yield) of the title compound as a yellow solid.

Step 2: 1-{1-[(tert-butoxy)carbonyl]piperidine-4-carbonyl}-4-methylpiperidine-4-carboxylic acid

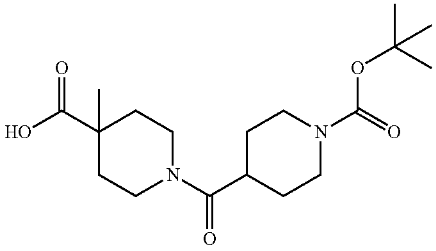 [SMILES: CC(C)(C)OC(=O)N1CCC(C(=O)N2CCC(C)(C(=O)O)CC2)CC1]

To a solution of methyl 1-{1-[(tert-butoxy)carbonyl]piperidine-4-carbonyl}-4-methylpiperidine-4-carboxylate (828 mg, 2.14 mmol) in THF (5 mL) and water (1 mL) was added lithium hydroxide monohydrate (138 mg, 3.21 mmol) at 25° C. The reaction mixture was stirred for 16 h at 25° C., and then the THF was evaporated under reduced pressure. Then an aqueous solution of $KHSO_4$ was added to the aqueous layer until the pH reached 2. The precipitated crystalline solid was filtered, washed with water, and then dried under reduced pressure to provide 736 mg (97% yield) of the title compound as a white solid.

Step 3: 4-methyl-1-(piperidine-4-carbonyl)piperidine-4-carboxylic acid

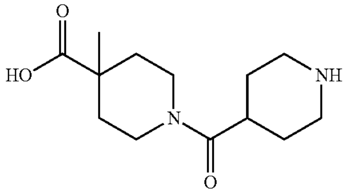 [SMILES: CC1(C(=O)O)CCN(C(=O)C2CCNCC2)CC1]

To 1-{1-[(tert-butoxy)carbonyl]piperidine-4-carbonyl}-4-methylpiperidine-4-carboxylic acid (499 mg, 1.41 mmol) was added HFIP (3.06 mL, 29.07 mmol) at 25° C. The reaction mixture was stirred for 2 h at 150° C. in a microwave reactor, and then the mixture was concentrated under reduced pressure. The residue was triturated with $Et_2O$ (3×15 mL) to provide 564 mg (90% yield) of the title compound as a cream-white solid.

Step 4: 1-{1-[2-(2,6-dioxopiperidin-3-yl)-1,3-dioxo-2,3-dihydro-1H-isoindol-5-yl]piperidine-4-carbonyl}-4-methylpiperidine-4-carboxylic acid

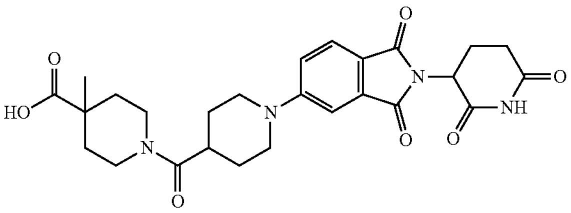 [SMILES: CC1(C(=O)O)CCN(C(=O)C2CCN(c3ccc4c(c3)C(=O)N(C3CCC(=O)NC3=O)C4=O)CC2)CC1]

To a solution of 4-methyl-1-(piperidine-4-carbonyl)piperidine-4-carboxylic acid (565 mg, 1.27 mmol) in anhydrous DMSO (2.8 mL) were added 2-(2,6-dioxopiperidin-3-yl)-5-fluoro-2,3-dihydro-1H-isoindole-1,3-dione (233 mg, 0.84 mmol) and potassium fluoride (196 mg, 3.37 mmol) at 25° C. The reaction mixture was stirred for 16 h at 120° C., and then poured into 50 mL of water and extracted with EtOAc (5×30 mL). The combined organic extracts were dried with $Na_2SO_4$ and evaporated under reduced pressure. The residue was purified by silica gel chromatography using a mobile phase of DCM and MeOH to provide 136 mg (32% yield) of the title compound as a yellow solid. LCMS: $C_{26}H_{30}N_4O_7$, desired mass=510.6, found: m/z=511.2 $[M+H]^+$.

Intermediate 59

4-(4-{2-[2,6-dioxopiperidin-3-yl]-1,3-dioxoisoindol-5-yl}piperazine-1-carbonyl)-2-methylbenzoic acid

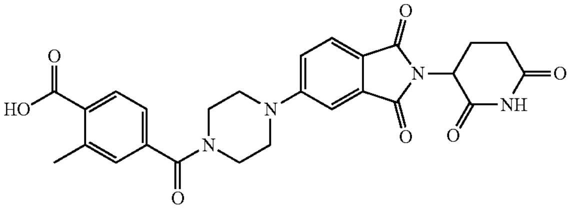 [SMILES: Cc1cc(C(=O)N2CCN(c3ccc4c(c3)C(=O)N(C3CCC(=O)NC3=O)C4=O)CC2)ccc1C(=O)O]

Step-1: benzyl 4-(4-bromo-3-methylbenzoyl)piperazine-1-carboxylate

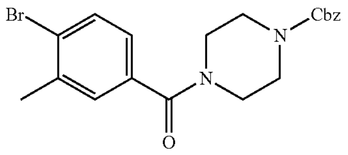 [SMILES: Cc1cc(C(=O)N2CCN(C(=O)OCc3ccccc3)CC2)ccc1Br]

Procedures similar to those in step 1 of Intermediate 19 were followed using 4-bromo-3-methylbenzoic acid (3 g, 13.951 mmol), DCM (15 mL), HATU (7.96 g, 20.926 mmol), benzyl piperazine-1-carboxylate (3.07 g, 13.937 mmol) and DIEA (5.41 g, 41.852 mmol). The residue was purified by silica gel chromatography using a mobile phase of [PE and EA] to provide 5 g (81.59%) of the title compound as a colorless oil. LCMS: $(C_{20}H_{21}BrN_2O_3)$ desired mass=416.1; found: m/z=417.1 $[M+H]^+$.

Step-2: benzyl 4-[4-(methoxycarbonyl)-3-methylbenzoyl]piperazine-1-carboxylate

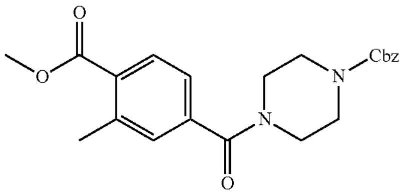 [SMILES: COC(=O)c1ccc(C(=O)N2CCN(C(=O)OCc3ccccc3)CC2)cc1C]

To a mixture of benzyl 4-(4-bromo-3-methylbenzoyl)piperazine-1-carboxylate (2.5 g, 5.991 mmol) in MeOH (10 mL) was added TEA (1.82 g, 17.973 mmol) and $Pd(dppf)Cl_2$ (0.88 g, 1.198 mmol). The resulting mixture was stirred for 5 h at 100° C. under carbon monoxide atmosphere (1 atm). The resulting mixture was concentrated under reduced pressure. The residue was purified by silica gel chromatography using a mobile phase of [PE and EA] to provide 900 mg (34.10%) of the title compound as a dark red solid. LCMS: $(C_{22}H_{24}N_2O_5)$ desired mass=396.2; found: m/z=397.0 $[M+H]^+$.

Step-3: methyl 2-methyl-4-(piperazine-1-carbonyl)benzoate

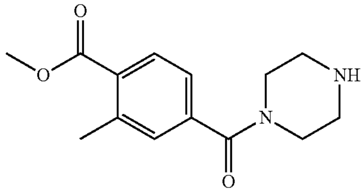 [SMILES: COC(=O)c1ccc(C(=O)N2CCNCC2)cc1C]

Procedures similar to those in step 5 of Intermediate 15 were followed using benzyl 4-[4-(methoxycarbonyl)-3-methylbenzoyl]piperazine-1-carboxylate (900 mg, 2.270 mmol) in MeOH (10 mL) and added Pd/C (900 mg). The residue was purified by silica gel chromatography using a mobile phase of $[CH_2Cl_2$ and MeOH] to provide 560 mg (86.52%) of the title compound as a brown oil. LCMS: ($C_{14}H_{18}N_2O_3$) desired mass=262.1; found: m/z=263.0 $[M+H]^+$.

Step-4: 2-methyl-4-(piperazine-1-carbonyl)benzoic acid

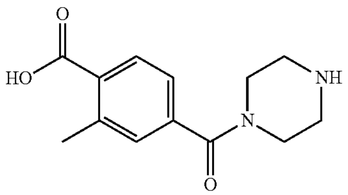 [SMILES: Cc1cc(C(=O)N2CCNCC2)ccc1C(=O)O]

To a mixture of methyl 2-methyl-4-(piperazine-1-carbonyl)benzoate (500 mg, 1.906 mmol) in THF (2 mL) and $H_2O$ (2 mL) was added LiOH (456 mg, 19.060 mmol). The resulting mixture was stirred at room temperature for 1 h. The mixture was acidified to pH 2 with HCl aqueous (2 M). The resulting mixture was concentrated under reduced pressure to provide 400 mg (crude) of the title compound as a brown solid. The residue was used directly for the next step. LCMS: ($C_{13}H_{16}N_2O_3$) desired mass=248.1; found: m/z=249.1 $[M+H]^+$.

Step-5: 4-(4-{2-[2,6-dioxopiperidin-3-yl]-1,3-dioxoisoindol-5-yl}piperazine-1-carbonyl)-2-methylbenzoic acid

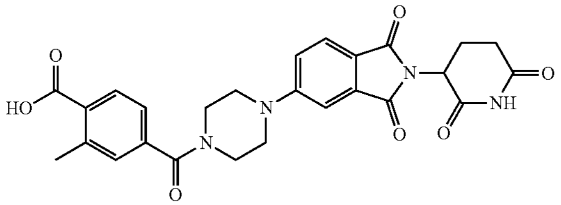

Procedures similar to those in step-4 of Intermediate 15 were followed using 2-methyl-4-(piperazine-1-carbonyl) benzoic acid (400 mg, 1.611 mmol), 2-(2,6-dioxopiperidin-3-yl)-5-fluoroisoindole-1,3-dione (222 mg, 0.806 mmol), DMSO (5 mL) and DIEA (312.33 mg, 2.417 mmol). The mixture was purified by reverse phase flash chromatography [ACN and $H_2O$] to provide 111.5 mg (26.75%) of the title compound as a yellow solid. LCMS (Method 6): ($C_{26}H_{24}N_4O_7$) desired mass=504.2; found: m/z=505.1 $[M+H]^+$.

Intermediate 60

4-{4-[2-(2,6-dioxopiperidin-3-yl)-1,3-dioxo-2,3-dihydro-1H-isoindol-5-yl]piperazine-1-carbonyl}-3-methylbenzoic acid

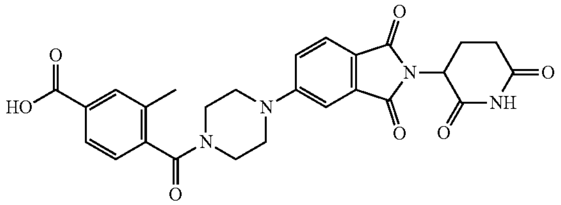

Step 1: benzyl 4-[4-(methoxycarbonyl)-2-methylbenzoyl]piperazine-1-carboxylate

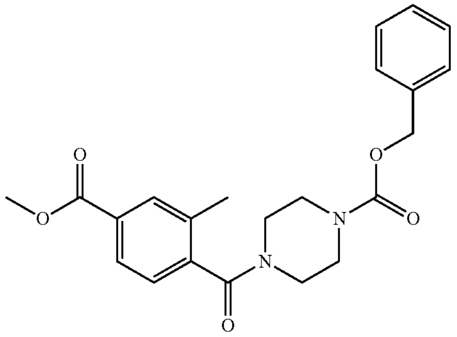 [SMILES: COC(=O)c1ccc(C(=O)N2CCN(C(=O)OCc3ccccc3)CC2)c(C)c1]

The title compound was synthesized using a similar method to step 1 for intermediate 58, and substituting 1-[(tert-butoxy)carbonyl]piperidine-4-carboxylic acid for 4-(methoxycarbonyl)-2-methylbenzoic acid and methyl 4-methylpiperidine-4-carboxylate hydrochloride for benzyl 1-piperazinecarboxylate to provide 500 mg (98% yield) of the title compound as a dark red oil. LCMS: $C_{22}H_{24}N_2O_5$, desired mass=396.4, found: m/z=397.4 $[M+H]^+$.

Step 2: 4-{4-[(benzyloxy)carbonyl]piperazine-1-carbonyl}-3-methylbenzoic acid

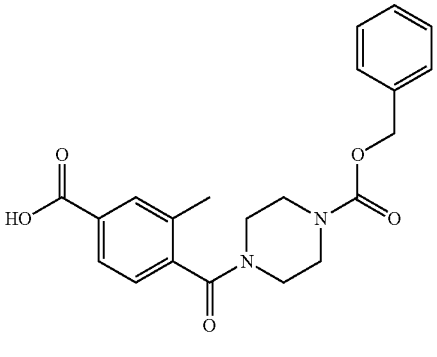 [SMILES: Cc1cc(C(=O)O)ccc1C(=O)N1CCN(C(=O)OCc2ccccc2)CC1]

The title compound was synthesized using similar method to step 2 for intermediate 58, and substituting methyl 1-{1-[(tert-butoxy)carbonyl]piperidine-4-carbonyl}-4-methylpiperidine-4-carboxylate for benzyl 4-[4-(methoxycarbonyl)-2-methylbenzoyl]piperazine-1-carboxylate to provide 417 mg (87% yield) of the title compound as a cream-white solid. LCMS: $C_{21}H_{22}N_2O_5$, desired mass=382.4, found: m/z=383.2 $[M+H]^+$.

Step 3: 3-methyl-4-(piperazine-1-carbonyl)benzoic acid

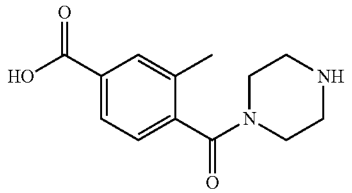 [SMILES: Cc1cc(C(=O)O)ccc1C(=O)N1CCNCC1]

To a solution of 4-{4-[(benzyloxy)carbonyl]piperazine-1-carbonyl}-3-methylbenzoic acid (414 mg, 1.08 mmol) in anhydrous THF (54 mL) was added 10% wt Pd/C (62 mg) at 25° C. The reaction mixture was stirred for 16 h at 25° C., followed by the addition of a $2^{nd}$ portion of 10% wt Pd/C (206 mg) at 25° C. The reaction mixture was stirred for another 72 h at 25° C., followed by the addition of a $3^{rd}$ portion of 10% wt Pd/C (206 mg) at 25° C. The reaction mixture was stirred for 16 h at 25° C., and then filtered through a Celite pad and evaporated to dryness under reduced pressure. The residue was triturated with $Et_2O$ (3×15 mL) to provide 230 mg (86% yield) of the title compound as a white solid. LCMS: $C_{13}H_{16}N_2O_3$, desired mass=248.3, found: m/z=249.4 $[M+H]^+$.

Step 4: benzyl 3-methyl-4-(piperazine-1-carbonyl)benzoate

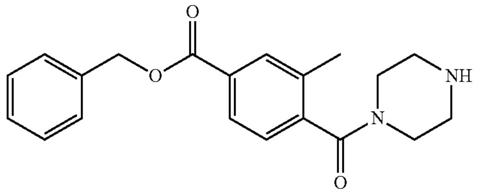 [SMILES: Cc1cc(C(=O)OCc2ccccc2)ccc1C(=O)N1CCNCC1]

To a solution of 3-methyl-4-(piperazine-1-carbonyl)benzoic acid (200 mg, 0.81 mmol) in anhydrous toluene (20.0 mL) was added anhydrous benzyl alcohol (0.83 mL, 8.05 mmol) and TsOH monohydrate (169 mg, 0.89 mmol) at 25° C. The reaction mixture was stirred for 16 h at 140° C. and then evaporated under reduced pressure. The residue was triturated with $Et_2O$ (3×15 mL) and diisopropyl ether (2×15 mL), and then sat aq $NaHCO_3$ solution (10 mL) was added into the residue, and the mixture was extracted with DCM (5×50 mL). The combined organic layers were dried with $Na_2SO_4$ and concentrated under reduced pressure to provide 169 mg (62% yield) of the title compound as a brown oil. LCMS: $C_{20}H_{22}N_2O_3$, desired mass=338.4, found: m/z=339.5 $[M+H]^+$.

Step 5: benzyl 4-{4-[2-(2,6-dioxopiperidin-3-yl)-1,3-dioxo-2,3-dihydro-1H-isoindol-5-yl]piperazine-1-carbonyl}-3-methylbenzoate

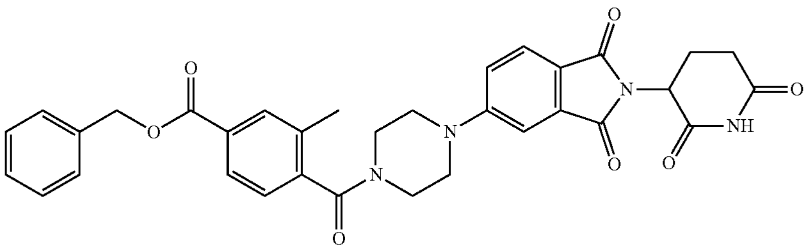 [SMILES: Cc1cc(C(=O)OCc2ccccc2)ccc1C(=O)N1CCN(c2ccc3c(c2)C(=O)N(C2CCC(=O)NC2=O)C3=O)CC1]

To a solution of benzyl 3-methyl-4-(piperazine-1-carbonyl)benzoate (169 mg, 0.50 mmol) in anhydrous DMSO (1.4 mL) were added 2-(2,6-dioxopiperidin-3-yl)-5-fluoro-2,3-dihydro-1H-isoindole-1,3-dione (115 mg, 0.42 mmol) and DIPEA (0.29 mL, 1.67 mmol) at 25° C. The reaction mixture was stirred for 72 h at 100° C. and then was concentrated under reduced pressure. The residue was purified by silica gel chromatography using a mobile phase of hexane and EtOAc to provide 121 mg (49% yield) of the title compound as a yellow solid. LCMS: $C_{33}H_{30}N_4O_7$, desired mass=594.6, found: m/z=595.2 $[M+H]^+$.

Step 6: 4-{4-[2-(2,6-dioxopiperidin-3-yl)-1,3-dioxo-2,3-dihydro-1H-isoindol-5-yl]piperazine-1-carbonyl}-3-methylbenzoic acid

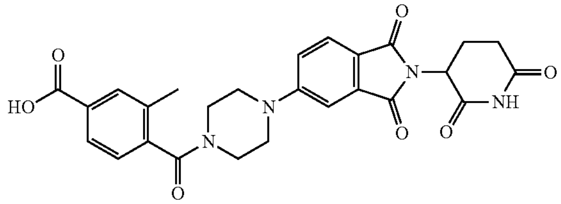

To a solution of benzyl 4-{4-[2-(2,6-dioxopiperidin-3-yl)-1,3-dioxo-2,3-dihydro-1H-isoindol-5-yl]piperazine-1-carbonyl}-3-methylbenzoate (120 mg, 0.20 mmol) in anhydrous THF (15 mL) was added 10% wt Pd/C (30 mg) at 25° C. The reaction mixture was stirred for 16 h at 25° C., followed by the addition of a $2^{nd}$ portion of 10% wt Pd/C (30 mg) at 25° C. The reaction mixture was stirred for another 48 h at 25° C., followed by the addition of a $3^{rd}$ portion of 10% wt Pd/C (12 mg) at 25° C. The reaction mixture was stirred for 96 h at 25° C., and then filtered through a Celite pad and evaporated to dryness. The residue was purified by silica gel chromatography using a mobile phase of DCM and MeOH to provide 62 mg (61% yield) of the title compound as a yellow solid. LCMS: $C_{26}H_{24}N_4O_7$, desired mass=504.5, found: m/z=505.2 $[M+H]^+$.

Intermediate 61

(3R)-1-((1R,4R)-4-((5-(2,6-dioxopiperidin-3-yl)pyridin-2-yl)(methyl)amino)cyclohexane-1-carbonyl)pyrrolidine-3-carboxylic acid

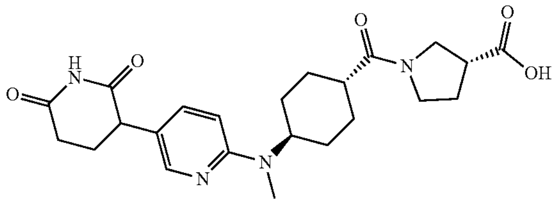 [SMILES: CN(c1ccc(C2CCC(=O)NC2=O)cn1)[C@H]1CC[C@H](C(=O)N2CC[C@@H](C(=O)O)C2)CC1]

Benzyl (3R)-pyrrolidine-3-carboxylate hydrochloride was synthesized using methods for intermediate 62: steps 5-6.

Step 1: methyl (1r,4r)-4-{[(tert-butoxy)carbonyl](methyl)amino}cyclohexane-1-carboxylate

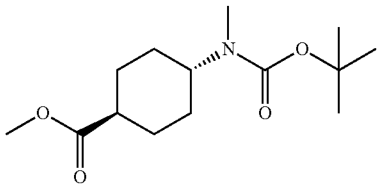 [SMILES: COC(=O)[C@H]1CC[C@H](N(C)C(=O)OC(C)(C)C)CC1]

To a solution of methyl trans-4-(N-Boc-amino)cyclohexanecarboxylate (17.0 g, 66.1 mmol), in anhydrous DMF (146.8 mL) was added sodium hydride (1.902 g, 79.27 mmol, 1.2 eq) at 0° C. The reaction mixture was stirred for 30 min at 0° C., then was added methyl iodide (6.17 mL, 99.1 mmol) at 0° C. and then the mixture was stirred overnight at room temperature. The reaction mixture was then evaporated to dryness and quenched with saturated aq $NH_4Cl$. The water phase was extracted with $Et_2O$ and the organic fractions were evaporated to dryness. The resulting 17.8 g (99% yield) of the title compound as a transparent oil was used as-is for the next step. LCMS: $C_{14}H_{25}NO_4$, desired mass=271.36, found: m/z=272.10 $[M+H]^+$.

Step 2: methyl (1r,4r)-4-(methylamino)cyclohexane-1-carboxylate hydrochloride

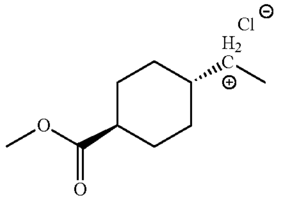

To a solution of methyl (1r,4r)-4-{[(tert-butoxy)carbonyl](methyl)amino}cyclohexane-1-carboxylate (17.8 g, 65.6 mmol) in DCM (262.4 mL, 0.25 M) was added dropwise 4M HCl in 1,4-dioxane (262.4 mL, 1050 mmol) at 0° C. The reaction mixture was overnight at room temperature, and the mixture was concentrated and reevaporated 3 times with DCM. The resulting 13.62 g (quantitative yield) of the title compound as a white powder was used as-is for the next step. LCMS: $C_9H_{18}ClNO_2$, desired mass=207.70, found: m/z=none $[M+H]^+$.

Step 3: methyl (1r,4r)-4-[(5-bromopyridin-2-yl)(methyl)amino]cyclohexane-1-carboxylate

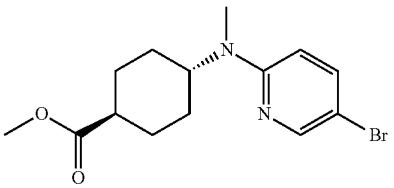 [SMILES: COC(=O)[C@H]1CC[C@H](N(C)c2ccc(Br)cn2)CC1]

To a solution of 5-bromo-2-fluoropyridine (5.43 g, 30.8 mmol) in anhydrous DMSO (30.85 mL) were added methyl (1r,4r)-4-(methylamino)cyclohexane-1-carboxylate hydrochloride (3.23 g, 15.4 mmol) and cesium carbonate (20.1 g, 61.7 mmol) at room temperature. The reaction mixture was stirred overnight at 130° C., and then the mixture was concentrated. The residue was suspended in DCM, formed solid was filtered, and the obtained filtrate was concentrated. The residue was purified by silica gel chromatography using a mobile phase of hexane and ethyl acetate (0 to 10%) to provide 1.53 g (30% yield) of the title compound as a yellow oil. LCMS: $C_{14}H_{19}BrN_2O_2$, desired mass=327.22, found: m/z=327.25 $[M+H]^+$.

Step 4: methyl (1r,4r)-4-{[2',6'-bis(benzyloxy)-[3,3'-bipyridin]-6-yl](methyl)amino}cyclohexane-1-carboxylate

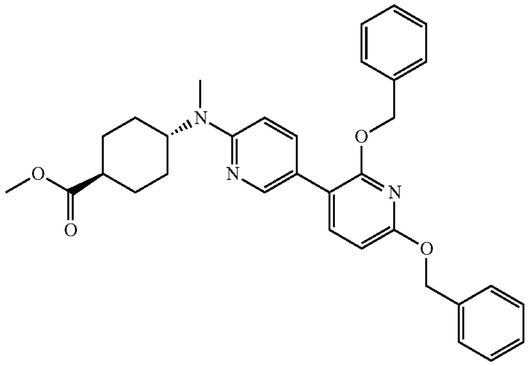

To a solution of methyl (1r,4r)-4-[(5-bromopyridin-2-yl)(methyl)amino]cyclohexane-1-carboxylate (1.53 g, 4.68 mmol) in degassed dimethylformamide (13.37 mL) was added 2,6-bis(benzyloxy)-3-(4,4,5,5-tetramethyl-1,3,2-dioxaborolan-2-yl)pyridine (1.95 g, 4.68 mmol), 1,1'-bis(diphenylphosphino)ferrocene dichloropalladium (II) (0.171 g, 0.234 mmol) and potassium carbonate (1.94 g, 14.0 mmol) at room temperature. The reaction mixture was stirred overnight at 85° C., and then the mixture was evaporated in vacuo. The residue was purified by silica gel chromatography using a mobile phase of hexane and ethyl acetate (0 to 30%) to provide 1.49 g (59% yield) of the title compound as a brown oil. LCMS: $C_{33}H_{35}N_3O_4$, desired mass=537.66, found: m/z=538.70 $[M+H]^+$.

Step 5: (1r,4r)-4-{[2',6'-bis(benzyloxy)-[3,3'-bipyridin]-6-yl](methyl)amino}cyclohexane-1-carboxylic acid

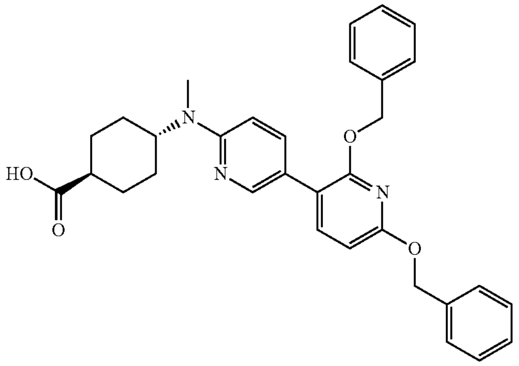 [SMILES: CN(c1ccc(-c2ccc(OCc3ccccc3)nc2OCc2ccccc2)cn1)[C@H]1CC[C@H](C(=O)O)CC1]

To a solution of methyl (1r,4r)-4-{[2',6'-bis(benzyloxy)-[3,3'-bipyridin]-6-yl](methyl)amino}cyclohexane-1-carboxylate (1.44 g, 2.68 mmol) in a mixture of THF (4.32 mL) and water (1.42 mL) was added lithium hydroxide monohydride (0.225 g, 5.36 mmol) at room temperature. The reaction mixture was stirred for 8 h at room temperature, and then THF was evaporated. To the remaining water layer was added $KHSO_4$ (0.729 g, 5.36 mmol) to adjust the pH at 4-5, formed solid was filtered, dissolved in DCM, dried under $Na_2SO_4$. The resulting 1.26 g (90% yield) of the title compound as a yellow solid was used as-is for the next step. LCMS: $C_{33}H_{34}N_2O_4$, desired mass=522.65, found: m/z=523.70 $[M+H]^+$.

Step 6: (1r,4r)-4-{[5-(2,6-dioxopiperidin-3-yl)pyridin-2-yl](methyl)amino}cyclohexane-1-carboxylic acid

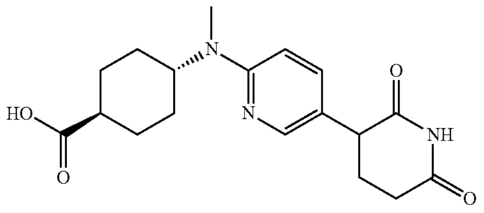 [SMILES: CN(c1ccc(C2CCC(=O)NC2=O)cn1)[C@H]1CC[C@H](C(=O)O)CC1]

To a solution of (1r,4r)-4-{[2',6'-bis(benzyloxy)-[3,3'-bipyridin]-6-yl](methyl)amino}cyclohexane-1-carboxylic acid (2.8 g, 5.347 mmol) in a mixture of degassed tetrahydrofuran (140.72 mL) and isopropanol (140.72 mL) was added palladium on carbon 60-65% wet (0.29 g, 2.72 mmol) at room temperature. The reaction mixture was stirred for 24 h at room temperature under $H_2$ (1 atm) and then was added another portion of palladium on carbon 60-65% wet (0.29 g, 2.72 mmol) and a mixture of degassed tetrahydrofuran (70.36 mL) and isopropanol (70.36 mL) at room temperature. The reaction mixture was stirred for another 24 h at room temperature under $H_2$ (1 atm) then the mixture was filtered, and the filtrate was concentrated under reduced pressure. The residue was purified by prep-HPLC method 1 to provide 179.8 mg (21% yield) of the title compound as a grey solid. LCMS: $C_{18}H_{23}N_3O_4$, desired mass=345.40, found: m/z=346.25 $[M+H]^+$.

Step 7: benzyl (3R)-1-[(1r,4r)-4-{[5-(2,6-dioxopiperidin-3-yl)pyridin-2-yl](methyl)amino}cyclohexanecarbonyl]pyrrolidine-3-carboxylate

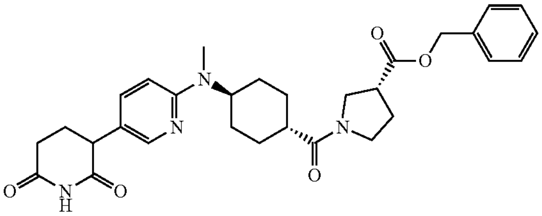 [SMILES: CN(c1ccc(C2CCC(=O)NC2=O)cn1)[C@H]1CC[C@H](C(=O)N2CC[C@@H](C(=O)OCc3ccccc3)C2)CC1]

To a solution of (1r,4r)-4-{[5-(2,6-dioxopiperidin-3-yl)pyridin-2-yl](methyl)amino}cyclohexane-1-carboxylic acid (0.12 g, 0.35 mmol) in anh. DMF (1.2 mL, 0.3 M) were added HATU (0.16 g, 0.42 mmol) and DIPEA (0.24 mL, 1.39 mmol) at 25° C. and stirred for 0.5 h at 25° C. Then solution of benzyl (3R)-pyrrolidine-3-carboxylate hydrochloride (0.1 g, 0.42 mmol) in anh. DMF (1.2 mL, 0.3 M) was added and the reaction mixture was stirred for 16 h at 25° C. The solvents were evaporated to dryness and the residue was purified by silica gel chromatography using mobile of DCM and MeOH to provide 0.075 g (39% yield) of title compound. LCMS: $C_{30}H_{36}N_4O_5$, desired mass=532.3, found: m/z=533.5 $[M+H]^+$.

Step 8: (3R)-1-((1r,4R)-4-((5-(2,6-dioxopiperidin-3-yl)pyridin-2-yl)(methyl)amino)cyclohexane-1-carbonyl)pyrrolidine-3-carboxylic acid

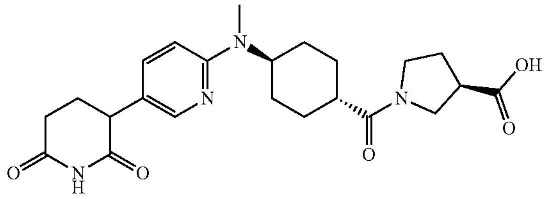 [SMILES: CN(c1ccc(C2CCC(=O)NC2=O)cn1)[C@H]1CC[C@H](C(=O)N2CC[C@@H](C(=O)O)C2)CC1]

Benzyl (3R)-1-[(1r,4r)-4-{[5-(2,6-dioxopiperidin-3-yl) pyridin-2-yl](methyl)amino}cyclohexanecarbonyl]pyrrolidine-3-carboxylate (0.075 g, 0.14 mmol) was dissolved in HBr solution in AcOH (10.30 mL, 4.22 mmol) at 25° C. and left stirring for 16 h at 25° C. Then reaction mixture was concentrated, triturated with $Et_2O$ and lyophilized to provide 0.061 g (77% yield) of title compound as an orange solid. LCMS: $C_{23}H_{30}N_4O_5$, desired mass=442.5, found: m/z=443.3 $[M+H]^+$.

Intermediate 62

(3R)-1-((1R,4R)-4-((2-(2,6-dioxopiperidin-3-yl)-1,3-dioxoisoindolin-4-yl)(methyl)amino)cyclohexane-1-carbonyl)pyrrolidine-3-carboxylic acid

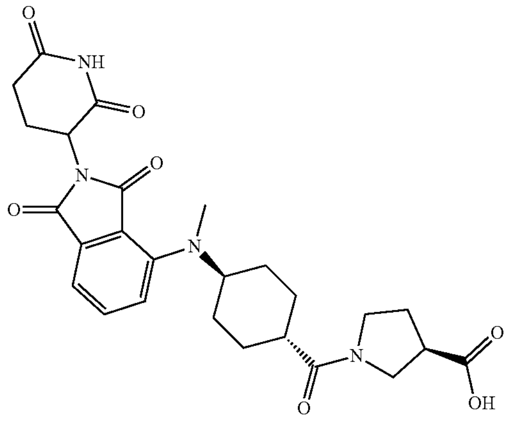 [SMILES: CN(c1cccc2c1C(=O)N(C1CCC(=O)NC1=O)C2=O)[C@H]1CC[C@H](C(=O)N2CC[C@@H](C(=O)O)C2)CC1]

Step 1: methyl (1r,4r)-4-{[(tert-butoxy)carbonyl](methyl)amino}cyclohexane-1-carboxylate

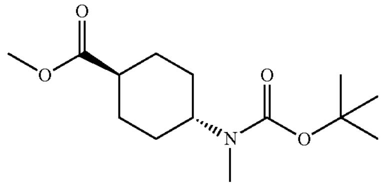 [SMILES: COC(=O)[C@H]1CC[C@H](N(C)C(=O)OC(C)(C)C)CC1]

To a solution of methyl trans-4-(N-Boc-amino)cyclohexanecarboxylate (3.0 g, 11.66 mmol) in anhydrous DMF (20.0 mL) was added sodium hydride (536 mg, 14.0 mmol) at 0° C. The reaction mixture was stirred for 30 min at 0° C., and then methyl iodide (1.09 mL, 17.50 mmol) was added at 0° C. The reaction mixture was stirred for 16 h at 25° C., and then the resulting mixture was coevaporated with toluene (3×100 mL) and quenched with saturated aq $NH_4Cl$. The water phase was extracted with $Et_2O$ (3×50 mL), and the organic fractions were concentrated to dryness to provide 3.276 g (99% yield) of the title compound as a transparent oil that was used as-is for the next step.

Step 2: (1r,4r)-4-{[(tert-butoxy)carbonyl](methyl)amino}cyclohexane-1-carboxylic acid

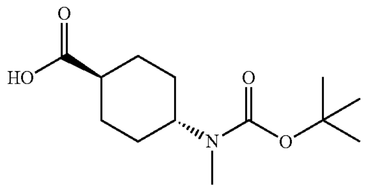 [SMILES: CN(C(=O)OC(C)(C)C)[C@H]1CC[C@H](C(=O)O)CC1]

To a solution of methyl (1r,4r)-4-{[(tert-butoxy)carbonyl](methyl)amino}cyclohexane-1-carboxylate (3.276 g, 12.07 mmol) in THF (25 mL) and water (5 mL) was added lithium hydroxide monohydrate (1.037 g, 24.15 mmol) at 25° C. The reaction mixture was stirred for 16 h at 25° C., and then THF was evaporated under reduced pressure. Then an aqueous solution of $KHSO_4$ was added to the aqueous layer until the pH reached 2, followed by extraction with EtOAc (4×25 mL). The combined organic extracts were dried with $Na_2SO_4$ and evaporated under reduced pressure to provide 2.510 g (81% yield) of the title compound as a white solid that was used as-is for the next step.

Step 3: (1r,4r)-4-(methylamino)cyclohexane-1-carboxylic acid hydrochloride

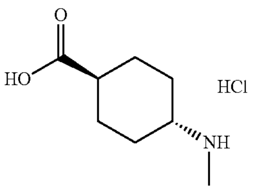

To a solution of (1r,4r)-4-{[(tert-butoxy)carbonyl](methyl)amino}cyclohexane-1-carboxylic acid (2.510 g, 9.75 mmol) in anhydrous DCM (130.0 mL) was added 2M HCl in $Et_2O$ (39.0 mL, 78.03 mmol) at 0° C. The reaction mixture was stirred for 16 h at 25° C., and then the solvents were evaporated to dryness under reduced pressure to provide 1.740 g (92% yield) of the title compound as a white solid that was used as-is for the next step.

Step 4: (1r,4r)-4-{[2-(2,6-dioxopiperidin-3-yl)-1,3-dioxo-2,3-dihydro-1H-isoindol-4-yl](methyl)amino}cyclohexane-1-carboxylic acid

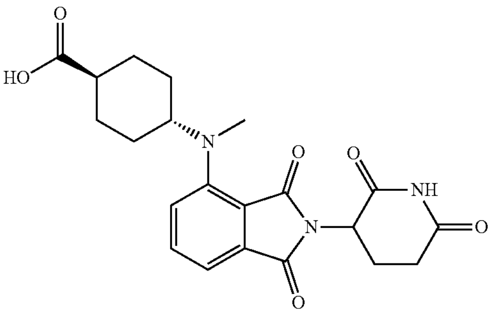 [SMILES: CN(c1cccc2c1C(=O)N(C1CCC(=O)NC1=O)C2=O)[C@H]1CC[C@H](C(=O)O)CC1]

To a solution of (1r,4r)-4-(methylamino)cyclohexane-1-carboxylic acid hydrochloride (1.737 g, 9.00 mmol) in anhydrous DMSO (50.0 mL) were added 2-(2,6-dioxopiperidin-3-yl)-5-fluoro-2,3-dihydro-1H-isoindole-1,3-dione (2.485 g, 9.0 mmol) and KF (2.090 g, 35.98 mmol) at 25° C. The reaction mixture was stirred for 16 h at 120° C., and then poured into 1000 mL of brine and extracted with EtOAc (5×100 mL). The combined organic extracts were dried with $Na_2SO_4$ and evaporated under reduced pressure. The residue was purified by silica gel chromatography using a mobile phase of DCM and MeOH, then MeCN and $H_2O$ to provide 768 mg (21% yield) of the title compound as a yellow solid. LCMS: $C_{21}H_{23}N_3O_6$, desired mass=413.4, found: m/z=414.3 $[M+H]^+$.

Step 5: 3-benzyl 1-tert-butyl (3R)-pyrrolidine-1,3-dicarboxylate

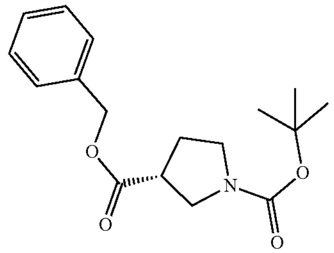 [SMILES: CC(C)(C)OC(=O)N1CC[C@@H](C(=O)OCc2ccccc2)C1]

To a solution of (3R)-1-[(tert-butoxy)carbonyl]pyrrolidine-3-carboxylic acid (5.00 g, 23.23 mmol) in anhydrous DMF (258 mL) was added $Cs_2CO_3$ (9.08 g, 27.87 mmol). The reaction mixture was placed in an ice bath and stirred for 1 h at 0° C. Then benzyl bromide (3.04 mL, 25.55 mmol) was added dropwise at 0° C. The reaction mixture was stirred for 12 h at 25° C., and then the mixture was poured into 1800 mL of brine and extracted with EtOAc (5×150 mL). Combined organic layers were dried with $MgSO_4$ and concentrated under reduced pressure to provide 6.228 g (88% yield) of the title compound as a yellow solid that was used as-is for the next step.

Step 6: benzyl (3R)-pyrrolidine-3-carboxylate hydrochloride

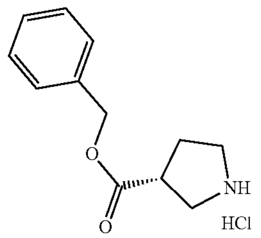 [SMILES: O=C(OCc1ccccc1)[C@@H]1CCNC1 ; Cl]

To a solution of 3-benzyl 1-tert-butyl (3R)-pyrrolidine-1,3-dicarboxylate (6.228 g, 20.39 mmol) in anhydrous DCM (255.0 mL) was added 2M HCl in $Et_2O$ (81.58 mL, 163.16 mmol) at 0° C. The reaction mixture was stirred for 16 h at 25° C., and then the solvents were evaporated to dryness under reduced pressure to provide 4.929 g (100% yield) of the title compound as a yellow oil that was used as-is for the next step.

Step 7: benzyl (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylate

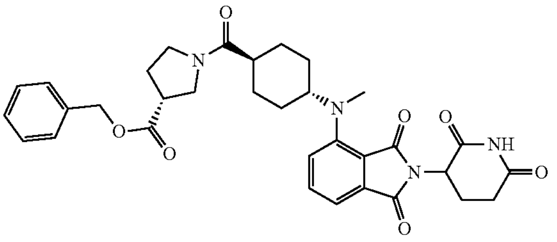 [SMILES: CN(c1cccc2c1C(=O)N(C1CCC(=O)NC1=O)C2=O)[C@H]1CC[C@H](C(=O)N2CC[C@@H](C(=O)OCc3ccccc3)C2)CC1]

To a solution of (1r,4r)-4-{[2-(2,6-dioxopiperidin-3-yl)-1,3-dioxo-2,3-dihydro-1H-isoindol-4-yl](methyl)amino}cyclohexane-1-carboxylic acid (450 mg, 1.09 mmol) in anhydrous DMF (22.0 mL) were added HATU (621 mg, 1.63 mmol) and DIPEA (0.76 mL, 4.35 mmol). The reaction mixture was stirred for 20 min at 25° C. Then benzyl (3R)-pyrrolidine-3-carboxylate hydrochloride (263 mg, 1.09 mmol) was added at 25° C. The reaction mixture was stirred for 16 h at 25° C., and then the mixture was poured into 250 mL of brine, extracted with EtOAc (4×40 mL). The combined organic layers were dried with $Na_2SO_4$ and concentrated under reduced pressure. The residue was purified by silica gel chromatography using a mobile phase of DCM and MeOH to provide 379 mg (58% yield) of the title compound as a yellow solid. LCMS: $C_{33}H_{36}N_4O_7$, desired mass=600.7, found: m/z=599.8 $[M-H^+]$.

Step 8: (3R)-1-((1r,4R)-4-((2-(2,6-dioxopiperidin-3-yl)-1,3-dioxoisoindolin-4-yl)(methyl)amino)cyclohexane-1-carbonyl)pyrrolidine-3-carboxylic acid

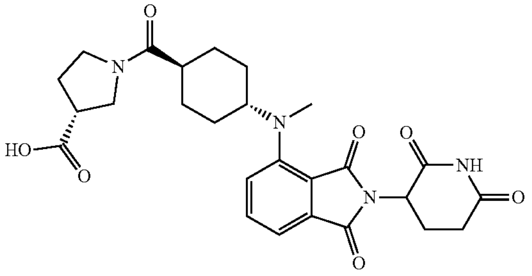 [SMILES: CN(c1cccc2c1C(=O)N(C1CCC(=O)NC1=O)C2=O)[C@H]1CC[C@H](C(=O)N2CC[C@@H](C(=O)O)C2)CC1]

To a solution of benzyl (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylate (379 mg, 0.63 mmol) in anhydrous THF (7.9 mL) was added 10% wt Pd/C (38 mg) at 25° C. The reaction mixture was stirred for 16 h at 25° C., followed by the addition of $2^{nd}$ portion of 10% wt Pd/C (38 mg) at 25° C. The reaction mixture was stirred for another 16 h at 25° C., and then filtered through a Celite pad and evaporated to dryness. The residue was purified by silica gel chromatography using a mobile phase of DCM and MeOH to provide 180 mg (56% yield) of the title compound as a yellow solid. LCMS: $C_{26}H_{30}N_4O_7$, desired mass=510.6, found: m/z=510.8 $[M+H]^+$.

Intermediate 63

1-((1R,4R)-4-((5-(2,6-dioxopiperidin-3-yl)pyridin-2-yl)(methyl)amino)cyclohexane-1-carbonyl)piperidine-4-carboxylic acid

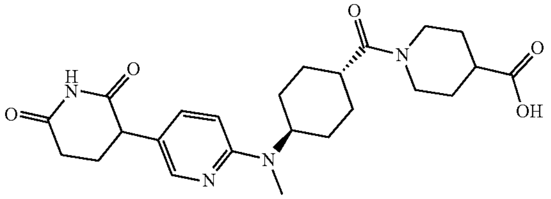 [SMILES: CN(c1ccc(C2CCC(=O)NC2=O)cn1)[C@H]1CC[C@H](C(=O)N2CCC(C(=O)O)CC2)CC1]

(1r,4r)-4-{[5-(2,6-dioxopiperidin-3-yl)pyridin-2-yl](methyl)amino}cyclohexane-1-carboxylic acid was synthesized according to procedures for intermediate 61: steps 1-6.

Step 1: tert-butyl 1-[(1r,4r)-4-{[5-(2,6-dioxopiperidin-3-yl)pyridin-2-yl](methyl)amino}cyclohexanecarbonyl]piperidine-4-carboxylate

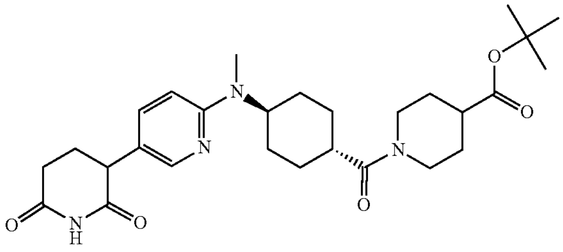 [SMILES: CN(c1ccc(C2CCC(=O)NC2=O)cn1)[C@H]1CC[C@H](C(=O)N2CCC(C(=O)OC(C)(C)C)CC2)CC1]

To a solution of (1r,4r)-4-{[5-(2,6-dioxopiperidin-3-yl)pyridin-2-yl](methyl)amino}cyclohexane-1-carboxylic acid (0.15 g, 0.43 mmol) in anh. DMF (1.5 mL, 0.3 M) were added HATU (0.2 g, 0.52 mmol) and DIPEA (0.3 mL, 1.74 mmol) at 25° C. and stirred for 0.5 h at 25° C. Then tert-butyl piperidine-4-carboxylate (0.12 g, 0.52 mmol) was added and the reaction mixture was stirred for 16 h at 25° C. The solvents were evaporated to dryness and the residue was purified by silica gel chromatography using mobile of hexane and EtOAc to provide 0.08 g (34% yield) of title compound. LCMS: $C_{28}H_{40}N_4O_5$, desired mass=512.3, found: m/z=513.6 [M+H$^+$].

Step 2: 1-[(1r,4r)-4-{[5-(2,6-dioxopiperidin-3-yl)pyridin-2-yl](methyl)amino}cyclohexanecarbonyl]piperidine-4-carboxylic acid trifluoroacetate

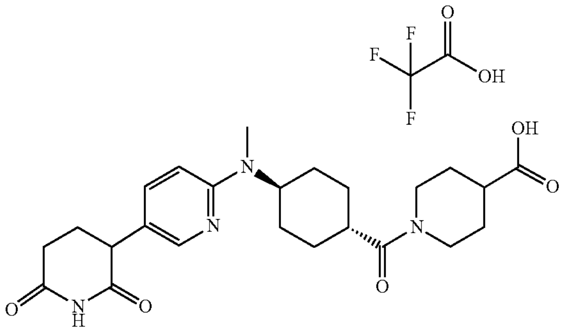 [SMILES: O=C(O)C(F)(F)F ; CN(c1ccc(C2CCC(=O)NC2=O)cn1)[C@H]1CC[C@H](C(=O)N2CCC(C(=O)O)CC2)CC1]

To solution of tert-butyl 1-[(1r,4r)-4-{[5-(2,6-dioxopiperidin-3-yl)pyridin-2-yl](methyl)amino}cyclohexanecarbonyl]piperidine-4-carboxylate (0.084 g, 0.16 mmol) in DCM (3.12 mL, 0.05 M) was added dropwise trifluoroacetic acid (0.36 mL, 4.69 mmol) at 25° C. and reaction mixture was left stirring for 1 h at 25° C. The mixture was concentrated under reduced pressure and residue was triturated with $Et_2O$ to provide 0.053 g (55% yield) of title compound as an off-white solid. LCMS: $C_{23}H_{30}N_4O_5$, desired mass=442.5, found: m/z=443.3 [M+H]$^+$.

Intermediate 64

1-((1R,4R)-4-((2-(2,6-dioxopiperidin-3-yl)-1,3-dioxoisoindolin-4-yl)(methyl)amino)cyclohexane-1-carbonyl)piperidine-4-carboxylic acid

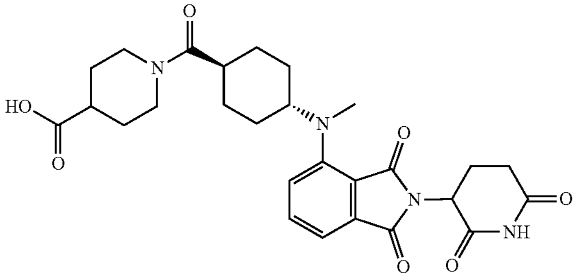 [SMILES: CN(c1cccc2c1C(=O)N(C1CCC(=O)NC1=O)C2=O)[C@H]1CC[C@H](C(=O)N2CCC(C(=O)O)CC2)CC1]

Following procedures similar to Intermediate 15 (steps 4 and 5) and using (1r,4r)-4-((2-(2,6-dioxopiperidin-3-yl)-1,3-dioxoisoindolin-4-yl)(methyl)amino)cyclohexane-1-carboxylic acid and benzyl piperidine-4-carboxylate as the coupling partners, the title compound was obtained as an off-white solid (52 mg, 39% yield over two steps).

Intermediate 65

3-(4-(methyl(piperidin-4-yl)amino)phenyl)piperidine-2,6-dione

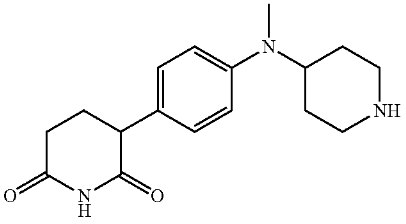 [SMILES: CN(c1ccc(C2CCC(=O)NC2=O)cc1)C1CCNCC1]

Using procedures similar to the preparation of Intermediate 31 (steps 1, 3, and 4) with 1,4-dibromobenzene and tert-butyl 4-(methylamino)piperidine-1-carboxylate as the starting materials in step 1, followed by procedures similar to step 2 of Intermediate 12, the title compound was obtained as an off-white solid (84 mg). LCMS: [$C_{17}H_{23}N_3O_2$], desired mass=301.2, found: m/z=302.3 [M+H]$^+$.

Intermediate 66

3-(4-(methyl(piperidin-4-yl)amino)phenyl)piperidine-2,6-dione

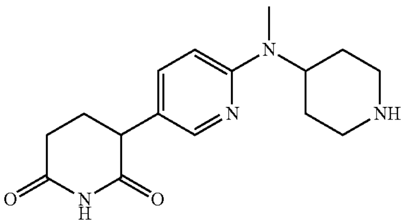 [SMILES: CN(c1ccc(C2CCC(=O)NC2=O)cn1)C1CCNCC1]

Procedures similar to those for Intermediate 12 (steps 1 and 2) were followed using tert-butyl 4-(methylamino) piperidine-1-carboxylate and 3-(6-Fluoro-3-pyridyl)-2,6-piperidinedione as the starting materials in step 1. The title compound was afforded as the HCl salt (off-white solid, 327 mg, 23% yield). LCMS: [$C_{16}H_{22}N_4O_2$], desired mass=302.2, found: m/z=303.1 $[M+H]^+$.

Intermediate 67

4-(4-((5-(2,6-dioxopiperidin-3-yl)pyridin-2-yl)(methyl)amino)piperidine-1-carbonyl)benzoic acid

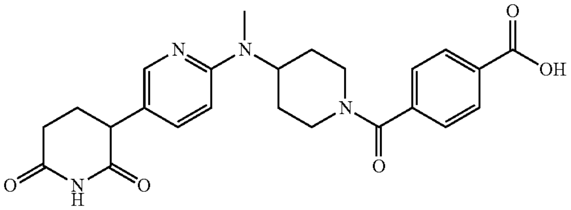 [SMILES: CN(c1ccc(C2CCC(=O)NC2=O)cn1)C1CCN(C(=O)c2ccc(C(=O)O)cc2)CC1]

Procedures similar to those for preparing Intermediate 1 (step 1) were carried out using 4-(tert-butoxycarbonyl)benzoic acid and 3-(4-(methyl(piperidin-4-yl)amino)phenyl)piperidine-2,6-dione as the starting materials, followed by tert-butyl ester deprotection using procedures similar to those in step 2 of Intermediate 68. The title compound was afforded as an off-white solid (48 mg, 72% yield). LCMS: [$C_{24}H_{26}N_4O_5$], desired mass=450.2, found: m/z=451.4 $[M+H]^+$.

Intermediate 68

4-((1-(5-(2,6-dioxopiperidin-3-yl)pyridin-2-yl)piperidin-4-yl)(methyl)carbamoyl)benzoic acid

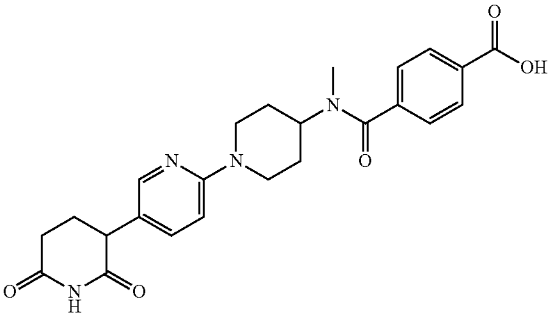 [SMILES: CN(C(=O)c1ccc(C(=O)O)cc1)C1CCN(c2ccc(C3CCC(=O)NC3=O)cn2)CC1]

Step 1: tert-butyl 4-({1-[5-(2,6-dioxopiperidin-3-yl)pyridin-2-yl]piperidin-4-yl}(methyl)carbamoyl)benzoate

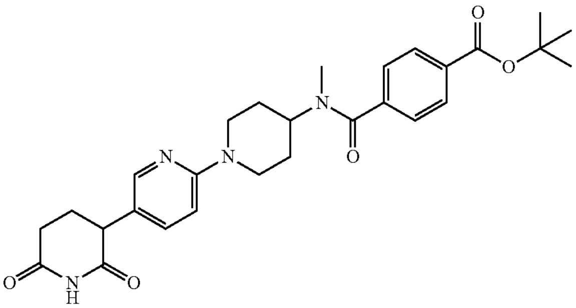 [SMILES: CN(C(=O)c1ccc(C(=O)OC(C)(C)C)cc1)C1CCN(c2ccc(C3CCC(=O)NC3=O)cn2)CC1]

Following a similar procedure to step 1 in intermediate 1 with 4-(tert-butoxycarbonyl)benzoic acid (837 mg, 3.770 mmol), DMF (8 mL), HATU (1075 mg, 2.828 mmol), 3-{6-[4-(methylamino)piperidin-1-yl]pyridin-3-yl}piperidine-2,6-dione (570 mg, 1.885 mmol) and DIEA (730 mg, 5.655 mmol). The residue was purified by reverse phase flash chromatography [ACN and $H_2O$ mobile phase] to yield 440 mg (41.47%) of the title compound as an orange solid. LCMS: ($C_{28}H_{34}N_4O_5$) desired mass=506.3; found: m/z=507.2 $[M+H]^+$.

Step 2: 4-((1-(5-(2,6-dioxopiperidin-3-yl)pyridin-2-yl)piperidin-4-yl)(methyl)carbamoyl)benzoic acid

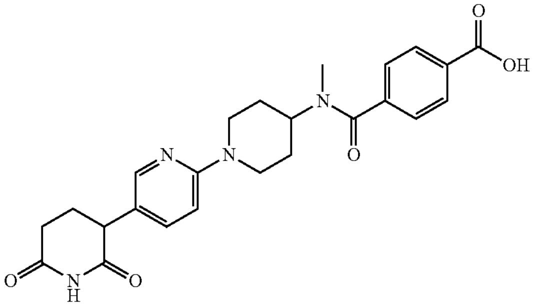 [SMILES: CN(C(=O)c1ccc(C(=O)O)cc1)C1CCN(c2ccc(C3CCC(=O)NC3=O)cn2)CC1]

A mixture of tert-butyl 4-({1-[5-(2,6-dioxopiperidin-3-yl)pyridin-2-yl]piperidin-4-yl}(methyl)carbamoyl)benzoate (100 mg, 0.197 mmol) and HCl (10 mL, 12M) was stirred for 2 h at room temperature, then the mixture was concentrated. The residue was purified by reverse phase flash chromatography [ACN and $H_2O$ mobile phase] to yield 41.9 mg (46.46%) of the title compound as a white solid. LCMS: ($C_{24}H_{26}N_4O_5$) desired mass=450.2; found: m/z=451.1 $[M+H]^+$.

Intermediate 69

1-((1-(1-(2,6-dioxopiperidin-3-yl)-3-methyl-2-oxo-2,3-dihydro-1H-benzo[d]imidazol-4-yl)piperidin-4-yl)methyl)piperidine-4-carboxylic acid

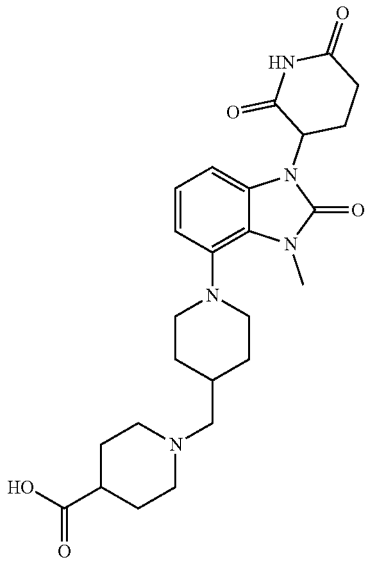 [SMILES: Cn1c(=O)n(C2CCC(=O)NC2=O)c2cccc(N3CCC(CN4CCC(C(=O)O)CC4)CC3)c21]

Step 1: 1-(1-(2,6-dioxopiperidin-3-yl)-3-methyl-2-oxo-2,3-dihydro-1H-benzo[d]imidazol-4-yl)piperidine-4-carbaldehyde

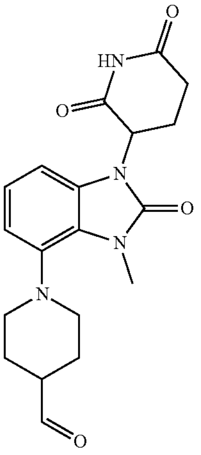 [SMILES: Cn1c(=O)n(C2CCC(=O)NC2=O)c2cccc(N3CCC(C=O)CC3)c21]

3-(4-(4-(hydroxymethyl)piperidin-1-yl)-3-methyl-2-oxo-2,3-dihydro-1H-benzo[d]imidazol-1-yl)piperidine-2,6-dione (prepared using procedures similar to step 3 of intermediate 70 using 4-benzyloxymethyl-piperidine and 1-[2,6-bis(benzyloxy)pyridin-3-yl]-4-bromo-3-methyl-1,3-benzodiazol-2-one as the starting materials, followed by using procedures similar to step 5 of intermediate 15) (49.7 mg, 0.13 mmol) was dissolved in DMSO (1 mL) then treated with polystyrene-supported 2-iodoxybenzoic acid (330 mg of 1.2 mmol/g, 0.39 mmol). The reaction mixture was stirred for 16 hours, then filtered, washing with DCM. The DCM was removed under reduced pressure and the title compound was carried forward to the next step as a DMSO solution. LCMS: ($C_{19}H_{22}N_4O_4$) desired mass=370.2; found: m/z=371.1 $[M+H]^+$.

Step 2: 1-((1-(1-(2,6-dioxopiperidin-3-yl)-3-methyl-2-oxo-2,3-dihydro-1H-benzo[d]imidazol-4-yl)piperidin-4-yl)methyl)piperidine-4-carboxylic acid 1-(1-(2,6-dioxopiperidin-3-yl)-3-methyl-2-oxo-2,3-dihydro-1H-benzo[d]imidazol-4-yl)piperidine-4-carbaldehyde (DMSO solution from above) was diluted in 1,2-dichloroethane (0.41 mL), then tert-butyl piperidine-4-carboxylate (43 mg, 0.26 mmol) and sodium triacetoxyborohydride (33 mg, 0.16 mmol) were added. The reaction mixture was stirred for 1 h, then a saturated solution of sodium bicarbonate was added (20 mL). The aqueous layer was extracted with DCM (3×10 mL), then the combine organic layers were washed with a saturated solution of sodium chloride (2×5 mL), dried over sodium sulfate, and purified by reverse phase chromatography (mobile phase: ACN and water). After lyophilization of the desired fractions, DCM (1 mL), followed by HCl (1 mL of a 4N solution in dioxane) was added to the residue. The reaction mixture was stirred overnight, then concentrated under reduced pressure to afford the title compound as the HCl salt (off-white solid, 42 mg, 76% yield). LCMS: ($C_{25}H_{33}N_5O_5$) desired mass=483.3; found: m/z=484.4 $[M+H]^+$.

Intermediate 70

(3S)-1-[(1R,4R)-4-({1-[(3RS)-2,6-dioxopiperidin-3-yl]-3-methyl-2-oxo-1,3-benzodiazol-4-cyl}amino)cyclohexanecarbonyl]pyrrolidine-3-carboxylic acid

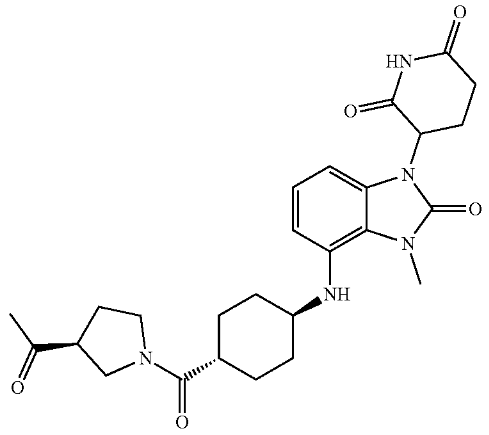 [SMILES: CC(=O)[C@H]1CCN(C(=O)[C@H]2CC[C@H](Nc3cccc4c3n(C)c(=O)n4C3CCC(=O)NC3=O)CC2)C1]

Step-1: 2,6-bis(benzyloxy)-N-(3-bromo-2-nitrophenyl)pyridin-3-amine

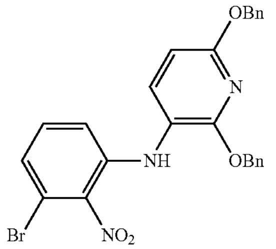

To a mixture of 2,6-bis(benzyloxy)pyridin-3-amine (3.48 g, 11.364 mmol) in THF (10 mL) was added t-BuOK (2.55 g, 22.728 mmol) and 1-bromo-3-fluoro-2-nitrobenzene (2.5 g, 11.364 mmol). The resulting mixture was stirred for 2 h at room temperature. The resulting mixture was concentrated under reduced pressure. The residue was purified by silica gel chromatography using a mobile phase of [PE and EA] to provide 2 g (24.33%) of the title compound as a red oil. LCMS: ($C_{25}H_{20}BrN_3O_2$) desired mass=505.1; found: m/z=506.2. $[M+H]^+$.

Step-2: N-1-[2,6-bis(benzyloxy)pyridin-3-yl]-3-bromobenzene-1,2-diamine

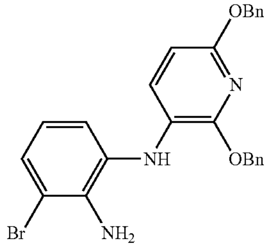 [SMILES: O=[N+]([O-])c1c(Br)cccc1Nc1ccc(OCc2ccccc2)nc1OCc1ccccc1]

To a mixture of 2,6-bis(benzyloxy)-N-(3-bromo-2-nitrophenyl)pyridin-3-amine (14 g, 27.649 mmol) in IPA (700 mL) was added Fe (7.72 g, 138.245 mmol) and saturated aqueous $NH_4Cl$ solution (100 mL). The resulting mixture was stirred overnight at 80° C. The resulting mixture was concentrated under reduced pressure. The residue was purified by silica gel chromatography using a mobile phase of [PE and EA] to provide 11 g (58.46%) of the title compound as a brown oil. LCMS: ($C_{25}H_{22}BrN_3O_2$) desired mass=475.1; found: m/z=476.0 $[M+H]^+$.

Step-3: 1-[2,6-bis(benzyloxy)pyridin-3-yl]-4-bromo-3H-1,3-benzodiazol-2-one

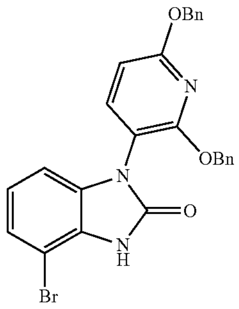 [SMILES: O=c1[nH]c2c(Br)cccc2n1-c1ccc(OCc2ccccc2)nc1OCc1ccccc1]

To a mixture of N-1-[2,6-bis(benzyloxy)pyridin-3-yl]-3-bromobenzene-1,2-diamine (700 mg, 1.469 mmol) in DCM (6 mL) was added DIEA (228 mg, 1.763 mmol) and triphosgene (262 mg, 0.881 mmol) at 0° C. The resulting mixture was stirred for 2 h at room temperature. The resulting mixture was concentrated under reduced pressure. The residue was purified by silica gel chromatography using a mobile phase of [PE and EA] to provide 590 mg (71.93%) of the title compound as a pink solid. LCMS: ($C_{26}H_{20}BrN_3O_3$) desired mass=501.1; found: m/z=502.1 $[M+H]^+$.

Step-4: 1-[2,6-bis(benzyloxy)pyridin-3-yl]-4-bromo-3-methyl-1,3-benzodiazol-2-one

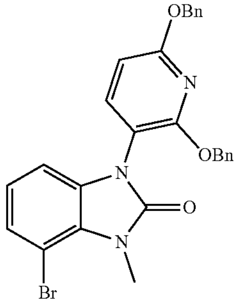 [SMILES: Cn1c(=O)n(-c2ccc(OCc3ccccc3)nc2OCc2ccccc2)c2cccc(Br)c21]

To a mixture of NaH (56 mg, 2.348 mmol) in THF (10 mL) was added 1-[2,6-bis(benzyloxy)pyridin-3-yl]-4-bromo-3H-1,3-benzodiazol-2-one (590 mg, 1.174 mmol) at 0° C. under nitrogen atmosphere. The resulting mixture was stirred for 30 min at room temperature. To the above mixture was added MeI (500 mg, 3.522 mmol) at 0° C. The resulting mixture was stirred for 2 h at room temperature. The resulting mixture was quenched with water at 0° C. The resulting mixture was concentrated under reduced pressure. The residue was purified by silica gel chromatography using a mobile phase of [PE and EA] to provide 580 mg (83.20%) of the title compound as a yellow solid. LCMS: ($C_{27}H_{22}BrN_3O_3$) desired mass=515.1; found: m/z=516.1 $[M+H]^+$.

Step-5: methyl (1r,4r)-4-({1-[2,6-bis(benzyloxy)pyridin-3-yl]-3-methyl-2-oxo-1,3-benzodiazol-4-yl}amino)cyclohexane-1-carboxylate

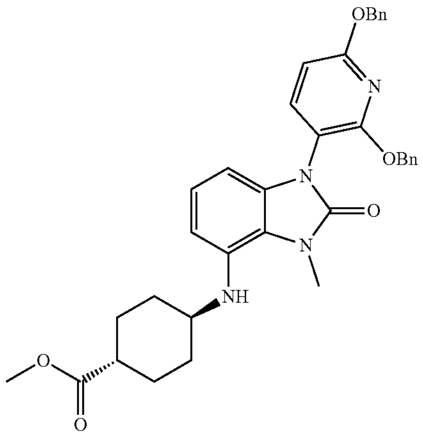 [SMILES: COC(=O)[C@H]1CC[C@H](Nc2cccc3c2n(C)c(=O)n3-c2ccc(OCc3ccccc3)nc2OCc2ccccc2)CC1]

To a mixture of 1-[2,6-bis(benzyloxy)pyridin-3-yl]-4-bromo-3-methyl-1,3-benzodiazol-2-one (5 g, 9.683 mmol) in toluene (30 mL) were added methyl (1r,4r)-4-aminocyclohexane-1-carboxylate hydrochloride (2.25 g, 11.620 mmol), RuPhos Palladacycle Gen.3 (0.81 g, 0.968 mmol) and $Cs_2CO_3$ (9.46 g, 29.049 mmol). The resulting mixture was stirred overnight at 100° C. under nitrogen atmosphere. The resulting mixture was concentrated under reduced pressure. The residue was purified by silica gel chromatography using a mobile phase of [PE and EA] to provide 4 g (62.73%) of the title compound as a white solid. LCMS: ($C_{35}H_{36}N_4O_5$) desired mass=592.3; found: m/z=593.4 $[M+H]^+$.

Step-6: (1r,4r)-4-({1-[2,6-bis(benzyloxy)pyridin-3-yl]-3-methyl-2-oxo-1,3-benzodiazol-4-yl}amino) cyclohexane-1-carboxylic acid

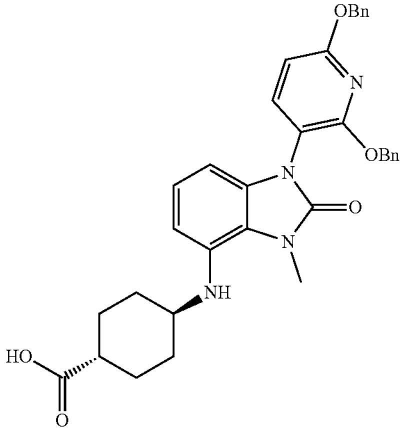 [SMILES: Cn1c(=O)n(-c2ccc(OCc3ccccc3)nc2OCc2ccccc2)c2cccc(N[C@H]3CC[C@H](C(=O)O)CC3)c21]

Procedures similar to those in step 4 of Intermediate 59 were followed using methyl (1r,4r)-4-({1-[2,6-bis(benzyloxy)pyridin-3-yl]-3-methyl-2-oxo-1,3-benzodiazol-4-yl}amino)cyclohexane-1-carboxylate (4 g, 6.749 mmol), water (10 mL), THF (10 mL), MeOH (10 mL) and LiOH (1.62 g, 67.490 mmol) to provide 3.2 g (crude) of the title compound as a white solid. The residue was used directly for the next step. LCMS: ($C_{34}H_{34}N_4O_5$) desired mass=578.3; found: m/z=579.3 $[M+H]^+$.

Step-7: tert-butyl (3S)-1-[(1r,4r)-4-({1-[2,6-bis(benzyloxy)pyridin-3-yl]-3-methyl-2-oxo-1,3-benzodiazol-4-yl}amino)cyclohexanecarbonyl]pyrrolidine-3-carboxylate

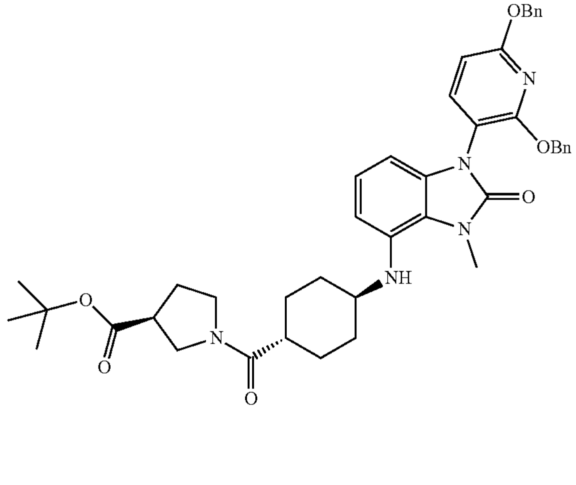 [SMILES: Cn1c(=O)n(-c2ccc(OCc3ccccc3)nc2OCc2ccccc2)c2cccc(N[C@H]3CC[C@H](C(=O)N4CC[C@H](C(=O)OC(C)(C)C)C4)CC3)c21]

Procedures similar to those in step 1 of Intermediate 19 were followed using (1r,4r)-4-({1-[2,6-bis(benzyloxy)pyridin-3-yl]-3-methyl-2-oxo-1,3-benzodiazol-4-yl}amino)cyclohexane-1-carboxylic acid (3 g, 5.184 mmol), HATU (2.96 g, 7.776 mmol), DMF (6 mL), tert-butyl (3S)-pyrrolidine-3-carboxylate (0.89 g, 5.184 mmol) and DIEA (2.01 g, 15.552 mmol). The residue was purified by reverse phase flash chromatography of [$CH_3CN$ and $H_2O$] to provide 2.5 g (62.59%) of the title compound as a white solid. LCMS: ($C_{43}H_{49}N_5O_6$) desired mass=731.4; found: m/z=732.4 $[M+H]^+$.

Step-8: tert-butyl (3S)-1-[(1r,4r)-4-{[1-(2,6-dioxopiperidin-3-yl)-3-methyl-2-oxo-1,3-benzodiazol-4-yl] amino}cyclohexanecarbonyl]pyrrolidine-3-carboxylate

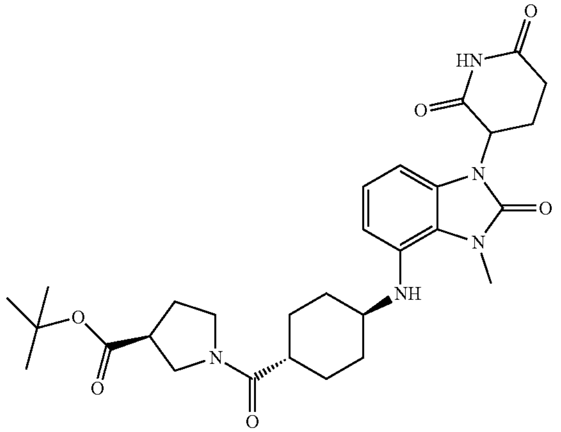 [SMILES: Cn1c(=O)n(C2CCC(=O)NC2=O)c2cccc(N[C@H]3CC[C@H](C(=O)N4CC[C@H](C(=O)OC(C)(C)C)C4)CC3)c21]

Procedures similar to those in step 5 of Intermediate 15 were followed using tert-butyl (3S)-1-[(1r,4r)-4-({1-[2,6-bis(benzyloxy)pyridin-3-yl]-3-methyl-2-oxo-1,3-benzodiazol-4-yl}amino)cyclohexanecarbonyl]pyrrolidine-3-carboxylate (0.5 g, 0.683 mmol), THF (25 mL) and Pd/C (1.6 g) to provide 260 mg (crude) of the title compound as a white solid. The residue was used directly in the next step. LCMS: ($C_{29}H_{39}N_5O_6$) desired mass=553.3; found: m/z=554.2 $[M+H]^+$.

Step-9: (3S)-1-[(1r,4r)-4-({1-[(3RS)-2,6-dioxopiperidin-3-yl]-3-methyl-2-oxo-1,3-benzodiazol-4-cyl}amino)cyclohexanecarbonyl]pyrrolidine-3-carboxylic acid

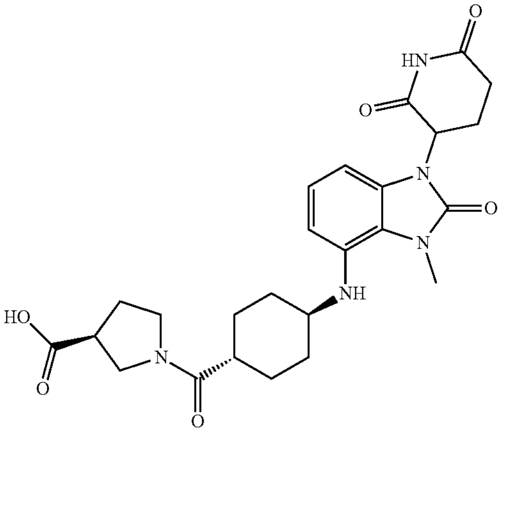 [SMILES: Cn1c(=O)n(C2CCC(=O)NC2=O)c2cccc(N[C@H]3CC[C@H](C(=O)N4CC[C@H](C(=O)O)C4)CC3)c21]

To a mixture of tert-butyl (3S)-1-[(1r,4r)-4-{[1-(2,6-dioxopiperidin-3-yl)-3-methyl-2-oxo-1,3-benzodiazol-4-yl]amino}cyclohexanecarbonyl]pyrrolidine-3-carboxylate (300 mg, 0.542 mmol) in DCM (6 mL) was added TFA (2 mL) at 0° C. The resulting mixture was stirred for 3 h at room temperature. The resulting mixture was concentrated under vacuum. The residue was triturated with acetonitrile. The precipitated solids were collected by filtration and washed with acetonitrile to provide 252.9 mg (92.02%) of the title compound as a white solid. LCMS (Method 7): ($C_{25}H_{31}N_5O_6$) desired mass=497.2; found: m/z=498.2 $[M+H]^+$.

Intermediate 71

(3R)-1-[(1R,4R)-4-({1-[(3RS)-2,6-dioxopiperidin-3-yl]-3-methyl-2-oxo-1,3-benzodiazol-4-yl}amino)cyclohexanecarbonyl]pyrrolidine-3-carboxylic acid

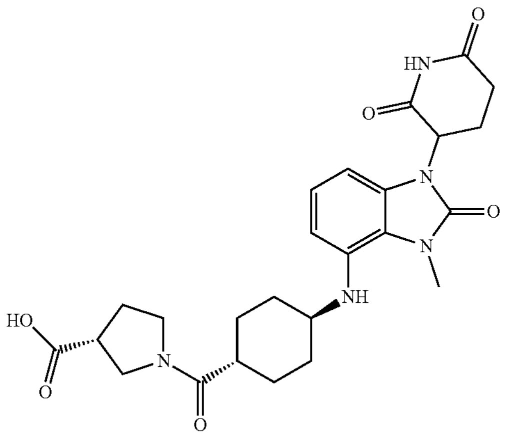 [SMILES: Cn1c(=O)n(C2CCC(=O)NC2=O)c2cccc(N[C@H]3CC[C@H](C(=O)N4CC[C@@H](C(=O)O)C4)CC3)c21]

Step-1: tert-butyl (3R)-1-[(1r,4r)-4-({1-[2,6-bis(benzyloxy)pyridin-3-yl]-3-methyl-2-oxo-1,3-benzodiazol-4-yl}amino)cyclohexanecarbonyl]pyrrolidine-3-carboxylate

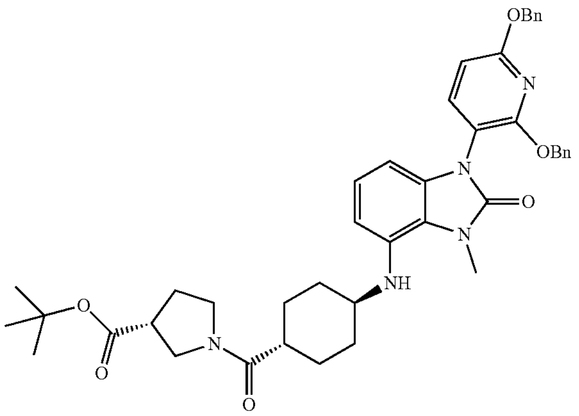 [SMILES: Cn1c(=O)n(-c2ccc(OCc3ccccc3)nc2OCc2ccccc2)c2cccc(N[C@H]3CC[C@H](C(=O)N4CC[C@@H](C(=O)OC(C)(C)C)C4)CC3)c21]

Procedures similar to those in step 1 of Intermediate 19 were followed using (1r,4r)-4-({1-[2,6-bis(benzyloxy)pyridin-3-yl]-3-methyl-2-oxo-1,3-benzodiazol-4-yl}amino)cyclohexane-1-carboxylic acid (2 g, 3.456 mmol), DMF (10 mL), HATU (1.97 g, 5.184 mmol), tert-butyl (3R)-pyrrolidine-3-carboxylate (0.71 g, 4.147 mmol) and DIEA (1.34 g, 10.368 mmol). The residue was purified by silica gel chromatography using a mobile phase of [PE and EA] to provide 1.4 g (52.58%) of the title compound as a white solid. LCMS: ($C_{43}H_{49}N_5O_6$) desired mass=731.4; found: m/z=732.3 $[M+H]^+$.

Step-2: tert-butyl (3R)-1-[(1r,4r)-4-{[1-(2,6-dioxopiperidin-3-yl)-3-methyl-2-oxo-1,3-benzodiazol-4-yl]amino}cyclohexanecarbonyl]pyrrolidine-3-carboxylate

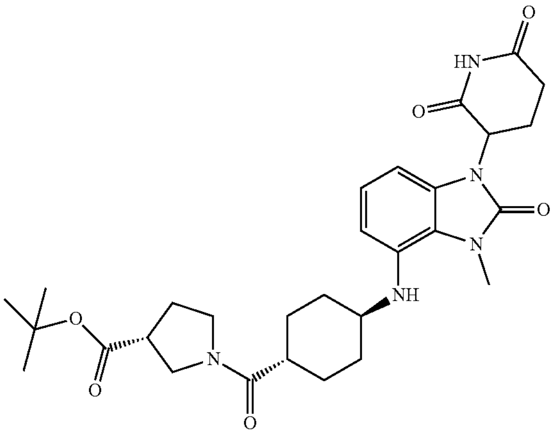 [SMILES: Cn1c(=O)n(C2CCC(=O)NC2=O)c2cccc(N[C@H]3CC[C@H](C(=O)N4CC[C@@H](C(=O)OC(C)(C)C)C4)CC3)c21]

Procedures similar to those in step 5 of Intermediate 15 were followed using tert-butyl (3R)-1-[(1r,4r)-4-({1-[2,6-bis(benzyloxy)pyridin-3-yl]-3-methyl-2-oxo-1,3-benzodiazol-4-yl}amino)cyclohexanecarbonyl]pyrrolidine-3-carboxylate (1 g, 1.366 mmol) in THF (20 mL), and Pd/C (2 g) to provide 500 mg (crude) of the title compound as a white solid. The residue was used directly in the next step. LCMS: ($C_{29}H_{39}N_5O_6$) desired mass=553.3; found: m/z=554.3 $[M+H]^+$.

Step-3: (3R)-1-[(1r,4r)-4-({1-[(3RS)-2,6-dioxopiperidin-3-yl]-3-methyl-2-oxo-1,3-benzodiazol-4-yl}amino)cyclohexanecarbonyl]pyrrolidine-3-carboxylic acid

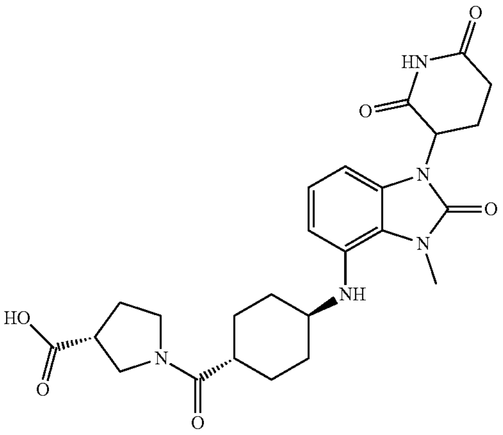 [SMILES: Cn1c(=O)n(C2CCC(=O)NC2=O)c2cccc(N[C@H]3CC[C@H](C(=O)N4CC[C@@H](C(=O)O)C4)CC3)c21]

Procedures similar to those in step 9 of Intermediate 70 were followed using tert-butyl (3R)-1-[(1r,4r)-4-{[1-(2,6-dioxopiperidin-3-yl)-3-methyl-2-oxo-1,3-benzodiazol-4-yl]amino}cyclohexanecarbonyl]pyrrolidine-3-carboxylate (500 mg, 0.903 mmol), DCM (15 mL) and TFA (3 mL). The residue was purified by reverse phase flash chromatography of [$CH_3CN$ and $H_2O$] to provide 300.9 mg (65.96%) of the title compound as an off-white solid. LCMS (Method 8): ($C_{25}H_{31}N_5O_6$) desired mass=497.2; found: m/z=498.2 $[M+H]^+$.

Intermediate 72

5-(4-{2-[2,6-dioxopiperidin-3-yl]-1,3-dioxoisoindol-5-yl}piperazine-1-carbonyl)-1-methylpyrazole-3-carboxylic acid

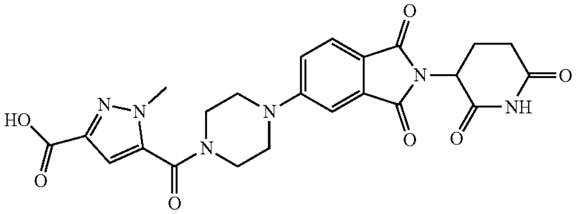 [SMILES: Cn1nc(C(=O)O)cc1C(=O)N1CCN(c2ccc3c(c2)C(=O)N(C2CCC(=O)NC2=O)C3=O)CC1]

Step-1: 5-bromo-2-methylpyrazole-3-carboxylic acid

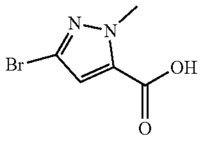

To a mixture of 3,5-dibromo-1-methylpyrazole (3 g, 12.505 mmol) in THF (30 mL) was added n-BuLi in n-hexane (6.5 mL, 16.236 mmol, 2.5 moL/L) dropwise at −70° C. The resulting mixture was stirred for 30 min at −70° C. under nitrogen atmosphere. To the above mixture was added dry ice (5.50 g, 124.973 mmol) at −70° C. The resulting mixture was stirred for additional 1 h at −65° C. The reaction mixture was quenched by the addition of aqueous HCl (6M) at −65° C. The resulting mixture was concentrated under reduced pressure. The aqueous layer was extracted with $CH_2Cl_2$ and dried over anhydrous $Na_2SO_4$. After filtration, the filtrate was concentrated under reduced pressure. The residue was purified by silica gel chromatography using a mobile phase of [PE and EA] to provide 680 mg (23.87%) of the title compound as a yellow solid. LCMS: ($C_5H_5BrN_2O_2$) desired mass=204.0; found: m/z=205.2 $[M+H]^+$.

Step-2: tert-butyl 4-(5-bromo-2-methylpyrazole-3-carbonyl)piperazine-1-carboxylate

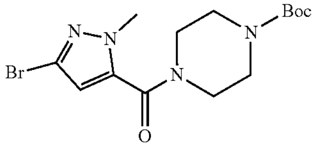 [SMILES: Cn1nc(Br)cc1C(=O)N1CCN(C(=O)OC(C)(C)C)CC1]

Procedures similar to those in step 2 of Intermediate 20 were followed using 5-bromo-2-methylpyrazole-3-carboxylic acid (650 mg, 3.171 mmol), DCM (8 mL), DMF (0.1 mL), Oxalyl chloride (2.4 mL, 4.756 mmol, 2 moL/L), tert-butyl piperazine-1-carboxylate (1181 mg, 6.341 mmol) and TEA (962 mg, 9.512 mmol, 3 equiv). The residue was purified by silica gel chromatography using a mobile phase of [PE and EA] to provide 0.9 g (68.45%) of the title compound as a white solid. LCMS: ($C_{14}H_{21}BrN_4O_3$) desired mass=372.1; found: m/z=373.1 $[M+H]^+$.

Step-3: tert-butyl 4-[5-(ethoxycarbonyl)-2-methylpyrazole-3-carbonyl]piperazine-1-carboxylate

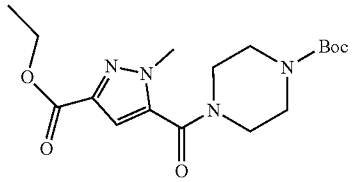 [SMILES: CCOC(=O)c1cc(C(=O)N2CCN(C(=O)OC(C)(C)C)CC2)n(C)n1]

To a solution of tert-butyl 4-(5-bromo-2-methylpyrazole-3-carbonyl)piperazine-1-carboxylate (350 mg, 0.938 mmol) in EtOH (8 mL) was added potassium acetate (184 mg, 1.876 mmol) and Pd(dppf)$Cl_2$ (137 mg, 0.188 mmol) in a pressure tank. The mixture was purged with nitrogen for 10 min and then was pressurized to 30 atm with CO overnight at 140° C. The reaction mixture was cooled to room temperature and filtered to remove insoluble solids. The resulting mixture was concentrated under reduced pressure. The residue was purified by silica gel chromatography using a mobile phase of [PE and EA] to provide 270 mg (70.72%) of the title compound as a white solid. LCMS: ($C_{17}H_{26}N_4O_5$) desired mass=366.2; found: m/z=367.1 $[M+H]^+$.

Step-4: ethyl 1-methyl-5-(piperazine-1-carbonyl)pyrazole-3-carboxylate

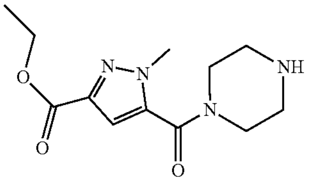 [SMILES: CCOC(=O)c1cc(C(=O)N2CCNCC2)n(C)n1]

Procedures similar to those in step 3 of Intermediate 15 were followed using tert-butyl 4-[5-(ethoxycarbonyl)-2- methylpyrazole-3-carbonyl]piperazine-1-carboxylate (200 mg, 0.546 mmol) and HCl/dioxane (3 mL, 4M) to provide 150 mg (crude) of the title compound as a white solid. The residue was used directly for the next step. LCMS: ($C_{12}H_{18}N_4O_3$) desired mass=266.1; found: m/z=267.1 $[M+H]^+$.

Step-5: 1-methyl-S-(piperazine-1-carbonyl)pyrazole-3-carboxylic acid

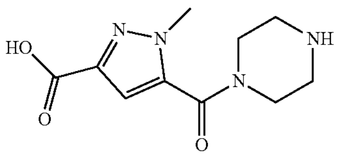 [SMILES: Cn1nc(C(=O)O)cc1C(=O)N1CCNCC1]

Procedures similar to those in step 4 of Intermediate 59 were followed using ethyl 1-methyl-5-(piperazine-1-carbonyl)pyrazole-3-carboxylate (250 mg, 0.939 mmol), THF (3 mL), $H_2O$ (3 mL), MeOH (3 mL) and LiOH (225 mg, 9.390 mmol) to provide 420 mg (crude) of the title compound as a white solid. The residue was used directly for the next step. LCMS: ($C_{10}H_{14}N_4O_3$) desired mass=238.1; found: m/z=239.3 $[M+H]^+$.

Step-6: 5-(4-{2-[2,6-dioxopiperidin-3-yl]-1,3-dioxoisoindol-5-yl}piperazine-1-carbonyl)-1-methylpyrazole-3-carboxylic acid

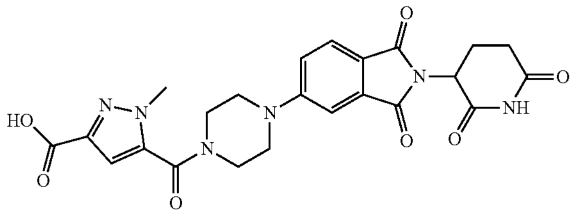 [SMILES: Cn1nc(C(=O)O)cc1C(=O)N1CCN(c2ccc3c(c2)C(=O)N(C2CCC(=O)NC2=O)C3=O)CC1]

Procedures similar to those in step 4 of Intermediate 15 were followed using 1-methyl-5-(piperazine-1-carbonyl)pyrazole-3-carboxylic acid (400 mg, 1.679 mmol), 2-(2,6-dioxopiperidin-3-yl)-5-fluoroisoindole-1,3-dione (557 mg, 2.015 mmol), DMSO (5 mL) and DIEA (1302 mg, 10.074 mmol). The resulting mixture was purified by reverse phase flash chromatography of [$CH_3CN$ and $H_2O$] to provide 114.3 mg (13.16%) of the title compound as an off-white solid. LCMS (Method 9): ($C_{23}H_{22}N_6O_7$) desired mass=494.2; found: m/z=495.2 $[M+H]^+$.

Intermediate 73

3-(6-Fluoropyridin-3-yl)Piperidine-2,6-Dione

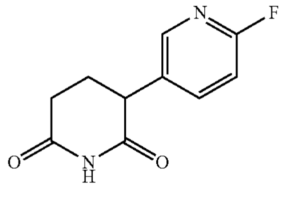 [SMILES: O=C1CCC(c2ccc(F)nc2)C(=O)N1]

Step 1: 2,6-bis(benzyloxy)-6'-fluoro-3,3'-bipyridine

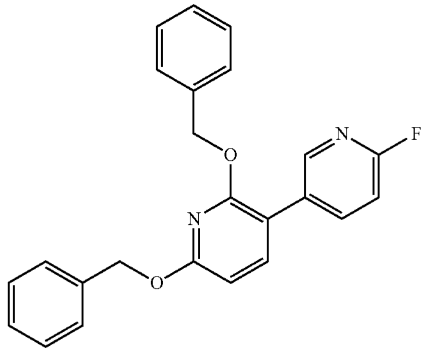 [SMILES: Fc1ccc(-c2ccc(OCc3ccccc3)nc2OCc2ccccc2)cn1]

To a mixture of 2,6-bis(benzyloxy)-3-bromopyridine (250 g, 675 mmol, 1.00 eq), (6-fluoropyridin-3-yl)boronic acid (104 g, 742 mmol, 1.10 eq) in dioxane (1.50 L) was added $K_3PO_4$ (429 g, 2.03 mol, 3.00 eq) in $H_2O$ (500 mL) and $Pd(dppf)Cl_2 \cdot DCM$ (27.6 g, 33.7 mmol, 0.05 eq) at 25° C. under $N_2$, and then the mixture was stirred at 90° C. for 16 hrs. under an $N_2$ atmosphere. To the reaction mixture was added water (2.00 L) and the mixture was extracted with ethyl acetate (2.00 L×3). The combined organic phase was washed with brine (3.00 L), dried over anhydrous $Na_2SO_4$, filtered, and concentrated in vacuo. The crude product was purified by column chromatography on silica gel to afford the title compound (400 g, 1.02 mol, 75.9% yield) as a white solid.

Step 2: 3-(6-fluoropyridin-3-yl)piperidine-2,6-dione

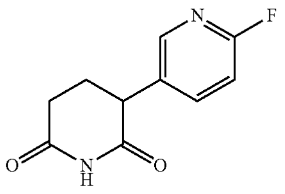 [SMILES: O=C1CCC(c2ccc(F)nc2)C(=O)N1]

A mixture of 2,6-bis(benzyloxy)-6'-fluoro-3,3'-bipyridine (150 g, 388 mmol, 1.00 eq), Pd/C (30.0 g, 10% purity) and $Pd(OH)_2$ (30.0 g, 42.7 mmol) in THF (500 mL) was degassed and purged with $N_2$ 3 times, and then the mixture was stirred at 25° C. for 16 hrs. under $H_2$ (50 psi). The mixture was filtered through celite and the filtrate was concentrated under vacuum. The residue was triturated with MTBE (300 mL) at 25° C. for 1 hr. to afford the title compound (105 g, 498 mmol, 64.2% yield) as a white solid. LCMS: $C_{10}H_9FN_2O_2$, desired mass=208.1, found: m/z=209.1 $[M+H]^+$.

Intermediate 74

1-(4-(2,6-dioxopiperidin-3-yl)phenyl)piperidine-4-carboxylic acid

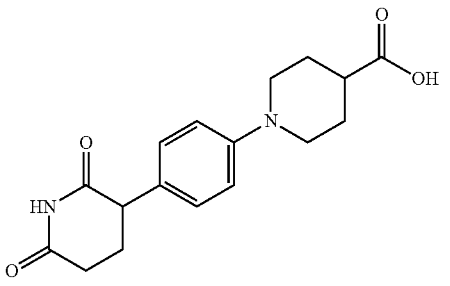

Step 1: 2,6-bis(benzyloxy)-3-(4-bromophenyl)pyridine

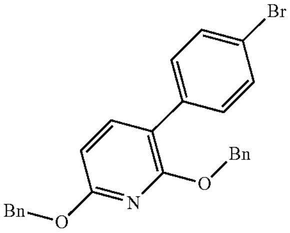 [SMILES: Brc1ccc(-c2ccc(OCc3ccccc3)nc2OCc2ccccc2)cc1]

To a 20 mL microwave reaction vial was added 4-bromoiodobenzene (800.00 mg, 2.83 mmol), 2,6-bis(benzyloxy)-3-(4,4,5,5-tetramethyl-1,3,2-dioxaborolan-2-yl)pyridine (944.05 mg, 2.26 mmol), potassium carbonate 1 M aqueous solution (8.48 mL, 8.48 mmol), Pd(dppf)Cl2 (0.23 g, 0.28 mmol), and dioxane (8.00 mL). The reaction mixture was purged with nitrogen for 5 min, then stirred at 115° C. for 25 min in a microwave reactor. The reaction mixture was filtered through a thin layer of celite. The filtrate was diluted with water and EtOAc. The organic layer was dried over sodium sulfate and concentrated under vacuum. The resulting residue was purified by silica gel chromatography eluting with 0-100% EtOAc/hexane to afford 400 mg (47% yield) of the title compound as a white solid. LCMS: [$C_{25}H_{20}BrNO_2$], desired mass=445.1, found: m/z=446.3 $[M+H]^+$.

Step 2: tert-butyl 1-(4-(2,6-bis(benzyloxy)pyridin-3-yl)phenyl)piperidine-4-carboxylate

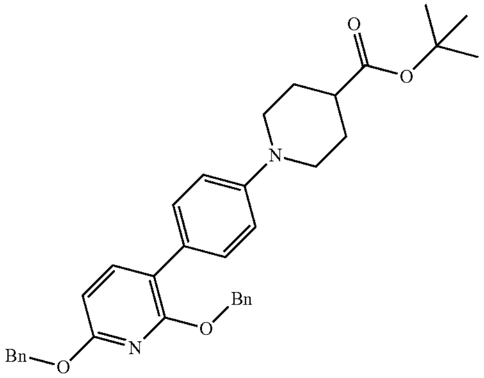 [SMILES: CC(C)(C)OC(=O)C1CCN(c2ccc(-c3ccc(OCc4ccccc4)nc3OCc3ccccc3)cc2)CC1]

To a solution of 2,6-bis(benzyloxy)-3-(4-bromophenyl)pyridine (400.00 mg, 0.90 mmol) and tert-butyl piperidine-4-carboxylate (182.63 mg, 0.99 mmol) in 1,4-dioxane (5 mL) was added cesium carbonate (875.97 mg, 2.69 mmol) and 1,3-bis[2,6-bis(pentan-3-yl)phenyl]-2H-imidazole; 3-chloropyridine; palladium chloride (35.56 mg, 0.04 mmol) at room temperature. The reaction mixture was purged with nitrogen and stirred at 100° C. overnight, and then the reaction mixture was quenched with water (20 mL) and extracted with ethyl acetate (3×10 mL). The combined organic layers were dried over anhydrous sodium sulfate and concentrated under reduced pressure. The residue was purified by silica gel chromatography eluting with 0-100% EtOAc/heptane to afford the title compound as a white solid (375 mg, 77%). LCMS: [$C_{35}H_{38}N_2O_4$], desired mass=550.3, found: m/z=551.4 $[M+H]^+$.

Step 3: tert-butyl 1-(4-(2,6-dioxopiperidin-3-yl)phenyl)piperidine-4-carboxylate

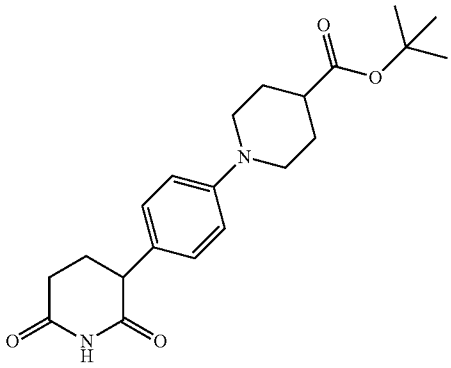 [SMILES: CC(C)(C)OC(=O)C1CCN(c2ccc(C3CCC(=O)NC3=O)cc2)CC1]

To a solution of tert-butyl 1-(4-(2,6-bis(benzyloxy)pyridin-3-yl)phenyl)piperidine-4-carboxylate (375 mg, 0.68 mmol) in a mixture of THF (3 mL) and isopropanol (3 mL) was added Pd/C (74 mg, 0.06 mmol). The reaction mixture was stirred for 36 h at room temperature under $H_2$ gas and then the mixture was diluted with ethyl acetate (30 mL) and filtered through Celite. The filtrate was then concentrated under reduced pressure. The residue was purified by silica gel chromatography eluting with 0-100% EtOAc/heptane to afford the title compound as a white solid (248 mg, 98%). LCMS: ($C_{21}H_{28}N_2O_4$) desired mass=372.2, found: m/z=373.4 $[M+H]^+$.

Step 4: 1-(4-(2,6-dioxopiperidin-3-yl)phenyl)piperidine-4-carboxylic acid

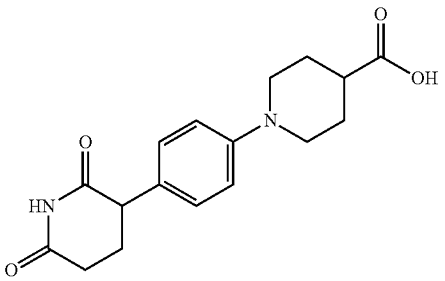

A mixture of tert-butyl 1-(4-(2,6-dioxopiperidin-3-yl)phenyl)piperidine-4-carboxylate (780 mg, 2.02 mmol) in HFIP (20 mL) was treated with TFA (1.55 mL, 20 mmol) and stirred at room temperature overnight. The resulting mixture was concentrated under vacuum. The residue was purified by reverse phase flash chromatography ($CH_3CN$ and $H_2O$ as mobile phase) to yield the title compound as a white solid (760 mg, 84%). LCMS: ($C_{17}H_{20}N_2O_4$) desired mass=316.1; found: m/z=317.4 $[M+H]^+$.

Intermediate 75

1-(5-(2,4-Dioxotetrahydropyrimidin-1(2H)-yl)Pyridin-2-yl)Piperidine-4-Carboxylic Acid

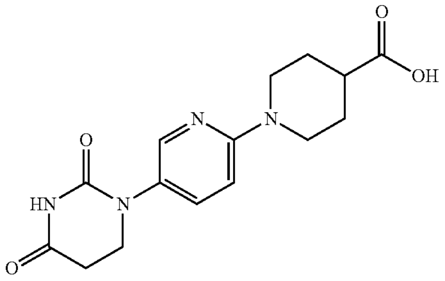

Step 1: tert-butyl 1-(5-nitropyridin-2-yl)piperidine-4-carboxylate

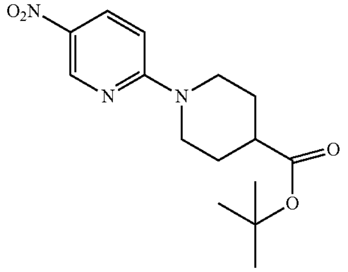 [SMILES: CC(C)(C)OC(=O)C1CCN(c2ccc([N+](=O)[O-])cn2)CC1]

A mixture of 2-fluoro-5-nitropyridine (1000.00 mg, 7.04 mmol), tert-butyl piperidine-4-carboxylate (1434.27 mg, 7.74 mmol) and N,N-diisopropylethylamine (2.46 mL, 14.08 mmol) in DMSO was stirred at 100° C. overnight. The reaction mixture was cooled to room temperature and diluted with water and EtOAc. The organic layer was separated and dried over sodium sulfate, then concentrated under vacuum. The resulting residue was purified by silica gel chromatography eluting with 0-100% EtOAc/hexane to afford the title compound as a white solid (1700 mg, 78% yield). LCMS: $[C_{15}H_{21}N_3O_4]$, desired mass=307.2, found: m/z=308.3 $[M+H]^+$.

Step 2: tert-butyl 1-(5-aminopyridin-2-yl)piperidine-4-carboxylate

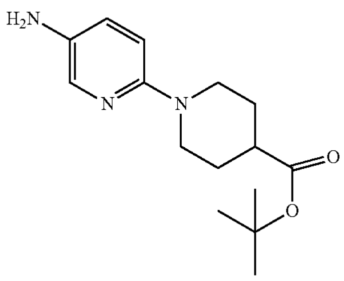

A mixture of tert-butyl 1-(4-nitrophenyl)piperidine-4-carboxylate (1000.00 mg, 3.25 mmol), iron powder (908 mg, 16 mmol), ammonium chloride 1M aqueous solution (16 mL, 16 mmol) in EtOH (5 mL) was heated at 50° C. for 30 minutes. The reaction mixture was cooled to room temperature and diluted with EtOAc. The organic layer was separated and dried over anhydrous sodium sulfate and concentrated under reduced pressure. The crude residue was purified by flash chromatography with 0 to 60% ethyl acetate/hexanes as the mobile phase to afford the title compound as a white solid (650 mg, 72%). LCMS: $[C_{15}H_{23}N_3O_2]$, desired mass=277.2, found: m/z=278.5 $[M+H]^+$.

Step 3: 3-({6-[4-(tert-butoxycarbonyl)piperidin-1-yl]pyridin-3-yl}amino)propanoic acid

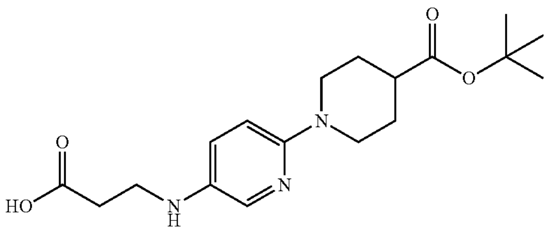 [SMILES: CC(C)(C)OC(=O)C1CCN(c2ccc(NCCC(=O)O)cn2)CC1]

To a solution of tert-butyl 1-(5-aminopyridin-2-yl)piperidine-4-carboxylate (420.00 mg, 1.51 mmol) in toluene (1.51 mL) was added acrylic acid (0.05 mL, 0.75 mmol). The reaction mixture was heated to 100° C. for 3 hours and then a second portion of acrylic acid (0.05 mL, 0.75 mmol) was added. Heating at 100° C. was continued for 16 hours, at which time LCMS analysis showed a mixture of mono and bis-substituted products. The reaction mixture was cooled to room temperature and concentrated in vacuo. The crude residue was purified with C18 reverse phase chromatography (eluting with $CH_3CN$ and water) to afford the title compound as a brown oil (290 mg, 55%). LCMS: $[C_{18}H_{27}N_3O_4]$ desired mass=349.2, found: m/z=350.4 $[M+H]^+$.

Step 4: tert-butyl 1-[5-(2,4-dioxo-1,3-diazinan-1-yl) pyridin-2-yl]piperidine-4-carboxylate

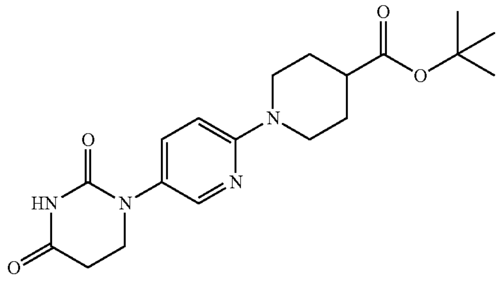

To a solution of 3-({6-[4-(tert-butoxycarbonyl)piperidin-1-yl]pyridin-3-yl}amino)propanoic acid (100.00 mg, 0.29 mmol) in toluene (1.51 mL) and acetic acid (0.16 mL, 2.86 mmol) was added urea (86 mg, 1.43 mmol). The resulting suspension was heated to reflux for 3 hours. The reaction mixture was cooled to room temperature and concentrated in vacuo. The crude residue was purified with C18 reverse phase chromatography (eluting with $CH_3CN$ and water) to afford the title compound as a brown oil (50 mg, 47%). LCMS: [$C_{19}H_{26}N_4O_4$] desired mass=374.2, found: m/z=375.4 $[M+H]^+$.

Step 5: 1-(5-(2,4-dioxotetrahydropyrimidin-1(2H)-yl)pyridin-2-yl)piperidine-4-carboxylic acid

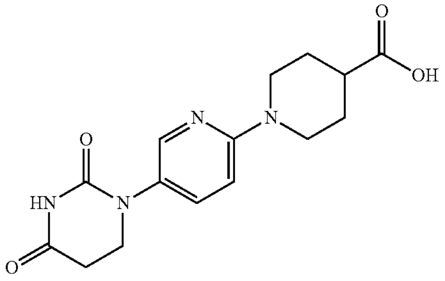

A mixture of tert-butyl 1-[5-(2,4-dioxo-1,3-diazinan-1-yl) pyridin-2-yl]piperidine-4-carboxylate (50 mg, 0.133 mmol) in HFIP (2 mL) was treated with TFA (0.1 mL, 1.33 mmol) and stirred at room temperature overnight. The resulting mixture was concentrated under vacuum. The residue was purified by reverse phase flash chromatography (eluting with $CH_3CN$ and $H_2O$) to yield the title compound as a white solid (40 mg, 94%). LCMS: [$C_{15}H_{18}N_4O_4$] desired mass=318.1; found: m/z=319.4 $[M+H]^+$.

Intermediate 76

1-(4-(2,6-dioxopiperidin-3-yl)-2-Fluorophenyl)Piperidine-4-Carboxylic Acid

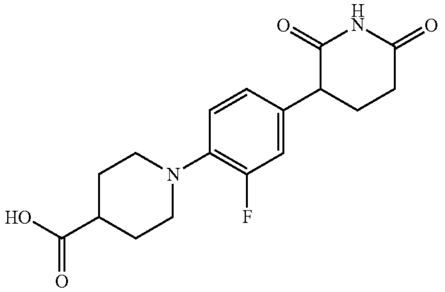 [SMILES: O=C1CCC(c2ccc(N3CCC(C(=O)O)CC3)c(F)c2)C(=O)N1]

Step 1: 2,6-bis(benzyloxy)-3-(4-chloro-3-fluorophenyl)pyridine

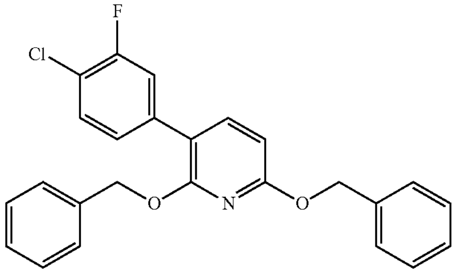 [SMILES: Fc1cc(-c2ccc(OCc3ccccc3)nc2OCc2ccccc2)ccc1Cl]

1-chloro-2-fluoro-4-iodobenzene (0.29 mL, 0.50 g, 2.3873 mmol), 2,6-bis(benzyloxy)pyridin-3-ylboronic acid (1.00 g, 2.3873 mmol), cesium carbonate 1 N aqueous solution (4.77 mL, 4.7746 mmol), Pd(dppf)Cl2-DCM (0.39 g, 0.4775 mmol), and dioxane (10.00 mL) were combined in a sealed vial and stirred at 70° C. for 3 hours. The reaction mixture was concentrated onto silica and purified by flash column chromatography to afford the title compound (0.912 g, 86% yield).

Step 2: tert-butyl 1-{4-[2,6-bis(benzyloxy)pyridin-3-yl]-2-fluorophenyl}piperidine-4-carboxylate

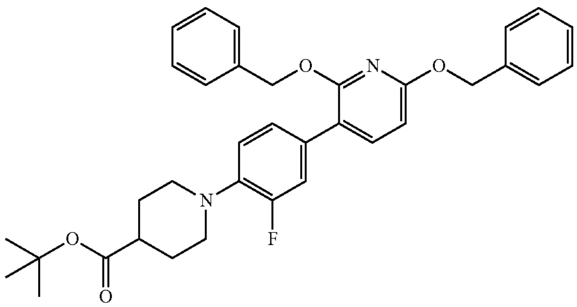 [SMILES: CC(C)(C)OC(=O)C1CCN(c2ccc(-c3ccc(OCc4ccccc4)nc3OCc3ccccc3)cc2F)CC1]

2,6-bis(benzyloxy)-3-(4-chloro-3-fluorophenyl)pyridine (0.58 mL, 1.00 g, 4.7746 mmol), tert-butyl piperidine-4- carboxylate (0.88 g, 4.7746 mmol), tris(dibenzylideneacetone) dipalladium(0) (0.44 g, 0.4775 mmol), xantphos (0.28 g, 0.4775 mmol), potassium tert-butoxide (1.07 g, 9.5493 mmol), and toluene (5.00 mL) were combined in a sealed vial and stirred at 70° C. for 4 hours. The reaction mixture was purified by flash column chromatography to afford the title compound (0.234 g, 8% yield).

Step 3: tert-butyl 1-(4-(2,6-dioxopiperidin-3-yl)-2-fluorophenyl)piperidine-4-carboxylate

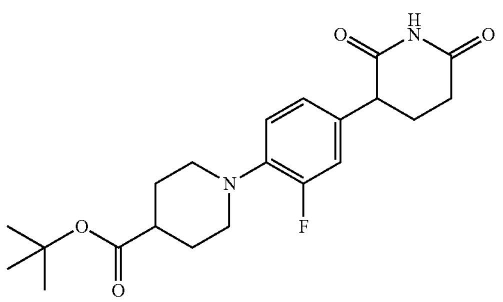 [SMILES: CC(C)(C)OC(=O)C1CCN(c2ccc(C3CCC(=O)NC3=O)cc2F)CC1]

Tert-butyl 1-{4-[2,6-bis(benzyloxy)pyridin-3-yl]-2-fluorophenyl}piperidine-4-carboxylate (0.25 g, 1.768 mmol) was dissolved in isopropanol (5.00 mL) and THF (5.00 mL). Palladium on carbon 10% (0.19 g, 0.1768 mmol) was added and the reaction mixture was stirred under a hydrogen balloon for 12 hours. The reaction mixture was filtered through celite and concentrated to afford the title compound (0.170 g, 98% yield)

Step 4: 1-(4-(2,6-dioxopiperidin-3-yl)-2-fluorophenyl)piperidine-4-carboxylic acid

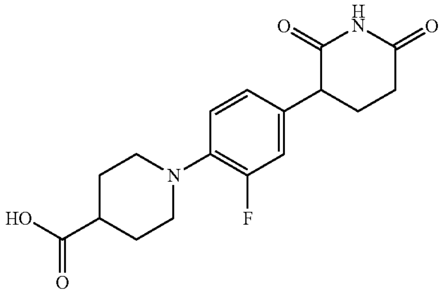 [SMILES: O=C1CCC(c2ccc(N3CCC(C(=O)O)CC3)c(F)c2)C(=O)N1]

Tert-butyl 1-(4-(2,6-dioxopiperidin-3-yl)-2-fluorophenyl) piperidine-4-carboxylate (0.170 g. 0.435 mmol) was dissolved in DCM (2.0 mL). 4M HCl in dioxane (2.0 mL) was added and the reaction mixture was stirred at room temperature for 4 hours. The crude reaction mixture was evaporated onto silica gel and purified by reverse phase flash column chromatography eluting with acetonitrile/water to afford the title compound (0.134 g, 93% yield). LCMS: $C_{17}H_{19}FN_2O_4$, desired mass=334.3, found: m/z=335.4 $[M+H]^+$.

Intermediate 77

1-(1-(5-(2,6-dioxopiperidin-3-yl)-3-methylpyridin-2-yl)piperidine-4-carbonyl)-4-methylpiperidine-4-carboxylic acid

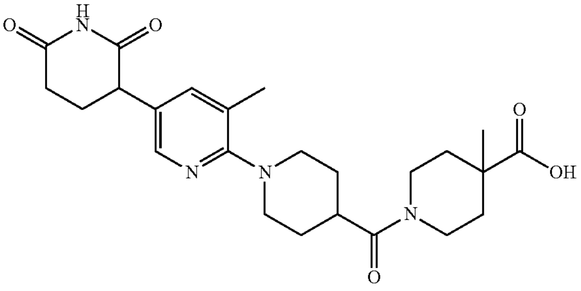 [SMILES: Cc1cc(C2CCC(=O)NC2=O)cnc1N1CCC(C(=O)N2CCC(C)(C(=O)O)CC2)CC1]

Step 1: tert-butyl 1-(5-bromo-3-methylpyridin-2-yl) piperidine-4-carboxylate

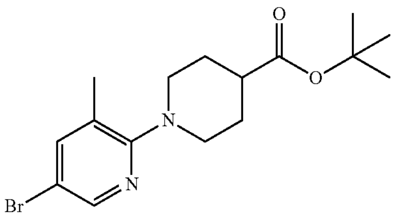 [SMILES: Cc1cc(Br)cnc1N1CCC(C(=O)OC(C)(C)C)CC1]

To a solution of tert-butyl piperidine-4-carboxylate hydrochloride (4.00 g, 18.04 mmol) in anhydrous DMSO (36.0 mL) was added 5-bromo-2-fluoro-3-methylpyridine (6.856 g, 36.08 mmol) and $Cs_2CO_3$ (23.511 g, 72.16 mmol) at 25° C. The reaction mixture was stirred for 24 h at 130° C., and then poured into 400 mL of brine and extracted with EtOAc (4×400 mL). The combined organic extracts were dried with $Na_2SO_4$ and evaporated under reduced pressure. The residue was purified by silica gel chromatography using a mobile phase of hexane and EtOAc to provide the title compound (5.082 g, 79% yield) as a yellow solid. LCMS: $C_{16}H_{23}BrN_2O_2$, desired mass=355.3, found: m/z=357.0 $[M+H^+]$.

Step 2: tert-butyl 1-[2',6'-bis(benzyloxy)-5-methyl-[3,3'-bipyridin]-6-yl]piperidine-4-carboxylate

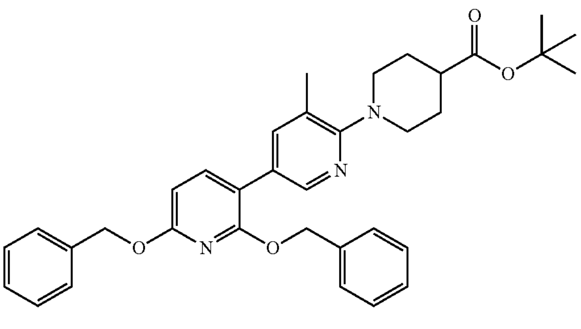

To a solution of tert-butyl 1-(5-bromo-3-methylpyridin-2-yl)piperidine-4-carboxylate (4.00 g, 11.26 mmol) in degassed anhydrous DMF (22.5 mL) was added 2,6-bis(benzyloxy)-3-(4,4,5,5-tetramethyl-1,3,2-dioxaborolan-2-yl)pyridine (4.699 g, 11.26 mmol), $K_2CO_3$ (4.669 g, 33.78 mmol) and [1,1'-bis(diphenylphosphino)ferrocene]dichloropalladium(II) (0.494 g, 0.68 mmol) at 25° C. The reaction mixture was stirred for 16 h at 85° C., and then the mixture was poured into 250 mL of water, and extracted with EtOAc (4×120 mL). The combined organic layers were washed with water (2×120 mL) and brine (120 mL), dried with $Na_2SO_4$ and concentrated under reduced pressure. The residue was purified by silica gel chromatography using a mobile phase of hexane and EtOAc to provide the title compound (5.363 g, 84% yield) as a yellow solid. LCMS: $C_{35}H_{39}N_3O_4$, desired mass=565.7, found: m/z=566.8 [$M+H^+$].

Step 3: tert-butyl 1-[5-(2,6-dioxopiperidin-3-yl)-3-methylpyridin-2-yl]piperidine-4-carboxylate

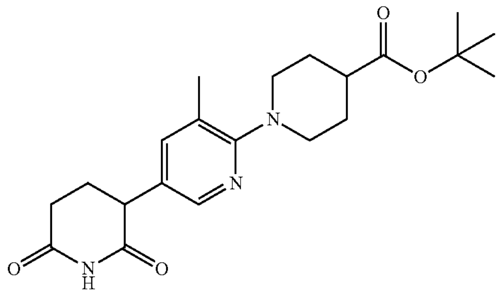 [SMILES: Cc1cc(C2CCC(=O)NC2=O)cnc1N1CCC(C(=O)OC(C)(C)C)CC1]

To a solution of tert-butyl 1-[2',6'-bis(benzyloxy)-5-methyl-[3,3'-bipyridin]-6-yl]piperidine-4-carboxylate (3.00 g, 5.30 mmol) in anhydrous THF (220.0 mL) was added 10% wt Pd/C (900 mg) at 25° C. The reaction mixture was stirred for 16 h at 25° C., and then filtered through a Celite pad and evaporated to dryness. The residue was purified by silica gel chromatography using a mobile phase of DCM and MeOH to provide the title compound (1.605 g, 78% yield) as a grey solid. LCMS: $C_{21}H_{29}N_3O_4$, desired mass=387.5, found: m/z=388.6 [$M+H^+$].

Step 4:1-[5-(2,6-dioxopiperidin-3-yl)-3-methylpyridin-2-yl]piperidine-4-carboxylic acid hydrochloride

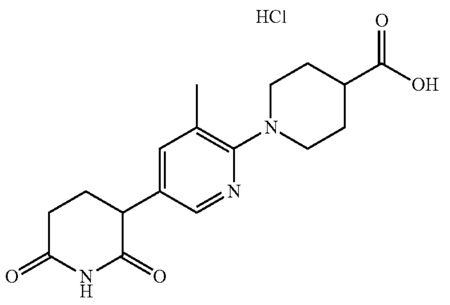 [SMILES: Cl ; Cc1cc(C2CCC(=O)NC2=O)cnc1N1CCC(C(=O)O)CC1]

To a solution of tert-butyl 1-[5-(2,6-dioxopiperidin-3-yl)-3-methylpyridin-2-yl]piperidine-4-carboxylate (1.467 g, 3.79 mmol) in anhydrous DCM (57.4 mL) was added 4M HCl in DCM (22.72 ml, 90.86 mmol) at 25° C. The reaction mixture was stirred for 16 h at 25° C., and then the solvents were evaporated to dryness under reduced pressure. The residue was triturated with DCM (3×20 mL) and dried under reduced pressure to provide the title compound (1.293 g, 93% yield) as a white solid. LCMS: $C_{17}H_{21}N_3O_4$, desired mass=331.4, found: m/z=332.2 [$M+H^+$].

Step 5: tert-butyl 1-(1-(5-(2,6-dioxopiperidin-3-yl)-3-methylpyridin-2-yl)piperidine-4-carbonyl)-4-methylpiperidine-4-carboxylate

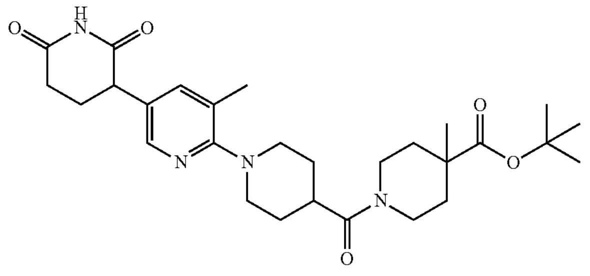 [SMILES: Cc1cc(C2CCC(=O)NC2=O)cnc1N1CCC(C(=O)N2CCC(C)(C(=O)OC(C)(C)C)CC2)CC1]

1-[5-(2,6-dioxopiperidin-3-yl)-3-methylpyridin-2-yl]piperidine-4-carboxylic acid hydrochloride (50.00 mg, 0.1509 mmol), (1,2,3-benzotriazol-1-yloxy)tris(dimethylamino)phosphanium; hexafluoro-lambda5-phosphanuide (86.76 mg, 0.1962 mmol), and tert-butyl 4-methylpiperidine-4-carboxylate (30.07 mg, 0.1509 mmol) were dissolved in dimethylformamide (1.00 mL) and N,N-diisopropylethylamine (0.11 mL, 78.01 mg, 0.6036 mmol) and stirred at room temperature for 6 hours. The product was isolated by reverse phase flash column chromatography eluting with $CH_3CN$/water to afford the title compound (0.065 g, 84% yield).

Step 6: 1-(1-(5-(2,6-dioxopiperidin-3-yl)-3-methylpyridin-2-yl)piperidine-4-carbonyl)-4-methylpiperidine-4-carboxylic acid

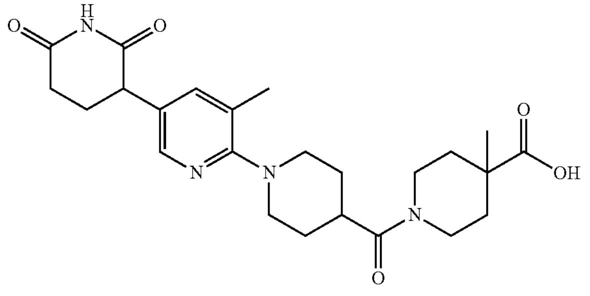 [SMILES: Cc1cc(C2CCC(=O)NC2=O)cnc1N1CCC(C(=O)N2CCC(C)(C(=O)O)CC2)CC1]

Tert-butyl 1-(1-(5-(2,6-dioxopiperidin-3-yl)-3-methylpyridin-2-yl)piperidine-4-carbonyl)-4-methylpiperidine-4-carboxylate (0.065 g, 0.126 mmol) was dissolved in DCM (1.0 mL). 4M HCl in dioxane (1.0 mL) was added and the reaction mixture was stirred at room temperature for 4 hours. The crude reaction mixture was purified by reverse phase flash column chromatography eluting with acetonitrile/water to afford the title compound (0.042 g, 69% yield). LCMS: $C_{24}H_{32}N_4O_5$, desired mass=456.5, found: m/z=457.4 $[M+H]^+$.

Intermediate 78

1-((1R,4R)-4-((4-(2,6-dioxopiperidin-3-yl)phenyl)(methyl)amino)cyclohexane-1-carbonyl)-4-methylpiperidine-4-carboxylic acid

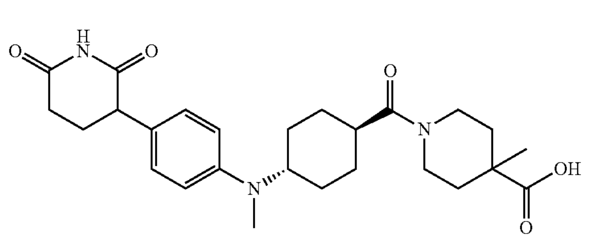 [SMILES: CN(c1ccc(C2CCC(=O)NC2=O)cc1)[C@H]1CC[C@H](C(=O)N2CCC(C)(C(=O)O)CC2)CC1]

Step 1: methyl (1r,4r)-4-[(4-bromophenyl)(methyl)amino]cyclohexane-1-carboxylate

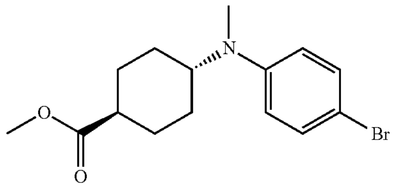 [SMILES: COC(=O)[C@H]1CC[C@H](N(C)c2ccc(Br)cc2)CC1]

To a solution of methyl (1r,4r)-4-(methylamino)cyclohexane-1-carboxylate (1.0 g, 4.82 mmol), in degassed anhydrous dioxane (9.63 ml) was added 1-bromo-4-iodobenzene (1.36 g, 4.82 mmol), cesium carbonate (6.28 g, 19.3 mmol), palladium (II) acetate (0.108 g, 0.481 mmol) and 4,5-bis(diphenylphosphino)-9,9-dimethylxanthene (0.418 g, 0.722 mmol) at room temperature. The reaction mixture was stirred for 16 h at 100° C., and then the mixture was concentrated. The residue was purified by silica gel chromatography using a mobile phase of hexane and dichloromethane (0 to 40%) to provide the title compound (0.231 g, 15% yield) as a yellow oil. LCMS: [$C_{15}H_{20}BrNO_2$], desired mass=326.23, found: m/z=328.10 [M+$H^+$].

Step 2: methyl (1r,4r)-4-({4-[2,6-bis(benzyloxy)pyridin-3-yl]phenyl}(methyl)amino) cyclohexane-1-carboxylate

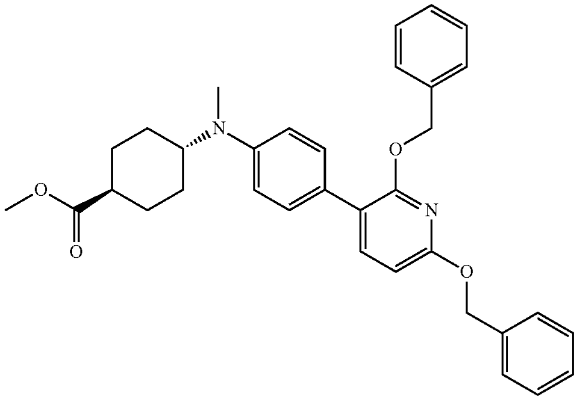 [SMILES: COC(=O)[C@H]1CC[C@H](N(C)c2ccc(-c3ccc(OCc4ccccc4)nc3OCc3ccccc3)cc2)CC1]

To a solution of (1r,4r)-4-[(4-bromophenyl)(methyl)amino]cyclohexane-1-carboxylate (2.24 g, 6.87 mmol) in dimethylformamide (19.6 ml) was added 2,6-bis(benzyloxy)-3-(4,4,5,5-tetramethyl-1,3,2-dioxaborolan-2-yl)pyridine (2.87 g, 6.87 mmol), 1,1'-bis(diphenylphosphino)ferrocene dichloropalladium (II) (0.251 g, 0.343 mmol) and potassium carbonate (2.85 g, 20.60 mmol) at room temperature. The reaction mixture was stirred for 16 h at 85° C., and then the mixture was evaporated in vacuo. The residue was purified by silica gel chromatography using a mobile phase of hexane and ethyl acetate (0 to 30%) to provide the title compound (1.15 g, 31% yield) as a brown oil. LCMS: [$C_{34}H_{36}N_2O_4$], desired mass=536.67, found: m/z=537.65 [M+$H^+$].

Step 3: (1r,4r)-4-({4-[2,6-bis(benzyloxy)pyridin-3-yl]phenyl}(methyl)amino)cyclohexane-1-carboxylic acid

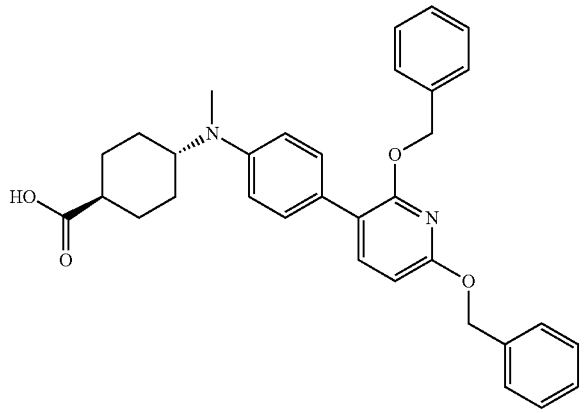 [SMILES: CN(c1ccc(-c2ccc(OCc3ccccc3)nc2OCc2ccccc2)cc1)[C@H]1CC[C@H](C(=O)O)CC1]

To a solution of methyl (1r,4r)-4-({4-[2,6-bis(benzyloxy)pyridin-3-yl]phenyl}(methyl)amino)cyclohexane-1-carboxylate (1.15 g, 2.14 mmol) in a mixture of tetrahydrofuran (3.46 ml) and water (1.13 ml) was added lithium hydroxide monohydride (0.18 g, 4.29 mmol) at room temperature. The reaction mixture was stirred for 8 h at room temperature, and then the THF was removed under vacuum. To the remaining water layer was added $KHSO_4$ (0.584 g, 4.29 mmol) to adjust the pH to 4-5, and the resulting solid was filtered off, dissolved in DCM, and dried over $Na_2SO_4$. Filtration, followed by concentration of the filtrate under vacuum afforded the title compound (0.962 g, 86% yield) which was used as-is for the next step. LCMS: [$C_{33}H_{34}N_2O_4$], desired mass=522.65, found: m/z=523.70 [M+$H^+$].

Step 4: (1r,4r)-4-((4-(2,6-dioxopiperidin-3-yl)phenyl)(methyl)amino)cyclohexane-1-carboxylic acid

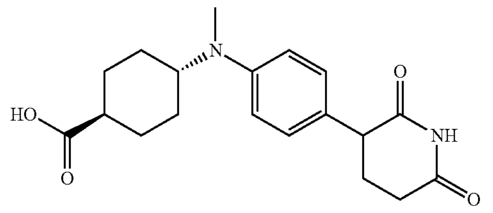 [SMILES: CN(c1ccc(C2CCC(=O)NC2=O)cc1)[C@H]1CC[C@H](C(=O)O)CC1]

To a solution of (1r,4r)-4-({4-[2,6-bis(benzyloxy)pyridin-3-yl]phenyl}(methyl)amino)cyclohexane-1-carboxylic acid (0.962 g, 1.84 mmol) in degassed tetrahydrofuran (108.27 ml) was added 10% Palladium on carbon 60-65% wet (0.29 g, 2.72 mmol) at room temperature. The reaction mixture was stirred for 16 h at room temperature under and atmosphere of $H_2$ (balloon), and then the mixture was filtered, and the filtrate was concentrated under vacuum. The residue was purified by preparative HPLC to provide the title compound (0.171 g, 27% yield) as a grey solid. LCMS: [$C_{19}H_{24}N_2O_4$], desired mass=344.41, found: m/z=345.20 $[M+H]^+$.

Step 5: tert-butyl 1-((1r,4r)-4-((4-(2,6-dioxopiperidin-3-yl)phenyl)(methyl)amino)cyclohexane-1-carbonyl)-4-methylpiperidine-4-carboxylate

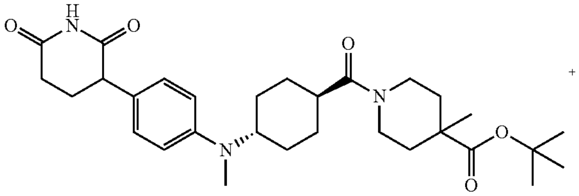 [SMILES: CN(c1ccc(C2CCC(=O)NC2=O)cc1)[C@H]1CC[C@H](C(=O)N2CCC(C)(C(=O)OC(C)(C)C)CC2)CC1]

(1r,4r)-4-((4-(2,6-dioxopiperidin-3-yl)phenyl)(methyl)amino)cyclohexane-1-carboxylic acid (50.00 mg, 0.1452 mmol), (1,2,3-benzotriazol-1-yloxy)tris(dimethylamino)phosphanium; hexafluoro-lambda5-phosphanuide (83.47 mg, 0.1887 mmol), and tert-butyl 4-methylpiperidine-4-carboxylate (28.93 mg, 0.1452 mmol) were dissolved in dimethylformamide (1.00 mL) and N,N-diisopropylethylamine (0.10 mL, 75.05 mg, 0.5807 mmol) and stirred at room temperature for 6 hours. The reaction mixture was purified by reverse phase flash column chromatography eluting with $CH_3CN$/water to afford the title compound (0.071 g, 93% yield).

Step 6: 1-((1r,4r)-4-((4-(2,6-dioxopiperidin-3-yl)phenyl)(methyl)amino)cyclohexane-1-carbonyl)-4-methylpiperidine-4-carboxylic acid

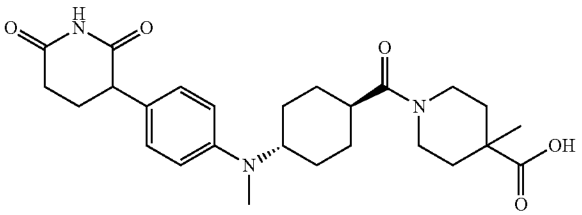 [SMILES: CN(c1ccc(C2CCC(=O)NC2=O)cc1)[C@H]1CC[C@H](C(=O)N2CCC(C)(C(=O)O)CC2)CC1]

Tert-butyl 1-((1r,4r)-4-((4-(2,6-dioxopiperidin-3-yl)phenyl)(methyl)amino)cyclohexane-1-carbonyl)-4-methylpiperidine-4-carboxylate (0.071 g, 0.135 mmol) was dissolved in DCM (1.0 mL). 4M HCl in dioxane (1.0 mL) was added and the reaction mixture was stirred at room temperature for 4 hours. The crude reaction mixture was purified by reverse phase flash column chromatography eluting with $CH_3CN$/water to afford the title compound (0.051 g, 80% yield). LCMS: $C_{26}H_{35}N_3O_5$, desired mass=469.6, found: m/z=470.4 $[M+H]^+$.

Intermediate 79

1-(1-(5-(2,6-Dioxopiperidin-3-yl)Pyridin-2-yl)-4-Methylpiperidine-4-Carbonyl)-4-Methylpiperidine-4-Carboxylic Acid

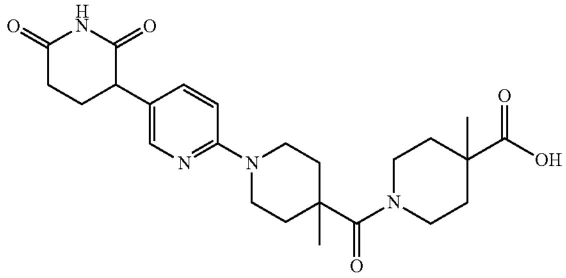 [SMILES: CC1(C(=O)O)CCN(C(=O)C2(C)CCN(c3ccc(C4CCC(=O)NC4=O)cn3)CC2)CC1]

Step 1: tert-butyl 1-(5-(2,6-dioxopiperidin-3-yl)pyridin-2-yl)-4-methylpiperidine-4-carboxylate

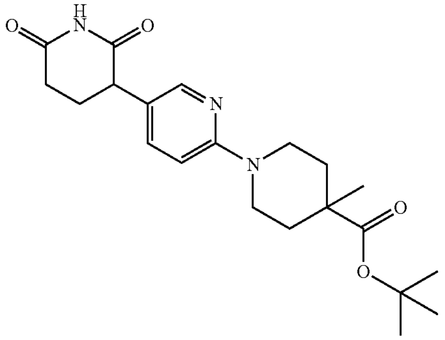 [SMILES: CC(C)(C)OC(=O)C1(C)CCN(c2ccc(C3CCC(=O)NC3=O)cn2)CC1]

3-(6-fluoropyridin-3-yl)piperidine-2,6-dione (200.00 mg, 0.96 mmol) and tert-butyl 4-methylpiperidine-4-carboxylate (191.45 mg, 0.96 mmol) were dissolved in DMSO (7.20 mL) and N,N-diisopropylethylamine (0.34 mL, 248.32 mg, 1.92 mmol) in a sealed vial. The reaction mixture was heated to 120° C. for 12 hours. After cooling to room temperature, the crude reaction mixture was purified by reverse phase flash column chromatography eluting with acetonitrile/water to afford the title compound (0.254 g, 68% yield).

Step 2: 1-(5-(2,6-dioxopiperidin-3-yl)pyridin-2-yl)-4-methylpiperidine-4-carboxylic acid

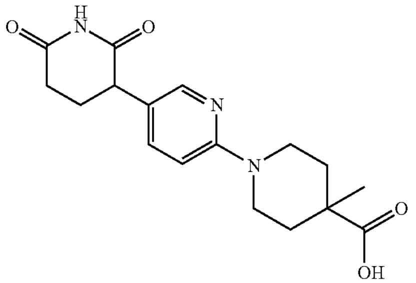 [SMILES: CC1(C(=O)O)CCN(c2ccc(C3CCC(=O)NC3=O)cn2)CC1]

Tert-butyl 1-(5-(2,6-dioxopiperidin-3-yl)pyridin-2-yl)-4-methylpiperidine-4-carboxylate (0.254 g, 0.655 mmol) was dissolved in DCM (3.0 mL). 4M HCl in dioxane (2.0 mL) was added and the reaction mixture was stirred at room temperature for 4 hours. The crude reaction mixture was purified by reverse phase flash column chromatography eluting with acetonitrile/water to afford the title compound (0.214 g, 97% yield).

Step 3: tert-butyl 1-(1-(5-(2,6-dioxopiperidin-3-yl)pyridin-2-yl)-4-methylpiperidine-4-carbonyl)-4-methylpiperidine-4-carboxylate

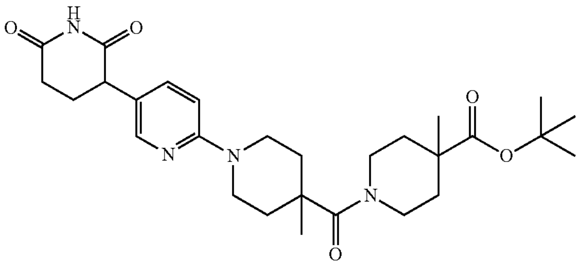 [SMILES: CC(C)(C)OC(=O)C1(C)CCN(C(=O)C2(C)CCN(c3ccc(C4CCC(=O)NC4=O)cn3)CC2)CC1]

1-(5-(2,6-dioxopiperidin-3-yl)pyridin-2-yl)-4-methylpiperidine-4-carboxylic acid (50.00 mg, 0.1509 mmol), (1,2,3-benzotriazol-1-yloxy)tris(dimethylamino)phosphanium; hexafluoro-lambda5-phosphanuide (86.76 mg, 0.1962 mmol), and tert-butyl 4-methylpiperidine-4-carboxylate (30.07 mg, 0.1509 mmol) were dissolved in dimethylformamide (1.00 mL) and N,N-diisopropylethylamine (0.11 mL, 78.01 mg, 0.6036 mmol) and stirred at room temperature for 6 hours. The crude reaction mixture was purified by reverse phase flash column chromatography eluting with acetonitrile/water to afford the title compound (0.068 g, 88% yield).

Step 4: 1-(1-(5-(2,6-dioxopiperidin-3-yl)pyridin-2-yl)-4-methylpiperidine-4-carbonyl)-4-methylpiperidine-4-carboxylic acid

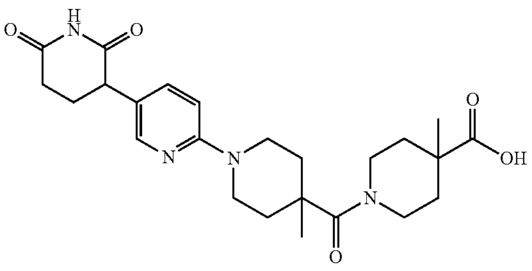 [SMILES: CC1(C(=O)O)CCN(C(=O)C2(C)CCN(c3ccc(C4CCC(=O)NC4=O)cn3)CC2)CC1]

Tert-butyl 1-(1-(5-(2,6-dioxopiperidin-3-yl)pyridin-2-yl)-4-methylpiperidine-4-carbonyl)-4-methylpiperidine-4-carboxylate (0.068 g, 0.132 mmol) was dissolved in DCM (1.0 mL). 4M HCl in dioxane (1.0 mL) was added and the reaction mixture was stirred at room temperature for 4 hours. The crude reaction mixture was purified by reverse phase flash column chromatography eluting with acetonitrile/water to afford the title compound (0.052 g, 86% yield). LCMS: $C_{24}H_{32}N_4O_5$, desired mass=456.5, found: m/z=457.4 $[M+H]^+$.

Intermediate 80

1-{1-[5-(2,4-Dioxo-1,3-Diazinan-1-yl)Pyridin-2-yl]-3,3-Difluoropiperidine-4-Carbonyl}-4-Methylpiperidine-4-Carboxylic Acid

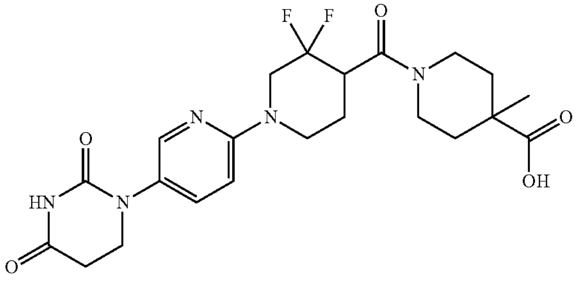 [SMILES: CC1(C(=O)O)CCN(C(=O)C2CCN(c3ccc(N4CCC(=O)NC4=O)cn3)CC2(F)F)CC1]

Step 1: methyl 3,3-difluoro-1-(5-nitropyridin-2-yl)piperidine-4-carboxylate

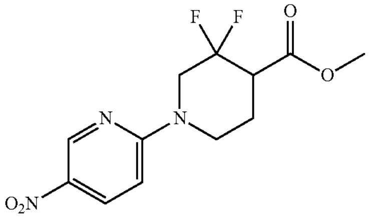

To a stirred solution of 2-fluoro-5-nitropyridine (3.30 g, 23.2 mmol, 1.00 eq) in NMP (33.0 mL) was added DIEA (81.2 mmol, 14.1 mL), followed by methyl 3,3-difluoropiperidine-4-carboxylate hydrochloride (5.01 g, 23.2 mmol) at 25° C. The resulting reaction mixture was heated at 90° C. for 0.5 hr. The reaction mixture was cooled to room temperature and was poured into water (100 mL), extracted with ethyl acetate (100 mL×2), the combined organic phases were washed with brine (100 mL×4), dried over $Na_2SO_4$, filtered and concentrated under vacuum. The crude product was triturated with Petroleum ether/ethyl acetate=5/1 (30.0 mL) at 25° C. for 15 mins, then filtered off and dried under vacuum to afford the title compound (6.00 g, 19.6 mmol, 73.6% yield).

Step 2: methyl 1-(5-aminopyridin-2-yl)-3,3-difluoropiperidine-4-carboxylate

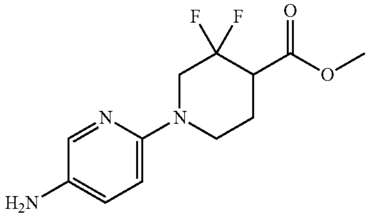 [SMILES: COC(=O)C1CCN(c2ccc([N+](=O)[O-])cn2)CC1(F)F]

To a solution of methyl 3,3-difluoro-1-(5-nitropyridin-2-yl)piperidine-4-carboxylate (5.90 g, 19.5 mmol, 1.00 eq) in EtOAc (60.0 mL) was added Pd/C (1.00 g, 10.0% Pd) under $N_2$ atmosphere. The suspension was degassed and purged with $H_2$ 3 times. The mixture was stirred under $H_2$ (15 Psi) at 25° C. for 12 hrs, then was filtered through a layer of diatomite, and the filtrate was concentrated under vacuum to afford the title compound (5.00 g, 18.0 mmol, 91.9% yield) as a red solid.

Step 3: 3-((6-(3,3-difluoro-4-(methoxycarbonyl)piperidin-1-yl)pyridin-3-yl)amino)propanoic acid

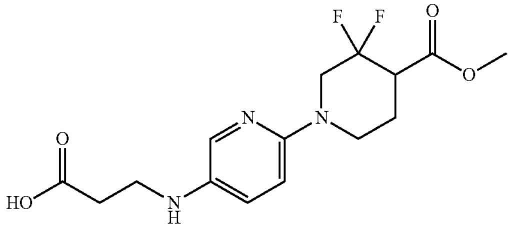 [SMILES: COC(=O)C1CCN(c2ccc(NCCC(=O)O)cn2)CC1(F)F]

To a solution of methyl 1-(5-aminopyridin-2-yl)-3,3-difluoropiperidine-4-carboxylate (4.50 g, 16.2 mmol, 1.00 eq) in dioxane (45.0 mL) was added acrylic acid (2.03 g, 28.1 mmol, 1.93 mL, 1.74 eq), then the mixture was stirred at 100° C. for 48 hrs. After cooling to room temperature, the reaction mixture was concentrated under vacuum to afford the title compound (5.60 g, crude) as a red oil.

Step 4: methyl 1-(5-(2,4-dioxotetrahydropyrimidin-1(2H)-yl)pyridin-2-yl)-3,3-difluoropiperidine-4-carboxylate

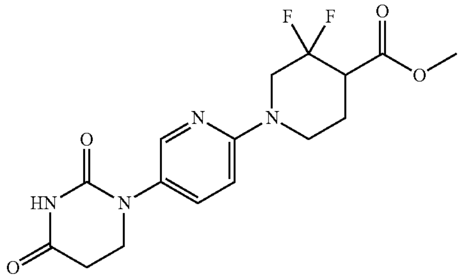 [SMILES: COC(=O)C1CCN(c2ccc(N3CCC(=O)NC3=O)cn2)CC1(F)F]

A solution of 3-((6-(3,3-difluoro-4-(methoxycarbonyl)piperidin-1-yl)pyridin-3-yl)amino)propanoic acid (5.60 g, 16.3 mmol, 1.00 eq) and urea (1.96 g, 32.6 mmol, 1.75 mL, 2.00 eq) in acetic acid (50.0 mL) was stirred at 110° C. for 12 hrs. After cooling to room temperature, the reaction mixture was concentrated under vacuum, then poured into water (60.0 mL), extracted with ethyl acetate (100 mL), and the combined organic phases were washed with brine (100 mL×4), dried over $Na_2SO_4$, filtered, and concentrated under vacuum. The residue was purified by column chromatography to afford the title compound (2.80 g, 7.60 mmol, 46.6% yield) as white solid.

Step 5: 1-(5-(2,4-dioxotetrahydropyrimidin-1(2H)-yl)pyridin-2-yl)-3,3-difluoropiperidine-4-carboxylic acid

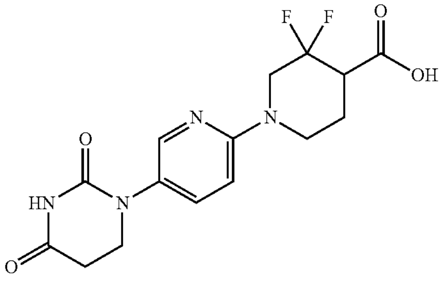 [SMILES: O=C1CCN(c2ccc(N3CCC(C(=O)O)C(F)(F)C3)nc2)C(=O)N1]

To a solution of methyl 1-(5-(2,4-dioxotetrahydropyrimidin-1(2H)-yl)pyridin-2-yl)-3,3-difluoropiperidine-4-carboxylate (800 mg, 2.17 mmol, 1.00 eq) in acetic acid (7.50 mL) was added $H_2SO_4$ (2.77 g, 28.2 mmol, 1.51 mL, 13.0 eq). The reaction mixture was stirred at 50° C. for 48 hrs, then stirred at 70° C. for an additional 48 hrs. After cooling to room temperature, the reaction mixture was concentrated under vacuum. The residue was purified by preparative HPLC to afford the title compound (0.37 g, 45.9% yield) as a light-yellow solid.

Step 6: tert-butyl 1-{1-[5-(2,4-dioxo-1,3-diazinan-1-yl)pyridin-2-yl]-3,3-difluoropiperidine-4-carbonyl}-4-methylpiperidine-4-carboxylate

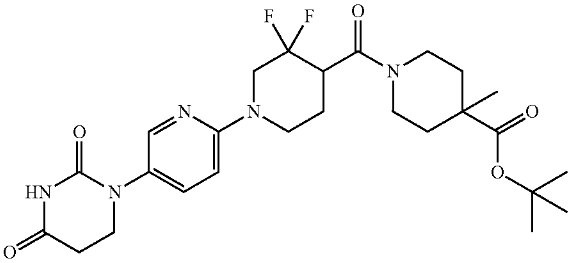 [SMILES: CC(C)(C)OC(=O)C1(C)CCN(C(=O)C2CCN(c3ccc(N4CCC(=O)NC4=O)cn3)CC2(F)F)CC1]

1-(5-(2,4-dioxotetrahydropyrimidin-1(2H)-yl)pyridin-2-yl)-3,3-difluoropiperidine-4-carboxylic acid (0.05 g, 0.1576 mmol), (1,2,3-benzotriazol-1-yloxy)tris(dimethylamino)phosphanium; hexafluoro-lambda5-phosphanuide (0.09 g, 0.2048 mmol), and tert-butyl 4-methylpiperidine-4-carboxylate (0.03 g, 0.1576 mmol) were dissolved in dimethylformamide (1.00 mL) and N,N-diisopropylethylamine (0.11 mL, 0.08 g, 0.6302 mmol) and stirred at room temperature for 6 hours. The crude reaction mixture was purified by reverse phase flash column chromatography eluting with acetonitrile/water to afford the title compound (0.062 g, 73% yield).

Step 7: 1-{1-[5-(2,4-dioxo-1,3-diazinan-1-yl)pyridin-2-yl]-3,3-difluoropiperidine-4-carbonyl}-4-methylpiperidine-4-carboxylic acid

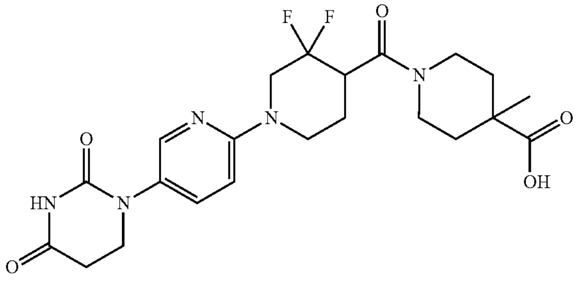 [SMILES: CC1(C(=O)O)CCN(C(=O)C2CCN(c3ccc(N4CCC(=O)NC4=O)cn3)CC2(F)F)CC1]

Tert-butyl 1-{1-[5-(2,4-dioxo-1,3-diazinan-1-yl)pyridin-2-yl]-3,3-difluoropiperidine-4-carbonyl}-4-methylpiperidine-4-carboxylate (0.062 g, 0.115 mmol) was dissolved in DCM (1.0 mL). 4M HCl in dioxane was added and the reaction mixture was stirred at room temperature for 4 hours. The crude reaction mixture was evaporated to dryness and the residue was purified by reverse phase flash column chromatography eluting with acetonitrile/water to afford the title compound (0.043 g, 78% yield). LCMS: $C_{22}H_{27}F_2N_5O_5$, desired mass=479.5, found: m/z=480.4 $[M+H]^+$.

Intermediate 81

1-(2-((3R)-1-(5-(2,6-dioxopiperidin-3-yl)pyridin-2-yl)pyrrolidin-3-yl)acetyl)-4-methylpiperidine-4-carboxylic acid

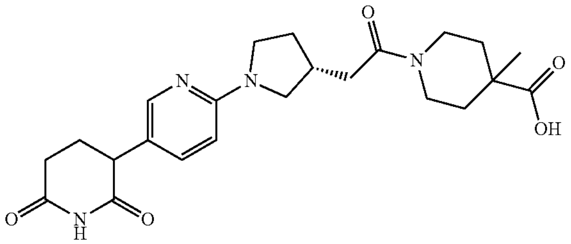 [SMILES: CC1(C(=O)O)CCN(C(=O)C[C@H]2CCN(c3ccc(C4CCC(=O)NC4=O)cn3)C2)CC1]

Step 1: methyl (R)-2-(1-(5-bromopyridin-2-yl)pyrrolidin-3-yl)acetate

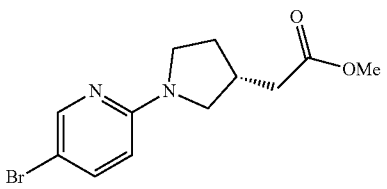 [SMILES: COC(=O)C[C@H]1CCN(c2ccc(Br)cn2)C1]

A mixture of 5-bromo-2-fluoropyridine (6.00 g, 34.1 mmol, 3.51 mL), methyl (R)-2-(pyrrolidin-3-yl)acetate hydrochloride (7.35 g, 40.9 mmol) and DIEA (17.6 g, 136 mmol, 23.8 mL) in NMP (60.0 mL) was stirred at 135° C. for 16 hrs. under $N_2$. The mixture was poured into ice-water (200 mL) and extracted with Ethyl acetate (100 mL×3). The combined organic layer was washed with brine (100 mL×2), dried over $Na_2SO_4$, filtered and concentrated, and the resulting residue was purified by column chromatography (silica gel, Ethyl acetate/Petroleum ether=0/1 to 1/15) to afford the title compound (8.75 g, 29.1 mmol, 85.5% yield) as a yellow oil. LCMS: $C_{12}H_{15}BrN_2O_2$, desired mass=298.0, found: m/z=300.8 $[M+H]^+$.

Step 2: methyl (R)-2-(1-(2',6'-bis(benzyloxy)-[3,3'-bipyridin]-6-yl)pyrrolidin-3-yl)acetate

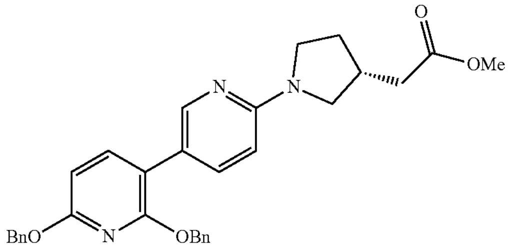 [SMILES: COC(=O)C[C@H]1CCN(c2ccc(-c3ccc(OCc4ccccc4)nc3OCc3ccccc3)cn2)C1]

To a mixture of methyl (R)-2-(1-(5-bromopyridin-2-yl)pyrrolidin-3-yl)acetate (8.75 g, 29.1 mmol, 1.00 eq), 2,6-bis(benzyloxy)-3-(4,4,5,5-tetramethyl-1,3,2-dioxaborolan-2-yl)pyridine (13.4 g, 32.0 mmol, 1.10 eq) and $K_3PO_4$ (12.4 g, 58.3 mmol, 2.00 eq) in THF (130 mL) and $H_2O$ (13.0 mL) was added Pd(dppf)$Cl_2$ (4.26 g, 5.83 mmol, 0.20 eq) at 25° C. under $N_2$. The mixture was stirred at 50° C. for 12 hrs. under $N_2$. The mixture was poured into water (300 mL) and extracted with Ethyl acetate (200 mL×3). The combined organic layer was washed with brine (200 mL×2), dried over $Na_2SO_4$, filtered, and concentrated, and the residue was purified by column chromatography (silica gel, Ethyl acetate/Petroleum ether=0/1 to 1/5) to afford the title compound (11.7 g, 22.8 mmol, 78.4% yield) as a yellow oil. LCMS: $C_{31}H_{31}N_3O_4$, desired mass=509.2, found: m/z=510.1 $[M+H]^+$.

Step 3: (R)-2-(1-(2',6'-bis(benzyloxy)-[3,3'-bipyridin]-6-yl)pyrrolidin-3-yl)acetic acid

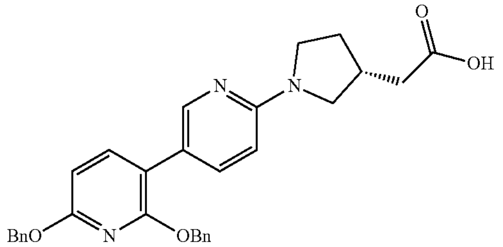 [SMILES: O=C(O)C[C@H]1CCN(c2ccc(-c3ccc(OCc4ccccc4)nc3OCc3ccccc3)cn2)C1]

To a solution of methyl (R)-2-(1-(2',6'-bis(benzyloxy)-[3,3'-bipyridin]-6-yl)pyrrolidin-3-yl)acetate (4.20 g, 8.20 mmol, 1.00 eq) in THF (20.0 mL) and MeOH (8.00 mL) was added a solution of LiOH·$H_2O$ (516 mg, 12.3 mmol, 1.50 eq) in $H_2O$ (8.00 mL) at 25° C. The mixture was stirred at 25° C. for 1 hr. The mixture was concentrated to remove THF and MeOH, and the residue was poured into water (150 mL). The mixture was adjusted to pH=6-7 with 1 N aqueous HCl solution and extracted with Ethyl acetate (100 mL×2).

The combined organic layer was washed with brine (100 mL×2), dried over $Na_2SO_4$, filtered, and concentrated, and the residue was stirred as a slurry in Ethyl acetate/Petroleum ether=1/5 (150 mL) at 25° C. for 0.5 hr. The mixture was filtered to collect the solid. The solid was dried under vacuum at 45° C. for 0.5 hr. to afford the title compound (3.62 g, 6.44 mmol, 78.5% yield) as a white solid. LCMS: $C_{30}H_{29}N_3O_4$, desired mass=495.2, found: m/z=496.1 $[M+H]^+$.

Step 4: 2-((3R)-1-(5-(2,6-dioxopiperidin-3-yl)pyridin-2-yl)pyrrolidin-3-yl)acetic acid

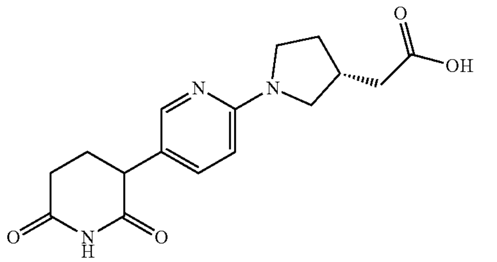 [SMILES: O=C(O)C[C@H]1CCN(c2ccc(C3CCC(=O)NC3=O)cn2)C1]

To a solution of (R)-2-(1-(2',6'-bis(benzyloxy)-[3,3'-bipyridin]-6-yl)pyrrolidin-3-yl)acetic acid (3.00 g, 6.05 mmol, 1.00 eq) in THF (150 mL) was added Pd/C (3.00 g, 10% purity) and $Pd(OH)_2$ (3.00 g, 20% purity) under $N_2$. The mixture was degassed under vacuum and purged with $H_2$ three times. The mixture was stirred at 25° C. for 12 hrs. under $H_2$ (15 psi). The mixture was filtered through a pad of Celite. The filtrate was concentrated to afford the title compound (0.73 g, 2.27 mmol, 37.5% yield) as a white solid. LCMS: $C_{16}H_{19}N_3O_4$, desired mass=317.1, found: m/z=318.1 $[M+H]^+$.

Step 5: tert-butyl 1-{2-[3R)-1-{5-[(3RS)-2,6-dioxopiperidin-3-yl]pyridin-2-yl}pyrrolidin-3-yl]acetyl}-4-methylpiperidine-4-carboxylate

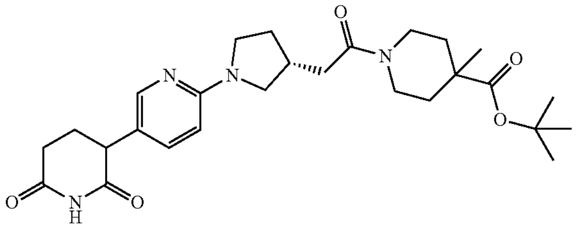 [SMILES: CC(C)(C)OC(=O)C1(C)CCN(C(=O)C[C@H]2CCN(c3ccc(C4CCC(=O)NC4=O)cn3)C2)CC1]

[(3R)-1-{5-[(3RS)-2,6-dioxopiperidin-3-yl]pyridin-2-yl}pyrrolidin-3-yl]acetic acid (0.05 g, 0.1576 mmol), (1,2,3-benzotriazol-1-yloxy)tris(dimethylamino)phosphanium; hexafluoro-lambda5-phosphanuide (0.09 g, 0.2048 mmol), and tert-butyl 4-methylpiperidine-4-carboxylate (0.03 g, 0.1576 mmol) were dissolved in dimethylformamide (10.00 mL) and N,N-diisopropylethylamine (0.11 mL, 0.08 g, 0.6302 mmol) and stirred at room temperature for 6 hours. The crude reaction mixture was purified by reverse phase flash column chromatography eluting with acetonitrile/water to afford the title compound (0.066 g, 84% yield). LCMS: $C_{27}H_{38}N_4O_5$, desired mass=498.6, found: m/z=499.4 $[M+H]^+$.

Step 6: 1-(2-((3R)-1-(5-(2,6-dioxopiperidin-3-yl)pyridin-2-yl)pyrrolidin-3-yl)acetyl)-4-methylpiperidine-4-carboxylic acid

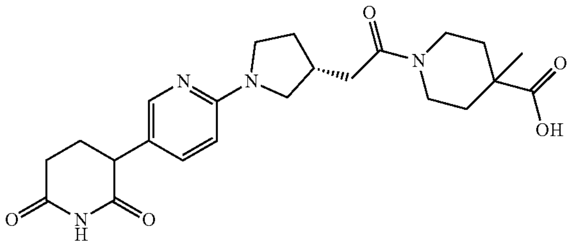 [SMILES: CC1(C(=O)O)CCN(C(=O)C[C@H]2CCN(c3ccc(C4CCC(=O)NC4=O)cn3)C2)CC1]

Tert-butyl 1-{2-[(3R)-1-{5-[(3RS)-2,6-dioxopiperidin-3-yl]pyridin-2-yl}pyrrolidin-3-yl]acetyl}-4-methylpiperidine-4-carboxylate (0.066 g, 0.132 mmol) was dissolved in DCM (1.0 mL). 4M HCl in dioxane (1.0 mL) was added and the reaction mixture was stirred at room temperature for 4 hours. The crude reaction mixture was concentrated under vacuum and the residue was purified by reverse phase flash column chromatography eluting with acetonitrile/water to afford the title compound (0.043 g, 74% yield). LCMS: $C_{23}H_{30}N_4O_5$, desired mass=442.5, found: m/z=443.2 $[M+H]^+$.

Intermediate 82

1-{3-[5-(2,4-dioxo-1,3-diazinan-1-yl)pyridin-2-yl]-3-azabicyclo[3.2.1]octane-8-carbonyl}-4-methylpiperidine-4-carboxylic acid

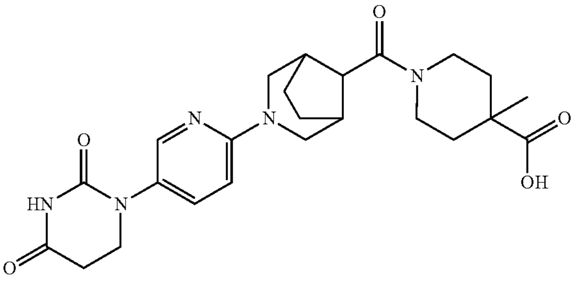 [SMILES: CC1(C(=O)O)CCN(C(=O)C2C3CCC2CN(c2ccc(N4CCC(=O)NC4=O)cn2)C3)CC1]

Step 1: methyl 3-(5-nitropyridin-2-yl)-3-azabicyclo[3.2.1]octane-8-carboxylate

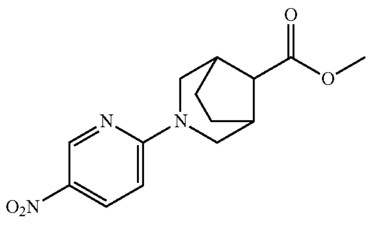

To a solution of 2-fluoro-5-nitropyridine (3.00 g, 21.1 mmol) and methyl 3-azabicyclo[3.2.1]octane-8-carboxylate hydrochloride (3.95 g, 19.2 mmol, 1.00 eq) in NMP (10.0 mL) was added DIEA (8.68 g, 67.2 mmol, 11.7 mL, 3.50 eq).

The reaction mixture was stirred at 100° C. for 1.5 hours, cooled to room temperature, poured into $H_2O$ (300 mL), then was extracted with ethyl acetate (100 mL×3). The combined organic layers were washed with brine (100 mL×2), dried over $Na_2SO_4$, filtered, and concentrated to afford the title compound (6.90 g, 23.4 mmol, 79.5% yield) as a yellow solid.

Step 2: methyl 3-(5-aminopyridin-2-yl)-3-azabicyclo[3.2.1]octane-8-carboxylate

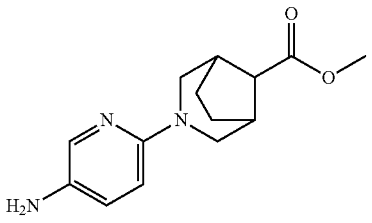 [SMILES: COC(=O)C1C2CCC1CN(c1ccc(N)cn1)C2]

To a solution of methyl 3-(5-nitropyridin-2-yl)-3-azabicyclo[3.2.1]octane-8-carboxylate (5.90 g, 20.3 mmol, 1.00 eq) in THF (60.0 mL) was added Pd/C (2.95 g, 3.43 mmol, 10% Pd) under $N_2$. The suspension was degassed under vacuum and purged with $H_2$ 3 times. The reaction mixture was stirred under $H_2$ (15 psi) at 25° C. for 12 hours. The suspension was filtered through a pad of celite and the pad was washed with THF (100 mL×4). Concentration under reduced pressure afforded the title compound (5.20 g, 19.9 mmol, 98.3% yield) as a yellow oil.

Step 3: 3-((6-(8-(methoxycarbonyl)-3-azabicyclo[3.2.1]octan-3-yl)pyridin-3-yl)amino)propanoic acid

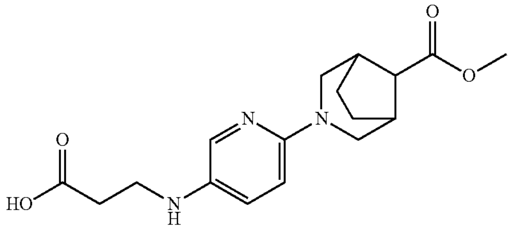 [SMILES: COC(=O)C1C2CCC1CN(c1ccc(NCCC(=O)O)cn1)C2]

To a solution of methyl 3-(5-aminopyridin-2-yl)-3-azabicyclo[3.2.1]octane-8-carboxylate (2.40 g, 8.69 mmol, 1.00 eq) in dioxane (25.0 mL) was added acrylic acid (939 mg, 13.0 mmol, 894 uL, 1.50 eq), The reaction mixture was stirred at 100° C. for 24 hours. The reaction mixture was concentrated under vacuum to afford the title compound (4.50 g, 8.30 mmol, 95.5% yield) as a black oil.

Step 4: methyl 3-(5-(2,4-dioxotetrahydropyrimidin-1(2H)-yl)pyridin-2-yl)-3-azabicyclo[3.2.1]octane-8-carboxylate

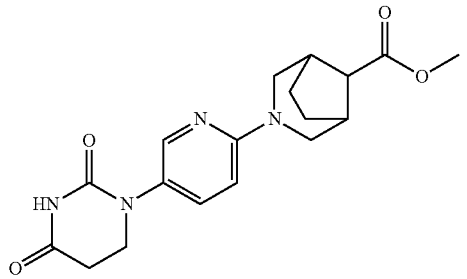 [SMILES: COC(=O)C1C2CCC1CN(c1ccc(N3CCC(=O)NC3=O)cn1)C2]

To a solution of 3-((6-(8-(methoxycarbonyl)-3-azabicyclo[3.2.1]octan-3-yl)pyridin-3-yl)amino)propanoic acid (4.50 g, 8.30 mmol, 1.00 eq) in acetic acid (40.0 mL) was added urea (997 mg, 16.6 mmol, 890 uL, 2.00 eq), Then reaction mixture was stirred 100° C. for 12 hrs, then concentrated under vacuum and purified by flash column chromatography to afford the title compound (1.00 g, 2.64 mmol, 31.8% yield).

Step 5: 3-(5-(2,4-dioxotetrahydropyrimidin-1(2H)-yl)pyridin-2-yl)-3-azabicyclo[3.2.1]octane-8-carboxylic acid

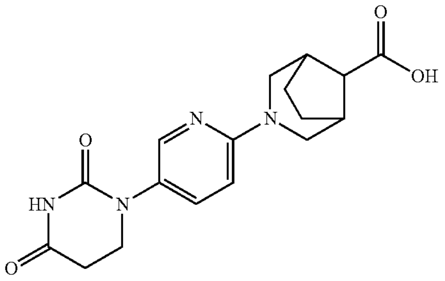 [SMILES: O=C1CCN(c2ccc(N3CC4CCC(C3)C4C(=O)O)nc2)C(=O)N1]

To a solution of methyl 3-(5-(2,4-dioxotetrahydropyrimidin-1(2H)-yl)pyridin-2-yl)-3-azabicyclo[3.2.1]octane-8-carboxylate (900 mg, 2.38 mmol, 1.00 eq) in acetic acid (9.00 mL) was added $H_2SO_4$ (3.31 g, 33.7 mmol, 1.80 mL, 14.2 eq), the reaction mixture was stirred at 70° C. for 12 hrs, then concentrated under vacuum. The residue was purified by preparative HPLC to afford the title compound (230 mg, 0.648 mmol, 27.3% yield) as a yellow solid.

Step 6: tert-butyl 1-{3-[5-(2,4-dioxo-1,3-diazinan-1-yl)pyridin-2-yl]-3-azabicyclo[3.2.1]octane-8-carbonyl}-4-methylpiperidine-4-carboxylate

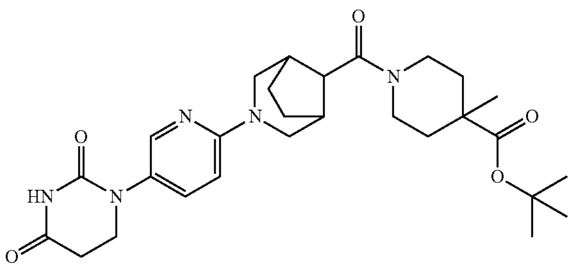 [SMILES: CC(C)(C)OC(=O)C1(C)CCN(C(=O)C2C3CCC2CN(c2ccc(N4CCC(=O)NC4=O)cn2)C3)CC1]

3-[5-(2,4-dioxo-1,3-diazinan-1-yl)pyridin-2-yl]-3-azabicyclo[3.2.1]octane-8-carboxylic acid (0.05 g, 0.1576 mmol), (1,2,3-benzotriazol-1-yloxy)tris(dimethylamino)phosphanium; hexafluoro-lambda5-phosphanuide (0.09 g, 0.2048 mmol), and tert-butyl 4-methylpiperidine-4-carboxylate (0.03 g, 0.1576 mmol) were dissolved in dimethylformamide (10.00 mL) and N,N-diisopropylethylamine (0.11 mL, 0.08 g, 0.6302 mmol) and stirred at room temperature for 6 hours. The crude reaction mixture was purified by reverse phase flash column chromatography eluting with acetonitrile/water to afford the title compound (0.058 g, 70% yield).

Step 7: 1-{3-[5-(2,4-dioxo-1,3-diazinan-1-yl)pyridin-2-yl]-3-azabicyclo[3.2.1]octane-8-carbonyl}-4-methylpiperidine-4-carboxylic acid

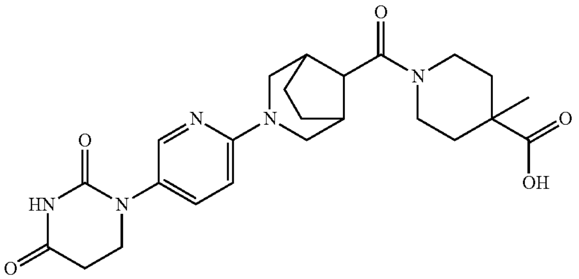 [SMILES: CC1(C(=O)O)CCN(C(=O)C2C3CCC2CN(c2ccc(N4CCC(=O)NC4=O)cn2)C3)CC1]

Tert-butyl 1-{3-[5-(2,4-dioxo-1,3-diazinan-1-yl)pyridin-2-yl]-3-azabicyclo[3.2.1]octane-8-carbonyl}-4-methylpiperidine-4-carboxylate (0.058 g, 0.110 mmol) was dissolved in DCM (1.0 mL). 4M HCl in dioxane (1.0 mL) was added and the reaction mixture was stirred at room temperature for 6 hours. The crude reaction mixture was concentrated under vacuum and the residue was purified by reverse phase flash column chromatography eluting with acetonitrile/water to afford the title compound (0.041 g, 80% yield). LCMS: $C_{24}H_{31}N_5O_5$, desired mass=469.5, found: m/z=470.4 $[M+H]^+$.

Intermediate 83

4-Methyl-1-[(1R,4R)-4-{4-[(3RS)-2,6-Dioxopiperidin-3-yl]-2-Methylphenoxy}Cyclohexanecarbonyl] Piperidine-4-Carboxylic Acid

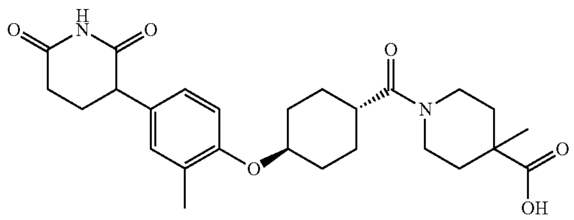 [SMILES: Cc1cc(C2CCC(=O)NC2=O)ccc1O[C@H]1CC[C@H](C(=O)N2CCC(C)(C(=O)O)CC2)CC1]

Step 1: benzyl (1s,4s)-4-hydroxycyclohexane-1-carboxylate

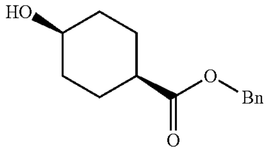 [SMILES: O=C(OCc1ccccc1)[C@H]1CC[C@@H](O)CC1]

To a solution of cis-4-hydroxycyclohexanecarboxylic acid (5.5 g, 38.15 mmol) in anhydrous dimethylformamide (63.6 mL, 0.6 M) was added potassium carbonate (10.55 g, 76.30 mmol). The reaction mixture was heated to 55° C. Then benzyl chloride (5.71 ml, 49.59 mmol) was added dropwise and the reaction mixture was stirred at 55° C. for 12 h. After cooling to room temperature, water (180 mL) was poured into the reaction mixture, followed by extraction with DCM (4×150 ml). The combined organic layers were washed with a saturated solution of aqueous $NaHCO_3$ (100 ml) and brine, then dried over $Na_2SO_4$. The solvent was evaporated in vacuo. The residue was purified by flash chromatography eluting with DCM/MeOH (100 to 90% of DCM) to provide 7.5 g (84%) of the title compound as a yellow oil. LCMS: $C_{14}H_{18}O_3$, desired mass=234.1, found: m/z=234.8 $[M+H]^+$.

Step 2: benzyl (1r,4r)-4-(4-bromo-2-methylphenoxy)cyclohexane-1-carboxylate

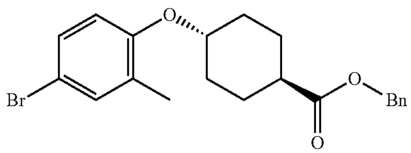 [SMILES: Cc1cc(Br)ccc1O[C@H]1CC[C@H](C(=O)OCc2ccccc2)CC1]

A solution of 4-bromo-2-methylphenol (1.19 g, 6.362 mmol), benzyl (1s,4s)-4-hydroxycyclohexane-1-carboxylate (1.789 g, 7.635 mmol), triethylamine (1.06 ml, 7.635 mmol) and triphenylphosphine (3.338 g, 12.725 mmol) in anhydrous tetrahydrofuran (9.5 ml, 0.67 M) was cooled to 0° C., followed by slow addition of diisopropyl azodicarboxylate (2.573 g, 12.725 mmol) under an argon atmosphere. The reaction mixture was stirred at room temperature overnight. Then the solvent was removed under reduced pressure. The residue was purified by flash chromatography eluting with hexane/DCM (100 to 30% of hex) to provide 1.23 g (46% yield) of the title compound as a colorless oil.

Step 3: benzyl 4-{4-[2,6-bis(benzyloxy)pyridin-3-yl]-2-methylphenoxy}cyclohexane-1-carboxylate

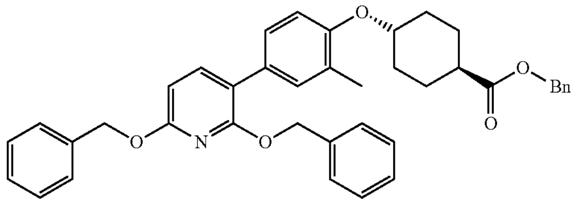

A mixture of 2,6-bis(benzyloxy)-3-(4,4,5,5-tetramethyl-1,3,2-dioxaborolan-2-yl)pyridine (0.618 g, 1.845 mmol) and benzyl (1r,4r)-4-(4-bromo-2-methylphenoxy)cyclohexane-1-carboxylate (0.744 g, 1.845 mmol) in anhydrous dimethylformamide (5.27 ml, 0.35 M) was degassed with Argon, followed by addition of 1,1'-bis(diphenylphosphino)ferrocene dichloropalladium (II) (0.068 g, 0.092 mmol) and potassium carbonate (0.765 g, 5.534 mmol). The reaction mixture was stirred at 85° C. for 16 h, then cooled to room temperature and concentrated in vacuo. The residue was purified by flash chromatography eluting with hexane/EtOAc (from 0 to 15% of EtOAc) to provide 0.352 g (31% yield) of the title compound as a yellow oil. LCMS: $C_{40}H_{39}NO_5$, desired mass=613.3, found: m/z=614.5.

Step 4: 4-[4-(2,6-dioxopiperidin-3-yl)-2-methylphenoxy]cyclohexane-1-carboxylic acid

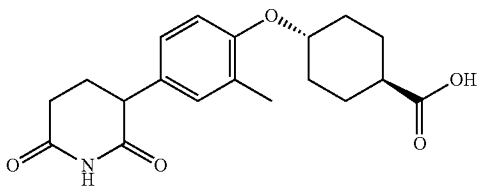 [SMILES: Cc1cc(C2CCC(=O)NC2=O)ccc1O[C@H]1CC[C@H](C(=O)O)CC1]

To a solution of benzyl 4-{4-[2,6-bis(benzyloxy)pyridin-3-yl]-2-methylphenoxy}cyclohexane-1-carboxylate (0.352 g, 0.574 mmol) dissolved in degassed tetrahydrofuran (33.75 ml, 0.017 M) and isopropanol (11.47 ml, 0.05 M) was added palladium on carbon 60-65% wet (0.105 g, 0.987 mmol) and the mixture was stirred under $H_2$ (balloon) at room temperature for 16 hours. The mixture was filtered, and the filtrate was concentrated in vacuo, then the residue was washed with DCM and EtOAc to provide 0.11 g (55% yield) of the title compound as a yellow solid.

Step 5: tert-butyl 4-methyl-1-[(1r,4r)-4-{4-[(3RS)-2,6-dioxopiperidin-3-yl]-2-methylphenoxy}cyclohexanecarbonyl]piperidine-4-carboxylate

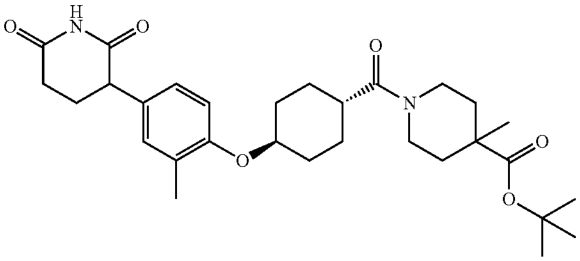 [SMILES: Cc1cc(C2CCC(=O)NC2=O)ccc1O[C@H]1CC[C@H](C(=O)N2CCC(C)(C(=O)OC(C)(C)C)CC2)CC1]

(1r,4r)-4-{4-[(3RS)-2,6-dioxopiperidin-3-yl]-2-methylphenoxy}cyclohexane-1-carboxylic acid (110.00 mg, 0.3185 mmol), (1,2,3-benzotriazol-1-yloxy)tris(dimethylamino)phosphanium; hexafluoro-lambda5-phosphanuide (183.12 mg, 0.4140 mmol), and tert-butyl 4-methylpiperidine-4-carboxylate (63.47 mg, 0.3185 mmol) were dissolved in dimethylformamide (1.00 mL) and N,N-diisopropylethylamine (0.22 mL, 164.65 mg, 1.2739 mmol) and stirred at room temperature for 6 hours. The crude reaction mixture was purified by reverse phase flash column chromatography eluting with acetonitrile/water to afford the title compound (0.123 g, 73% yield).

Step 6: 4-methyl-1-[(1r,4r)-4-{4-[(3RS)-2,6-dioxopiperidin-3-yl]-2-methylphenoxy}cyclohexanecarbonyl]piperidine-4-carboxylic acid

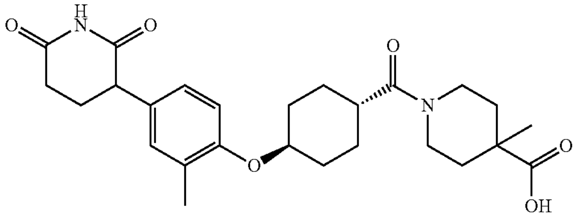 [SMILES: Cc1cc(C2CCC(=O)NC2=O)ccc1O[C@H]1CC[C@H](C(=O)N2CCC(C)(C(=O)O)CC2)CC1]

Tert-butyl 4-methyl-1-[(1r,4r)-4-{4-[(3RS)-2,6-dioxopiperidin-3-yl]-2-methylphenoxy}cyclohexanecarbonyl]piperidine-4-carboxylate (0.123 g, 0.233 mmol) was dissolved in DCM (2.0 mL). 4M HCL in dioxane (2.0 mL) was added and the reaction mixture was stirred at room temperature for 6 hours. The crude reaction mixture was concentrated under vacuum and the residue purified by reverse phase flash column chromatography eluting with acetonitrile/water to afford the title compound (0.082 g, 75% yield). LCMS: $C_{26}H_{34}N_2O_6$ desired mass=470.6, found: m/z=471.3 $[M+H]^+$.

Intermediate 84

1-((1-(5-(2,6-Dioxopiperidin-3-yl)Pyridin-2-yl)Piperidin-4-yl)Sulfonyl)Piperidine-4-Carboxylic Acid

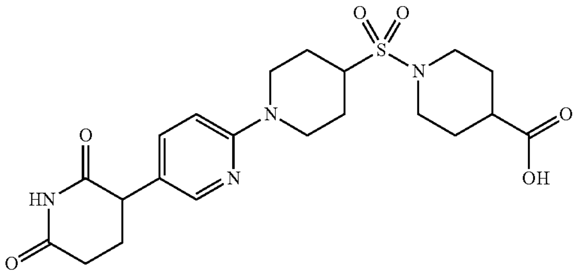 [SMILES: O=C1CCC(c2ccc(N3CCC(S(=O)(=O)N4CCC(C(=O)O)CC4)CC3)nc2)C(=O)N1]

Step 1: tert-butyl 4-[4-(tert-butoxycarbonyl)piperidin-1-ylsulfonyl]piperidine-1-carboxylate

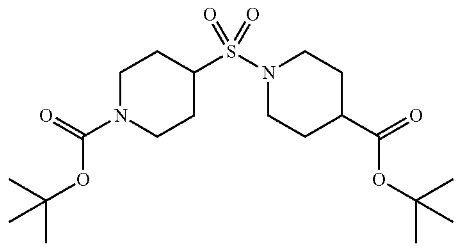 [SMILES: CC(C)(C)OC(=O)C1CCN(S(=O)(=O)C2CCN(C(=O)OC(C)(C)C)CC2)CC1]

Tert-butyl piperidine-4-carboxylate (130.58 mg, 0.7048 mmol) and tert-butyl 4-(chlorosulfonyl)piperidine-1-carboxylate (200.00 mg, 0.7048 mmol) were dissolved in DCM (5.00 mL) and N,N-diisopropylethylamine (0.49 mL, 2.8192 mmol) and stirred at room temperature for 4 hours. The crude reaction mixture was evaporated onto silica gel and purified by flash column chromatography to afford the title compound. (0.144 g, 47% yield).

Step 2: 1-(piperidine-4-sulfonyl)piperidine-4-carboxylic acid

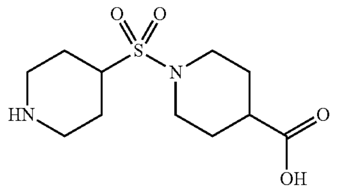 [SMILES: O=C(O)C1CCN(S(=O)(=O)C2CCNCC2)CC1]

Tert-butyl 4-[4-(tert-butoxycarbonyl)piperidin-1-ylsulfonyl]piperidine-1-carboxylate (0.144 g, 0.332 mmol) was dissolved in DCM (5.0 mL). TFA (1.0 mL) was added, and the reaction mixture was stirred at room temperature for 16 h. The reaction mixture was then concentrated under reduced pressure to afford the title compound (0.088 g, 97% yield).

Step 3: 1-((1-(5-(2,6-dioxopiperidin-3-yl)pyridin-2-yl)piperidin-4-yl)sulfonyl)piperidine-4-carboxylic acid

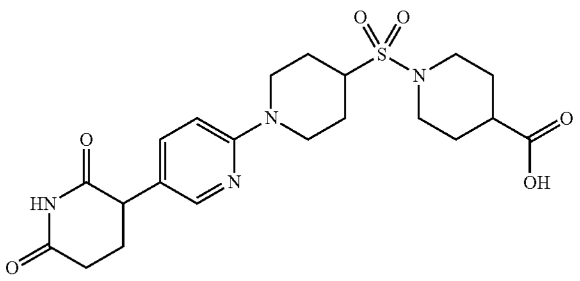 [SMILES: O=C1CCC(c2ccc(N3CCC(S(=O)(=O)N4CCC(C(=O)O)CC4)CC3)nc2)C(=O)N1]

3-(6-fluoropyridin-3-yl)piperidine-2,6-dione (0.15 g, 0.7205 mmol) and 1-(piperidine-4-sulfonyl)piperidine-4-carboxylic acid (0.23 mL, 0.22 g, 0.7925 mmol) were dissolved in DMSO (7.20 mL) and N,N-diisopropylethylamine (0.25 mL, 1.441 mmol) in a sealed vial. The vial was heated to 120° C. for 12 hours. The crude reaction mixture was purified by reverse phase flash column chromatography eluting with acetonitrile/water to afford the title compound (0.15 g, 40% yield).

Intermediate 85

1-(2-{1-[5-(2,6-Dioxopiperidin-3-yl)Pyridin-2-yl]Piperidin-4-yl}Acetyl)-4-Methylpiperidine-4-Carboxylic Acid

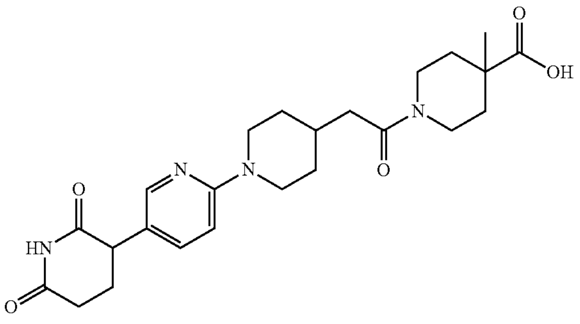 [SMILES: CC1(C(=O)O)CCN(C(=O)CC2CCN(c3ccc(C4CCC(=O)NC4=O)cn3)CC2)CC1]

Step 1: tert-butyl 2-(1-(5-(2,6-dioxopiperidin-3-yl)pyridin-2-yl)piperidin-4-yl)acetate

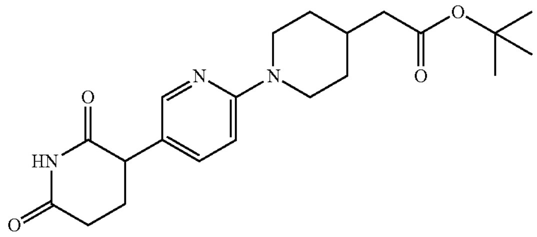 [SMILES: CC(C)(C)OC(=O)CC1CCN(c2ccc(C3CCC(=O)NC3=O)cn2)CC1]

3-(6-fluoropyridin-3-yl)piperidine-2,6-dione (0.50 g, 2.4016 mmol) and tert-butyl 2-(piperidin-4-yl)acetate (0.60 mL, 0.57 g, 2.8820 mmol) were dissolved in DMSO (7.20 mL) and N,N-diisopropylethylamine (0.84 mL, 4.8033 mmol) in a sealed vial. The reaction mixture was heated to 120° C. for 12 hours. The crude reaction mixture was purified by reverse phase flash column chromatography eluting with acetonitrile/water to afford the title compound (0.813 g, 83% yield).

Step 2: 2-(1-(5-(2,6-dioxopiperidin-3-yl)pyridin-2-yl)piperidin-4-yl)acetic acid

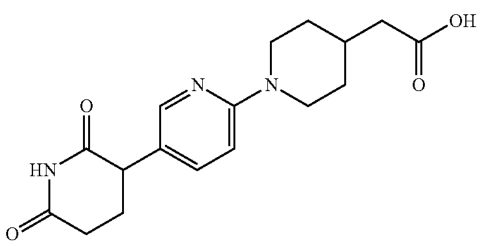 [SMILES: O=C(O)CC1CCN(c2ccc(C3CCC(=O)NC3=O)cn2)CC1]

Tert-butyl 2-(1-(5-(2,6-dioxopiperidin-3-yl)pyridin-2-yl)piperidin-4-yl)acetate (0.813 g, 1.993 mmol) was dissolved in DCM (10.0 mL). 4M HCl in dioxane was added and the reaction mixture was stirred at room temperature overnight.

The crude reaction mixture was concentrated under vacuum and purified by reverse phase flash column chromatography eluting with acetonitrile/water to afford the title compound (0.657 g, 95% yield)

Step 3: tert-butyl 1-(2-{1-[5-(2,6-dioxopiperidin-3-yl)pyridin-2-yl]piperidin-4-yl}acetyl)-4-methylpiperidine-4-carboxylate

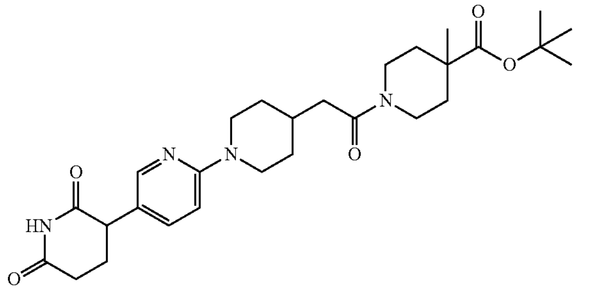 [SMILES: CC(C)(C)OC(=O)C1(C)CCN(C(=O)CC2CCN(c3ccc(C4CCC(=O)NC4=O)cn3)CC2)CC1]

2-(1-(5-(2,6-dioxopiperidin-3-yl)pyridin-2-yl)piperidin-4-yl)acetic acid (0.04 g, 0.1207 mmol), (1,2,3-benzotriazol-1-yloxy)tris(dimethylamino)phosphanium; hexafluoro-lambda5-phosphanuide (0.07 g, 0.1569 mmol), and tert-butyl 4-methylpiperidine-4-carboxylate (0.02 g, 0.1207 mmol) were dissolved in dimethylformamide (2.00 mL) and N,N-diisopropylethylamine (0.08 mL, 0.4828 mmol) and stirred at room temperature for 6 hours. The crude reaction mixture was purified by reverse phase flash column chromatography eluting with acetonitrile/water to afford the title compound (0.052 g, 84% yield).

Step 4: 1-(2-{1-[5-(2,6-dioxopiperidin-3-yl)pyridin-2-yl]piperidin-4-yl}acetyl)-4-methylpiperidine-4-carboxylic acid

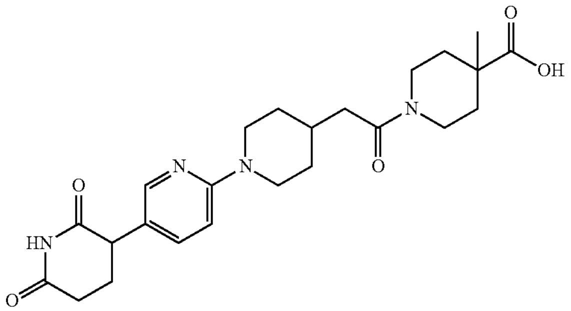 [SMILES: CC1(C(=O)O)CCN(C(=O)CC2CCN(c3ccc(C4CCC(=O)NC4=O)cn3)CC2)CC1]

Tert-butyl 1-(2-{1-[5-(2,6-dioxopiperidin-3-yl)pyridin-2-yl]piperidin-4-yl}acetyl)-4-methylpiperidine-4-carboxylate (0.052 g, 0.101 mmol) was dissolved in DCM (2.0 mL). 4M HCl in dioxane (1.0 mL) was added and the reaction mixture was stirred at room temperature for 6 hours. The solvents were removed via a stream of nitrogen, and the residue was dissolved in DMF and purified by reverse phase flash column chromatography eluting with acetonitrile/water to afford the title compound (0.038 g, 85% yield, 95% purity). LCMS: $C_{24}H_{32}N_4O_5$, desired mass=456.2, found: m/z=457.6 $[M+H]^+$.

Intermediate 86

3-{6-[4-(piperazine-1-carbonyl)piperidin-1-yl]pyridin-3-yl}piperidine-2,6-dione

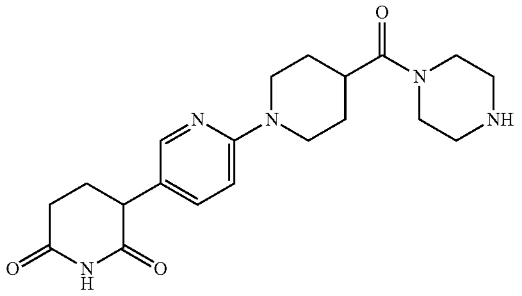 [SMILES: O=C1CCC(c2ccc(N3CCC(C(=O)N4CCNCC4)CC3)nc2)C(=O)N1]

Step-1: tert-butyl 4-{1-[5-(2,6-dioxopiperidin-3-yl)pyridin-2-yl]piperidine-4-carbonyl}piperazine-1-carboxylate

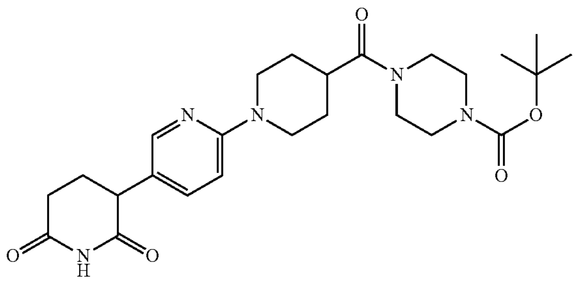 [SMILES: CC(C)(C)OC(=O)N1CCN(C(=O)C2CCN(c3ccc(C4CCC(=O)NC4=O)cn3)CC2)CC1]

To a solution of 1-[5-(2,6-dioxopiperidin-3-yl)pyridin-2-yl]piperidine-4-carboxylic acid (Intermediate 11, step 2) (0.1 g, 0.254 mmol) in anhydrous DMF (2.5 mL) was added N,N-diisopropylethylamine (0.22 mL, 1.27 mmol) and BOP (0.135 g, 0.305 mmol). The reaction mixture was stirred for 1 h at room temperature. Then t-Butyl piperazine-1-carboxylate (0.057 g, 0.254 mmol) was added and stirring was continued for 1.5 h. The reaction mixture was evaporated to dryness, diluted with DCM, washed with $NaHCO_3$, dried over $Na_2SO_4$ and the organic phase was filtered and evaporated to dryness. The crude residue was purified by flash chromatography eluting with DCM:MeOH (0-15%) to provide 0.12 g (97% yield) of title compound as an off-white solid. LCMS: ($C_{25}H_{35}N_5O_5$) desired mass=485.3; found: m/z=486.2 $[M+H]^+$.

Step 2: 3-{6-[4-(piperazine-1-carbonyl)piperidin-1-yl]pyridin-3-yl}piperidine-2,6-dione

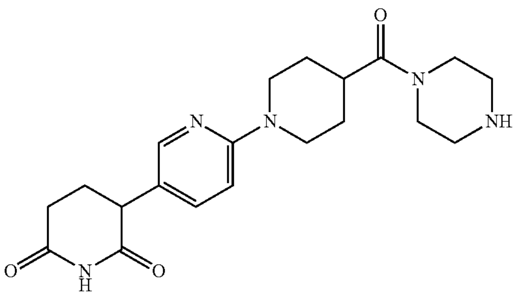 [SMILES: O=C1CCC(c2ccc(N3CCC(C(=O)N4CCNCC4)CC3)nc2)C(=O)N1]

To a solution of tert-butyl 4-{1-[5-(2,6-dioxopiperidin-3-yl)pyridin-2-yl]piperidine-4-carbonyl}piperazine-1-carboxylate (0.12 g, 0.247 mmol) in anhydrous DCM (2.5 mL, 0.1 M) was added TFA (2.8 mL, 24.7 mmol). The reaction mixture was stirred at room temperature for 2 h. On completion of the reaction, the solvents were evaporated and the crude residue was triturated with $Et_2O$ to provide 151 mg (100% yield) of the title compound as an orange viscous solid. LCMS: ($C_{20}H_{27}N_5O_3$) desired mass=385.2; found: m/z=386.0 $[M+H]^+$.

Intermediate 87

3-{2-[4-(piperazine-1-carbonyl)piperidin-1-yl]pyridin-4-yl}piperidine-2,6-dione

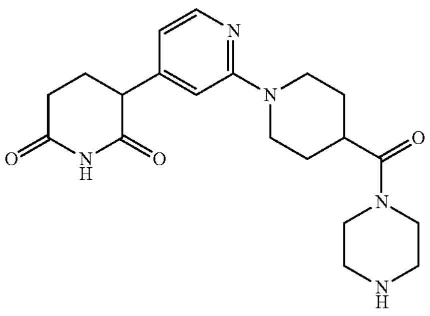 [SMILES: O=C1CCC(c2ccnc(N3CCC(C(=O)N4CCNCC4)CC3)c2)C(=O)N1]

Step-1: tert-butyl 1-[4-(2,6-dioxopiperidin-3-yl)pyridin-2-yl]piperidine-4-carboxylate

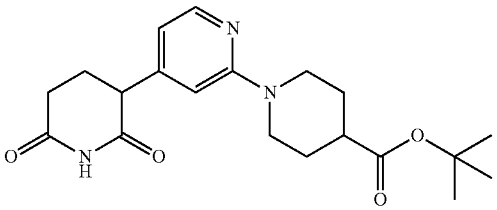 [SMILES: CC(C)(C)OC(=O)C1CCN(c2cc(C3CCC(=O)NC3=O)ccn2)CC1]

To a solution of 3-(2-fluoropyridin-4-yl)piperidine-2,6-dione (1.0 g, 4.8 mmol) in anhydrous DMSO (10 mL, 0.5 M) in a pressure vessel, was added 4-piperidinecarboxylic acid t-butyl ester HCl (2.13 g, 9.61 mmol) and DIPEA (0.84 mL, 4.8 mmol). The reaction mixture was stirred at 120° C. for 48 h, then was cooled to room temperature, quenched with water and extracted with DCM. The organic phase was washed with brine, dried over $Na_2SO_4$ and evaporated to dryness. The crude residue was purified by flash chromatography eluting with DCM:MeOH (0-10%) to provide 1.32 g (66% yield) of title compound as a yellow semi-solid. LCMS: ($C_{20}H_{27}N_3O_4$) desired mass=373.2; found: m/z=374.0 $[M+H]^+$.

Step 2: 1-[4-(2,6-dioxopiperidin-3-yl)pyridin-2-yl]piperidine-4-carboxylic acid

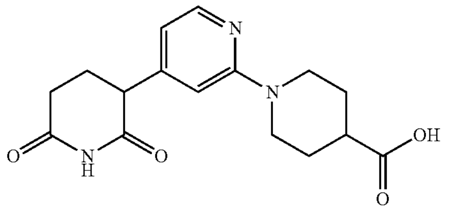 [SMILES: O=C1CCC(c2ccnc(N3CCC(C(=O)O)CC3)c2)C(=O)N1]

To a solution of tert-butyl 1-[4-(2,6-dioxopiperidin-3-yl)pyridin-2-yl]piperidine-4-carboxylate (1.32 g, 3.18 mmol) in anhydrous DCM (45.0 mL) was added a 4 M HCl solution in Dioxane (16.0 mL, 63.6 mmol). The reaction mixture was stirred at room temperature for 2 h, then the solvents were evaporated and the crude residue was triturated with $Et_2O$ to provide 1.32 g (100% yield) of the title compound as a pale orange solid. LCMS: ($C_{20}H_{27}N_5O_3$) desired mass=317.1; found: m/z=318.4 $[M+H]^+$.

Step 3: tert-butyl 4-{1-[4-(2,6-dioxopiperidin-3-yl)pyridin-2-yl]piperidine-4-carbonyl}piperazine-1-carboxylate

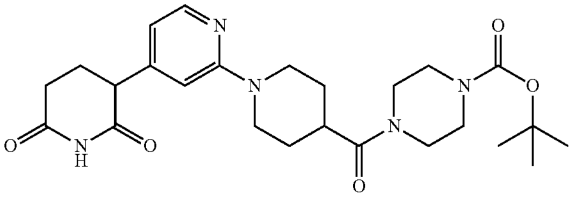 [SMILES: CC(C)(C)OC(=O)N1CCN(C(=O)C2CCN(c3cc(C4CCC(=O)NC4=O)ccn3)CC2)CC1]

To a solution of 1-[4-(2,6-dioxopiperidin-3-yl)pyridin-2-yl]piperidine-4-carboxylic acid (0.12 g, 0.25 mmol) in anhydrous DMF (2.5 mL) was added DIPEA (0.22 mL, 1.27 mmol) and BOP (0.135 g, 0.305 mmol). The reaction mixture was stirred for 1 h at room temperature, then t-Butyl piperazine-1-carboxylate (0.057 g, 0.254 mmol) was added and stirring was continued for 1.5 h. The solvents were evaporated to dryness, and the crude residue was diluted with DCM, washed with saturated aqueous $NaHCO_3$ solution, dried over $Na_2SO_4$, filtered, and evaporated to dryness. The crude residue was purified by flash chromatography eluting with DCM:MeOH (0-15%) to provide 0.12 g (98% yield) of the title compound as a pale yellow solid. LCMS: ($C_{25}H_{35}N_5O_5$) desired mass=485.3; found: m/z=486.5 $[M+H]^+$.

Step 4: 4-{1-[4-(2,6-dioxopiperidin-3-yl)pyridin-2-yl]piperidine-4-carbonyl}piperazine-1-carboxylic acid

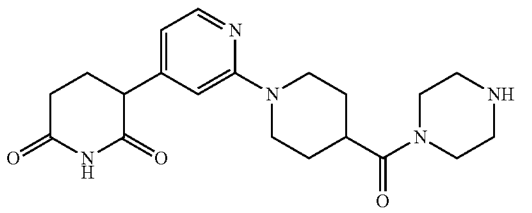 [SMILES: O=C1CCC(c2ccnc(N3CCC(C(=O)N4CCNCC4)CC3)c2)C(=O)N1]

To a solution of tert-butyl 4-{1-[4-(2,6-dioxopiperidin-3-yl)pyridin-2-yl]piperidine-4-carbonyl}piperazine-1-carboxylate (0.12 g, 0.25 mmol) in anhydrous DCM (2.5 mL) was added TFA (2.8 mL, 24.9 mmol). The reaction mixture was stirred at room temperature for 2 h, then the solvents were evaporated and the crude residue was triturated with $Et_2O$ to provide 180 mg (100% yield) of the title compound as an orange viscous solid. LCMS: ($C_{20}H_{27}N_5O_3$) desired mass=385.2; found: m/z=385.9 $[M+H]^+$.

Intermediate 88

1-[(1R,4R)-4-[5-(2,6-dioxopiperidin-3-yl)-2H-indazol-2-yl]cyclohexanecarbonyl]piperidine-4-carboxylic acid hydrochloride

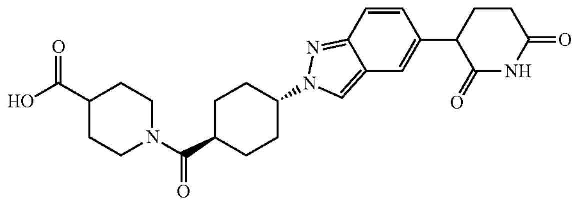 [SMILES: O=C1CCC(c2ccc3nn([C@H]4CC[C@H](C(=O)N5CCC(C(=O)O)CC5)CC4)cc3c2)C(=O)N1]

Step 1: methyl (1r,4r)-4-{[(5-bromo-2-nitrophenyl)methylidene]amino}cyclohexane-1-carboxylate

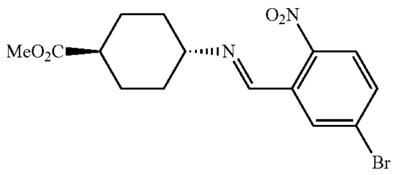 [SMILES: COC(=O)[C@H]1CC[C@H](/N=C/c2cc(Br)ccc2[N+](=O)[O-])CC1]

Triethylamine (7.272 mL, 52.17 mmol) was added dropwise to a suspension of methyl trans-4-aminocyclohexanecarboxylate hydrochloride (7.409 g, 38.258 mmol) and 5-bromo-2-nitrobenzaldehyde (8.0 g, 34.78 mmol) in acetonitrile (347.8 mL, 0.1 M) and the mixture was stirred for 4 hours at room temperature. The reaction mixture was concentrated under reduced pressure and mixed with water. The resulting precipitate was collected by filtration and dried in vacuo to provide 12.72 g (quantitative yield) of the title compound as a yellow solid. LCMS: $C_{15}H_{17}BrN_2O_4$, desired mass=369.2, found: m/z=371.6 $[M+H]^+$.

Step 2: methyl (1r,4r)-4-(5-bromo-2H-indazol-2-yl)cyclohexane-1-carboxylate

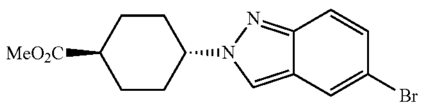 [SMILES: COC(=O)[C@H]1CC[C@H](n2cc3cc(Br)ccc3n2)CC1]

Methyl (1r,4r)-4-{[(5-bromo-2-nitrophenyl)methylidene]amino}cyclohexane-1-carboxylate (12.87 g, 34.86 mmol) was dissolved in isopropanol (345 mL, 0.1 M) and tri-n-butylphosphine (25.8 mL, 104.57 mmol) was added in one portion followed by stirring at 80° C. for 3 h. The mixture was cooled to room temperature, concentrated in vacuo, dissolved in DCM, and purified by silica gel chromatography (Hexane/ethyl acetate 0-35%) to provide 10.1 g (86% yield) of the title compound as a yellow solid. LCMS: $C_{15}H_{17}BrN_2O_2$, desired mass=337.2, found: m/z=337.0 $[M+H]^+$.

Step 3: methyl (1r,4r)-4-{5-[2,6-bis(benzyloxy)pyridin-3-yl]-2H-indazol-2-yl}cyclohexane-1-carboxylate

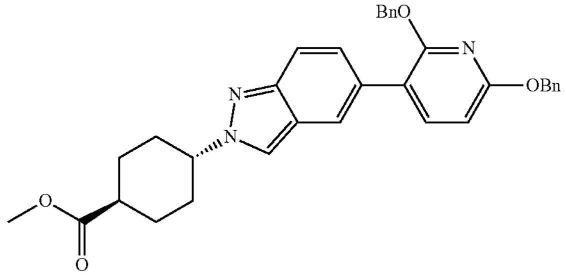 [SMILES: COC(=O)[C@H]1CC[C@H](n2cc3cc(-c4ccc(OCc5ccccc5)nc4OCc4ccccc4)ccc3n2)CC1]

A vial was charged with methyl (1r,4r)-4-(5-bromo-2H-indazol-2-yl)cyclohexane-1-carboxylate (1.0 g, 2.965 mmol), 2,6-bis(benzyloxy)-3-(4,4,5,5-tetramethyl-1,3,2-dioxaborolan-2-yl)pyridine (1.42 g, 3.41 mmol), and $K_2CO_3$ (1.23 g, 8.90 mmol). Then, a mixture 5:1 of 1,4-dioxane (29.65 mL, 0.1 M) and water (5.93 mL, 0.5 M) was added and Ar was bubbled through the system (sonication bath) for 10 min. After that, Pd(dppf)Cl2-DCM (0.242 g, 0.297 mmol) was added and the reaction mixture was stirred at 95° C. for 16 h. The reaction mixture was cooled to room temperature, diluted with water and extracted with DCM (2×5 mL). The organic layers were dried over sodium sulphate, filtered and evaporated to obtain the crude product. The crude product was purified using flash column chromatography (Hexane:EtOAc 100:0 to 40:60) to provide 1.38 g (85% yield) of the title compound as pale yellow solid. LCMS: $C_{34}H_{33}N_3O_4$, desired mass=547.7, found: m/z=548.4 $[M+H]^+$.

Step 4: methyl (1r,4r)-4-[5-(2,6-dioxopiperidin-3-yl)-2H-indazol-2-yl]cyclohexane-1-carboxylate

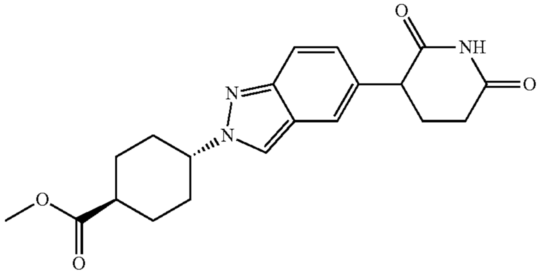 [SMILES: COC(=O)[C@H]1CC[C@H](n2cc3cc(C4CCC(=O)NC4=O)ccc3n2)CC1]

Methyl (1r,4r)-4-{5-[2,6-bis(benzyloxy)pyridin-3-yl]-2H-indazol-2-yl}cyclohexane-1-carboxylate (1.38 g, 2.52 mmol) was dissolved in anhydrous THF (251.98 mL, 0.01 M) and 10% Palladium on carbon 55-65% wet (0.145 g, 1.361 mmol) was added to the mixture. After that the system was evacuated and backfilled with $H_2$ (1 atm, balloon) four times. The reaction was stirred at 25° C. for 16 h, then was filtered over a pad of celite and washed with EtOAc (500 mL). The solvent was evaporated and the crude mixture was purified using flash column chromatography (DCM/EtOAc 0-100%) to provide 0.545 g (59% yield) of the title compound as a tan solid. LCMS: $C_{20}H_{23}N_3O_4$, desired mass=369.4, found: m/z=370.2 $[M+H]^+$.

Step 5: (1r,4r)-4-[5-(2,6-dioxopiperidin-3-yl)-2H-indazol-2-yl]cyclohexane-1-carboxylic acid

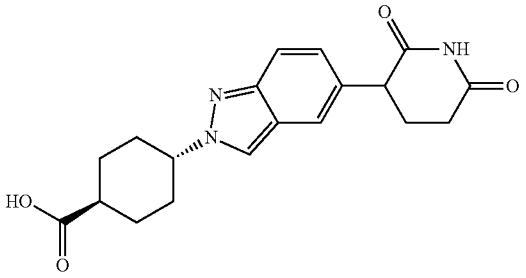 [SMILES: O=C1CCC(c2ccc3nn([C@H]4CC[C@H](C(=O)O)CC4)cc3c2)C(=O)N1]

Methyl (1r,4r)-4-[5-(2,6-dioxopiperidin-3-yl)-2H-indazol-2-yl]cyclohexane-1-carboxylate (0.436 g, 1.18 mmol) was dissolved in 30% HCl aqueous solution (1.87 mL, 17.70 mmol) and stirred at 25° C. for 16 h. The solvent was then evaporated and the crude mixture was triturated with diethyl ether (3×20 mL) to provide 0.344 g (82% yield) of the title compound as an orange solid. LCMS: $C_{19}H_{21}N_3O_4$, desired mass=355.4, found: m/z=356.1 $[M+H]^+$.

Step 6: tert-butyl 1-{1-[5-(2,6-dioxopiperidin-3-yl)pyridin-2-yl]piperidine-4-carbonyl}-4-methylpiperidine-4-carboxylate

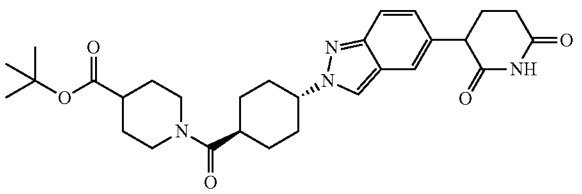 [SMILES: CC(C)(C)OC(=O)C1CCN(C(=O)[C@H]2CC[C@H](n3cc4cc(C5CCC(=O)NC5=O)ccc4n3)CC2)CC1]

(1r,4r)-4-[5-(2,6-dioxopiperidin-3-yl)-2H-indazol-2-yl]cyclohexane-1-carboxylic acid (0.344 g, 0.968 mmol), N,N-diisopropylethylamine (0.674 mL, 3.872 mmol) and benzotriazol-1-yloxy)tris(dimethylamino)phosphonium hexafluorophosphate (0.514 g, 1.162 mmol) were dissolved in anhydrous DMF (19.36 mL) under argon. The reaction mixture was stirred for 20 min, then 4-piperidinecarboxylic acid t-butyl ester hydrochloride (0.258 g, 1.162 mmol) was added and the reaction mixture was stirred for 3 h at 25° C. The reaction mixture was poured into water (20 mL) and extracted with EtOAc (3×20 mL). The combined organic layers were washed with brine (3×20 mL), dried over $Na_2SO_4$, filtered and evaporated. The crude mixture was purified using flash column chromatography (DCM/EtOAc 0-100%) to provide 0.384 g (76% yield) of the title compound as an off-white solid. LCMS: $C_{29}H_{38}N_4O_5$, desired mass=522.7, found: m/z=523.4 $[M+H]^+$.

Step 7: 1-[(1r,4r)-4-[5-(2,6-dioxopiperidin-3-yl)-2H-indazol-2-yl]cyclohexanecarbonyl]piperidine-4-carboxylic acid hydrochloride

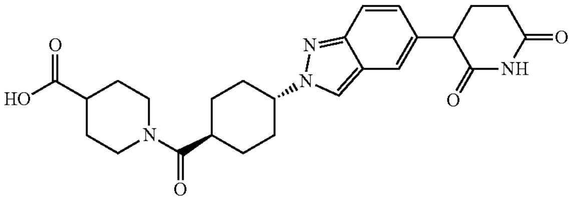 [SMILES: O=C1CCC(c2ccc3nn([C@H]4CC[C@H](C(=O)N5CCC(C(=O)O)CC5)CC4)cc3c2)C(=O)N1]

Tert-butyl 1-{1-[5-(2,6-dioxopiperidin-3-yl)pyridin-2-yl]piperidine-4-carbonyl}-4-methylpiperidine-4-carboxylate (0.38 g, 0.727 mmol) was placed in a 25 mL flask, dissolved in dichloromethane (7.27 mL, 0.1 M) and stirred at 0° C. Then 4 M HCl in dioxane (4.362 mL, 17.45 mmol) was added dropwise and the reaction was allowed to reach room temperature and stirred at this temperature overnight. The resulting solid residue was filtered off and triturated with $Et_2O$ (5×5 mL), then dried under vacuum to provide 0.364 g (99% yield) of the title compound as white solid. LCMS: $C_{25}H_{30}N_4O_5$, desired mass=466.5, found: m/z=$[M+H]^+$.

Intermediate 89

3-[6-(piperazin-1-yl)pyridin-3-yl]piperidine-2,6-dione; bis trifluoroacetic acid

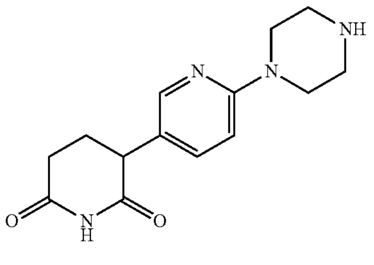 [SMILES: O=C1CCC(c2ccc(N3CCNCC3)nc2)C(=O)N1]

Step 1: tert-butyl 4-[5-(2,6-dioxopiperidin-3-yl)pyridin-2-yl]piperazine-1-carboxylate

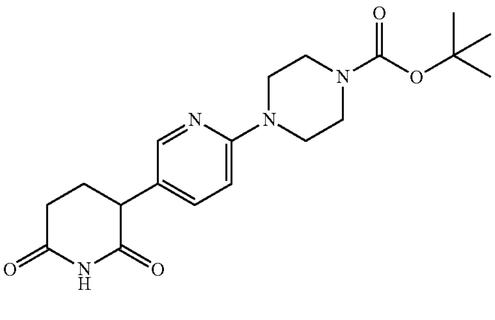 [SMILES: CC(C)(C)OC(=O)N1CCN(c2ccc(C3CCC(=O)NC3=O)cn2)CC1]

A solution of 3-(6-fluoropyridin-3-yl)piperidine-2,6-dione (1.2 g, 5.5 mmol), t-butyl piperazine-1-carboxylate (5.1 g, 27.4 mmol) and (6.93 mL, 54.75 mmol) in anhydrous dimethyl sulfoxide (27.38 mL, 0.2 M) was heated with vigorous stirring at 120° C. overnight. The resulting mixture was cooled to room temperature, poured into water and extracted with DCM twice. The organic phase was dried over anhydrous magnesium sulfate, evaporated to dryness under vacuum, then the crude residue was purified with flash chromatography (mobile phase: DCM-MeOH, 0 to 10%) to provide 1.3 g (62% yield) of the title compound as an off-white solid. LCMS: $C_{19}H_{26}N_4O_4$, desired mass=374.4, found: m/z=375.0 $[M+H]^+$.

Step 2: 3-[6-(piperazin-1-yl)pyridin-3-yl]piperidine-2,6-dione; bis(trifluoroacetic acid)

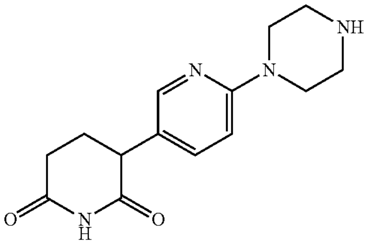 [SMILES: O=C1CCC(c2ccc(N3CCNCC3)nc2)C(=O)N1]

A solution of tert-butyl 4-[5-(2,6-dioxopiperidin-3-yl)pyridin-2-yl]piperazine-1-carboxylate (1.3 g, 3.37 mmol) and trifluoroacetic acid (11.5 g, 101 mmol) in anhydrous dichloromethane (11.23 mL, 0.3 M) was stirred at room temperature for 3 h. After evaporating to dryness under vacuum, the residue was triturated with dry diethyl ether to provide 1.7 g (90% yield) of the title compound as a bis TFA salt. LCMS: $C_{14}H_{18}N_4O_2$, desired mass=274.3, found: m/z=274.8 $[M+H]^+$.

Intermediate 90

3-{6-[4-(piperazine-1-carbonyl)piperidin-1-yl]pyridin-3-yl}piperidine-2,6-dione

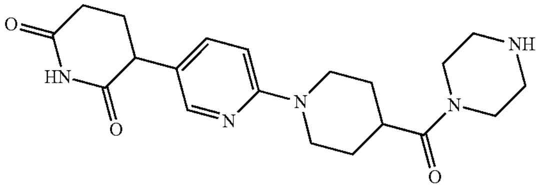 [SMILES: O=C1CCC(c2ccc(N3CCC(C(=O)N4CCNCC4)CC3)nc2)C(=O)N1]

Step 1: tert-butyl 4-{1-[5-(2,6-dioxopiperidin-3-yl)pyridin-2-yl]piperidine-4-carbonyl}piperazine-1-carboxylate

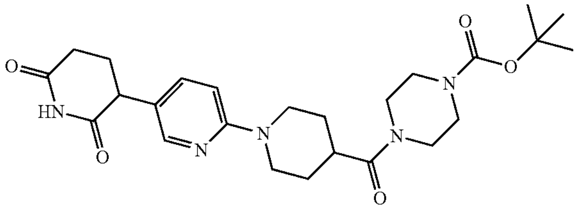 [SMILES: CC(C)(C)OC(=O)N1CCN(C(=O)C2CCN(c3ccc(C4CCC(=O)NC4=O)cn3)CC2)CC1]

To a solution of 1-[5-(2,6-dioxopiperidin-3-yl)pyridin-2-yl]piperidine-4-carboxylic acid (0.1 g, 0.25 mmol) in anhydrous DMF (2.5 mL, 0.1 M) was added DIPEA (0.22 mL, 1.27 mmol) and BOP (0.135 g, 0.31 mmol). The mixture was stirred for 1 h at rt. Tert-butyl piperazine-1-carboxylate (0.057 g, 0.25 mmol) was added and the reaction was stirred at rt for 1.5 h. The volatiles were evaporated in vacuo, the residue was dissolved in DCM, quenched with saturated aqueous $NaHCO_3$ solution and stirred vigorously for 30 min. The organic phase was separated, dried over $Na_2SO_4$, and concentrated to dryness. The crude residue was purified by column chromatography eluting with DCM/MeOH (0-15%) to provide 0.12 g (97% yield) of the title compound as an off-white solid. LCMS: $C_{25}H_{35}N_5O_5$, desired mass=485.58, found m/z=486.20 $[M+H]^+$.

Step 2: 3-{6-[4-(piperazine-1-carbonyl)piperidin-1-yl]pyridin-3-yl}piperidine-2,6-dione

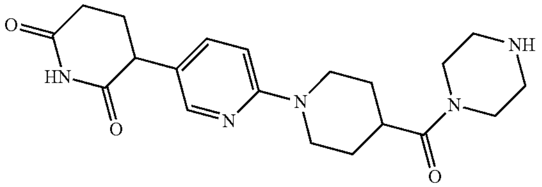 [SMILES: O=C1CCC(c2ccc(N3CCC(C(=O)N4CCNCC4)CC3)nc2)C(=O)N1]

To a solution of tert-butyl 4-{1-[5-(2,6-dioxopiperidin-3-yl)pyridin-2-yl]piperidine-4-carbonyl}piperazine-1-carboxylate (0.12 g, 0.247 mmol) in anhydrous DCM (2.5 mL, 0.1 M) was added TFA (2.8 mL, 24.71 mmol). The reaction mixture was stirred at rt for 2 h. The solvents were evaporated under vacuum and the crude residue was triturated with $Et_2O$ to provide 151 mg (100% yield) of the title compound as an orange viscous solid. LCMS: $C_{20}H_{27}N_5O_3$, desired mass=385.47, found m/z=386.00 $[M+H]^+$.

Intermediate 91

1-{6-[5-(2,6-dioxopiperidin-3-yl)pyridin-2-yl]-2,6-diazaspiro[3.3]heptane-2-carbonyl}-4-methylpiperidine-4-carboxylic acid

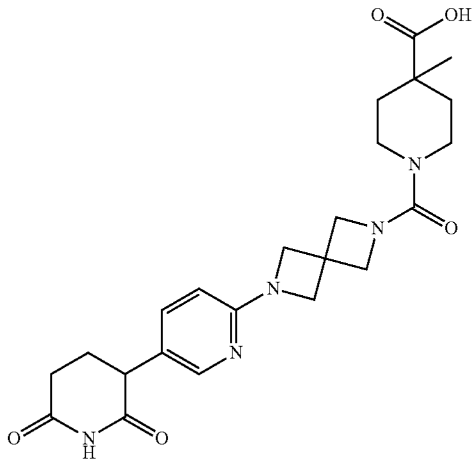 [SMILES: CC1(C(=O)O)CCN(C(=O)N2CC3(C2)CN(c2ccc(C4CCC(=O)NC4=O)cn2)C3)CC1]

Step 1: tert-butyl 6-[5-(2,6-dioxopiperidin-3-yl)pyridin-2-yl]-2,6-diazaspiro[3.3]heptane-2-carboxylate

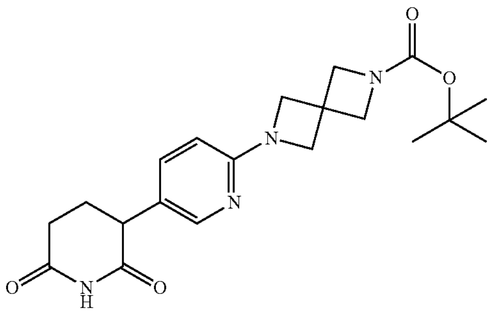 [SMILES: CC(C)(C)OC(=O)N1CC2(C1)CN(c1ccc(C3CCC(=O)NC3=O)cn1)C2]

A solution of 3-(6-fluoropyridin-3-yl)piperidine-2,6-dione (0.8 g, 3.65 mmol), tert-butyl 2,6-diazaspiro[3.3]heptane-2-carboxylate (4.09 g, 8.396 mmol) and triethylamine (4.62 mL, 36.51 mmol) in anhydrous DMSO (18.25 mL, 0.2 M) was stirred at 120° C. for 16 h. The reaction was cooled to room temperature, quenched with water, treated with a saturated aqueous solution of $NaHCO_3$, and washed with DCM. The organic layer was dried over $Na_2SO_4$, filtrated and concentrated to dryness. The crude residue was purified by flash column chromatography eluting with DCM/MeOH (0-10% of MeOH) to provide 0.53 g (34% yield) of the title compound. LCMS: $C_{20}H_{26}N_4O_4$, desired mass=386.45, found m/z=387.05 $[M+H]^+$.

Step 2:3-(6-{2,6-diazaspiro[3.3]heptan-2-yl}pyridin-3-yl)piperidine-2,6-dione

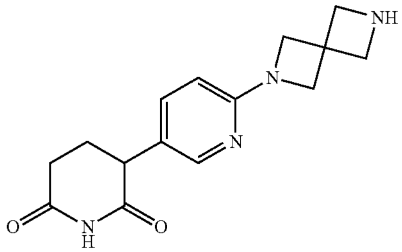 [SMILES: O=C1CCC(c2ccc(N3CC4(CNC4)C3)nc2)C(=O)N1]

To a solution of tert-butyl 6-[5-(2,6-dioxopiperidin-3-yl)pyridin-2-yl]-2,6-diazaspiro[3.3]heptane-2-carboxylate (0.53 g, 1.23 mmol) in anhydrous DCM (6.2 mL, 0.2 M) was added trifluoroacetic acid (4.222 g, 37.03 mmol). The reaction mixture was stirred at rt for 3 h. The volatiles were evaporated in vacuo, then the crude residue was triturated with $Et_2O$ to obtain 0.52 g (74% yield) of title compound. LCMS: $C_{15}H_{18}N_4O_2$, desired mass=286.34, found m/z=286.85 $[M]^+$.

Step 3: tert-butyl 1-(chlorocarbonyl)-4-methylpiperidine-4-carboxylate

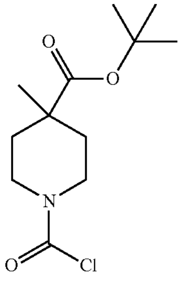 [SMILES: CC(C)(C)OC(=O)C1(C)CCN(C(=O)Cl)CC1]

To a solution of triphosgene (0.101 g, 0.34 mmol) in DCM (2.83 mL) at 0° C. was slowly added a solution of tert-butyl 4-methylpiperidine-4-carboxylate hydrochloride (0.2 g, 0.85 mmol) and pyridine (0.137 mL, 1.7 mmol) in DCM (1.0 mL). The mixture was warmed to room temperature over 30 min followed by addition of aqueous HCl solution (0.1 N, 200 mL). The organic layer was separated and dried over anhydrous $MgSO_4$. The mixture was filtered and the filtrate was concentrated to dryness to provide 0.21 g (90% yield) of the title compound. $^1H$ NMR (300 MHz, Chloroform-d), δ: 4.09 (d, J=13.7 Hz, 2H), 3.29 (t, J=11.6 Hz, 1H), 3.11 (t, J=13.8 Hz, 1H), 2.17 (d, J=13.7 Hz, 2H), 1.48 (s, 9H), 1.45-1.34 (m, 2H), 1.22 (s, 3H).

Step 4: tert-butyl 1-{6-[5-(2,6-dioxopiperidin-3-yl)pyridin-2-yl]-2,6-diazaspiro[3.3]heptane-2-carbonyl}-4-methylpiperidine-4-carboxylate

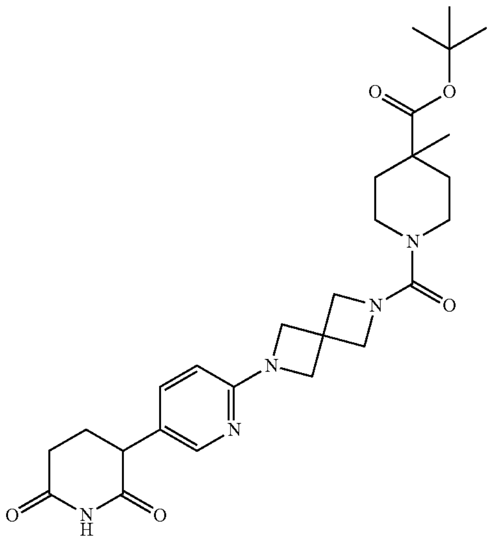 [SMILES: CC(C)(C)OC(=O)C1(C)CCN(C(=O)N2CC3(C2)CN(c2ccc(C4CCC(=O)NC4=O)cn2)C3)CC1]

A solution of 3-(6-{2,6-diazaspiro[3.3]heptan-2-yl}pyridin-3-yl)piperidine-2,6-dione (0.48 g, 0.84 mmol), tert-butyl 1-(chlorocarbonyl)-4-methylpiperidine-4-carboxylate (0.185 g, 0.67 mmol) and triethylamine (0.607 mL, 4.2 mmol) in DCM (4.2 mL, 0.2 M) was stirred vigorously at 45° C. for 2 h. Then, the reaction mixture was evaporated to dryness under vacuum, and the crude residue was purified by flash column chromatography (DCM/IPA, 8:2) to give 0.15 g (34% yield) of the title compound. LCMS: $C_{27}H_{37}N_5O_5$, desired mass=511.62, found m/z=512.25 $[M+H]^+$.

Step 5: 1-{6-[5-(2,6-dioxopiperidin-3-yl)pyridin-2-yl]-2,6-diazaspiro[3.3]heptane-2-carbonyl}-4-methylpiperidine-4-carboxylic acid

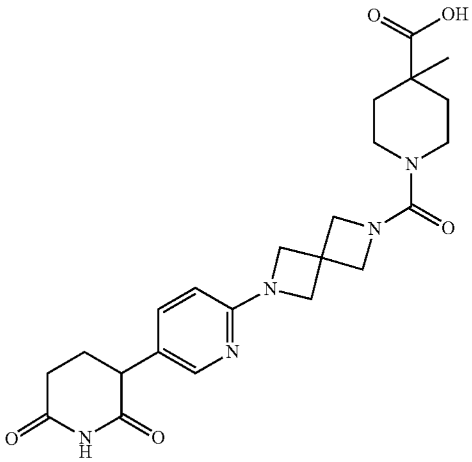 [SMILES: CC1(C(=O)O)CCN(C(=O)N2CC3(C2)CN(c2ccc(C4CCC(=O)NC4=O)cn2)C3)CC1]

To a solution of tert-butyl 1-{6-[5-(2,6-dioxopiperidin-3-yl)pyridin-2-yl]-2,6-diazaspiro[3.3]heptane-2-carbonyl}-4-methylpiperidine-4-carboxylate (0.15 g, 0.28 mmol) in anhydrous DCM (0.95 mL) was added trifluoroacetic acid (0.973 g, 8.53 mmol). The reaction mixture was stirred at room temperature for 3 h. The volatiles were evaporated in vacuo, and the crude residue was triturated with $Et_2O$ to provide 0.11 g (79% yield) of the title compound. LCMS: $C_{23}H_{29}N_5O_5$, desired mass=455.51, found m/z=456.35 $[M+H]^+$.

Intermediate 92

1-[5-(2,6-dioxopiperidin-3-yl)-4-methylpyridin-2-yl]piperidine-4-carboxylic acid hydrochloride

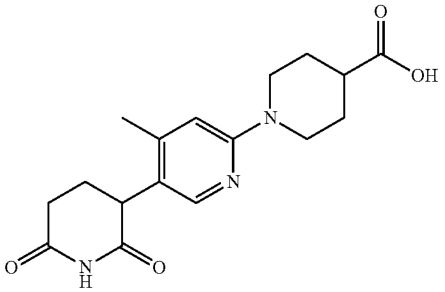 [SMILES: Cc1cc(N2CCC(C(=O)O)CC2)ncc1C1CCC(=O)NC1=O]

Step 1: tert-butyl 1-(5-bromo-4-methylpyridin-2-yl)piperidine-4-carboxylate

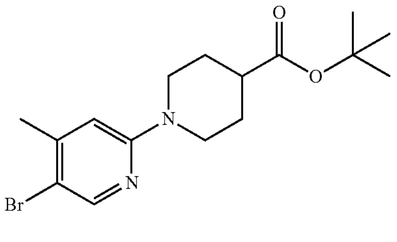 [SMILES: Cc1cc(N2CCC(C(=O)OC(C)(C)C)CC2)ncc1Br]

To a solution of tert-butyl piperidine-4-carboxylate hydrochloride (3.60 g, 16.24 mmol) in anhydrous DMSO (32.5 mL) was added 5-bromo-2-fluoro-4-methylpyridine (6.170 g, 32.47 mmol) and $Cs_2CO_3$ (21.160 g, 64.94 mmol) at 25° C. The reaction mixture was stirred for 24 h at 130° C., then cooled to room temperature, poured into 350 mL of brine and extracted with EtOAc (3×300 mL). The combined organic extracts were dried with $Na_2SO_4$ and evaporated under reduced pressure. The residue was purified by silica gel chromatography using a mobile phase of hexane and EtOAc (gradient 100:0 to 70:30) to provide 4.478 g (78% yield) of the title compound as a white solid. LCMS: $C_{16}H_{23}BrN_2O_2$, desired mass=355.3, found: m/z=357.2 $[M+H^+]$.

Step 2: tert-butyl 1-[2',6'-bis(benzyloxy)-4-methyl-[3,3'-bipyridin]-6-yl]piperidine-4-carboxylate

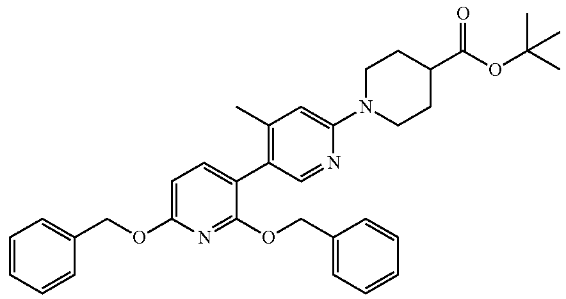 [SMILES: Cc1cc(N2CCC(C(=O)OC(C)(C)C)CC2)ncc1-c1ccc(OCc2ccccc2)nc1OCc1ccccc1]

To a solution of tert-butyl 1-(5-bromo-4-methylpyridin-2-yl)piperidine-4-carboxylate (4.00 g, 11.26 mmol) and 2,6-bis(benzyloxy)-3-(4,4,5,5-tetramethyl-1,3,2-dioxaborolan-2-yl)pyridine (4.699 g, 11.26 mmol) in degassed anhydrous DMF (22.5 mL) was added $K_2CO_3$ (4.669 g, 33.78 mmol) and [1,1'-bis(diphenylphosphino)ferrocene]dichloropalladium(II) (0.494 g, 0.68 mmol) at 25° C. The reaction mixture was stirred for 16 h at 85° C., then the mixture cooled to room temperature, poured into 250 mL of water, and extracted with EtOAc (4×120 mL). The combined organic layers were washed with water (2×120 mL) and brine (120 mL), dried with $Na_2SO_4$ and concentrated under reduced pressure. The residue was purified by silica gel chromatography using a mobile phase of hexane and EtOAc (gradient 100:0 to 70:30%) to provide 5.130 g (81% yield) of the title compound as a yellow solid. LCMS: $C_{35}H_{39}N_3O_4$, desired mass=565.7, found: m/z=567.1 [M+H$^+$].

Step 3: tert-butyl 1-[5-(2,6-dioxopiperidin-3-yl)-4-methylpyridin-2-yl]piperidine-4-carboxylate

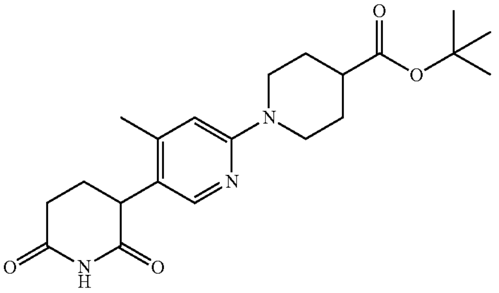 [SMILES: Cc1cc(N2CCC(C(=O)OC(C)(C)C)CC2)ncc1C1CCC(=O)NC1=O]

To a solution of tert-butyl 1-[2',6'-bis(benzyloxy)-4-methyl-[3,3'-bipyridin]-6-yl]piperidine-4-carboxylate (3.00 g, 5.30 mmol) in anhydrous THF (220.0 mL) was added 10% wt Pd/C (900 mg) at 25° C. The reaction mixture was stirred for 16 h at 25° C. under an atmosphere of $H_2$ gas (balloon), followed by the addition of IPA (220.0 mL, 0.02 M) and a second portion of 10% wt Pd/C (450 mg) at 25° C. The reaction mixture was stirred for another 16 h at 25° C., followed by the addition of a third portion of 10% wt Pd/C (450 mg) at 25° C. The reaction mixture was stirred for 16 h at 25° C., followed by the addition of a fourth portion of 10% wt Pd/C (600 mg) at 25° C. The reaction mixture was stirred for 16 h at 25° C. and then filtered through a Celite pad and evaporated to dryness. The residue was purified by silica gel chromatography using a mobile phase of DCM and MeOH (gradient 100:0 to 90:10%) and DCM:EtOAc:IPA (100:0:0 to 70:20:10%) to provide 0.909 g (44% yield) of the title compound as a light blue solid. LCMS: $C_{21}H_{29}N_3O_4$, desired mass=387.5, found: m/z=388.7 [M+H$^+$].

Step 4: 1-[5-(2,6-dioxopiperidin-3-yl)-4-methylpyridin-2-yl]piperidine-4-carboxylic acid hydrochloride

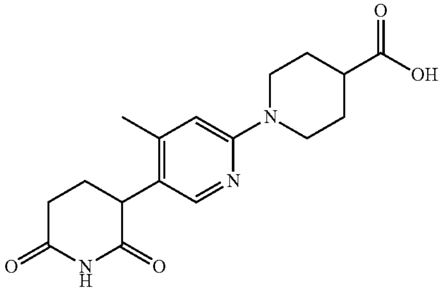 [SMILES: Cc1cc(N2CCC(C(=O)O)CC2)ncc1C1CCC(=O)NC1=O]

To a solution of tert-butyl 1-[5-(2,6-dioxopiperidin-3-yl)-4-methylpyridin-2-yl]piperidine-4-carboxylate (0.796 g, 2.05 mmol) in anhydrous DCM (31.1 mL) was added 4M HCl solution in DCM (12.33 mL, 49.30 mmol) at 25° C. The reaction mixture was stirred for 16 h at 25° C., and then the solvents were evaporated to dryness under reduced pressure. The crude compound was triturated with $Et_2O$ (3×20 mL) and dried under reduced pressure to provide 0.622 g (82% yield) of the title compound as a pale brown solid. LCMS: $C_{17}H_{21}N_3O_4$, desired mass=331.4, found: m/z=332.4 [M+H$^+$].

Intermediate 93

(1R,4R)-4-{[5-(2,6-dioxopiperidin-3-yl)pyrimidin-2-yl]oxy}cyclohexane-1-carboxylic acid hydrochloride

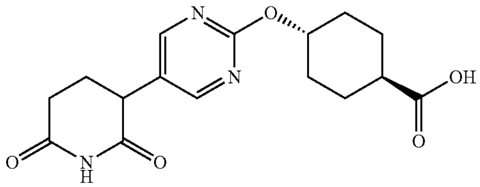 [SMILES: O=C1CCC(c2cnc(O[C@H]3CC[C@H](C(=O)O)CC3)nc2)C(=O)N1]

Step 1: tert-butyl (1r,4r)-4-hydroxycyclohexane-1-carboxylate

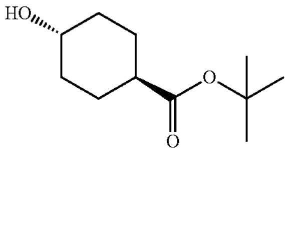

To a suspension of trans-4-hydroxycyclohexanecarboxylic acid (5.0 g, 34.67 mmol) in anhydrous toluene (160 mL) stirred at 90° C. was added N,N-dimethylformamide di-tert-butyl acetal (16.6 mL, 69.35 mmol) in one portion. The resulting solution was stirred at 90° C. for 1 h, then another portion of N,N-dimethylformamide di-tert-butyl acetal (16.63 mL, 69.35 mmol) was added and the reaction mixture was stirred for 30 min at 90° C. and then at room temperature overnight. An additional portion of N,N-dimethylformamide di-tert-butyl acetal (10.0 mL, 34.67 mmol) was added dropwise over 10 minutes, the reaction mixture was stirred at 70° C. for 1.5 h and then cooled to room temperature. The reaction mixture was washed with 2M aqueous NaOH solution (50 mL), brine (100 mL) and the organic phase was separated and evaporated to provide 5.5 g (79% yield) of the title compound as an orange waxy-solid. $^1H$ NMR (300 MHz, DMSO-$d_6$) δ 4.55 (d, J=4.3 Hz, 1H), 3.32-3.26 (m, 1H), 2.06 (tt, J=11.7, 3.3 Hz, 1H), 1.87-1.75 (m, 4H), 1.38 (s, 9H), 1.33-1.03 (m, 4H).

Step 2: tert-butyl (1r,4r)-4-[(5-bromopyrimidin-2-yl)oxy]cyclohexane-1-carboxylate

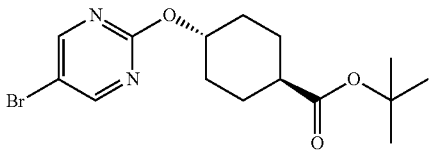 [SMILES: CC(C)(C)OC(=O)[C@H]1CC[C@H](Oc2ncc(Br)cn2)CC1]

5-Bromo-2-chloropyrimidine (5.31 g, 27.46 mmol) and tert-butyl (1r,4r)-4-hydroxycyclohexane-1-carboxylate (5.5 g, 27.46 mmol) were dissolved in a pressure vessel in anhydrous DMF (54.0 mL). $Cs_2CO_3$ (17.9 g, 54.92 mmol) was added and the reaction mixture was stirred at 60° C. overnight. The inorganic solids were filtered off and the filtrate was evaporated to dryness. The crude residue was purified by flash chromatography eluting with Hexane-EtOAc (0-30%) to provide 2.47 g (25% yield) of the title compound as a white solid. LCMS: $C_{15}H_{21}BrN_2O_3$, desired mass=356.1, found: m/z=359.1 [M+H$^+$].

Step 3: tert-butyl (1r,4r)-4-({5-[2,6-bis(benzyloxy)pyridin-3-yl]pyrimidin-2-yl}oxy)cyclohexane-1-carboxylate

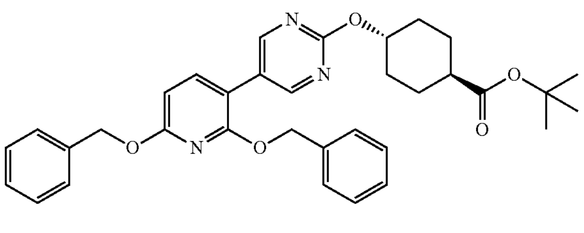 [SMILES: CC(C)(C)OC(=O)[C@H]1CC[C@H](Oc2ncc(-c3ccc(OCc4ccccc4)nc3OCc3ccccc3)cn2)CC1]

2,6-bis(benzyloxy)-3-(4,4,5,5-tetramethyl-1,3,2-dioxaborolan-2-yl)pyridine (2.89 g, 6.91 mmol) and tert-butyl (1r,4r)-4-[(5-bromopyrimidin-2-yl)oxy]cyclohexane-1-carboxylate (2.47 g, 6.91 mmol) were dissolved in anhydrous dimethylformamide (19.8 mL). The reaction mixture was degassed by bubbling with argon, then 1,1'-Bis(diphenylphosphino)ferrocene dichloropalladium (II) (0.25 g, 0.35 mmol) and $K_2CO_3$ (2.87 g, 20.74 mmol) were added. The mixture was placed in oil bath heated to 85° C. and stirred overnight. The mixture was cooled to room temperature, evaporated to dryness, and the crude residue was purified by FC eluting with Hexane:EtOAc (0-30%) to provide 2.2 g (56% yield) of the title compound as a white solid. LCMS: $C_{34}H_{37}N_3O_5$, desired mass=567.3, found: m/z=568.5 [M+H$^+$].

Step 4: tert-butyl (1r,4r)-4-{[5-(2,6-dioxopiperidin-3-yl)pyrimidin-2-yl]oxy}cyclohexane-1-carboxylate

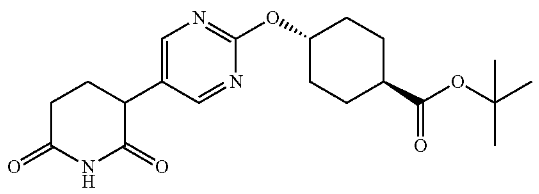 [SMILES: CC(C)(C)OC(=O)[C@H]1CC[C@H](Oc2ncc(C3CCC(=O)NC3=O)cn2)CC1]

Tert-butyl (1r,4r)-4-({5-[2,6-bis(benzyloxy)pyridin-3-yl]pyrimidin-2-yl}oxy)cyclohexane-1-carboxylate (2.2 g, 3.88 mmol) was dissolved in mixture of tetrahydrofuran (97 mL) and isopropyl alcohol (97 mL), then degassed with Argon, charged with 10% Palladium on carbon (0.66 g, 6.18 mmol) and stirred under an atmosphere of $H_2$ (balloon) at room temperature overnight. The mixture was filtered, the filtrate was concentrated under vacuum, and the crude residue was purified by flash chromatography eluting with DCM:MeOH (0-7%) to provide 0.71 g (47% yield) of the title compound as a white solid. LCMS: $C_{20}H_{27}N_3O_5$, desired mass=390.0, found: m/z=389.2 [M−H$^+$].

Step 5: (1r,4r)-4-{[5-(2,6-dioxopiperidin-3-yl)pyrimidin-2-yl]oxy}cyclohexane-1-carboxylic acid hydrochloride

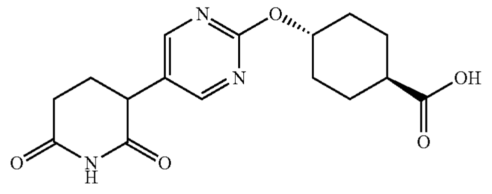 [SMILES: O=C1CCC(c2cnc(O[C@H]3CC[C@H](C(=O)O)CC3)nc2)C(=O)N1]

Tert-butyl (1r,4r)-4-{[5-(2,6-dioxopiperidin-3-yl)pyrimidin-2-yl]oxy}cyclohexane-1-carboxylate (0.71 g, 0.18 mmol) was dissolved in acetic acid (26 mL) followed by addition of 4M HCl solution in dioxane (9.11 mL, 36.46 mmol). The reaction mixture was stirred at room temperature for 4 h. The solvents were evaporated to dryness and the crude solid was triturated with $Et_2O$ to provide 650 mg (96% yield) of the title compound as a white solid. LCMS: $C_{20}H_{27}N_3O_5$, desired mass=333.3, found: m/z=334.3, [M+H$^+$].

Intermediate 94

1-{1-[6-(2,6-dioxopiperidin-3-yl)pyridazin-3-yl]piperidine-4-carbonyl}-4-methylpiperidine-4-carboxylic acid hydrochloride

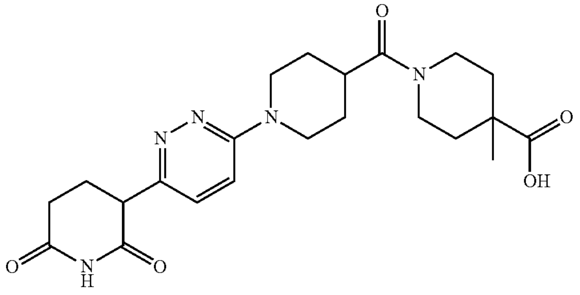 [SMILES: CC1(C(=O)O)CCN(C(=O)C2CCN(c3ccc(C4CCC(=O)NC4=O)nn3)CC2)CC1]

Step 1: tert-butyl 1-(6-chloropyridazin-3-yl)piperidine-4-carboxylate

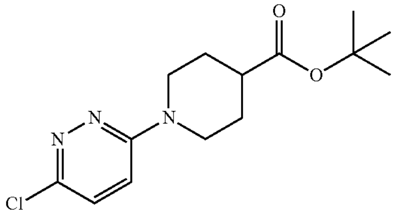 [SMILES: CC(C)(C)OC(=O)C1CCN(c2ccc(Cl)nn2)CC1]

Tert-butyl piperidine-4-carboxylate hydrochloride (8.93 g, 40.27 mmol), 3,6-dichloropyridazine (6.0 g, 40.27 mmol) and potassium carbonate (8.34 g, 60.42 mmol) were dissolved in ACN (60.0 mL) and stirred at 85° C. overnight. The solvent was evaporated under vacuum to dryness and the crude mixture was purified by FC eluting with Hexane: EtOAC (0-30%) to provide 8.93 g (74% yield) of the title compound. LCMS: $C_{14}H_{20}ClN_3O_2$, desired mass=297.1, found: m/z=298.7 $[M+H]^+$.

Step 2: tert-butyl 1-{6-[2,6-bis(benzyloxy)pyridin-3-yl]pyridazin-3-yl}piperidine-4-carboxylate

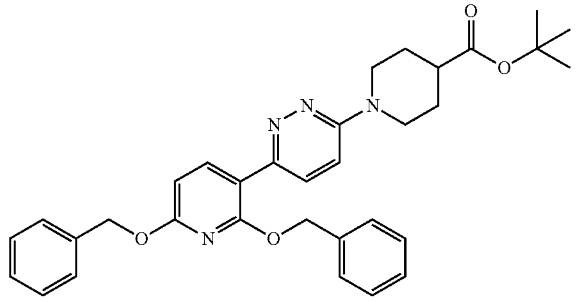 [SMILES: CC(C)(C)OC(=O)C1CCN(c2ccc(-c3ccc(OCc4ccccc4)nc3OCc3ccccc3)nn2)CC1]

To a solution of tert-butyl 1-(6-chloropyridazin-3-yl)piperidine-4-carboxylate (2.0 g, 6.7 mmol) in anhydrous DME (67 mL) in a pressure vessel was added 2,6-bis(benzyloxy)-3-(4,4,5,5-tetramethyl-1,3,2-dioxaborolan-2-yl)pyridine (4.2 g, 10.08 mmol) and a 2M solution of potassium phosphate (2.85 g, 13.43 mmol) in water (6.7 mL). The mixture was degassed by bubbling argon and XPhos Pd G3 (0.57 g, 0.67 mmol) was added. Then reaction mixture was stirred at 100° C. for 16 h, then cooled to room temperature, with water (15 mL), and extracted with EtOAc (3×10 mL). The combined organic phases were washed with brine (10 mL), dried over $Na_2SO_4$ and evaporated to dryness. The crude residue was purified by FC eluting with DCM:EtOAc (0-70%) to provide 3.05 g (82% yield) of title compound as a white solid. LCMS: $C_{33}H_{36}N_4O_4$, desired mass=552.3, found: m/z=533.7 $[M+H]^+$.

Step 3: tert-butyl 1-[6-(2,6-dioxopiperidin-3-yl)pyridazin-3-yl]piperidine-4-carboxylate

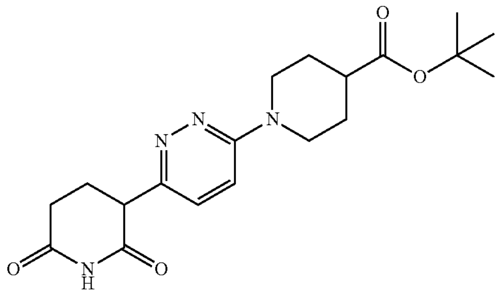 [SMILES: CC(C)(C)OC(=O)C1CCN(c2ccc(C3CCC(=O)NC3=O)nn2)CC1]

Tert-butyl 1-{6-[2,6-bis(benzyloxy)pyridin-3-yl]pyridazin-3-yl}piperidine-4-carboxylate (3.05 g, 1.6 mmol) was dissolved in Tetrahydrofuran (230.7 mL), degassed with Argon, charged with 10% Palladium on carbon (0.94 g, 8.8 mmol) and stirred under an atmosphere of $H_2$ (balloon) at room temperature for 16 hours. The mixture was filtered and the filtrate was concentrated to dryness under vacuum. The crude residue was purified by FC eluting with DCM:EtOAc (0-70%) to provide 0.81 g (39%) of the title compound as a white solid. LCMS: $C_{19}H_{26}N_4O_4$, desired mass=374.2, found: m/z=375.6 $[M+H]^+$.

Step 4: 1-[6-(2,6-dioxopiperidin-3-yl)pyridazin-3-yl]piperidine-4-carboxylic acid hydrochloride

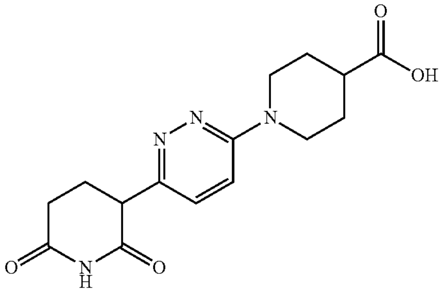 [SMILES: O=C1CCC(c2ccc(N3CCC(C(=O)O)CC3)nn2)C(=O)N1]

To a solution of tert-butyl 1-[6-(2,6-dioxopiperidin-3-yl)pyridazin-3-yl]piperidine-4-carboxylate (0.81 g, 0.61 mmol) in anhydrous DCM (33.0 mL) was added 4 M HCl in Dioxane solution (13.0 mL, 52.0 mmol) and the reaction mixture was stirred at room temperature for 16 h. The reaction mixture was evaporated to dryness under vacuum and the crude residue was triturated with $Et_2O$ to provide 0.74 mg (96% yield) of the title compound as a white solid. LCMS: $C_{15}H_{18}N_4O_4$, desired mass=318.3, found: m/z=319.3 $[M+H]^+$.

Step 5: tert-butyl 1-{1-[6-(2,6-dioxopiperidin-3-yl)pyridazin-3-yl]piperidine-4-carbonyl}-4-methylpiperidine-4-carboxylate

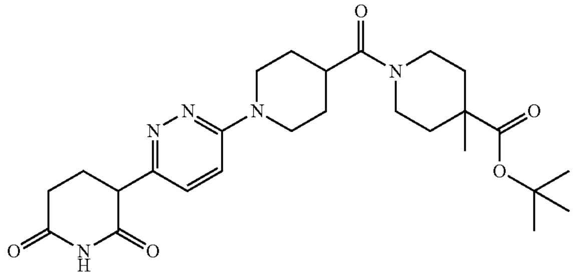 [SMILES: CC(C)(C)OC(=O)C1(C)CCN(C(=O)C2CCN(c3ccc(C4CCC(=O)NC4=O)nn3)CC2)CC1]

1-[6-(2,6-dioxopiperidin-3-yl)pyridazin-3-yl]piperidine-4-carboxylic acid hydrochloride (0.135 g, 0.424 mmol), HATU (0.24 g, 0.63 mmol) and DIPEA (0.29 mL, 1.38 mmol) were dissolved in anhydrous DMF (8.5 mL). After 30 min of stirring at room temperature, tert-butyl 4-methylpiperidine-4-carboxylate hydrochloride (0.112 g, 0.51 mmol) was added to the reaction mixture and stirring was continued for an additional 16 h. The reaction mixture was quenched with brine and extracted with EtOAc. The organic layer was evaporated to dryness under vacuum, and the crude residue was purified by preparative TLC developed with DCM:MeOH (95:5) to provide 120 mg (57% yield) of the title compound as a white solid. LCMS: $C_{26}H_{37}N_5O_5$, desired mass=499.3, found: m/z=500.9 $[M+H]^+$.

Step 6: 1-{1-[6-(2,6-dioxopiperidin-3-yl)pyridazin-3-yl]piperidine-4-carbonyl}-4-methylpiperidine-4-carboxylic acid hydrochloride

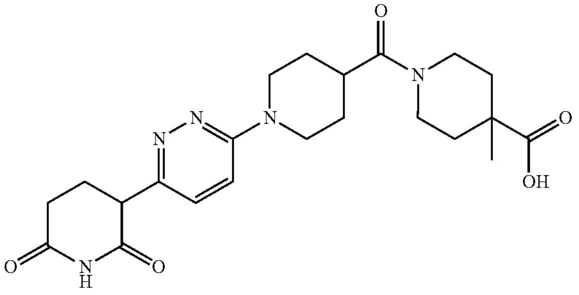 [SMILES: CC1(C(=O)O)CCN(C(=O)C2CCN(c3ccc(C4CCC(=O)NC4=O)nn3)CC2)CC1]

Tert-butyl 1-{1-[6-(2,6-dioxopiperidin-3-yl)pyridazin-3-yl]piperidine-4-carbonyl}-4-methylpiperidine-4-carboxylate (0.18 g, 0.37 mmol) was dissolved in anhydrous DCM (5.3 mL) followed by addition of 2 M HCl in Dioxane solution (1.8 mL, 7.4 mmol) and stirred at room temperature overnight. The reaction mixture was evaporated to dryness under vacuum and the residue was triturated with $Et_2O$ to provide 177.4 mg (95% yield) of the title compound as a pale yellow solid. LCMS: $C_{22}H_{29}N_5O_5$, desired mass=443.5, found: m/z=444.1 $[M+H]^+$.

Intermediate 95

1-{1-[6-(2,6-dioxopiperidin-3-yl)pyridazin-3-yl]piperidine-4-carbonyl}piperidine-4-carboxylic acid hydrochloride

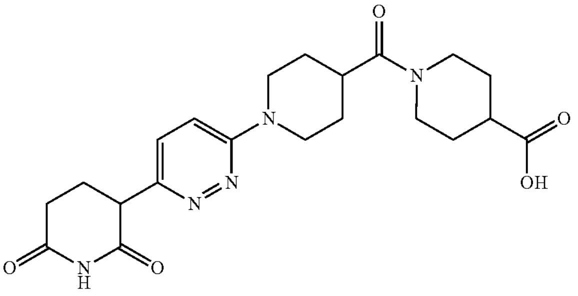

Step 1: tert-butyl 1-{1-[6-(2,6-dioxopiperidin-3-yl)pyridazin-3-yl]piperidine-4-carbonyl}piperidine-4-carboxylate

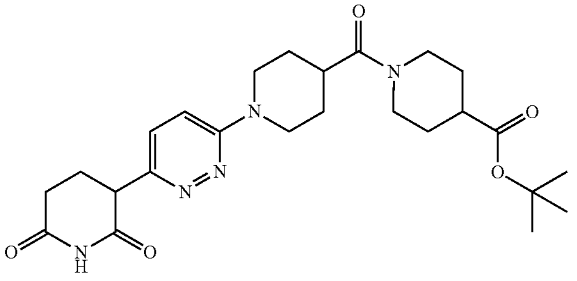 [SMILES: CC(C)(C)OC(=O)C1CCN(C(=O)C2CCN(c3ccc(C4CCC(=O)NC4=O)nn3)CC2)CC1]

1-[6-(2,6-dioxopiperidin-3-yl)pyridazin-3-yl]piperidine-4-carboxylic acid hydrochloride (0.15 g, 0.676 mmol), HATU (0.321 g, 0.846 mmol) and DIPEA (0.39 mL, 2.26 mmol) were dissolved in anh. DMF (11.3 mL). After 30 min of stirring in room temperature, tert-butyl piperidine-4-carboxylate hydrochloride (0.2 g, 0.676 mmol) was added to the reaction mixture and stirring was continued for an additional 16 h. The reaction mixture was quenched with water and extracted with EtOAc. The organic phase was dried over $Na_2SO_4$ and evaporated to dryness under vacuum. The crude residue was purified by flash chromatography eluting with DCM:MeOH (0-5%) to provide 0.18 g (66% yield) of the title compound as a yellow solid. LCMS: $C_{25}H_{35}N_5O_5$, desired mass=485.3, found: m/z=486.4 $[M+H]^+$.

Step 2: 1-{1-[6-(2,6-dioxopiperidin-3-yl)pyridazin-3-yl]piperidine-4-carbonyl}piperidine-4-carboxylic acid hydrochloride

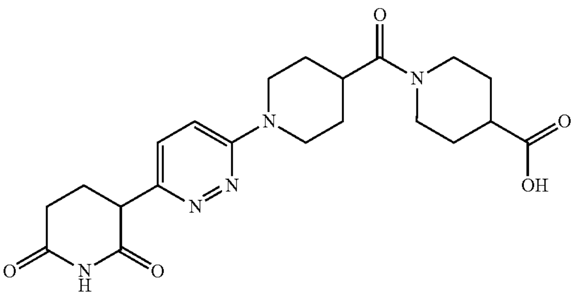 [SMILES: O=C1CCC(c2ccc(N3CCC(C(=O)N4CCC(C(=O)O)CC4)CC3)nn2)C(=O)N1]

Tert-butyl 1-{1-[6-(2,6-dioxopiperidin-3-yl)pyridazin-3-yl]piperidine-4-carbonyl}piperidine-4-carboxylate (0.18 g, 0.37 mmol) was dissolved in anhydrous DCM (5.3 mL) followed by addition of 2M HCl solution in Dioxane (1.8 mL, 7.4 mmol) and stirred at room temperature for 16 h. The reaction mixture was evaporated to dryness and the residue was triturated with $Et_2O$ to provide 177.4 mg (95% yield) of the title compound as a pale yellow solid. LCMS: $C_{21}H_{27}N_5O$, desired mass=429.5, found: m/z=430.4 $[M+H]^+$.

Intermediate 96

1-(2-{1-[4-(2,6-Dioxopiperidin-3-yl)Phenyl]Piperidin-4-yl}Acetyl)-4-Methylpiperidine-4-Carboxylic Acid

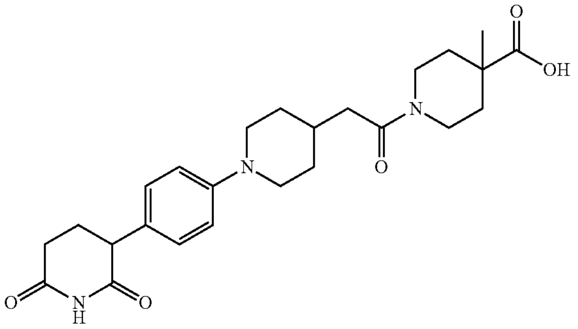 [SMILES: CC1(C(=O)O)CCN(C(=O)CC2CCN(c3ccc(C4CCC(=O)NC4=O)cc3)CC2)CC1]

Step 1: 2,6-bis(benzyloxy)-3-(4-bromophenyl)pyridine

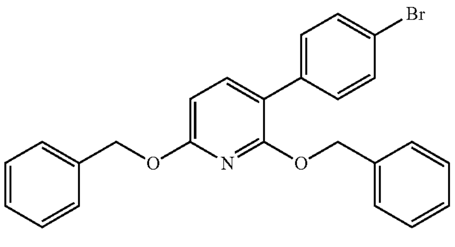 [SMILES: Brc1ccc(-c2ccc(OCc3ccccc3)nc2OCc2ccccc2)cc1]

To a solution of [2,6-bis(benzyloxy)pyridin-3-yl]boronic acid (14 g, 29.2 mmol) in anhydrous dioxane (150 mL) and water (30 mL) was added anhydrous potassium carbonate (12.12 g, 87.7 mmol) and 1-bromo-4-iodobenzene (12.4 g, 43.9 mmol). Under argon atmosphere Pd(dppf)$Cl_2$-DCM (2.39 g, 2.92 mmol) was added and the mixture was stirred in a sealed vessel at 80° C. for 16 h. The mixture was cooled to room temperature and water (50 mL) and ethyl acetate (50 mL) were added. The phases were separated and the aqueous phase was extracted with ethyl acetate (2×50 mL). The combined organic layers were dried over $Na_2SO_4$, filtered and concentrated under vacuum. The crude residue was purified by flash column chromatography eluting with hexane/EtOAc (0 to 2% of EtOAc) to provide 14.12 g (87% yield) of the title compound as a pale yellow solid. LCMS: $C_{25}H_{20}BrNO_2$ requires 446.34, observed m/z=447.65 $[M+H]^+$.

Step 2: tert-butyl 2-(1-{4-[2,6-bis(benzyloxy)pyridin-3-yl]phenyl}piperidin-4-yl)acetate

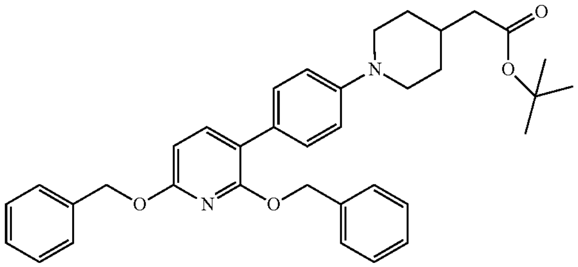 [SMILES: CC(C)(C)OC(=O)CC1CCN(c2ccc(-c3ccc(OCc4ccccc4)nc3OCc3ccccc3)cc2)CC1]

To a suspension of 2,6-bis(benzyloxy)-3-(4-bromophenyl)pyridine (8 g, 14.34 mmol) in anhydrous dioxane (143 mL) was added cesium carbonate (11.68 g, 35.85 mmol) and tert-butyl 2-(piperidin-4-yl)acetate hydrochloride (3.91 g, 18.64 mmol). Under argon atmosphere XPhos Pd G3 (2.43 g, 2.87 mmol) was added and the mixture was stirred in a sealed vessel at 100° C. for 16 h. The mixture was cooled to rt, filtered and washed with EtOAc. The volatiles were evaporated in vacuo and the crude residue was purified by flash column chromatography eluting with hexane/EtOAc (0 to 10% of EtOAc) to provide 5.39 g (65% yield) of title compound as a pale yellow solid. LCMS: $C_{36}H_{40}N_2O_4$ requires 564.73, observed m/z=564.95 $[M+H]^+$.

Step 3: tert-butyl 2-{1-[4-(2,6-dioxopiperidin-3-yl)phenyl]piperidin-4-yl}acetate

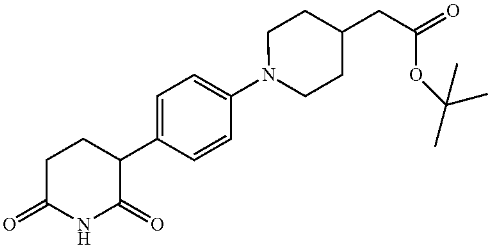 [SMILES: CC(C)(C)OC(=O)CC1CCN(c2ccc(C3CCC(=O)NC3=O)cc2)CC1]

To a solution of tert-butyl 2-(1-{4-[2,6-bis(benzyloxy)pyridin-3-yl]phenyl}piperidin-4-yl)acetate (1.1 g, 1.95 mmol) in THF (208 mL) and IPA (208 mL) degassed with argon, 10% Palladium on carbon (0.33 g, 3.12 mmol) was added and stirred under an atmosphere of $H_2$ (balloon) at rt for 16 h. The mixture was filtered and the filtrate was concentrated to dryness to obtain 3.38 g (90% yield) of title compound as a white solid. LCMS: $C_{22}H_{30}N_2O_4$ requires 386.49, observed m/z=387.26 $[M+H]^+$.

Step 4: 2-{1-[4-(2,6-dioxopiperidin-3-yl)phenyl] piperidin-4-yl}acetic acid

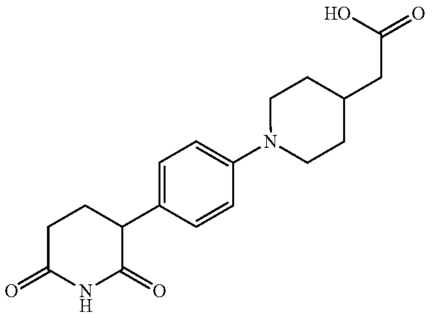 [SMILES: O=C(O)CC1CCN(c2ccc(C3CCC(=O)NC3=O)cc2)CC1]

To a solution of tert-butyl 2-{1-[4-(2,6-dioxopiperidin-3-yl)phenyl]piperidin-4-yl}acetate (3.38 g, 8.4 mmol) in anhydrous DCM (84 mL, 0.1 M) was added trifluoroacetic acid (65 mL, 843.4 mmol), and the reaction mixture was stirred for 2 h at room temperature. The reaction mixture was concentrated to dryness, the crude residue was triturated with $Et_2O$ and filtered off to provide 3.75 g (91% yield) of the title compound as a yellow solid. LCMS: $C_{18}H_{22}N_2O_4$ requires 330.38, observed m/z=331.23 $[M+H]^+$.

Step 5: tert-butyl 1-(2-{1-[4-(2,6-dioxopiperidin-3-yl)phenyl]piperidin-4-yl}acetyl)-4-methylpiperidine-4-carboxylate

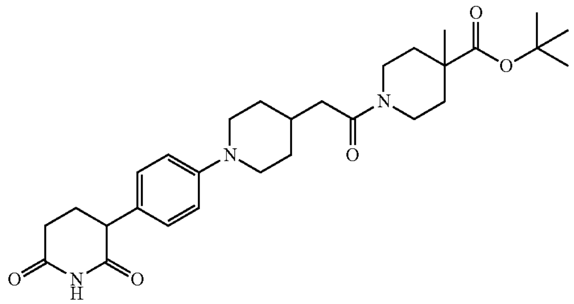 [SMILES: CC(C)(C)OC(=O)C1(C)CCN(C(=O)CC2CCN(c3ccc(C4CCC(=O)NC4=O)cc3)CC2)CC1]

To a solution of 2-{1-[4-(2,6-dioxopiperidin-3-yl)phenyl] piperidin-4-yl}acetic acid (3.0 g, 6.14 mmol) in anhydrous DMF (51.0 mL) was added DIPEA (8.9 mL, 51.2 mmol) and BOP (2.72 g, 6.14 mmol). The reaction mixture was stirred for 1 h at room temperature under an argon atmosphere. Tert-butyl 4-methylpiperidine-4-carboxylate hydrochloride (1.21 g, 5.12 mmol) was added and the reaction was stirred for 1 h. The volatiles were evaporated in vacuo, and the residue was dissolved in DCM, quenched with saturated aqueous $NaHCO_3$ and stirred vigorously for 30 min. The organic phase was separated, dried over $Na_2SO_4$, and concentrated to dryness under vacuum. The crude residue was purified by flash chromatography eluting with DCM/MeOH (0 to 4% of MeOH) to provide 2.9 g (99%) of the title compound as an off-white solid. LCMS: $C_{29}H_{41}N_3O_5$ requires 511.66, observed m/z=512.33 $[M+H]^+$.

Step 6: 1-(2-{1-[4-(2,6-dioxopiperidin-3-yl)phenyl] piperidin-4-yl}acetyl)-4-methylpiperidine-4-carboxylic acid

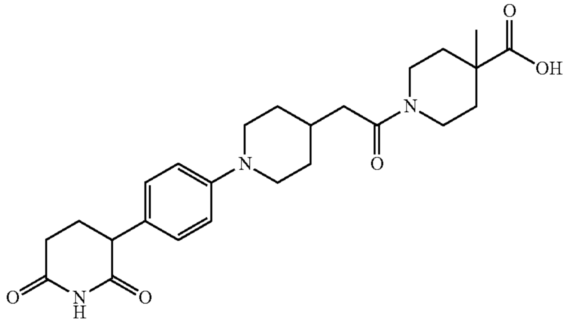 [SMILES: CC1(C(=O)O)CCN(C(=O)CC2CCN(c3ccc(C4CCC(=O)NC4=O)cc3)CC2)CC1]

To a solution of tert-butyl 1-(2-{1-[4-(2,6-dioxopiperidin-3-yl)phenyl]piperidin-4-yl}acetyl)-4-methylpiperidine-4-carboxylate (2.9 g, 5.08 mmol) in anhydrous DCM (17 mL) was added trifluoroacetic acid (38 mL, 508.46 mmol), and the reaction mixture was stirred for 2 h at room temperature. The reaction mixture was then concentrated to dryness under vacuum, and the crude residue was triturated with $Et_2O$ and filtered off to provide 3.21 mg (88% yield) of the title compound as an off-white solid. LCMS: $C_{25}H_{33}N_3O_5$ requires 455.56, observed m/z=456.30 $[M+H]^+$.

Intermediate 97

1-(4-(2,4-Dioxotetrahydropyrimidin-1(2H)-yl)Phenyl)Piperidine-4-Carboxylic Acid

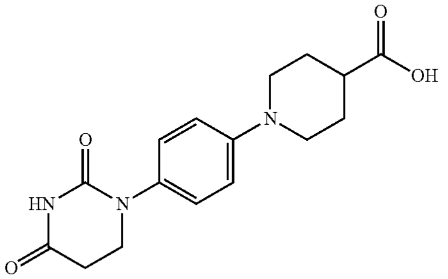 [SMILES: O=C1CCN(c2ccc(N3CCC(C(=O)O)CC3)cc2)C(=O)N1]

Step 1: tert-butyl 1-(4-bromophenyl)piperidine-4-carboxylate

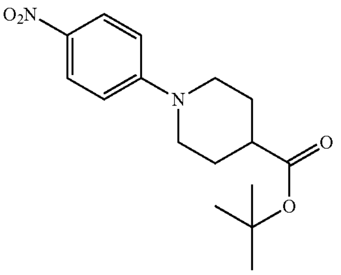 [SMILES: CC(C)(C)OC(=O)C1CCN(c2ccc([N+](=O)[O-])cc2)CC1]

A mixture of 4-bromo-1-nitrobenzene (1000.00 mg, 4.95 mmol), tert-butyl piperidine-4-carboxylate (917 mg, 4.95 mmol), cesium carbonate (4800 mg, 14.8 mmol) and 1,3-bis[2,6-bis(pentan-3-yl)phenyl]-2H-imidazole; 3-chloropyridine; palladium chloride (196 mg, 0.25 mmol) in dioxane was purged with nitrogen and stirred at 100° C. overnight. LCMS showed complete conversion to the desired product. The reaction mixture was cooled to room temperature and filtered through a thin layer of celite. The filtrate was diluted with water and EtOAc. The organic layer was separated and dried over sodium sulfate, then concentrated under vacuum. The resulting residue was purified by silica gel chromatography eluting with 0-100% EtOAc/hexane to afford of product as white solid (1200 mg, 80% yield) of the title compound as a white solid. LCMS: $[C_{16}H_{22}N_2O_4]$, desired mass=306.2, found: m/z=307.3 $[M+H]^+$.

Step 2: tert-butyl 1-(4-aminophenyl)piperidine-4-carboxylate

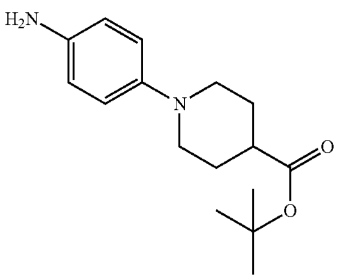

A mixture of tert-butyl 1-(4-nitrophenyl)piperidine-4-carboxylate (1200.00 mg, 3.9 mmol), zinc powder (2770 mg, 42 mmol), and ammonium chloride 1M aqueous solution (40 mL, 40 mmol) in THF (15 mL) was heated at room temperature for 4 hours. The reaction mixture was cooled to room temperature, filtered, and diluted with EtOAc. The organic layer was dried over anhydrous sodium sulfate and concentrated under reduced pressure. The crude residue was purified by flash chromatography, eluting with 0 to 60% ethyl acetate/hexanes to afford the title compound as a white solid (1100 mg, 100%). LCMS: $[C_{16}H_{24}N_2O_2]$, desired mass=276.2, found: m/z=277.5 $[M+H]^+$.

Step 3: 3-({4-[4-(tert-butoxycarbonyl)piperidin-1-yl]phenyl}amino)propanoic acid

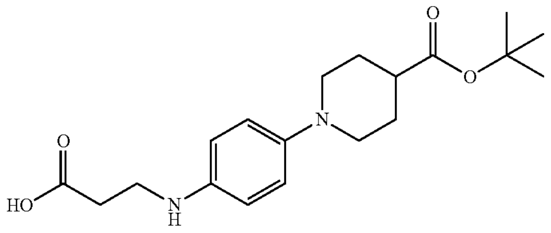 [SMILES: CC(C)(C)OC(=O)C1CCN(c2ccc(NCCC(=O)O)cc2)CC1]

To a solution of tert-butyl 1-(4-aminophenyl)piperidine-4-carboxylate (1100.00 mg, 3.99 mmol) in toluene (1.51 mL) was added acrylic acid (84 mg, 1.2 mmol). The reaction mixture was heated for 3 hours at 100° C., then a second portion of acrylic acid (84 mg, 1.2 mmol) was added. Heating at 100° C. was continued for an additional 16 hours at which time LCMS analysis showed a mixture of mono and bis-substituted products. The reaction mixture was cooled to room temperature and concentrated in vacuo. The crude residue was purified with C18 reverse phase chromatography (eluting with $CH_3CN$ and water) to afford the title compound as a brown oil (1100 mg, 67%). LCMS: $[C_{19}H_{28}N_2O_4]$ desired mass=348.2, found: m/z=349.4 $[M+H]^+$.

Step 4: tert-butyl 1-[5-(2,4-dioxo-1,3-diazinan-1-yl)pyridin-2-yl]piperidine-4-carboxylate

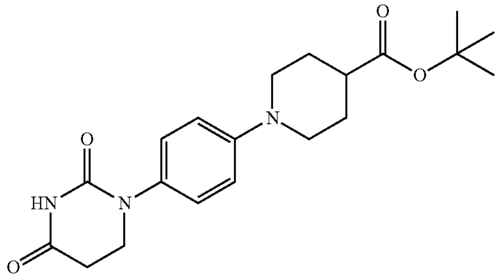 [SMILES: CC(C)(C)OC(=O)C1CCN(c2ccc(N3CCC(=O)NC3=O)cc2)CC1]

To a solution of 3-({6-[4-(tert-butoxycarbonyl)piperidin-1-yl]pyridin-3-yl}amino)propanoic acid (1100.00 mg, 3.16 mmol) in acetic acid (1.81 mL, 31.6 mmol) was added urea (227 mg, 3.8 mmol). The resulting suspension was heated to reflux for 3 hours. The reaction mixture was cooled to room temperature and concentrated in vacuo. The crude residue was purified with C18 reverse phase chromatography (eluting with $CH_3CN$ and water) to afford the title compound as a brown oil (170 mg, 14%). LCMS: $[C_{20}H_{27}N_3O_4]$ desired mass=373.2, found: m/z=374.4 $[M+H]^+$.

Step 5: 1-(4-(2,4-dioxotetrahydropyrimidin-1(2h)-yl)phenyl)piperidine-4-carboxylic acid

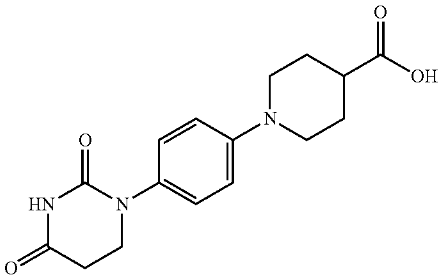 [SMILES: O=C1CCN(c2ccc(N3CCC(C(=O)O)CC3)cc2)C(=O)N1]

A mixture of tert-butyl 1-[4-(2,4-dioxo-1,3-diazinan-1-yl)phenyl]piperidine-4-carboxylate (170 mg, 0.455 mmol) in HFIP (2 mL) was treated with TFA (0.35 mL, 1.33 mmol) and stirred at room temperature overnight. The resulting mixture was concentrated under vacuum. The residue was purified by reverse phase flash chromatography (eluting with $CH_3CN$ and $H_2O$) to yield the title compound as a white solid (160 mg, 104%). LCMS: $[C_{16}H_{19}N_3O_4]$ desired mass=317.1; found: m/z=318.4 $[M+H]^+$.

Intermediate 98

1-(4-(2,6-Dioxopiperidin-3-yl)-3-Fluorophenyl)Piperidine-4-Carboxylic Acid

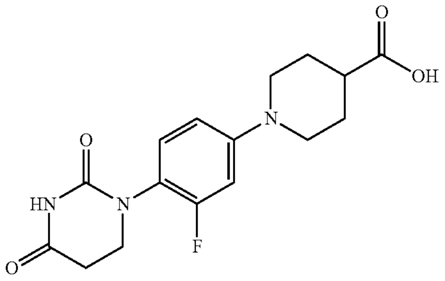 [SMILES: O=C1CCN(c2ccc(N3CCC(C(=O)O)CC3)cc2F)C(=O)N1]

Step 1: 2,6-bis(benzyloxy)-3-(4-chloro-2-fluorophenyl)pyridine

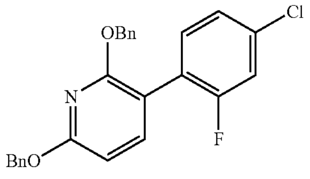 [SMILES: Fc1cc(Cl)ccc1-c1ccc(OCc2ccccc2)nc1OCc1ccccc1]

To a solution of 1-bromo-4-chloro-2-fluorobenzene (2 g, 9.54 mmol) and 2,6-bis(benzyloxy)pyridin-3-ylboronic acid (2.4 g, 5.73 mmol) in 1,4-dioxane (8 mL) was added a 1N aqueous solution of potassium carbonate (28 mL, 28 mmol). The mixture was degassed with argon gas for 10 min, then Pd(dppf)$Cl_2$-DCM (780 mg, 0.95 mmol) was added and the vial was sealed. The reaction mixture was stirred for 0.5 h at 115° C. under microwave radiation, and then the reaction mixture was quenched with water (10 mL) and extracted with ethyl acetate (3×10 mL). The combined organic layers were dried over anhydrous sodium sulfate and concentrated under reduced pressure. The residue was purified by silica gel chromatography eluting with 0-100% EtOAc/heptane to afford the title compound as a white solid (1.9 g, 47% yield). LCMS: [$C_{25}H_{19}ClFNO_2$], desired mass=419.1, found: m/z=420.5 $[M+H]^+$.

Step 2: tert-butyl 1-{4-[2,6-bis(benzyloxy)pyridin-3-yl]-3-fluorophenyl}piperidine-4-carboxylate

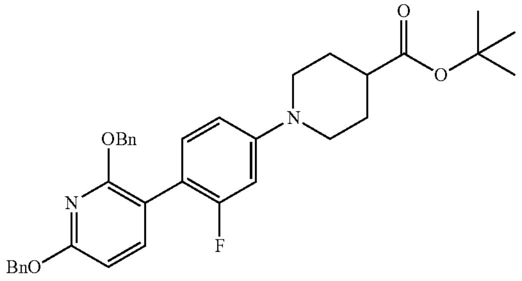 [SMILES: CC(C)(C)OC(=O)C1CCN(c2ccc(-c3ccc(OCc4ccccc4)nc3OCc3ccccc3)c(F)c2)CC1]

To a solution of 2,6-bis(benzyloxy)-3-(4-chloro-2-fluorophenyl)pyridine (2 g, 4.76 mmol) and tert-butyl piperidine-4-carboxylate (882 mg, 4.76 mmol) in 1,4-dioxane (5 mL) was added cesium carbonate (3.1 g, 9.53 mmol) and 1,3-bis[2,6-bis(pentan-3-yl)phenyl]-2H-imidazole; 3-chloropyridine; palladium chloride (350 mg, 0.4 mmol) at room temperature. The reaction mixture was stirred at 100° C. overnight, and then the reaction mixture was cooled to room temperature, quenched with water (20 mL) and extracted with ethyl acetate (3×10 mL). The combined organic layers were dried over anhydrous sodium sulfate and concentrated under reduced pressure. The residue was purified by silica gel chromatography eluting with 0-100% EtOAc/heptane to afford the title compound as a white solid (2.1 g, 77%). LCMS: [$C_{35}H_{37}FN_2O_4$], desired mass=568.3, found: m/z=569.4 $[M+H]^+$.

Step 3: tert-butyl 1-[4-(2,6-dioxopiperidin-3-yl)-3-fluorophenyl]piperidine-4-carboxylate

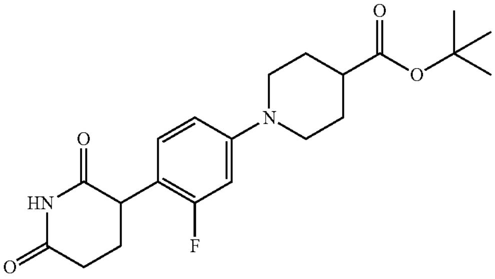 [SMILES: CC(C)(C)OC(=O)C1CCN(c2ccc(C3CCC(=O)NC3=O)c(F)c2)CC1]

To a solution of tert-butyl 1-{4-[2,6-bis(benzyloxy)pyridin-3-yl]-3-fluorophenyl}piperidine-4-carboxylate (1.5 g, 2.64 mmol) in a mixture of THF (5 mL) and isopropanol (5 mL) was added Pd/C (280 mg, 0.26 mmol). The reaction mixture was stirred for 36 hours at room temperature under $H_2$ gas and then the mixture was diluted with ethyl acetate (30 mL) and filtered through Celite. The filtrate was then concentrated under reduced pressure. The residue was purified by silica gel chromatography eluting with 0-100% EtOAc/heptane to afford the title compound as a white solid (1.01 g, 98%). LCMS: ($C_{21}H_{27}FN_2O_4$) desired mass=390.2, found: m/z=391.4 $[M+H]^+$.

Step 4: 1-(4-(2,6-dioxopiperidin-3-yl)-3-fluorophenyl)piperidine-4-carboxylic acid

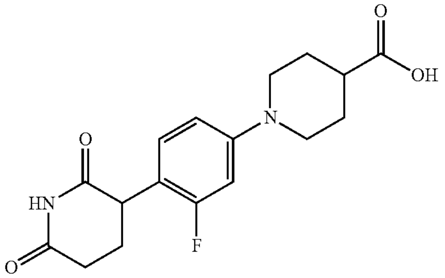 [SMILES: O=C1CCC(c2ccc(N3CCC(C(=O)O)CC3)cc2F)C(=O)N1]

A mixture of tert-butyl 1-[4-(2,6-dioxopiperidin-3-yl)-3-fluorophenyl]piperidine-4-carboxylate (1010 mg, 2.02 mmol) in HFIP (2 mL) was treated with TFA (1.55 mL, 20 mmol) and stirred at room temperature overnight. The resulting mixture was concentrated under vacuum. The residue was purified by reverse phase flash chromatography [eluting with $CH_3CN$ and $H_2O$] to afford the title compound as a white solid (750 mg, 84%). LCMS: ($C_{17}H_{19}FN_2O_4$) desired mass=334.1; found: m/z=335.4 $[M+H]^+$.

Intermediate 99

(3S)-1-(1-(4-(2,6-Dioxopiperidin-3-yl)Phenyl)Piperidine-4-Carbonyl)Pyrrolidine-3-Carboxylic Acid

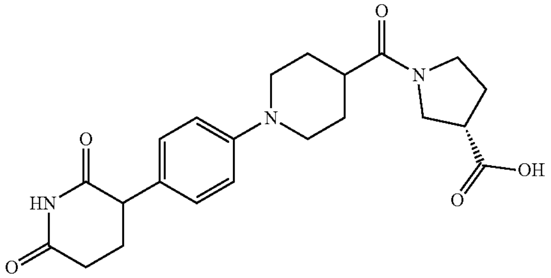 [SMILES: O=C1CCC(c2ccc(N3CCC(C(=O)N4CC[C@H](C(=O)O)C4)CC3)cc2)C(=O)N1]

Step 1: tert-butyl (3S)-1-(1-(4-(2,6-dioxopiperidin-3-yl)phenyl)piperidine-4-carbonyl)pyrrolidine-3-carboxylate

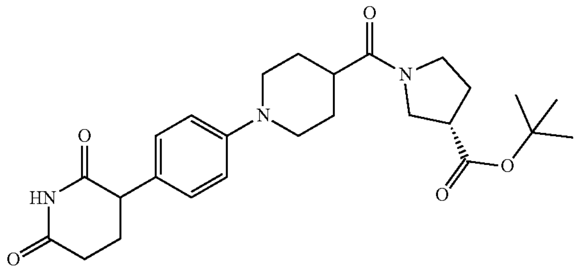 [SMILES: CC(C)(C)OC(=O)[C@H]1CCN(C(=O)C2CCN(c3ccc(C4CCC(=O)NC4=O)cc3)CC2)C1]

Prepared by similar procedures as Intermediate 5 (step 1) using 1-(4-(2,6-dioxopiperidin-3-yl)phenyl)piperidine-4-carboxylic acid (Intermediate 74) (100 mg, 0.32 mmol) and tert-butyl (3S)-pyrrolidine-3-carboxylate (81 mg, 0.47 mmol) as starting materials. The title compound was isolated as an off-white solid (80 mg, 54%). LCMS: $[C_{26}H_{35}N_3O_5]$, desired mass=469.3, found: m/z=470.5 $[M+H]^+$.

Step 2: (3S)-1-(1-(4-(2,6-dioxopiperidin-3-yl)phenyl)piperidine-4-carbonyl)pyrrolidine-3-carboxylic acid

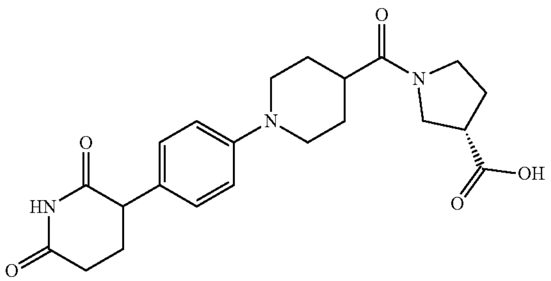 [SMILES: O=C1CCC(c2ccc(N3CCC(C(=O)N4CC[C@H](C(=O)O)C4)CC3)cc2)C(=O)N1]

Prepared by similar procedures as Intermediate 5 (step 2) using tert-butyl (3S)-1-(1-(4-(2,6-dioxopiperidin-3-yl)phenyl)piperidine-4-carbonyl)pyrrolidine-3-carboxylate (80 mg, 0.17 mmol) as the starting material. The title compound was isolated as an off-white solid (66 mg, 94%). LCMS: $[C_{22}H_{27}N_3O_5]$, desired mass=413.2, observed mass=414.4 $[M+H]^+$.

Intermediate 100

(3R)-1-(1-(4-(2,6-dioxopiperidin-3-yl)phenyl)piperidine-4-carbonyl)pyrrolidine-3-carboxylic

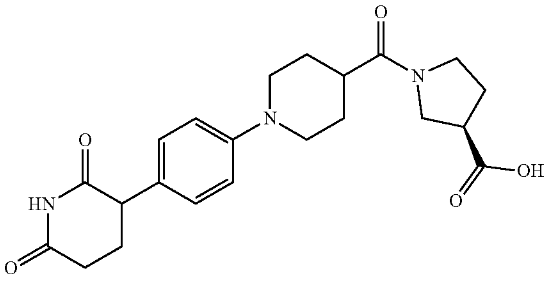 [SMILES: O=C1CCC(c2ccc(N3CCC(C(=O)N4CC[C@@H](C(=O)O)C4)CC3)cc2)C(=O)N1]

Prepared by similar procedures as Intermediate 99 using tert-butyl (3S)-pyrrolidine-3-carboxylate in step 1. The title compound was isolated as an off-white solid (60 mg, 85%). LCMS: $[C_{22}H_{27}N_3O_5]$, desired mass=413.2, observed mass=414.3 $[M+H]^+$.

Intermediate 101

(R)-1-(1-(4-(2,4-Dioxotetrahydropyrimidin-1(2H)-yl)Phenyl)Piperidine-4-Carbonyl)Pyrrolidine-3-Carboxylic Acid

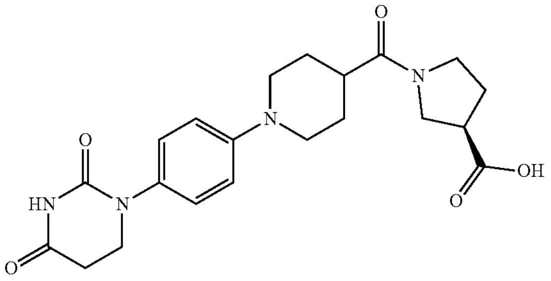 [SMILES: O=C1CCN(c2ccc(N3CCC(C(=O)N4CC[C@@H](C(=O)O)C4)CC3)cc2)C(=O)N1]

Step 1: tert-butyl (3R)-1-{1-[4-(2,4-dioxo-1,3-diazinan-1-yl)phenyl]piperidine-4-carbonyl}pyrrolidine-3-carboxylate

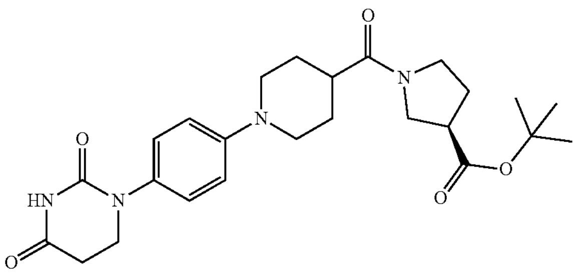 [SMILES: CC(C)(C)OC(=O)[C@@H]1CCN(C(=O)C2CCN(c3ccc(N4CCC(=O)NC4=O)cc3)CC2)C1]

Prepared by similar procedures as Intermediate 5 (step 1) using 1-(4-(2,4-dioxotetrahydropyrimidin-1(2H)-yl)phenyl) piperidine-4-carboxylic acid (80 mg, 0.25 mmmol) and tert-butyl (3R)-pyrrolidine-3-carboxylate (56 mg, 0.33 mmol) as starting materials. The title compound was isolated as an off-white solid (79 mg, 67%). LCMS: [$C_{25}H_{34}N_4O_5$], desired mass=470.3, found: m/z=471.5 $[M+H]^+$.

Step 2: (R)-1-(1-(4-(2,4-dioxotetrahydropyrimidin-1(2H)-yl)phenyl)piperidine-4-carbonyl)pyrrolidine-3-carboxylic acid

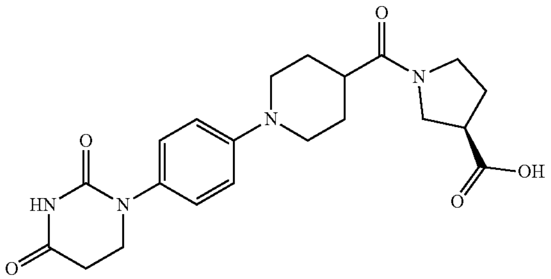

Prepared by similar procedures as Intermediate 5 (step 2) using tert-butyl (3R)-1-{1-[4-(2,4-dioxo-1,3-diazinan-1-yl)phenyl]piperidine-4-carbonyl}pyrrolidine-3-carboxylate (80 mg, 0.17 mmol) as the starting material. The title compound was isolated as an off-white solid (60 mg, 88%). LCMS: [$C_{21}H_{26}N_4O_5$], desired mass=414.2, found: m/z=415.4 $[M+H]^+$.

Intermediate 102

1-((1-(5-(2,6-Dioxopiperidin-3-yl)Pyridin-2-yl)Piperidin-4-yl)Methyl)-4-Methylpiperidine-4-Carboxylic Acid

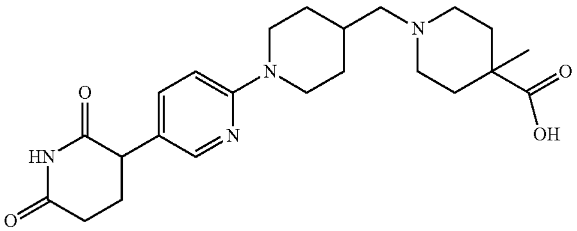 [SMILES: CC1(C(=O)O)CCN(CC2CCN(c3ccc(C4CCC(=O)NC4=O)cn3)CC2)CC1]

Step 1: 2,6-bis(benzyloxy)pyridine

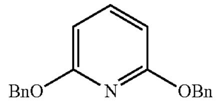 [SMILES: c1ccc(COc2cccc(OCc3ccccc3)n2)cc1]

Into a 5-L 4-necked round-bottom flask purged and maintained with an inert atmosphere of nitrogen, was placed 2,6-dichloropyridine (150.00 g, 1013.58 mmol, 1.00 equiv), dimethylformamide (3 L), and NaH (272.00 g, 11334.41 mmol, 11.18 equiv, 65%). BnOH (329.50 g, 3050.88 mmol, 3.01 equiv) was added dropwise with stirring at 0° C. The resulting solution was stirred for 4 h at 80° C., then cooled and quenched by the addition of 7 L of water/ice. The solids were collected by filtration and concentrated to afford 276 g (93.46%) of the title compound as a grey solid. LCMS: (ES, m/z): $[M+H]^+$=292.

Step 2: 2,6-bis(benzyloxy)-3-bromopyridine

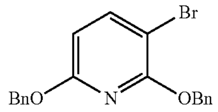 [SMILES: Brc1ccc(OCc2ccccc2)nc1OCc1ccccc1]

Into a 3-L 4-necked round-bottom flask purged and maintained with an inert atmosphere of nitrogen, was placed 2,6-bis(benzyloxy)pyridine (276.00 g, 947.314 mmol, 1.00 equiv), $CH_3CN$ (2.76 L), and $K_2CO_3$ (445.00 g, 3196.54 mmol, 3.37 equiv). $Br_2$ (151.70 g, 949.26 mmol, 1.00 equiv) was added dropwise with stirring at 0° C. The resulting solution was stirred for 4 h at room temperature, then was concentrated and the residue was purified by silica gel chromatography eluting with ethyl acetate/petroleum ether (10%) to afford 253 g (72.13%) of the title compound as a white solid. LCMS: (ES, m/z): $[M+H]^+$=370.

Step 3: 2,6-bis(benzyloxy)-3-(4,4,5,5-tetramethyl-1,3,2-dioxaborolan-2-yl)pyridine

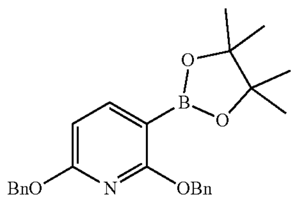 [SMILES: CC1(C)OB(c2ccc(OCc3ccccc3)nc2OCc2ccccc2)OC1(C)C]

Into a 3-L 4-necked round-bottom flask purged and maintained with an inert atmosphere of nitrogen, was placed 2,6-bis(benzyloxy)-3-bromopyridine (253.00 g, 683.32 mmol, 1.00 equiv), Dioxane (2.53 L), bis(pinacolato)diboron (261.00 g, 1027.80 mmol, 1.50 equiv), potassium acetate (134.00 g, 1365.36 mmol, 2.00 equiv), and $Pd(dppf)Cl_2$ (25.10 g, 34.290 mmol, 0.05 equiv). The resulting solution was stirred for 16 h at 100° C. The reaction mixture was cooled, concentrated under vacuum, and purified by silica gel column chromatography eluting with ethyl acetate/petroleum ether (15%) to provide 200 g (70.14%) of the title compound as a white solid.

Step 4: (1-(5-iodopyridin-2-yl)piperidin-4-yl)methanol

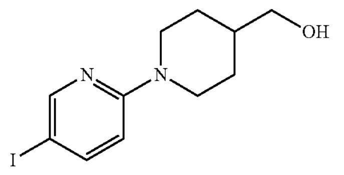 [SMILES: OCC1CCN(c2ccc(I)cn2)CC1]

Into a 3-L 4-necked round-bottom flask purged and maintained with an inert atmosphere of nitrogen, was placed 2-fluoro-5-iodopyridine (200.00 g, 896.90 mmol, 1.00 equiv), DMSO (2.00 L), piperidin-4-ylmethanol (128.90 g, 1119.15 mmol, 1.25 equiv), and DIEA (347.00 g, 2684.86 mmol, 3.00 equiv). The resulting solution was stirred for 3 days at 90° C., then the reaction mixture was cooled and exacted with 2×2 L of EtOAc. The combined organic layers were washed with 3×2 L of brine, then concentrated, and the residue purified by silica gel column chromatography eluting with ethyl acetate/petroleum ether (35%) to provide 182 g (63.78%) of the title compound as yellow oil. LCMS: (ES, m/z): $[M+H]^+=319$.

Step 5: (1-(2',6'-bis(benzyloxy)-[3,3'-bipyridin]-6-yl)piperidin-4-yl)methanol

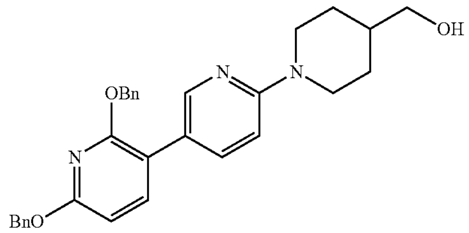 [SMILES: OCC1CCN(c2ccc(-c3ccc(OCc4ccccc4)nc3OCc3ccccc3)cn2)CC1]

Into a 3-L 4-necked round-bottom flask purged and maintained with an inert atmosphere of nitrogen, was placed [1-(5-iodopyridin-2-yl)piperidin-4-yl]methanol (182.00 g, 572.04 mmol, 1.00 equiv), tetrahydrofuran (1.82 L), water (364.00 mL), 2,6-bis(benzyloxy)-3-(4,4,5,5-tetramethyl-1,3,2-dioxaborolan-2-yl)pyridine (298.40 g, 715.05 mmol, 1.25 equiv), $K_2CO_3$ (157.90 g, 1134.23 mmol, 1.98 equiv), and tetrakis(triphenylphosphine)palladium(0) (66.00 g, 57.114 mmol, 0.10 equiv). The resulting solution was stirred for 16 h at 90° C. The reaction mixture was cooled, exacted with 2×3 L of EtOAc, and the combined organic layers were washed with 3×3 L of brine. After concentrating under reduced pressure, the residue was purified with silica gel column chromatography eluting with ethyl acetate/petroleum ether (85%) to provide 140 g (50.82%) of the title compound as a green solid. LCMS: (ES, m/z): $[M+H]^+=482$.

Step 6: 3-(6-(4-(hydroxymethyl)piperidin-1-yl)pyridin-3-yl)piperidine-2,6-dione

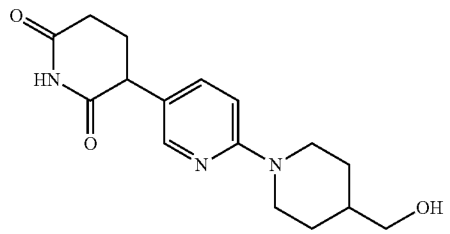 [SMILES: O=C1CCC(c2ccc(N3CCC(CO)CC3)nc2)C(=O)N1]

Into a 2-L round-bottom flask, was placed [1-[2',6'-bis(benzyloxy)-[3,3'-bipyridin]-6-yl]piperidin-4-yl]methanol (35.00 g, 72.67 mmol, 1.00 equiv), tetrahydrofuran (120 mL), and Pd/C (10.00 g, 10%). The resulting solution was stirred for 16 h under hydrogen atmosphere (4 atm). Then reaction mixture was filtered and another 10 g of Pd/C (10%), then the reaction mixture was stirred under hydrogen atmosphere (4 atm). This was repeated an additional three times. The solids were filtered off, the filtrate was concentrated and washed with 3×100 mL EtOAc to provide 64 g of the crude title compound. LCMS: (ES, m/z): $[M+H]^+=304$.

Step 7: 1-(5-(2,6-dioxopiperidin-3-yl)pyridin-2-yl)piperidine-4-carbaldehyde

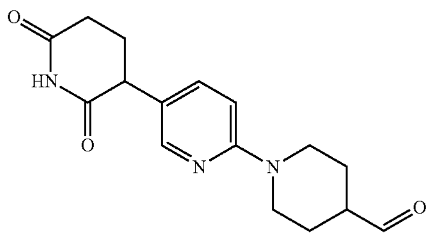 [SMILES: O=CC1CCN(c2ccc(C3CCC(=O)NC3=O)cn2)CC1]

Into a 1-L 3-necked round-bottom flask purged and maintained with an inert atmosphere of nitrogen, was placed 3-[6-[4-(hydroxymethyl)piperidin-1-yl]pyridin-3-yl]piperidine-2,6-dione (8.00 g, 26.37 mmol, 1.00 equiv), DCM (400.00 mL), then Dess-Martin (12.30 g, 31.59 mmol, 1.20 equiv) at 0° C. The resulting solution was stirred for 2 h at 0° C., then the solids were filtered off and the filtrate was washed with brine (200 mL), dried over $Na_2SO_4$ and concentrated under vacuum. The residue was purified by silica gel column chromatography eluting with DCM/EtOAc (3:2) to provide 5 g (62.92%) of 1-[5-(2,6-dioxopiperidin-3-yl)pyridin-2-yl]piperidine-4-carbaldehyde as a grey solid. LCMS: (ES, m/z): $[M+H]^+=302$; T=1.33 min $^1$H-NMR: (300 MHZ, DMSO-$d_6$, ppm): δ10.80 (s, 1H), 9.62 (s, 1H), 7.95 (d, J=2.5 Hz, 1H), 7.39 (dd, J=8.9, 2.5 Hz, 1H), 6.83 (d, J=8.8 Hz, 1H), 4.12 (dd, J=13.1, 4.2 Hz, 2H), 3.73 (dd, J=12.0, 4.9 Hz, 1H), 3.10-2.95 (m, 2H), 2.64 (tdd, J=24.6, 11.1, 4.8 Hz, 2H), 2.18 (qd, J=12.4, 4.4 Hz, 1H), 2.03-1.93 (m, 1H), 1.89 (dd, J=13.2, 3.6 Hz, 3H), 1.57-1.39 (m, 2H).

Step 8: tert-butyl 1-((1-(5-(2,6-dioxopiperidin-3-yl)pyridin-2-yl)piperidin-4-yl)methyl)-4-methylpiperidine-4-carboxylate

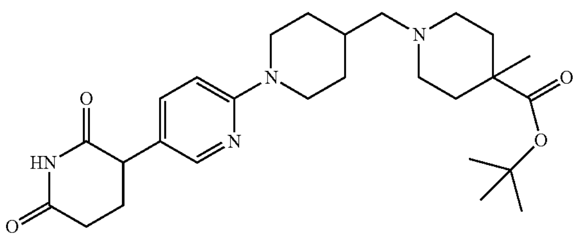 [SMILES: CC(C)(C)OC(=O)C1(C)CCN(CC2CCN(c3ccc(C4CCC(=O)NC4=O)cn3)CC2)CC1]

1-(5-(2,6-dioxopiperidin-3-yl)pyridin-2-yl)piperidine-4-carbaldehyde (100 mg, 0.33 mmol, triethylamine (0.23 mL, 1.66 mmol), and tert-butyl 4-methylpiperidine-4-carboxylate (68 mg. 0.37 mmol) were dissolved in DCM (1.0 mL) and DMSO (0.1 mL). The mixture was treated with sodium bis(acetyloxy)boranuidyl acetate (212 mg, 0.99 mmol), and stirred at room temperature for 3 hours before being poured over saturated aqueous ammonium chloride and extracted with ethyl acetate. The organic layer was concentrated and purified with reverse phase C18 chromatography eluting with ACN/water to afford an off-white solid (170 mg, 100%). LCMS: [$C_{27}H_{40}N_4O_4$], desired mass=484.3, found: m/z=485.5 $[M+H]^+$.

Step 9: 1-((1-(5-(2,6-dioxopiperidin-3-yl)pyridin-2-yl)piperidin-4-yl)methyl)-4-methylpiperidine-4-carboxylic acid

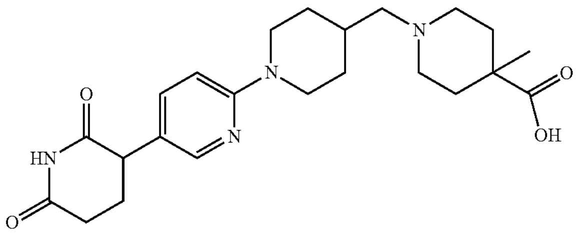 [SMILES: CC1(C(=O)O)CCN(CC2CCN(c3ccc(C4CCC(=O)NC4=O)cn3)CC2)CC1]

Prepared by similar procedures as Intermediate 5 (step 2) using tert-butyl 1-((1-(5-(2,6-dioxopiperidin-3-yl)pyridin-2-yl)piperidin-4-yl)methyl)-4-methylpiperidine-4-carboxylate (110 mg, 0.21 mmol) as the starting material. The title compound was isolated as an off-white solid (80 mg, 75%). LCMS: [$C_{23}H_{32}N_4O_4$], desired mass=428.2, found: m/z=429.4 $[M+H]^+$.

Intermediate 103

1-(1-(5-(2,6-Dioxopiperidin-3-yl)Pyrimidin-2-yl)Piperidine-4-Carbonyl)-4-Methylpiperidine-4-Carboxylic Acid

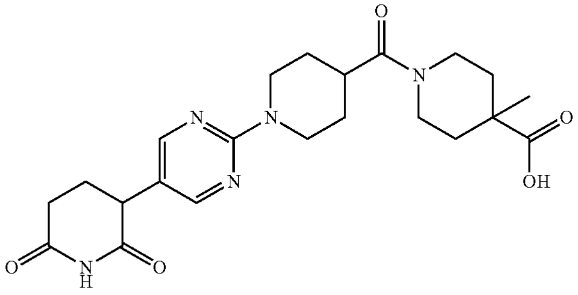 [SMILES: CC1(C(=O)O)CCN(C(=O)C2CCN(c3ncc(C4CCC(=O)NC4=O)cn3)CC2)CC1]

Step 1: tert-butyl 1-(5-bromopyrimidin-2-yl)piperidine-4-carboxylate

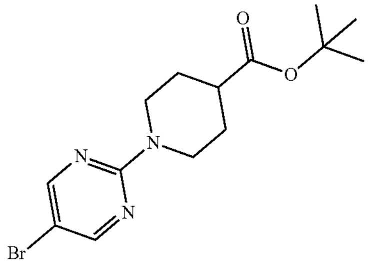 [SMILES: CC(C)(C)OC(=O)C1CCN(c2ncc(Br)cn2)CC1]

To a mixture of 5-bromo-2-chloropyrimidine (20 g, 103.397 mmol) in EtOH (300 mL) was added tert-butyl piperidine-4-carboxylate (19.16 g, 103.397 mmol) at room temperature. The resulting mixture was stirred at 80° C. overnight. The resulting mixture was concentrated under reduced pressure. The residue was purified by silica gel column chromatography, eluted with PE/EA (10/1) to afford tert-butyl 1-(5-bromopyrimidin-2-yl)piperidine-4-carboxylate (14 g, 37.59%) as a white solid.

LCMS: ($C_{14}H_{20}BrN_3O_2$) desired mass=342.0; observed mass=342.1$[M+H]^+$.

Step 2: tert-butyl 1-(5-(2,6-bis(benzyloxy)pyridin-3-yl)pyrimidin-2-yl)piperidine-4-carboxylate

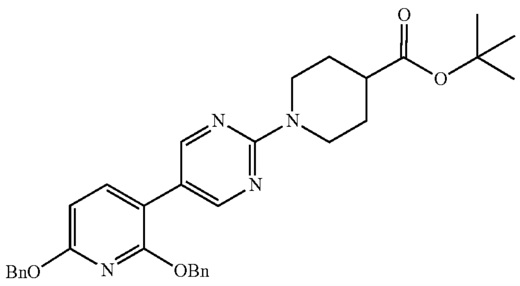 [SMILES: CC(C)(C)OC(=O)C1CCN(c2ncc(-c3ccc(OCc4ccccc4)nc3OCc3ccccc3)cn2)CC1]

To a mixture of tert-butyl 1-(5-bromopyrimidin-2-yl)piperidine-4-carboxylate (14 g, 40.907 mmol) in dioxane (100 mL) and $H_2O$ (20 mL) were added 2,6-bis(benzyloxy)-3-(4,4,5,5-tetramethyl-1,3,2-dioxaborolan-2-yl)pyridine (17.07 g, 40.905 mmol), $Pd(dppf)Cl_2 \cdot CH_2Cl_2$ (6.66 g, 8.176 mmol) and $K_2CO_3$ (16.96 g, 122.716 mmol) at room temperature. The resulting mixture was stirred at 100° C. for 1 h under nitrogen atmosphere. The resulting mixture was concentrated under reduced pressure. The residue was purified by silica gel column chromatography, eluted with PE/EA (1/1) to afford tert-butyl 1-{5-[2,6-bis(benzyloxy)pyridin-3-yl]pyrimidin-2-yl}piperidine-4-carboxylate (5.8 g, 23.09%) as a light brown solid. LCMS: ($C_{33}H_{36}N_4O_4$) desired mass=553.2; observed mass=553.3[M+H]$^+$.

Step-3: tert-butyl 1-(5-(2,6-dioxopiperidin-3-yl)pyrimidin-2-yl)piperidine-4-carboxylate

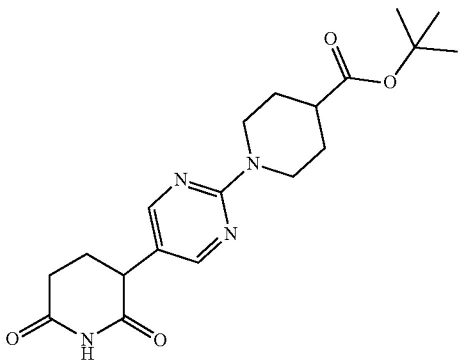 [SMILES: CC(C)(C)OC(=O)C1CCN(c2ncc(C3CCC(=O)NC3=O)cn2)CC1]

To a mixture of tert-butyl 1-{5-[2,6-bis(benzyloxy)pyridin-3-yl]pyrimidin-2-yl}piperidine-4-carboxylate (5.8 g, 10.494 mmol) in THF (50 mL) and EtOH (5 mL) was added Pd/C (11.6 g) at room temperature. The resulting mixture was stirred at room temperature overnight under hydrogen atmosphere. The resulting mixture was filtered. The filtrate was concentrated under reduced pressure. The residue was purified by silica gel column chromatography, eluted with PE/EA (1/1) to afford tert-butyl 1-[5-(2,6-dioxopiperidin-3-yl)pyrimidin-2-yl]piperidine-4-carboxylate (580 mg, 14.76%) as a light yellow solid. LCMS: ($C_{19}H_{26}N_4O_4$) desired mass=375.2; observed mass=375.1 [M+H]$^+$.

Step-4: 1-(5-(2,6-dioxopiperidin-3-yl)pyrimidin-2-yl)piperidine-4-carboxylic acid

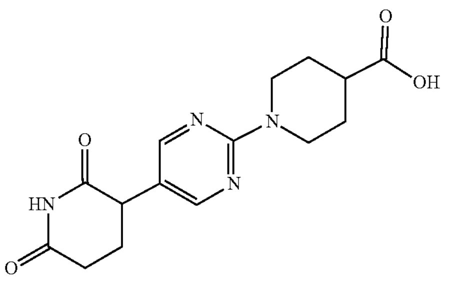 [SMILES: O=C1CCC(c2cnc(N3CCC(C(=O)O)CC3)nc2)C(=O)N1]

A mixture of tert-butyl 1-[5-(2,6-dioxopiperidin-3-yl)pyrimidin-2-yl]piperidine-4-carboxylate (780 mg, 2.083 mmol) in HCl (gas) in 1,4-dioxane (25 mL, 4M) was stirred at room temperature for 4 h. The resulting mixture was concentrated under reduced pressure. This resulted in rac-1-{5-[(3R)-2,6-dioxopiperidin-3-yl]pyrimidin-2-yl}piperidine-4-carboxylic acid (662.2 mg, crude) as a white solid. LCMS: ($C_{15}H_{18}N_4O_4$) desired mass=319.2; observed mass=319.1 [M+H]$^+$. $^1H$ NMR (400 MHz, $D_2O$) δ 8.46 (s, 2H), 4.39-4.31 (m, 2H), 4.06-3.97 (m, 1H), 3.84-3.60 (m, 1H), 3.51-3.25 (m, 2H), 2.87-2.70 (m, 3H), 2.43-2.18 (m, 2H), 2.14-2.06 (m, 2H), 1.88-1.60 (m, 2H).

Step 5: tert-butyl 1-(1-(5-(2,6-dioxopiperidin-3-yl)pyrimidin-2-yl)piperidine-4-carbonyl)-4-methylpiperidine-4-carboxylate

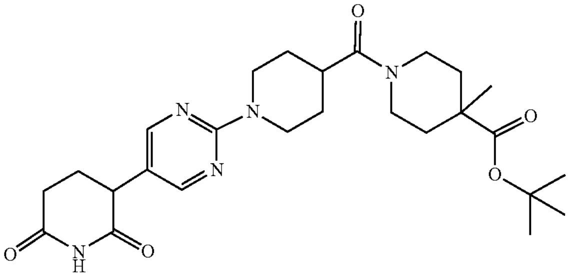 [SMILES: CC(C)(C)OC(=O)C1(C)CCN(C(=O)C2CCN(c3ncc(C4CCC(=O)NC4=O)cn3)CC2)CC1]

Prepared by similar procedures as Intermediate 5 (step 1) using 1-(5-(2,6-dioxopiperidin-3-yl)pyrimidin-2-yl)piperidine-4-carboxylic acid (100 mg, 0.314 mmmol) and tert-butyl 4-methylpiperidine-4-carboxylate (63 mg, 0.31 mmol) as starting materials. The title compound (TFA salt) was isolated as an off-white solid (81 mg, 52% yield). LCMS: [$C_{26}H_{37}N_5O_5$], desired mass=499.3, found: m/z=500.3 [M+H]$^+$.

Step 6: 1-(1-(5-(2,6-dioxopiperidin-3-yl)pyrimidin-2-yl)piperidine-4-carbonyl)-4-methylpiperidine-4-carboxylic acid

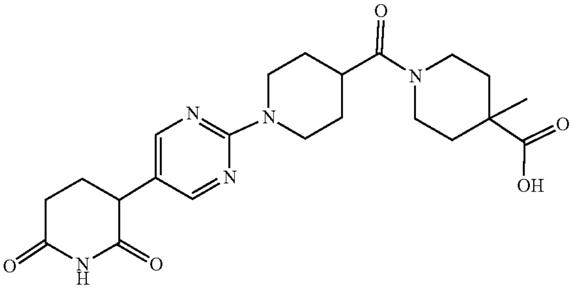 [SMILES: CC1(C(=O)O)CCN(C(=O)C2CCN(c3ncc(C4CCC(=O)NC4=O)cn3)CC2)CC1]

Prepared by similar procedures as Intermediate 5 (step 2) using tert-butyl 1-(1-(5-(2,6-dioxopiperidin-3-yl)pyrimidin-2-yl)piperidine-4-carbonyl)-4-methylpiperidine-4-carboxylate (81 mg, 0.16 mmol) as the starting material. The title compound (TFA salt) was isolated as an off-white solid (60 mg, 83% yield). LCMS: [$C_{22}H_{29}N_5O_5$], desired mass=443.2, found: m/z=444.2 [M+H]$^+$.

Intermediate 104

1-(4-(2,6-Dioxopiperidin-3-yl)-2-Methylphenyl) Piperidine-4-Carboxylic Acid

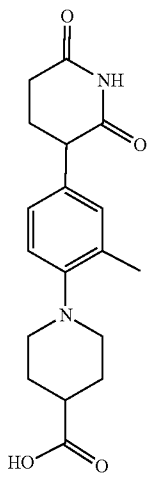

Step-1: ethyl 1-(4-chloro-2-methylphenyl) piperidine-4-carboxylate

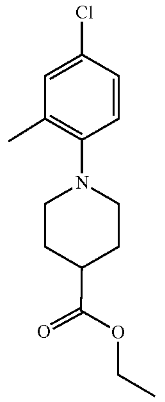 [SMILES: CCOC(=O)C1CCN(c2ccc(Cl)cc2C)CC1]

To a mixture of 1-bromo-4-chloro-2-methylbenzene (16 g, 77.866 mmol) and ethyl piperidine-4-carboxylate (12.24 g, 77.866 mmol) in toluene (15 mL) was added BINAP (4.85 g, 7.787 mmol), $Cs_2CO_3$ (76.11 g, 233.598 mmol) and $Pd_2(dba)_3$ (4.59 g, 7.787 mmol). The resulting mixture was stirred overnight at 100° C. under nitrogen atmosphere. The resulting mixture was concentrated under reduced pressure. The residue was purified by silica gel chromatography using a mobile phase of [PE and EtOAc] to provide 14.5 g (66.09%) of the title compound as a yellow oil. LCMS: ($C_{15}H_{20}ClNO_2$) desired mass=282.1; found: m/z=282.2 $[M+H]^+$.

Step-2: ethyl 1-{4-[2,6-bis(benzyloxy)pyridin-3-yl]-2-methylphenyl}piperidine-4-carboxylate

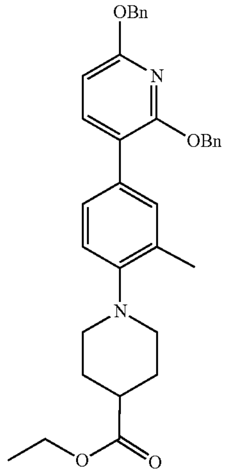 [SMILES: CCOC(=O)C1CCN(c2ccc(-c3ccc(OCc4ccccc4)nc3OCc3ccccc3)cc2C)CC1]

To a mixture of ethyl 1-(4-chloro-2-methylphenyl) piperidine-4-carboxylate (14 g, 49.684 mmol) and 2,6-bis(benzyloxy)-3-(4,4,5,5-tetramethyl-1,3,2-dioxaborolan-2-yl) pyridine (20.73 g, 49.684 mmol) in dioxane (20 mL) were added $K_2CO_3$ (13.73 g, 99.368 mmol) in $H_2O$ (4 mL) and $Pd(dppf)Cl_2$ (2.93 g, 4.968 mmol) at room temperature. The resulting mixture was stirred at 100° C. overnight under nitrogen atmosphere. The resulting mixture was concentrated under reduced pressure. The residue was purified by silica gel chromatography using a mobile phase of [PE and EtOAc] to provide 1.8 g (6.01%) of the title compound as a white solid. LCMS: ($C_{34}H_{36}N_2O_4$) desired mass=537.3; found: m/z=537.3 $[M+H]^+$.

Step-3: 1-{4-[2,6-bis(benzyloxy)pyridin-3-yl]-2-methyl phenyl}piperidine-4-carboxylic acid

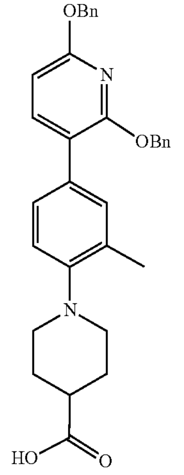

To a mixture of ethyl 1-{4-[2,6-bis(benzyloxy)pyridin-3-yl]-2-methylphenyl}piperidine-4-carboxylate (1.7 g, 3.168 mmol) in THF (10 mL) and EtOH (10 mL) was added LiOH (0.76 g, 31.680 mmol) in $H_2O$ (10 mL). The resulting mixture was stirred overnight at room temperature. The resulting mixture was concentrated under reduced pressure. The residue was neutralized to pH 6 with HCl (2M). The aqueous layer was extracted with EtOAc and concentrated. The residue was purified by reverse phase flash chromatography [ACN and $H_2O$ as mobile phase] to provide 1.3 g (80.69%) of the title compound as an off-white solid. LCMS: ($C_{32}H_{32}N_2O_4$) desired mass=509.2; found: m/z=509.4 $[M+H]^+$.

Step-4: 1-(4-(2,6-dioxopiperidin-3-yl)-2-methylphenyl)piperidine-4-carboxylic acid

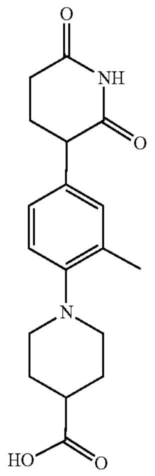

To a mixture of 1-{4-[2,6-bis(benzyloxy)pyridin-3-yl]-2-methyl phenyl}piperidine-4-carboxylic acid (1 g, 1.966 mmol) in THF (30 mL) was added Pd/C (1 g). The resulting mixture was stirred overnight at room temperature under hydrogen atmosphere. The resulting mixture was filtered. The filtrate was concentrated under reduced pressure. The residue was purified by reverse phase flash chromatography [ACN and $H_2O$ as mobile phase] to provide 494.8 mg (71.91%) of the title compound as a brown solid. LCMS: ($C_{18}H_{22}N_2O_4$) desired mass=331.2; found: m/z=331.1 $[M+H]^+$.

Intermediate 105

1-(4-(2,6-Dioxopiperidin-3-yl)-3-Methylphenyl) Piperidine-4-Carboxylic Acid

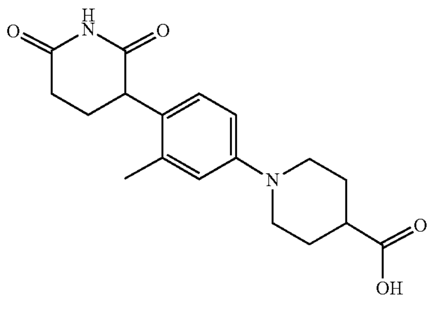 [SMILES: Cc1cc(N2CCC(C(=O)O)CC2)ccc1C1CCC(=O)NC1=O]

Step-1: tert-butyl 1-(4-bromo-3-methylphenyl)piperidine-4-carboxylate

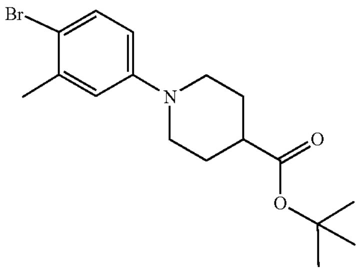 [SMILES: Cc1cc(N2CCC(C(=O)OC(C)(C)C)CC2)ccc1Br]

To a mixture of 1-bromo-4-iodo-2-methylbenzene (8 g, 26.942 mmol) in DMSO (30 mL) was added tert-butyl piperidine-4-carboxylate (4.99 g, 26.942 mmol), CuI (1.03 g, 5.388 mmol), L-proline (1.24 g, 10.777 mmol) and $K_2CO_3$ (14.89 g, 107.768 mmol) at room temperature. The resulting mixture was stirred at 80° C. for 2 h under nitrogen atmosphere. The resulting mixture was extracted with EtOAc (3×50 mL). The combined organic layers were washed with water (3×50 mL), dried over anhydrous $Na_2SO_4$. After filtration, the filtrate was concentrated under reduced pressure. The residue was purified by silica gel chromatography using a mobile phase of [PE and EtOAc] to provide 4.5 g (42.43%) of the title compound as a yellow solid. LCMS: ($C_{17}H_{24}BrNO_2$) desired mass=354.1; found: m/z=354.0 $[M+H]^+$.

Step-2: tert-butyl 1-{4-[2,6-bis(benzyloxy)pyridin-3-yl]-3-methylphenyl}piperidine-4-carboxylate

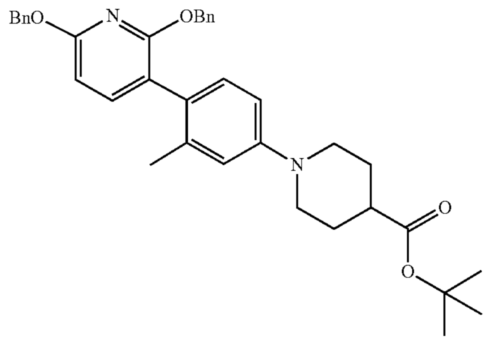 [SMILES: Cc1cc(N2CCC(C(=O)OC(C)(C)C)CC2)ccc1-c1ccc(OCc2ccccc2)nc1OCc1ccccc1]

To a mixture of tert-butyl 1-(4-bromo-3-methylphenyl) piperidine-4-carboxylate (4.5 g, 12.702 mmol) in dioxane (50 mL) and $H_2O$ (10 mL) were added 2,6-bis(benzyloxy)-3-(4,4,5,5-tetramethyl-1,3,2-dioxaborolan-2-yl)pyridine (5.83 g, 13.972 mmol), $Pd(dppf)Cl_2 \cdot CH_2Cl_2$ (2.07 g, 2.540 mmol) and $K_3PO_4$ (5.39 g, 25.404 mmol) at room temperature. The resulting mixture was stirred at 60° C. for 3 h under nitrogen atmosphere. The resulting mixture was concentrated under reduced pressure. The residue was purified by silica gel chromatography using a mobile phase of [PE and EtOAc] to provide 4.2 g (52.70%) of the title compound as a yellow oil. LCMS: ($C_{36}H_{40}N_2O_4$) desired mass=565.3; found: m/z=565.2 $[M+H]^+$.

Step-3: tert-butyl 1-[4-(2,6-dioxopiperidin-3-yl)-3-methylphenyl]piperidine-4-carboxylate

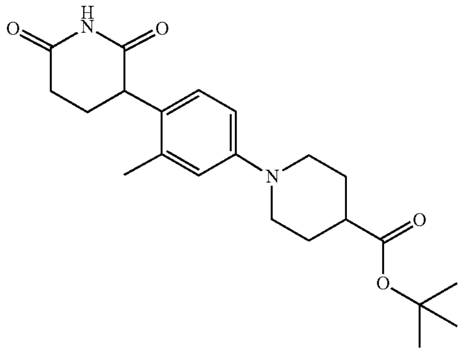 [SMILES: Cc1cc(N2CCC(C(=O)OC(C)(C)C)CC2)ccc1C1CCC(=O)NC1=O]

To a mixture of tert-butyl 1-{4-[2,6-bis(benzyloxy)pyridin-3-yl]-3-methylphenyl}piperidine-4-carboxylate (2 g, 3.542 mmol) in THF (50 mL) was added Pd/C (2 g) at room temperature. The resulting mixture was stirred at room temperature for 2 h under hydrogen atmosphere. The resulting mixture was filtered. The filtrate was concentrated under reduced pressure. The residue was purified by reverse phase flash chromatography [ACN and $H_2O$ as mobile phase] to provide 1.05 g (76.70%) of the title compound as a white solid. LCMS: ($C_{22}H_{30}N_2O_4$) desired mass=387.2; found: m/z=387.1 $[M+H]^+$.

Step-4: 1-(4-(2,6-dioxopiperidin-3-yl)-3-methylphenyl)piperidine-4-carboxylic acid

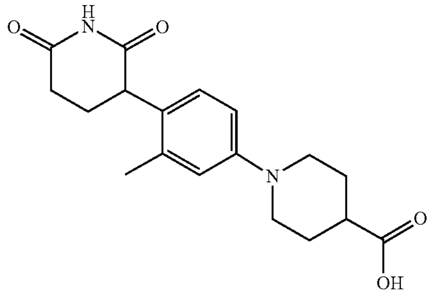 [SMILES: Cc1cc(N2CCC(C(=O)O)CC2)ccc1C1CCC(=O)NC1=O]

A mixture of tert-butyl 1-[4-(2,6-dioxopiperidin-3-yl)-3-methylphenyl]piperidine-4-carboxylate (1 g, 2.587 mmol) in HCl (gas) in 1,4-dioxane (20 mL, 4M) was stirred at room temperature for 2 h. The resulting mixture was concentrated under reduced pressure. The filtrate was concentrated under reduced pressure. The residue was purified by reverse phase flash chromatography [ACN and $H_2O$ as mobile phase] to provide 542.7 mg (62.92%) of the title compound as a white solid. LCMS: ($C_{18}H_{22}N_2O_4$) desired mass=331.1; found: m/z=331.3 $[M+H]^+$.

Intermediate 106

(1R,4R)-4-((4-(2,6-Dioxopiperidin-3-yl)Phenyl)Amino)Cyclohexane-1-Carboxylic Acid

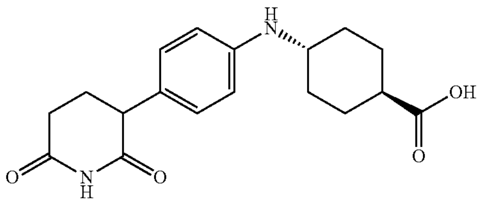 [SMILES: O=C1CCC(c2ccc(N[C@H]3CC[C@H](C(=O)O)CC3)cc2)C(=O)N1]

Step-1: (1r,4r)-4-[(4-bromophenyl)amino]cyclohexane-1-carboxylic acid

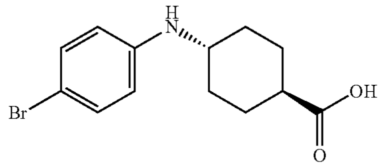 [SMILES: O=C(O)[C@H]1CC[C@H](Nc2ccc(Br)cc2)CC1]

To a mixture of methyl (1r,4r)-4-aminocyclohexane-1-carboxylate hydrochloride (40 g, 206.537 mmol) in toluene (300 mL) was added dibromobenzene (97.45 g, 413.074 mmol), $Pd_2(dba)_3$ (18.91 g, 20.654 mmol), BINAP (25.72 g, 41.307 mmol) and t-BuONa (39.70 g, 413.074 mmol) at room temperature. The resulting mixture was stirred at 100° C. for 2 h under a nitrogen atmosphere. The resulting mixture was concentrated under reduced pressure. The resulting mixture was diluted with water (100 mL). The aqueous layer was washed with EtOAc (3×100 mL). The aqueous layer was acidified to pH 4 with 1 M aqueous HCl solution and extracted with EtOAc (3×100 mL). The combine organic layers were concentrated under reduced pressure to afford the title compound (4.5 g) as a brown solid. LCMS: ($C_{13}H_{16}BrNO_2$) desired mass=298.0; found: m/z=297.9$[M+H]^+$.

Step-2: (1r,4r)-4-({4-[2,6-bis(benzyloxy)pyridin-3-yl]phenyl}amino)cyclohexane-1-carboxylic acid

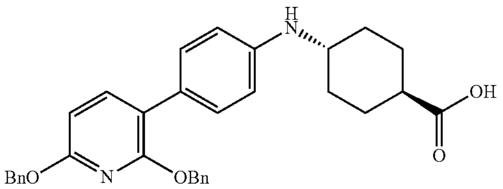 [SMILES: O=C(O)[C@H]1CC[C@H](Nc2ccc(-c3ccc(OCc4ccccc4)nc3OCc3ccccc3)cc2)CC1]

To a mixture of (1r,4r)-4-[(4-bromophenyl)amino]cyclohexane-1-carboxylic acid (5.5 g, 18.445 mmol) in dioxane (100 mL) and $H_2O$ (20 mL) was added 2,6-bis(benzyloxy)-3-(4,4,5,5-tetramethyl-1,3,2-dioxaborolan-2-yl)pyridine (7.70 g, 18.445 mmol), $Pd(dppf)Cl_2 \cdot CH_2Cl_2$ (3.01 g, 3.689 mmol) and $K_3PO_4$ (11.75 g, 55.335 mmol) at room temperature. The resulting mixture was stirred at 100° C. for 2 h under a nitrogen atmosphere. The resulting mixture was concentrated under reduced pressure. The residue was purified by C18 reverse phase column chromatography eluting with ACN/$H_2O$ (3/1) to afford the title compound (1.1 g, 11.14%) as a brown oil. LCMS: ($C_{32}H_{32}N_2O_4$) desired mass=509.2; found: m/z=509.2 $[M+H]^+$.

Step-3: (1r,4r)-4-((4-(2,6-dioxopiperidin-3-yl)phenyl)amino)cyclohexane-1-carboxylic acid

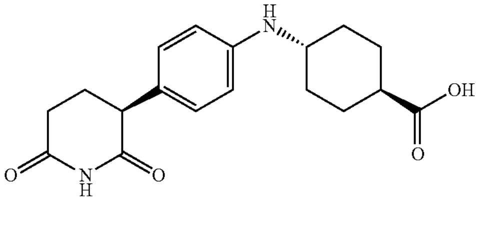 [SMILES: O=C1CC[C@@H](c2ccc(N[C@H]3CC[C@H](C(=O)O)CC3)cc2)C(=O)N1]

To a mixture of (1r,4r)-4-({4-[2,6-bis(benzyloxy)pyridin-3-yl]phenyl}amino)cyclohexane-1-carboxylic acid (1.06 g, 2.084 mmol) in EtOH (50 mL) and THF (50 mL) was added Pd/C (2.12 g) at room temperature. The resulting mixture was stirred at room temperature for 8 h under a hydrogen atmosphere (balloon). The resulting mixture was filtered. The filtrate was concentrated under reduced pressure to afford the title compound (503.4 mg) as an off-white solid. LCMS: ($C_{18}H_{22}N_2O_4$) desired mass=331.1; found: m/z=331.1$[M+H]^+$.

$^1H$ NMR (400 MHz, DMSO-$d_6$) δ 10.72 (s, 1H), 6.92-6.84 (m, 2H), 6.56-6.48 (m, 2H), 5.32 (s, 1H), 3.67-3.59 (m, 1H), 3.14 (s, 1H), 2.67-2.54 (m, 1H), 2.50-2.39 (m, 1H), 2.24-2.10 (m, 1H), 2.12-2.02 (m, 1H), 2.02-1.98 (m, 3H), 1.96-1.87 (m, 3H), 1.52-1.33 (m, 2H), 1.21-1.03 (m, 2H).

Intermediate 107

(1R,4R)-4-((5-(2,4-Dioxotetrahydropyrimidin-1(2H)-yl)Pyridin-2-yl)Amino)Cyclohexane-1-Carboxylic Acid

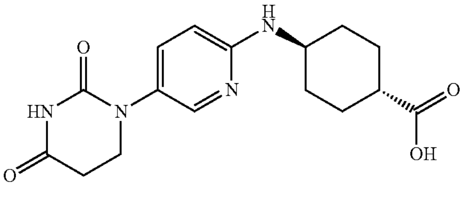 [SMILES: O=C1CCN(c2ccc(N[C@H]3CC[C@H](C(=O)O)CC3)nc2)C(=O)N1]

Step-1: of 3-[(6-chloropyridin-3-yl)amino]propanoic acid

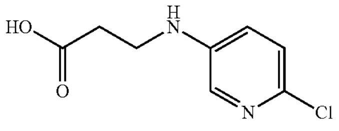 [SMILES: O=C(O)CCNc1ccc(Cl)nc1]

To a mixture of 6-chloropyridin-3-amine (30 g, 233.354 mmol) in toluene (300 mL) was added acrylic acid (16.82 g, 233.354 mmol) at room temperature. The resulting mixture was stirred at 110° C. overnight. The resulting mixture was concentrated under reduced pressure to afford the title compound as a brown oil. LCMS: ($C_8H_9ClN_2O_2$) desired mass=201.0; found: m/z=201.0 $[M+H]^+$.

Step-2: Methyl 3-[(6-chloropyridin-3-yl)amino]propanoate

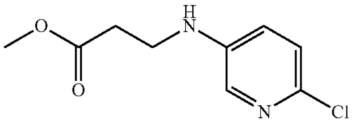

To a mixture of 3-[(6-chloropyridin-3-yl)amino]propanoic acid (30 g, 149.536 mmol) in MeOH (300 mL) was added $SOCl_2$ (76 mL, 1046.752 mmol) at 0° C. The resulting mixture was warmed to room temperature and stirred for 1 h. The resulting mixture was concentrated under reduced pressure. The residue was purified by silica gel column chromatography, eluting with PE/EtOAc (1/1) to afford the title compound (18 g, 44.86%) as a brown oil. LCMS: ($C_9H_{11}ClN_2O_2$) desired mass=215.1; found: m/z=215.0 $[M+H]^+$.

Step-3: Methyl 3-[carbamoyl(6-chloropyridin-3-yl)amino]propanoate

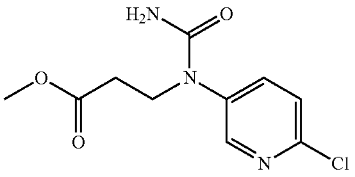 [SMILES: COC(=O)CCN(C(N)=O)c1ccc(Cl)nc1]

To a mixture of methyl 3-[(6-chloropyridin-3-yl)amino]propanoate (18 g, 83.857 mmol) in AcOH (20 mL) and DCM (20 mL) was added potassium cyanate (20.41 g, 251.571 mmol) at room temperature. The resulting mixture was stirred at room temperature for 16 h. The resulting mixture was extracted with $CH_2Cl_2$ (3×40 mL). The combined organic layers were washed with water (3×10 mL), dried over anhydrous $Na_2SO_4$, filtered, and the filtrate was concentrated under reduced pressure. The residue was purified by C18 reverse phase chromatography eluting with ACN/$H_2O$ (1/1) to afford the title compound (8 g, 29.62%) as a white solid. LCMS: ($C_{10}H_{12}ClN_3O_3$) desired mass=258.1; found: m/z=258.0 $[M+H]^+$.

Step-4: 1-(6-chloropyridin-3-yl)-1,3-diazinane-2,4-dione

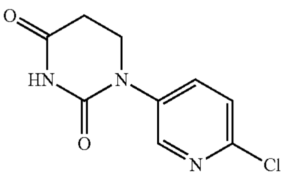 [SMILES: O=C1CCN(c2ccc(Cl)nc2)C(=O)N1]

To a mixture of methyl 3-[carbamoyl(6-chloropyridin-3-yl)amino]propanoate (8 g, 31.047 mmol) in THF (30 mL) was added potassium trimethylsilanolate (7.97 g, 62.094 mmol). The resulting mixture was stirred at room temperature for 1 h. The resulting mixture was extracted with EtOAc three times. The combined organic layers were washed with water, and dried over anhydrous $Na_2SO_4$. After filtration, the filtrate was concentrated under reduced pressure to provide the title compound (2 g) as a white solid. LCMS: ($C_9H_8ClN_3O_2$) desired mass=226.0; found: m/z=226.0 $[M+H]^+$.

Step-5: tert-butyl (1r,4r)-4-{[5-(2,4-dioxo-1,3-diazinan-1-yl)pyridin-2-yl]amino}cyclohexane-1-carboxylate

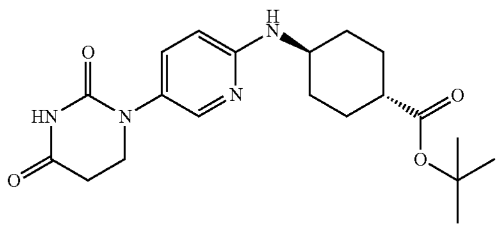 [SMILES: CC(C)(C)OC(=O)[C@H]1CC[C@H](Nc2ccc(N3CCC(=O)NC3=O)cn2)CC1]

To a mixture of 1-(6-chloropyridin-3-yl)-1,3-diazinane-2,4-dione (1.3 g, 5.762 mmol) and tert-butyl (1r,4r)-4-aminocyclohexane-1-carboxylate (1.38 g, 6.914 mmol) in 1,4-dioxane (10 mL) was added $Cs_2CO_3$ (3.75 g, 11.524 mmol) and Pd-PEPPSI-IPentCl 2-methylpyridine (o-picoline) (0.24 g, 0.288 mmol) at room temperature under a nitrogen atmosphere. The resulting mixture was stirred at 100° C. for 2 h under a nitrogen atmosphere. The residue was purified by silica gel column chromatography, eluting with EtOAc/MeOH (10/1) to afford the title compound (920 mg, 39.05%) as a white solid. LCMS: ($C_{20}H_{28}N_4O_4$) desired mass=389.2; found: m/z=389.2 $[M+H]^+$.

Step-6: (1r,4r)-4-((5-(2,4-dioxotetrahydropyrimidin-1(2h)-yl)pyridin-2-yl)amino)cyclohexane-1-carboxylic acid

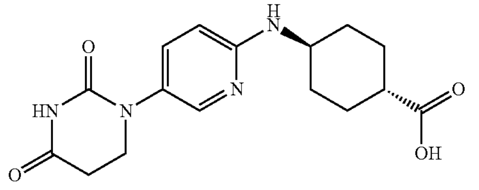 [SMILES: O=C1CCN(c2ccc(N[C@H]3CC[C@H](C(=O)O)CC3)nc2)C(=O)N1]

A mixture of tert-butyl (1r,4r)-4-{[5-(2,4-dioxo-1,3-diazinan-1-yl)pyridin-2-yl]amino}cyclohexane-1-carboxylate (830 mg, 2.137 mmol) and HCl in 1,4-dioxane (20 mL, 4M) was stirred at room temperature for 3 h. The resulting mixture was concentrated under reduced pressure to afford the title compound (920 mg, crude) as a white solid. LCMS: ($C_{16}H_{20}N_4O_4$) desired mass=333.2; found: m/z=333.1 $[M+H]^+$.

Intermediate 108

3-(3-methyl-2-oxo-4-(3-(piperidin-4-yloxy)prop-1-yn-1-yl)-2,3-dihydro-1h-benzo[d]imidazol-1-yl)piperidine-2,6-dione

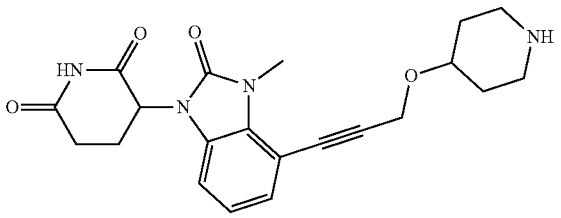 [SMILES: Cn1c(=O)n(C2CCC(=O)NC2=O)c2cccc(C#CCOC3CCNCC3)c21]

Step-1: tert-butyl 4-((3-(1-(2,6-dioxopiperidin-3-yl)-3-methyl-2-oxo-2,3-dihydro-1H-benzo[d]imidazol-4-yl)prop-2-yn-1-yl)oxy)piperidine-1-carboxylate

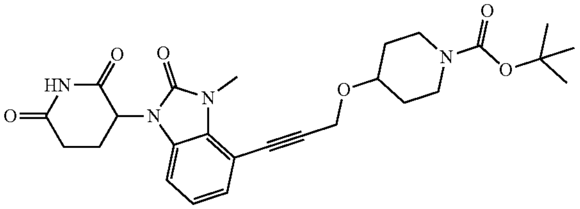 [SMILES: Cn1c(=O)n(C2CCC(=O)NC2=O)c2cccc(C#CCOC3CCN(C(=O)OC(C)(C)C)CC3)c21]

To a solution of 3-(4-bromo-3-methyl-2-oxo-2,3-dihydro-1H-benzo[d]imidazol-1-yl)piperidine-2,6-dione (30.0 g, 88.7 mmol, 1.00 eq) in DMF (300 mL) was added tert-butyl 4-(prop-2-yn-1-yloxy)piperidine-1-carboxylate (42.5 g, 177 mmol, 2.00 eq), CuI (1.69 g, 8.87 mmol, 0.10 eq), $Cs_2CO_3$ (86.7 g, 266 mmol, 3.00 eq), and 4 Å molecular sieves (10.0 g), and the mixture was stirred at 25° C. for 30 min. $Pd(PPh_3)_2Cl_2$ (1.04 g, 1.48 mmol, 0.10 eq) was added in one portion at 25° C., then the reaction was stirred at 80° C. for 3 hrs under $N_2$. The reaction mixture was cooled to room temperature and filtered, then the filtrate was poured into ice water (2.00 L), and extracted with EtOAc (500 mL×3). The combined organic layers were dried over $Na_2SO_4$, filtered and concentrated under vacuum. The residue was purified by column chromatography ($SiO_2$, Petroleum ether/Ethyl acetate=10/1 to 2/1) to give the title compound (29.5 g, 59.4 mmol, 66.9% yield) as a light yellow solid.

Step-2: 3-(3-methyl-2-oxo-4-(3-(piperidin-4-yloxy)prop-1-yn-1-yl)-2,3-dihydro-1H-benzo[d]imidazol-1-yl)piperidine-2,6-dione

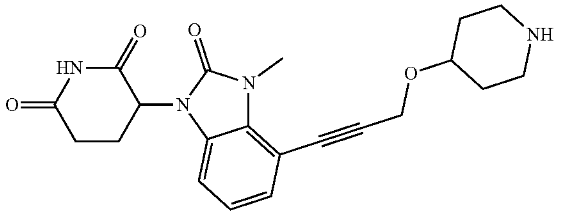 [SMILES: Cn1c(=O)n(C2CCC(=O)NC2=O)c2cccc(C#CCOC3CCNCC3)c21]

To a solution of tert-butyl 4-((3-(1-(2,6-dioxopiperidin-3-yl)-3-methyl-2-oxo-2,3-dihydro-1H-benzo[d]imidazol-4-yl)prop-2-yn-1-yl)oxy)piperidine-1-carboxylate (29.5 g, 59.4 mmol, 1.00 eq) in DCM (300 mL) was added TFA (20.3 g, 178 mmol, 13.2 mL, 3.00 eq), then the mixture was stirred at 25° C. for 2 hrs. MTBE (400 mL) was added to the mixture, and the resulting precipitate was isolated by filtration. The filter cake was dried under reduced pressure to give the title compound (27.5 g, 48.2 mmol, 81.1% yield, 89.4% purity, TFA salt) as a gray solid. LCMS: $(C_{21}H_{24}N_4O_4)$ desired mass=396.2; observed mass=397.3 $[M+H]^+$.

Intermediate 109

1-[5-(2,6-Dioxopiperidin-3-yl)-6-Methylpyridin-2-yl]Piperidine-4-Carboxylic Acid

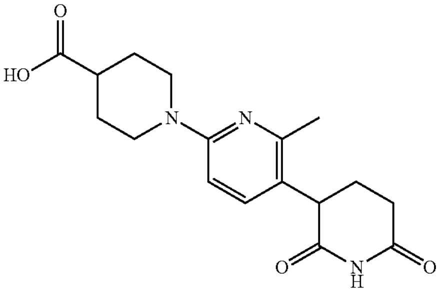 [SMILES: Cc1nc(N2CCC(C(=O)O)CC2)ccc1C1CCC(=O)NC1=O]

Step 1: tert-butyl 1-(5-bromo-6-methylpyridin-2-yl)piperidine-4-carboxylate

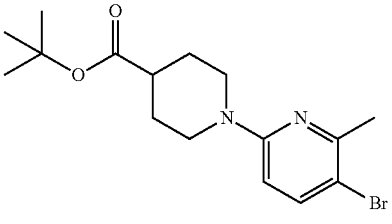 [SMILES: Cc1nc(N2CCC(C(=O)OC(C)(C)C)CC2)ccc1Br]

3-bromo-6-fluoro-2-methylpyridine (0.31 mL, 0.50 g, 2.63 mmol) and tert-butyl piperidine-4-carboxylate (0.49 g, 2.63 mmol) were dissolved in DMSO (5.00 mL) and N,N-diisopropylethylamine (0.92 mL, 5.26 mmol). The reaction was heated to 120° C. for 4 hours. The crude reaction mixture was purified by reverse phase flash column chromatography to afford the title compound (0.822 g, 87% yield).

Step 2: tert-butyl 1-(2',6'-bis(benzyloxy)-2-methyl-[3,3'-bipyridin]-6-yl)piperidine-4-carboxylate

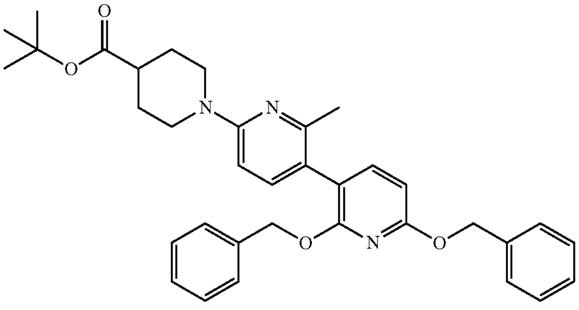 [SMILES: Cc1nc(N2CCC(C(=O)OC(C)(C)C)CC2)ccc1-c1ccc(OCc2ccccc2)nc1OCc1ccccc1]

Tert-butyl 1-(5-bromo-6-methylpyridin-2-yl)piperidine-4-carboxylate (0.82 g, mmol), Pd(dppf)Cl2-DCM (0.46 g, 0.5629 mmol), cesium carbonate 1N solution (7.04 mL, 2.29 g, 7.0368 mmol), 2,6-bis(benzyloxy)pyridin-3-ylboronic acid (0.94 g, 2.8147 mmol), and dioxane (5.00 mL) were combined in a sealed vial. The vial was purged with nitrogen gas and stirred for 60 minutes at 100° C. The reaction was poured over brine, extracted with ethyl acetate, filtered, concentrated on to silica, then purified by flash column chromatography to afford the title compound (1.23 g, 94% yield).

Step 3: tert-butyl 1-(5-(2,6-dioxopiperidin-3-yl)-6-methylpyridin-2-yl)piperidine-4-carboxylate

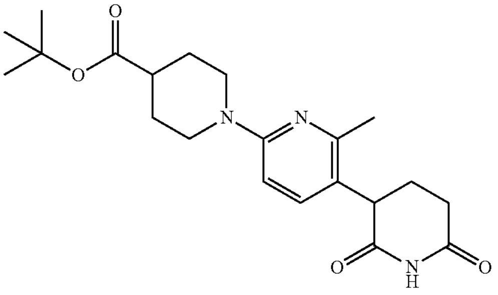 [SMILES: Cc1nc(N2CCC(C(=O)OC(C)(C)C)CC2)ccc1C1CCC(=O)NC1=O]

Tert-butyl 1-[2',6'-bis(benzyloxy)-2-methyl-[3,3'-bipyridin]-6-yl]piperidine-4-carboxylate (1.00 g, mmol) was dissolved in EtOH (5.00 mL) and THF (5.00 mL). Palladium on carbon 10% (0.19 g, 0.1768 mmol) was added and the reaction was stirred under hydrogen balloon for 12 hours. The reaction was filtered through celite and concentrated to afford the title compound (0.684 g, 97% yield).

Step 4: 1-[5-(2,6-dioxopiperidin-3-yl)-6-methylpyridin-2-yl]piperidine-4-carboxylic acid

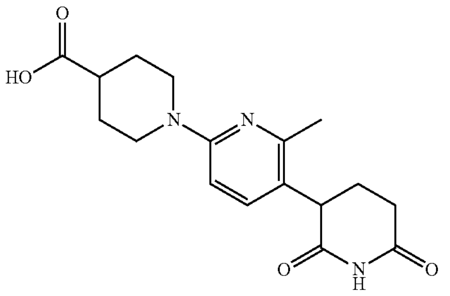 [SMILES: Cc1nc(N2CCC(C(=O)O)CC2)ccc1C1CCC(=O)NC1=O]

Tert-butyl 1-(5-(2,6-dioxopiperidin-3-yl)-6-methylpyridin-2-yl)piperidine-4-carboxylate (0.684 g, 1.677 mmol) was dissolved in DCM (10.0 mL). 4M HCl in dioxanes (4.0 mL) was added and the reaction was stirred at room temperature overnight. The crude reaction mixture was evaporated on to silica gel and purified by reverse phase flash column chromatography to afford the title compound (0.551 g, 95% yield). LCMS: $C_{17}H_{21}N_3O_4$, desired mass=331.4, found: m/z=332.3 $[M+H]^+$.

Intermediate A

Tert-butyl 6-{4-chloro-3-isopropylimidazo[4,5-c]pyridin-6-yl}-2-oxo-1-[(1s,3s)-3-(piperidin-1-yl)cyclobutyl]spiro[indole-3,4'-piperidine]-1'-carboxylate

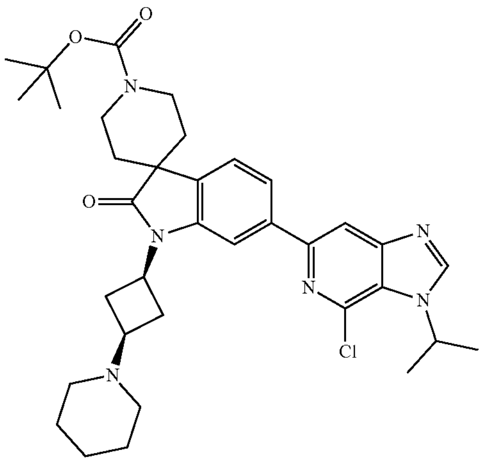 [SMILES: CC(C)n1cnc2cc(-c3ccc4c(c3)N([C@H]3C[C@@H](N5CCCCC5)C3)C(=O)C43CCN(C(=O)OC(C)(C)C)CC3)nc(Cl)c21]

Tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate (Intermediate 0558 in WO2020092528A1) (2.00 g, 3.5 mmol), tetrakis(triphenylphosphine) palladium(0) (0.41 g, 0.35 mmol), 6-bromo-4-chloro-3-isopropyl-3H-imidazo[4,5-c]pyridine (Intermediate 0540 in WO2020092528A1) (0.97 g, 3.54 mmol), sodium carbonate (1.50 g, 14.15 mmol), water (6.37 mL, 6.37 g, 353.63 mmol), and 1,2-dimethoxyethane (29.41 mL, 25.50 g, 282.91 mmol) were combined in a microwave vial, sealed, and irradiated at 100° C. for 90 mins. The reaction mixture was filtered then concentrated onto silica gel and purified by normal phase flash column chromatography to afford the title compound (1.06 g, 94% yield). LCMS: $C_{35}H_{45}ClN_6O_3$ desired mass: 633.2, found: m/z=633.8 $[M+H]^+$.

Intermediate B

6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one

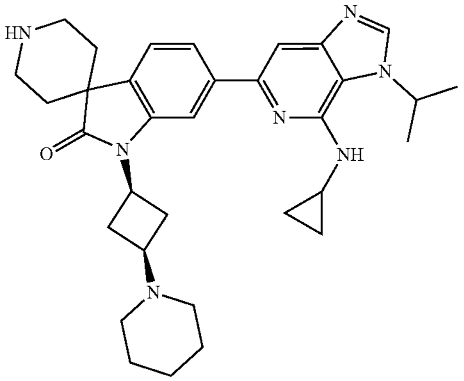 [SMILES: CC(C)n1cnc2cc(-c3ccc4c(c3)N([C@H]3C[C@@H](N5CCCCC5)C3)C(=O)C43CCNCC3)nc(NC3CC3)c21]

Step 1: 6-bromo-N-cyclopropyl-3-isopropylimidazo[4,5-c]pyridin-4-amine 6-bromo-4-fluoro-3-isopropyl-3H-imidazo[4,5-c]pyridine (Intermediate 0542 in WO2020092528A1) (1.5 g, 5.81 mmol) and aminocyclopropane (3.41 g, 59.8 mmol) were combined and heated at 50° C. for 48 hours. The reaction mixture was cooled to RT and purified by silica gel chromatography to afford the title compound (1.7 g, 98% yield). LCMS: $C_{12}H_{15}BrN_4$ desired mass: 295.2, found: m/z=297.0 $[M+H]^+$.

Step 2: 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one Tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate (Intermediate 0558 in WO2020092528A1) (3.50 g, 6.2 mmol), tetrakis(triphenylphosphine) palladium(0) (0.72 g, 0.62 mmol), 6-bromo-N-cyclopropyl-3-isopropylimidazo[4,5-c]pyridin-4-amine (1.8, 6.2 mmol), sodium carbonate (2.62 g, 24.75 mmol), water (11.15 mL, 11.15 g, 618.86 mmol), and 1,2-dimethoxyethane (51.46 mL, 44.62 g, 495.08 mmol) were combined in a microwave vial, sealed, and irradiated at 100° C. for 90 mins. The reaction mixture was filtered then concentrated onto silica gel and purified by normal phase flash column chromatography. This material was dissolved in DCM (20 mL) and treated with 4M HCl (6 mL). The reaction mixture was stirred at room temperature for 4 hours then concentrated onto silica gel and purified by reverse phase flash chromatography to afford the title compound (2.45 g, 72% yield). LCMS: $C_{33}H_{43}N_7O$ desired mass: 553.8, found: m/z=554.7 $[M+H]^+$.

Intermediate C

6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one

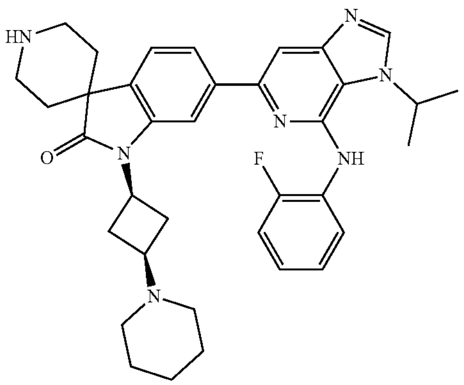

tert-butyl 6-{4-chloro-3-isopropylimidazo[4,5-c]pyridin-6-yl}-2-oxo-1-[(1s,3s)-3-(piperidin-1-yl)cyclobutyl]spiro[indole-3,4'-piperidine]-1'-carboxylate (1.50 g, 2.37 mmol), tris(dibenzylideneacetone)dipalladium(0) (0.22 g, 0.24 mmol), xantphos (0.14 g, 0.24 mmol), cesium carbonate (1.93 g, 5.92 mmol), and 2-fluoroaniline (0.23 mL, 0.26 g, 2.37 mmol) were combined in two microwave vials and irradiated at 120° C. for 60 minutes. The reaction mixtures were poured over brine and extracted with ethyl acetate. The Boc protected product was isolated by normal phase flash chromatography (hexanes/ethyl acetate). The resulting material was dissolved in DCM (15.00 mL), treated with 4M HCl in dioxane and stirred overnight. The reaction mixture was concentrated onto silica gel and purified by reverse phase flash column chromatography to afford the title compound (1.2 g, 81% yield). LCMS: $C_{36}H_{46}FN_7O$ desired mass: 607.8, found: m/z=608.7 $[M+H]^+$.

Intermediate D

6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one

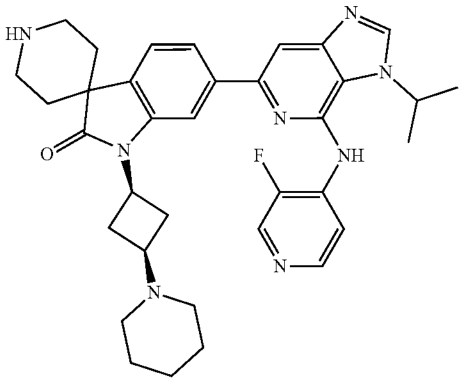 [SMILES: CC(C)n1cnc2cc(-c3ccc4c(c3)N([C@H]3C[C@@H](N5CCCCC5)C3)C(=O)C43CCNCC3)nc(Nc3ccncc3F)c21]

tert-butyl 6-{4-chloro-3-isopropylimidazo[4,5-c]pyridin-6-yl}-2-oxo-1-[(1s,3s)-3-(piperidin-1-yl)cyclobutyl]spiro[indole-3,4'-piperidine]-1'-carboxylate (0.2 g, 0.32 mmol), tris(dibenzylideneacetone)dipalladium(0) (29.0 mg, 0.03 mmol), xantphos (18.3 mg, 0.03 mmol), cesium carbonate (0.26 g, 0.79 mmol), and 3-fluoropyridin-4-amine (35.4 mg, 0.32 mmol) were combined and irradiated at 120° C. for 60 minutes. The reaction mixture was poured over brine and extracted with ethyl acetate. The Boc protected product was isolated by normal phase flash column (hexanes/ethyl acetate). The resulting material was dissolved in DCM (15.00 mL), treated with 4M HCl in dioxane and stirred overnight. The reaction mixture was concentrated on to silica gel and purified by reverse phase flash column chromatography to afford the title compound (0.150 g, 67% yield). LCMS: $C_{35}H_{41}FN_8O$ desired mass: 608.8, found: m/z=609.5 $[M+H]^+$.

Intermediate E

6-[3-isopropyl-4-(oxan-4-ylamino)imidazo[4,5-c]pyridin-6-yl]-1-[(1s,3s)-3-(piperidin-1-yl)cyclobutyl]spiro[indole-3,4'-piperidin]-2-one

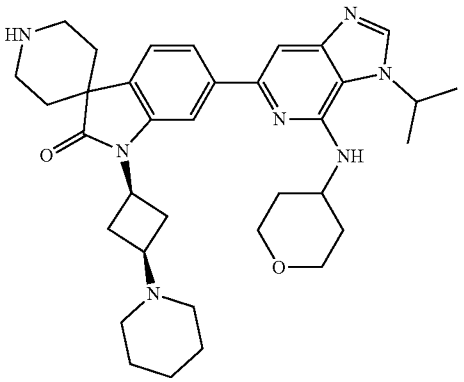 [SMILES: CC(C)n1cnc2cc(-c3ccc4c(c3)N([C@H]3C[C@@H](N5CCCCC5)C3)C(=O)C43CCNCC3)nc(NC3CCOCC3)c21]

Step 1: 6-bromo-3-isopropyl-n-(oxan-4-yl)imidazo[4,5-c]pyridin-4-amine 6-bromo-4-fluoro-3-isopropyl-3H-imidazo[4,5-c]pyridine (Intermediate 0542 in WO2020092528A1) (0.50 g, 1.94 mmol) and oxan-4-amine (0.98 g, 9.69 mmol) were combined in a microwave vial with DIEA (0.5 mL) and NMP (3.00 mL). The vial was irradiated at 120° C. for 3 hours. The reaction mixture was purified by reverse phase flash column chromatography to afford the title compound (0.21 g, 32% yield). LCMS: $C_{14}H_{19}BrN_4O$ desired mass: 339.2, found: m/z=341.2 $[M+H]^+$.

Step 2: 6-[3-isopropyl-4-(oxan-4-ylamino)imidazo[4,5-c]pyridin-6-yl]-1-[(1s,3s)-3-(piperidin-1-yl)cyclobutyl]spiro[indole-3,4'-piperidin]-2-one Tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate (Intermediate 0558 in WO2020092528A1) (0.35 g, 0.62 mmol), tetrakis(triphenylphosphine) palladium(0) (0.07 g, 0.06 mmol), 6-bromo-3-isopropyl-n-(oxan-4-yl)imidazo[4,5-c]pyridin-4-amine (0.2 g, 0.62 mmol), sodium carbonate (0.26 g, 2.5 mmol), water (1.11 mL, 62.0 mmol), and 1,2-dimethoxyethane (5.0 mL, 50.0 mmol) were combined in a microwave vial, sealed, and irradiated at 100° C. for 90 mins. The reaction mixture was filtered then concentrated onto silica gel and purified by normal phase flash column chromatography. This material was dissolved in DCM (20 mL) and treated with 4M HCl (6 mL). The reaction mixture was stirred at room temperature for 4 hours then concentrated onto silica gel and purified by reverse phase flash column to afford the title compound (0.3 g, 81% yield). LCMS: $C_{35}H_{47}N_7O_2$ desired mass: 597.8, found: m/z=598.7 $[M+H]^+$.

Intermediate F

6-{4-[(2-fluorophenyl)amino]-3-isopropylimidazo[4,5-c]pyridin-6-yl}-1-[(1s,3s)-3-(dimethylamino)cyclobutyl]spiro[indole-3,4'-piperidin]-2-one

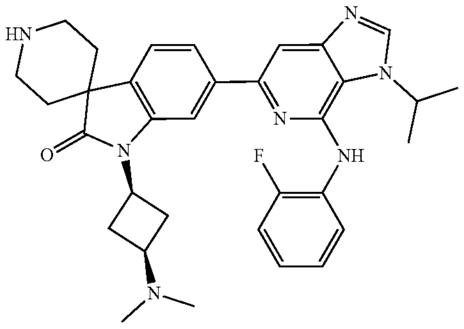 [SMILES: CC(C)n1cnc2cc(-c3ccc4c(c3)N([C@H]3C[C@@H](N(C)C)C3)C(=O)C43CCNCC3)nc(Nc3ccccc3F)c21]

Step 1: tert-butyl 2-oxo-1-[(1s,3s)-3-(dimethylamino)cyclobutyl]-6-(4,4,5,5-tetramethyl-1,3,2-dioxaborolan-2-yl)spiro[indole-3,4'-piperidine]-1'-carboxylate Tert-butyl 2-oxo-1-(3-oxocyclobutyl)-6-(4,4,5,5-tetramethyl-1,3,2-dioxaborolan-2-yl)spiro[indoline-3,4'-piperidine]-r-carboxylate (Intermediate 0557 in WO2020092528A1) (1.0 g, 2.0 mmol, acetic acid (0.46 mL, 0.48 g, 8.06 mmol), sodium bis(acetyloxy)boranuidyl acetate (2.56 g, 12.09 mmol), and dimethylamine (0.095 g. 2.0 mmol) were dissolved in DCM (25.0 mL) and stirred at room temperature for 3 hours. The reaction mixture was poured over saturated ammonium chloride and extracted with ethyl acetate. The organic layer was concentrated to afford the title compound as a white foam (0.85 g, 88% yield). LCMS: $C_{29}H_{44}BN_3O_5$ desired mass: 525.5, found: m/z=526.6 $[M+H]^+$.

Step 2: tert-butyl 6-{4-chloro-3-isopropylimidazo[4,5-c]pyridin-6-yl}-2-oxo-1-[(1s,3s)-3-(dimethylamino)cyclobutyl]spiro[indole-3,4'-piperidine]-1'-carboxylate tert-butyl 2-oxo-1-[(1s,3s)-3-(dimethylamino)cyclobutyl]-6-(4,4,5,5-tetramethyl-1,3,2-dioxaborolan-2-yl)spiro[indole-3,4'-piperidine]-1'-carboxylate (90.0 mg, 1.71 mmol) tetrakis(triphenylphosphine) palladium(0) (20.0 mg, 0.17 mmol), 6-bromo-4-chloro-3-isopropyl-3H-imidazo[4,5-c]pyridine (Intermediate 0540 in WO2020092528A1) (470 mg g, 0.17 mmol), sodium carbonate (0.73 g, 6.85 mmol), water (3.09 mL, 171.5 mmol), and 1,2-dimethoxyethane (14.1 mL, 137.0 mmol) were combined in a microwave vial, sealed, and irradiated at 100° C. for 90 mins. The reaction mixture was filtered then concentrated onto silica gel and purified by normal phase flash column chromatography to afford the title compound (0.795 g, 74% yield). LCMS: $C_{32}H_{41}ClN_6O_3$ desired mass: 593.2, found: m/z=593.7 $[M+H]^+$.

Step 3: 6-{4-[(2-fluorophenyl)amino]-3-isopropylimidazo[4,5-c]pyridin-6-yl}-1-[(1s,3s)-3-(dimethylamino)cyclobutyl]spiro[indole-3,4'-piperidin]-2-one tert-butyl 6-{4-chloro-3-isopropylimidazo[4,5-c]pyridin-6-yl}-2-oxo-1-[(1s,3s)-3-(dimethylamino)cyclobutyl]spiro[indole-3,4'-piperidine]-1'-carboxylate (0.25 g, 1.68 mmol), tris(dibenzylideneacetone)dipalladium(0) (0.04 g, 0.04 mmol), xantphos (0.02 g, 0.04 mmol), caesium carbonate (0.34 g, 1.05 mmol), and 2-fluoroaniline (0.04 mL, 1.68 mmol) and Dioxane (15.0 mL) were combined in a microwave vial and irradiated at 120° C. for 60 minutes. The reaction mixture was poured over brine and extracted with ethyl acetate. The Boc protected product was isolated by normal phase flash column (hexanes/ethyl acetate). The resulting material was dissolved in DCM (15.00 mL), treated with 4M HCl in dioxane and stirred overnight. The reaction mixture was evaporated to dryness to afford the title compound as an off-white solid (0.232 g, 21% yield). LCMS: $C_{33}H_{38}FN_7O$ desired mass: 567.7, found: m/z=568.5 $[M+H]^+$.

Intermediate G

6-[4-(2-fluorophenoxy)-3-isopropylimidazo[4,5-c]pyridin-6-yl]-1-[(1s,3s)-3-(piperidin-1-yl)cyclobutyl]spiro[indole-3,4'-piperidin]-2-one

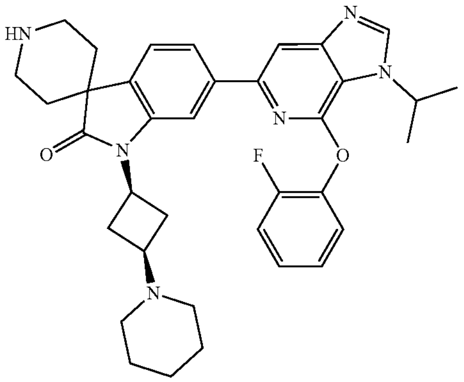 [SMILES: CC(C)n1cnc2cc(-c3ccc4c(c3)N([C@H]3C[C@@H](N5CCCCC5)C3)C(=O)C43CCNCC3)nc(Oc3ccccc3F)c21]

Step 1: 6-bromo-4-(2-fluorophenoxy)-3-isopropylimidazo[4,5-c]pyridine

To a suspension of 2-fluorophenol (0.354 mL, 3.97 mmol) and $K_2CO_3$ (1.097 g, 7.937 mmol) in N-methyl-2-pyrrolidone (7.94 mL, 0.5 M) stirred for 0.5 h at 25° C. was added 6-bromo-4-chloro-3-isopropyl-3H-imidazo[4,5-c]pyridine (Intermediate 0540 in WO2020092528A1) (1.199 g, 4.367 mmol) at 25° C. The reaction mixture was stirred at 90° C. for 2 days and then diluted with DCM (50 mL) and washed with water (3×100 mL) and brine (2×100 mL). The organic layer was dried over $Na_2SO_4$ and concentrated to dryness under reduced pressure. The residue was purified by silica gel chromatography using a mobile phase of hexane and EtOAc to provide 1.0 g (70% yield) of the title compound as pale beige solid. LCMS: $C_{15}H_{13}BrFN_3O$, desired mass=349.0, found: m/z=350.0 [M+H]$^+$.

Step 2: 6-[4-(2-fluorophenoxy)-3-isopropylimidazo [4,5-c]pyridin-6-yl]-1-[(1s,3s)-3-(piperidin-1-yl) cyclobutyl]spiro[indole-3,4'-piperidin]-2-one tert-butyl 2-oxo-1-[(1s,3s)-3-(piperidin-1-yl)cyclobutyl]-6-(4,4,5,5-tetramethyl-1,3,2-dioxaborolan-2-yl)spiro[indole-3,4'-piperidine]-1'-carboxylate (0.5 g, 0.884 mmol), tetrakis(triphenylphosphine) palladium(0) (0.1 g, 0.088 mmol), 6-bromo-4-(2-fluorophenoxy)-3-isopropylimidazo [4,5-c]pyridine (0.31 g, 0.884 mmol), sodium carbonate (0.37 g, 3.53 mmol), water (1.6 mL, 88.0 mmol), and 1,2-dimethoxyethane (7.35 mL, 70.7 mmol) were combined in a microwave vial, sealed, and irradiated at 100° C. for 90 mins. The reaction mixture was filtered then concentrated onto silica gel and purified by normal phase flash column chromatography. This material was dissolved in DCM (20 mL) and treated with 4M HCl (6 mL). The reaction mixture was stirred at room temperature for 4 hours then concentrated onto silica gel and purified by reverse phase flash column to afford the title compound (0.4 g, 76% yield). LCMS: $C_{36}H_{41}FN_6O_2$ desired mass: 608.8, found: m/z=609.6 [M+H]$^+$.

Intermediate H

6-[4-(Cyclopropylamino)-3-Isopropylimidazo[4,5-C] Pyridin-6-yl]-1'-[2-(Piperidin-4-yl)Acetyl]-1-[(1S, 3S)-3-(Piperidin-1-yl)Cyclobutyl]Spiro[Indole-3,4'-Piperidin]-2-One

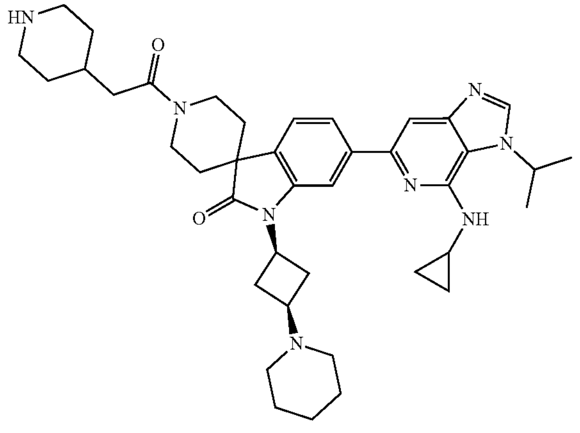 [SMILES: CC(C)n1cnc2cc(-c3ccc4c(c3)N([C@H]3C[C@@H](N5CCCCC5)C3)C(=O)C43CCN(C(=O)CC4CCNCC4)CC3)nc(NC3CC3)c21]

Step 1: tert-butyl 4-(2-{6-[4-(cyclopropylamino)-3-isopropylimidazo[4,5-c]pyridin-6-yl]-2-oxo-1-[(1s, 3s)-3-(piperidin-1-yl)cyclobutyl]spiro[indole-3,4'-piperidin]-1'-yl}-2-oxoethyl)piperidine-1-carboxylate

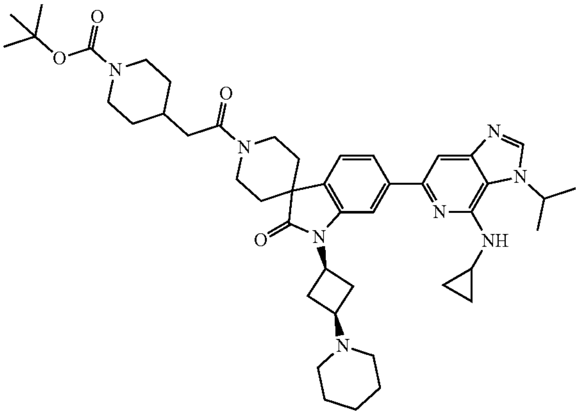 [SMILES: CC(C)n1cnc2cc(-c3ccc4c(c3)N([C@H]3C[C@@H](N5CCCCC5)C3)C(=O)C43CCN(C(=O)CC4CCN(C(=O)OC(C)(C)C)CC4)CC3)nc(NC3CC3)c21]

6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (250.00 mg, 0.4515 mmol), (1,2,3-benzotriazol-1-yloxy)tris(dimethylamino)phosphanium; hexafluoro-lambda5-phosphanuide (259.58 mg, 0.586 mmol) and [1-(tert-butoxycarbonyl)piperidin-4-yl]acetic acid (109.84 mg, 0.4515 mmol) were dissolved in dimethylformamide (0.80 mL) and N,N-diisopropylethylamine (0.31 mL, 1.8059 mmol) and stirred at room temperature for 4 hours. The crude reaction mixture was purified by reverse phase flash column chromatography eluting with acetonitrile/water to afford the title compound (0.301 g, 85% yield).

Step 2: 6-[4-(cyclopropylamino)-3-isopropylimidazo [4,5-c]pyridin-6-yl]-1'-[2-(piperidin-4-yl)acetyl]-1-[(1s,3s)-3-(piperidin-1-yl)cyclobutyl]spiro[indole-3, 4'-piperidin]-2-one

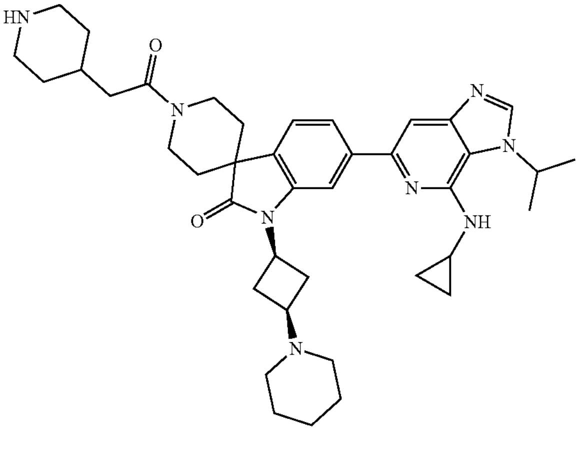 [SMILES: CC(C)n1cnc2cc(-c3ccc4c(c3)N([C@H]3C[C@@H](N5CCCCC5)C3)C(=O)C43CCN(C(=O)CC4CCNCC4)CC3)nc(NC3CC3)c21]

Tert-butyl 4-(2-{6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}-2-oxoethyl)piperidine-1-carboxylate (0.301 g, 0.386 mmol) was dissolved in DCM (5.0 mL). 4M HCl in dioxanes (2.0 mL) was added and the reaction mixture was stirred at room temperature overnight. The crude reaction mixture was evaporated under vacuum and the residue purified by reverse phase flash column chromatography eluting with acetonitrile/water to afford the title compound (0.234 g, 93% yield). LCMS: $C_{40}H_{54}N_8O_2$, desired mass=678.9, found: m/z=679.8 $[M+H]^+$.

Intermediate I

6-[4-(cyclopropylamino)-3-isopropylimidazo[4,5-c]pyridin-6-yl]-1'-(piperidine-4-sulfonyl)-1-[(1S,3S)-3-(piperidin-1-yl)cyclobutyl]spiro[indole-3,4'-piperidin]-2-one

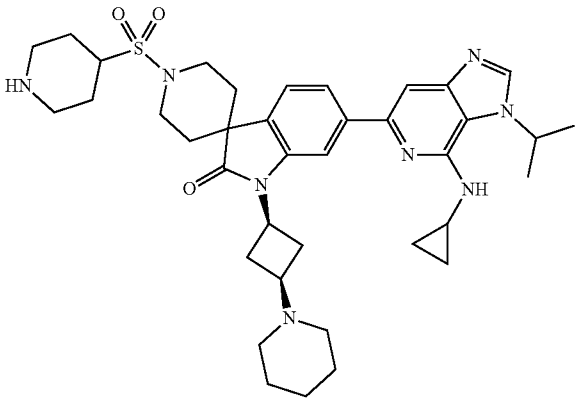 [SMILES: CC(C)n1cnc2cc(-c3ccc4c(c3)N([C@H]3C[C@@H](N5CCCCC5)C3)C(=O)C43CCN(S(=O)(=O)C4CCNCC4)CC3)nc(NC3CC3)c21]

Step 1: tert-butyl 4-((6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)sulfonyl)piperidine-1-carboxylate

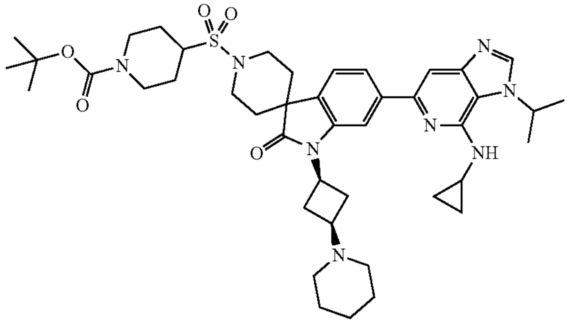 [SMILES: CC(C)n1cnc2cc(-c3ccc4c(c3)N([C@H]3C[C@@H](N5CCCCC5)C3)C(=O)C43CCN(S(=O)(=O)C4CCN(C(=O)OC(C)(C)C)CC4)CC3)nc(NC3CC3)c21]

6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (200.00 mg, 0.3612 mmol), tert-butyl 4-(chlorosulfonyl)piperidine-1-carboxylate (102.49 mg, 0.3612 mmol), and N,N-diisopropylethylamine (0.25 mL, 1.4447 mmol) were dissolved in DMF (5.00 mL) and N,N-diisopropylethylamine (0.25 mL, 186.72 mg, 1.4447 mmol) and stirred at room temperature for 4 hours. The crude reaction mixture was purified by reverse phase flash column chromatography eluting with acetonitrile/water to afford the title compound (0.234 g, 80% yield).

Step 2: 6-[4-(cyclopropylamino)-3-isopropylimidazo[4,5-c]pyridin-6-yl]-1'-(piperidine-4-sulfonyl)-1-[(1s,3s)-3-(piperidin-1-yl)cyclobutyl]spiro[indole-3,4'-piperidin]-2-one

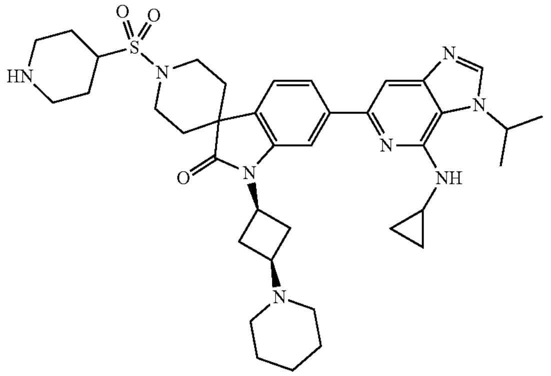 [SMILES: CC(C)n1cnc2cc(-c3ccc4c(c3)N([C@H]3C[C@@H](N5CCCCC5)C3)C(=O)C43CCN(S(=O)(=O)C4CCNCC4)CC3)nc(NC3CC3)c21]

Tert-butyl 4-((6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)sulfonyl)piperidine-1-carboxylate (0.234 g, 0.292 mmol) was dissolved in DCM (5.0 mL). 4M HCl in dioxane (3.0 mL) was added and the reaction mixture was stirred at room temperature overnight. The crude reaction mixture was concentrated under vacuum and the residue purified by reverse phase flash column chromatography eluting with acetonitrile/water to afford the title compound (0.170 g, 83% yield). LCMS: $C_{38}H_{52}N_8O_3S$, desired mass=700.9, found: m/z=701.7 $[M+H]^+$.

Intermediate J

6-{4-[(2-Fluorophenyl)Amino]-3-isopropylimidazol[4,5-C]Pyridin-6-yl}-1'-(4-Methylpiperidine-4-Carbonyl)-1-[(1S,3S)-3-(Piperidin-1-yl)Cyclobutyl]Spiro[Indole-3,4'-Piperidin]-2-One

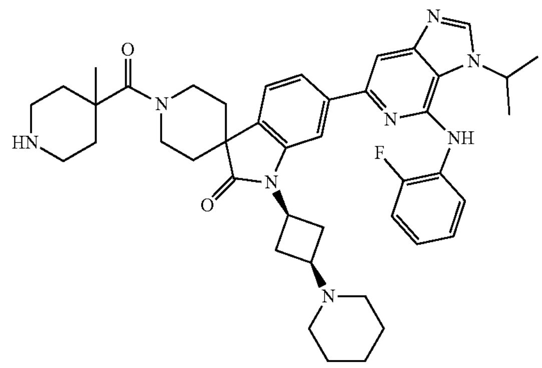 [SMILES: CC(C)n1cnc2cc(-c3ccc4c(c3)N([C@H]3C[C@@H](N5CCCCC5)C3)C(=O)C43CCN(C(=O)C4(C)CCNCC4)CC3)nc(Nc3ccccc3F)c21]

Step 1: tert-butyl 4-[(6-{4-[(2-fluorophenyl)amino]-3-isopropylimidazo[4,5-c]pyridin-6-yl}-2-oxo-1-[(1s,3s)-3-(piperidin-1-yl)cyclobutyl]spiro[indole-3,4'-piperidin]-1'-yl)carbonyl]-4-methylpiperidine-1-carboxylate

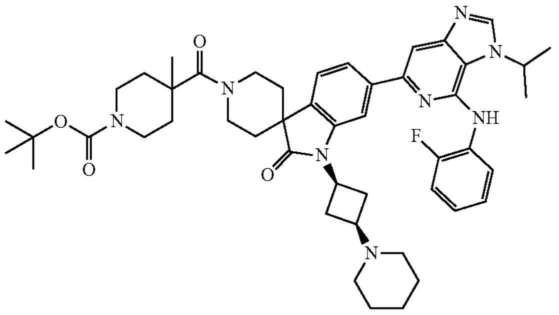 [SMILES: CC(C)n1cnc2cc(-c3ccc4c(c3)N([C@H]3C[C@@H](N5CCCCC5)C3)C(=O)C43CCN(C(=O)C4(C)CCN(C(=O)OC(C)(C)C)CC4)CC3)nc(Nc3ccccc3F)c21]

6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (Intermediate C) (200.00 mg, 0.3291 mmol), (1,2,3-benzotriazol-1-yloxy)tris(dimethylamino)phosphanium; hexafluoro-lambda5-phosphanuide (189.20 mg, 0.4278 mmol), N,N-diisopropylethylamine (0.23 mL, 1.3163 mmol), and 1-(tert-butoxycarbonyl)-4-methylpiperidine-4-carboxylic acid (80.06 mg, 0.3291 mmol) were dissolved in dimethylformamide (3.00 mL) and stirred at room temperature for 4 hours. The crude mixture was purified by reverse phase flash column chromatography eluting with acetonitrile/water to afford the title compound (0.147 g, 53% yield).

Step 2: 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one

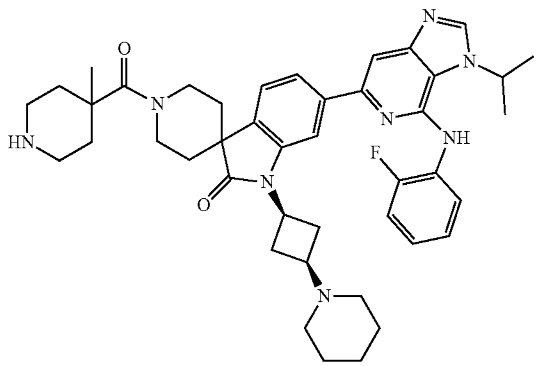 [SMILES: CC(C)n1cnc2cc(-c3ccc4c(c3)N([C@H]3C[C@@H](N5CCCCC5)C3)C(=O)C43CCN(C(=O)C4(C)CCNCC4)CC3)nc(Nc3ccccc3F)c21]

Tert-butyl 4-[(6-{4-[(2-fluorophenyl)amino]-3-isopropylimidazo[4,5-c]pyridin-6-yl}-2-oxo-1-[(1s,3s)-3-(piperidin-1-yl)cyclobutyl]spiro[indole-3,4'-piperidin]-1'-yl)carbonyl]-4-methylpiperidine-1-carboxylate (0.147 g, 0.176 mmol) was dissolved in DCM (5.0 mL). TFA (1.0 mL) was added, and the reaction mixture was stirred at room temperature overnight. The crude reaction mixture was concentrated under vacuum and the residue purified by reverse phase flash column chromatography eluting with acetonitrile/water to afford the title compound (0.11 g, 86% yield). LCMS: $C_{43}H_{53}FN_8O_2$, desired mass=732.9, found: m/z=733.8 $[M+H]^+$.

Intermediate K

6-[4-(Cyclopropylamino)-3-Isopropylimidazo[4,5-C]Pyridin-6-yl]-1'-[2-(4-Methylpiperidin-4-yl)Acetyl]-1-[(1S,3S)-3-(Piperidin-1-yl)Cyclobutyl]Spiro[Indole-3,4'-Piperidin]-2-One

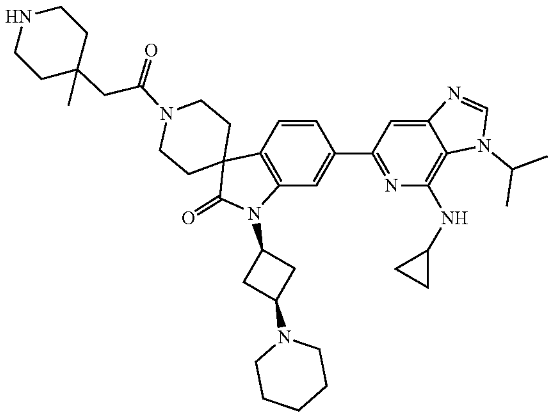 [SMILES: CC(C)n1cnc2cc(-c3ccc4c(c3)N([C@H]3C[C@@H](N5CCCCC5)C3)C(=O)C43CCN(C(=O)CC4(C)CCNCC4)CC3)nc(NC3CC3)c21]

Step 1: tert-butyl 4-(2-{6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}-2-oxoethyl)-4-methylpiperidine-1-carboxylate

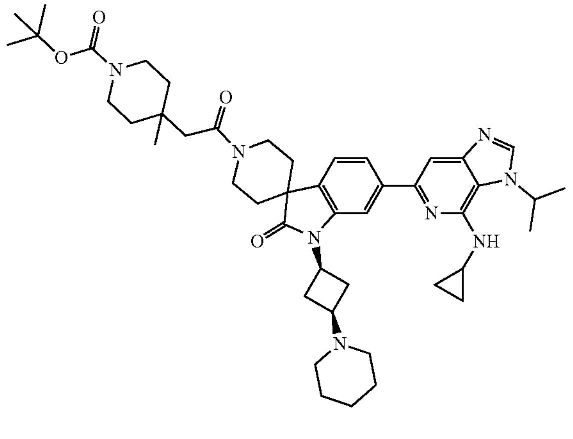 [SMILES: CC(C)n1cnc2cc(-c3ccc4c(c3)N([C@H]3C[C@@H](N5CCCCC5)C3)C(=O)C43CCN(C(=O)CC4(C)CCN(C(=O)OC(C)(C)C)CC4)CC3)nc(NC3CC3)c21]

6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (350.00 mg, 0.6320 mmol), (1,2,3-benzotriazol-1-yloxy)tris(dimethylamino)phosphanium; hexafluoro-lambda5-phosphanuide (363.41 mg, 0.8217 mmol) and [1-(tert-butoxycarbonyl)-4-methylpiperidin-4-yl]acetic acid (162.65 mg, 0.6320 mmol) were dissolved in dimethylformamide (0.80 mL) and N,N-diisopropylethylamine (0.44 mL, 2.5282 mmol) and stirred at room temperature for 4 hours. The crude reaction mixture was purified by reverse phase flash column chromatography eluting with acetonitrile/water to afford the title compound (0.284 g, 56% yield).

Step 2: 6-[4-(cyclopropylamino)-3-isopropylimidazo[4,5-c]pyridin-6-yl]-1'-[2-(4-methylpiperidin-4-yl)acetyl]-1-[(1s,3s)-3-(piperidin-1-yl)cyclobutyl]spiro[indole-3,4'-piperidin]-2-one

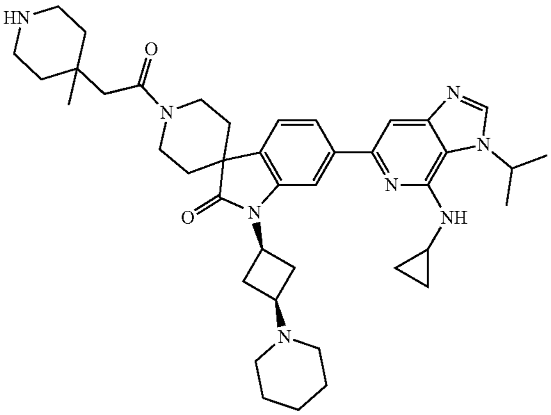 [SMILES: CC(C)n1cnc2cc(-c3ccc4c(c3)N([C@H]3C[C@@H](N5CCCCC5)C3)C(=O)C43CCN(C(=O)CC4(C)CCNCC4)CC3)nc(NC3CC3)c21]

Tert-butyl 4-(2-{6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}-2-oxo-ethyl)-4-methylpiperidine-1-carboxylate (0.284 g, 0.358 mmol) was dissolved in DCM (5.0 mL). 4M HCl in dioxanes (3.0 mL) was added and the reaction mixture was stirred at room temperature overnight. The crude reaction mixture was evaporated onto silica gel and purified by reverse phase flash column chromatography eluting with acetonitrile/water to afford the title compound (0.204 g, 82% yield). LCMS: $C_{41}H_{56}N_8O_2$, desired mass=692.9, found: m/z=693.9 $[M+H]^+$.

Intermediate L

Tert-Butyl 6-[4-(Oxan-4-yloxy)-3-(Propan-2-yl)-3H-Imidazo[4,5-C]Pyridin-6-yl]-2-Oxo-1-[(1S,3S)-3-(Piperidin-1-yl)Cyclobutyl]-1,2-Dihydrospiro[Indole-3,4'-Piperidine]-1'-Carboxylate

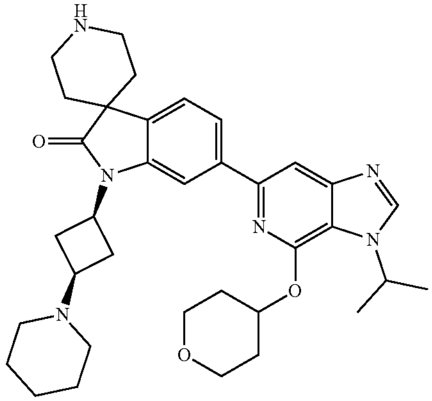 [SMILES: CC(C)n1cnc2cc(-c3ccc4c(c3)N([C@H]3C[C@@H](N5CCCCC5)C3)C(=O)C43CCNCC3)nc(OC3CCOCC3)c21]

Step 1: 6-bromo-4-(oxan-4-yloxy)-3-(propan-2-yl)-3H-imidazo[4,5-c]pyridine

Sodium (0.048 g, 2.076 mmol) was added carefully to Tetrahydro-2H-pyran-4-ol (0.707 g, 6.92 mmol) in anhydrous Tetrahydrofuran (6.92 mL) at room temperature and stirred at 80° C. for 1 hour. 6-bromo-4-chloro-3-isopropyl-3H-imidazo[4,5-c]pyridine (Intermediate 0540 in WO2020092528A1) (0.2 g, 0.692 mmol) was added to the reaction mixture and stirred at 80° C. overnight. The reaction mixture was cooled to room temperature and diluted with DCM and washed with saturated aqueous $KHSO_4$. The organic layer was dried over sodium sulphate and evaporated to obtain 199 mg (78% yield) of the crude title compound as a pale yellow oil. LCMS: $C_{14}H_{18}BrN_3O_2$ desired mass: 340.22, found: m/z=340.10$[M+H]^+$.

Step 2: tert-butyl 6-[4-(oxan-4-yloxy)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate 6-bromo-4-(oxan-4-yloxy)-3-(propan-2-yl)-3H-imidazo[4,5-c]pyridine (0.199 g, 0.538 mmol) and tert-butyl 2-oxo-1-[(1s,3s)-3-(piperidin-1-yl)cyclobutyl]-6-(4,4,5,5-tetramethyl-1,3,2-dioxaborolan-2-yl)spiro[indole-3,4'-piperidine]-1'-carboxylate (prepared as described in WO2020092528A1) (0.32 g, 0.538 mmol) were dissolved in anhydrous dioxane (5.38 mL) and a solution of cesium carbonate (0.526 g, 1.614 mmol) and water (0.54 mL) was added. The reaction mixture was degassed by bubbling argon and 1,1'-Bis(diphenylphosphino)ferrocene-palladium (II)dichloride dichloromethane (0.044 g, 0.054 mmol) was added to it. The reaction vessel was sealed and heated at 80° C. for 1 h. The reaction mixture was cooled to room temperature and diluted with water and DCM. The aqueous layer was extracted with DCM (3×10 mL), dried over sodium sulphate, filtered and evaporated to obtain the crude product. The crude was purified using reverse phase flash column chromatography eluting with ACN and water to obtain 194 mg (52% yield) of the title compound as a white solid. LCMS: C40H54N6O5 desired mass: 698.91, found: m/z=699.63 $[M+H]^+$.

Step 3: 6-[4-(oxan-4-yloxy)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one Tert-butyl 6-[4-(oxan-4-yloxy)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate (0.194 g, 0.278 mmol) was dissolved in 1:1 Trifluoroacetic acid (0.95 g, 8.327 mmol):Dichloromethane (2.78 mL) and stirred at room temperature for 1 h. The solvents were evaporated under vacuum and the residue was diluted with DCM and stirred for 10 minutes with saturated aqueous $K_2CO_3$ solution. The aqueous layer was extracted with DCM (3×10 mL). The combined organic layers were dried over sodium sulphate, filtered and evaporated to obtain the crude product, which was triturated with diethyl ether to obtain 179 mg (97% yield) of the title compound as a brown solid. LCMS: C35H46N6O3, desired mass: 598.79, found: m/z=599.40$[M+H]^+$.

Intermediate M

6-[3-(propan-2-yl)-4-(propan-2-yloxy)-3H-imidazo[4,5-c]pyridin-6-yl]-1-[(1s,3s)-3-(piperidin-1-yl)cyclobutyl]-1,2-dihydrospiro[indole-3,4'-piperidin]-2-one

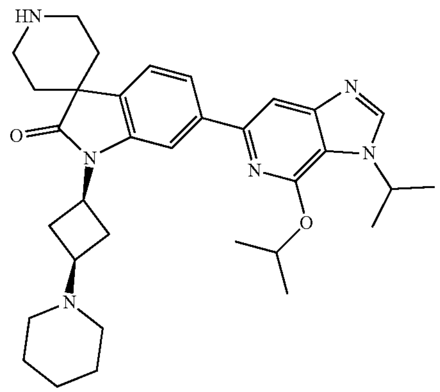 [SMILES: CC(C)Oc1nc(-c2ccc3c(c2)N([C@H]2C[C@@H](N4CCCCC4)C2)C(=O)C32CCNCC2)cc2ncn(C(C)C)c12]

Step 1: 6-bromo-3-(propan-2-yl)-4-(propan-2-yloxy)-3H-imidazo[4,5-c]pyridine

Sodium (0.119 g, 5.19 mmol) was added carefully to anhydrous 2-propanol (1.428 mL, 18.683 mmol) at room temperature and stirred at 80° C. for 1 hour. 6-bromo-4-chloro-3-(propan-2-yl)-3H-imidazo[4,5-c]pyridine (Intermediate 0540 in WO2020092528A1) (0.5 g, 1.73 mmol) was added to the reaction mixture stirring was continued at 80° C. for 30 hours. The reaction mixture was cooled to room temperature and concentrated to dryness under vacuum. The residue was diluted with DCM and washed with saturated aqueous $KHSO_4$ solution. The organic layer was dried over sodium sulphate and evaporated to obtain 513 mg (99% yield) of the title compound as a pale yellow solid. LCMS: $C_{12}H_{16}BrN_3O$, desired mass=298.18, found: m/z=299.95 $[M+H]^+$.

Step 2: 6-[3-(propan-2-yl)-4-(propan-2-yloxy)-3H-imidazo[4,5-c]pyridin-6-yl]-1-[(1s,3s)-3-(piperidin-1-yl)cyclobutyl]-1,2-dihydrospiro[indole-3,4'-piperidin]-2-one Tert-butyl 2-oxo-1-[(1s,3s)-3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (prepared as described in WO2020092528A1) (0.973 g, 1.72 mmol) and 6-bromo-3-(propan-2-yl)-4-(propan-2-yloxy)-3H-imidazo[4,5-c]pyridine (0.513 g, 1.72 mmol) were dissolved in anhydrous dioxane (17.0 mL) and a solution of cesium carbonate (1.682 g, 5.161 mmol) in water (1.7 mL) was added. The reaction mixture was thoroughly degassed by bubbling argon, then 1,1'-bis(diphenylphosphino)ferrocene-palladium(II)dichloride dichloromethane (0.141 g, 0.172 mmol) was added. The reaction vessel was sealed and heated at 85° C. for 3 h. The reaction mixture was degassed again and second portion of tert-butyl 2-oxo-1-[(1s,3s)-3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (0.292 g, 0.517 mmol) and 1,1'-bis(diphenylphosphino)ferrocene-palladium(II)dichloride dichloromethane (0.028 g, 0.034 mmol) were added. The reaction mixture was stirred at 85° C. for an additional 2 h. The reaction mixture was cooled to room temperature and diluted with water and extracted with EtOAc. The organic layer was washed with brine, dried over $Na_2SO_4$, filtered and evaporated. The residue was purified by silica gel chromatography using a mobile phase of DCM and MeOH and repurified by reverse phase flash column chromatography using a mobile phase of ACN and $H_2O$. The resulting material was dissolved in DCM (3.5 mL) and treated with TFA (3.5 mL) for 3 h. The residue was partitioned between DCM and saturated $K_2CO_3$ aqueous solution. The mixture was stirred for 30 min and separated. The organic layer was washed with water, brine, dried over $Na_2SO_4$, filtered and evaporated to afford the title compound as a tan solid (0.399 g, 42% yield). LCMS: $C_{33}H_{44}N_6O_2$ desired mass: 556.8, found: m/z=557.4 $[M+H]^+$.

Intermediate N

6-[4-phenoxy-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one

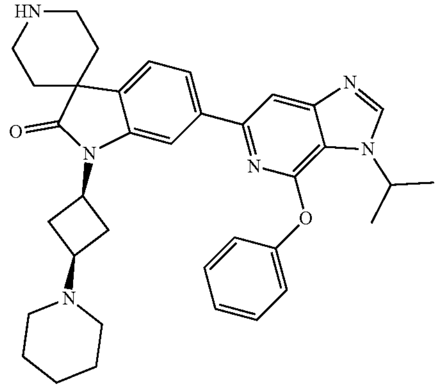 [SMILES: CC(C)n1cnc2cc(-c3ccc4c(c3)N([C@H]3C[C@@H](N5CCCCC5)C3)C(=O)C43CCNCC3)nc(Oc3ccccc3)c21]

Step 1: 6-bromo-4-phenoxy-3-(propan-2-yl)-3H-imidazo[4,5-c]pyridine

To a suspension of phenol (0.2 g, 2.125 mmol) and potassium carbonate (0.587 g, 4.25 mmol) in anhydrous dimethylformamide (4.25 mL) stirred at room temperature under argon for 30 minutes, was added 6-bromo-4-chloro-3-(propan-2-yl)-3H-imidazo[4,5-c]pyridine (Intermediate 0540 in WO2020092528A1) (0.676 g, 2.338 mmol) and stirred at 90° C. for 48 hours. The reaction mixture was evaporated, the residue was diluted with DCM and washed with water and brine. The organic layer was dried over $Na_2SO_4$, filtered and evaporated to obtain the crude product which was purified by silica gel chromatography using a mobile phase of hexane and EtOAc to afford the title compound as a white solid (0.53 g, 75% yield). LCMS: $C_{15}H_{14}BrN_3O$, desired mass=332.2, found: m/z=334.0 $[M+H]^+$.

Step 2: 6-[4-phenoxy-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one In a pressure vessel under an argon atmosphere tert-butyl 2-oxo-1-[(1s,3s)-3-(piperidin-1-yl)cyclobutyl]-6-(4,4,5,5- tetramethyl-1,3,2-dioxaborolan-2-yl)-1,2-dihydrospiro[indole-3,4'-piperidine]-1'-carboxylate (prepared as described in WO2020092528A1) (0.908 g, 1.526 mmol) and 6-bromo-4-phenoxy-3-(propan-2-yl)-3H-imidazo[4,5-c]pyridine (0.512 g, 1.526 mmol) were dissolved in anhydrous dioxane (28 mL), and cesium carbonate (1.491 g, 4.577 mmol) solution in water (2.5 mL) was added. The reaction mixture was degassed with argon for 20 min and 1,1'-bis(diphenylphosphino)ferrocene-palladium(II)dichloride dichloromethane (0.125 g, 0.153 mmol) was added. The reaction mixture was stirred at 100° C. for 3 h, then concentrated to dryness under vacuum. The residue was partitioned between EtOAc and brine. The organic layer separated and dried over $Na_2SO_4$, then filtered and evaporated. The crude residue was purified by silica gel chromatography using a mobile phase of DCM and i-PrOH. The resulting material was dissolved in DCM (5.5 mL) and TFA (5.5 mL) and stirred for 1 h at room temperature. The residue was partitioned between DCM and saturated $K_2CO_3$ aqueous solution. The mixture was stirred for 30 min and separated. The organic layer was washed with water, brine, dried over $Na_2SO_4$, filtered and evaporated to afford the title compound as an off-white solid (0.471 g, 52% yield). LCMS: $C_{36}H_{42}N_6O_2$ desired mass: 590.8, found: m/z=591.4 $[M+H]^+$.

Intermediate O

6-[3-(propan-2-yl)-4-[(propan-2-yl)amino]-3H-imidazo[4,5-c]pyridin-6-yl]-1-[(1s,3s)-3-(piperidin-1-yl)cyclobutyl]-1,2-dihydrospiro[indole-3,4'-piperidin]-2-one

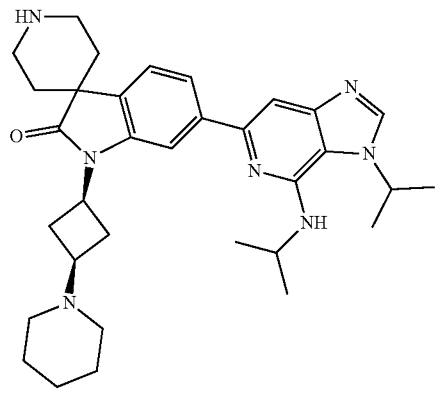 [SMILES: CC(C)Nc1nc(-c2ccc3c(c2)N([C@H]2C[C@@H](N4CCCCC4)C2)C(=O)C32CCNCC2)cc2ncn(C(C)C)c12]

Step 1: 6-bromo-N,3-bis(propan-2-yl)-3H-imidazo[4,5-c]pyridin-4-amine

Isopropylamine (0.949 mL, 11.042 mmol) was added to 6-bromo-4-fluoro-3-(propan-2-yl)-3H-imidazo[4,5-c]pyridine (Intermediate 0540 in WO2020092528A1) (0.2 g, 0.736 mmol) in anhydrous dioxane (1 mL), and the reaction mixture was stirred at 60° C. for 16 h. The reaction mixture was concentrated under vacuum and triturated with $H_2O$. The resulting material was filtered off, dried under high vacuum, then purified by silica gel chromatography using a mobile phase of hexane and EtOAc to afford the title compound as a purple solid (0.19 g, 86% yield). LCMS: $C_{12}H_{17}BrN_4$, desired mass=297.2, found: m/z=298.9 $[M+H]^+$.

Step 2: 6-[3-(propan-2-yl)-4-[(propan-2-yl)amino]-3H-imidazo[4,5-c]pyridin-6-yl]-1-[(1s,3s)-3-(piperidin-1-yl)cyclobutyl]-1,2-dihydrospiro[indole-3,4'-piperidin]-2-one In a pressure vessel under argon atmosphere tert-butyl 2-oxo-1-[(1s,3s)-3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (prepared as described in WO2020092528A1) (0.429 g, 0.759 mmol) and 6-bromo-N,3-bis(propan-2-yl)-3H-imidazo[4,5-c]pyridin-4-amine (0.188 g, 0.633 mmol) were dissolved in anhydrous dioxane (6.3 mL) and cesium carbonate (0.618 g, 1.898 mmol) solution in water (0.6 mL) was added. The reaction mixture was degassed with argon for 20 min and 1,1'-bis(diphenylphosphino)ferrocene-palladium(II)dichloride dichloromethane (0.052 g, 0.063 mmol) was added. The reaction mixture was stirred at 90° C. for 3 h. The reaction mixture was degassed again and a second portion of tert-butyl 2-oxo-1-[(1s,3s)-3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (0.215 g, 0.380 mmol), cesium carbonate (0.309 g, 0.949 mmol) and 1,1'-bis(diphenylphosphino)ferrocene-palladium(II)dichloride dichloromethane (0.015 g, 0.019 mmol) was added. The reaction mixture was stirred at 90° C. for an additional 2 h. The reaction mixture was cooled to room temperature, diluted with water and was extracted with EtOAc. The organic layer was separated, washed with brine, dried over $Na_2SO_4$, filtered and evaporated. The residue was purified by silica gel chromatography using a mobile phase of DCM and MeOH. The resulting material was dissolved in DCM (3.5 mL) and TFA (3.5 mL) and stirred for 1 h. After concentrating under vacuum, the residue was partitioned between DCM (10 mL) and saturated aqueous $K_2CO_3$ solution (10 mL). The mixture was stirred for 10 minutes, then the organic layer was separated and washed with brine (10 mL), dried over $Na_2SO_4$ and concentrated to provide the title compound as a white solid (0.16 g; 45% yield). LCMS: $C_{33}H_{45}N_7O$, desired mass=555.4, found: m/z=556.3 $[M+H]^+$.

Intermediate P

6-[3-(propan-2-yl)-4-(pyrrolidin-1-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one

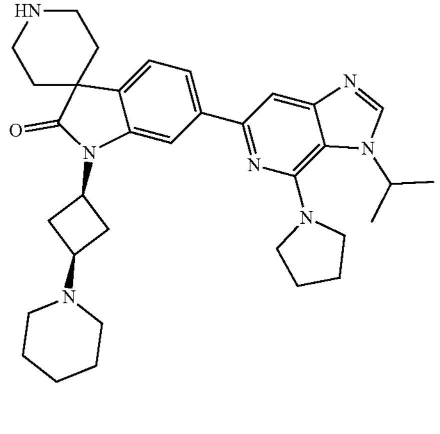 [SMILES: CC(C)n1cnc2cc(-c3ccc4c(c3)N([C@H]3C[C@@H](N5CCCCC5)C3)C(=O)C43CCNCC3)nc(N3CCCC3)c21]

Step 1: 1-[6-bromo-3-(propan-2-yl)-3H-imidazo[4,5-c]pyridin-4-yl]pyrrolidine 6-bromo-4-fluoro-3-isopropyl-3H-imidazo[4,5-c]pyridine (Intermediate 0542 in WO2020092528A1) (0.1 g, 0.35 mmol) and pyrrolidine (0.498 g, 7.00 mmol) were combined and heated at 80° C. for 16 hours. The reaction mixture was cooled to RT and purified by silica gel chromatography to afford the title compound (0.090 g, 83% yield). LCMS: $C_{13}H_{17}BrN_4$ desired mass: 308.2, found: m/z=309.2 $[M+H]^+$.

Step 2: 6-[3-(propan-2-yl)-4-(pyrrolidin-1-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one Tert-butyl 2-oxo-1-[(1s,3s)-3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (prepared as described in WO2020092528A1) (0.173 g, 0.28 mmol), $Pd(dppf)Cl_2DCM$ (23 mg, 0.028 mmol), 1-[6-bromo-3-(propan-2-yl)-3H-imidazo[4,5-c]pyridin-4-yl]pyrrolidine (0.087 g, 0.28 mmol), cesium carbonate (0.272 g, 0.84 mmol), water (0.28 mL), and 1,4-dioxane (2.8 mL) were combined in a vial, degassed with bubbling argon for 10 min, sealed, and stirred at 80° C. for 60 mins. The reaction mixture was cooled to room temperature, filtered, then concentrated onto silica gel and purified by flash column chromatography eluting with DCM/MeOH. The resulting material was dissolved in DCM (2.5 mL) and treated with TFA (2 mL). The reaction mixture was stirred at room temperature for 2 hours then neutralized with aqueous sodium bicarbonate solution. The aqueous layer was extracted with DCM (3×10 mL), then the combined organic layers were washed with a saturated solution of sodium chloride (5 mL), dried over sodium sulfate and concentrated under vacuum to afford the title compound (0.14 g, 86% yield). LCMS: $C_{34}H_{45}N_7O$ desired mass: 567.4, found: m/z=568.4 $[M+H]^+$.

Intermediate Q

6-{4-[cyclopropyl(methyl)amino]-3-(propan-2-yl)-3H-imidazo[4,5-c]pyridin-6-yl}-1-[(1s,3s)-3-(piperidin-1-yl)cyclobutyl]-1,2-dihydrospiro[indole-3,4'-piperidin]-2-one

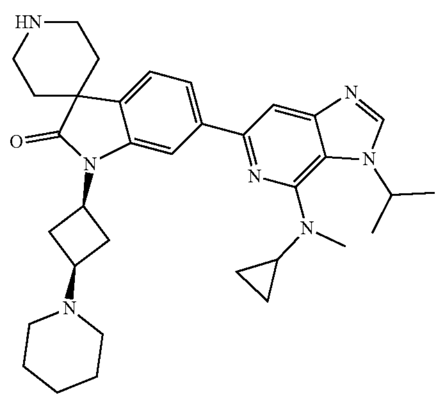 [SMILES: CC(C)n1cnc2cc(-c3ccc4c(c3)N([C@H]3C[C@@H](N5CCCCC5)C3)C(=O)C43CCNCC3)nc(N(C)C3CC3)c21]

Step 1: 6-bromo-N-cyclopropyl-N-methyl-3-(propan-2-yl)-3H-imidazo[4,5-c]pyridin-4-amine 6-bromo-4-fluoro-3-isopropyl-3H-imidazo[4,5-c]pyridine (Intermediate 0542 in WO2020092528A1) (0.4 g, 1.47 mmol) and N-methylcyclopropaneamine (0.257 g, 5.89 mmol), DIPEA (1.54 g, 8.83 mmol) and DMSO (2.9 mL) were combined and heated at 100° C. for 30 hours. The reaction mixture was cooled to RT and purified by silica gel chromatography to afford the title compound (0.264 g, 56% yield). LCMS: $C_{13}H_{17}BrN_4$ desired mass: 308.2, found: m/z=309.2 $[M+H]^+$.

Step 2: tert-butyl 6-{4-[cyclopropyl(methyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidine]-1'-carboxylate Tert-butyl 2-oxo-1-((1s,3s)-3-(piperidin-1-yl)cyclobutyl)-6-(4,4,5,5-tetramethyl-1,3,2-dioxaborolan-2-yl)spiro[indoline-3,4'-piperidine]-1'-carboxylate (Intermediate 0558 in WO2020092528A1) (0.36 g, 0.64 mmol), XPhos Pd G3 (36 mg, 0.042 mmol), 6-bromo-N-cyclopropyl-N-methyl-3-(propan-2-yl)-3H-imidazo[4,5-c]pyridin-4-amine (0.135 g, 0.42 mmol), potassium phosphate tribasic (0.270 g, 1.27 mmol), water (0.42 mL), and 1,4-dioxane (4.2 mL) were combined in a vial, degassed with argon for 10 min, sealed, and stirred at 80° C. for 240 mins. The reaction mixture was filtered then concentrated onto silica gel and purified by normal phase flash column chromatography. This material was dissolved in DCM (2.5 mL) and treated with TFA. The crude was purified by preparative HPLC to afford the title compound (0.133 g, 53% yield). LCMS: $C_{34}H_{45}N_7O$ desired mass: 567.4, found: m/z=568.4 $[M+H]^+$.

Intermediate R (1s,3s)-3-[(6-{2-oxo-1-[(1s,3s)-3-(piperidin-yl)cyclobutyl]-1,2-dihydrospiro[indole-3,4'-piperidin]-6-yl}-3-(propan-2-yl)-3h-imidazo[4,5-c]pyridin-4-yl)amino]cyclobutane-1-carbonitrile

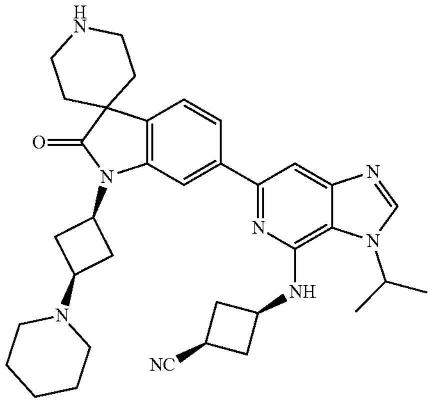 [SMILES: CC(C)n1cnc2cc(-c3ccc4c(c3)N([C@H]3C[C@@H](N5CCCCC5)C3)C(=O)C43CCNCC3)nc(N[C@H]3C[C@@H](C#N)C3)c21]

Step 1: tert-butyl 2-oxo-6-[3-(propan-2-yl)-4-{[(1s,3s)-3-cyanocyclobutyl]amino}-3H-imidazo[4,5-c]pyridin-6-yl]-1-[(1s,3s)-3-(piperidin-1-yl)cyclobutyl]-1,2-dihydrospiro[indole-3,4'-piperidine]-1'-carboxylate Argon was bubbled through a mixture of tert-butyl 6-[4-chloro-3-(propan-2-yl)-3H-imidazo[4,5-c]pyridin-6-yl]-2- oxo-1-[(1s,3s)-3-(piperidin-1-yl)cyclobutyl]-1,2-dihydrospiro[indole-3,4'-piperidine]-1'-carboxylate (prepared as described in WO2020092621A1) (0.7 g, 0.995 mmol), cis-3-aminocyclobutane carbonitrile hydrochloride (0.264 g, 1.99 mmol), sodium tert-butoxide (0.246 g, 2.56 mmol), and XPhos Pd G3 (0.084 g, 0.1 mmol) in anhydrous toluene (20 mL) for 20 minutes and then the reaction mixture was stirred at 115° C. for 16 h. The reaction mixture was cooled to room temperature, concentrated under vacuum, and the residue was purified by silica gel flash chromatography (DCM/MeOH, 9:1) and by reverse-phase flash chromatography (water/acetonitrile) to provide 0.23 g (31% yield) of the title compound as an off-white solid. LCMS: $C_{40}H_{52}N_8O_3$, desired mass=692.4, found: m/z=693.3 $[M+H]^+$.

Step 2: (1s,3s)-3-[(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]cyclobutane-1-carbonitrile A solution of tert-butyl 2-oxo-6-[3-(propan-2-yl)-4-{[(1s,3s)-3-cyanocyclobutyl]amino}-3H-imidazo[4,5-c]pyridin-6-yl]-1-[(1s,3s)-3-(piperidin-1-yl)cyclobutyl]-1,2-dihydrospiro[indole-3,4'-piperidine]-1'-carboxy-late (0.225 g, 0.31 mmol) and TFA (1.1 mL, 9.3 mmol) in dichloromethane (4.4 mL) was stirred at rt for 2 hours. The reaction mixture was concentrated under vacuum and the resulting residue was triturated with dry diethyl ether to provide 0.17 g (89% yield) of trifluoroacetate salt of the title compound as an off-white solid (0.17 g, 89% yield). LCMS: $C_{35}H_{44}N_8O$, desired mass=592.4, found: m/z=593.3 $[M+H]^+$.

Intermediate S 1-(6-{2-oxo-1-[(1s,3s)-3-(piperidin-1-yl)cyclobutyl]-1,2-dihydrospiro[indole-3,4'-piperidin]-6-yl}-3-(propan-2-yl)-3h-imidazo[4,5-c]pyridin-4-yl)azetidine-3-carbonitrile; bis(trifluoroacetic acid)

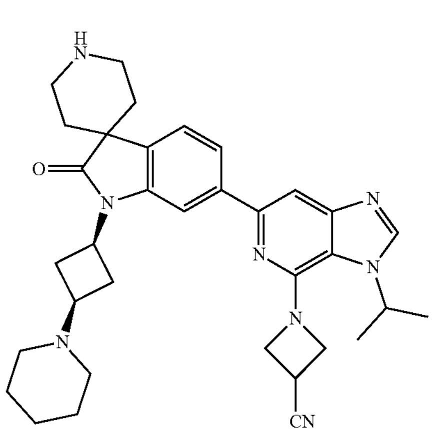 [SMILES: CC(C)n1cnc2cc(-c3ccc4c(c3)N([C@H]3C[C@@H](N5CCCCC5)C3)C(=O)C43CCNCC3)nc(N3CC(C#N)C3)c21]

Step 1: tert-butyl 6-[4-(3-cyanoazetidin-1-yl)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate Argon was bubbled through a mixture of tert-butyl 6-[4-chloro-3-(propan-2-yl)-3H-imidazo[4,5-c]pyridin-6-yl]-2- oxo-1-[(1s,3s)-3-(piperidin-1-yl)cyclobutyl]-1,2-dihydrospiro[indole-3,4'-piperidine]-1'-carboxylate (prepared as described in WO2020092621A1) (0.6 g, 0.85 mmol), azetidine-3-carbonitrile hydrochloride (0.20 g, 1.71 mmol), sodium tert-butoxide (0.25 g, 2.56 mmol) and XPhos Pd G3 (0.072 g, 0.085 mmol) in dry toluene (17.1 mL) for 30 minutes, then the reaction mixture was stirred at 115° C. for 16 h. After cooling to room temperature, the reaction mixture was concentrated to dryness under vacuum and the residue was purified by silica gel flash chromatography (DCM/MeOH, 9:1) and reverse-phase flash chromatography eluting with ACN/water to provide 0.28 g (48% yield) of the title compound as an off-white solid. LCMS: $C_{39}H_{50}N_8O_3$, desired mass=678.4, found: m/z=680.1 $[M+H]^+$.

Step 2: 1-(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)azetidine-3-carbonitrile; bis(trifluoroacetic acid)

A solution of tert-butyl 6-[4-(3-cyanoazetidin-1-yl)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate (0.31 g, 0.45 mmol) and TFA (1.51 g, 13.5 mmol) in anhydrous dichloromethane (5.8 mL) was stirred at room temperature for 2 hours. The reaction mixture was concentrated to dryness under vacuum, then the residue was triturated with dry diethyl ether to provide 0.39 g (95% yield) of the title compound as a double trifluoroacetate salt. LCMS: $C_{34}H_{42}N_8O$, desired mass=578.3, found: m/z=579.35 $[M+H]^+$.

Intermediate T (1R,3R)-3-[(6-{2-Oxo-1-[(1S,3S)-3-(Piperidin-1-yl)Cyclobutyl]-1,2-Dihydrospiro[Indole-3,4'-Piperidin]-6-yl}-3-(Propan-2-yl)-3H-Imidazo[4,5-C]Pyridin-4-yl)Amino]Cyclobutane-1-Carbonitrile; Tris(Trifluoroacetic Acid)

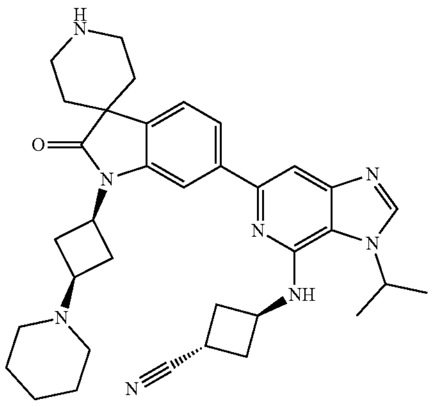 [SMILES: CC(C)n1cnc2cc(-c3ccc4c(c3)N([C@H]3C[C@@H](N5CCCCC5)C3)C(=O)C43CCNCC3)nc(N[C@H]3C[C@H](C#N)C3)c21]

Step 1: tert-butyl 2-oxo-6-[3-(propan-2-yl)-4-{[(1r,3r)-3-cyanocyclobutyl]amino}-3H-imidazo[4,5-c]pyridin-6-yl]-1-[(1s,3s)-3-(piperidin-1-yl)cyclobutyl]-1,2-dihydrospiro[indole-3,4'-piperidine]-1'-carboxylate A mixture of tert-butyl 6-[4-chloro-3-(propan-2-yl)-3H-imidazo[4,5-c]pyridin-6-yl]-2-oxo-1-[(1s,3s)-3-(piperidin- 1-yl)cyclobutyl]-1,2-dihydrospiro[indole-3,4'-piperidine]-1'-carboxylate (prepared as described in WO2020092621A1) (0.7 g, 1.11 mmol), $Pd_2(dba)_3$ (0.5 g, 0.06 mmol), Xantphos (0.064 g, 0.11 mmol), t-BuONa (0.32 g, 3.32 mmol) and trans-3-aminocyclobutanecarbonitrile hydrochloride (0.290 g, 2.21 mmol) in anhydrous toluene (22.2 mL) was stirred at 110° C. for 16 h. After cooling to room temperature, the reaction mixture was filtered, and concentrated under vacuum. The residue was purified by silica gel flash chromatography eluting with DCM/MeOH (0 to 10% of MeOH) to provide 270 mg (35% yield) of title compound as orange solid. LCMS: $C_{40}H_{52}N_8O_3$ desired mass=692.4, found: m/z=693.0 $[M+H]^+$.

Step 2: (1r,3r)-3-[(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]cyclobutane-1-carbonitrile; tris(trifluoroacetic acid)

To a solution of tert-butyl 2-oxo-6-[3-(propan-2-yl)-4-{[(1r,3r)-3-cyanocyclobutyl]amino}-3H-imidazo[4,5-c]pyridin-6-yl]-1-[(1s,3s)-3-(piperidin-1-yl)cyclobutyl]-1,2-dihydrospiro[indole-3,4'-piperidine]-1'-carboxylate (0.257 g, 0.37 mmol in anhydrous DCM (3.7 mL) was added trifluoroacetic acid (2.8 mL, 37.1 mmol), and the reaction mixture was stirred for 1 h at room temperature. Then reaction mixture was concentrated under vacuum to dryness, then the crude residue was triturated with $Et_2O$ and filtered off to provide 321 mg (93% yield) of the title compound as a yellow solid. LCMS: $C_{35}H_{44}N_8O$ desired mass=592.4, found m/z=593.3 $[M+H]^+$.

Intermediate U

6-[4-({2-oxaspiro[3.3]heptan-6-yl}amino)-3-(propan-2-yl)-3H-imidazo[4,5-c]pyridin-6-yl]-1-[(1S,3S)-3-(piperidin-1-yl)cyclobutyl]-1,2-dihydrospiro[indole-3,4'-piperidin]-2-one

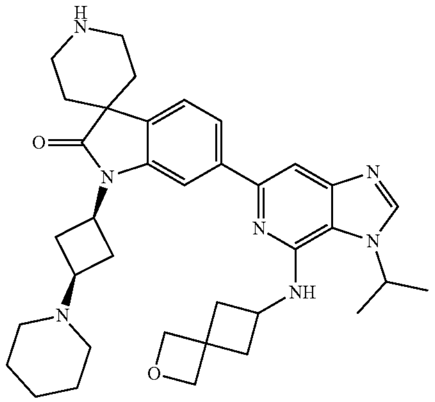 [SMILES: CC(C)n1cnc2cc(-c3ccc4c(c3)N([C@H]3C[C@@H](N5CCCCC5)C3)C(=O)C43CCNCC3)nc(NC3CC4(COC4)C3)c21]

Step 1: tert-butyl 6-[4-({2-oxaspiro[3.3]heptan-6-yl}amino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate To a solution of tert-butyl 6-[4-chloro-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate (prepared as described in WO2020092621A1) (388 mg, 0.55 mmol) in degassed anhydrous toluene (1.8 mL) was added 6-amino-2-oxaspiro[3.3]heptane hydrochloride (165 mg, 1.10 mmol), sodium tert-butoxide (159 mg, 1.65 mmol), tris(dibenzylideneacetone)dipalladium(0) (25 mg, 0.028 mmol), 4,5-bis(diphenylphosphino)-9,9-dimethylxanthene (32 mg, 0.055 mmol) at 25° C. The reaction mixture was stirred for 16 h at 90° C., and then the temperature was increased to 100° C. and stirring was continued for a further 16 h. The reaction mixture was cooled to room temperature, filtered and concentrated under reduced pressure. The residue was purified by silica gel chromatography using a mobile phase of DCM and MeOH (gradient 100:0 to 80:20%) to provide 177 mg (44% yield) of the title compound as a tan solid. LCMS: $C_{41}H_{55}N_7O_4$, desired mass=709.9, found: m/z=710.5 $[M+H]^+$.

Step 2: 6-[4-({2-oxaspiro[3.3]heptan-6-yl}amino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one To a solution of tert-butyl 6-[4-({2-oxaspiro[3.3]heptan-6-yl}amino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate (134 mg, 0.18 mmol) in anhydrous DCM (2.6 mL) was added TFA (0.4 mL, 5.44 mmol) at 25° C. The reaction mixture was stirred for 20 min at 25° C., and then diluted with DCM (5 mL) and poured into a saturated aqueous solution of $NaHCO_3$ (10 mL). Then resulting mixture was stirred vigorously for 10 min then the layers were separated and the aqueous layer was extracted with DCM (2×5 mL). Then organic layers were combined, dried with $Na_2SO_4$ and evaporated to dryness to provide 105 mg (95% yield) of the title compound as a tan solid. LCMS: $C_{36}H_{47}N_7O_2$, desired mass=609.8, found: m/z=610.3 $[M+H]^+$.

Intermediate V

6-[4-cyclopropoxy-3-(propan-2-yl)-3h-imidazo[4,5-c]pyridin-6-yl]-1-[(1s,3s)-3-(piperidin-1-yl)cyclobutyl]-1,2-dihydrospiro[indole-3,4'-piperidin]-2-one

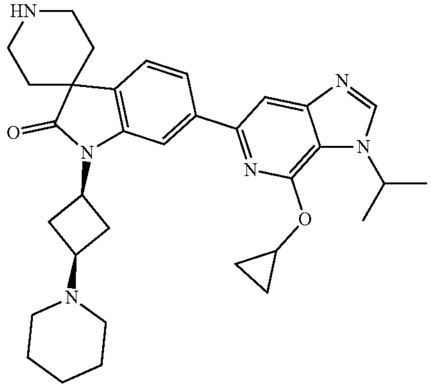 [SMILES: CC(C)n1cnc2cc(-c3ccc4c(c3)N([C@H]3C[C@@H](N5CCCCC5)C3)C(=O)C43CCNCC3)nc(OC3CC3)c21]

Step 1: tert-butyl 6-[4-cyclopropoxy-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate To a mixture of 1,1'-bis(diphenylphosphino)ferrocene dichloropalladium (II) (28 mg, 0.03 mmol), potassium carbonate (0.14 g, 1.0 mmol), tert-butyl 2-oxo-1-[3-(piperidin-1-yl)cyclobutyl]-6-(4,4,5,5-tetramethyl-1,3,2-dioxaborolan-2-yl)-1,2-dihydrospiro[indole-3,4'-piperidine]-1'-carboxylate (Intermediate 0558 in WO2020092528A1) (0.20 g, 0.34 mmol), 6-bromo-4-cyclopropoxy-3-(propan-2-yl)-3H-imidazo[4,5-c]pyridine (0.10 g, 0.34 mmol) was added dioxane (5.7 mL) and water (1.4 mL). The reaction mixture was degassed for 0.5 h with bubbling argon. The reaction mixture was stirred at 110° C., under an Ar atmosphere for 1 h, then cooled to room temperature, diluted with $CH_2Cl_2$, and filtered through a pad of celite and $MgSO_4$. The filtrate was concentrated under vacuum and the residue was purified by silica-gel flash chromatography eluting with $CH_3OH/CH_2Cl_2$ (gradient from 0% to 10% of $CH_3OH$) to provide 136 mg (60%) of the title compound as a brown solid. LCMS: $C_{38}H_{50}N_6O_4$, desired mass=654.9, found: m/z=655.3 $[M+H]^+$.

Step 2: 6-[4-cyclopropoxy-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one To a solution of tert-butyl 6-[4-cyclopropoxy-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-carboxylate (136 mg, 0.208 mmol) in anhydrous $CH_2Cl_2$ (0.32 mL) was added TFA (0.32 mL, 4.2 mmol). The reaction mixture was stirred at room temperature for 1 h, then concentrated to dryness under vacuum. The residue was triturated with diethyl ether to provide 148 mg (quantitative yield) of the title compound as a brown solid (TFA salt). LCMS: $C_{33}H_{42}N_6O_2$ desired mass: 554.7, found: m/z=555.2 $[M+H]^+$.

Intermediate W

2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}acetic acid

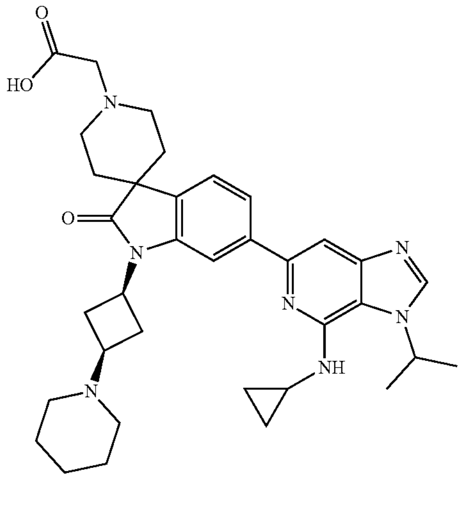 [SMILES: CC(C)n1cnc2cc(-c3ccc4c(c3)N([C@H]3C[C@@H](N5CCCCC5)C3)C(=O)C43CCN(CC(=O)O)CC3)nc(NC3CC3)c21]

Step 1: tert-butyl 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}acetate A mixture of 6-[4-(cyclopropylamino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate B) (1.5 g, 2.44 mmol, 1.0 eq), triethylamine (1.02 ml, 7.31 mmol, 3.0 eq) and tert-butyl bromoacetate (0.71 g, 3.66 mmol, 1.5 eq) in dichloromethane (16.3 mL) was stirred at room temperature for 18 h. The reaction mixture was concentrated under vacuum, and the residue was purified with reverse phase flash chromatography eluting with $CH_3CN$/water to give the title product as an off-white solid (1.25 g, 76%). LCMS: $C_{39}H_{53}N_7O_3$ desired mass=667.90, found m/z=669.30 $[M+H]^+$. $^1H$ NMR (500 MHz, DMSO-$d_6$) δ: 8.34 (s, 1H), 8.15 (s, 1H), 7.91 (d, J=7.8 Hz, 1H), 7.72 (s, 1H), 7.62 (d, J=7.8 Hz, 1H), 6.46 (s, 1H), 5.15-5.01 (m, 1H), 4.71-4.51 (m, 1H), 3.28 (s, 2H), 3.00 (m, 1H), 2.95-2.78 (m, 3H), 2.70-2.57 (m, 2H), 2.52 (m, 6H), 2.27 (m, 3H), 1.82 (m, 2H), 1.71-1.54 (m, 5H), 1.50 (d, J=6.5 Hz, 6H), 1.47 (s, 9H), 0.86-0.75 (m, 2H), 0.58 (m, 2H).

Step 2: 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}acetic acid dihydrochloride To a mixture of tert-butyl 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospi-ro[indole-3,4'-piperidin]-1'-yl}acetate (1.25 g, 1.85 mmol, 0.5 eq) in glacial acetic acid (12 ml), a 4.0 M hydrogen chloride in dioxane solution (11.56 ml, 46.25 mmol, 25.0 eq) was added and the mixture was stirred at room temperature for 3 h. The reaction mixture was concentrated under vacuum and the residue was dissolved in water (15 ml) and treated with activated charcoal. After filtration the reaction mixture was concentrated under vacuum to afford the title compound as an off-white hydroscopic crystalline salt (1.35 g, 83%, HCl salt). LCMS: $C_{35}H_{45}N_7O_3$ desired mass=611.79, found m/z=612.30 $[M+H]^+$. $^1H$ NMR (500 MHz, DMSO-$d_6$) δ: 10.85 (br s, 1H), 8.36 (s, 1H), 7.92 (d, J=8.5 Hz, 1H), 7.73 (s, 1H), 7.65 (s, 1H), 7.58 (m, 1H), 6.50 (s, 1H), 5.15-5.01 (m, 1H), 4.35-4.22 (m, 1H), 3.46-3.37 (m, 8H), 3.12-2.87 (m, 5H), 2.87-2.60 (m, 2H), 2.05 (m, 4H), 1.76 (m, 5H), 1.50 (m, 8H), 0.79 (m, 2H), 0.60 (m, 2H).

Intermediate X

2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-n-methyl-n-(piperidin-4-yl) acetamide

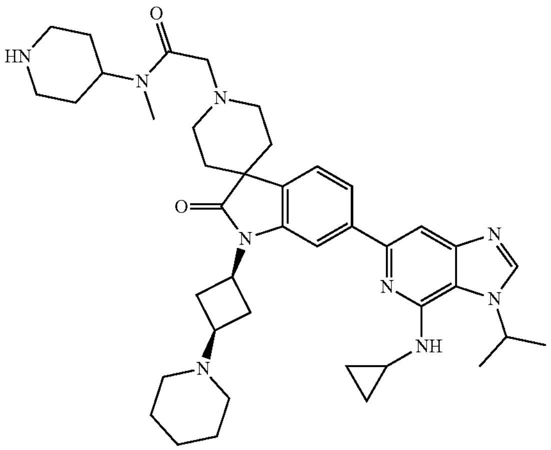 [SMILES: CC(C)n1cnc2cc(-c3ccc4c(c3)N([C@H]3C[C@@H](N5CCCCC5)C3)C(=O)C43CCN(CC(=O)N(C)C4CCNCC4)CC3)nc(NC3CC3)c21]

Step 1: tert-butyl 4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-n-methylacetamido)piperidine-1-carboxylate To solution of 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}acetic acid (Intermediate W) (0.12 g, 0.173 mmol) in anhydrous DMF (1.7 mL) was added DIPEA (0.3 mL, 1.7 mmol) and BOP (0.08 g, 0.185 mmol). The reaction mixture was stirred for 1 h at room temperature, then tert-butyl 4-(methylamino)piperidine-1-carboxylate (0.045 g, 0.210 mmol) was added. Stirring was continued for an additional 1.5 h, then the reaction mixture was concentrated to dryness under vacuum. The residue was diluted with DCM, washed with saturated aqueous $NaHCO_3$ solution, and the layers separated. The organic layer was dried over $Na_2SO_4$, filtered and evaporated to dryness. The residue was purified by flash chromatography eluting with DCM:MeOH (0-15%) to provide 0.07 g (50% yield) of title compound as an orange solid. LCMS: ($C_{46}H_{65}N_9O_4$) desired mass=807.5; found: m/z=808.3 $[M+H]^+$.

Step 2: 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-N-methyl-N-(piperidin-4-yl)acetamide Tert-Butyl 4-(2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-N-methylacetamido)piperidine-1-carboxylate (0.07 g, 0.1 mmol) was dissolved in anhydrous DCM (0.8 mL), then TFA was added (0.8 mL, 8.66 mmol). The reaction mixture was stirred at room temperature for 2 h, then concentrated to dryness under vacuum. The crude residue was triturated with $Et_2O$ to provide 90 mg (100% yield) of the title compound as an orange solid. LCMS: ($C_{41}H_{57}N_9O_2$) desired mass=707.5; found: m/z=708.2 $[M+H]^+$.

Intermediate Y

6-[4-(cyclopropylamino)-3-(propan-2-yl)-3h-imidazo[4,5-c]pyridin-6-yl]-1'-(piperazine-1-carbonyl)-1-[(1s,3s)-3-(piperidin-1-yl)cyclobutyl]-1,2-dihydrospiro[indole-3,4'-piperidin]-2-one

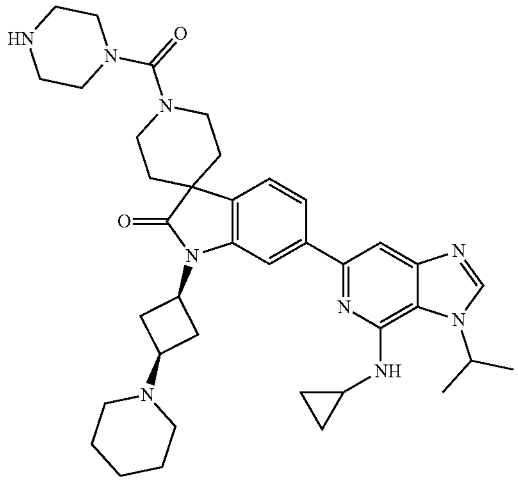 [SMILES: CC(C)n1cnc2cc(-c3ccc4c(c3)N([C@H]3C[C@@H](N5CCCCC5)C3)C(=O)C43CCN(C(=O)N4CCNCC4)CC3)nc(NC3CC3)c21]

Step 1: tert-butyl 4-(carbonochloridoyl)piperazine-1-carboxylate

To a solution of bis(trichloromethyl)carbonate (0.25 g, 0.84 mmol) in dichloromethane (2 mL) at 0° C. was slowly added a solution of tert-butyl 1-piperazinecarboxylate (0.4 g, 2.14 mmol) and pyridine (0.35 mL, 4.33 mmol) in dichloromethane (1.6 mL). The mixture was warmed to room temperature and stirred for 2 hours followed by addition of aqueous HCl solution (0.1 N, 200 mL). The organic layer was separated and dried over anhydrous magnesium sulfate, filtered and concentered to provide 0.51 g (93% yield) of the title compound as a pale-yellow solid. $^1H$ NMR (300 MHz, Chloroform-d) δ 3.71 (m, 2H), 3.68-3.60 (m, 2H), 3.52 (s, 4H), 1.50 (s, 9H).

Step 2: tert-butyl 4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl) piperazine-1-carboxylate A mixture of 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.25 g, 0.44 mmol), tert-butyl 4-(carbonochloridoyl)piperazine-1-carboxylate (0.13 g, 0.50 mmol) and DIPEA (0.21 mL, 1.31 mmol) in anhydrous dichloromethane (8 mL) was stirred at 50° C. for 4 h. The volatiles were removed in vacuo and the crude residue was purified by silica gel flash chromatography eluting with DCM/MeOH (9:1) to provide 0.29 g (82% yield) of the title compound. LCMS: $C_{43}H_{59}N_9O_4$, desired mass=765.5, found: m/z=767.3 $[M+H]^+$.

Step 3: 6-[4-(cyclopropylamino)-3-(propan-2-yl)-3H-imidazo[4,5-c]pyridin-6-yl]-1'-(piperazine-1-carbonyl)-1-[(1s,3s)-3-(piperidin-1-yl)cyclobutyl]-1,2-dihydrospiro[indole-3,4'-piperidin]-2-one A solution of tert-butyl 4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperazine-1-carboxylate (0.29 g, 0.36 mmol) and trifluoroacetic acid (1.23 g, 10.79 mmol) in anhydrous dichloromethane (5.14 mL) was stirred at rt for 2 h. All volatiles were removed in vacuo, and the crude product was triturated with dry diethyl ether to obtain the title compound a trifluoroacetate salt. The residue was triturated with aqueous potassium carbonate solution to provide 0.17 g (62% yield) of the title compound as a brown solid. LCMS: $C_{30}H_{51}N_9O_2$, desired mass=665.4, found: m/z=666.4 $[M+H]^+$.

Intermediate Z 2-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)propanoic acid

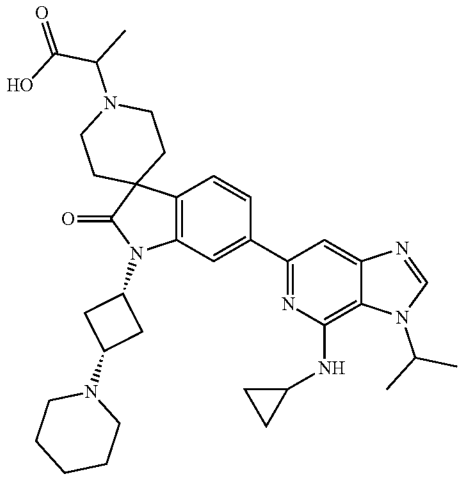 [SMILES: CC(C(=O)O)N1CCC2(CC1)C(=O)N([C@H]1C[C@@H](N3CCCCC3)C1)c1cc(-c3cc4ncn(C(C)C)c4c(NC4CC4)n3)ccc12]

The title compound was synthesized by similar procedures to Intermediate W using tert-butyl 2-bromopropanoate as the alkylating agent in step 1. LCMS: $C_{36}H_{47}N_7O_3$ desired mass=625.82, found m/z=626.35 $[M+H]^+$. $^1H$ NMR (500 MHz, DMSO-$d_6$) δ: 11.42 (s, 1H), 11.27 (s, 1H), 9.43 (s, 1H), 7.78 (d, J=7.7 Hz, 1H), 7.66 (d, J=13.1 Hz, 2H), 7.41 (d, J=7.7 Hz, 1H), 4.31 (m, 2H), 3.89 (m, 2H), 3.51 (m, 3H), 3.27 (m, 2H), 3.10 m, 3H), 2.93 (m, 2H), 2.75 (m, 3H), 2.06 (m, 1H), 1.77 (s, 3H), 1.59 (m, 6H), 1.36 (m, 1H), 0.92 (m, 2H), 0.79 (m, 2H).

Intermediate AA 1-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carboxylic acid; bis(trifluoroacetic acid)

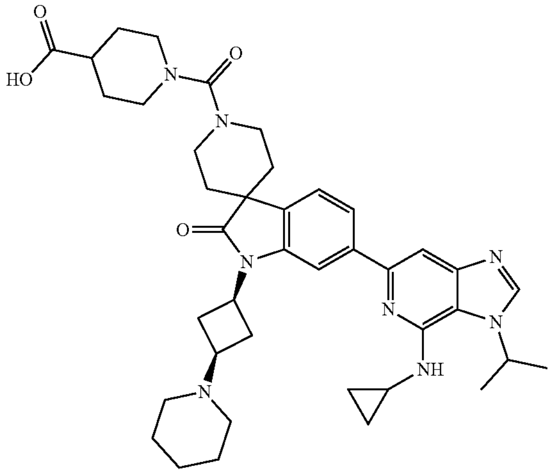 [SMILES: CC(C)n1cnc2cc(-c3ccc4c(c3)N([C@H]3C[C@@H](N5CCCCC5)C3)C(=O)C43CCN(C(=O)N4CCC(C(=O)O)CC4)CC3)nc(NC3CC3)c21]

Step 1: tert-butyl 1-(carbonochloridoyl)piperidine-4-carboxylate

To triphosgene (0.214 g, 0.72 mmol) in dichloromethane (6.01 mL) at 0° C. was slowly added a solution of 4-piperidinecarboxylic acid t-butyl ester HCl (0.4 g, 1.80 mmol) and pyridine (0.29 mL, 3.61 mmol) in dichloromethane (2.0 mL). The mixture was warmed to room temperature over 30 min followed by addition of aqueous HCl solution (0.1 N, 200 mL). The organic layer was separated, dried over anhydrous magnesium sulfate, filtered and concentrated to provide 0.41 g (83% yield) of the title compound as a brown solid. $^1H$ NMR (300 MHz, Chloroform-d), δ: 4.19 (m, 2H), 3.28 (t, J=12.5 Hz, 1H), 3.13 (t, J=12.5 Hz, 1H), 2.58-2.40 (m, 1H), 1.96 (m, 2H), 1.75 (m, 2H), 1.47 (s, 9H).

Step 2: tert-butyl 1-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carboxylate A mixture of 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.2 g, 0.33 mmol), tert-butyl 1-(carbono-chloridoyl)piperidine-4-carboxylate (0.11 g, 0.39 mmol) and triethylamine (0.24 mL, 1.63 mmol) in anhydrous dichloromethane (1.63 mL) was heated with vigorous stirring at 45° C. for 2 h. The reaction mixture was concentrated to dryness under vacuum and the residue was purified by flash chromatography (eluting with DCM-MeOH, 0 to 10%) to provide 0.25 g (94%) of the title compound as an off-white solid. LCMS: $C_{44}H_{60}N_8O_4$, desired mass=764.5, found m/z=765.5 $[M+H]^+$.

Step 3: 1-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carboxylic acid; bis(trifluoroacetic acid)

A solution of tert-butyl 1-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carboxylate (0.25 g, 0.30 mmol) and trifluoroacetic acid (1.04 g, 9.12 mmol) in anhydrous dichloromethane (3.04 mL) was stirred at room temperature for 3 h. The mixture was concentrated to dryness under vacuum and the residue was triturated with dry diethyl ether to provide 0.3 g (95%) of the title compound as a double TFA salt. LCMS: $C_{40}H_{52}N_8O_4$, desired mass=708.9, found: m/z=709.4 $[M+H]^+$.

Intermediate BB

1'-{2-azaspiro[3.3]heptane-6-carbonyl}-6-[4-(cyclopropylamino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidine]-2-one

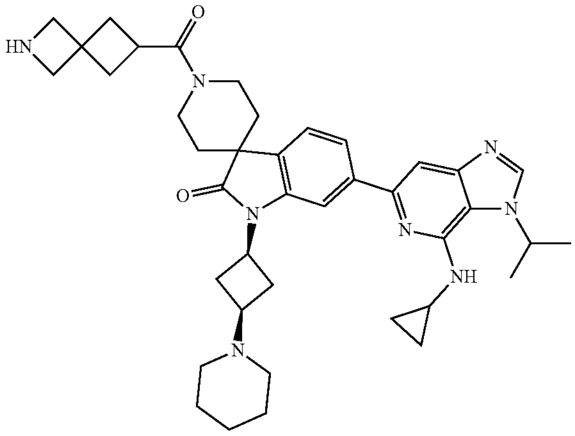 [SMILES: CC(C)n1cnc2cc(-c3ccc4c(c3)N([C@H]3C[C@@H](N5CCCCC5)C3)C(=O)C43CCN(C(=O)C4CC5(CNC5)C4)CC3)nc(NC3CC3)c21]

Step 1: tert-butyl 6-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-yl}carbonyl)-2-azaspiro[3.3]heptane-2-carboxylate To a solution of 2-[(tert-butoxy)carbonyl]-2-azaspiro[3.3]heptane-6-carboxylic acid (0.226 g, 0.93 mmol) in anhydrous DMF (7.22 mL, 0.1 M) was added DIPEA (0.63 mL, 3.62 mmol) and BOP (0.38 g, 0.87 mmol). The reaction mixture was stirred 1 h at rt, then 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.4 g, 0.72 mmol) was added and stirring was continued for an additional 1.5 h. The volatiles were evaporated in vacuo, the residue was dissolved in DCM, then saturated aqueous $NaHCO_3$ solution was added and the mixture stirred vigorously for 30 min. The organic phase was separated, dried over $Na_2SO_4$, and concentrated to dryness. The residue was purified flash column chromatography eluting with DCM:MeOH (0-15% of MeOH) to provide 0.36 g (64% yield) of the title compound as a brown solid. LCMS: $C_{45}H_{60}N_8O_4$ desired mass=777.03, found m/z=778.40 $[M+H]^+$.

Step 2: 1'-{2-azaspiro[3.3]heptane-6-carbonyl}-6-[4-(cyclopropylamino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidine]-2-one To a solution of tert-butyl 6-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-yl}carbonyl)-2-azaspiro[3.3]heptane-2-carboxylate (0.36 g, 0.46 mmol) in anhydrous DCM (6.6 mL) was added TFA (5.28 mL, 46.33 mmol). The reaction mixture was stirred at rt for 2 h, then concentrated to dryness under vacuum. The crude residue was triturated with $Et_2O$ to provide 360 mg (100% yield) of the title compound as a white solid. LCMS: $C_{40}H_{52}N_8O_2$ desired mass=676.91, found m/z=678.30 $[M+H]^+$.

Intermediate CC

6-[4-(Cyclopropylamino)-3-Isopropylimidazo[4,5-c]Pyridin-6-yl]-1'-[(3R)-3-Methylpyrrolidine-3-Carbonyl]-1-[(1S,3S)-3-(Piperidin-1-yl)Cyclobutyl]Spiro[Indole-3,4'-Piperidin]-2-One

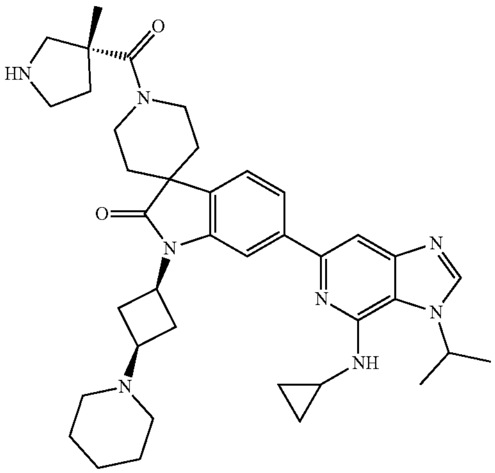 [SMILES: CC(C)n1cnc2cc(-c3ccc4c(c3)N([C@H]3C[C@@H](N5CCCCC5)C3)C(=O)C43CCN(C(=O)[C@]4(C)CCNC4)CC3)nc(NC3CC3)c21]

Step 1: benzyl (R)-3-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)-3-methylpyrrolidine-1-carboxylate To (3R)-1-[(benzyloxy)carbonyl]-3-methylpyrrolidine-3-carboxylic acid (57 mg, 0.22 mmol) in DMF was added (1,2,3-benzotriazol-1-yloxy)tris(dimethylamino)phosphanium; hexafluoro-lambda5-phosphanuide (BOP) (76 mg, 0.27 mmol) followed by N,N-diisopropylethylamine (0.07 mL, 0.9 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (100 mg, 0.18 mmol). The reaction mixture was stirred at rt overnight. The crude mixture was purified with C18 reverse phase chromatography (eluting with $CH_3CN$ and water). The title compound (TFA salt) was isolated as an off-white solid (116 mg, 80% yield). LCMS: [$C_{47}H_{58}N_8O_4$], desired mass=798.5, found: m/z=799.4 $[M+H]^+$.

Step 2: 6-[4-(cyclopropylamino)-3-isopropylimidazo [4,5-c]pyridin-6-yl]-1'-[(3R)-3-methylpyrrolidine-3-carbonyl]-1-[(1s,3s)-3-(piperidin-1-yl)cyclobutyl] spiro[indole-3,4'-piperidin]-2-one A mixture of benzyl (R)-3-(6-(4-(cyclopropylamino)-3-isopropyl-3H-imidazo[4,5-c]pyridin-6-yl)-2-oxo-1-((1s, 3S)-3-(piperidin-1-yl)cyclobutyl)spiro[indoline-3,4'-piperidine]-1'-carbonyl)-3-methylpyrrolidine-1-carboxylate (116.00 mg, 0.1452 mmol) in ethanol (2 ml) and THF (2 mL) was placed in a 40 mL vial and stirred until dissolution was complete. The vial was evacuated/backfilled with $N_2$ three times. Palladium 10% (154 mg, 1.45 mmol) was added, and the mixture was evacuated/backfilled with $H_2$ three times. The mixture was stirred at rt under an $H_2$ balloon for 3 hours. The reaction mixture was filtered through a thin layer of celite and concentrated to dryness. The residue was purified with C18 reverse phase chromatography eluting with $CH_3CN$ and water. The title compound (TFA salt) was isolated as an off-white solid (90 mg, 93% yield). LCMS: [$C_{39}H_{52}N_8O_2$], desired mass=664.4, found: m/z=665.4 $[M+H]^+$.

Intermediate DD

6-[4-(Cyclopropylamino)-3-Isopropylimidazo[4,5-C] Pyridin-6-yl]-1'-[2-(Piperidin-4-yl)Propanoyl]-1-[(1S,3S)-3-(Piperidin-1-yl)Cyclobutyl]Spiro[Indole-3,4'-Piperidin]-2-One

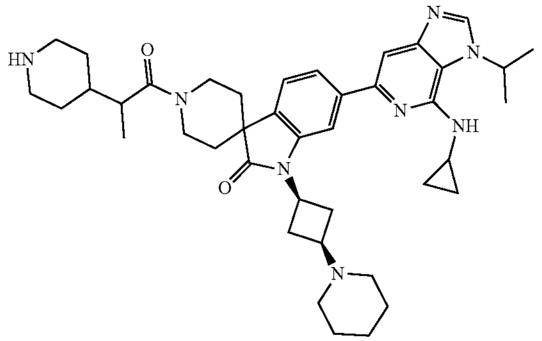 [SMILES: CC(C(=O)N1CCC2(CC1)C(=O)N([C@H]1C[C@@H](N3CCCCC3)C1)c1cc(-c3cc4ncn(C(C)C)c4c(NC4CC4)n3)ccc12)C1CCNCC1]

Step 1: tert-butyl 4-(1-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-1-oxopropan-2-yl)piperidine-1-carboxylate A mixture of 2-[1-(tert-butoxycarbonyl)piperidin-4-yl] propanoic acid (111 mg, 0.43 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (200 mg, 0.36 mmol) in DMF and $CH_3CN$ was treated with chloro(dimethylamino)methylidene]dimethylazanium; hexafluoro-lambda5-phosphanuide (TCFH) (152 mg, 0.54 mmol) followed by 1-methylimidazole (0.14 mL, 1.81 mmol). The reaction mixture was stirred at rt for 1 hour. The crude mixture was purified with C18 reverse phase chromatography eluting with $CH_3CN$ and water. The desired product was isolated as an off-white solid (116 mg, 80% yield). LCMS: [$C_{46}H_{64}N_8O_4$], desired mass=792.5, found: m/z=793.5 $[M+H]^+$.

Step 2: 6-[4-(cyclopropylamino)-3-isopropylimidazo [4,5-c]pyridin-6-yl]-1'-[2-(piperidin-4-yl)propanoyl]-1-[(1s,3s)-3-(piperidin-1-yl)cyclobutyl]spiro[indole-3,4'-piperidin]-2-one A mixture of tert-butyl 4-(1-{6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}-1-oxopropan-2-yl)piperidine-1-carboxylate (200 mg, 0.25 mmol) in HFIP (4 mL) was treated with TFA (0.2 mL, 2.5 mmol) and stirred at room temperature for 1 hour. The resulting mixture was concentrated under vacuum. The residue was purified by reverse phase flash chromatography [CH3CN and H2O mobile phase] to yield 150 mg (83%) of the title compound as a white solid. LCMS: [$C_{41}H_{56}N_8O_2$] desired mass=692.5; found: m/z=693.4 $[M+H]^+$.

Intermediate EE

6-[4-(Cyclopropylamino)-3-Isopropylimidazo[4,5-C] Pyridin-6-yl]-1'-[2-(Piperazin-1-yl)Acetyl]-1-[(1S, 3S)-3-(Piperidin-1-yl)Cyclobutyl]Spiro[Indole-3,4'-Piperidin]-2-One

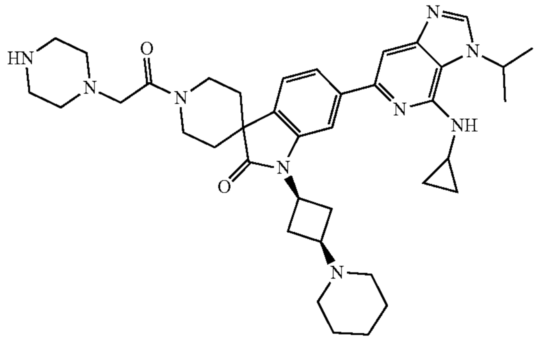 [SMILES: CC(C)n1cnc2cc(-c3ccc4c(c3)N([C@H]3C[C@@H](N5CCCCC5)C3)C(=O)C43CCN(C(=O)CN4CCNCC4)CC3)nc(NC3CC3)c21]

Step 1: tert-butyl 4-(2-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperazine-1-carboxylate Using procedures similar to those for Intermediate DD (step 1) and using 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (200 mg, 0.36 mmmol) and [4-(tert-butoxycarbonyl)piperazin-1-yl]acetic acid (105 mg, 0.43 mmol) as the starting materials, the desired product (TFA salt) was isolated as an off-white solid (210 mg, 74% yield). LCMS: [$C_{44}H_{61}N_9O_4$], desired mass=779.5, found: m/z=780.5 $[M+H]^+$.

Step 2: 6-[4-(cyclopropylamino)-3-isopropylimidazo [4,5-c]pyridin-6-yl]-1'-[2-(piperazin-1-yl)acetyl]-1-[(1s,3s)-3-(piperidin-1-yl)cyclobutyl]spiro[indole-3, 4'-piperidin]-2-one Using procedures similar to those for Intermediate DD (step 2) and using tert-butyl 4-(2-(6-(4-(cyclopropylamino)-

3-isopropyl-3H-imidazo[4,5-c]pyridin-6-yl)-2-oxo-1-((1s, 3s)-3-(piperidin-1-yl)cyclobutyl)spiro[indoline-3,4'-piperidin]-1'-yl)-2-oxoethyl)piperazine-1-carboxylate (210 mg, 0.269 mmol) as the starting material, the title compound (TFA salt) was isolated as an off-white solid (160 mg, 87% yield). LCMS: [$C_{39}H_{53}N_9O_2$], desired mass=679.4, found: m/z=680.4 $[M+H]^+$.

Intermediate FF

6-[4-(cyclopropylamino)-3-isopropylimidazo[4,5-c]pyridin-6-yl]-1'-[2-methyl-2-(piperazin-1-yl)propanoyl]-1-[(1S,3S)-3-(piperidin-1-yl)cyclobutyl]spiro[indole-3,4'-piperidin]-2-one

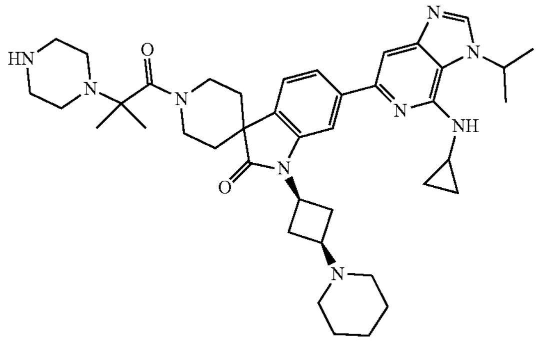 [SMILES: CC(C)n1cnc2cc(-c3ccc4c(c3)N([C@H]3C[C@@H](N5CCCCC5)C3)C(=O)C43CCN(C(=O)C(C)(C)N4CCNCC4)CC3)nc(NC3CC3)c21]

Step 1: tert-butyl 4-(1-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-methyl-1-oxopropan-2-yl)piperazine-1-carboxylate Using procedures similar to those for Intermediate DD (step 1) and using 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (200 mg, 0.36 mmmol) and 2-[4-(tert-butoxycarbonyl)piperazin-1-yl]-2-methylpropanoic acid (118 mg, 0.43 mmol) as starting materials, the desired product (TFA salt) was isolated as an off-white solid (160 mg, 64% yield). LCMS: [$C_{46}H_{65}N_9O_4$], desired mass=807.5, found: m/z=808.5 $[M+H]^+$.

Step 2: 6-[4-(cyclopropylamino)-3-isopropylimidazo[4,5-c]pyridin-6-yl]-1'-[2-methyl-2-(piperazin-1-yl)propanoyl]-1-[(1s,3s)-3-(piperidin-1-yl)cyclobutyl]spiro[indole-3,4'-piperidin]-2-one Using procedures similar to those for Intermediate DD (step 2) and using tert-butyl 4-(1-(6-(4-(cyclopropylamino)-3-isopropyl-3H-imidazo[4,5-c]pyridin-6-yl)-2-oxo-1-((1s, 3s)-3-(piperidin-1-yl)cyclobutyl)spiro[indoline-3,4'-piperidin]-1'-yl)-2-methyl-1-oxopropan-2-yl)piperazine-1-carboxylate (159 mg, 0.197 mmol) as the starting material, the title compound (TFA salt) was isolated as an off-white solid (120 mg, 86% yield). LCMS: [$C_{41}H_{57}N_9O_2$], desired mass=707.5, found: m/z=708.4 $[M+H]^+$.

Intermediate GG

6-[4-(cyclopropylamino)-3-isopropylimidazo[4,5-c]pyridin-6-yl]-1'-[(3S)-piperidine-3-carbonyl]-1-[(1S,3S)-3-(piperidin-1-yl)cyclobutyl]spiro[indole-3,4'-piperidin]-2-one

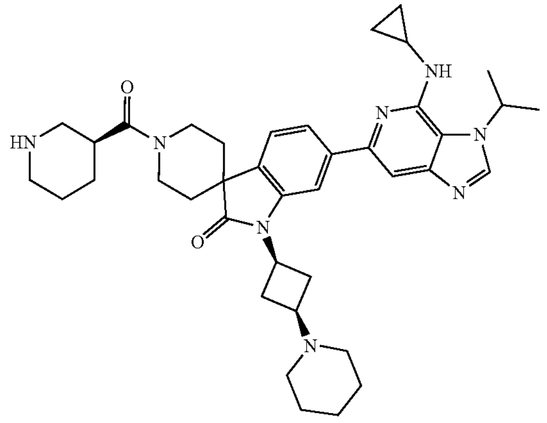 [SMILES: CC(C)n1cnc2cc(-c3ccc4c(c3)N([C@H]3C[C@@H](N5CCCCC5)C3)C(=O)C43CCN(C(=O)[C@H]4CCCNC4)CC3)nc(NC3CC3)c21]

Step 1: tert-butyl (S)-3-(6-(4-(cyclopropylamino)-3-isopropyl-3H-imidazo[4,5-c]pyridin-6-yl)-2-oxo-1-((1s,3R)-3-(piperidin-1-yl)cyclobutyl)spiro[indoline-3,4'-piperidine]-1'-carbonyl)piperidine-1-carboxylate Using procedures similar to those for Intermediate DD (step 1) and using 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) and (3S)-1-(tert-butoxycarbonyl)piperidine-3-carboxylic acid (112 mg, 0.43 mmol) as starting materials, the desired product (TFA salt) was isolated as an off-white solid (200 mg, 72% yield). LCMS: [$C_{44}H_{60}N_8O_4$], desired mass=764.5, found: m/z=765.9 $[M+H]^+$.

Step 2: 6-[4-(cyclopropylamino)-3-isopropylimidazo[4,5-c]pyridin-6-yl]-1'-[(3S)-piperidine-3-carbonyl]-1-[(1s,3s)-3-(piperidin-1-yl)cyclobutyl]spiro[indole-3,4'-piperidin]-2-one Using procedures similar to those for Intermediate DD (step 2) and using tert-butyl (S)-3-(6-(4-(cyclopropylamino)-3-isopropyl-3H-imidazo[4,5-c]pyridin-6-yl)-2-oxo-1-((1s,3R)-3-(piperidin-1-yl)cyclobutyl)spiro[indoline-3,4'-piperidine]-1'-carbonyl)piperidine-1-carboxylate (200 mg, 0.261 mmol) as the starting material, the title compound (TFA salt) was isolated as an off-white solid (120 mg, 69% yield). LCMS: [$C_{39}H_{52}N_8O_2$], desired mass=664.4, found: m/z=665.4 $[M+H]^+$.

Intermediate HH

6-[4-(cyclopropylamino)-3-isopropylimidazo[4,5-c]pyridin-6-yl]-1'-[(3R)-piperidine-3-carbonyl]-1-[(1s,3s)-3-(piperidin-1-yl)cyclobutyl]spiro[indole-3,4'-piperidin]-2-one

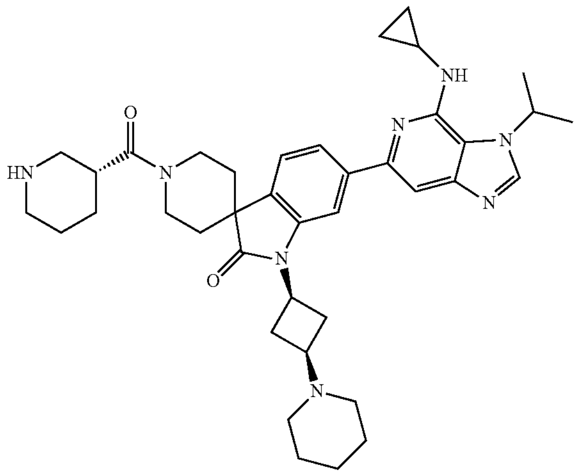 [SMILES: CC(C)n1cnc2cc(-c3ccc4c(c3)N([C@H]3C[C@@H](N5CCCCC5)C3)C(=O)C43CCN(C(=O)[C@@H]4CCCNC4)CC3)nc(NC3CC3)c21]

Step 1: tert-butyl (R)-3-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)piperidine-1-carboxylate Using procedures similar to those for Intermediate DD (step 1) and using 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) and (3R)-1-(tert-butoxycarbonyl)piperidine-3-carboxylic acid (111 mg, 0.43 mmol) as starting materials, the desired product was isolated as an off-white solid (220 mg, 79% yield). LCMS: [$C_{44}H_{60}N_8O_4$], desired mass=764.5, found: m/z=765.9 $[M+H]^+$.

Step 2: 6-[4-(cyclopropylamino)-3-isopropylimidazo[4,5-c]pyridin-6-yl]-1'-[(3R)-piperidine-3-carbonyl]-1-[(1s,3s)-3-(piperidin-1-yl)cyclobutyl]spiro[indole-3,4'-piperidin]-2-one Using procedures similar to those for Intermediate DD (step 2) using tert-butyl (R)-3-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)piperidine-1-carboxylate (210 mg, 0.275 mmol) as the starting material, the title compound was isolated as an off-white solid (110 mg, 60% yield). LCMS: [$C_{39}H_{52}N_8O_2$], desired mass=664.4, found: m/z=665.4 $[M+H]^+$.

Intermediate II

6-[4-(Cyclopropylamino)-3-Isopropylimidazo[4,5-C]Pyridin-6-yl]-1'-[(1R,5S,6S)-3-Azabicyclo[3.1.1]Heptane-6-Carbonyl]-1-[(1S,3S)-3-(Piperidin-1-yl)Cyclobutyl]Spiro[Indole-3,4'-Piperidin]-2-One

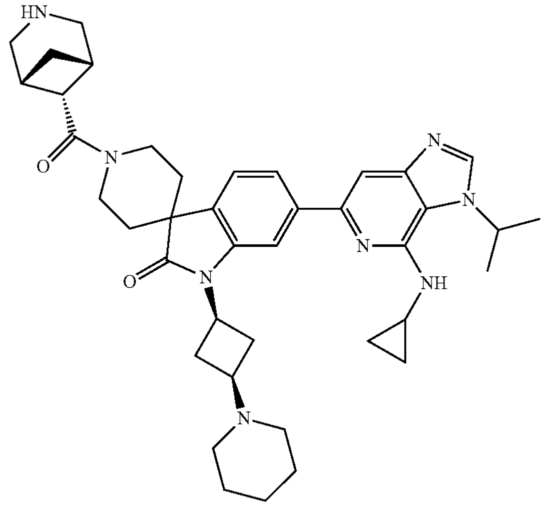 [SMILES: CC(C)n1cnc2cc(-c3ccc4c(c3)N([C@H]3C[C@@H](N5CCCCC5)C3)C(=O)C43CCN(C(=O)[C@@H]4[C@@H]5CNC[C@H]4C5)CC3)nc(NC3CC3)c21]

Step 1: tert-butyl (1R,5S,6s)-6-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)-3-azabicyclo[3.1.1]heptane-3-carboxylate Using procedures similar to those for Intermediate DD (step 1) and using 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (200 mg, 0.36 mmmol) and (1R,5S,6s)-3-(tert-butoxycarbonyl)-3-azabicyclo[3.1.1]heptane-6-carboxylic acid (106 mg, 0.43 mmol) as starting materials, the desired product was isolated as an off-white solid (180 mg, 64% yield). LCMS: [$C_{45}H_{60}N_8O_4$], desired mass=776.5, found: m/z=777.9 $[M+H]^+$.

Step 2: 6-[4-(cyclopropylamino)-3-isopropylimidazo[4,5-c]pyridin-6-yl]-1'-[(1R,5S,6s)-3-azabicyclo[3.1.1]heptane-6-carbonyl]-1-[(1s,3s)-3-(piperidin-1-yl)cyclobutyl]spiro[indole-3,4'-piperidin]-2-one Using procedures similar to those for Intermediate DD (step 2) using tert-butyl (1R,5S,6s)-6-({6-[4-(cyclopropylamino)-3-isopropylimidazo[4,5-c]pyridin-6-yl]-2-oxo-1-[(1 s,3s)-3-(piperidin-1-yl)cyclobutyl]spiro[indole-3,4'-piperidin]-1'-yl}carbonyl)-3-azabicyclo[3.1.1]heptane-3-carboxylate (200 mg, 0.257 mmol) as the starting material, the title compound was isolated as an off-white solid (190 mg, 100% yield). LCMS: [$C_{40}H_{52}N_8O_2$], desired mass=676.4, found: m/z=677.7 $[M+H]^+$.

Intermediate JJ

1'-(azetidine-3-carbonyl)-6-{4-[(2-fluorophenyl)amino]-3-isopropylimidazo[4,5-c]pyridin-6-yl}-1-[(1S,3S)-3-(piperidin-1-yl)cyclobutyl]spiro[indole-3,4'-piperidin]-2-one

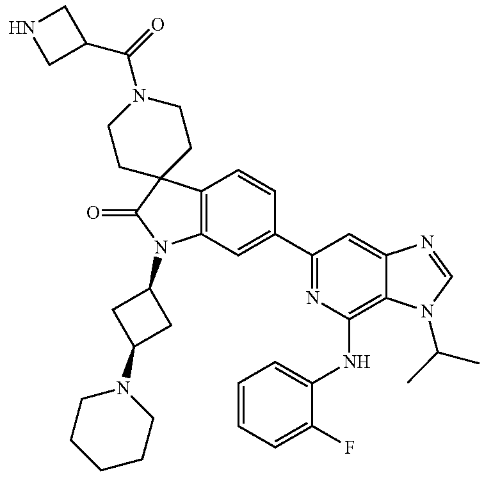 [SMILES: CC(C)n1cnc2cc(-c3ccc4c(c3)N([C@H]3C[C@@H](N5CCCCC5)C3)C(=O)C43CCN(C(=O)C4CNC4)CC3)nc(Nc3ccccc3F)c21]

Step 1: tert-butyl 3-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)azetidine-1-carboxylate Using procedures similar to those for Intermediate DD (step 1) 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (Intermediate C) (20 mg, 0.033 mmmol) and 1-(tert-butoxycarbonyl)azetidine-3-carboxylic acid (6.6 mg, 0.033 mmol) as starting materials, the desired product was isolated as an off-white solid (21 mg, 81% yield). LCMS: [$C_{45}H_{55}N_8O_4$], desired mass=790.4, found: m/z=791.9 $[M+H]^+$.

Step 2: 1'-(azetidine-3-carbonyl)-6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one Using procedures similar to those for Intermediate DD (step 2) using tert-butyl 3-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)azetidine-1-carboxylate (21 mg, 0.025 mmol) as the starting material, the title compound was isolated as an off-white solid (8 mg, 30% yield). LCMS: [$C_{40}H_{47}FN_8O_2$], desired mass=690.4, found: m/z=691.7 $[M+H]^+$.

Intermediate KK 1-((1S,3S)-3-(3-oxa-8-azabicyclo[3.2.1]octan-8-yl)cyclobutyl)-6-(4-(cyclopropylamino)-3-isopropyl-3h-imidazo[4,5-c]pyridin-6-yl)spiro[indoline-3,4'-piperidin]-2-one

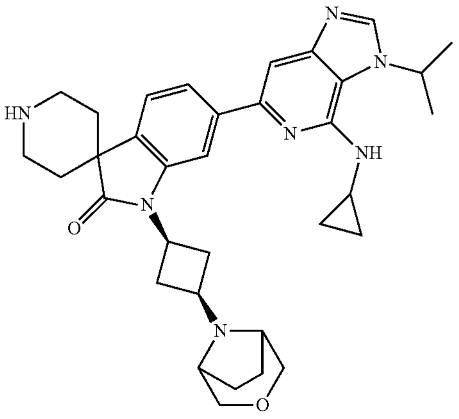 [SMILES: CC(C)n1cnc2cc(-c3ccc4c(c3)N([C@H]3C[C@@H](N5C6CCC5COC6)C3)C(=O)C43CCNCC3)nc(NC3CC3)c21]

Step 1: 6-bromo-N-cyclopropyl-3-isopropylimidazo[4,5-c]pyridin-4-amine

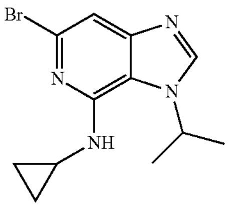 [SMILES: CC(C)n1cnc2cc(Br)nc(NC3CC3)c21]

A mixture of 6-bromo-4-chloro-3-isopropyl-3H-imidazo[4,5-c]pyridine (Intermediate 0540 in WO2020092528A1) (3 g, 11.6 mmol) and aminocyclopropane (6.8 g, 119 mmol) was heated to 50° C. for 16 hours. The reaction mixture was cooled to room temperature, then diluted with EtOAc, washed with water and dried with sodium sulfate. The organic layer was concentrated to afford the title compound as a white foam (2.6 g, 75% yield). LCMS: $C_{12}H_{15}BrN_4$ desired mass: 294.1, found: m/z=295.6 $[M+H]^+$.

Step 2: tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate

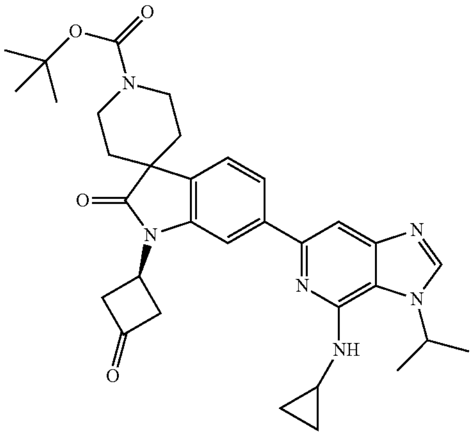

Tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate (Intermediate 0557 in WO2020092528A1) (2 g, 4.03 mmol), Pd(dppf)$Cl_2$ (329.0 mg, 0.4 mmol), 6-bromo-N-cyclopropyl-3-isopropylimidazo[4,5-c]pyridin-4-amine (1.2 g g, 0.17 mmol), 1N aqueous sodium carbonate (12 mL, 12.1 mmol) and 1,4-dioxane (10 mL) were combined in a microwave vial, sealed, and irradiated at 100° C. for 60 mins.

The reaction mixture was filtered then concentrated onto silica gel and purified by normal phase flash column chromatography to afford the title compound (1.8 g, 76% yield). LCMS: $C_{33}H_{40}N_6O_4$ desired mass: 584.7, found: m/z=585.7 $[M+H]^+$.

Step 3: 1-((1s,3s)-3-(3-oxa-8-azabicyclo[3.2.1]octan-8-yl)cyclobutyl)-6-(4-(cyclopropylamino)-3-isopropyl-3H-imidazo[4,5-c]pyridin-6-yl)spiro[indoline-3,4'-piperidin]-2-one

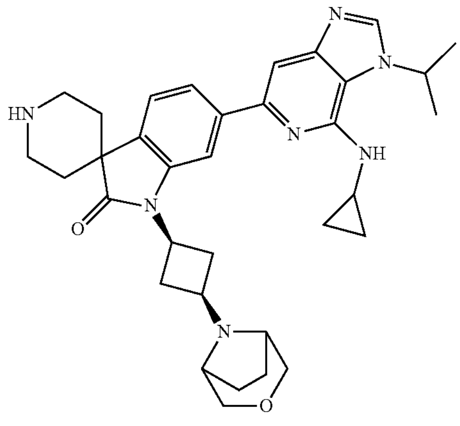 [SMILES: CC(C)n1cnc2cc(-c3ccc4c(c3)N([C@H]3C[C@@H](N5C6CCC5COC6)C3)C(=O)C43CCNCC3)nc(NC3CC3)c21]

A mixture of tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (0.2 g, 0.34 mmol, triethylamine (0.24 mL, 1.71 mmol), and 3-oxa-8-azabicyclo[3.2.1]octane (0.046 g. 0.41 mmol) were dissolved in DCM (1.0 mL) and DMSO (0.1 mL) and was treated with sodium triacetoxyborohydride (217 mg, 1.03 mmol). The reaction mixture was stirred at room temperature for 3 hours and poured over saturated aqueous ammonium chloride and extracted with ethyl acetate. The organic layer was concentrated and treated with TFA (0.2 mL, 2.6 mmol) in HFIP (3.8 mL) at room temperature for 1 hour. The reaction mixture was concentrated and purified by C18 reverse phase column eluting with $CH_3CN/H_2O$ to afford the title compound as a white foam (120 mg, 69% yield). LCMS: $C_{34}H_{43}N_7O_2$ desired mass: 581.4, found: m/z=582.6 $[M+H]^+$.

Intermediate LL 6-(4-(cyclopropylamino)-3-isopropyl-3h-imidazo[4,5-c]pyridin-6-yl)-1-((1S,3S)-3-morpholinocyclobutyl)spiro[indoline-3,4'-piperidin]-2-one

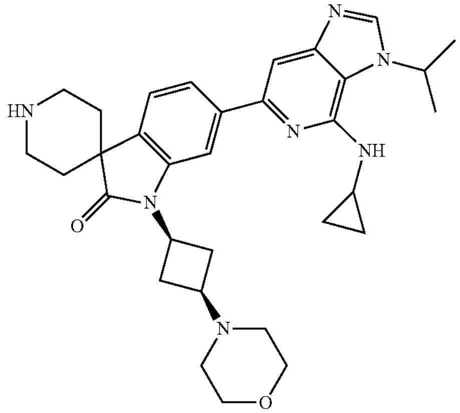 [SMILES: CC(C)n1cnc2cc(-c3ccc4c(c3)N([C@H]3C[C@@H](N5CCOCC5)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (100 mg, 0.2 mmol), and morpholine (100 mg, 1.01 mmol), the title compound was isolated as an off-white solid (95 mg, 100% yield) as a TFA salt. LCMS: $[C_{32}H_{41}N_7O_2]$, desired mass=555.3, found: m/z=556.5 $[M+H]^+$.

Intermediate MM 1-((1S,3S)-3-(3-Azabicyclo[3.2.1]Octan-3-yl)Cyclobutyl)-6-(4-(Cyclopropylamino)-3-Isopropyl-3H-Imidazo[4,5-C]Pyridin-6-yl)Spiro[Indoline-3,4'-Piperidin]-2-One

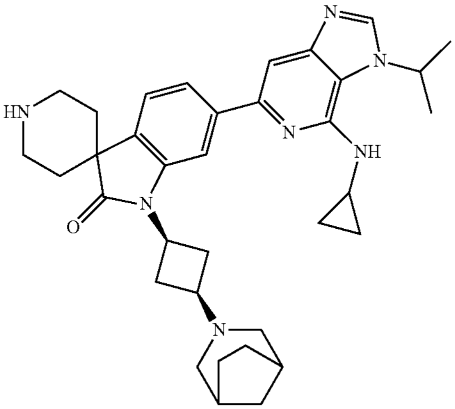 [SMILES: CC(C)n1cnc2cc(-c3ccc4c(c3)N([C@H]3C[C@@H](N5CC6CCC(C6)C5)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (300 mg, 0.51 mmol), and 3-azabicyclo[3.2.1]octane (111 mg, 0.77 mmol), the title compound was isolated as an off-white solid (195 mg, 66% yield) as a TFA salt. LCMS: [$C_{35}H_{45}N_7O$], desired mass=579.4, found: m/z=580.5 $[M+H]^+$.

Intermediate NN 1-((1S,3S)-3-(3-oxa-6-azabicyclo[3.1.1]heptan-6-yl)cyclobutyl)-6-(4-(cyclopropylamino)-3-isopropyl-3h-imidazo[4,5-c]pyridin-6-yl)spiro[indoline-3,4'-piperidin]-2-one

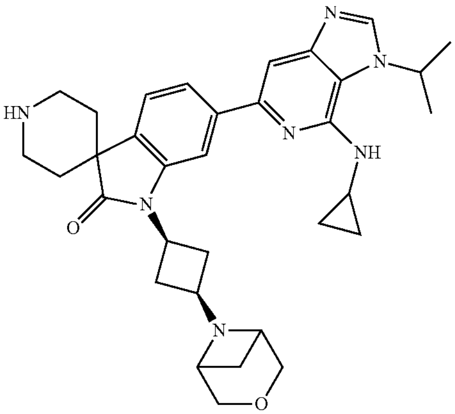 [SMILES: CC(C)n1cnc2cc(-c3ccc4c(c3)N([C@H]3C[C@@H](N5C6COCC5C6)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (200 mg, 0.34 mmol), and 3-oxa-6-azabicyclo[3.1.1]heptane (139 mg, 0.51 mmol), the title compound was isolated as an off-white solid (180 mg, 94% yield) as a TFA salt. LCMS: [$C_{33}H_{41}N_7O_2$], desired mass=567.3, found: m/z=568.5 $[M+H]^+$.

Intermediate OO 6-(4-(cyclopropylamino)-3-isopropyl-3h-imidazo[4,5-c]pyridin-6-yl)-1-((1R,3S)-3-((S)-3-fluoropiperidin-1-yl)cyclobutyl)spiro[indoline-3,4'-piperidin]-2-one

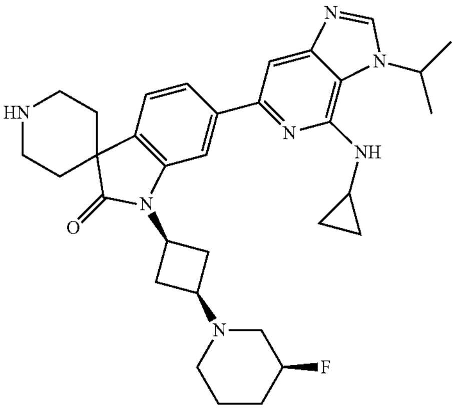 [SMILES: CC(C)n1cnc2cc(-c3ccc4c(c3)N([C@H]3C[C@@H](N5CCC[C@H](F)C5)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (320 mg, 0.55 mmol), and (3S)-3-fluoropiperidine (68 mg, 0.66 mmol), the title compound was isolated as an off-white solid (120 mg, 40% yield) as a TFA salt. LCMS: [$C_{33}H_{42}FN_7O$], desired mass=571.3, found: m/z=572.5 $[M+H]^+$.

Intermediate PP 6-(4-(cyclopropylamino)-3-isopropyl-3h-imidazo[4,5-c]pyridin-6-yl)-1-((1R,3S)-3-((S)-3-fluoropiperidin-1-yl)cyclobutyl)spiro[indoline-3,4'-piperidin]-2-one

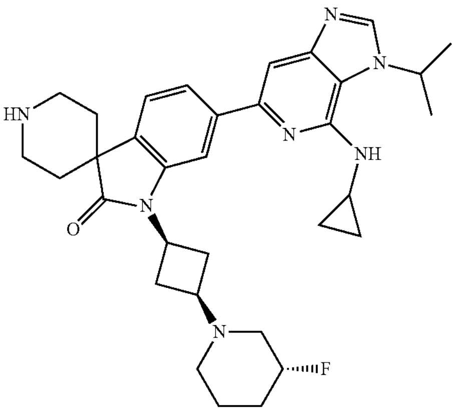 [SMILES: CC(C)n1cnc2cc(-c3ccc4c(c3)N([C@H]3C[C@@H](N5CCC[C@@H](F)C5)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (320 mg, 0.55 mmol), and (3R)-3-fluoropiperidine (68 mg, 0.66 mmol), the title compound was isolated as an off-white solid (140 mg, 45% yield) as a TFA salt. LCMS: [$C_{33}H_{42}FN_7O$], desired mass=571.3, found: m/z=572.5 [M+H]$^+$.

Intermediate QQ 1-((1S,3S)-3-(8-oxa-3-azabicyclo[3.2.1]octan-3-yl) cyclobutyl)-6-(4-(cyclopropylamino)-3-isopropyl-3h-imidazo[4,5-c]pyridin-6-yl)spiro[indoline-3,4'-piperidin]-2-one

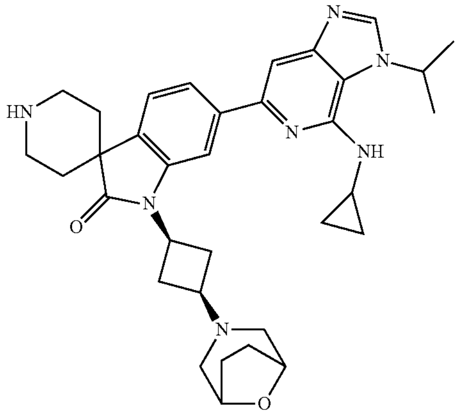 [SMILES: CC(C)n1cnc2cc(-c3ccc4c(c3)N([C@H]3C[C@@H](N5CC6CCC(C5)O6)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (200 mg, 0.34 mmol), and 8-oxa-3-azabicyclo[3.2.1]octane (46 mg, 0.41 mmol), the title compound was isolated as an off-white solid (120 mg, 73% yield) as a TFA salt. LCMS: $C_{34}H_{43}N_7O_2$ desired mass: 581.4, found: m/z=582.6 [M+H]$^+$.

Intermediate RR (1S,4S)-4-(6-(4-(cyclopropylamino)-3-isopropyl-3h-imidazo[4,5-c]pyridin-6-yl)-2-oxo-1-((1S,3S)-3-(piperidin-1-yl)cyclobutyl)spiro[indoline-3,4'-piperidine]-1'-carbonyl)cyclohexane-1-carboxylic acid

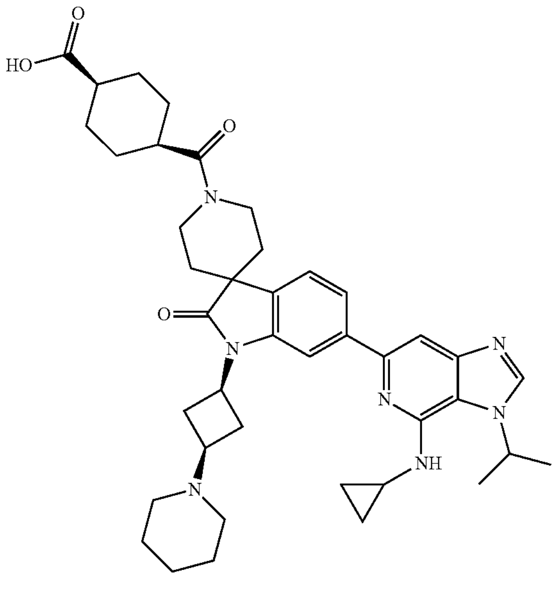 [SMILES: CC(C)n1cnc2cc(-c3ccc4c(c3)N([C@H]3C[C@@H](N5CCCCC5)C3)C(=O)C43CCN(C(=O)[C@H]4CC[C@@H](C(=O)O)CC4)CC3)nc(NC3CC3)c21]

Step 1: methyl (1S,4s)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylate A mixture of (1s,4s)-4-(methoxycarbonyl)cyclohexane-1-carboxylic acid (40.35 mg, 0.22 mmol), (1,2,3-benzotriazol-1-yloxy)tris(dimethylamino)phosphanium; hexafluoro-lambda5-phosphanuide (95.84 mg, 0.22 mmol), and N,N-diisopropylethylamine (0.13 mL, 0.10 g, 0.74 mmol) in DMF was stirred for 10 minutes. 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (80.00 mg, 0.14 mmol) was added and the reaction mixture was stirred at rt for 30 min, then purified by silica gel chromatography eluting with DCM/MeOH to afford the title compound as an off-white solid (0.059 g, 56% yield). LCMS: [$C_{42}H_{55}N_7O_4$], desired mass=721.4, found: m/z=722.8 [M+H]$^+$.

Step 2: (1S,4s)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid 0.08 mL of 1 N aqueous lithium hydroxide hydrate solution was added to methyl (1S,4s)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylate (50 mg, 0.069 mmol) in THF (1 mL). The reaction mixture was stirred for 16 h at room temperature, then acidified to pH 4 with aqueous 1 N HCl solution. The aqueous layer was extracted with EtOAc, then the organic layer was concentrated, and the residue purified by reverse phase chromatography eluting with $CH_3CN$ and water to afford the title compound as an off-white solid (0.030 g, 61% yield). LCMS: [$C_{41}H_{53}N_7O_4$], desired mass=707.4, found: m/z=708.7 [M+H]$^+$.

Intermediate SS 6-(4-(cyclopropylamino)-3-isopropyl-3h-imidazo[4,5-c]pyridin-6-yl)-1-((1S,3S)-3-(4-fluoropiperidin-1-yl)cyclobutyl)spiro[indoline-3,4'-piperidin]-2-one

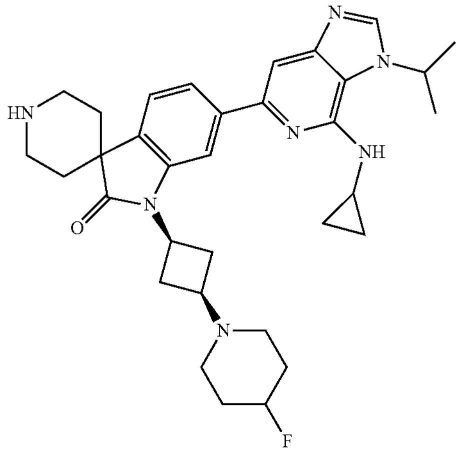 [SMILES: CC(C)n1cnc2cc(-c3ccc4c(c3)N([C@H]3C[C@@H](N5CCC(F)CC5)C3)C(=O)C43CCNCC3)nc(NC3CC3)c21]

Using similar procedures to those in step 3 of Intermediate KK and using tert-butyl 6-[4-(cyclopropylamino)-3-isopropylimidazo[4,5-c]pyridin-6-yl]-2-oxo-1-(3-oxocyclobutyl)spiro[indole-3,4'-piperidine]-1'-carboxylate (200 mg, 0.34 mmol), and 4-fluoropiperidine (46 mg, 0.41 mmol), the title compound was isolated as an off-white solid (120 mg, 63% yield) as a TFA salt. LCMS: [$C_{33}H_{42}FN_7O$], desired mass=571.3, found: m/z=572.5 $[M+H]^+$.

Intermediate TT

1'-(2-bromoacetyl)-6-[4-(cyclopropylamino)-3-isopropylimidazo[4,5-c]pyridin-6-yl]-1-[(1S,3S)-3-(piperidin-1-yl)cyclobutyl]spiro[indole-3,4'-piperidin]-2-one

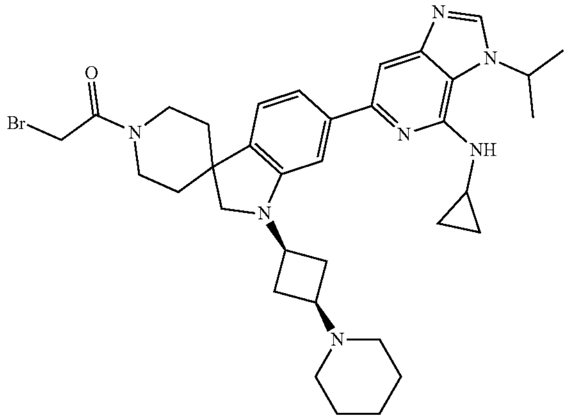 [SMILES: CC(C)n1cnc2cc(-c3ccc4c(c3)N([C@H]3C[C@@H](N5CCCCC5)C3)CC43CCN(C(=O)CBr)CC3)nc(NC3CC3)c21]

To a cooled (0° C.) solution of 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (50 mg, 0.903 mmol) and triethylamine (0.038 mL, 0.27 mmol) in DCM (1 mL) was added 2-bromoacetyl bromide (18 mg, 0.093 mmol). The mixture was stirred for 1 h at 0° C., then the reaction mixture was poured into water (10 mL) and extracted with DCM (3×10 mL). The combined organic layers were dried over anhydrous sodium sulfate and concentrated under reduced pressure. The residue was purified by reverse phase isco (eluting with $CH_3CN$/water) to afford the title compound as a white solid (20 mg, 33%). LCMS: [$C_{35}H_{44}BrN_7O_2$], desired mass=674.3, found: m/z=675.5 $[M+H]^+$.

EXAMPLES

Purification Procedures

Preparative-scale HPLC was performed using columns such as SunFire Prep C18 OBD, XBridge Prep OBD C18 and Xbridge Shield RP18 OBD, using solvent systems such as (water-0.1% formic acid)/acetonitrile, (water-10 mmol/L $NH_4HCO_3$)/acetonitrile, or (water-10 mmol/L $NH_4HCO_3$)/acetonitrile. Chromatography A refers to purification over silica gel, typically in pre-packed cartridges, eluting with mixtures of EtOAc in hexanes or petroleum ether; Chromatography B refers to elution with mixtures of MeOH in DCM; Chromatography C refers to use of C18 reverse-phase silica gel, eluting with mixtures of acetonitrile in water. Compounds drawn without stereochemistry were tested as racemic or diasteromeric mixtures in the Biological Examples.

Abbreviations

Abbreviations used in the Examples include the following: aq (aqueous), BOP (Benzotriazol-1-yloxy)tris(dimethylamino)phosphonium hexafluorophosphate, BINAP (2,2-bis(diphenylphosphino)-1,1-binaphthyl), Bn (benzyl), Boc (tert-butoxycarbonyl), CBz: (benzyloxycarbonyl), HATU (N-[(Dimethylamino)-1H-1,2,3-triazolo-[4,5-b]pyridin-1-ylmethylene]-N-methylmethanaminium hexafluorophosphate N-oxide), IPA (isopropyl alcohol), DMSO (dimethyl sulfoxide), THF (tetrahydrofuran), EtOAc (ethyl acetate), ACN (acetonitrile), $Et_2O$ (diethyl ether), DCM (dichloromethane), MeOH (methanol), EtOH (ethanol), DCE (1,2-dichloroethane), DIC (N,N'-Diisopropylcarbodiimide), DME (ethylene glycol dimethyl ether), TEA (trimethylamine), TFA (trifluoroacetic acid), DIEA (N,N-diisopropylethlamine), DIPEA (N,N-Diisopropylethylamine), DMF (N,N-dimethylformamide), MTBE (methyl tert-butyl ether), NMP (N-methyl-2-pyrrolidone), N,N-dimethylacetamide (DMA), EDCI (1-ethyl-3-(3-dimethylaminopropyl)carbodiimide), HFIP (hexafluoroisopropanol), HOBT (hydroxybenzotriazole), STAB (sodium triacetoxyborohydride), $Pd_2(dba)_3$ (tris(dibenzylideneacetone)dipalladium), Pd(dppf)$Cl_2$ ([1,1'-bis(diphenylphosphino)ferrocene]dichloropalladium(II)), PE (petroleum ether), RuPhos (palladacycle Gen.3: Methanesulfonato(2-dicyclohexylphosphino-2',6'-bis(dimethylamino)-1,1'-biphenyl)(2'-amino-1,1'-biphenyl-2-yl)palladium(II)), SFC (supercritical fluid chromatography), $T_3P$ (propanephosphonic acid cyclic anhydride), XantPhos (9,9-dimethyl-4,5-bis(diphenylphosphino)xanthene), TFA (trifluoroacetic acid), rt or RT (room temperature), anh (anhydrous), eq. or equiv. (equivalent), FC (flash chromatography), h or hr (hour), LCMS (liquid chromatography-mass spectrometry), min (minute), NMR (nuclear magnetic resonance spectroscopy), uplc (ultra performance liquid chromatography).

Example 1

(3RS)-3-(2-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-4-yl)piperidine-2,6-dione

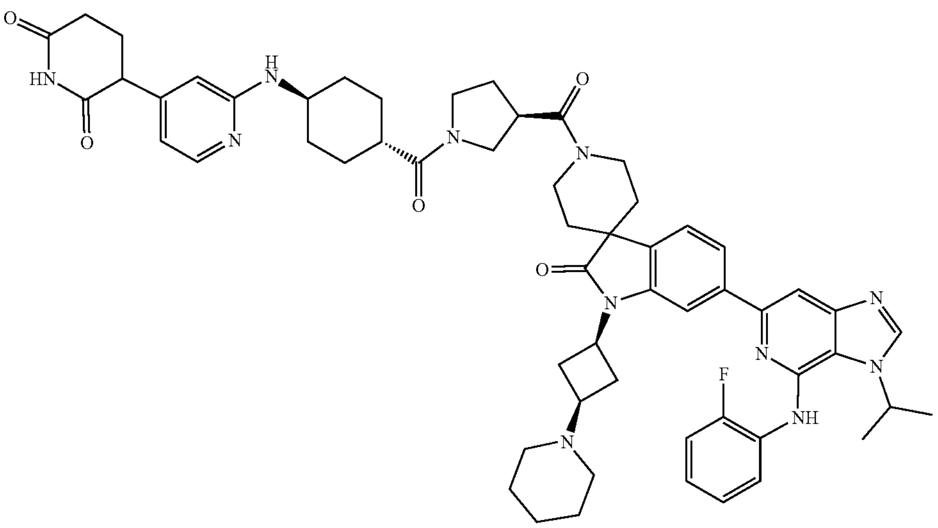 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cc(C7CCC(=O)NC7=O)ccn6)CC5)C4)CC3)nc(Nc3ccccc3F)c21]

A mixture of (3R)-1-((1r,4R)-4-((4-(2,6-dioxopiperidin-3-yl)pyridin-2-yl)amino)cyclohexane-1-carbonyl)pyrrolidine-3-carboxylic acid (intermediate 1) (7 mg, 0.016 mmol), EDCI (4.7 mg, 0.025 mmol) and HOBT (3.8 mg, 0.025 mmol) was dissolved in DMF (0.2 mL) and DIPEA (0.013 mL, 9.4 mg, 0.074 mmol), and stirred at room temperature for 5 minutes. 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) was added and the reaction mixture was stirred for overnight at room temperature. The crude reaction mixture was purified by reverse phase HPLC to provide the title compound (TFA salt) as an off-white solid (4.6 mg, 26% yield). LCMS: [$C_{58}H_{68}FN_{11}O_5$], desired mass=1018.2, found: m/z=1018.8 $[M+H]^+$, $^1H$ NMR (500 MHz, DMSO) δ 11.04 (s, 1H), 9.40 (s, 1H), 8.61 (d, J=4.7 Hz, 1H), 8.36 (s, 1H), 7.90 (t, J=4.3 Hz, 2H), 7.70 (d, J=7.8 Hz, 1H), 7.57 (td, J=8.5, 4.1 Hz, 2H), 7.50 (s, 1H), 7.32 (dd, J=11.6, 8.1 Hz, 1H), 7.22 (dp, J=8.9, 5.2, 4.5 Hz, 2H), 6.90 (s, 1H), 6.80 (d, J=6.7 Hz, 1H), 5.29 (p, J=6.7 Hz, 1H), 4.28 (s, 4H), 4.09 (d, J=8.7 Hz, 1H), 4.03 (dd, J=12.2, 4.7 Hz, 1H), 3.83 (s, 3H), 3.74 (t, J=6.8 Hz, 1H), 3.68 (s, 2H), 3.61 (s, 2H), 3.58-3.41 (m, 1H), 2.88 (dq, J=19.6, 12.1, 8.9 Hz, 4H), 2.74 (s, 3H), 2.69 (ddd, J=17.4, 12.0, 5.0 Hz, 1H), 2.61-2.53 (m, 1H), 2.28 (d, J=12.5 Hz, 1H), 2.14 (s, 1H), 2.02 (s, 3H), 1.88 (d, J=13.5 Hz, 3H), 1.82-1.77 (m, 5H), 1.71 (s, 3H), 1.60 (d, J=6.6 Hz, 6H), 1.44 (q, J=12.5 Hz, 2H), 1.37 (d, J=12.2 Hz, 3H).

Example 2

(3RS)-3-(4-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]amino}phenyl)piperidine-2,6-dione

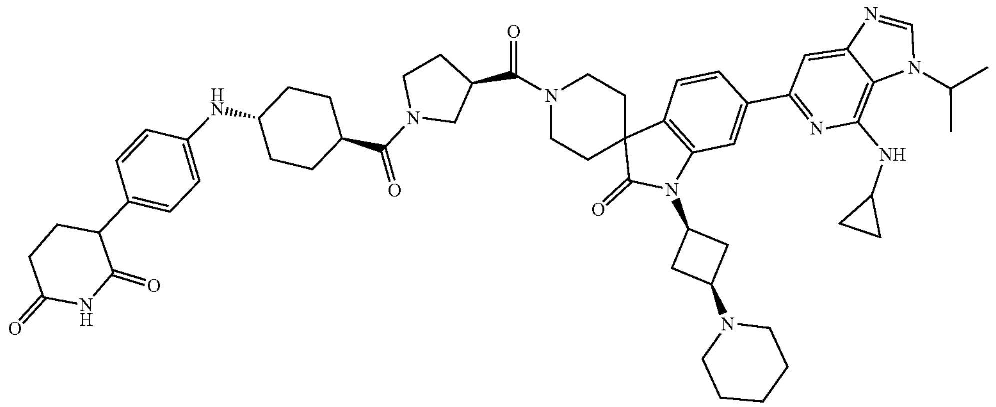 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C7CCC(=O)NC7=O)cc6)CC5)C4)CC3)nc(NC3CC3)c21]

Example 2 was prepared by similar procedures as Example 1 using (R)-1-((1R,4R)-4-((4-((RS)-2,6-dioxopiperidin-3-yl)phenyl)amino)cyclohexane-1-carbonyl)pyrrolidine-3-carboxylic acid (intermediate 2) (7 mg, 0.018) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018) as starting materials. The title compound (TFA salt) was isolated as an off-white solid (10.4 mg, 57% yield). LCMS: [$C_{56}H_{70}N_{10}O_5$], desired mass=963.2, found: m/z=964.8 $[M+H]^+$, $^1H$ NMR (500 MHz, MeOD) δ 8.92 (s, 1H), 7.71-7.61 (m, 3H), 7.56 (s, 1H), 7.46 (d, J=8.1 Hz, 2H), 7.35 (d, J=8.0 Hz, 2H), 5.17-5.09 (m, 1H), 4.53-4.45 (m, 1H), 4.15 (s, 2H), 3.97 (dt, J=15.0, 7.5 Hz, 2H), 3.80 (m, 1H), 3.74-3.64 (m, 1H), 3.67-3.49 (m, 5H), 3.07 (s, 1H), 3.01 (s, 2H), 2.91 (d, J=12.8 Hz, 2H), 2.81-2.65 (m, 1H), 2.60 (d, J=13.1 Hz, 1H), 2.27 (dd, J=33.5, 7.1 Hz, 3H), 2.15 (s, 2H), 2.08-1.93 (m, 7H), 1.91 (s, 3H), 1.79 (d, J=14.0 Hz, 2H), 1.72-1.57 (m, 9H), 1.53 (d, J=14.6 Hz, 3H), 1.31 (s, 2H), 1.13 (s, 2H), 0.93 (d, J=6.2 Hz, 3H).

Example 3

(3RS)-3-(4-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}phenyl)piperidine-2,6-dione

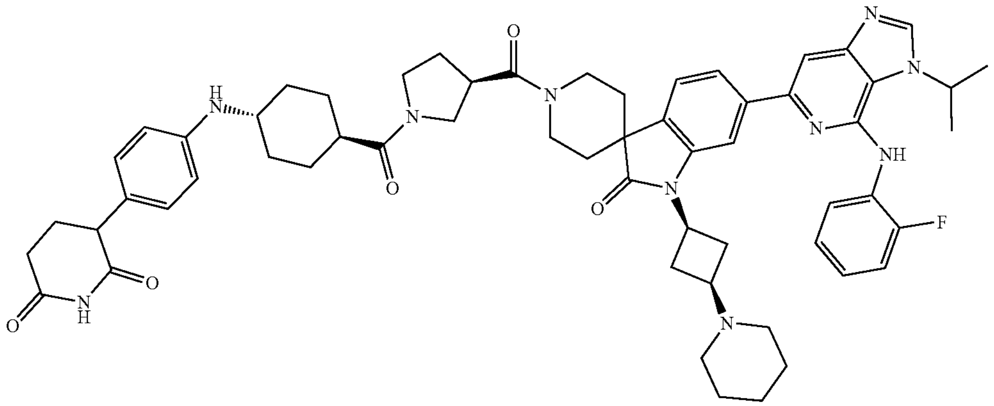 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C7CCC(=O)NC7=O)cc6)CC5)C4)CC3)nc(Nc3ccccc3F)c21]

Example 3 was prepared by similar procedures as Example 1 using (R)-1-((1R,4R)-4-((4-((RS)-2,6-dioxopiperidin-3-yl)phenyl)amino)cyclohexane-1-carbonyl)pyrrolidine-3-carboxylic acid (intermediate 2) (7 mg, 0.016 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (10.2 mg, 55% yield). LCMS: [$C_{59}H_{69}FN_{10}O_5$], desired mass=1017.2, found: m/z=1017.7 $[M+H]^+$, $^1H$ NMR (500 MHz, MeOD) δ 8.92 (s, 1H), 7.84-7.74 (m, 2H), 7.70 (t, J=7.9 Hz, 1H), 7.63 (d, J=6.7 Hz, 1H), 7.53 (q, J=8.3, 7.8 Hz, 1H), 7.47 (d, J=8.2 Hz, 2H), 7.36 (d, J=8.0 Hz, 2H), 7.33-7.22 (m, 3H), 5.32 (s, 1H), 4.25 (s, 1H), 4.10 (s, 2H), 3.98 (dd, J=11.9, 5.1 Hz, 1H), 3.78 (d, J=7.7 Hz, 1H), 3.69 (t, J=14.2 Hz, 2H), 3.64-3.54 (m, 2H), 3.55 (s, 4H), 3.08 (s, 2H), 3.05-2.90 (m, 3H), 2.90 (s, 2H), 2.81-2.65 (m, 1H), 2.59 (d, J=13.2 Hz, 1H), 2.30 (s, 2H), 2.15 (s, 5H), 2.08-1.88 (m, 7H), 1.86 (d, J=6.0 Hz, 2H), 1.74 (d, J=6.6 Hz, 8H), 1.58 (dt, J=32.9, 12.9 Hz, 5H), 1.31 (s, 1H).

Example 4

3-(4-(((1R,4R)-4-((R)-3-(6-(4-((3-fluoropyridin-4-yl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)pyrrolidine-1-carbonyl)cyclohexyl)amino)phenyl)piperidine-2,6-dione

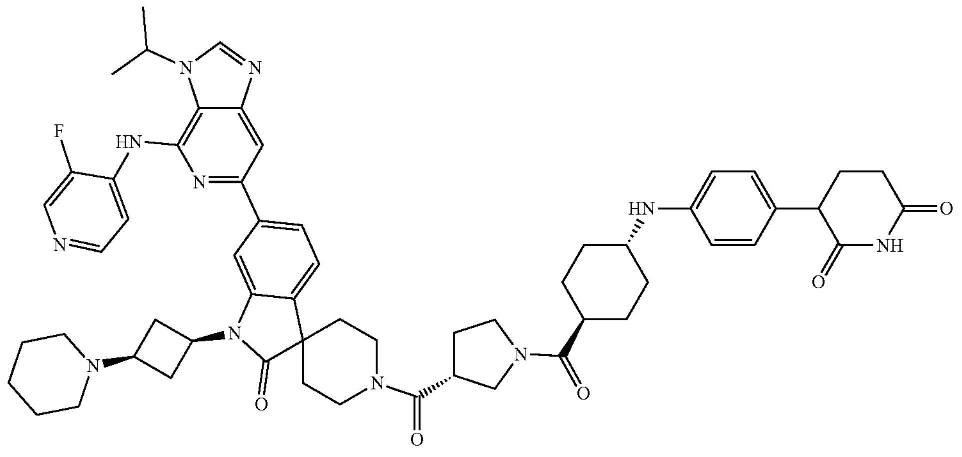 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C7CCC(=O)NC7=O)cc6)CC5)C4)CC3)nc(Nc3ccncc3F)c21]

The title compound was synthesized using similar methods to example 10, using BOP coupling. Afforded an off-white solid (5 mg, 0.0049 mmol, 8 yield) as a free base. LCMS: [$C_{58}H_{68}FN_{11}O_5$], desired mass=1017.5, found: m/z=1018.9 $[M+H]^+$. $^1H$ NMR (500 MHz, DMSO-$d_6$) δ 10.70 (s, 1H), 9.05 (s, 1H), 8.60 (s, 1H), 8.42 (s, 1H), 8.17 (s, 2H), 8.03 (s, 1H), 7.88-7.67 (m, 1H), 7.67-7.50 (m, 2H), 6.87 (d, J=8.1 Hz, 2H), 6.51 (d, J=8.9 Hz, 1H), 5.31 (d, J=7.6 Hz, 1H), 5.18 (p, J=6.7, 6.7, 6.6, 6.6 Hz, 1H), 4.49 (s, 1H), 3.92 (s, 1H), 3.80 (s, 1H), 3.61 (dd, J=10.5, 5.2 Hz, 1H), 3.27-3.17 (m, 9H), 3.14 (s, 2H), 2.64-2.55 (m, 1H), 2.45-2.36 (m, 7H), 2.25 (s, 2H), 2.10-1.94 (m, 3H), 1.82-1.63 (m, 6H), 1.56 (dd, J=37.1, 6.6 Hz, 11H), 1.28-1.07 (m, 4H).

Example 5

(3RS)-3-(6-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]amino}pyridin-3-yl)piperidine-2,6-dione

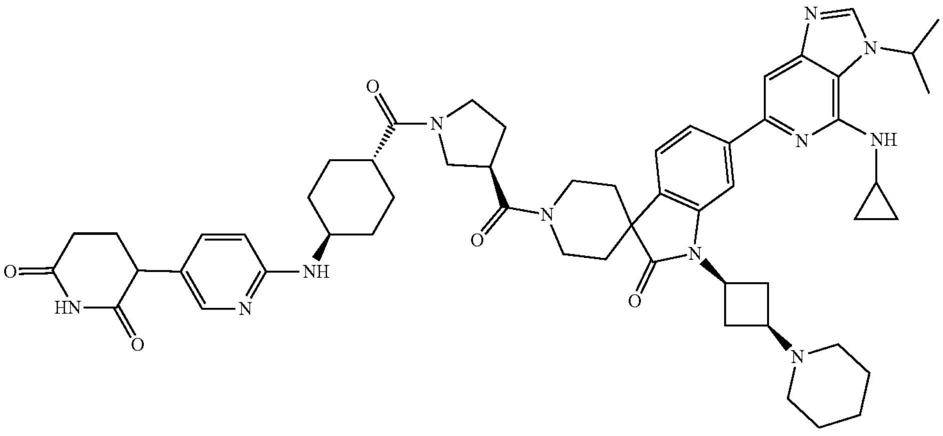 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C7CCC(=O)NC7=O)cn6)CC5)C4)CC3)nc(NC3CC3)c21]

Example 5 was prepared by similar procedures as Example 1 using (3R)-1-((1r,4R)-4-((5-(2,6-dioxopiperidin-3-yl)pyridin-2-yl)amino)cyclohexane-1-carbonyl)pyrrolidine-3-carboxylic acid (intermediate 3) (9 mg, 0.022 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (4.6 mg, 25% yield). LCMS: $C_{55}H_{69}N_{11}O_5$ desired mass 964.2, found m/z=964.7 $[M+H]^+$.

Example 6

(3RS)-3-(6-{1[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione

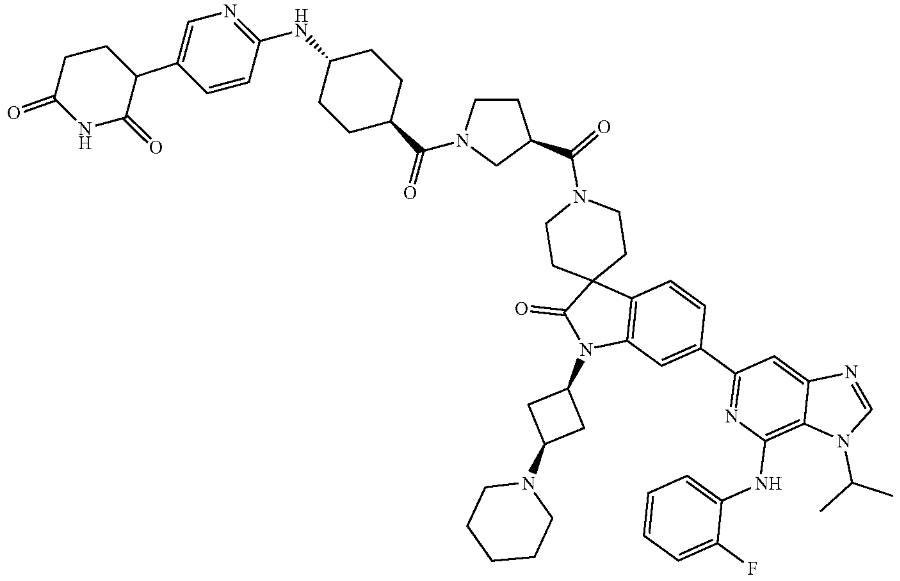 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C7CCC(=O)NC7=O)cn6)CC5)C4)CC3)nc(Nc3ccccc3F)c21]

The title compound was synthesized using similar methods to Example 24, using BOP coupling. (White solid, 67 mg, 68% yield). LCMS: [$C_{58}H_{68}FN_{11}O_5$], desired mass=1017.5, found: m/z=1018.9 $[M+H]^+$. $^1H$ NMR (500 MHz, DMSO-$d_6$): δ (ppm): 10.93 (s, 1H), 9.39 (s, 1H), 8.67 (d, J=7.9 Hz, 1H), 8.37 (s, 1H), 7.87 (d, J=3.3 Hz, 1H), 7.80 (d, J=9.8 Hz, 1H), 7.76 (s, 1H), 7.67 (d, J=7.9 Hz, 1H), 7.53 (td, J=12.6, 10.9, 5.9 Hz, 2H), 7.46 (s, 1H), 7.29 (d, J=10.5 Hz, 1H), 7.20 (dd, J=7.4, 4.1 Hz, 2H), 7.08-6.95 (m, 1H), 5.28 (p, J=6.6, 6.6, 6.5, 6.5 Hz, 1H), 4.06 (t, J=8.4, 8.4 Hz, 1H), 3.89 (dd, J=12.9, 5.0 Hz, 3H), 3.80 (s, 3H), 3.42 (s, 4H), 3.35 (d, J=13.2 Hz, 3H), 2.86 (dt, J=21.7, 12.7, 12.7 Hz, 5H), 2.69 (ddt, J=17.7, 12.7, 6.3, 6.3 Hz, 4H), 2.60-2.52 (m, 1H), 2.24 (tt, J=12.3, 12.3, 6.2, 6.2 Hz, 1H), 2.14-2.07 (m, 1H), 2.03-1.93 (m, 4H), 1.86 (d, J=15.1 Hz, 3H), 1.78 (d, J=15.1 Hz, 4H), 1.68 (t, J=6.3, 6.3 Hz, 3H), 1.61 (s, 1H), 1.58 (d, J=6.6 Hz, 7H), 1.52 (d, J=11.2 Hz, 2H), 1.42-1.29 (m, 3H).

Example 7

N-[(3RS)-2,6-dioxopiperidin-3-yl]-5-{1[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridine-2-carboxamide

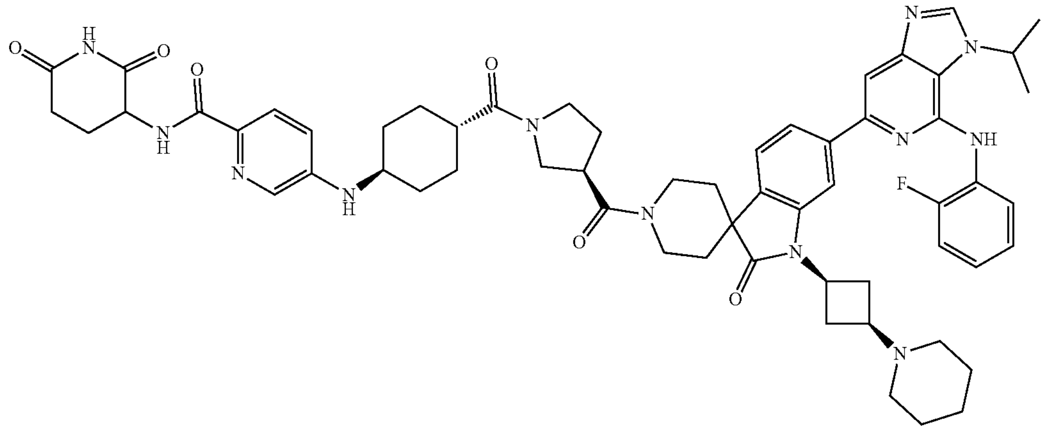 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc(C(=O)NC7CCC(=O)NC7=O)nc6)CC5)C4)CC3)nc(Nc3ccccc3F)c21]

Example 7 was prepared by similar procedures as Example 1 using tert-butyl (3R)-1-((1r,4R)-4-((6-((2,6-dioxopiperidin-3-yl)carbamoyl)pyridin-3-yl)amino)cyclohexane-1-carbonyl)pyrrolidine-3-carboxylate (intermediate 4) (12 mg, 0.026 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (3.6 mg, 19% yield). LCMS: [$C_{59}H_{69}FN_{12}O_6$], desired mass=1061.2, found: m/z=1062.0 $[M+H]^+$.

Example 8

(3RS)-3-(6-{1[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-2-yl)piperidine-2,6-dione

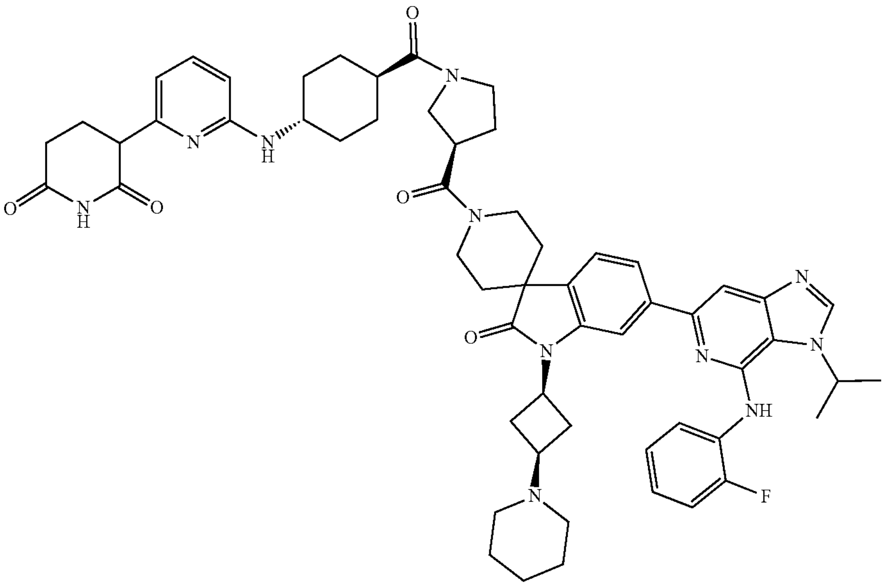 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc(C7CCC(=O)NC7=O)n6)CC5)C4)CC3)nc(Nc3ccccc3F)c21]

Example 8 was prepared by similar procedures as Example 1 using (3R)-1-((1r,4R)-4-((6-(2,6-dioxopiperidin-3-yl)pyridin-2-yl)amino)cyclohexane-1-carbonyl)pyrrolidine-3-carboxylic acid (7 mg, 0.016 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (4.9 mg, 29% yield). LCMS: [$C_{58}H_{68}FN_{11}O_5$], desired mass=1018.2, found: m/z=1019.6 $[M+H]^+$, $^1H$ NMR (500 MHz, DMSO) δ 10.97 (s, 1H), 9.35 (s, 1H), 8.70 (s, 1H), 8.39 (s, 1H), 7.90 (d, J=3.8 Hz, 1H), 7.70 (d, J=7.8 Hz, 1H), 7.61-7.53 (m, 2H), 7.49 (s, 1H), 7.33 (s, 1H), 7.27-7.20 (m, 2H), 6.59 (s, 1H), 5.35-5.25 (m, 1H), 4.14-4.05 (m, 1H), 3.84 (s, 2H), 3.51 (dd, J=17.1, 8.3 Hz, 2H), 3.44 (s, 1H), 3.37 (s, 2H), 2.90 (d, J=12.7 Hz, 1H), 2.86 (s, 4H), 2.74 (s, 2H), 2.14 (dd, J=14.8, 8.1 Hz, 6H), 2.04-1.96 (m, 2H), 1.88 (d, J=13.8 Hz, 2H), 1.77 (d, J=13.9 Hz, 4H), 1.71 (s, 4H), 1.60 (d, J=6.5 Hz, 6H), 1.55-1.40 (m, 4H), 1.29 (m, 2H).

Example 9

2-[(3RS)-2,6-dioxopiperidin-3-yl]-4-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-isoindole-1,3-dione

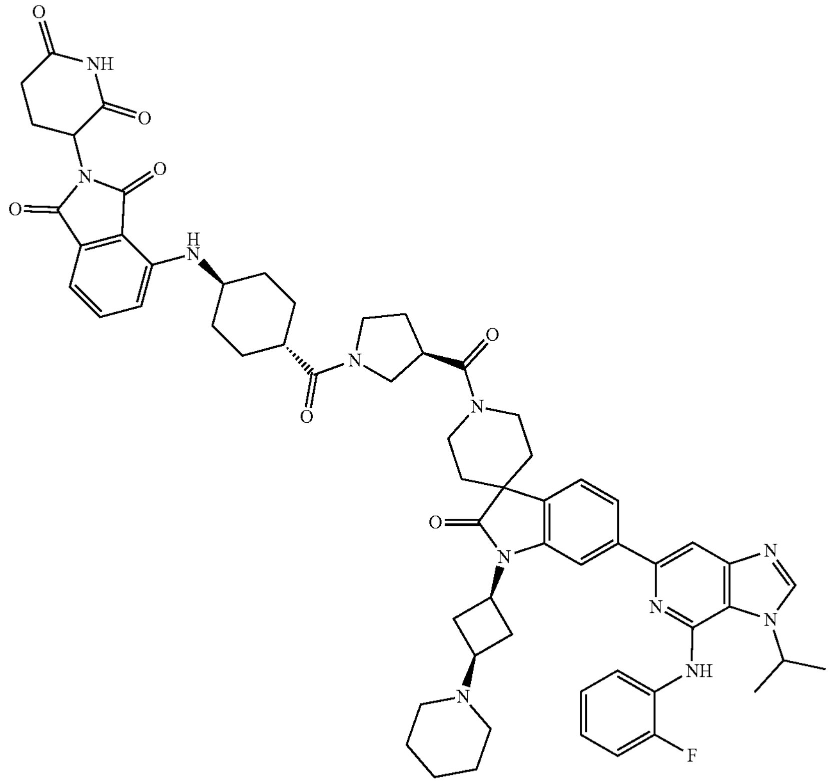 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc7c6C(=O)N(C6CCC(=O)NC6=O)C7=O)CC5)C4)CC3)nc(Nc3ccccc3F)c21]

6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (50.00 mg, 0.08 mmol) and BOP (47.30 mg, 0.11 mmol) were dissolved in dimethylformamide (2.00 mL) and N,N-diisopropylethylamine (0.06 mL, 42.53 mg, 0.33 mmol) and stirred at room temperature for 5 minutes. (3R)-1-((1r,4R)-4-((2-(2,6-dioxopiperidin-3-yl)-1,3-dioxoisoindolin-4-yl)amino)cyclohexane-1-carbonyl)pyrrolidine-3-carboxylic acid (intermediate 6) (40.85 mg, 0.08 mmol) was added and the reaction mixture was stirred for 2 hours at room temperature. The crude reaction mixture was purified by reverse HPLC to afford the title compound (TFA salt) as an off-white solid (42.3 mg, 46% yield). LCMS: [$C_{61}H_{68}FN_{11}O_7$], desired mass=1085.5, found: m/z=1087.0 $[M+H]^+$. $^1H$ NMR (500 MHz, MeOD) δ 9.03 (s, 1H), 9.02-8.97 (m, 1H), 7.82 (s, 1H), 7.77 (d, J=7.7 Hz, 1H), 7.69 (d, J=7.9 Hz, 1H), 7.63-7.49 (m, 3H), 7.28-7.24 (m, 2H), 7.17-7.11 (m, 1H), 7.07 (d, J=7.1 Hz, 1H), 5.35 (s, 1H), 5.07 (dd, J=12.5, 5.4 Hz, 1H), 4.24 (s, 1H), 4.11 (s, 2H), 3.97 (d, J=14.5 Hz, 3H), 3.82 (dd, J=15.6, 8.1 Hz, 1H), 3.77-3.63 (m, 1H), 3.63-3.51 (m, 5H), 3.09 (s, 1H), 3.02 (d, J=9.2 Hz, 1H), 2.90 (q, J=15.6 Hz, 6H), 2.75 (t, J=14.5 Hz, 2H), 2.61 (t, J=12.0 Hz, 1H), 2.28 (s, 2H), 2.22 (d, J=12.9 Hz, 3H), 2.13 (s, 1H), 2.04 (d, J=14.3 Hz, 3H), 1.94 (s, 5H), 1.86 (s, 2H), 1.75 (d, J=6.7 Hz, 8H), 1.70 (s, 1H), 1.59 (d, J=14.2 Hz, 1H), 1.40 (q, J=12.2 Hz, 2H).

Example 10

2-[(3RS)-2,6-dioxopiperidin-3-yl]-4-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]amino}-2,3-dihydro-1H-isoindole-1,3-dione

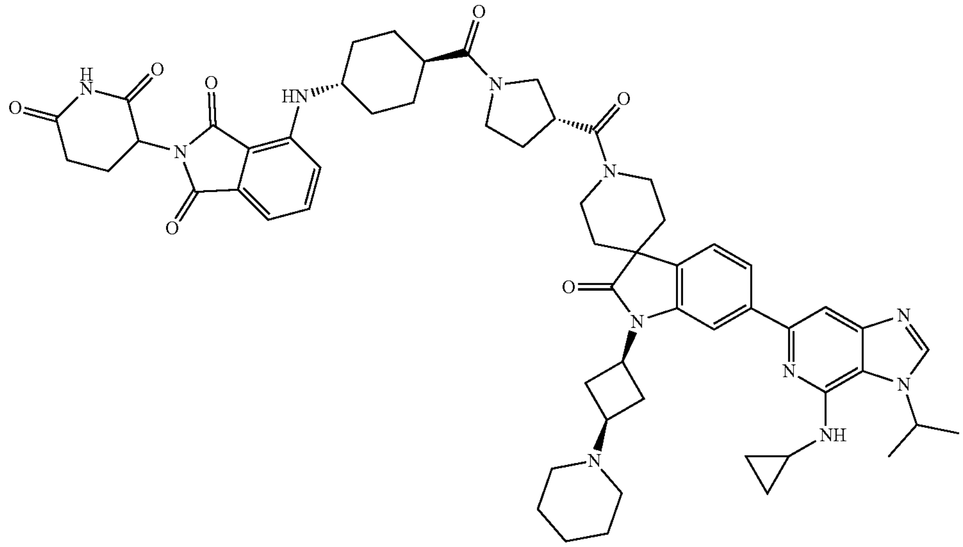 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc7c6C(=O)N(C6CCC(=O)NC6=O)C7=O)CC5)C4)CC3)nc(NC3CC3)c21]

To a solution of Intermediate 6 (100 mg, 0.2016 mmol) in DMF (3 mL) was added BOP (9 mg, 0.2016 mmol), and N,N-diisopropylethylamine (0.12 mL, 0.62 mmol, 4 eq) at room temperature for 10 min. 6-[4-(Cyclopropylamino)-3-isopropyl-1,3,5-triaza-3H-inden-6-yl]-1-[(1s,3s)-3-piperidinocyclobutyl]spiro[indoline-3,4'-piperidin]-2-one (86 mg, 0.155 mmol, 1 eq) was added and stirring was continued at room temperature for 1 hour. The reaction mixture was directly loaded to HPLC without work up to afford desired product as a TFA salt which was treated with aqueous $NH_4OH$ (0.3%, 0.5 mL, 1.2 eq) and extracted with DCM (3×0.5 mL). The combined organic layers were dried using $Na_2SO_4$ and concentrated to afford (Bright yellow solid, 71 mg, 0.0689 mmol, 34% yield) title compound as a free base. LCMS: [$C_{58}H_{69}N_{11}O_7$], desired mass=1031.5, found: m/z=1033.4 $[M+H]^+$. $^1H$ NMR (500 MHz, DMSO-$d_6$) δ 11.07 (s, 1H), 9.37 (s, 1H), 8.61 (s, 1H), 7.85 (s, 1H), 7.72 (s, 2H), 7.63 (s, 1H), 7.57 (ddd, J=9.0, 7.0, 2.4 Hz, 1H), 7.20 (dd, J=8.7, 3.7 Hz, 1H), 7.02 (d, J=7.1 Hz, 1H), 6.15 (d, J=8.5 Hz, 1H), 5.13-5.07 (m, 1H), 5.03 (dd, J=12.7, 5.5 Hz, 1H), 4.39-4.25 (m, 1H), 3.97-3.74 (m, 4H), 3.68 (dd, J=32.4, 8.5 Hz, 2H), 3.05-2.73 (m, 11H), 2.64-2.52 (m, 1H), 2.48-2.43 (m, 5H), 2.20-1.99 (m, 4H), 1.90-1.66 (m, 8H), 1.64-1.52 (m, 4H), 1.50 (d, J=6.5 Hz, 6H), 1.43-1.28 (m, 3H), 1.28-1.20 (m, 1H), 0.82 (m, 1H), 0.62 (m, 1H).

Example 11

2-[(3RS)-2,6-dioxopiperidin-3-yl]-4-{[(1R,4R)-4-[(3R)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-isoindole-1,3-dione

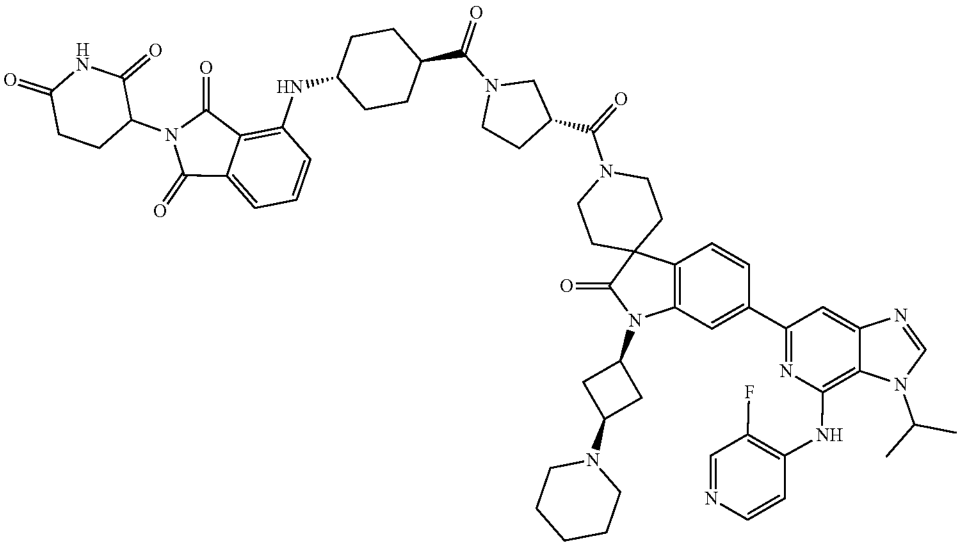 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc7c6C(=O)N(C6CCC(=O)NC6=O)C7=O)CC5)C4)CC3)nc(Nc3ccncc3F)c21]

Example 11 was prepared by similar procedures as Example 1 using (3R)-1-((1r,4R)-4-((2-(2,6-dioxopiperidin-3-yl)-1,3-dioxoisoindolin-4-yl)amino)cyclohexane-1-carbonyl)pyrrolidine-3-carboxylic acid (intermediate 6) (9 mg, 0.018 mmol) and 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (11.2 mg, 61% yield). LCMS: [$C_{60}H_{67}FN_{12}O_7$], desired mass=1087.2, found: m/z=1087.3 $[M+H]^+$, Example 12

(3RS)-3-(5-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione

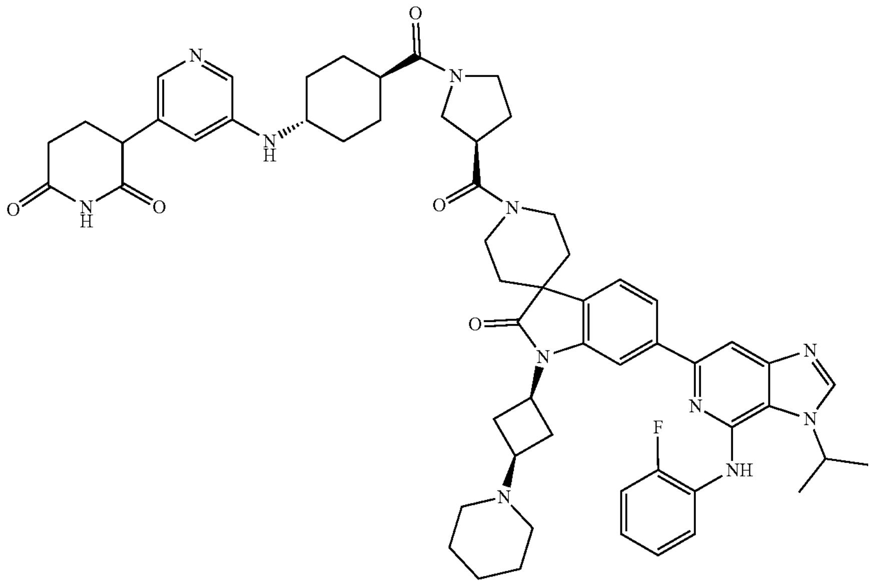 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cncc(C7CCC(=O)NC7=O)c6)CC5)C4)CC3)nc(Nc3ccccc3F)c21]

Example 12 was prepared by similar procedures as Example 1 using (3R)-1-((1r,4R)-4-((5-(2,6-dioxopiperidin-3-yl)pyridin-3-yl)amino)cyclohexane-1-carbonyl)pyrrolidine-3-carboxylic acid (intermediate 7) (10 mg, 0.023 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (14 mg, 0.023 mmol) as starting materials. The title compound (TFA salt) was isolated as an off-white solid (6 mg, 24% yield). LCMS: [$C_{58}H_{68}FN_{11}O_5$], desired mass=1018.2, found: m/z=1018.6 $[M+H]^+$, $^1H$ NMR (500 MHz, DMSO) δ 11.03 (s, 1H), 9.39 (s, 1H), 8.63 (d, J=5.5 Hz, 1H), 8.37 (s, 1H), 8.03 (s, 1H), 7.95 (s, 1H), 7.90 (d, J=3.3 Hz, 1H), 7.70 (d, J=7.9 Hz, 1H), 7.58 (d, J=7.7 Hz, 2H), 7.50 (s, 1H), 7.32 (t, J=9.7 Hz, 1H), 7.27-7.16 (m, 2H), 6.99-6.94 (m, 1H), 5.29 (p, J=6.7 Hz, 1H), 4.08 (td, J=14.6, 12.7, 6.4 Hz, 1H), 3.94-3.84 (s, 3H), 3.38 (d, J=11.0 Hz, 6H), 2.97-2.66 (m, 6H), 2.62 (d, J=4.0 Hz, 1H), 2.51 (s, 3H), 2.39-2.29 (m, 1H), 2.14 (d, J=7.6 Hz, 1H), 2.15-2.04 (m, 1H), 2.01 (d, J=11.4 Hz, 2H), 1.88 (d, J=14.2 Hz, 2H), 1.85-1.75 (m, 4H), 1.75-1.62 (m, 2H), 1.60 (d, J=6.7 Hz, 6H), 1.56 (s, 1H), 1.45 (t, J=12.9 Hz, 1H), 1.27 (m, 4H).

Example 13

3-(4-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}phenyl)piperidine-2,6-dione

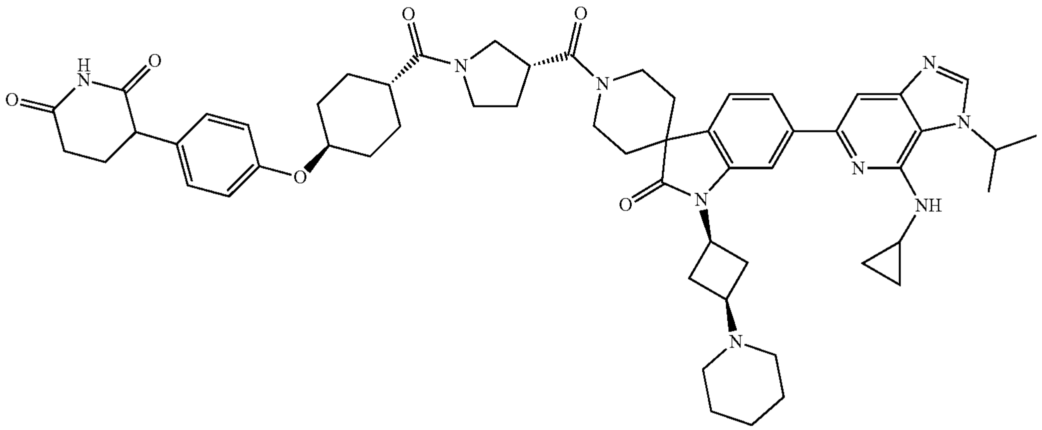 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cc6)CC5)C4)CC3)nc(NC3CC3)c21]

(3R)-1-((1r,4R)-4-(4-(2,6-dioxopiperidin-3-yl)phenoxy)cyclohexane-1-carbonyl)pyrrolidine-3-carboxylic acid (Intermediate 8) (15.5 mg, 0.036 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (20.0 mg, 0.036 mmol), and (1,2,3-benzotriazol-1-yloxy)tris(dimethylamino)phosphanium, hexafluorolambda5-phosphanuide (20.77 mg, 0.05 mmol) were dissolved in DMF (1.0 mL) and DIEA (0.03 mL, 0.14 mmol) and stirred at room temperature for 2 hours. The crude reaction mixture was purified by prep-HPLC to afford the title compound (TFA salt) as an off-white solid (29.1 mg, 79% yield). LCMS: $C_{56}H_{69}N_9O_6$ desired mass=963.5, found: m/z=964.5 $[M+H]^+$. $^1H$ NMR (500 MHz, Methanol-$d_4$) δ 7.67 (s, 2H), 7.63 (s, 1H), 7.57 (s, 1H), 7.17 (dd, J=8.2, 3.7 Hz, 3H), 6.97-6.89 (m, 2H), 4.54-4.46 (m, 1H), 4.33-4.26 (m, 2H), 4.15 (s, 2H), 4.03 (s, 1H), 3.93 (dq, J=17.4, 9.2, 7.8 Hz, 1H), 3.81 (q, J=9.2, 7.7 Hz, 3H), 3.77-3.54 (m, 5H), 3.16 (d, J=6.7 Hz, 1H), 3.09-3.04 (m, 1H), 3.03-2.95 (m, 2H), 2.90 (t, J=12.3 Hz, 2H), 2.65 (ddd, J=36.7, 20.8, 10.9 Hz, 4H), 2.35-2.19 (m, 9H), 2.05 (d, J=5.3 Hz, 1H), 2.01 (s, 2H), 1.91 (s, 6H), 1.79 (d, J=13.7 Hz, 1H), 1.69 (d, J=6.5 Hz, 6H), 1.67 (s, 2H), 1.52 (dd, J=22.5, 11.6 Hz, 3H), 1.31 (s, 1H), 1.15 (s, 2H), 0.95 (s, 2H).

Example 14

3-(4-{[(1R,4R)-4-[(3R)-3-[(6-{4-[(2-fluorophenyl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]pyrrolidine-1-carbonyl]cyclohexyl] oxy}phenyl)piperidine-2,6-dione

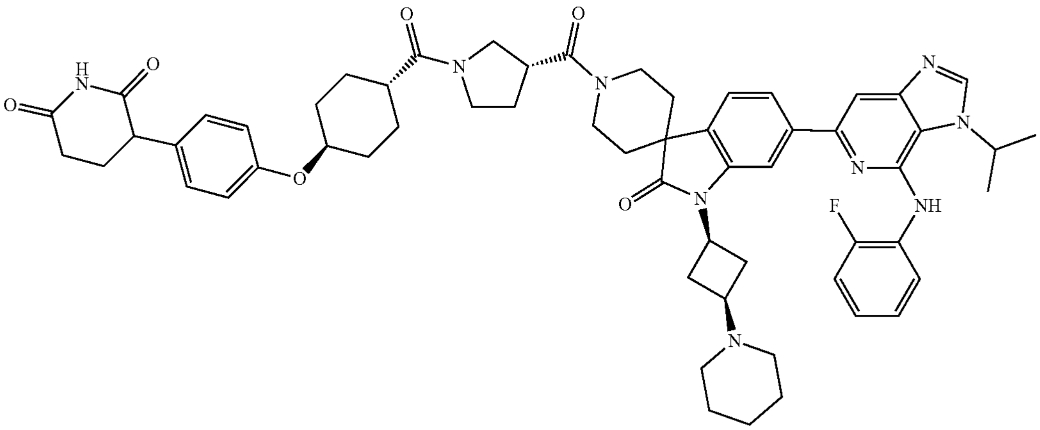 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cc6)CC5)C4)CC3)nc(Nc3ccccc3F)c21]

Using procedures similar to those used for Example 13 but using (3R)-1-((1r,4R)-4-(4-(2,6-dioxopiperidin-3-yl) phenoxy)cyclohexane-1-carbonyl)pyrrolidine-3-carboxylic acid (Intermediate 8) (15.5 mg, 0.036 mmol) and 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (20.0 mg, 0.036 mmol) afforded the title compound (TFA salt) as an off white solid (27.4 mg, 79% yield). LCMS: $C_{59}H_{68}FN_9O_6$ desired mass=1017.5, found: m/z=1018.8 $[M+H]^+$. $^1H$ NMR (500 MHz, Methanol-$d_4$) δ 7.81 (s, 1H), 7.77 (d, J=7.5 Hz, 1H), 7.70 (s, 1H), 7.61 (s, 1H), 7.59-7.49 (m, 1H), 7.31 (s, 1H), 7.27 (s, 3H), 7.20-7.14 (m, 3H), 6.93 (d, J=8.5 Hz, 1H), 4.30 (s, 2H), 4.25 (s, 1H), 4.10 (d, J=6.3 Hz, 1H), 3.98 (s, 2H), 3.94 (d, J=7.5 Hz, 1H), 3.82 (d, J=15.8 Hz, 1H), 3.82 (s, 2H), 3.74 (d, J=6.7 Hz, 1H), 3.67 (d, J=12.5 Hz, 1H), 3.58 (dd, J=16.8, 7.9 Hz, 1H), 3.54 (s, 2H), 3.31 (s, 4H), 3.10 (s, 1H), 3.01 (d, J=10.2 Hz, 1H), 2.92 (t, J=13.9 Hz, 5H), 2.74-2.60 (m, 1H), 2.59 (s, 1H), 2.25-2.19 (m, 1H), 2.04 (d, J=15.0 Hz, 2H), 1.92 (d, J=17.4 Hz, 6H), 1.86 (s, 2H), 1.75 (d, J=6.6 Hz, 6H), 1.65 (dd, J=29.0, 14.5 Hz, 2H), 1.50 (d, J=12.1 Hz, 2H), 1.31 (s, 2H).

Example 15

3-(4-{[(1R,4R)-4-[(3R)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl] oxy}phenyl)piperidine-2,6-dione

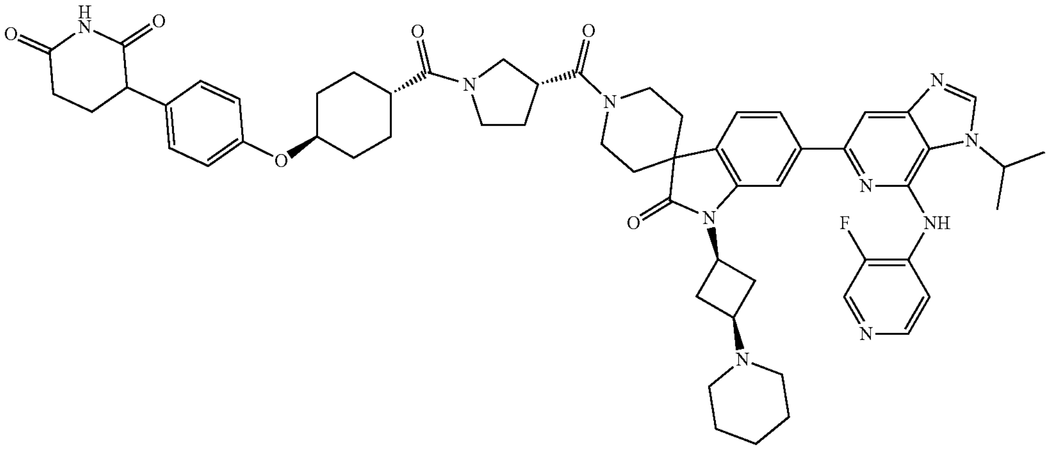 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cc6)CC5)C4)CC3)nc(Nc3ccncc3F)c21]

Using procedures similar to those used for Example 13 but using (3R)-1-((1r,4R)-4-(4-(2,6-dioxopiperidin-3-yl) phenoxy)cyclohexane-1-carbonyl)pyrrolidine-3-carboxylic acid (Intermediate 8) (15.0 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.0 mg, 0.033 mmol) afforded the title compound (TFA salt) as an off white solid (29.7 mg, 88% yield). LCMS: $C_{58}H_{67}FN_{10}O_6$ desired mass=1018.5, found: m/z=1020.3 $[M+H]^+$. $^1$H NMR (500 MHz, Methanol-$d_4$) δ 8.80-8.73 (m, 2H), 8.30 (s, 1H), 8.24 (s, 1H), 7.77 (d, J=7.5 Hz, 1H), 7.72 (s, 1H), 7.57 (s, 1H), 7.20-7.14 (m, 3H), 6.97-6.90 (m, 3H), 5.17 (d, J=6.7 Hz, 1H), 4.52 (t, J=8.3 Hz, 1H), 4.30 (s, 1H), 4.14 (s, 3H), 3.99 (s, 3H), 3.93 (s, 1H), 3.83 (q, J=8.8, 7.4 Hz, 2H), 3.79-3.71 (m, 1H), 3.68 (s, 3H), 3.60 (dd, J=18.7, 10.1 Hz, 5H), 2.97 (d, J=2.9 Hz, 1H), 2.90 (t, J=12.4 Hz, 2H), 2.76-2.56 (m, 4H), 2.25-2.19 (m, 1H), 2.04 (d, J=14.8 Hz, 3H), 1.97 (s, 2H), 1.91 (d, J=18.2 Hz, 5H), 1.79 (d, J=14.5 Hz, 2H), 1.74-1.61 (m, 8H), 1.61-1.51 (m, 1H), 1.50 (d, J=12.3 Hz, 2H), 1.31 (s, 2H).

Example 16

(3RS)-3-(6-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}pyridin-3-yl)piperidine-2,6-dione

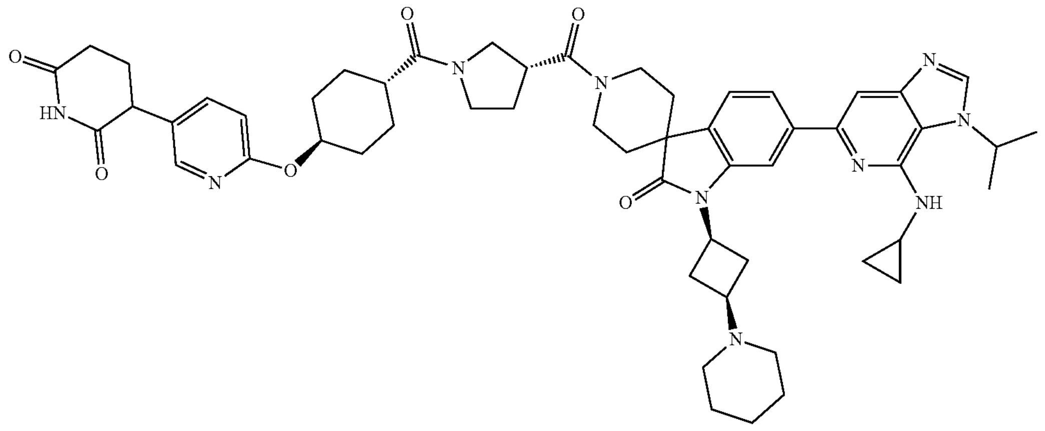 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cn6)CC5)C4)CC3)nc(NC3CC3)c21]

Step 1: 6-[4-(cyclopropylamino)-3-isopropylimidazo[4,5-c]pyridin-6-yl]-1'-[(3R)-pyrrolidine-3-carbonyl]-1-[(1S,3S)-3-(piperidin-1-yl)cyclobutyl]spiro[indole-3,4'-piperidin]-2-one 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (50.00 mg, 0.090 mmol) and (1,2,3-benzotriazol-1-yloxy)tris(dimethylamino)phosphanium, hexafluoro-lambda5-phosphanuide (51.92 mg, 0.117 mmol) were dissolved in dimethylformamide (1.00 mL) and N,N-diisopropylethylamine (0.06 mL, 46.68 mg, 0.361 mmol) and stirred at room temperature for 5 minutes. (3R)-1-(tert-butoxycarbonyl)pyrrolidine-3-carboxylic acid (19.44 mg, 0.090 mmol) was added and the reaction mixture was stirred for 2 hours at room temperature. The protected intermediate was isolated by reverse phase flash column, dissolved in DCM and treated with 4M HCl in dioxane for 2 hours. The reaction mixture was evaporated to dryness and taken forward as the HCl salt. (52.4 mg, 89% yield).

Step 2: (3rs)-3-(6-{[(1r,4r)-4-[(3r)-3-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)pyrrolidine-1-carbonyl]cyclohexyl]oxy}pyridin-3-yl)piperidine-2,6-dione Using procedures similar to those used for Example 36 and using 6-[4-(cyclopropylamino)-3-isopropylimidazo[4,5-c]pyridin-6-yl]-1'-[(3R)-pyrrolidine-3-carbonyl]-1-[(1s,3s)-3-(piperidin-1-yl)cyclobutyl]spiro[indole-3,4'-piperidin]-2-one (15.00 mg, 0.02 mmol) and (1r,4r)-4-((5-(2,6-dioxopiperidin-3-yl)pyridin-2-yl)oxy)cyclohexane-1-carboxylic acid (intermediate 9) (7.66 mg, 0.02 mmol) as coupling partners afforded the title compound (TFA salt) as an off white solid (8.1 mg, 35% yield). LCMS: $C_{55}H_{68}N_{10}O_6$ desired mass=964.5, found: m/z=965.9 $[M+H]^+$. $^1$H NMR (500 MHz, DMSO-$d_6$) δ 10.86 (s, 1H), 8.04-7.98 (m, 1H), 7.77 (s, 1H), 7.66 (s, 1H), 7.60-7.53 (m, 1H), 6.74 (d, J=8.6 Hz, 1H), 4.92 (s, 2H), 4.35 (s, 2H), 3.85 (dd, J=12.3, 4.9 Hz, 2H), 3.55 (d, J=7.7 Hz, 1H), 3.48-3.37 (m, 4H), 3.02 (s, 2H), 2.92 (d, J=15.2 Hz, 4H), 2.82 (d, J=10.6 Hz, 1H), 2.82 (s, 2H), 2.77-2.66 (m, 1H), 2.56 (d, J=5.8 Hz, 1H), 2.50-2.45 (m, 3H), 2.24 (d, J=12.0 Hz, 1H), 2.15 (s, 4H), 1.85 (d, J=17.2 Hz, 6H), 1.75 (s, 4H), 1.61 (dd, J=18.1, 9.6 Hz, 2H), 1.53 (d, J=6.5 Hz, 6H), 1.49 (s, 8H), 1.25 (s, 1H), 0.84 (s, 3H), 0.63 (s, 2H).

Example 17

(3RS)-3-(6-{1[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)piperidine-2,6-dione

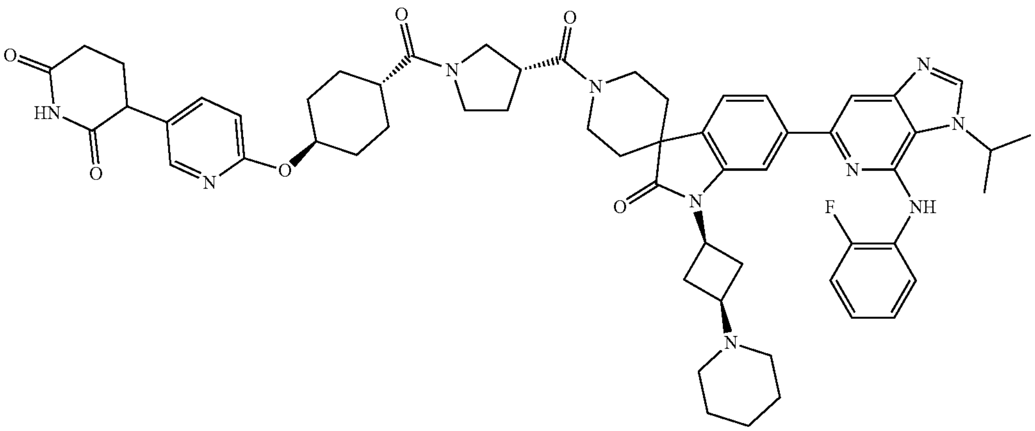 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cn6)CC5)C4)CC3)nc(Nc3ccccc3F)c21]

Step 1: 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (3R)-1-(tert-butoxycarbonyl)pyrrolidine-3-carboxylic acid (24.79 mg, 0.12 mmol) and (1,2,3-benzotriazol-1-yloxy)tris(dimethylamino)phosphanium, hexafluoro-lambda5-phosphanuide (66.22 mg, 0.15 mmol) were dissolved in dimethylformamide (1.00 mL) and N,N-diisopropylethylamine (0.08 mL, 59.54 mg, 0.46 mmol) and stirred at room temperature for 5 minutes. 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (70.00 mg, 0.12 mmol) was added and the reaction mixture was stirred for 2 hours at room temperature. The protected intermediate was isolated by reverse phase flash column, dissolved in DCM and treated with 4M HCl in dioxane for 2 hours. The reaction mixture was evaporated to dryness and taken forward as the HCl salt. (75 mg, 92% yield).

Step 2: Using procedures similar to those used for Example 36 and using 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (15.00 mg, 0.02 mmol) and (1r,4r)-4-((5-(2,6-dioxopiperidin-3-yl)pyridin-2-yl)oxy)cyclohexane-1-carboxylic acid (intermediate 9) (7.07 mg, 0.02 mmol) as coupling partners afforded the title compound (TFA salt) as an off white solid (12.3 mg, 56% yield). LCMS: $C_{58}H_{67}FN_{10}O_6$ desired mass=1018.5, found: m/z=1020.0 $[M+H]^+$. $^1H$ NMR (500 MHz, Methanol-$d_4$) δ 8.04 (s, 1H), 7.82 (s, 1H), 7.77 (d, J=7.8 Hz, 1H), 7.69 (d, J=7.8 Hz, 1H), 7.62 (s, 2H), 7.54 (d, J=7.9 Hz, 1H), 7.30 (s, 1H), 7.26 (s, 3H), 6.79 (d, J=8.9 Hz, 1H), 4.83 (d, J=16.9 Hz, 1H), 4.25 (s, 1H), 4.11 (s, 2H), 3.97 (s, 3H), 3.92-3.80 (m, 2H), 3.68 (s, 4H), 3.63-3.51 (m, 4H), 3.29 (ddd, J=12.9, 10.0, 1.7 Hz, 4H), 2.97-2.86 (m, 4H), 2.81-2.66 (m, 2H), 2.60 (s, 1H), 2.28 (d, J=6.8 Hz, 6H), 2.20 (s, 2H), 2.04 (d, J=13.9 Hz, 2H), 1.94 (s, 4H), 1.86 (s, 1H), 1.74 (d, J=6.7 Hz, 8H), 1.56 (s, 3H).

Example 18

(3RS)-3-(6-{[(1R,4R)-4-[(3R)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)piperidine-2,6-dione

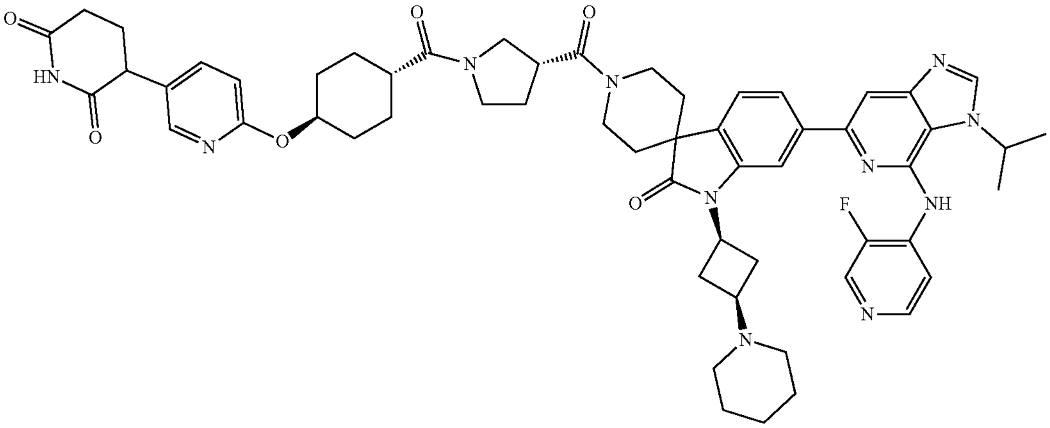 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cn6)CC5)C4)CC3)nc(Nc3ccncc3F)c21]

Using procedures similar to those used for Example 17 but using 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)-1'-((R)-pyrrolidine-3-carbonyl)spiro[indoline-3,4'-piperidin]-2-one (10.00 mg, 0.02 mmol) and (1r,4r)-4-((5-(2,6-dioxopiperidin-3-yl)pyridin-2-yl)oxy)cyclohexane-1-carboxylic acid (intermediate 9) (7.05 mg, 0.02 mmol) as the coupling partners in step 2 afforded the title compound (TFA salt) as an off white solid (7.8 mg, 43% yield). LCMS: $C_{57}H_{66}FN_{11}O_6$ desired mass=1019.5, found: m/z=1021.1 $[M+H]^+$. $^1H$ NMR (500 MHz, Methanol-$d_4$) δ 8.74 (s, 1H), 8.30 (d, J=6.5 Hz, 1H), 8.22 (s, 1H), 8.03 (d, J=3.2 Hz, 1H), 7.87 (d, J=6.7 Hz, 1H), 7.77 (d, J=8.3 Hz, 1H), 7.72 (s, 1H), 7.64-7.54 (m, 2H), 6.78 (dd, J=8.6, 2.1 Hz, 1H), 5.21-5.13 (m, 1H), 4.96 (s, 1H), 4.54-4.45 (m, 1H), 3.99 (s, 1H), 3.96-3.80 (m, 2H), 3.78-3.59 (m, 3H), 3.59 (s, 4H), 3.31 (s, 1H), 3.23 (d, J=10.3 Hz, 1H), 2.97 (s, 2H), 2.90 (t, J=12.6 Hz, 2H), 2.81-2.66 (m, 2H), 2.61 (d, J=12.5 Hz, 1H), 2.28 (s, 5H), 2.32-2.24 (m, 2H), 2.19 (s, 2H), 2.03 (d, J=15.0 Hz, 4H), 1.97 (s, 2H), 1.91 (d, J=15.9 Hz, 5H), 1.83-1.62 (m, 8H), 1.61-1.51 (m, 3H), 1.33 (d, J=13.9 Hz, 2H).

Example 19

(3RS)-3-(6-{[(1R,4R)-4-[(3R)-3-[(6-{4-[(oxan-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)piperidine-2,6-dione

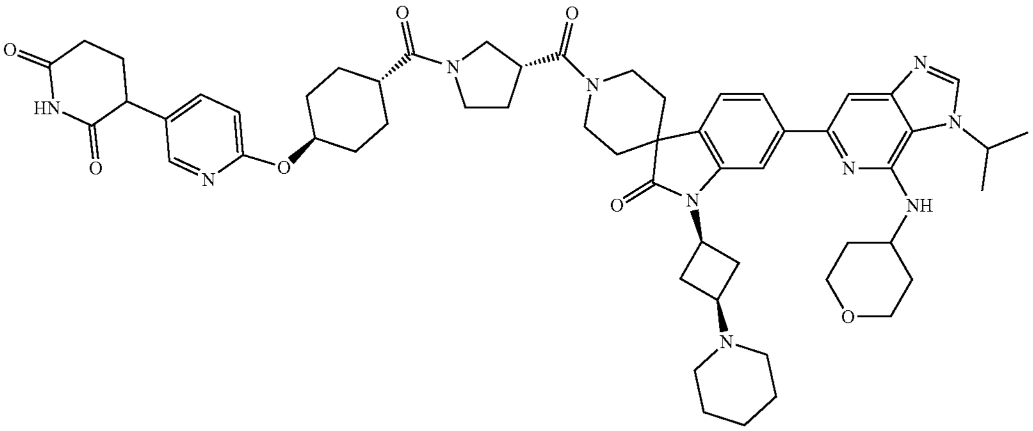 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(C7CCC(=O)NC7=O)cn6)CC5)C4)CC3)nc(NC3CCOCC3)c21]

Using procedures similar to those used for Example 17 but using (1r,4r)-4-((5-(2,6-dioxopiperidin-3-yl)pyridin-2-yl)oxy)cyclohexane-1-carboxylic acid (Intermediate 9) (14.4 mg, 0.03 mmol) and 6-(3-isopropyl-4-((tetrahydro-2H-pyran-4-yl)amino)-3H-imidazo[4,5-c]pyridin-6-yl)-1-((1s,3s)-3-(piperidin-1-yl)cyclobutyl)-1'-((R)-pyrrolidine-3-carbonyl)spiro[indoline-3,4'-piperidin]-2-one (20.00 mg, 0.03 mmol) as the coupling partners in step 2 afforded the title compound (TFA salt) as an off white solid (15.1 mg, 44% yield). LCMS: $C_{57}H_{72}N_{10}O_7$ desired mass=1008.6, found: m/z=1010.5 $[M+H]^+$. $^1H$ NMR (500 MHz, Methanol-$d_4$) δ 8.05 (t, J=2.6 Hz, 1H), 7.86 (d, J=7.8 Hz, 1H), 7.77 (s, 1H), 7.69-7.57 (m, 2H), 7.55 (s, 1H), 6.84 (d, J=8.6 Hz, 1H), 4.58-4.51 (m, 2H), 4.49 (s, 2H), 4.12 (d, J=11.8 Hz, 5H), 4.05-3.90 (m, 2H), 3.94-3.80 (m, 2H), 3.77 (dd, J=11.7, 7.7 Hz, 1H), 3.72-3.61 (m, 4H), 3.60 (t, J=10.5 Hz, 4H), 3.56-3.48 (m, 2H), 3.02 (s, 2H), 2.92 (t, J=12.5 Hz, 2H), 2.83-2.67 (m, 2H), 2.62 (d, J=12.4 Hz, 1H), 2.34-2.25 (m, 5H), 2.18 (s, 2H), 2.00 (q, J=15.0, 14.5 Hz, 9H), 1.90 (s, 4H), 1.75 (d, J=6.5 Hz, 6H), 1.69 (d, J=12.5 Hz, 1H), 1.57 (t, J=12.0 Hz, 4H), 1.31 (s, 1H).

Example 20

1-(6-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}pyridin-3-yl)-1,3-diazinane-2,4-dione

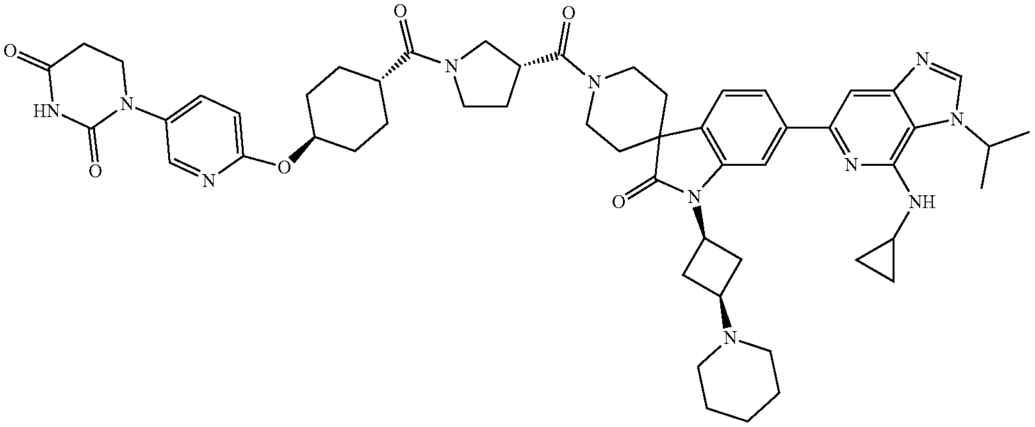 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(N7CCC(=O)NC7=O)cn6)CC5)C4)CC3)nc(NC3CC3)c21]

Using procedures similar to those used for Example 13 but using (R)-1-((1r,4R)-4-((5-(2,4-dioxotetrahydropyrimidin-1(2H)-yl)pyridin-2-yl)oxy)cyclohexane-1-carbonyl)pyrrolidine-3-carboxylic acid (Intermediate 10) (15.5 mg, 0.036 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (20.00 mg, 0.04 mmol) as coupling partners afforded the title compound (TFA salt) as an off white solid (19.5 mg, 54% yield). LCMS: $C_{54}H_{67}N_{11}O_6$ desired mass=965.5, found: m/z=966.4 $[M+H]^+$. $^1H$ NMR (500 MHz, Methanol-$d_4$) δ 8.95 (s, 1H), 8.15 (t, J=2.9 Hz, 1H), 7.73-7.64 (m, 3H), 7.62 (s, 1H), 7.57 (s, 1H), 6.81 (d, J=8.8 Hz, 1H), 5.17-5.10 (m, 1H), 4.54-4.46 (m, 1H), 4.16 (s, 3H), 4.03 (d, J=12.0 Hz, 1H), 3.94 (dd, J=13.8, 7.0 Hz, 1H), 3.84 (dt, J=16.2, 7.5 Hz, 4H), 3.80-3.66 (m, 2H), 3.60 (dd, J=21.3, 9.8 Hz, 4H), 3.21 (s, 1H), 3.10-3.04 (m, 2H), 3.00 (s, 2H), 2.95-2.81 (m, 5H), 2.62 (d, J=12.4 Hz, 1H), 2.29 (s, 1H), 2.04 (s, 1H), 2.01 (s, 4H), 1.92 (s, 7H), 1.83-1.72 (m, 2H), 1.69 (d, J=6.5 Hz, 6H), 1.56 (t, J=12.2 Hz, 4H), 1.31 (s, 1H), 1.15 (s, 2H), 0.96 (s, 2H).

Example 21

1-(6-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)-1,3-diazinane-2,4-dione

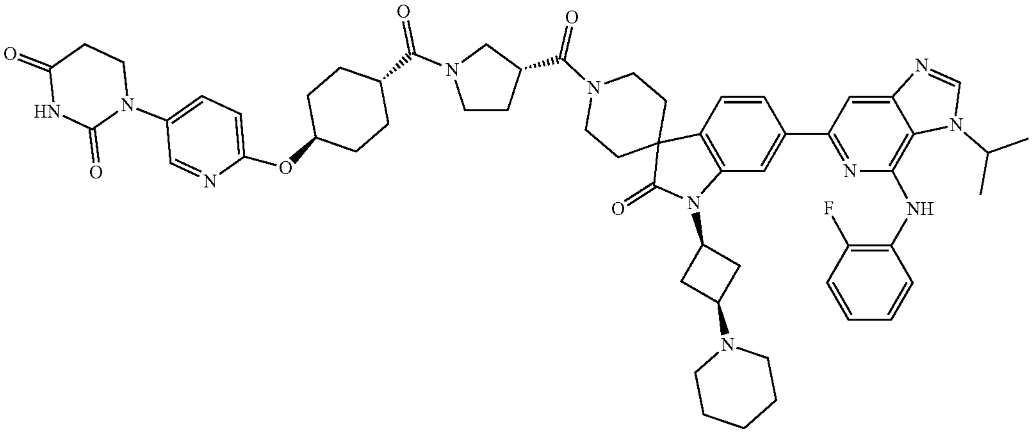 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(N7CCC(=O)NC7=O)cn6)CC5)C4)CC3)nc(Nc3ccccc3F)c21]

Using procedures similar to those used for Example 13 but using (R)-1-((1r,4R)-4-((5-(2,4-dioxotetrahydropyrimidin-1(2H)-yl)pyridin-2-yl)oxy)cyclohexane-1-carbonyl)pyrrolidine-3-carboxylic acid (Intermediate 10) (15.5 mg, 0.036 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (20.0 mg, 0.036 mmol) as coupling partners afforded the title compound (TFA salt) as an off white solid (21.7 mg, 72% yield). LCMS: $C_{57}H_{66}FN_{11}O_6$ desired mass=1019.5, found: m/z=1020.4 $[M+H]^+$. $^1H$ NMR (500 MHz, Methanol-$d_4$) δ 9.33-9.18 (m, 1H), 8.14 (d, J=2.8 Hz, 1H), 7.82 (s, 1H), 7.77 (d, J=7.7 Hz, 1H), 7.69 (dd, J=8.8, 2.7 Hz, 2H), 7.59 (d, J=4.7 Hz, 1H), 7.57-7.50 (m, 1H), 7.32 (d, J=11.3 Hz, 3H), 6.81 (d, J=8.8 Hz, 1H), 5.40 (d, J=7.4 Hz, 1H), 4.21 (s, 1H), 4.11 (d, J=10.4 Hz, 2H), 4.04-3.38 (m, 14H), 3.25-2.99 (m, 3H), 2.98-2.78 (m, 7H), 2.72 (s, 1H), 2.54 (s, 2H), 2.42-2.22 (m, 4H), 2.18-1.83 (m, 11H), 1.78 (d, J=6.7 Hz, 8H), 1.75-1.25 (m, 8H).

Example 22

1-(6-{[(1R,4R)-4-[(3R)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)-1,3-diazinane-2,4-dione

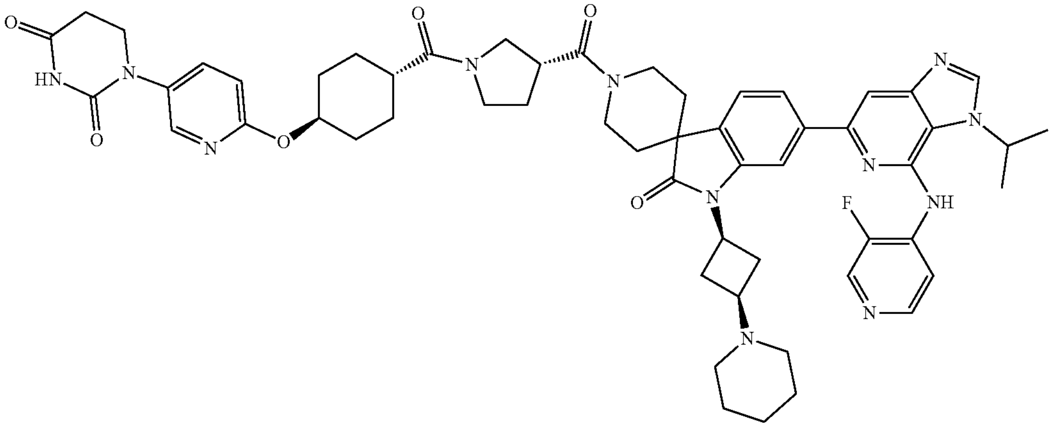 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Oc6ccc(N7CCC(=O)NC7=O)cn6)CC5)C4)CC3)nc(Nc3ccncc3F)c21]

Using procedures similar to those used for Example 13 but using (R)-1-((1r,4R)-4-((5-(2,4-dioxotetrahydropyrimidin-1(2H)-yl)pyridin-2-yl)oxy)cyclohexane-1-carbonyl) pyrrolidine-3-carboxylic acid (Intermediate 10) (15.5 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.00 mg, 0.033 mmol) as coupling partners afforded the title compound (TFA salt) as an off white solid (27.7 mg, 80% yield). LCMS: $C_{56}H_{65}FN_{12}O_6$ desired mass=1020.5, found: m/z=1021.4 $[M+H]^+$. $^1$H NMR (500 MHz, Methanol-$d_4$) δ 8.79 (d, J=9.2 Hz, 2H), 8.31 (d, J=6.4 Hz, 1H), 8.25 (d, J=6.8 Hz, 1H), 8.14 (d, J=3.1 Hz, 1H), 7.89 (t, J=6.4 Hz, 1H), 7.86-7.65 (m, 3H), 7.58 (t, J=9.8 Hz, 1H), 6.81 (d, J=8.8 Hz, 1H), 5.21-5.10 (m, 1H), 4.51 (q, J=8.4 Hz, 1H), 4.14 (s, 2H), 4.07-3.39 (m, 12H), 3.16 (d, J=6.7 Hz, 3H), 3.05-2.76 (m, 6H), 2.61 (d, J=11.3 Hz, 1H), 2.29 (d, J=7.9 Hz, 4H), 2.10-1.86 (m, 9H), 1.85-1.68 (m, 4H), 1.65 (dd, J=6.7, 3.0 Hz, 6H), 1.61-1.27 (m, 4H).

Example 23

(3RS)-3-(6-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl) pyrrolidine-1-carbonyl]piperidin-1-yl}pyridin-3-yl) piperidine-2,6-dione

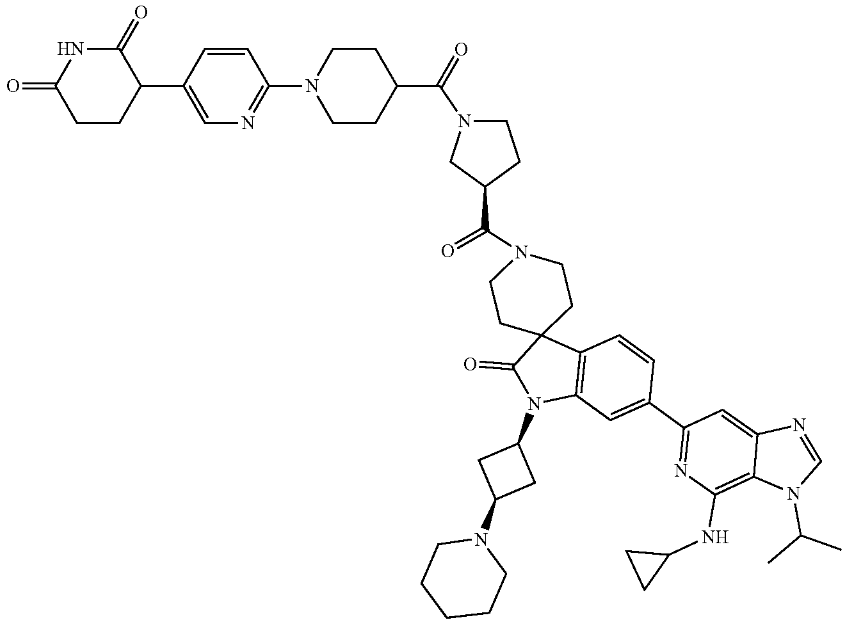 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ccc(C7CCC(=O)NC7=O)cn6)CC5)C4)CC3)nc(NC3CC3)c21]

Example 23 was prepared by similar procedures as Example 1 using (3R)-1-(1-(5-(2,6-dioxopiperidin-3-yl) pyridin-2-yl)piperidine-4-carbonyl)pyrrolidine-3-carboxylic acid (intermediate 11) (10 mg, 0.024 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro [indoline-3,4'-piperidin]-2-one (13.3 mg, 0.024 mmol) as starting materials. The title compound (TFA salt) was isolated as an off-white solid (7.8 mg, 33% yield). LCMS: $[C_{54}H7N_{11}O_5]$, desired mass=950.2, found: m/z=950.7 $[M+H]^+$, $^1$H NMR (500 MHz, DMSO) δ 10.93 (s, 1H), 9.51 (s, 1H), 8.87 (s, 1H), 7.92 (s, 1H), 7.78 (s, 3H), 7.67 (s, 2H), 7.26 (s, 1H), 5.17 (s, 1H), 4.34 (s, 3H), 4.29-4.20 (m, 4H), 3.97 (s, 1H), 3.90 (d, J=11.5 Hz, 1H), 3.58 (s, 2H), 3.48 (s, 1H), 3.41 (d, J=10.3 Hz, 2H), 3.17 (s, 2H), 3.03 (s, 2H), 2.94 (s, 3H), 2.83 (s, 3H), 2.69 (d, J=14.0 Hz, 1H), 2.60 (s, 1H), 2.28 (d, J=12.9 Hz, 1H), 2.20-2.13 (m, 2H), 2.00 (s, 1H), 1.86 (d, J=14.8 Hz, 5H), 1.76 (s, 4H), 1.67-1.59 (m, 5H), 1.54 (d, J=6.7 Hz, 6H), 1.42 (d, J=12.4 Hz, 1H), 0.87 (s, 2H), 0.68 (s, 2H).

Example 24

3-(6-(4-((R)-3-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)pyrrolidine-1-carbonyl)piperidin-1-yl)pyridin-3-yl)piperidine-2,6-dione

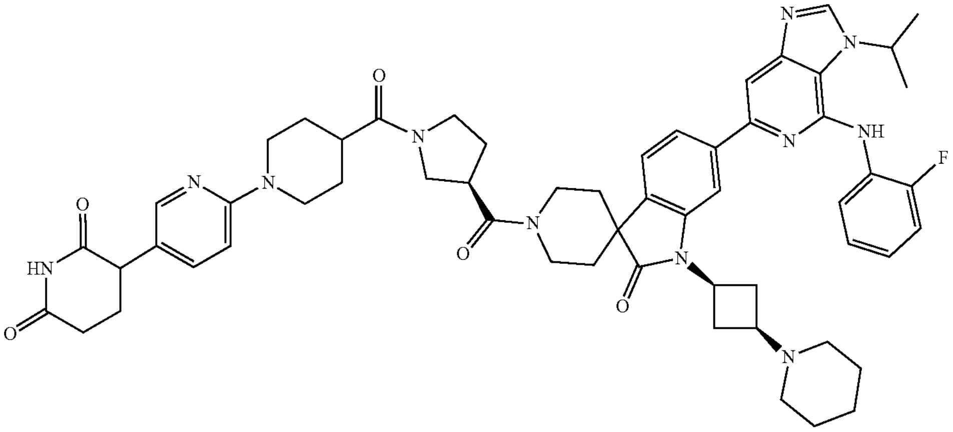 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ccc(C7CCC(=O)NC7=O)cn6)CC5)C4)CC3)nc(Nc3ccccc3F)c21]

To a solution of intermediate 11 (31 mg, 0.07 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (35 mg, 0.06 mmol) in anhydrous DMF (0.6 mL) was added BOP (33 mg, 0.07 mmol) and after 10 min of stirring at room temperature, DIPEA (0.04 mL, 0.23 mmol) was added. The reaction mixture was stirred for 1 h at room temperature, and then was purified directly without workup by HPLC to provide the desired product as a TFA salt. The combined HPLC fractions were concentrated under reduced pressure and the residue was treated with aqueous $NH_4OH$ (0.3%, 0.5 mL), then extracted with DCM (3×0.5 mL). 45 mg (79% yield) of the title compound as a white solid was obtained. LCMS: [$C_{57}H_{66}FN_{11}O_5$], desired mass=1003.5, found: m/z=1003.9 $[M+H]^+$. $^1H$ NMR (500 MHz, DMSO-$d_6$): δ (ppm): 10.87 (s, 1H), 9.41 (s, 1H), 8.66 (s, 1H), 8.36 (s, 1H), 7.88 (d, J=6.5 Hz, 1H), 7.77-7.64 (m, 1H), 7.54 (t, J=7.8, 7.8 Hz, 2H), 7.46 (s, 1H), 7.33-7.21 (m, 1H), 7.20 (d, J=9.0 Hz, 2H), 5.31-5.19 (m, 1H), 4.22 (d, J=11.8 Hz, 2H), 4.06 (q, J=8.8, 8.1, 8.1 Hz, 2H), 3.95-3.68 (m, 26H), 3.58-3.40 (m, 6H), 3.10 (s, 1H), 2.89-2.79 (m, 3H), 2.74-2.64 (m, 2H), 2.24 (q, J=12.7, 12.5, 12.5 Hz, 1H), 2.13 (s, 1H), 2.02-1.92 (m, 1H), 1.86 (d, J=12.8 Hz, 2H), 1.76 (s, 2H), 1.69 (s, 3H), 1.41 (d, J=12.7 Hz, 1H).

Example 25

(3RS)-3-(6-{4-[(3R)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione

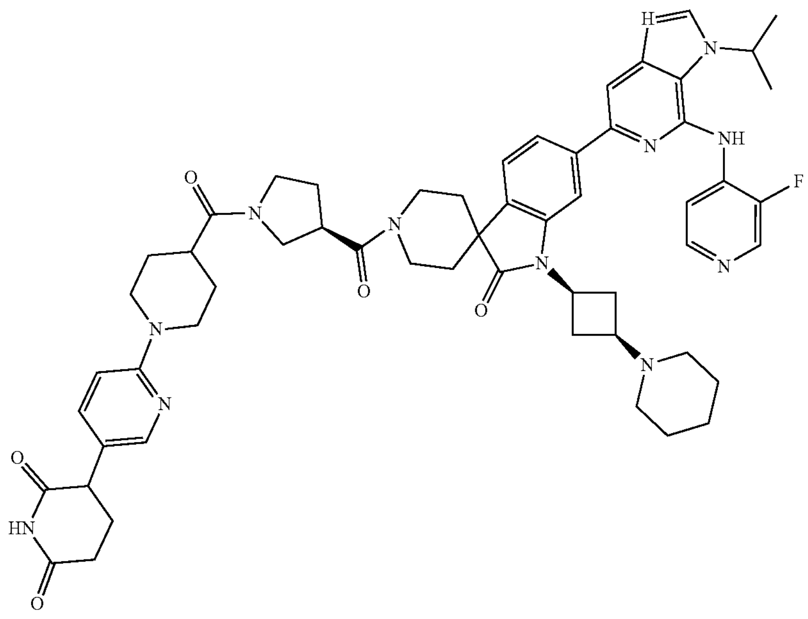

The title compound was synthesized using similar methods to example 10, using BOP coupling. Afforded an off-white solid (45 mg, 0.044 mmol, 18%) as a free base. LCMS: [$C_{56}H_{65}FN_{12}O_5$], desired mass=1004.5, found: m/z=1005.1 $[M+H]^+$. $^1H$ NMR (500 MHz, DMSO-$d_6$) δ 10.88 (s, 1H), 8.81 (s, 1H), 8.72 (s, 1H), 8.41-8.26 (m, 2H), 7.89 (d, J=2.6 Hz, 1H), 7.74 (d, J=28.8 Hz, 2H), 7.61 (dd, J=15.1, 7.4 Hz, 3H), 7.20 (s, 1H), 7.09 (s, 1H), 6.99 (s, 1H), 5.18-5.06 (m, 1H), 4.28 (d, J=7.1 Hz, 2H), 4.22 (d, J=13.2 Hz, 2H), 3.88-3.74 (m, 11H), 3.58 (d, J=14.9 Hz, 1H), 3.44 (d, J=7.0 Hz, 2H), 3.38 (d, J=6.6 Hz, 2H), 3.12 (d, J=12.1 Hz, 1H), 3.04-2.87 (m, 1H), 2.82 (s, 5H), 2.72-2.59 (m, 1H), 2.30-2.19 (m, 1H), 2.14 (d, J=6.8 Hz, 1H), 2.01-1.93 (m, 1H), 1.89-1.55 (m, 14H), 1.51 (d, J=6.7 Hz, 6H), 1.39 (d, J=12.7 Hz, 1H).

Example 26

3-(6-((1-((1R,4R)-4-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carbonyl)piperidin-4-yl)amino)pyridin-3-yl)piperidine-2,6-dione

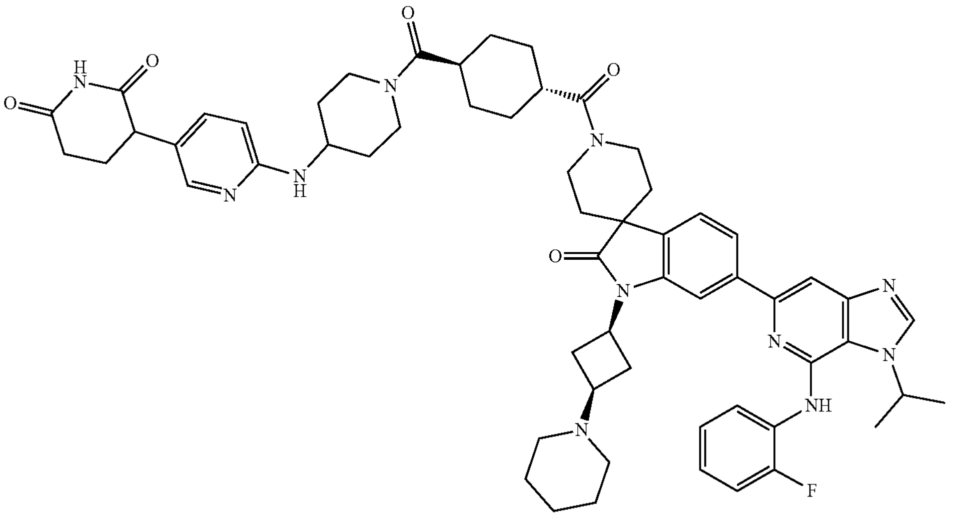 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(Nc6ccc(C7CCC(=O)NC7=O)cn6)CC5)CC4)CC3)nc(Nc3ccccc3F)c21]

The title compound was synthesized using similar methods to Example 10, using BOP coupling. Afforded an off-white powder (18 mg, 0.0174 mmol) as a free base. LCMS: [$C_{59}H_{70}FN_{11}O_5$], desired mass=1031.2, found: m/z=1032.5 $[M+H]^+$. $^1$H NMR (500 MHz, DMSO-$d_6$) δ 10.90 (s, 1H), 9.31 (s, 1H), 8.55 (s, 1H), 8.30 (s, 1H), 7.87 (s, 1H), 7.79 (d, J=2.3 Hz, 1H), 7.67 (dd, J=7.9, 1.6 Hz, 1H), 7.58-7.49 (m, 2H), 7.48 (s, 1H), 7.29 (ddd, J=11.3, 7.6, 2.1 Hz, 1H), 7.23-7.14 (m, 3H), 7.07 (s, 1H), 6.97 (s, 1H), 5.25 (p, J=6.5, 6.5, 6.4, 6.4 Hz, 1H), 4.30 (s, 1H), 4.08 (p, J=9.6, 9.6, 9.1, 9.1 Hz, 1H), 4.00 (d, J=13.3 Hz, 1H), 3.83 (m, 6H), 2.95-2.78 (m, 10H), 2.77-2.62 (m, 9H), 2.28-2.17 (m, 2H), 2.01-1.59 (m, 14H), 1.57 (m, 9H), 1.41 (q, J=12.7, 12.4, 12.4 Hz, 2H).

Example 27

(3RS)-3-[6-({1-[(1R,4R)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl}oxy)pyridin-3-yl]piperidine-2,6-dione

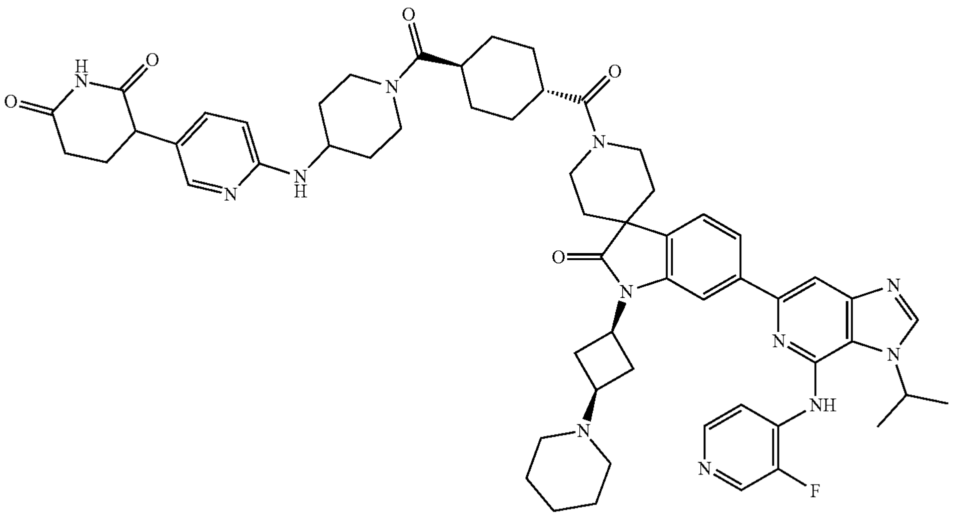 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(Nc6ccc(C7CCC(=O)NC7=O)cn6)CC5)CC4)CC3)nc(Nc3ccncc3F)c21]

EDCI (9.5 mg, 0.049 mmol) was added to a mixture of 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20 mg, 0.033 mmol), HOBT hydrate (7.6 mg, 0.049 mmol), (1r,4r)-4-[4-({5-[(3RS)-2,6-dioxopiperidin-3-yl]pyridin-2-yl}amino)piperidine-1-carbonyl]cyclohexane-1-carboxylic acid (intermediate 12) (14.5 mg, 0.033 mmol), and DIPEA (26 μL, 0.15 mmol) in DMF (250 μL). The reaction mixture was stirred for 16 hours at room temperature, then the crude reaction mixture was purified by reverse phase HPLC to afford the title compound (TFA salt) as an off-white solid (16 mg, 46% yield). LCMS: [$C_{58}H_{69}FN_{12}O_5$], desired mass=1032.5, found: m/z=1034.4 $[M+H]^+$. $^1$H NMR (500 MHz, DMSO) δ 10.94 (s, 1H), 9.32 (s, 1H), 8.69 (s, 1H), 8.29 (d, J=6.1 Hz, 1H), 8.24 (s, 1H), 7.83-7.74 (m, 3H), 7.64 (s, 1H), 7.62-7.53 (m, 2H), 7.18 (s, 1H), 7.08 (s, 1H), 6.98 (s, 1H), 5.15 (s, 1H), 4.32 (s, 2H), 4.02 (s, 1H), 3.88 (s, 5H), 3.80 (s, 2H), 3.16 (s, 2H), 2.97 (d, J=9.6 Hz, 1H), 2.83 (s, 5H), 2.68 (d, J=12.8 Hz, 6H), 2.59 (s, 1H), 2.25 (d, J=13.9 Hz, 1H), 2.07 (s, 3H), 1.99 (s, 3H), 1.86 (d, J=13.9 Hz, 1H), 1.79 (s, 2H), 1.71 (s, 7H), 1.53 (d, J=6.7 Hz, 8H), 1.41 (s, 2H), 1.25 (dd, J=12.4, 5.4 Hz, 2H).

Example 28

(3RS)-3-[6-({1-[(1R,4R)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl}oxy)pyridin-3-yl]piperidine-2,6-dione

Step 1: (1r,4r)-4-(4-((5-(2,6-dioxopiperidin-3-yl)pyridin-2-yl)oxy)piperidine-1-carbonyl)cyclohexane-1-carboxylic acid 3-(6-(piperidin-4-yloxy)pyridin-3-yl)piperidine-2,6-dione (100.00 mg, 0.35 mmol), (1r,4r)-cyclohexane-1,4-dicarboxylic acid (65.46 mg, 0.38 mmol), (1,2,3-benzotriazol-1-yloxy)tris(dimethylamino)phosphanium, hexafluoro-lambda5-phosphanuide (168.15 mg, 0.38 mmol), and N,N-diisopropylethylamine (0.24 mL, 178.68 mg, 1.38 mmol) were dissolved in dimethylformamide (2.00 mL) and stirred at room temperature for 4 hours. The reaction mixture was purified by reverse phase flash column to afford the title compound as a white solid (20.0 mg, 26% yield).

Step 2

Using procedures similar to those used for Example 36 and using 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (20.00 mg, 0.033 mmol) and (1r,4r)-4-(4-((5-(2,6-dioxopiperidin-3-yl)pyridin-2-yl)oxy)piperidine-1-carbonyl)cyclohexane-1-carboxylic acid (14.59 mg, 0.03 mmol) as coupling partners afforded the title compound (TFA salt) as an off white solid (10.4 mg, 30% yield). LCMS: $C_{59}H_{69}FN_{10}O_6$ desired mass=1032.5, found: m/z=1033.5 $[M+H]^+$. $^1$H NMR (500 MHz, Methanol-$d_4$) δ 8.50 (s, 1H), 8.05 (d, J=2.6 Hz, 1H), 7.81 (s, 1H), 7.79-7.69 (m, 2H), 7.66 (s, 1H), 7.61 (dd, J=8.7, 2.6 Hz, 1H), 7.52 (d, J=7.8 Hz, 1H), 7.30-7.17 (m, 2H), 7.14 (d, J=6.7 Hz, 1H), 6.82 (d, J=8.5 Hz, 1H), 4.60 (s, 1H), 4.12-4.02 (m, 2H), 3.97 (s, 1H), 3.94 (s, 5H), 3.89 (dd, J=12.1, 5.1 Hz, 1H), 2.89 (s, 9H), 2.84-2.67 (m, 2H), 2.29 (dd, J=12.7, 4.7 Hz, 1H), 2.23-2.18 (m, 2H), 2.11 (s, 1H), 2.05 (s, 1H), 1.85 (m, 20H), 1.65 (s, 4H), 1.31 (s, 3H).

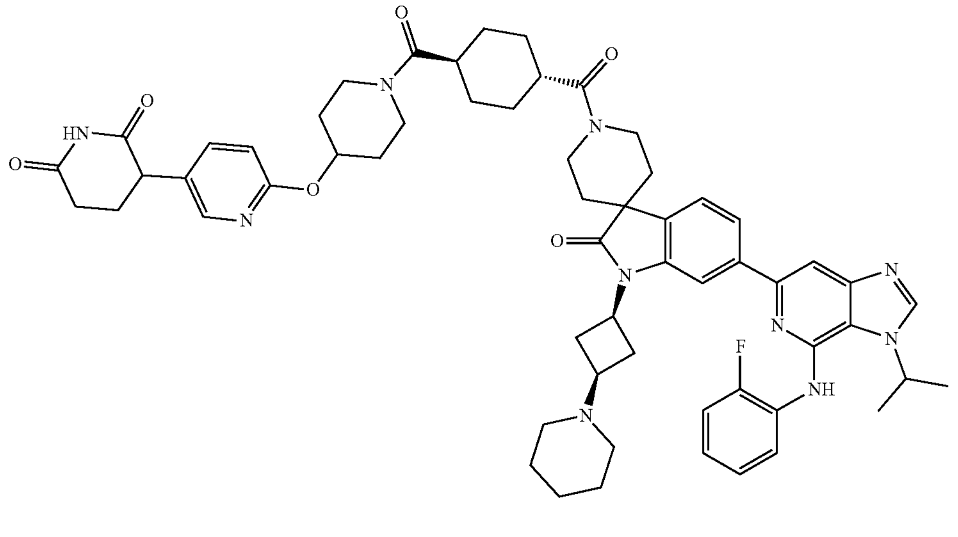 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(Oc6ccc(C7CCC(=O)NC7=O)cn6)CC5)CC4)CC3)nc(Nc3ccccc3F)c21]

Example 29

(3RS)-3-[6-({1-[(1S,4S)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexanecarbonyl]piperidin-4-yl}amino)pyridin-3-yl]piperidine-2,6-dione

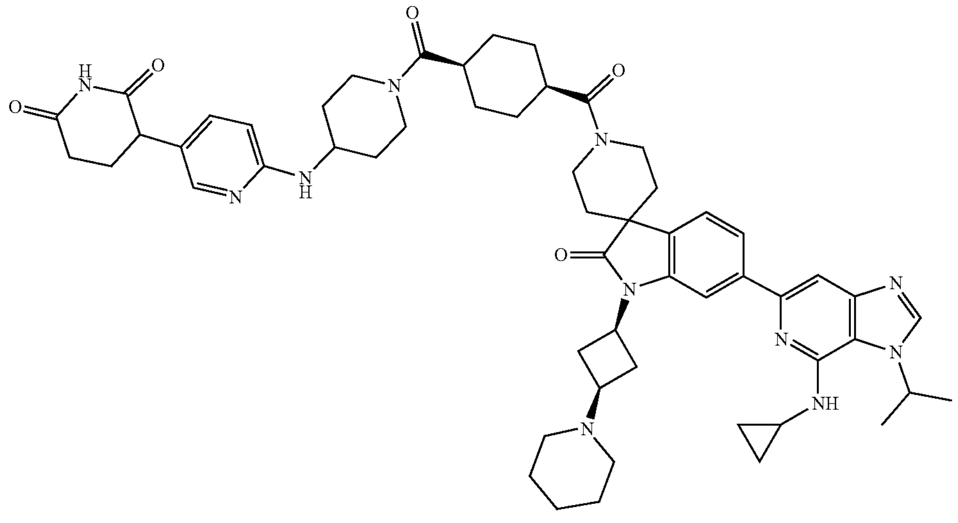 [SMILES: CC(C)n1cnc2cc(-c3ccc4c(c3)N([C@H]3C[C@@H](N5CCCCC5)C3)C(=O)C43CCN(C(=O)[C@H]4CC[C@@H](C(=O)N5CCC(Nc6ccc(C7CCC(=O)NC7=O)cn6)CC5)CC4)CC3)nc(NC3CC3)c21]

Using procedures similar to those used for Example 27, and using (1s,4s)-4-(4-((5-(2,6-dioxopiperidin-3-yl)pyridin-2-yl)amino)piperidine-1-carbonyl)cyclohexane-1-carboxylic acid (intermediate 14) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one as the coupling partners, the title compound (TFA salt) was isolated as an off-white solid (10.2 mg, 42% yield). LCMS: [C56H71N11O5], desired mass=977.6, found: m/z=978.7 $[M+H]^+$. $^1H$ NMR (500 MHz, MeOD) δ 8.86 (s, 1H), 7.90 (d, J=9.5 Hz, 1H), 7.80 (s, 1H), 7.71 (s, 1H), 7.65 (d, J=7.3 Hz, 2H), 7.56 (s, 1H), 7.09 (d, J=9.3 Hz, 1H), 5.15-5.09 (m, 1H), 4.54 (s, 2H), 4.49 (t, J=8.3 Hz, 1H), 4.11 (s, 3H), 3.97-3.87 (m, 2H), 3.63 (t, J=8.2 Hz, 1H), 3.57 (s, 3H), 3.37 (dd, J=3.3, 1.6 Hz, 1H), 3.01 (s, 3H), 2.90 (s, 6H), 2.83-2.75 (m, 2H), 2.32 (dd, J=12.6, 5.4 Hz, 1H), 2.17 (s, 1H), 2.03 (d, J=15.3 Hz, 9H), 1.96 (s, 1H), 1.89 (s, 2H), 1.75-1.66 (m, 12H), 1.58 (s, 4H), 1.31 (s, 1H), 1.11 (s, 2H), 0.91 (s, 3H).

Example 30

(3RS)-3-[6-({1-[(1S,4S)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl}amino)pyridin-3-yl]piperidine-2,6-dione

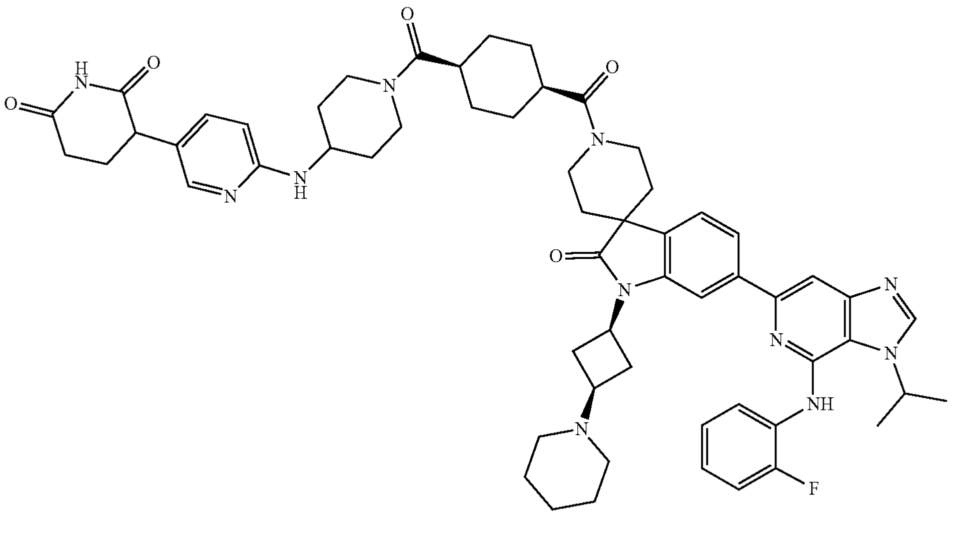 [SMILES: CC(C)n1cnc2cc(-c3ccc4c(c3)N([C@H]3C[C@@H](N5CCCCC5)C3)C(=O)C43CCN(C(=O)[C@H]4CC[C@@H](C(=O)N5CCC(Nc6ccc(C7CCC(=O)NC7=O)cn6)CC5)CC4)CC3)nc(Nc3ccccc3F)c21]

Using procedures similar to those for Example 27, and using (1s,4s)-4-(4-((5-(2,6-dioxopiperidin-3-yl)pyridin-2-yl)amino)piperidine-1-carbonyl)cyclohexane-1-carboxylic acid (intermediate 14) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one as the coupling partners, the title compound (formate salt) was isolated as an off-white solid (5.0 mg, 24% yield). LCMS: [C59H70FN11O5], desired mass=1031.6, found: m/z=517.2 $[(M+2H)/2]^+$. $^1$H NMR (500 MHz, MeOD) δ 8.53 (s, 1H), 8.49 (s, 1H), 7.85 (s, 1H), 7.80 (s, 1H), 7.75 (d, J=7.9 Hz, 2H), 7.69 (s, 1H), 7.51 (d, J=7.7 Hz, 1H), 7.35 (d, J=8.7 Hz, 1H), 7.28-7.17 (m, 2H), 7.13 (s, 1H), 6.57 (d, J=8.7 Hz, 1H), 5.28-5.21 (m, 1H), 4.60 (s, 1H), 4.46 (s, 2H), 4.23 (s, 2H), 3.97 (s, 14H), 3.76 (dd, J=11.5, 5.1 Hz, 1H), 2.92 (s, 2H), 2.88 (s, 3H), 2.80 (s, 6H), 2.78-2.72 (m, 1H), 2.68 (d, J=17.5 Hz, 1H), 2.04 (s, 4H), 1.70 (d, J=6.7 Hz, 9H), 1.43 (s, 3H), 1.31 (s, 3H).

Example 31

2-[(3RS)-2,6-dioxopiperidin-3-yl]-5-{4-[(1S,4s)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperazin-1-yl}-2,3-dihydro-1H-isoindole-1,3-dione

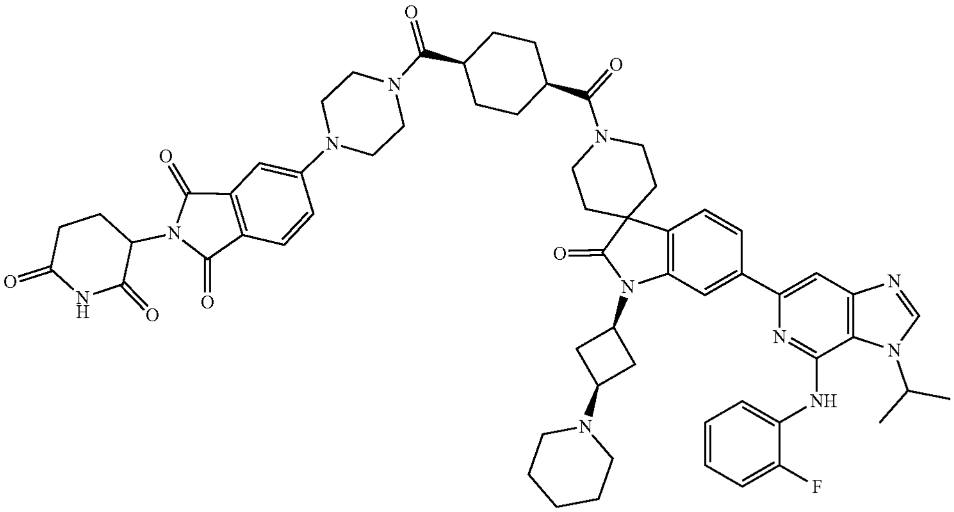 [SMILES: CC(C)n1cnc2cc(-c3ccc4c(c3)N([C@H]3C[C@@H](N5CCCCC5)C3)C(=O)C43CCN(C(=O)[C@H]4CC[C@@H](C(=O)N5CCN(c6ccc7c(c6)C(=O)N(C6CCC(=O)NC6=O)C7=O)CC5)CC4)CC3)nc(Nc3ccccc3F)c21]

BOP (8.8 mg, 0.020 mmol), was added to a mixture of 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride (9.9 mg, 0.015 mmol), (1S,4s)-4-(4-(2-(2,6-dioxopiperidin-3-yl)-1,3-dioxoisoindolin-5-yl)piperazine-1-carbonyl)cyclohexane-1-carboxylic acid (9.4 mg, 0.018 mmol), and DIPEA (10.7 μL, 0.062 mmol) in DMF. The reaction mixture was stirred at room temperature for 16 hours, then the crude mixture was purified by reverse phase HPLC to afford the title compound (TFA salt) as an off-white solid (10.4 mg, 62% yield). LCMS: [C61H68FN11O7], desired mass=1085.5, found: m/z=1086.9 $[M+H]^+$. $^1$H NMR (500 MHz, DMSO) δ 11.09 (s, 1H), 9.31 (d, J=8.8 Hz, 1H), 8.77 (s, 1H), 8.42 (s, 1H), 7.89 (s, 1H), 7.71 (dd, J=14.7, 8.1 Hz, 2H), 7.56 (t, J=6.4 Hz, 2H), 7.48 (s, 1H), 7.39-7.29 (m, 2H), 7.25 (dtd, J=13.5, 7.8, 3.0 Hz, 3H), 5.32 (p, J=6.7 Hz, 2H), 5.09 (dd, J=12.7, 5.5 Hz, 1H), 4.09 (p, J=8.4 Hz, 2H), 3.76-3.72 (m, 5H), 3.62 (d, J=6.2 Hz, 6H), 3.52 (d, J=7.8 Hz, 2H), 3.48 (s, 3H), 2.94-2.82 (m, 5H), 2.76-2.69 (m, 4H), 2.64-2.57 (m, 2H), 2.04 (dd, J=11.1, 5.6 Hz, 2H), 1.89 (d, J=13.8 Hz, 2H), 1.75 (d, J=15.4 Hz, 5H), 1.68 (s, 2H), 1.61 (d, J=6.5 Hz, 6H), 1.57-1.54 (m, 1H), 1.53 (s, 2H), 1.44 (d, J=12.9 Hz, 1H).

Example 32

(3RS)-3-(6-{4-[(3S)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]piperidin-1-yl}pyridin-3-yl)piperidine-2,6-dione

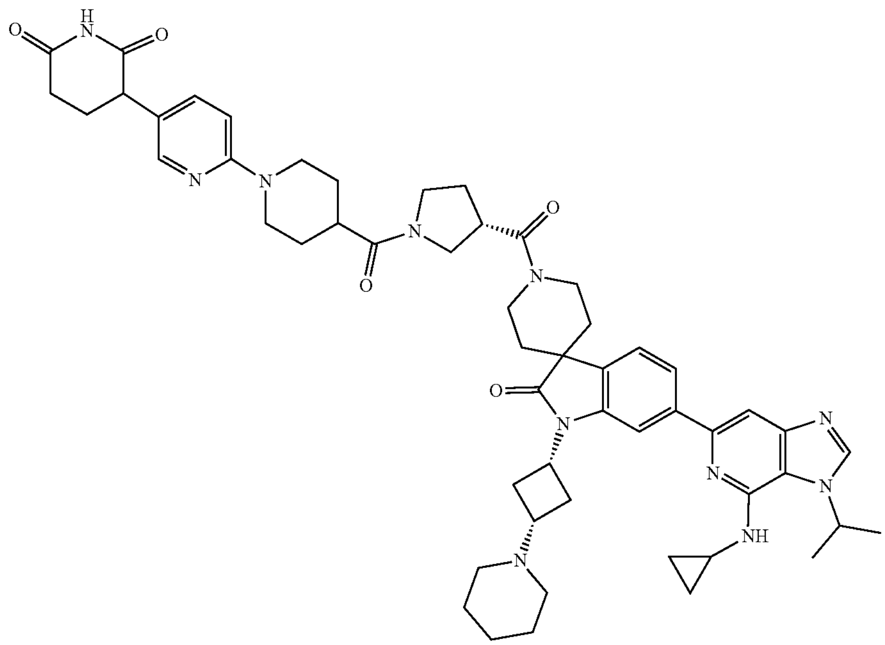 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)C5CCN(c6ccc(C7CCC(=O)NC7=O)cn6)CC5)C4)CC3)nc(NC3CC3)c21]

Example 32 was prepared by similar procedures as Example 1 using (3S)-1-(1-(5-(2,6-dioxopiperidin-3-yl)pyridin-2-yl)piperidine-4-carbonyl)pyrrolidine-3-carboxylic acid (intermediate 16) (10 mg, 0.024 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (13 mg, 0.024 mmol) as starting materials. The title compound (TFA salt) was isolated as an off-white solid (6.7 mg, 29% yield). LCMS: [$C_{54}H7N_{11}O_5$], desired mass=950.2, found: m/z=950.6 $[M+H]^+$, $^1H$ NMR (500 MHz, DMSO) δ 10.89 (s, 1H), 9.41 (s, 1H), 8.67 (s, 1H), 7.93 (s, 1H), 7.87 (s, 1H), 7.75 (s, 1H), 7.66 (d, J=2.9 Hz, 2H), 7.13 (s, 1H), 6.65 (s, 1H), 5.18-5.09 (m, 1H), 4.39 (s, 4H), 4.37-4.30 (m, 1H), 4.27 (d, J=12.6 Hz, 2H), 3.84 (s, 1H), 3.66-3.51 (m, 4H), 3.44 (dd, J=30.3, 9.4 Hz, 3H), 3.10-2.98 (m, 3H), 2.93 (d, J=8.6 Hz, 3H), 2.82 (t, J=11.2 Hz, 3H), 2.69 (td, J=12.6, 6.2 Hz, 1H), 2.61-2.53 (m, 1H), 2.32-2.19 (m, 1H), 2.16 (s, 2H), 1.99 (d, J=11.2 Hz, 1H), 1.85 (d, J=14.5 Hz, 5H), 1.74 (d, J=21.5 Hz, 5H), 1.63 (d, J=14.0 Hz, 4H), 1.53 (d, J=6.5 Hz, 6H), 1.48-1.37 (m, 1H), 0.84 (s, 2H), 0.64 (s, 2H).

Example 33

(3RS)-3-(6-{4-[(3S)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione

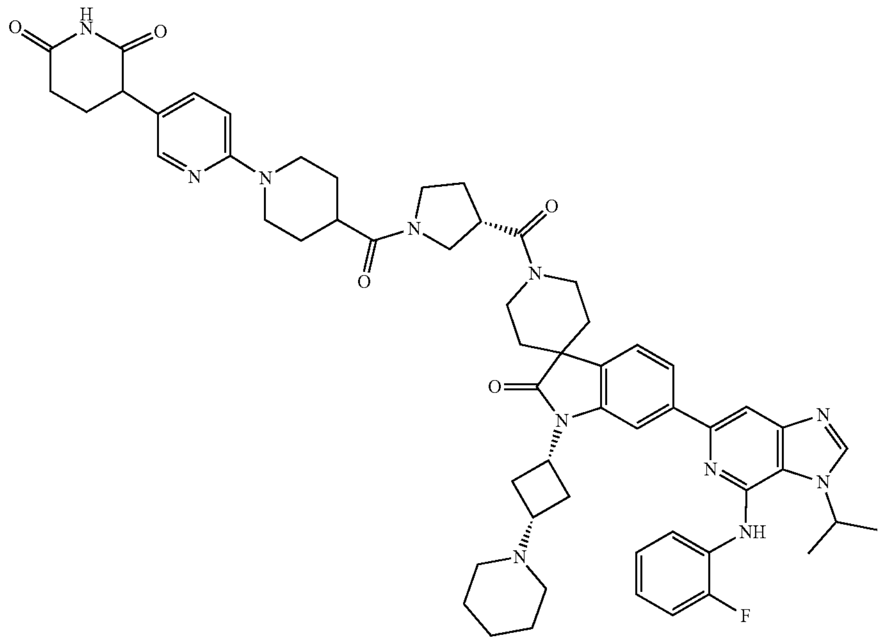 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)C5CCN(c6ccc(C7CCC(=O)NC7=O)cn6)CC5)C4)CC3)nc(Nc3ccccc3F)c21]

Example 33 was prepared by similar procedures as Example 1 using (3S)-1-(1-(5-(2,6-dioxopiperidin-3-yl)pyridin-2-yl)piperidine-4-carbonyl)pyrrolidine-3-carboxylic acid (intermediate 16) (10 mg, 0.024 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (15 mg, 0.024 mmol) as starting materials. The title compound (TFA salt) was isolated as an off-white solid (3.6 mg, 15% yield). LCMS: [$C_{57}H_{66}FN_{11}O_5$], desired mass=1004.2, found: m/z=1004.6 $[M+H]^+$, $^1$H NMR (500 MHz, DMSO) δ 10.89 (s, 1H), 9.34 (s, 1H), 8.63 (d, J=3.8 Hz, 1H), 8.36 (s, 1H), 7.91 (dd, J=10.8, 3.1 Hz, 2H), 7.70 (d, J=7.5 Hz, 1H), 7.67 (s, 1H), 7.62-7.52 (m, 2H), 7.50 (d, J=3.3 Hz, 1H), 7.32 (t, J=9.8 Hz, 1H), 7.22 (dt, J=9.7, 4.4 Hz, 2H), 5.29 (p, J=6.6 Hz, 1H), 4.26 (d, J=12.5 Hz, 2H), 4.10 (q, J=8.2 Hz, 1H), 3.85 (s, 3H), 3.38 (d, J=10.6 Hz, 3H), 3.08 (s, 2H), 2.96-2.87 (m, 1H), 2.85 (s, 6H), 2.74 (s, 3H), 2.69 (td, J=12.5, 6.3 Hz, 1H), 2.61-2.52 (m, 1H), 2.48 (s, 2H), 2.32-2.19 (m, 1H), 2.18-2.10 (m, 2H), 1.99 (d, J=11.7 Hz, 1H), 1.88 (d, J=14.1 Hz, 2H), 1.78 (s, 5H), 1.71 (s, 3H), 1.67 (m, 3H), 1.60 (d, J=6.6 Hz, 6H), 1.45 (t, J=12.8 Hz, 1H).

Example 34

(3RS)-3-(6-{4-[(3S)-3-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione

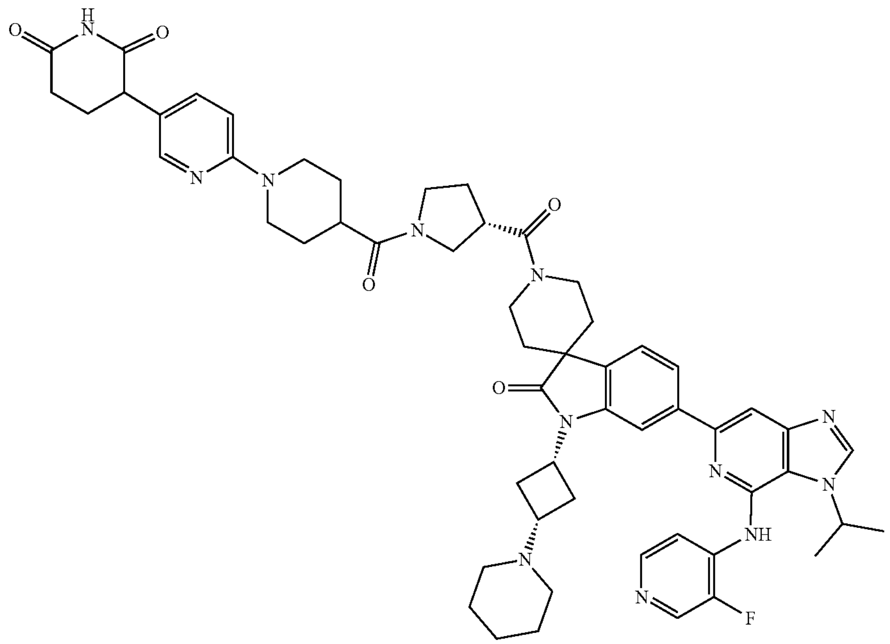 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)C5CCN(c6ccc(C7CCC(=O)NC7=O)cn6)CC5)C4)CC3)nc(Nc3ccncc3F)c21]

Example 34 was prepared by similar procedures as Example 1 using (3S)-1-(1-(5-(2,6-dioxopiperidin-3-yl)pyridin-2-yl)piperidine-4-carbonyl)pyrrolidine-3-carboxylic acid (intermediate 16) (10 mg, 0.024 mmol) and 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (15 mg, 0.024 mmol) as starting materials. The title compound (TFA salt) was isolated as an off-white solid (4.7 mg, 18% yield). LCMS: $[C_{56}H_{65}FN_{12}O_5]$, desired mass=1005.2, found: m/z=1005.6 $[M+H]^+$, $^1H$ NMR (500 MHz, DMSO) δ 10.89 (s, 1H), 10.03 (s, 1H), 9.40 (s, 1H), 8.74 (d, J=12.2 Hz, 2H), 8.39-8.26 (m, 2H), 7.93 (d, J=2.5 Hz, 1H), 7.79 (s, 1H), 7.63 (dt, J=20.5, 5.3 Hz, 2H), 7.12 (s, 1H), 5.20-5.12 (m, 1H), 4.28 (s, 3H), 4.25 (s, 1H), 3.95 (s, 2H), 3.89-3.75 (m, 2H), 3.06 (s, 4H), 2.99 (d, J=9.5 Hz, 1H), 2.84 (s, 6H), 2.69 (td, J=12.4, 6.1 Hz, 1H), 2.56 (d, J=12.9 Hz, 1H), 2.49 (s, 5H), 2.29-2.21 (m, 1H), 2.15 (s, 3H), 2.03-1.95 (m, 2H), 1.85 (t, J=15.8 Hz, 6H), 1.74 (s, 5H), 1.63 (d, J=6.6 Hz, 1H), 1.55 (dd, J=9.4, 6.7 Hz, 6H), 1.44 (s, 1H).

Example 35

2-[(3RS)-2,6-dioxopiperidin-3-yl]-4-{[(1R,4R)-4-[(3S)-3-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)pyrrolidine-1-carbonyl]cyclohexyl]amino}-2,3-dihydro-1H-isoindole-1,3-dione

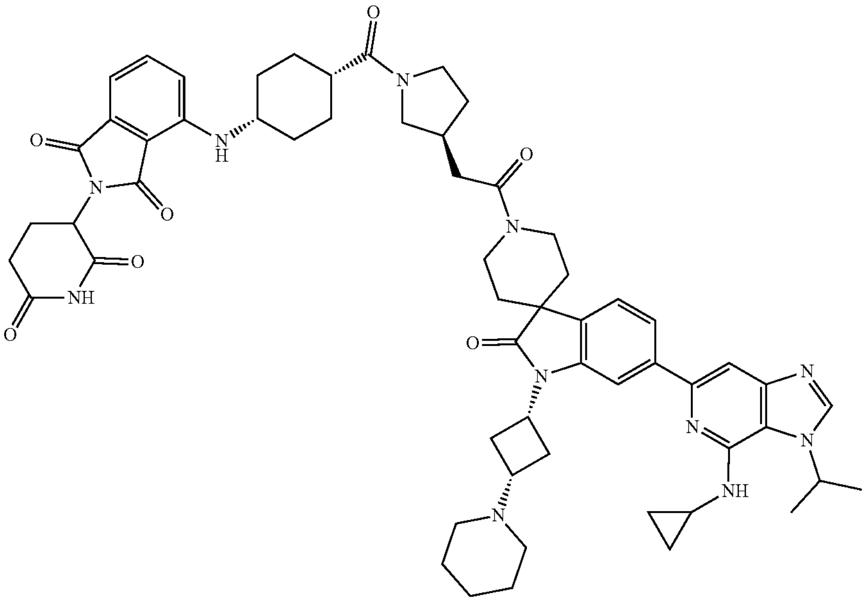 [SMILES: CC(C)n1cnc2cc(-c3ccc4c(c3)N([C@H]3C[C@@H](N5CCCCC5)C3)C(=O)C43CCN(C(=O)C[C@@H]4CCN(C(=O)[C@H]5CC[C@@H](Nc6cccc7c6C(=O)N(C6CCC(=O)NC6=O)C7=O)CC5)C4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 2-((3S)-1-((1s,4R)-4-((2-(2,6-dioxopiperidin-3-yl)-1,3-dioxoisoindolin-4-yl)amino)cyclohexane-1-carbonyl)pyrrolidin-3-yl)acetic acid (intermediate 17) as the coupling partners, the title compound (TFA salt) was isolated as an off-white solid (6.7 mg, 48% yield). LCMS: [C59H71N11O7], desired mass=1045.6, found: m/z=1046.7 $[M+H]^+$.

Example 36

4-fluoro-2-methyl-5-{[6-(2-oxo-1'-{1-[(1R,4R)-4-({2-[(3RS)-2,6-dioxopiperidin-3-yl]-1,3-dioxo-2,3-dihydro-1H-isoindol-4-yl}amino)cyclohexanecarbonyl]-1,2,3,6-tetrahydropyridine-4-carbonyl}-1-[(1S,3S)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide

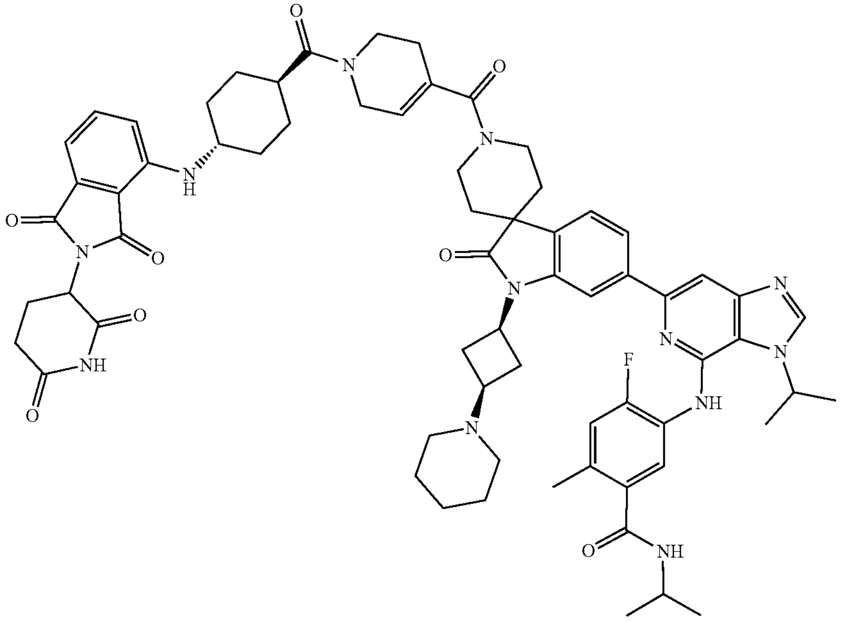 [SMILES: Cc1cc(F)c(Nc2nc(-c3ccc4c(c3)N([C@H]3C[C@@H](N5CCCCC5)C3)C(=O)C43CCN(C(=O)C4=CCN(C(=O)[C@H]5CC[C@H](Nc6cccc7c6C(=O)N(C6CCC(=O)NC6=O)C7=O)CC5)CC4)CC3)cc3ncn(C(C)C)c23)cc1C(=O)NC(C)C]

Step 1: 4-fluoro-N-isopropyl-5-((3-isopropyl-6-(2-oxo-1-((1s,3s)-3-(piperidin-1-yl)cyclobutyl)-1'-(1,2,3,6-tetrahydropyridine-4-carbonyl)spiro[indoline-3,4'-piperidin]-6-yl)-3H-imidazo[4,5-c]pyridin-4-yl)amino)-2-methylbenzamide hydrochloride To a mixture of 4-fluoro-N-isopropyl-5-[(3-isopropyl-6-{2-oxo-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide hydrochloride (33 mg, 0.044 mmol), 1-(tert-butoxycarbonyl)-3,6-dihydro-2H-pyridine-4-carboxylic acid (10 mg, 0.044 mmol), and DIPEA (31 μL, 0.18 mmol) in DMF (440 μL) was added BOP (22 mg, 0.051 mmol). The reaction mixture was stirred at room temperature for 16 hours, then concentrated in vacuo. The residue was diluted in DCM (300 μL), the HCl (4N solution in dioxane) was added. The reaction mixture was stirred for an additional 18 hours, then concentrated in vacuo to afford the title compound as a yellow oil which was used without further purification in the next step.

Step 2: 4-fluoro-2-methyl-5-{[6-(2-oxo-1'-{1-[(1r,4r)-4-({2-[(3RS)-2,6-dioxopiperidin-3-yl]-1,3-dioxo-2,3-dihydro-1H-isoindol-4-yl}amino)cyclohexanecarbonyl]-1,2,3,6-tetrahydropyridine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide Using procedures similar to those for Example 31 and using 4-fluoro-N-isopropyl-5-((3-isopropyl-6-(2-oxo-1-((1s,3s)-3-(piperidin-1-yl)cyclobutyl)-1'-(1,2,3,6-tetrahydropyridine-4-carbonyl)spiro[indoline-3,4'-piperidin]-6-yl)-3H-imidazo[4,5-c]pyridin-4-yl)amino)-2-methylbenzamide hydrochloride and (1r,4r)-4-((2-(2,6-dioxopiperidin-3-yl)-1,3-dioxoisoindolin-4-yl)amino)cyclohexane-1-carboxylic acid (step 1, Intermediate 17) as the coupling partners, the title compound (TFA salt) was isolated as an off-white solid (4.1 mg, 22% yield). LCMS: [$C67H77FN_{12}O_8$], desired mass=1196.6, found: m/z=1198.3 $[M+H]^+$.

Example 37

5-[(6-{1'-[1-(1-{2-[(3RS)-2,6-dioxopiperidin-3-yl]-1,3-dioxo-2,3-dihydro-1H-isoindol-5-yl}piperidine-4-carbonyl)-1,2,3,6-tetrahydropyridine-4-carbonyl]-2-oxo-1-[(1S,3S)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

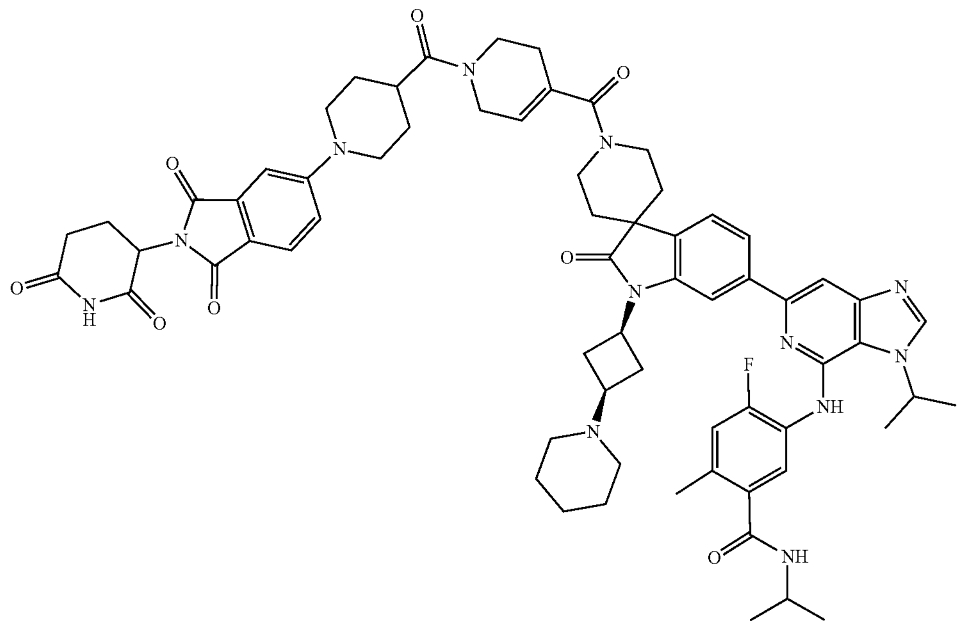 [SMILES: Cc1cc(F)c(Nc2nc(-c3ccc4c(c3)N([C@H]3C[C@@H](N5CCCCC5)C3)C(=O)C43CCN(C(=O)C4=CCN(C(=O)C5CCN(c6ccc7c(c6)C(=O)N(C6CCC(=O)NC6=O)C7=O)CC5)CC4)CC3)cc3ncn(C(C)C)c23)cc1C(=O)NC(C)C]

Using procedures similar to those for Example 36 and using 4-fluoro-N-isopropyl-5-((3-isopropyl-6-(2-oxo-1-((1s,3s)-3-(piperidin-1-yl)cyclobutyl)-1'-(1,2,3,6-tetrahydropyridine-4-carbonyl)spiro[indoline-3,4'-piperidin]-6-yl)-3H-imidazo[4,5-c]pyridin-4-yl)amino)-2-methylbenzamide hydrochloride and 1-(2-(2,6-dioxopiperidin-3-yl)-1,3-dioxoisoindolin-5-yl)piperidine-4-carboxylic acid (intermediate 18) as the coupling partners in the final step, the title compound (TFA salt) was isolated as an off-white solid (6.2 mg, 35% yield). LCMS: [C66H75FN12O8], desired mass=1182.6, found: m/z=1183.3 $[M+H]^+$.

Example 38

(3RS)-3-(6-{4-[6-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione

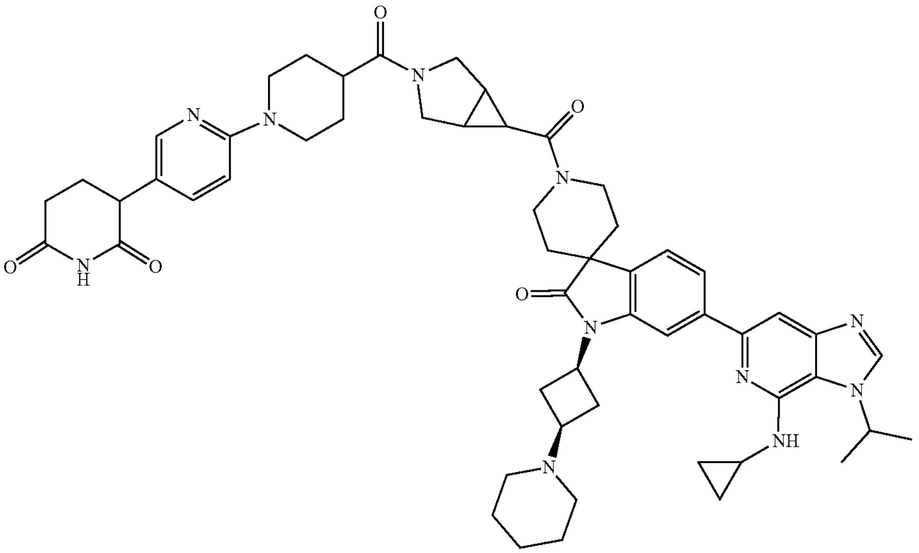 [SMILES: CC(C)n1cnc2cc(-c3ccc4c(c3)N([C@H]3C[C@@H](N5CCCCC5)C3)C(=O)C43CCN(C(=O)C4C5CN(C(=O)C6CCN(c7ccc(C8CCC(=O)NC8=O)cn7)CC6)CC54)CC3)nc(NC3CC3)c21]

Step 1: 1'-(3-azabicyclo[3.1.0]hexane-6-carbonyl)-6-(4-(cyclopropylamino)-3-isopropyl-3h-imidazo[4,5-c]pyridin-6-yl)-1-((1s,3s)-3-(piperidin-1-yl)cyclobutyl)spiro[indoline-3,4'-piperidin]-2-one

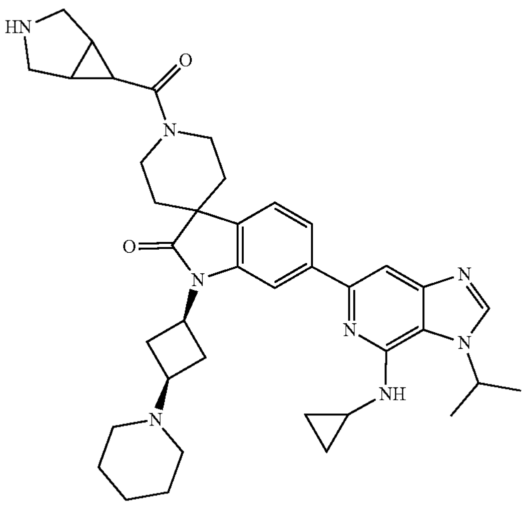 [SMILES: CC(C)n1cnc2cc(-c3ccc4c(c3)N([C@H]3C[C@@H](N5CCCCC5)C3)C(=O)C43CCN(C(=O)C4C5CNCC54)CC3)nc(NC3CC3)c21]

Step 2: tert-butyl 4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carboxylate

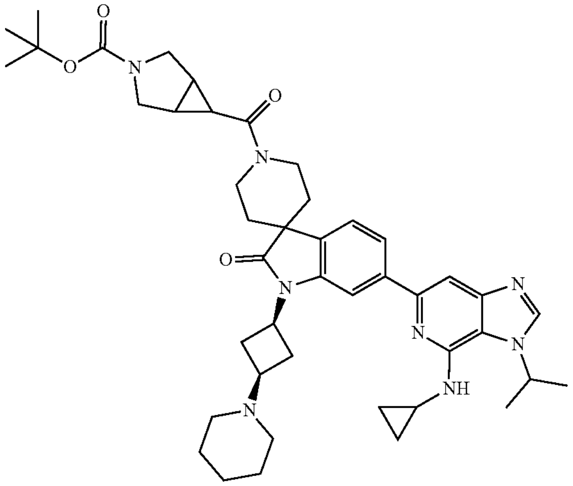 [SMILES: CC(C)n1cnc2cc(-c3ccc4c(c3)N([C@H]3C[C@@H](N5CCCCC5)C3)C(=O)C43CCN(C(=O)C4C5CN(C(=O)OC(C)(C)C)CC54)CC3)nc(NC3CC3)c21]

Prepared by similar procedures as Intermediate 5 (step 1) using 3-(2-(tert-butoxy)acetyl)-3-azabicyclo[3.1.0]hexane-6-carboxylic acid (10 mg, 0.043 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (20 mg, 0.036 mmol) as starting materials. The title compound (TFA salt) was isolated as an off-white solid (20 mg, 70% yield). LCMS: [$C_{44}H_{58}N_8O_4$], desired mass=763.0, found: m/z=763.6 [M+H]$^+$.

Step 3: 1'-(3-azabicyclo[3.1.0]hexane-6-carbonyl)-6-(4-(cyclopropylamino)-3-isopropyl-3h-imidazo[4,5-c]pyridin-6-yl)-1-((1s,3s)-3-(piperidin-1-yl)cyclobutyl)spiro[indoline-3,4'-piperidin]-2-one

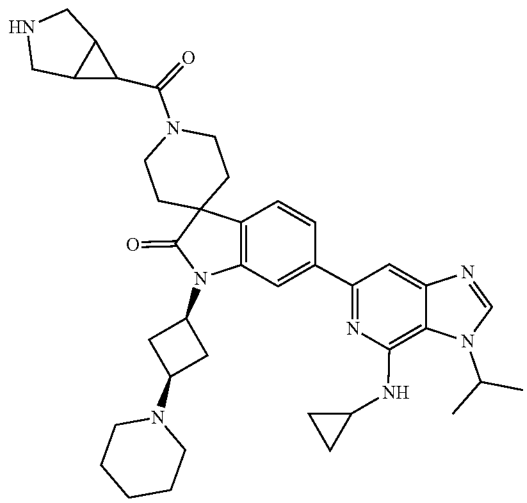 [SMILES: CC(C)n1cnc2cc(-c3ccc4c(c3)N([C@H]3C[C@@H](N5CCCCC5)C3)C(=O)C43CCN(C(=O)C4C5CNCC54)CC3)nc(NC3CC3)c21]

Prepared by similar procedures as Intermediate 5 (step 2) using tert-butyl 4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carboxylate (20 mg, 0.026 mmol) as starting materials. The title compound (TFA salt) was isolated as an off-white solid (16 mg, 96% yield). LCMS: [$C_{39}H_{50}N_8O_2$], desired mass=662.9, found: m/z=663.4 [M+H]$^+$.

Step 4

Example 38 was prepared by similar procedures as Example 1 using 1'-(3-azabicyclo[3.1.0]hexane-6-carbonyl)-6-(4-(cyclopropylamino)-3-isopropyl-3h-imidazo[4,5-c]pyridin-6-yl)-1-((1s,3s)-3-(piperidin-1-yl)cyclobutyl) spiro[indoline-3,4'-piperidin]-2-one (16 mg, 0.024 mmol) and 1-(5-(2,6-dioxopiperidin-3-yl)pyridin-2-yl)piperidine-4-carboxylic acid (prepared in step 2 of intermediate 11) (8 mg, 0.024 mmol) as starting materials. The title compound (TFA salt) was isolated as an off-white solid (14 mg, 556). LCMS: [$C_{55}H_{67}N_{11}O_5$], desired mass=962.2, found: m/z=962.7 [M+H]$^+$.

Example 39

(3RS)-3-[6-(4-{6-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-3-azabicyclo[3.1.0]hexane-3-carbonyl}piperidin-1-yl)pyridin-3-yl]piperidine-2,6-dione

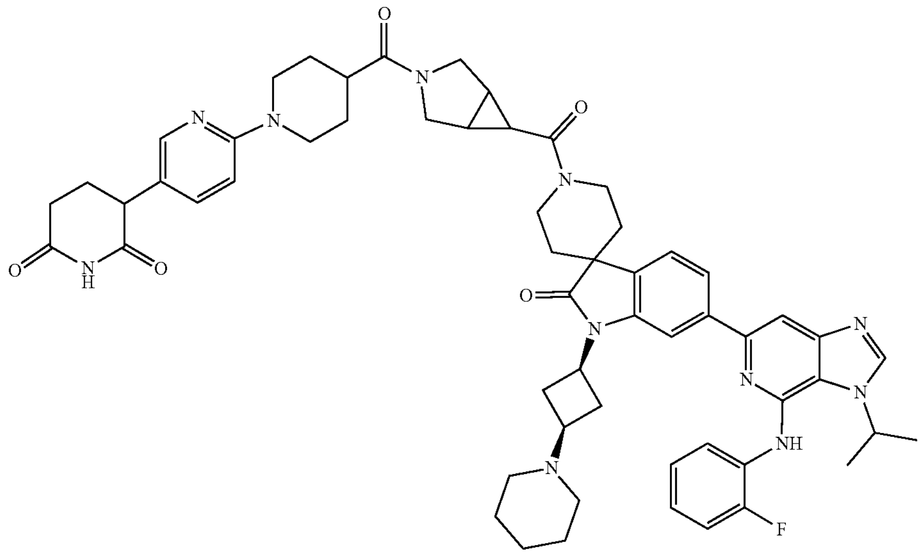 [SMILES: CC(C)n1cnc2cc(-c3ccc4c(c3)N([C@H]3C[C@@H](N5CCCCC5)C3)C(=O)C43CCN(C(=O)C4C5CN(C(=O)C6CCN(c7ccc(C8CCC(=O)NC8=O)cn7)CC6)CC54)CC3)nc(Nc3ccccc3F)c21]

Step 1: tert-butyl 4-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carboxylate

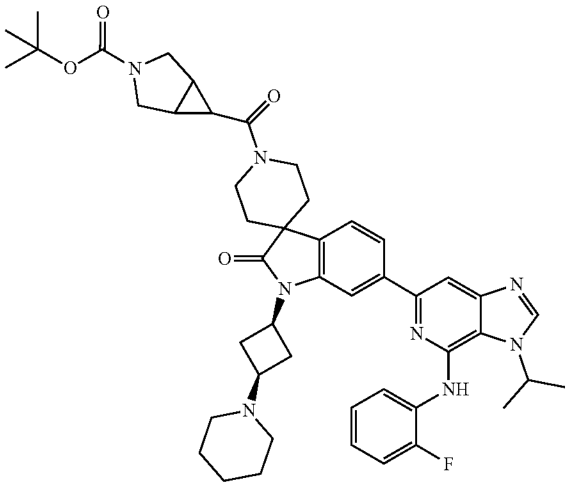 [SMILES: CC(C)n1cnc2cc(-c3ccc4c(c3)N([C@H]3C[C@@H](N5CCCCC5)C3)C(=O)C43CCN(C(=O)C4C5CN(C(=O)OC(C)(C)C)CC54)CC3)nc(Nc3ccccc3F)c21]

Prepared by similar procedures as Intermediate 5 (step 1) using 3-(tert-butoxycarbonyl)-3-azabicyclo[3.1.0]hexane-6-carboxylic acid (9.7 mg, 0.043 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (20 mg, 0.033 mmol) as starting materials. The title compound (TFA salt) was isolated as an off-white solid (22 mg, 82% yield). LCMS: $[C_{47}H_{57}FN_8O_4]$, desired mass=817.0, found: m/z=817.7 $[M+H]^+$.

Step 2: 1'-(3-azabicyclo[3.1.0]hexane-6-carbonyl)-6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one

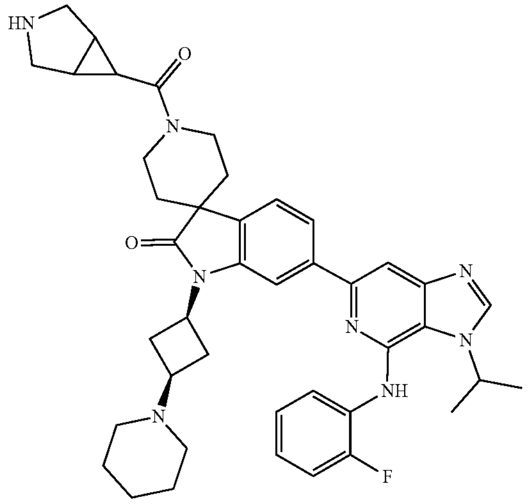 [SMILES: CC(C)n1cnc2cc(-c3ccc4c(c3)N([C@H]3C[C@@H](N5CCCCC5)C3)C(=O)C43CCN(C(=O)C4C5CNCC54)CC3)nc(Nc3ccccc3F)c21]

Prepared by similar procedures as Intermediate 5 (step 1) using tert-butyl 4-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carboxylate (22 mg, 0.027 mmol) as starting materials. The title compound (TFA salt) was isolated as an off-white solid (18 mg, 93% yield). LCMS: $[C_{42}H_{49}FN_8O_2]$, desired mass=716.9, found: m/z=717.4 $[M+H]^+$.

Step 3

Example 39 was prepared by similar procedures as Example 1 using 1'-(3-azabicyclo[3.1.0]hexane-6-carbonyl)-6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (18 mg, 0.025 mmol) and 1-(5-(2,6-dioxopiperidin-3-yl)pyridin-2-yl)piperidine-4-carboxylic acid (prepared in step 2 of intermediate 11) (8 mg, 0.025 mmol) as starting materials. The title compound (TFA salt) was isolated as an off-white solid (16 mg, 61% yield). LCMS: $[C_{58}H_{66}FN_{11}O_5]$, desired mass=1016.2, found: m/z=1016.7 $[M+H]^+$, $^1$H NMR (500 MHz, DMSO) δ 10.90 (s, 1H), 9.32 (s, 1H), 8.67 (s, 1H), 8.38 (s, 1H), 7.90 (s, 2H), 7.70 (d, J=7.9 Hz, 2H), 7.57 (td, J=7.3, 2.9 Hz, 2H), 7.49 (s, 1H), 7.37-7.28 (m, 1H), 7.23 (dt, J=9.6, 4.2 Hz, 2H), 5.34-5.26 (m, 1H), 4.22 (d, J=13.1 Hz, 4H), 4.09 (t, J=8.3 Hz, 1H), 3.84 (d, J=10.6 Hz, 3H), 3.77 (s, 4H), 3.68 (d, J=12.0 Hz, 1H), 3.54-3.46 (m, 1H), 3.08 (s, 2H), 2.95 (d, J=8.9 Hz, 1H), 2.88 (q, J=12.6, 12.0 Hz, 2H), 2.75-2.64 (m, 1H), 2.58 (s, 1H), 2.25 (d, J=13.1 Hz, 1H), 2.07-1.94 (m, 2H), 1.88 (d, J=10.0 Hz, 3H), 1.81 (s, 5H), 1.79-1.67 (m, 4H), 1.64-1.51 (m, 11H), 1.43 (d, J=15.2 Hz, 1H).

Example 40

(3RS)-3-[4-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]benzoyl}piperazin-1-yl)phenyl]piperidine-2,6-dione

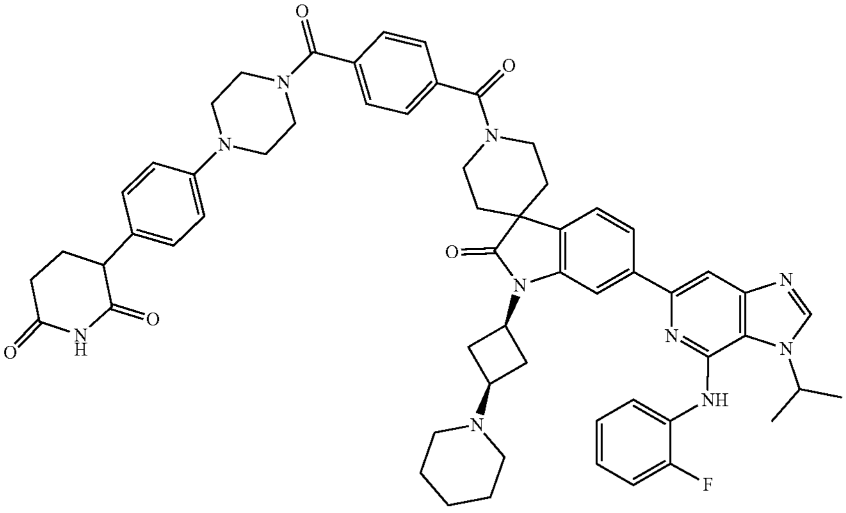 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc(C7CCC(=O)NC7=O)cc6)CC5)cc4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 4-(4-(4-(2,6-dioxopiperidin-3-yl)phenyl)piperazine-1-carbonyl)benzoic acid (intermediate 19) as the coupling partners, the title compound (TFA salt) was isolated as an off-white solid (10 mg, 58% yield). LCMS: [C59H63FN10O5], desired mass=1010.5, found: m/z=1011.7 $[M+H]^+$.

Example 41

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]benzoyl}piperazin-1-yl)-2,3-dihydro-1H-isoindole-1,3-dione

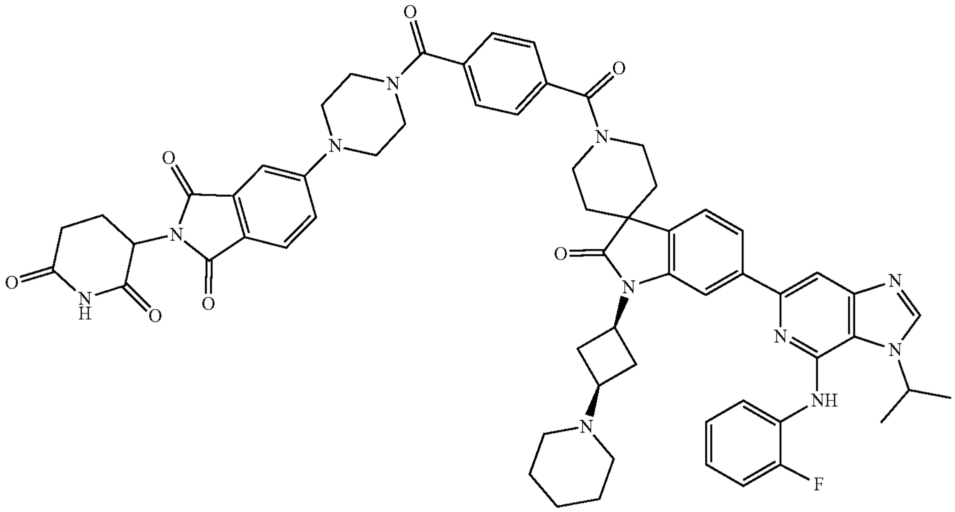 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)cc4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 4-(4-(2-(2,6-dioxopiperidin-3-yl)-1,3-dioxoisoindolin-5-yl)piperazine-1-carbonyl)benzoic acid (intermediate 20) as the coupling partners, the title compound (TFA salt) was isolated as an off-white solid (7.4 mg, 41% yield). LCMS: [C61H62FN11O7], desired mass=1079.5, found: m/z=1080.4 [M+H]$^+$.

Example 42

2-[(3RS)-2,6-dioxopiperidin-3-yl]-5-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]benzoyl}piperazin-1-yl)-2,3-dihydro-1H-isoindole-1,3-dione

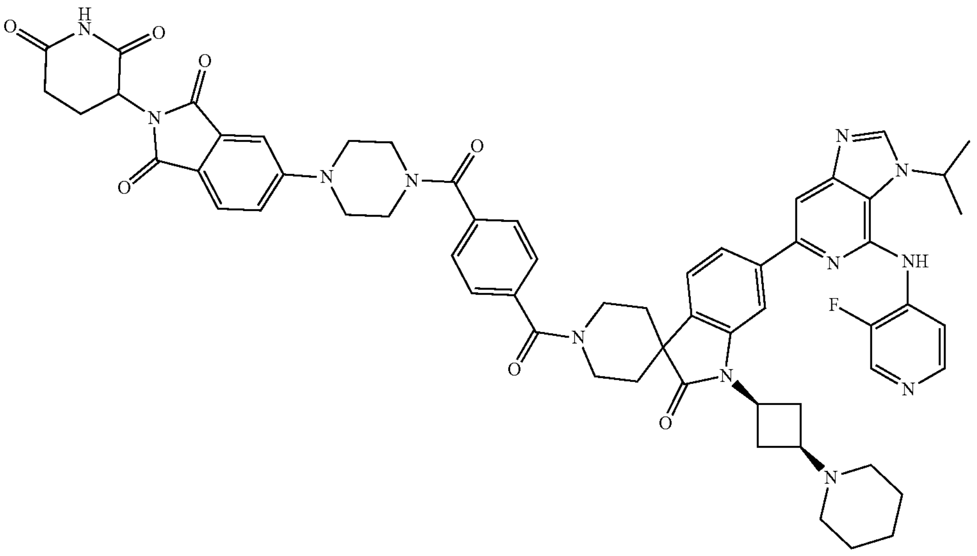 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)cc4)CC3)nc(Nc3ccncc3F)c21]

Example 42 was prepared by similar procedures as Example 1 using 4-(4-(2-(2,6-dioxopiperidin-3-yl)-1,3-dioxoisoindolin-5-yl)piperazine-1-carbonyl)benzoic acid (intermediate 21) (9 mg, 0.018 mmol) and 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as a yellow solid (8.8 mg, 49% yield). LCMS: [$C_{60}H_{61}FN_{12}O_7$], desired mass=1081.1, found: m/z=1082.0 [M+H]$^+$.

Example 43

4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-N-(1-{2-[(3RS)-2,6-dioxopiperidin-3-yl]-1,3-dioxo-2,3-dihydro-1H-isoindol-5-yl}piperidin-4-yl)benzamide

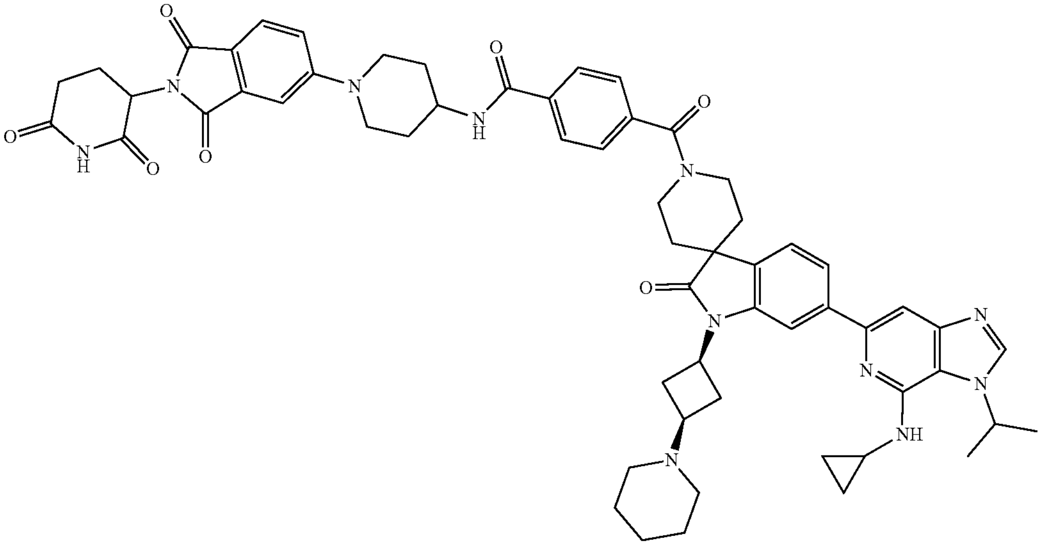 [SMILES: CC(C)n1cnc2cc(-c3ccc4c(c3)N([C@H]3C[C@@H](N5CCCCC5)C3)C(=O)C43CCN(C(=O)c4ccc(C(=O)NC5CCN(c6ccc7c(c6)C(=O)N(C6CCC(=O)NC6=O)C7=O)CC5)cc4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 4-((1-(2-(2,6-dioxopiperidin-3-yl)-1,3-dioxoisoindolin-5-yl)piperidin-4-yl)carbamoyl)benzoic acid (intermediate 22) as the coupling partners, the title compound (TFA salt) was isolated as an off-white solid (8.4 mg, 41% yield). LCMS: [C59H65N11O7], desired mass=1039.5, found: m/z=1040.3 $[M+H]^+$. $^1$H NMR (500 MHz, MeOD) δ 8.95 (s, 1H), 7.99-7.94 (m, 2H), 7.75-7.65 (m, 3H), 7.63 (dd, J=9.2, 7.5 Hz, 3H), 7.56 (s, 1H), 7.41 (d, J=2.3 Hz, 1H), 7.29 (dd, J=8.6, 2.4 Hz, 1H), 5.18-5.06 (m, 2H), 4.49 (p, J=8.3 Hz, 1H), 4.35 (s, 1H), 4.27-4.19 (m, 1H), 4.12 (t, J=15.7 Hz, 3H), 4.01 (s, 1H), 3.74 (s, 1H), 3.67-3.54 (m, 4H), 3.22 (s, 4H), 3.18 (d, J=13.1 Hz, 1H), 3.07 (tt, J=6.9, 3.7 Hz, 1H), 3.00 (s, 2H), 2.94-2.83 (m, 4H), 2.81-2.67 (m, 2H), 2.16-2.08 (m, 3H), 2.07-1.98 (m, 4H), 1.90 (d, J=15.9 Hz, 1H), 1.83-1.72 (m, 3H), 1.69 (d, J=6.5 Hz, 7H), 1.14 (dd, J=7.1, 5.1 Hz, 2H), 0.98-0.93 (m, 2H).

Example 44

4-({6-[4-(cyclopropylamino)-3-(propan-2-yl)-3H-imidazo[4,5-c]pyridin-6-yl]-2-oxo-1-{[(1S,3S)-3-(piperidin-1-yl)cyclobutyl]-1,2-dihydrospiro[indole-3,4'-piperidin]-1'-yl}carbonyl)-N-(1-{2-[(3RS)-2,6-dioxopiperidin-3-yl]-1,3-dioxo-2,3-dihydro-1H-isoindol-5-yl}piperidin-4-yl)benzamide

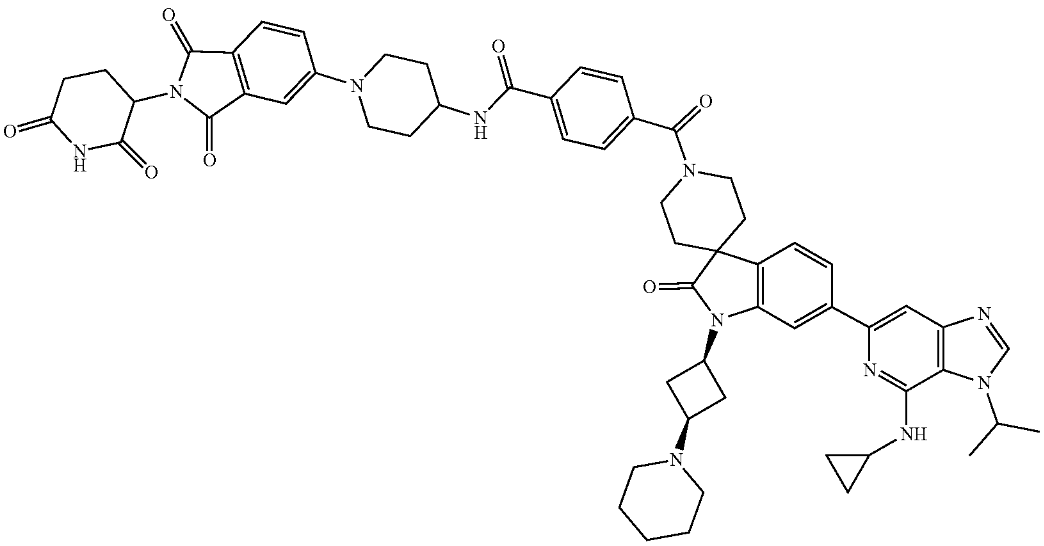 [SMILES: CC(C)n1cnc2cc(-c3ccc4c(c3)N([C@H]3C[C@@H](N5CCCCC5)C3)C(=O)C43CCN(C(=O)c4ccc(C(=O)NC5CCN(c6ccc7c(c6)C(=O)N(C6CCC(=O)NC6=O)C7=O)CC5)cc4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl) spiro[indoline-3,4'-piperidin]-2-one hydrochloride and 4-((1-(2-(2,6-dioxopiperidin-3-yl)-1,3-dioxoisoindolin-5-yl)piperidin-4-yl)carbamoyl)benzoic acid (intermediate 22) as the coupling partners, the title compound (TFA salt) was isolated as an off-white solid (8.4 mg, 41% yield). LCMS: [C59H65N11O7], desired mass=1039.5, found: m/z=1040.3 $[M+H]^+$. $^1$H NMR (500 MHz, MeOD) δ 8.95 (s, 1H), 7.99-7.94 (m, 2H), 7.75-7.65 (m, 3H), 7.63 (dd, J=9.2, 7.5 Hz, 3H), 7.56 (s, 1H), 7.41 (d, J=2.3 Hz, 1H), 7.29 (dd, J=8.6, 2.4 Hz, 1H), 5.18-5.06 (m, 2H), 4.49 (p, J=8.3 Hz, 1H), 4.35 (s, 1H), 4.27-4.19 (m, 1H), 4.12 (t, J=15.7 Hz, 3H), 4.01 (s, 1H), 3.74 (s, 1H), 3.67-3.54 (m, 4H), 3.22 (s, 4H), 3.18 (d, J=13.1 Hz, 1H), 3.07 (tt, J=6.9, 3.7 Hz, 1H), 3.00 (s, 2H), 2.94-2.83 (m, 4H), 2.81-2.67 (m, 2H), 2.16-2.08 (m, 3H), 2.07-1.98 (m, 4H), 1.90 (d, J=15.9 Hz, 1H), 1.83-1.72 (m, 3H), 1.69 (d, J=6.5 Hz, 7H), 1.14 (dd, J=7.1, 5.1 Hz, 2H), 0.98-0.93 (m, 2H).

Example 45

2-[(3RS)-2,6-dioxopiperidin-3-yl]-5-(4-{5-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyridine-2-carbonyl}piperazin-1-yl)-2,3-dihydro-1H-isoindole-1,3-dione

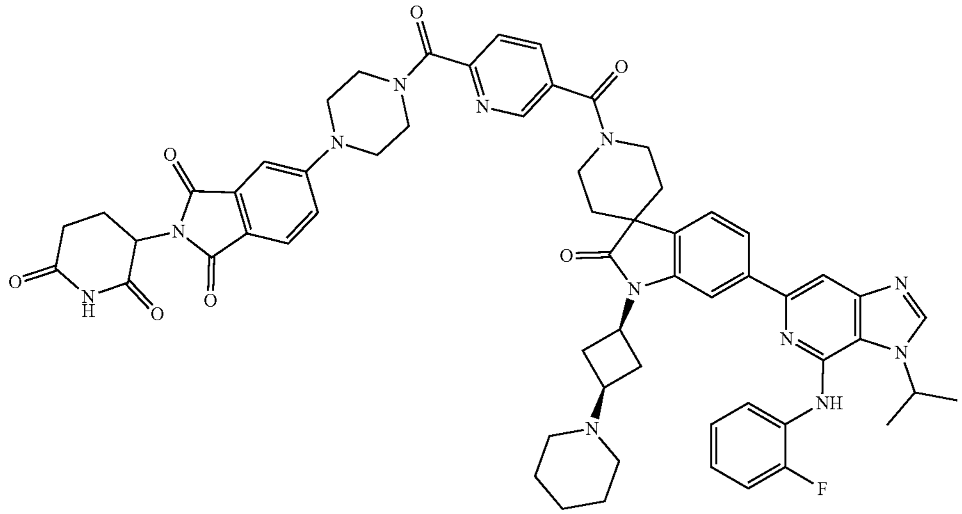 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)nc4)CC3)nc(Nc3ccccc3F)c21]

Using procedures similar to those for Example 27 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (intermediate 23) as the coupling partners, the title compound (TFA salt) was isolated as an off-white solid (11 mg, 46% yield). LCMS: [$C_{60}H_{61}FN_{12}O_7$], desired mass=1080.5, found: m/z=1081.8 $[M+H]^+$. $^1H$ NMR (500 MHz, MeOD) δ 9.15 (s, 1H), 8.80 (d, J=1.9 Hz, 1H), 8.14 (dd, J=7.9, 2.1 Hz, 1H), 7.84-7.66 (m, 5H), 7.60 (s, 2H), 7.59 (d, J=5.4 Hz, 1H), 7.41 (d, J=2.3 Hz, 1H), 7.31 (s, 1H), 7.35-7.26 (m, 3H), 5.39 (p, J=6.6 Hz, 1H), 5.10 (dd, J=12.4, 5.5 Hz, 1H), 4.31 (s, 1H), 4.23 (p, J=8.3 Hz, 1H), 4.13 (s, 1H), 3.99 (t, J=6.7 Hz, 2H), 3.81-3.76 (m, 3H), 3.67 (d, J=5.4 Hz, 2H), 3.60 (q, J=7.9 Hz, 1H), 3.57-3.52 (m, 5H), 3.07 (s, 3H), 2.94 (d, J=13.2 Hz, 2H), 2.91-2.83 (m, 4H), 2.81-2.67 (m, 3H), 2.13 (dd, J=10.1, 5.0 Hz, 1H), 2.04 (d, J=14.7 Hz, 3H), 1.92 (d, J=16.1 Hz, 1H), 1.77 (d, J=6.5 Hz, 8H), 1.59 (d, J=13.0 Hz, 1H).

Example 46

(3RS)-3-{2-{[(1R,4R)-4-({4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidin-1-yl}methyl) cyclohexanecarbonyl]-1,2,3,4-tetrahydroisoquinolin-6-yl}piperidine-2,6-dione

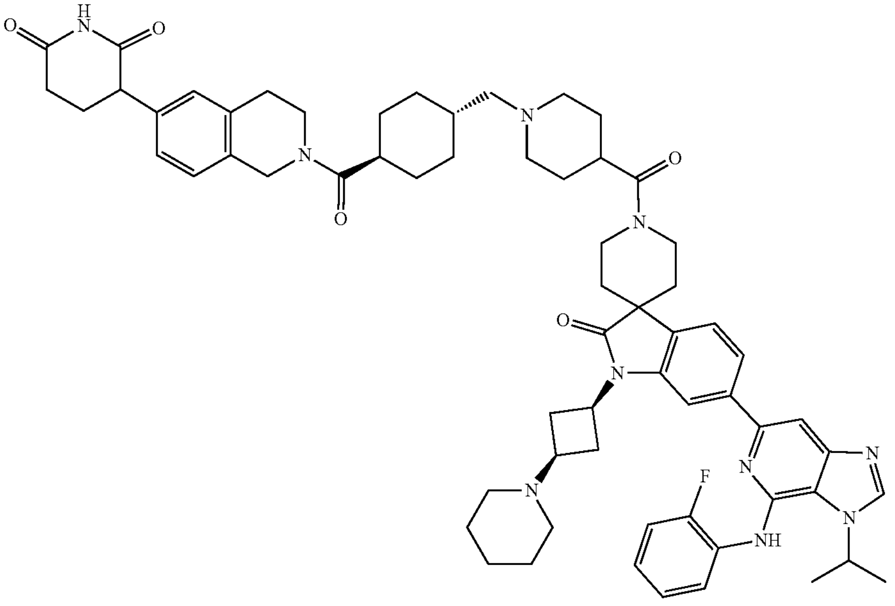 [SMILES: CC(C)n1cnc2cc(-c3ccc4c(c3)N([C@H]3C[C@@H](N5CCCCC5)C3)C(=O)C43CCN(C(=O)C4CCN(C[C@H]5CC[C@H](C(=O)N6CCc7cc(C8CCC(=O)NC8=O)ccc7C6)CC5)CC4)CC3)nc(Nc3ccccc3F)c21]

Step 1: 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro [indoline-3,4'-piperidin]-2-one hydrochloride Using procedures similar to those used to make 4-fluoro-N-isopropyl-5-((3-isopropyl-6-(2-oxo-1-((1s,3s)-3-(piperidin-1-yl)cyclobutyl)-1'-(1,2,3,6-tetrahydropyridine-4-carbonyl)spiro[indoline-3,4'-piperidin]-6-yl)-3H-imidazo[4,5-c]pyridin-4-yl)amino)-2-methylbenzamide hydrochloride (example 36, step 1), and using 6-(4-((2-fluorophenyl) amino)-3-isopropyl-3H-imidazo[4,5-c]pyridin-6-yl)-1-((1s, 3s)-3-(piperidin-1-yl)cyclobutyl)spiro[indoline-3,4'-piperidin]-2-one and 1-(tert-butoxycarbonyl)piperidine-4-carboxylic acid as the coupling partners, the title compound was obtained as an off-white solid that was used without purification in the next step.

Step 2: (3RS)-3-{2-[(1r,4r)-4-({4-[(6-{4-[(2-fluorophenyl)amino]-3-(propan-2-yl)-3H-imidazo[4,5-c] pyridin-6-yl}-2-oxo-1-[(1s,3s)-3-(piperidin-1-yl) cyclobutyl]-1,2-dihydrospiro[indole-3,4'-piperidin]-1'-yl)carbonyl]piperidin-1-yl}methyl) cyclohexanecarbonyl]-1,2,3,4-tetrahydroisoquinolin-6-yl}piperidine-2,6-dione Polymer supported cyanoborohydride (~2 mmol/g, 10 equiv, 50 mg) was added to a mixture of (1r,4r)-4-{6-[(3RS)-2,6-dioxopiperidin-3-yl]-3,4-dihydro-1H-isoquinoline-2-carbonyl}cyclohexane-1-carbaldehyde (intermediate 24) (4.00 mg, 0.01 mmol), 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride (6.32 mg, 0.01 mmol), triethylamine (14.50 μL, 0.01 g, 0.10 mmol), and DMSO (0.50 mL). The reaction mixture was stirred for 16 h at room temperature, then was filtered and the filtrate washed with ~5 mL of DCM and concentrated. 100 μL of TFA as added to the crude reaction mixture, and the mixture was purified by reverse phase flash chromatography (15.5 g C18 silica, 0-100% MeCN/water +0.1% TFA) to provide the title compound (TFA salt) as an off-white solid (3 mg, 21% yield). LCMS: [$C_{64}H_{77}FN_{10}O_5$], desired mass=1084.6, found: m/z=1085.8 $[M+H]^+$. $^1H$ NMR (500 MHz, DMSO) δ 10.82 (s, 1H), 9.31 (s, 1H), 8.58 (s, 1H), 8.33 (s, 1H), 7.89 (s, 1H), 7.69 (d, J=7.8 Hz, 1H), 7.59-7.45 (m, 3H), 7.35-7.26 (m, 1H), 7.25-7.12 (m, 3H), 7.04 (d, J=12.1 Hz, 2H), 5.34-5.22 (m, 1H), 4.70 (s, 1H), 4.58 (s, 1H), 4.13-4.05 (m, 1H), 3.67 (s, 1H), 3.57 (s, 2H), 3.00-2.92 (m, 3H), 2.90 (s, 3H), 2.85 (s, 2H), 2.72 (s, 5H), 2.18 (d, J=12.4 Hz, 1H), 1.94-1.84 (m, 3H), 1.82 (s, 2H), 1.78 (s, 1H), 1.73 (s, 3H), 1.58 (dd, J=6.6, 3.2 Hz, 6H), 1.44 (s, 3H), 1.10 (d, J=12.8 Hz, 2H).

Example 47

(3RS)-3-{6-[(3R)-3-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}pyrrolidin-1-yl]pyridin-3-yl}piperidine-2,6-dione

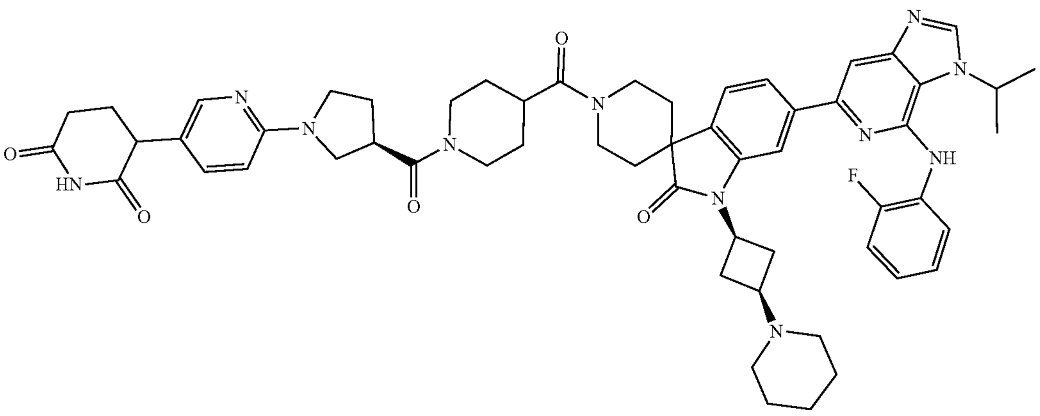 [SMILES: CC(C)n1cnc2cc(-c3ccc4c(c3)N([C@H]3C[C@@H](N5CCCCC5)C3)C(=O)C43CCN(C(=O)C4CCN(C(=O)[C@@H]5CCN(c6ccc(C7CCC(=O)NC7=O)cn6)C5)CC4)CC3)nc(Nc3ccccc3F)c21]

Step 1: 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one 1-(tert-butoxycarbonyl)piperidine-4-carboxylic acid (226.34 mg, 0.99 mmol) and (1,2,3-benzotriazol-1-yloxy)tris(dimethylamino)phosphanium, hexafluoro-lambda5-phosphanuide (473.01 mg, 1.07 mmol) were dissolved in dimethylformamide (1.00 mL) and N,N-diisopropylethylamine (0.57 mL, 425.31 mg, 3.29 mmol) and stirred at room temperature for 5 minutes. 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (500.00 mg, 0.82 mmol) was added and the reaction mixture was stirred for 2 hours at room temperature. The product was isolated by reverse phase flash column, then dissolved in DCM and treated with 1M HCl at room temperature. The reaction mixture was concentrated to afford the title compound as a pale yellow solid (420 mg, 71% yield).

Step 2

Using procedures similar to those used for Example 36 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one (15.00 mg, 0.02 mmol) and (3R)-1-(5-(2,6-dioxopiperidin-3-yl)pyridin-2-yl)pyrrolidine-3-carboxylic acid (intermediate 25) (6.33 mg, 0.02 mmol) as coupling partners afforded the title compound (TFA salt) as an off white solid (9.2 mg, 40% yield). LCMS: $C_{57}H_{66}FN_{11}O_5$ desired mass=1003.5, found: m/z=1005.0 $[M+H]^+$. $^1H$ NMR (500 MHz, DMSO-$d_6$) δ 10.95 (s, 1H), 9.36 (s, 1H), 8.61 (s, 1H), 8.36 (s, 1H), 7.90 (s, 1H), 7.88 (s, 1H), 7.70 (d, J=7.8 Hz, 1H), 7.56 (dd, J=8.0, 2.1 Hz, 1H), 7.50 (s, 1H), 7.32 (s, 1H), 7.22 (ddd, J=9.8, 5.9, 3.6 Hz, 2H), 5.28 (q, J=6.6 Hz, 1H), 4.42 (s, 1H), 4.14-4.06 (m, 2H), 3.95 (s, 1H), 3.87 (s, 3H), 3.51 (q, J=8.4 Hz, 1H), 3.38 (s, 2H), 3.19 (d, J=12.9 Hz, 1H), 3.04 (s, 1H), 2.95 (s, 2H), 2.92-2.79 (m, 2H), 2.74 (t, J=10.4 Hz, 6H), 2.61 (s, 1H), 2.59-2.47 (m, 3H), 2.31 (d, J=15.6 Hz, 3H), 2.13 (s, 1H), 2.00 (s, 1H), 1.89 (d, J=13.5 Hz, 2H), 1.78 (d, J=17.1 Hz, 4H), 1.69 (s, 6H), 1.66-1.56 (m, 7H), 1.45 (s, 3H), 1.25 (s, 1H).

Example 48

3-(2-((1R,4R)-4-(4-(6-(4-((2-fluorophenyl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidine-1-carbonyl)cyclohexane-1-carbonyl)-1,2,3,4-tetrahydroisoquinolin-6-yl)piperidine-2,6-dione

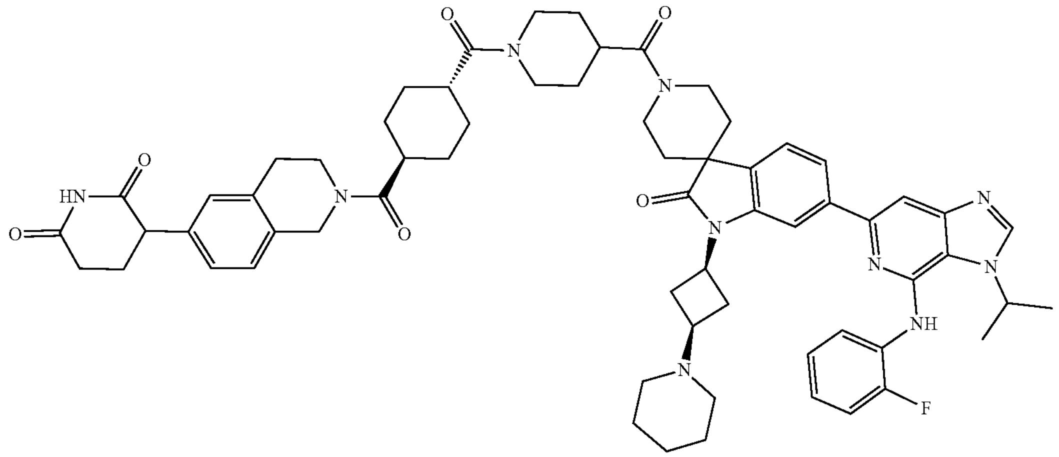 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](C(=O)N6CCc7cc(C8CCC(=O)NC8=O)ccc7C6)CC5)CC4)CC3)nc(Nc3ccccc3F)c21]

The title compound was synthesized using similar methods to Example 24, using BOP coupling. (White solid, 61 mg, 30% yield). LCMS: [$C_{64}H_{75}FN_{10}O_6$], desired mass=1099.3, found: m/z=1100.6 $[M+H]^+$. $^1H$ NMR (500 MHz, DMSO-$d_6$): δ (ppm): 10.79 (s, 1H), 9.29 (d, J=8.3 Hz, 1H), 8.57 (s, 1H), 8.31 (s, 1H), 7.87 (s, 1H), 7.67 (dd, J=7.9, 1.5 Hz, 1H), 7.55 (td, J=8.0, 7.9, 2.3 Hz, 2H), 7.48 (d, J=1.6 Hz, 1H), 7.29 (ddd, J=11.5, 7.5, 2.3 Hz, 1H), 7.22-7.15 (m, 3H), 7.12 (d, J=8.5 Hz, 1H), 7.02 (q, J=7.4, 7.4, 7.0 Hz, 2H), 5.26 (p, J=6.5, 6.5, 6.3, 6.3 Hz, 1H), 4.70 (s, 1H), 4.56 (s, 1H), 4.40 (d, J=11.5 Hz, 1H), 4.08 (p, J=9.1, 9.1, 9.1, 9.1 Hz, 2H), 4.01 (t, J=7.1, 7.1 Hz, 1H), 3.90 (s, 1H), 3.79 (dd, J=11.5, 5.0 Hz, 3H), 3.73 (d, J=6.1 Hz, 2H), 3.65 (s, 1H), 3.36 (s, 3H), 3.09 (s, 1H), 2.95 (d, J=14.3 Hz, 2H), 2.85-2.81 (m, 3H), 2.72 (s, 2H), 2.64-2.61 (m, 2H), 2.19-2.12 (m, 1H), 1.97 (s, 2H), 1.86 (d, J=14.1 Hz, 3H), 1.69 (q, J=26.6, 26.6, 22.9 Hz, 14H), 1.57 (d, J=6.6 Hz, 7H), 1.52-1.46 (m, 4H), 1.40 (s, 1H), 1.15 (d, J=7.1 Hz, 1H).

Example 49

1-{2-[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroisoquinolin-6-yl}-1,3-diazinane-2,4-dione

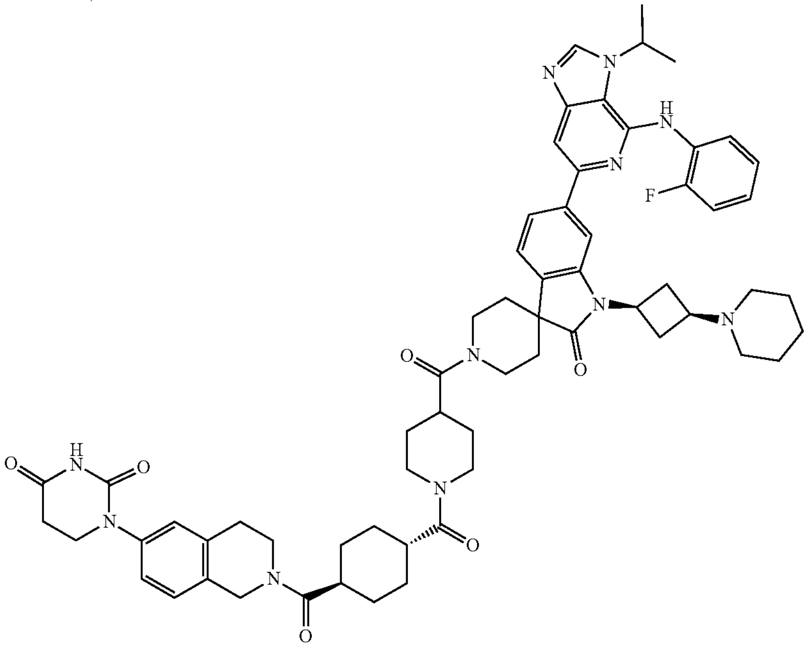 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](C(=O)N6CCc7cc(N8CCC(=O)NC8=O)ccc7C6)CC5)CC4)CC3)nc(Nc3ccccc3F)c21]

Using procedures similar to Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride (20 mg) and (1r,4r)-4-(6-(2,4-dioxotetrahydropyrimidin-1(2H)-yl)-1,2,3,4-tetrahydroisoquinoline-2-carbonyl)cyclohexane-1-carboxylic acid (intermediate 27) (15 mg) as the coupling partners, and HATU as the coupling reagent, the title compound (TFA salt) was isolated as a white solid (9 mg, 32% yield). LCMS: [$C_{63}H_{74}FN_{11}O_6$], desired mass=1099.6, found: m/z=1100.7 $[M+H]^+$. $^1$H NMR (500 MHz, DMSO) δ 10.82 (s, 1H), 9.31 (s, 1H), 8.58 (s, 1H), 8.33 (s, 1H), 7.89 (s, 1H), 7.69 (d, J=7.8 Hz, 1H), 7.59-7.45 (m, 3H), 7.35-7.26 (m, 1H), 7.25-7.12 (m, 3H), 7.04 (d, J=12.1 Hz, 2H), 5.34-5.22 (m, 1H), 4.70 (s, 1H), 4.58 (s, 1H), 4.13-4.05 (m, 1H), 3.67 (s, 1H), 3.57 (s, 2H), 3.00-2.92 (m, 3H), 2.90 (s, 3H), 2.85 (s, 2H), 2.72 (s, 5H), 2.18 (d, J=12.4 Hz, 1H), 1.94-1.84 (m, 3H), 1.82 (s, 2H), 1.78 (s, 1H), 1.73 (s, 3H), 1.58 (dd, J=6.6, 3.2 Hz, 6H), 1.44 (s, 3H), 1.10 (d, J=12.8 Hz, 2H).

Example 50

(3RS)-3-{2-[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroisoquinolin-7-yl}piperidine-2,6-dione

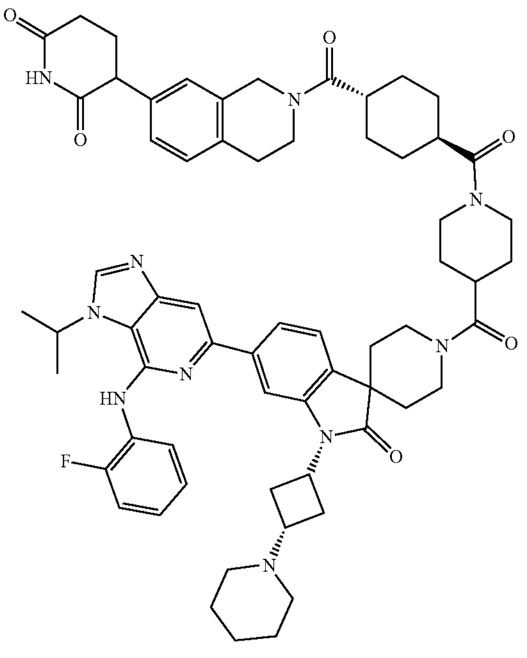

Using procedures similar to Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride and (1r,4r)-4-(7-(2,6-dioxopiperidin-3-yl)-1,2,3,4-tetrahydroisoquinoline-2-carbonyl)cyclohexane-1-carboxylic acid (intermediate 28) as the coupling partners, and HATU as the coupling reagent, the title compound (TFA salt) was isolated as an off-white solid. LCMS: [$C_{64}H_{75}FN_{10}O_6$], desired mass=1098.6, found: m/z=1099.4 $[M+H]^+$.

Example 51

(3RS)-3-{1-[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroquinolin-6-yl}piperidine-2,6-dione

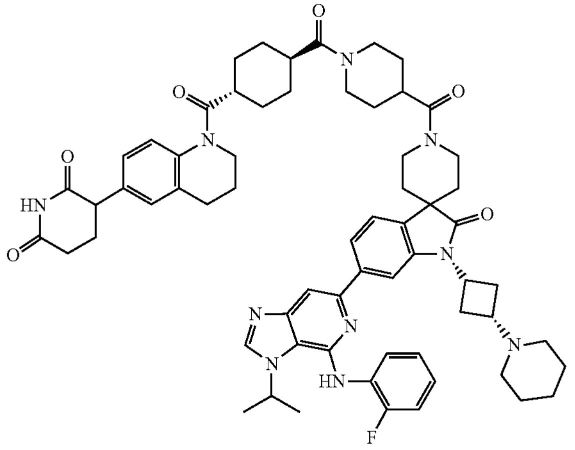

Using procedures similar to Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride and (1r,4r)-4-(6-(2,6-dioxopiperidin-3-yl)-1,2,3,4-tetrahydroquinoline-1-carbonyl)cyclohexane-1-carboxylic acid (intermediate 29) as the coupling partners, and HATU as the coupling reagent, the title compound (TFA salt) was isolated as an off-white solid. LCMS: [$C_{64}H_{75}FN_{10}O_6$], desired mass=1098.6, found: m/z=1099.3 $[M+H]^+$.

Example 52

(3RS)-3-(2-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-4-yl)piperidine-2,6-dione

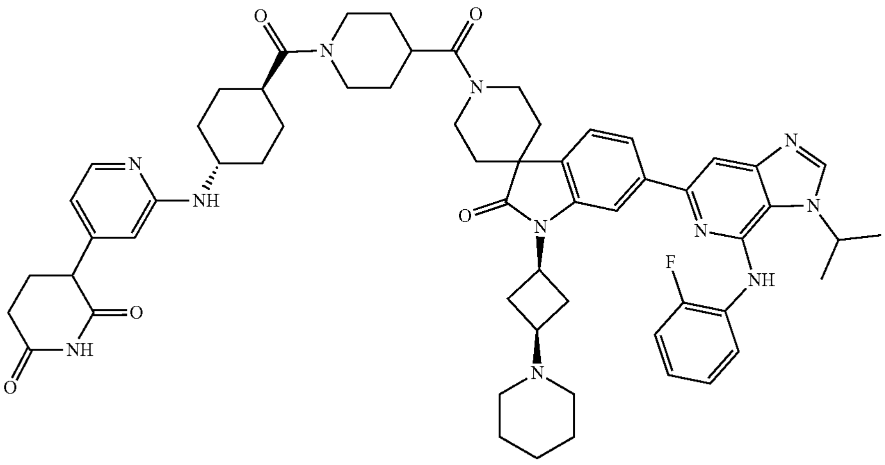 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6cc(C7CCC(=O)NC7=O)ccn6)CC5)CC4)CC3)nc(Nc3ccccc3F)c21]

Example 52 was prepared by similar procedures as Example 1 using 1-((1r,4r)-4-((4-(2,6-dioxopiperidin-3-yl)pyridin-2-yl)amino)cyclohexane-1-carbonyl)piperidine-4-carboxylic acid (intermediate 30) (7 mg, 0.016 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (4.2 mg, 26% yield). LCMS: [$C_{59}H_{70}FN_{11}O_5$], desired mass=1032.2, found: m/z=1032.8 $[M+H]^+$, $^1$H NMR (500 MHz, DMSO) δ 11.04 (s, 1H), 9.35 (s, 1H), 8.58 (s, 1H), 8.34 (s, 1H), 7.89 (d, J=8.0 Hz, 2H), 7.70 (d, J=7.7 Hz, 1H), 7.57 (td, J=7.8, 2.3 Hz, 1H), 7.53 (s, 1H), 7.50 (s, 1H), 7.32 (ddd, J=11.0, 7.8, 2.1 Hz, 1H), 7.27-7.16 (m, 2H), 6.89 (s, 1H), 6.79 (s, 1H), 5.28 (p, J=6.7 Hz, 1H), 4.42 (s, 1H), 4.10 (t, J=8.0 Hz, 1H), 4.03 (s, 3H), 3.93-3.78 (m, 4H), 3.13 (m, 1H), 3.06-2.82 (m, 4H), 2.75-2.53 (m, 3H), 2.47 (s, 1H), 2.27 (d, J=10.9 Hz, 1H), 2.12-1.99 (m, 1H), 1.89 (d, J=13.9 Hz, 3H), 1.77 (d, J=18.9 Hz, 12H), 1.59 (d, J=6.7 Hz, 6H), 1.44 (d, J=12.7 Hz, 1H), 1.39 (m, 5H).

Example 53

(3RS)-3-(4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]amino}phenyl)piperidine-2,6-dione

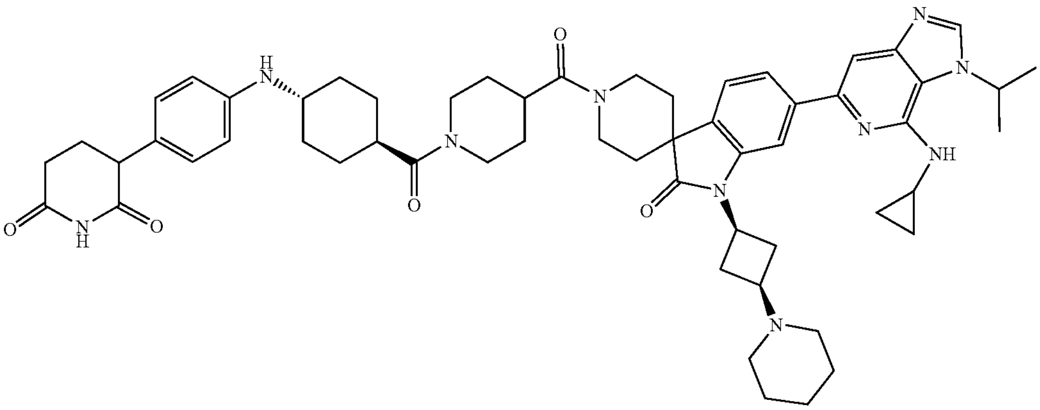 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6ccc(C7CCC(=O)NC7=O)cc6)CC5)CC4)CC3)nc(NC3CC3)c21]

Example 53 was prepared by similar procedures as Example 1 using 1-((1r,4r)-4-((4-(2,6-dioxopiperidin-3-yl)phenyl)amino)cyclohexane-1-carbonyl)piperidine-4-carboxylic acid (intermediate 31) (8 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (8.6 mg, 49% yield). LCMS: [$C_{57}H_{72}N_{12}O_5$], desired mass=977.2, found: m/z=978.6 $[M+H]^+$.

Example 54

(3RS)-3-(4-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}phenyl)piperidine-2,6-dione

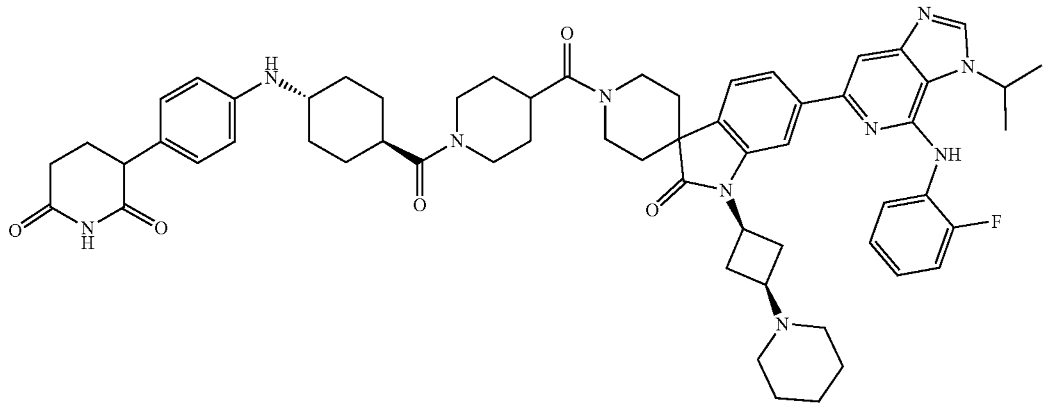 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6ccc(C7CCC(=O)NC7=O)cc6)CC5)CC4)CC3)nc(Nc3ccccc3F)c21]

Example 54 was prepared by similar procedures as Example 1 using 1-((1r,4r)-4-((4-(2,6-dioxopiperidin-3-yl)phenyl)amino)cyclohexane-1-carbonyl)piperidine-4-carboxylic acid (intermediate 31) (7 mg, 0.016 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (7 mg, 42% yield). LCMS: [$C_{60}H_{71}FN_{10}O_5$], desired mass=1031.2, found: m/z=1031.8 $[M+H]^+$, $^1H$ NMR (500 MHz, MeOD) δ 8.87 (s, 1H), 7.84-7.74 (m, 2H), 7.70 (t, J=7.7 Hz, 1H), 7.63 (s, 1H), 7.52 (d, J=7.9 Hz, 1H), 7.47 (d, J=8.0 Hz, 2H), 7.39-7.21 (m, 5H), 5.32 (s, 1H), 4.58 (s, 1H), 4.31-4.22 (m, 1H), 4.12 (s, 4H), 3.98 (dd, J=11.6, 5.1 Hz, 2H), 3.59 (t, J=8.3 Hz, 1H), 3.54 (s, 4H), 3.10 (d, J=11.8 Hz, 3H), 2.96 (dt, J=37.7, 11.1 Hz, 5H), 2.83-2.66 (m, 5H), 2.35-2.19 (m, 1H), 2.14 (s, 2H), 2.04 (d, J=13.5 Hz, 2H), 1.96-1.76 (m, 11H), 1.73 ((d, J=6.5 Hz, 6H), 1.59 (m, 3H), 1.31 (s, 2H).

Example 55

(3RS)-3-(4-{[(1R,4R)-4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}phenyl)piperidine-2,6-dione

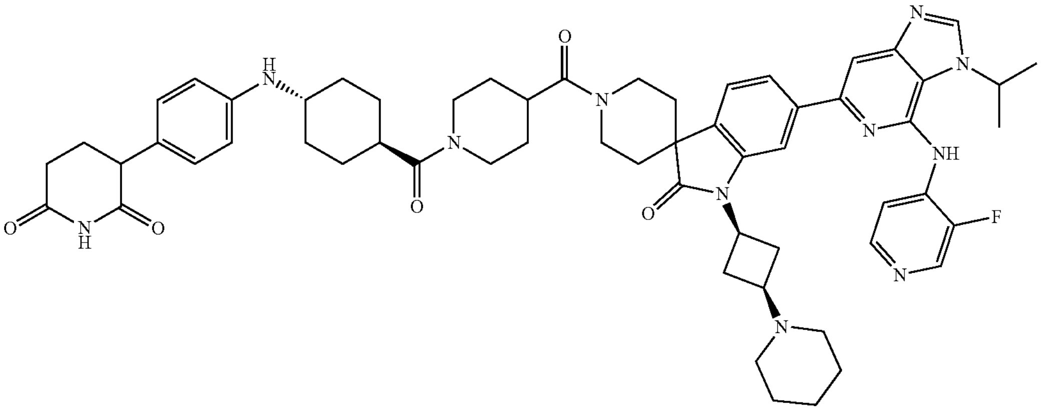 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6ccc(C7CCC(=O)NC7=O)cc6)CC5)CC4)CC3)nc(Nc3ccncc3F)c21]

1-((1r,4R)-4-((4-(2,6-dioxopiperidin-3-yl)phenyl)amino)cyclohexane-1-carbonyl)piperidine-4-carboxylic acid (intermediate 31) (7 mg, 0.016 mmol) and 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (6.8 mg, 39% yield). LCMS: [$C_{59}H_{70}FN_{11}O_5$], desired mass=1032.2, found: m/z=1032.8 $[M+H]^+$, Example 56

2-[(3RS)-2,6-dioxopiperidin-3-yl]-4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]amino}-2,3-dihydro-1H-isoindole-1,3-dione

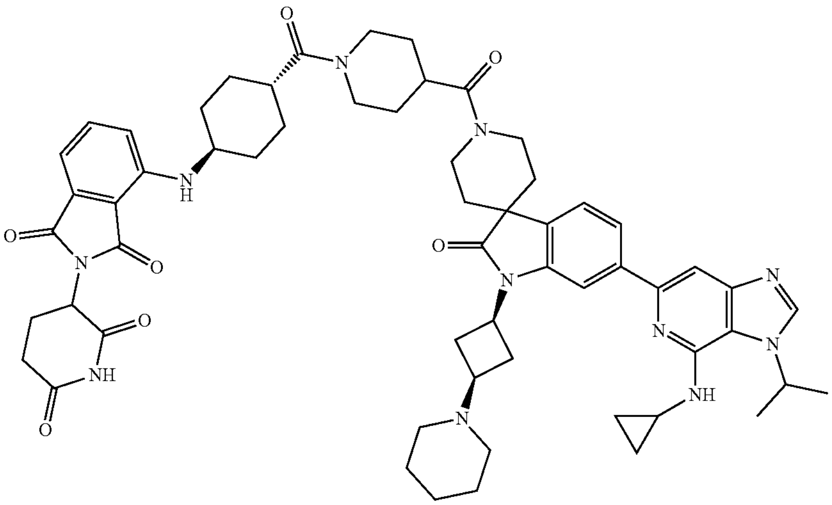 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6cccc7c6C(=O)N(C6CCC(=O)NC6=O)C7=O)CC5)CC4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl) spiro[indoline-3,4'-piperidin]-2-one hydrochloride and 1-((1r,4R)-4-((2-(2,6-dioxopiperidin-3-yl)-1,3-dioxoisoindolin-4-yl)amino)cyclohexane-1-carbonyl)piperidine-4-carboxylic acid (intermediate 32) as the coupling partners, the title compound (TFA salt) was isolated as an off-white solid (78 mg, 92% yield). LCMS: [C59H71N11O7], desired mass=1045.6, found: m/z=1046.8 $[M+H]^+$. $^1H$ NMR (500 MHz, MeOD) δ 8.90 (s, 1H), 7.67 (d, J=6.7 Hz, 2H), 7.63 (s, 1H), 7.57 (d, J=7.4 Hz, 2H), 7.14 (d, J=8.5 Hz, 1H), 7.07 (d, J=7.0 Hz, 1H), 5.16-5.09 (m, 1H), 5.07 (dd, J=12.4, 5.3 Hz, 1H), 4.61 (s, 1H), 4.48 (q, J=8.2 Hz, 1H), 4.17 (s, 3H), 4.04 (s, 1H), 3.92 (s, 1H), 3.66-3.55 (m, 4H), 3.25 (d, J=12.0 Hz, 1H), 3.15 (d, J=15.8 Hz, 1H), 3.07 (s, 1H), 3.01 (d, J=8.8 Hz, 2H), 2.91 (d, J=15.0 Hz, 3H), 2.79 (d, J=9.5 Hz, 3H), 2.76-2.68 (m, 1H), 2.22 (s, 2H), 2.16-2.10 (m, 1H), 2.01 (t, J=11.7 Hz, 4H), 1.90 (s, 8H), 1.77 (s, 7H), 1.69 (d, J=6.6 Hz, 6H), 1.57 (d, J=13.0 Hz, 1H), 1.44 (t, J=11.6 Hz, 2H), 1.13 (d, J=6.7 Hz, 2H), 0.93 (s, 2H).

Example 57

2-[(3RS)-2,6-dioxopiperidin-3-yl]-4-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}-2,3-dihydro-1H-isoindole-1,3-dione

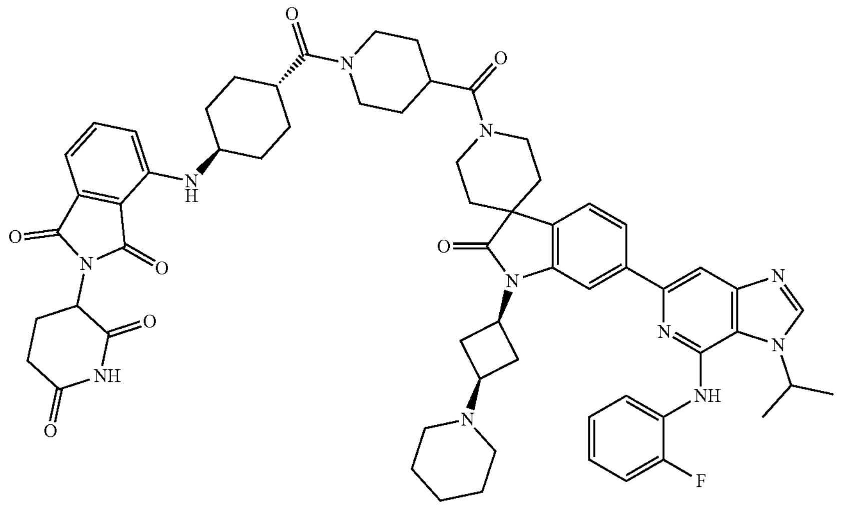 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6cccc7c6C(=O)N(C6CCC(=O)NC6=O)C7=O)CC5)CC4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-((1r,4R)-4-((2-(2,6-dioxopiperidin-3-yl)-1,3-dioxoisoindolin-4-yl)amino)cyclohexane-1-carbonyl)piperidine-4-carboxylic acid (intermediate 32) as the coupling partners, the title compound (TFA salt) was isolated as an off-white solid (10.1 mg, 56% yield). LCMS: [C62H70FN11O7], desired mass=1099.5, found: m/z=1100.2 $[M+H]^+$.

Example 58

(3RS)-3-(5-{[(1R,4R)-4-{4-[(6-{4-[(2-fluorophenyl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]piperidine-1-carbonyl}cyclohexyl] amino}pyridin-3-yl)piperidine-2,6-dione

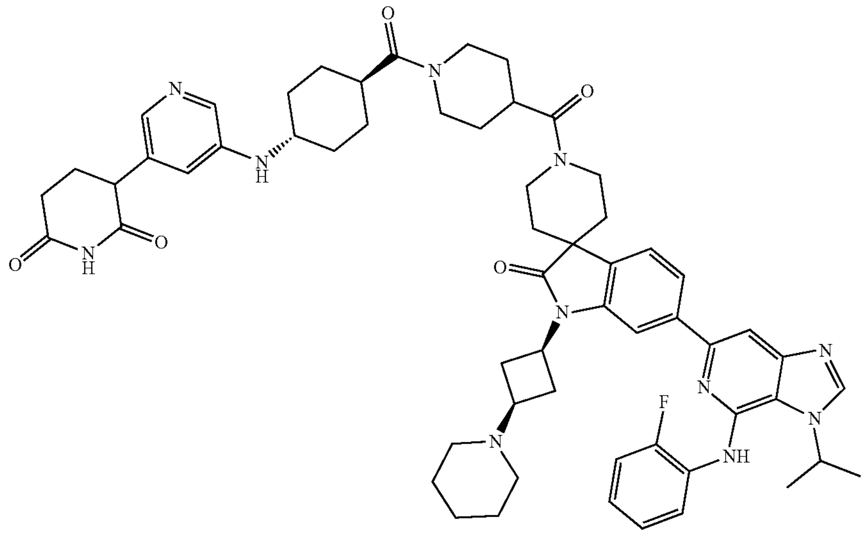 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Nc6cncc(C7CCC(=O)NC7=O)c6)CC5)CC4)CC3)nc(Nc3ccccc3F)c21]

Example 58 was prepared by similar procedures as Example 1 using 1-((1r,4r)-4-((5-(2,6-dioxopiperidin-3-yl) pyridin-3-yl)amino)cyclohexane-1-carbonyl)piperidine-4-carboxylic acid (intermediate 33) (11 mg, 0.025 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl) spiro[indoline-3,4'-piperidin]-2-one (15 mg, 0.025 mmol) as starting materials. The title compound (TFA salt) was isolated as an off-white solid (11 mg, 39% yield). LCMS: [$C_{59}H_{70}FN_{11}O_5$], desired mass=1032.2, found: m/z=1032.8 $[M+H]^+$, $^1H$ NMR (500 MHz, DMSO) δ 11.04 (s, 1H), 9.50-9.44 (m, 1H), 8.67 (s, 1H), 8.39 (s, 1H), 8.04 (s, 1H), 7.96 (s, 1H), 7.91 (d, J=5.1 Hz, 1H), 7.72 (dd, J=25.7, 7.9 Hz, 1H), 7.61-7.46 (m, 3H), 7.32 (t, J=9.4 Hz, 1H), 7.22 (dd, J=8.5, 5.5 Hz, 2H), 7.00 (s, 1H), 5.30 (p, J=6.7 Hz, 1H), 4.48-4.39 (m, 1H), 4.13-4.00 (m, 4H), 3.56-3.32 (m, 6H), 3.19-3.08 (m, 1H), 2.97-2.75 (m, 6H), 2.75-2.58 (m, 6H), 2.37 (d, J=10.9 Hz, 1H), 2.12-2.04 (m, 1H), 2.00 (s, 1H), 1.88 (d, J=13.6 Hz, 3H), 1.82-1.71 (m, 12H), 1.61 (d, J=6.5 Hz, 6H), 1.44 (q, J=12.9 Hz, 1H), 1.25 (m, 5H).

Example 59

(3RS)-3-(4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]oxy}phenyl)piperidine-2,6-dione

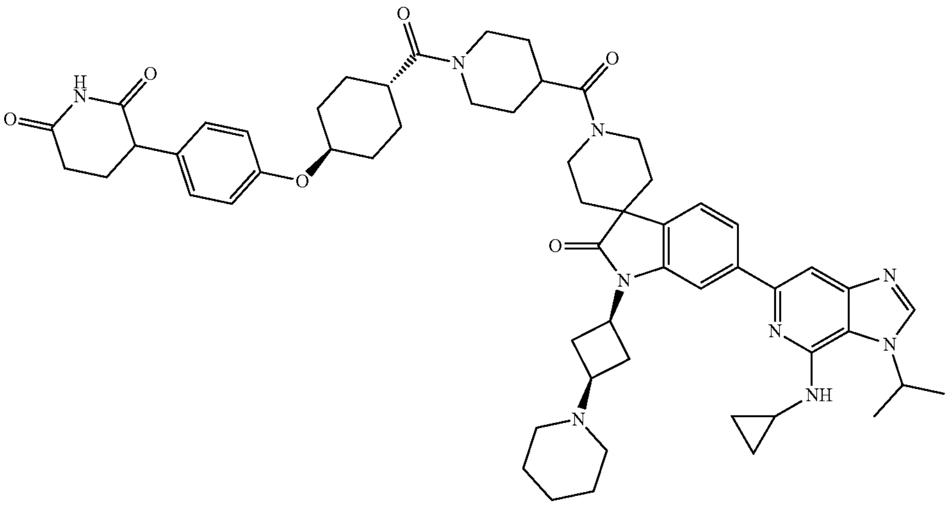 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Oc6ccc(C7CCC(=O)NC7=O)cc6)CC5)CC4)CC3)nc(NC3CC3)c21]

Using procedures similar to those used for Example 13 but using 1-((1r,4r)-4-(4-(2,6-dioxopiperidin-3-yl)phenoxy)cyclohexane-1-carbonyl)piperidine-4-carboxylic acid (Intermediate 34) (16 mg, 0.036 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (20.0 mg, 0.036 mmol) as coupling partners afforded the title compound (TFA salt) as an off white solid (24.2 mg, 67% yield). LCMS: $C_{57}H_{71}N_9O_6$ desired mass=977.6, found: m/z=978.5 $[M+H]^+$. $^1H$ NMR (500 MHz, Methanol-$d_4$) δ 7.67 (s, 2H), 7.63 (s, 1H), 7.57 (s, 1H), 7.17 (dd, J=7.4, 5.2 Hz, 2H), 6.93 (dd, J=8.6, 4.7 Hz, 2H), 5.17-5.10 (m, 1H), 4.60 (s, 1H), 4.49 (q, J=8.4 Hz, 1H), 4.30 (s, 2H), 4.16 (t, J=15.9 Hz, 3H), 4.05 (s, 1H), 3.91 (s, 1H), 3.82 (dd, J=9.6, 6.1 Hz, 1H), 3.68-3.54 (m, 3H), 3.26 (s, 1H), 3.16 (s, 1H), 3.07 (dt, J=6.6, 3.2 Hz, 1H), 3.00 (d, J=9.8 Hz, 2H), 2.97-2.85 (m, 2H), 2.84-2.72 (m, 2H), 2.74-2.66 (m, 1H), 2.69-2.59 (m, 1H), 2.22 (q, J=9.2, 5.8 Hz, 6H), 2.02 (dd, J=23.9, 7.3 Hz, 4H), 1.90 (s, 8H), 1.79 (d, J=13.5 Hz, 1H), 1.69 (d, J=6.6 Hz, 7H), 1.54 (q, J=13.0, 11.9 Hz, 2H), 1.31 (s, 1H), 1.14 (d, J=6.5 Hz, 2H), 0.95 (s, 2H).

Example 60

(3RS)-3-(4-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]oxy}phenyl)piperidine-2,6-dione

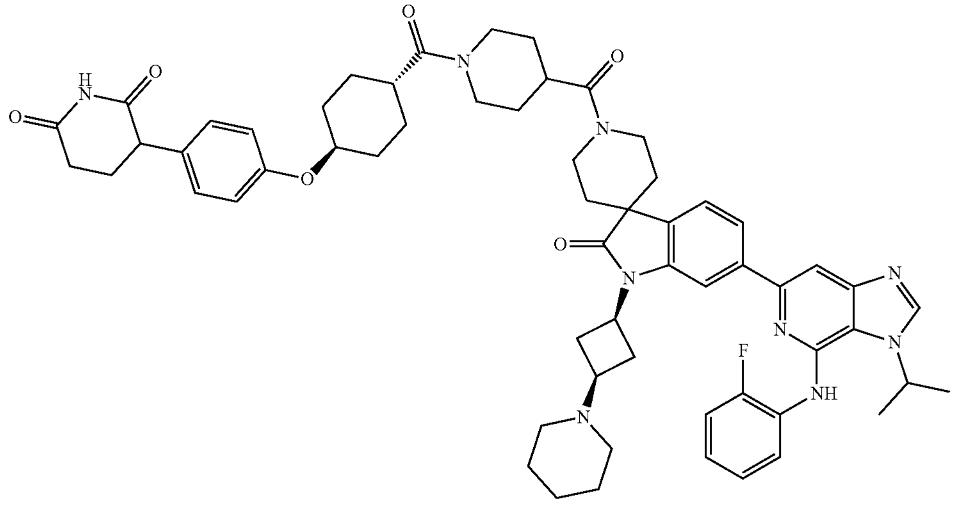 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Oc6ccc(C7CCC(=O)NC7=O)cc6)CC5)CC4)CC3)nc(Nc3ccccc3F)c21]

Using procedures similar to those used for Example 13 but using 1-((1r,4r)-4-(4-(2,6-dioxopiperidin-3-yl)phenoxy)cyclohexane-1-carbonyl)piperidine-4-carboxylic acid (Intermediate 34) (15.0 mg, 0.033 mmol) and 6-{4-[(2-fluorophenyl)amino]-3-isopropylimidazo[4,5-c]pyridin-6-yl}-1-[(1S,3s)-3-(piperidin-1-yl)cyclobutyl]spiro[indole-3,4'-piperidin]-2-one (20.0 mg, 0.033 mmol) as coupling partners afforded the title compound (TFA salt) as an off white solid (28.7 mg, 81% yield). LCMS: $C_{60}H_{70}FN_9O_6$ desired mass=1031.5, found: m/z=1033.4 $[M+H]^+$. $^1H$ NMR (500 MHz, Methanol-$d_4$) δ 7.81 (s, 1H), 7.80-7.74 (m, 1H), 7.74-7.66 (m, 1H), 7.60 (s, 1H), 7.53 (d, J=7.7 Hz, 1H), 7.36-7.24 (m, 3H), 7.20-7.14 (m, 2H), 6.93 (d, J=8.3 Hz, 2H), 4.60 (s, 1H), 4.30 (s, 1H), 4.27-4.11 (m, 2H), 4.10 (s, 2H), 4.02-3.91 (m, 2H), 3.82 (dd, J=9.6, 6.0 Hz, 1H), 3.58 (dt, J=29.6, 10.6 Hz, 4H), 3.30 (s, 4H), 3.24 (d, J=12.3 Hz, 1H), 3.10 (d, J=11.0 Hz, 2H), 3.01 (s, 1H), 2.97-2.86 (m, 4H), 2.78 (s, 2H), 2.77-2.66 (m, 1H), 2.64 (dt, J=17.4, 4.9 Hz, 1H), 2.22 (td, J=10.9, 10.3, 5.2 Hz, 5H), 2.04 (d, J=14.6 Hz, 2H), 1.92 (d, J=19.0 Hz, 6H), 1.85 (s, 3H), 1.76 (d, J=6.6 Hz, 7H), 1.70-1.48 (m, 2H), 1.31 (s, 1H).

Example 61

(3RS)-3-(4-{[(1R,4R)-4-{4-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]oxy}phenyl)piperidine-2,6-dione

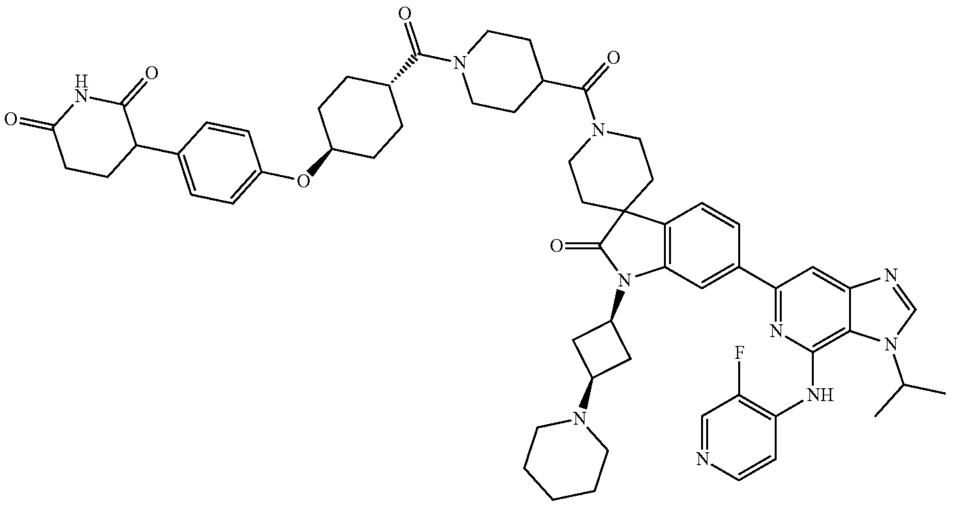 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Oc6ccc(C7CCC(=O)NC7=O)cc6)CC5)CC4)CC3)nc(Nc3ccncc3F)c21]

Using procedures similar to those used for Example 13 but using 1-((1r,4r)-4-(4-(2,6-dioxopiperidin-3-yl)phenoxy) cyclohexane-1-carbonyl)piperidine-4-carboxylic acid (Intermediate 34) (15.0 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.0 mg, 0.033 mmol) as coupling partners afforded the title compound (TFA salt) as an off white solid (29.8 mg, 87% yield). LCMS: $C_{59}H_{69}FN_{10}O_6$ desired mass=1032.5, found: m/z=1034.4 $[M+H]^+$. $^1$H NMR (500 MHz, Methanol-$d_4$) δ 8.77 (d, J=13.7 Hz, 2H), 8.31 (d, J=6.8 Hz, 1H), 8.24 (s, 1H), 7.89 (d, J=7.9 Hz, 1H), 7.77 (s, 1H), 7.72 (s, 1H), 7.57 (d, J=7.9 Hz, 1H), 7.17 (d, J=8.4 Hz, 2H), 6.93 (d, J=8.3 Hz, 3H), 5.20-5.12 (m, 1H), 4.59 (s, 1H), 4.51 (q, J=8.3 Hz, 1H), 4.34-4.26 (m, 1H), 4.15 (dd, J=21.7, 11.9 Hz, 4H), 4.02 (s, 1H), 3.94 (s, 2H), 3.82 (dd, J=9.6, 6.1 Hz, 1H), 3.59 (t, J=11.0 Hz, 4H), 3.25 (d, J=11.9 Hz, 1H), 3.12 (s, 1H), 2.98 (s, 2H), 2.91 (q, J=12.7, 12.3 Hz, 2H), 2.84-2.59 (m, 4H), 2.27-2.19 (m, 3H), 2.03 (d, J=14.5 Hz, 2H), 1.97 (s, 2H), 1.88 (s, 9H), 1.79 (d, J=13.6 Hz, 2H), 1.65 (dd, J=6.8, 2.9 Hz, 8H), 1.57-1.48 (m, 2H), 1.31 (s, 1H).

Example 62

(3RS)-3-(6-{[(1R,4R)-4-{4-[(6-{4-[(2-fluorophenyl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]piperidine-1-carbonyl}cyclohexyl] oxy}pyridin-3-yl)piperidine-2,6-dione

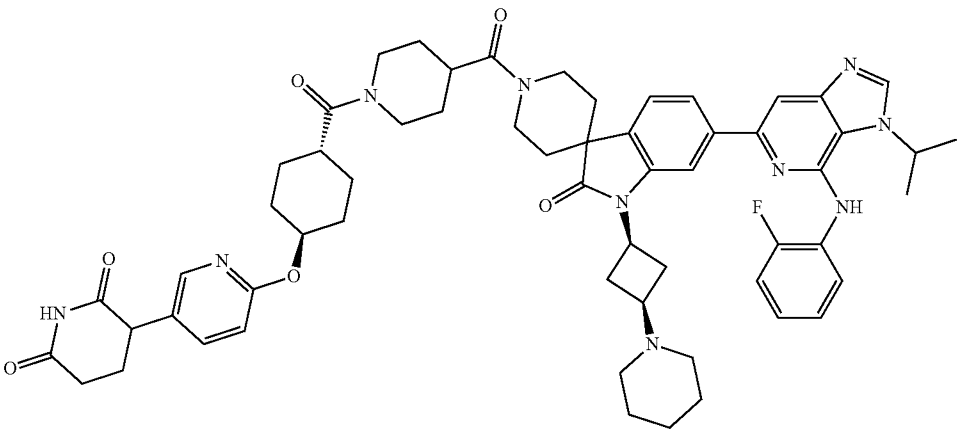 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Oc6ccc(C7CCC(=O)NC7=O)cn6)CC5)CC4)CC3)nc(Nc3ccccc3F)c21]

Step 1: 6-{4-[(2-fluorophenyl)amino]-3-isopropylimidazo[4,5-c]pyridin-6-yl}-1'-(piperidine-4-carbonyl)-1-[(1s,3s)-3-(piperidin-1-yl)cyclobutyl]spiro [indole-3,4'-piperidin]-2-one 1-(tert-butoxycarbonyl)piperidine-4-carboxylic acid (226.34 mg, 0.99 mmol) and (1,2,3-benzotriazol-1-yloxy) tris(dimethylamino)phosphanium, hexafluoro-lambda5-phosphanuide (473.01 mg, 1.07 mmol) were dissolved in dimethylformamide (1.00 mL) and N,N-diisopropylethylamine (0.57 mL, 425.31 mg, 3.29 mmol) and stirred at room temperature for 5 minutes. 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (500.00 mg, 0.82 mmol) was added and the reaction mixture was stirred for 2 hours at room temperature. The product was isolated by reverse phase flash column, then dissolved in DCM and treated with 1M HCl at room temperature. The reaction mixture was concentrated to afford the title compound as a pale yellow solid (420 mg, 71% yield).

Step 2

Using procedures similar to those used for Example 36 and using 6-{4-[(2-fluorophenyl)amino]-3-isopropylimidazo[4,5-c]pyridin-6-yl}-1'-(piperidine-4-carbonyl)-1-[(1s,3s)-3-(piperidin-1-yl)cyclobutyl]spiro[indole-3,4'-piperidin]-2-one (15.00 mg, 0.02 mmol) and (1r,4r)-4-((5-(2,6-dioxopiperidin-3-yl)pyridin-2-yl)oxy)cyclohexane-1-carboxylic acid (Intermediate 9) (6.93 mg, 0.02 mmol) as coupling partners afforded the title compound (TFA salt) as an off white solid (13.0 mg, 58% yield). LCMS: $C_{59}H_{69}FN_{10}O_6$ desired mass=1032.5, found: m/z=1034.1 $[M+H]^+$. $^1$H NMR (500 MHz, DMSO-$d_6$) δ 10.86 (s, 1H), 9.31 (s, 1H), 8.69 (s, 1H), 8.39 (s, 1H), 8.01 (d, J=2.6 Hz, 1H), 7.90 (s, 1H), 7.73-7.67 (m, 1H), 7.61-7.53 (m, 3H), 7.49 (s, 1H), 7.37-7.28 (m, 1H), 7.27-7.18 (m, 2H), 6.74 (d, J=8.5 Hz, 1H), 5.30 (q, J=6.6 Hz, 1H), 4.91 (s, 1H), 4.42 (s, 1H), 4.10 (t, J=8.2 Hz, 1H), 3.92 (s, 1H), 3.85 (dd, J=12.6, 4.9 Hz, 2H), 3.51 (q, J=8.1 Hz, 1H), 3.13 (s, 1H), 3.02-2.82 (m, 2H), 2.77-2.65 (m, 1H), 2.56 (t, J=4.8 Hz, 1H), 2.47 (s, 2H), 2.28-2.21 (m, 1H), 2.13 (s, 2H), 2.00 (d, J=12.7 Hz, 2H), 1.88 (d, J=13.8 Hz, 2H), 1.81-1.71 (m, 7H), 1.69 (s, 3H), 1.60 (d, J=6.6 Hz, 6H), 1.51 (s, 14H).

Example 63

(3RS)-3-(2-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]methyl}-2H-indazol-5-yl)piperidine-2,6-dione

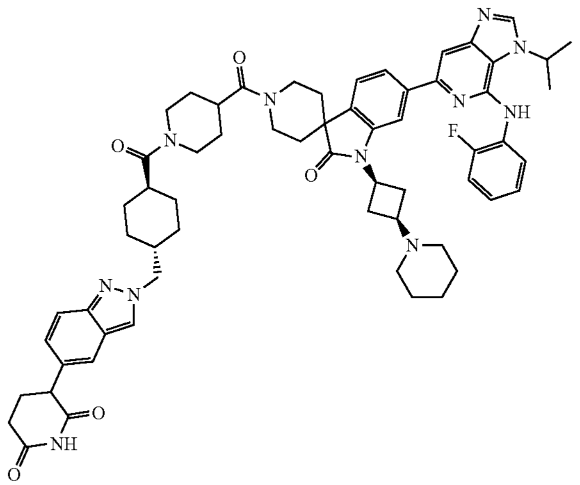 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Cn6cc7cc(C8CCC(=O)NC8=O)ccc7n6)CC5)CC4)CC3)nc(Nc3ccccc3F)c21]

Using procedures similar to Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride (20 mg) and (1r,4r)-4-((5-(2,6-dioxopiperidin-3-yl)-2H-indazol-2-yl)methyl)cyclohexane-1-carboxylic acid (intermediate 35) (10 mg) as the coupling partners, and HATU as the coupling reagent, the title compound (TFA salt) was isolated as an off-white solid (12 mg, 40% yield). LCMS: [$C_{62}H_{72}FN_{11}O_5$], desired mass=1069.6, found: m/z=1070.8 $[M+H]^+$. $^1$H NMR (500 MHz, DMSO) δ 10.82 (s, 1H), 9.31 (s, 1H), 8.58 (s, 1H), 8.33 (s, 1H), 7.89 (s, 1H), 7.69 (d, J=7.8 Hz, 1H), 7.59-7.45 (m, 3H), 7.35-7.26 (m, 1H), 7.25-7.12 (m, 3H), 7.04 (d, J=12.1 Hz, 2H), 5.34-5.22 (m, 1H), 4.70 (s, 1H), 4.58 (s, 1H), 4.13-4.05 (m, 1H), 3.67 (s, 1H), 3.57 (s, 2H), 3.00-2.92 (m, 3H), 2.90 (s, 3H), 2.85 (s, 2H), 2.72 (s, 5H), 2.18 (d, J=12.4 Hz, 1H), 1.94-1.84 (m, 3H), 1.82 (s, 2H), 1.78 (s, 1H), 1.73 (s, 3H), 1.58 (dd, J=6.6, 3.2 Hz, 6H), 1.44 (s, 3H), 1.10 (d, J=12.8 Hz, 2H).

Example 64

(3RS)-3-(1-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]methyl}-1H-indazol-5-yl)piperidine-2,6-dione

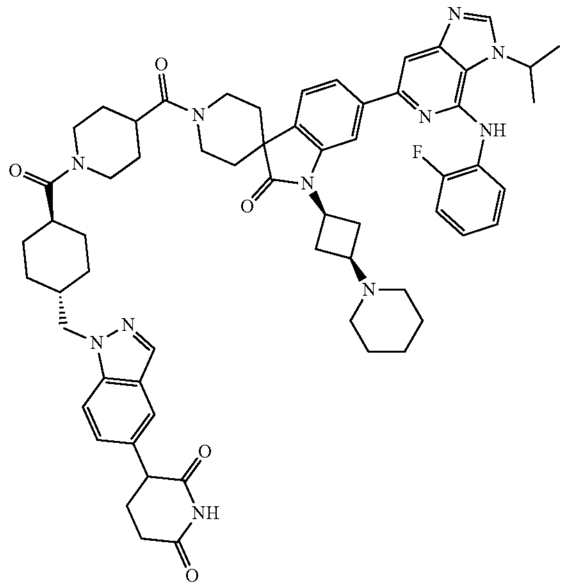 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](Cn6ncc7cc(C8CCC(=O)NC8=O)ccc76)CC5)CC4)CC3)nc(Nc3ccccc3F)c21]

Using procedures similar to Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride (20 mg) and (20 mg) and (1r,4r)-4-((5-(2,6-dioxopiperidin-3-yl)-1H-indazol-1-yl)methyl)cyclohexane-1-carboxylic acid (intermediate 36) (10 mg) as the coupling partners, and HATU as the coupling reagent, the title compound (TFA salt) was isolated as an off-white solid (11 mg, 39% yield). LCMS [$C_{62}H_{72}FN_{11}O_5$], desired mass=1069.6, found: m/z=1070.4 $[M+H]^+$. $^1$H NMR (500 MHz, DMSO) δ 10.84 (s, 1H), 9.24 (s, 1H), 8.60 (s, 1H), 8.34 (s, 1H), 8.02 (s, 1H), 7.89 (s, 1H), 7.68 (d, J=7.7 Hz, 1H), 7.62 (d, J=8.8 Hz, 1H), 7.59-7.52 (m, 3H), 7.49 (s, 1H), 7.30 (d, J=9.8 Hz, 1H), 7.23 (t, J=8.7 Hz, 1H), 7.20 (s, 2H), 5.30-5.24 (m, 1H), 4.37 (s, 1H), 4.26 (d, J=6.8 Hz, 2H), 4.12-4.06 (m, 1H), 3.96 (dd, J=11.6, 4.9 Hz, 1H), 3.91 (s, 1H), 3.83 (s, 4H), 3.07 (s, 1H), 2.93 (d, J=11.2 Hz, 2H), 2.89-2.80 (m, 2H), 2.71 (d, J=11.2 Hz, 2H), 2.27 (d, J=9.5 Hz, 1H), 2.08 (d, J=8.9 Hz, 1H), 1.87 (d, J=13.8 Hz, 3H), 1.76 (s, 1H), 1.66 (s, 11H), 1.58 (d, J=6.6 Hz, 6H), 1.31 (s, 4H), 1.23 (s, 1H), 1.14 (s, 2H).

Example 65

(3RS)-3-{6-[(3S)-3-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}pyrrolidin-1-yl]pyridin-3-yl}piperidine-2,6-dione

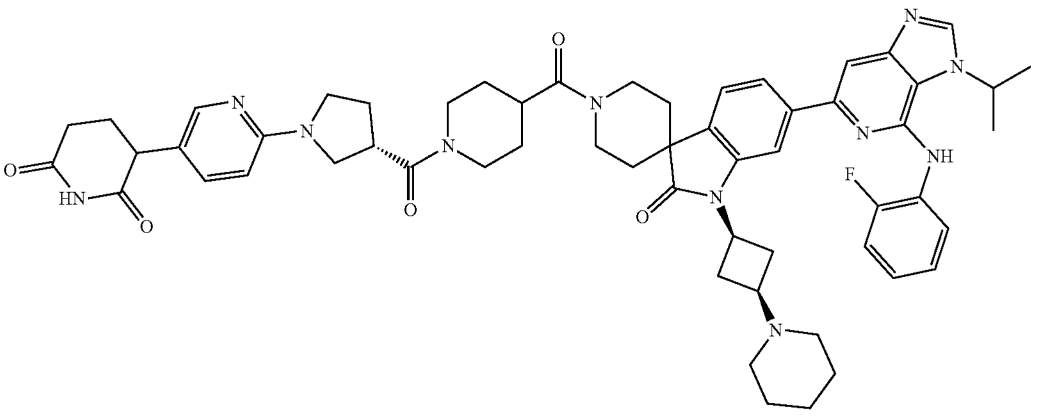 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CCN(c6ccc(C7CCC(=O)NC7=O)cn6)C5)CC4)CC3)nc(Nc3ccccc3F)c21]

Step 1: 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one 1-(tert-butoxycarbonyl)piperidine-4-carboxylic acid (226.34 mg, 0.99 mmol) and (1,2,3-benzotriazol-1-yloxy)tris(dimethylamino)phosphanium, hexafluoro-lambda5-phosphanuide (473.01 mg, 1.07 mmol) were dissolved in dimethylformamide (1.00 mL) and N,N-diisopropylethylamine (0.57 mL, 425.31 mg, 3.29 mmol) and stirred at room temperature for 5 minutes. 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (500.00 mg, 0.82 mmol) was added and the reaction mixture was stirred for 2 hours at room temperature. The product was isolated by reverse phase flash column, then dissolved in DCM and treated with 1M HCl at room temperature. The reaction mixture was concentrated to afford the title compound as a pale-yellow solid (420 mg, 71% yield).

Step 2: Using procedures similar to those used for Example 36 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one (15.00 mg, 0.02 mmol) and (3S)-1-(5-(2,6-dioxopiperidin-3-yl)pyridin-2-yl)pyrrolidine-3-carboxylic acid (Intermediate 37) (6.33 mg, 0.02 mmol) as coupling partners afforded the title compound (TFA salt) as an off white solid (4.1 mg, 17% yield). LCMS: $C_{57}H_{66}FN_{11}O_5$ desired mass=1003.5, found: m/z=1005.0 $[M+H]^+$. $^1H$ NMR (500 MHz, Methanol-$d_4$) δ 7.98 (d, J=9.5 Hz, 1H), 7.84 (d, J=10.1 Hz, 2H), 7.77 (d, J=8.2 Hz, 1H), 7.70 (s, 1H), 7.60 (s, 1H), 7.53 (d, J=8.0 Hz, 1H), 7.28 (s, 3H), 7.21-7.13 (m, 1H), 4.91 (d, J=1.7 Hz, 1H), 4.85 (d, J=5.6 Hz, 1H), 4.60 (s, 1H), 4.22 (d, J=8.6 Hz, 2H), 4.10 (d, J=13.5 Hz, 2H), 3.97 (s, 3H), 3.97-3.87 (m, 1H), 3.82 (d, J=7.4 Hz, 1H), 3.74 (s, 2H), 3.71 (d, J=6.9 Hz, 1H), 3.65-3.50 (m, 3H), 3.39-3.33 (m, 1H), 3.29 (s, 1H), 3.16 (s, 0H), 3.09 (d, J=9.7 Hz, 1H), 3.02 (d, J=9.7 Hz, 1H), 2.97-2.79 (m, 5H), 2.76 (d, J=17.8 Hz, 1H), 2.48 (t, J=6.9 Hz, 1H), 2.33 (d, J=12.1 Hz, 3H), 2.21 (s, 1H), 2.04 (d, J=14.6 Hz, 2H), 1.94 (s, 3H), 1.88 (d, J=18.6 Hz, 2H), 1.76 (d, J=6.5 Hz, 6H), 1.60 (t, J=12.7 Hz, 1H), 1.31 (s, 1H), 0.77-0.69 (m, 1H).

Example 66

3-(4-(4-(4-(6-(4-(cyclopropylamino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidine-1-carbonyl)piperidin-1-yl)phenyl)piperidine-2,6-dione

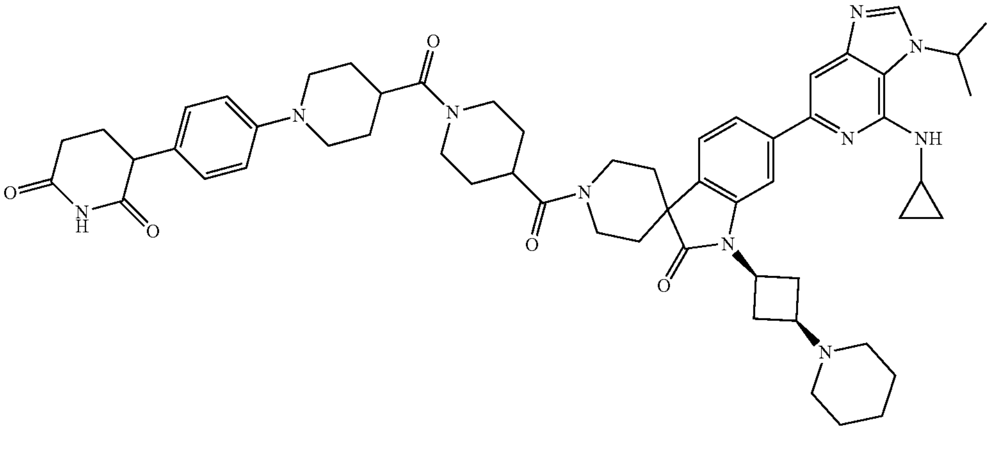 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cc6)CC5)CC4)CC3)nc(NC3CC3)c21]

The title compound was synthesized using similar methods to example 10, using BOP coupling. Afforded an off-white solid (76 mg, 0.079 mmol, 34% yield) as a free base. LCMS: [$C_{56}H_{70}N_{10}O_5$], desired mass=962.5, found: m/z=963.5 $[M+H]^+$. $^1H$ NMR (500 MHz, DMSO-$d_6$) δ 10.78 (s, 1H), 9.37 (s, 1H), 8.81 (s, 1H), 7.80 (s, 1H), 7.70 (s, 1H), 7.63 (s, 1H), 7.23-6.92 (m, 5H), 5.13 (p, J=5.9, 5.9, 5.5, 5.5 Hz, 1H), 4.42 (m, 1H), 4.31 (q, J=8.0, 8.0, 7.7 Hz, 1H), 4.10 (m, 1H), 4.02 (m, 1H), 3.00 (dd, J=6.8, 3.1 Hz, 7H), 2.91 (s, 5H), 2.80 (d, J=12.6 Hz, 4H), 2.70-2.57 (m, 4H), 2.14 (q, J=11.6, 11.3, 11.3 Hz, 1H), 2.06-1.94 (m, 1H), 1.81 (m, 5H), 1.72 (m, 10H), 1.60 (m, 3H), 1.51 (d, J=6.5 Hz, 6H), 1.39 (m, 2H), 0.84 (m, 4H), 0.65 (m, 2H).

Example 67

(3RS)-3-[4-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]piperidine-2,6-dione

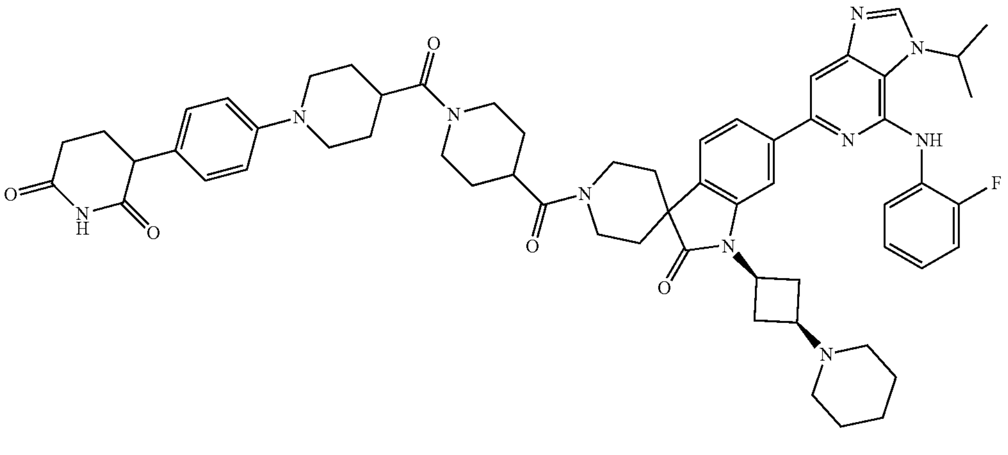 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cc6)CC5)CC4)CC3)nc(Nc3ccccc3F)c21]

Example 67 was prepared by similar procedures as Example 1 using 1-(1-(4-(2,6-dioxopiperidin-3-yl)phenyl)piperidine-4-carbonyl)piperidine-4-carboxylic acid (intermediate 38) (7 mg, 0.016 mmol) and 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.016 mmol) as starting materials. The title compound (TFA salt) was isolated as an off-white solid (7.3 mg, 42% yield). LCMS: [$C_{59}H_{69}FN_{10}O_5$], desired mass=1017.2, found: m/z=1017.8 $[M+H]^+$, $^1H$ NMR (500 MHz, DMSO) δ 10.81 (s, 1H), 9.34 (d, J=8.9 Hz, 1H), 8.66 (s, 1H), 8.38 (s, 1H), 7.90 (s, 1H), 7.70 (d, J=7.8 Hz, 1H), 7.61-7.53 (m, 2H), 7.49 (s, 1H), 7.32 (ddd, J=11.0, 7.3, 2.5 Hz, 1H), 7.22 (dt, J=7.9, 3.5 Hz, 1H), 7.13 (s, 2H), 7.03 (s, 2H), 5.30 (p, J=6.7 Hz, 1H), 4.44 (d, J=12.8 Hz, 1H), 4.04-3.98 (m, 2H), 3.54-3.45 (m, 1H), 3.37 (m, 3H), 3.16 (t, J=12.8 Hz, 1H), 3.10-2.74 (m, 6H), 2.77-2.50 (m, 6H), 2.22-2.09 (m, 1H), 2.03 (m, 1H), 1.88 (d, J=13.8 Hz, 3H), 1.84-1.64 (m, 15H), 1.60 (d, J=6.6 Hz, 7H), 1.42 (d, J=10.9 Hz, 2H).

Example 68

3-(4-(4-(4-(6-(4-((3-fluoropyridin-4-yl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidine-1-carbonyl)piperidin-1-yl)phenyl)piperidine-2,6-dione

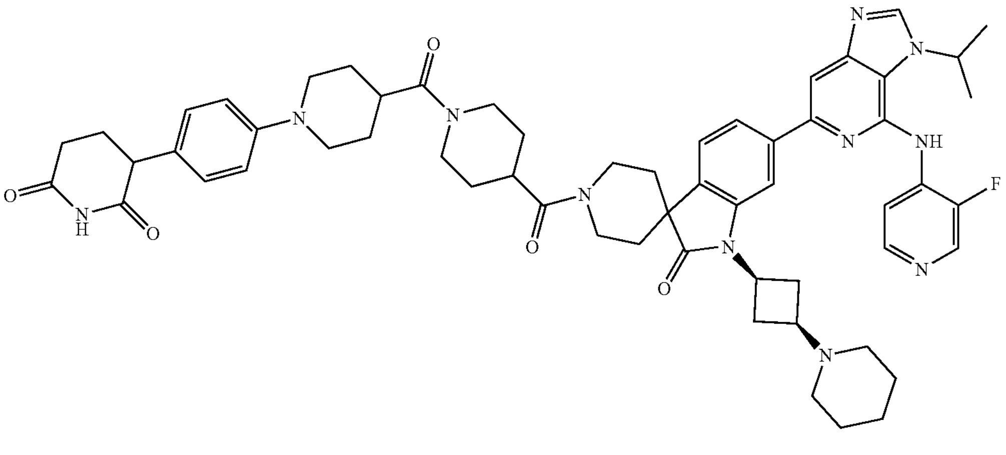 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cc6)CC5)CC4)CC3)nc(Nc3ccncc3F)c21]

The title compound was synthesized using similar methods to example 10, using BOP coupling. (Off-white solid, 29 mg, 0.027 mmol, 42%) title compound as a free base. LCMS: [$C_{58}H_{68}FN_{11}O_5$], desired mass=[1017.5], found: m/z=[1018.9] $[M+H]^+$. $^1H$ NMR (500 MHz, DMSO-$d_6$) δ 10.78 (s, 1H), 10.32 (s, 1H), 9.47 (s, 1H), 8.82 (d, J=4.5 Hz, 1H), 8.73 (s, 1H), 8.36-8.27 (m, 2H), 7.77 (d, J=9.3 Hz, 1H), 7.67-7.53 (m, 2H), 7.19 (s, 1H), 7.10 (d, J=11.7 Hz, 2H), 6.99 (s, 1H), 5.12 (p, J=6.7, 6.7, 6.5, 6.5 Hz, 1H), 4.41 (d, J=11.2 Hz, 1H), 4.29 (p, J=8.7, 8.7, 8.7, 8.7 Hz, 1H), 4.04-3.98 (m, 2H), 3.47 (s, 3H), 3.38 (d, J=9.3 Hz, 4H), 3.15 (d, J=7.7 Hz, 2H), 2.99 (d, J=7.8 Hz, 4H), 2.84 (m, 9H), 2.69-2.58 (m, 2H), 2.20-2.08 (m, 1H), 2.03-1.98 (m, 1H), 1.88-1.54 (m, 15H), 1.51 (d, J=6.6 Hz, 7H), 1.40 (d, J=10.9 Hz, 2H).

Example 69

1-(4-{4-[4-({6-[4-(cyclopropylamino)-3-(propan-2-yl)-3h-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}phenyl)-1,3-diazinane-2,4-dione

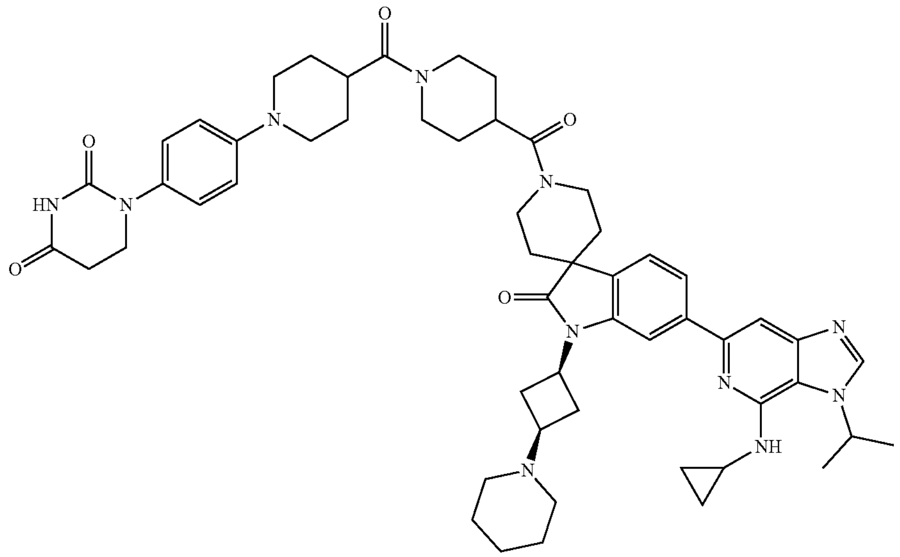 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)cc6)CC5)CC4)CC3)nc(NC3CC3)c21]

Example 69 was prepared by similar procedures as Example 1 using 1-((1r,4r)-4-((4-(2,6-dioxopiperidin-3-yl)pyridin-2-yl)amino)cyclohexane-1-carbonyl)piperidine-4-carboxylic acid (intermediate 39) (15 mg, 0.036 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (18 mg, 0.032 mmol) as starting materials. The title compound (TFA salt) was isolated as an off-white solid (12.4 mg, 38% yield). LCMS: [$C_{55}H_{69}N_{11}O_5$], desired mass=964.2, found: m/z=964.6 $[M+H]^+$, $^1H$ NMR (500 MHz, MeOD) δ 8.94 (s, 1H), 7.67 (s, 2H), 7.63 (s, 1H), 7.57 (s, 1H), 7.47 (q, J=8.7 Hz, 4H), 5.14 (p, J=6.4 Hz, 1H), 4.62 (s, 1H), 4.49 (t, J=8.2 Hz, 1H), 4.23-4.12 (m, 4H), 4.05 (m, 1H), 3.90 (t, J=6.7 Hz, 2H), 3.81 (t, J=11.9 Hz, 3H), 3.64 (m, 3H), 3.19-3.11 (m, 6H), 3.11-2.97 (m, 5H), 2.80 (t, J=6.7 Hz, 2H), 2.12-1.97 (m, 5H), 1.91 (d, J=7.1 Hz, 6H), 1.81 (t, J=13.2 Hz, 3H), 1.69 (d, J=6.5 Hz, 6H), 1.57 (d, J=13.0 Hz, 2H), 1.31 (s, 1H), 1.14 (d, J=6.6 Hz, 2H), 0.95 (s, 2H).

Example 70

1-[4-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]-1,3-diazinane-2,4-dione

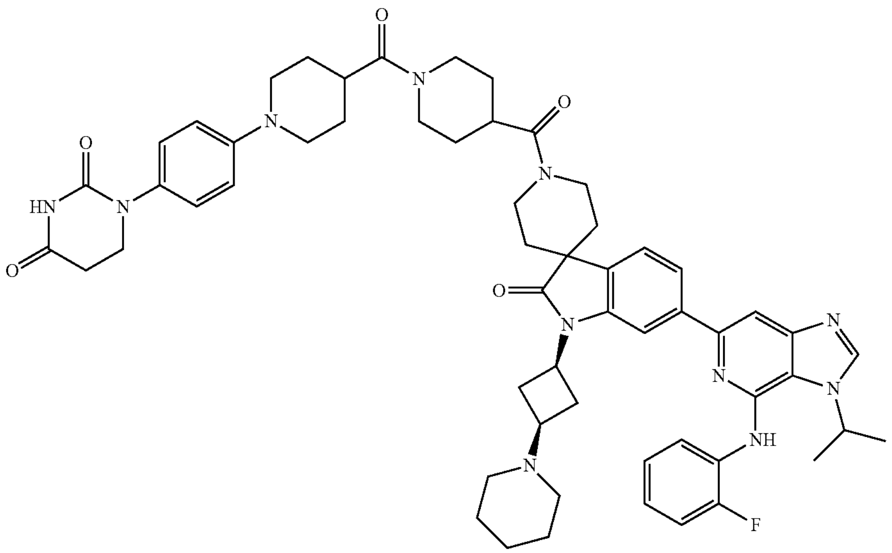 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)cc6)CC5)CC4)CC3)nc(Nc3ccccc3F)c21]

Example 70 was prepared by similar procedures as Example 1 using 1-((1r,4r)-4-((4-(2,6-dioxopiperidin-3-yl)pyridin-2-yl)amino)cyclohexane-1-carbonyl)piperidine-4-carboxylic acid (intermediate 39) (14 mg, 0.033 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (18 mg, 0.029 mmol) as starting materials. The title compound (TFA salt) was isolated as an off-white solid (11.3 mg, 37% yield). LCMS: [$C_{58}H_{68}FN_{11}O_5$], desired mass=1018.2, found: m/z=1018.6 $[M+H]^+$, $^1H$ NMR (500 MHz, MeOD) δ 9.00 (d, J=7.9, 1H), 7.84-7.74 (m, 2H), 7.70 (td, J=7.9, 2.4 Hz, 1H), 7.62 (s, 1H), 7.53 (t, J=6.6 Hz, 1H), 7.46 (d, J=8.6 Hz, 2H), 7.40 (d, J=8.7 Hz, 2H), 7.33-7.24 (m, 1H), 7.26 (s, 2H), 5.39-5.31 (m, 1H), 4.61 (s, 1H), 4.29-4.17 (m, 2H), 4.15-4.03 (m, 4H), 3.99 (d, J=18.0 Hz, 2H), 3.89 (t, J=6.7 Hz, 2H), 3.82 (m, 3H), 3.65-3.51 (m, 3H), 3.21-3.07 (m, 6H), 3.05-2.88 (m, 5H), 2.85 (t, J=6.7 Hz, 2H), 2.04 (d, J=14.7 Hz, 5H), 1.97-1.75 (m, 9H), 1.75 (d, J=6.6 Hz, 6H), 1.59 (d, J=15.6 Hz, 2H).

Example 71

1-[4-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]-1,3-diazinane-2,4-dione

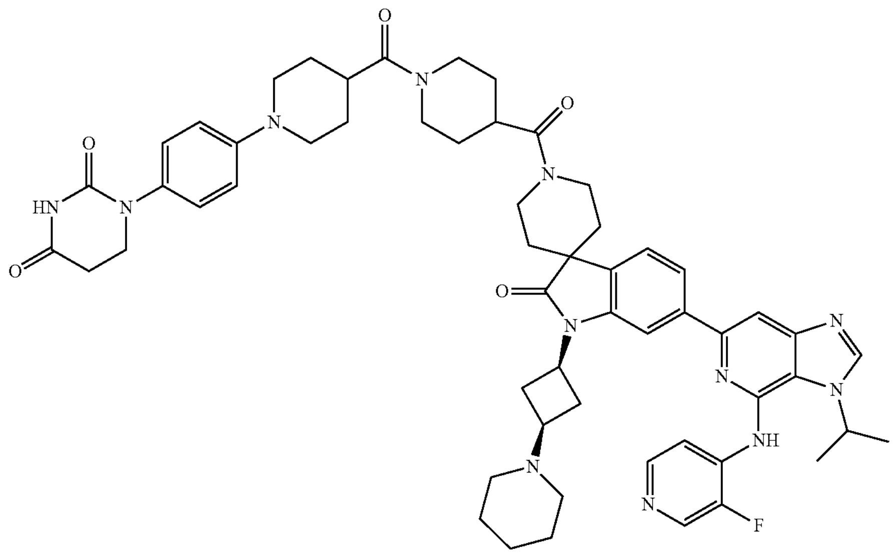 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)cc6)CC5)CC4)CC3)nc(Nc3ccncc3F)c21]

Example 71 was prepared by similar procedures as Example 1 using 1-((1r,4r)-4-((4-(2,6-dioxopiperidin-3-yl)pyridin-2-yl)amino)cyclohexane-1-carbonyl)piperidine-4-carboxylic acid (intermediate 39) (18 mg, 0.035 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (18 mg, 0.029 mmol) as starting materials. The title compound (TFA salt) was isolated as an off-white solid (15.9 mg, 53% yield). LCMS: [$C_{57}H_{67}FN_{12}O_5$], desired mass=1019.2, found: m/z=1019.6 $[M+H]^+$, $^1H$ NMR (500 MHz, MeOD) δ 8.83 ((d, J=6.8 Hz, 1H), 8.77 (s, 1H), 8.32 (d, J=6.8 Hz, 1H), 8.25 (s, 1H), 7.88 (d, J=7.8 Hz, 1H), 7.79-7.74 (m, 1H), 7.71 (s, 1H), 7.61-7.52 (m, 2H), 7.53 (s, 3H), 5.16 (p, J=6.6 Hz, 1H), 4.62 (s, 1H), 4.50 (p, J=8.4 Hz, 1H), 4.23-4.12 (m, 4H), 4.03 (s, 1H), 3.92 (t, J=6.7 Hz, 2H), 3.82 (t, J=11.1 Hz, 3H), 3.66-3.55 (m, 3H), 3.55-3.43 (m, 2H), 3.27-3.13 (m, 5H), 3.03-2.87 (m, 5H), 2.84 (t, J=6.7 Hz, 2H), 2.21-2.05 (m, 4H), 2.04-1.90 (m, 9H), 1.79 (d, J=13.9 Hz, 2H), 1.65 (dd, J=6.7, 2.6 Hz, 6H), 1.59-1.50 (m, 2H).

Example 72

5-[(6-{1'-[1-(1-{5-[(3RS)-2,6-dioxopiperidin-3-yl] pyridin-2-yl}piperidine-4-carbonyl)piperidine-4-carbonyl]-2-oxo-1-[(1S,3S)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl) amino]-4-fluoro-2-methyl-N-(propan-2-yl) benzamide

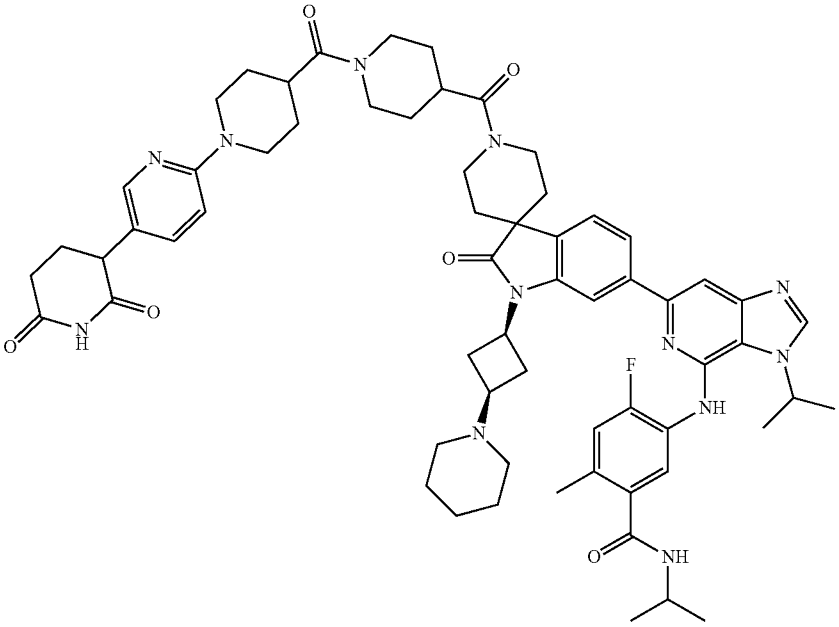 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4)CC3)cc3ncn(C(C)C)c23)cc1C(=O)NC(C)C]

Using procedures similar to those for Example 31 and using 4-fluoro-N-isopropyl-5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-2-methylbenzamide hydrochloride and 1-(1-(5-(2,6-dioxopiperidin-3-yl)pyridin-2-yl)piperidine-4-carbonyl) piperidine-4-carboxylic acid (intermediate 40) as the coupling partners, the title compound (TFA salt) was isolated as an off-white solid (4.5 mg, 28% yield). LCMS: [C63H77FN12O6], desired mass=1116.6, found: m/z=1118.1 $[M+H]^+$.

Example 73

3-(6-(4-(4-(6-(4-(cyclopropylamino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidine-1-carbonyl)piperidin-1-yl)pyridin-3-yl)piperidine-2,6-dione

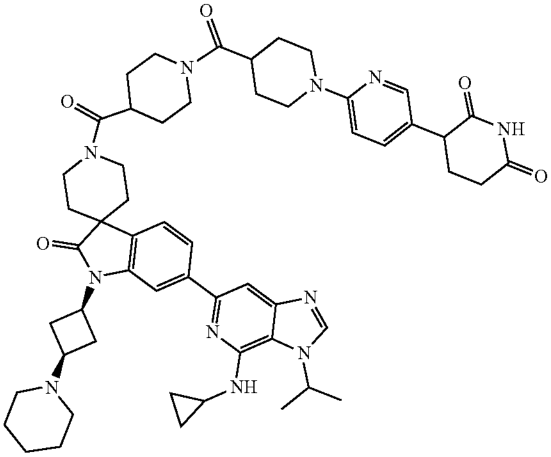 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4)CC3)nc(NC3CC3)c21]

The title compound was synthesized using similar methods to example 10, using BOP coupling. Afforded an off-white solid (76 mg, 0.079 mmol, 34%) as a free base. LCMS: [$C_{55}H_{69}N_{11}O_5$], desired mass=963.5, found: m/z=964.8 $[M+H]^+$. $^1H$ NMR (500 MHz, DMSO-$d_6$) δ 10.89 (s, 1H), 9.36 (s, 1H), 8.85 (s, 1H), 7.88 (d, J=2.6 Hz, 1H), 7.63 (s, 2H), 7.25 (s, 1H), 7.17 (s, 1H), 7.07 (s, 1H), 6.97 (s, 1H), 5.14 (q, J=6.6, 6.5, 6.5 Hz, 1H), 4.39 (s, 1H), 4.32 (p, J=8.7, 8.7, 8.6, 8.6 Hz, 1H), 4.19 (d, J=11.3 Hz, 2H), 4.10-4.03 (m, 1H), 3.97-3.83 (m, 11H), 3.52 (q, J=7.9, 7.9, 7.9 Hz, 2H), 3.41-3.34 (m, 2H), 3.22-3.10 (m, 2H), 3.01 (s, 3H), 2.91 (s, 2H), 2.80 (q, J=10.1, 10.1, 9.8 Hz, 1H), 2.72-2.60 (m, 1H), 2.32-2.20 (m, 1H), 1.96 (d, J=4.6 Hz, 1H), 1.86-1.55 (m, 16H), 1.52 (d, J=6.5 Hz, 6H), 1.39 (d, J=12.9 Hz, 2H), 0.85 (s, 2H), 0.66 (s, 1H).

Example 74

(3RS)-3-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione

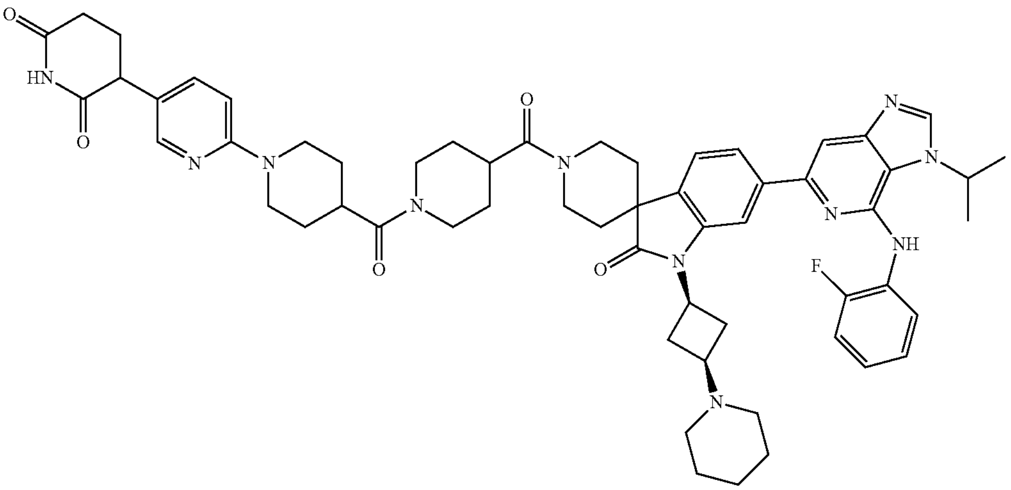 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4)CC3)nc(Nc3ccccc3F)c21]

Using procedures similar to those used for Example 13 but using 1-(1-{5-[2,6-dioxopiperidin-3-yl]pyridin-2-yl}piperidine-4-carbonyl)piperidine-4-carboxylic acid (intermediate 40) (15.0 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.0 mg, 0.033 mmol) as coupling partners afforded the title compound (TFA salt) as an off white solid (20.4 mg, 74% yield). LCMS: $C_{58}H_{68}FN_{11}O_5$ desired mass=1017.5, found: m/z=1018.9 $[M+H]^+$. $^1H$ NMR (500 MHz, Methanol-$d_4$) δ 7.99 (dd, J=9.6, 2.3 Hz, 1H), 7.87 (d, J=2.3 Hz, 1H), 7.82 (s, 1H), 7.77 (dd, J=7.8, 1.5 Hz, 1H), 7.70 (td, J=7.8, 2.4 Hz, 1H), 7.62 (s, 1H), 7.52 (d, J=8.0 Hz, 1H), 7.43 (d, J=9.6 Hz, 1H), 7.34-7.22 (m, 2H), 4.88 (s, 1H), 4.60 (s, 1H), 4.11 (s, 2H), 3.97 (dd, J=12.9, 5.0 Hz, 2H), 3.65-3.50 (m, 3H), 3.48-3.38 (m, 2H), 3.33-3.26 (m, 1H), 3.22 (s, 1H), 3.12 (dt, J=19.9, 10.3 Hz, 1H), 2.92 (t, J=12.0 Hz, 3H), 2.87-2.73 (m, 2H), 2.32 (tt, J=12.6, 6.3 Hz, 1H), 2.25-2.16 (m, 1H), 2.05 (s, 1H), 2.00 (d, J=17.7 Hz, 2H), 1.95 (s, 2H), 1.90 (s, 11H), 1.86 (s, 1H), 1.79 (s, 2H), 1.74 (d, J=6.7 Hz, 7H), 1.65-1.55 (m, 2H), 1.33 (d, J=18.7 Hz, 1H).

Example 75

(3RS)-3-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(dimethylamino)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione

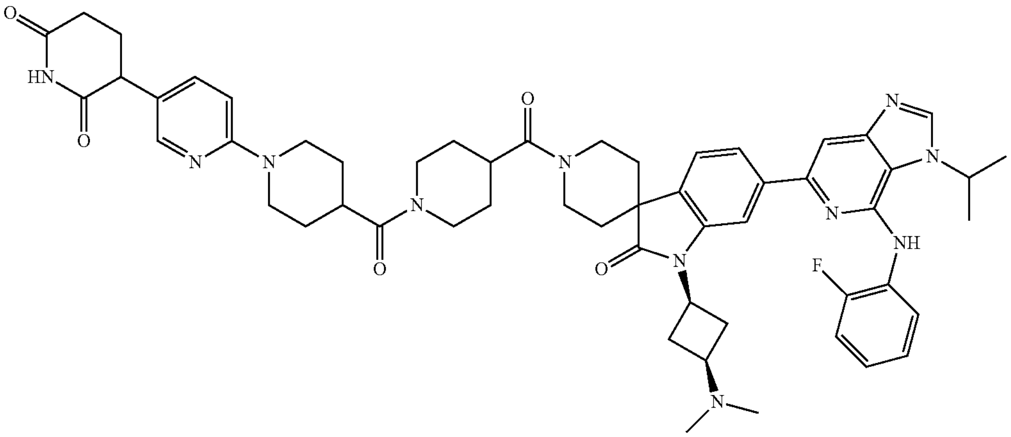 [SMILES: CC(C)n1cnc2cc(-c3ccc4c(c3)N([C@H]3C[C@@H](N(C)C)C3)C(=O)C43CCN(C(=O)C4CCN(C(=O)C5CCN(c6ccc(C7CCC(=O)NC7=O)cn6)CC5)CC4)CC3)nc(Nc3ccccc3F)c21]

Using procedures similar to those used for Example 13 but using 1-(1-{5-[2,6-dioxopiperidin-3-yl]pyridin-2-yl}piperidine-4-carbonyl)piperidine-4-carboxylic acid (intermediate 40) (11.3 mg, 0.026 mmol) and 6-{4-[(2-fluorophenyl)amino]-3-isopropylimidazo[4,5-c]pyridin-6-yl}-1-[(1s,3s)-3-(dimethylamino)cyclobutyl]spiro[indole-3,4'-piperidin]-2-one (15.0 mg, 0.026 mmol) as coupling partners afforded the title compound (TFA salt) as an off white solid (7.7 mg, 27% yield). LCMS: $C_{55}H_{64}FN_{11}O_5$ desired mass=977.5, found: m/z=978.9 $[M+H]^+$. $^1H$ NMR (500 MHz, Methanol-$d_4$) δ 7.98 (dd, J=9.5, 2.3 Hz, 1H), 7.87 (d, J=2.3 Hz, 1H), 7.82 (s, 1H), 7.80-7.74 (m, 1H), 7.70 (td, J=8.0, 2.0 Hz, 1H), 7.63 (s, 1H), 7.52 (d, J=7.9 Hz, 1H), 7.42 (d, J=9.6 Hz, 1H), 7.32-7.21 (m, 2H), 5.35-5.28 (m, 1H), 4.59 (s, 1H), 4.29 (d, J=8.2 Hz, 1H), 4.11 (s, 3H), 4.03-3.92 (m, 2H), 3.67 (p, J=8.2 Hz, 1H), 3.52 (s, 1H), 3.46-3.37 (m, 2H), 3.33-3.26 (m, 2H), 3.22 (s, 1H), 3.14 (s, 3H), 3.07 (s, 1H), 2.90 (s, 1H), 2.93-2.86 (m, 1H), 2.83-2.72 (m, 2H), 2.32 (tt, J=12.7, 6.4 Hz, 1H), 2.24-2.17 (m, 1H), 1.90 (dd, J=29.9, 15.5 Hz, 13H), 1.73 (d, J=6.7 Hz, 6H), 1.63 (dd, J=23.9, 13.4 Hz, 2H), 1.33 (d, J=16.5 Hz, 1H).

Example 76

(3RS)-3-(6-{4-[4-({6-[4-(2-fluorophenoxy)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

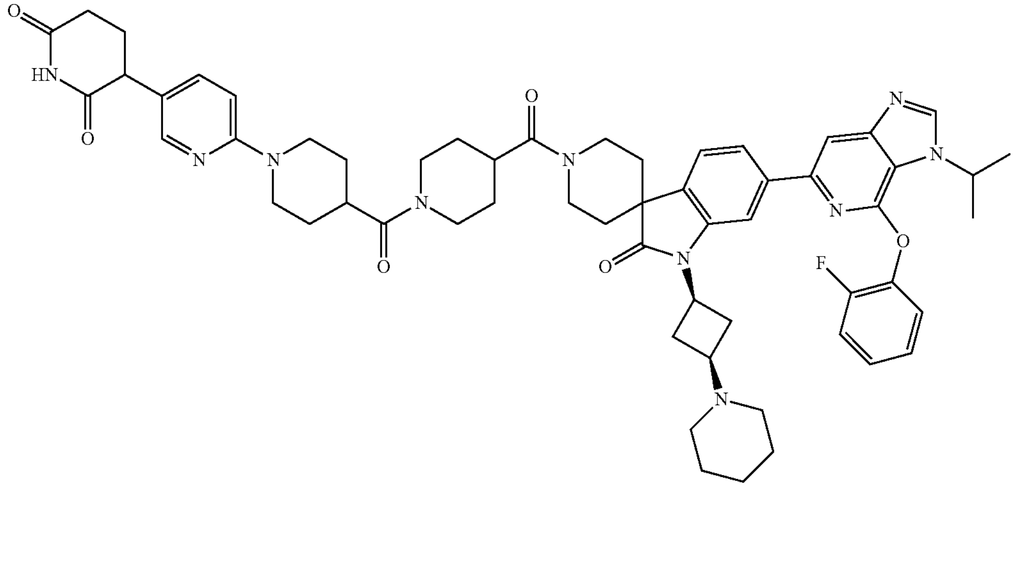 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4)CC3)nc(Oc3ccccc3F)c21]

Using procedures similar to those used for Example 13 but using 1-(1-{5-[2,6-dioxopiperidin-3-yl]pyridin-2-yl}piperidine-4-carbonyl)piperidine-4-carboxylic acid (intermediate 40) (11.3 mg, 0.026 mmol) (7.4 mg, 0.016 mmol) and 6-[4-(2-fluorophenoxy)-3-isopropylimidazo[4,5-c]pyridin-6-yl]-1-[(1s,3s)-3-(piperidin-1-yl)cyclobutyl]spiro[indole-3,4'-piperidin]-2-one (10.0 mg, 0.016 mmol) as coupling partners afforded the title compound (TFA salt) as an off white solid (16.3 mg, 94% yield). LCMS: $C_{58}H_{67}FN_{10}O_6$ desired mass=1018.5, found: m/z=1020.0 $[M+H]^+$. $^1H$ NMR (500 MHz, Methanol-$d_4$) δ 8.65 (s, 1H), 8.02-7.96 (m, 1H), 7.95 (s, 1H), 7.87 (d, J=2.4 Hz, 1H), 7.67 (d, J=7.7 Hz, 1H), 7.53 (t, J=7.7 Hz, 1H), 7.44 (s, 6H), 7.39 (q, J=8.2, 7.2 Hz, 2H), 4.59 (s, 1H), 4.22 (s, 4H), 4.17 (d, J=7.9 Hz, 1H), 4.10 (s, 2H), 4.04 (s, 1H), 3.96 (dd, J=13.2, 4.8 Hz, 3H), 3.59 (dd, J=24.0, 10.4 Hz, 4H), 3.43 (d, J=11.5 Hz, 2H), 3.22 (s, 1H), 3.16-3.04 (m, 1H), 2.96 (d, J=12.5 Hz, 2H), 2.93-2.83 (m, 1H), 2.83-2.72 (m, 2H), 2.37-2.26 (m, 1H), 2.06 (d, J=14.2 Hz, 2H), 1.98 (s, 1H), 1.91 (s, 5H), 1.78 (d, J=6.7 Hz, 11H), 1.60 (d, J=14.6 Hz, 3H), 1.33 (d, J=20.0 Hz, 2H).

Example 77

(3RS)-3-[6-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione

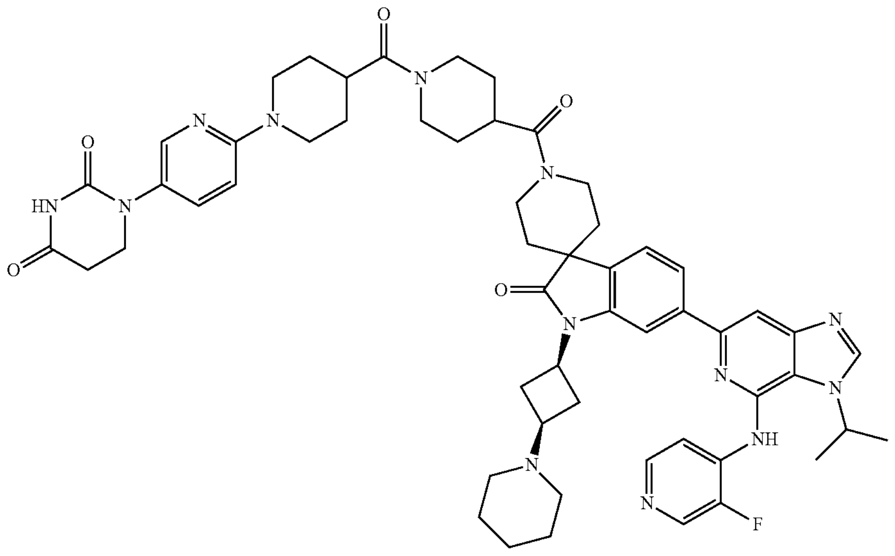 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)cn6)CC5)CC4)CC3)nc(Nc3ccncc3F)c21]

Example 77 was prepared by similar procedures as Example 1 using 1-(1-{5-[2,6-dioxopiperidin-3-yl]pyridin-2-yl}piperidine-4-carbonyl)piperidine-4-carboxylic acid (intermediate 40) (15 mg, 0.025 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3, 4'-piperidin]-2-one (13 mg, 0.03 mmol) as starting materials. The title compound (TFA salt) was isolated as an off-white solid (15.5 mg, 62% yield). LCMS: $[C_{57}H_{67}FN_{12}O_5]$, desired mass=1019.2, found: m/z=1019.6 $[M+H]^+$, $^1H$ NMR (500 MHz, MeOD) δ 9.00 (d, J=7.9, 1H), 7.84-7.74 (m, 2H), 7.70 (td, J=7.9, 2.4 Hz, 1H), 7.62 (s, 1H), 7.53 (t, J=6.6 Hz, 1H), 7.46 (d, J=8.6 Hz, 2H), 7.40 (d, J=8.7 Hz, 2H), 7.33-7.24 (m, 1H), 7.26 (s, 2H), 5.39-5.31 (m, 1H), 4.61 (s, 1H), 4.29-4.17 (m, 2H), 4.15-4.03 (m, 4H), 3.99 (d, J=18.0 Hz, 2H), 3.89 (t, J=6.7 Hz, 2H), 3.82 (m, 3H), 3.65-3.51 (m, 3H), 3.21-3.07 (m, 6H), 3.05-2.88 (m, 5H), 2.85 (t, J=6.7 Hz, 2H), 2.04 (d, J=14.7 Hz, 5H), 1.97-1.75 (m, 9H), 1.75 (d, J=6.6 Hz, 6H), 1.59 (d, J=15.6 Hz, 2H).

Example 78

(3RS)-3-[6-(4-{4-[(6-{4-[(oxan-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione

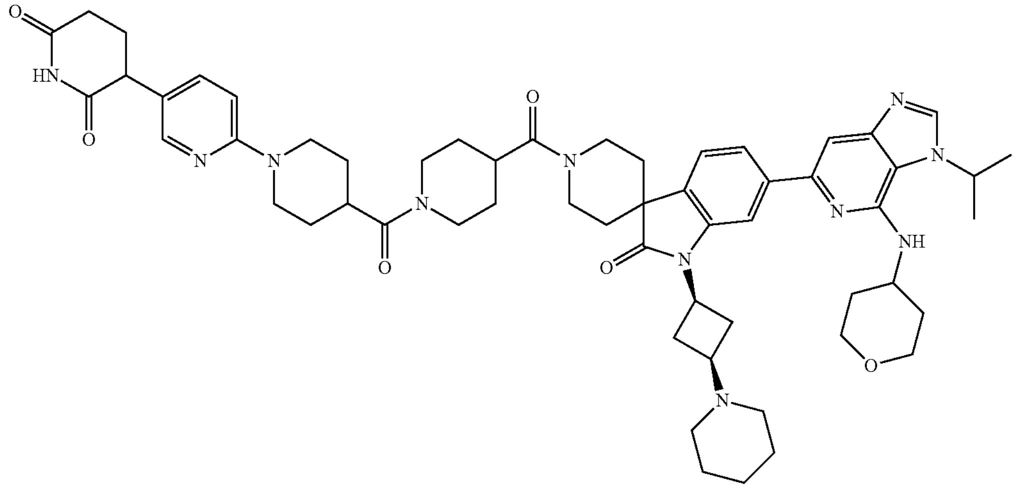 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4)CC3)nc(NC3CCOCC3)c21]

Using procedures similar to those used for Example 13 but using 1-(1-{5-[2,6-dioxopiperidin-3-yl]pyridin-2-yl}piperidine-4-carbonyl)piperidine-4-carboxylic acid (intermediate 40) (11.3 mg, 0.026 mmol) (15.0 mg, 0.033 mmol) and 6-[3-isopropyl-4-(oxan-4-ylamino)imidazo[4,5-c]pyridin-6-yl]-1-[(1s,3s)-3-(piperidin-1-yl)cyclobutyl]spiro[indole-3,4'-piperidin]-2-one (20.0 mg, 0.033 mmol) as coupling partners afforded the title compound (TFA salt) as an off white solid (17.9 mg, 51% yield). LCMS: $C_{57}H_{73}N_{11}O_6$ desired mass=1007.6, found: m/z=1008.5 $[M+H]^+$. $^1H$ NMR (500 MHz, Methanol-$d_4$) δ 8.00 (dd, J=9.5, 2.3 Hz, 1H), 7.89-7.83 (m, 3H), 7.76 (s, 1H), 7.59 (d, J=7.8 Hz, 1H), 7.55 (s, 1H), 7.44 (d, J=9.6 Hz, 2H), 4.60 (s, 2H), 4.51 (dd, J=28.6, 9.8 Hz, 1H), 4.22 (s, 4H), 4.13 (t, J=13.7 Hz, 5H), 4.04 (s, 1H), 3.97 (dd, J=12.9, 4.9 Hz, 2H), 3.76 (q, J=7.1, 6.2 Hz, 1H), 3.71-3.55 (m, 7H), 3.44 (s, 1H), 3.02 (s, 2H), 2.96-2.72 (m, 7H), 2.33 (qd, J=12.4, 5.0 Hz, 1H), 2.23-2.16 (m, 4H), 2.04-1.92 (m, 3H), 1.90 (s, 7H), 1.74 (d, J=6.5 Hz, 8H), 1.60 (d, J=18.4 Hz, 3H), 1.31 (s, 1H).

Example 79

1-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)-1,3-diazinane-2,4-dione

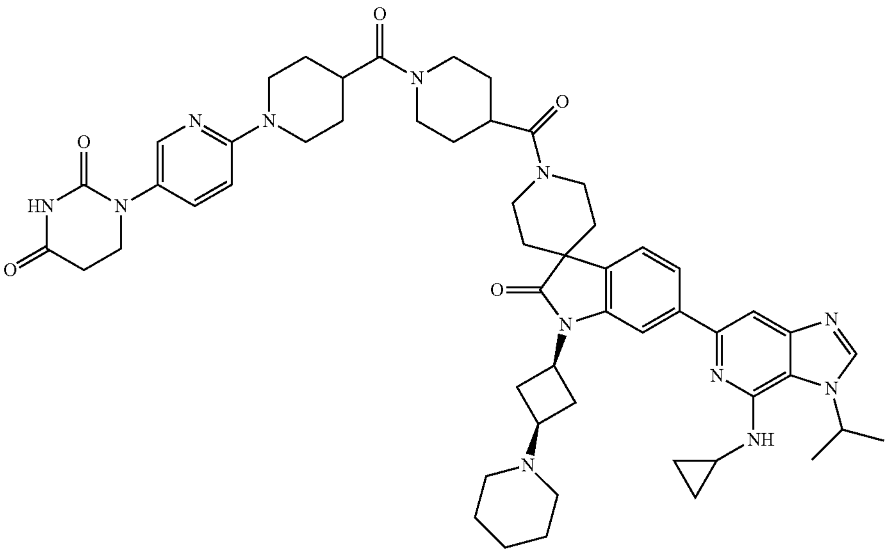 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)cn6)CC5)CC4)CC3)nc(NC3CC3)c21]

Example 79 was prepared by similar procedures as Example 1 using 1-(1-(5-(2,4-dioxotetrahydropyrimidin-1(2H)-yl)pyridin-2-yl)piperidine-4-carbonyl)piperidine-4-carboxylic acid (intermediate 41) (11 mg, 0.025 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (13.6 mg, 74% yield). LCMS: [$C_{54}H_{68}N_{12}O_5$], desired mass=965.2, found: m/z=965.6 $[M+H]^+$, $^1H$ NMR (500 MHz, MeOD) δ 8.94 (s, 1H), 8.05 (d, J=2.7 Hz, 1H), 7.98 (d, J=9.6 Hz, 1H), 7.68 (s, 2H), 7.64 (s, 1H), 7.57 (s, 1H), 7.34 (d, J=9.6 Hz, 1H), 5.17-5.10 (m, 1H), 4.60 (s, 1H), 4.54-4.46 (m, 1H), 4.25 (m, 4H), 4.23-4.05 (m, 4H), 3.87 (t, J=6.7 Hz, 2H), 3.60 (m, 3H), 3.17 (m, 6H), 3.15-2.97 (m, 5H), 2.96 (t, J=6.7 Hz, 2H), 2.05-1.96 (m, 5H), 1.94-1.81 (m, 11H), 1.69 (d, J=6.6 Hz, 6H), 1.59 (m, 2H), 1.31 (s, 1H), 1.14 (s, 2H), 0.94 (s, 2H).

Example 80

1-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]-1,3-diazinane-2,4-dione

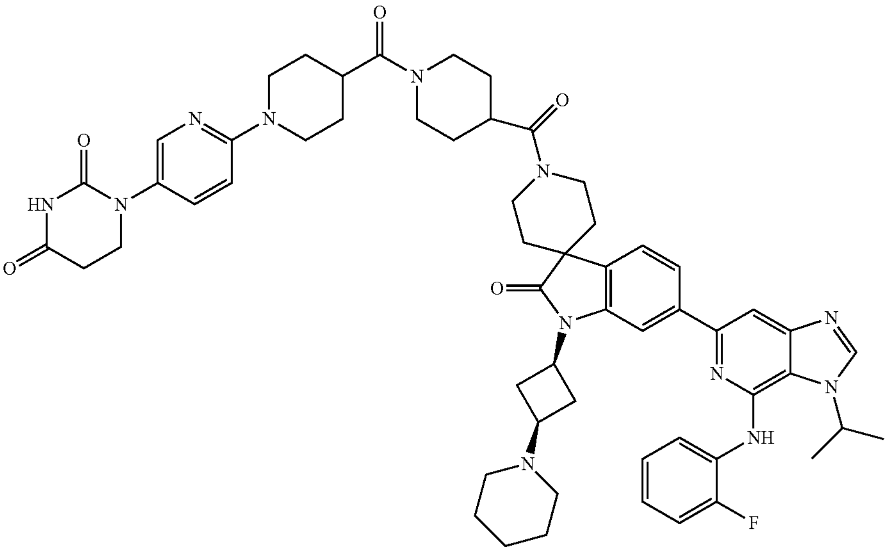

Example 80 was prepared by similar procedures as Example 1 using 1-(1-(5-(2,4-dioxotetrahydropyrimidin-1(2H)-yl)pyridin-2-yl)piperidine-4-carbonyl)piperidine-4-carboxylic acid (intermediate 41) (10 mg, 0.023 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl) spiro[indoline-3,4'-piperidin]-2-one (10 mg, 0.016 mmol) as starting materials. The title compound (TFA salt) was isolated as an off-white solid (11 mg, 60% yield). LCMS: [$C_{57}H_{67}FN_{12}O_5$], desired mass=1019.2, found: m/z=1019.6 $[M+H]^+$, $^1H$ NMR (500 MHz, MeOD) δ 8.95 (d, J=7.9, 1H), 8.05 (d, J=2.6 Hz, 1H), 7.96 (d, J=10.1 Hz, 1H), 7.84-7.74 (m, 2H), 7.70 (t, J=8.0 Hz, 1H), 7.62 (s, 1H), 7.53 (d, J=7.8 Hz, 1H), 7.36-7.22 (m, 4H), 5.34 (s, 1H), 4.60 (s, 1H), 4.3-4.21 (m, 4H), 4.20-4.06 (m, 4H), 3.98 (m, 2H), 3.87 (t, J=6.7 Hz, 2H), 3.64-3.54 (m, 3H), 3.25-3.11 (m, 6H), 3.10-2.76 (m, 7H), 2.09-2.05 (m, 5H), 2.03-1.78 (m, 9H), 1.74 (d, J=6.8 Hz, 6H), 1.61 (s, 2H).

Example 81

1-[6-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]-1,3-diazinane-2,4-dione

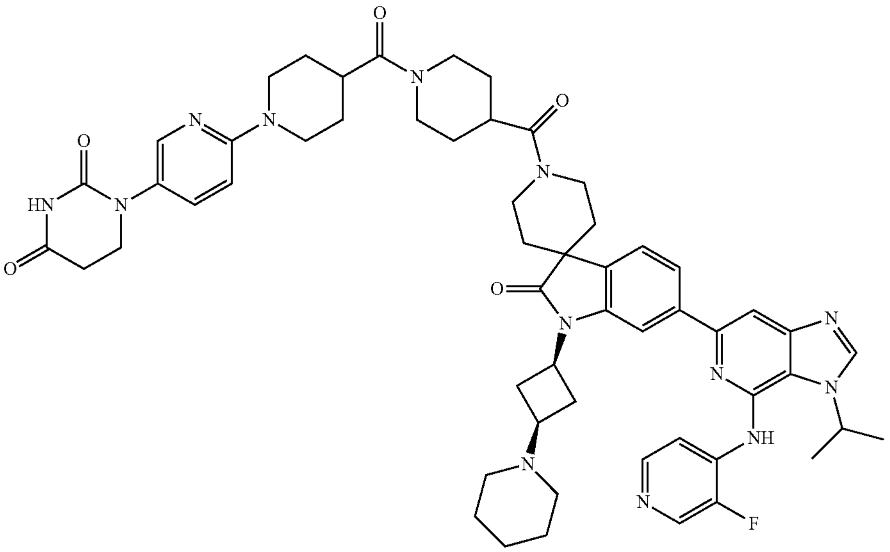

Example 81 was prepared by similar procedures as Example 1 using 1-(1-(5-(2,4-dioxotetrahydropyrimidin-1(2H)-yl)pyridin-2-yl)piperidine-4-carbonyl)piperidine-4-carboxylic acid (intermediate 41) (7 mg, 0.016 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl] spiro[indole-3,4'-piperidin]-2-one (10 mg, 0.016 mmol) as starting materials. The title compound (TFA salt) was isolated as an off-white solid (3.6 mg, 21% yield). LCMS: [$C_{56}H_{66}FN_{13}O_5$], desired mass=1020.2, found: m/z=1020.4 $[M+H]^+$.

Example 82

(3RS)-3-[5-(4-{4-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-2-yl]piperidine-2,6-dione

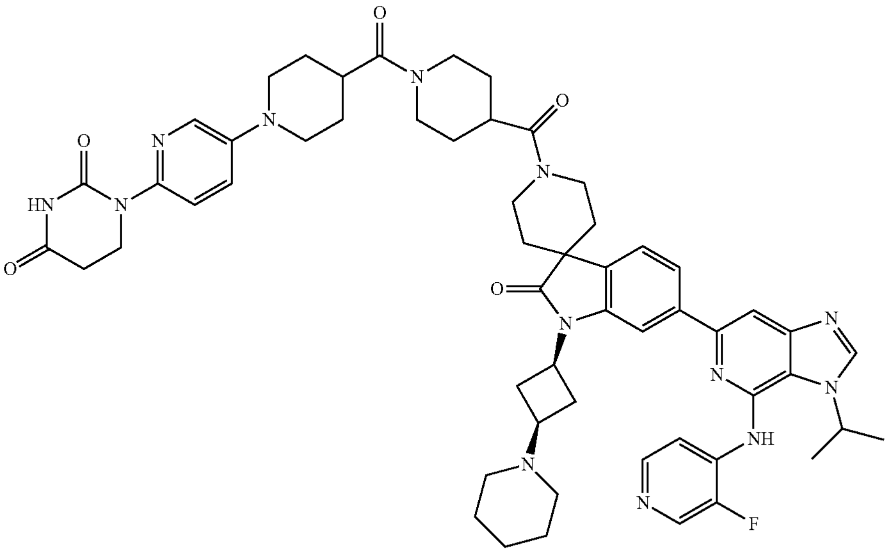 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(N7CCC(=O)NC7=O)nc6)CC5)CC4)CC3)nc(Nc3ccncc3F)c21]

Example 82 was prepared by similar procedures as Example 1 using 1-(1-(6-(2,6-dioxopiperidin-3-yl)pyridin-3-yl)piperidine-4-carbonyl)piperidine-4-carboxylic acid (intermediate 42) (10 mg, 0.023 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.016 mmol) as starting materials. The title compound (TFA salt) was isolated as an off-white solid (8.1 mg, 49% yield). LCMS: [$C_{57}H_{67}FN_{12}O_5$], desired mass=1019.2, found: m/z=1019.7 $[M+H]^+$, $^1H$ NMR (500 MHz, MeOD) δ 8.74 (s, 2H), 8.36-8.26 (m, 2H), 8.22 (s, 1H), 7.95 (d, J=8.6 Hz, 1H), 7.87 (s, 1H), 7.75-7.64 (m, 3H), 7.58 (d, J=7.8 Hz, 1H), 5.21-5.13 (m, 1H), 4.60 (m, 1H), 4.50 (m, 1H), 4.22 (m, 2H), 4.18-4.07 (m, 2H), 4.01 (m, 4H), 3.58 (m, 6H), 3.25-3.06 (m, 4H), 2.98 (m, 2H), 2.90-2.81 (m, 5H), 2.42 (s, 1H), 2.33 (s, 1H), 2.05-1.90 (m, 5H), 1.89-1.75 (m, 9H), 1.65 (dd, J=6.6, 3.0 Hz, 6H), 1.59 (m, 2H).

Example 83

N-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridine-2-carboxamide

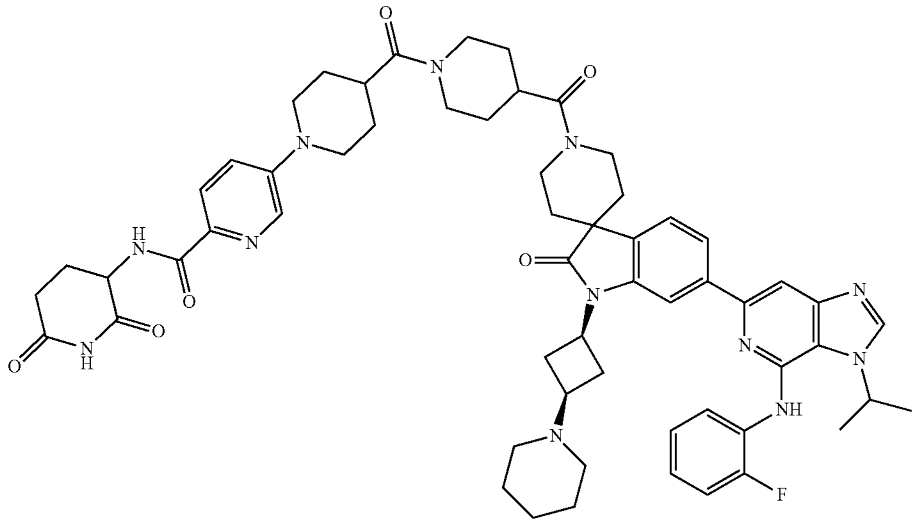 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C(=O)NC7CCC(=O)NC7=O)nc6)CC5)CC4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-(1-(5-(2,6-dioxopiperidin-3-yl)pyridin-2-yl)piperidine-4-carbonyl) piperidine-4-carboxylic acid (intermediate 43) as the coupling partners, the title compound (TFA salt) was isolated as an off-white solid (7.0 mg, 39% yield). LCMS: [C59H69FN12O6], desired mass=1060.5, found: m/z=1061.4 $[M+H]^+$. $^1$H NMR (500 MHz, MeOD) δ 8.91 (d, J=3.6 Hz, 1H), 8.05 (dd, J=12.4, 8.1 Hz, 1H), 7.82-7.68 (m, 4H), 7.68-7.61 (m, 1H), 7.58 (d, J=9.2 Hz, 2H), 7.43 (d, J=2.3 Hz, 1H), 7.30 (dd, J=8.7, 2.3 Hz, 1H), 7.18 (d, J=11.8 Hz, 1H), 5.34 (p, J=6.6 Hz, 1H), 5.10 (dd, J=12.4, 5.5 Hz, 1H), 4.36 (t, J=8.0 Hz, 1H), 4.21-4.11 (m, 1H), 3.96 (s, 3H), 3.68 (s, 4H), 3.56 (d, J=12.6 Hz, 7H), 3.12 (s, 2H), 2.93 (s, 3H), 2.97-2.83 (m, 2H), 2.75 (t, J=13.9 Hz, 2H), 2.46 (s, 3H), 2.16-2.10 (m, 1H), 2.03 (d, J=13.7 Hz, 5H), 1.89 (s, 3H), 1.75 (d, J=6.6 Hz, 7H), 1.59 (t, J=13.2 Hz, 1H), 1.31 (s, 1H), 1.21-1.14 (m, 6H).

Example 84

3-(5-{4-[4-({6-[4-(cyclopropylamino)-3-(propan-2-yl)-3H-imidazo[4,5-c]pyridin-6-yl]-2-Oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-2-yl)piperidine-2,6-dione

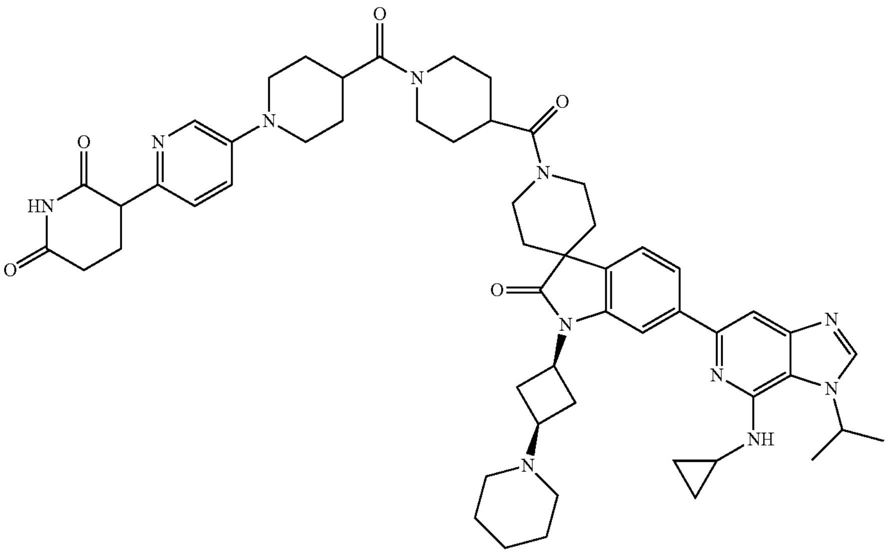 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)nc6)CC5)CC4)CC3)nc(NC3CC3)c21]

Example 84 was prepared by similar procedures as Example 1 using 1-(1-(6-(2,6-dioxopiperidin-3-yl)pyridin-3-yl)piperidine-4-carbonyl)piperidine-4-carboxylic acid (intermediate 42) (7.7 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (10.6 mg, 55% yield). LCMS: $[C_{55}H_{69}N_{11}O_5]$, desired mass=964.2, found: m/z=964.6 $[M+H]^+$.

Example 85

3-[5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-2-yl]piperidine-2,6-dione

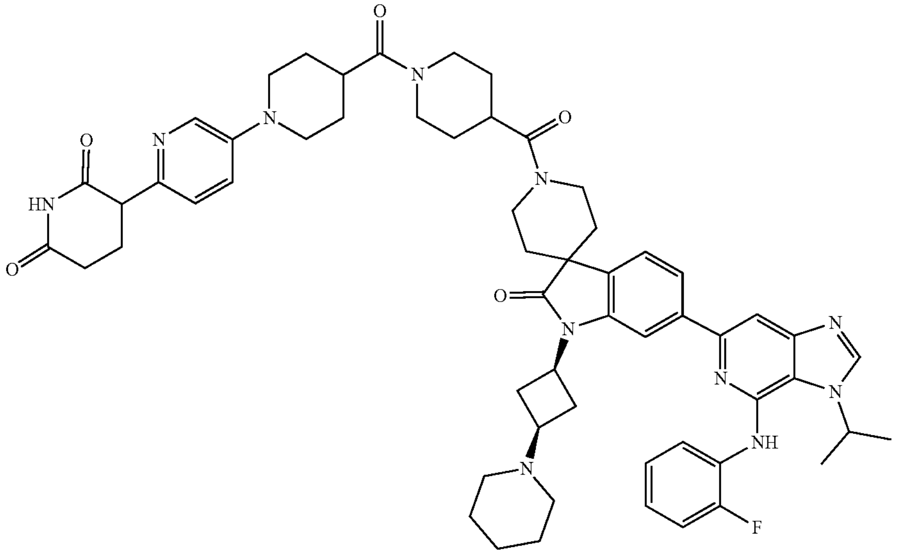 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)nc6)CC5)CC4)CC3)nc(Nc3ccccc3F)c21]

Example 85 was prepared by similar procedures as Example 1 using 1-(1-(6-(2,6-dioxopiperidin-3-yl)pyridin-3-yl)piperidine-4-carbonyl)piperidine-4-carboxylic acid (intermediate 42) (10 mg, 0.023 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (8.3 mg, 45% yield). LCMS: [$C_{58}H_{68}FN_{11}O_5$], desired mass=1018.2, found: m/z=1018.6 $[M+H]^+$.

Example 86

5-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}-2-[(3RS)-2,6-dioxopiperidin-3-yl]-2,3-dihydro-1H-isoindole-1,3-dione

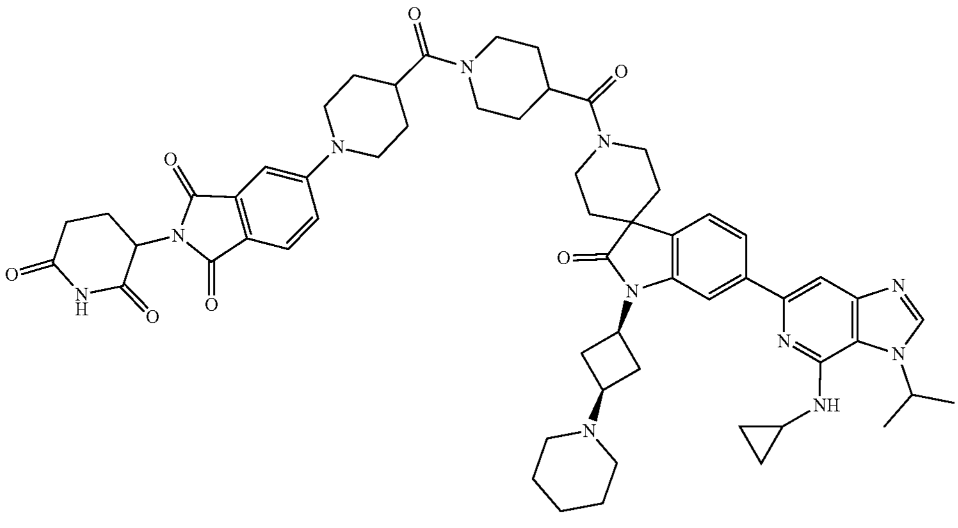 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc7c(c6)C(=O)N(C6CCC(=O)NC6=O)C7=O)CC5)CC4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 1-(1-(2-(2,6-dioxopiperidin-3-yl)-1,3-dioxoisoindolin-5-yl)piperidine-4-carbonyl)piperidine-4-carboxylic acid (intermediate 44) as the coupling partners, the title compound (TFA salt) was isolated as an off-white solid (31 mg, 86% yield). LCMS: [C58H69N11O7], desired mass=1031.5, found: m/z=1032.9 $[M+H]^+$. $^1H$ NMR (500 MHz, DMSO) δ 11.09 (s, 1H), 9.38 (s, 1H), 8.91 (s, 1H), 7.85 (s, 1H), 7.74 (s, 1H), 7.71-7.64 (m, 3H), 7.35 (d, J=2.3 Hz, 1H), 7.27 (dd, J=8.7, 2.3 Hz, 1H), 5.21-5.14 (m, 1H), 5.08 (dd, J=12.8, 5.4 Hz, 2H), 4.42 (s, 1H), 4.34 (q, J=8.2 Hz, 3H), 4.08 (s, 4H), 3.94 (s, 5H), 3.54 (q, J=8.2 Hz, 2H), 3.43-3.36 (m, 3H), 3.19-3.07 (m, 3H), 3.03 (s, 2H), 2.93 (s, 2H), 2.83 (td, J=15.1, 7.6 Hz, 3H), 2.69 (d, J=12.7 Hz, 1H), 2.62 (d, J=3.8 Hz, 1H), 2.59 (d, J=4.8 Hz, 1H), 2.06-2.00 (m, 1H), 1.84 (s, 2H), 1.74 (s, 3H), 1.63 (d, J=13.7 Hz, 3H), 1.55 (d, J=6.4 Hz, 6H), 1.41 (d, J=13.0 Hz, 2H), 1.25 (s, 1H), 0.88 (s, 1H), 0.68 (s, 1H).

Example 87

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)-2,3-dihydro-1H-isoindole-1,3-dione

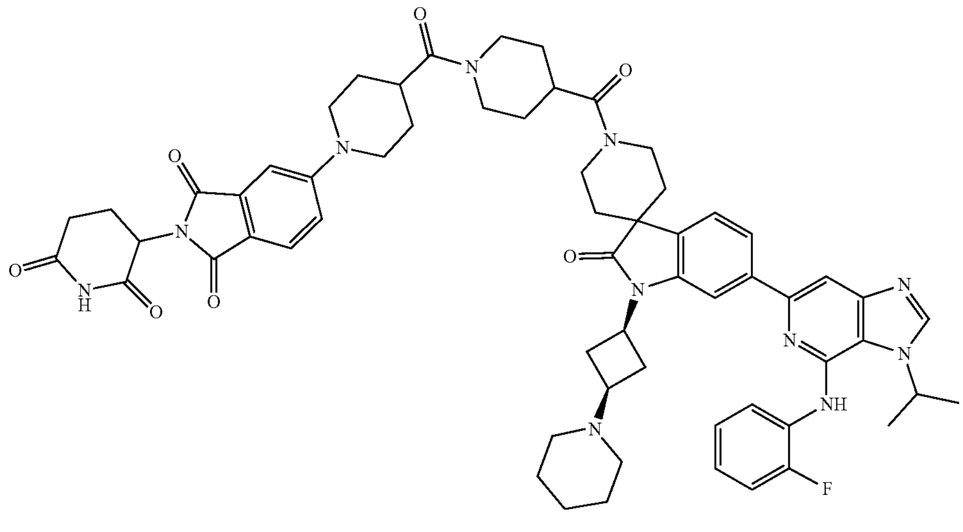 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc7c(c6)C(=O)N(C6CCC(=O)NC6=O)C7=O)CC5)CC4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 1-(1-(2-(2,6-dioxopiperidin-3-yl)-1,3-dioxoisoindolin-5-yl)piperidine-4-carbonyl)piperidine-4-carboxylic acid (intermediate 44) as the coupling partners, the title compound (TFA salt) was isolated as an off-white solid (9.6 mg, 54% yield). LCMS: [C61H68FN11O7], desired mass=1085.5, found: m/z=1086.5 $[M+H]^+$.

Example 88

2-[(3RS)-2,6-dioxopiperidin-3-yl]-5-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)-2,3-dihydro-1H-isoindole-1,3-dione

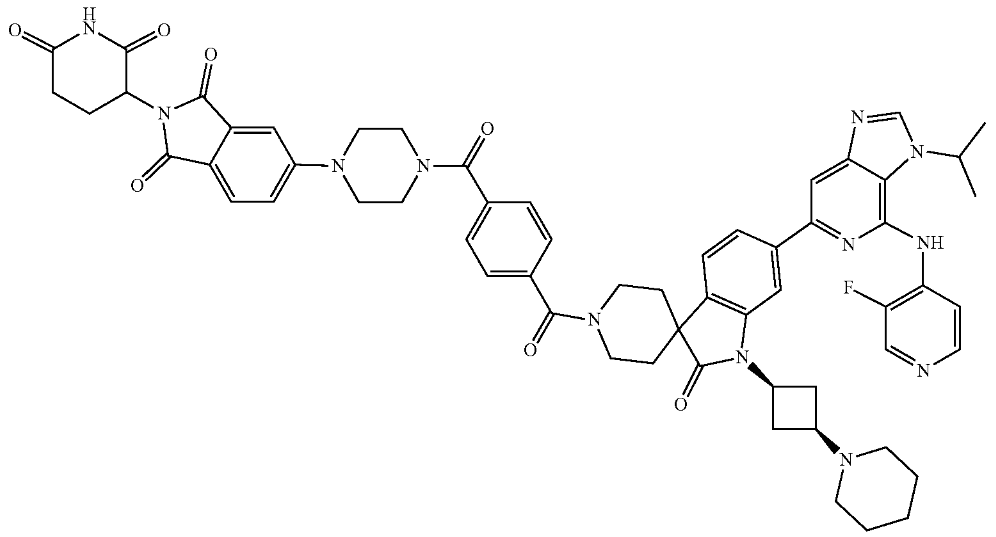 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)cc4)CC3)nc(Nc3ccncc3F)c21]

Example 88 was prepared by similar procedures as Example 1 using 1-(1-(2-(2,6-dioxopiperidin-3-yl)-1,3-dioxoisoindolin-5-yl)piperidine-4-carbonyl)piperidine-4-carboxylic acid (intermediate 44) (56 mg, 0.144 mmol) and 6-(4-((3-fluoropyridin-4-yl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (65 mg, 0.090 mmol) as starting materials. The title compound (TFA salt) was isolated as an off-white solid (49 mg, 50% yield). LCMS: [$C_{60}H_{67}FN_{12}O_7$], desired mass=1087.2, found: m/z=1088.3 $[M+H]^+$.

Example 89

(3RS)-3-(2-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyrimidin-5-yl)piperidine-2,6-dione

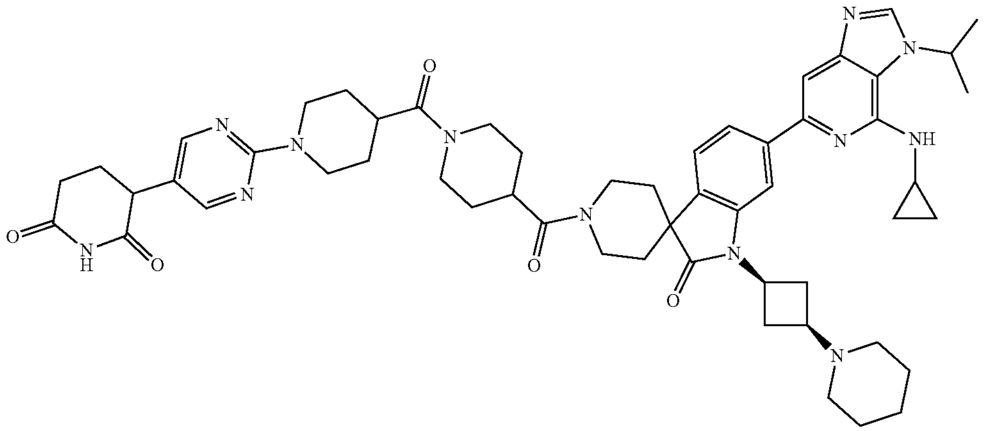 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ncc(C7CCC(=O)NC7=O)cn6)CC5)CC4)CC3)nc(NC3CC3)c21]

Example 89 was prepared by similar procedures as Example 1 using 1-(1-(6-(2,6-dioxopiperidin-3-yl)pyridin-3-yl)piperidine-4-carbonyl)piperidine-4-carboxylic acid (intermediate 45) (7.7 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (3 mg, 17% yield). LCMS: [$C_{54}H_{68}N_{12}O_5$], desired mass=965.2, found: m/z=965.8 $[M+H]^+$, $^1H$ NMR (500 MHz, DMSO) δ 10.88 (s, 1H), 9.41 (s, 1H), 8.77 (s, 1H), 8.25 (s, 2H), 7.86 (s, 1H), 7.74 (s, 1H), 7.66 (s, 1H), 6.70 (s, 1H), 5.27 (m, J=6.7, 6.7, 6.6, 6.6 Hz, 1H), 4.62 (s, 2H), 4.39 (d, J=10.5 Hz, 1H), 4.08 (m, J=9.6, 9.6, 9.5, 9.5 Hz, 2H), 3.87 (d, J=30.9 Hz, 4H), 3.72 (dd, J=12.7, 4.8 Hz, 2H), 3.13 (t, J=12.2, 12.2 Hz, 2H), 3.02-2.58 (m, 15H), 2.22 (qd, J=12.9, 12.8, 12.8, 4.3 Hz, 1H), 2.04-1.94 (m, 1H), 1.86 (d, J=13.9 Hz, 2H), 1.80-1.61 (m, 10H), 1.53 (d, J=6.4 Hz, 6H), 1.51 (m, 2H), 1.08 (m, 1H), 0.88 (s, 2H), 0.66 (s, 2H).

Example 90

3-(2-(4-(4-(6-(4-((2-fluorophenyl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidine-1-carbonyl)piperidin-1-yl)pyrimidin-5-yl)piperidine-2,6-dione

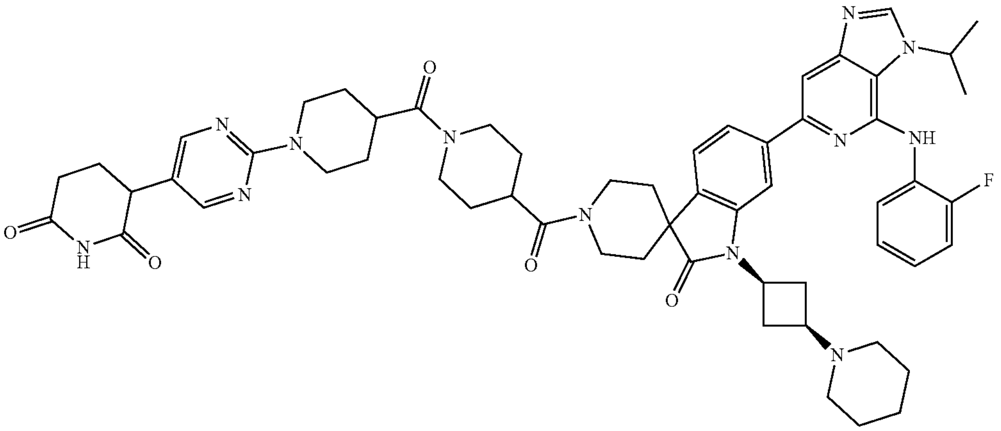 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ncc(C7CCC(=O)NC7=O)cn6)CC5)CC4)CC3)nc(Nc3ccccc3F)c21]

The title compound was synthesized using similar methods to example 10, using BOP coupling to condense 1-(1-(6-(2,6-dioxopiperidin-3-yl)pyridin-3-yl)piperidine-4-carbonyl)piperidine-4-carboxylic acid (intermediate 45) with 6-(4-((2-fluorophenyl)amino)-3-isopropyl-3H-imidazo[4,5-c]pyridin-6-yl)-1-((1s,3s)-3-(piperidin-1-yl)cyclobutyl) spiro[indoline-3,4'-piperidin]-2-one. Afforded a pale white solid (62 mg, 0.0609 mmol, 35%) as a free base. LCMS: [$C_{57}H_{67}FN_{12}O_5$], exact mass=1018.5, found: m/z=1019.8 $[M+H]^+$. $^1H$ NMR (500 MHz, DMSO-$d_6$) δ 10.84 (s, 1H), 9.32 (s, 1H), 8.61 (s, 1H), 8.33 (s, 1H), 8.22 (s, 2H), 7.87 (s, 1H), 7.67 (d, J=7.8 Hz, 1H), 7.55 (td, J=7.9, 7.9, 2.6 Hz, 2H), 7.47 (s, 1H), 7.29 (ddd, J=11.5, 7.3, 2.7 Hz, 1H), 7.19 (td, J=8.2, 7.6, 2.1 Hz, 2H), 5.27 (p, J=6.7, 6.7, 6.6, 6.6 Hz, 1H), 4.62 (s, 2H), 4.39 (d, J=10.5 Hz, 1H), 4.08 (p, J=9.6, 9.6, 9.5, 9.5 Hz, 2H), 3.87 (d, J=30.9 Hz, 4H), 3.72 (dd, J=12.7, 4.8 Hz, 2H), 3.13 (t, J=12.2, 12.2 Hz, 2H), 3.02-2.58 (m, 15H), 2.22 (qd, J=12.9, 12.8, 12.8, 4.3 Hz, 1H), 2.04-1.94 (m, 1H), 1.86 (d, J=13.9 Hz, 2H), 1.80-1.61 (m, 10H), 1.57 (d, J=6.6 Hz, 7H), 1.44 (dt, J=38.7, 12.0, 12.0 Hz, 4H).

Example 91

(3RS)-3-[2-(4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyrimidin-5-yl]piperidine-2,6-dione

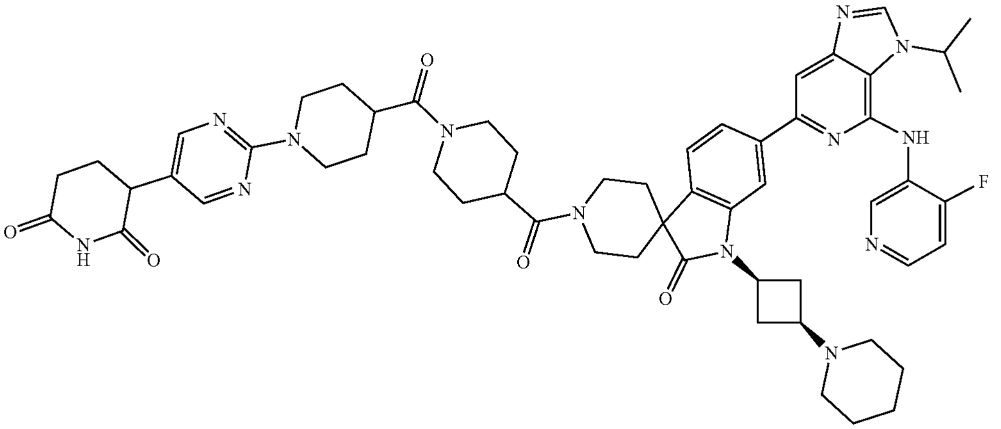 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ncc(C7CCC(=O)NC7=O)cn6)CC5)CC4)CC3)nc(Nc3cnccc3F)c21]

Example 91 was prepared by similar procedures as Example 1 using 1-(1-(6-(2,6-dioxopiperidin-3-yl)pyridin-3-yl)piperidine-4-carbonyl)piperidine-4-carboxylic acid (7 mg, 0.016 mmol) (intermediate 45) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.016 mmol) as starting materials. The title compound (TFA salt) was isolated as an off-white solid (8 mg, 47% yield). LCMS: [$C_{56}H66FN_{13}O_5$], desired mass=1020.2, found: m/z=1020.8 $[M+H]^+$, $^1H$ NMR (500 MHz, DMSO) δ 10.88 (s, 1H), 10.29 (s, 1H), 9.42 (s, 1H), 8.83 (d, J=4.5 Hz, 1H), 8.75 (s, 1H), 8.39-8.30 (m, 2H), 8.25 (s, 2H), 7.80 (d, J=7.8 Hz, 1H), 7.70-7.58 (m, 2H), 5.15 (m, J=6.7, 6.7, 6.6, 6.6 Hz, 1H), 4.62 (s, 2H), 4.39 (d, J=10.5 Hz, 1H), 4.08 (m, J=9.6, 9.6, 9.5, 9.5 Hz, 2H), 3.87 (d, J=30.9 Hz, 4H), 3.72 (dd, J=12.7, 4.8 Hz, 2H), 3.13 (t, J=12.2, 12.2 Hz, 2H), 3.04-2.51 (m, 15H), 2.22 (qd, J=12.9, 12.8, 12.8, 4.3 Hz, 1H), 2.07-1.9 (m, 1H), 1.86 (d, J=13.9 Hz, 2H), 1.78-1.6 (m, 10H), 1.53 (d, J=6.4 Hz, 6H), 1.41 (m, 2H).

Example 92

3-(6-(4-(2-(4-(6-(4-((2-fluorophenyl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)piperidin-1-yl)-2-oxoethyl)piperidin-1-yl)pyridin-3-yl)piperidine-2,6-dione

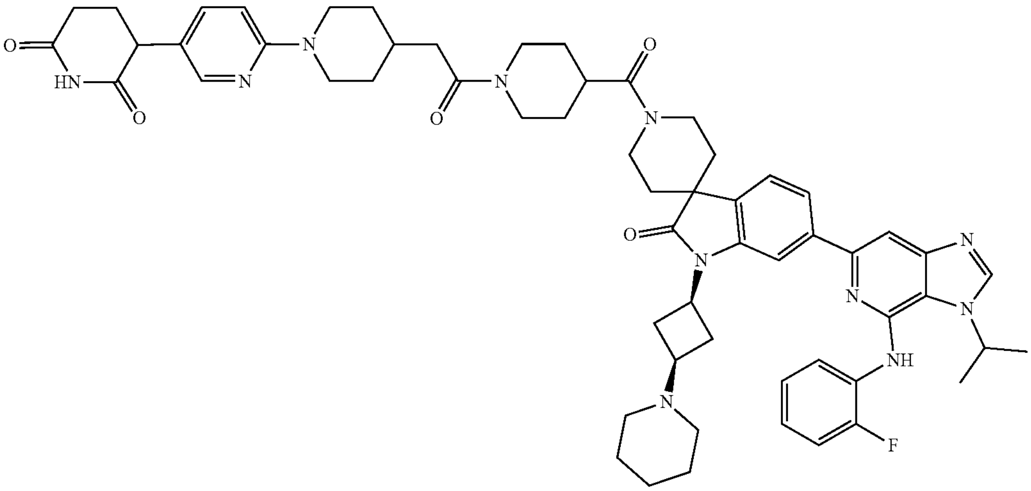 [SMILES: CC(C)n1cnc2cc(-c3ccc4c(c3)N([C@H]3C[C@@H](N5CCCCC5)C3)C(=O)C43CCN(C(=O)C4CCN(C(=O)CC5CCN(c6ccc(C7CCC(=O)NC7=O)cn6)CC5)CC4)CC3)nc(Nc3ccccc3F)c21]

The title compound was synthesized using similar methods to Example 24, using BOP coupling to condense 1-(2-(1-(5-(2,6-dioxopiperidin-3-yl)pyridin-2-yl)piperidin-4-yl)acetyl)piperidine-4-carboxylic acid (intermediate 46) with 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one. Afforded a white solid (16 mg, 25% yield). LCMS: [$C_{59}H_{70}FN_{11}O_5$], desired mass=1031.5, found: m/z=1032.8 $[M+H]^+$. $^1H$ NMR (500 MHz, DMSO-$d_6$): δ (ppm): 10.80 (s, 1H), 9.26 (s, 1H), 8.52 (s, 1H), 8.31 (s, 1H), 7.92-7.86 (m, 2H), 7.67 (d, J=7.8 Hz, 1H), 7.53 (d, J=8.2 Hz, 2H), 7.48 (s, 1H), 7.35 (d, J=7.9 Hz, 1H), 7.31-7.26 (m, 1H), 7.19 (q, J=6.2, 6.2, 5.2 Hz, 3H), 6.78 (d, J=8.9 Hz, 1H), 5.27-5.21 (m, 1H), 4.41 (s, 1H), 4.23 (d, J=10.9 Hz, 2H), 4.10-4.06 (m, 1H), 3.90 (s, 3H), 3.81 (d, J=17.2 Hz, 2H), 3.71 (dd, J=12.2, 5.0 Hz, 2H), 3.05 (d, J=12.1 Hz, 3H), 2.95-2.90 (m, 3H), 2.84 (d, J=11.8 Hz, 3H), 2.76 (s, 4H), 2.66-2.60 (m, 3H), 2.26 (s, 1H), 2.17-2.13 (m, 1H), 1.97-1.92 (m, 3H), 1.84 (s, 1H), 1.75 (s, 2H), 1.71 (d, J=12.0 Hz, 3H), 1.66 (s, 2H), 1.58-1.54 (m, 9H), 1.40 (d, J=11.8 Hz, 3H), 1.22 (s, 1H), 1.13 (s, 1H).

Example 93

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione

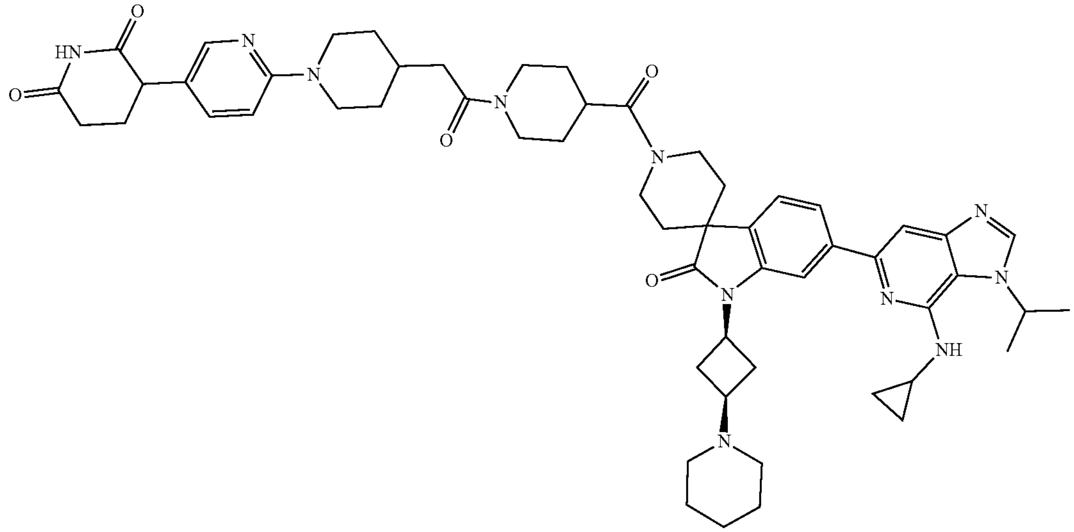 [SMILES: CC(C)n1cnc2cc(-c3ccc4c(c3)N([C@H]3C[C@@H](N5CCCCC5)C3)C(=O)C43CCN(C(=O)C4CCN(C(=O)CC5CCN(c6ccc(C7CCC(=O)NC7=O)cn6)CC5)CC4)CC3)nc(NC3CC3)c21]

Example 93 was prepared by similar procedures as Example 1 using 1-(2-(1-(5-(2,6-dioxopiperidin-3-yl)pyridin-2-yl)piperidin-4-yl)acetyl)piperidine-4-carboxylic acid (intermediate 46) (8 mg, 0.024 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (9 mg, 55% yield). LCMS: [$C_6H_{71}N_{11}O_5$], desired mass=978.2, found: m/z=978.8 $[M+H]^+$, $^1H$ NMR (500 MHz, DMSO) δ 10.92 (s, 1H), 9.44 (s, 1H), 8.75 (s, 1H), 7.90 (d, J=2.3 Hz, 1H), 7.85 (s, 1H), 7.74 (s, 1H), 7.66 (s, 1H), 7.25 (s, 1H), 6.72 (s, 1H), 5.18-5.10 (m, 1H), 4.45 (s, 1H), 4.38-4.30 (m, 1H), 4.20 (d, J=12.9 Hz, 1H), 3.54 (q, J=8.2 Hz, 1H), 3.40 (d, J=11.5 Hz, 2H), 3.10 (m, 2H), 2.93 (m, 4H), 2.83 (d, J=11.6 Hz, 2H), 2.69 (td, J=12.5, 5.8 Hz, 2H), 2.57 (d, J=19.0 Hz, 1H), 2.38-2.24 (m, 2H), 2.06-1.95 (m, 2H), 1.93-1.59 (m, 20H), 1.54 (d, J=6.4 Hz, 6H), 1.41 (d, J=12.7 Hz, 2H), 1.25 (s, 1H), 0.85 (s, 2H), 0.66 (s, 2H).

Example 94

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]-2-oxoethyl}piperazin-1-yl)pyridin-3-yl]piperidine-2,6-dione

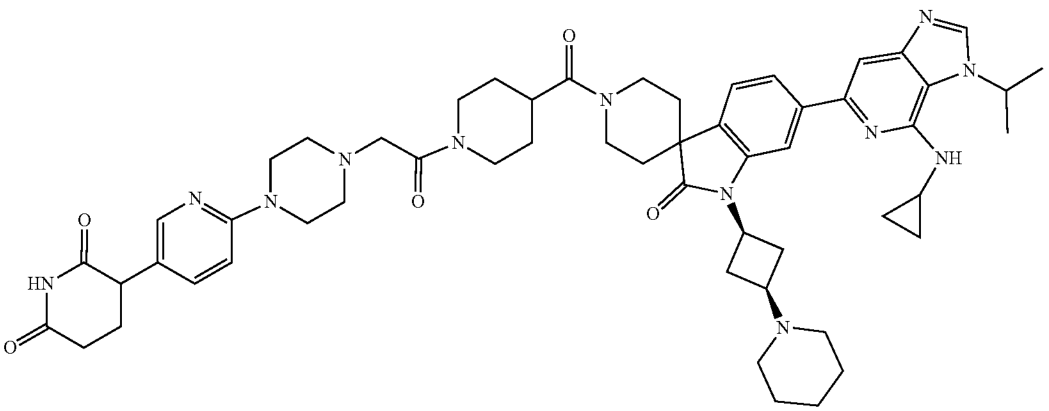 [SMILES: CC(C)n1cnc2cc(-c3ccc4c(c3)N([C@H]3C[C@@H](N5CCCCC5)C3)C(=O)C43CCN(C(=O)C4CCN(C(=O)CN5CCN(c6ccc(C7CCC(=O)NC7=O)cn6)CC5)CC4)CC3)nc(NC3CC3)c21]

Example 94 was prepared by similar procedures as Example 1 using 1-(2-(4-(5-(2,6-dioxopiperidin-3-yl)pyridin-2-yl)piperazin-1-yl)acetyl)piperidine-4-carboxylic acid (intermediate 47) (8 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (10.6 mg, 55% yield). LCMS: [$C_{55}H_{70}N_{12}O_5$], desired mass=979.2, found: m/z=979.7 $[M+H]^+$.

Example 95

(3RS)-3-{6-[4-(2-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidin-1-yl}-2-oxoethyl)piperazin-1-yl]pyridin-3-yl}piperidine-2,6-dione Example 95 was prepared by similar procedures as Example 1 using 1-(1-(6-(2,6-dioxopiperidin-3-yl)pyridin-3-yl)piperidine-4-carbonyl)piperidine-4-carboxylic acid (intermediate 47) (10 mg, 0.023 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.016 mmol) as starting materials. The title compound (TFA salt) was isolated as an off-white solid (8.3 mg, 45% yield). LCMS: [$C_{58}H_{69}FN_{12}O_5$], desired mass=1018.2, found: m/z=1018.6 $[M+H]^+$, $^1H$ NMR (500 MHz, MeOD) δ 8.75 (d, J=8.8 Hz, 1H), 8.11 (s, 1H), 7.79 (d, J=22.8 Hz, 2H), 7.70 (t, J=7.9 Hz, 1H), 7.66-7.57 (m, 2H), 7.53 (t, J=7.3 Hz, 1H), 7.25 (dq, J=18.7, 10.9, 10.1 Hz, 3H), 7.00 (d, J=8.8 Hz, 1H), 5.16 (m, 1H), 4.60 (s, 1H), 4.49 (q, J=8.5 Hz, 1H), 4.42 (d, J=16.1 Hz, 1H), 4.32 (d, J=16.0 Hz, 1H), 4.14 (m, 2H), 4.06-3.94 (m, 5H), 3.92-3.77 (m, 2H), 3.66-3.43 (m, 4H), 3.24 (d, J=9.5 Hz, 1H), 3.16 (m, 2H), 3.04-2.85 (m, 6H), 2.84-2.62 (m, 5H), 2.33-2.24 (m, 1H), 2.23-2.14 (m, 1H), 2.05-1.90 (m, 5H), 1.89-1.75 (m, 9H), 1.72 (d, J=6.6 Hz, 6H), 1.60 (m, 2H).

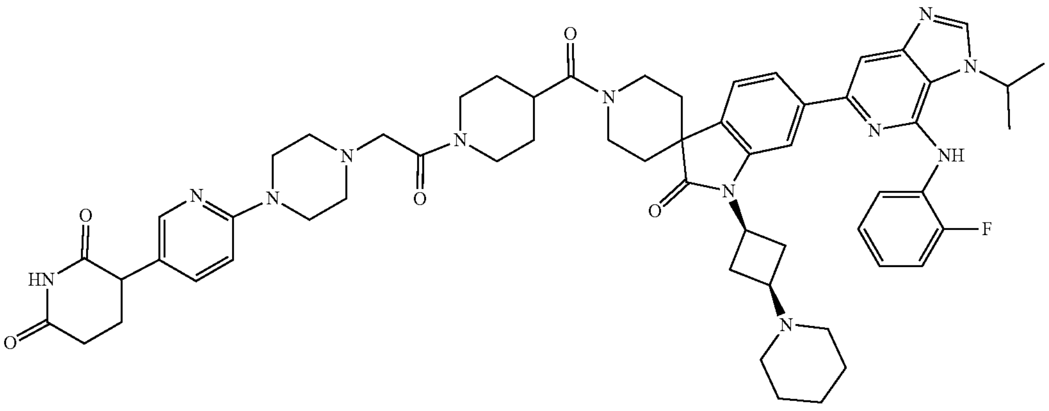 [SMILES: CC(C)n1cnc2cc(-c3ccc4c(c3)N([C@H]3C[C@@H](N5CCCCC5)C3)C(=O)C43CCN(C(=O)C4CCN(C(=O)CN5CCN(c6ccc(C7CCC(=O)NC7=O)cn6)CC5)CC4)CC3)nc(Nc3ccccc3F)c21]

Example 96

(3RS)-3-{6-[4-(2-{4-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidin-1-yl}-2-oxoethyl)piperazin-1-yl]pyridin-3-yl}piperidine-2,6-dione

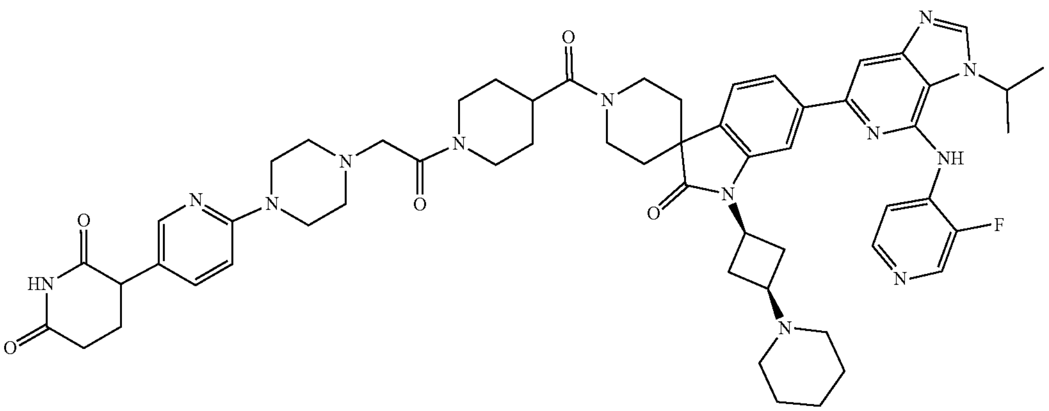 [SMILES: CC(C)n1cnc2cc(-c3ccc4c(c3)N([C@H]3C[C@@H](N5CCCCC5)C3)C(=O)C43CCN(C(=O)C4CCN(C(=O)CN5CCN(c6ccc(C7CCC(=O)NC7=O)cn6)CC5)CC4)CC3)nc(Nc3ccncc3F)c21]

Example 96 was prepared by similar procedures as Example 1 using 1-(1-(6-(2,6-dioxopiperidin-3-yl)pyridin-3-yl)piperidine-4-carbonyl)piperidine-4-carboxylic acid (intermediate 47) (7.3 mg, 0.0165 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.0165 mmol) as starting materials. The title compound (TFA salt) was isolated as an off-white solid (7.9 mg, 45% yield). LCMS: [$C_{57}H_{68}FN_{13}O_5$], desired mass=1034.2, found: m/z=1034.6 $[M+H]^+$, $^1$H NMR (500 MHz, MeOD) δ 8.83-8.75 (m, 2H), 8.31 (d, J=6.8 Hz, 1H), 8.25 (s, 1H), 8.11 (d, J=2.4 Hz, 1H), 7.88 (d, J=7.6 Hz, 1H), 7.79-7.69 (m, 2H), 7.69-7.62 (m, 1H), 7.57 (d, J=7.7 Hz, 1H), 7.05 (d, J=8.9 Hz, 1H), 5.16 (m, 1H), 4.60 (s, 1H), 4.49 (q, J=8.5 Hz, 1H), 4.42 (d, J=16.1 Hz, 1H), 4.32 (d, J=16.0 Hz, 1H), 4.14 (m, 2H), 4.06-3.94 (m, 5H), 3.92-3.77 (m, 2H), 3.66-3.43 (m, 4H), 3.24 (d, J=9.5 Hz, 1H), 3.16 (m, 2H), 3.04-2.85 (m, 6H), 2.84-2.62 (m, 5H), 2.33-2.24 (m, 1H), 2.23-2.14 (m, 1H), 2.05-1.90 (m, 5H), 1.89-1.75 (m, 9H), 1.69 (d, J=6.6 Hz, 6H), 1.60 (d, J=16.0 Hz, 2H).

Example 97

(3RS)-3-[6-(1-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-4-yl)pyridin-3-yl]piperidine-2,6-dione

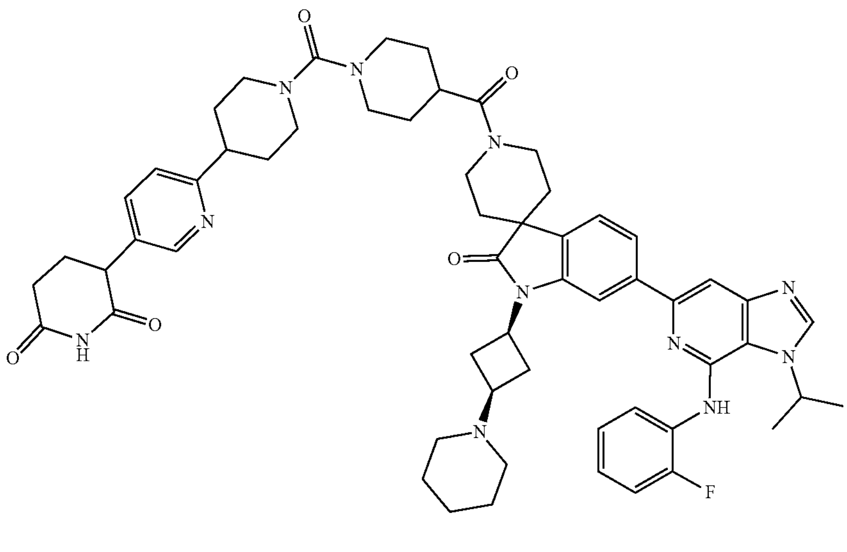 [SMILES: CC(C)n1cnc2cc(-c3ccc4c(c3)N([C@H]3C[C@@H](N5CCCCC5)C3)C(=O)C43CCN(C(=O)C4CCN(C(=O)N5CCC(c6ccc(C7CCC(=O)NC7=O)cn6)CC5)CC4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 1-(4-(5-(2,6-dioxopiperidin-3-yl)pyridin-2-yl)piperidine-1-carbonyl)piperidine-4-carboxylic acid (intermediate 48) as the coupling partners, the title compound (TFA salt) was isolated as an off-white solid (2.3 mg, 8.9% yield). LCMS: [C58H68FN11O5], desired mass=1017.5, found: m/z=510.2 [(M+2H)/2]$^+$.

Example 98

(3RS)-3-{6-[4-(2-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidin-1-yl}ethyl)piperidin-1-yl]pyridin-3-yl}piperidine-2,6-dione

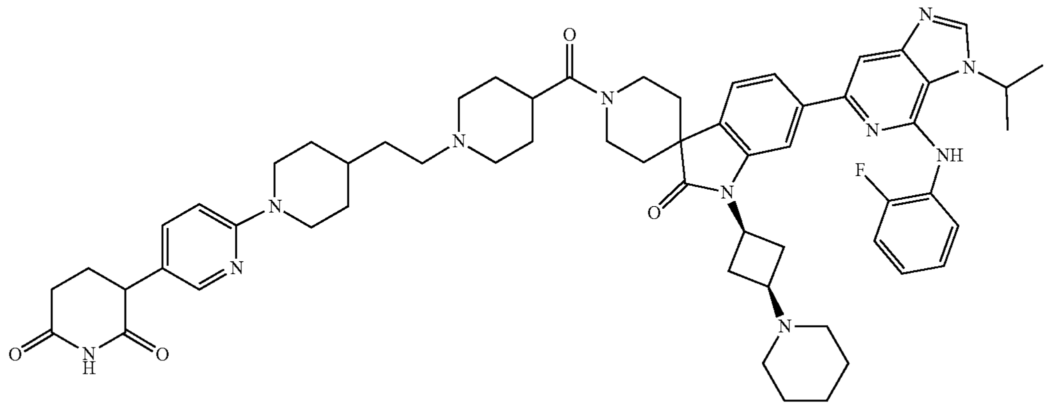 [SMILES: CC(C)n1cnc2cc(-c3ccc4c(c3)N([C@H]3C[C@@H](N5CCCCC5)C3)C(=O)C43CCN(C(=O)C4CCN(CCC5CCN(c6ccc(C7CCC(=O)NC7=O)cn6)CC5)CC4)CC3)nc(Nc3ccccc3F)c21]

Using procedures similar to step 2 of Example 46 and using 6-(4-((2-fluorophenyl)amino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one hydrochloride (19 mg) and 2-(1-(5-(2,6-dioxopiperidin-3-yl)pyridin-2-yl)piperidin-4-yl)acetaldehyde (intermediate 49) (9 mg) as the reductive amination partners, the title compound (TFA salt) was isolated as an off-white solid (12 mg, 42% yield). LCMS: [$C_{59}H_{72}FN_{11}O_4$], desired mass=1017.6, found: m/z=1018.5 [M+H]$^+$. $^1$H NMR (500 MHz, DMSO) δ 10.84 (s, 1H), 9.24 (s, 1H), 8.60 (s, 1H), 8.34 (s, 1H), 8.02 (s, 1H), 7.89 (s, 1H), 7.68 (d, J=7.7 Hz, 1H), 7.62 (d, J=8.8 Hz, 1H), 7.59-7.52 (m, 3H), 7.49 (s, 1H), 7.30 (d, J=9.8 Hz, 1H), 7.23 (t, J=8.7 Hz, 1H), 7.20 (s, 2H), 5.30-5.24 (m, 1H), 4.37 (s, 1H), 4.26 (d, J=6.8 Hz, 2H), 4.12-4.06 (m, 1H), 3.96 (dd, J=11.6, 4.9 Hz, 1H), 3.91 (s, 1H), 3.83 (s, 4H), 3.07 (s, 1H), 2.93 (d, J=11.2 Hz, 2H), 2.89-2.80 (m, 2H), 2.71 (d, J=11.2 Hz, 2H), 2.27 (d, J=9.5 Hz, 1H), 2.08 (d, J=8.9 Hz, 1H), 1.87 (d, J=13.8 Hz, 3H), 1.76 (s, 1H), 1.66 (s, 11H), 1.58 (d, J=6.6 Hz, 6H), 1.31 (s, 4H), 1.23 (s, 1H), 1.14 (s, 2H).

Example 99

5-[(6-{1'-[2-(1-{1-[2-({2-[(3RS)-2,6-dioxopiperidin-3-yl]-1,3-dioxo-2,3-dihydro-1H-isoindol-4-yl}amino)acetyl]piperidine-4-carbonyl}piperidin-4-yl)acetyl]-2-oxo-1-[(1S,3S)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

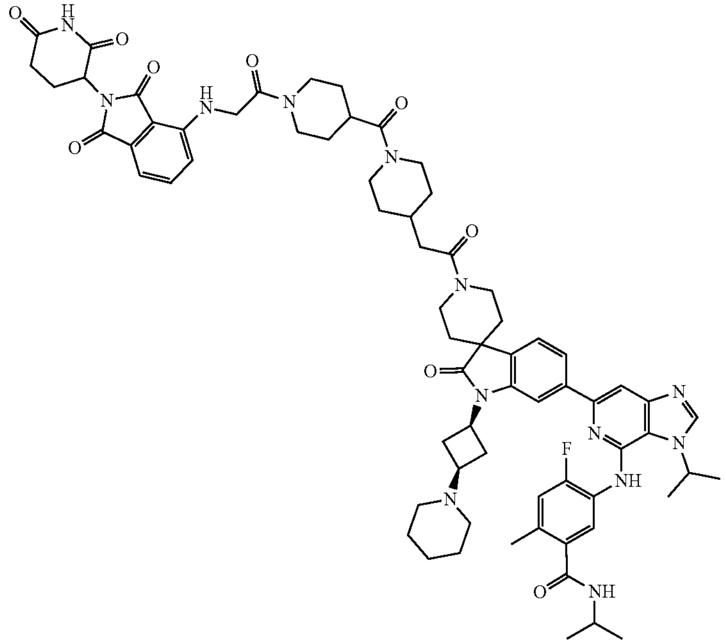 [SMILES: Cc1cc(F)c(Nc2nc(-c3ccc4c(c3)N([C@H]3C[C@@H](N5CCCCC5)C3)C(=O)C43CCN(C(=O)CC4CCN(C(=O)C5CCN(C(=O)CNc6cccc7c6C(=O)N(C6CCC(=O)NC6=O)C7=O)CC5)CC4)CC3)cc3ncn(C(C)C)c23)cc1C(=O)NC(C)C]

Using procedures similar to those for Example 31 and using 4-fluoro-N-isopropyl-5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-2-methylbenzamide and 2-(1-(1-((2-(2,6-dioxopiperidin-3-yl)-1,3-dioxoisoindolin-4-yl)glycyl)piperidine-4-carbonyl)piperidin-4-yl)acetic acid (intermediate 50) as the coupling partners, the title compound (TFA salt) was isolated as an off-white solid (2.3 mg, 8.9% yield). LCMS: [C69H82FN13O9], desired mass=1255.6, found: m/z=1257.1 $[M+H]^+$. $^1$H NMR (500 MHz, DMSO) δ 11.11 (s, 1H), 9.33 (s, 1H), 8.68 (s, 1H), 8.41 (s, 1H), 8.15 (d, J=7.8 Hz, 1H), 7.89 (s, 1H), 7.68 (d, J=7.9 Hz, 1H), 7.62 (dd, J=8.3, 4.8 Hz, 2H), 7.53 (d, J=6.7 Hz, 2H), 7.19 (d, J=12.1 Hz, 1H), 7.15-7.06 (m, 3H), 5.30 (p, J=6.6 Hz, 1H), 5.08 (dd, J=12.9, 5.4 Hz, 1H), 4.43-4.36 (m, 3H), 4.28-4.13 (m, 3H), 4.04 (dt, J=13.6, 6.6 Hz, 2H), 3.92 (d, J=14.1 Hz, 2H), 3.53 (q, J=8.1 Hz, 1H), 3.41 (d, J=11.5 Hz, 2H), 3.08 (t, J=13.4 Hz, 1H), 2.97 (s, 4H), 2.90 (s, 1H), 2.82 (t, J=10.1 Hz, 6H), 2.62 (d, J=3.4 Hz, 1H), 2.60-2.53 (m, 1H), 2.38 (s, 6H), 2.04 (s, 2H), 1.86 (d, J=14.6 Hz, 2H), 1.78-1.66 (m, 5H), 1.60 (d, J=6.6 Hz, 8H), 1.43 (d, J=13.3 Hz, 3H), 1.16 (s, 1H), 1.11 (d, J=6.5 Hz, 7H), 1.04 (s, 2H).

Example 100

(3RS)-3-{6-[(3R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]benzoyl}-3-methylpiperazin-1-yl]pyridin-3-yl}piperidine-2,6-dione

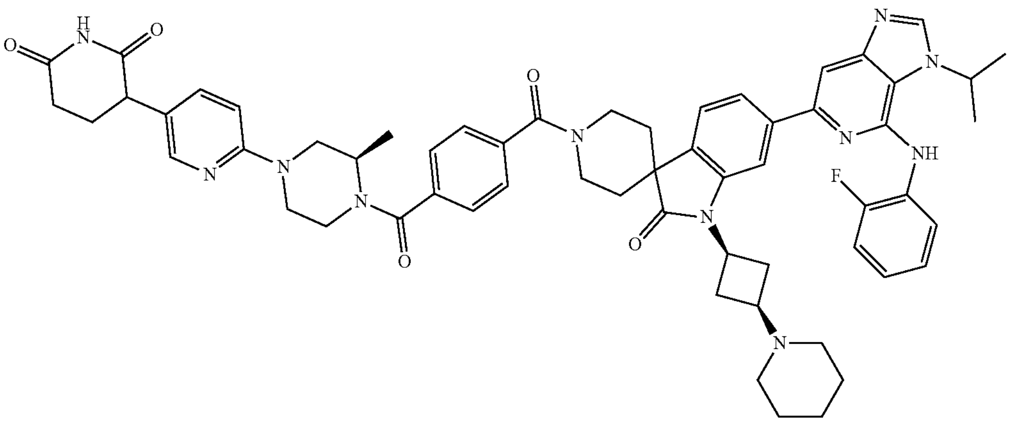 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCN(c6ccc(C7CCC(=O)NC7=O)cn6)C[C@H]5C)cc4)CC3)nc(Nc3ccccc3F)c21]

Step 1: 4-[(6-{4-[(2-fluorophenyl)amino]-3-isopropylimidazo[4,5-c]pyridin-6-yl}-2-oxo-1-[(1s,3s)-3-(piperidin-1-yl)cyclobutyl]spiro[indole-3,4'-piperidin]-1'-yl)carbonyl]benzoic acid 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (50.00 mg, 0.08 mmol), methyl terephthalate (14.82 mg, 0.08 mmol), and (1,2,3-benzotriazol-1-yloxy)tris(dimethylamino)phosphanium, hexafluoro-lambda5-phosphanuide (47.30 mg, 0.11 mmol) were dissolved in dimethylformamide (1.00 mL) and N,N-diisopropylethylamine (0.06 mL, 42.53 mg, 0.33 mmol) and stirred at room temperature for 4 hours. The reaction mixture was concentrated via nitrogen blowdown, then dissolved in MeOH (1 mL), treated with 1M LiOH (1 mL), and stirred at 50° C. for 2 hours. The product was isolated by reverse phase flash column chromatography to afford the title compound as a white solid (41.1 mg, 62% yield).

Step 2

Using procedures similar to those used for Example 36 and using 4-[(6-{4-[(2-fluorophenyl)amino]-3-isopropylimidazo[4,5-c]pyridin-6-yl}-2-oxo-1-[(1s,3s)-3-(piperidin-1-yl)cyclobutyl]spiro[indole-3,4'-piperidin]-1'-yl)carbonyl]benzoic acid (15.00 mg, 0.02 mmol) and 3-(6-((R)-3-methylpiperazin-1-yl)pyridin-3-yl)piperidine-2,6-dione (intermediate 51) (5.72 mg, 0.02 mmol) as coupling partners afforded the title compound (TFA salt) as an off white solid (18.2 mg, 88% yield). LCMS: $C_{59}H_{64}FN_{11}O_5$ desired mass=1025.5, found: m/z=1026.8 $[M+H]^+$. $^1$H NMR (500 MHz, Methanol-$d_4$) δ 8.83 (s, 1H), 7.97 (d, J=2.3 Hz, 1H), 7.85-7.76 (m, 2H), 7.74-7.64 (m, 2H), 7.64-7.56 (m, 3H), 7.32-7.18 (m, 3H), 5.31 (p, J=6.7 Hz, 1H), 4.85 (d, J=2.8 Hz, 1H), 4.26 (p, J=8.6 Hz, 2H), 4.14 (s, 2H), 4.07 (d, J=13.3 Hz, 1H), 3.99 (s, 1H), 3.91 (dd, J=12.4, 4.9 Hz, 1H), 3.75 (p, J=6.6 Hz, 1H), 3.58 (dd, J=18.1, 10.1 Hz, 2H), 3.53 (s, 1H), 3.36 (dt, J=3.4, 1.7 Hz, 1H), 3.33-3.21 (m, 5H), 3.05 (s, 2H), 2.95-2.87 (m, 2H), 2.85-2.69 (m, 1H), 2.66 (d, J=9.4 Hz, 1H), 2.30 (qd, J=12.7, 5.0 Hz, 1H), 2.23-2.15 (m, 1H), 2.03 (d, J=17.8 Hz, 3H), 1.89 (s, 4H), 1.78 (d, J=7.7 Hz, 1H), 1.59 (d, J=13.3 Hz, 1H), 1.46-1.29 (m, 11H).

Example 101

(3RS)-3-(4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}phenyl)piperidine-2,6-dione

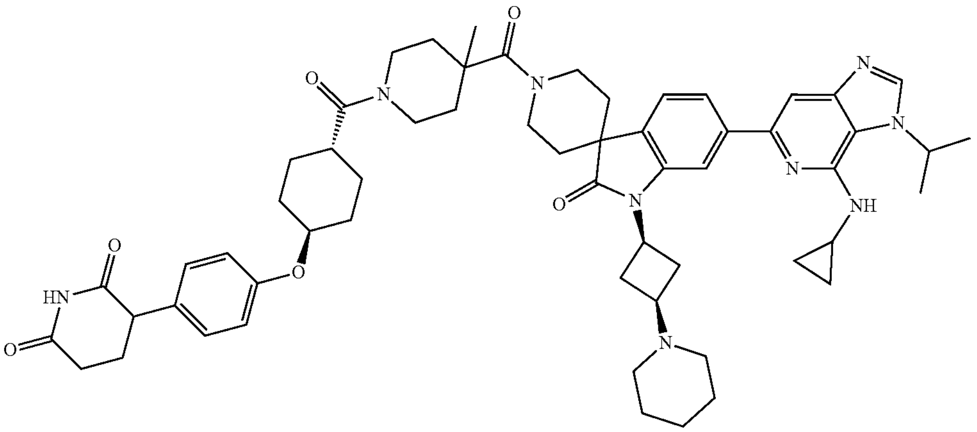 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cc6)CC5)CC4)CC3)nc(NC3CC3)c21]

Step 1: 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (200.00 mg, 0.36 mmol), (1,2,3-benzotriazol-1-yloxy)tris(dimethylamino)phosphanium, hexafluoro-lambda5-phosphanuide (207.66 mg, 0.47 mmol), N,N-diisopropylethylamine (0.25 mL, 186.72 mg, 1.44 mmol), and 1-(tert-butoxycarbonyl)-4-methylpiperidine-4-carboxylic acid (87.87 mg, 0.36 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (140.0 mg, 57% yield).

Step 2

Using procedures similar to those used for Example 36 and using 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one (20.00 mg, 0.03 mmol) and (1r,4r)-4-(4-(2,6-dioxopiperidin-3-yl)phenoxy)cyclohexane-1-carboxylic acid (Intermediate 52) (9.76 mg, 0.03 mmol) as coupling partners afforded the title compound (TFA salt) as an off white solid (11.1 mg, 35% yield). LCMS: $C_{58}H_{73}N_9O_6$ desired mass=991.6, found: m/z=992.4 $[M+H]^+$. $^1H$ NMR (500 MHz, Methanol-$d_4$) δ 7.69 (s, 2H), 7.63 (s, 1H), 7.57 (s, 1H), 7.17 (dd, J=8.6, 3.5 Hz, 3H), 6.96-6.89 (m, 3H), 5.17-5.09 (m, 1H), 4.49 (q, J=8.4 Hz, 1H), 4.29 (dd, J=10.4, 4.9 Hz, 1H), 4.15 (d, J=11.8 Hz, 2H), 4.10 (s, 2H), 4.03 (d, J=14.3 Hz, 1H), 3.86-3.78 (m, 2H), 3.67-3.54 (m, 4H), 3.22 (d, J=9.6 Hz, 1H), 3.14 (s, 1H), 3.07 (t, J=3.6 Hz, 1H), 3.04-2.97 (m, 1H), 2.97-2.85 (m, 2H), 2.81-2.58 (m, 2H), 2.34 (d, J=15.1 Hz, 1H), 2.23 (q, J=7.3, 5.3 Hz, 2H), 2.08-1.99 (m, 2H), 1.92 (d, J=10.3 Hz, 3H), 1.88 (d, J=14.0 Hz, 4H), 1.79 (d, J=13.7 Hz, 1H), 1.69 (d, J=6.6 Hz, 6H), 1.61 (s, 7H), 1.52 (q, J=11.6 Hz, 2H), 1.44 (s, 3H), 1.31 (s, 1H), 1.14 (d, J=6.6 Hz, 2H), 0.94 (s, 2H).

Example 102

(3RS)-3-(4-{[(1R,4R)-4-{4-[(6-{4-[(2-fluorophenyl)amino]-3-isopropylimidazo[4,5-c]pyridin-6-yl}-2-oxo-1-[(1S,3S)-3-(piperidin-1-yl)cyclobutyl]spiro[indole-3,4'-piperidin]-1'-yl)carbonyl]-4-methylpiperidine-1-carbonyl}cyclohexyl]oxy}phenyl)piperidine-2,6-dione

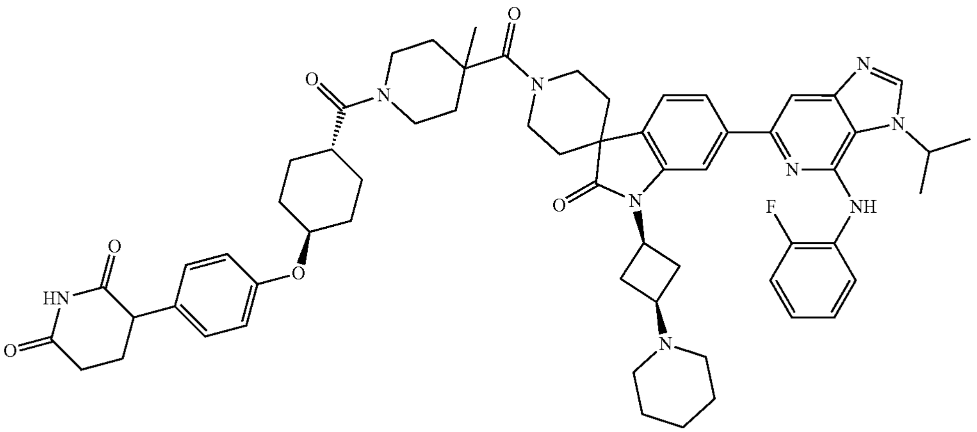 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cc6)CC5)CC4)CC3)nc(Nc3ccccc3F)c21]

Step 1: 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (110.0 mg, 45% yield).

Step 2

Using procedures similar to those used for Example 36 and using 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.03 mmol) and (1r,4r)-4-(4-(2,6-dioxopiperidin-3-yl)phenoxy)cyclohexane-1-carboxylic acid (Intermediate 52) (9.76 mg, 0.03 mmol) as coupling partners afforded the title compound (TFA salt) as an off white solid (16.2 mg, 57% yield). LCMS: $C_{61}H_{72}FN_9O_6$ desired mass=1045.6, found: m/z=1046.4 $[M+H]^+$. $^1H$ NMR (500 MHz, Methanol-$d_4$) δ 7.81 (s, 1H), 7.78 (d, J=7.9 Hz, 1H), 7.70 (t, J=7.8 Hz, 1H), 7.62 (s, 1H), 7.55 (d, J=7.9 Hz, 1H), 7.32-7.23 (m, 1H), 7.17 (d, J=8.4 Hz, 2H), 6.93 (d, J=8.2 Hz, 2H), 4.26 (dd, J=19.2, 10.1 Hz, 2H), 4.08 (s, 6H), 3.82 (t, J=7.8 Hz, 2H), 3.57 (dd, J=18.7, 10.4 Hz, 5H), 3.05 (d, J=10.6 Hz, 3H), 2.97-2.88 (m, 4H), 2.78-2.59 (m, 2H), 2.24 (d, J=15.4 Hz, 1H), 2.23 (s, 5H), 2.04 (d, J=14.5 Hz, 2H), 1.89 (t, J=15.3 Hz, 8H), 1.74 (d, J=6.6 Hz, 8H), 1.66 (d, J=13.3 Hz, 1H), 1.63-1.55 (m, 3H), 1.52 (d, J=11.9 Hz, 1H), 1.43 (s, 3H), 1.31 (s, 2H).

Example 103

(3RS)-3-(4-{[(1R,4R)-4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}phenyl)piperidine-2,6-dione

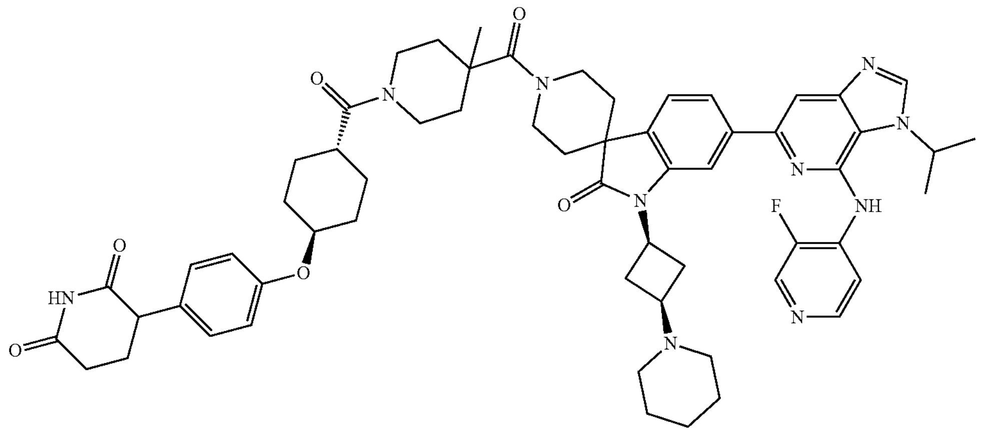 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cc6)CC5)CC4)CC3)nc(Nc3ccncc3F)c21]

Step 1: 6-{4-[(3-fluoropyridin-4-yl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one 6-{4-[(2-fluoropyridine)amino]-3-isopropylimidazo[4,5-c]pyridin-6-yl}-1-[(1s,3s)-3-(piperidin-1-yl)cyclobutyl]spiro[indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (120.0 mg, 50% yield).

Step 2

Using procedures similar to those used for Example 36 and using 6-{4-[(2-fluoropyridine)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.03 mmol) and (1r,4r)-4-(4-(2,6-dioxopiperidin-3-yl)phenoxy)cyclohexane-1-carboxylic acid (Intermediate 52) (9.0 mg, 0.03 mmol) as coupling partners afforded the title compound (TFA salt) as an off white solid (13.1 mg, 44% yield). LCMS: $C_{60}H_{71}FN_{10}O_6$ desired mass=1046.6, found: m/z=1047.4 $[M+H]^+$. $^1H$ NMR (500 MHz, Methanol-$d_4$) δ 8.81-8.74 (m, 2H), 8.31 (d, J=6.7 Hz, 1H), 8.25 (s, 1H), 7.89 (d, J=7.9 Hz, 1H), 7.77 (t, J=7.3 Hz, 1H), 7.72 (s, 1H), 7.59 (d, J=7.8 Hz, 1H), 7.17 (dd, J=8.7, 3.5 Hz, 3H), 6.93 (dd, J=8.6, 3.2 Hz, 3H), 5.20-5.12 (m, 1H), 4.52 (t, J=8.3 Hz, 1H), 4.29 (q, J=4.8 Hz, 1H), 4.11 (s, 4H), 4.03 (d, J=14.0 Hz, 1H), 3.83 (s, 2H), 3.60 (dd, J=19.8, 10.4 Hz, 4H), 3.31 (s, 3H), 3.22 (s, 1H), 3.14 (s, 1H), 3.01-2.85 (m, 4H), 2.78-2.59 (m, 3H), 2.34 (d, J=14.0 Hz, 1H), 2.23 (s, 5H), 2.03 (d, J=14.8 Hz, 2H), 1.92 (s, 1H), 1.89 (s, 7H), 1.86 (s, 1H), 1.79 (d, J=13.4 Hz, 1H), 1.65 (d, J=6.6 Hz, 6H), 1.61 (s, 4H), 1.53 (dt, J=24.5, 12.9 Hz, 3H), 1.44 (s, 3H), 1.31 (s, 1H).

Example 104

(3RS)-3-(6-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyridin-3-yl)piperidine-2,6-dione

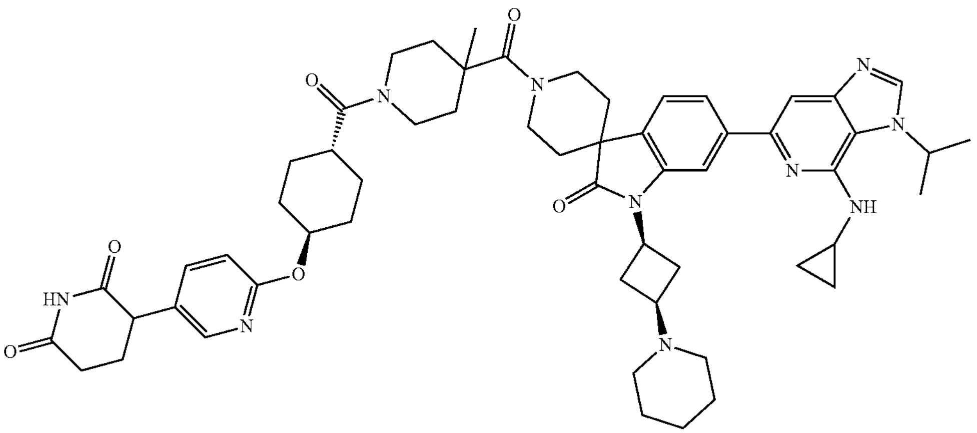 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cn6)CC5)CC4)CC3)nc(NC3CC3)c21]

Step 1: 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (200.00 mg, 0.36 mmol), (1,2,3-benzotriazol-1-yloxy)tris(dimethylamino)phosphanium, hexafluoro-lambda5-phosphanuide (207.66 mg, 0.47 mmol), N,N-diisopropylethylamine (0.25 mL, 186.72 mg, 1.44 mmol), and 1-(tert-butoxycarbonyl)-4-methylpiperidine-4-carboxylic acid (87.87 mg, 0.36 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (140.0 mg, 57% yield).

Step 2

Using procedures similar to those used for Example 36 and using 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one (20.00 mg, 0.03 mmol) and (1r,4r)-4-((5-(2,6-dioxopiperidin-3-yl)pyridin-2-yl)oxy)cyclohexane-1-carboxylic acid (Intermediate 9) (9.79 mg, 0.03 mmol) as coupling partners afforded the title compound (TFA salt) as an off white solid (15.8 mg, 53% yield). LCMS: $C_{57}H_{72}N_{10}O_6$ desired mass=992.6, found: m/z=994.5 $[M+H]^+$. $^1H$ NMR (500 MHz, Methanol-$d_4$) δ 8.94 (s, 1H), 8.04 (d, J=2.5 Hz, 1H), 7.70 (d, J=7.6 Hz, 1H), 7.66-7.59 (m, 2H), 7.57 (s, 1H), 6.81 (d, J=8.7 Hz, 1H), 5.14 (d, J=6.6 Hz, 1H), 4.49 (q, J=8.4 Hz, 1H), 4.14 (s, 2H), 4.12-4.00 (m, 4H), 3.93-3.81 (m, 2H), 3.60 (dd, J=20.7, 10.1 Hz, 4H), 3.22 (s, 1H), 3.06 (dd, J=6.9, 3.5 Hz, 1H), 3.00 (d, J=9.4 Hz, 2H), 2.90 (t, J=12.2 Hz, 2H), 2.81-2.67 (m, 2H), 2.34 (d, J=14.0 Hz, 1H), 2.30-2.23 (m, 5H), 2.19 (dd, J=11.2, 6.4 Hz, 1H), 2.03 (d, J=14.7 Hz, 2H), 1.92 (d, J=9.9 Hz, 4H), 1.79 (d, J=13.8 Hz, 1H), 1.69 (d, J=6.6 Hz, 7H), 1.60 (q, J=13.0, 12.0 Hz, 4H), 1.45 (s, 3H), 1.31 (s, 1H), 1.14 (d, J=6.6 Hz, 2H), 0.95 (s, 2H).

Example 105

(3RS)-3-(6-{1[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)piperidine-2,6-dione

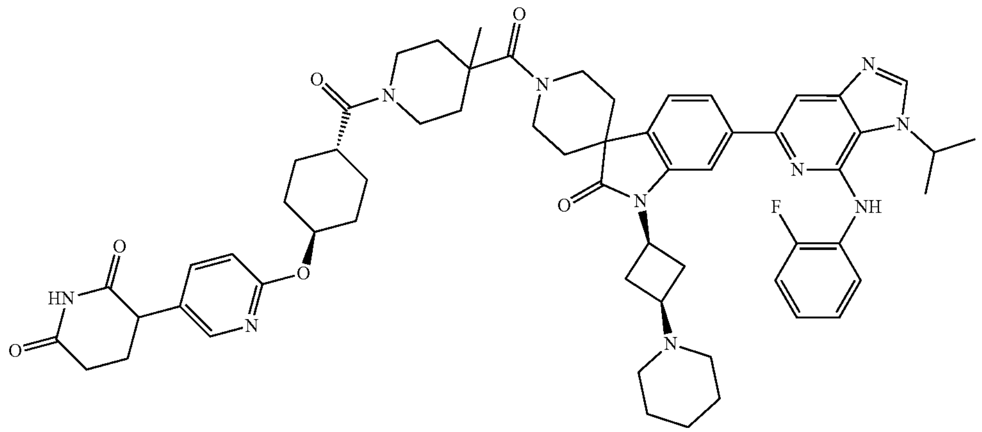 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cn6)CC5)CC4)CC3)nc(Nc3ccccc3F)c21]

Step 1: 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one 6-{4-[(2-fluorophenyl)amino]-3-isopropylimidazo[4,5-c]pyridin-6-yl}-1-[(1s,3s)-3-(piperidin-1-yl)cyclobutyl]spiro[indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (110.0 mg, 45% yield).

Step 2

Using procedures similar to those used for Example 36 and using 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.027 mmol) and (1r,4r)-4-((5-(2,6-dioxopiperidin-3-yl)pyridin-2-yl)oxy)cyclohexane-1-carboxylic acid (Intermediate 9) (9.07 mg, 0.027 mmol) as coupling partners afforded the title compound (TFA salt) as an off white solid (16.2 mg, 55% yield). LCMS: $C_{60}H_{71}FN_{10}O_6$ desired mass=1046.6, found: m/z=1047.5 $[M+H]^+$. $^1$H NMR (500 MHz, Methanol-$d_4$) δ 8.04 (d, J=2.5 Hz, 1H), 7.81 (s, 1H), 7.77 (dd, J=7.8, 1.5 Hz, 1H), 7.70 (t, J=8.7 Hz, 1H), 7.64 (dd, J=8.6, 2.5 Hz, 1H), 7.60 (d, J=1.6 Hz, 1H), 7.55 (d, J=7.9 Hz, 1H), 7.36-7.25 (m, 3H), 6.82 (d, J=8.7 Hz, 1H), 4.23 (p, J=8.2 Hz, 1H), 4.08 (s, 5H), 4.02 (s, 1H), 3.89 (dd, J=12.2, 5.1 Hz, 1H), 3.83 (s, 1H), 3.57 (dt, J=21.3, 9.9 Hz, 5H), 3.05 (d, J=9.1 Hz, 1H), 2.94 (d, J=12.1 Hz, 1H), 2.84-2.67 (m, 3H), 2.34 (d, J=14.0 Hz, 1H), 2.26 (s, 6H), 2.20 (dq, J=8.5, 4.5 Hz, 1H), 2.05 (d, J=14.5 Hz, 2H), 1.87 (td, J=14.2, 13.6, 6.2 Hz, 8H), 1.79-1.67 (m, 9H), 1.67-1.54 (m, 6H), 1.43 (s, 3H), 1.31 (s, 1H).

Example 106

(3RS)-3-(6-{1[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)piperidine-2,6-dione

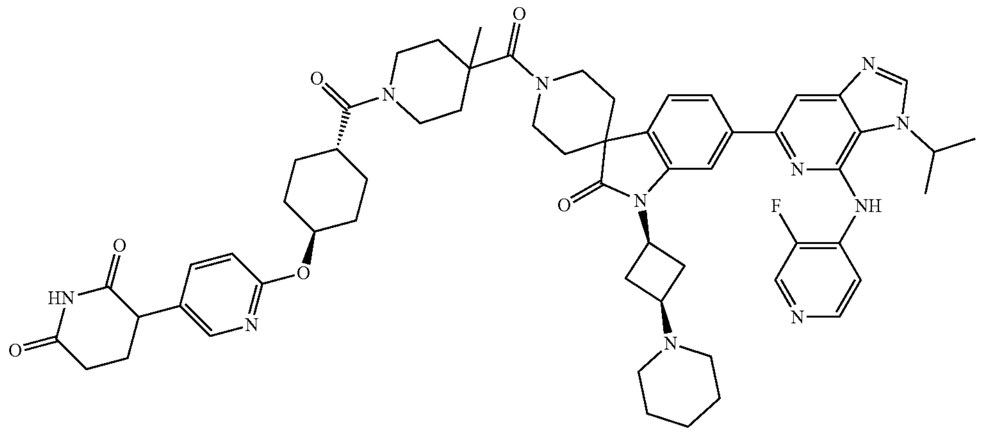 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cn6)CC5)CC4)CC3)nc(Nc3ccncc3F)c21]

Step 1: 6-{4-[(3-fluoropyridin-4-yl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one 6-{4-[(2-fluoropyridine)amino]-3-isopropylimidazo[4,5-c]pyridin-6-yl}-1-[(1s,3s)-3-(piperidin-1-yl)cyclobutyl] spiro[indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (120.0 mg, 50% yield).

Step 2

Using procedures similar to those used for Example 36 and using 6-{4-[(2-fluoropyridine)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.027 mmol) and (1r,4r)-4-((5-(2,6-dioxopiperidin-3-yl)pyridin-2-yl)oxy)cyclohexane-1-carboxylic acid (Intermediate 9) (9.0 mg, 0.027 mmol) as coupling partners afforded the title compound (TFA salt) as an off white solid (12 mg, 41% yield). LCMS: $C_{59}H_{70}FN_{11}O_6$ desired mass=1047.5, found: m/z=1049.4 $[M+H]^+$. $^1H$ NMR (500 MHz, Methanol-$d_4$) δ 8.82-8.75 (m, 2H), 8.31 (d, J=6.8 Hz, 1H), 8.25 (s, 1H), 8.05 (d, J=2.5 Hz, 1H), 7.89 (d, J=7.9 Hz, 1H), 7.78 (t, J=7.3 Hz, 1H), 7.72 (s, 1H), 7.66 (dd, J=8.6, 2.5 Hz, 1H), 7.59 (d, J=7.9 Hz, 1H), 6.84 (d, J=8.7 Hz, 1H), 5.21-5.12 (m, 1H), 4.53 (q, J=8.3 Hz, 1H), 4.11 (s, 5H), 4.04 (d, J=14.2 Hz, 1H), 3.94-3.81 (m, 2H), 3.60 (dd, J=21.6, 10.8 Hz, 5H), 3.21 (d, J=9.5 Hz, 2H), 2.98 (q, J=8.8 Hz, 3H), 2.90 (t, J=12.0 Hz, 2H), 2.85-2.67 (m, 2H), 2.34 (d, J=15.2 Hz, 2H), 2.30-2.23 (m, 1H), 2.23-2.15 (m, 1H), 2.04 (d, J=15.0 Hz, 2H), 1.90 (dd, J=14.1, 7.3 Hz, 7H), 1.79 (d, J=13.9 Hz, 2H), 1.72 (d, J=13.1 Hz, 1H), 1.65 (d, J=6.6 Hz, 7H), 1.59 (s, 5H), 1.55 (d, J=11.6 Hz, 1H), 1.44 (s, 3H), 1.31 (s, 1H).

Example 107

1-(6-{1[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyridin-3-yl)-1,3-diazinane-2,4-dione

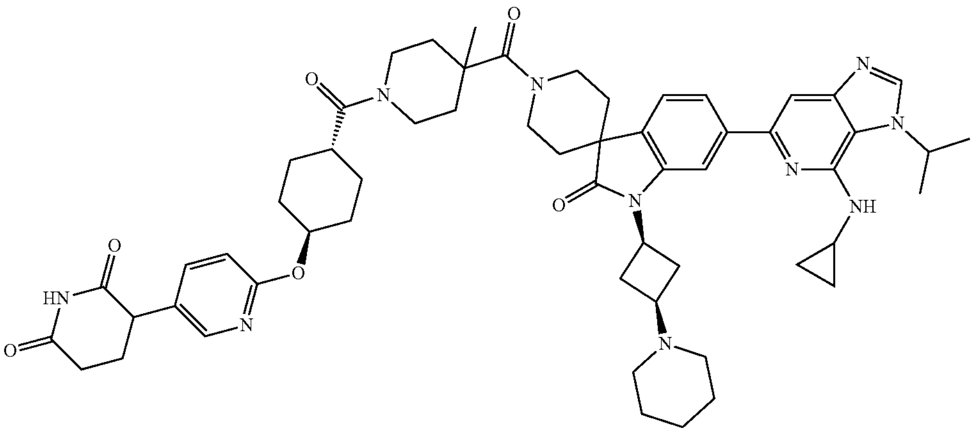 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(C7CCC(=O)NC7=O)cn6)CC5)CC4)CC3)nc(NC3CC3)c21]

Step 1: 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (200.00 mg, 0.36 mmol), (1,2,3-benzotriazol-1-yloxy)tris(dimethylamino)phosphanium, hexafluoro-lambda5-phosphanuide (207.66 mg, 0.47 mmol), N,N-diisopropylethylamine (0.25 mL, 186.72 mg, 1.44 mmol), and 1-(tert-butoxycarbonyl)-4-methylpiperidine-4-carboxylic acid (87.87 mg, 0.36 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (140.0 mg, 57% yield).

Step 2

Using procedures similar to those used for Example 36 and using 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one (20.00 mg, 0.03 mmol) and (1r,4r)-4-((5-(2,4-dioxotetrahydropyrimidin-1(2H)-yl)pyridin-2-yl)oxy)cyclohexane-1-carboxylic acid (Intermediate 53) (9.82 mg, 0.03 mmol) as coupling partners afforded the title compound (TFA salt) as an off white solid (12.6 mg, 42% yield). LCMS: $C_{56}H_{71}N_{11}O_6$ desired mass=993.6, found: m/z=995.0 $[M+H]^+$.

Example 108

1-(6-{[(1R,4R)-4-{4-[(6-{4-[(2-fluorophenyl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]-4-methylpiperidine-1-carbonyl}cyclohexyl]oxy}pyridin-3-yl)-1,3-diazinane-2,4-dione

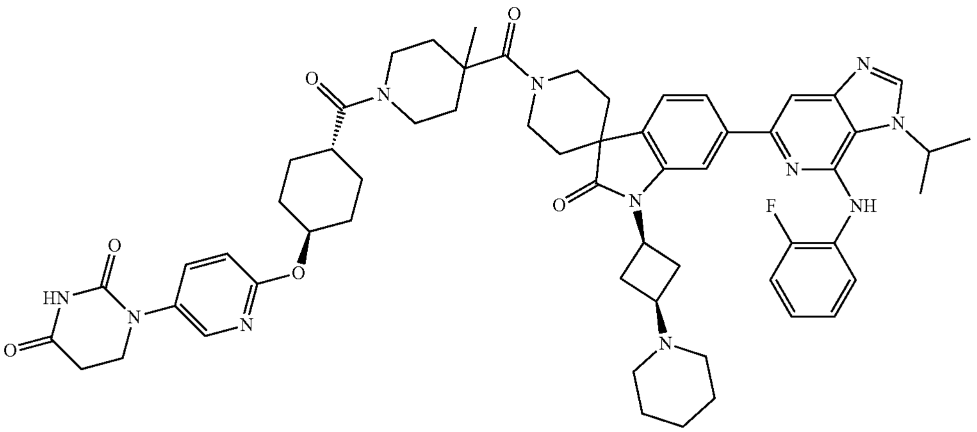 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(N7CCC(=O)NC7=O)cn6)CC5)CC4)CC3)nc(Nc3ccccc3F)c21]

Step 1: 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl] spiro[indole-3,4'-piperidin]-2-one 6-{4-[(2-fluorophenyl)amino]-3-isopropylimidazo[4,5-c] pyridin-6-yl}-1-[(1s,3s)-3-(piperidin-1-yl)cyclobutyl]spiro [indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (110.0 mg, 45% yield).

Step 2

Using procedures similar to those used for Example 36 and using 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.027 mmol) and (1r,4r)-4-((5-(2,4-dioxotetrahydropyrimidin-1(2H)-yl)pyridin-2-yl) oxy)cyclohexane-1-carboxylic acid (Intermediate 53) (9.1 mg, 0.027 mmol) as coupling partners afforded the title compound (TFA salt) as an off white solid (16.5 mg, 57% yield). LCMS: $C_{59}H_{70}FN_{11}O_6$ desired mass=1047.5, found: m/z=1049.4 $[M+H]^+$. $^1H$ NMR (500 MHz, Methanol-$d_4$) δ 9.22 (s, 1H), 8.14 (d, J=2.8 Hz, 1H), 7.81 (s, 1H), 7.77 (dd, J=7.9, 1.5 Hz, 1H), 7.69 (dd, J=8.7, 2.8 Hz, 2H), 7.59 (d, J=1.5 Hz, 1H), 7.55 (d, J=7.9 Hz, 1H), 7.35-7.26 (m, 3H), 6.80 (d, J=8.8 Hz, 1H), 4.89 (s, 2H), 4.22 (q, J=8.3 Hz, 1H), 4.08 (s, 5H), 4.02 (s, 1H), 3.86 (s, 1H), 3.86 (t, J=6.8 Hz, 3H), 3.74 (s, 1H), 3.57 (dt, J=20.2, 9.7 Hz, 4H), 2.94 (d, J=11.4 Hz, 1H), 2.92-2.81 (m, 3H), 2.77 (t, J=11.8 Hz, 1H), 2.34 (d, J=14.2 Hz, 1H), 2.26 (s, 4H), 2.05 (d, J=12.8 Hz, 2H), 1.92-1.80 (m, 8H), 1.77 (d, J=6.6 Hz, 6H), 1.75-1.65 (m, 1H), 1.43 (s, 3H), 1.31 (s, 1H), 1.25 (s, 1H).

Example 109

1-(6-{[(1R,4R)-4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)-1,3-diazinane-2,4-dione

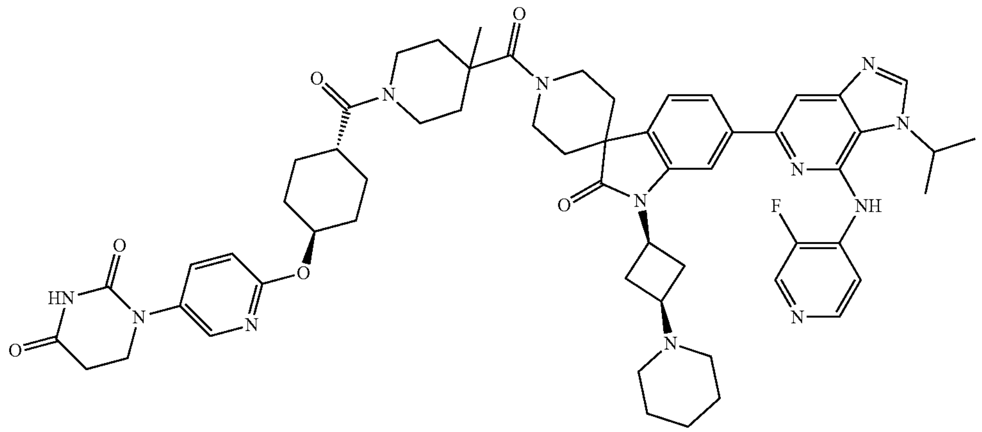 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ccc(N7CCC(=O)NC7=O)cn6)CC5)CC4)CC3)nc(Nc3ccncc3F)c21]

Step 1: 6-{4-[(3-fluoropyridin-4-yl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one 6-{4-[(2-fluoropyridine)amino]-3-isopropylimidazo[4,5-c]pyridin-6-yl}-1-[(1s,3s)-3-(piperidin-1-yl)cyclobutyl]spiro[indole-3,4'-piperidin]-2-one (200.00 mg, 0.33 mmol), (1,2,3-benzotriazol-1-yloxy)tris(dimethylamino)phosphanium, hexafluoro-lambda5-phosphanuide (189.20 mg, 0.43 mmol), N,N-diisopropylethylamine (0.23 mL, 170.12 mg, 1.32 mmol), and 1-(tert-butoxycarbonyl)-4-methylpiperidine-4-carboxylic acid (80.06 mg, 0.33 mmol) were dissolved in dimethylformamide (3.00 mL) and stirred at room temperature for 4 hours. The solvents were removed via nitrogen blowdown and the resulting material was dissolved in DCM (5.0 mL), treated with 4M HCL in dioxane (2.0 mL), and stirred at room temperature for 4 hours. The crude reaction mixture was purified by reverse phase flash column chromatography to afford the title compound (120.0 mg, 50% yield).

Step 2

Using procedures similar to those used for Example 36 and using 6-{4-[(2-fluoropyridine)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (20.00 mg, 0.027 mmol) and (1r,4r)-4-((5-(2,4-dioxotetrahydropyrimidin-1(2H)-yl)pyridin-2-yl)oxy)cyclohexane-1-carboxylic acid (Intermediate 53) (9.1 mg, 0.027 mmol) as coupling partners afforded the title compound (TFA salt) as an off white solid (11.1 mg, 38% yield). LCMS: $C_{58}H_{69}FN_{12}O_6$ desired mass=1048.5, found: m/z=1049.7 $[M+H]^+$. $^1H$ NMR (500 MHz, Methanol-$d_4$) δ 8.78 (d, J=12.7 Hz, 2H), 8.31 (d, J=6.9 Hz, 1H), 8.25 (s, 1H), 8.14 (d, J=2.7 Hz, 1H), 7.89 (d, J=7.7 Hz, 1H), 7.77 (t, J=7.3 Hz, 1H), 7.74-7.66 (m, 2H), 7.59 (d, J=7.8 Hz, 1H), 6.80 (d, J=8.8 Hz, 1H), 4.51 (d, J=8.1 Hz, 1H), 4.11 (s, 4H), 4.05 (s, 1H), 3.86 (t, J=6.7 Hz, 3H), 3.59 (t, J=11.4 Hz, 5H), 3.21 (d, J=9.4 Hz, 1H), 2.98 (d, J=9.3 Hz, 2H), 2.95-2.82 (m, 4H), 2.78 (d, J=12.4 Hz, 1H), 2.34 (d, J=13.8 Hz, 1H), 2.26 (d, J=12.4 Hz, 3H), 2.04 (d, J=15.0 Hz, 2H), 1.92 (s, 1H), 1.79 (d, J=14.1 Hz, 2H), 1.76-1.68 (m, 1H), 1.65 (d, J=6.6 Hz, 6H), 1.60 (s, 7H), 1.57 (d, J=12.3 Hz, 1H), 1.44 (s, 3H), 1.31 (s, 1H).

Example 110

(3RS)-3-[4-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)phenyl]piperidine-2,6-dione

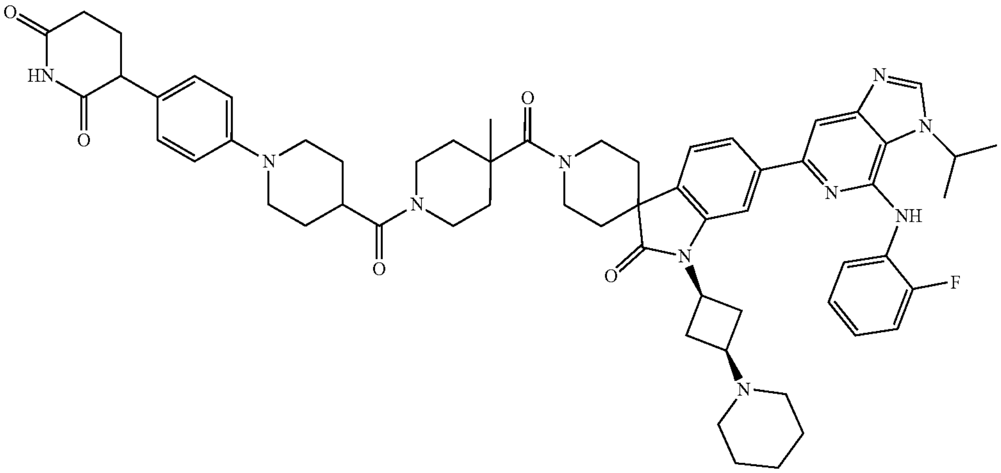 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cc6)CC5)CC4)CC3)nc(Nc3ccccc3F)c21]

Example 110 was prepared by similar procedures as Example 1 using 1-(1-(6-(2,6-dioxopiperidin-3-yl)pyridin-3-yl)piperidine-4-carbonyl)piperidine-4-carboxylic acid (intermediate 54) (8 mg, 0.018 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (4.7 mg, 33% yield). LCMS: [$C_{60}H_{71}FN_{10}O_5$], desired mass=1031.2, observed=1031.4 $[M+H]^+$, $^1H$ NMR (500 MHz, MeOD) δ 8.87 (s, 1H), 7.84-7.74 (m, 2H), 7.70 (dd, J=8.5, 6.7 Hz, 1H), 7.63 (s, 1H), 7.55 (d, J=7.8 Hz, 1H), 7.45 (s, 4H), 7.33-7.19 (m, 3H), 5.32 (m, 1H), 4.26 (m, 1H), 4.08 (m, 6H), 3.96 (dd, J=11.4, 5.0 Hz, 1H), 3.87 (m, 2H), 3.81 (m, 2H), 3.71-3.53 (m, 4H), 3.23-2.85 (m, 10H), 2.82-2.64 (m, 2H), 2.36-2.18 (m, 3H), 2.15-1.83 (m, 10H), 1.73 (d, J=6.7 Hz, 6H), 1.64 (m, 2H), 1.45 (s, 3H).

Example 111

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione

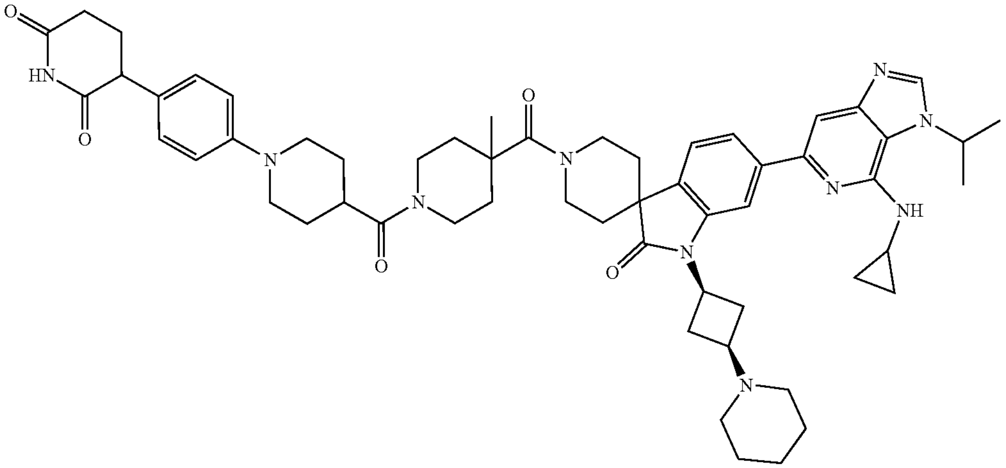 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cc6)CC5)CC4)CC3)nc(NC3CC3)c21]

Example 111 was prepared by similar procedures as Example 1 using 1-(1-(6-(2,6-dioxopiperidin-3-yl)pyridin-3-yl)piperidine-4-carbonyl)piperidine-4-carboxylic acid (intermediate 54) (8 mg, 0.018 mmol) and 6-(4-(cyclopropylamino)-3-isopropyl-3H-imidazo[4,5-c]pyridin-6-yl)-1-((1s, 3s)-3-(piperidin-1-yl)cyclobutyl)spiro[indoline-3,4'-piperidin]-2-one (10 mg, 0.018 mmol) as starting materials. The title compound (TFA salt) was isolated as an off-white solid (6.2 mg, 40% yield). LCMS: [$C_{57}H_{72}N_{10}O_5$], desired mass=977.2, found: m/z=977.5 $[M+H]^+$.

Example 112

(3RS)-3-[4-(4-{4-[(6-{4-[(3-fluoropyridin-4-yl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]-4-methylpiperidine-1-carbonyl}piperidin-1-yl)phenyl]piperidine-2,6-dione

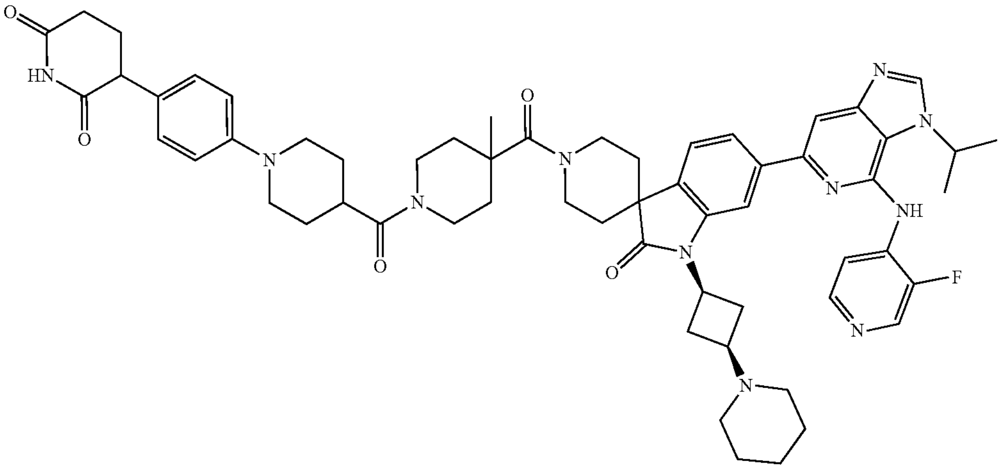 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cc6)CC5)CC4)CC3)nc(Nc3ccncc3F)c21]

Example 112 was prepared by similar procedures as Example 1 using 1-(1-(6-(2,6-dioxopiperidin-3-yl)pyridin-3-yl)piperidine-4-carbonyl)piperidine-4-carboxylic acid (intermediate 54) (8 mg, 0.018 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.018 mmol) as starting materials. The title compound (TFA salt) was isolated as an off-white solid (5.8 mg, 35% yield). LCMS: [$C_{59}H_{70}FN_{10}O_5$], desired mass=1032.2, found: m/z=1032.4 $[M+H]^+$, $^1H$ NMR (500 MHz, DMSO) δ 10.80 (s, 1H), 9.33 (s, 1H), 8.76 (d, J=22.1 Hz, 2H), 8.36-8.28 (m, 2H), 7.80 (d, J=7.8 Hz, 1H), 7.70-7.57 (m, 3H), 7.15-7.06 (m, 2H), 6.99 (s, 2H), 5.19-5.11 (m, 1H), 4.37-4.28 (m, 1H), 3.95 (s, 5H), 3.72 (m, 2H), 3.6-3.10 (m, 11H), 3.07-2.73 (m, 10H), 2.3-2.05 (m, 5H), 1.87-1.62 (m, 10H), 1.55 (dd, J=10.6, 6.7 Hz, 6H), 1.49 (m, 2H), 1.34 (d, J=4.7 Hz, 3H).

Example 113

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

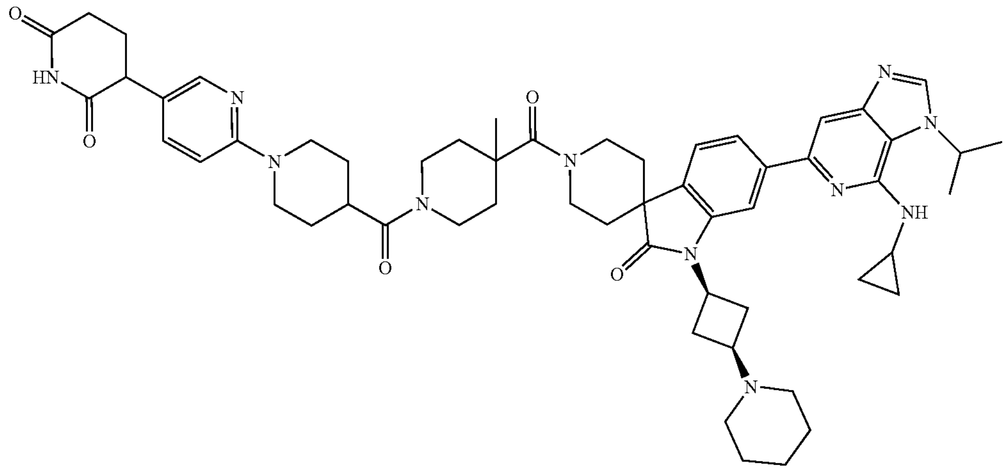 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Example 113 was prepared by similar procedures as Example 1 using 1-(1-(5-(2,6-dioxopiperidin-3-yl)pyridin-2-yl)piperidine-4-carbonyl)-4-methylpiperidine-4-carboxylic acid (intermediate 55) (96 mg, 0.22 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (100 mg, 0.18 mmol) as starting materials. Purification by reverse phase flash chromatography (5-95% MeCN/$H_2O$) afforded the title compound (free base) as an off-white solid (65 mg, 37% yield). LCMS: [$C_{56}H_{71}N_{11}O_5$], desired mass=978.2, found: m/z=978.9 $[M+H]^+$, $^1H$ NMR (500 MHz, DMSO) δ 10.81 (s, 1H), 8.35 (s, 1H), 8.18 (s, 1H), 8.01-7.89 (m, 2H), 7.72 (s, 1H), 7.58 (d, J=7.9 Hz, 1H), 7.39 (dd, J=8.8, 2.5 Hz, 1H), 6.82 (d, J=8.9 Hz, 1H), 6.47 (s, 1H), 5.07 (p, J=6.6 Hz, 1H), 4.63 (d, J=10.1 Hz, 1H), 4.29 (d, J=12.3 Hz, 2H), 3.95 (d, J=22.5 Hz, 5H), 3.85-3.69 (m, 3H), 3.00 (s, 1H), 2.89 (t, J=13.0 Hz, 4H), 2.75-2.61 (m, 4H), 2.31-1.97 (m, 7H), 1.75-1.60 (s, 13H), 1.51 (d, J=6.4 Hz, 6H), 1.44 (m, 5H), 1.33 (s, 3H), 0.79 (dd, J=7.1, 5.0 Hz, 2H), 0.59 (dd, J=6.4, 3.7 Hz, 2H).

Example 114

(3RS)-3-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]piperidine-2,6-dione

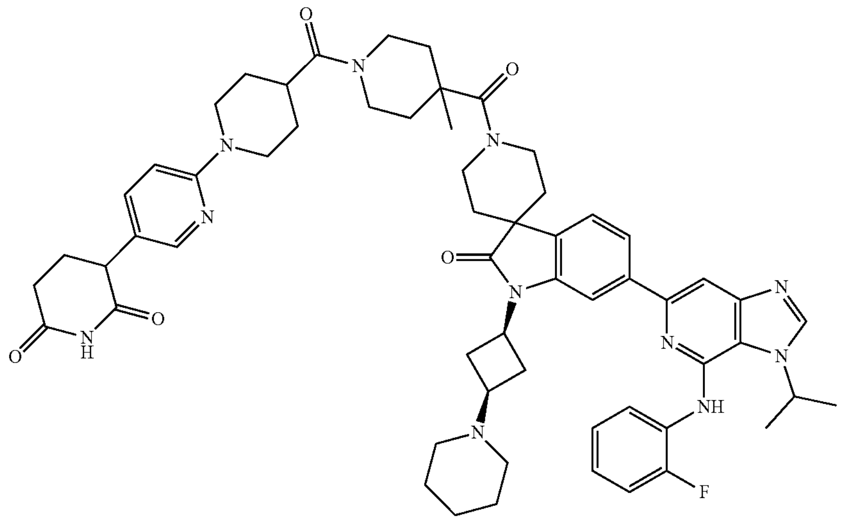 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(Nc3ccccc3F)c21]

Using procedures similar to those for Example 27 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-(1-(5-(2,6-dioxopiperidin-3-yl)pyridin-2-yl)piperidine-4-carbonyl)-4-methylpiperidine-4-carboxylic acid (intermediate 55) as the coupling partners, the title compound (TFA salt) was isolated as an off-white solid (12.2 mg, 57% yield). LCMS: [C59H70FN11O5], desired mass=1031.6, found: m/z=1032.3 $[M+H]^+$. $^1$H NMR (500 MHz, MeOD) δ 9.05 (s, 1H), 8.00 (d, J=9.3 Hz, 1H), 7.91-7.80 (m, 2H), 7.80-7.65 (m, 2H), 7.61 (s, 1H), 7.58-7.37 (m, 2H), 7.36-7.15 (m, 3H), 5.36 (s, 1H), 4.23 (d, J=12.6 Hz, 2H), 4.00-3.78 (m, 2H), 3.72-3.37 (m, 6H), 3.38-3.22 (m, 12H), 3.13-2.99 (m, 2H), 2.99-2.62 (m, 5H), 2.46-2.12 (m, 4H), 2.44-1.81 (m, 12H), 1.75 (d, J=6.5 Hz, 5H), 1.61 (s, 2H), 1.45 (s, 2H), 1.31 (s, 1H).

Example 115

1-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)-1,3-diazinane-2,4-dione

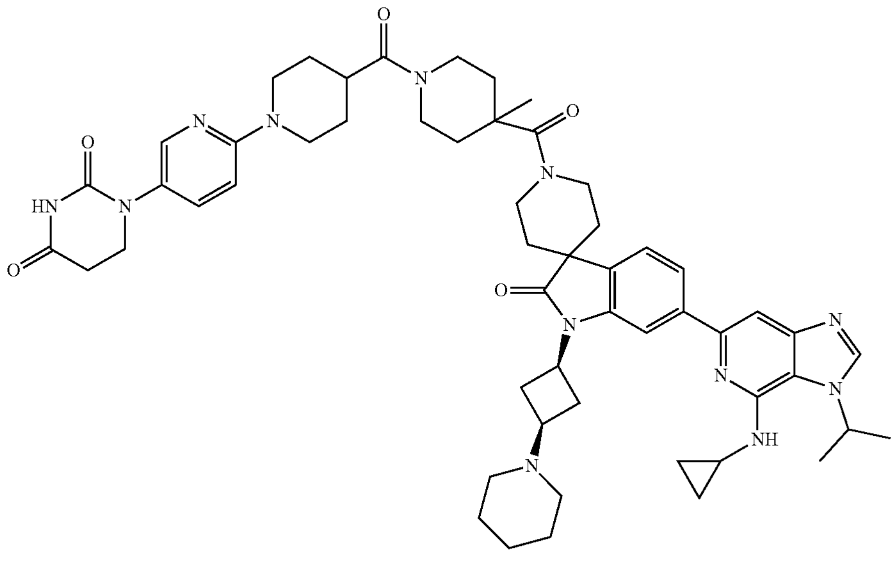 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(N7CCC(=O)NC7=O)cn6)CC5)CC4)CC3)nc(NC3CC3)c21]

Example 115 was prepared by similar procedures as Example 1 using 1-(1-(5-(2,4-dioxotetrahydropyrimidin-1(2H)-yl)pyridin-2-yl)piperidine-4-carbonyl)-4-methylpiperidine-4-carboxylic acid (intermediate 56) (9 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.0165 mmol) as starting materials. The title compound (TFA salt) was isolated as an off-white solid (7.1 mg, 39% yield). LCMS: [$C_{55}H_{70}N_{12}O$], desired mass=979.2, found: m/z=979.5 $[M+H]^+$, Example 116

1-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]-1,3-diazinane-2,4-dione

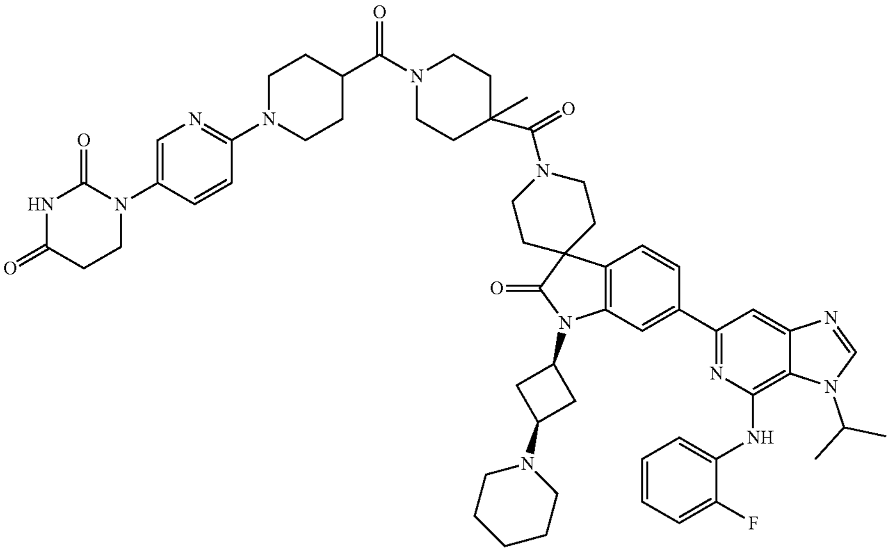 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(N7CCC(=O)NC7=O)cn6)CC5)CC4)CC3)nc(Nc3ccccc3F)c21]

Example 116 was prepared by similar procedures as Example 1 using 1-(1-(5-(2,4-dioxotetrahydropyrimidin-1(2H)-yl)pyridin-2-yl)piperidine-4-carbonyl)-4-methylpiperidine-4-carboxylic acid (intermediate 56) (8.2 mg, 0.018 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.0165 mmol) as starting materials. The title compound (TFA salt) was isolated as an off-white solid (4.7 mg, 33% yield). LCMS: [$C_{58}H_{69}FN_{12}O_5$], desired mass=1033.2, found: m/z=1033.4 $[M+H]^+$, $^1$H NMR (500 MHz, MeOD) δ 8.92 (s, 1H), 8.06 (d, J=2.6 Hz, 1H), 7.94 (dd, J=9.5, 2.6 Hz, 1H), 7.68 (s, 2H), 7.63 (s, 1H), 7.56 (s, 1H), 7.30 (d, J=9.7 Hz, 1H), 5.13 (q, J=6.5 Hz, 1H), 4.49 (p, J=8.4 Hz, 1H), 4.27 (d, J=13.4 Hz, 2H), 4.09 (m, 6H), 3.86 (t, J=6.7 Hz, 2H), 3.69-3.54 (m, 4H), 3.22-3.11 (m, 5H), 3.10-2.94 (m, 3H), 2.95-2.82 (m, 4H), 2.41-2.23 (m, 2H), 2.08-1.99 (m, 2H), 1.94-1.71 (m, 13H), 1.69 (d, J=6.5 Hz, 6H), 1.62 (d, J=12.2 Hz, 2H), 1.46 (s, 3H), 1.31 (s, 1H), 1.13 (d, J=6.8 Hz, 2H), 0.93 (d, J=8.0 Hz, 2H).

Example 117

1-[6-(4-{4-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]-1,3-diazinane-2,4-dione

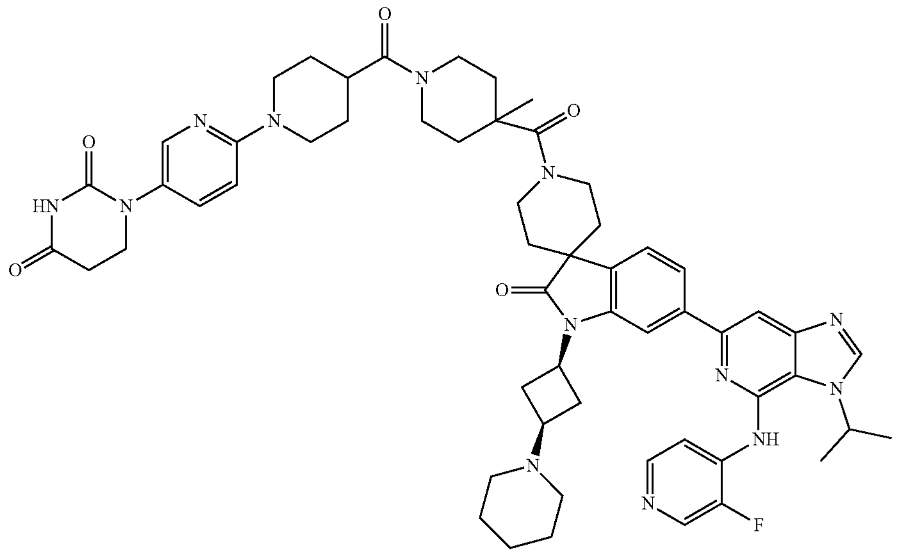 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(N7CCC(=O)NC7=O)cn6)CC5)CC4)CC3)nc(Nc3ccncc3F)c21]

Example 117 was prepared by similar procedures as Example 1 using 1-(1-(5-(2,4-dioxotetrahydropyrimidin-1(2H)-yl)pyridin-2-yl)piperidine-4-carbonyl)-4-methylpiperidine-4-carboxylic acid (intermediate 56) (8.2 mg, 0.016 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (10 mg, 0.0165 mmol) as starting materials. The title compound (TFA salt) was isolated as an off-white solid (7.3 mg, 44% yield). LCMS: [$C_{57}H_{68}FN_{13}O_5$], desired mass=1034.2, found: m/z=1034.5 $[M+H]^+$, $^1H$ NMR (500 MHz, MeOD) δ 8.81-8.73 (m, 2H), 8.38-8.27 (m, 1H), 8.24 (s, 1H), 8.05 (d, J=2.6 Hz, 1H), 7.97 (dd, J=9.6, 2.7 Hz, 1H), 7.88 (d, J=7.8 Hz, 1H), 7.80-7.68 (m, 2H), 7.59 (d, J=7.9 Hz, 1H), 7.35 (dd, J=22.8, 9.7 Hz, 1H), 5.16 (p, J=6.5 Hz, 1H), 4.49 (q, J=8.4 Hz, 1H), 4.26 (d, J=13.3 Hz, 2H), 4.12 (s, 6H), 4.05 (d, J=13.8 Hz, 2H), 3.87 (t, J=6.7 Hz, 4H), 3.65 (d, J=11.2 Hz, 1H), 3.60 (dd, J=20.5, 10.6 Hz, 4H), 3.19 (d, J=19.7 Hz, 2H), 3.01-2.82 (m, 9H), 2.36 (d, J=11.2 Hz, 1H), 2.26 (d, J=13.7 Hz, 1H), 1.94-1.71 (m, 12H), 1.69 (d, J=6.7 Hz, 6H), 1.45 (s, 3H).

Example 118

(3RS)-3-(5-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-2-yl)piperidine-2,6-dione

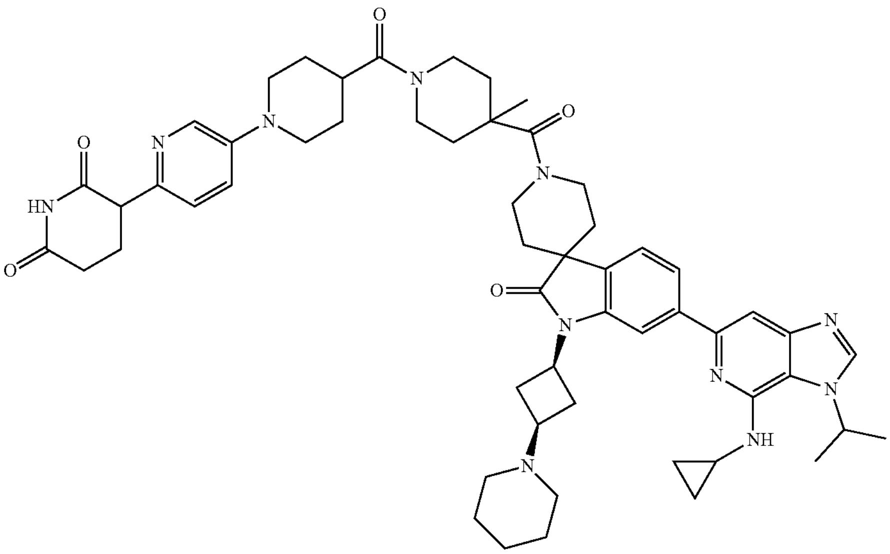 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)nc6)CC5)CC4)CC3)nc(NC3CC3)c21]

Step 3

Example 118 was prepared by similar procedures as Example 1 using 1-(1-(6-(2,6-dioxopiperidin-3-yl)pyridin-3-yl)piperidine-4-carbonyl)-4-methylpiperidine-4-carboxylic acid (intermediate 57) (8 mg, 0.018 mmol) and 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.0165 mmol) as starting materials. The title compound (TFA salt) was isolated as an off-white solid (6.1 mg, 34% yield). LCMS: [$C_{56}H_{71}N_{11}O_5$], desired mass=978.2, found: m/z=978.4 $[M+H]^+$, $^1H$ NMR (500 MHz, MeOD) δ 8.93 (s, 1H), 8.34 (d, J=3.0 Hz, 1H), 8.00 (dd, J=9.4, 3.0 Hz, 1H), 7.72 (d, J=9.1 Hz, 1H), 7.68 (s, 2H), 7.63 (s, 1H), 7.56 (s, 1H), 5.13 (p, J=6.5 Hz, 1H), 4.49 (p, J=8.5 Hz, 1H), 4.16-4.10 (m, 8H), 3.89 (d, J=13.8 Hz, 1H), 3.69-3.51 (m, 4H), 3.27-2.76 (m, 10H), 2.42-2.18 (m, 5H), 1.96-1.76 (m, 13H), 1.69 (d, J=6.5 Hz, 6H), 1.64-1.53 (m, 2H), 1.46 (s, 3H), 1.32 (d, J=10.0 Hz, 1H), 1.13 (d, J=6.5 Hz, 2H), 0.94 (s, 2H).

Example 119

(3RS)-3-[5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-2-yl]piperidine-2,6-dione

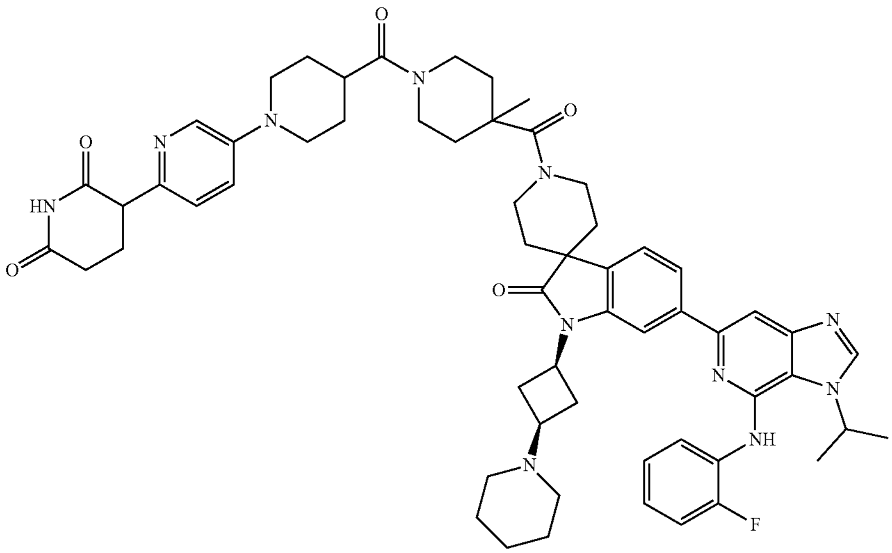 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)nc6)CC5)CC4)CC3)nc(Nc3ccncc3F)c21]

Example 119 was prepared by similar procedures as Example 1 using 1-(1-(6-(2,6-dioxopiperidin-3-yl)pyridin-3-yl)piperidine-4-carbonyl)-4-methylpiperidine-4-carboxylic acid (intermediate 57) (7.3 mg, 0.0165 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.0165 mmol) as starting materials. The title compound (TFA salt) was isolated as an off-white solid (6.4 mg, 37% yield). LCMS: [$C_{59}H_{70}FN_{11}O_5$], desired mass=1032.2, found: m/z=1032.4 $[M+H]^+$, $^1H$ NMR (500 MHz, MeOD) δ 8.84 (s, 1H), 8.33 (d, J=3.0 Hz, 1H), 7.97 (d, J=8.1 Hz, 1H), 7.84-7.75 (m, 2H), 7.70 (t, J=10.3 Hz, 2H), 7.63 (s, 1H), 7.55 (d, J=7.9 Hz, 1H), 7.33-7.21 (m, 2H), 5.35-5.28 (m, 1H), 4.27 (t, J=8.1 Hz, 1H), 4.16-4.10 (m, 8H), 3.89 (d, J=13.8 Hz, 1H), 3.69-3.51 (m, 4H), 3.17-2.76 (m, 10H), 2.42-2.18 (m, 5H), 2.11-1.76 (m, 13H), 1.71 (d, J=6.5 Hz, 6H), 1.64-1.53 (m, 2H), 1.43 (s, 3H).

Example 120

(3RS)-3-[5-(4-{4-[(6-{4-[(3-fluoropyridin-4-yl) amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl) carbonyl]-4-methylpiperidine-1-carbonyl}piperidin-1-yl)pyridin-2-yl]piperidine-2,6-dione

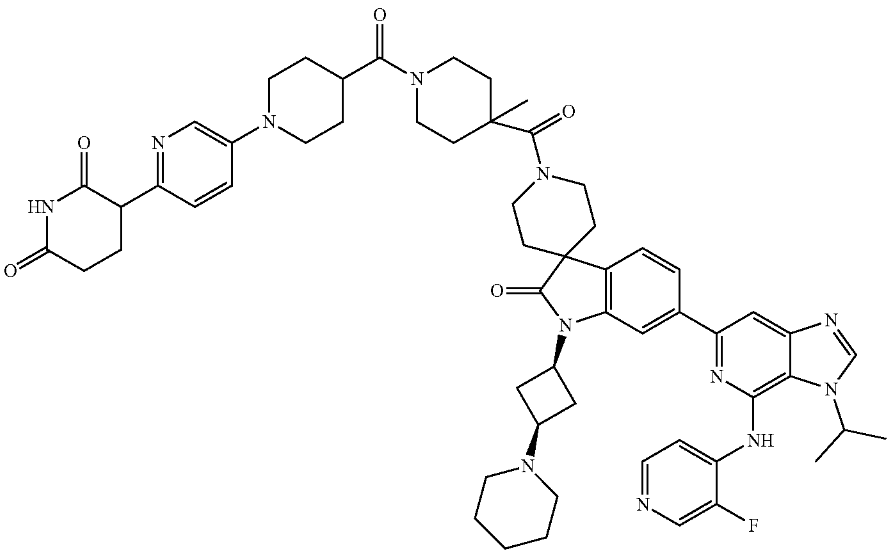

Example 120 was prepared by similar procedures as Example 1 using 1-(1-(6-(2,6-dioxopiperidin-3-yl)pyridin-3-yl)piperidine-4-carbonyl)-4-methylpiperidine-4-carboxylic acid (intermediate 57) (7.3 mg, 0.0165 mmol) and 6-{4-[(3-fluoropyridin-4-yl)amino]-3-isopropylimidazo[4,5-c]pyridin-6-yl}-1-[(1S,3S)-3-(piperidin-1-yl)cyclobutyl]spiro[indole-3,4'-piperidin]-2-one (10 mg, 0.0165 mmol) as starting materials. The title compound (TFA salt) was isolated as an off-white solid (5.9 mg, 34% yield). LCMS: $[C_{58}H_{69}FN_{12}O_5]$, desired mass=1033.2, found: m/z=1033.7 $[M+H]^+$, $^1H$ NMR (500 MHz, MeOD) δ 8.74 (s, 2H), 8.36-8.26 (m, 2H), 8.22 (s, 1H), 7.96 (d, J=9.0 Hz, 1H), 7.88 (d, J=7.7 Hz, 1H), 7.78-7.64 (m, 3H), 7.59 (d, J=7.8 Hz, 1H), 5.20-5.12 (m, 1H), 4.49 (t, J=8.0 Hz, 1H), 4.16-3.89 (m, 9H), 3.69-3.51 (m, 4H), 3.17-2.76 (m, 10H), 2.42-2.18 (m, 5H), 2.11-1.76 (m, 13H), 1.71-1.62 (m, 6H), 1.60 (m, 2H), 1.45 (s, 3H).

Example 121

5-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-(2,6-dioxopiperidin-3-yl)-2,3-dihydro-1H-isoindole-1,3-dione

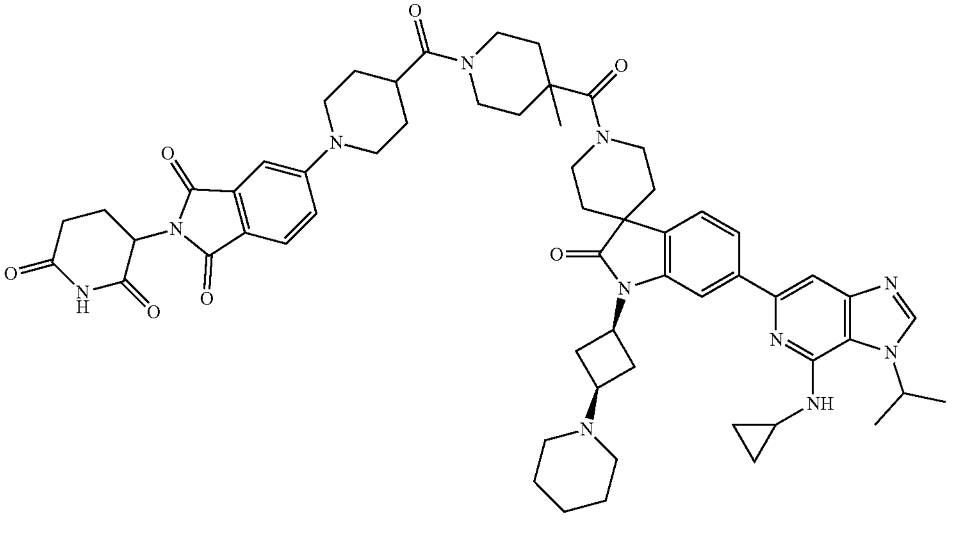 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc7c(c6)C(=O)N(C6CCC(=O)NC6=O)C7=O)CC5)CC4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-(1-(2-(2,6-dioxopiperidin-3-yl)-1,3-dioxoisoindolin-5-yl)piperidine-4-carbonyl)-4-methylpiperidine-4-carboxylic acid (intermediate 58) as the coupling partners, the title compound (TFA salt) was isolated as an off-white solid (5.5 mg, 30% yield). LCMS: [C59H71N11O7], desired mass=1045.6, found: m/z=1046.3 $[M+H]^+$.

Example 122

2-(2,6-dioxopiperidin-3-yl)-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)-2,3-dihydro-1H-isoindole-1,3-dione

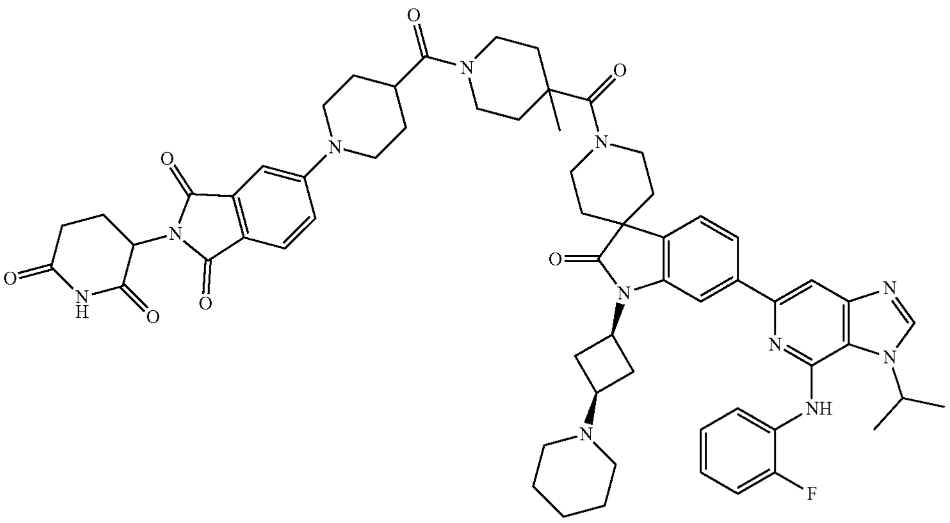 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc7c(c6)C(=O)N(C6CCC(=O)NC6=O)C7=O)CC5)CC4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-(1-(2-(2,6-dioxopiperidin-3-yl)-1,3-dioxoisoindolin-5-yl)piperidine-4-carbonyl)-4-methylpiperidine-4-carboxylic acid (intermediate 58) as the coupling partners, the title compound (TFA salt) was isolated as an off-white solid (4.4 mg, 25% yield). LCMS: [C62H70FN11O7], desired mass=1099.5, found: m/z=1100.4 $[M+H]^+$. $^1$H NMR (500 MHz, MeOD) δ 9.19 (s, 1H), 7.82 (s, 1H), 7.77 (d, J=7.9 Hz, 1H), 7.69 (d, J=8.2 Hz, 2H), 7.60 (s, 1H), 7.55 (d, J=7.9 Hz, 1H), 7.38 (s, 1H), 7.29 (d, J=5.8 Hz, 3H), 7.26 (d, J=9.0 Hz, 1H), 5.39 (p, J=6.7 Hz, 1H), 5.09 (dd, J=12.4, 5.5 Hz, 1H), 4.22 (p, J=8.4 Hz, 1H), 4.09 (s, 7H), 4.03 (s, 1H), 3.89 (d, J=13.8 Hz, 1H), 3.63-3.52 (m, 4H), 3.12 (t, J=12.4 Hz, 2H), 3.05 (s, 3H), 3.08-3.01 (m, 1H), 2.97-2.83 (m, 5H), 2.75 (t, J=14.0 Hz, 2H), 2.36 (d, J=13.8 Hz, 1H), 2.26 (d, J=14.4 Hz, 1H), 2.13 (d, J=12.1 Hz, 1H), 2.04 (d, J=14.6 Hz, 2H), 1.98-1.81 (m, 9H), 1.77 (d, J=6.6 Hz, 7H), 1.60 (t, J=11.3 Hz, 3H), 1.44 (s, 3H).

Example 123

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperazin-1-yl)pyridin-3-yl]piperidine-2,6-dione

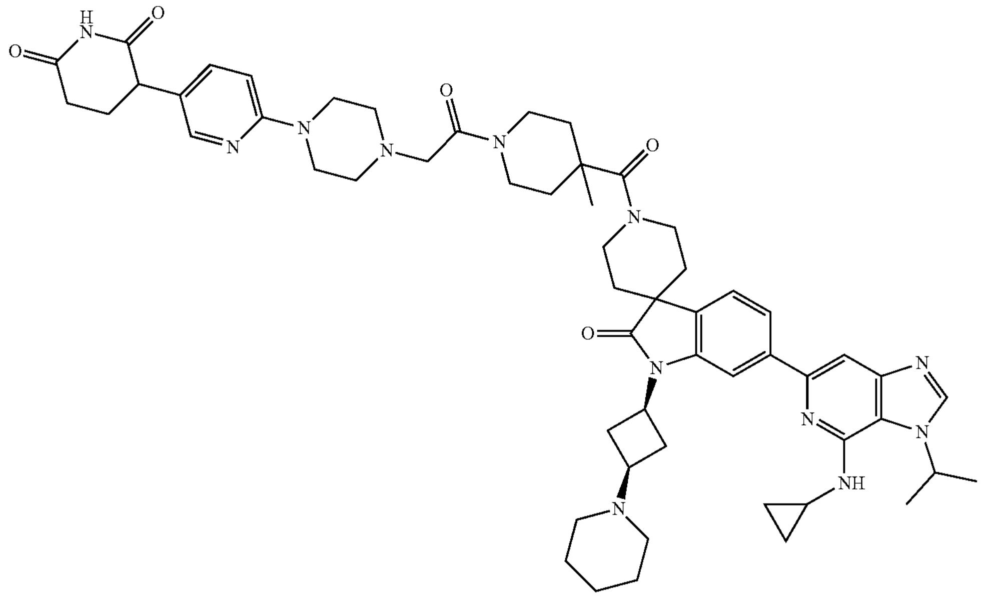 [SMILES: CC(C)n1cnc2cc(-c3ccc4c(c3)N([C@H]3C[C@@H](N5CCCCC5)C3)C(=O)C43CCN(C(=O)C4(C)CCN(C(=O)CN5CCN(c6ccc(C7CCC(=O)NC7=O)cn6)CC5)CC4)CC3)nc(NC3CC3)c21]

Using a sequence of procedures similar to those for Example 36 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 1-(tert-butoxycarbonyl)-4-methylpiperidine-4-carboxylic acid as the coupling partners for the first step, and 6-(4-(cyclopropylamino)-3-isopropyl-3H-imidazo[4,5-c]pyridin-6-yl)-1'-(4-methylpiperidine-4-carbonyl)-1-((1s,3s)-3-(piperidin-1-yl)cyclobutyl)spiro[indoline-3,4'-piperidin]-2-one hydrochloride and 2-(4-(5-(2,6-dioxopiperidin-3-yl)pyridin-2-yl)piperazin-1-yl)acetic acid (intermediate 47, step 2) as the coupling partners for the final step, the title compound (TFA salt) was isolated as an off-white solid (6.1 mg, 19% yield). LCMS: [C56H72N12O5], desired mass=992.6, found: m/z=993.4 $[M+H]^+$.

Example 124

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-3-methylbenzoyl}piperazin-1-yl)-2,3-dihydro-1H-isoindole-1,3-dione

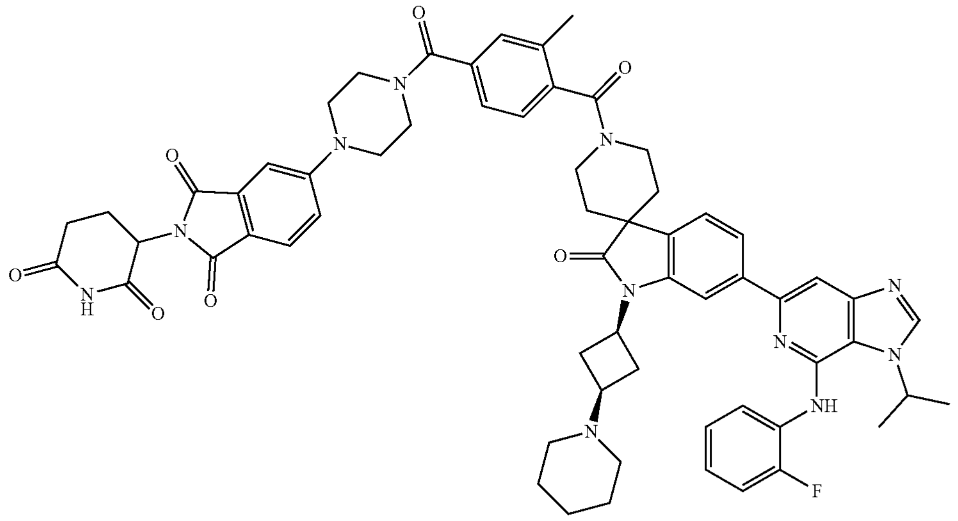 [SMILES: Cc1cc(C(=O)N2CCN(c3ccc4c(c3)C(=O)N(C3CCC(=O)NC3=O)C4=O)CC2)ccc1C(=O)N1CCC2(CC1)C(=O)N([C@H]1C[C@@H](N3CCCCC3)C1)c1cc(-c3cc4ncn(C(C)C)c4c(Nc4ccccc4F)n3)ccc12]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 4-(4-(2-(2,6-dioxopiperidin-3-yl)-1,3-dioxoisoindolin-5-yl)piperazine-1-carbonyl)-2-methylbenzoic acid (intermediate 59) as the coupling partners, the title compound (TFA salt) was isolated as an off-white solid (12.1 mg, 55% yield). LCMS: [C62H64FN11O7], desired mass=1093.5, found: m/z=1094.1 $[M+H]^+$. $^1$H NMR (500 MHz, MeOD) δ 9.20 (s, 1H), 7.82 (s, 1H), 7.78 (dd, J=7.9, 1.5 Hz, 1H), 7.71 (dd, J=15.9, 6.6 Hz, 2H), 7.58 (d, J=8.3 Hz, 1H), 7.50 (d, J=7.7 Hz, 1H), 7.48-7.39 (m, 4H), 7.35-7.26 (m, 4H), 5.39 (p, J=6.6 Hz, 1H), 5.09 (dd, J=12.4, 5.4 Hz, 1H), 4.36 (s, 1H), 4.21 (dd, J=16.5, 8.1 Hz, 2H), 4.09 (s, 1H), 3.95 (s, 2H), 3.89 (s, 1H), 3.82 (s, 1H), 3.68 (s, 3H), 3.63 (s, 3H), 3.61-3.54 (m, 1H), 3.53 (s, 6H), 3.03 (s, 1H), 2.97-2.82 (m, 5H), 2.80-2.66 (m, 2H), 2.49 (d, J=7.6 Hz, 1H), 2.42 (s, 2H), 2.13 (dd, J=9.3, 4.2 Hz, 1H), 2.05 (s, 1H), 2.03 (s, 2H), 1.91 (d, J=14.1 Hz, 1H), 1.79-1.74 (m, 8H), 1.67-1.56 (m, 1H).

Example 125

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-2-methylbenzoyl}piperazin-1-yl)-2,3-dihydro-1H-isoindole-1,3-dione

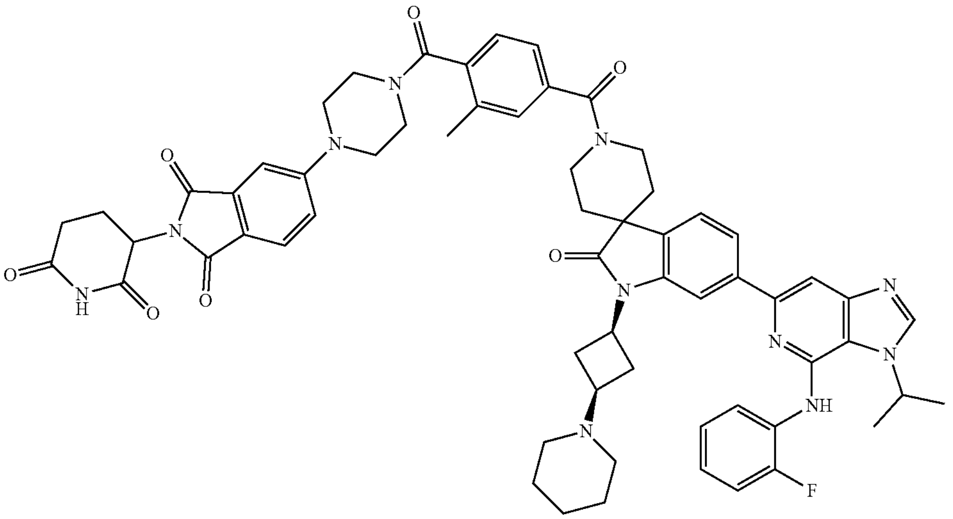 [SMILES: Cc1cc(C(=O)N2CCC3(CC2)C(=O)N([C@H]2C[C@@H](N4CCCCC4)C2)c2cc(-c4cc5ncn(C(C)C)c5c(Nc5ccccc5F)n4)ccc23)ccc1C(=O)N1CCN(c2ccc3c(c2)C(=O)N(C2CCC(=O)NC2=O)C3=O)CC1]

Using procedures similar to those for Example 27 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one and 4-(4-(2-(2,6-dioxopiperidin-3-yl)-1,3-dioxoisoindolin-5-yl)piperazine-1-carbonyl)-3-methylbenzoic acid (intermediate 60) as the coupling partners, the title compound (TFA salt) was isolated as an off-white solid (6.0 mg, 24% yield). LCMS: [C62H64FN11O7], desired mass=1093.5, found: m/z=1094.2 $[M+H]^+$. $^1H$ NMR (500 MHz, MeOD) δ 9.06 (s, 1H), 8.01-7.93 (m, 1H), 7.84-7.66 (m, 4H), 7.60 (d, J=7.9 Hz, 2H), 7.49 (s, 1H), 7.47-7.36 (m, 4H), 7.34-7.24 (m, 4H), 5.36 (p, J=6.6 Hz, 1H), 5.09 (dd, J=12.4, 5.5 Hz, 1H), 4.27-4.19 (m, 2H), 4.12 (s, 1H), 3.99 (s, 4H), 3.65 (s, 3H), 3.63-3.52 (m, 1H), 3.52-3.45 (m, 5H), 3.06 (s, 2H), 2.97-2.82 (m, 5H), 2.78 (d, J=3.1 Hz, 1H), 2.74 (s, 1H), 2.78-2.66 (m, 1H), 2.41 (d, J=6.1 Hz, 4H), 2.03 (s, 1H), 1.99 (s, 2H), 1.90 (s, 3H), 1.75 (d, J=6.5 Hz, 7H), 1.60 (t, J=13.3 Hz, 1H), 1.31 (s, 1H).

Example 126

(3RS)-3-(6-{methyl[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]amino}pyridin-3-yl)piperidine-2,6-dione

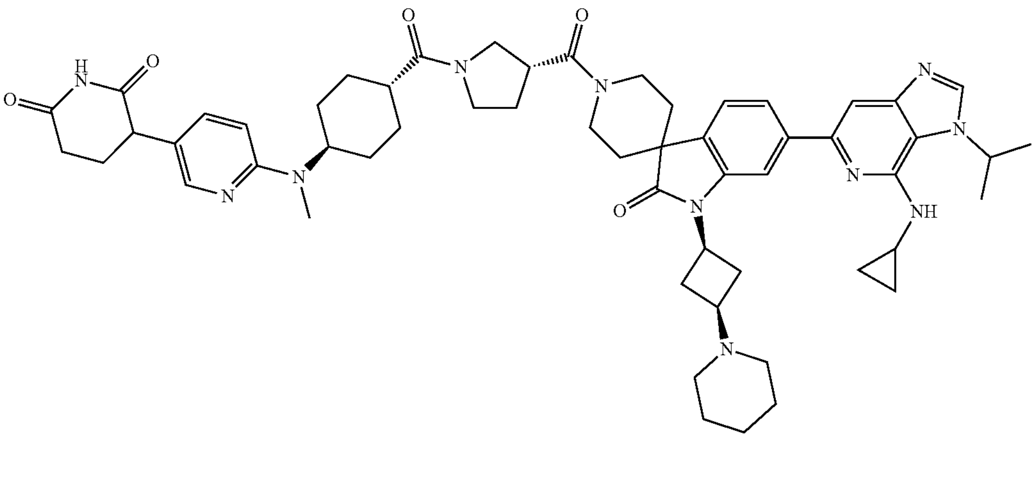 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](N(C)c6ccc(C7CCC(=O)NC7=O)cn6)CC5)C4)CC3)nc(NC3CC3)c21]

Using procedures similar to those used for Example 13 but using (3R)-1-((1r,4R)-4-((5-(2,6-dioxopiperidin-3-yl)pyridin-2-yl)(methyl)amino)cyclohexane-1-carbonyl)pyrrolidine-3-carboxylic acid (Intermediate 61) (16 mg, 0.036 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (20.0 mg, 0.036 mmol) as coupling partners afforded the title compound (TFA salt) as an off white solid (19.7 mg, 55% yield). LCMS: $C_{56}H_{71}N_{11}O_5$ desired mass=977.6, found: m/z=978.5 $[M+H]^+$. $^1H$ NMR (500 MHz, Methanol-$d_4$) δ 8.93 (s, 1H), 7.98 (d, J=9.6 Hz, 1H), 7.84 (d, J=2.2 Hz, 1H), 7.68 (s, 2H), 7.61 (s, 1H), 7.56 (s, 1H), 7.43 (d, J=9.7 Hz, 1H), 5.17-5.10 (m, 1H), 4.53-4.45 (m, 1H), 4.04 (s, 2H), 3.96 (dt, J=13.0, 6.4 Hz, 1H), 3.84 (d, J=8.9 Hz, 1H), 3.73 (q, J=10.1, 8.8 Hz, 1H), 3.62 (dd, J=18.7, 10.6 Hz, 3H), 3.56 (s, 1H), 3.16 (d, J=3.7 Hz, 2H), 3.07 (tt, J=6.8, 3.7 Hz, 1H), 3.01 (s, 3H), 2.90 (t, J=12.3 Hz, 2H), 2.84-2.73 (m, 2H), 2.69-2.59 (m, 1H), 2.34 (td, J=13.5, 12.9, 5.5 Hz, 3H), 2.21 (dd, J=11.6, 7.5 Hz, 1H), 2.12 (s, 1H), 2.02 (d, J=15.7 Hz, 6H), 1.92 (s, 8H), 1.79 (s, 5H), 1.69 (d, J=6.5 Hz, 6H), 1.57 (d, J=13.0 Hz, 1H), 1.31 (s, 1H), 1.14 (d, J=6.5 Hz, 2H), 0.95 (s, 2H).

Example 127

(3RS)-3-(6-{METHYL [(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione

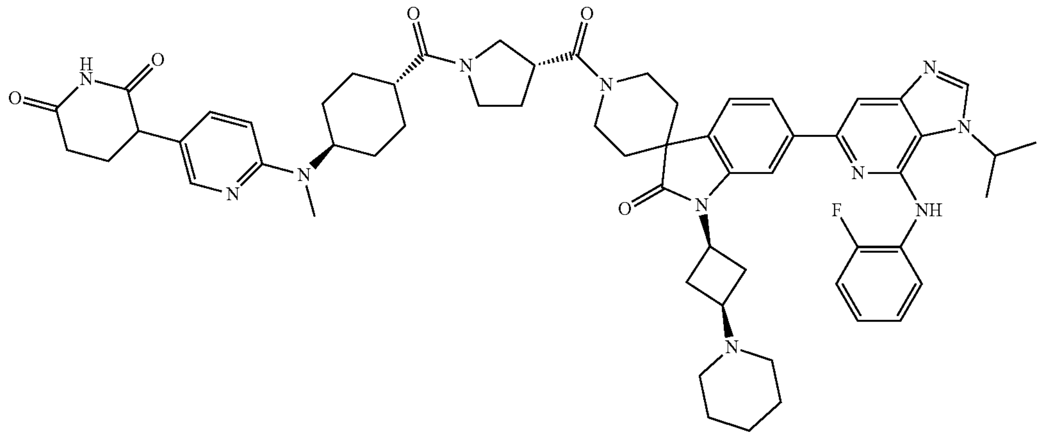 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](N(C)c6ccc(C7CCC(=O)NC7=O)cn6)CC5)C4)CC3)nc(Nc3ccccc3F)c21]

Using procedures similar to those used for Example 13 but using (3R)-1-((1r,4R)-4-((5-(2,6-dioxopiperidin-3-yl)pyridin-2-yl)(methyl)amino)cyclohexane-1-carbonyl)pyrrolidine-3-carboxylic acid (Intermediate 61) (15.5 mg, 0.033 mmol) and 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (20.0 mg, 0.033 mmol) afforded the title compound (TFA salt) as an off white solid (27.6 mg, 80% yield). LCMS: $C_{59}H_{70}FN_{11}O_5$ desired mass=1031.6, found: m/z=1032.8 $[M+H]^+$. $^1H$ NMR (500 MHz, Methanol-$d_4$) δ 7.98 (d, J=9.6 Hz, 1H), 7.84 (d, J=2.2 Hz, 1H), 7.82 (s, 1H), 7.77 (dd, J=7.8, 1.6 Hz, 1H), 7.70 (t, J=8.2 Hz, 1H), 7.62 (s, 1H), 7.53 (q, J=7.5, 6.8 Hz, 1H), 7.43 (d, J=9.5 Hz, 1H), 7.32-7.22 (m, 2H), 4.26 (s, 1H), 4.10 (s, 4H), 3.97 (dd, J=12.8, 5.2 Hz, 1H), 3.82 (t, J=8.7 Hz, 1H), 3.77-3.64 (m, 2H), 3.60 (t, J=8.1 Hz, 1H), 3.57-3.51 (m, 4H), 3.19-3.13 (m, 3H), 3.09 (s, 1H), 3.01 (t, J=9.6 Hz, 1H), 2.92 (t, J=12.4 Hz, 3H), 2.84-2.75 (m, 1H), 2.65 (d, J=13.4 Hz, 1H), 2.40-2.27 (m, 1H), 2.31 (s, 2H), 2.21 (s, 1H), 2.05 (s, 1H), 2.03 (s, 2H), 1.95 (d, J=4.7 Hz, 1H), 1.93 (s, 9H), 1.87 (d, J=4.7 Hz, 1H), 1.84-1.70 (m, 8H), 1.59 (d, J=14.7 Hz, 1H), 1.31 (s, 1H).

Example 128

(3RS)-3-(6-{methyl[(1R,4R)-4-[(3R)-3-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione

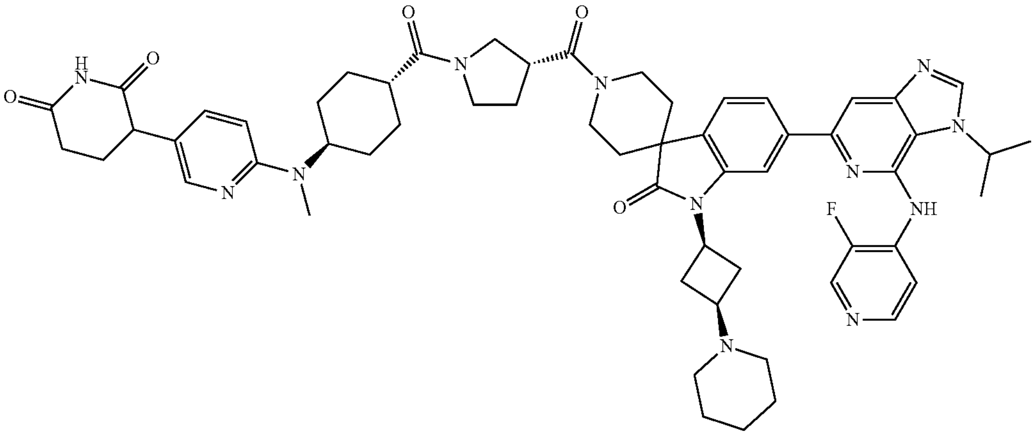 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](N(C)c6ccc(C7CCC(=O)NC7=O)cn6)CC5)C4)CC3)nc(Nc3ccncc3F)c21]

Using procedures similar to those used for Example 13 but using (3R)-1-((1r,4R)-4-((5-(2,6-dioxopiperidin-3-yl)pyridin-2-yl)(methyl)amino)cyclohexane-1-carbonyl)pyrrolidine-3-carboxylic acid (Intermediate 61) (15.0 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.0 mg, 0.033 mmol) afforded the title compound (TFA salt) as an off white solid (13.9 mg, 40% yield). LCMS: $C_{58}H_{69}FN_{12}O_5$ desired mass=1032.5, found: m/z=1033.4 $[M+H]^+$. $^1H$ NMR (500 MHz, Methanol-$d_4$) δ 8.81-8.74 (m, 2H), 8.31 (d, J=6.7 Hz, 1H), 8.24 (s, 1H), 7.98 (dd, J=9.7, 2.2 Hz, 1H), 7.90-7.82 (m, 2H), 7.80-7.69 (m, 2H), 7.59 (s, 1H), 7.43 (d, J=9.6 Hz, 1H), 5.20-5.13 (m, 1H), 4.53-4.45 (m, 1H), 4.15 (s, 2H), 4.09-3.92 (m, 3H), 3.82 (d, J=11.5 Hz, 1H), 3.73 (t, J=6.9 Hz, 1H), 3.63 (ddd, J=32.3, 21.4, 13.6 Hz, 5H), 3.16 (d, J=3.8 Hz, 3H), 2.98 (s, 3H), 2.90 (t, J=12.4 Hz, 2H), 2.83-2.72 (m, 2H), 2.64 (t, J=13.7 Hz, 1H), 2.40-2.25 (m, 3H), 2.24-2.16 (m, 1H), 2.11 (s, 1H), 2.01 (t, J=15.6 Hz, 6H), 1.91 (d, J=14.7 Hz, 8H), 1.78 (d, J=12.8 Hz, 6H), 1.65 (dd, J=6.7, 2.7 Hz, 7H), 1.57 (d, J=13.2 Hz, 1H), 1.31 (s, 1H).

Example 129

2-[(3RS)-2,6-dioxopiperidin-3-yl]-4-{methyl[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]amino}-2,3-dihydro-1H-isoindole-1,3-dione

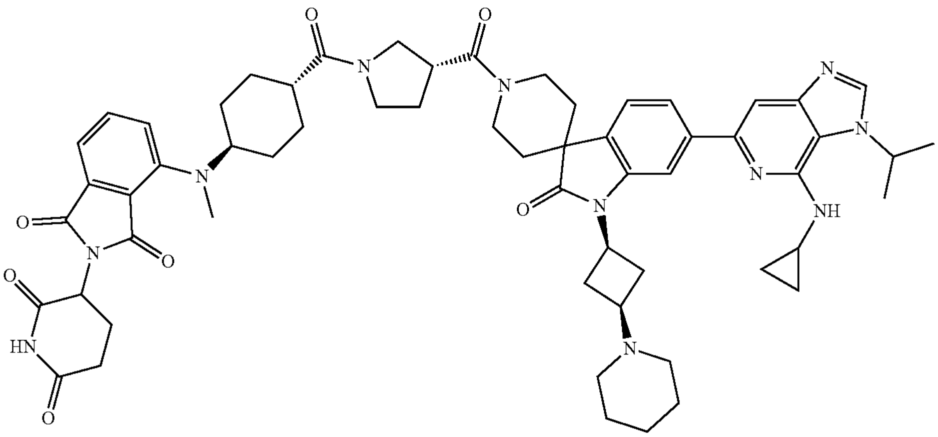 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](N(C)c6cccc7c6C(=O)N(C6CCC(=O)NC6=O)C7=O)CC5)C4)CC3)nc(NC3CC3)c21]

Using procedures similar to those used for Example 13 but using (3R)-1-((1r,4R)-4-((2-(2,6-dioxopiperidin-3-yl)-1,3-dioxoisoindolin-4-yl)(methyl)amino)cyclohexane-1-carbonyl)pyrrolidine-3-carboxylic acid (Intermediate 62) (64.0 mg, 0.126 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (70.0 mg, 0.126 mmol) as coupling partners afforded the title compound (TFA salt) as an off white solid (75.5 mg, 56% yield). LCMS: $C_{59}H_{71}N_{11}O_7$ desired mass=1045.6, found: m/z=1047.1 $[M+H]^+$. $^1H$ NMR (500 MHz, Methanol-$d_4$) δ 7.70-7.58 (m, 4H), 7.56 (s, 1H), 7.30 (dd, J=12.2, 7.8 Hz, 2H), 5.13 (dt, J=12.0, 5.9 Hz, 2H), 4.53-4.45 (m, 1H), 4.16 (dd, J=26.0, 15.4 Hz, 2H), 4.02 (s, 1H), 3.94 (s, 1H), 3.86 (t, J=11.8 Hz, 2H), 3.79-3.63 (m, 1H), 3.57 (d, J=11.1 Hz, 4H), 3.24 (dt, J=23.2, 11.6 Hz, 2H), 3.07 (s, 1H), 3.01 (s, 2H), 2.97-2.84 (m, 6H), 2.77 (d, J=19.1 Hz, 3H), 2.54 (d, J=12.3 Hz, 1H), 2.33-2.26 (m, 2H), 2.15 (d, J=10.3 Hz, 1H), 2.00 (s, 8H), 1.91 (s, 5H), 1.83-1.73 (m, 4H), 1.69 (d, J=6.6 Hz, 6H), 1.56 (d, J=12.6 Hz, 1H), 1.14 (t, J=6.2 Hz, 2H), 0.95 (s, 2H).

Example 130

(3RS)-3-(6-{methyl[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]amino}pyridin-3-yl)piperidine-2,6-dione

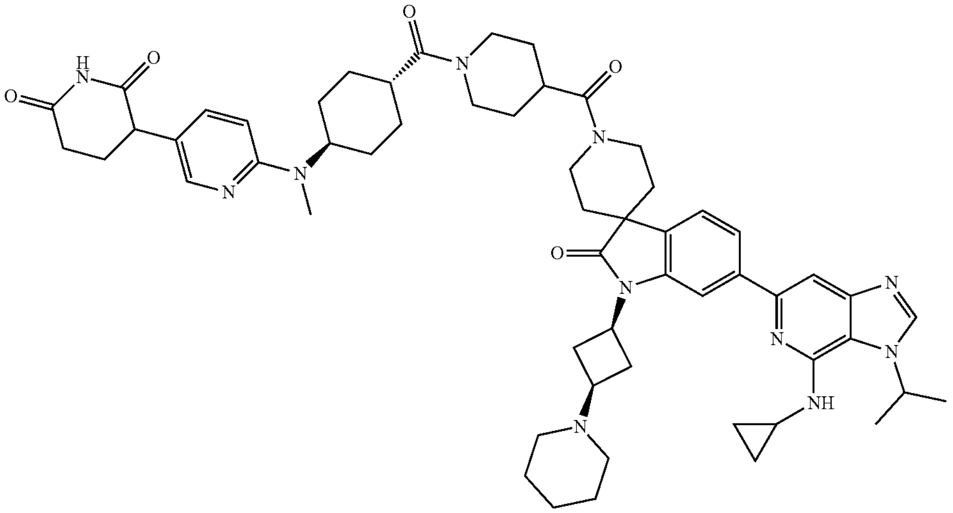 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](N(C)c6ccc(C7CCC(=O)NC7=O)cn6)CC5)CC4)CC3)nc(NC3CC3)c21]

Using procedures similar to those used for Example 13 but using 1-((1r,4r)-4-((5-(2,6-dioxopiperidin-3-yl)pyridin-2-yl)(methyl)amino)cyclohexane-1-carbonyl)piperidine-4-carboxylic acid (Intermediate 63) (16.5 mg, 0.036 mmol) and 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (20.0 mg, 0.036 mmol) as coupling partners afforded the title compound (TFA salt) as an off white solid (27.8 mg, 75% yield). LCMS: $C_{57}H_{73}N_{11}O_5$ desired mass=991.6, found: m/z=992.7 $[M+H]^+$. $^1H$ NMR (500 MHz, Methanol-$d_4$) δ 8.92 (s, 1H), 7.98 (dd, J=9.6, 2.2 Hz, 1H), 7.84 (d, J=2.1 Hz, 1H), 7.66 (d, J=7.7 Hz, 1H), 7.64 (s, 1H), 7.56 (s, 1H), 7.42 (d, J=9.6 Hz, 1H), 4.54-4.45 (m, 1H), 4.19 (s, 3H), 4.14 (s, 1H), 4.06 (s, 2H), 3.97 (dd, J=12.9, 5.0 Hz, 1H), 3.67-3.54 (m, 4H), 3.16 (s, 3H), 3.10-3.04 (m, 1H), 3.01 (s, 2H), 2.90 (t, J=11.7 Hz, 1H), 2.84-2.75 (m, 2H), 2.40-2.29 (m, 1H), 2.05 (d, J=6.2 Hz, 1H), 2.00 (s, 5H), 1.91 (d, J=12.4 Hz, 12H), 1.80 (s, 6H), 1.69 (d, J=6.6 Hz, 6H), 1.64 (s, 1H), 1.59 (s, 2H), 1.39 (dd, J=6.7, 3.9 Hz, 2H), 1.31 (s, 2H), 1.13 (s, 2H), 0.93 (s, 3H).

Example 131

(3RS)-3-(6-{methyl[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-3-yl)piperidine-2,6-dione

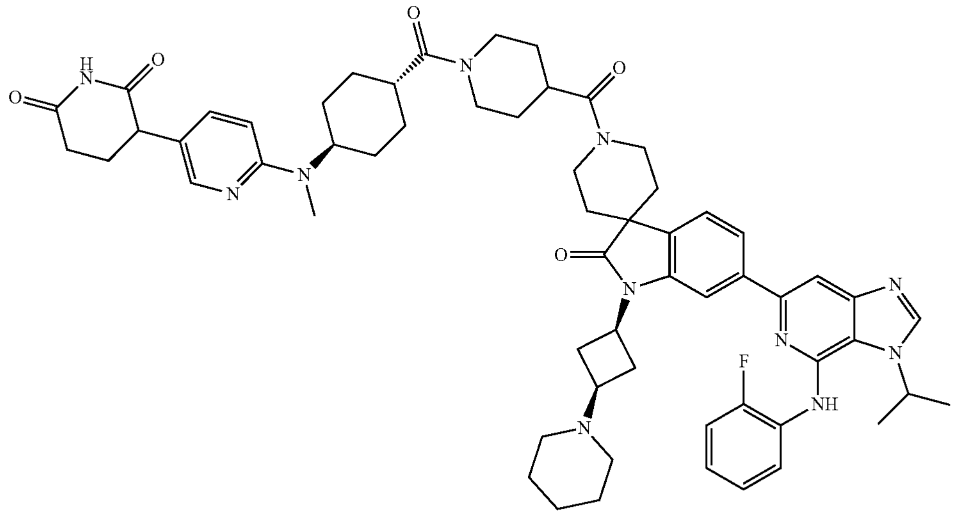 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](N(C)c6ccc(C7CCC(=O)NC7=O)cn6)CC5)CC4)CC3)nc(Nc3ccccc3F)c21]

Using procedures similar to those used for Example 13 but using 1-((1r,4r)-4-((5-(2,6-dioxopiperidin-3-yl)pyridin-2-yl)(methyl)amino)cyclohexane-1-carbonyl)piperidine-4-carboxylic acid (Intermediate 63) (15.0 mg, 0.033 mmol) and 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (20.0 mg, 0.033 mmol) afforded the title compound (TFA salt) as an off white solid (24.1 mg, 69% yield). LCMS: $C_{60}H_{72}FN_{11}O_5$ desired mass=1045.6, found: m/z=1046.5 $[M+H]^+$. $^1H$ NMR (500 MHz, Methanol-$d_4$) δ 8.92 (s, 1H), 7.98 (dd, J=9.6, 2.2 Hz, 1H), 7.84 (d, J=2.1 Hz, 1H), 7.66 (d, J=7.7 Hz, 1H), 7.64 (s, 1H), 7.56 (s, 1H), 7.42 (d, J=9.6 Hz, 1H), 4.54-4.45 (m, 1H), 4.19 (s, 3H), 4.14 (s, 1H), 4.06 (s, 2H), 3.97 (dd, J=12.9, 5.0 Hz, 1H), 3.67-3.54 (m, 4H), 3.16 (s, 3H), 3.10-3.04 (m, 1H), 3.01 (s, 2H), 2.90 (t, J=11.7 Hz, 1H), 2.84-2.75 (m, 2H), 2.40-2.29 (m, 1H), 2.05 (d, J=6.2 Hz, 1H), 2.00 (s, 5H), 1.91 (d, J=12.4 Hz, 12H), 1.80 (s, 6H), 1.64 (s, 1H), 1.59 (s, 2H), 1.39 (dd, J=6.7, 3.9 Hz, 2H), 1.31 (s, 2H), 1.13 (s, 2H), 0.93 (s, 3H).

Example 132

(3RS)-3-(6-{methyl[(1R,4R)-4-{4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-3-yl)piperidine-2,6-dione

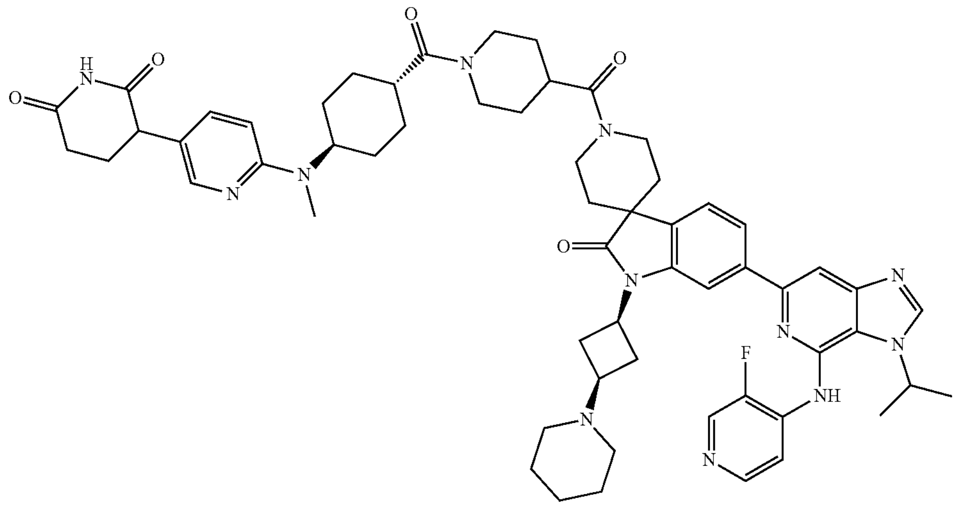 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](N(C)c6ccc(C7CCC(=O)NC7=O)cn6)CC5)CC4)CC3)nc(Nc3ccncc3F)c21]

Using procedures similar to those used for Example 13 but using 1-((1r,4r)-4-((5-(2,6-dioxopiperidin-3-yl)pyridin-2-yl)(methyl)amino)cyclohexane-1-carbonyl)piperidine-4-carboxylic acid (Intermediate 63) (15.0 mg, 0.033 mmol) and 6-{4-[(3-fluoropyridin-4-yl)amino]-3-isopropylimidazo[4,5-c]pyridin-6-yl}-1-[(1s,3s)-3-(piperidin-1-yl)cyclobutyl]spiro[indole-3,4'-piperidin]-2-one (20.0 mg, 0.033 mmol) afforded the title compound (TFA salt) as an off white solid (29.7 mg, 84% yield). LCMS: $C_{59}H_{71}FN_{12}O_5$ desired mass=1046.6, found: m/z=1047.3 $[M+H]^+$. $^1H$ NMR (500 MHz, Methanol-$d_4$) δ 8.80-8.73 (m, 2H), 8.30 (d, J=6.8 Hz, 1H), 8.24 (s, 1H), 7.98 (dd, J=9.6, 2.1 Hz, 1H), 7.88 (s, 1H), 7.84 (d, J=2.2 Hz, 1H), 7.74 (dd, J=16.2, 5.9 Hz, 2H), 7.60 (dd, J=19.5, 7.7 Hz, 1H), 7.44 (dd, J=20.2, 8.8 Hz, 1H), 5.20-5.12 (m, 1H), 4.54-4.46 (m, 1H), 4.20 (d, J=15.1 Hz, 1H), 4.14 (s, 3H), 4.04 (s, 3H), 3.97 (dd, J=13.0, 4.9 Hz, 1H), 3.60 (dd, J=21.1, 10.7 Hz, 4H), 3.16 (s, 4H), 2.98 (s, 2H), 2.90 (t, J=12.2 Hz, 2H), 2.80 (dt, J=17.6, 6.3 Hz, 4H), 2.40-2.27 (m, 1H), 2.24-2.16 (m, 1H), 2.07-1.95 (m, 2H), 1.93 (s, 3H), 1.90 (s, 14H), 1.83-1.73 (m, 4H), 1.72-1.61 (m, 6H), 1.59 (s, 2H), 1.31 (s, 1H).

Example 133

2-[(3RS)-2,6-dioxopiperidin-3-yl]-4-{methyl[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]amino}-2,3-dihydro-1H-isoindole-1,3-dione

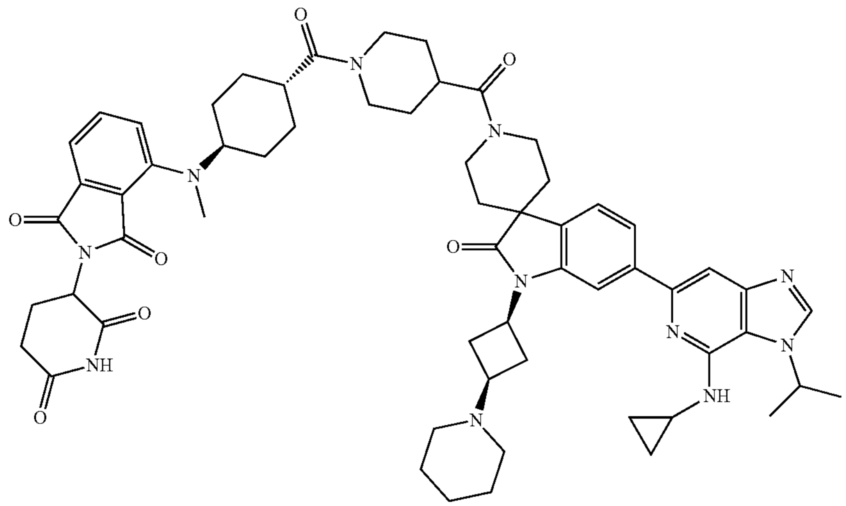 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](N(C)c6cccc7c6C(=O)N(C6CCC(=O)NC6=O)C7=O)CC5)CC4)CC3)nc(NC3CC3)c21]

Using procedures similar to those for Example 31 and using 6-(4-(cyclopropylamino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 1-((1r,4r)-4-((2-(2,6-dioxopiperidin-3-yl)-1,3-dioxoisoindolin-4-yl)(methyl)amino)cyclohexane-1-carbonyl)piperidine-4-carboxylic acid (intermediate 64) as the coupling partners, the title compound (TFA salt) was isolated as an off-white solid (7.4 mg, 40% yield). LCMS: [C60H73N11O7], desired mass=1059.6, found: m/z=1060.6 [M+H]+.

Example 134

(3RS)-3-{4-[methyl({1-[(1R,4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexanecarbonyl]piperidin-4-yl})amino]phenyl}piperidine-2,6-dione

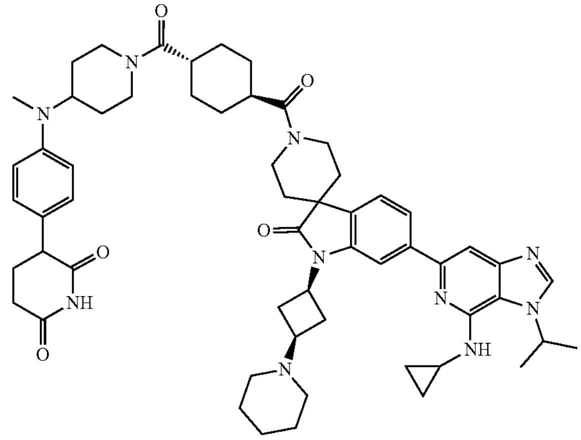 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cc6)CC5)CC4)CC3)nc(NC3CC3)c21]

Step 1: methyl (1R,4r)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylate

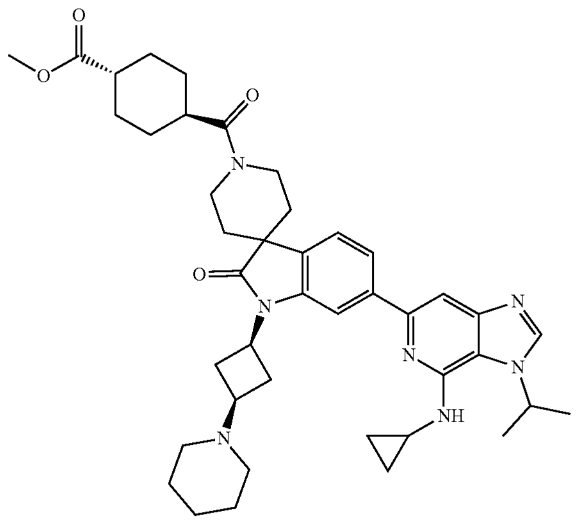 [SMILES: COC(=O)[C@H]1CC[C@H](C(=O)N2CCC3(CC2)C(=O)N([C@H]2C[C@@H](N4CCCCC4)C2)c2cc(-c4cc5ncn(C(C)C)c5c(NC5CC5)n4)ccc23)CC1]

To a solution of (1r,4r)-4-(methoxycarbonyl)cyclohexane-1-carboxylic acid (15 mg, 0.081 mmol) in DMF was added BOP (36, 0.082 mmol) and DIPEA (0.05 mL, 34 mg, 0.27 mmol). 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (30 mg, 0.054 mmol) was added last and the reaction mixture was stirred at room temperature for 1 hour. The reaction mixture was diluted with DMF, and further purified by reverse phase FC (5-50% MeCN/H2O +0.1% TFA) to afford the title compound (TFA salt) as an off-white solid (27 mg, 69% yield). LCMS: [$C_{42}H_{55}N_7O_4$], desired mass=721.9, found: m/z=722.6 [M+H]+.

Step 2: (1R,4r)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid

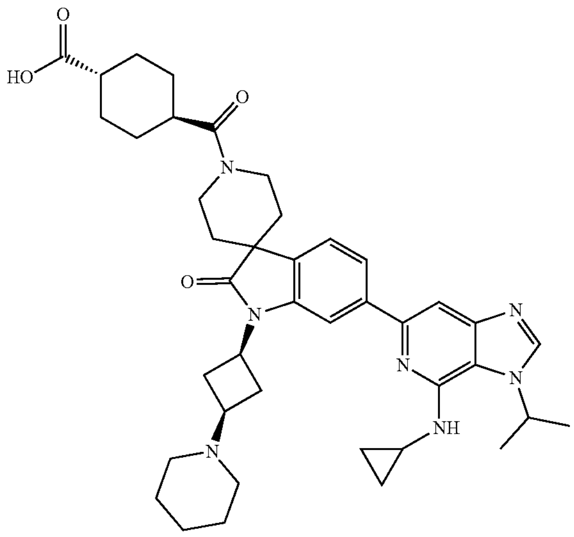 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)O)CC4)CC3)nc(NC3CC3)c21]

Methyl (1R,4r)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylate (27 mg, 0.035 mmol) was dissolved in THF at rt. To this solution was added lithium hydroxide and the resulting mixture was stirred vigorously overnight. LCMS at this point showed full consumption of starting material. The reaction mixture was concentrated to dryness and further purified by reverse phase FC (5-50% MeCN/H2O) to provide the title compound as an off-white solid (23 mg, 94% yield). LCMS: [$C_{41}H_{53}N_7O_4$], desired mass=707.9, found: m/z=708.6 [M+H]$^+$.

Step 3

Example 134 was prepared by similar procedures as Example 1 using (1R,4r)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (15 mg, 0.021 mmol) and 3-(4-(methyl(piperidin-4-yl)amino)phenyl)piperidine-2,6-dione (9 mg, 0.032 mmol) as starting materials. The title compound (TFA salt) was isolated as an off-white solid (7 mg, 33% yield). LCMS: [$C_{58}H_{74}N_{10}O_5$], desired mass=991.3, found: m/z=991.5 [M+H]$^+$, $^1$H NMR (500 MHz, MeOD) δ 8.92 (s, 1H), 7.67 (s, 2H), 7.63 (s, 1H), 7.56 (s, 1H), 7.39 (d, J=8.1 Hz, 2H), 7.31 (s, 2H), 5.13 (p, J=6.8 Hz, 1H), 4.72 (d, J=13.3 Hz, 1H), 4.49 (q, J=8.1 Hz, 1H), 4.25 (d, J=13.6 Hz, 1H), 4.14-4.10 (m, 3H), 3.99-3.89 (m, 2H), 3.61 (m, 4H), 3.12 (s, 3H), 3.10-2.62 (m, 9H), 2.33-2.20 (m, 4H), 2.08-1.75 (m, 13H), 1.69 (d, J=6.6 Hz, 6H), 1.65 (m, 2H), 1.59 (m, 6H), 1.31 (s, 2H), 1.13 (d, J=6.8 Hz, 2H), 0.93 (d, J=7.2 Hz, 2H).

Example 135

(3RS)-3-{4-[methyl({1-[(1R,4R)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl})amino]phenyl}piperidine-2,6-dione

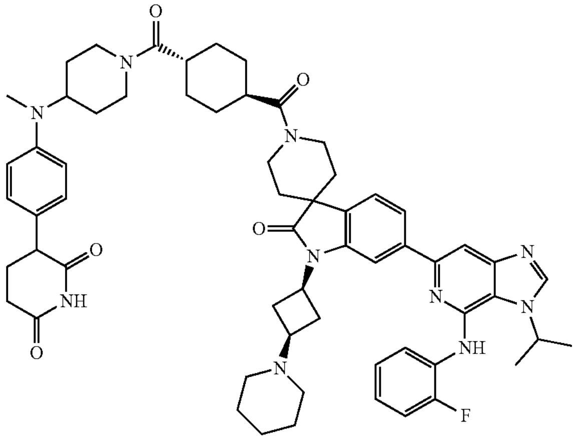 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cc6)CC5)CC4)CC3)nc(Nc3ccccc3F)c21]

Example 135 was prepared by similar procedures as Example 134 (step 1 to step 3) using (1R,4r)-4-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (10 mg, 0.013 mmol) and 3-(4-(methyl(piperidin-4-yl)amino)phenyl)piperidine-2,6-dione (4 mg, 0.013 mmol) as starting materials. The title compound (TFA salt) was isolated as an off-white solid (5.5 mg, 40% yield). LCMS: [$C_{61}H_{73}FN_{10}O_5$], desired mass=1045.3, found: m/z=1045.7 [M+H]$^+$, $^1$H NMR (500 MHz, MeOD) δ 8.88 (s, 1H), 7.84-7.74 (m, 2H), 7.70 (t, J=7.6 Hz, 1H), 7.62 (s, 1H), 7.52 (d, J=7.9 Hz, 1H), 7.37 (s, 2H), 7.32-7.20 (m, 5H), 5.32 (p, J=6.6 Hz, 1H), 4.71 (d, J=13.3 Hz, 1H), 4.25 (q, J=8.5 Hz, 1H), 4.07 (m, 3H), 3.95 (d, J=12.5 Hz, 2H), 3.63-3.55 (m, 4H), 3.13 (s, 3H), 3.05-2.62 (m, 9H), 2.25 (m, 4H), 2.05 (s, 1H), 2.03-1.75 (m, 13H), 1.73 (d, J=6.7 Hz, 6H), 1.61 (m, 8H), 1.31 (s, 2H).

Example 136

(3RS)-3-{4-[methyl({1-[(1R,4R)-4-[(6-{4-[(3-fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-11'-yl)carbonyl]cyclohexanecarbonyl]piperidin-4-yl})amino]phenyl}piperidine-2,6-dione

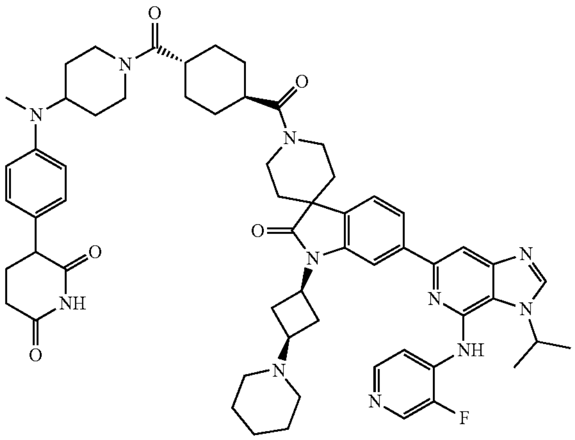 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cc6)CC5)CC4)CC3)nc(Nc3ccncc3F)c21]

Example 136 was prepared by similar procedures as Example 134 (step 1 to step 3) using (1R,4r)-4-(6-(4-((3-fluoropyridin-4-yl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (15 mg, 0.020 mmol) and 3-(4-(methyl(piperidin-4-yl)amino)phenyl)piperidine-2,6-dione (7 mg, 0.024 mmol) as starting materials. The title compound (TFA salt) was isolated as an off-white solid (10 mg, 46% yield). LCMS: [$C_{60}H_{72}FN_{11}O_5$], desired mass=1046.3, found: m/z=1046.7 $[M+H]^+$, $^1H$ NMR (500 MHz, MeOD) δ 8.76 (d, J=12.3 Hz, 2H), 8.30 (d, J=6.9 Hz, 1H), 8.23 (s, 1H), 7.88 (d, J=7.8 Hz, 1H), 7.79-7.69 (m, 2H), 7.59 (dd, J=20.0, 7.8 Hz, 1H), 7.48-7.25 (m, 4H), 5.20 (p, J=6.6 Hz, 1H), 4.72 (d, J=13.7 Hz, 1H), 4.50 (p, J=8.6 Hz, 1H), 4.25 (d, J=13.3 Hz, 1H), 4.11 (d, J=14.5 Hz, 3H), 3.96 (m, 2H), 3.65-3.51 (m, 4H), 3.21 (s, 1H), 3.25-3.12 (m, 5H), 3.08-2.65 (m, 7H), 2.4-2.12 (m, 4H), 2.11-1.67 (m, 13H), 1.64 (d, J=6.7 Hz, 6H), 1.62-1.53 (m, 8H), 1.31 (s, 1H).

Example 137

(3RS)-3-{6-[methyl({1-[(1R,4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexanecarbonyl]piperidin-4-yl})amino]pyridin-3-yl}piperidine-2,6-dione

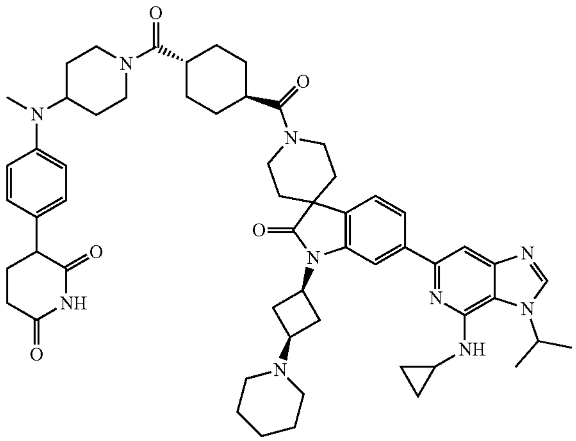 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cc6)CC5)CC4)CC3)nc(NC3CC3)c21]

Example 137 was prepared by similar procedures as Example 1 using (1R,4r)-4-(6-(4-(cyclopropylamino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (10 mg, 0.014 mmol) and 3-(6-(methyl(piperidin-4-yl)amino)pyridin-3-yl)piperidine-2,6-dione (4 mg, 0.014 mmol) as starting materials. The title compound (TFA salt) was isolated as an off-white solid (6.3 mg, 44% yield). LCMS: [$C_{57}H_{73}N_{11}O_5$], desired mass=992.3, found: m/z=992.5 $[M+H]^+$, Example 138

(3RS)-3-{6-[methyl({1-[(1R,4R)-4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl})amino]pyridin-3-yl}piperidine-2,6-dione

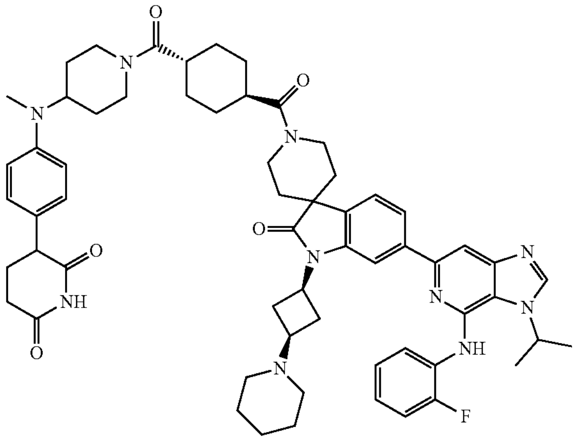 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cc6)CC5)CC4)CC3)nc(Nc3ccccc3F)c21]

Example 138 was prepared by similar procedures as Example 134 (step 1 to step 3) using (1R,4r)-4-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (10 mg, 0.013 mmol) and 3-(6-(methyl(piperidin-4-yl)amino)pyridin-3-yl)piperidine-2,6-dione (6 mg, 0.019 mmol) as starting materials. The title compound (TFA salt) was isolated as an off-white solid (5.7 mg, 41% yield). LCMS: [$C_{60}H_{72}FN_{11}O_5$], desired mass=1046.3, found: m/z=1046.7 $[M+H]^+$.

Example 139

(3RS)-3-{6-[methyl({1-[(1R,4R)-4-[(6-{4-[(3-Fluoropyridin-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]cyclohexanecarbonyl]piperidin-4-yl})amino]pyridin-3-yl}piperidine-2,6-dione

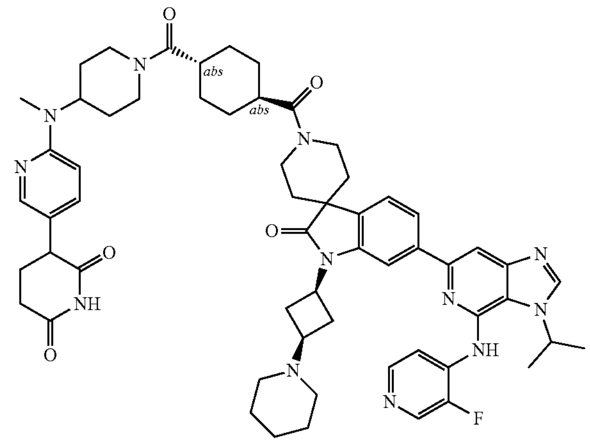 [SMILES: CC(C)n1cnc2cc(-c3ccc4c(c3)N([C@H]3C[C@@H](N5CCCCC5)C3)C(=O)C43CCN(C(=O)[C@H]4CC[C@H](C(=O)N5CCC(N(C)c6ccc(C7CCC(=O)NC7=O)cn6)CC5)CC4)CC3)nc(Nc3ccncc3F)c21]

Example 139 was prepared by similar procedures as Example 134 (step 1 to step 3) using (1R,4r)-4-(6-(4-((3-fluoropyridin-4-yl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carboxylic acid (10 mg, 0.013 mmol) and 3-(6-(methyl(piperidin-4-yl)amino)pyridin-3-yl)piperidine-2,6-dione (6 mg, 0.020 mmol) as starting materials. The title compound (TFA salt) was isolated as an off-white solid (5 mg, 36% yield). LCMS: [$C_{59}H_{71}FN_{12}O_5$], desired mass=1047.2, found: m/z=1047.4 $[M+H]^+$ Example 140

(3RS)-3-{6-[(1-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]benzoyl}piperidin-4-yl)(methyl)amino]pyridin-3-yl}piperidine-2,6-dione

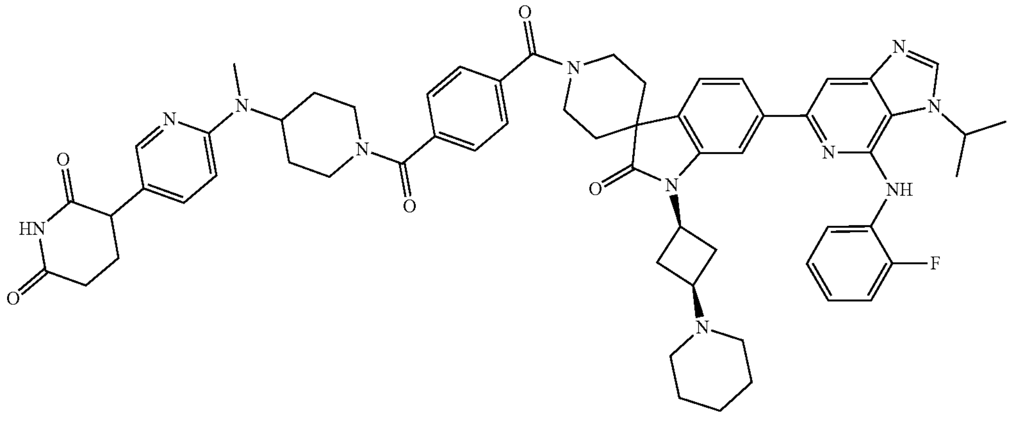 [SMILES: CC(C)n1cnc2cc(-c3ccc4c(c3)N([C@H]3C[C@@H](N5CCCCC5)C3)C(=O)C43CCN(C(=O)c4ccc(C(=O)N5CCC(N(C)c6ccc(C7CCC(=O)NC7=O)cn6)CC5)cc4)CC3)nc(Nc3ccccc3F)c21]

Example 140 was prepared by similar procedures as Example 1 using 4-(4-((5-(2,6-dioxopiperidin-3-yl)pyridin-2-yl)(methyl)amino)piperidine-1-carbonyl)benzoic acid (intermediate 67) (7.4 mg, 0.0165 mmol) and 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one (10 mg, 0.0165 mmol) as starting materials. The title compound (TFA salt) was isolated as an off-white solid (7.2 mg, 41% yield). LCMS: [$C_{60}H_{66}FN_{11}O_5$], desired mass=1040.2, found: m/z=1040.8 $[M+H]^+$, $^1H$ NMR (500 MHz, DMSO) δ 10.92 (s, 1H), 9.36 (d, J=9.1 Hz, 1H), 8.68 (s, 1H), 8.38 (s, 1H), 7.91 (s, 2H), 7.78 (s, 1H), 7.72 (d, J=7.8 Hz, 1H), 7.64 (d, J=7.9 Hz, 1H), 7.61-7.50 (m, 5H), 7.49 (s, 1H), 7.37-7.28 (m, 1H), 7.23 (qt, J=8.0, 3.9 Hz, 2H), 5.30 (p, J=6.8 Hz, 1H), 4.65 (s, 2H), 4.50 (s, 2H), 4.10 (p, J=8.3 Hz, 2H), 3.90-3.62 (m, 6H), 3.51 (q, J=8.1 Hz, 1H), 3.38 (d, J=11.6 Hz, 2H), 3.23 (s, 1H), 3.00 (s, 3H), 2.77-2.5 (m, 5H), 2.28 (d, J=12.4 Hz, 2H), 2.03-1.64 (m, 13H), 1.60 (d, J=6.5 Hz, 6H), 1.45 (m, 2H).

Example 141

N-(1-{5-[(3RS)-2,6-dioxopiperidin-3-yl]pyridin-2-yl}piperidin-4-yl)-4-[(6-{4-[(2-Fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-N-methylbenzamide

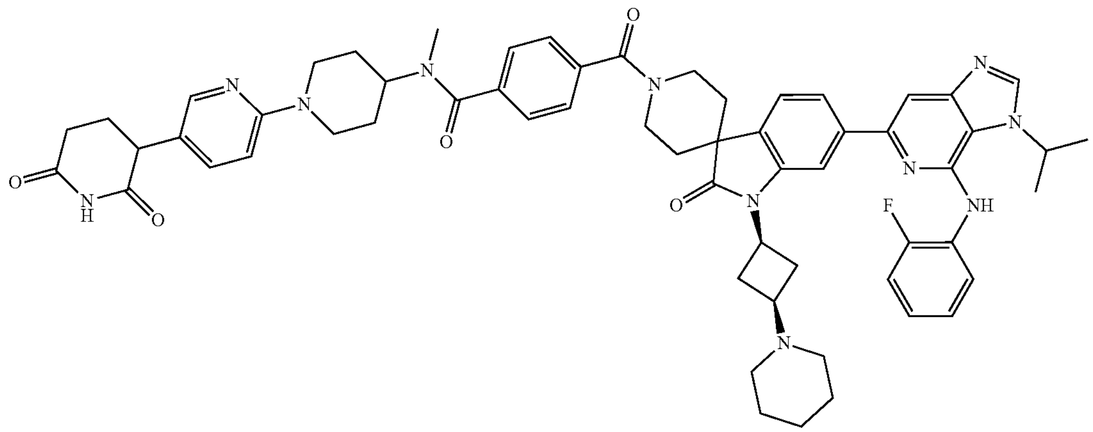 [SMILES: CC(C)n1cnc2cc(-c3ccc4c(c3)N([C@H]3C[C@@H](N5CCCCC5)C3)C(=O)C43CCN(C(=O)c4ccc(C(=O)N(C)C5CCN(c6ccc(C7CCC(=O)NC7=O)cn6)CC5)cc4)CC3)nc(Nc3ccccc3F)c21]

Using procedures similar to those used for Example 13 but using 4-((1-(5-(2,6-dioxopiperidin-3-yl)pyridin-2-yl)piperidin-4-yl)(methyl)carbamoyl)benzoic acid (Intermediate 68) (7.4 mg, 0.017 mmol) and 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (10.0 mg, 0.017 mmol) afforded the title compound (TFA salt) as an off white solid (15.3 mg, 84% yield). LCMS: $C_{60}H_{66}FN_{11}O_5$ desired mass=1039.5, found: m/z=1040.9 $[M+H]^+$. $^1H$ NMR (500 MHz, Methanol-$d_4$) δ 8.83 (s, 1H), 7.96 (s, 1H), 7.90 (s, 1H), 7.82 (s, 1H), 7.78 (dd, J=8.0, 1.5 Hz, 1H), 7.70 (td, J=7.9, 2.0 Hz, 1H), 7.64 (dd, J=13.9, 4.7 Hz, 3H), 7.58 (dd, J=8.1, 1.6 Hz, 3H), 7.42 (s, 1H), 7.32-7.18 (m, 2H), 5.31 (p, J=6.6 Hz, 1H), 4.36 (s, 1H), 4.30-4.22 (m, 3H), 4.13 (s, 1H), 3.75 (s, 1H), 3.58 (dd, J=18.8, 10.7 Hz, 2H), 3.52 (s, 1H), 3.43 (s, 1H), 3.37 (s, 1H), 3.34-3.27 (m, 4H), 3.02 (s, 3H), 2.92 (s, 6H), 2.89 (d, J=2.6 Hz, 1H), 2.77 (s, 2H), 2.31 (s, 1H), 2.20 (s, 1H), 2.03 (d, J=15.9 Hz, 8H), 1.91 (d, J=13.9 Hz, 1H), 1.73 (d, J=6.6 Hz, 6H), 1.58 (d, J=13.7 Hz, 1H), 1.31 (s, 1H).

Example 142

5-{[6-(1'-{1-[(1-{1-[(3RS)-2,6-dioxopiperidin-3-yl]-3-methyl-2-oxo-2,3-dihydro-1H-1,3-benzodiazol-4-yl}piperidin-4-yl)methyl]piperidine-4-carbonyl}-2-oxo-1-[(1S,3S)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

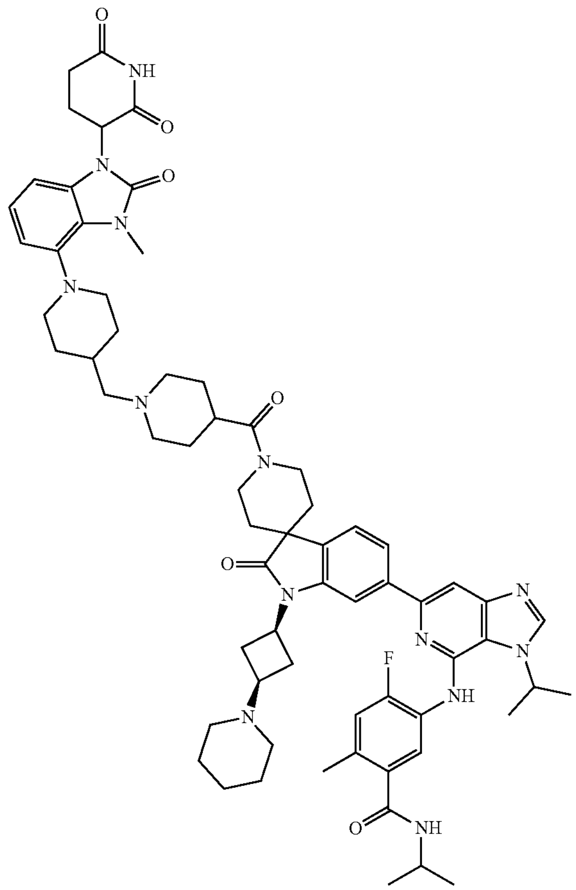 [SMILES: Cc1cc(F)c(Nc2nc(-c3ccc4c(c3)N([C@H]3C[C@@H](N5CCCCC5)C3)C(=O)C43CCN(C(=O)C4CCN(CC5CCN(c6cccc7c6n(C)c(=O)n7C6CCC(=O)NC6=O)CC5)CC4)CC3)cc3ncn(C(C)C)c23)cc1C(=O)NC(C)C]

Using procedures similar to those for Example 31 and using 4-fluoro-N-isopropyl-5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-2-methylbenzamide hydrochloride and 1-((1-(1-(2,6-dioxopiperidin-3-yl)-3-methyl-2-oxo-2,3-dihydro-1H-benzo[d]imidazol-4-yl)piperidin-4-yl)methyl)piperidine-4-carboxylic acid (intermediate 69) as the coupling partners, the title compound (TFA salt) was isolated as an off-white solid (15 mg, 36% yield). LCMS: [C66H82FN13O6], desired mass=1171.6, found: m/z=1173.1 $[M+H]^+$. $^1$H NMR (500 MHz, DMSO) δ 11.10 (s, 1H), 9.42 (s, 1H), 8.95 (s, 1H), 8.60 (s, 1H), 8.38 (s, 1H), 8.15 (d, J=7.9 Hz, 1H), 7.89 (s, 1H), 7.68 (d, J=7.9 Hz, 1H), 7.61 (d, J=8.2 Hz, 1H), 7.53 (d, J=6.8 Hz, 2H), 7.22-7.16 (m, 1H), 7.01 (t, J=8.0 Hz, 1H), 6.91 (t, J=8.0 Hz, 2H), 5.37 (dd, J=12.8, 5.5 Hz, 1H), 5.32-5.26 (m, 1H), 4.26-4.19 (m, 1H), 4.09-4.01 (m, 1H), 3.92 (s, 2H), 3.65 (s, 3H), 3.18 (s, 2H), 3.07 (s, 2H), 3.01 (d, J=10.7 Hz, 3H), 2.92-2.85 (m, 1H), 2.82 (s, 5H), 2.76-2.67 (m, 3H), 2.55 (s, 5H), 2.37 (s, 4H), 2.02-1.94 (m, 4H), 1.94-1.79 (m, 7H), 1.72 (s, 2H), 1.65 (s, 1H), 1.60 (d, J=6.5 Hz, 7H), 1.45 (d, J=12.5 Hz, 4H), 1.25 (s, 1H), 1.11 (d, J=6.6 Hz, 7H).

Example 143

(3RS)-3-(3-methyl-2-oxo-4-{[(1R,4R)-4-[(3S)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-1,3-benzodiazol-1-yl)piperidine-2,6-dione

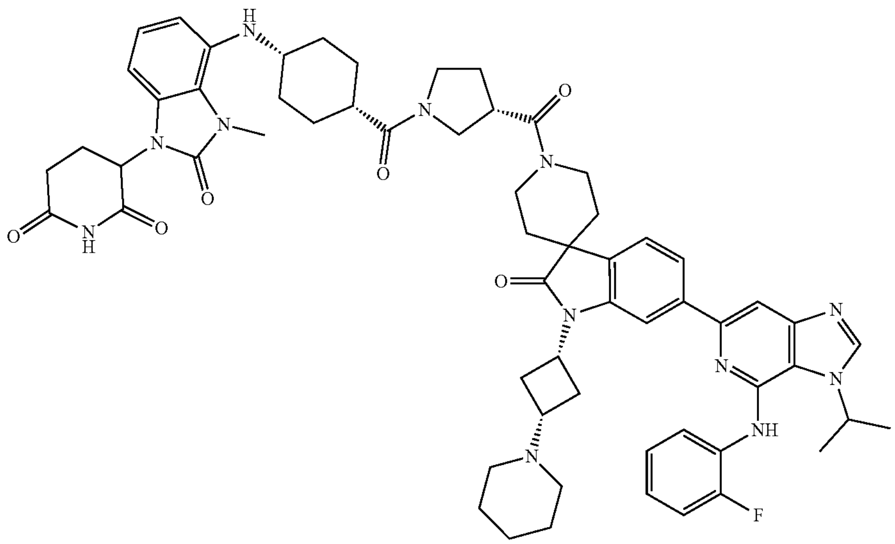 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)[C@H]5CC[C@@H](Nc6cccc7c6n(C)c(=O)n7C6CCC(=O)NC6=O)CC5)C4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and (3S)-1-((1s,4R)-4-((1-(2,6-dioxopiperidin-3-yl)-3-methyl-2-oxo-2,3-dihydro-1H-benzo[d]imidazol-4-yl)amino)cyclohexane-1-carbonyl)pyrrolidine-3-carboxylic acid (intermediate 70) as the coupling partners, the title compound (TFA salt) was isolated as an off-white solid (14 mg, 63% yield). LCMS: [C61H71FN12O6], desired mass=1086.6, found: m/z=544.1 $[(M+2H)/2]^+$. $^1$H NMR (500 MHz, MeOD) δ 9.08 (d, J=5.8 Hz, 1H), 7.81 (s, 1H), 7.77 (d, J=7.6 Hz, 1H), 7.70 (s, 1H), 7.60 (d, J=4.9 Hz, 1H), 7.55 (dd, J=11.9, 8.1 Hz, 1H), 7.33-7.25 (m, 2H), 7.00 (t, J=8.1 Hz, 1H), 6.67 (dd, J=12.3, 7.8 Hz, 3H), 5.39-5.27 (m, 2H), 4.24 (s, 1H), 4.11 (d, J=13.0 Hz, 3H), 4.00-3.91 (m, 3H), 3.82 (d, J=10.1 Hz, 1H), 3.79-3.67 (m, 4H), 3.69-3.54 (m, 2H), 3.32-3.27 (m, 1H), 3.10 (t, J=9.3 Hz, 1H), 3.01 (s, 2H), 2.91 (d, J=12.6 Hz, 4H), 2.84 (d, J=16.6 Hz, 2H), 2.79 (s, 1H), 2.60 (d, J=11.9 Hz, 1H), 2.28 (d, J=7.1 Hz, 1H), 2.25 (s, 4H), 2.16 (s, 1H), 2.04 (d, J=14.5 Hz, 2H), 1.94 (s, 6H), 1.86 (s, 1H), 1.76 (d, J=6.5 Hz, 7H), 1.68 (s, 1H), 1.65 (s, 1H), 1.64-1.56 (m, 1H), 1.40 (q, J=12.7 Hz, 2H), 1.31 (s, 1H).

Example 144

(3RS)-3-(3-methyl-2-oxo-4-{[(1R,4R)-4-[(3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-1,3-benzodiazol-1-yl)piperidine-2,6-dione

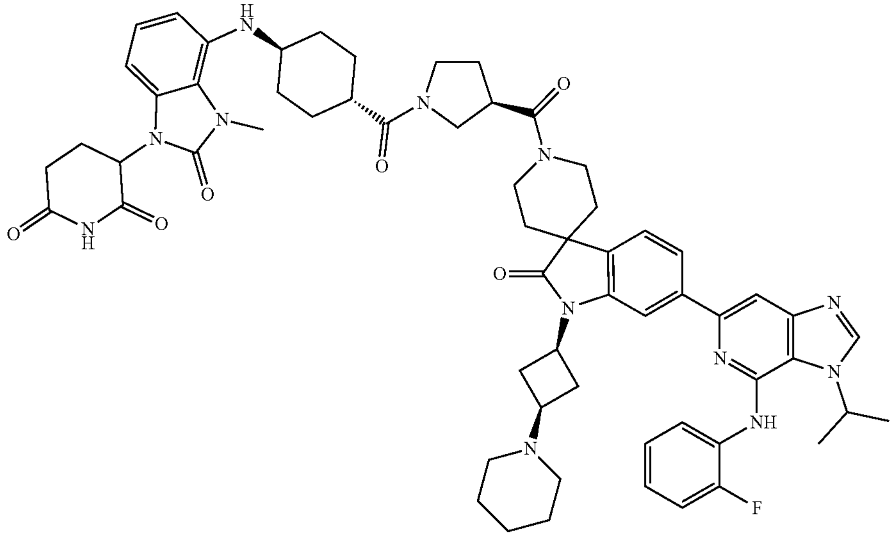 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc7c6n(C)c(=O)n7C6CCC(=O)NC6=O)CC5)C4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and (3R)-1-((1r,4R)-4-((1-(2,6-dioxopiperidin-3-yl)-3-methyl-2-oxo-2,3-dihydro-1H-benzo[d]imidazol-4-yl)amino)cyclohexane-1-carbonyl)pyrrolidine-3-carboxylic acid (intermediate 71) as the coupling partners, the title compound (TFA salt) was isolated as an off-white solid (8.1 mg, 21% yield). LCMS: [C61H71FN12O6], desired mass=1086.6, found: m/z=544.6 $[(M+2H)/2]^+$. $^1$H NMR (500 MHz, MeOD) δ 9.11-8.99 (m, 1H), 7.83-7.75 (m, 2H), 7.70 (s, 1H), 7.61 (s, 1H), 7.54 (d, J=8.1 Hz, 1H), 7.27 (s, 3H), 7.00 (t, J=8.2 Hz, 1H), 6.67 (dd, J=13.9, 8.1 Hz, 2H), 5.35 (s, 1H), 5.31 (d, J=11.8 Hz, 1H), 4.92 (s, 1H), 4.82 (s, 1H), 4.10 (s, 3H), 3.96 (s, 3H), 3.74 (d, J=2.9 Hz, 3H), 3.61-3.54 (m, 3H), 2.93 (s, 1H), 2.91 (s, 6H), 2.81 (d, J=14.4 Hz, 1H), 2.59 (s, 1H), 2.26 (s, 5H), 2.05 (s, 5H), 1.94 (s, 8H), 1.86 (s, 1H), 1.75 (d, J=6.5 Hz, 7H), 1.65 (s, 3H), 1.39 (d, J=12.5 Hz, 1H), 1.31 (s, 2H), 1.15 (s, 1H).

Example 145

5-[(6-{1'-[5-(4-{2-[(3RS)-2,6-dioxopiperidin-3-yl]-1,3-dioxo-2,3-dihydro-1H-isoindol-5-yl}piperazine-1-carbonyl)-1-methyl-1H-pyrazole-3-carbonyl]-2-oxo-1-[(1S,3S)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

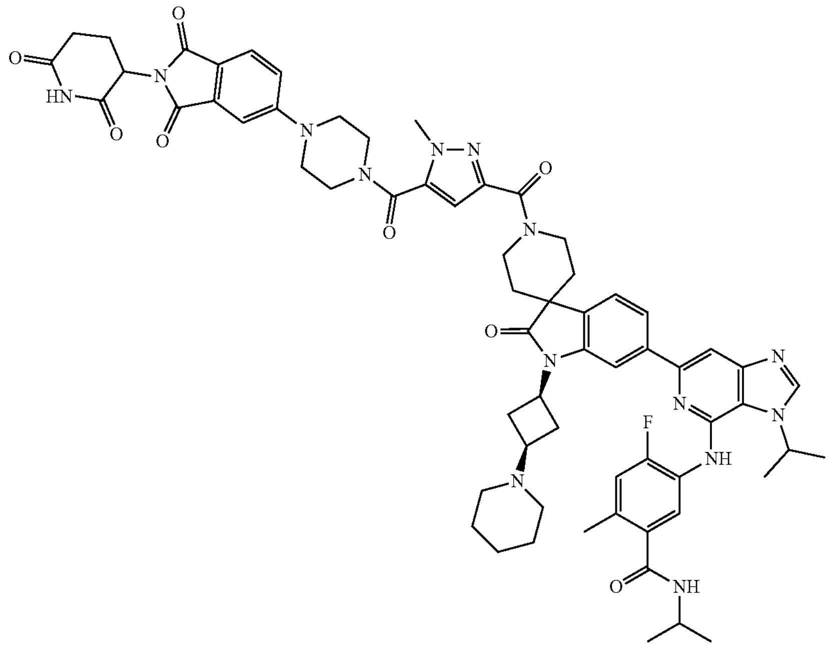 [SMILES: Cc1cc(F)c(Nc2nc(-c3ccc4c(c3)N([C@H]3C[C@@H](N5CCCCC5)C3)C(=O)C43CCN(C(=O)c4cc(C(=O)N5CCN(c6ccc7c(c6)C(=O)N(C6CCC(=O)NC6=O)C7=O)CC5)n(C)n4)CC3)cc3ncn(C(C)C)c23)cc1C(=O)NC(C)C]

Using procedures similar to those for Example 31 and using 4-fluoro-N-isopropyl-5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-2-methylbenzamide hydrochloride and 5-(4-(2-(2,6-dioxopiperidin-3-yl)-1,3-dioxoisoindolin-5-yl)piperazine-1-carbonyl)-1-methyl-1H-pyrazole-3-carboxylic acid (intermediate 72) as the coupling partners, the title compound (TFA salt) was isolated as an off-white solid (11.3 mg, 53% yield). LCMS: [C64H71FN14O8], desired mass=1182.6, found: m/z=1184.3 [(M+H)+]. $^{1}$H NMR (500 MHz, MeOD) δ 9.10 (s, 1H), 8.00 (d, J=8.1 Hz, 1H), 7.80 (s, 1H), 7.79-7.72 (m, 2H), 7.62 (d, J=1.5 Hz, 1H), 7.56 (d, J=7.8 Hz, 1H), 7.44 (d, J=2.3 Hz, 1H), 7.31 (dd, J=8.6, 2.4 Hz, 1H), 7.19 (d, J=11.7 Hz, 1H), 6.95 (s, 1H), 5.38 (p, J=6.5 Hz, 1H), 5.10 (dd, J=12.4, 5.5 Hz, 1H), 4.46 (d, J=13.7 Hz, 1H), 4.37 (dq, J=16.6, 8.6 Hz, 2H), 4.21-4.06 (m, 2H), 4.03 (s, 3H), 3.96 (s, 2H), 3.88 (s, 3H), 3.69 (p, J=8.1 Hz, 1H), 3.57 (d, J=12.8 Hz, 3H), 3.14 (s, 2H), 2.99-2.83 (m, 5H), 2.80-2.66 (m, 3H), 2.47 (s, 3H), 2.12 (s, 1H), 2.07-2.00 (m, 3H), 1.96 (d, J=6.9 Hz, 5H), 1.91 (d, J=14.2 Hz, 1H), 1.77 (d, J=6.6 Hz, 8H), 1.59 (t, J=13.0 Hz, 1H), 1.18 (d, J=6.6 Hz, 7H).

Example 146

2-[(3RS)-2,6-dioxopiperidin-3-yl]-5-(4-{3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-1-methyl-1H-pyrazole-5-carbonyl}piperazin-1-yl)-2,3-dihydro-1H-isoindole-1,3-dione

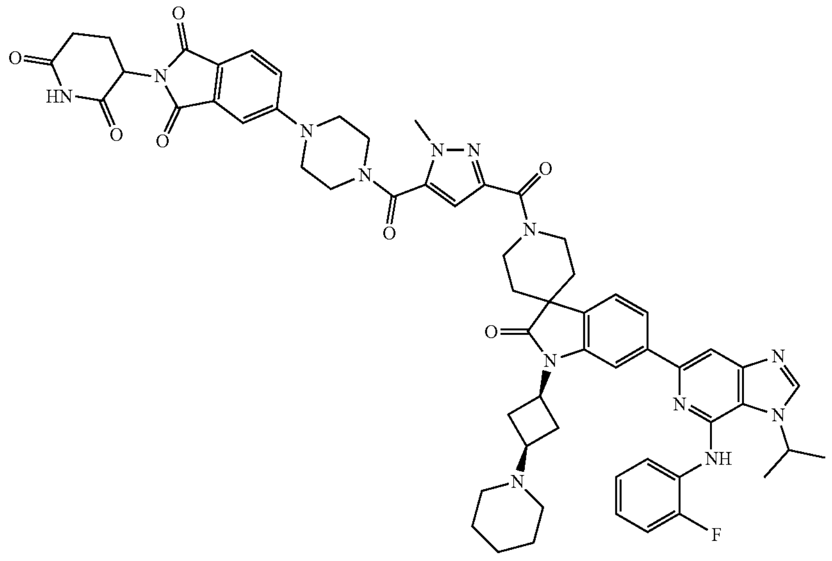 [SMILES: CC(C)n1cnc2cc(-c3ccc4c(c3)N([C@H]3C[C@@H](N5CCCCC5)C3)C(=O)C43CCN(C(=O)c4cc(C(=O)N5CCN(c6ccc7c(c6)C(=O)N(C6CCC(=O)NC6=O)C7=O)CC5)n(C)n4)CC3)nc(Nc3ccccc3F)c21]

Using procedures similar to those for Example 31 and using 6-(4-((2-fluorophenyl)amino)-3-isopropyl-3H-imidazo[4,5-c]pyridin-6-yl)-1-((1s,3s)-3-(piperidin-1-yl)cyclobutyl)spiro[indoline-3,4'-piperidin]-2-one hydrochloride and 5-(4-(2-(2,6-dioxopiperidin-3-yl)-1,3-dioxoisoindolin-5-yl)piperazine-1-carbonyl)-1-methyl-1H-pyrazole-3-carboxylic acid (intermediate 72) as the coupling partners, the title compound (TFA salt) was isolated as an off-white solid (9.6 mg, 49% yield). LCMS: [C59H62FN13O7], desired mass=1083.5, found: m/z=1085.3 $[M+H]^+$. $^1H$ NMR (500 MHz, MeOD) δ 9.26 (s, 1H), 7.82 (s, 1H), 7.80-7.66 (m, 3H), 7.59 (s, 1H), 7.55 (d, J=7.8 Hz, 1H), 7.42 (s, 1H), 7.29 (d, J=8.6 Hz, 4H), 6.94 (d, J=1.5 Hz, 1H), 5.40 (s, 1H), 5.10 (dd, J=12.4, 5.4 Hz, 1H), 4.89 (s, 1H), 4.44 (d, J=14.2 Hz, 1H), 4.39 (d, J=7.9 Hz, 1H), 4.24 (s, 2H), 4.09 (dd, J=13.3, 6.8 Hz, 1H), 4.03 (s, 2H), 3.95 (s, 3H), 3.87 (s, 2H), 3.59 (dd, J=16.3, 8.3 Hz, 2H), 3.54 (s, 1H), 3.07 (s, 2H), 2.97-2.83 (m, 6H), 2.81-2.68 (m, 2H), 2.14 (dd, J=9.8, 4.8 Hz, 1H), 2.04 (d, J=12.6 Hz, 2H), 1.96 (s, 5H), 1.91 (s, 1H), 1.78 (d, J=6.7 Hz, 9H), 1.61 (t, J=13.1 Hz, 1H).

Example 147

(3RS)-3-(4-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}-3-fluorophenyl)piperidine-2,6-dione

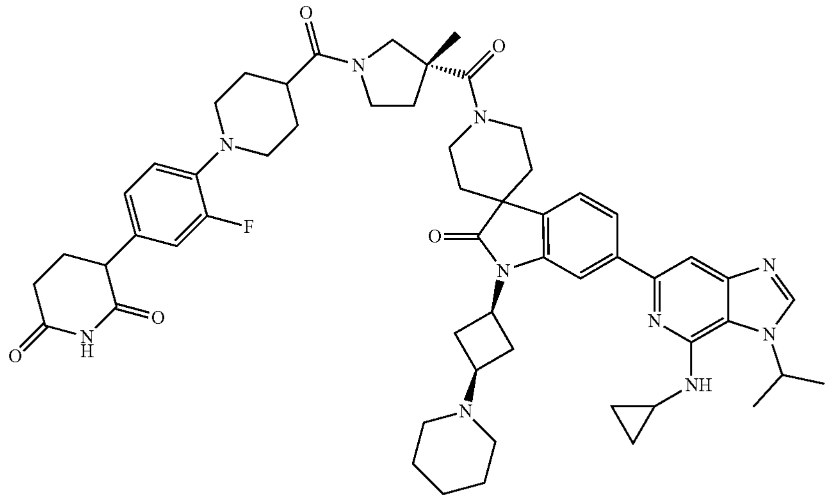 [SMILES: CC(C)n1cnc2cc(-c3ccc4c(c3)N([C@H]3C[C@@H](N5CCCCC5)C3)C(=O)C43CCN(C(=O)[C@]4(C)CCN(C(=O)C5CCN(c6ccc(C7CCC(=O)NC7=O)cc6F)CC5)C4)CC3)nc(NC3CC3)c21]

Intermediate 76 (11.06 mg, 0.0331 mmol), 6-[4-(cyclopropylamino)-3-isopropylimidazo[4,5-c]pyridin-6-yl]-1'-[(3R)-3-methylpyrrolidine-3-carbonyl]-1-[(1s,3s)-3-(piperidin-1-yl)cyclobutyl]spiro[indole-3,4'-piperidin]-2-one (Intermediate CC) (20.00 mg, 0.0301 mmol), and (1,2,3-benzotriazol-1-yloxy)tris(dimethylamino)phosphanium, hexafluoro-lambda5-phosphanuide (18.98 mg, 0.0429 mmol) were dissolved in DMF (0.6 mL) and N,N-diisopropylethylamine (0.02 mL, 15.55 mg, 0.1203 mmol) and stirred at room temperature for 4 hours. The crude reaction mixture was purified by preparative HPLC to afford the title compound (TFA salt) as an off-white solid (7.4 mgs, 25% yield). LCMS: $C_{56}H_{69}FN_{10}O_5$, desired mass=980.5, found: m/z=981.6 $[M+H]^+$. $^1H$ NMR (500 MHz, Methanol-$d_4$) δ 7.69 (s, 2H), 7.64 (s, 1H), 7.57 (d, J=6.9 Hz, 1H), 7.13-7.05 (m, OH), 7.05-6.98 (m, 1H), 4.23 (s, 1H), 4.09 (s, 5H), 3.84 (s, 1H), 3.62 (dd, J=17.3, 8.9 Hz, 1H), 3.57 (s, 3H), 3.23 (s, 8H), 3.07 (s, 1H), 3.01 (s, 2H), 2.89 (q, J=14.8, 13.9 Hz, 3H), 2.70 (s, 6H), 2.21 (s, 2H), 2.01 (s, 4H), 1.96 (s, 4H), 1.91 (s, 4H), 1.79 (d, J=15.7 Hz, 3H), 1.69 (d, J=6.5 Hz, 6H), 1.64-1.48 (m, 4H), 1.31 (s, 2H), 1.14 (s, 2H), 0.93 (d, J=10.7 Hz, 2H).

Example 148

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-5-Methylpyridin-3-yl)piperidine-2,6-dione

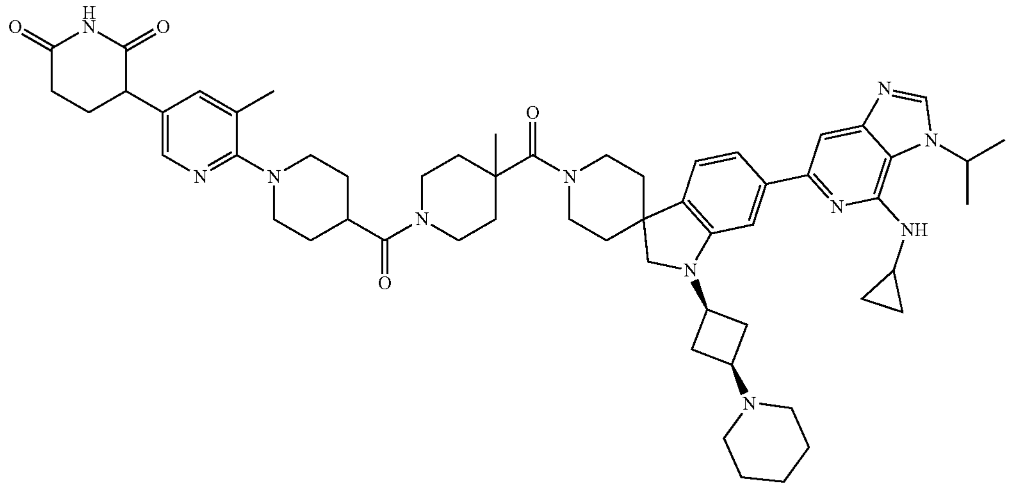 [SMILES: Cc1cc(C2CCC(=O)NC2=O)cnc1N1CCC(C(=O)N2CCC(C)(C(=O)N3CCC4(CC3)CN([C@H]3C[C@@H](N5CCCCC5)C3)c3cc(-c5cc6ncn(C(C)C)c6c(NC6CC6)n5)ccc34)CC2)CC1]

6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (15.00 mg, 0.0271 mmol), Intermediate 77 (12.37 mg, 0.0271 mmol), and (1,2,3-benzotriazol-1-yloxy)tris(dimethylamino)phosphanium, hexafluoro-lambda5-phosphanuide (15.57 mg, 0.0352 mmol) were dissolved in dimethylformamide (0.6 mL) and N,N-diisopropylethylamine (0.05 mL, 35.01 mg, 0.2709 mmol) and stirred at room temperature for 6 hours. The crude reaction mixture was purified by preparative HPLC to afford the title compound. (12.7 mgs, 47% yield). LCMS: $C_{57}H_{73}N_{11}O_5$, desired mass=991.6, found: m/z=992.6 $[M+H]^+$. $^1H$ NMR (500 MHz, Methanol-$d_4$) δ 8.93 (s, 1H), 8.01 (s, 1H), 7.98 (d, J=2.2 Hz, 1H), 7.69 (s, 2H), 7.62 (s, 1H), 7.56 (s, 1H), 5.17-5.10 (m, 1H), 4.85 (s, 2H), 4.48 (q, J=8.3 Hz, 1H), 4.16 (d, J=14.3 Hz, 3H), 4.09 (s, 4H), 4.01 (dd, J=12.9, 4.9 Hz, 1H), 3.85 (t, J=13.5 Hz, 3H), 3.69-3.54 (m, 5H), 3.30 (dd, J=3.3, 1.6 Hz, 2H), 3.10-2.98 (m, 1H), 2.90 (t, J=12.2 Hz, 2H), 2.84-2.72 (m, 1H), 2.78 (s, 1H), 2.48 (s, 3H), 2.36 (dt, J=12.7, 6.4 Hz, 1H), 2.32-2.18 (m, 2H), 2.08-1.99 (m, 3H), 1.95 (s, 9H), 1.91 (d, J=9.8 Hz, 1H), 1.79 (d, J=13.8 Hz, 2H), 1.72-1.53 (m, 10H), 1.46 (s, 3H), 1.31 (s, 1H), 1.15 (t, J=6.5 Hz, 2H), 0.95 (s, 2H).

Example 149

(3RS)-3-(6-{4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)-4-methylpiperidine-1-carbonyl]piperidin-1-yl}pyridin-3-yl)piperidine-2,6-dione

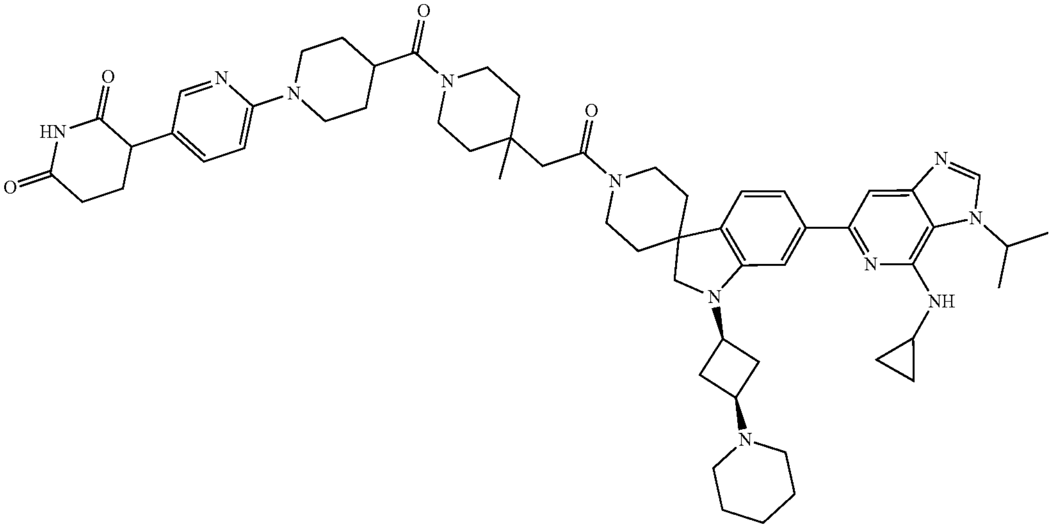 [SMILES: CC(C)n1cnc2cc(-c3ccc4c(c3)N([C@H]3C[C@@H](N5CCCCC5)C3)CC43CCN(C(=O)CC4(C)CCN(C(=O)C5CCN(c6ccc(C7CCC(=O)NC7=O)cn6)CC5)CC4)CC3)nc(NC3CC3)c21]

Intermediate K (25.00 mg, 0.0361 mmol), (1,2,3-benzotriazol-1-yloxy)tris(dimethylamino)phosphanium, hexafluoro-lambda5-phosphanuide (20.74 mg, 0.0469 mmol) and 1-[5-(2,6-dioxopiperidin-3-yl)pyridin-2-yl]piperidine-4-carboxylic acid (Intermediate 55, step 2) (11.45 mg, 0.0361 mmol) were dissolved in dimethylformamide (0.80 mL) and N,N-diisopropylethylamine (0.03 mL, 18.65 mg, 0.1443 mmol) and stirred at room temperature for 4 hours. The crude reaction mixture was purified by preparative HPLC to afford the title compound (27.8 mgs, 76% yield). LCMS: $C_{57}H_{73}N_{11}O_5$, desired mass=991.6, found: m/z=992.4 $[M+H]^+$. $^1H$ NMR (500 MHz, Methanol-$d_4$) δ 7.98 (d, J=9.5 Hz, 1H), 7.86 (d, J=2.4 Hz, 1H), 7.69 (s, 1H), 7.65 (d, J=7.5 Hz, 2H), 7.56 (s, 1H), 7.42 (d, J=9.5 Hz, 1H), 4.49 (t, J=8.3 Hz, 1H), 4.20 (t, J=14.8 Hz, 3H), 4.12 (d, J=6.8 Hz, 1H), 4.04 (s, 1H), 3.96 (dd, J=13.0, 4.9 Hz, 1H), 3.80 (s, 1H), 3.63 (t, J=8.3 Hz, 1H), 3.59 (s, 3H), 3.56 (s, 1H), 3.44 (d, J=12.1 Hz, 3H), 2.89 (d, J=12.1 Hz, 1H), 2.83-2.72 (m, 2H), 2.67-2.58 (m, 1H), 2.58-2.49 (m, 1H), 2.40-2.28 (m, 1H), 2.23-2.16 (m, 1H), 2.08-1.99 (m, 2H), 1.97 (s, 3H), 1.90 (s, 7H), 1.79 (d, J=13.4 Hz, 1H), 1.69 (d, J=6.5 Hz, 6H), 1.58 (s, 2H), 1.31 (s, 2H), 1.24 (d, J=5.8 Hz, 3H), 1.12 (s, 2H), 0.93 (s, 2H).

Example 150

(3RS)-3-(4-{methyl[(1R,4R)-4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]cyclohexyl]amino}phenyl)piperidine-2,6-dione

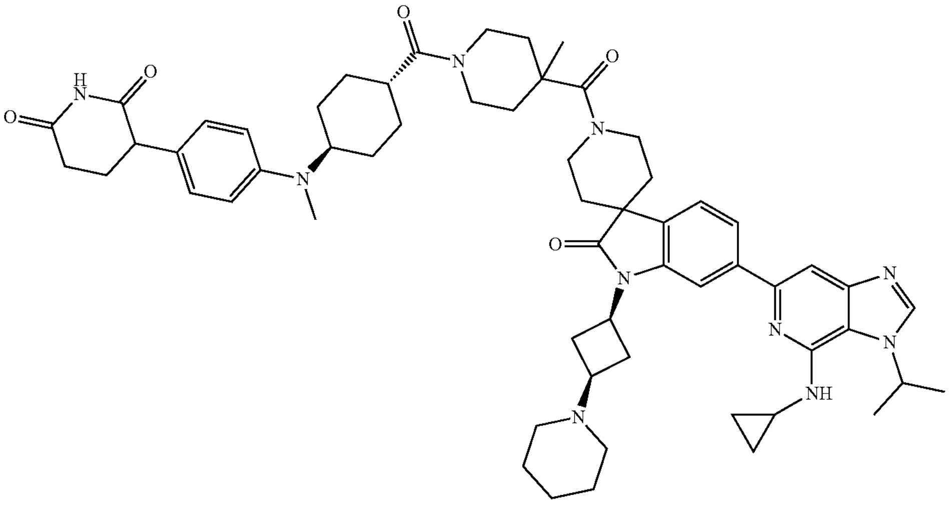 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](N(C)c6ccc(C7CCC(=O)NC7=O)cc6)CC5)CC4)CC3)nc(NC3CC3)c21]

Intermediate 78 (12.72 mg, 0.0271 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (15.00 mg, 0.0271 mmol), and (1,2,3-benzotriazol-1-yloxy)tris(dimethylamino)phosphanium, hexafluoro-lambda5-phosphanuide (15.57 mg, 0.0352 mmol) were dissolved in dimethylformamide (0.80 mL) and N,N-diisopropylethylamine (0.02 mL, 14.00 mg, 0.1084 mmol) and stirred at room temperature for 4 hours. The crude reaction mixture was purified by preparative HPLC to afford the title compound. (11.3 mgs, 41% yield). LCMS: $C_{59}H_{76}N_{10}O_5$, desired mass=1004.6, found: m/z=1005.5 $[M+H]^+$. $^1$H NMR (500 MHz, Methanol-$d_4$) δ 7.67 (d, J=7.9 Hz, 1H), 7.63 (s, 0H), 7.56 (s, 1H), 7.51 (s, 3H), 4.84 (d, J=2.3 Hz, 2H), 4.49 (t, J=8.3 Hz, OH), 4.13 (s, 1H), 4.09 (s, 1H), 4.01 (dt, J=11.9, 7.4 Hz, 1H), 3.79 (d, J=14.0 Hz, 1H), 3.61 (dd, J=30.9, 10.2 Hz, 3H), 3.33-3.26 (m, 4H), 3.01 (d, J=9.1 Hz, 1H), 2.90 (t, J=10.4 Hz, 1H), 2.68 (s, 33H), 2.65 (d, J=2.3 Hz, 1H), 2.36-2.28 (m, 1H), 2.27-2.19 (m, 1H), 2.03 (d, J=21.7 Hz, 2H), 1.93 (s, 1H), 1.80 (t, J=9.8 Hz, 1H), 1.72-1.53 (m, 8H), 1.46-1.36 (m, 2H), 1.32 (d, J=10.0 Hz, 2H), 1.12 (d, J=6.4 Hz, 1H), 0.93 (s, 1H).

Example 151

(3RS)-3-(6-{4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]-4-methylpiperidin-1-yl}pyridin-3-yl)piperidine-2,6-dione

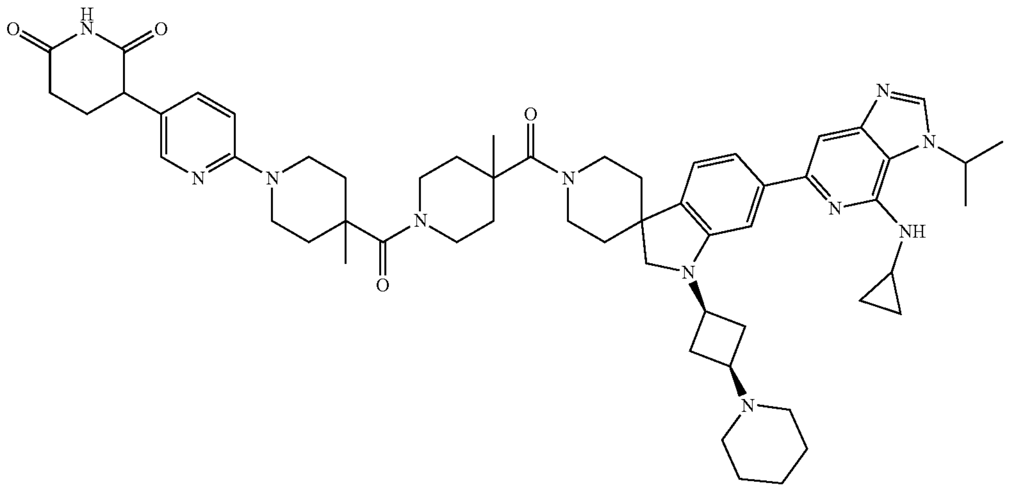 [SMILES: CC(C)n1cnc2cc(-c3ccc4c(c3)N([C@H]3C[C@@H](N5CCCCC5)C3)CC43CCN(C(=O)C4(C)CCN(C(=O)C5(C)CCN(c6ccc(C7CCC(=O)NC7=O)cn6)CC5)CC4)CC3)nc(NC3CC3)c21]

Intermediate 79 (49.47 mg, 0.1084 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (50.00 mg, 0.0903 mmol), and (1,2,3-benzotriazol-1-yloxy)tris(dimethylamino)phosphanium, hexafluoro-lambda5-phosphanuide (51.92 mg, 0.1174 mmol) were dissolved in dimethylformamide (3.00 mL) and N,N-diisopropylethylamine (0.16 mL, 116.70 mg, 0.9029 mmol) and stirred at room temperature for 6 hours. The crude reaction mixture was purified by preparative HPLC to afford the title compound (32.1 mgs, 35% yield). LCMS: $C_{57}H_{73}N_{11}O_5$, desired mass=991.6, found: m/z=1014.7 $[M+H]^+$. $^1$H NMR (500 MHz, Methanol-$d_4$) δ 8.91 (s, 1H), 7.96 (dd, J=9.6, 2.2 Hz, 1H), 7.84 (d, J=2.2 Hz, 1H), 7.67 (d, J=7.6 Hz, 1H), 7.64 (s, 1H), 7.56 (s, 1H), 7.37 (d, J=9.7 Hz, 1H), 4.49 (t, J=8.4 Hz, 1H), 4.14 (s, 4H), 4.05-3.91 (m, 4H), 3.87 (d, J=13.6 Hz, 3H), 3.67-3.54 (m, 1H), 3.58 (s, 5H), 3.22 (d, J=11.0 Hz, 2H), 3.10-3.04 (m, OH), 3.01 (d, J=8.3 Hz, 2H), 2.90 (t, J=10.6 Hz, 2H), 2.83-2.72 (m, 2H), 2.46 (d, J=14.2 Hz, 2H), 2.33 (t, J=6.3 Hz, 1H), 2.30 (s, 3H), 2.23-2.17 (m, 1H), 2.08-1.99 (m, 2H), 1.94 (s, 4H), 1.90 (d, J=9.3 Hz, OH), 1.88-1.76 (m, 2H), 1.69 (d, J=6.5 Hz, 7H), 1.61 (d, J=11.7 Hz, 3H), 1.45 (d, J=8.6 Hz, 7H), 1.31 (s, 1H), 1.12 (d, J=6.7 Hz, 2H), 0.93 (s, 2H).

Example 152

(3RS)-3-(4-{4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]piperidin-1-yl}-3-Fluorophenyl)piperidine-2,6-dione

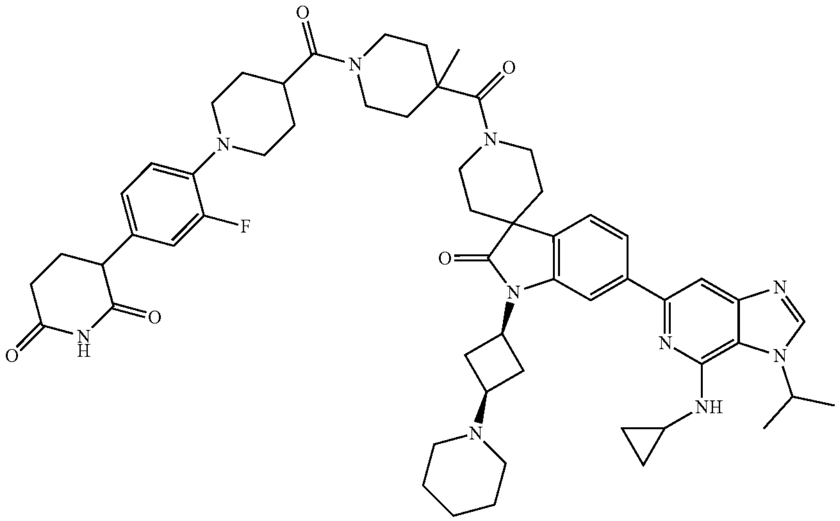 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cc6F)CC5)CC4)CC3)nc(NC3CC3)c21]

Intermediate 76 (13.54 mg, 0.0405 mmol) and 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one (Example 189, step 2) (25.00 mg, 0.0368 mmol) were dissolved in DMF (0.60 mL) and N,N-diisopropylethylamine (0.03 mL, 19.04 mg, 0.1473 mmol) and stirred at room temperature for 4 hours. The crude reaction mixture was purified by preparative HPLC to afford the title compound (20.2 mgs, 55% yield). LCMS: $C_{57}H_{71}FN_{10}O_5$, desired mass=994.6, found: m/z=995.6 $[M+H]^+$. $^1$H NMR (500 MHz, Methanol-$d_4$) δ 7.69 (s, 2H), 7.63 (s, 1H), 7.57 (s, 1H), 7.11 (t, J=8.5 Hz, 1H), 7.03 (d, J=10.7 Hz, 2H), 5.14 (q, J=6.6 Hz, 1H), 4.90 (s, 1H), 4.50 (p, J=8.4 Hz, 1H), 4.15 (s, 3H), 4.09 (d, J=13.3 Hz, 3H), 3.85 (dd, J=10.8, 5.4 Hz, 1H), 3.67-3.49 (m, 6H), 3.39-3.33 (m, 1H), 3.22 (s, 1H), 3.06 (dq, J=6.8, 3.4 Hz, 1H), 3.05-2.97 (m, 2H), 2.89 (q, J=12.9, 11.8 Hz, 5H), 2.78-2.61 (m, 2H), 2.36 (d, J=13.5 Hz, 1H), 2.26 (d, J=7.8 Hz, 3H), 2.26-2.16 (m, 1H), 2.08-1.96 (m, 3H), 1.94 (s, 6H), 1.86 (d, J=14.0 Hz, 2H), 1.79 (d, J=13.8 Hz, 1H), 1.69 (d, J=6.6 Hz, 6H), 1.65-1.59 (m, 3H), 1.45 (s, 3H), 1.31 (s, 1H), 1.14 (d, J=6.7 Hz, 2H), 0.95 (s, 2H).

Example 153

1-(6-{4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]-3,3-difluoropiperidin-1-yl}pyridin-3-yl)-1,3-diazinane-2,4-dione

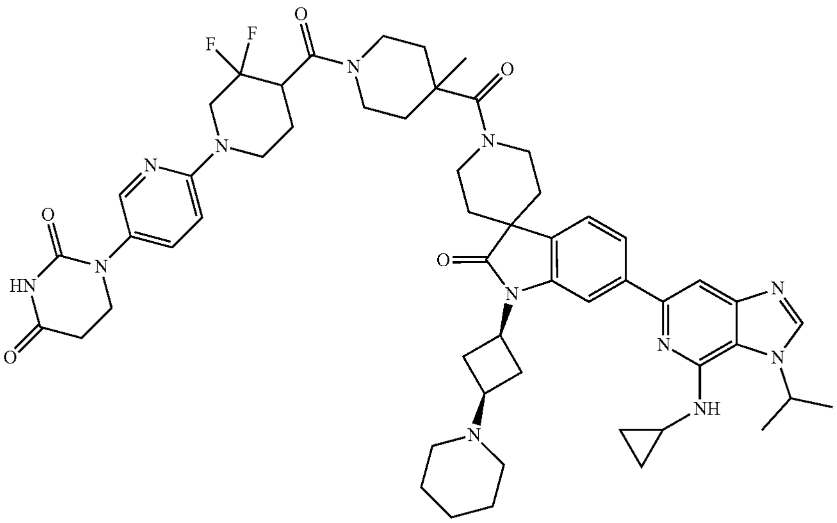 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(N7CCC(=O)NC7=O)cn6)CC5(F)F)CC4)CC3)nc(NC3CC3)c21]

Intermediate 80 (33.99 mg, 0.0722 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B)(40.00 mg, 0.0722 mmol), and (1,2,3-benzotriazol-1-yloxy)tris(dimethylamino)phosphanium, hexafluoro-lambda5-phosphanuide (41.53 mg, 0.0939 mmol) were dissolved in dimethylformamide (0.80 mL) and N,N-diisopropylethylamine (0.05 mL, 37.34 mg, 0.2889 mmol) and stirred at room temperature for 4 hours. The crude reaction mixture was purified by preparative HPLC to afford the title compound (64.9 mgs, 87% yield). LCMS: $C_{55}H_{68}F_2N_{12}O_5$, desired mass=1014.5, found: m/z=1015.4 $[M+H]^+$. $^1H$ NMR (500 MHz, Methanol-$d_4$) δ 8.94 (s, 1H), 8.13 (d, J=2.7 Hz, 1H), 7.67 (d, J=9.4 Hz, 3H), 7.62 (s, 1H), 7.57 (s, 1H), 7.04 (dd, J=9.3, 2.3 Hz, 1H), 5.14 (p, J=6.6 Hz, 1H), 4.50 (dq, J=16.7, 8.4 Hz, 2H), 4.21-4.06 (m, 6H), 3.84 (t, J=6.7 Hz, 2H), 3.73 (d, J=26.2 Hz, 1H), 3.71-3.53 (m, 6H), 3.42 (d, J=11.1 Hz, 2H), 3.23 (d, J=10.6 Hz, 3H), 3.07 (tt, J=6.8, 3.7 Hz, 1H), 3.00 (d, J=9.7 Hz, 3H), 2.96-2.79 (m, 4H), 2.40-2.27 (m, 2H), 2.23 (d, J=14.1 Hz, 2H), 2.02 (d, J=14.5 Hz, 2H), 1.93 (q, J=5.9, 5.1 Hz, 6H), 1.86-1.70 (m, 2H), 1.69 (d, J=6.5 Hz, 6H), 1.60 (dd, J=29.4, 14.6 Hz, 1H), 1.45 (d, J=5.1 Hz, 3H), 1.15 (d, J=6.6 Hz, 2H), 0.95 (s, 2H).

Example 154

3-{6-[(3R)-3-{2-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidin-1-yl]-2-oxoethyl}pyrrolidin-1-yl]pyridin-3-yl}piperidine-2,6-dione

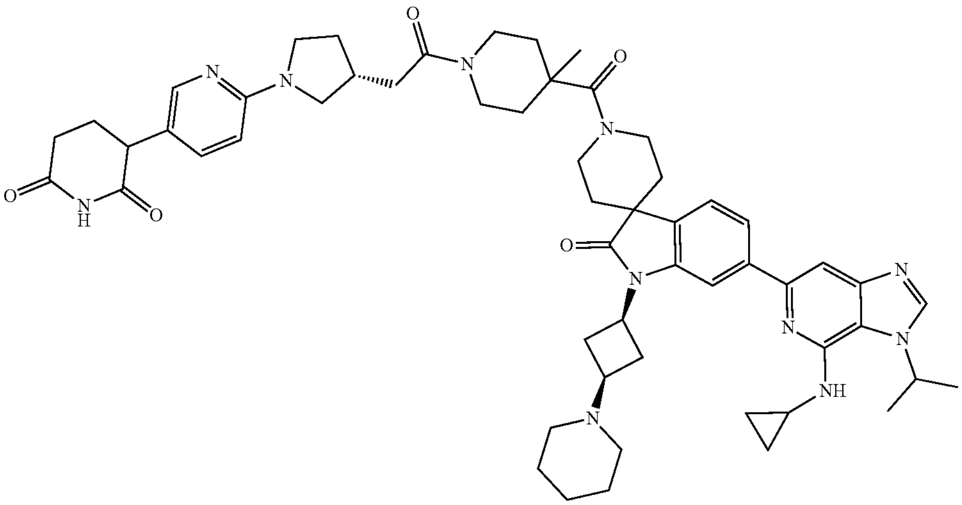 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C[C@H]5CCN(c6ccc(C7CCC(=O)NC7=O)cn6)C5)CC4)CC3)nc(NC3CC3)c21]

Intermediate 81 (0.040 g, 0.090 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.050 g, 0.090 mmol), and (1,2,3-benzotriazol-1-yloxy)tris(dimethylamino)phosphanium, hexafluoro-lambda5-phosphanuide (0.052 g, 0.117 mmol) were dissolved in dimethylformamide (0.80 mL) and N,N-diisopropylethylamine (0.06 mL, 0.361 mmol) and stirred at room temperature for 4 hours. The crude reaction mixture was purified by preparative HPLC to afford the title compound (0.064 g, 71% yield). LCMS: $C_{56}H_{71}N_{11}O_5$ desired mass=977.6, found: m/z=978.4 $[M+H]^+$. $^1H$ NMR (500 MHz, Methanol-$d_4$) δ 8.92 (s, 1H), 7.99-7.92 (m, 1H), 7.81 (d, J=2.2 Hz, 1H), 7.68 (s, 2H), 7.63 (s, 1H), 7.56 (s, 1H), 7.12 (d, J=9.5 Hz, 1H), 4.48 (q, J=8.3 Hz, 1H), 4.12 (d, J=20.3 Hz, 5H), 4.05 (s, 1H), 3.99-3.90 (m, 2H), 3.76 (s, 3H), 3.62 (d, J=8.3 Hz, 2H), 3.57 (d, J=12.3 Hz, 4H), 3.22 (d, J=9.8 Hz, 1H), 3.11-2.98 (m, 3H), 2.90 (t, J=12.3 Hz, 3H), 2.83-2.74 (m, 3H), 2.65 (s, 1H), 2.41 (s, 1H), 2.36-2.29 (m, 1H), 2.33-2.23 (m, 1H), 2.19 (dd, J=9.8, 5.0 Hz, 1H), 2.08-1.99 (m, 2H), 1.91 (dd, J=15.0, 7.7 Hz, 6H), 1.79 (d, J=13.9 Hz, 2H), 1.69 (d, J=6.5 Hz, 6H), 1.59 (dd, J=24.0, 12.2 Hz, 4H), 1.45 (d, J=1.9 Hz, 3H), 1.31 (s, 1H), 1.13 (d, J=6.7 Hz, 2H), 0.93 (s, 2H).

Example 155

1-(6-{8-[4-({6-[4-(cyclopropylamino)-3-(propan-2-yl)-3H-imidazo[4,5-c]pyridin-6-yl]-2-oxo-1-[(1(1S,3S)-3-(piperidin-1-yl)cyclobutyl]-1,2-dihydrospiro[indole-3,4'-piperidin]-1'-yl}carbonyl)-4-methylpiperidine-1-carbonyl]-3-azabicyclo[3.2.1]octan-3-yl}pyridin-3-yl)-1,3-diazinane-2,4-dione

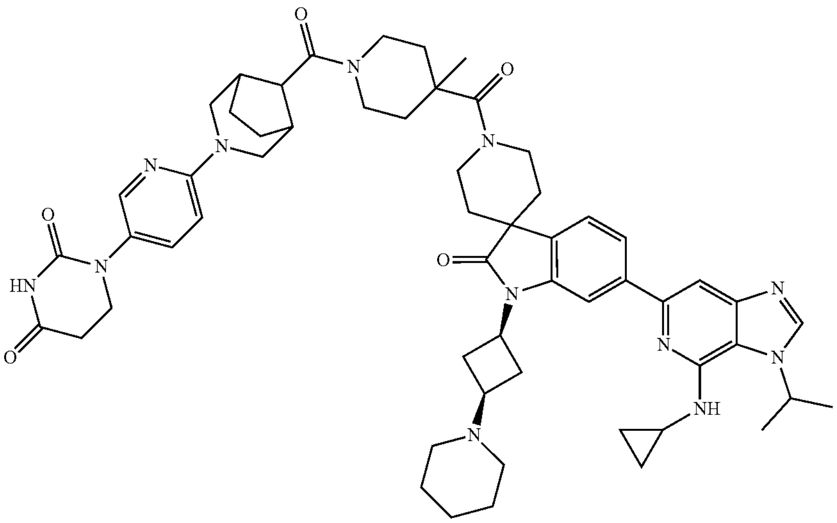 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5C6CCC5CN(c5ccc(N7CCC(=O)NC7=O)cn5)C6)CC4)CC3)nc(NC3CC3)c21]

Intermediate 82 (33.99 mg, 0.0722 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (40.00 mg, 0.0722 mmol), and (1,2,3-benzotriazol-1-yloxy)tris(dimethylamino)phosphanium, hexafluoro-lambda5-phosphanuide (41.53 mg, 0.0939 mmol) were dissolved in dimethylformamide (0.80 mL) and N,N-diisopropylethylamine (0.05 mL, 0.2889 mmol) and stirred at room temperature for 4 hours. The crude reaction mixture was purified by preparative HPLC to afford the title compound (43.7 mgs, 58% yield). LCMS: $C_{57}H_{72}N_{12}O_5$, desired mass=1004.6, found: m/z=1005.6 $[M+H]^+$. $^1$H NMR (500 MHz, Methanol-$d_4$) δ 8.08 (d, J=2.6 Hz, 1H), 8.04 (d, J=2.5 Hz, OH), 7.93 (d, J=9.6 Hz, 1H), 7.69 (s, 3H), 7.64 (s, 1H), 7.56 (d, J=1.8 Hz, 1H), 7.21 (d, J=9.6 Hz, 1H), 4.53-4.45 (m, 1H), 3.98 (s, 0H), 3.95 (s, 1H), 3.87 (td, J=6.7, 3.4 Hz, 2H), 3.71 (s, 1H), 3.69 (s, 1H), 3.64 (q, J=8.6, 7.8 Hz, 1H), 3.59 (s, 2H), 3.56 (s, 1H), 3.23 (s, 1H), 3.21 (s, 1H), 3.08 (s, 1H), 3.06 (q, J=3.7 Hz, OH), 3.01 (d, J=9.2 Hz, 2H), 2.90 (s, 1H), 2.86 (t, J=6.8 Hz, 2H), 2.67 (s, 2H), 2.35 (s, 1H), 2.27 (d, J=14.2 Hz, 1H), 1.92 (d, J=18.8 Hz, 5H), 1.83-1.71 (m, 3H), 1.69 (d, J=6.6 Hz, 7H), 1.63 (s, 4H), 1.46 (s, 3H), 1.31 (s, 1H), 1.12 (s, 2H), 0.92 (s, 2H).

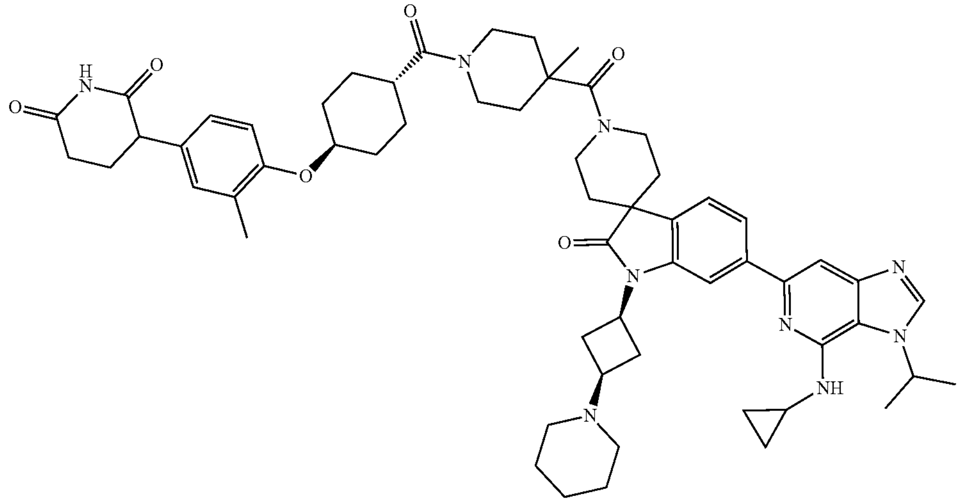 [SMILES: Cc1cc(C2CCC(=O)NC2=O)ccc1O[C@H]1CC[C@H](C(=O)N2CCC(C)(C(=O)N3CCC4(CC3)C(=O)N([C@H]3C[C@@H](N5CCCCC5)C3)c3cc(-c5cc6ncn(C(C)C)c6c(NC6CC6)n5)ccc34)CC2)CC1]

Intermediate 83 (33.99 mg, 0.0722 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (40.00 mg, 0.0722 mmol), and (1,2,3-benzotriazol-1-yloxy)tris(dimethylamino)phosphanium, hexafluoro-lambda5-phosphanuide (41.53 mg, 0.0939 mmol) were dissolved in dimethylformamide (0.80 mL) and N,N-diisopropylethylamine (0.05 mL, 0.2889 mmol) and stirred at room temperature for 4 hours. The crude reaction mixture was purified by preparative HPLC to afford the title compound (39.4 mgs, 53% yield). LCMS: $C_{59}H_{75}N_9O_6$, desired mass=1005.6, found: m/z=1007.4 $[M+H]^+$. $^1H$ NMR (500 MHz, Methanol-$d_4$) δ 7.69 (s, 2H), 7.64 (s, 1H), 7.57 (s, 1H), 7.02 (d, J=8.0 Hz, 2H), 6.94 (d, J=8.3 Hz, 1H), 5.17-5.09 (m, 1H), 4.50 (p, J=8.3 Hz, 1H), 4.14 (s, 2H), 4.10 (s, 4H), 4.05 (s, 1H), 4.02 (s, 0H), 3.84 (s, 2H), 3.78 (dd, J=9.4, 6.0 Hz, 1H), 3.63 (t, J=8.2 Hz, 1H), 3.56 (s, 1H), 3.07 (dt, J=6.7, 3.2 Hz, 1H), 2.93 (s, 0H), 2.90 (s, 1H), 2.88 (s, 1H), 2.74-2.57 (m, 2H), 2.35 (d, J=14.4 Hz, 1H), 2.23 (dd, J=20.9, 8.4 Hz, 2H), 2.19 (s, 4H), 2.08-1.99 (m, 3H), 1.96-1.87 (m, 1H), 1.79 (d, J=13.5 Hz, 1H), 1.69 (d, J=6.6 Hz, 8H), 1.58 (dd, J=21.3, 11.5 Hz, 7H), 1.44 (s, 4H), 1.31 (s, 2H), 1.14 (d, J=6.6 Hz, 3H), 0.94 (s, 3H).

Example 157

(3RS)-3-[6-(4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)-2-Methylpyridin-3-yl]piperidine-2,6-dione

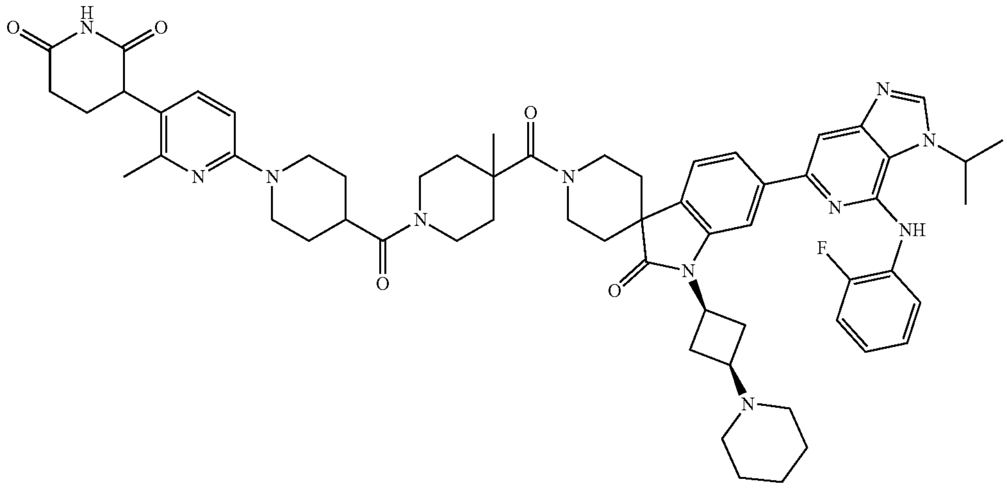 [SMILES: Cc1nc(N2CCC(C(=O)N3CCC(C)(C(=O)N4CCC5(CC4)C(=O)N([C@H]4C[C@@H](N6CCCCC6)C4)c4cc(-c6cc7ncn(C(C)C)c7c(Nc7ccccc7F)n6)ccc45)CC3)CC2)ccc1C1CCC(=O)NC1=O]

Intermediate J (20.00 mg, 0.0273 mmol), Intermediate 109 (9.04 mg, 0.0273 mmol), and (1,2,3-benzotriazol-1-yloxy)tris(dimethylamino)phosphanium, hexafluoro-lambda5-phosphanuide (15.69 mg, 0.0355 mmol) were dissolved in dimethylformamide (1.00 mL) and N,N-diisopropylethylamine (0.05 mL, 0.2729 mmol) and stirred at room temperature for 6 hours. The crude product mixture was purified by preparative HPLC to afford the title compound (1.3 mgs, 5% yield). LCMS: $C_{60}H_{72}FN_{11}O_5$, desired mass=1045.6, found: m/z=1046.5 $[M+H]^+$.

Example 158

3-(2-(4-((R)-3-(6-(4-((2-fluorophenyl)amino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)pyrrolidine-1-carbonyl)piperidin-1-yl)pyrimidin-5-yl)piperidine-2,6-dione

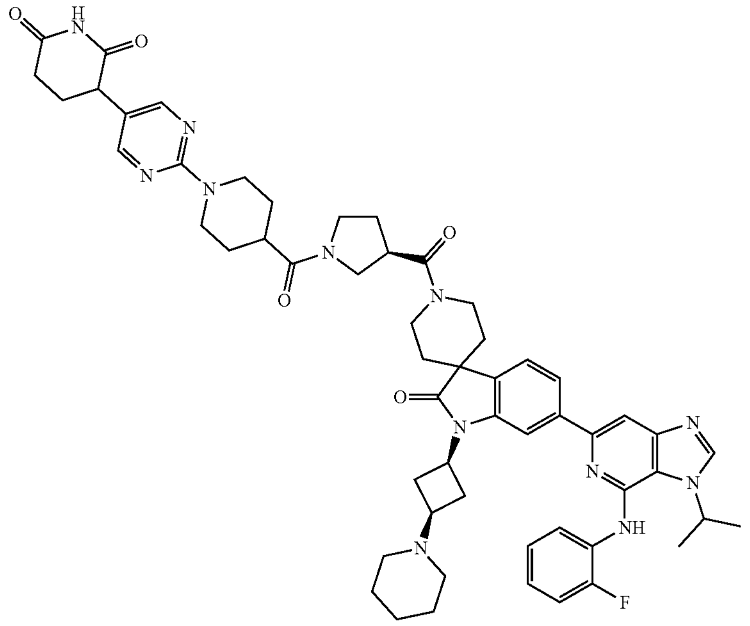 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ncc(C7CCC(=O)NC7=O)cn6)CC5)C4)CC3)nc(Nc3ccccc3F)c21]

Using procedures similar to Example 157 and using 6-{4-[(2-fluorophenyl)amino]-3-isopropylimidazo[4,5-c]pyridin-6-yl}-1'-[(3R)-pyrrolidine-3-carbonyl]-1-[(1s,3s)-3-(piperidin-1-yl)cyclobutyl]spiro[indole-3,4'-piperidin]-2-one (example 17, step 1) and intermediate 103 (step 4) as the coupling partners, the title compound was isolated as an off-white solid (26 mgs, 77% yield). LCMS: $C_{56}H_{65}FN_{12}O_5$, desired mass=1004.5, found: m/z=1005.4 $[M+H]^+$.

Example 159

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}sulfonyl)piperidine-1-carbonyl]piperidin-1-yl}pyridin-3-yl)piperidine-2,6-dione

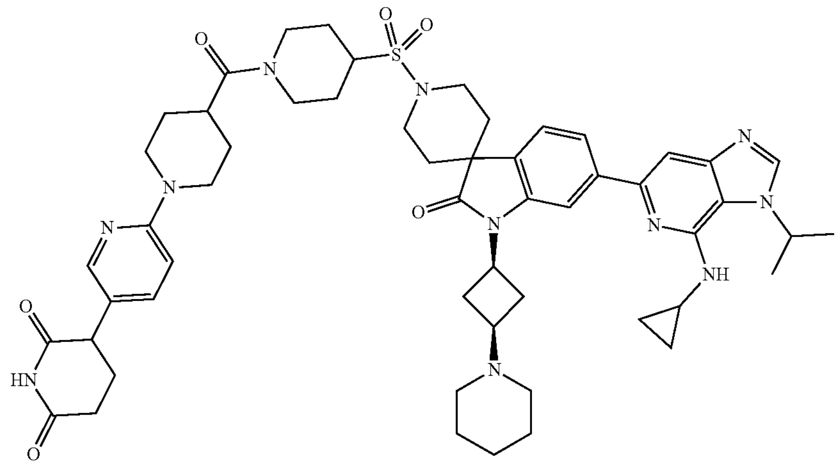 [SMILES: CC(C)n1cnc2cc(-c3ccc4c(c3)N([C@H]3C[C@@H](N5CCCCC5)C3)C(=O)C43CCN(S(=O)(=O)C4CCN(C(=O)C5CCN(c6ccc(C7CCC(=O)NC7=O)cn6)CC5)CC4)CC3)nc(NC3CC3)c21]

Intermediate I (25.00 mg, 0.0361 mmol), (1,2,3-benzotriazol-1-yloxy)tris(dimethylamino)phosphanium, hexafluoro-lambda5-phosphanuide (20.74 mg, 0.0469 mmol) and 1-[5-(2,6-dioxopiperidin-3-yl)pyridin-2-yl]piperidine-4-carboxylic acid (Intermediate 55, step 2) (11.45 mg, 0.0361 mmol) were dissolved in dimethylformamide (0.80 mL) and N,N-diisopropylethylamine (0.03 mL, 0.1443 mmol) and stirred at room temperature for 4 hours. The crude reaction mixture was purified by preparative HPLC to afford the title compound (7.5 mgs, 14% yield). LCMS: $C_{54}H_{69}N_{11}O_6S$, desired mass=999.5, found: m/z=1000.4 $[M+H]^+$. $^1H$ NMR (500 MHz, Methanol-$d_4$) δ 8.92 (s, 1H), 8.03-7.96 (m, 1H), 7.87 (s, 1H), 7.66 (s, 3H), 7.61 (s, 1H), 7.56 (d, J=3.9 Hz, 1H), 7.47-7.40 (m, 1H), 5.16-5.10 (m, 1H), 4.85 (s, 2H), 4.70 (d, J=13.6 Hz, 1H), 4.48 (s, 2H), 4.32 (d, J=13.6 Hz, 1H), 4.23 (s, 3H), 3.97 (d, J=12.9 Hz, 1H), 3.90 (s, 3H), 3.77 (s, 2H), 3.57 (s, 4H), 3.07 (s, 1H), 3.01 (s, 3H), 2.90 (s, 3H), 2.82 (s, 1H), 2.79 (s, 3H), 2.30 (s, 4H), 2.20 (d, J=12.8 Hz, 2H), 2.08-1.99 (m, 4H), 1.97 (s, 2H), 1.92 (d, J=16.9 Hz, 1H), 1.84-1.78 (m, 1H), 1.69 (t, J=5.4 Hz, 7H), 1.57 (d, J=12.5 Hz, 1H), 1.32 (s, 1H), 1.14 (s, 2H), 0.95 (s, 2H).

Example 160

(3RS)-3-[6-(4-{[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]sulfonyl}piperidin-1-yl)pyridin-3-yl]piperidine-2,6-dione

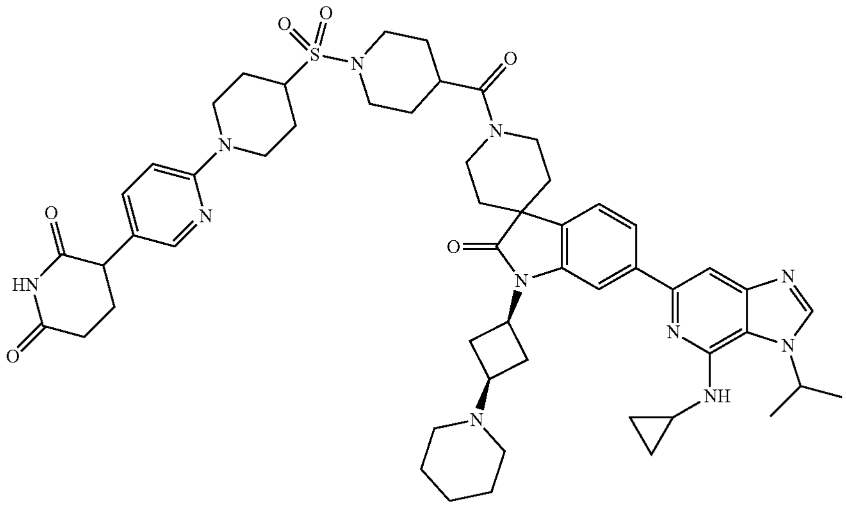 [SMILES: CC(C)n1cnc2cc(-c3ccc4c(c3)N([C@H]3C[C@@H](N5CCCCC5)C3)C(=O)C43CCN(C(=O)C4CCN(S(=O)(=O)C5CCN(c6ccc(C7CCC(=O)NC7=O)cn6)CC5)CC4)CC3)nc(NC3CC3)c21]

-

Intermediate 84 (25.93 mg, 0.0542 mmol), 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B), and (1,2,3-benzotriazol-1-yloxy)tris(dimethylamino)phosphanium, hexafluoro-lambda5-phosphanuide (28.75 mg, 0.0650 mmol) were dissolved in DMF (2.00 mL) and N,N-diisopropylethylamine (0.04 mL, 0.2167 mmol) and stirred at room temperature for 4 hours. The crude reaction mixture was purified by preparative HPLC to afford the title compound (6.9 mgs, 13% yield). LCMS: $C_{54}H_{69}N_{11}O_6S$, desired mass=999.5, found: m/z=1001.4 $[M+H]^+$. $^1H$ NMR (500 MHz, Methanol-$d_4$) δ 8.89 (s, 1H), 7.98-7.90 (m, 2H), 7.70 (s, 1H), 7.65 (d, J=6.4 Hz, 2H), 7.56 (s, 1H), 7.37 (d, J=9.5 Hz, 1H), 4.32 (d, J=13.6 Hz, 2H), 4.16 (s, 2H), 4.12 (s, 1H), 4.02 (s, 0H), 3.95 (dd, J=12.6, 5.0 Hz, 1H), 3.88 (s, 4H), 3.63 (t, J=8.1 Hz, 1H), 3.57 (s, 4H), 3.11 (t, J=12.4 Hz, 1H), 3.02 (s, 4H), 2.90 (t, J=12.1 Hz, 2H), 2.77 (s, 1H), 2.27 (d, J=13.4 Hz, 2H), 2.21 (s, 1H), 2.05 (s, 0H), 1.99 (s, 4H), 1.90 (s, 8H), 1.81 (s, 2H), 1.69 (d, J=6.5 Hz, 6H), 1.58 (s, 1H), 1.31 (s, 2H), 1.12 (s, 2H), 0.92 (s, 2H).

Example 161

3-(6-{[(1R,4R)-4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidine-1-carbonyl]cyclohexyl]oxy}pyridin-3-yl)piperidine-2,6-dione

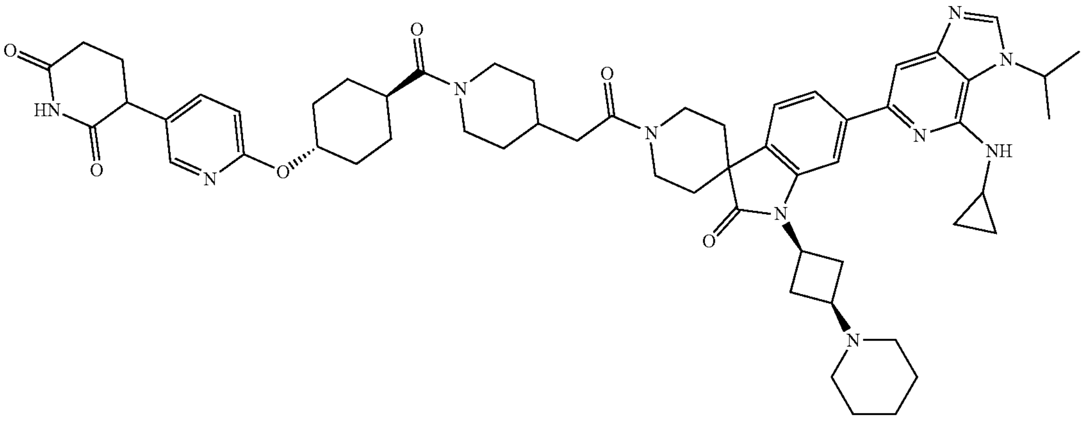 [SMILES: CC(C)n1cnc2cc(-c3ccc4c(c3)N([C@H]3C[C@@H](N5CCCCC5)C3)C(=O)C43CCN(C(=O)CC4CCN(C(=O)[C@H]5CC[C@H](Oc6ccc(C7CCC(=O)NC7=O)cn6)CC5)CC4)CC3)nc(NC3CC3)c21]

Intermediate H (25.00 mg, 0.0361 mmol), (1,2,3-benzotriazol-1-yloxy)tris(dimethylamino)phosphanium, hexafluoro-lambda5-phosphanuide (20.74 mg, 0.0469 mmol) and (1r,4r)-4-((5-(2,6-dioxopiperidin-3-yl)pyridin-2-yl)oxy)cyclohexane-1-carboxylic acid (Intermediate 9) (11.45 mg, 0.0361 mmol) were dissolved in dimethylformamide (0.80 mL) and N,N-diisopropylethylamine (0.03 mL, 0.1443 mmol) and stirred at room temperature for 4 hours. The crude reaction mixture was purified by preparative HPLC to afford the title compound (14.2 mgs, 39% yield). LCMS: $C_{57}H_{72}N_{10}O_6$, desired mass=992.6, found: m/z=993.5 $[M+H]^+$. $^1H$ NMR (500 MHz, Methanol-$d_4$) δ 8.95 (s, 1H), 8.05 (d, J=2.5 Hz, 1H), 7.64 (d, J=22.8 Hz, 5H), 7.57 (s, 1H), 6.83 (d, J=8.6 Hz, 1H), 5.17-5.10 (m, 1H), 4.59 (d, J=13.5 Hz, 1H), 4.53-4.45 (m, 1H), 4.16 (d, J=15.8 Hz, 2H), 4.11 (s, 1H), 4.07 (d, J=7.0 Hz, 1H), 3.97-3.85 (m, 1H), 3.63 (t, J=8.0 Hz, 1H), 3.58 (d, J=12.6 Hz, 3H), 3.23 (d, J=10.3 Hz, 2H), 3.17 (s, 0H), 3.10-3.04 (m, 1H), 3.00 (d, J=10.1 Hz, 3H), 2.90 (t, J=12.5 Hz, 2H), 2.85-2.68 (m, 4H), 2.55-2.44 (m, 2H), 2.30-2.23 (m, 3H), 2.23-2.15 (m, OH), 2.08-1.99 (m, 3H), 1.96 (s, 4H), 1.89 (d, J=5.9 Hz, 2H), 1.79 (d, J=13.6 Hz, 1H), 1.69 (d, J=6.7 Hz, 9H), 1.57 (d, J=12.9 Hz, 4H), 1.31 (s, 1H), 1.21 (d, J=12.5 Hz, 1H), 1.15 (d, J=6.6 Hz, 3H), 0.95 (s, 3H).

Example 162

(3RS)-3-(6-{4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione

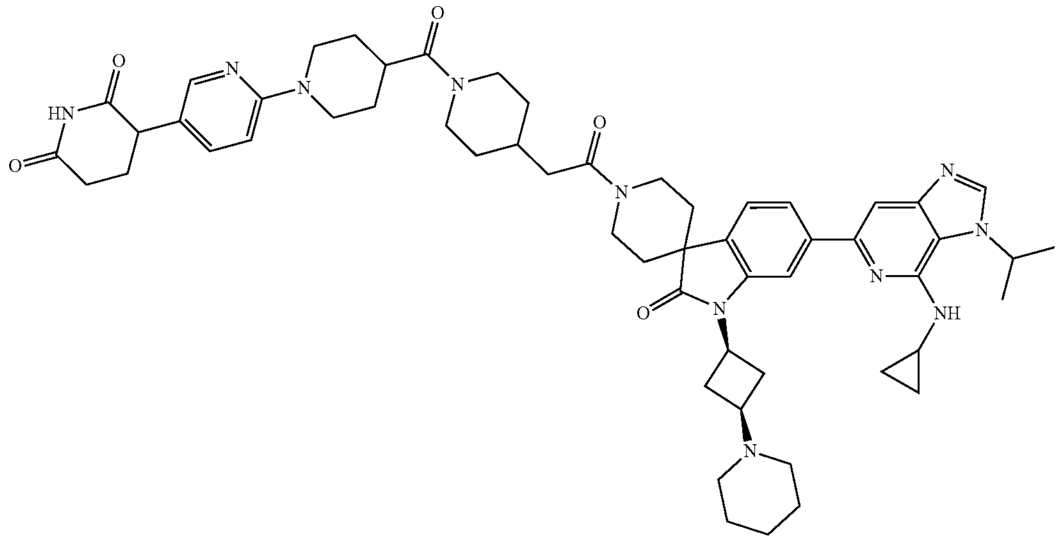 [SMILES: CC(C)n1cnc2cc(-c3ccc4c(c3)N([C@H]3C[C@@H](N5CCCCC5)C3)C(=O)C43CCN(C(=O)CC4CCN(C(=O)C5CCN(c6ccc(C7CCC(=O)NC7=O)cn6)CC5)CC4)CC3)nc(NC3CC3)c21]

Intermediate H (25.00 mg, 0.0361 mmol), (1,2,3-benzotriazol-1-yloxy)tris(dimethylamino)phosphanium, hexafluoro-lambda5-phosphanuide (20.74 mg, 0.0469 mmol) and 1-[5-(2,6-dioxopiperidin-3-yl)pyridin-2-yl]piperidine-4-carboxylic acid (Intermediate 55, step 2) (11.45 mg, 0.0361 mmol) were dissolved in dimethylformamide (0.80 mL) and N,N-diisopropylethylamine (0.03 mL, 0.1443 mmol) and stirred at room temperature for 4 hours. The crude reaction mixture was purified by preparative HPLC to afford the title compound (14.4 mgs, 37% yield). LCMS: $C_{56}H_{71}N_{11}O_5$, desired mass=977.6, found: m/z=978.5 $[M+H]^+$. $^1H$ NMR (500 MHz, Methanol-$d_4$) δ 8.94 (s, 1H), 7.99 (dd, J=9.6, 2.3 Hz, 1H), 7.86 (d, J=2.3 Hz, 1H), 7.66 (s, 2H), 7.62 (s, 1H), 7.56 (s, 1H), 7.43 (d, J=9.6 Hz, 1H), 5.17-5.10 (m, 1H), 4.58 (d, J=13.4 Hz, 1H), 4.49 (p, J=8.5 Hz, 1H), 4.08 (s, 1H), 3.96 (dd, J=13.0, 4.9 Hz, 2H), 3.67-3.54 (m, 4H), 3.43 (s, 2H), 3.36 (s, 1H), 3.24 (s, 1H), 3.07 (dt, J=6.7, 3.2 Hz, 1H), 3.01 (d, J=9.5 Hz, 3H), 2.90 (t, J=12.4 Hz, 2H), 2.84-2.76 (m, 1H), 2.78 (s, 1H), 2.74 (t, J=14.3 Hz, 1H), 2.60-2.40 (m, 2H), 2.33 (qd, J=13.0, 5.8 Hz, 1H), 2.24-2.16 (m, 1H), 2.04 (s, 1H), 2.01 (s, 3H), 1.96 (s, 4H), 1.91 (s, 1H), 1.90 (s, 5H), 1.86-1.71 (m, 2H), 1.69 (dd, J=6.6, 1.4 Hz, 6H), 1.57 (d, J=12.9 Hz, 1H), 1.31 (s, 1H), 1.22 (d, J=12.8 Hz, 1H), 1.14 (d, J=6.4 Hz, 2H), 0.94 (s, 2H).

Example 163

3-(6-(((1R,4R)-4-((R)-3-(6-(4-(cyclopropylamino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)-3-methylpyrrolidine-1-carbonyl)cyclohexyl)oxy)pyridin-3-yl)piperidine-2,6-dione

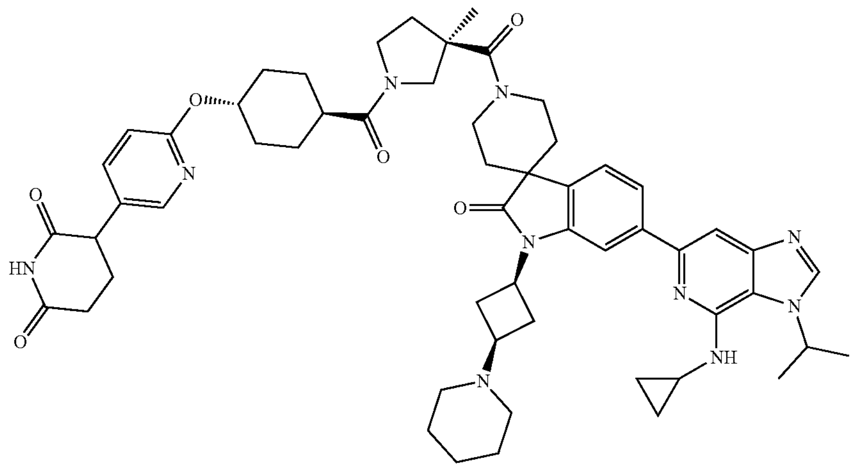 [SMILES: CC(C)n1cnc2cc(-c3ccc4c(c3)N([C@H]3C[C@@H](N5CCCCC5)C3)C(=O)C43CCN(C(=O)[C@]4(C)CCN(C(=O)[C@H]5CC[C@H](Oc6ccc(C7CCC(=O)NC7=O)cn6)CC5)C4)CC3)nc(NC3CC3)c21]

Using procedures similar to Example 185 and using Intermediate 9 as the acid coupling partner afforded the title compound (42.5 mg, 30% yield) as an off-white solid. LCMS: $C_{56}H_{70}N_{10}O_6$, desired mass=978.6, found: m/z=979.5 $[M+H]^+$.

Example 164

3-(6-{4-[4-({6-[4-(2-fluorophenoxy)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

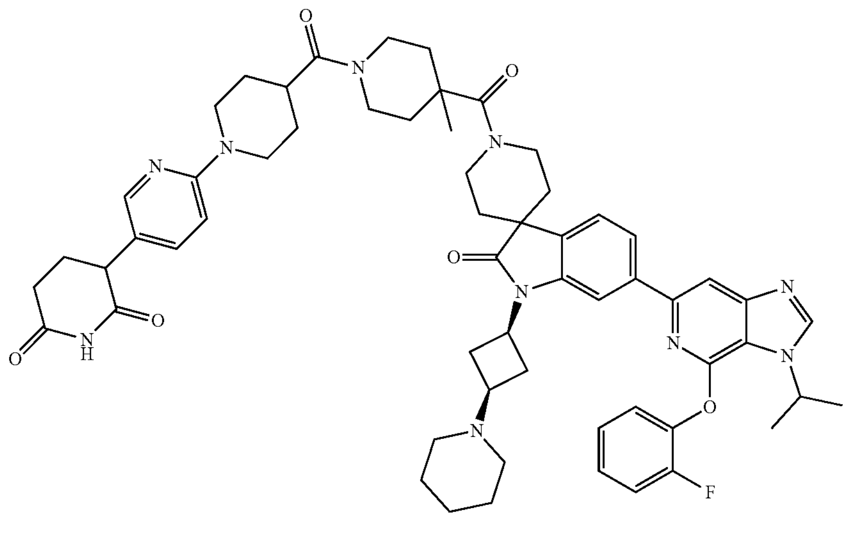 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(Oc3ccccc3F)c21]

To a solution of tert-butyl 1-(1-(4-(2,6-dioxopiperidin-3-yl)phenyl)piperidine-4-carbonyl)-4-methylpiperidine-4-carboxylate (Intermediate 55) (0.07 g, 0.149 mmol) in anhydrous Dimethylformamide (4.96 mL, 0.03 M) was added (Benzotriazol-1-yloxy)tris(dimethylamino)phosphonium hexafluorophosphate (0.072 g, 0.164 mmol) and the reaction mixture was stirred at room temperature for 10 min. A solution of 6-[4-(2-fluorophenoxy)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate G) (0.1 g, 0.164 mmol) and N,N-Diisopropylethylamine (DIPEA) (0.13 mL, 0.743 mmol) in DMF was added and stirring was continued for an additional 16 h at room temperature. The solvents were evaporated under vacuum and the residue was diluted with DCM and stirred vigorously with saturated sodium bicarbonate solution for 30 min. The aqueous layer was extracted with DCM (3×10 mL) and the combined organic layers were dried over sodium sulphate, filtered and evaporated. The crude residue was purified twice using reverse phase flash column chromatography (eluting with 10-90% ACN in water) to obtain 36 mg (24% yield) of the title compound as a white solid. LCMS: C59H69FN10O6, desired mass=1033.26, found: m/z=1034.30 $[M+H]^+$ $^1H$ NMR (300 MHz, DMSO-$d_6$) δ 10.82 (s, 1H), 8.64 (s, 1H), 8.14 (s, 1H), 7.95 (d, J=2.5 Hz, 1H), 7.77 (s, 1H), 7.64-7.29 (m, 6H), 6.81 (d, J=8.8 Hz, 1H), 5.14 (p, J=6.7 Hz, 1H), 4.29 (d, J=12.5 Hz, 3H), 4.02-3.63 (m, 7H), 3.48 (d, J=21.4 Hz, 1H), 3.17 (t, J=11.2 Hz, 1H), 2.88 (t, J=11.8 Hz, 3H), 2.72-2.59 (m, 1H), 2.24-1.93 (m, 2H), 1.67 (d, J=6.8 Hz, 8H), 1.55-1.37 (m, 5H), 1.30 (s, 3H).

Example 165

3-(6-{4-[4-methyl-4-({6-[4-(oxan-4-yloxy)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

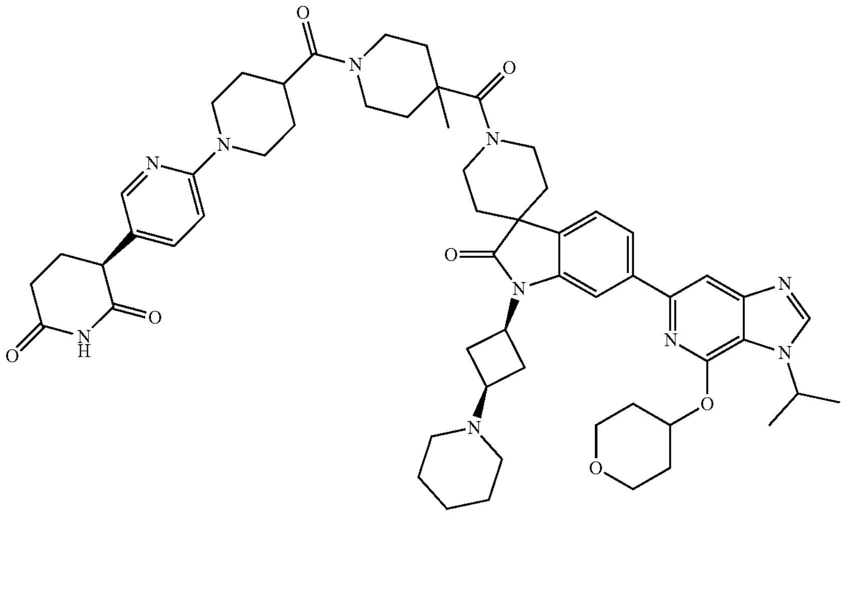 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc([C@@H]7CCC(=O)NC7=O)cn6)CC5)CC4)CC3)nc(OC3CCOCC3)c21]

Tert-butyl 1-(1-(4-(2,6-dioxopiperidin-3-yl)phenyl)piperidine-4-carbonyl)-4-methylpiperidine-4-carboxylate (Intermediate 55) (0.07 g, 0.149 mmol) was dissolved in anhydrous Dimethylformamide (4.96 mL). (Benzotriazol-1-yloxy)tris(dimethylamino)phosphonium hexafluorophosphate (0.099 g, 0.223 mmol) was added and the reaction mixture was stirred at room temperature for 10 mins. A solution of 6-[4-(oxan-4-yloxy)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate L) (0.109 g, 0.164 mmol) and N,N-Diisopropylethylamine (DIPEA) (0.13 mL, 0.743 mmol) in DMF was added and the mixture stirred for 16 h at room temperature. The reaction mixture was evaporated to dryness under vacuum, and the residue was diluted with DCM and vigorously stirred with aqueous saturated sodium bicarbonate solution for 30 min. The aqueous layer was extracted with DCM and the organic layer was dried over sodium sulphate, filtered and evaporated. The crude residue was purified by reverse phase flash column chromatography eluting with ACN/Water to obtain 55 mg (36% yield) of the title compound as a white solid. LCMS: C58H74N10O7 desired mass=1023.29, found: m/z=1023.30$[M+H]^+$. $^1H$ NMR (300 MHz, DMSO-$d_6$) δ 10.82 (s, 1H), 8.49 (s, 1H), 8.10 (s, 1H), 8.01 (s, 1H), 7.96 (d, J=2.4 Hz, 1H), 7.86 (d, J=8.0 Hz, 1H), 7.62 (d, J=7.9 Hz, 1H), 7.39 (dd, J=8.8, 2.4 Hz, 1H), 6.82 (d, J=8.9 Hz, 1H), 5.61 (s, 1H), 5.08 (t, J=6.7 Hz, 1H), 4.63 (d, J=8.9 Hz, 1H), 4.30 (d, J=12.6 Hz, 2H), 4.02-3.86 (m, 5H), 3.74 (dd, J=11.9, 4.8 Hz, 1H), 3.64 (t, J=8.4 Hz, 1H), 3.20 (s, 1H), 2.89 (t, J=12.0 Hz, 3H), 2.18 (s, 3H), 2.01 (s, 1H), 1.86 (d, J=8.6 Hz, 1H), 1.75 (s, 4H), 1.61 (d, J=6.7 Hz, 6H), 1.47 (s, 6H), 1.33 (s, 3H).

Example 166

3-(6-{4-[4-methyl-4-({2-oxo-6-[3-(propan-2-yl)-4-[(propan-2-yl)amino]-3H-imidazo[4,5-c]pyridin-6-yl]-1-[((1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

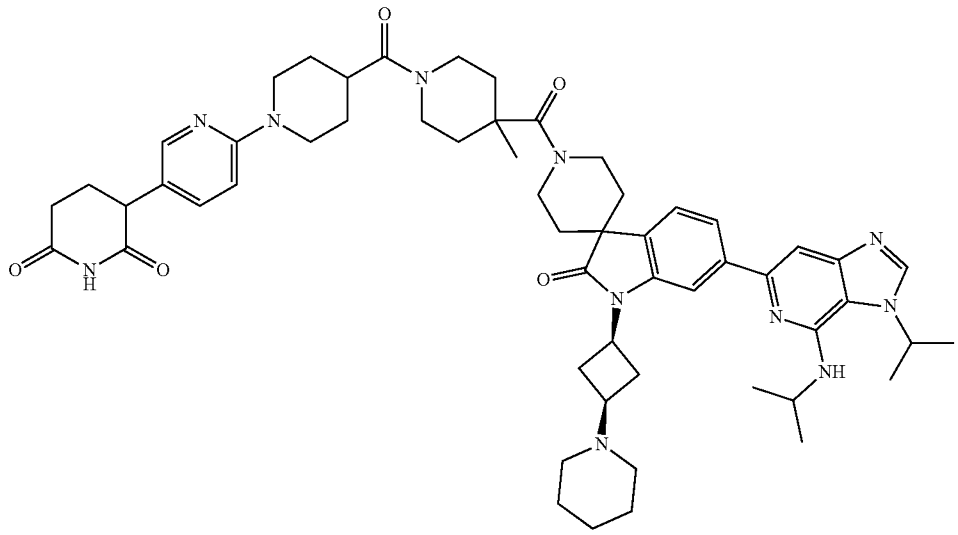 [SMILES: CC(C)Nc1nc(-c2ccc3c(c2)N([C@H]2C[C@@H](N4CCCCC4)C2)C(=O)C32CCN(C(=O)C3(C)CCN(C(=O)C4CCN(c5ccc(C6CCC(=O)NC6=O)cn5)CC4)CC3)CC2)cc2ncn(C(C)C)c12]

To a solution of tert-butyl 1-(1-(4-(2,6-dioxopiperidin-3-yl)phenyl)piperidine-4-carbonyl)-4-methylpiperidine-4-carboxylate (Intermediate 55) (134 mg, 0.227 mmol) in anhydrous dimethylformamide (10.32 mL) at 0° C. was added (benzotriazol-1-yloxy)tris(dimethylamino)phosphonium hexafluorophosphate (96 mg, 0.217 mmol) and N,N-diisopropylethylamine (0.18 mL, 1.032 mmol). The reaction mixture was warmed to room temperature and stirred for 30 minutes, then recooled in an ice water bath. 3-(6-{4-[4-methyl-4-({2-oxo-6-[3-(propan-2-yl)-4-[(propan-2-yl)amino]-3H-imidazo[4,5-c]pyridin-6-yl]-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione (Intermediate 0) (122 mg, 0.206 mmol) was added and the mixture was warmed to room temperature at stirred for 16 h. The mixture was concentrated under vacuum and the residue was partitioned between dichloromethane (20 mL) and saturated aqueous sodium bicarbonate solution. The organic layer was separated, washed with brine (20 mL), dried over sodium sulfate, filtered and concentrated. The residue was purified by silica gel flash chromatography (eluting with dichloromethane/methanol 100:0 to 90:10) to obtain 42 mg (20% yield) of title compound as a beige solid. LCMS: C56H73N11O5, desired mass=979.57, found: m/z=980.66 $[M+H]^+$. $^1H$ NMR (300 MHz, DMSO-$d_6$) δ 10.82 (s, 1H), 8.33 (s, 1H), 8.10 (s, 1H), 8.00-7.92 (m, 1H), 7.87 (d, J=8.4 Hz, 1H), 7.67 (s, 1H), 7.58 (d, J=7.9 Hz, 1H), 7.39 (dd, J=8.8, 2.4 Hz, 1H), 6.82 (d, J=8.8 Hz, 1H), 5.77 (s, 1H), 5.70 (d, J=6.8 Hz, 1H), 5.13 (p, J=6.9 Hz, 1H), 4.68-4.42 (m, 2H), 4.30 (d, J=11.3 Hz, 2H), 4.07-3.65 (m, 7H), 3.46 (s, 1H), 3.27-3.11 (m, 1H), 2.89 (t, J=11.6 Hz, 4H), 2.72-2.57 (m, 6H), 2.30 (s, 3H), 2.23-2.11 (m, 2H), 2.01 (dd, J=10.0, 4.9 Hz, 1H), 1.82-1.39 (m, 23H), 1.34 (d, J=6.6 Hz, 9H).

Example 167

3-[6-(4-{2-[4-({6-[4-(2-fluorophenoxy)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione

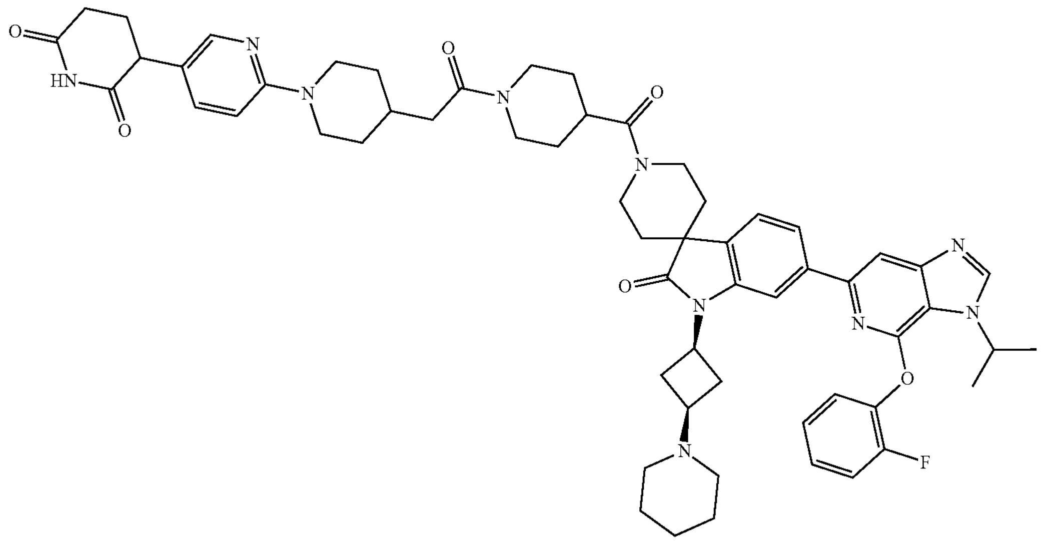 [SMILES: CC(C)n1cnc2cc(-c3ccc4c(c3)N([C@H]3C[C@@H](N5CCCCC5)C3)C(=O)C43CCN(C(=O)C4CCN(C(=O)CC5CCN(c6ccc(C7CCC(=O)NC7=O)cn6)CC5)CC4)CC3)nc(Oc3ccccc3F)c21]

In a pre-dried flask under argon 1-(2-{1-[5-(2,6-dioxopiperidin-3-yl)pyridin-2-yl]piperidin-4-yl}acetyl)piperidine-4-carboxylic acid, trifluoroacetic acid (Intermediate 46) (0.098 g, 0.154 mmol), DIPEA (0.061 mL, 0.351 mmol), DMAP (0.021 g, 0.169 mmol) and 1-(3-dimethylaminopropyl)-3-ethylcarbodiimide hydrochloride (0.032 g, 0.169 mmol) were combined in anhydrous dichloromethane (4.0 mL) and the mixture was stirred at room temperature for 20 min. A solution of 6-[4-(2-fluorophenoxy)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate G) (0.09 g, 0.14 mmol) and DIPEA (0.061 mL, 0.351 mmol) in anhydrous dichloromethane (3.0 mL) was added dropwise to the reaction mixture and it was stirred at room temperature for 3 days. A solution of 1-(2-{1-[5-(2,6-dioxopiperidin-3-yl)pyridin-2-yl]piperidin-4-yl}acetyl)piperidine-4-carboxylic acid, trifluoroacetic acid (Intermediate 46) (0.044 g, 0.071 mmol), DIPEA (0.025 mL, 0.141 mmol), DMAP (0.008 g, 0.070 mmol) and 1-(3-dimethylaminopropyl)-3-ethylcarbodiimide hydrochloride (0.014 g, 0.070 mmol) in anhydrous dichloromethane (1.0 mL) was stirred at room temperature for 20 min and added to the reaction mixture, which was stirred at room temperature overnight. A solution of 1-(2-{1-[5-(2,6-dioxopiperidin-3-yl)pyridin-2-yl]piperidin-4-yl}acetyl)piperidine-4-carboxylic acid, trifluoroacetic acid (Intermediate 46) (0.036 g, 0.056 mmol), DIPEA (0.025 mL, 0.141 mmol), DMAP (0.007 g, 0.056 mmol) and 1-(3-dimethylaminopropyl)-3-ethylcarbodiimide hydrochloride (0.011 g, 0.056 mmol) in anhydrous dichloromethane (1.0 mL) was stirred at room temperature for 20 min and added to the reaction mixture, which was stirred at room temperature overnight. The reaction mixture was diluted with DCM, washed with $NaHCO_3$, water and brine, dried over $Na_2SO_4$, filtered and evaporated, then purified by reverse phase flash column chromatography using a mobile phase of ACN and $H_2O$. 26 mg (17% yield) of the title compound as an off-white solid was obtained. LCMS: $C_{59}H_{69}FN_{10}O_6$, desired mass=1033.3, found: m/z=1033.4 $[M+H]^+$. $^1H$ NMR (300 MHz, DMSO-$d_6$) δ 10.81 (s, 1H), 8.64 (s, 1H), 8.14 (s, 1H), 7.94 (d, J=2.4 Hz, 1H), 7.77 (s, 1H), 7.62-7.29 (m, 7H), 6.80 (d, J=8.8 Hz, 1H), 5.21-5.07 (m, 1H), 4.43 (d, J=12.6 Hz, 1H), 4.30-4.20 (m, 3H), 3.99-3.67 (m, 7H), 3.56-3.39 (m, 2H), 3.13-3.03 (m, 1H), 3.02-2.89 (m, 1H), 2.84-2.71 (m, 3H), 2.71-2.57 (m, 2H), 2.47-2.38 (m, 4H), 2.34-2.22 (m, 5H), 2.24-2.13 (m, 1H), 2.04-1.89 (m, 2H), 1.66 (d, J=6.7 Hz, 6H), 1.81-1.53 (m, 10H), 1.52-1.32 (m, 4H), 1.22-1.09 (m, 3H).

Example 168

3-(6-{4-[4-methyl-4-({2-oxo-6-[4-phenoxy-3-(propan-2-yl)-3H-imidazo[4,5-c]pyridin-6-yl]-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

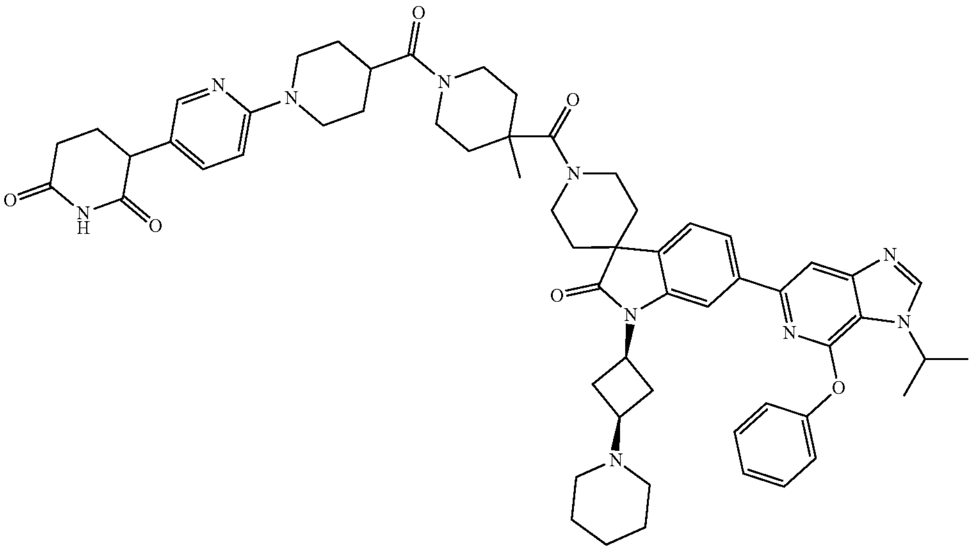 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(Oc3ccccc3)c21]

A mixture of tert-butyl 1-(1-(4-(2,6-dioxopiperidin-3-yl)phenyl)piperidine-4-carbonyl)-4-methylpiperidine-4-carboxylate (Intermediate 55) (0.079 g, 0.168 mmol), DIPEA (0.067 mL, 0.381 mmol) and 1-hydroxybenzotriazole hydrate (0.026 g, 0.168 mmol) in anhydrous dimethylformamide (1.5 mL) was stirred at room temperature for 5 min. 1-(3-dimethylaminopropyl)-3-ethylcarbodiimide hydrochloride (0.032 g, 0.168 mmol) was added and the mixture was stirred for additional 20 min. A solution of 6-[4-phenoxy-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate N) (0.09 g, 0.152 mmol) and DIPEA (0.067 mL, 0.381 mmol) in anhydrous dimethylformamide (1.5 mL) was added dropwise to the reaction mixture and stirring continued at room temperature for 16 h. The reaction mixture was evaporated under vacuum and the residue was partitioned between EtOAc and saturated $NaHCO_3$ aqueous solution. The organic layer was separated and washed with water and brine, dried over $Na_2SO_4$, filtered and evaporated, then purified by reverse phase flash column chromatography using a mobile phase of ACN and $H_2O$ to afford 54 mg (33% yield) of the title compound as a white solid. LCMS: $C_{59}H_{70}N_{10}O_6$, desired mass=1015.3, found: m/z=1015.4 $[M+H]^+$. $^1H$ NMR (300 MHz, DMSO-$d_6$) δ 10.82 (s, 1H), 8.62 (s, 1H), 8.12 (s, 1H), 7.95 (d, J=2.3 Hz, 1H), 7.83 (s, 1H), 7.59 (d, J=7.9 Hz, 1H), 7.55-7.46 (m, 3H), 7.43-7.34 (m, 3H), 7.34-7.25 (m, 1H), 6.81 (d, J=8.9 Hz, 1H), 5.15 (p, J=13.4, 6.9 Hz, 1H), 4.40-4.22 (m, 3H), 3.94-3.65 (m, 7H), 3.44 (dd, J=13.4, 7.1 Hz, 2H), 3.23-3.11 (m, 1H), 2.98-2.80 (m, 4H), 2.71-2.60 (m, 2H), 2.48-2.39 (m, 4H), 2.34-2.23 (m, 3H), 2.23-2.11 (m, 2H), 2.07-1.94 (m, 2H), 1.65 (d, J=6.7 Hz, 6H), 1.71-1.36 (m, 16H), 1.30 (s, 3H).

Example 169

3-(6-{4-[4-methyl-4-({2-oxo-6-[3-(propan-2-yl)-4-(propan-2-yloxy)-3H-imidazo[4,5-c]pyridin-6-yl]-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

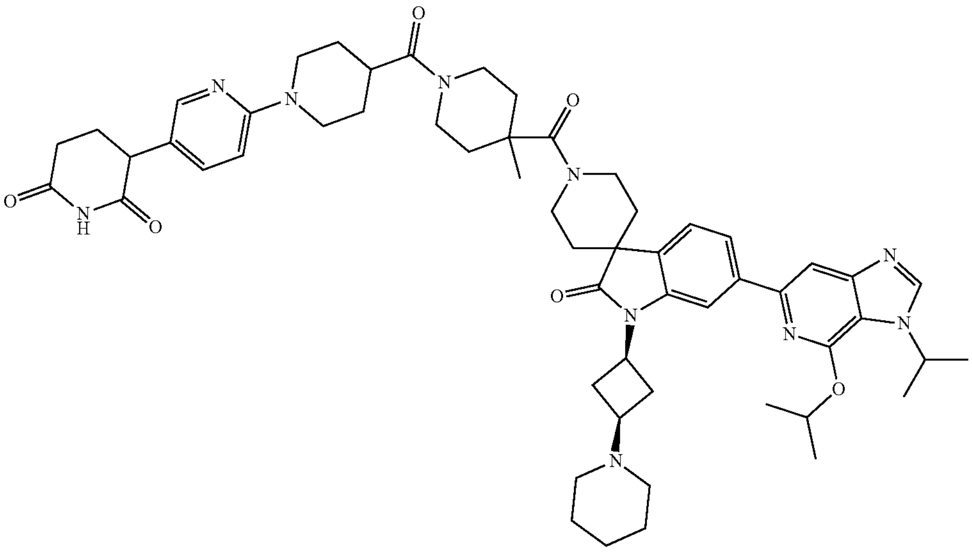 [SMILES: CC(C)Oc1nc(-c2ccc3c(c2)N([C@H]2C[C@@H](N4CCCCC4)C2)C(=O)C32CCN(C(=O)C3(C)CCN(C(=O)C4CCN(c5ccc(C6CCC(=O)NC6=O)cn5)CC4)CC3)CC2)cc2ncn(C(C)C)c12]

To a solution of tert-butyl 1-(1-(4-(2,6-dioxopiperidin-3-yl)phenyl)piperidine-4-carbonyl)-4-methylpiperidine-4-carboxylate (Intermediate 55) (0.157 g, 0.283 mmol) in anhydrous dimethylformamide (6.0 mL) was added DIPEA (0.205 mL, 1.177 mmol) and BOP (0.125 g, 0.283 mmol). The reaction mixture was stirred for 30 min and 6-[3-(propan-2-yl)-4-(propan-2-yloxy)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate M) (0.138 g, 0.235 mmol) was added. The reaction mixture was stirred at room temperature for 16 h, then was evaporated under vacuum. The residue was dissolved in DCM and $NaHCO_3$ aqueous solution and stirred vigorously for 20 min. The layers were separated and organic phase was washed with water and brine, dried over $Na_2SO_4$, filtered and evaporated. The crude residue was purified by reverse phase flash column chromatography using a mobile phase of ACN and $H_2O$ to afford 105 mg (43% yield) of the title compound as an off-white solid. LCMS: $C_{56}H_{72}N_{10}O_6$, desired mass=981.3, found: m/z=982.2 $[M+H]^+$. $^1H$ NMR (300 MHz, DMSO-$d_6$) δ 10.81 (s, 1H), 8.45 (s, 1H), 8.13 (s, 1H), 7.98 (s, 1H), 7.95 (d, J=2.5 Hz, 1H), 7.90-7.83 (m, 1H), 7.60 (d, J=7.9 Hz, 1H), 7.38 (dd, J=8.8, 2.5 Hz, 1H), 6.82 (d, J=8.9 Hz, 1H), 5.62 (p, J=6.2 Hz, 1H), 5.04 (p, J=6.7 Hz, 1H), 4.71-4.58 (m, 1H), 4.29 (d, J=12.7 Hz, 2H), 4.05-3.84 (m, 4H), 3.74 (dd, J=12.0, 4.9 Hz, 3H), 3.53-3.39 (m, 2H), 3.26-3.12 (m, 1H), 2.98-2.81 (m, 4H), 2.66 (dd, J=12.2, 5.1 Hz, 7H), 2.51-2.40 (m, 3H), 2.38-2.24 (m, 3H), 2.23-1.90 (m, 4H), 1.82-1.39 (m, 24H), 1.32 (s, 3H).

Example 170

3-(6-{4-[4-methyl-4-({2-oxo-6-[3-(propan-2-yl)-4-(pyrrolidin-1-yl)-3H-imidazo[4,5-c]pyridin-6-yl]-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

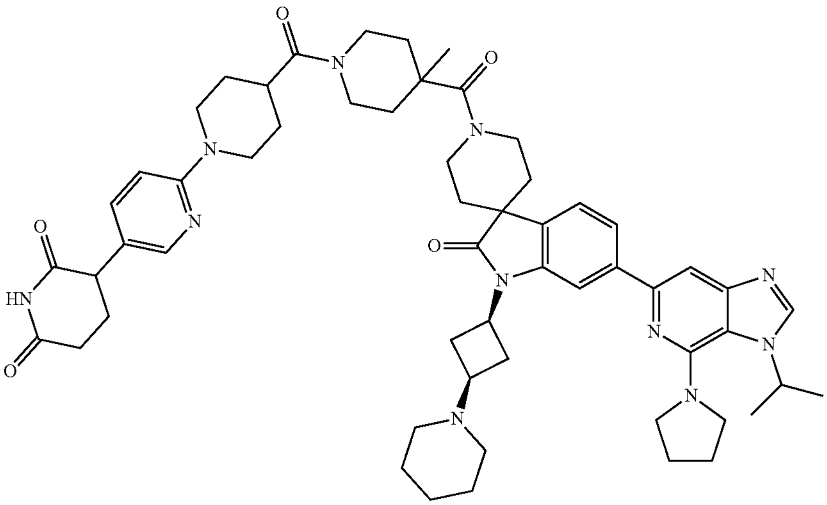 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(N3CCCC3)c21]

Using similar procedures to Example 169 and using 6-[3-(propan-2-yl)-4-(pyrrolidin-1-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate P) as the amine coupling partner, the title compound (23.0 mg, 22% yield) was isolated as an off-white solid. LCMS: $C_{57}H_{73}N_{11}O_5$, desired mass=991.6, found: m/z=992.6 $[M+H]^+$. $^1$H NMR (300 MHz, DMSO-$d_6$) δ 10.81 (s, 1H), 8.61 (s, 1H), 8.12 (s, 1H), 7.97 (s, 1H), 7.95 (d, J=2.7 Hz, 2H), 7.86 (d, J=7.8 Hz, 1H), 7.59 (d, J=7.9 Hz, 1H), 7.38 (dd, J=8.8, 2.5 Hz, 1H), 6.82 (d, J=8.9 Hz, 1H), 5.15 (p, J=6.8 Hz, 1H), 4.66 (d, J=11.3 Hz, 1H), 4.29 (d, J=12.6 Hz, 2H), 3.94 (d, J=13.7 Hz, 4H), 3.74 (dd, J=12.0, 5.0 Hz, 2H), 3.50 (q, J=5.5, 4.6 Hz, 5H), 3.20 (t, J=10.9 Hz, 1H), 2.88 (t, J=12.0 Hz, 3H), 2.66 (dd, J=12.2, 5.3 Hz, 1H), 2.28 (q, J=1.9 Hz, 3H), 2.17 (dt, J=12.0, 5.8 Hz, 1H), 2.06-1.95 (m, 1H), 1.74 (s, 5H), 1.61 (s, 5H), 1.55 (d, J=6.7 Hz, 10H), 1.49-1.42 (m, 5H), 1.32 (s, 3H), 1.24 (s, 1H).

Example 171

3-[6-(4-{4-[(6-{4-[cyclopropyl(methyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]piperidine-2,6-dione

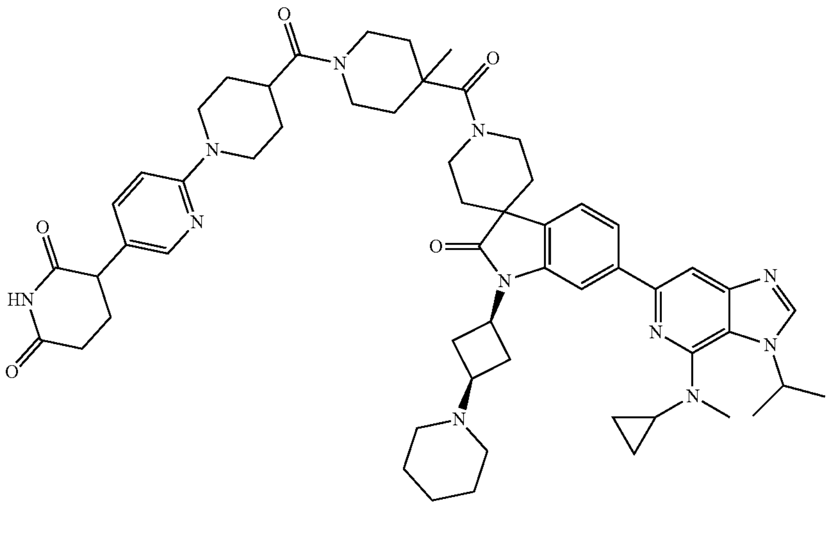 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(N(C)C3CC3)c21]

Using similar procedures to Example 169 and using 6-{4-[cyclopropyl(methyl)amino]-3-(propan-2-yl)-3H-imidazo[4,5-c]pyridin-6-yl}-1-[(1s,3s)-3-(piperidin-1-yl)cyclobutyl]-1,2-dihydrospiro[indole-3,4'-piperidin]-2-one (Intermediate Q) as the amine coupling partner, the title compound (32.0 mg, 22% yield) was isolated as an off-white solid. LCMS: $C_{57}H_{73}N_{11}O_5$, desired mass=991.6, found: m/z=992.6 $[M+H]^+$. $^1H$ NMR (300 MHz, DMSO-$d_6$) δ 10.82 (s, 1H), 8.60 (s, 1H), 8.18 (s, 1H), 8.08 (s, 1H), 7.95 (d, J=2.5 Hz, 1H), 7.90 (dd, J=7.8, 1.3 Hz, 1H), 7.59 (d, J=7.9 Hz, 1H), 7.38 (dd, J=8.9, 2.5 Hz, 1H), 6.81 (d, J=8.8 Hz, 1H), 5.13 (p, J=6.7 Hz, 1H), 4.66 (d, J=10.5 Hz, 1H), 4.29 (d, J=12.4 Hz, 2H), 3.94 (d, J=12.9 Hz, 4H), 3.74 (dd, J=12.0, 4.9 Hz, 3H), 3.44 (d, J=14.3 Hz, 1H), 3.20 (t, J=10.7 Hz, 1H), 3.02 (tt, J=6.8, 3.7 Hz, 1H), 2.90 (s, 6H), 2.75-2.60 (m, 3H), 2.34-2.24 (m, 4H), 2.21-1.94 (m, 5H), 1.78-1.56 (m, 12H), 1.50 (d, J=6.7 Hz, 11H), 1.32 (s, 3H), 1.25 (d, J=4.6 Hz, 2H), 0.66 (dt, J=6.4, 3.0 Hz, 2H), 0.45-0.38 (m, 2H).

Example 172

3-(6-{4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}propanoyl)piperazine-1-carbonyl]piperidin-1-yl}pyridin-3-yl)piperidine-2,6-dione

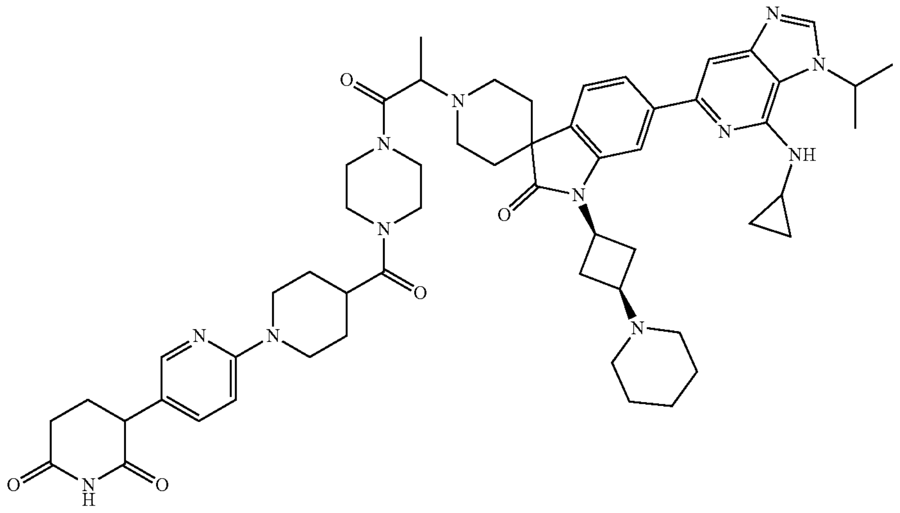 [SMILES: CC(C(=O)N1CCN(C(=O)C2CCN(c3ccc(C4CCC(=O)NC4=O)cn3)CC2)CC1)N1CCC2(CC1)C(=O)N([C@H]1C[C@@H](N3CCCCC3)C1)c1cc(-c3cc4ncn(C(C)C)c4c(NC4CC4)n3)ccc12]

To a solution of 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}propanoic acid (Intermediate Z) (0.05 g, 0.064 mmol) in anhydrous DMF (0.5 mL) was added N,N-diisopropylethylamine (0.04 mL, 0.244 mmol) and BOP (0.036 g, 0.059 mmol). The reaction mixture was stirred for 1 h at room temperature, then Intermediate 86 (0.03 g, 0.049 mmol) was added and stirring was continued for 1.5 h. Then reaction mixture was evaporated to dryness, diluted with DCM, washed with saturated aqueous $NaHCO_3$ solution, dried over $Na_2SO_4$, filtered and evaporated to dryness. The crude residue was purified by preparative HPLC to afford the title compound (white foamy solid, 21.7 mg, 42% yield). LCMS: [C56H72$N_{12}$O5], desired mass=992.6, found: m/z=993.7 $[M+H]^+$, 1H NMR (300 MHz, DMSO-$d_6$) δ 10.82 (s, 1H), 8.34 (s, 1H), 8.14 (s, 1H), 8.04-7.86 (m, 2H), 7.71 (s, 1H), 7.53 (s, 1H), 7.39 (d, J=8.9 Hz, 1H), 6.83 (d, J=8.9 Hz, 1H), 6.46 (s, 1H), 5.15-4.98 (m, 1H), 4.67-4.49 (m, 1H), 4.41-4.20 (m, 2H), 3.92-3.66 (m, 5H), 3.64-3.50 (m, 1H), 3.48-3.35 (m, 2H), 3.28-3.15 (m, 2H), 3.07-2.81 (m, 5H), 2.81-2.54 (m, 6H), 2.32-2.11 (m, 5H), 2.05-1.91 (m, 2H), 1.89-1.36 (m, 16H), 1.17 (d, J=6.4 Hz, 3H), 0.80 (d, J=6.1 Hz, 2H), 0.58 (d, J=4.2 Hz, 2H).

Example 173

3-(2-{4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}propanoyl)piperazine-1-carbonyl]piperidin-1-yl}pyridin-4-yl)piperidine-2,6-dione

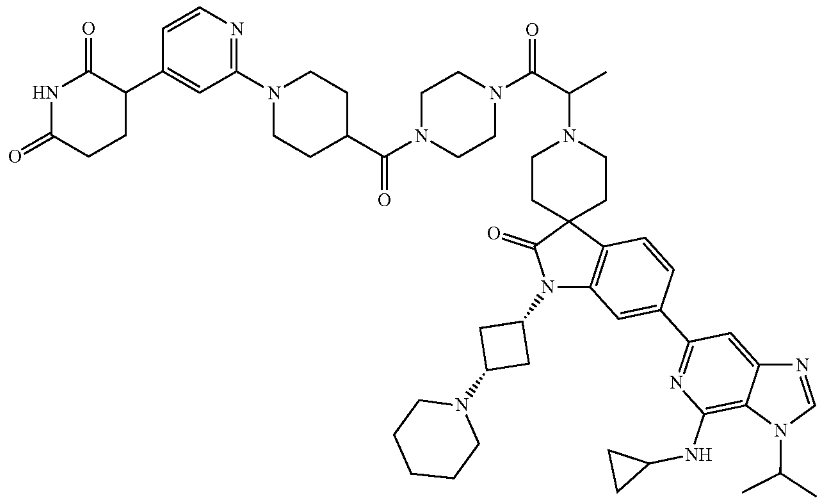 [SMILES: CC(C(=O)N1CCN(C(=O)C2CCN(c3cc(C4CCC(=O)NC4=O)ccn3)CC2)CC1)N1CCC2(CC1)C(=O)N([C@H]1C[C@@H](N3CCCCC3)C1)c1cc(-c3cc4ncn(C(C)C)c4c(NC4CC4)n3)ccc12]

To a solution of 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}propanoic acid (Intermediate Z) (0.07 g, 0.09 mmol) in anhydrous DMF (0.8 mL) was added N,N-diisopropylethylamine (0.1 mL. 480 mmol) and BOP (0.042 g, 0.094 mmol). The reaction mixture was stirred for 1 h at room temperature, then Intermediate 87 (0.06 g, 0.08 mmol) was added and stirring was continued for 1.5 h. Then reaction was evaporated to dryness, diluted with DCM, washed with $NaHCO_3$, dried over Na2SO4 and organic phase was filtered off and evaporated to dryness. Crude residue was submitted for pHPLC (basic conditions) to afford title compound (white solid, 12.9 mg, 17% yield). LCMS: [C56H72N12O5], desired mass=992.6, found: m/z=993.8 $[M+H]^+$, 1H NMR (300 MHz, DMSO-$d_6$) δ 10.87 (s, 1H), 8.34 (s, 1H), 8.13 (s, 1H), 8.04 (d, J=5.1 Hz, 1H), 7.92 (d, J=7.7 Hz, 1H), 7.70 (s, 1H), 7.52 (s, 1H), 6.73 (s, 1H), 6.51-6.39 (m, 2H), 5.12-5.01 (m, 1H), 4.63-4.53 (m, 1H), 4.43-4.24 (m, 3H), 3.89-3.68 (m, 6H), 3.54 (dd, J=9.4, 6.5 Hz, 5H), 3.05-2.81 (m, 6H), 2.62 (s, 5H), 2.34-2.18 (m, 5H), 2.07-1.94 (m, 2H), 1.91-1.75 (m, 3H), 1.76-1.33 (m, 16H), 1.17 (d, J=6.4 Hz, 3H), 0.83-0.72 (m, 2H), 0.61-0.52 (m, 2H).

Example 174

(1S,3S)-3-({6-[1'-(1-{1-[5-(2,6-dioxopiperidin-3-yl) pyridin-2-yl]piperidine-4-carbonyl}-4-methylpiperidine-4-carbonyl)-2-oxo-1-[(1S,3S)-3-(piperidin-1-yl) cyclobutyl]-1,2-dihydrospiro-[indole-3,4'-piperidin]-6-yl]-3-(propan-2-yl)-3H-imidazo[4,5-c]pyridin-4-yl}amino)cyclobutane-1-carbonitrile

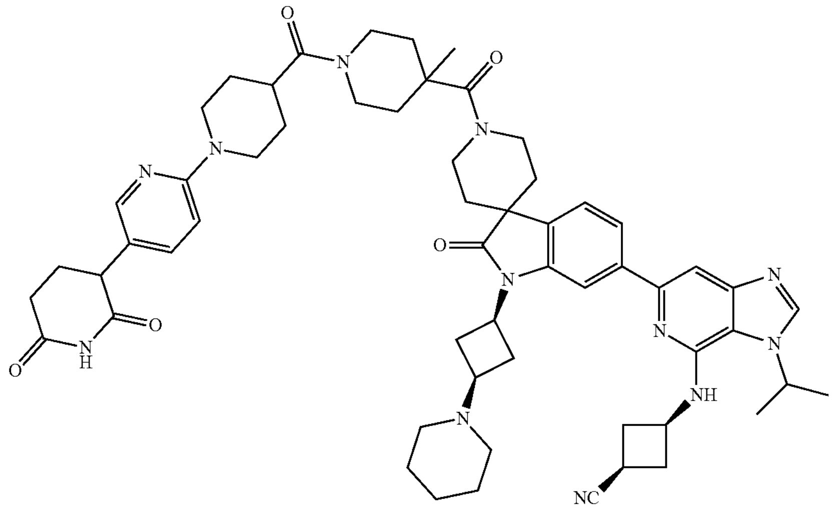 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(N[C@H]3C[C@@H](C#N)C3)c21]

To a solution of tert-butyl 1-(1-(4-(2,6-dioxopiperidin-3-yl)phenyl)piperidine-4-carbonyl)-4-methylpiperidine-4-carboxylate (Intermediate 55) (0.168 g, 0.315 mmol) and DIPEA (0.239 mL, 1.37 mmol) in DMF (2.74 mL, 0.1 M) was added BOP (0.151 g, 0.342 mmol), and the mixture was stirred for 90 min at room temperature. (1s,3s)-3-[(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]cyclo-butane-1-carbonitrile (Intermediate R) (0.171 g, 0.274 mmol) was added, the reaction mixture was stirred for 3 hours, then concentrated under vacuum. The residue was dissolved in dichloromethane and treated with saturated aqueous $NaHCO_3$ solution. The organic phase was separated and dried over $Na_2SO_4$ and concentrated in vacuo. The residue was purified by silica gel flash chromatography eluting with DCM/MeOH (0 to 15% of MeOH) to provide 0.09 g (30% yield) of the title compound as an off-white solid. LCMS: $C_{58}H_{72}N_{12}O_5$, desired mass=1016.6, found: m/z=1017.6 $[M+H]^+$. $^1H$ NMR (300 MHz, DMSO-$d_6$) δ 10.81 (s, 1H), 8.39 (s, 1H), 8.07 (s, 1H), 7.95 (d, J=2.2 Hz, 1H), 7.86 (d, J=8.3 Hz, 1H), 7.72 (s, 1H), 7.55 (s, 1H), 7.37 (s, 1H), 6.81 (d, J=8.9 Hz, 1H), 6.45 (s, 1H), 5.20-5.10 (m, 1H), 4.81-4.57 (m, 3H), 4.29 (d, J=12.5 Hz, 2H), 4.03-3.86 (m, 4H), 3.85-3.66 (m, 4H), 3.53-3.38 (m, 2H), 3.24-3.09 (m, 3H), 2.98-2.77 (m, 7H), 2.74-2.60 (m, 5H), 2.28 (d, J=8.2 Hz, 4H), 2.15 (s, 2H), 2.06-1.92 (m, 2H), 1.82-1.67 (m, 5H), 1.67-1.58 (m, 6H), 1.50 (m, 10H), 1.32 (s, 3H), 1.24 (s, 1H).

Example 175

1-{6-[1'-(1-{1-[5-(2,6-dioxopiperidin-3-yl)pyridin-2-yl]piperidine-4-carbonyl}-4-methylpipe-ridine-4-carbonyl)-2-oxo-1-[(1S,3S)-3-(piperidin-1-yl)cyclobutyl]-1,2-dihydrospiro[indole-3,4'-pi-peridin]-6-yl]-3-(propan-2-yl)-3H-imidazo[4,5-c]pyridin-4-yl}azetidine-3-carbonitrile

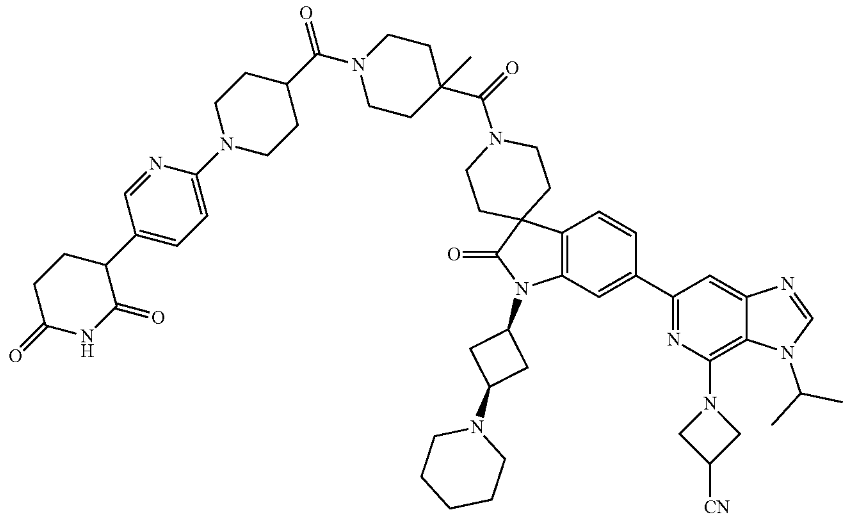 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(N3CC(C#N)C3)c21]

To a solution of tert-butyl 1-(1-(4-(2,6-dioxopiperidin-3-yl)phenyl)piperidine-4-carbonyl)-4-methylpiperidine-4-carboxylate (Intermediate 55) (0.18 g, 0.34 mmol) and DIPEA (0.26 mL, 1.49 mmol) in anhydrous DMF (3 mL) was added BOP (0.15 g, 0.34 mmol) and the mixture was stirred for 90 min at room temperature. 1-(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl) azetidine-3-carbonitrile bis trifluoroacetic acid salt (Intermediate S) (0.3 g, 0.3 mmol) was added and stirring was continued for 2 hours. The reaction mixture was concentrated to dryness under vacuum, then the residue was dissolved in DCM and treated with saturated aqueous $NaHCO_3$ solution. The organic phase was dried over $Na_2SO_4$ and concentrated in vacuo. The residue was purified with silica gel flash chromatography eluting with DCM/MeOH (8.5:1.5, v/v) to provide 0.085 g (28% yield) of the title compound. LCMS: $C_{57}H_{70}N_{12}O_5$, desired mass=1002.6, found: m/z=1003.6 $[M+H]^+$. $^1H$ NMR (300 MHz, DMSO-$d_6$) δ 10.82 (s, 1H), 8.61 (s, 1H), 8.16 (s, 1H), 8.12-7.87 (m, 3H), 7.61 (d, J=8.0 Hz, 1H), 7.39 (d, J=11.2 Hz, 1H), 6.82 (d, J=8.9 Hz, 1H), 4.96-4.85 (m, 1H), 4.67 (m, 1H), 4.50 (t, J=8.9 Hz, 2H), 4.44-4.36 (m, 2H), 4.30 (m, 2H), 3.92 (m, 4H), 3.74 (m, 3H), 3.52-3.39 (m, 1H), 3.27-3.13 (m, 1H), 2.91 (m, 3H), 2.77-2.62 (m, 3H), 2.55 (m, 13H), 2.30 (m, 4H), 2.18 (m, 2H), 2.09 (m, 1H), 1.99 (m, 1H), 1.75 (m, 4H), 1.48 (m, 16H), 1.33 (s, 3H).

Example 176

(1R,3R)-3-({6-[1'-(1-{1-[5-(2,6-dioxopiperidin-3-yl)pyridin-2-yl]piperidine-4-carbonyl}-4-methylpiperidine-4-carbonyl)-2-oxo-1-[(1S,3S)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)cyclobutane-1-carbonitrile

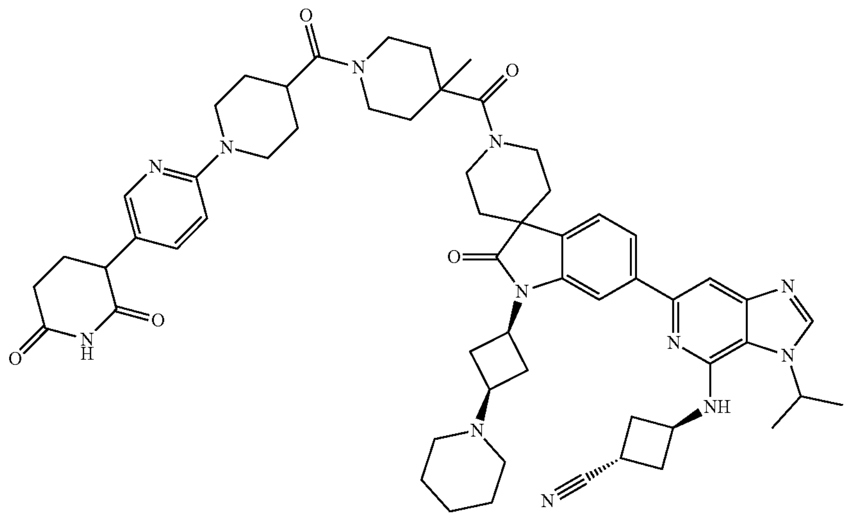 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(N[C@H]3C[C@H](C#N)C3)c21]

To a solution of tert-butyl 1-(1-(4-(2,6-dioxopiperidin-3-yl)phenyl)piperidine-4-carbonyl)-4-methylpiperidine-4-carboxylate (Intermediate 55) (0.12 g, 0.22 mmol) in anhydrous DMF (2.0 mL) was added DIPEA (0.2 mL, 1.03 mmol) and BOP (0.09 g, 0.205 mmol). The reaction mixture was stirred for 1 h at room temperature, then, (1r,3r)-3-[(6-{2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]cyclobutane-1-carbonitrile tris (trifluoroacetic acid) (Intermediate T) (0.16 g, 0.17 mmol) and stirring was continued for 1.5 h. The reaction mixture was concentrated to dryness under vacuum, and the residue was dissolved in DCM, quenched with saturated aqueous $NaHCO_3$ solution and stirred vigorously for 20 min. The organic phase was separated, dried over $Na_2SO_4$, and concentrated to dryness. The crude residue was purified by flash chromatography eluting with DCM/MeOH (0 to 15% of MeOH) to provide 0.1 g of impure product, which was further purified by reverse-phase flash chromatography eluting with Water/ACN (0 to 60% of ACN) to provide 37.6 mg (22% yield) of the title compound as an off-white solid. LCMS: C58H72N12O5 desired mass: 1016.6, found m/z=1017.6 [M+H]+, 1H NMR (300 MHz, DMSO-$d_6$) δ 10.82 (s, 1H), 8.40 (s, 1H), 8.08 (s, 1H), 7.96 (d, J=2.4 Hz, 1H), 7.87 (d, J=7.9 Hz, 1H), 7.73 (s, 1H), 7.57 (d, J=7.9 Hz, 1H), 7.39 (d, J=8.8 Hz, 1H), 6.82 (d, J=8.8 Hz, 1H), 6.48 (d, J=7.7 Hz, 1H), 5.27-5.05 (m, 1H), 4.81-4.58 (m, 3H), 4.30 (d, J=12.3 Hz, 2H), 3.95 (s, 4H), 3.74 (dd, J=12.0, 5.0 Hz, 3H), 3.22-3.10 (m, 3H), 2.98-2.79 (m, 6H), 2.67 (d, J=16.9 Hz, 4H), 2.29 (s, 5H), 2.10 (d, J=47.1 Hz, 5H), 1.81-1.41 (m, 20H), 1.33 (s, 3H).

Example 177

3-(6-{4-[4-methyl-4-({6-[4-({2-oxaspiro[3.3]heptan-6-yl}amino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

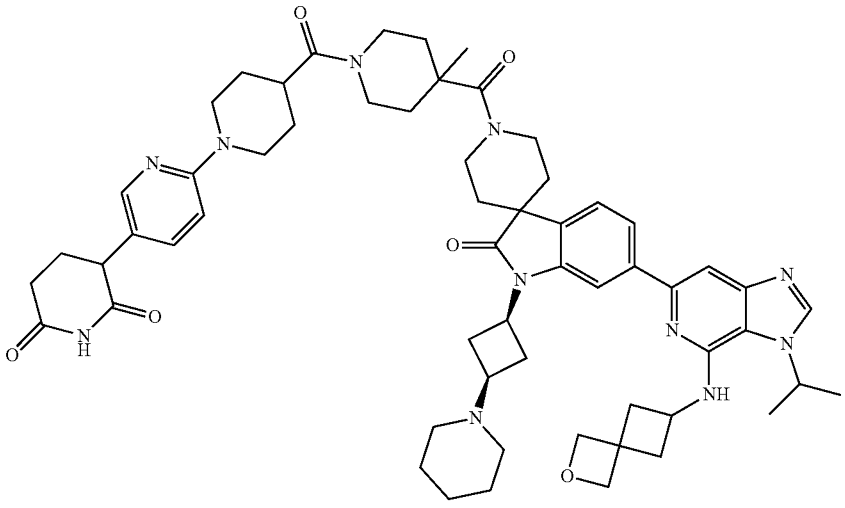 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(NC3CC4(COC4)C3)c21]

To a solution of tert-butyl 1-(1-(4-(2,6-dioxopiperidin-3-yl)phenyl)piperidine-4-carbonyl)-4-methylpiperidine-4-carboxylate (Intermediate 55) (93 mg, 0.17 mmol) in anhydrous DMF (1.3 mL) was added BOP (68 mg, 0.15 mmol) and DIPEA (0.12 mL, 0.67 mmol) at 25° C. The reaction mixture was stirred for 1 h at 25° C., then 6-[4-({2-oxaspiro[3.3]heptan-6-yl}amino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate U) (83 mg, 0.13 mmol) was added. The reaction mixture was stirred for an additional 1 h at 25° C. and then concentrated under reduced pressure. The residue was dissolved in DCM (20 mL) and stirred vigorously with a saturated aqueous solution of $NaHCO_3$ (30 mL) for 30 min, then the layers were separated and the organic layer was washed with saturated aqueous $NaHCO_3$ solution (3×20 mL) and brine (20 mL). The organic layer was dried over $Na_2SO_4$ and evaporated to dryness. The residue was purified by silica gel chromatography using a mobile phase of DCM and MeOH (gradient 100:0 to 80:20%) and preparative HPLC to provide 32.2 mg (23% yield) of the title compound as a white solid. LCMS: $C_{59}H_{75}N_{11}O_6$, desired mass=1034.3, found: m/z=1034.6 $[M+H]^+$. $^1H$ NMR (300 MHz, DMSO-$d_6$) δ 10.81 (s, 1H), 8.35 (s, 1H), 8.07 (s, 1H), 7.95 (d, J=2.5 Hz, 1H), 7.85 (d, J=7.8 Hz, 1H), 7.69 (s, 1H), 7.59 (d, J=7.8 Hz, 1H), 7.38 (dd, J=8.8, 2.6 Hz, 1H), 6.81 (d, J=8.9 Hz, 1H), 6.21 (d, J=6.0 Hz, 1H), 5.17-5.07 (m, 1H), 4.70 (s, 2H), 4.57 (s, 3H), 4.50-4.39 (m, 1H), 4.34-4.23 (m, 2H), 4.00-3.88 (m, 3H), 3.88-3.67 (m, 4H), 3.52-3.38 (m, 2H), 3.26-3.13 (m, 2H), 2.97-2.82 (m, 3H), 2.78 (s, 3H), 2.69-2.54 (m, 5H), 2.36-2.23 (m, 6H), 2.22-2.11 (m, 2H), 2.06-1.92 (m, 2H), 1.83-1.57 (m, 10H), 1.53 (d, J=6.5 Hz, 6H), 1.49-1.37 (m, 4H), 1.32 (s, 3H), 1.27-1.21 (m, 1H).

Example 178

3-(6-{4-[4-({6-[4-cyclopropoxy-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

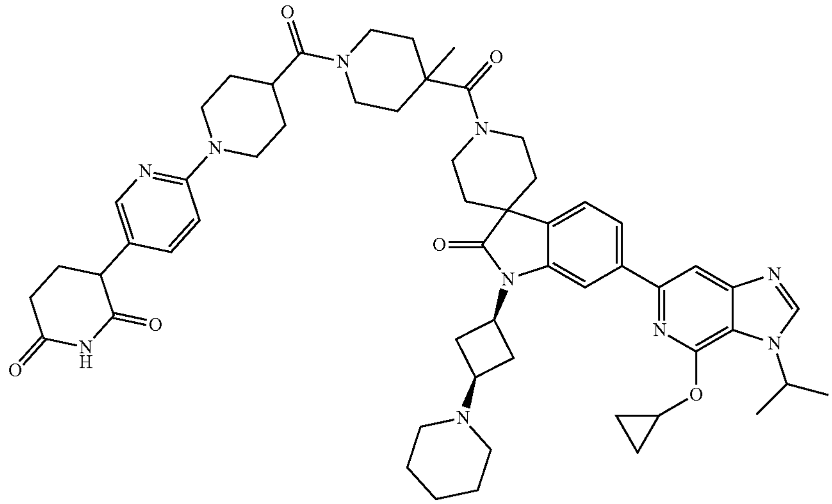 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(OC3CC3)c21]

To a solution of (benzotriazol-1-yloxy)tris(dimethylamino)phosphonium hexafluorophosphate (61 mg, 0.14 mmol) and tert-butyl 1-(1-(4-(2,6-dioxopiperidin-3-yl)phenyl)piperidine-4-carbonyl)-4-methylpiperidine-4-carboxylate (Intermediate 55) (67 mg, 0.15 mmol) in anhydrous DMF (1.3 mL, 0.1 M) was added DIPEA (110 μl, 0.63 mmol) at 0° C., under Argon. The reaction mixture was stirred at room temperature for 0.5 h then 6-[4-cyclopropoxy-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidin]-2-one (Intermediate V) (70 mg, 0.13 mmol) was added. The reaction mixture was stirred at room temperature for 1 h, then concentrated to dryness under vacuum. The residue was re-dissolved in $CH_2Cl_2$, washed with aqueous saturated $NaHCO_3$ solution. The organic layer was separated, dried over anhydrous $MgSO_4$, and concentrated under vacuum. The residue was purified by reverse phase flash chromatography eluting with $CH_3CN$/water (gradient from 5% to 90% of $CH_3CN$) to provide 8.4 mg (7%) of the title compound as a tan solid. LCMS: $C_{56}H_{70}N_{10}O_6$, desired mass=979.2, found: m/z=979.5 $[M+H]^+$. $^1H$ NMR (500 MHz, DMSO-$d_6$) δ 10.81 (s, 1H), 8.47 (s, 1H), 8.18 (s, 1H), 8.03 (s, 1H), 7.98-7.89 (m, 2H), 7.60 (d, J=7.8 Hz, 1H), 7.38 (d, J=8.7 Hz, 1H), 6.81 (d, J=8.7 Hz, 1H), 5.01-4.83 (m, 1H), 4.74-4.49 (m, 2H), 4.37-4.20 (m, 2H), 4.10-3.87 (m, 4H), 3.83-3.61 (m, 4H), 2.98-2.78 (m, 3H), 2.70-2.59 (m, 3H), 2.36-2.12 (m, 7H), 2.08-1.89 (m, 2H), 1.79-1.66 (m, 4H), 1.66-1.38 (m, 19H), 1.37-1.20 (m, 6H), 0.97-0.76 (m, 4H).

Example 179

3-{2-[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl]-2H-indazol-5-yl}piperidine-2,6-dione

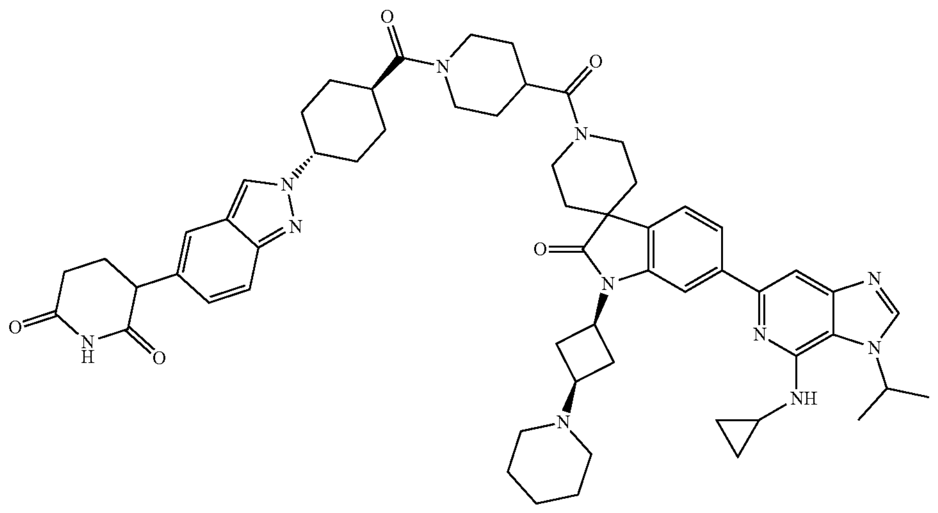 [SMILES: CC(C)n1cnc2cc(-c3ccc4c(c3)N([C@H]3C[C@@H](N5CCCCC5)C3)C(=O)C43CCN(C(=O)C4CCN(C(=O)[C@H]5CC[C@H](n6cc7cc(C8CCC(=O)NC8=O)ccc7n6)CC5)CC4)CC3)nc(NC3CC3)c21]

BOP (0.121 g, 0.273 mmol) was added to a solution of 1-[(1r,4r)-4-[5-(2,6-dioxopiperidin-3-yl)-2H-indazol-2-yl]cyclohexanecarbonyl]piperidine-4-carboxylic acid hydrochloride (Intermediate 88) (0.137 g, 0.273 mmol) and DIPEA (0.198 mL, 1.139 mmol) in anhydrous DMF (4.55 mL), and the reaction mixture was stirred 60 for min. 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.13 g, 0.228 mmol) was added and stirring was continued for 2 h. The reaction mixture was concentrated under vacuum and the residue was dissolved in DCM and treated with a saturated aqueous solution of $NaHCO_3$. The organic layer was separated, dried over $Na_2SO_4$, filtered, and evaporated to dryness. The residue was purified by reverse phase flash chromatography (eluting with DCM-MeOH, 0-15%) to provide 55 mg (23% yield) of the title compound. LCMS: $C_{58}H_{71}N_{11}O_5$, desired mass=1002.3, found: m/z=1002.6 $[M+H]^+$. $^1H$ NMR (300 MHz, DMSO-$d_6$) δ 10.83 (s, 1H), 8.34 (s, 2H), 8.17 (s, 1H), 7.92 (d, J=8.3 Hz, 1H), 7.71 (s, 1H), 7.61-7.47 (m, 3H), 7.09 (d, J=9.0 Hz, 1H), 6.47 (s, 1H), 5.06 (m, 1H), 4.69-4.38 (m, 4H), 4.05 (m, 2H), 3.90 (m, 4H), 3.77 (m, 1H), 3.02 (s, 2H), 2.86-2.52 (m, 10H), 2.27 (m, 4H), 2.21-1.97 (m, 5H), 1.98-1.55 (m, 14H), 1.55-1.33 (m, 9H), 0.79 (m, 2H), 0.58 (m, 2H).

Example 180

(3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperazine-1-carbonyl]piperidin-1-yl}pyridin-3-yl)piperidine-2,6-dione

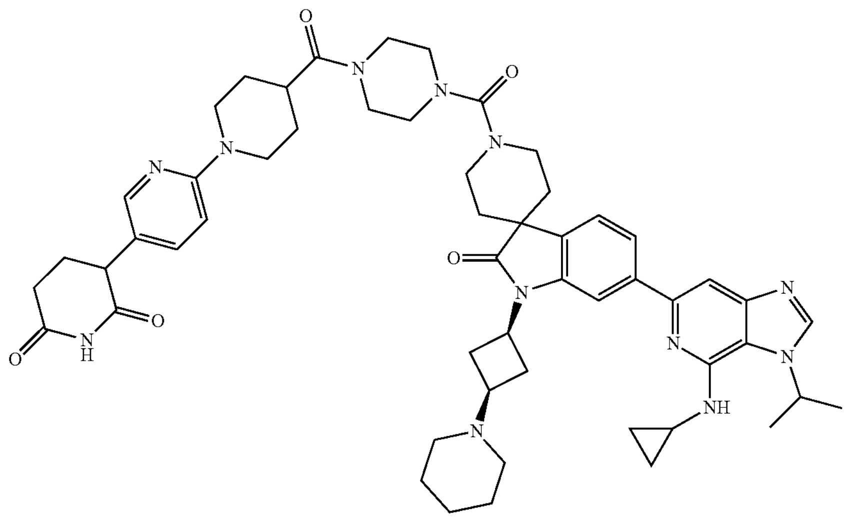 [SMILES: CC(C)n1cnc2cc(-c3ccc4c(c3)N([C@H]3C[C@@H](N5CCCCC5)C3)C(=O)C43CCN(C(=O)N4CCN(C(=O)C5CCN(c6ccc(C7CCC(=O)NC7=O)cn6)CC5)CC4)CC3)nc(NC3CC3)c21]

To a solution of 1-[5-(2,6-dioxopiperidin-3-yl)pyridin-2-yl]piperidine-4-carboxylic acid (Intermediate 55, step 2) (0.114 g, 0.29 mmol) and DIPEA (0.194 mL, 1.115 mmol) in DMF (2.23 mL, 0.1 M) was added BOP (0.128 g, 0.29 mmol) and the resulting mixture was stirred for 90 min. 6-[4-(cyclopropylamino)-3-(propan-2-yl)-3H-imidazo[4,5-c]pyridin-6-yl]-1'-(piperazine-1-carbonyl)-1-[(1s,3s)-3-(piperidin-1-yl)cyclobutyl]-1,2-dihydrospiro[indole-3,4'-piperidin]-2-one (Intermediate Y) (0.15 g, 0.22 mmol) was added and stirring was continued for an additional 2 h. The reaction mixture was evaporated to dryness under vacuum and the crude residue was dissolved in DCM was treated with saturated aqueous $NaHCO_3$ solution. The organic layer was separated, dried over $Na_2SO_4$, filtered, and concentrated in vacuo. The residue was purified by silica gel flash chromatography eluting with DCM/MeOH (0 to 15% of MeOH) to provide 34 mg (16% yield) of the title compound as an off-white solid. LCMS: $C_{54}H_{68}N_{12}O_5$, desired mass=964.5, found: m/z=965.6 $[M+H]^+$. $^1H$ NMR (300 MHz, DMSO-$d_6$) δ 10.82 (s, 1H), 8.35 (s, 1H), 8.18 (s, 1H), 7.99-7.89 (m, 2H), 7.72 (s, 1H), 7.56 (d, J=7.9 Hz, 1H), 7.39 (d, J=8.7 Hz, 1H), 6.83 (d, J=4.4 Hz, 1H), 6.48 (s, 1H), 5.07 (m, 1H), 4.64 (m, 1H), 4.30 (m, 2H), 3.78-3.44 (br m, 10H), 3.29-3.11 (m, 5H), 3.07-2.79 (m, 6H), 2.62 (m, 4H), 2.39-2.11 (m, 5H), 2.00 (m, 1H), 1.72 (m, 6H), 1.59 (m, 5H), 1.47 (m, 8H), 0.80 (m, 2H), 0.60 (m, 2H).

Example 181

3-(6-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-4-carbonyl]piperazin-1-yl}pyridin-3-yl)piperidine-2,6-dione

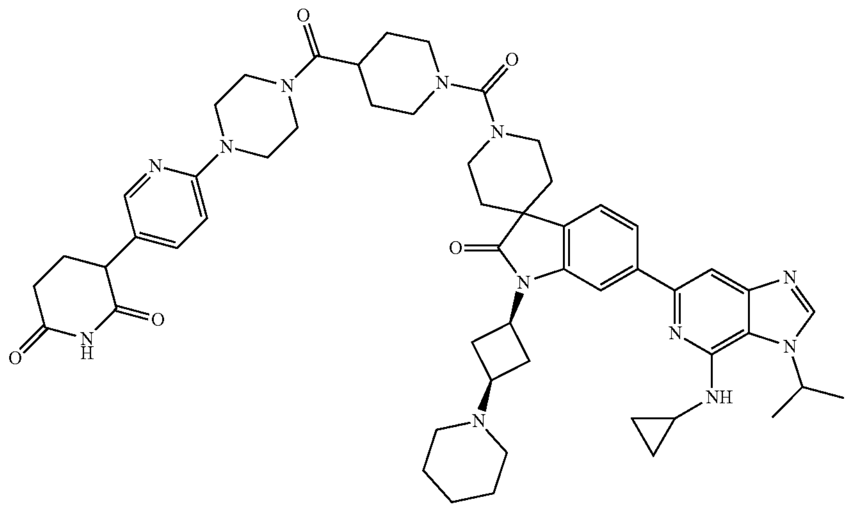 [SMILES: CC(C)n1cnc2cc(-c3ccc4c(c3)N([C@H]3C[C@@H](N5CCCCC5)C3)C(=O)C43CCN(C(=O)N4CCC(C(=O)N5CCN(c6ccc(C7CCC(=O)NC7=O)cn6)CC5)CC4)CC3)nc(NC3CC3)c21]

To a solution of 1-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carboxylic acid, bis (trifluoroacetic acid) (Intermediate AA) (0.3 g, 0.29 mmol) and DIPEA (0.21 mL, 1.44 mmol) in anhydrous DMF (5.8 mL) BOP (0.127 g, 0.29 mmol) was added and resulting mixture was stirred for 60 min. Intermediate 89 (0.145 g, 0.26 mmol) was added and stirring was continued for 4 hours. The mixture was evaporated to dryness under vacuum, and the residue was dissolved in dichloromethane and washed with saturated aqueous $NaHCO_3$ solution. The organic layer was separated and evaporated. The residue was purified with preparative HPLC to provide 67 mg (23%) of the title compound as an off white solid. LCMS: $C_{54}H_{68}N_{12}O_5$, desired mass=965.2, found: m/z=965.6 $[M+H]^+$. $^1H$ NMR (300 MHz, DMSO-$d_6$) δ 10.83 (s, 1H), 8.35 (s, 1H), 8.18 (s, 1H), 8.01 (s, 1H), 7.92 (d, J=7.8 Hz, 1H), 7.72 (s, 1H), 7.57 (d, J=7.8 Hz, 1H), 7.45 (d, J=10.9 Hz, 1H), 6.86 (d, J=8.9 Hz, 1H), 6.47 (s, 1H), 5.12-5.01 (m, 1H), 4.68-4.55 (m, 1H), 3.77 (m, 1H), 3.63 (m, 8H), 3.47 (m, 3H), 3.01 (m, 1H), 2.87 (m, 3H), 2.65 (br m, 16H), 2.36-2.16 (m, 4H), 2.05-1.93 (m, 1H), 1.80-1.68 (m, 3H), 1.66 (m, 6H), 1.51 (m, 6H), 0.80 (m, 2H), 0.63-0.55 (m, 2H).

Example 182

3-(6-{4-[6-({6-[4-(cyclopropylamino)-3-(propan-2-yl)-3H-imidazo[4,5-c]pyridin-6-yl]-2-oxo-1-[(1S, 3S)-3-(piperidin-1-yl)cyclobutyl]-1,2-dihydrospiro [indole-3,4'-piperidine]-1'-yl}carbonyl)-2-azaspiro [3.3]heptane-2-carbonyl]piperidin-1-yl}pyridin-3-yl) piperidine-2,6-dione

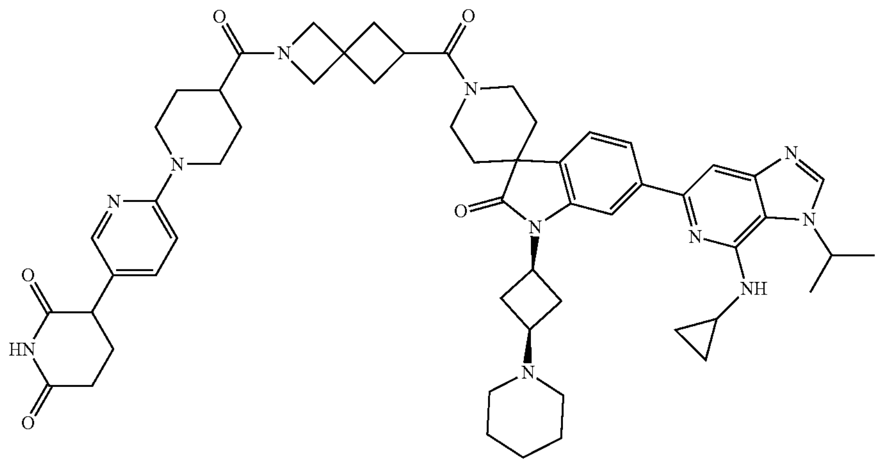 [SMILES: CC(C)n1cnc2cc(-c3ccc4c(c3)N([C@H]3C[C@@H](N5CCCCC5)C3)C(=O)C43CCN(C(=O)C4CC5(C4)CN(C(=O)C4CCN(c6ccc(C7CCC(=O)NC7=O)cn6)CC4)C5)CC3)nc(NC3CC3)c21]

BOP (0.123 g, 0.27 mmol) was added to a mixture of 1-[5-(2,6-dioxopiperidin-3-yl)pyridin-2-yl]piperidine-4-carboxylic acid (Intermediate 11, step 2) (0.117 g, 0.297 mmol) in anhydrous DMF (2.3 mL, 0.1 M) and added DIPEA (0.2 mL, 1.14 mmol). The reaction mixture was stirred for 1 h at rt, then 1'-{2-azaspiro[3.3]heptane-6-carbonyl}-6-[4-(cyclopropylamino)-3-(propan-2-yl)-3H-imidazo[4,5-c]pyridin-6-yl]-1-[(1s,3s)-3-(piperidin-1-yl)cyclobutyl]-1,2-dihydrospiro[indole-3,4'-piperidine]-2-one (Intermediate BB) (0.18 g, 0.229 mmol) was added and stirring was continued for an additional 1.5 h. The volatiles were evaporated in vacuo, the residue was dissolved in DCM, to which saturated aqueous $NaHCO_3$ solution was added, followed by vigorous stirring for 30 min. The organic phase was separated, dried over $Na_2SO_4$, and concentrated to dryness. The residue was purified by preparative HPLC to provide 59.7 mg (64% yield) of the title compound as a white solid. LCMS: $C_{56}H_{69}N_{11}O_5$ desired mass=976.24, found m/z=976.64 $[M]^+$. 1H NMR (300 MHz, DMSO-$d_6$) δ 10.81 (s, 1H), 8.34 (s, 1H), 8.16 (s, 1H), 8.07-7.84 (m, 2H), 7.71 (s, 1H), 7.54 (d, J=7.8 Hz, 1H), 7.37 (dd, J=8.9, 2.4 Hz, 1H), 6.81 (d, J=8.9 Hz, 1H), 6.47 (s, 1H), 5.13-4.97 (m, 1H), 4.59 (q, J=8.6, 8.1 Hz, 1H), 4.32-4.19 (m, 3H), 4.13 (s, 1H), 3.97-3.84 (m, 2H), 3.82-3.53 (m, 5H), 3.00 (s, 1H), 2.83 (t, J=12.4 Hz, 2H), 2.71-2.54 (m, 4H), 2.45-2.35 (m, 4H), 2.32-2.15 (m, 5H), 2.00 (s, 1H), 1.79-1.35 (m, 19H), 0.79 (d, J=6.2 Hz, 2H), 0.58 (d, J=3.5 Hz, 2H).

Example 183

3-(6-{4-[4-(2-{6-[4-(cyclopropylamino)-3-(propan-2-yl)-3H-imidazo[4,5-c]pyridin-6-yl]-2-oxo-1-[3-(piperidin-1-yl)cyclobutyl]-1,2-dihydrospiro[indole-3,4'-piperidine]-1'-yl}Acetyl)piperazine-1-carbonyl]piperidin-1-yl}pyridin-3-yl)piperidine-2,6-dione

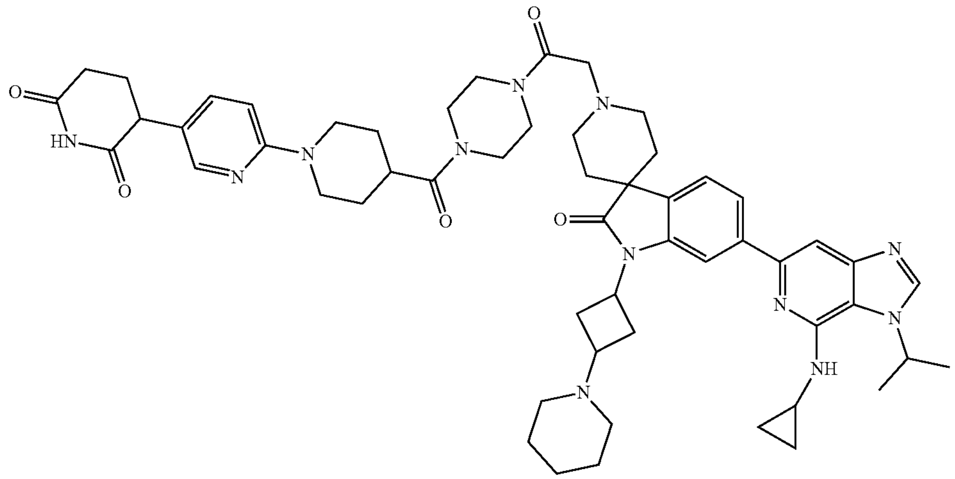 [SMILES: CC(C)n1cnc2cc(-c3ccc4c(c3)N(C3CC(N5CCCCC5)C3)C(=O)C43CCN(CC(=O)N4CCN(C(=O)C5CCN(c6ccc(C7CCC(=O)NC7=O)cn6)CC5)CC4)CC3)nc(NC3CC3)c21]

BOP (0.035 g, 0.078 mmol) was added to a mixture of 2-{6-[4-(cyclopropylamino)-3-(propan-2-yl)-3H-imidazo[4,5-c]pyridin-6-yl]-2-oxo-1-[3-(piperidin-1-yl)cyclobutyl]-1,2-dihydrospiro[indole-3,4'-piperidine]-1'-yl}acetic acid (Intermediate W) (0.06 g, 0.078 mmol) in anhydrous DMF (0.7 mL) and DIPEA (0.06 mL, 0.326 mmol). The reaction mixture was stirred for 1 h at rt, then Intermediate 90 (0.04 g, 0.065 mmol) was stirring was continued for an additional 1.5 h. The volatiles were evaporated in vacuo, the residue was dissolved in DCM, saturated aqueous $NaHCO_3$ solution was added and the mixture stirred vigorously for 30 min. The organic phase was separated, dried over $Na_2SO_4$, and concentrated to dryness. The residue was purified by preparative HPLC to provide 8.8 mg (14% yield) of the title compound as a white solid. LCMS: $C_{55}H_{70}N_{12}O_5$, desired mass=979.24, found m/z=979.57 $[M]^+$. 1H NMR (300 MHz, DMSO-$d_6$) δ 10.81 (s, 1H), 8.34 (s, 1H), 8.16 (s, 1H), 8.03-7.88 (m, 2H), 7.71 (s, 1H), 7.65 (d, J=8.1 Hz, 1H), 7.39 (d, J=6.9 Hz, 1H), 6.82 (d, J=9.0 Hz, 1H), 6.46 (s, 1H), 5.11-5.01 (m, 1H), 4.64-4.56 (m, 1H), 4.30 (d, J=12.6 Hz, 2H), 3.77-3.36 (m, 12H), 3.05-2.75 (m, 8H), 2.67-2.57 (m, 4H), 2.30-2.15 (m, 5H), 2.05-1.92 (m, 2H), 1.91-1.78 (m, 2H), 1.74-1.35 (m, 15H), 0.85-0.75 (m, 2H), 0.58 (s, 2H).

Example 184

3-(6-{6-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidine]-1'-yl}carbonyl)-4-methylpiperidine-1-carbonyl]-2,6-diazaspiro[3.3]heptan-2-yl}pyridin-3-yl)piperidine-2,6-dione

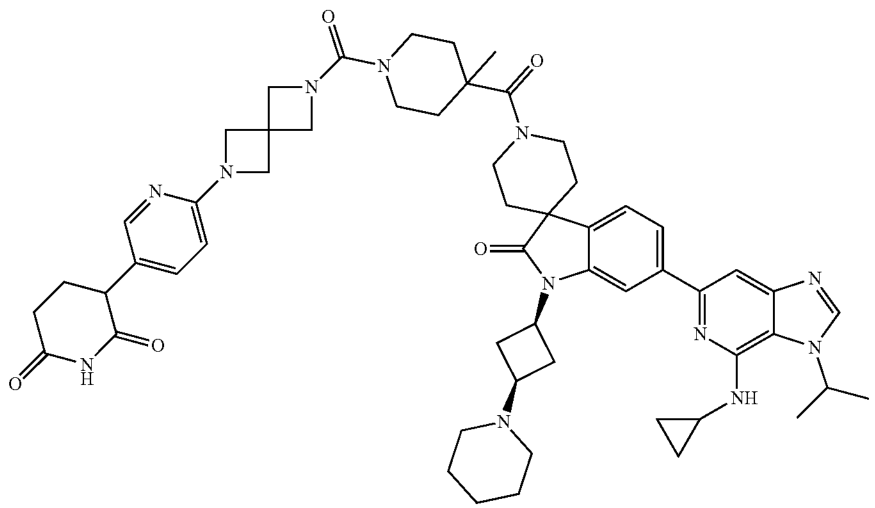 [SMILES: CC(C)n1cnc2cc(-c3ccc4c(c3)N([C@H]3C[C@@H](N5CCCCC5)C3)C(=O)C43CCN(C(=O)C4(C)CCN(C(=O)N5CC6(C5)CN(c5ccc(C7CCC(=O)NC7=O)cn5)C6)CC4)CC3)nc(NC3CC3)c21]

BOP (0.099 g, 0.23 mmol) was added to a mixture of Intermediate 91 (0.11 g, 0.23 mmol) and DIPEA (0.162 mL, 1.12 mmol) in anhydrous DMF (4.49 mL). The reaction mixture was stirred for 1 h, then, 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (0.138 g, 0.23 mmol) was added and stirring was continued for an additional 1.5 h. The volatiles were evaporated under vacuum, and the residue was dissolved in DCM and treated with saturated aqueous $NaHCO_3$ solution. The organic phase was separated, dried over $Na_2SO_4$, filtered and evaporated to dryness. The residue was purified by reverse phase flash column chromatography eluting with ACN/water and then by flash column chromatography eluting with DCM/MeOH (0-15% of MeOH) to obtain 18 mg, 0.016 (7% yield) of the title compound. LCMS: $C_{56}H_{70}N_{12}O_5$, desired mass=991.25, found m/z=991.60 $[M+H]^+$. 1H NMR (300 MHz, DMSO-$d_6$) δ 10.82 (s, 1H), 8.35 (s, 1H), 8.14 (s, 1H), 7.92 (m, 2H), 7.71 (s, 1H), 7.57 (d, J=7.9 Hz, 1H), 7.40 (d, J=10.9 Hz, 1H), 6.48 (s, 1H), 6.39 (d, J=8.6 Hz, 1H), 5.13-5.03 (m, 1H), 4.59 (s, 1H), 4.09 (m, 4H), 4.05 (m, 4H), 3.99-3.86 (m, 4H), 3.75 (m, 1H), 3.44 (m, 4H), 3.18 (m, 1H), 3.12 (m, 2H), 3.04-2.96 (m, 1H), 2.78-2.59 (m, 6H), 2.31 (m, 3H), 2.19 (m, 1H), 1.98 (m, 3H), 1.74 (m, 4H), 1.62 (m, 4H), 1.51 (m, 9H), 1.30 (m, 3H), 1.26 (s, 3H), 0.79 (m, 2H), 0.60 (m, 2H).

Example 185

(3RS)-3-(4-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}-2-fluorophenyl)piperidine-2,6-dione

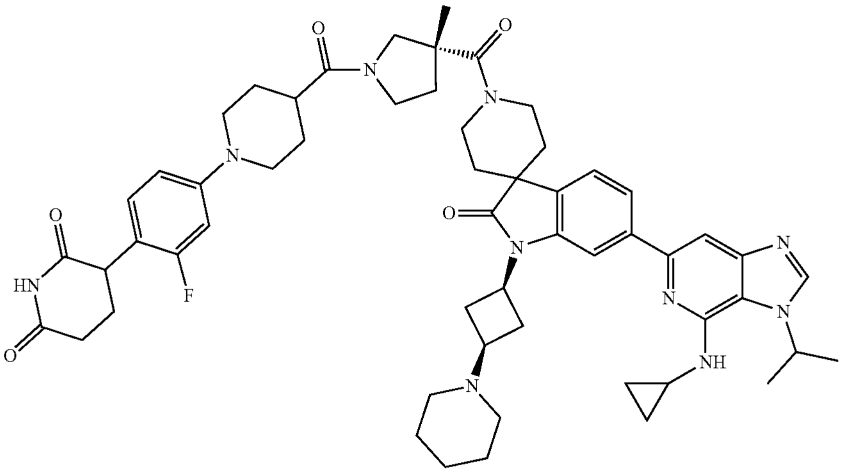 [SMILES: CC(C)n1cnc2cc(-c3ccc4c(c3)N([C@H]3C[C@@H](N5CCCCC5)C3)C(=O)C43CCN(C(=O)[C@]4(C)CCN(C(=O)C5CCN(c6ccc(C7CCC(=O)NC7=O)c(F)c6)CC5)C4)CC3)nc(NC3CC3)c21]

To a mixture of 6-[4-(cyclopropylamino)-3-isopropylimidazo[4,5-c]pyridin-6-yl]-1'-[(3r)-3-methylpyrrolidine-3-carbonyl]-1-[(1s,3s)-3-(piperidin-1-yl)cyclobutyl]spiro[indole-3,4'-piperidin]-2-one (Intermediate CC) (33.2 mg, 0.0496 mmol) and 1-(4-(2,6-dioxopiperidin-3-yl)-3-fluorophenyl)piperidine-4-carboxylic acid (Intermediate 98) (16.59 mg, 0.0496 mmol) in $CH_3CN$ (0.1 mL) and DMF (0.1 mL) was added 1-methylimidazole (NMI) (0.02 mL, 0.02 g) at 0° C. under a nitrogen atmosphere. To the above mixture was added N,N,N',N'-tetramethylchloroformamidinium hexafluorophosphate (TCFH) ([chloro(dimethylamino)methylidene]dimethylazanium, hexafluoro-lambda5-phosphanuide (0.02 mL, 0.02 g, 0.2256 mmol) at 0° C. The resulting mixture was stirred for 1 h under a nitrogen atmosphere, then warmed to room temperature. The mixture was purified by C18 reverse phase chromatography eluting with $CH_3CN/H_2O$ to afford the title compound as an off-white solid (13.1 mg, 27%). LCMS: [$C_{56}H_{69}FN_{10}O_5$], desired mass=980.5, observed mass=981.6 $[M+H]^+$.

Example 186

(3RS)-3-(6-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}pyridin-3-yl)piperidine-2,6-dione

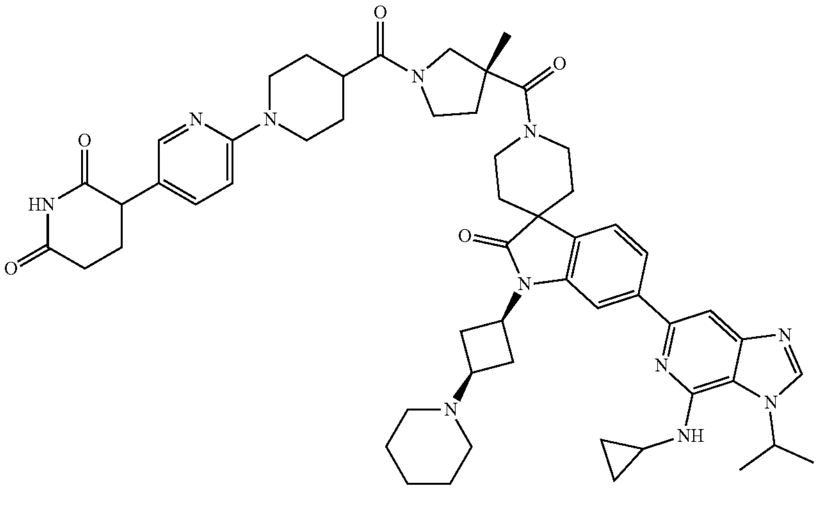 [SMILES: CC(C)n1cnc2cc(-c3ccc4c(c3)N([C@H]3C[C@@H](N5CCCCC5)C3)C(=O)C43CCN(C(=O)[C@]4(C)CCN(C(=O)C5CCN(c6ccc(C7CCC(=O)NC7=O)cn6)CC5)C4)CC3)nc(NC3CC3)c21]

To a mixture of 6-[4-(cyclopropylamino)-3-isopropylimidazo[4,5-c]pyridin-6-yl]-1'-[(3R)-3-methylpyrrolidine-3-carbonyl]-1-[(1s,3s)-3-(piperidin-1-yl)cyclobutyl]spiro[indole-3,4'-piperidin]-2-one (30.00 mg, 0.041 mmol) (Intermediate CC) and 1-[5-(2,6-dioxopiperidin-3-yl)pyridin-2-yl]piperidine-4-carboxylic acid hydrochloride (step 2 of Intermediate 55) (13 mg, 0.041 mmol) in $CH_3CN$ (0.1 mL) and DMF (0.1 mL) were added 1-methylimidazole (NMI) (16 uL, 0.21 mmol) at 0° C. under a nitrogen atmosphere. To the above mixture was added N,N,N',N'-tetramethylchloroformamidinium hexafluorophosphate (TCFH) ([chloro(dimethylamino)methylidene]dimethylazanium, hexafluoro-lambda5-phosphanuide (11 mg, 0.041 mmol)) at 0° C. The resulting mixture was stirred for 1 h under a nitrogen atmosphere and then warmed to room temperature. The mixture was purified by preparative HPLC provide the title compound as an off-white solid (13.3 mg, 0.0134 mmol, 32% yield) as a TFA salt. LCMS: [$C_{58}H_{69}N_{11}O_5$], desired mass=963.5, found: m/z=964.5 $[M+H]^+$, 1H NMR (500 MHz, MeOD) δ 8.95 (s, 1H), 8.00 (dt, J=9.6, 1.9 Hz, 1H), 7.87 (d, J=2.3 Hz, 1H), 7.68 (d, J=9.1 Hz, 2H), 7.62 (d, J=3.8 Hz, 1H), 7.56 (d, J=1.4 Hz, 1H), 7.45 (dd, J=9.6, 3.8 Hz, 1H), 5.14 (p, J=6.5 Hz, 2H), 4.49 (p, J=8.5 Hz, 1H), 4.28 (dd, J=34.4, 12.1 Hz, 3H), 4.11 (s, 3H), 3.96 (dt, J=10.7, 5.3 Hz, 2H), 3.84-3.74 (m, 1H), 3.68-3.51 (m, 4H), 3.44 (q, J=12.9 Hz, 3H), 3.22 (d, J=10.1 Hz, 2H), 3.11-2.96 (m, 3H), 2.90 (t, J=12.3 Hz, 2H), 2.83-2.71 (m, 2H), 2.65 (dt, J=12.4, 8.1 Hz, 1H), 2.46 (dd, J=13.3, 6.5 Hz, 1H), 2.33 (ddd, J=17.9, 15.1, 8.6 Hz, 2H), 2.17 (ddd, J=31.9, 12.4, 6.8 Hz, 3H), 2.09-1.85 (m, 8H), 1.81 (t, J=14.4 Hz, 2H), 1.69 (d, J=6.5 Hz, 4H), 1.52 (d, J=12.

Example 187

(3RS)-3-(6-{4-[4-(1-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-1-oxopropan-2-yl)piperidine-1-carbonyl]piperidin-1-yl}pyridin-3-yl)piperidine-2,6-dione

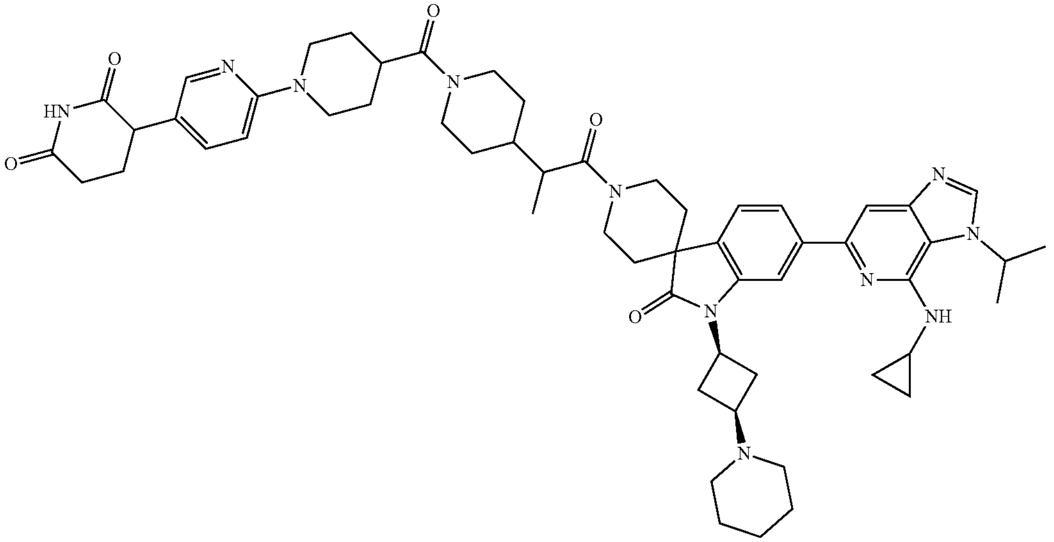 [SMILES: CC(C(=O)N1CCC2(CC1)C(=O)N([C@H]1C[C@@H](N3CCCCC3)C1)c1cc(-c3cc4ncn(C(C)C)c4c(NC4CC4)n3)ccc12)C1CCN(C(=O)C2CCN(c3ccc(C4CCC(=O)NC4=O)cn3)CC2)CC1]

A mixture of 1-[5-(2,6-dioxopiperidin-3-yl)pyridin-2-yl] piperidine-4-carboxylic acid hydrochloride (step 2 of Intermediate 55) (13 mg, 0.043 mmol), EDCI (10.3 mg, 0.054 mmol), HOBT (8.3 mg, 0.054 mmol) and DIPEA (0.03 mL, 0.18 mmol) was dissolved in DMF (0.1 mL) and stirred at room temperature for 15 minutes. 6-[4-(cyclopropylamino)-3-isopropylimidazo[4,5-c]pyridin-6-yl]-1'-[2-(piperidin-4-yl)propanoyl]-1-[(1s,3s)-3-(piperidin-1-yl)cyclobutyl]spiro [indole-3,4'-piperidin]-2-one (Intermediate DD (25 mg, 0.036 mmol) was added and the reaction mixture was stirred at room temperature overnight. The crude reaction mixture was purified by preparative HPLC to provide the title compound as an off-white solid (7.8 mg, 0.0078 mmol, 21% yield) as a TFA salt. LCMS: [$C_{57}H_{73}N_{11}O_5$], desired mass=991.6, found: m/z=992.4 $[M+H]^+$, 1H NMR (500 MHz, MeOD) δ 8.89 (s, 1H), 7.97 (d, J=9.4 Hz, 1H), 7.87 (s, 1H), 7.74-7.62 (m, 3H), 7.56 (s, 1H), 7.41 (d, J=9.2 Hz, 1H), 5.17-5.09 (m, 1H), 4.60 (s, 1H), 4.49 (d, J=8.9 Hz, 1H), 4.22 (t, J=13.1 Hz, 3H), 4.15 (s, 4H), 4.03 (s, 1H), 3.96 (d, J=11.0 Hz, 2H), 3.64 (d, J=8.2 Hz, 1H), 3.57 (s, 3H), 3.04 (d, J=26.6 Hz, 3H), 2.89 (d, J=13.4 Hz, 1H), 2.79 (d, J=16.3 Hz, 1H), 2.66 (d, J=13.4 Hz, 1H), 2.41-2.28 (m, 2H), 2.21 (s, 1H), 2.02 (s, 2H), 1.97 (s, 1H), 1.93 (s, 11H), 1.81 (s, 4H), 1.68 (d, J=6.4 Hz, 6H), 1.31 (s, 5H), 1.22 (s, 3H), 1.19 (d, J=6.5 Hz, 1H), 1.12 (s, 2H), 0.92 (s, 2H).

Example 188

(3RS)-3-(6-{4-[4-(1-{6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}-2-methyl-1-oxopropan-2-yl)piperazine-1-carbonyl]piperidin-1-yl}pyridin-3-yl)piperidine-2,6-dione

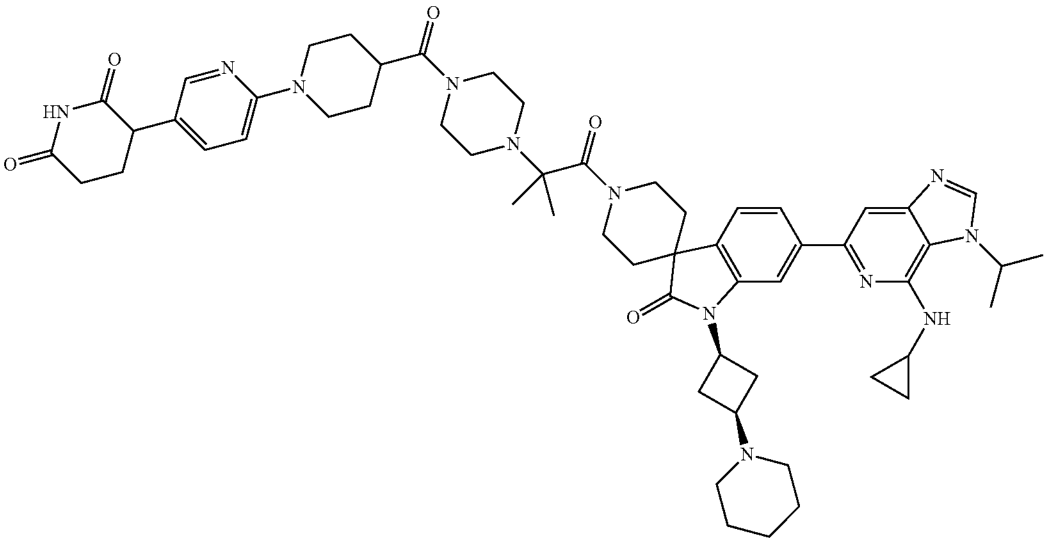 [SMILES: CC(C)n1cnc2cc(-c3ccc4c(c3)N([C@H]3C[C@@H](N5CCCCC5)C3)C(=O)C43CCN(C(=O)C(C)(C)N4CCN(C(=O)C5CCN(c6ccc(C7CCC(=O)NC7=O)cn6)CC5)CC4)CC3)nc(NC3CC3)c21]

A mixture of 1-[5-(2,6-dioxopiperidin-3-yl)pyridin-2-yl]piperidine-4-carboxylic acid hydrochloride (step 2 of Intermediate 55) (8.4 mg, 0.0265 mmol), EDCI (6.3 mg, 0.033 mmol) and HOBT (5.1 mg, 0.033 mmol) was dissolved in DMF (0.1 mL) and DIPEA (0.02 mL, 0.11 mmol) and stirred at room temperature for 15 minutes. 6-[4-(cyclopropylamino)-3-isopropylimidazo[4,5-c]pyridin-6-yl]-1'-[2-methyl-2-(piperazin-1-yl)propanoyl]-1-[(1s,3s)-3-(piperidin-1-yl)cyclobutyl]spiro[indole-3,4'-piperidin]-2-one (Intermediate FF (15 mg, 0.022 mmol) was added and the reaction mixture was stirred at room temperature overnight. The crude reaction mixture was purified by reverse phase UPLC to provide the title compound (TFA salt) as an off-white solid (10.3 mg, 44%). LCMS: [$C_{57}H_{74}N_{12}O_5$], desired mass=1006.5, observed mass=1007.4 $[M+H]^+$, Example 189

(3RS)-3-(6-{4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]piperidin-1-yl}-4-Methylpyridin-3-yl)piperidine-2,6-dione

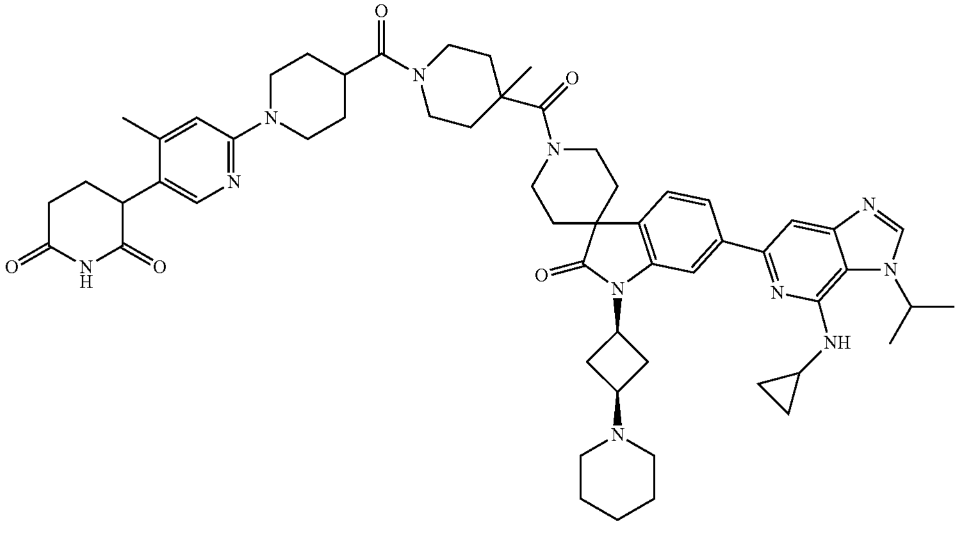 [SMILES: Cc1cc(N2CCC(C(=O)N3CCC(C)(C(=O)N4CCC5(CC4)C(=O)N([C@H]4C[C@@H](N6CCCCC6)C4)c4cc(-c6cc7ncn(C(C)C)c7c(NC7CC7)n6)ccc45)CC3)CC2)ncc1C1CCC(=O)NC1=O]

Step 1: tert-butyl 4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)-4-methylpiperidine-1-carboxylate 6-[4-(cyclopropylamino)-3-isopropylimidazo[4,5-c]pyridin-6-yl]-1-[(1s,3s)-3-(piperidin-1-yl)cyclobutyl]spiro[indole-3,4'-piperidin]-2-one (Intermediate B) (1.00 g, 1.8059 mmol), (1,2,3-benzotriazol-1-yloxy)tris(dimethylamino) phosphanium, hexafluoro-lambda5-phosphanuide (1.04 g, 2.3476 mmol), and 1-(tert-butoxycarbonyl)-4-methylpiperidine-4-carboxylic acid (0.44 g, 1.8059 mmol) were dissolved in dimethylformamide (10.00 mL) and N,N-diisopropylethylamine (1.26 mL, 7.2234 mmol) and stirred at room temperature for 6 hours. The crude reaction mixture was poured over brine and extracted with ethyl acetate (2×100 mL). The organic layer was dried over anhydrous sodium sulfate, filtered, evaporated onto silica gel, then purified by reverse phase flash column chromatography to afford the title compound (1.12 g, 79% yield).

Step 2: 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one Tert-butyl 4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)-4-methylpiperidine-1-carboxylate (1.12 g, 1.43 mmol) was dissolved in DCM (10.0 mL). 4M HCl in dioxane (5.0 mL) was added and the reaction mixture was stirred at room temperature overnight. The crude reaction mixture was evaporated onto silica gel and purified by reverse phase flash column chromatography to afford the title compound (0.925 g, 94% yield). LCMS: $C_{40}H_{54}N_8O_2$, desired mass=678.9, found: m/z=679.8 $[M+H]^+$.

Step 3: (3rs)-3-(6-{4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]piperidin-1-yl}-4-methylpyridin-3-yl)piperidine-2,6-dione A mixture of Intermediate 92 (16 mg, 0.049 mmol), EDCI (12 mg, 0.061 mmol) and HOBT (9.4 mg, 0.061 mmol) was dissolved in DMF (0.1 mL) and DIPEA (0.04 mL, 0.2 mmol) and stirred at room temperature for 15 minutes. 6-[4-(cyclopropylamino)-3-isopropylimidazo[4,5-c]pyridin-6-yl]-1'-(4-methylpiperidine-4-carbonyl)-1-[(1s,3s)-3-(piperidin-1-yl)cyclobutyl]spiro[indole-3,4'-piperidin]-2-one (30 mg, 0.041 mmol) was added and the reaction mixture was stirred at room temperature overnight. The crude reaction mixture was purified by reverse phase UPLC to provide the title compound (TFA salt) as an off-white solid (29.4 mg, 72%). LCMS: $[C_{57}H_{73}N_{11}O_5]$, desired mass=991.5, observed mass=992.6 $[M+H]^+$, H NMR (500 MHz, MeOD) δ 8.89 (s, 1H), 7.73 (s, 1H), 7.67 (dd, J=17.1, 9.7 Hz, 3H), 7.56 (s, 1H), 7.33 (s, 1H), 5.18-5.09 (m, 1H), 4.48 (q, J=8.5 Hz, 1H), 4.25-4.10 (m, 5H), 4.08 (s, 4H), 3.89 (d, J=14.2 Hz, 1H), 3.64 (d, J=8.8 Hz, 1H), 3.59 (t, J=13.5 Hz, 3H), 3.42 (d, J=12.9 Hz, 2H), 3.22 (d, J=10.7 Hz, 2H), 3.12-2.97 (m, 1H), 3.02 (s, 3H), 2.95-2.81 (m, 3H), 2.78 (d, J=17.0 Hz, 1H), 2.49 (s, 3H), 2.42-2.35 (m, 1H), 2.36 (s, 1H), 2.26 (d, J=13.7 Hz, 1H), 2.19 (d, J=13.5 Hz, 1H), 2.08-1.99 (m, 2H), 1.99-1.89 (m, 8H), 1.89 (t, J=13.2 Hz, 1H), 1.86-1.75 (m, 2H), 1.69 (d, J=6.5 Hz, 6H), 1.66-1.56 (m, 1H), 1.46 (s, 3H), 1.31 (s, 1H), 1.12 (d, J=6.5 Hz, 2H), 0.92 (s, 2H).

Example 190

(3RS)-3-(2-{[(1R,4R)-4-{4-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-4-methylpiperidine-1-carbonyl}cyclohexyl]methyl}-2H-indazol-5-yl)piperidine-2,6-dione

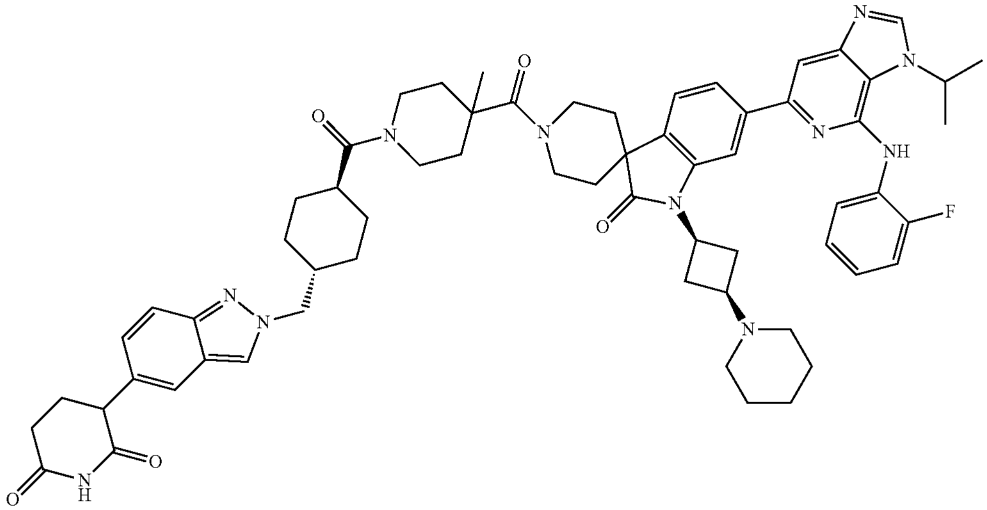 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Cn6cc7cc(C8CCC(=O)NC8=O)ccc7n6)CC5)CC4)CC3)nc(Nc3ccccc3F)c21]

A mixture of (1r,4r)-4-((5-(2,6-dioxopiperidin-3-yl)-2H-indazol-2-yl)methyl)cyclohexane-1-carboxylic acid (Intermediate 35) (15 mg, 0.041 mmol), EDCI (12 mg, 0.061 mmol) and HOBT (9.4 mg, 0.061 mmol) was dissolved in DMF (0.1 mL) and DIPEA (0.03 mL, 0.17 mmol) and stirred at room temperature for 15 minutes. 6-{4-[(2-fluorophenyl)amino]-3-isopropylimidazo[4,5-c]pyridin-6-yl}-1'-(4-methylpiperidine-4-carbonyl)-1-[(1s,3s)-3-(piperidin-1-yl)cyclobutyl]spiro[indole-3,4'-piperidin]-2-one (Example 102, step 1) (25 mg, 0.041 mmol) was added and the reaction mixture was stirred at room temperature overnight. The crude reaction mixture was purified by reverse phase UPLC to provide the title compound (TFA salt) as an off-white solid (17 mg, 37%). LCMS: [$C_{63}H_{74}FN_{11}O_5$], desired mass=1083.6, observed mass=1085.5 $[M+H]^+$, 1H NMR (500 MHz, MeOD) δ 8.97 (s, 1H), 8.21 (s, 1H), 7.84-7.74 (m, 2H), 7.70 (s, 1H), 7.61 (t, J=8.7 Hz, 3H), 7.54 (d, J=7.9 Hz, 1H), 7.33-7.19 (m, 3H), 5.35 (q, J=6.7 Hz, 1H), 4.33 (d, J=7.1 Hz, 3H), 4.24 (t, J=8.2 Hz, 1H), 4.07 (s, 5H), 4.04-3.92 (m, 3H), 3.79 (d, J=13.5 Hz, 1H), 3.6-3.5 (m, 5H), 3.08-2.81 (m, 5H), 2.79-2.6 (m, 3H), 2.40-2.19 (m, 3H), 2.15-1.75 (m, 11H), 1.7 (d, J=6.5 Hz, 6H), 1.65-1.52 (m, 5H), 1.41 (s, 3H), 1.31 (s, 2H), 1.22 (q, J=12.8 Hz, 2H).

Example 191

(3RS)-3-(4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]amino}phenyl)piperidine-2,6-dione

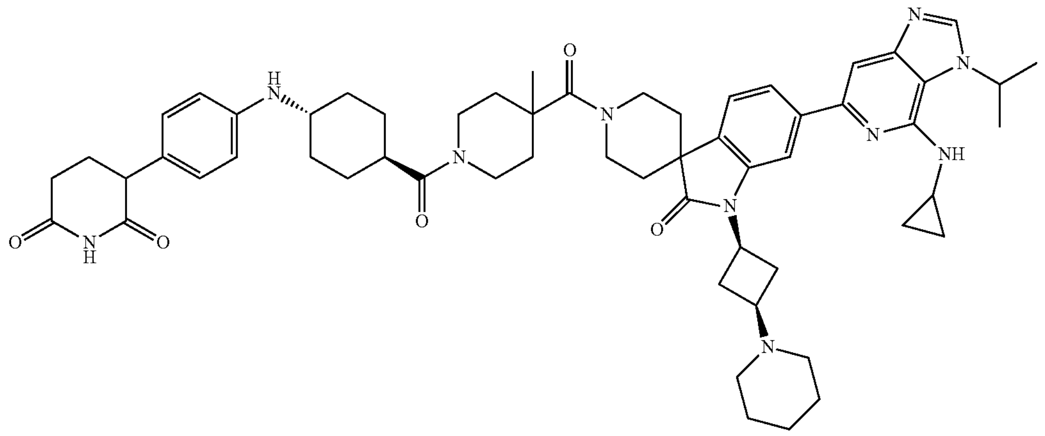 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Nc6ccc(C7CCC(=O)NC7=O)cc6)CC5)CC4)CC3)nc(NC3CC3)c21]

Using similar procedures to Example 189 and using (1r,4r)-4-((4-(2,6-dioxopiperidin-3-yl)phenyl)amino)cyclohexane-1-carboxylic acid (Intermediate 106) as the acid coupling partner in step 3, the title compound (TFA salt) was isolated as an off-white solid (8.8 mg, 48%). LCMS: [$C_{58}H_{74}N_{10}O_5$], desired mass=990.5, observed mass=991.5 $[M+H]^+$, Example 192

1-(6-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]amino}pyridin-3-yl)-1,3-diazinane-2,4-dione

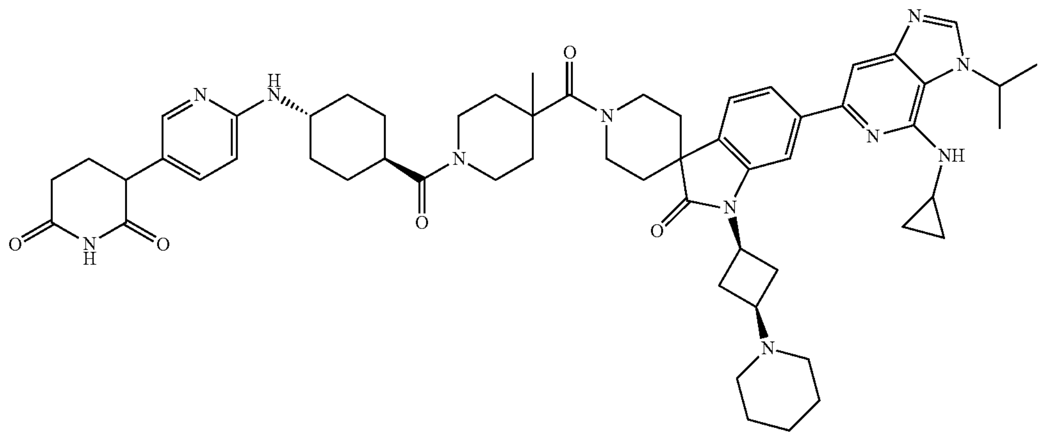 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Nc6ccc(C7CCC(=O)NC7=O)cn6)CC5)CC4)CC3)nc(NC3CC3)c21]

Using similar procedures to Example 189 and using (1r,4r)-4-((5-(2,4-dioxotetrahydropyrimidin-1(2H)-yl)pyridin-2-yl)amino)cyclohexane-1-carboxylic acid (Intermediate 107) as the acid coupling partner in step 3, the title compound was isolated as an off-white solid (16.1 mg, 0.0162 mmol, 44% yield) as a TFA salt. LCMS: $[C_{56}H_{72}N_{12}O_5]$, desired mass=992.5, found: m/z=993.5 $[M+H]^+$, 1H NMR (500 MHz, MeOD) δ 8.91 (s, 1H), 8.01-7.91 (m, 2H), 7.68 (s, 2H), 7.63 (s, 1H), 7.56 (s, 1H), 7.06 (d, J=9.6 Hz, 1H), 5.13 (p, J=6.4 Hz, 1H), 4.49 (p, J=8.4 Hz, 1H), 4.10 (dt, J=26.5, 14.2 Hz, 5H), 3.85 (t, J=6.7 Hz, 3H), 3.69-3.52 (m, 5H), 3.23 (t, J=10.6 Hz, 3H), 3.11-2.95 (m, 4H), 2.95-2.74 (m, 5H), 2.35 (d, J=14.0 Hz, 2H), 2.26 (d, J=14.3 Hz, 2H), 2.17 (d, J=12.5 Hz, 2H), 2.09-1.98 (m, 2H), 1.92 (d, J=10.0 Hz, 5H), 1.76 (dd, J=29.5, 13.5 Hz, 3H), 1.69 (d, J=6.6 Hz, 6H), 1.56 (dq, J=25.0, 12.6, 11.0 Hz, 5H), 1.45 (s, 3H), 1.31 (s, 1H), 1.13 (d, J=6.7 Hz, 2H), 0.93 (s, 2H).

Example 193

(3RS)-3-(4-{[(1R,4R)-4-[4-({6-[4-(cyclopropylamino)-3-(propan-2-yl)-3H-imidazo[4,5-c]pyridin-6-yl]-2-oxo-1-[(1S,3S)-3-{3-oxa-8-Azabicyclo[3.2.1]octan-8-yl}cyclobutyl]-1,2-dihydrospiro[indole-3,4'-piperidin]-1'-yl}carbonyl)-4-methylpiperidine-1-carbonyl]cyclohexyl]oxy}phenyl)piperidine-2,6-dione

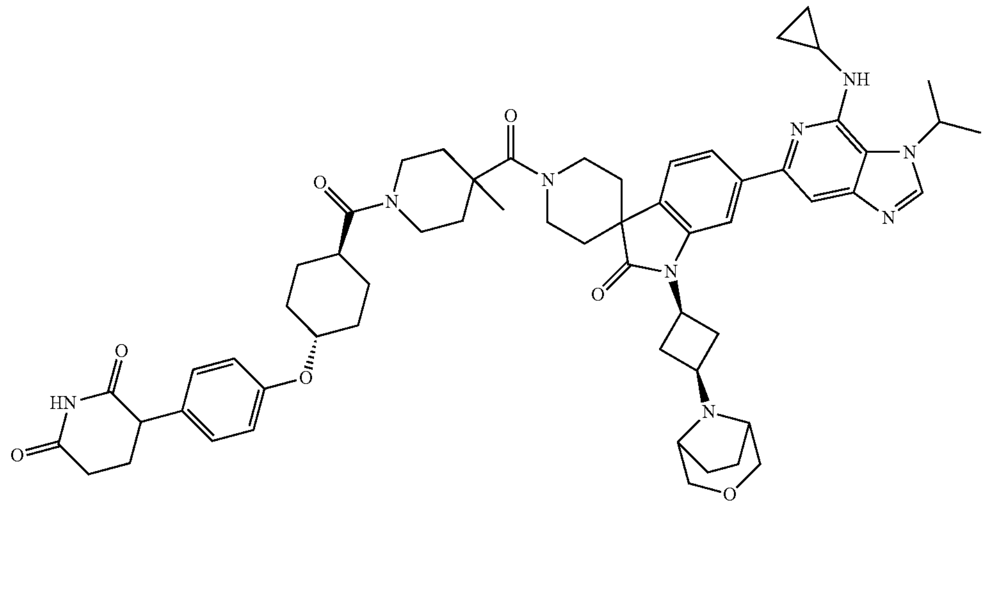 [SMILES: CC(C)n1cnc2cc(-c3ccc4c(c3)N([C@H]3C[C@@H](N5C6CCC5COC6)C3)C(=O)C43CCN(C(=O)C4(C)CCN(C(=O)[C@H]5CC[C@H](Oc6ccc(C7CCC(=O)NC7=O)cc6)CC5)CC4)CC3)nc(NC3CC3)c21]

Using procedures similar to Example 189 and using Intermediate KK as the amine coupling partner in step 1, and Intermediate 52 as the acid coupling partner in step 3, the title compound was isolated as an off-white solid (22.9 mg, 0.022 mmol, 49% yield) as a TFA salt. LCMS: [$C_{59}H_{73}N_9O_7$], desired mass=1019.5, found: m/z=1020.4 $[M+H]^+$, 1H NMR (500 MHz, MeOD) δ 8.36 (s, 1H), 8.32 (d, J=2.6 Hz, 1H), 7.95-7.88 (m, 2H), 7.60-7.52 (m, 2H), 7.17 (d, J=8.5 Hz, 2H), 6.96-6.91 (m, 2H), 5.04 (p, J=6.6 Hz, 1H), 4.46 (p, J=8.4 Hz, 1H), 4.29 (t, J=10.7 Hz, 1H), 4.2-4.05 (m, 7H), 4.04 (d, J=13.5 Hz, 1H), 3.89-3.79 (m, 5H), 3.72 (d, J=11.5 Hz, 2H), 3.63 (s, 2H), 3.57 (t, J=11.6 Hz, 1H), 3.07 (dq, J=7.1, 3.5 Hz, 1H), 2.98-2.91 (m, 2H), 2.81-2.59 (m, 2H), 2.55 (s, 1H), 2.35 (d, J=13.9 Hz, 1H), 2.23 (dd, J=12.0, 7.8 Hz, 5H), 2.17-2.09 (m, 2H), 2.05 (s, 1H), 1.98-1.85 (m, 7H), 1.69 (d, J=13.0 Hz, 1H), 1.63 (dd, J=6.7, 2.1 Hz, 7H), 1.52 (q, J=12.6 Hz, 2H), 1.44 (s, 3H), 0.90 (td, J=6.7, 4.7 Hz, 2H), 0.68 (p, J=4.8 Hz, 2H).

Example 194

(3RS)-3-(2-{[(1R,4R)-4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyrimidin-5-yl)piperidine-2,6-dione

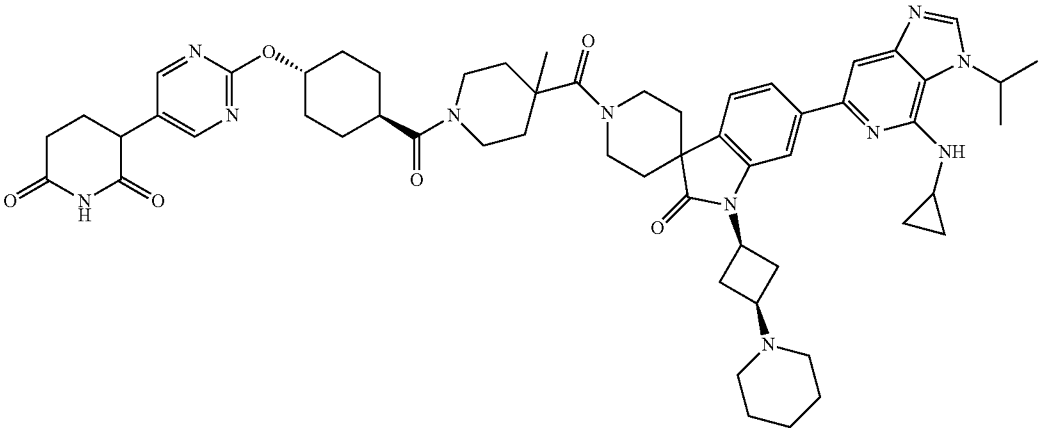 [SMILES: CC(C)n1cnc2cc(-c3ccc4c(c3)N([C@H]3C[C@@H](N5CCCCC5)C3)C(=O)C43CCN(C(=O)C4(C)CCN(C(=O)[C@H]5CC[C@H](Oc6ncc(C7CCC(=O)NC7=O)cn6)CC5)CC4)CC3)nc(NC3CC3)c21]

Using similar procedures to Example 189 and using Intermediate 93 as the acid coupling partner in step 3, the title compound was isolated as an off-white solid (27.1 mg, 0.026 mmol, 59% yield) as a TFA salt. LCMS: [$C_{56}H_{71}N_{11}O_6$], desired mass=993.5, found: m/z=994.4 $[M+H]^+$, 1H NMR (500 MHz, MeOD) δ 8.95 (s, 1H), 8.50 (s, 2H), 7.68 (d, J=6.2 Hz, 2H), 7.63 (s, 1H), 7.57 (s, 1H), 5.14 (p, J=6.5 Hz, 1H), 5.05 (dt, J=10.5, 5.9 Hz, 1H), 4.50 (p, J=8.4 Hz, 1H), 4.16 (d, J=13.9 Hz, 2H), 4.09 (s, 4H), 4.03 (s, 1H), 3.98-3.82 (m, 2H), 3.60 (dd, J=20.9, 10.3 Hz, 4H), 3.23 (d, J=9.8 Hz, 1H), 3.06 (dq, J=6.8, 3.5 Hz, 1H), 2.90 (t, J=12.0 Hz, 2H), 2.86-2.71 (m, 3H), 2.42-2.18 (m, 3H), 2.30 (s, 6H), 2.08-1.99 (m, 3H), 1.91 (d, J=16.5 Hz, 7H), 1.83-1.69 (m, 2H), 1.68 (d, J=6.6 Hz, 6H), 1.63-1.52 (m, 2H), 1.45 (s, 3H), 1.31 (s, 1H), 1.15 (d, J=6.2 Hz, 2H), 0.95 (s, 2H).

Example 195

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-{3-oxa-6-Azabicyclo[3.1.1]heptan-6-yl}cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione

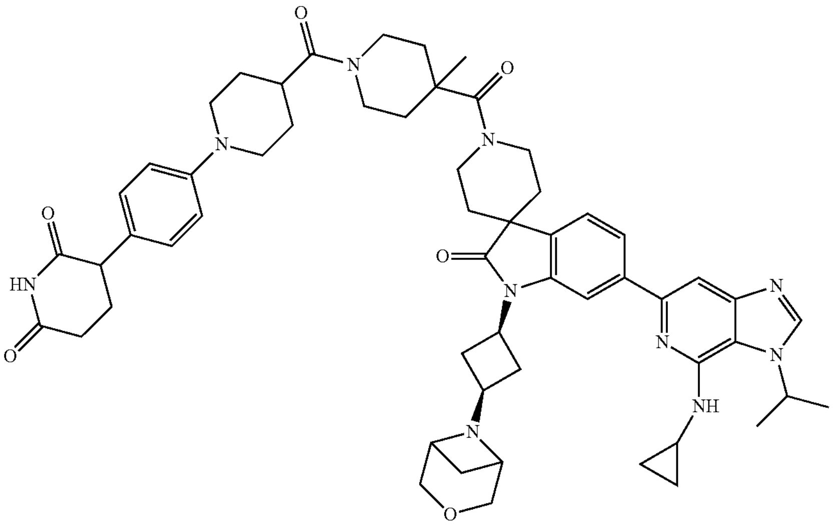 [SMILES: CC(C)n1cnc2cc(-c3ccc4c(c3)N([C@H]3C[C@@H](N5C6COCC5C6)C3)C(=O)C43CCN(C(=O)C4(C)CCN(C(=O)C5CCN(c6ccc(C7CCC(=O)NC7=O)cc6)CC5)CC4)CC3)nc(NC3CC3)c21]

Using similar procedures to Example 202, and using Intermediate NN as the amine coupling partner, and Intermediate 54 as the acid coupling partner, the title compound was isolated as an off-white solid (8 mg, 0.0078 mmol, 56% yield) as a free base. LCMS: [$C_{57}H_{70}N_{10}O_6$], desired mass=990.6, found: m/z=991.5 $[M+H]^+$, 1H NMR (500 MHz, MeOD) δ 8.31 (d, J=3.5 Hz, 1H), 8.14 (s, 1H), 7.99 (s, 1H), 7.84 (dd, J=17.8 Hz, 8.8 Hz, 1H), 7.59-7.51 (m, 2H), 7.14 (d, J=8.4 Hz, 2H), 7.01 (d, J=8.3 Hz, 2H), 5.07-5.01 (m, 1H), 4.59 (s, 1H), 4.24 (d, J=10.8 Hz, 1H), 4.2-3.97 (m, 6H), 4.04 (s, 1H), 3.86 (s, 1H), 3.78 (q, J=8.2 Hz, 4H), 3.64-3.54 (m, 3H), 3.13 (s, 1H), 3.18-3.08 (m, 1H), 3.02 (s, 1H), 2.85 (d, J=37.2 Hz, 4H), 2.74-2.59 (m, 3H), 2.36 (d, J=14.4 Hz, 1H), 2.27 (s, 2H), 2.21 (q, J=6.0 Hz, 1H), 1.92-1.84 (m, 10H), 1.64 (dd, J=6.7, 2.2 Hz, 6H), 1.45 (s, 3H), 1.39-1.29 (m, 3H), 0.95 (d, J=6.6 Hz, 1H), 0.92-0.87 (m, 2H), 0.70-0.65 (m, 2H).

Example 196

(3RS)-3-[4-(4-{4-methyl-4-[(6-{4-[(oxan-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]piperidine-2,6-dione

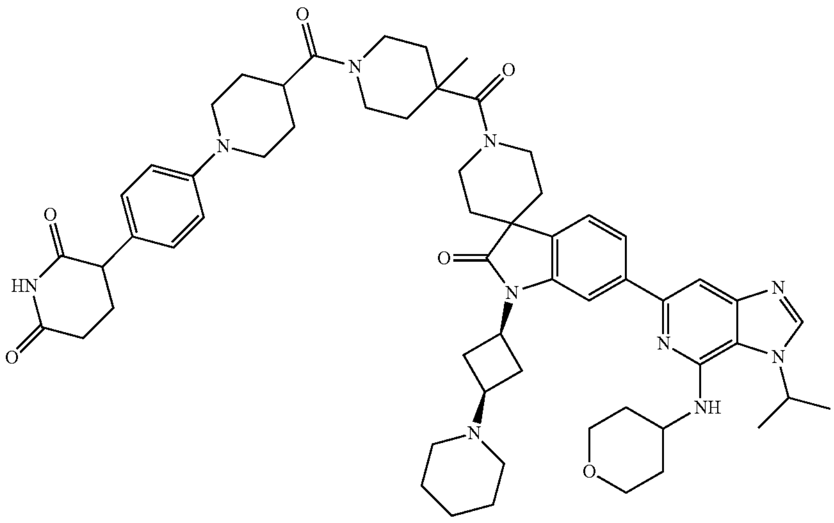 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cc6)CC5)CC4)CC3)nc(NC3CCOCC3)c21]

Using similar procedures to Example 189, and using Intermediate E as the amine coupling partner in step 1 and 1-(4-(2,6-dioxopiperidin-3-yl)phenyl)piperidine-4-carboxylic acid as the acid coupling partner in step 3, the title compound was isolated as an off-white solid (8 mg, 0.0078 mmol, 56% yield) as a TFA salt. LCMS: [$C_{59}H_{76}N_{10}O_6$], desired mass=1020.6, found: m/z=1021.5 $[M+H]^+$.

Example 197

(3RS)-3-(4-{4-[4-({6-[4-(cyclopropylamino)-3-(propan-2-yl)-3H-imidazo[4,5-c]pyridin-6-yl]-2-oxo-1-{[(1S,3S)-3-{8-oxa-3-azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione

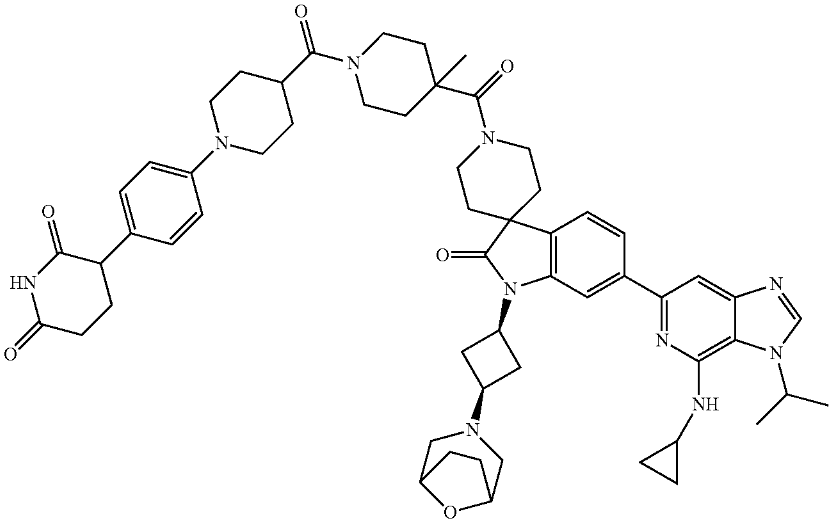 [SMILES: CC(C)n1cnc2cc(-c3ccc4c(c3)N([C@H]3C[C@@H](N5CC6CCC(C5)O6)C3)C(=O)C43CCN(C(=O)C4(C)CCN(C(=O)C5CCN(c6ccc(C7CCC(=O)NC7=O)cc6)CC5)CC4)CC3)nc(NC3CC3)c21]

Using similar procedures to Example 202, and using Intermediate QQ as the amine coupling partner, and Intermediate 54 as the acid coupling partner, the title compound was isolated as an off-white solid (20 mg, 0.018 mmol, 27% yield) as a formate. LCMS: [$C_{58}H_{72}N_{10}O_6$], desired mass=1004.5, found: m/z=1005.4 $[M+H]^+$. $^1H$ NMR (500 MHz, DMSO) δ 10.78 (s, 1H), 8.36 (s, 1H), 7.87 (d, J=10.6 Hz, 2H), 7.62-7.55 (m, 2H), 7.05 (d, J=8.2 Hz, 2H), 6.91 (d, J=8.3 Hz, 2H), 6.47 (s, 1H), 5.07 (p, J=6.7 Hz, 1H), 4.53 (s, 1H), 4.43 (s, 1H), 4.25 (s, 2H), 3.95 (s, 5H), 3.81 (s, 1H), 3.73 (dt, J=15.2, 7.7 Hz, 4H), 3.08-2.95 (m, 2H), 2.85-2.68 (m, 4H), 2.60 (q, J=8.3 Hz, 4H), 2.19-2.11 (m, 2H), 2.11-1.99 (m, 3H), 1.89 (d, J=6.8 Hz, 2H), 1.76 (s, 5H), 1.70 (s, 7H), 1.50 (d, J=6.4 Hz, 6H), 1.44 (s, 2H), 1.33 (s, 3H), 1.27 (t, J=6.9 Hz, 1H), 0.79 (d, J=6.4 Hz, 2H), 0.59 (s, 2H).

Example 198

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-[(3S)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione

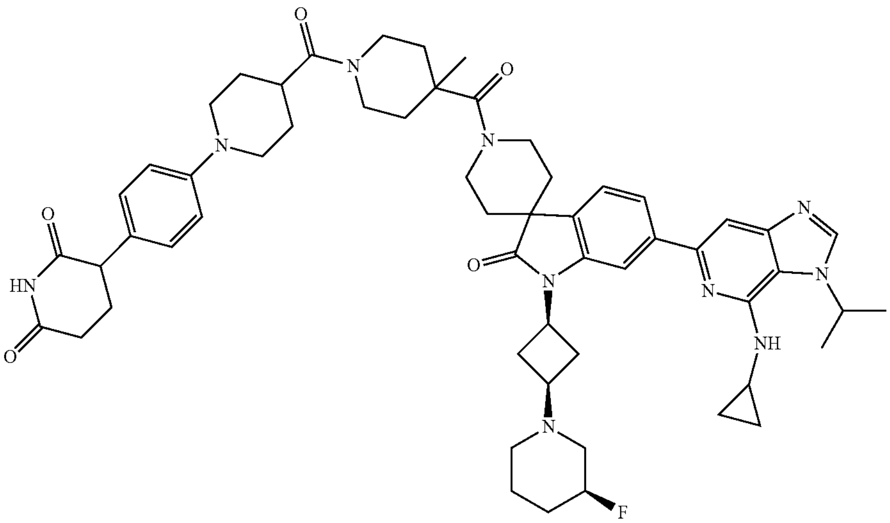 [SMILES: CC(C)n1cnc2cc(-c3ccc4c(c3)N([C@H]3C[C@@H](N5CCC[C@H](F)C5)C3)C(=O)C43CCN(C(=O)C4(C)CCN(C(=O)C5CCN(c6ccc(C7CCC(=O)NC7=O)cc6)CC5)CC4)CC3)nc(NC3CC3)c21]

Using similar procedures to Example 202, and using Intermediate 00 as the amine coupling partner, and Intermediate 54 as the acid coupling partner, the title compound was isolated as an off-white solid (25 mg, 0.024 mmol, 28% yield) as a free base. LCMS: [$C_{57}H_{71}FN_{10}O_5$], desired mass=994.5, found: m/z=996.2 $[M+H]^+$, 1H NMR (500 MHz, MeOD) δ 8.30 (s, 1H), 7.97 (d, J=1.5 Hz, 1H), 7.86 (dd, J=7.8, 1.5 Hz, 1H), 7.57-7.51 (m, 2H), 7.14 (d, J=8.7 Hz, 2H), 7.01 (d, J=8.5 Hz, 2H), 5.04 (p, J=6.5 Hz, 1H), 4.72 (s, 1H), 4.60 (s, 7H), 4.41-4.35 (m, 1H), 4.11 (s, 4H), 4.04 (s, 1H), 3.86 (s, 1H), 3.83-3.73 (m, 3H), 3.58 (t, J=11.6 Hz, 2H), 3.22-3.13 (m, 2H), 3.07 (dt, J=6.8, 3.3 Hz, 2H), 2.94-2.56 (m, 9H), 2.56-2.15 (m, 8H), 1.93-1.84 (m, 9H), 1.63 (d, J=6.6 Hz, 6H), 1.44 (s, 3H), 1.38 (d, J=6.5 Hz, 1H), 1.31 (s, 1H), 1.11 (t, J=7.2 Hz, 1H), 0.90 (td, J=7.1, 5.2 Hz, 2H), 0.68 (dt, J=6.5, 4.4 Hz, 2H)

Example 199

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-[(3R)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione

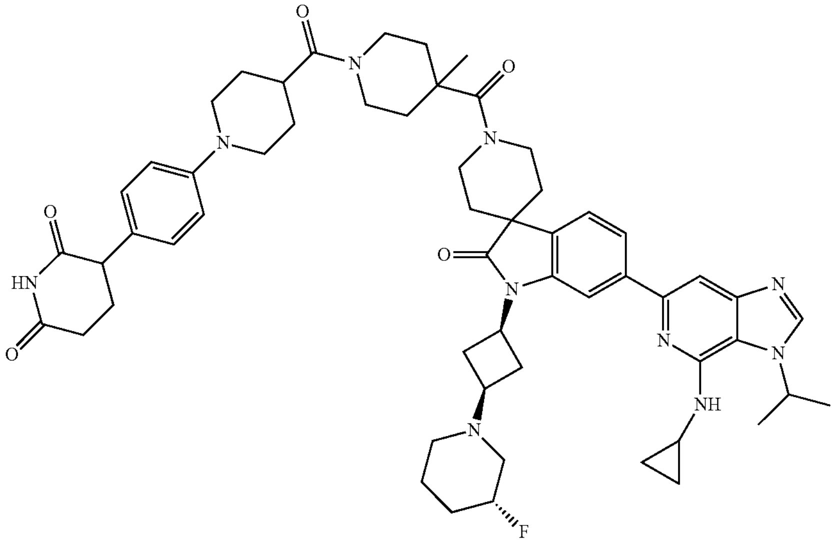 [SMILES: CC(C)n1cnc2cc(-c3ccc4c(c3)N([C@H]3C[C@@H](N5CCC[C@@H](F)C5)C3)C(=O)C43CCN(C(=O)C4(C)CCN(C(=O)C5CCN(c6ccc(C7CCC(=O)NC7=O)cc6)CC5)CC4)CC3)nc(NC3CC3)c21]

Using similar procedures to Example 202, and using Intermediate PP as the amine coupling partner, and Intermediate 54 as the acid coupling partner, the title compound was isolated as an off-white solid (31 mg, 0.030 mmol, 35% yield) as a free base. LCMS: [$C_{57}H_{71}FN_{10}O_5$], desired mass=994.5, found: m/z=996.2 $[M+H]^+$, 1H NMR (500 MHz, MeOD) δ 8.30 (s, 1H), 7.98 (d, J=1.4 Hz, 1H), 7.86 (dd, J=7.8, 1.4 Hz, 1H), 7.53 (t, J=3.9 Hz, 2H), 7.17-7.11 (m, 2H), 7.01 (d, J=8.4 Hz, 2H), 5.04 (p, J=6.6 Hz, 1H), 4.72 (s, 1H), 4.62 (s, 1H), 4.38 (t, J=8.4 Hz, 1H), 4.11 (s, 5H), 4.05 (d, J=14.0 Hz, 1H), 3.87 (d, J=13.6 Hz, 1H), 3.79 (dd, J=15.0, 6.7 Hz, 2H), 3.75 (s, 1H), 3.62-3.54 (m, 1H), 3.07 (tt, J=6.9, 3.7 Hz, 1H), 2.89-2.66 (m, 7H), 2.68-2.57 (m, 1H), 2.49 (s, 1H), 2.43 (s, 1H), 2.35 (d, J=15.8 Hz, 1H), 2.31-2.17 (m, 3H), 1.89 (dd, J=23.1, 10.0 Hz, 10H), 1.63 (d, J=6.5 Hz, 6H), 1.44 (s, 3H), 1.30 (d, J=6.4 Hz, 3H), 0.90 (td, J=6.9, 4.8 Hz, 2H), 0.71-0.64 (m, 2H).

Example 200

2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-N-(1-{1-[5-(2,6-dioxopiperidin-3-yl)pyridin-2-yl]piperidine-4-carbonyl}piperidin-4-yl)-N-methylacetamide

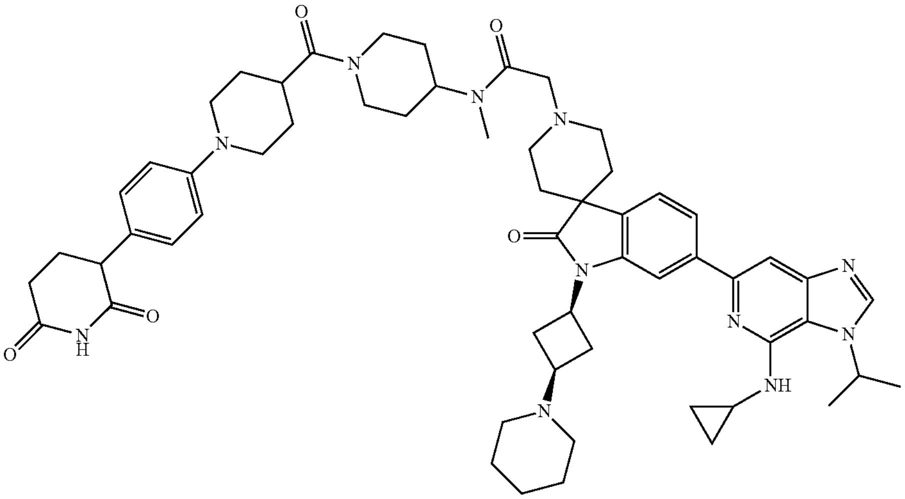 [SMILES: CC(C)n1cnc2cc(-c3ccc4c(c3)N([C@H]3C[C@@H](N5CCCCC5)C3)C(=O)C43CCN(CC(=O)N(C)C4CCN(C(=O)C5CCN(c6ccc(C7CCC(=O)NC7=O)cc6)CC5)CC4)CC3)nc(NC3CC3)c21]

To a solution of 1-[5-(2,6-dioxopiperidin-3-yl)pyridin-2-yl]piperidine-4-carboxylic acid (Intermediate 55, step 2) (0.032 g, 0.056 mmol) in anhydrous DMF (0.5 mL) was added N,N-diisopropylethylamine (0.08 mL, 0.42 mmol) and BOP (0.023 g, 0.051 mmol). The reaction mixture was stirred for 1 h at room temperature, then 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-N-methyl-N-(piperidin-4-yl)acetamide (Intermediate X) (0.045 g, 0.043 mmol) was added and stirring was continued for 1.5 h. The reaction mixture was evaporated to dryness under vacuum, diluted with DCM, washed with saturated aqueous $NaHCO_3$ solution, dried over $Na_2SO_4$, filtered, and evaporated to dryness. The residue was purified by preparative HPLC to afford the title compound as a white foamy solid (11.3 mg, 25% yield). LCMS: [C57H74$N_{12}$O5], desired mass=1006.6, found: m/z=1008.3 [M+H]+, 1H NMR (300 MHz, DMSO-$d_6$) δ 10.81 (s, 1H), 8.34 (s, 1H), 8.15 (s, 1H), 7.94 (d, J=10.9 Hz, 2H), 7.66 (d, J=28.4 Hz, 2H), 7.38 (d, J=8.5 Hz, 1H), 6.81 (d, J=8.8 Hz, 1H), 6.45 (s, 1H), 5.14-4.99 (m, 1H), 4.67-4.45 (m, 3H), 4.36-4.04 (m, 4H), 3.74 (dd, J=12.2, 4.9 Hz, 1H), 3.46-3.37 (m, 4H), 3.21-3.10 (m, 2H), 3.03-2.77 (m, 9H), 2.71-2.56 (m, 6H), 2.31-2.09 (m, 5H), 2.04-1.91 (m, 2H), 1.92-1.34 (m, 23H), 0.80 (d, J=6.6 Hz, 2H), 0.58 (d, J=3.2 Hz, 2H).

Example 201

2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-N-(1-{1-[4-(2,6-dioxopiperidin-3-yl)pyridin-2-yl]piperidine-4-carbonyl}piperidin-4-yl)-N-methylacetamide

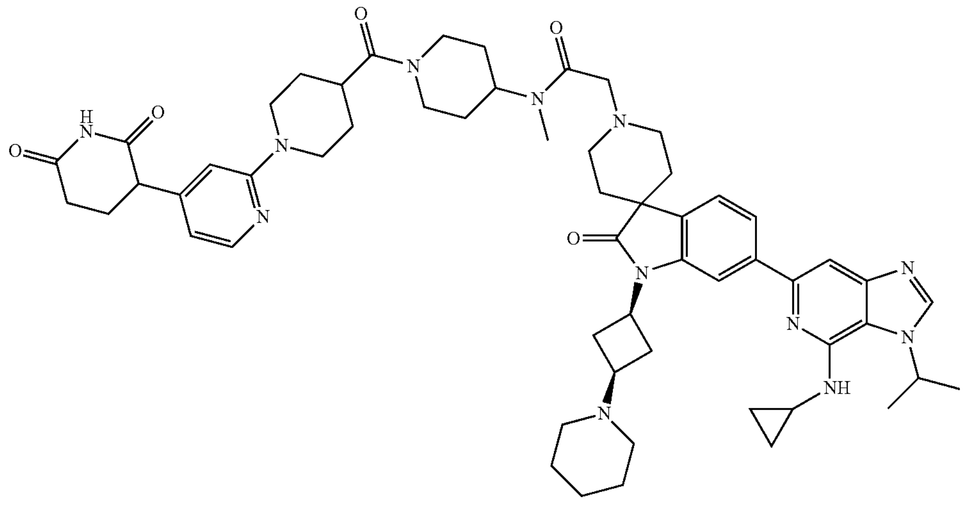 [SMILES: CC(C)n1cnc2cc(-c3ccc4c(c3)N([C@H]3C[C@@H](N5CCCCC5)C3)C(=O)C43CCN(CC(=O)N(C)C4CCN(C(=O)C5CCN(c6cc(C7CCC(=O)NC7=O)ccn6)CC5)CC4)CC3)nc(NC3CC3)c21]

To a solution of 1-[4-(2,6-dioxopiperidin-3-yl)pyridin-2-yl]piperidine-4-carboxylic acid (Intermediate 87) (0.026 g, 0.056 mmol) in anhydrous DMF (0.5 mL) was added N,N-diisopropylethylamine (0.08 mL, 0.42 mmol) and BOP (0.023 g, 0.051 mmol). The reaction mixture was stirred for 1 h at room temperature, then 2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-N-methyl-N-(piperidin-4-yl) acetamide (Intermediate X) (0.045 g, 0.043 mmol) was added and stirring was continued for 1.5 h. The reaction mixture was evaporated to dryness under vacuum, diluted with DCM, washed with saturated aqueous $NaHCO_3$ solution, dried over $Na_2SO_4$, filtered, and evaporated to dryness. The residue was purified by preparative HPLC to afford the title compound (white foamy solid, 7.7 mg, 16% yield). LCMS: [C57H74N12O5], desired mass=1006.6, found: m/z=1007.6 [M+H]+, 1H NMR (300 MHz, DMSO-d6) δ 10.86 (s, 1H), 8.34 (s, 1H), 8.15 (s, 1H), 8.03 (d, J=5.3 Hz, 1H), 7.95-7.89 (m, 1H), 7.71 (s, 1H), 7.60 (d, J=8.1 Hz, 1H), 6.72 (s, 1H), 6.52-6.39 (m, 2H), 5.10-5.01 (m, 1H), 4.65-4.43 (m, 3H), 4.38-4.09 (m, 4H), 3.81-3.72 (m, 1H), 3.43-3.38 (m, 4H), 3.21-3.02 (m, 2H), 3.03-2.76 (m, 9H), 2.72-2.55 (m, 6H), 2.34-2.20 (m, 5H), 2.08-1.95 (m, 2H), 1.92-1.38 (m, 23H), 0.80 (d, J=6.7 Hz, 2H), 0.58 (s, 2H).

Example 202

(3RS)-3-[4-(4-{2-[4-({6-[4-(cyclopropylamino)-3-(propan-2-yl)-3H-imidazo[4,5-c]pyridin-6-yl]-2-oxo-1-[(1S,3S)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidin-1-yl]-2-oxoethyl}piperidin-1-yl)phenyl]piperidine-2,6-dione

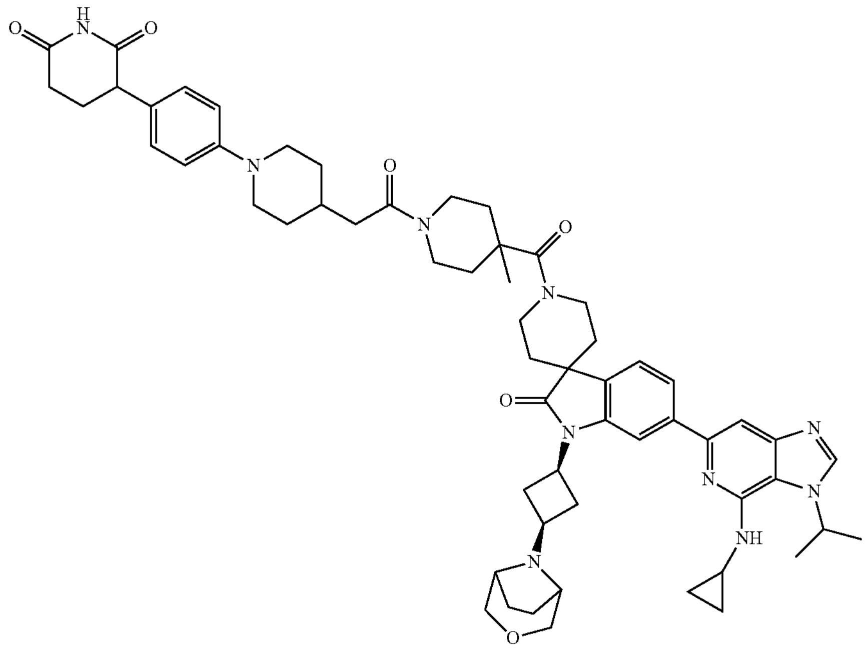 [SMILES: CC(C)n1cnc2cc(-c3ccc4c(c3)N([C@H]3C[C@@H](N5C6CCC5COC6)C3)C(=O)C43CCN(C(=O)C4(C)CCN(C(=O)CC5CCN(c6ccc(C7CCC(=O)NC7=O)cc6)CC5)CC4)CC3)nc(NC3CC3)c21]

A mixture of Intermediate KK (45.00 mg, 0.0774 mmol), EDCI, (22.24 mg, 0.1160 mmol), HOBT, (17.77 mg, 0.1160 mmol) and N,N-diisopropylethylamine (0.07 mL, 49.99 mg, 0.3868 mmol) in dimethylformamide (0.30 mL) was stirred for 15 minutes at room temperature. Intermediate 96 (42.29 mg, 0.0928 mmol) was added and the mixture was stirred at room temperature for 16 hours, then the crude mixture was purified by SFC to provide the title compound as an off-white solid (29.8 mg, 0.0286 mmol, 37% yield) as a free base. LCMS: [$C_{59}H_{74}N_{10}O_{6}$], desired mass=1018.6, found: m/z=1019.4 $[M+H]^+$, 1H NMR (500 MHz, MeOD) δ 8.31 (d, J=5.8 Hz, 1H), 8.02 (d, J=1.5 Hz, 1H), 7.86 (dd, J=7.8, 1.4 Hz, 1H), 7.57-7.51 (m, 2H), 7.13 (d, J=8.6 Hz, 2H), 6.99 (d, J=8.7 Hz, 2H), 5.08-4.99 (m, 1H), 4.44-4.35 (m, 1H), 4.11 (s, 5H), 4.08-4.01 (m, 1H), 3.82-3.67 (m, 6H), 3.63-3.50 (m, 4H), 3.36 (s, 1H), 3.24 (s, 1H), 3.17 (s, 2H), 3.07 (td, J=7.0, 3.5 Hz, 1H), 2.96 (t, J=7.6 Hz, 1H), 2.81-2.56 (m, 8H), 2.48-2.30 (m, 2H), 2.29 (s, 2H), 2.27-2.16 (m, 2H), 2.02-1.97 (m, 2H), 1.96-1.84 (m, 4H), 1.63 (dd, J=6.6, 2.4 Hz, 8H), 1.48 (d, J=12.2 Hz, 2H), 1.44 (s, 3H), 1.31 (s, 1H), 0.89 (td, J=6.8, 4.7 Hz, 2H), 0.72-0.64 (m, 2H).

Example 203

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-[(3S)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

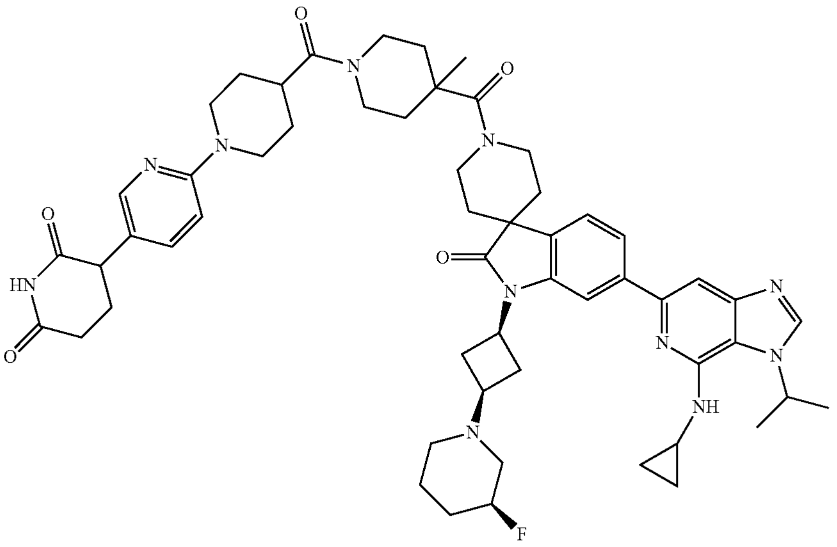 [SMILES: CC(C)n1cnc2cc(-c3ccc4c(c3)N([C@H]3C[C@@H](N5CCC[C@H](F)C5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate 00 as the amine coupling partner, and Intermediate 55 as the acid coupling partner, the title compound was isolated as an off-white solid (31.5 mg, 0.0310 mmol, 35% yield) as a free base. LCMS: [$C_{56}H_{70}FN_{11}O_5$], desired mass=995.5, found: m/z=997.1 $[M+H]^+$, 1H NMR (500 MHz, MeOD) δ 8.30 (s, 1H), 8.02-7.96 (m, 2H), 7.86 (d, J=8.0 Hz, 1H), 7.53 (d, J=7.6 Hz, 2H), 7.47 (dd, J=8.9, 2.5 Hz, 1H), 6.87 (d, J=8.9 Hz, 1H), 5.04 (p, J=6.6 Hz, 1H), 4.72 (s, 1H), 4.62 (s, 1H), 4.43-4.31 (m, 3H), 4.11 (s, 6H), 4.04 (d, J=13.7 Hz, 1H), 3.89 (d, J=13.9 Hz, 1H), 3.79 (dd, J=11.5, 5.2 Hz, 1H), 3.59 (t, J=11.6 Hz, 1H), 3.08 (dt, J=7.2, 3.7 Hz, 1H), 3.03 (d, J=23.1 Hz, 2H), 2.97 (d, J=11.9 Hz, 2H), 2.81-2.64 (m, 8H), 2.48 (s, 1H), 2.43 (s, 1H), 2.36 (d, J=16.1 Hz, 1H), 2.26 (s, 3H), 2.33-2.14 (m, 1H), 1.92-1.84 (m, 5H), 1.82-1.75 (m, 2H), 1.63 (d, J=6.6 Hz, 7H), 1.44 (s, 3H), 1.33-1.25 (m, 2H), 0.90 (td, J=6.9, 4.8 Hz, 2H), 0.71-0.64 (m, 2H).

Example 204

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-{8-oxa-3-Azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

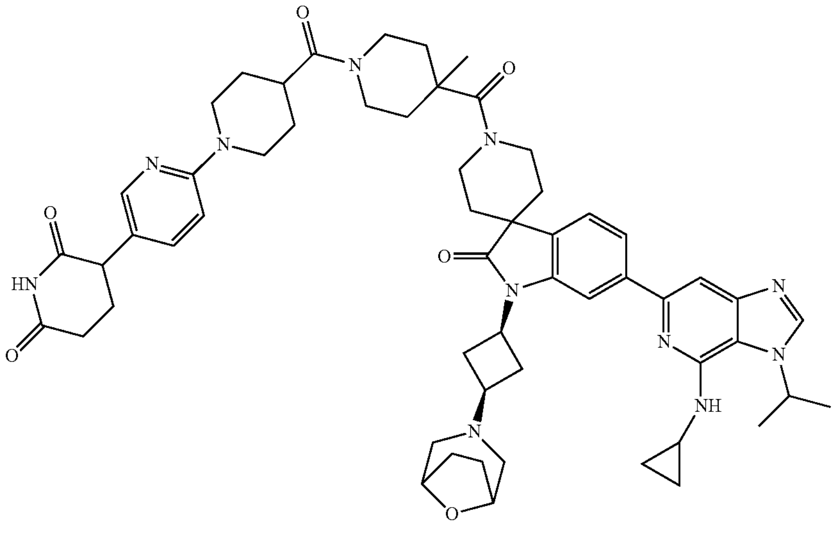 [SMILES: CC(C)n1cnc2cc(-c3ccc4c(c3)N([C@H]3C[C@@H](N5CC6CCC(C5)O6)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate QQ as the amine coupling partner, and Intermediate 55 as the acid coupling partner, the title compound was isolated as an off-white solid (27.6 mg, 0.0274 mmol, 53% yield) as a formate. LCMS: [$C_{57}H_{71}N_{11}O_6$], desired mass=1005.6, found: m/z=1006.6 [M+H]$^+$.

Example 205

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-[(3R)-3-fluoropiperidin-1-yl]cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

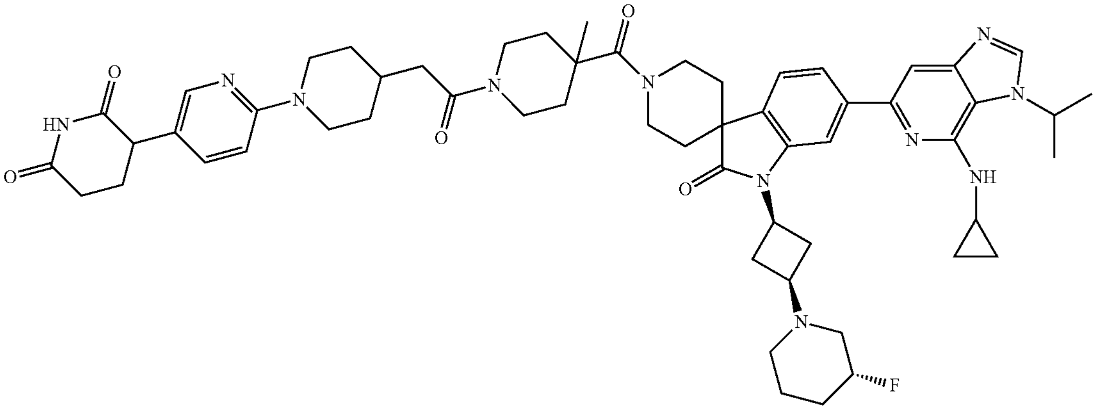 [SMILES: CC(C)n1cnc2cc(-c3ccc4c(c3)N([C@H]3C[C@@H](N5CCC[C@@H](F)C5)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate PP as the amine coupling partner, and Intermediate 85 as the acid coupling partner, the title compound was isolated as an off-white solid (20.7 mg, 0.0191 mmol, 27% yield) as a TFA salt. LCMS: [$C_{57}H_{72}FN_{11}O_5$], desired mass=1009.5, found: m/z=1010.3 [M+H]$^+$. 1H NMR (500 MHz, MeOD) δ 8.93 (s, 1H), 7.97 (dd, J=9.6, 2.3 Hz, 1H), 7.84 (d, J=2.3 Hz, 1H), 7.69 (s, 2H), 7.64 (s, 1H), 7.57 (s, 1H), 7.43 (d, J=9.7 Hz, 1H), 5.13 (dd, J=13.2, 6.6 Hz, 1H), 4.56-4.49 (m, 1H), 4.20-4.09 (m, 8H), 3.95 (dd, J=12.9, 5.0 Hz, 1H), 3.87-3.52 (m, 9H), 3.02 (s, 2H), 2.83-2.75 (m, 1H), 2.45 (d, J=7.0 Hz, 2H), 2.32 (dd, J=12.7, 5.0 Hz, 1H), 2.23 (s, 6H), 2.22-2.16 (m, 1H), 2.03 (d, J=29.1 Hz, 4H), 1.94 (s, 7H), 1.69 (d, J=6.5 Hz, 6H), 1.66-1.56 (m, 1H), 1.45 (s, 3H), 1.31 (s, 1H), 1.13 (d, J=6.0 Hz, 2H), 0.93 (s, 2H).

Example 206

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-[(3S)-3-fluoropiperidin-1-yl]cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

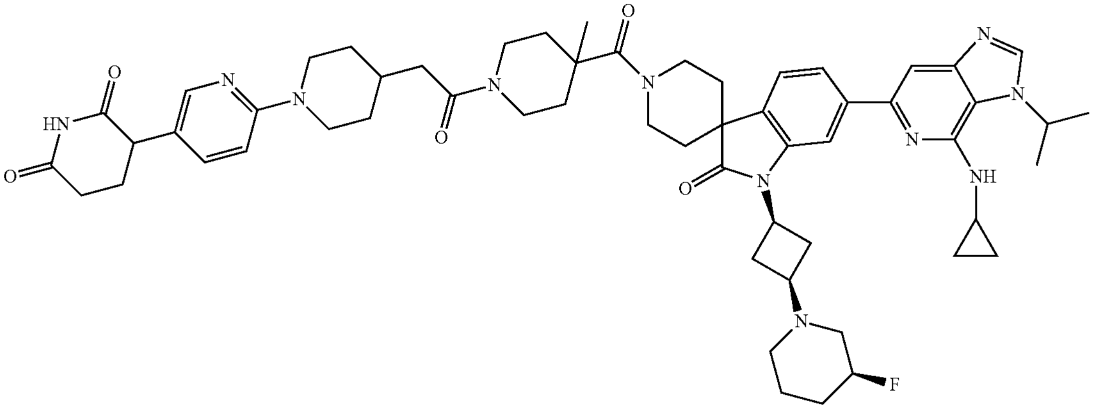 [SMILES: CC(C)n1cnc2cc(-c3ccc4c(c3)N([C@H]3C[C@@H](N5CCC[C@H](F)C5)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate 00 the amine coupling partner, and Intermediate 85 as the acid coupling partner, the title compound was isolated as an off-white solid (16 mg, 0.0158 mmol, 23% yield) as a formate. LCMS: [$C_{57}H_{72}FN_{11}O_5$], desired mass=1009.5, found: m/z=1010.3 $[M+H]^+$, 1H NMR (500 MHz, MeOD) δ 8.31 (s, 1H), 7.99-7.93 (m, 2H), 7.87 (d, J=7.9 Hz, 1H), 7.53 (d, J=5.4 Hz, 2H), 7.48-7.43 (m, 1H), 6.85 (d, J=8.9 Hz, 1H), 5.07-5.01 (m, 1H), 4.60 (s, 1H), 4.44-4.37 (m, 1H), 4.28 (d, J=13.1 Hz, 2H), 4.11 (s, 5H), 4.03 (s, 1H), 3.78 (dd, J=11.6, 5.3 Hz, 1H), 3.55 (d, J=13.0 Hz, 1H), 3.12-3.02 (m, 2H), 2.95-2.87 (m, 3H), 2.80 (s, 6H), 2.77-2.64 (m, 1H), 2.55 (s, 1H), 2.40 (t, J=7.3 Hz, 2H), 2.24 (d, J=13.0 Hz, 1H), 2.06 (s, 1H), 1.87 (dd, J=27.9, 14.6 Hz, 9H), 1.63 (d, J=6.5 Hz, 6H), 1.59 (s, 2H), 1.44 (s, 3H), 1.33 (d, J=18.0 Hz, 6H), 0.91 (t, J=7.0 Hz, 2H), 0.68 (s, 2H).

Example 207

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-{8-oxa-3-Azabicyclo[3.2.1]octan-3-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

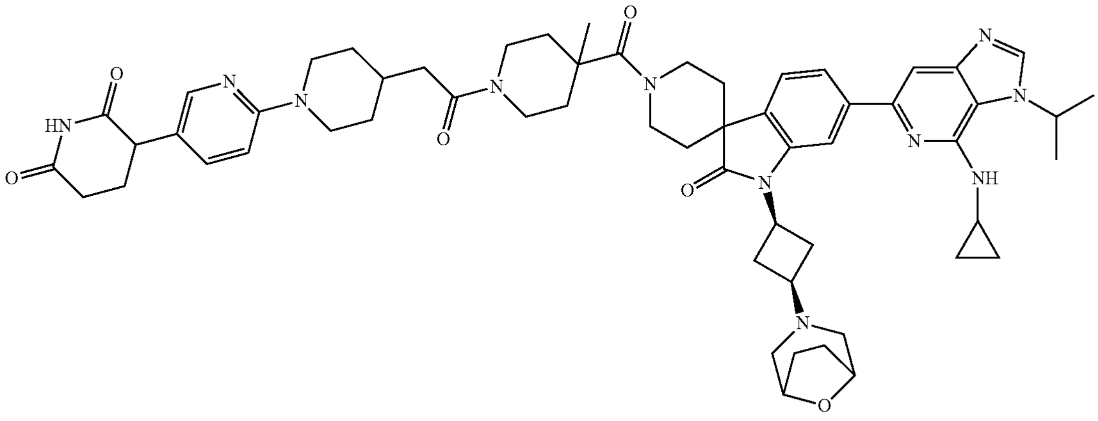 [SMILES: CC(C)n1cnc2cc(-c3ccc4c(c3)N([C@H]3C[C@@H](N5CC6CCC(C5)O6)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate QQ as the amine coupling partner, and Intermediate 85 as the acid coupling partner, the title compound was isolated as an off-white solid (15.7 mg, 0.0149 mmol, 29% yield) as a formate. LCMS: [$C_{58}H_{73}N_{11}O_6$], desired mass=1019.5, found: m/z=1020.4 $[M+H]^+$.

Example 208

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(4-fluoropiperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

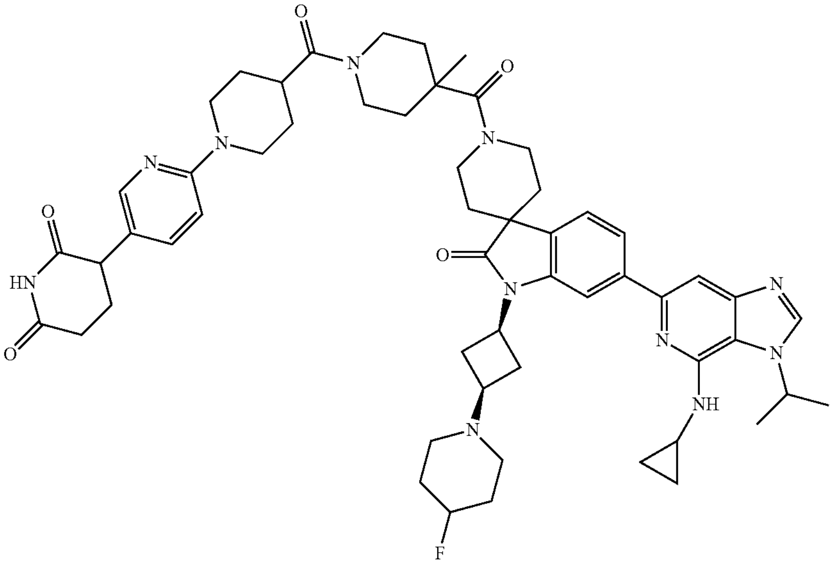 [SMILES: CC(C)n1cnc2cc(-c3ccc4c(c3)N([C@H]3C[C@@H](N5CCC(F)CC5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate SS as the amine coupling partner, and Intermediate 55 as the acid coupling partner, the title compound was isolated as an off-white solid (20.5 mg, 0.0205 mmol, 39% yield) as a formate. LCMS: [$C_{56}H_{70}FN_{11}O_5$], desired mass=995.5, found: m/z=996.4 $[M+H]^+$, 1H NMR (500 MHz, MeOD) δ 8.31 (s, 1H), 8.02-7.95 (m, 2H), 7.87 (d, J=7.8 Hz, 1H), 7.54 (t, J=3.9 Hz, 2H), 7.47 (dd, J=8.8, 2.6 Hz, 1H), 6.88 (d, J=8.9 Hz, 1H), 5.04 (p, J=6.6 Hz, 1H), 4.68 (s, 1H), 4.60 (s, 1H), 4.42 (d, J=8.7 Hz, 1H), 4.33 (s, 3H), 4.11 (s, 5H), 4.04 (d, J=14.7 Hz, 1H), 3.90 (d, J=14.1 Hz, 1H), 3.80 (dd, J=11.5, 5.2 Hz, 1H), 3.59 (t, J=11.7 Hz, 1H), 3.06 (dd, J=7.4, 3.8 Hz, 1H), 2.99 (t, J=12.2 Hz, 3H), 2.82 (s, 3H), 2.77 (s, 2H), 2.77-2.68 (m, 1H), 2.67 (t, J=10.0 Hz, 1H), 2.59-2.48 (m, 4H), 2.36 (d, J=13.0 Hz, 1H), 2.30-2.21 (m, 2H), 2.23-2.14 (m, 1H), 1.93-1.85 (m, 1H), 1.78 (d, J=16.5 Hz, 3H), 1.63 (d, J=6.5 Hz, 6H), 1.59-1.55 (m, 2H), 1.45 (s, 3H), 1.31 (s, 1H), 0.94-0.86 (m, 2H), 0.68 (t, J=3.1 Hz, 2H).

Example 209

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridazin-3-yl)piperidine-2,6-dione

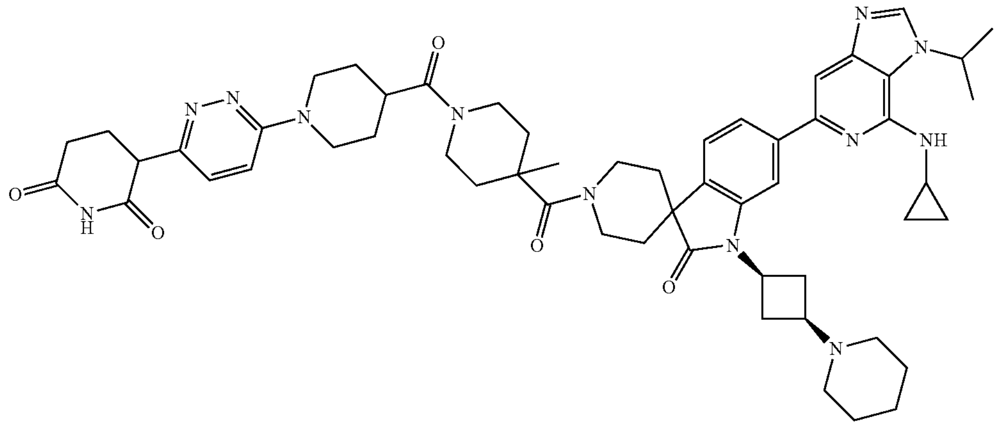 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)nn6)CC5)CC4)CC3)nc(NC3CC3)c21]

Following procedures similar to Example 202 by using Intermediate B and Intermediate 94 as the amine and acid coupling partners, respectively, the title compound was isolated as an off-white solid (15 mg, 0.015 mmol, 33% yield) as a TFA salt. LCMS: [$C_{55}H_{70}N_{12}O_5$], desired mass=978.5, found: m/z=979.7 $[M+H]^+$, 1H NMR (500 MHz, MeOD) δ 8.85 (s, 1H), 7.84 (q, J=9.8 Hz, 2H), 7.72 (s, 1H), 7.67 (d, J=8.1 Hz, 2H), 7.56 (s, 1H), 5.16-5.08 (m, 1H), 4.49 (t, J=8.4 Hz, 1H), 4.33 (d, J=13.5 Hz, 2H), 4.21-4.14 (m, 5H), 4.07 (s, 3H), 3.89 (d, J=13.7 Hz, 1H), 3.74-3.60 (m, 1H), 3.57 (s, 6H), 3.43 (s, 1H), 3.21 (d, J=9.7 Hz, 3H), 3.10-2.98 (m, 3H), 2.90 (s, 2H), 2.77 (d, J=6.0 Hz, 2H), 2.41-2.21 (m, 2H), 2.09 (s, 1H), 2.1-1.76 (m, 11H), 1.68 (d, J=6.5 Hz, 6H), 1.60 (d, J=12.1 Hz, 1H), 1.46 (s, 3H), 1.31 (s, 2H), 1.11 (s, 2H), 0.91 (s, 2H).

Example 210

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-Fluorophenyl)piperidine-2,6-dione

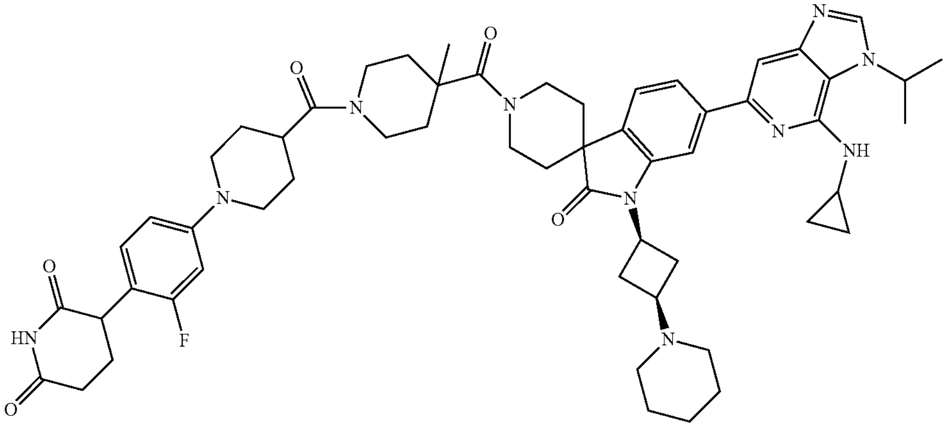 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)c(F)c6)CC5)CC4)CC3)nc(NC3CC3)c21]

Using similar procedures to Example 189, and using Intermediate 98 as the acid coupling partner in step 3, the title compound was isolated as an off-white solid (27.3 mg, 0.0269 mmol, 61% yield) as a TFA salt. LCMS: [$C_{57}H_{71}FN_{10}O_5$], desired mass=994.5, found: m/z=995.6 $[M+H]^+$, 1H NMR (500 MHz, MeOD) δ 8.93 (s, 1H), 7.66 (d, J=23.3 Hz, 3H), 7.57 (s, 1H), 7.16 (t, J=8.6 Hz, 1H), 6.87-6.75 (m, 2H), 5.17-5.09 (m, 1H), 4.50 (t, J=8.3 Hz, 1H), 4.17-4.04 (m, 6H), 3.95 (dd, J=11.8, 5.1 Hz, 1H), 3.84 (d, J=20.8 Hz, 3H), 3.79 (s, 1H), 3.67-3.59 (m, 1H), 3.59 (s, 4H), 3.23 (d, J=9.9 Hz, 1H), 2.92 (d, J=12.3 Hz, 5H), 2.83-2.63 (m, 2H), 2.37 (s, 1H), 2.31-2.23 (m, 1H), 2.19-2.10 (m, 1H), 2.05 (s, 1H), 2.02 (s, 2H), 1.96-1.84 (m, 10H), 1.79 (d, J=13.4 Hz, 1H), 1.69 (d, J=6.5 Hz, 6H), 1.62 (s, 3H), 1.45 (s, 3H), 1.31 (s, 2H), 1.14 (s, 2H), 0.94 (s, 2H).

Example 211

1-(4-{4-[4-({6-[4-(cyclopropylamino)-3-(propan-2-yl)-3H-imidazo[4,5-c]pyridin-6-yl]-2-oxo-1-[(1S, 3S)-3-(piperidin-1-yl)cyclobutyl]-1,2-dihydrospiro [indole-3,4'-piperidin]-1'-yl}carbonyl)-4-methylpiperidine-1-carbonyl]piperidin-1-yl}phenyl)-1,3-diazinane-2,4-dione

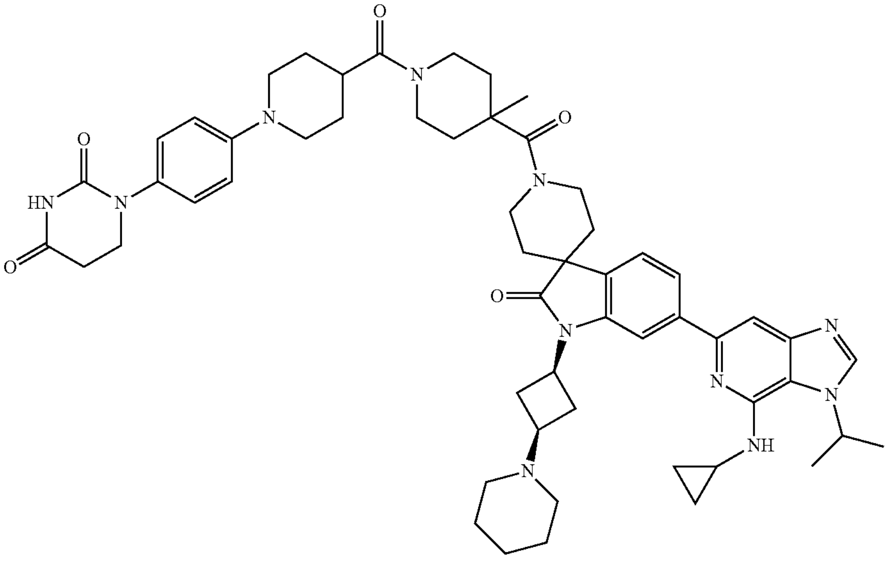 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(N7CCC(=O)NC7=O)cc6)CC5)CC4)CC3)nc(NC3CC3)c21]

Using similar procedures to Example 189, and using Intermediate 97 as the acid coupling partner in step 3, the title compound was isolated as an off-white solid (9.7 mg, 0.0097 mmol, 26% yield) as a TFA salt. LCMS: [$C_{56}H71FN_{11}O_5$], desired mass=977.5, found: m/z=978.6 $[M+H]^+$, 1H NMR (500 MHz, MeOD) δ 8.30 (s, 1H), 7.95 (d, J=1.4 Hz, 1H), 7.85 (dd, J=7.8, 1.5 Hz, 1H), 7.53 (d, J=10.2 Hz, 2H), 7.26-7.17 (m, 2H), 7.04 (dd, J=7.1, 4.6 Hz, 2H), 5.30 (s, 2H), 5.03 (p, J=6.6 Hz, 1H), 4.60 (s, 2H), 4.37-4.27 (m, 1H), 4.15-4.00 (m, 5H), 3.84 (d, J=10.1 Hz, 1H), 3.85-3.74 (m, 3H), 3.58 (dd, J=13.3, 9.5 Hz, 1H), 3.28 (dd, J=13.6, 3.3 Hz, 1H), 3.06 (tt, J=7.0, 3.8 Hz, 1H), 2.92-2.76 (m, 6H), 2.71-2.63 (m, 3H), 2.42 (s, 4H), 2.35 (d, J=13.5 Hz, 1H), 2.27 (d, J=14.3 Hz, 1H), 1.96-1.79 (m, 8H), 1.63 (d, J=6.6 Hz, 6H), 1.59-1.51 (m, 7H), 1.44 (s, 3H), 1.31 (s, 1H), 0.89 (dt, J=6.9, 3.5 Hz, 2H), 0.72-0.63 (m, 2H).

Example 212 and Example 213

(3R)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione And (3R)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

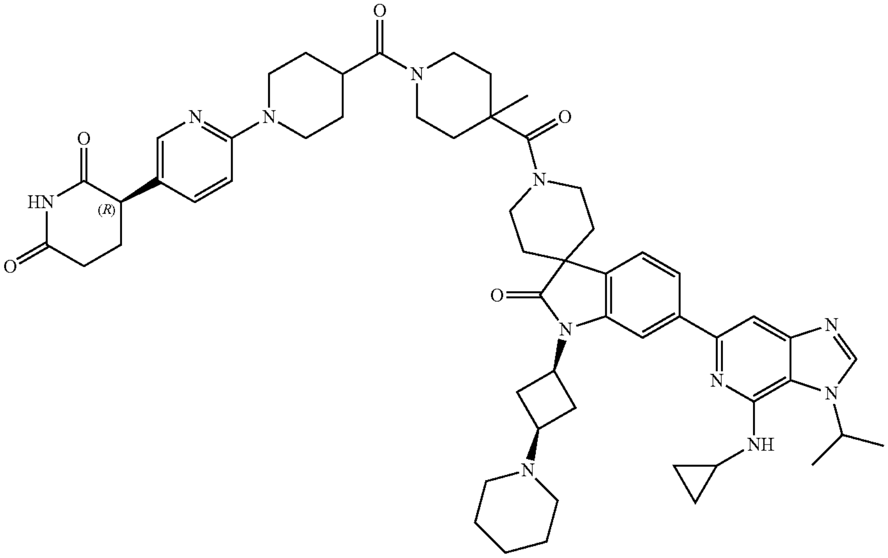

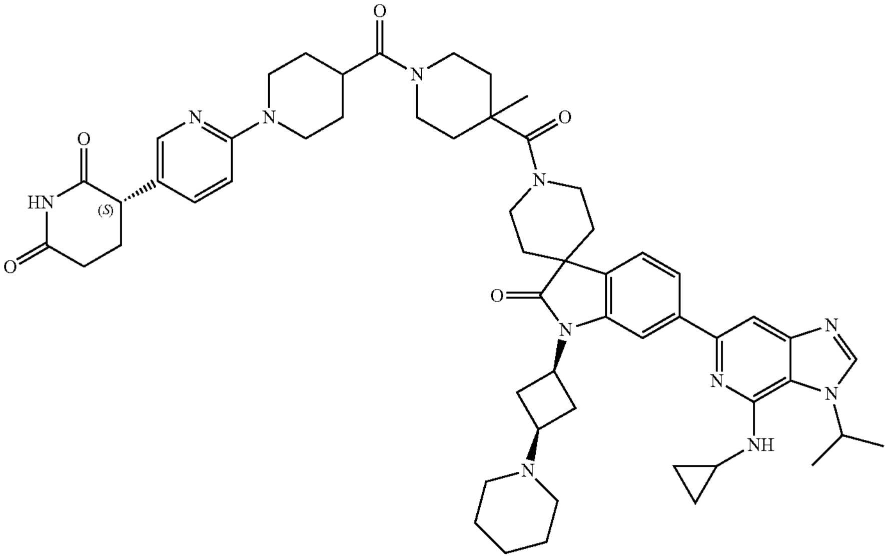

Examples 212 (peak 2, off-white solid, 94 mg) and 213 (peak 1, off-white solid, 86 mg) were obtained by subjecting 200 mg of Example 113 to chiral SFC chromatography using the following conditions:

Chiral Stationary Phase—Regis (R,R)—Whelk-O 1 Sum Kromasil
Column Dimensions—150 mm×4.6 mm
Mobile Phase A—IPA: Acetonitrile (4:6)+0.1% ammonia hydroxide
Mobile Phase B—CO2
Method—Isocratic A—80%, B—20%
Runtime—12 minutes
Flow Rate—3 ml/min
UV—254 nm
Column Temp—40 C
BPR—100 Bar The absolute stereochemistry of each product was not determined, and was randomly assigned. Example 212 LCMS: $[C_{56}H_{71}N_{11}O_5]$, desired mass=977.6, found: m/z=978.6 $[M+H]^+$, 1H NMR (500 MHz, MeOD) δ 8.31 (s, 1H), 8.00 (s, 1H), 7.94 (s, 1H), 7.86 (d, J=7.8 Hz, 1H), 7.54 (t, J=3.9 Hz, 2H), 7.50-7.43 (m, 1H), 6.88 (d, J=8.8 Hz, 1H), 5.04 (p, J=6.6 Hz, 1H), 4.60 (s, 1H), 4.38-4.28 (m, 4H), 4.18-4.01 (m, 5H), 3.89 (d, J=22.5 Hz, 2H), 3.79 (d, J=22.5 Hz, 2H), 3.59 (t, J=11.4 Hz, 1H), 3.11-2.93 (m, 5H), 2.86-2.64 (m, 7H), 2.5-2.15 (m, 9H), 1.97-1.72 (m, 7H), 1.63 (d, J=6.7 Hz, 6H), 1.53 (s, 2H), 1.45 (s, 3H), 0.89 (d, J=6.6 Hz, 2H), 0.68 (s, 2H). Example 213 LCMS: $[C_{56}H_{71}N_{11}O_5]$, desired mass=977.6, found: m/z=978.6 $[M+H]^+$.

Example 214

(3RS)-3-[6-(4-{4-methyl-4-[(6-{4-[(oxan-4-yl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione

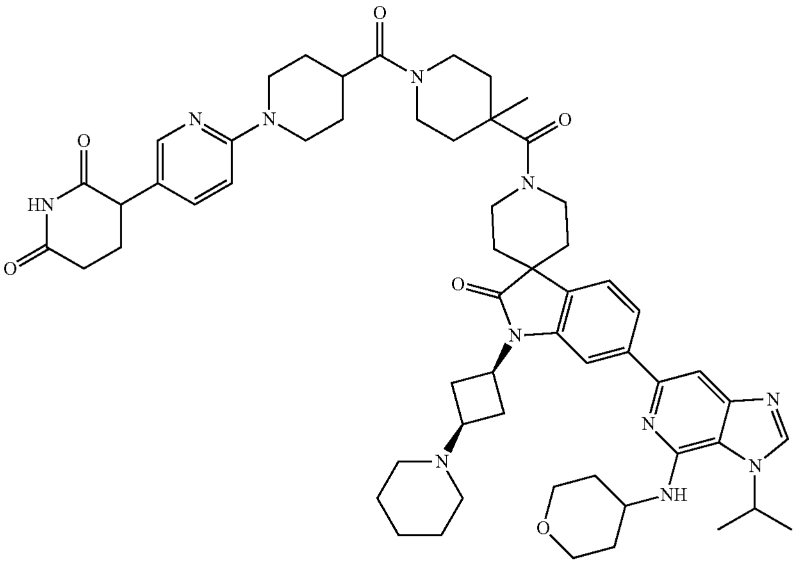 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ccc(C7CCC(=O)NC7=O)cn6)CC5)CC4)CC3)nc(NC3CCOCC3)c21]

Using similar procedures to Example 202, and using Intermediate E as the amine coupling partner, and Intermediate 5 as the acid coupling partner, the title compound was isolated as an off-white solid (6.7 mg, 0.0067 mmol, 20% yield) as a TFA salt. LCMS: $[C_{58}H_{71}N_1O_6]$, desired mass=1021.6, found: m/z=1022.4 $[M+H]^+$.

Example 215

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

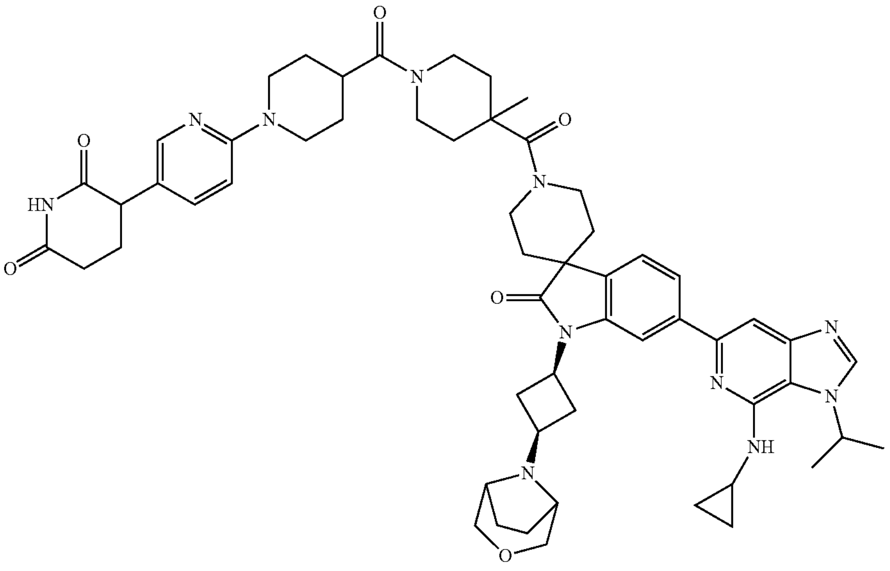 [SMILES: CC(C)n1cnc2cc(-c3ccc4c(c3)N([C@H]3C[C@@H](N5C6CCC5COC6)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate KK as the amine coupling partner, and Intermediate 55 as the acid coupling partner, the title compound was isolated as an off-white solid (41 mg, 0.039 mmol, 32% yield) as a free base. LCMS: [$C_{57}H_{71}N_{11}O_6$], desired mass=1005.6, found: m/z=1006.6 $[M+H]^+$, 1H NMR (500 MHz, MeOD) δ 8.96 (s, 1H), 8.00 (dd, J=9.6, 2.3 Hz, 1H), 7.87 (d, J=2.3 Hz, 1H), 7.68 (d, J=7.6 Hz, 2H), 7.60 (s, 1H), 7.56 (s, 1H), 7.44 (d, J=9.6 Hz, 1H), 5.14 (p, J=6.6 Hz, 1H), 4.50 (p, J=8.1 Hz, 1H), 4.23 (dd, J=13.2, 3.6 Hz, 2H), 4.16 (s, 1H), 4.09 (d, J=20.2 Hz, 1H), 4.05-3.92 (m, 5H), 3.88 (d, J=12.3 Hz, 3H), 3.75-3.60 (m, 2H), 3.43 (d, J=12.2 Hz, 2H), 3.22 (d, J=21.7 Hz, 1H), 3.21 (s, 3H), 3.16-3.06 (m, 1H), 3.10 (s, 1H), 3.07 (dt, J=6.9, 3.5 Hz, 1H), 2.87-2.71 (m, 2H), 2.41-2.26 (m, 1H), 2.30 (s, 5H), 2.26-2.15 (m, 1H), 1.99 (s, 1H), 1.96 (d, J=4.6 Hz, 5H), 1.97-1.83 (m, 4H), 1.69 (d, J=6.5 Hz, 6H), 1.65-1.57 (m, 2H), 1.47 (s, 3H), 1.14 (dd, J=7.3, 5.2 Hz, 2H), 0.99-0.90 (m, 2H).

Example 216

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(MORPHOLIN-4-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

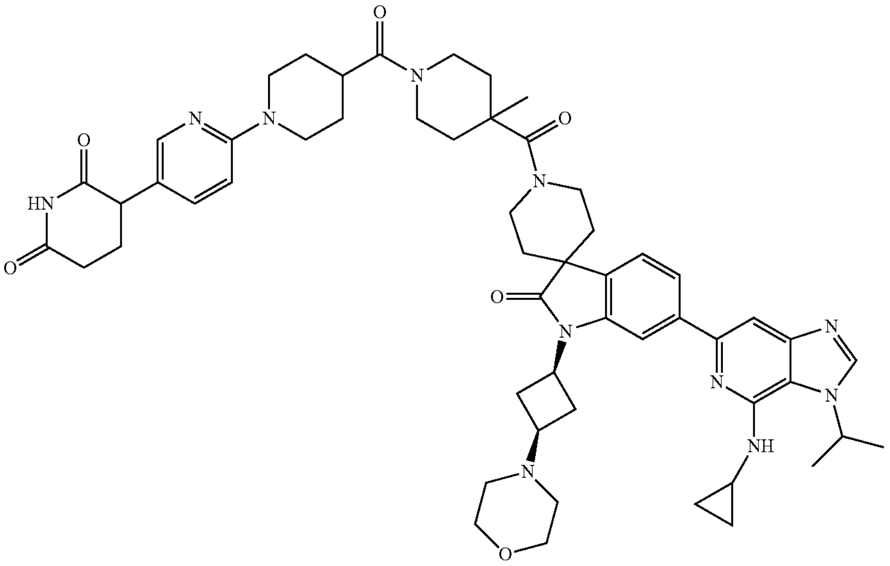 [SMILES: CC(C)n1cnc2cc(-c3ccc4c(c3)N([C@H]3C[C@@H](N5CCOCC5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 189, and using Intermediate LL the amine coupling partner in step 1, and 1-[5-(2,6-dioxopiperidin-3-yl)pyridin-2-yl]piperidine-4-carboxylic acid hydrochloride (intermediate 55, step 2) as the acid coupling partner in step 3, the title compound was isolated as an off-white solid (2.9 mg, 0.0026 mmol, 5% yield) as a TFA salt. LCMS: [$C_{55}H_{69}N_{11}O_6$], desired mass=979.5, found: m/z=980.4 $[M+H]^+$, Example 217

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-{3-Azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

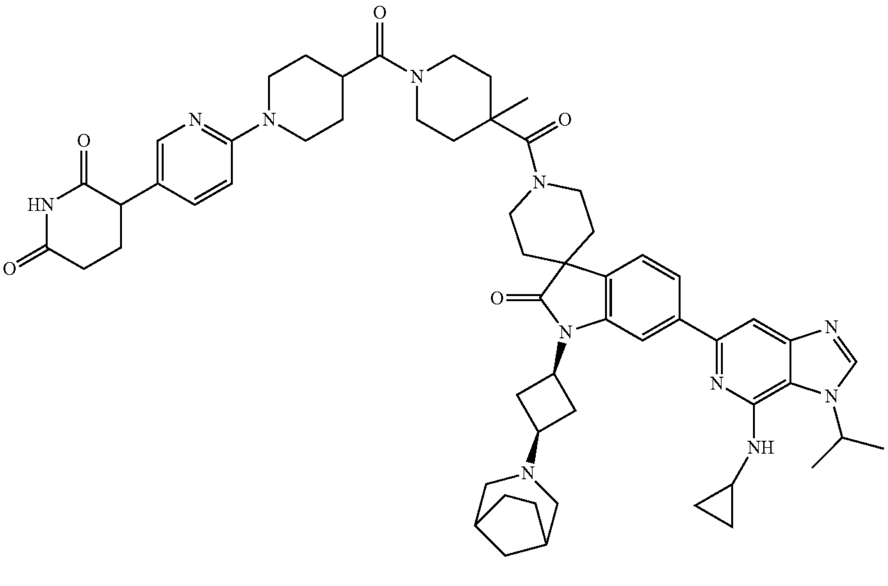 [SMILES: CC(C)n1cnc2cc(-c3ccc4c(c3)N([C@H]3C[C@@H](N5CC6CCC(C6)C5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate MM as the amine coupling partner, and Intermediate 55 as the acid coupling partner, the title compound was isolated as an off-white solid (113 mg, 0.107 mmol, 41% yield) as a free base. LCMS: [$C_{58}H_{73}N_{11}O_5$], desired mass=1003.5, found: m/z=1004.4 $[M+H]^+$, 1H NMR (500 MHz, DMSO) δ 10.81 (s, 1H), 8.35 (s, 1H), 7.96 (s, 1H), 7.90 (s, 1H), 7.86 (d, J=7.6 Hz, 1H), 7.62-7.55 (m, 2H), 7.39 (d, J=8.8 Hz, 1H), 6.82 (d, J=8.8 Hz, 1H), 6.46 (s, 1H), 5.10-5.04 (m, 1H), 4.43 (s, 1H), 4.29 (s, 2H), 4.01-3.88 (m, 7H), 3.80 (s, 2H), 3.77-3.71 (m, 2H), 3.47 (s, 1H), 3.20 (s, 2H), 3.00 (s, 2H), 2.93-2.85 (m, 4H), 2.18 (s, 2H), 2.13 (s, 2H), 2.00 (s, 2H), 1.90 (d, J=10.1 Hz, 2H), 1.76 (s, 6H), 1.66 (t, J=14.5 Hz, 4H), 1.50 (d, J=6.5 Hz, 6H), 1.44 (s, 2H), 1.33 (s, 3H), 1.25 (s, 1H), 0.78 (d, J=6.8 Hz, 2H), 0.59 (s, 2H).

Example 218

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-{3-oxa-6-azabicyclo[3.1.1]heptan-6-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

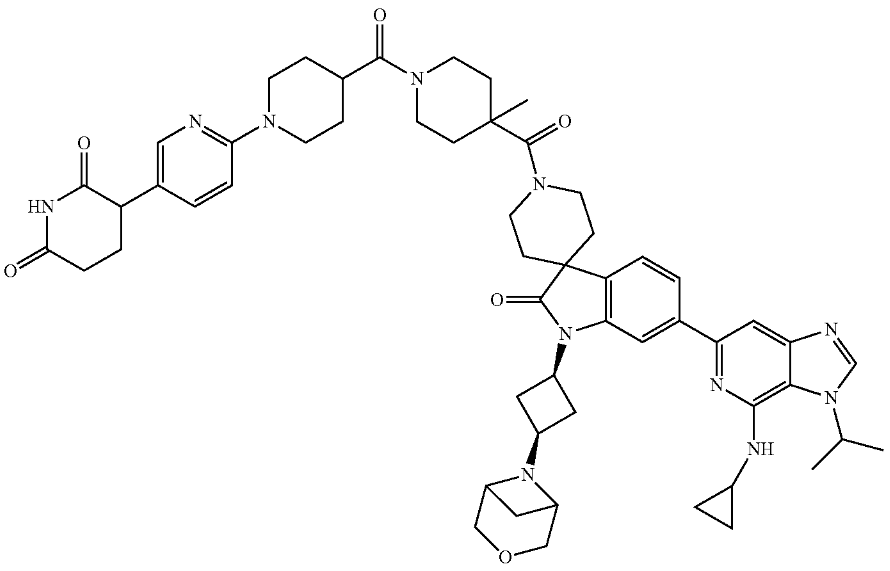 [SMILES: CC(C)n1cnc2cc(-c3ccc4c(c3)N([C@H]3C[C@@H](N5C6COCC5C6)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate NN as the amine coupling partner, and Intermediate 55 as the acid coupling partner, the title compound was isolated as an off-white solid (32 mg, 0.0316 mmol, 61% yield) as a free base. LCMS: [$C_{56}H_{69}N_{11}O_6$], desired mass=991.5, found: m/z=992.4 $[M+H]^+$, 1H NMR (500 MHz, MeOD) δ 8.31 (d, J=3.4 Hz, 1H), 8.17 (d, J=17.8 Hz, 1H), 7.99 (d, J=2.5 Hz, 1H), 7.85 (dd, J=17.8 Hz, 8.8 Hz, 1H), 7.57 (s, 1H), 7.53 (dd, J=7.9, 3.9 Hz, 1H), 7.47 (dd, J=8.9, 2.5 Hz, 1H), 6.87 (d, J=8.8 Hz, 1H), 5.30 (p, J=8.8 Hz, 1H), 5.04 (td, J=6.6, 3.4 Hz, 1H), 4.57 (dd, J=17.1, 8.6 Hz, 1H), 4.33 (s, 2H), 4.24 (d, J=10.8 Hz, 1H), 4.15 (d, J=10.8 Hz, 1H), 4.10 (s, 5H), 4.04 (d, J=16.2 Hz, 2H), 3.89 (d, J=14.1 Hz, 1H), 3.79 (td, J=9.0, 4.6 Hz, 3H), 3.70-3.55 (m, 4H), 3.19-3.05 (m, 2H), 2.98 (t, J=11.9 Hz, 4H), 2.73 (dddd, J=31.1, 17.6, 12.4, 6.1 Hz, 4H), 2.36 (d, J=14.2 Hz, 1H), 2.30-2.14 (m, 1H), 1.89 (s, 4H), 1.86 (d, J=4.9 Hz, 1H), 1.82-1.72 (m, 4H), 1.64 (dd, J=6.6, 2.2 Hz, 6H), 1.59-1.52 (m, 2H), 1.44 (s, 3H), 0.92 (dtd, J=29.2, 6.8, 4.8 Hz, 2H), 0.68 (dt, J=17.1, 4.0 Hz, 1H), 0.68 (s, 2H).

Example 219

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-[(3R)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione

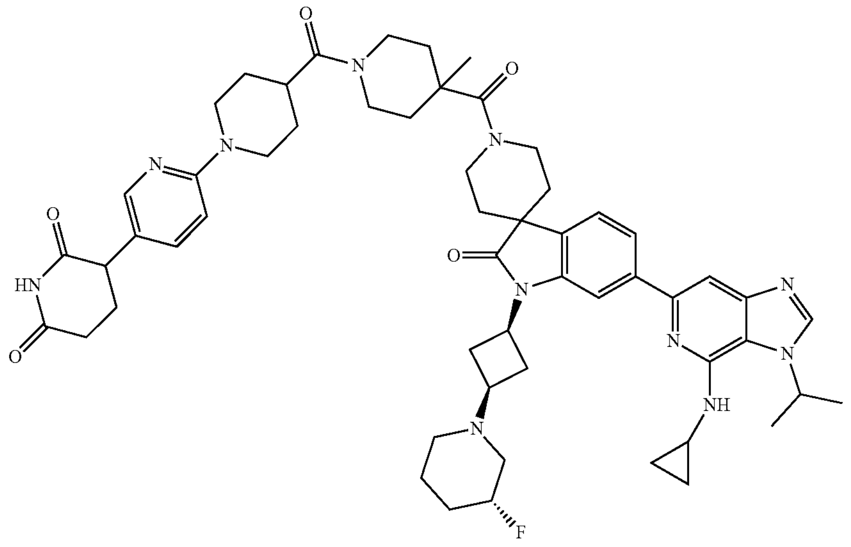 [SMILES: CC(C)n1cnc2cc(-c3ccc4c(c3)N([C@H]3C[C@@H](N5CCC[C@@H](F)C5)C3)C(=O)C43CCN(C(=O)C4(C)CCN(C(=O)C5CCN(c6ccc(C7CCC(=O)NC7=O)cn6)CC5)CC4)CC3)nc(NC3CC3)c21]

Using similar procedures to Example 202, and using Intermediate PP as the amine coupling partner, and Intermediate 55 as the acid coupling partner, the title compound was isolated as an off-white solid (20.3 mg, 0.0203 mmol, 23% yield) as a free base. LCMS: [$C_{56}H_{70}FN_{11}O_5$], desired mass=995.6, found: m/z=997.1 [M+H]$^+$.

Example 220

(3RS)-3-(2-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyrimidin-5-yl)piperidine-2,6-dione

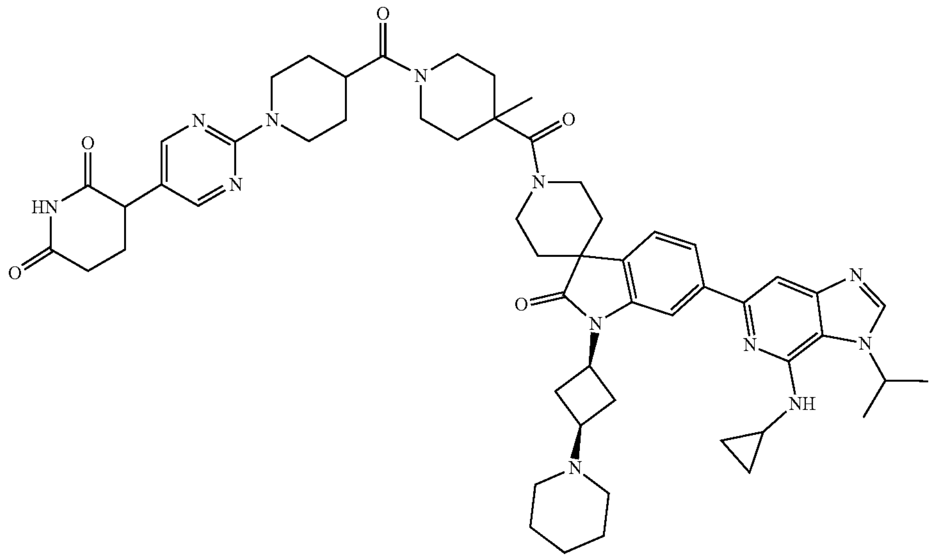 [SMILES: CC(C)n1cnc2cc(-c3ccc4c(c3)N([C@H]3C[C@@H](N5CCCCC5)C3)C(=O)C43CCN(C(=O)C4(C)CCN(C(=O)C5CCN(c6ncc(C7CCC(=O)NC7=O)cn6)CC5)CC4)CC3)nc(NC3CC3)c21]

Using similar procedures to Example 189, and using Intermediate 103 as the acid coupling partner in step 3, the title compound was isolated as an off-white solid (17.2 mg, 0.017 mmol, 64% yield) as a TFA salt. LCMS: [$C_{55}H_{60}N_{12}O_5$], desired mass=978.5, found: m/z=979.4 [M+H]$^+$.

Example 221

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

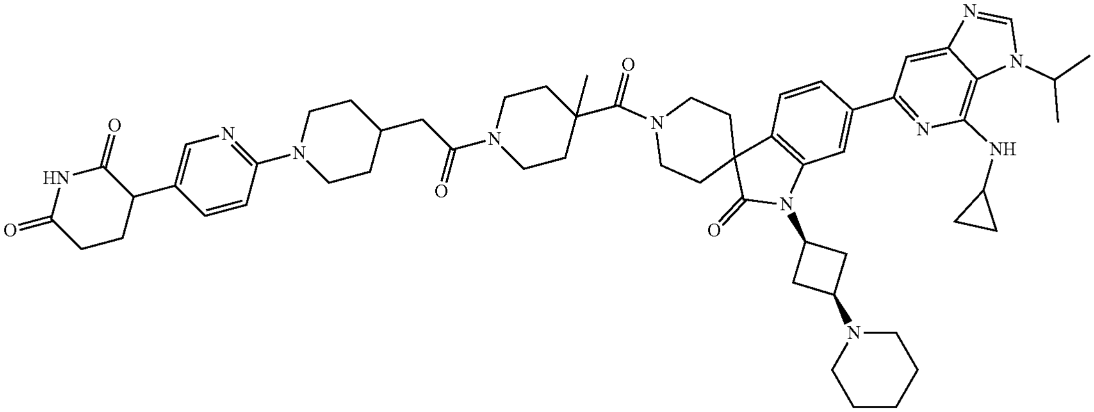 [SMILES: CC(C)n1cnc2cc(-c3ccc4c(c3)N([C@H]3C[C@@H](N5CCCCC5)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate B as the amine coupling partner, and Intermediate 85 as the acid coupling partner, the title compound was isolated as an off-white solid (19 mg, 0.019 mmol, 42% yield) as a free base. LCMS: [$C_{57}H_{73}N_{11}O_5$], desired mass=991.6, found: m/z=992.4 [M+H]$^+$.

Example 222

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-{3-oxa-8-Azabicyclo[3.2.1]octan-8-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

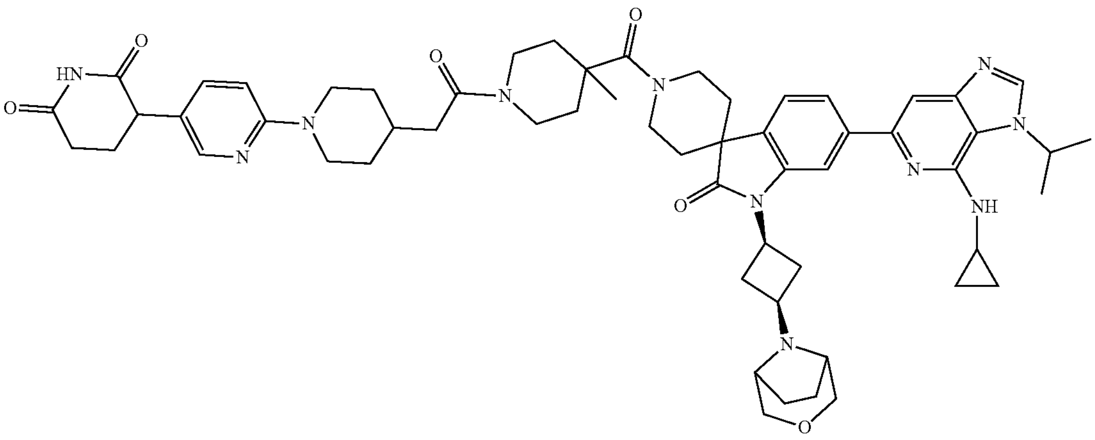 [SMILES: CC(C)n1cnc2cc(-c3ccc4c(c3)N([C@H]3C[C@@H](N5C6CCC5COC6)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate KK as the amine coupling partner, and Intermediate 85 as the acid coupling partner, the title compound was isolated as an off-white solid (11.7 mg, 0.0111 mmol, 21% yield) as a TFA salt. LCMS: [$C_{58}H_{73}N_{11}O_6$], desired mass=1019.6, found: m/z=1020.4 [M+H]$^+$, 1H NMR (500 MHz, MeOD) δ 8.95 (s, 1H), 7.98 (dd, J=9.7, 2.3 Hz, 1H), 7.84 (d, J=2.3 Hz, 1H), 7.70 (s, 2H), 7.62 (s, 1H), 7.56 (s, 1H), 7.43 (d, J=9.6 Hz, 1H), 5.14 (p, J=6.6 Hz, 1H), 4.55-4.47 (m, 1H), 4.25-4.13 (m, 4H), 4.10 (s, 7H), 4.09-3.92 (m, 5H), 3.89 (d, J=12.7 Hz, 2H), 3.82-3.66 (m, 2H), 3.56 (t, J=10.6 Hz, 1H), 3.16-3.03 (m, 3H), 2.86-2.72 (m, 2H), 2.46 (d, J=6.9 Hz, 2H), 2.34 (d, J=5.4 Hz, 1H), 2.30 (s, 5H), 2.27-2.18 (m, 1H), 2.08-1.90 (m, 7H), 1.69 (d, J=6.5 Hz, 6H), 1.58 (dd, J=25.8, 11.9 Hz, 2H), 1.45 (s, 3H), 1.31 (s, 1H), 1.14 (d, J=5.7 Hz, 2H), 0.94 (s, 2H).

Example 223

(3RS)-3-[6-(4-{2-[4-({6-[4-(cyclopropylamino)-3-(propan-2-yl)-3H-imidazo[4,5-c]pyridin-6-yl]-2-oxo-1-[(1S,3S)-3-{3-azabicyclo[3.2.1]octan-3-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione

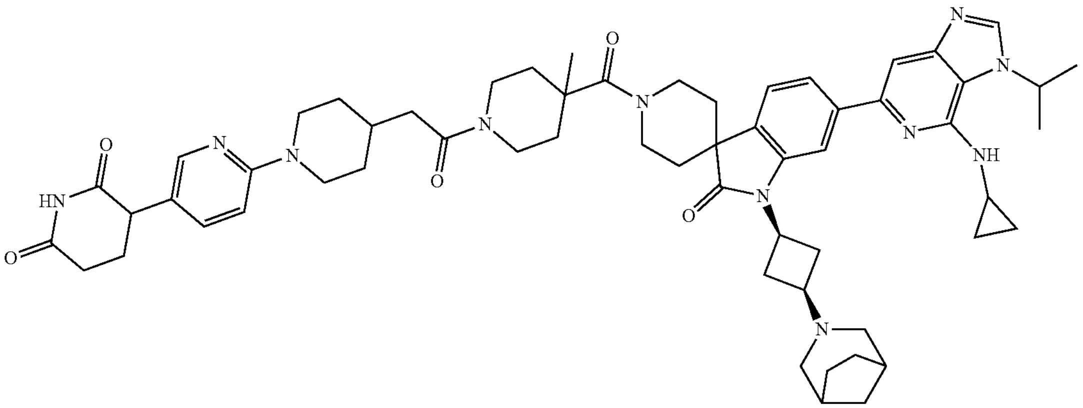 [SMILES: CC(C)n1cnc2cc(-c3ccc4c(c3)N([C@H]3C[C@@H](N5CC6CCC(C6)C5)C3)C(=O)C43CCN(C(=O)C4(C)CCN(C(=O)CC5CCN(c6ccc(C7CCC(=O)NC7=O)cn6)CC5)CC4)CC3)nc(NC3CC3)c21]

Using similar procedures to Example 202, and using Intermediate MM as the amine coupling partner, and Intermediate 85 as the acid coupling partner, the title compound was isolated as an off-white solid (9.9 mg, 0.0097 mmol, 24% yield) as a TFA salt. LCMS: [$C_{59}H_{75}N_{11}O_5$], desired mass=1017.6, found: m/z=1018.4 [M+H]$^+$.

Example 224

(3RS)-3-[6-(1-{2-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperidin-4-yl)pyridin-3-yl]piperidine-2,6-dione

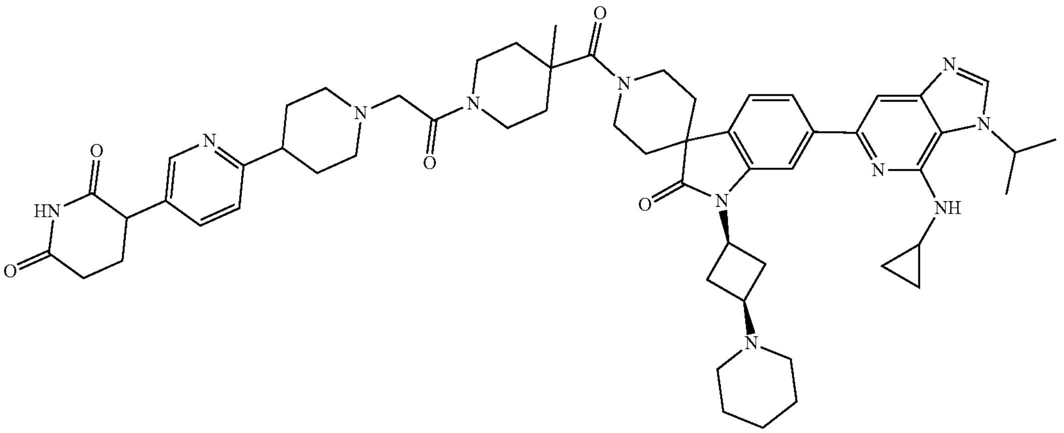 [SMILES: CC(C)n1cnc2cc(-c3ccc4c(c3)N([C@H]3C[C@@H](N5CCCCC5)C3)C(=O)C43CCN(C(=O)C4(C)CCN(C(=O)CN5CCC(c6ccc(C7CCC(=O)NC7=O)cn6)CC5)CC4)CC3)nc(NC3CC3)c21]

Using similar procedures to Example 189, and using Intermediate 85 (step 2) as the acid coupling partner in step 3, the title compound was isolated as an off-white solid (2.7 mg, 0.0027 mmol, 12% yield) as a TFA salt. LCMS: [$C_{57}H_{73}N_{11}O_5$], desired mass=991.6, found: m/z=992.4 $[M+H]^+$.

Example 225

(3RS)-3-[6-(4-{[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidin-1-yl]methyl}piperidin-1-yl)pyridin-3-yl]piperidine-2,6-dione

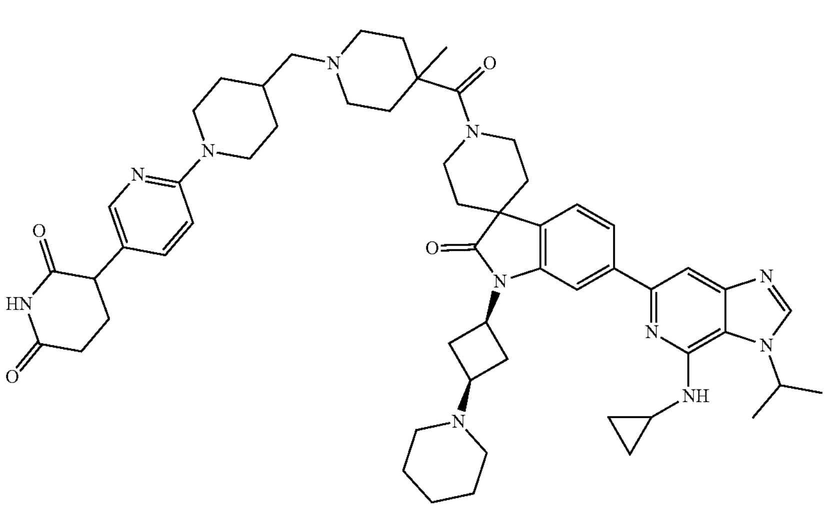 [SMILES: CC(C)n1cnc2cc(-c3ccc4c(c3)N([C@H]3C[C@@H](N5CCCCC5)C3)C(=O)C43CCN(C(=O)C4(C)CCN(CC5CCN(c6ccc(C7CCC(=O)NC7=O)cn6)CC5)CC4)CC3)nc(NC3CC3)c21]

Using similar procedures to Example 202, and using Intermediate B as the amine coupling partner, and Intermediate 102 as the acid coupling partner, the title compound was isolated as an off-white solid (19.6 mg, 0.0194 mmol, 52% yield) as a TFA salt. LCMS: [$C_{56}H_{73}N_{11}O_4$], desired mass=963.6, found: m/z=964.6 $[M+H]^+$, 1H NMR (500 MHz, MeOD) δ 8.91 (s, 1H), 7.94 (d, J=10.2 Hz, 1H), 7.90 (s, 1H), 7.67 (dd, J=18.0, 10.4 Hz, 3H), 7.56 (s, 1H), 7.38 (d, J=9.5 Hz, 1H), 5.19-5.09 (m, 1H), 4.52-4.44 (m, 1H), 4.29 (d, J=13.9 Hz, 2H), 4.2-4.02 (m, 7H), 3.95 (dd, J=12.7, 5.0 Hz, 1H), 3.62 (dt, J=37.4, 12.3 Hz, 6H), 3.13 (d, J=6.9 Hz, 2H), 3.03 (s, 2H), 2.88 (d, J=13.2 Hz, 2H), 2.83-2.73 (m, 2H), 2.60 (d, J=14.7 Hz, 2H), 2.32 (dd, J=12.7, 5.0 Hz, 1H), 2.18 (s, 1H), 2.05 (s, 8H), 1.94 (s, 5H), 1.88 (s, 1H), 1.83 (d, J=17.9 Hz, 1H), 1.79-1.71 (m, 1H), 1.69 (d, J=6.5 Hz, 6H), 1.56 (s, 1H), 1.49 (s, 3H), 1.11 (d, J=6.0 Hz, 2H), 0.93 (s, 2H).

Example 226

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-3-methylphenyl)piperidine-2,6-dione

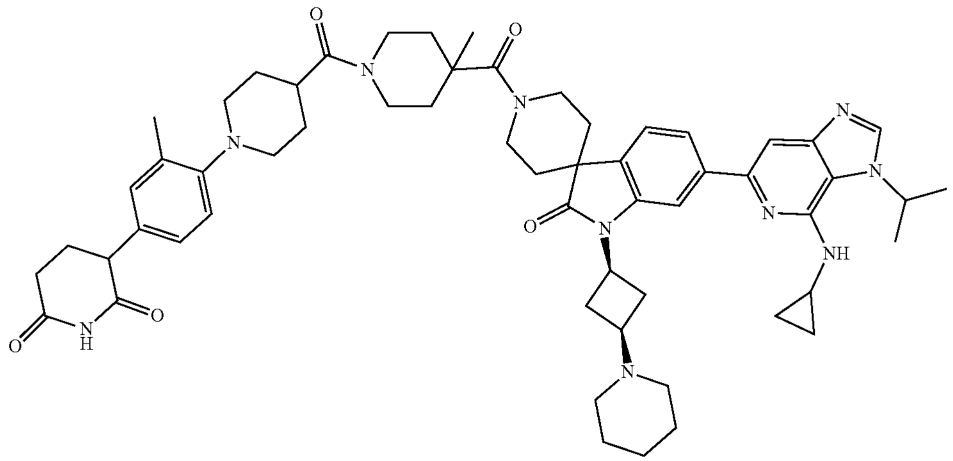 [SMILES: Cc1cc(C2CCC(=O)NC2=O)ccc1N1CCC(C(=O)N2CCC(C)(C(=O)N3CCC4(CC3)C(=O)N([C@H]3C[C@@H](N5CCCCC5)C3)c3cc(-c5cc6ncn(C(C)C)c6c(NC6CC6)n5)ccc34)CC2)CC1]

Using similar procedures to Example 189, and using Intermediate 104 as the acid coupling partner in step 3, the title compound was isolated as an off-white solid (27 mg, 0.027 mmol, 65% yield) as a TFA salt. LCMS: [$C_{58}H_{74}N_{10}O_5$], desired mass=990.6, found: m/z=991.9 $[M+H]^+$, 1H NMR (500 MHz, MeOD) δ 8.93 (s, 1H), 7.69 (s, 2H), 7.64 (s, 1H), 7.57 (s, 1H), 7.27 (s, 1H), 7.18 (d, J=11.3 Hz, 2H), 5.19-5.09 (m, 1H), 4.49 (q, J=8.4 Hz, 1H), 4.15 (s, 2H), 4.09 (s, 4H), 3.86 (dd, J=10.5, 5.2 Hz, 2H), 3.62 (d, J=8.8 Hz, 2H), 3.58 (d, J=12.9 Hz, 3H), 3.23 (d, J=9.8 Hz, 1H), 3.04 (dd, J=32.6, 6.7 Hz, 5H), 2.96-2.86 (m, 2H), 2.78-2.60 (m, 2H), 2.41 (s, 3H), 2.38-2.33 (m, 1H), 2.32-2.18 (m, 2H), 2.04 (d, J=19.0 Hz, 2H), 1.94 (s, 8H), 1.79 (d, J=13.7 Hz, 2H), 1.68 (t, J=7.1 Hz, 6H), 1.65-1.53 (m, 4H), 1.46 (s, 3H), 1.31 (s, 2H), 1.13 (d, J=6.9 Hz, 2H), 0.94 (s, 2H).

Example 227

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-methylphenyl)piperidine-2,6-dione

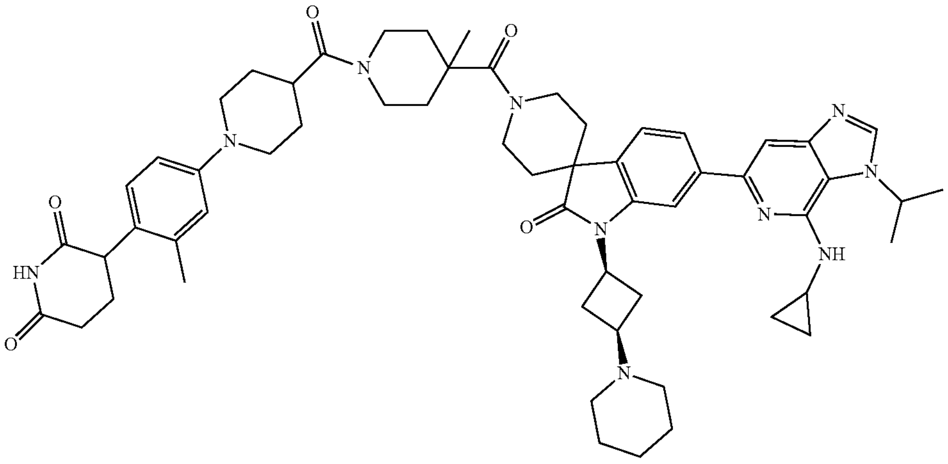 [SMILES: Cc1cc(N2CCC(C(=O)N3CCC(C)(C(=O)N4CCC5(CC4)C(=O)N([C@H]4C[C@@H](N6CCCCC6)C4)c4cc(-c6cc7ncn(C(C)C)c7c(NC7CC7)n6)ccc45)CC3)CC2)ccc1C1CCC(=O)NC1=O]

Using similar procedures to Example 189, and using Intermediate 105 as the acid coupling partner in step 3, the title compound was isolated as an off-white solid (25 mg, 0.0248 mmol, 67% yield) as a TFA salt. LCMS: $[C_{58}H_{74}N_{10}O_5]$, desired mass=990.6, found: m/z=991.9 $[M+H]^+$, 1H NMR (500 MHz, MeOD) δ 8.94 (s, 1H), 7.68 (s, 2H), 7.62 (s, 1H), 7.56 (s, 1H), 7.46 (s, 1H), 7.41 (d, J=2.9 Hz, 2H), 5.14 (p, J=6.5 Hz, 1H), 4.49 (p, J=8.3 Hz, 1H), 4.23-4.05 (m, 6H), 3.89 (d, J=13.0 Hz, 1H), 3.80 (d, J=11.2 Hz, 2H), 3.70-3.53 (m, 6H), 3.22 (d, J=10.8 Hz, 1H), 3.22 (s, 3H), 3.12-2.96 (m, 2H), 3.01 (s, 1H), 2.95-2.65 (m, 5H), 2.46 (s, 3H), 2.42-2.25 (m, 1H), 2.25-2.11 (m, 1H), 2.15 (s, 4H), 2.10-1.86 (m, 8H), 1.80 (q, J=14.5, 13.6 Hz, 2H), 1.69 (d, J=6.6 Hz, 8H), 1.46 (s, 3H), 1.18-1.10 (m, 2H), 0.95 (s, 2H).

Example 228

(3RS)-3-{4-[methyl({1-[(1S,4S)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexanecarbonyl]piperidin-4-yl})amino]phenyl}piperidine-2,6-dione

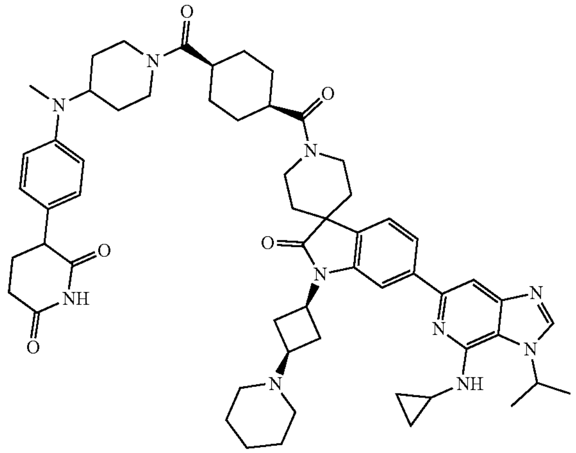 [SMILES: CC(C)n1cnc2cc(-c3ccc4c(c3)N([C@H]3C[C@@H](N5CCCCC5)C3)C(=O)C43CCN(C(=O)[C@H]4CC[C@@H](C(=O)N5CCC(N(C)c6ccc(C7CCC(=O)NC7=O)cc6)CC5)CC4)CC3)nc(NC3CC3)c21]

Using similar procedures to Example 202, and using Intermediate RR as the acid coupling partner and intermediate 65 as the amine coupling partner, the title compound was isolated as an off-white solid (7.5 mg, 0.0076 mmol, 54% yield) as a TFA salt. LCMS: $[C_{58}H_{74}N_{10}O_5]$, desired mass=990.6, found: m/z=991.4 $[M+H]^+$.

Example 229

(3RS)-3-[4-(3-{[1-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidin-4-yl]oxy}prop-1-yn-1-yl)-3-methyl-2-oxo-2,3-dihydro-1H-1,3-benzodiazol-1-yl]piperidine-2,6-dione

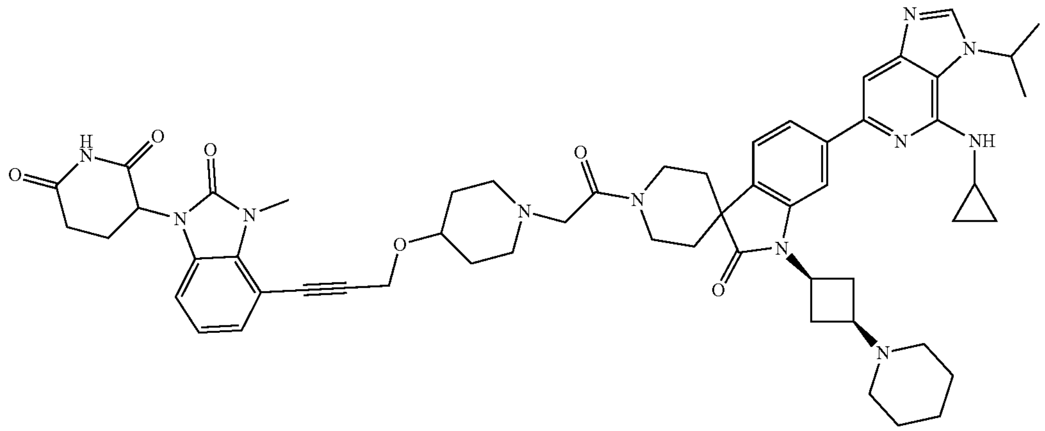 [SMILES: CC(C)n1cnc2cc(-c3ccc4c(c3)N([C@H]3C[C@@H](N5CCCCC5)C3)C(=O)C43CCN(C(=O)CN4CCC(OCC#Cc5cccc6c5n(C)c(=O)n6C5CCC(=O)NC5=O)CC4)CC3)nc(NC3CC3)c21]

Using similar procedures to Intermediate W (step 1), and using Intermediate 108, and Intermediate TT as starting materials, the title compound was isolated as an off-white solid (2.1 mg, 0.0021 mmol, 7% yield) as a TFA salt. LCMS: [$C_{56}H_{67}N_{11}O_6$], desired mass=989.53, found: m/z=990.4 [M+H]$^+$.

Example 230

(3RS)-3-[4-({1-[(1R,4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexanecarbonyl]piperidin-4-yl}methoxy)phenyl]piperidine-2,6-dione

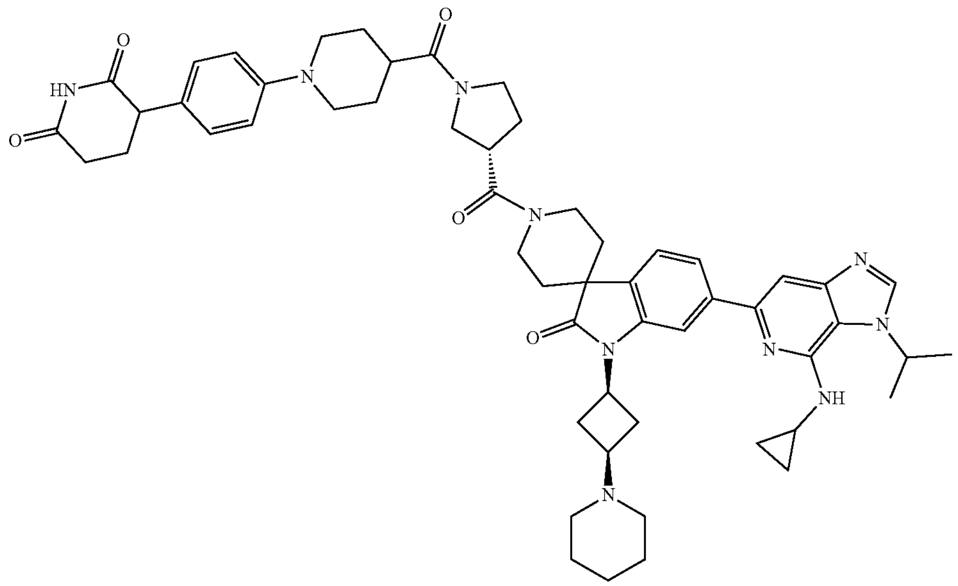 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)C5CCN(c6ccc(C7CCC(=O)NC7=O)cc6)CC5)C4)CC3)nc(NC3CC3)c21]

Using similar procedures to Example 202, and using Intermediate B as the amine coupling partner, and Intermediate 99 as the acid coupling partner, the title compound was isolated as an off-white solid (9.3 mg, 0.0098 mmol, 54% yield) as a TFA salt. LCMS: [$C_{58}H_{73}N_9O_6$], desired mass=991.6, found: m/z=992.5 [M+H]$^+$.

Example 231

(3RS)-3-[6-(4-{2-[(3S)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione

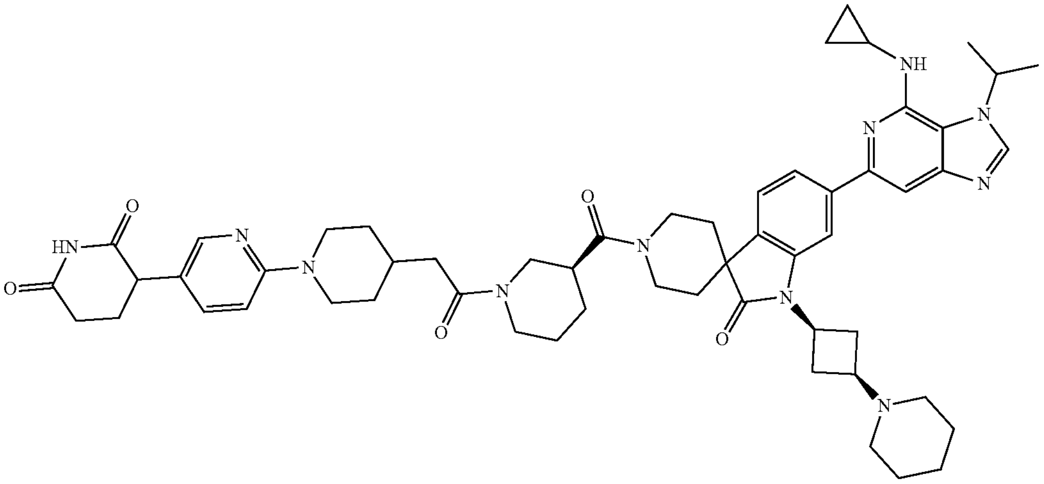 [SMILES: CC(C)n1cnc2cc(-c3ccc4c(c3)N([C@H]3C[C@@H](N5CCCCC5)C3)C(=O)C43CCN(C(=O)[C@H]4CCCN(C(=O)CC5CCN(c6ccc(C7CCC(=O)NC7=O)cn6)CC5)C4)CC3)nc(NC3CC3)c21]

Using similar procedures to Example 189, and using Intermediate GG as the amine coupling partner in step 1 and Intermediate 85 (step 2) as the acid coupling partner in step 3, the title compound was isolated as an off-white solid (13.6 mg, 0.0132 mmol, 29% yield) as a formate. LCMS: [$C_{56}H_{71}N_{11}O_5$], desired mass=977.6, found: m/z=978.4 $[M+H]^+$.

Example 232

(3RS)-3-(4-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]piperidin-1-yl}phenyl)piperidine-2,6-dione

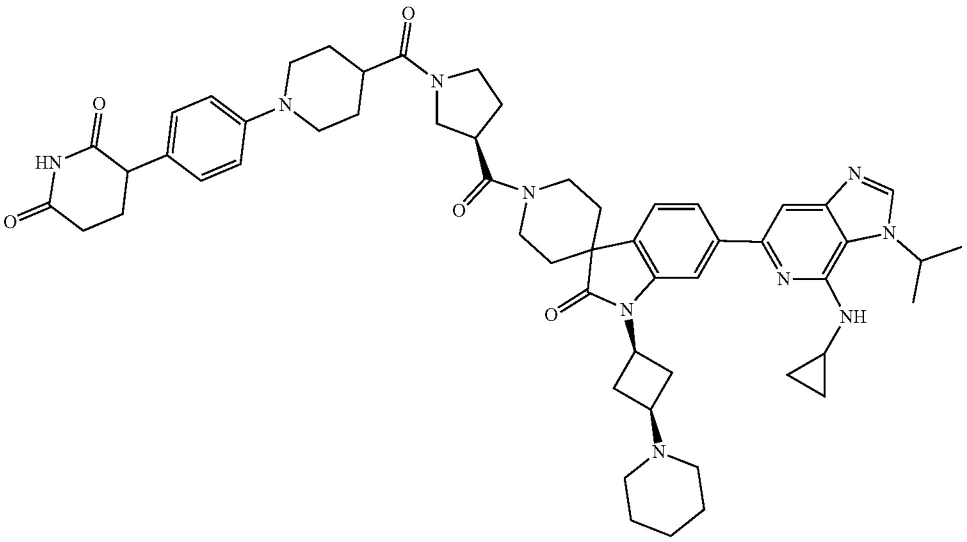 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ccc(C7CCC(=O)NC7=O)cc6)CC5)C4)CC3)nc(NC3CC3)c21]

Using similar procedures to Example 202, and using Intermediate B as the amine coupling partner and Intermediate 100 as the acid coupling partner, the title compound was isolated as an off-white solid (25 mg, 0.0263 mmol, 49% yield) as a free base. LCMS: [$C_{55}H_{68}N_{10}O_5$], desired mass=948.5, found: m/z=949.5 $[M+H]^+$, 1H NMR (500 MHz, MeOD) δ 8.30 (s, 1H), 7.94 (d, J=3.9 Hz, 1H), 7.85 (t, J=6.6 Hz, 1H), 7.59-7.46 (m, 2H), 7.14 (d, J=8.2 Hz, 2H), 7.01 (dd, J=8.6, 4.3 Hz, 2H), 5.04 (p, J=6.6 Hz, 2H), 4.60 (s, 1H), 4.33 (q, J=8.2 Hz, 1H), 4.12 (d, J=14.5 Hz, 2H), 3.98 (d, J=14.3 Hz, 2H), 3.93-3.85 (m, 1H), 3.85-3.73 (m, 4H), 3.73-3.45 (m, 4H), 3.06 (td, J=7.2, 3.7 Hz, 1H), 2.81 (d, J=9.2 Hz, 4H), 2.76-2.57 (m, 5H), 2.45 (s, 4H), 2.38-2.25 (m, 2H), 2.21 (q, J=6.8, 6.0 Hz, 2H), 1.92 (d, J=31.5 Hz, 7H), 1.64 (t, J=7.1 Hz, 6H), 1.52 (s, 2H), 1.31 (s, 2H), 0.90 (dt, J=7.0, 3.6 Hz, 2H), 0.68 (t, J=3.1 Hz, 2H).

Example 233

1-(4-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl) pyrrolidine-1-carbonyl]piperidin-1-yl}phenyl)-1,3-diazinane-2,4-dione

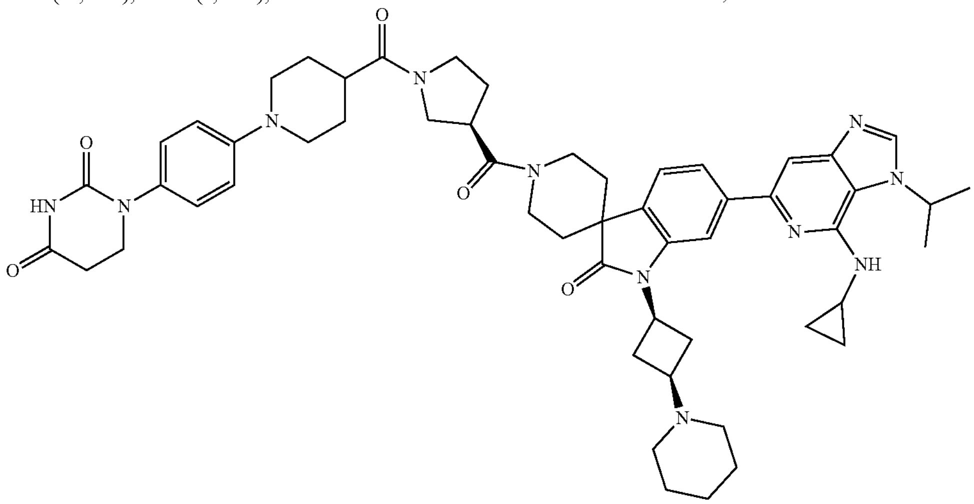

Using similar procedures to Example 202, and using Intermediate B as the amine coupling partner and Intermediate 101 as the acid coupling partner, the title compound was isolated as an off-white solid (11.9 mg, 0.0125 mmol, 69% yield) as a TFA salt. LCMS: [$C_{54}H_{67}N_{11}O_5$], desired mass=949.5, found: m/z=950.5 $[M+H]^+$, Example 234

(3RS)-3-(4-{[(1R,4R)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]cyclohexyl] oxy}phenyl)piperidine-2,6-dione

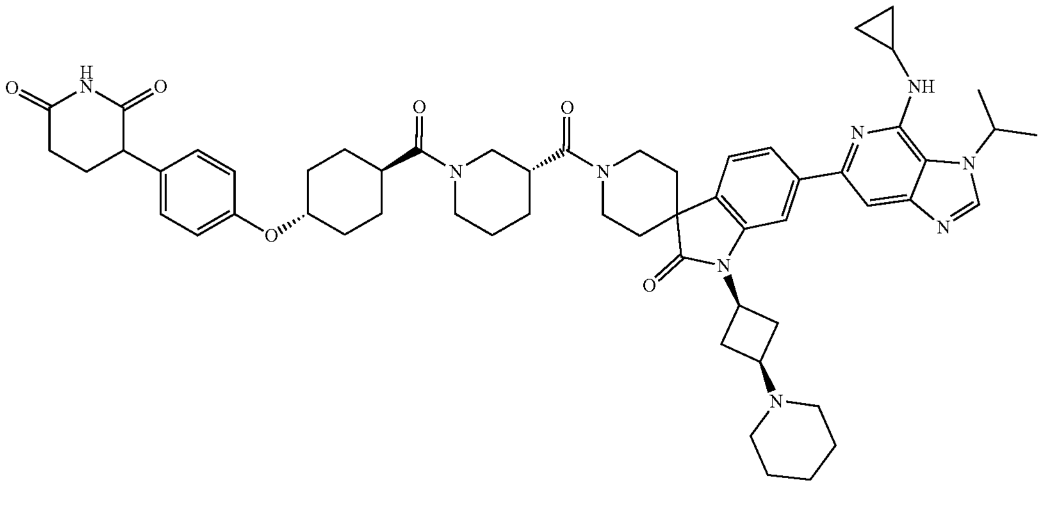 [SMILES: CC(C)n1cnc2cc(-c3ccc4c(c3)N([C@H]3C[C@@H](N5CCCCC5)C3)C(=O)C43CCN(C(=O)[C@@H]4CCCN(C(=O)[C@H]5CC[C@H](Oc6ccc(C7CCC(=O)NC7=O)cc6)CC5)C4)CC3)nc(NC3CC3)c21]

Using similar procedures to Example 202, and using Intermediate HH as the amine coupling partner and intermediate 52 as the acid coupling partner, the title compound was isolated as an off-white solid (11.7 mg, 0.0114 mmol, 25% yield) as a formate. LCMS: [$C_{57}H_{71}N_9O_6$], desired mass=977.6, found: m/z=978.4 [M+H]$^+$.

Example 235

(3RS)-3-[6-(4-{2-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione

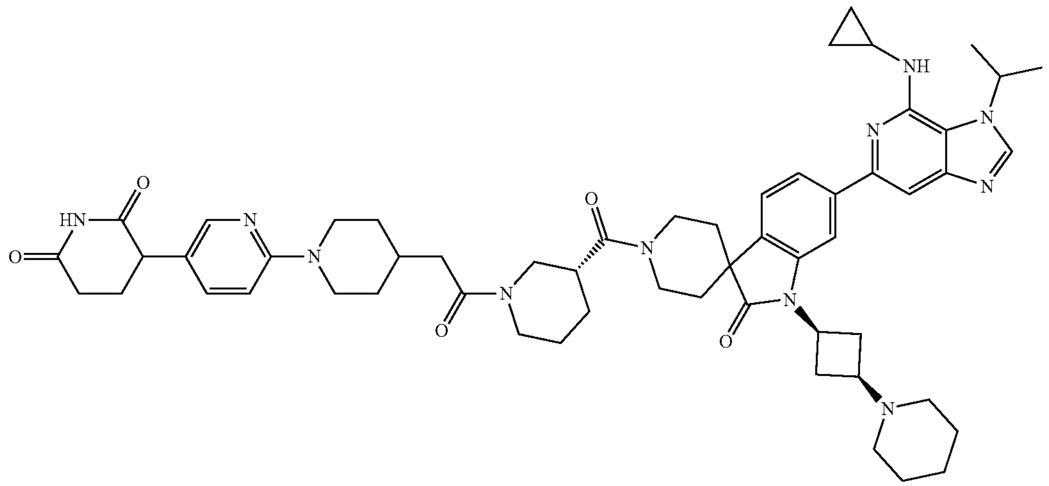 [SMILES: CC(C)n1cnc2cc(-c3ccc4c(c3)N([C@H]3C[C@@H](N5CCCCC5)C3)C(=O)C43CCN(C(=O)[C@@H]4CCCN(C(=O)CC5CCN(c6ccc(C7CCC(=O)NC7=O)cn6)CC5)C4)CC3)nc(NC3CC3)c21]

Using similar procedures to Example 202, and using Intermediate HH as the amine coupling partner and Intermediate 85 (step 2) as the acid coupling partner, the title compound was isolated as an off-white solid (21 mg, 0.0212 mmol, 47% yield) as a TFA salt. LCMS: [$C_{56}H_{71}N_{11}O_5$], desired mass=977.6, found: m/z=978.4 [M+H]$^+$.

Example 236

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridazin-3-yl)piperidine-2,6-dione

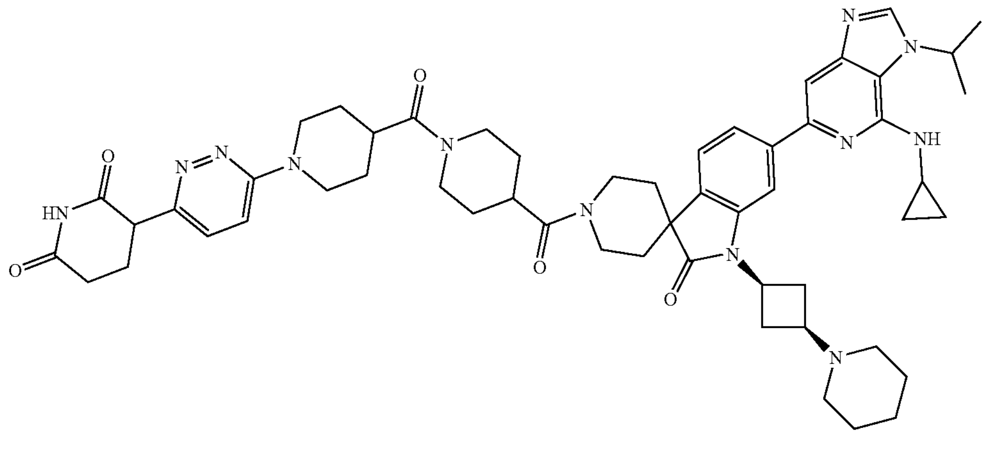 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)nn6)CC5)CC4)CC3)nc(NC3CC3)c21]

Using similar procedures to Example 202, and using Intermediate B as the amine coupling partner and Intermediate 95 as the acid coupling partner, the title compound was isolated as an off-white solid (27.7 mg, 0.0287 mmol, 53% yield) as a TFA salt. LCMS: [$C_{54}H_{68}N_{12}O_5$], desired mass=964.5, found: m/z=965.4 $[M+H]^+$, 1H NMR (500 MHz, MeOD) δ 8.95 (s, 1H), 7.99 (d, J=10.0 Hz, 1H), 7.91 (d, J=9.9 Hz, 1H), 7.67 (s, 2H), 7.62 (s, 1H), 7.56 (s, 1H), 5.14 (p, J=6.5 Hz, 1H), 4.60 (s, 1H), 4.53-4.45 (m, 2H), 4.35-4.11 (m, 7H), 4.04 (s, 1H), 3.93 (dd, J=14.1, 7.5 Hz, 1H), 3.64 (q, J=8.3 Hz, 1H), 3.57 (d, J=12.6 Hz, 3H), 3.49 (s, 1H), 3.31 (s, 4H), 3.25 (s, 3H), 3.15 (d, J=12.0 Hz, 1H), 3.10-3.04 (m, 1H), 3.01 (s, 2H), 2.95-2.75 (m, 6H), 2.49-2.38 (m, 1H), 2.31 (dt, J=13.4, 4.7 Hz, 1H), 2.02 (d, J=17.2 Hz, 6H), 1.91 (d, J=5.5 Hz, 3H), 1.80 (d, J=13.5 Hz, 2H), 1.69 (d, J=6.6 Hz, 6H), 1.58 (s, 1H), 1.14 (d, J=6.4 Hz, 2H), 0.95 (s, 2H).

Example 237

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}-2-fluorophenyl)piperidine-2,6-dione

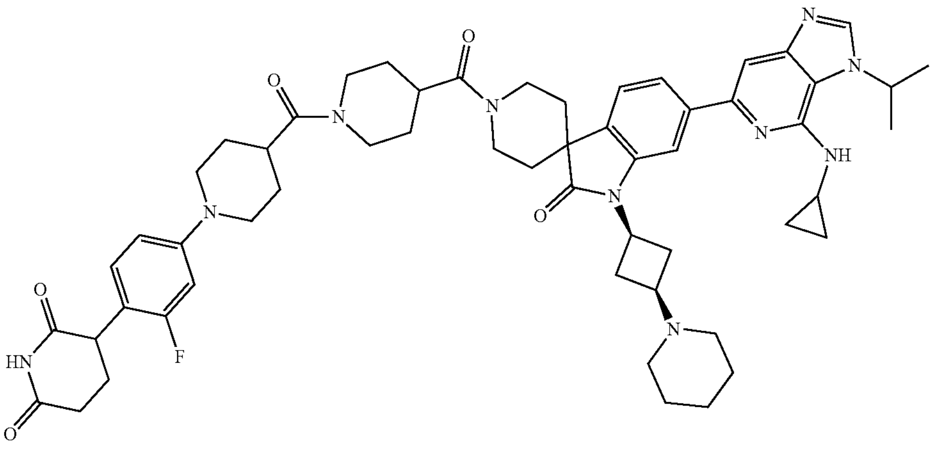 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)c(F)c6)CC5)CC4)CC3)nc(NC3CC3)c21]

6-(4-(cyclopropylamino)-3-isopropyl-3H-imidazo[4,5-c]pyridin-6-yl)-1-((1s,3s)-3-(piperidin-1-yl)cyclobutyl)-1'-(piperidine-4-carbonyl)spiro[indoline-3,4'-piperidin]-2-one was prepared by similar procedures to Example 202 (steps 1 and 2) using Intermediate B as the amine coupling partner and 1-(tert-butoxycarbonyl)piperidine-4-carboxylic acid as the acid coupling partner in step 1. Coupling with Intermediate 98 using conditions similar to NRX-0412246 afforded the title compound as an off-white solid (25.6 mg, 0.0254 mmol, 47% yield) as a TFA salt. LCMS: [$C_{56}H_{69}FN_{10}O_5$], desired mass=980.5, found: m/z=981 $[M+H]^+$, 1H NMR (500 MHz, MeOD) δ 8.94 (s, 1H), 7.65 (d, J=22.0 Hz, 3H), 7.57 (s, 1H), 7.19 (t, J=8.6 Hz, 1H), 6.86 (dd, J=18.5, 11.1 Hz, 2H), 5.14 (p, J=6.5 Hz, 1H), 4.60 (s, 1H), 4.51 (q, J=8.2 Hz, 1H), 4.23-4.12 (m, 4H), 4.05 (s, 1H), 3.96 (dd, J=11.9, 5.1 Hz, 1H), 3.92 (s, 1H), 3.81 (s, 3H), 3.74-3.60 (m, 1H), 3.59 (t, J=11.6 Hz, 3H), 3.06 (dd, J=6.9, 3.4 Hz, 1H), 3.02-2.64 (m, 6H), 2.34-2.22 (m, 1H), 2.19-2.10 (m, 1H), 2.03 (dd, J=22.9, 6.7 Hz, 5H), 1.90 (s, 12H), 1.79 (d, J=14.0 Hz, 2H), 1.69 (d, J=6.5 Hz, 6H), 1.57 (d, J=13.1 Hz, 2H), 1.31 (s, 1H), 1.14 (d, J=6.5 Hz, 2H), 0.95 (s, 2H).

Example 238

3-(4-(((1R,4R)-4-((1R,5S,6S)-6-(6-(4-(cyclopropylamino)-3-isopropyl-3H-imidazo[4,5-c]pyridin-6-yl)-2-oxo-1-((1S,3S)-3-(piperidin-1-yl)cyclobutyl) spiro[indoline-3,4'-piperidine]-1'-carbonyl)-3-azabicyclo[3.1.1]heptane-3-carbonyl)cyclohexyl) oxy)phenyl)piperidine-2,6-dione

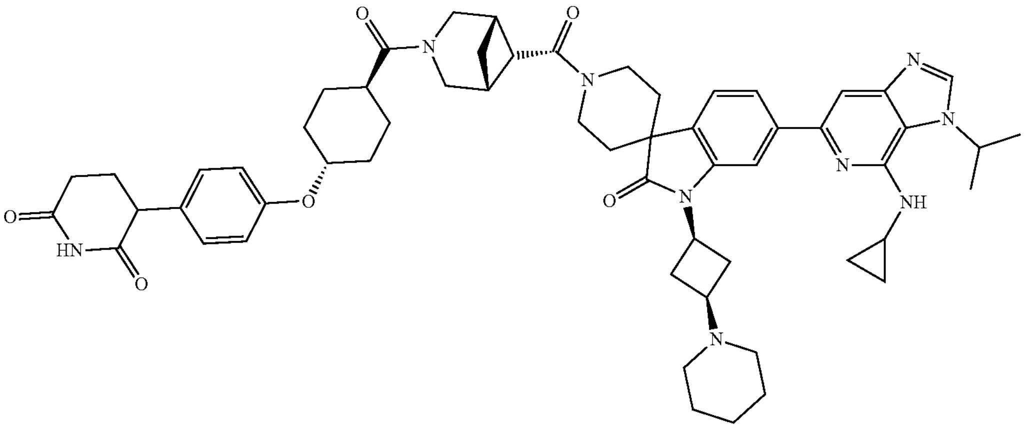

Using similar methods to Example 202 with EDCI/HOBt coupling of Intermediate II and intermediate 52, the title compound was isolated as an off-white solid (8.2 mg, 0.0077 mmol, 17% yield) as a TFA salt. LCMS: [$C_{58}H_{71}N_9O_6$], desired mass=989.5, found: m/z=990.5 $[M+H]^+$.

Example 239

3-(6-(4-((1R,5S,6S)-6-(6-(4-(cyclopropylamino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)-3-Azabicyclo[3.1.1] heptane-3-carbonyl)piperidin-1-yl)pyridin-3-yl) piperidine-2,6-dione Using similar methods to Example 202 with EDCI/HOBt coupling of Intermediate II and 1-(5-(2,6-dioxopiperidin-3-yl)pyridin-2-yl)piperidine-4-carboxylic acid (Intermediate 11, step 2), the title compound was isolated as an off-white solid (30.7 mg, 0.0304 mmol, 68% yield) as a TFA salt. LCMS: [$C_{56}H_{69}N_{11}O_5$], desired mass=975.5, found: m/z=976.6 $[M+H]^+$, 1H NMR (500 MHz, MeOD) δ 8.92 (s, 1H), 7.97 (d, J=8.5 Hz, 1H), 7.86 (s, 1H), 7.69 (s, 1H), 7.63-7.59 (m, 2H), 7.56 (s, 1H), 7.48-7.40 (m, 1H), 5.13 (t, J=6.5 Hz, 1H), 4.58 (dd, J=23.4, 10.1 Hz, 1H), 4.52-4.44 (m, 1H), 4.25 (s, 2H), 4.15 (d, J=13.1 Hz, 1H), 4.01 (s, 4H), 3.84 (dd, J=22.8, 13.0 Hz, 3H), 3.62 (t, J=8.0 Hz, 1H), 3.57 (s, 4H), 3.52 (d, J=13.9 Hz, 1H), 3.44 (s, 1H), 3.06 (s, 1H), 2.99 (s, 3H), 2.90-2.81 (m, 4H), 2.78 (s, 1H), 2.27 (s, 2H), 2.13 (d, J=13.3 Hz, 1H), 2.06 (s, 1H), 2.01 (s, 3H), 1.96 (s, 1H), 1.92 (s, 6H), 1.80 (t, J=12.9 Hz, 3H), 1.69 (d, J=6.5 Hz, 6H), 1.57 (s, 1H), 1.44 (dd, J=9.7, 4.5 Hz, 1H), 1.31 (s, 2H), 1.13 (s, 2H), 0.93 (s, 2H).

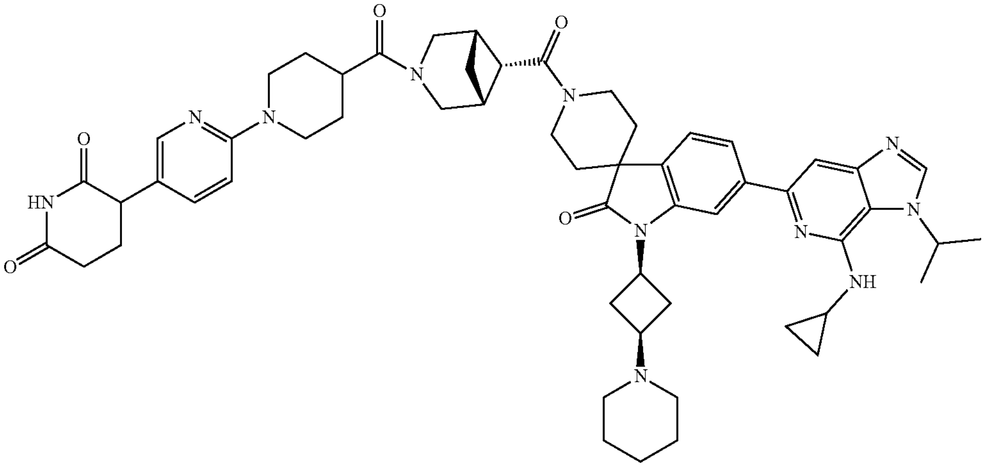 [SMILES: CC(C)n1cnc2cc(-c3ccc4c(c3)N([C@H]3C[C@@H](N5CCCCC5)C3)C(=O)C43CCN(C(=O)[C@H]4[C@@H]5C[C@H]4CN(C(=O)C4CCN(c6ccc(C7CCC(=O)NC7=O)cn6)CC4)C5)CC3)nc(NC3CC3)c21]

Example 240

3-(6-(4-(2-((1R,5S,6S)-6-(6-(4-(cyclopropylamino)-3-isopropyl-3H-imidazo[4,5-c]pyridin-6-yl)-2-oxo-1-((1S,3S)-3-(piperidin-1-yl)cyclobutyl)spiro[indoline-3,4'-piperidine]-1'-carbonyl)-3-azabicyclo[3.1.1]heptan-3-yl)-2-oxoethyl)piperidin-1-yl)pyridin-3-yl)piperidine-2,6-dione

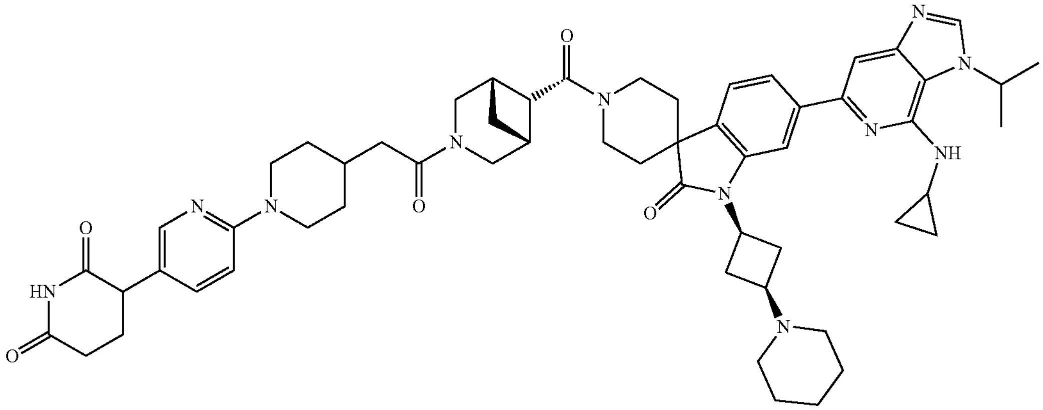

Using similar methods to Example 202 with EDCI/HOBt coupling of Intermediate II and 1-(5-(2,6-dioxopiperidin-3-yl)pyridin-2-yl)piperidine-4-carboxylic acid (Intermediate 85 (step 2)), the title compound was isolated as an off-white solid (3.7 mg, 0.0033 mmol, 7.4% yield) as a TFA salt. LCMS: [$C_{57}H_{71}N_{11}O_5$], desired mass=989.6, found: m/z=990.4 $[M+H]^+$.

Example 241

3-(4-{[(1R,4R)-4-[6-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]cyclohexyl]oxy}phenyl)piperidine-2,6-dione

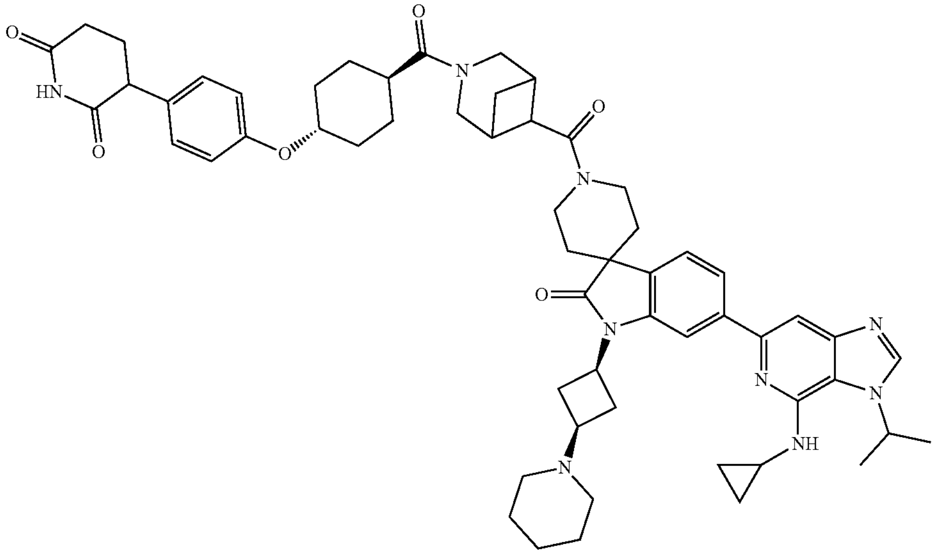 [SMILES: CC(C)n1cnc2cc(-c3ccc4c(c3)N([C@H]3C[C@@H](N5CCCCC5)C3)C(=O)C43CCN(C(=O)C4C5CC4CN(C(=O)[C@H]4CC[C@H](Oc6ccc(C7CCC(=O)NC7=O)cc6)CC4)C5)CC3)nc(NC3CC3)c21]

Using similar methods to Example 238, and substituting 3-(tert-butoxycarbonyl)-3-azabicyclo[3.1.1]heptane-6-carboxylic acid (mixture of isomers) for (1R,5S,6s)-3-(tert-butoxycarbonyl)-3-azabicyclo[3.1.1]heptane-6-carboxylic acid, the title compound was isolated as an off-white solid (17.5 mg, 0.0168 mmol, 38% yield) as a TFA salt. LCMS: [$C_{58}H_{71}N_9O_6$], desired mass=989.5, found: m/z=990.4 $[M+H]^+$.

Example 242

(3RS)-3-[6-(4-{3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]azetidine-1-carbonyl}piperidin-1-yl)pyridin-3-yl]piperidine-2,6-dione

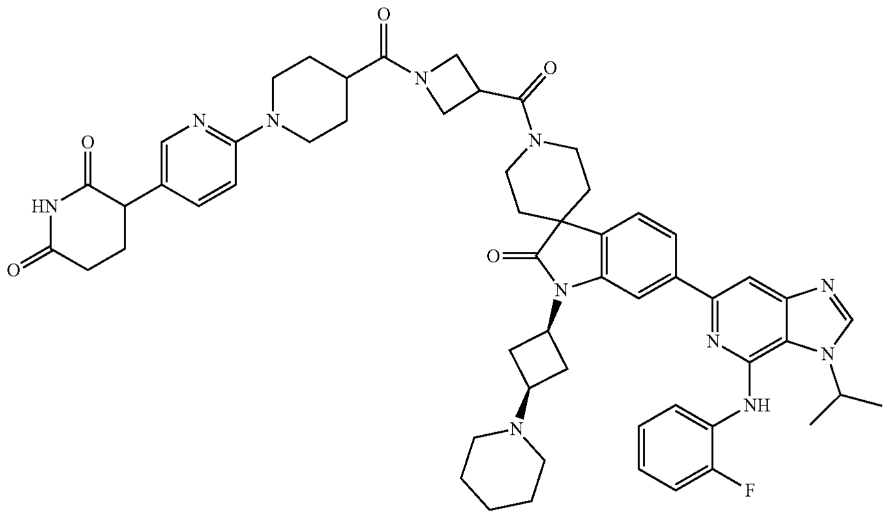 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cn6)CC5)C4)CC3)nc(Nc3ccccc3F)c21]

Using similar methods to Example 202 with EDCI/HOBt coupling of Intermediate JJ and intermediate 11 (step 2), the title compound was isolated as an off-white solid (2.3 mg, 0.0023 mmol, 20% yield) as a TFA salt. LCMS: [$C_{56}H_{64}FN_{11}O_5$], desired mass=989.5, found: m/z=990.4 $[M+H]^+$.

Example 243

(3RS)-3-(6-{4-[4-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperazine-1-carbonyl]piperidin-1-yl}pyridin-3-yl)piperidine-2,6-dione

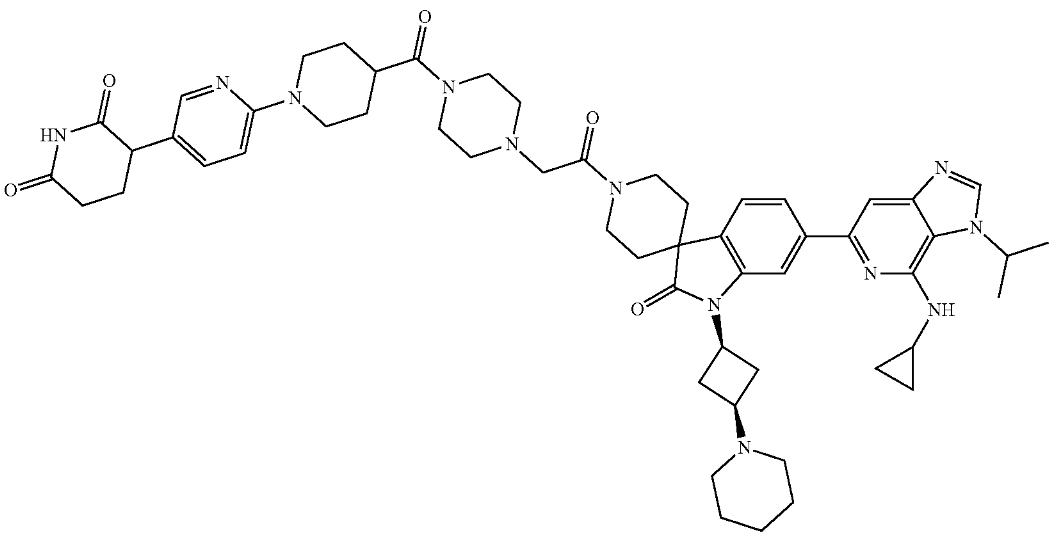 [SMILES: CC(C)n1cnc2cc(-c3ccc4c(c3)N([C@H]3C[C@@H](N5CCCCC5)C3)C(=O)C43CCN(C(=O)CN4CCN(C(=O)C5CCN(c6ccc(C7CCC(=O)NC7=O)cn6)CC5)CC4)CC3)nc(NC3CC3)c21]

Using procedures similar to Example 185 and using Intermediate EE and intermediate 11 (step 2) as the coupling partners, the title compound was isolated as an off-white solid (19.6 mg, 0.0194 mmol, 52% yield) as a TFA salt. LCMS: [$C_{55}H_{70}N_{12}O_5$], desired mass=978.5, found: m/z=979.6 $[M+H]^+$, 1H NMR (500 MHz, MeOD) δ 8.89 (s, 1H), 7.96 (dd, J=9.4, 2.2 Hz, 1H), 7.89 (d, J=2.3 Hz, 1H), 7.71 (d, J=7.9 Hz, 1H), 7.67-7.58 (m, 2H), 7.56 (s, 1H), 7.40 (d, J=9.5 Hz, 1H), 5.13 (p, J=6.6 Hz, 1H), 4.48 (q, J=8.2 Hz, 1H), 4.47-4.33 (m, 2H), 4.29-4.20 (m, 4H), 4.04 (s, 5H), 3.96 (dd, J=12.6, 4.8 Hz, 2H), 3.69-3.53 (m, 4H), 3.46-3.33 (m, 4H), 3.22 (d, J=9.0 Hz, 4H), 3.12-2.98 (m, 2H), 3.02 (s, 2H), 2.88 (q, J=11.5, 10.3 Hz, 3H), 2.86-2.71 (m, 2H), 2.32 (qd, J=12.8, 5.3 Hz, 1H), 2.24-2.16 (m, 1H), 2.02-1.85 (m, 2H), 1.80 (d, J=13.2 Hz, 1H), 1.69 (d, J=6.5 Hz, 6H), 1.58 (s, 2H), 1.31 (s, 1H), 1.11 (d, J=6.4 Hz, 2H), 0.96-0.92 (m, 2H).

Examples 244-303 were synthesized as summarized by Reaction Scheme AA using automated synthesis with a Hamilton Robotics Vantage system. In step 1, the HPK1 binder moieties (Intermediates B or C) were coupled to commercially-available Boc-protected amino acids under standard amide bond forming conditions. In step 2, the Boc groups were removed under acidic conditions. In step 3, the LHM moieties (Intermediate 11 (step 2) and Intermediate 74) were appended using standard amide bond forming conditions to give the final products.

Example 244

(3RS)-3-(4-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}phenyl)piperidine-2,6-dione

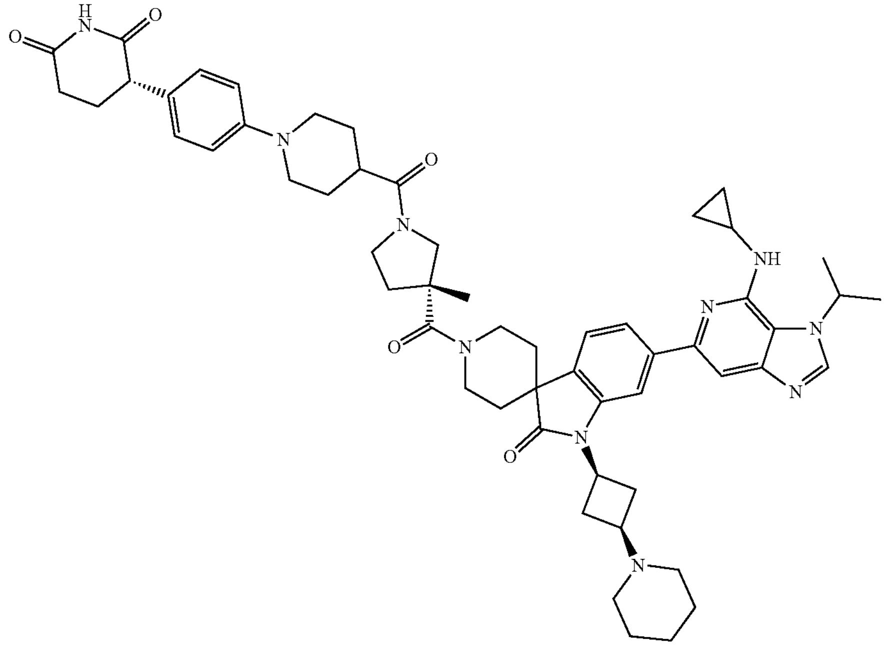 [SMILES: CC(C)n1cnc2cc(-c3ccc4c(c3)N([C@H]3C[C@@H](N5CCCCC5)C3)C(=O)C43CCN(C(=O)[C@]4(C)CCN(C(=O)C5CCN(c6ccc([C@@H]7CCC(=O)NC7=O)cc6)CC5)C4)CC3)nc(NC3CC3)c21]

LCMS: $C_{56}H_{70}N_{10}O_5$ desired mass: 962.5, found: m/z=963.3 $[M+H]^+$.

Example 245

(3RS)-3-(6-{4-[(2R,4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-2-methylpiperidine-1-carbonyl]piperidin-1-yl}pyridin-3-yl)piperidine-2,6-dione

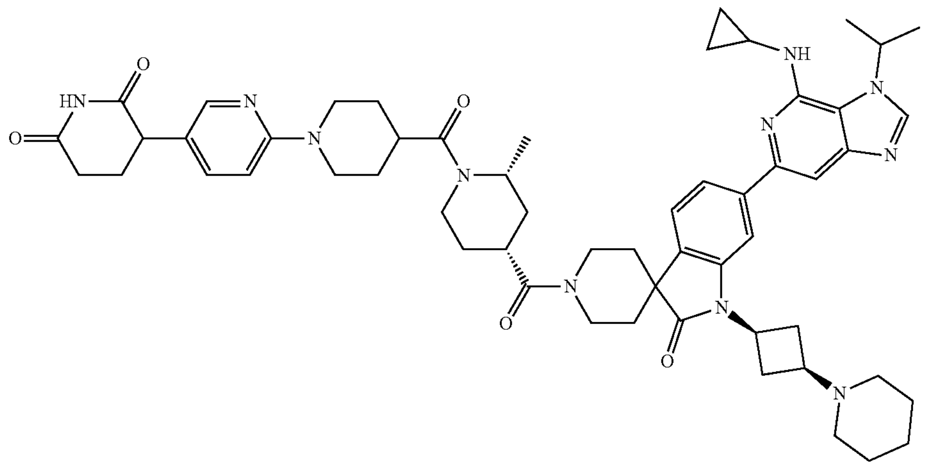 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ccc(C7CCC(=O)NC7=O)cn6)CC5)[C@H](C)C4)CC3)nc(NC3CC3)c21]

LCMS: $C_{56}H_{71}N_{11}O_5$ desired mass: 977.6, found: m/z=978.4 $[M+H]^+$.

Example 246

(3RS)-3-(6-{4-[(3S,5R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-methylpiperidine-1-carbonyl]piperidin-1-yl}pyridin-3-yl)piperidine-2,6-dione

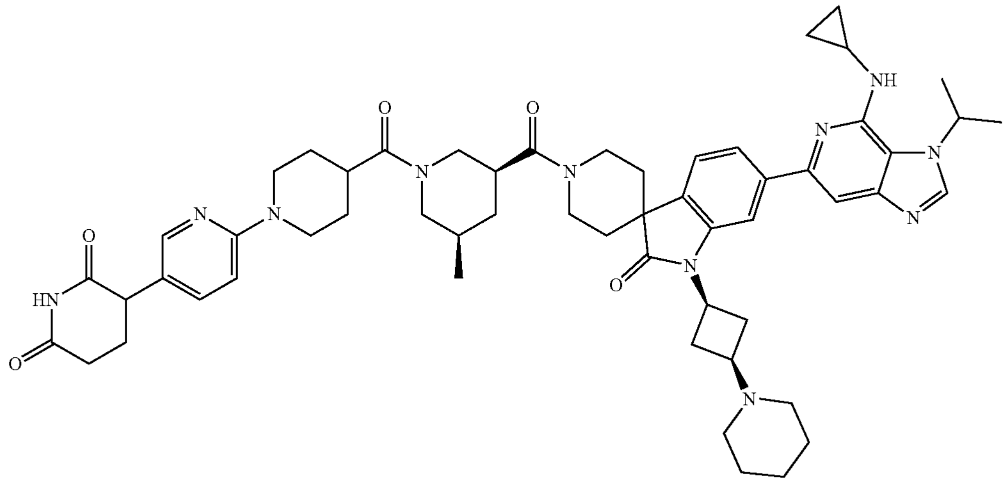 [SMILES: CC(C)n1cnc2cc(-c3ccc4c(c3)N([C@H]3C[C@@H](N5CCCCC5)C3)C(=O)C43CCN(C(=O)[C@H]4C[C@@H](C)CN(C(=O)C5CCN(c6ccc(C7CCC(=O)NC7=O)cn6)CC5)C4)CC3)nc(NC3CC3)c21]

LCMS: $C_{56}H_{71}N_{11}O_5$ desired mass: 977.6, found: m/z=979.5 $[M+H]^+$.

Example 247

(3RS)-3-(6-{4-[(3S,4S)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpiperidine-1-carbonyl]piperidin-1-yl}pyridin-3-yl)piperidine-2,6-dione

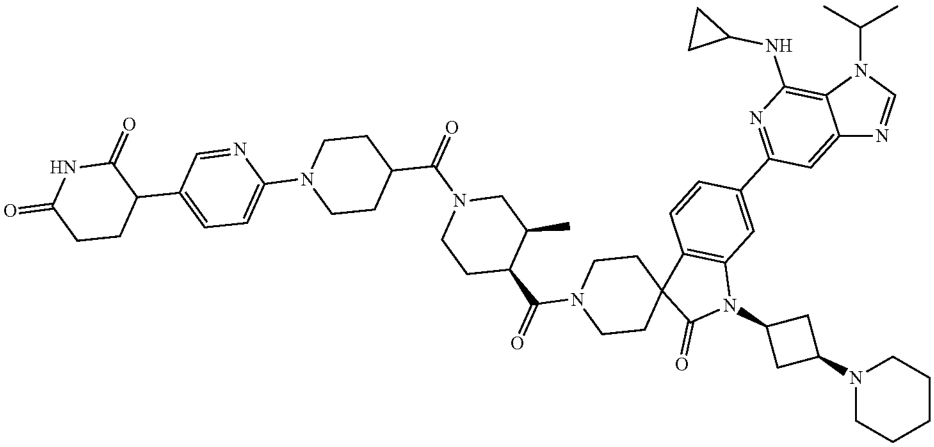 [SMILES: CC(C)n1cnc2cc(-c3ccc4c(c3)N([C@H]3C[C@@H](N5CCCCC5)C3)C(=O)C43CCN(C(=O)[C@H]4CCN(C(=O)C5CCN(c6ccc(C7CCC(=O)NC7=O)cn6)CC5)C[C@H]4C)CC3)nc(NC3CC3)c21]

LCMS: $C_{56}H_{71}N_{11}O_5$ desired mass: 977.6, found: m/z=978.4 $[M+H]^+$.

Example 248

(3RS)-3-(6-{4-[(3R,4S)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpyrrolidine-1-carbonyl]piperidin-1-yl}pyridin-3-yl)piperidine-2,6-dione

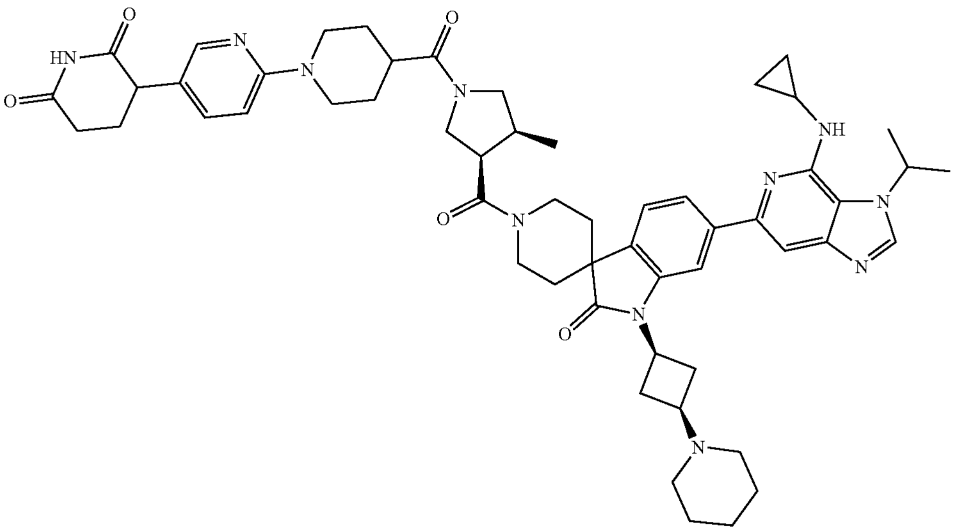 [SMILES: CC(C)n1cnc2cc(-c3ccc4c(c3)N([C@H]3C[C@@H](N5CCCCC5)C3)C(=O)C43CCN(C(=O)[C@H]4CN(C(=O)C5CCN(c6ccc(C7CCC(=O)NC7=O)cn6)CC5)C[C@H]4C)CC3)nc(NC3CC3)c21]

LCMS: $C_{55}H_{69}N_{11}O_5$ desired mass: 963.5, found: m/z=986.1 $[M+Na]^+$.

Example 249

(3RS)-3-(6-{4-[(2R,3R)-3-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-2-methylpyrrolidine-1-carbonyl]piperidin-1-yl}pyridin-3-yl)piperidine-2,6-dione

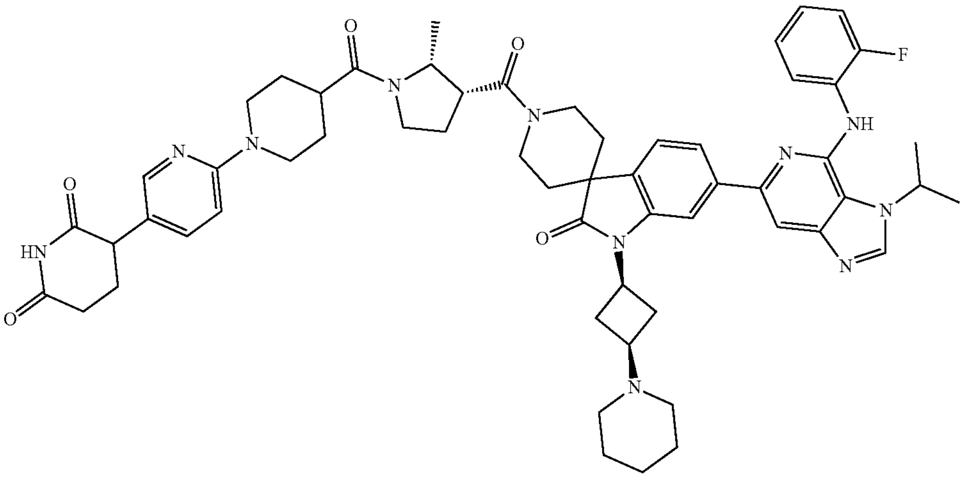 [SMILES: CC(C)n1cnc2cc(-c3ccc4c(c3)N([C@H]3C[C@@H](N5CCCCC5)C3)C(=O)C43CCN(C(=O)[C@@H]4CCN(C(=O)C5CCN(c6ccc(C7CCC(=O)NC7=O)cn6)CC5)[C@@H]4C)CC3)nc(Nc3ccccc3F)c21]

LCMS: $C_{58}H_{68}FN_{11}O_5$ desired mass: 1017.5, found: m/z=1018.4 $[M+H]^+$.

Example 250

(3RS)-3-(6-{4-[5-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3,3-dimethylpiperidine-1-carbonyl]piperidin-1-yl}pyridin-3-yl)piperidine-2,6-dione

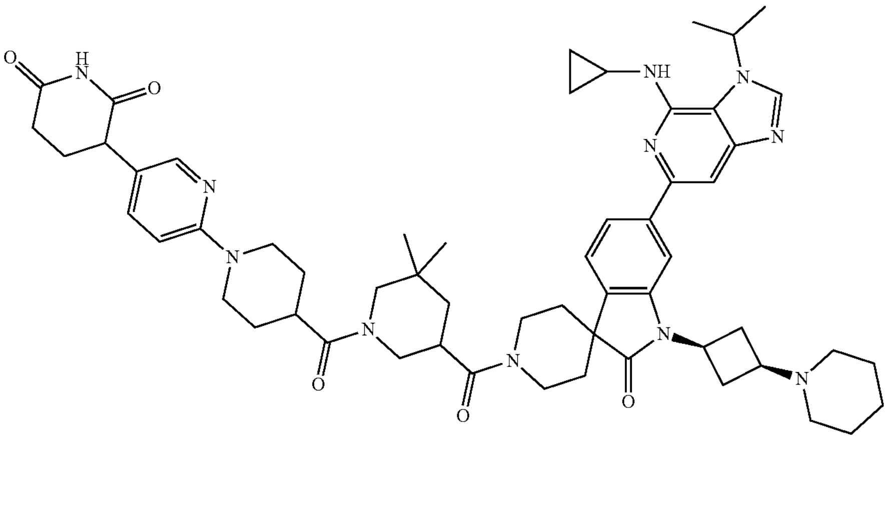 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cn6)CC5)CC(C)(C)C4)CC3)nc(NC3CC3)c21]

LCMS: $C_{57}H_{73}N_{11}O_5$ desired mass: 991.6, found: m/z=992.3 $[M+H]^+$.

Example 251

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-1-methyl-2-azabicyclo[2.2.1]heptane-2-carbonyl]piperidin-1-yl}pyridin-3-yl)piperidine-2,6-dione

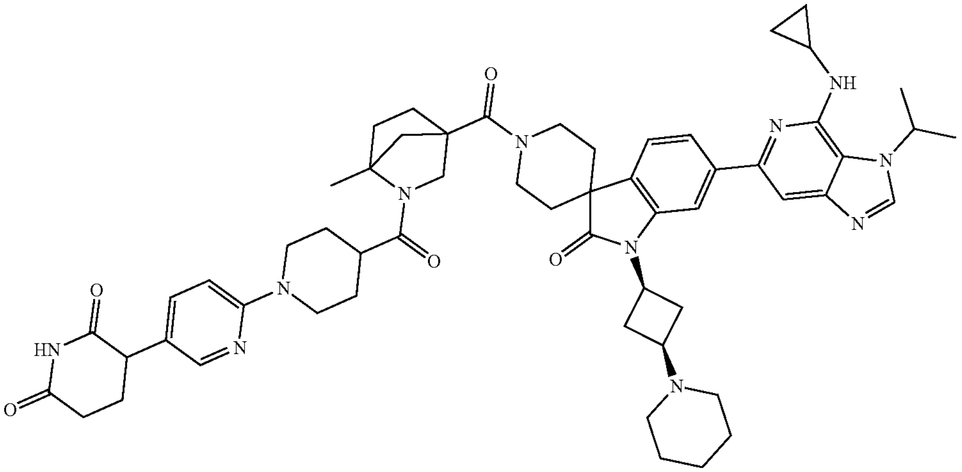 [SMILES: CC(C)n1cnc2cc(-c3ccc4c(c3)N([C@H]3C[C@@H](N5CCCCC5)C3)C(=O)C43CCN(C(=O)C45CCC(C)(C4)N(C(=O)C4CCN(c6ccc(C7CCC(=O)NC7=O)cn6)CC4)C5)CC3)nc(NC3CC3)c21]

LCMS: $C_{57}H_{71}N_{11}O_5$ desired mass: 989.6, found: m/z=990.4 $[M+H]^+$.

Example 252

(3RS)-3-(4-{4-[(4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3,3-dimethylpyrrolidine-1-carbonyl]piperidin-1-yl}phenyl)piperidine-2,6-dione

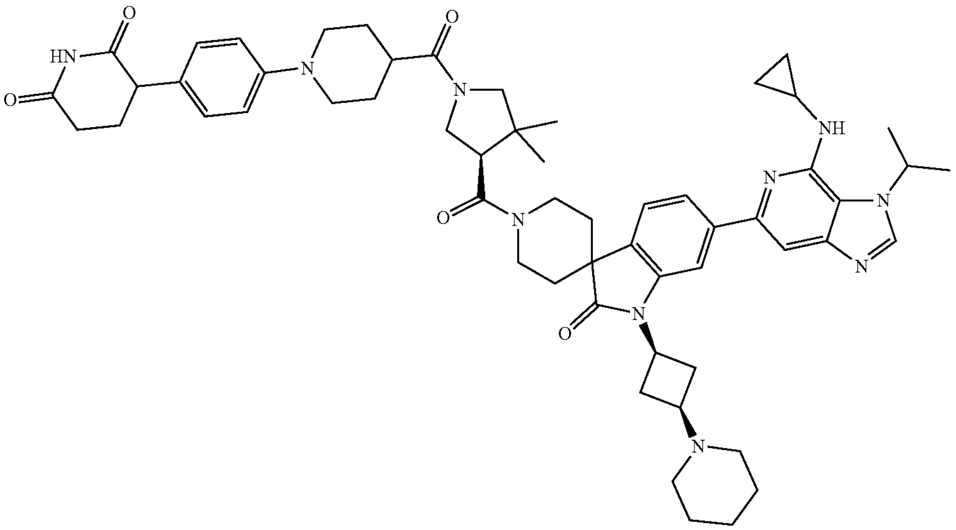 [SMILES: CC(C)n1cnc2cc(-c3ccc4c(c3)N([C@H]3C[C@@H](N5CCCCC5)C3)C(=O)C43CCN(C(=O)[C@H]4CN(C(=O)C5CCN(c6ccc(C7CCC(=O)NC7=O)cc6)CC5)CC4(C)C)CC3)nc(NC3CC3)c21]

LCMS: $C_{57}H_{72}N_{10}O_5$ desired mass: 976.5, found: m/z=977.3 $[M+H]^+$.

Example 253

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methylpiperidine-1-carbonyl]piperidin-1-yl}pyridin-3-yl)piperidine-2,6-dione

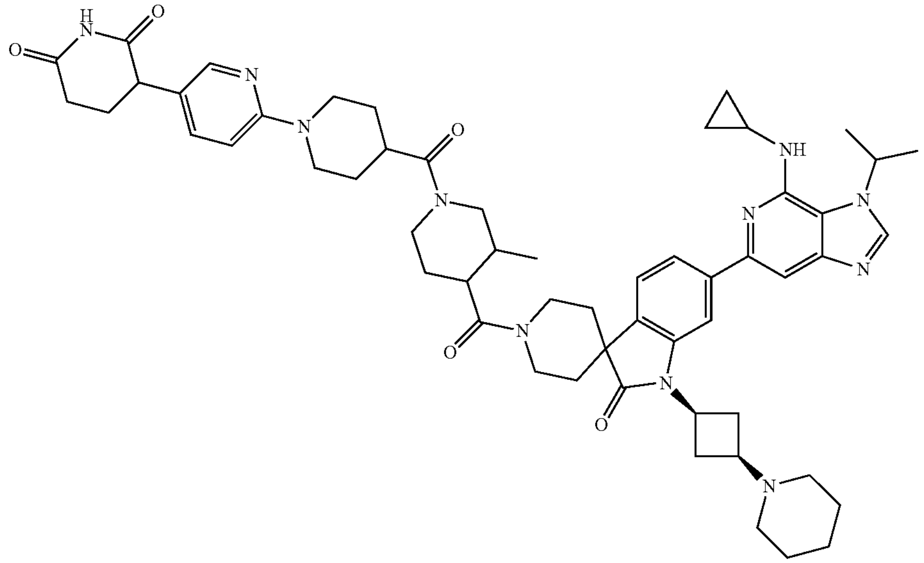 [SMILES: CC1CN(C(=O)C2CCN(c3ccc(C4CCC(=O)NC4=O)cn3)CC2)CCC1C(=O)N1CCC2(CC1)C(=O)N([C@H]1C[C@@H](N3CCCCC3)C1)c1cc(-c3cc4ncn(C(C)C)c4c(NC4CC4)n3)ccc12]

LCMS: $C_{56}H_{71}N_{11}O_5$ desired mass: 977.6, found: m/z=979.3 $[M+H]^+$.

Example 254

(3RS)-3-(4-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-2-methylpiperidine-1-carbonyl]piperidin-1-yl}phenyl)piperidine-2,6-dione

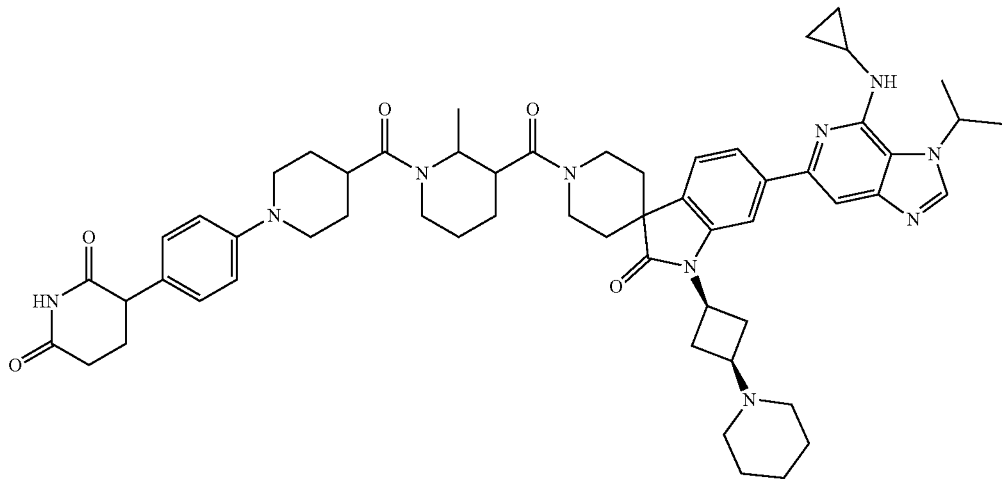 [SMILES: CC1C(C(=O)N2CCC3(CC2)C(=O)N([C@H]2C[C@@H](N4CCCCC4)C2)c2cc(-c4cc5ncn(C(C)C)c5c(NC5CC5)n4)ccc23)CCCN1C(=O)C1CCN(c2ccc(C3CCC(=O)NC3=O)cc2)CC1]

LCMS: $C_{57}H_{72}N_{10}O_5$ desired mass: 975.5, found: m/z=976.3 $[M+H]^+$.

Example 255

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-ethylpiperidine-1-carbonyl]piperidin-1-yl}pyridin-3-yl)piperidine-2,6-dione

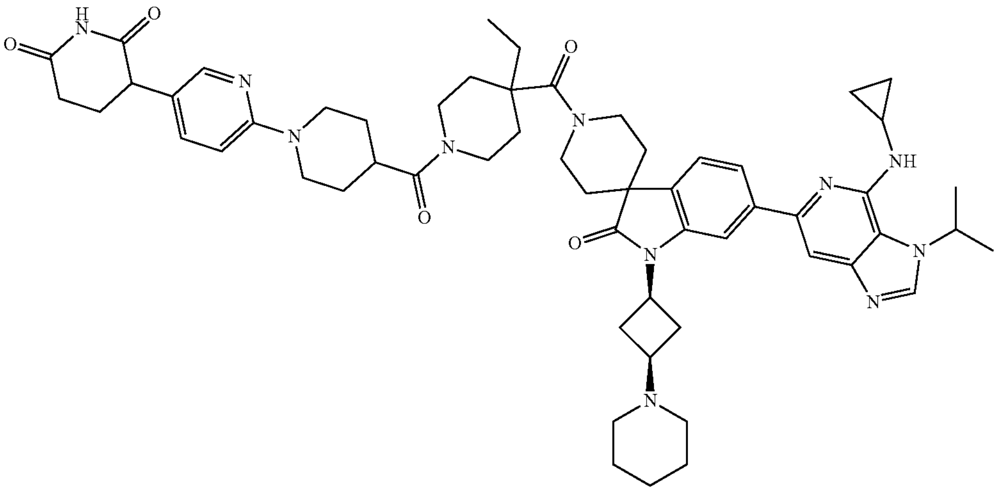 [SMILES: CCC1(C(=O)N2CCC3(CC2)C(=O)N([C@H]2C[C@@H](N4CCCCC4)C2)c2cc(-c4cc5ncn(C(C)C)c5c(NC5CC5)n4)ccc23)CCN(C(=O)C2CCN(c3ccc(C4CCC(=O)NC4=O)cn3)CC2)CC1]

LCMS: $C_{57}H_{73}N_{11}O_5$ desired mass: 991.6, found: m/z=993.2 $[M+H]^+$.

Example 256

(3RS)-3-(6-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-methoxypiperidine-1-carbonyl]piperidin-1-yl}pyridin-3-yl)piperidine-2,6-dione

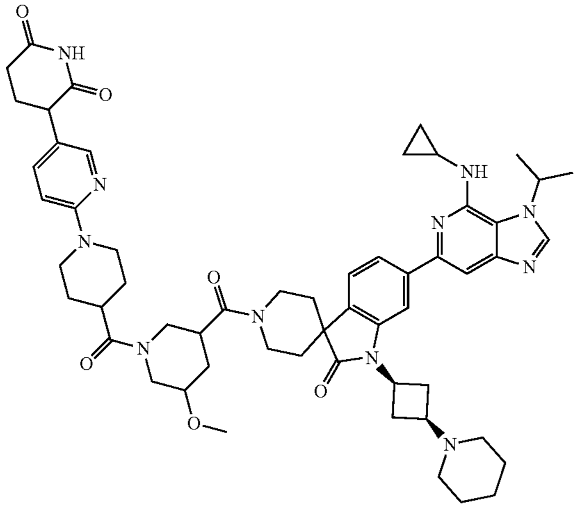 [SMILES: COC1CC(C(=O)N2CCC3(CC2)C(=O)N([C@H]2C[C@@H](N4CCCCC4)C2)c2cc(-c4cc5ncn(C(C)C)c5c(NC5CC5)n4)ccc23)CN(C(=O)C2CCN(c3ccc(C4CCC(=O)NC4=O)cn3)CC2)C1]

LCMS: $C_{56}H_{71}N_{11}O_6$ desired mass: 993.6, found: m/z=994.6 $[M+H]^+$.

Example 257

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-methoxypiperidine-1-carbonyl]piperidin-1-yl}phenyl)piperidine-2,6-dione

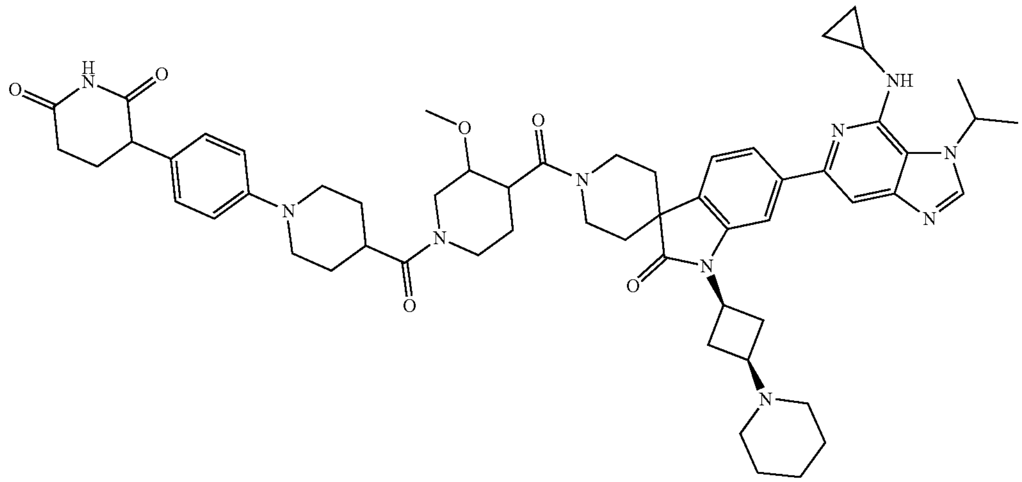 [SMILES: COC1CN(C(=O)C2CCN(c3ccc(C4CCC(=O)NC4=O)cc3)CC2)CCC1C(=O)N1CCC2(CC1)C(=O)N([C@H]1C[C@@H](N3CCCCC3)C1)c1cc(-c3cc4ncn(C(C)C)c4c(NC4CC4)n3)ccc12]

LCMS: $C_{57}H_{72}N_{10}O_6$ desired mass: 992.5, found: m/z=993.3 $[M+H]^+$.

Example 258

4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-1-(1-{4-[(3RS)-2,6-dioxopiperidin-3-yl]phenyl}piperidine-4-carbonyl)piperidine-4-carbonitrile

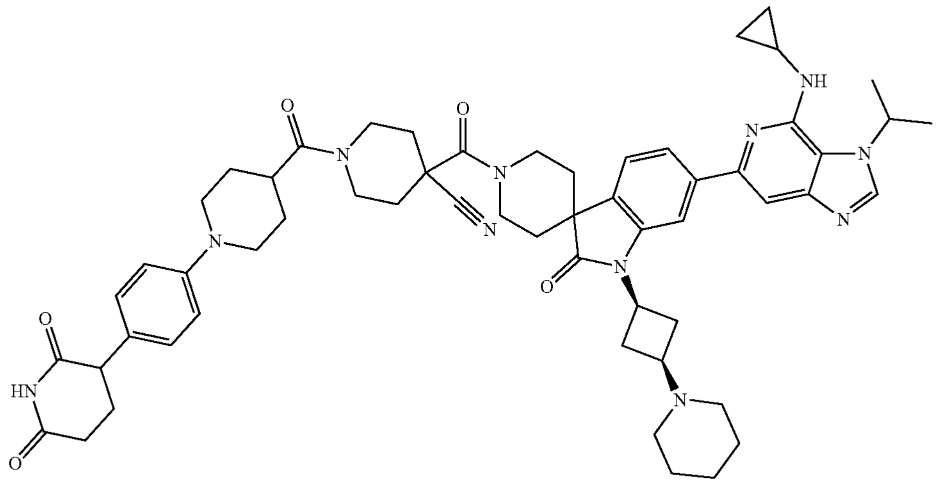 [SMILES: CC(C)n1cnc2cc(-c3ccc4c(c3)N([C@H]3C[C@@H](N5CCCCC5)C3)C(=O)C43CCN(C(=O)C4(C#N)CCN(C(=O)C5CCN(c6ccc(C7CCC(=O)NC7=O)cc6)CC5)CC4)CC3)nc(NC3CC3)c21]

LCMS: $C_{57}H_{69}N_{11}O_5$ desired mass: 987.5, found: m/z=988.3 $[M+H]^+$.

Example 259

(3RS)-3-(6-{4-[(1S,5S)-1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione

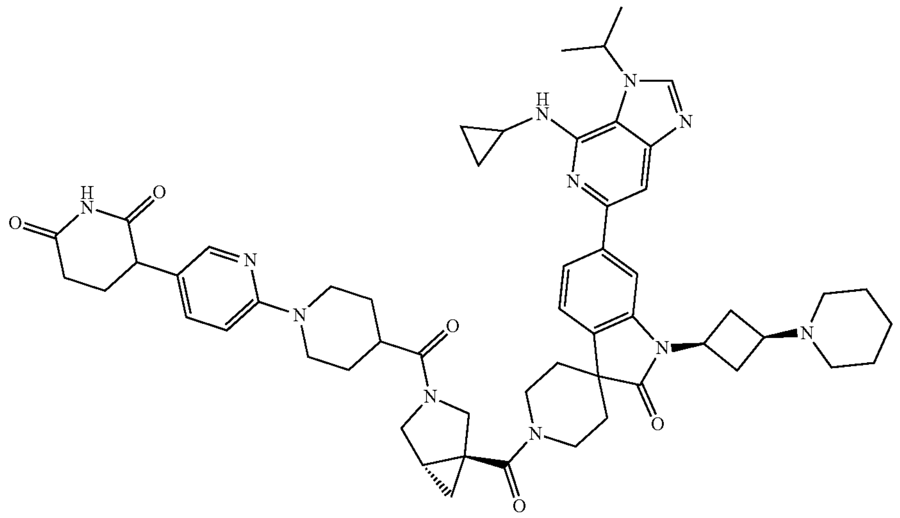 [SMILES: CC(C)n1cnc2cc(-c3ccc4c(c3)N([C@H]3C[C@@H](N5CCCCC5)C3)C(=O)C43CCN(C(=O)[C@@]45C[C@@H]4CN(C(=O)C4CCN(c6ccc(C7CCC(=O)NC7=O)cn6)CC4)C5)CC3)nc(NC3CC3)c21]

LCMS: $C_{55}H_{67}N_{11}O_5$ desired mass: 961.5, found: m/z=962.5 $[M+H]^+$.

Example 260

(3RS)-3-(6-{4-[(1R,5S,6S)-6-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione

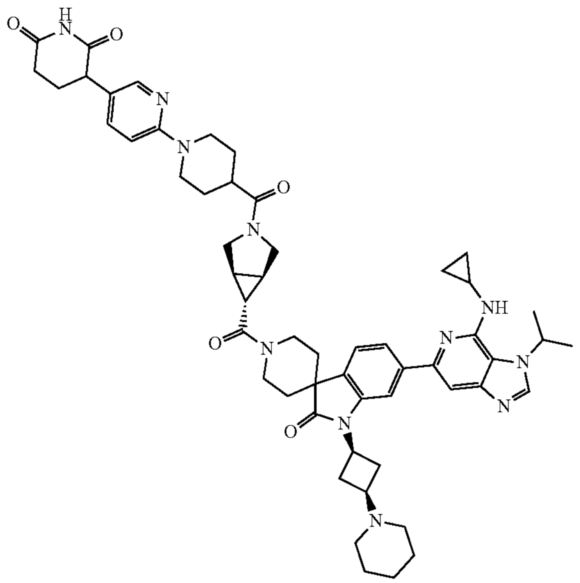 [SMILES: CC(C)n1cnc2cc(-c3ccc4c(c3)N([C@H]3C[C@@H](N5CCCCC5)C3)C(=O)C43CCN(C(=O)[C@H]4[C@@H]5CN(C(=O)C6CCN(c7ccc(C8CCC(=O)NC8=O)cn7)CC6)C[C@@H]54)CC3)nc(NC3CC3)c21]

LCMS: $C_{55}H_{67}N_{11}O_5$ desired mass: 961.5, found: m/z=962.4 $[M+H]^+$.

Example 261

(3RS)-3-(6-{4-[(1R,4S,5S)-5-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-2-azabicyclo[2.2.1]heptane-2-carbonyl]piperidin-1-yl}pyridin-3-yl)piperidine-2,6-dione

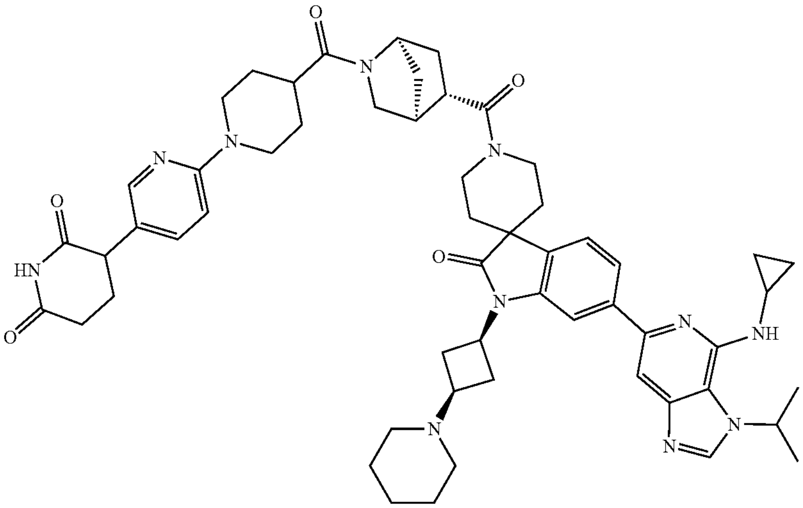 [SMILES: CC(C)n1cnc2cc(-c3ccc4c(c3)N([C@H]3C[C@@H](N5CCCCC5)C3)C(=O)C43CCN(C(=O)[C@H]4C[C@H]5C[C@@H]4CN5C(=O)C4CCN(c5ccc(C6CCC(=O)NC6=O)cn5)CC4)CC3)nc(NC3CC3)c21]

LCMS: $C_{56}H_{69}N_{11}O_5$ desired mass: 975.5, found: m/z=976.5 $[M+H]^+$.

Example 262

(3RS)-3-(4-{4-[(1R,3R,5S)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-8-azabicyclo[3.2.1]Octane-8-carbonyl]piperidin-1-yl}phenyl)piperidine-2,6-dione

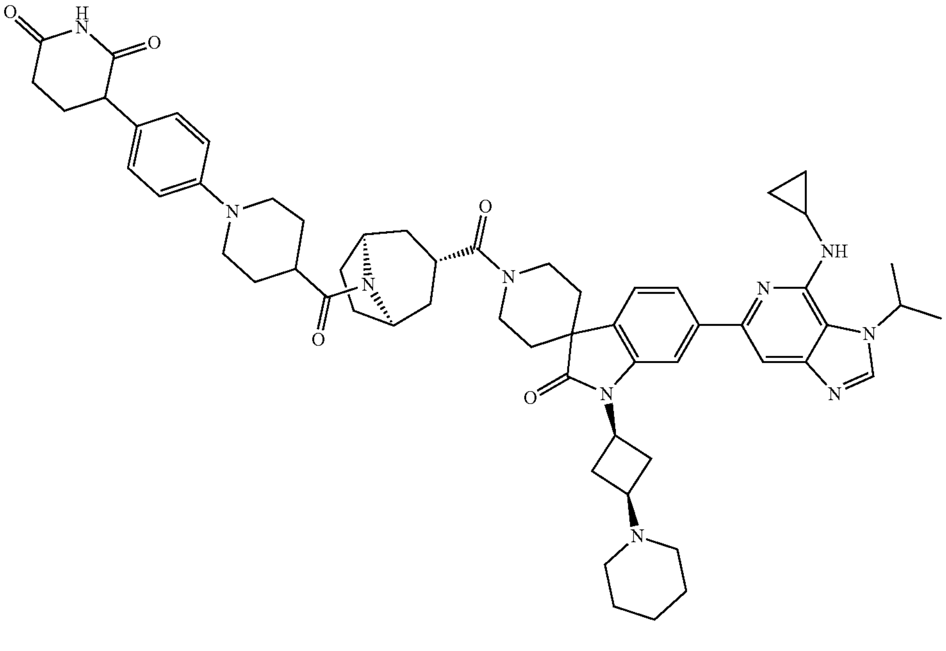 [SMILES: CC(C)n1cnc2cc(-c3ccc4c(c3)N([C@H]3C[C@@H](N5CCCCC5)C3)C(=O)C43CCN(C(=O)[C@@H]4C[C@H]5CC[C@@H](C4)N5C(=O)C4CCN(c5ccc(C6CCC(=O)NC6=O)cc5)CC4)CC3)nc(NC3CC3)c21]

LCMS: $C_{58}H_{72}N_{10}O_5$ desired mass: 988.5, found: m/z=989.3 $[M+H]^+$.

Example 263

(3RS)-3-(4-{4-[(1R,5R)-1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}phenyl)piperidine-2,6-dione

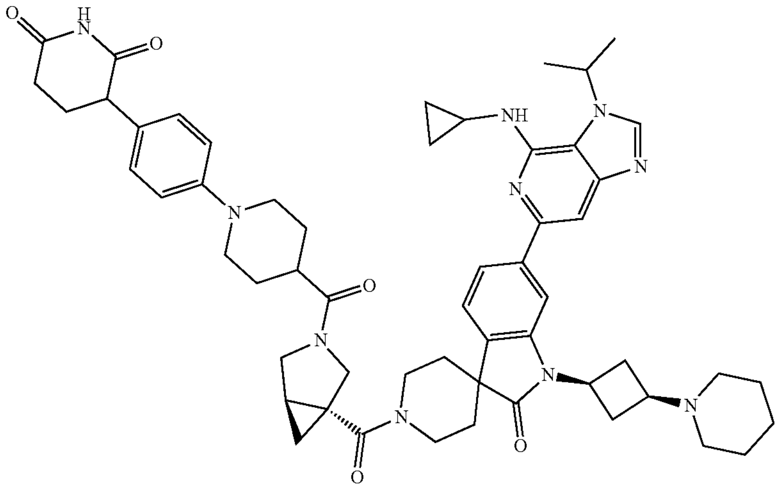 [SMILES: CC(C)n1cnc2cc(-c3ccc4c(c3)N([C@H]3C[C@@H](N5CCCCC5)C3)C(=O)C43CCN(C(=O)[C@]45C[C@H]4CN(C(=O)C4CCN(c6ccc(C7CCC(=O)NC7=O)cc6)CC4)C5)CC3)nc(NC3CC3)c21]

LCMS: $C_{56}H_{68}N_{10}O_5$ desired mass: 960.5, found: m/z=961.3 $[M+H]^+$.

Example 264

(3RS)-3-(6-{4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

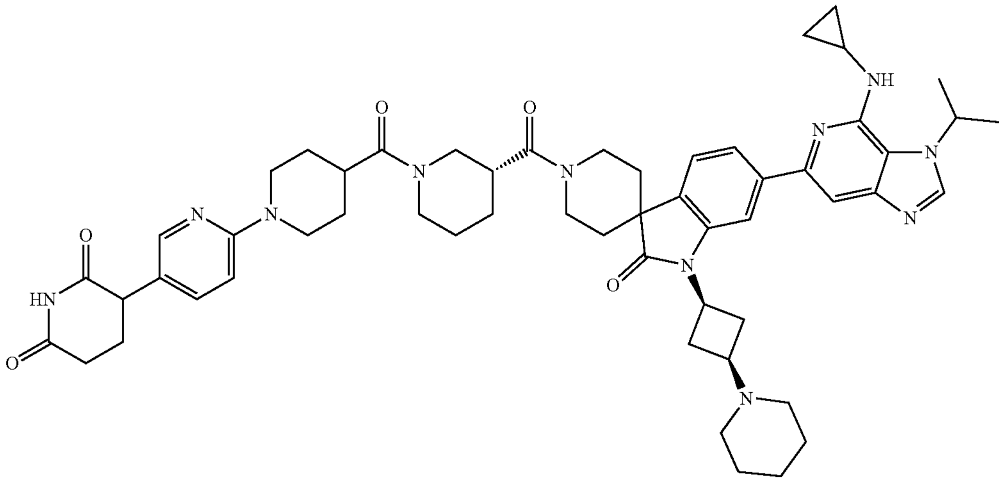 [SMILES: CC(C)n1cnc2cc(-c3ccc4c(c3)N([C@H]3C[C@@H](N5CCCCC5)C3)C(=O)C43CCN(C(=O)[C@@H]4CCCN(C(=O)C5CCN(c6ccc(C7CCC(=O)NC7=O)cn6)CC5)C4)CC3)nc(NC3CC3)c21]

LCMS: $C_{58}H_{69}N_{11}O_5$ desired mass s: 963.5, found: m/z=964.2 $[M+H]^+$.

Example 265

(3RS)-3-(6-{4-[(S,4R,5R)-5-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-2-azabicyclo[2.2.1]heptane-2-carbonyl]piperidin-1-yl}pyridin-3-yl)piperidine-2,6-dione

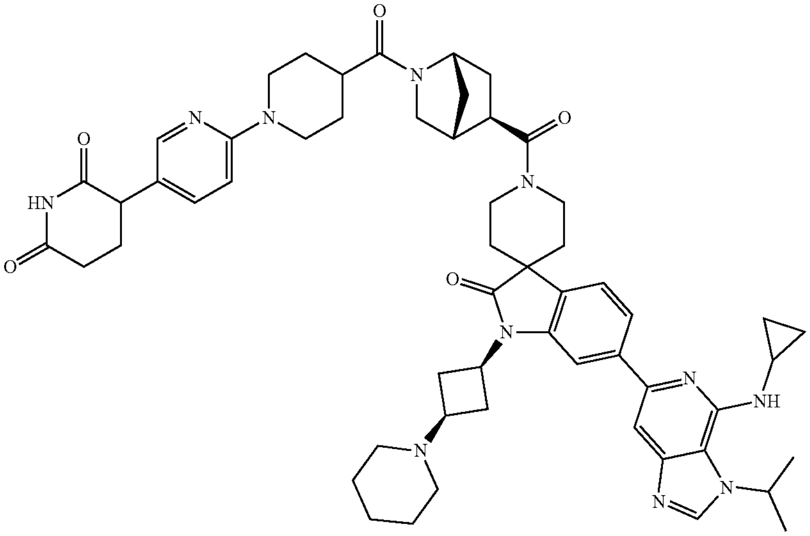 [SMILES: CC(C)n1cnc2cc(-c3ccc4c(c3)N([C@H]3C[C@@H](N5CCCCC5)C3)C(=O)C43CCN(C(=O)[C@@H]4C[C@@H]5C[C@H]4CN5C(=O)C4CCN(c5ccc(C6CCC(=O)NC6=O)cn5)CC4)CC3)nc(NC3CC3)c21]

LCMS: $C_{56}H_{69}N_{11}O_5$ desired mass: 975.5, found: m/z=976.7 $[M+H]^+$.

Example 266

(3RS)-3-(6-{4-[(1R,5R,6R)-6-[(6-{4-[(2-fluorophenyl)amino]-3-(propan-2-yl)-3H-imidazo[4,5-c]pyridin-6-yl}-2-oxo-1-[(1S,3S)-3-(piperidin-1-yl)cyclobutyl]-1,2-dihydrospiro[indole-3,4'-piperidin]-1'-yl)carbonyl]-2-azabicyclo[3.1.0]hexane-2-carbonyl]piperidin-1-yl}pyridin-3-yl)piperidine-2,6-dione

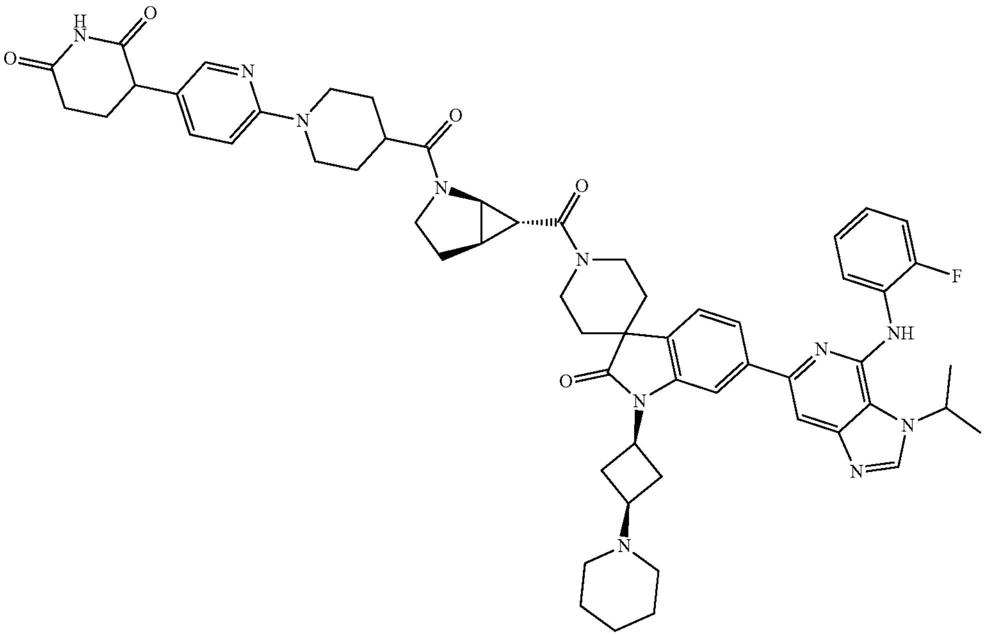 [SMILES: CC(C)n1cnc2cc(-c3ccc4c(c3)N([C@H]3C[C@@H](N5CCCCC5)C3)C(=O)C43CCN(C(=O)[C@@H]4[C@H]5CCN(C(=O)C6CCN(c7ccc(C8CCC(=O)NC8=O)cn7)CC6)[C@H]54)CC3)nc(Nc3ccccc3F)c21]

LCMS: $C_{58}H_{66}FN_{11}O_5$ desired mass: 1015.5, found: m/z=1016.7 $[M+H]^+$.

Example 267

(3RS)-3-(6-{4-[8-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-6-azaspiro[3.5]nonane-6-carbonyl]piperidin-1-yl}pyridin-3-yl)piperidine-2,6-dione

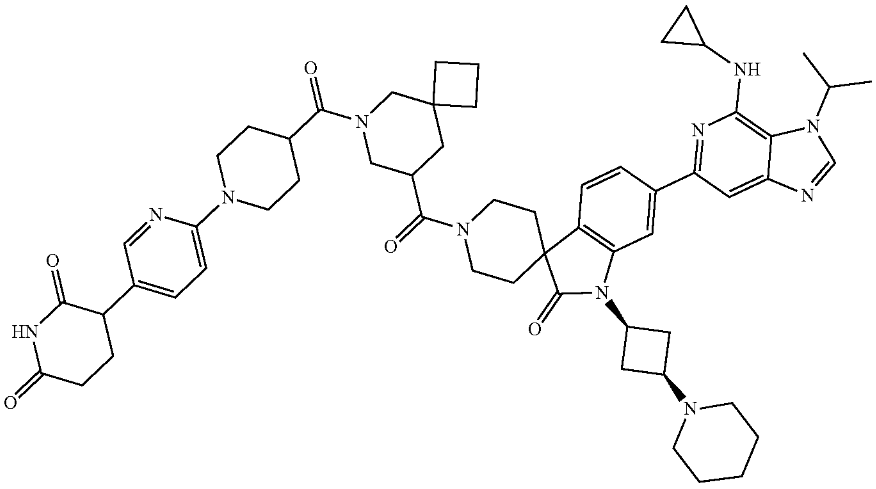 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cn6)CC5)CC5(CCC5)C4)CC3)nc(NC3CC3)c21]

LCMS: $C_{58}H_{73}N_{11}O_5$ desired mass: 1003.6, found: m/z=1005.2 $[M+H]^+$.

Example 268

(3RS)-3-(4-{4-[5-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3,3-Difluoropiperidine-1-carbonyl]piperidin-1-yl}phenyl)piperidine-2,6-dione

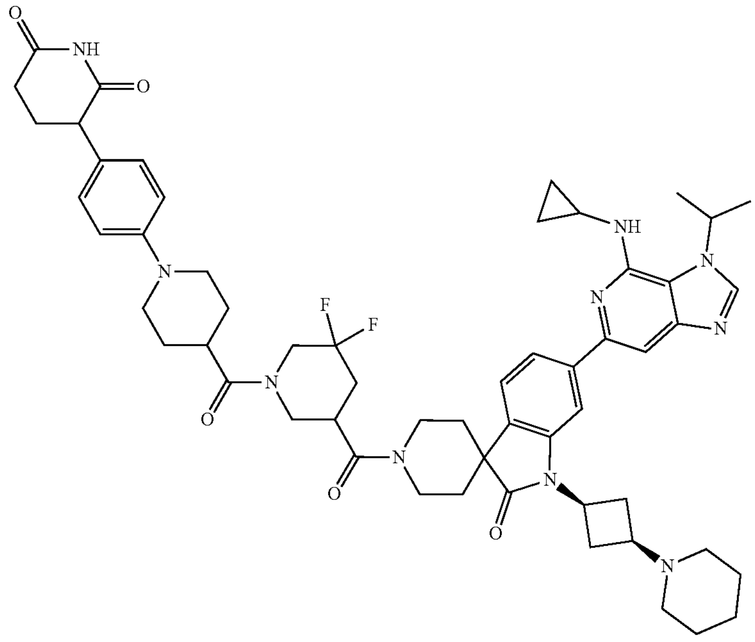 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cc6)CC5)CC(F)(F)C4)CC3)nc(NC3CC3)c21]

LCMS: $C_{56}H_{68}F_2N_{10}O_5$ desired mass: 998.5, found: m/z=999.3 $[M+H]^+$.

Example 269

(3RS)-3-(6-{4-[7-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-azaspiro[2.5]Octane-4-carbonyl]piperidin-1-yl}pyridin-3-yl)piperidine-2,6-dione

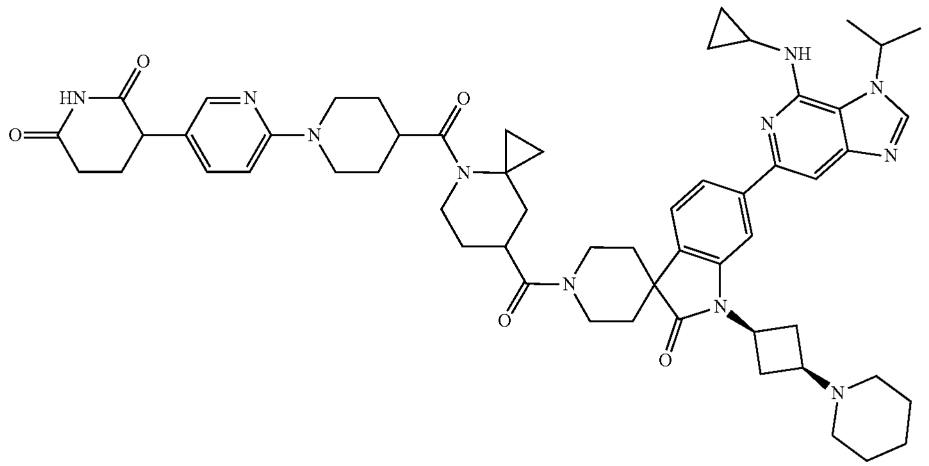 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)C5(CC5)C4)CC3)nc(NC3CC3)c21]

LCMS: $C_{57}H_{71}N_{11}O_5$ desired mass: 989.6, found: m/z=990.5 $[M+H]^+$.

Example 270

(3RS)-3-(6-{4-[8-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-azaspiro[3.5]nonane-5-carbonyl]piperidin-1-yl}pyridin-3-yl)piperidine-2,6-dione

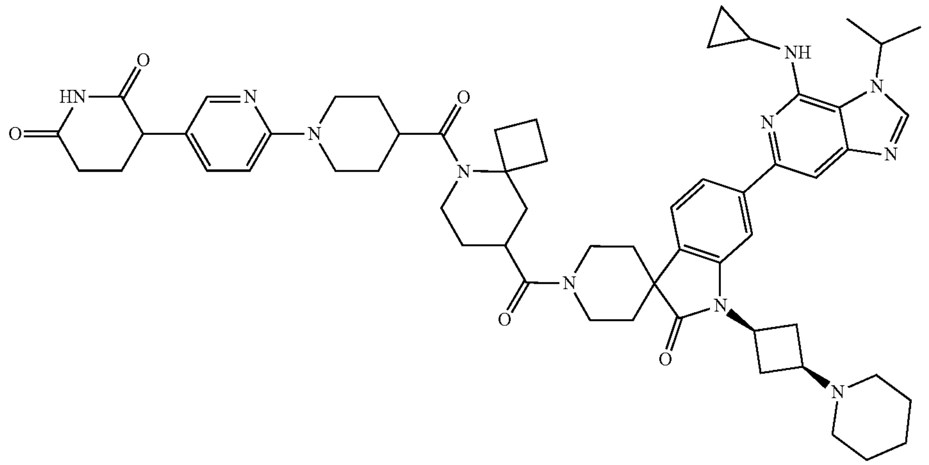 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)C5(CCC5)C4)CC3)nc(NC3CC3)c21]

LCMS: $C_{58}H_{73}N_{11}O_5$ desired mass: 1003.6, found: m/z=1027.3 $[M+Na]^+$.

Example 271

(3RS)-3-(6-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]piperidin-1-yl}pyridin-3-yl)piperidine-2,6-dione

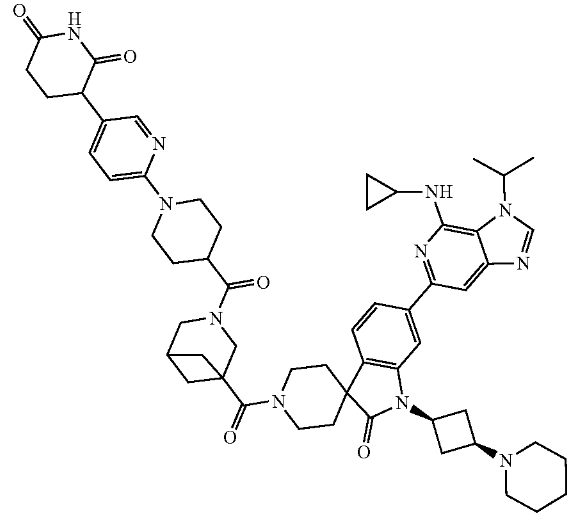 [SMILES: CC(C)n1cnc2cc(-c3ccc4c(c3)N([C@H]3C[C@@H](N5CCCCC5)C3)C(=O)C43CCN(C(=O)C45CC(CN(C(=O)C6CCN(c7ccc(C8CCC(=O)NC8=O)cn7)CC6)C4)C5)CC3)nc(NC3CC3)c21]

LCMS: $C_{56}H_{69}N_{11}O_5$ desired mass: 975.5, found: m/z=977.6 $[M+H]^+$.

Example 272

(3RS)-3-(6-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione

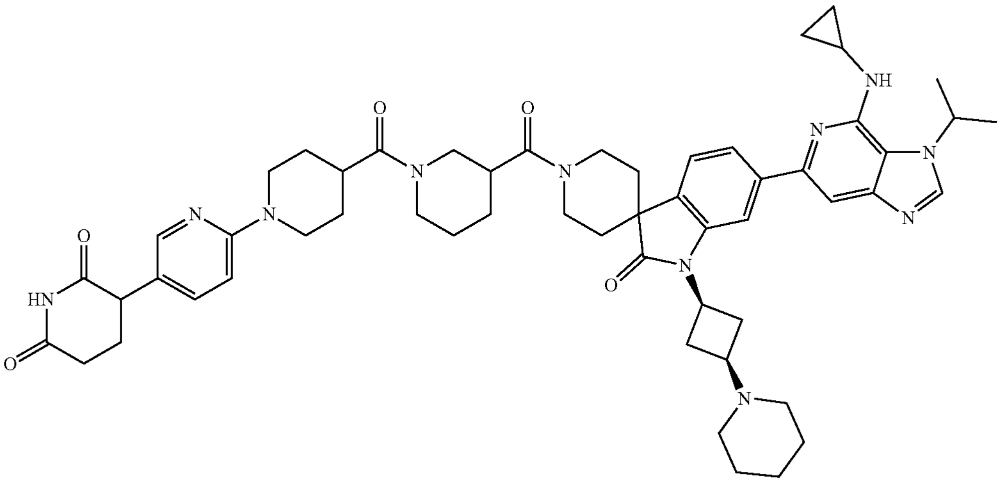 [SMILES: CC(C)n1cnc2cc(-c3ccc4c(c3)N([C@H]3C[C@@H](N5CCCCC5)C3)C(=O)C43CCN(C(=O)C4CCCN(C(=O)C5CCN(c6ccc(C7CCC(=O)NC7=O)cn6)CC5)C4)CC3)nc(NC3CC3)c21]

LCMS: $C_{55}H_{69}N_{11}O_5$ desired mass: 963.5, found: m/z=964.5 $[M+H]^+$.

Example 273

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3,3-Difluoropiperidine-1-carbonyl]piperidin-1-yl}pyridin-3-yl)piperidine-2,6-dione

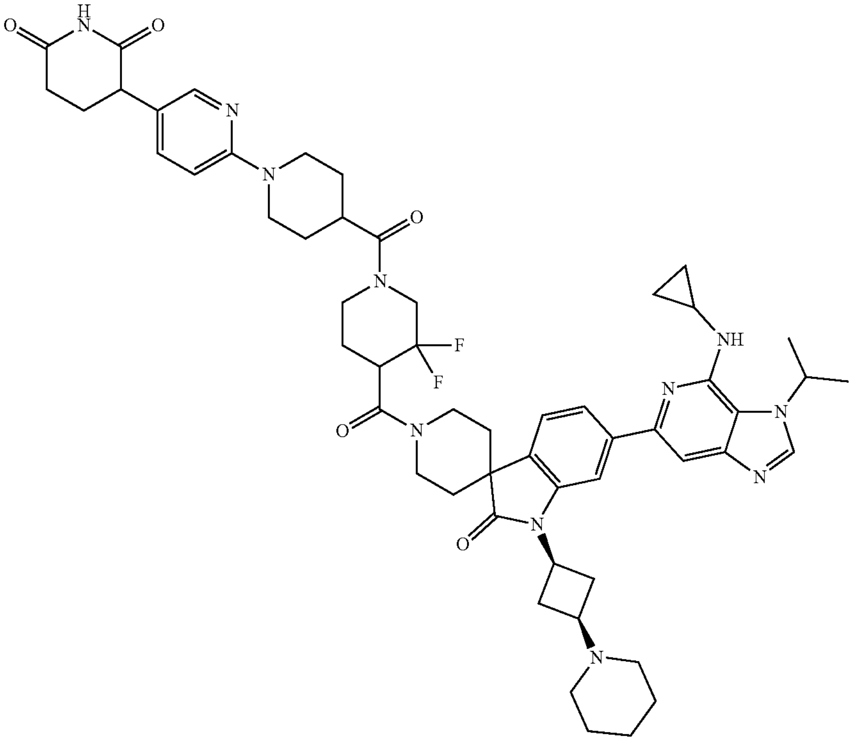 [SMILES: CC(C)n1cnc2cc(-c3ccc4c(c3)N([C@H]3C[C@@H](N5CCCCC5)C3)C(=O)C43CCN(C(=O)C4CCN(C(=O)C5CCN(c6ccc(C7CCC(=O)NC7=O)cn6)CC5)CC4(F)F)CC3)nc(NC3CC3)c21]

LCMS: $C_{55}H_{67}F_2N_{11}O_5$ desired mass: 999.5, found: m/z=1000.4 $[M+H]^+$.

Example 274

(3RS)-3-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-hydroxypiperidine-1-carbonyl]piperidin-1-yl}phenyl)piperidine-2,6-dione

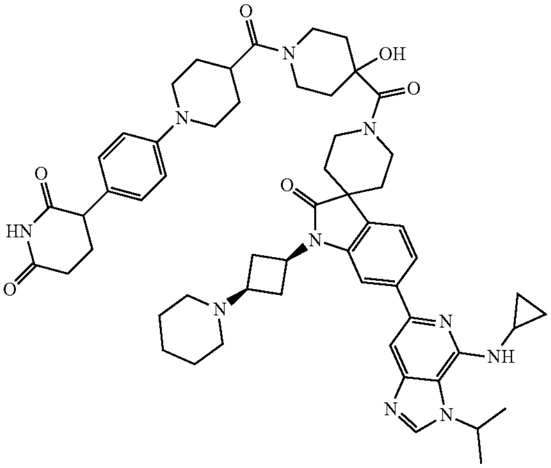 [SMILES: CC(C)n1cnc2cc(-c3ccc4c(c3)N([C@H]3C[C@@H](N5CCCCC5)C3)C(=O)C43CCN(C(=O)C4(O)CCN(C(=O)C5CCN(c6ccc(C7CCC(=O)NC7=O)cc6)CC5)CC4)CC3)nc(NC3CC3)c21]

LCMS: $C_{56}H_{70}N_{10}O_6$ desired mass: 978.5, found: m/z=979.3 $[M+H]^+$.

Example 275

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-(trifluoromethyl)piperidine-1-carbonyl]piperidin-1-yl}pyridin-3-yl)piperidine-2,6-dione

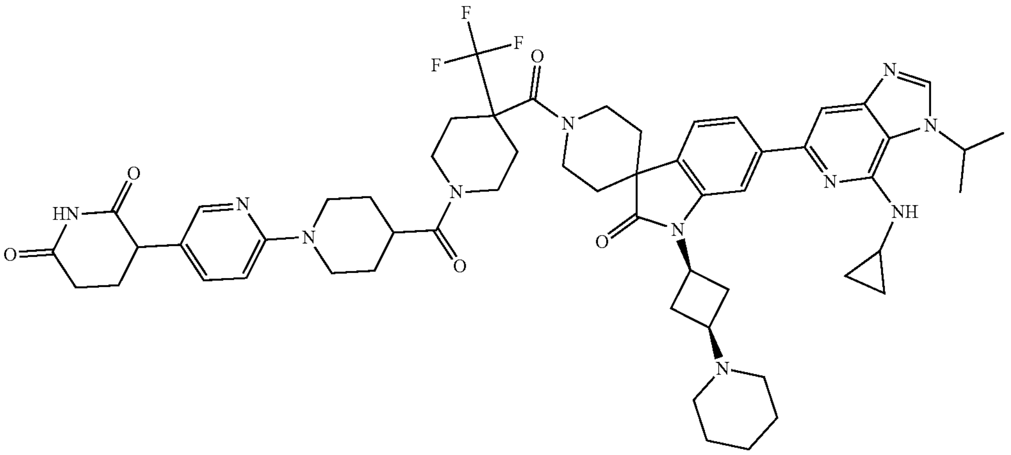 [SMILES: CC(C)n1cnc2cc(-c3ccc4c(c3)N([C@H]3C[C@@H](N5CCCCC5)C3)C(=O)C43CCN(C(=O)C4(C(F)(F)F)CCN(C(=O)C5CCN(c6ccc(C7CCC(=O)NC7=O)cn6)CC5)CC4)CC3)nc(NC3CC3)c21]

LCMS: $C_{56}H_{68}F_3N_{11}O_5$ desired mass: 1031.5, found: m/z=1033.0 [M+H]$^+$.

Example 276

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-(difluoromethyl)piperidine-1-carbonyl]piperidin-1-yl}pyridin-3-yl)piperidine-2,6-dione

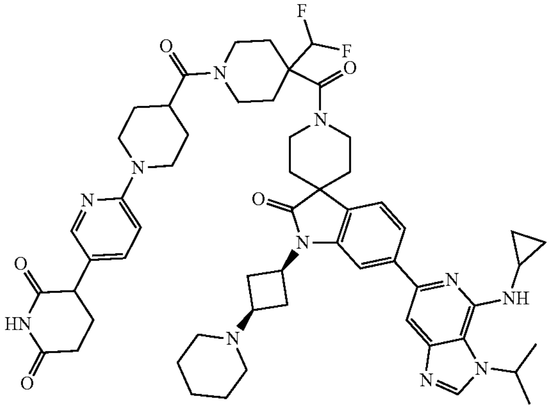 [SMILES: CC(C)n1cnc2cc(-c3ccc4c(c3)N([C@H]3C[C@@H](N5CCCCC5)C3)C(=O)C43CCN(C(=O)C4(C(F)F)CCN(C(=O)C5CCN(c6ccc(C7CCC(=O)NC7=O)cn6)CC5)CC4)CC3)nc(NC3CC3)c21]

LCMS: $C_{56}H_{69}F_2N_{11}O_5$ desired mass: 1013.5, found: m/z=1014.4 [M+H]$^+$.

Example 277

(3RS)-3-(6-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-fluoropiperidine-1-carbonyl]piperidin-1-yl}pyridin-3-yl)piperidine-2,6-dione

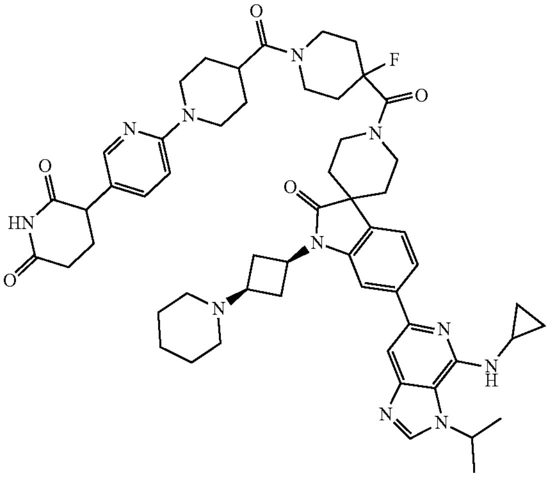 [SMILES: CC(C)n1cnc2cc(-c3ccc4c(c3)N([C@H]3C[C@@H](N5CCCCC5)C3)C(=O)C43CCN(C(=O)C4(F)CCN(C(=O)C5CCN(c6ccc(C7CCC(=O)NC7=O)cn6)CC5)CC4)CC3)nc(NC3CC3)c21]

LCMS: $C_{58}H_{68}FN_{11}O_5$ desired mass: 981.5, found: m/z=982.4 [M+H]$^+$.

Example 278

(3RS)-3-(6-{4-[4-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-(fluoromethyl)piperidine-1-carbonyl]piperidin-1-yl}pyridin-3-yl)piperidine-2,6-dione

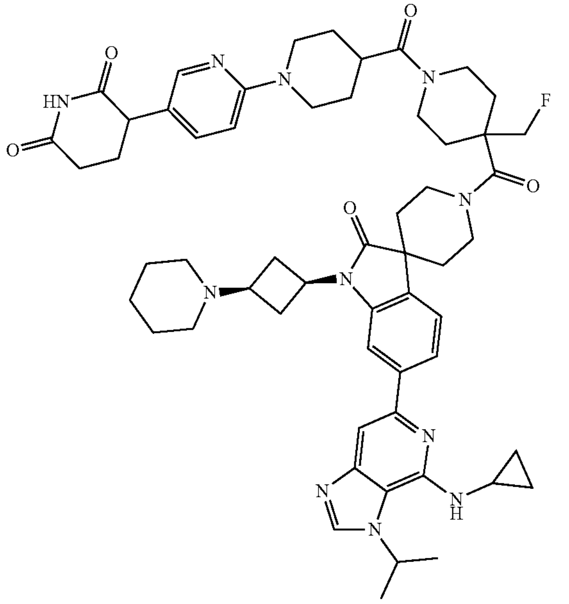 [SMILES: CC(C)n1cnc2cc(-c3ccc4c(c3)N([C@H]3C[C@@H](N5CCCCC5)C3)C(=O)C43CCN(C(=O)C4(CF)CCN(C(=O)C5CCN(c6ccc(C7CCC(=O)NC7=O)cn6)CC5)CC4)CC3)nc(NC3CC3)c21]

LCMS: $C_{56}H_{70}FN_{11}O_5$ desired mass: 995.6, found: m/z=996.4 $[M+H]^+$.

Example 279

(3RS)-3-(6-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-fluoro-3-azabicyclo[3.1.1]heptane-3-carbonyl]piperidin-1-yl}pyridin-3-yl)piperidine-2,6-dione

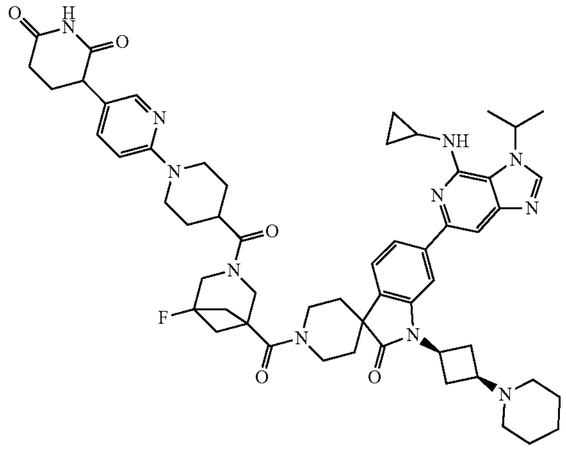 [SMILES: CC(C)n1cnc2cc(-c3ccc4c(c3)N([C@H]3C[C@@H](N5CCCCC5)C3)C(=O)C43CCN(C(=O)C45CN(C(=O)C6CCN(c7ccc(C8CCC(=O)NC8=O)cn7)CC6)CC(F)(C4)C5)CC3)nc(NC3CC3)c21]

LCMS: $C_{56}H_{68}FN_{11}O_5$ desired mass: 993.5, found: m/z=994.4 $[M+H]^+$.

Example 280

(3RS)-3-(6-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-fluoropiperidine-1-carbonyl]piperidin-1-yl}pyridin-3-yl)piperidine-2,6-dione

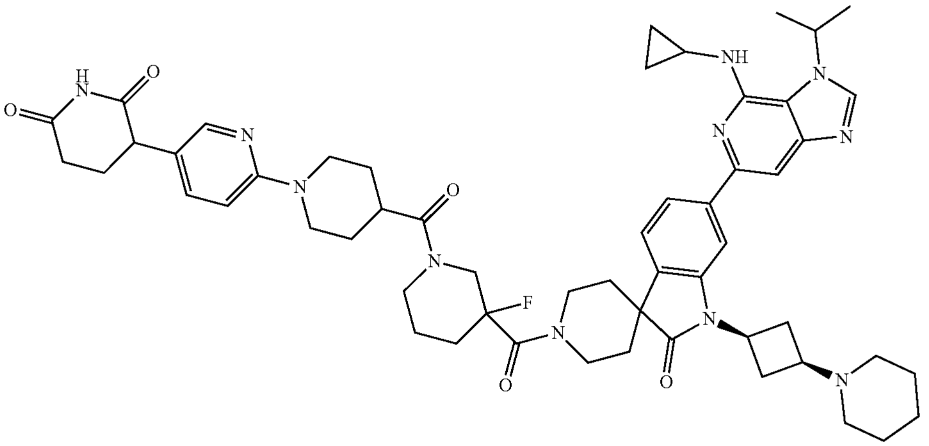 [SMILES: CC(C)n1cnc2cc(-c3ccc4c(c3)N([C@H]3C[C@@H](N5CCCCC5)C3)C(=O)C43CCN(C(=O)C4(F)CCCN(C(=O)C5CCN(c6ccc(C7CCC(=O)NC7=O)cn6)CC5)C4)CC3)nc(NC3CC3)c21]

LCMS: $C_{55}H_{68}FN_{11}O_5$ desired mass: 981.5, found: m/z=982.4 $[M+H]^+$.

Example 281

(3RS)-3-(6-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-6,6-difluoro-3-azabicyclo[3.1.0]hexane-3-carbonyl]piperidin-1-yl}pyridin-3-yl)piperidine-2,6-dione

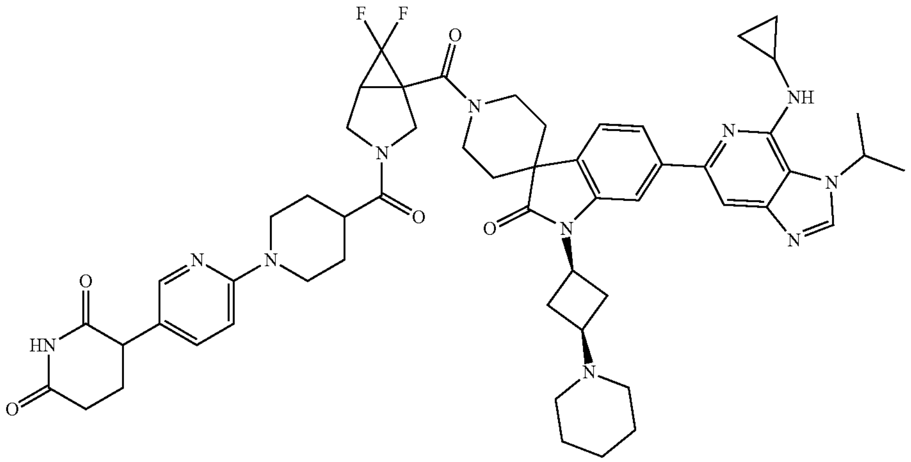 [SMILES: CC(C)n1cnc2cc(-c3ccc4c(c3)N([C@H]3C[C@@H](N5CCCCC5)C3)C(=O)C43CCN(C(=O)C45CN(C(=O)C6CCN(c7ccc(C8CCC(=O)NC8=O)cn7)CC6)CC4C5(F)F)CC3)nc(NC3CC3)c21]

LCMS: $C_{58}H_{68}F_2N_{11}O_5$ desired mass: 997.5, found: m/z=998.7 $[M+H]^+$.

Example 282

(3RS)-3-(6-{4-[6-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]piperidin-1-yl}pyridin-3-yl)piperidine-2,6-dione

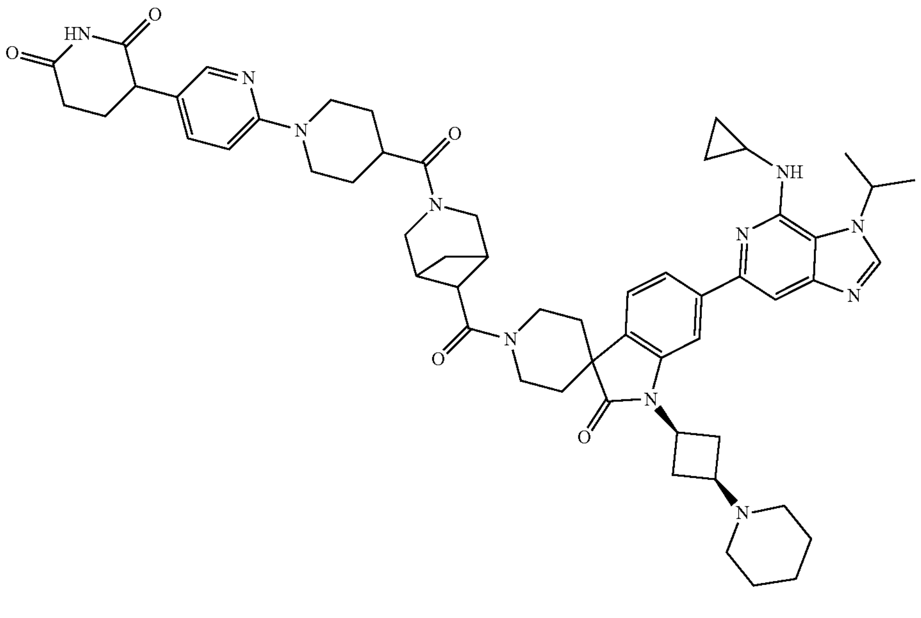 [SMILES: CC(C)n1cnc2cc(-c3ccc4c(c3)N([C@H]3C[C@@H](N5CCCCC5)C3)C(=O)C43CCN(C(=O)C4C5CC4CN(C(=O)C4CCN(c6ccc(C7CCC(=O)NC7=O)cn6)CC4)C5)CC3)nc(NC3CC3)c21]

LCMS: $C_{56}H_{69}N_{11}O_5$ desired mass: 975.5, found: m/z=976.2 $[M+H]^+$.

Example 283

(3RS)-3-(6-{4-[6-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-2-azabicyclo[2.2.2]Octane-2-carbonyl]piperidin-1-yl}pyridin-3-yl)piperidine-2,6-dione

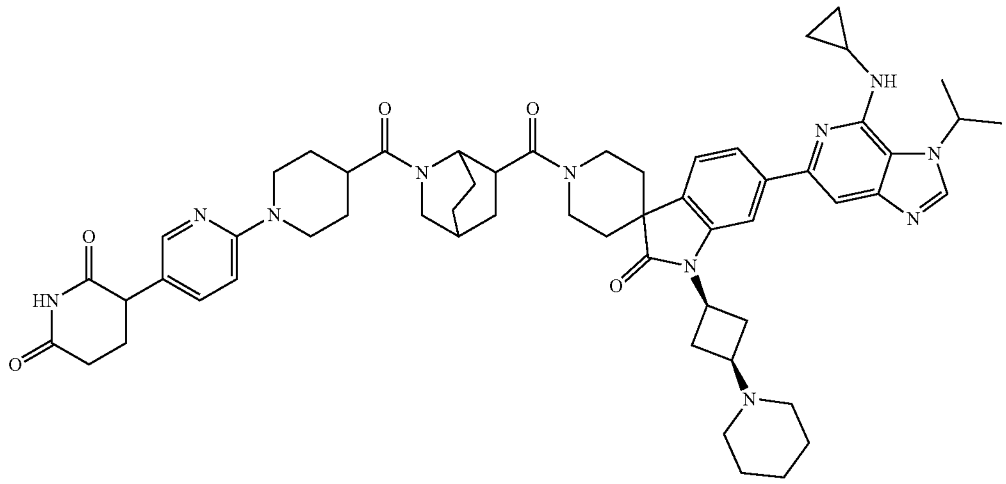 [SMILES: CC(C)n1cnc2cc(-c3ccc4c(c3)N([C@H]3C[C@@H](N5CCCCC5)C3)C(=O)C43CCN(C(=O)C4CC5CCC4N(C(=O)C4CCN(c6ccc(C7CCC(=O)NC7=O)cn6)CC4)C5)CC3)nc(NC3CC3)c21]

LCMS: $C_{57}H_{71}N_{11}O_5$ desired mass: 989.6, found: m/z=990.6 $[M+H]^+$.

Example 284

(3RS)-3-(6-{4-[8-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azabicyclo[3.2.1]Octane-3-carbonyl]piperidin-1-yl}pyridin-3-yl)piperidine-2,6-dione

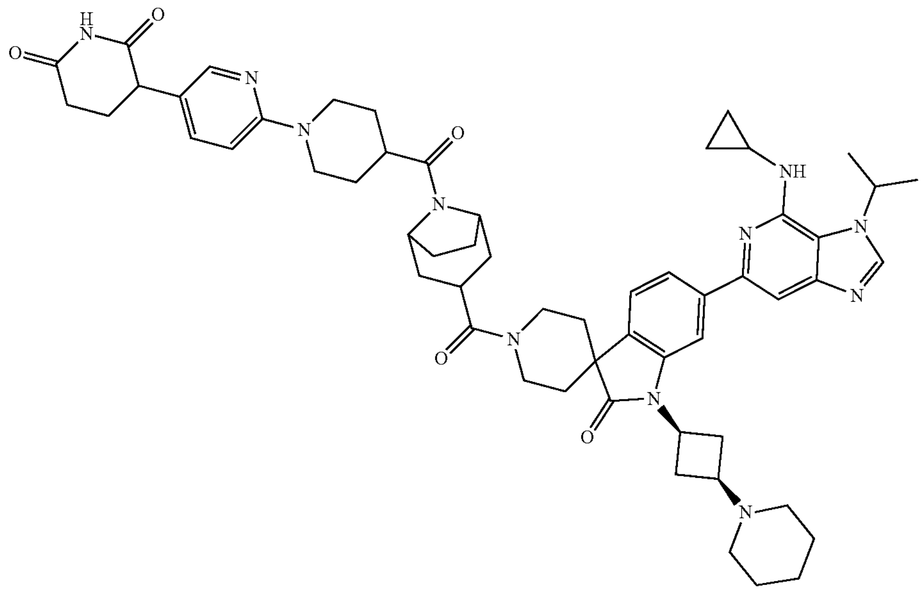 [SMILES: CC(C)n1cnc2cc(-c3ccc4c(c3)N([C@H]3C[C@@H](N5CCCCC5)C3)C(=O)C43CCN(C(=O)C4CC5CCC(C4)N5C(=O)C4CCN(c5ccc(C6CCC(=O)NC6=O)cn5)CC4)CC3)nc(NC3CC3)c21]

LCMS: $C_{57}H_{71}N_{11}O_5$ desired mass: 989.6, found: m/z=990.8 $[M+H]^+$.

Example 285

(3RS)-3-(6-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4,4-Difluoropiperidine-1-carbonyl]piperidin-1-yl}pyridin-3-yl)piperidine-2,6-dione

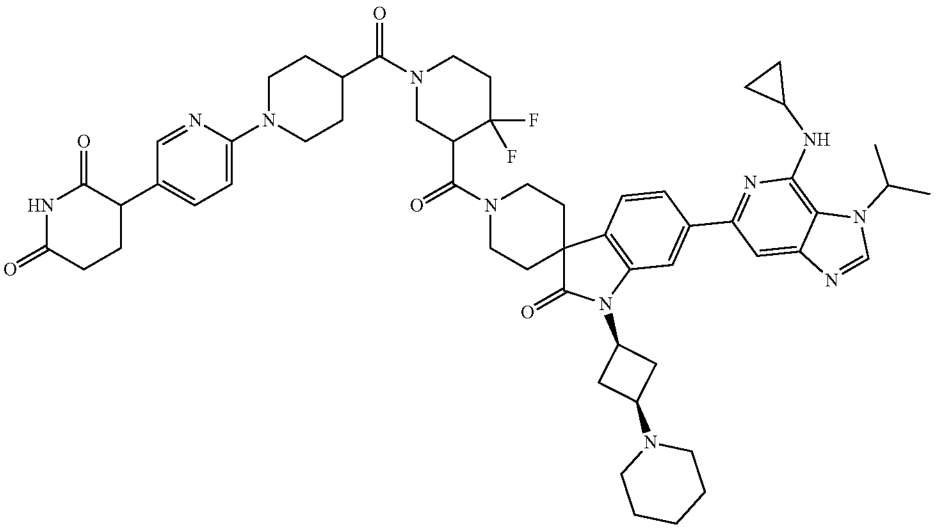 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cn6)CC5)CCC4(F)F)CC3)nc(NC3CC3)c21]

LCMS: $C_{55}H_{67}F_2N_{11}O_5$ desired mass: 999.5, found: m/z=1000.6 $[M+H]^+$.

Example 286 (3SR)-3-(6-{4-[(1S,3R,5RS)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-8-azabicyclo[3.2.1]octane-8-carbonyl]piperidin-1-yl}pyridin-3-yl)piperidine-2,6-dione

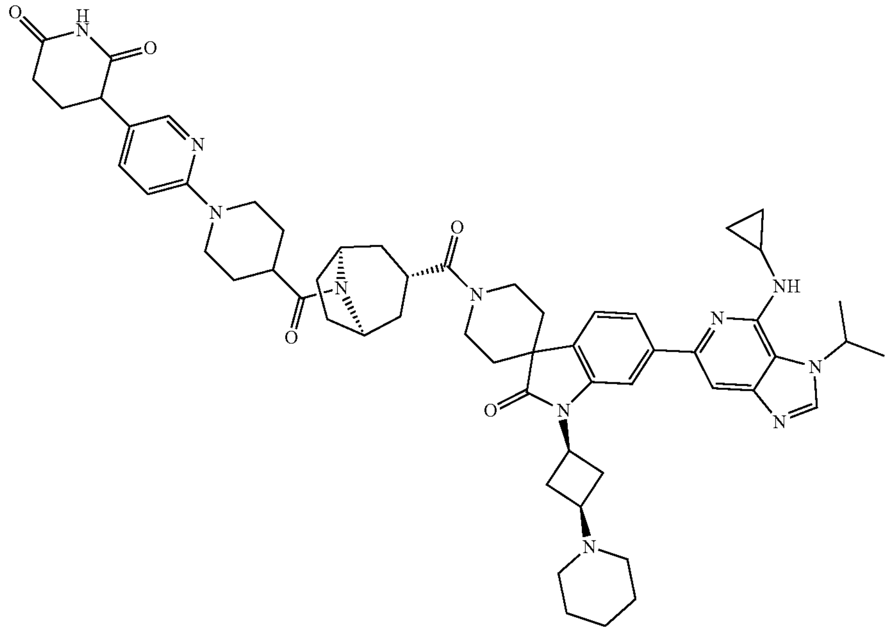 [SMILES: CC(C)n1cnc2cc(-c3ccc4c(c3)N([C@H]3C[C@@H](N5CCCCC5)C3)C(=O)C43CCN(C(=O)[C@@H]4C[C@H]5CC[C@@H](C4)N5C(=O)C4CCN(c5ccc(C6CCC(=O)NC6=O)cn5)CC4)CC3)nc(NC3CC3)c21]

LCMS: $C_{57}H_{71}N_{11}O_5$ desired mass: 989.6, found: m/z=990.4 $[M+H]^+$.
Example 287
(3RS)-3-(6-{4-[5-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-7-azaspiro[3.5]nonane-7-carbonyl]piperidin-1-yl}pyridin-3-yl)piperidine-2,6-dione
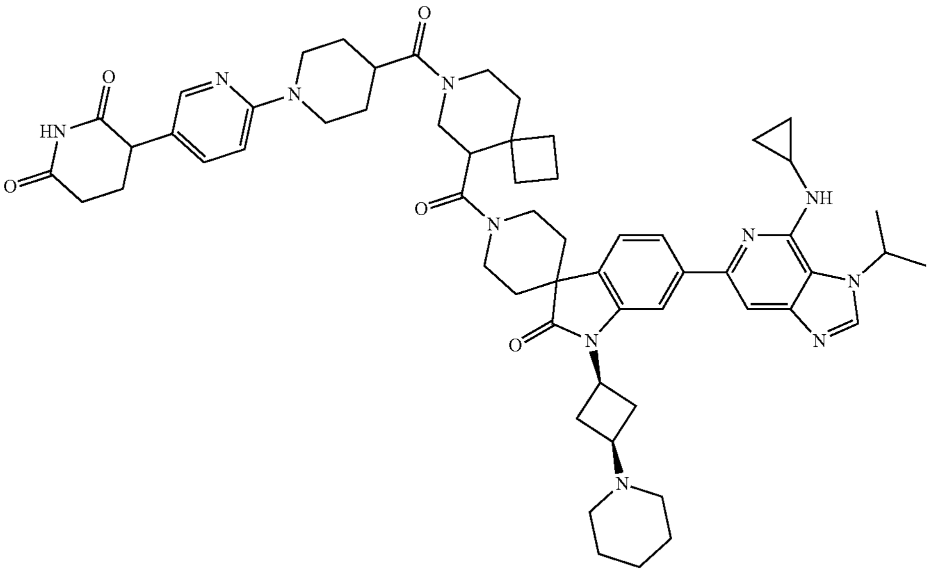 [SMILES: CC(C)n1cnc2cc(-c3ccc4c(c3)N([C@H]3C[C@@H](N5CCCCC5)C3)C(=O)C43CCN(C(=O)C4CN(C(=O)C5CCN(c6ccc(C7CCC(=O)NC7=O)cn6)CC5)CCC45CCC5)CC3)nc(NC3CC3)c21]
LCMS: $C_{58}H_{73}N_{11}O_5$ desired mass: 1003.6, found: m/z=1004.6 $[M+H]^+$.

Example 288

(3RS)-3-(6-{4-[9-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-oxa-7-azabicyclo[3.3.1]nonane-7-carbonyl]piperidin-1-yl}pyridin-3-yl)piperidine-2,6-dione

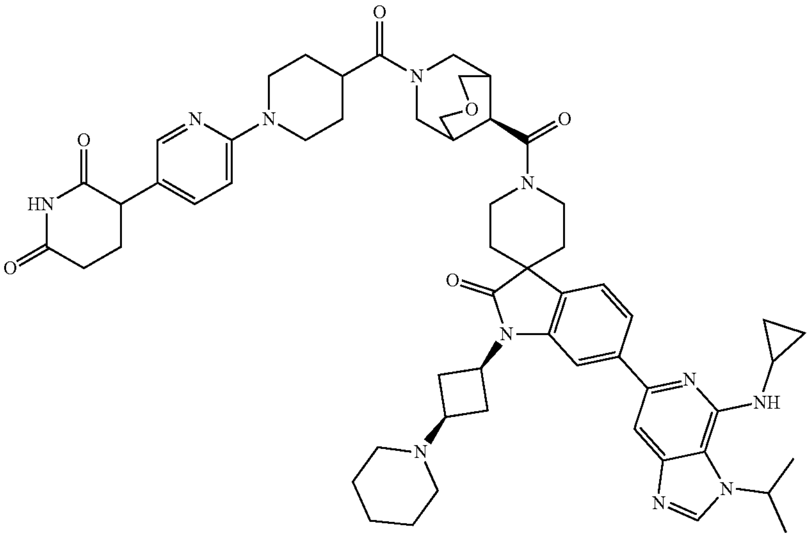

LCMS: $C_{57}H_{71}N_{11}O_6$ desired mass: 1005.6, found: m/z=1007.4 $[M+H]^+$.

Example 289

(3RS)-3-(4-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-8-azabicyclo[3.2.1]Octane-8-carbonyl]piperidin-1-yl}phenyl)piperidine-2,6-dione

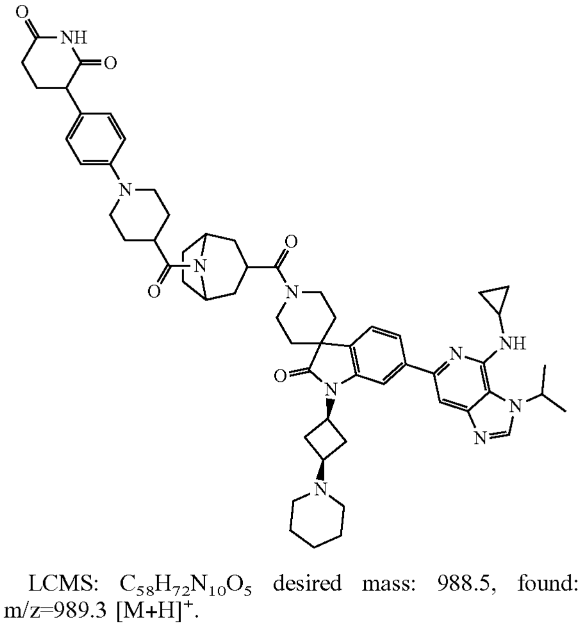

LCMS: $C_{58}H_{72}N_{10}O_5$ desired mass: 988.5, found: m/z=989.3 $[M+H]^+$.

Example 290

(3RS)-3-(6-{4-[7-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-azaspiro[3.5]nonane-5-carbonyl]piperidin-1-yl}pyridin-3-yl)piperidine-2,6-dione

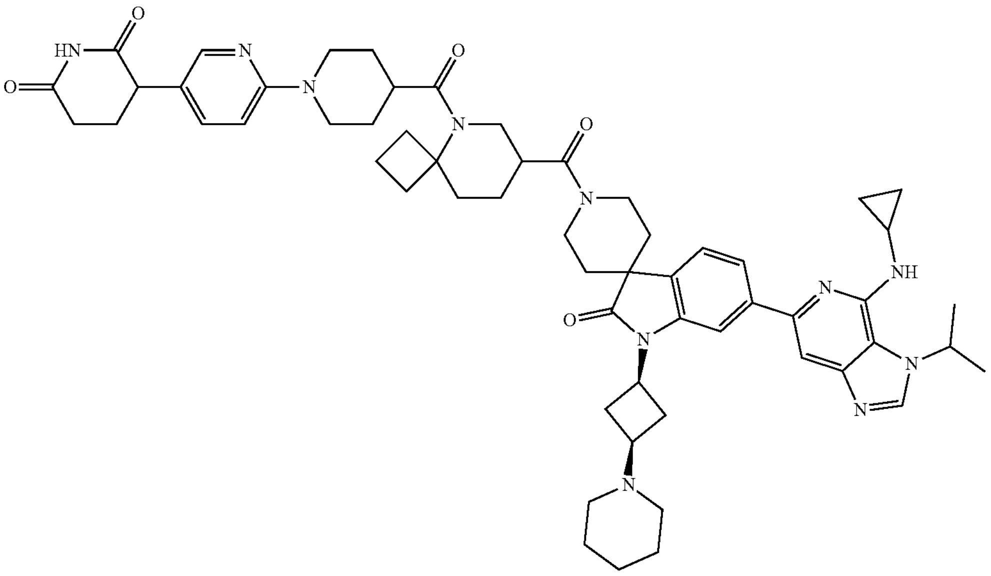 [SMILES: CC(C)n1cnc2cc(-c3ccc4c(c3)N([C@H]3C[C@@H](N5CCCCC5)C3)C(=O)C43CCN(C(=O)C4CCC5(CCC5)N(C(=O)C5CCN(c6ccc(C7CCC(=O)NC7=O)cn6)CC5)C4)CC3)nc(NC3CC3)c21]

LCMS: $C_{58}H_{73}N_{11}O_5$ desired mass: 1003.6, found: m/z=1004.1 $[M+H]^+$.

Example 291

1-{5-[(3RS)-2,6-dioxopiperidin-3-yl]pyridin-2-yl}-N-{[(1R,4R)-4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclohexyl]methyl}piperidine-4-carboxamide

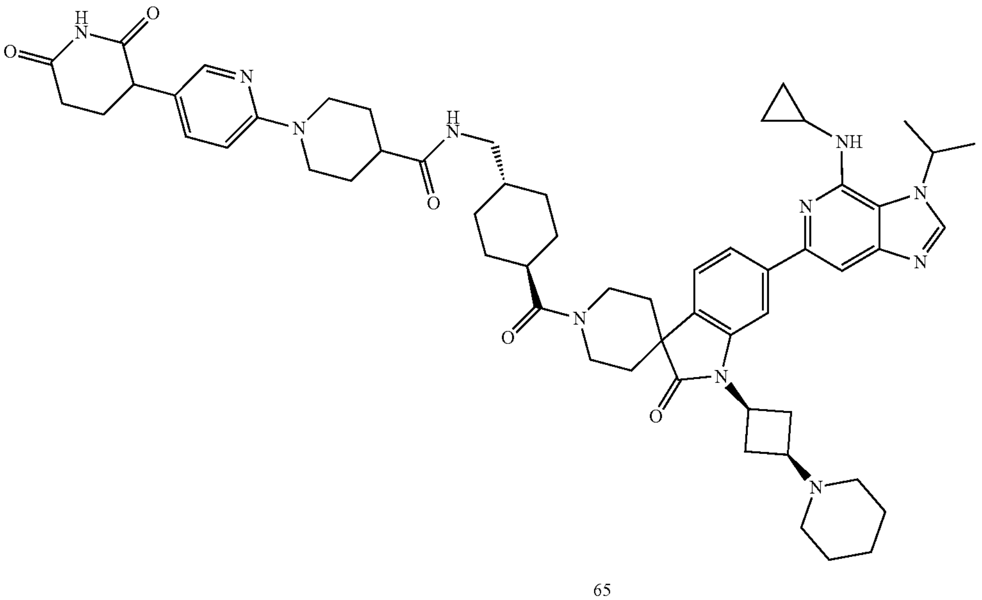

LCMS: $C_{57}H_{73}N_{11}O_5$ desired mass: 991.5, found: m/z=992.3 $[M+H]^+$.

Example 292

N-[(1S,3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexyl]-2-(1-{5-[(3RS)-2,6-dioxopiperidin-3-yl]pyridin-2-yl}piperidin-4-yl)acetamide

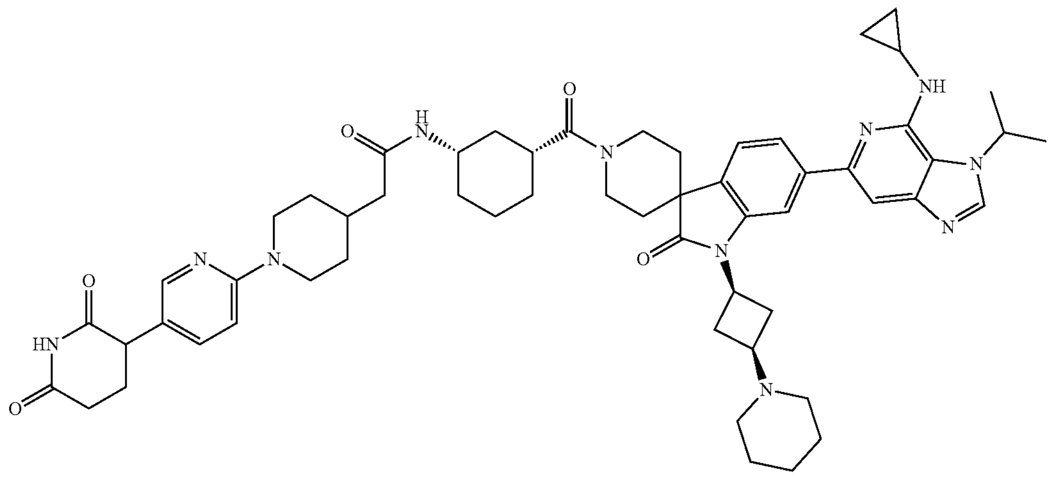 [SMILES: CC(C)n1cnc2cc(-c3ccc4c(c3)N([C@H]3C[C@@H](N5CCCCC5)C3)C(=O)C43CCN(C(=O)[C@@H]4CCC[C@H](NC(=O)CC5CCN(c6ccc(C7CCC(=O)NC7=O)cn6)CC5)C4)CC3)nc(NC3CC3)c21]

LCMS: $C_{57}H_{73}N_{11}O_5$ desired mass: 991.5, found: m/z=992.3 $[M+H]^+$.

Example 293

(3RS)-3-{6-[4-(4-{[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)phenyl]methyl}piperazine-1-carbonyl)piperidin-1-yl]pyridin-3-yl}piperidine-2,6-dione

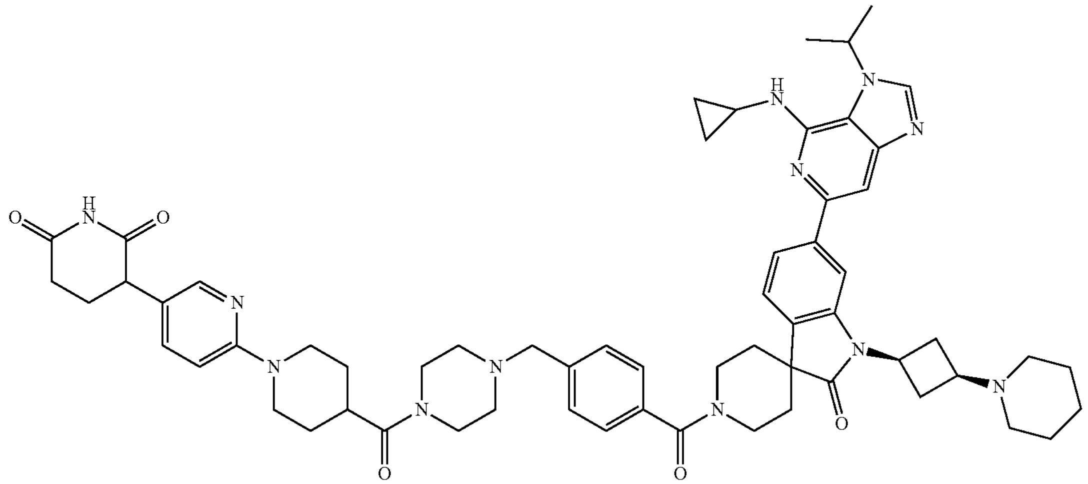 [SMILES: CC(C)n1cnc2cc(-c3ccc4c(c3)N([C@H]3C[C@@H](N5CCCCC5)C3)C(=O)C43CCN(C(=O)c4ccc(CN5CCN(C(=O)C6CCN(c7ccc(C8CCC(=O)NC8=O)cn7)CC6)CC5)cc4)CC3)nc(NC3CC3)c21]

LCMS: $C_{61}H_{74}N_{12}O_5$ desired mass: 1054.6, found: m/z=1055.3 $[M+H]^+$.

Example 294

(3RS)-3-(6-{4-[2-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-8-azaspiro[4.5]decane-8-carbonyl]piperidin-1-yl}pyridin-3-yl)piperidine-2,6-dione

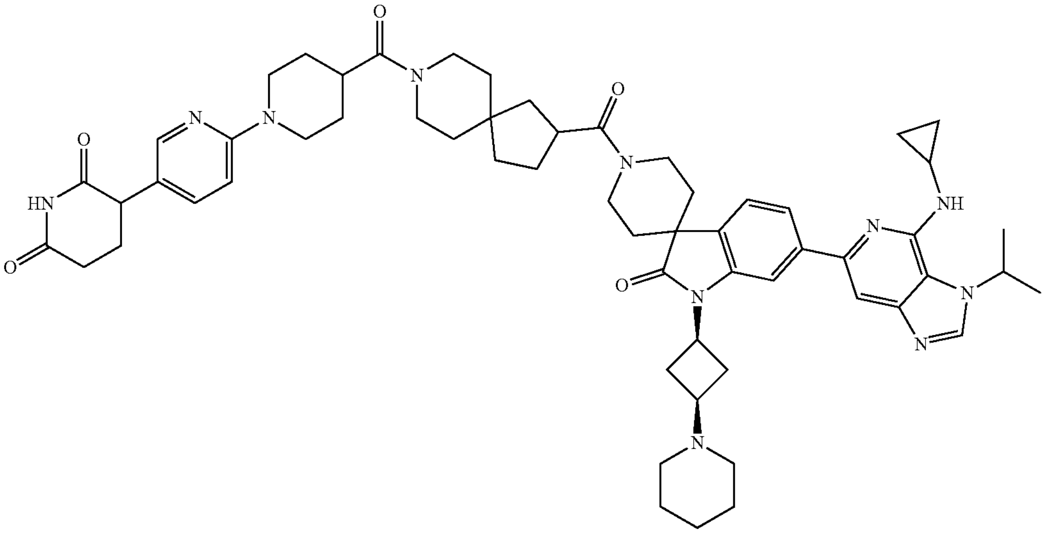 [SMILES: CC(C)n1cnc2cc(-c3ccc4c(c3)N([C@H]3C[C@@H](N5CCCCC5)C3)C(=O)C43CCN(C(=O)C4CCC5(CCN(C(=O)C6CCN(c7ccc(C8CCC(=O)NC8=O)cn7)CC6)CC5)C4)CC3)nc(NC3CC3)c21]

LCMS: $C_{59}H_{75}N_{11}O_5$ desired mass: 1017.6, found: m/z=1018.3 $[M+H]^+$.

Example 295

(3RS)-3-(6-{4-[9-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-3-azaspiro[5.5]undecane-3-carbonyl]piperidin-1-yl}pyridin-3-yl)piperidine-2,6-dione

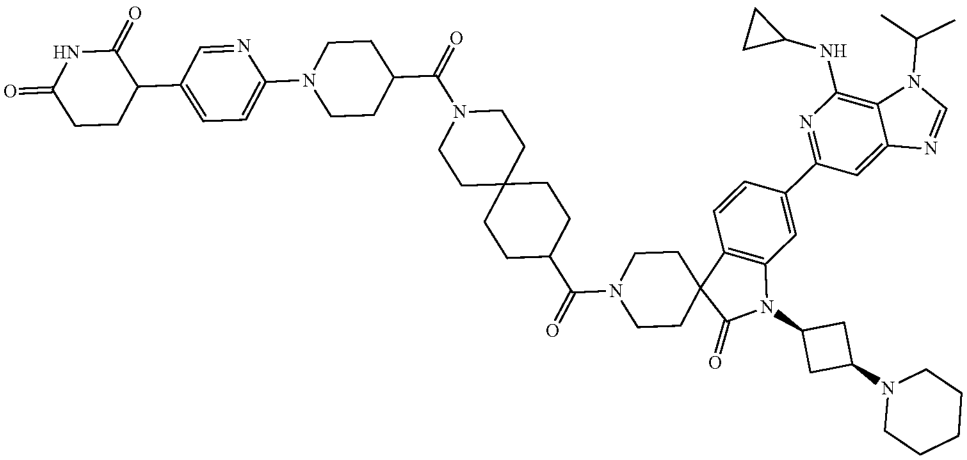 [SMILES: CC(C)n1cnc2cc(-c3ccc4c(c3)N([C@H]3C[C@@H](N5CCCCC5)C3)C(=O)C43CCN(C(=O)C4CCC5(CC4)CCN(C(=O)C4CCN(c6ccc(C7CCC(=O)NC7=O)cn6)CC4)CC5)CC3)nc(NC3CC3)c21]

LCMS: $C_{60}H_{77}N_{11}O_5$ desired mass: 1031.6, found: m/z=1032.4 $[M+H]^+$.

Example 296

(3RS)-3-(6-{4-[(3R)-3-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione

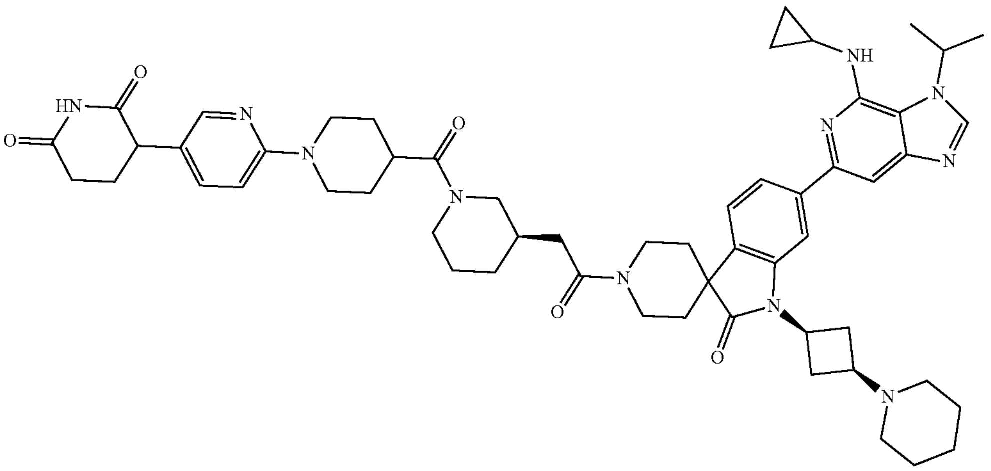 [SMILES: CC(C)n1cnc2cc(-c3ccc4c(c3)N([C@H]3C[C@@H](N5CCCCC5)C3)C(=O)C43CCN(C(=O)C[C@H]4CCCN(C(=O)C5CCN(c6ccc(C7CCC(=O)NC7=O)cn6)CC5)C4)CC3)nc(NC3CC3)c21]

LCMS: $C_{56}H_{71}N_{11}O_5$ desired mass: 977.5, found: m/z=978.3 $[M+H]^+$.

Example 297

(3RS)-3-[6-(4-{2-[(3R)-3-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidin-1-yl]-2-oxoethyl}piperidin-1-yl)pyridin-3-yl]piperidine-2,6-dione

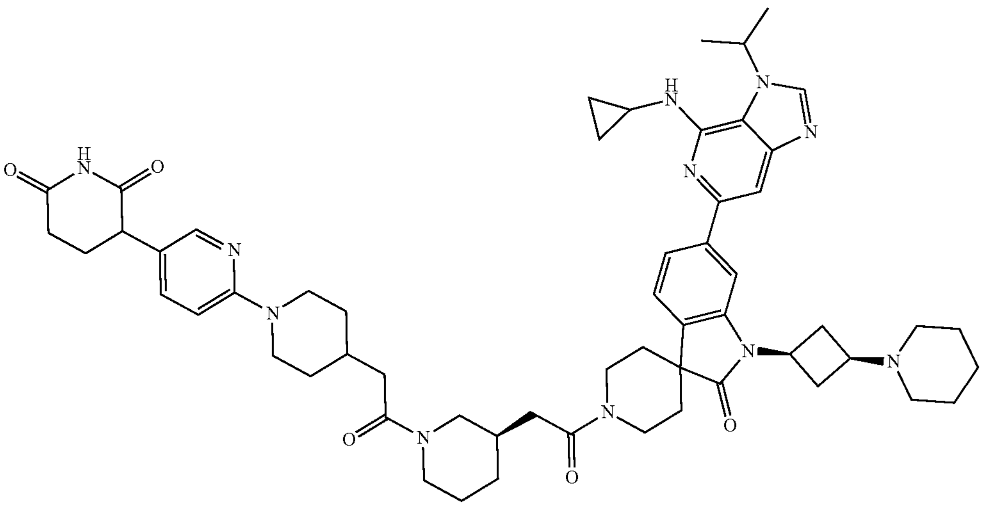 [SMILES: CC(C)n1cnc2cc(-c3ccc4c(c3)N([C@H]3C[C@@H](N5CCCCC5)C3)C(=O)C43CCN(C(=O)C[C@H]4CCCN(C(=O)CC5CCN(c6ccc(C7CCC(=O)NC7=O)cn6)CC5)C4)CC3)nc(NC3CC3)c21]

LCMS: $C_{57}H_{71}N_{11}O_5$ desired mass: 991.5, found: m/z=992.3 $[M+H]^+$.

Example 298

(3RS)-3-(6-{4-[(3S)-3-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione

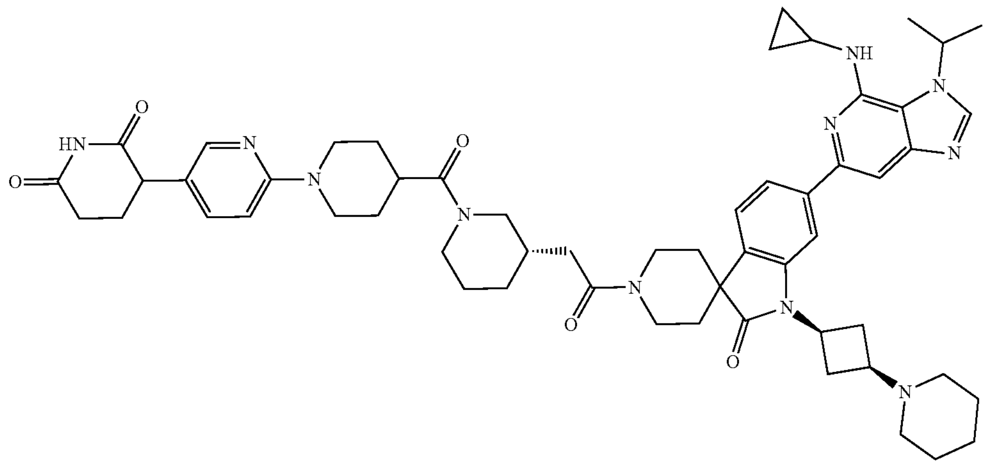 [SMILES: CC(C)n1cnc2cc(-c3ccc4c(c3)N([C@H]3C[C@@H](N5CCCCC5)C3)C(=O)C43CCN(C(=O)C[C@@H]4CCCN(C(=O)C5CCN(c6ccc(C7CCC(=O)NC7=O)cn6)CC5)C4)CC3)nc(NC3CC3)c21]

LCMS: $C_{56}H_{71}N_{11}O_5$ desired mass: 977.5, found: m/z=978.3 $[M+H]^+$.

Example 299

(3RS)-3-[6-(4-{2-[(3S)-3-(2-{6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}-2-oxoethyl)piperidin-1-yl]-2-oxoethyl}piperidin-1-yl)pyridin-3-yl]piperidine-2,6-dione

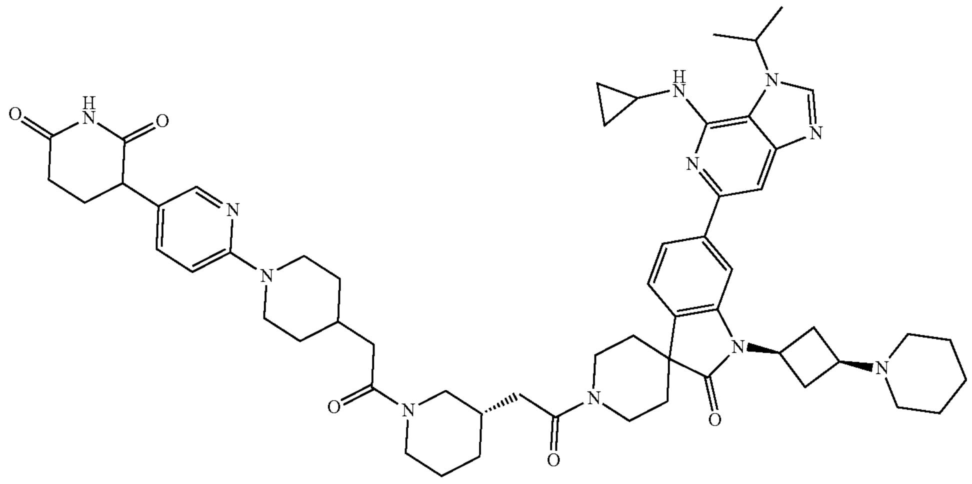 [SMILES: CC(C)n1cnc2cc(-c3ccc4c(c3)N([C@H]3C[C@@H](N5CCCCC5)C3)C(=O)C43CCN(C(=O)C[C@@H]4CCCN(C(=O)CC5CCN(c6ccc(C7CCC(=O)NC7=O)cn6)CC5)C4)CC3)nc(NC3CC3)c21]

LCMS: $C_{57}H_{71}N_{11}O_5$ desired mass: 991.5, found: m/z=992.3 $[M+H]^+$.

Example 300
(3RS)-3-[6-(4-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)cyclobutyl]piperidine-1-carbonyl}piperidin-1-yl)pyridin-3-yl]piperidine-2,6-dione
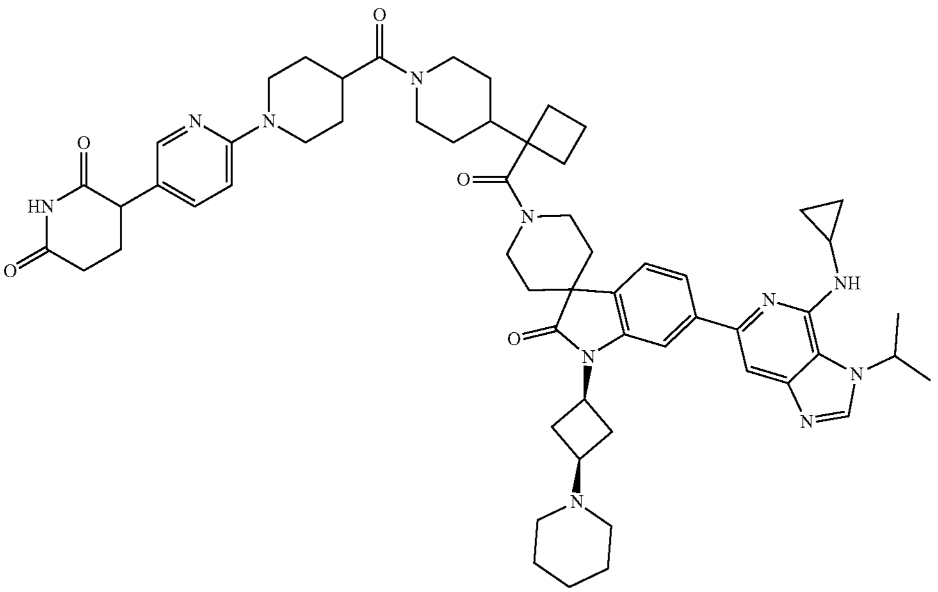 [SMILES: CC(C)n1cnc2cc(-c3ccc4c(c3)N([C@H]3C[C@@H](N5CCCCC5)C3)C(=O)C43CCN(C(=O)C4(C5CCN(C(=O)C6CCN(c7ccc(C8CCC(=O)NC8=O)cn7)CC6)CC5)CCC4)CC3)nc(NC3CC3)c21]
LCMS: $C_{59}H_{75}N_{11}O_5$ desired mass: 1017.6, found: m/z=1018.3 [M+H]⁺.

Example 301
(3RS)-3-[6-(4-{4-[3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)phenyl]piperidine-1-carbonyl}piperidin-1-yl)pyridin-3-yl]piperidine-2,6-dione
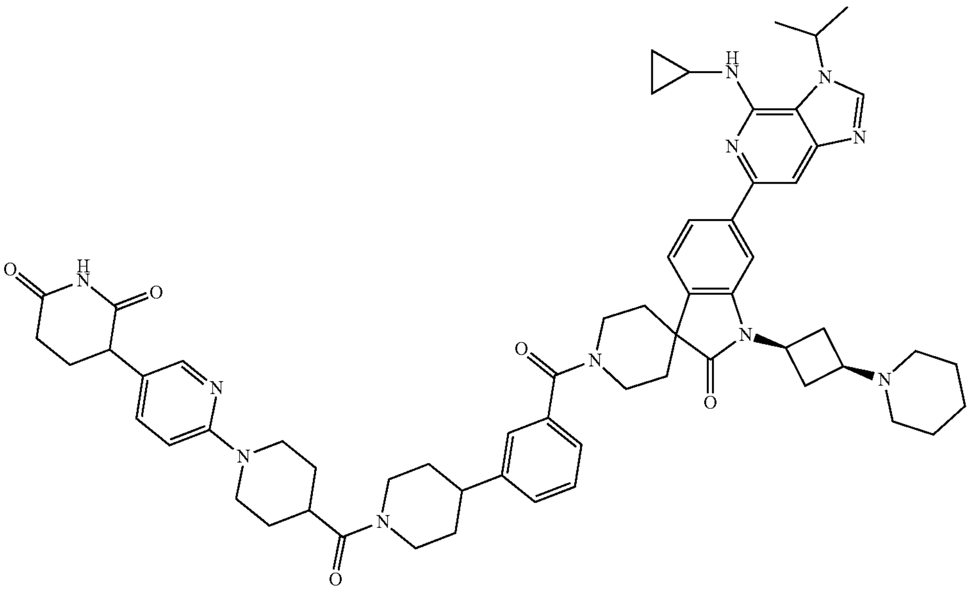 [SMILES: CC(C)n1cnc2cc(-c3ccc4c(c3)N([C@H]3C[C@@H](N5CCCCC5)C3)C(=O)C43CCN(C(=O)c4cccc(C5CCN(C(=O)C6CCN(c7ccc(C8CCC(=O)NC8=O)cn7)CC6)CC5)c4)CC3)nc(NC3CC3)c21]
LCMS: $C_{61}H_{73}N_{11}O_5$ desired mass: 1039.5, found: m/z=1040.3 [M+H]$^+$.

Example 302

(3RS)-3-[6-(4-{4-[4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)phenyl]piperidine-1-carbonyl}piperidin-1-yl)pyridin-3-yl]piperidine-2,6-dione

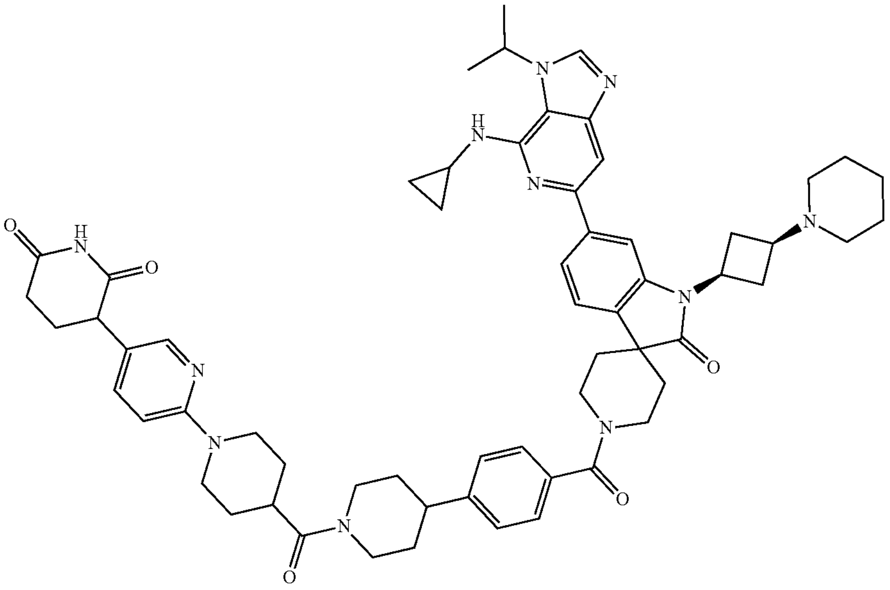 [SMILES: CC(C)n1cnc2cc(-c3ccc4c(c3)N([C@H]3C[C@@H](N5CCCCC5)C3)C(=O)C43CCN(C(=O)c4ccc(C5CCN(C(=O)C6CCN(c7ccc(C8CCC(=O)NC8=O)cn7)CC6)CC5)cc4)CC3)nc(NC3CC3)c21]

LCMS: $C_{61}H_{73}N_{11}O_5$ desired mass: 1039.5, found: m/z=1040.3 $[M+H]^+$.

Example 303

(3RS)-3-(6-{4-[1-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-azaspiro[2.4]heptane-5-carbonyl]piperidin-1-yl}pyridin-3-yl)piperidine-2,6-dione

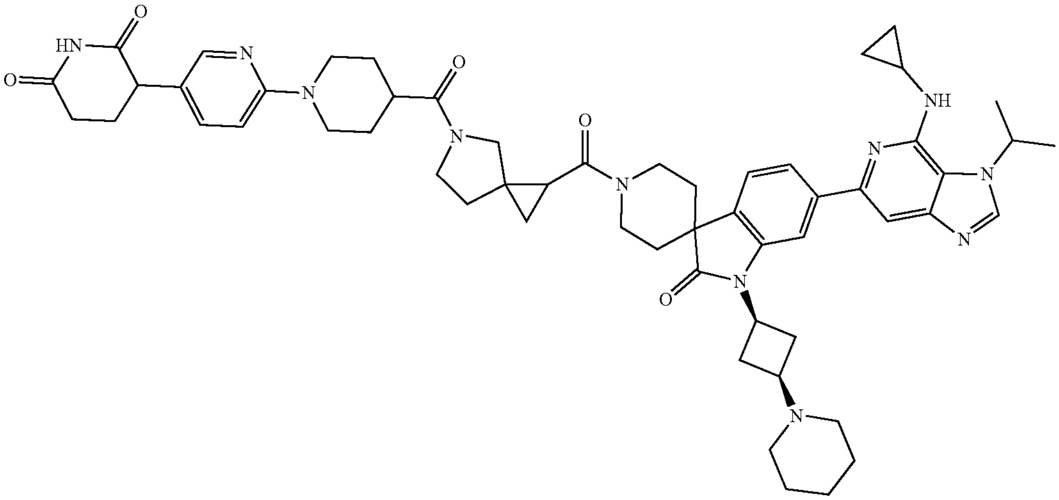 [SMILES: CC(C)n1cnc2cc(-c3ccc4c(c3)N([C@H]3C[C@@H](N5CCCCC5)C3)C(=O)C43CCN(C(=O)C4CC45CCN(C(=O)C4CCN(c6ccc(C7CCC(=O)NC7=O)cn6)CC4)C5)CC3)nc(NC3CC3)c21]

LCMS: $C_{56}H_{69}N_{11}O_5$ desired mass: 975.5, found: m/z=976.3 $[M+H]^+$.

Biological Example

HPK1 Cellular HiBit Degradation Assay

Materials and Methods

A HiBiT tag was introduced by CRISPR on the N terminus of HPK1 in Jurkat cells (ATCC® TIB-152) to allow quantitation of HPK1 protein levels in a monoclonal human cell line. Cells were plated at $1\times10^6$ cells/mL, 30 uL/well ($3\times10^4$ cells/well) in complete RPMI 1640 (10% heat inactivated FBS, 1% L-glutamine) in 384-well assay plates (Corning, cat. no. 3570). HPK1 chimeric targeting molecules (CTMs) were added in an 11 point dilution series (11-point, 3.16-fold) with a final assay concentration range of 10 uM to 0.1 nM. The parental Jurkat cell line, with no HiBiT insertion, was included in the assay as a background control. Cell treated with a DMSO vehicle control was used to determine the maximum signal defining 100% HPK1 in the cell. Cells were incubated for 24 hrs at 37° C./5% $CO_2$. Following incubation, 30 uL of complete Nano-Glo HiBiT Lytic Detection Reagent (Promega cat. no. N3040) was added. Cells were incubated for 10 min at room temperature and luminescence was read on an EnVision plate reader (Perkin Elmer, 0.1 sec per well). Viability was assessed in the same plate using Cell Titer Fluor (Promega) and read on an EnVision plate reader to ensure results were not the effect of cytotoxicity. Percent HPK1 remaining per sample was calculated as follows:

$$\%\ HPK1\ \text{remaining} = \left[\frac{\text{sample } RLU - \text{parental } RLU}{\text{average } DMSO\ RLU - \text{average parental } RLU}\right]\times 100$$

% HPK1 remaining values were plotted as a function of compound concentration and curves were fit using the Prism (GraphPad) equation "log(inhibitor) vs response−Variable slope (four parameters)". $D_{max}$ values were calculated by identifying the lowest % remaining and subtracting from 100. $DC_{50}$ values were determined by extrapolating from the curve the concentration at which 50% of HPK1 was remaining based on the DMSO control.

HiBiT HPK1 Jurkat cell lines were used to evaluate the total protein levels of HPK1 in a robust human cellular high throughput format. The level of HPK1 remaining following treatment with HPK1 CTMs is reported as $D_{max}$ (maximum degradation) achieved at 24 hours when compared to vehicle treated controls. These results indicate that HPK1 CTMs are able to degrade HPK1. These decreases were not a result of cytotoxicity measured by a viability assessment.

Table 1 and Table 2 summarize the $DC_{50}$ and $D_{max}$ values of certain selected HPK1 CTMs in the HiBiT HPK1 Degradation assay conducted in Jurkat cells. The $DC_{50}$ categories are as follows: A: <100 nM, B: >100 nM-<500 nM, C: >500 nM-<1000 nM. The $D_{max}$ categories are as follows: A: >85%, B: >70%-<85%, C: >50%-<70%.

TABLE 1

Activities of Representative Compounds

| Example number | $DC_{50}$ Category | $D_{max}$ Category |
|---|---|---|
| 1 | B | B |
| 2 | A | B |
| 3 | A | A |
| 4 | A | A |
| 5 | B | B |
| 6 | B | B |
| 7 | C | C |
| 8 | C | B |
| 9 | B | A |
| 10 | A | B |
| 11 | B | C |
| 12 | C | B |
| 13 | A | A |
| 14 | A | A |
| 15 | A | A |
| 16 | C | B |
| 17 | A | A |
| 18 | B | B |
| 19 | A | B |
| 20 | A | B |
| 21 | A | A |
| 22 | A | B |
| 23 | A | B |
| 24 | A | A |
| 25 | A | B |
| 26 | A | B |
| 27 | A | C |
| 28 | A | B |
| 29 | A | C |
| 30 | A | B |
| 31 | B | B |
| 32 | B | C |
| 33 | A | B |
| 34 | B | C |
| 35 | C | C |
| 36 | B | C |
| 37 | B | C |
| 38 | B | C |
| 39 | A | A |
| 40 | C | C |
| 41 | B | A |
| 42 | C | C |
| 43 | C | C |
| 44 | C | B |
| 45 | B | B |
| 46 | B | A |
| 47 | B | C |
| 48 | A | B |
| 49 | B | C |
| 50 | A | B |
| 51 | A | B |
| 52 | C | C |
| 53 | B | C |
| 54 | A | B |
| 55 | B | C |
| 56 | C | C |
| 57 | B | B |
| 58 | B | C |
| 59 | A | C |
| 60 | A | B |
| 61 | A | C |
| 62 | B | C |
| 63 | A | C |
| 64 | A | B |
| 65 | B | B |
| 66 | A | B |
| 67 | A | B |
| 68 | A | B |
| 69 | A | B |
| 70 | A | A |
| 71 | A | B |
| 72 | B | B |
| 73 | B | B |
| 74 | A | A |
| 75 | B | B |

TABLE 1-continued

| Activities of Representative Compounds | | |
|---|---|---|
| Example number | $DC_{50}$ Category | $D_{max}$ Category |
| 76 | B | A |
| 77 | A | B |
| 78 | A | C |
| 79 | A | C |
| 80 | A | B |
| 81 | A | C |
| 82 | A | B |
| 83 | B | C |
| 84 | B | C |
| 85 | A | B |
| 86 | B | B |
| 87 | A | B |
| 88 | A | C |
| 89 | B | C |
| 90 | A | B |
| 91 | B | C |
| 92 | A | B |
| 93 | A | C |
| 94 | A | C |
| 95 | A | B |
| 96 | B | B |
| 97 | C | C |
| 98 | C | A |
| 99 | C | C |
| 100 | B | B |
| 101 | A | B |
| 102 | A | A |
| 103 | A | B |
| 104 | A | B |
| 105 | A | A |
| 106 | A | B |
| 107 | B | B |
| 108 | A | B |
| 109 | B | C |
| 110 | A | A |
| 111 | A | B |
| 112 | A | B |
| 113 | A | B |
| 114 | A | B |
| 115 | A | B |
| 116 | A | A |
| 117 | A | A |
| 118 | A | C |
| 119 | A | B |
| 120 | A | B |
| 121 | C | C |
| 122 | B | B |
| 123 | A | C |
| 124 | B | B |
| 125 | C | C |
| 126 | A | A |
| 127 | A | A |
| 128 | A | A |
| 129 | B | B |
| 130 | A | C |
| 131 | A | B |
| 132 | A | C |
| 133 | C | C |
| 134 | B | C |
| 135 | A | B |
| 136 | A | B |
| 137 | A | B |
| 138 | A | A |
| 139 | A | B |
| 140 | C | C |
| 141 | C | C |
| 142 | C | B |
| 143 | A | C |
| 144 | A | C |
| 145 | C | C |
| 146 | B | B |

TABLE 2

| Activities of Additional Representative Compounds | | |
|---|---|---|
| Example number | $DC_{50}$ Category | $D_{max}$ Category |
| 147 | B | A |
| 148 | A | B |
| 149 | A | B |
| 150 | B | C |
| 151 | A | B |
| 152 | A | B |
| 153 | A | B |
| 154 | B | C |
| 155 | A | B |
| 156 | B | A |
| 157 | B | B |
| 158 | A | B |
| 159 | A | A |
| 160 | A | A |
| 161 | A | A |
| 162 | A | B |
| 163 | B | A |
| 164 | B | A |
| 165 | A | B |
| 166 | A | A |
| 167 | A | B |
| 168 | A | A |
| 169 | A | A |
| 170 | B | C |
| 171 | B | B |
| 172 | A | A |
| 173 | B | B |
| 174 | A | A |
| 175 | A | B |
| 176 | B | B |
| 177 | A | B |
| 178 | A | A |
| 179 | B | B |
| 180 | A | B |
| 181 | B | C |
| 182 | A | A |
| 183 | A | A |
| 184 | B | C |
| 185 | B | B |
| 186 | B | B |
| 187 | A | B |
| 188 | A | B |
| 189 | A | B |
| 190 | A | C |
| 191 | A | B |
| 192 | A | B |
| 193 | B | C |
| 194 | B | B |
| 195 | C | C |
| 196 | A | B |
| 197 | B | C |
| 198 | B | B |
| 199 | B | C |
| 200 | B | A |
| 201 | B | C |
| 202 | C | C |
| 203 | A | B |
| 204 | B | B |
| 205 | B | C |
| 206 | B | C |
| 207 | C | C |
| 208 | B | C |
| 209 | A | B |
| 210 | A | B |
| 211 | A | B |
| 212 | A | B |
| 213 | A | B |
| 214 | A | B |
| 215 | A | B |
| 216 | B | C |
| 217 | A | A |
| 218 | B | C |
| 219 | B | B |
| 220 | A | B |
| 221 | A | B |

TABLE 2-continued

| Activities of Additional Representative Compounds | | |
|---|---|---|
| Example number | $DC_{50}$ Category | $D_{max}$ Category |
| 222 | B | C |
| 223 | A | B |
| 224 | B | B |
| 225 | C | C |
| 226 | B | B |
| 227 | B | B |
| 228 | B | C |
| 229 | A | B |
| 230 | A | C |
| 231 | B | C |
| 232 | A | B |
| 233 | A | B |
| 234 | A | B |
| 235 | A | B |
| 236 | A | B |
| 237 | A | B |
| 238 | A | A |
| 239 | A | C |
| 240 | A | A |
| 241 | A | A |
| 242 | A | A |
| 243 | A | B |
| 244 | A | B |
| 245 | A | B |
| 246 | B | C |
| 247 | A | B |
| 248 | A | A |
| 249 | A | C |
| 250 | A | B |
| 251 | A | C |
| 252 | A | B |
| 253 | A | B |
| 254 | B | C |
| 255 | A | A |
| 256 | B | C |
| 257 | A | C |
| 258 | A | B |
| 259 | A | B |
| 260 | A | B |
| 261 | A | B |
| 262 | A | B |
| 263 | A | C |
| 264 | A | B |
| 265 | A | B |
| 266 | A | B |
| 267 | A | C |
| 268 | B | C |
| 269 | A | B |
| 270 | A | B |
| 271 | A | B |
| 272 | A | B |
| 273 | A | B |
| 274 | A | B |
| 275 | B | A |
| 276 | A | A |
| 277 | A | B |
| 278 | A | A |
| 279 | A | B |
| 280 | A | B |
| 281 | A | C |
| 282 | A | B |
| 283 | B | C |
| 284 | A | B |
| 285 | B | C |
| 286 | A | B |
| 287 | A | B |
| 288 | A | A |
| 289 | A | B |
| 290 | B | B |
| 291 | B | B |
| 292 | B | B |
| 293 | B | B |
| 294 | B | B |
| 295 | B | B |
| 296 | B | B |
| 297 | C | C |
| 298 | B | C |
| 299 | B | B |
| 300 | A | B |
| 301 | B | C |
| 302 | B | B |
| 303 | C | C |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having a structure represented by Formula (I):

Formula (I)

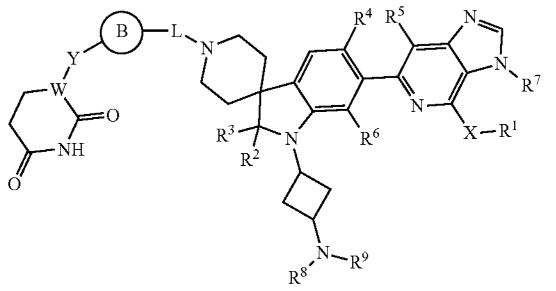

or a pharmaceutically acceptable salt thereof, wherein:

$R^1$ is i) phenyl optionally substituted with 1-3 groups independently selected from halogen, $C_{1-3}$ alkyl, —$C(O)N(R^{11})_2$, —CN, —OH, and $C_{1-3}$ alkoxy, ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy; or v) $C_{1-6}$ alkyl optionally substituted with 1-3 groups independently selected from halogen, $C_{1-3}$ alkyl, —C(O)N($R^{11}$)$_2$, —CN, —OH, and $C_{1-3}$ alkoxy, $R^2$ and $R^3$ are each H, or $R^2$ and $R^3$ together form ═O;

$R^4$, $R^5$, $R^6$, and $R^{10}$ are each independently H, halogen, $C_{1-3}$ alkyl, or $C_{1-3}$ alkoxy;

$R^7$ is H or $C_{1-6}$ alkyl optionally substituted with 1-3 groups independently selected from —OH, halogen, $C_{1-3}$ alkoxy, and $C_{3-7}$ monocyclic cycloalkyl;

$R^8$ and $R^9$ are independently i) H, ii) $C_{3-7}$ monocyclic cycloalkyl optionally substituted with 1-3 groups independently selected from —OH, halogen, $C_{1-3}$ alkyl, and $C_{1-3}$ alkoxy, iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, iv) $C_{1-6}$ alkyl optionally substituted with 1-6 groups independently selected from a) —CN, a) —OH, b) halogen, c) $C_{1-3}$ alkoxy, d) $C_{3-7}$ monocyclic cycloalkyl optionally substituted with 1-3 groups independently selected from —OH, halogen, $C_{1-3}$ alkyl, and $C_{1-3}$ alkoxy, and e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or $R^8$ and $R^9$, together with the nitrogen to which they are attached, form 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{12}$;

each $R^{11}$ is independently i) H, ii) $C_{1-6}$ alkyl optionally substituted with 1-6 groups independently selected from —CN, —OH, halogen, $C_{1-3}$ alkoxy, and $C_{3-7}$ monocyclic cycloalkyl, iii) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or iv) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy;

each $R^{12}$ is independently i) —CN, ii) a halogen, iii) —OH, iv) $C_{1-6}$ alkoxy optionally substituted with 1-3 groups independently selected from —OH, halogen, $C_{1-3}$ alkoxy, and $C_{3-7}$ monocyclic cycloalkyl, v) $C_{1-6}$ alkyl optionally substituted with 1-3 groups independently selected from —OH, halogen, $C_{1-3}$ alkoxy, and $C_{3-7}$ monocyclic cycloalkyl, vi) —COOH, or vii) —C(O)N($R^{13}$)$_2$, wherein each $R^{13}$ is independently H or $C_{1-6}$ alkyl;

X is —N($R^{11}$)— or —O—, wherein $R^{11}$, together with $R^1$ and the nitrogen atom to which they are connected, may form a 4-12 membered heterocylcle optionally substituted with 1-3 $R^b$, L is -$L_1$-$L_2$-$L_3$-$L_4$-$L_5$-$L_6$-, each $L_1$, $L_2$, $L_3$, $L_4$, $L_5$ and $L_6$ being independently:

i) $C_{3-12}$ cycloalkyl optionally substituted with 1-3 $R^b$, ii) $C_{6-12}$ aryl optionally substituted with 1-3 $R^b$;

iii) 4-12 membered heterocyclyl optionally substituted with 1-3 $R^b$, iv) 5-12 membered heteroaryl optionally substituted with 1-3 $R^b$, v) direct bond;

vi) $C_{1-12}$ alkylene chain optionally substituted with 1-3 $R^d$, vii) $C_{2-12}$ alkenylene chain optionally substituted with 1-3 $R^d$, viii) $C_{2-12}$ alkynylene chain optionally substituted with 1 to 3 $R^d$, ix) —C(O)—, —C(O)O—, —O—, —N($R^c$)—, —($CH_2$)$_m$—C(O)—, —S—, —C(S)—, —C(S)—O—, —S(O)$_2$—, —S(O)—N—, —S(O)$_2$NH—, —C(O)—N($R^c$)—, —C═N—, —O—C(O)—N($R^c$)—, —O—C(O)—O—, or —NH—($CH_2$)$_m$—C(O)—, wherein m is 0, 1, 2 or 3;

each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$;

each $R^b$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —N$R^c$S(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$, each $R^c$ is independently hydrogen or $C_{1-6}$ alkyl;

each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro;

W is —C($R^g$)— or —N—;

Y is direct bond, $C_{1-4}$ alkylene chain, —C(O)—, —C(O)O—, —O—, —N($R^g$)—, —S—, —C(S)—, —C(S)—O—, —O—C(O)O—, —C(O)—N($R^g$)—, or —O—C(O)—N($R^g$)—;

B ring is $C_{6-12}$ aryl, 5-12 membered heteroaryl, or 4-12 membered heterocyclyl, each being optionally substituted with 1 to 3 $R^j$;

each $R^j$ is independently hydrogen, oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N($R^g$)($R^g$), —N($R^g$)($R^g$), —N($R^g$)C(O)—$R^g$, —N($R^g$)C(O)O—$R^g$, —N($R^g$)C(O)N($R^g$)($R^g$), —N(R)S(O)$_2$($R^g$), —NR$^c$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)(NH)$R^g$, —S(O)$_2R^g$ or —S(O)$_2$N($R^g$)($R^g$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$, $R^g$ is hydrogen or $C_{1-6}$ alkyl; and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro, provided that, either $R^1$ is not

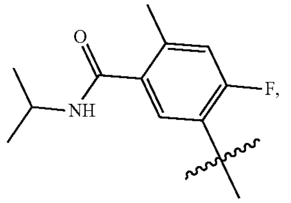 [SMILES: *c1cc(C(=O)NC(C)C)c(C)cc1F]

or if $R^1$ is

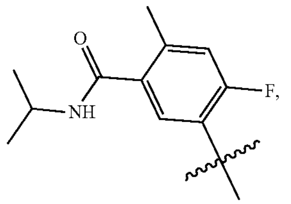 [SMILES: *c1cc(C(=O)NC(C)C)c(C)cc1F]

then

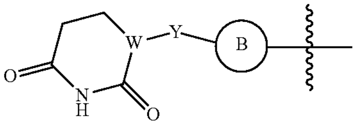

is not

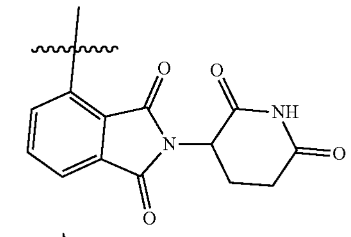

, or

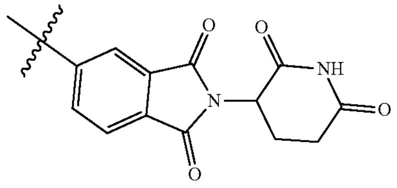

.

2. The compound of Formula (I) according to claim 1:

Formula (I)

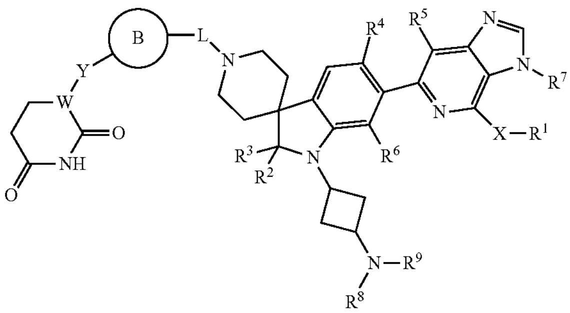

or a pharmaceutically acceptable salt thereof, wherein:

$R^1$ is i) phenyl optionally substituted with 1-3 groups independently selected from halogen, $C_{1-3}$ alkyl, —C(O)N($R^{11}$)$_2$, —CN, —OH, and $C_{1-3}$ alkoxy, ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, or iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy, $R^2$ and $R^3$ are each H, or $R^2$ and $R^3$ together form =O, $R^4$, $R^5$, $R^6$, and $R^{10}$ are each independently H, halogen, $C_{1-3}$ alkyl, or $C_{1-3}$ alkoxy, $R^7$ is H or $C_{1-6}$ alkyl optionally substituted with 1-3 groups independently selected from —OH, halogen, $C_{1-3}$ alkoxy, and $C_{3-7}$ monocyclic cycloalkyl, $R^8$ and $R^9$ are independently i) H, ii) $C_{3-7}$ monocyclic cycloalkyl optionally substituted with 1-3 groups independently selected from —OH, halogen, $C_{1-3}$ alkyl, and $C_{1-3}$ alkoxy, iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, iv) $C_{1-6}$ alkyl optionally substituted with 1-6 groups independently selected from a) —CN, b) —OH, c) halogen, d) $C_{1-3}$ alkoxy, e) $C_{3-7}$ monocyclic cycloalkyl optionally substituted with 1-3 groups independently selected from —OH, halogen, $C_{1-3}$ alkyl, and $C_{1-3}$ alkoxy, and f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy, or $R^8$ and $R^9$, together with the nitrogen to which they are attached, form 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{12}$, each $R^{11}$ is independently i) H, ii) $C_{1-6}$ alkyl optionally substituted with 1-6 groups independently selected from —CN, —OH, halogen, $C_{1-3}$ alkoxy, and $C_{3-7}$ monocyclic cycloalkyl, iii) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or iv) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy, each $R^{12}$ is independently i) —CN, ii) a halogen, iii) —OH, iv) $C_{1-6}$ alkoxy optionally substituted with 1-3 groups independently selected from —OH, halogen, $C_{1-3}$ alkoxy, and $C_{3-7}$ monocyclic cycloalkyl, v) $C_{1-6}$ alkyl optionally substituted with 1-3 groups independently selected from —OH, halogen, $C_{1-3}$ alkoxy, and $C_{3-7}$ monocyclic cycloalkyl, vi) —COOH, or vii) —C(O)N($R^{13}$)$_2$, wherein each $R^{13}$ is independently H or $C_{1-6}$ alkyl, X is —N($R^{11}$)— or —O—, L is -$L_1$-$L_2$-$L_3$-$L_4$-$L_5$-, each $L_1$, $L_2$, $L_3$, $L_4$ and $L_5$ being independently:

i) $C_{3-12}$ cycloalkyl optionally substituted with 1-3 $R^b$, ii) $C_{6-12}$ aryl optionally substituted with 1-3 $R^b$, iii) 4-12 membered heterocyclyl optionally substituted with 1-3 $R^b$, iv) 5-12 membered heteroaryl optionally substituted with 1-3 $R^b$, v) direct bond, vi) $C_{1-12}$ alkylene chain optionally substituted with 1-3 $R^d$, vii) $C_{2-12}$ alkenylene chain optionally substituted with 1-3 $R^d$, viii) $C_{2-12}$ alkynylene chain optionally substituted with 1 to 3 $R^d$, or ix) —C(O)—, —C(O)O—, —O—, —N($R^c$)—, —$(CH_2)_m$—C(O)—, —S—, —C(S)—, —C(S)—O—, —S(O)$_2$—, —S(O)═N—, —S(O)$_2$NH—, —C(O)—N($R^c$)—, —C═N—, —O—C(O)—N($R^c$)—, —O—C(O)—O—, or —NH—$(CH_2)_m$—C(O)—, wherein m is 0, 1, 2 or 3, each $R^a$ is independently halo, —CN, $C_{1-3}$ alkyl optionally substituted with 1 to 3 $R^d$, $C_{3-6}$ cycloalkyl optionally substituted with 1 to 3 $R^d$, or —O$R^c$, each $R^b$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^c$, —C(O)—$R^c$, —C(O)O—$R^c$, —C(O)—N($R^c$)($R^c$), —N($R^c$)($R^c$), —N($R^c$)C(O)—$R^c$, —N($R^c$)C(O)O—$R^c$, —N($R^c$)C(O)N($R^c$)($R^c$), —N($R^c$)S(O)$_2$($R^c$), —NRCS(O)$_2$N($R^c$)($R^c$), —N($R^c$)S(O)$_2$O($R^c$), —OC(O)$R^c$, —OC(O)—N($R^c$)($R^c$), —Si($R^c$)$_3$, —S—$R^c$, —S(O)$R^c$, —S(O)(NH)$R^c$, —S(O)$_2R^c$ or —S(O)$_2$N($R^c$)($R^c$), wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^d$, each $R^c$ is independently hydrogen or $C_{1-6}$ alkyl, each $R^d$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro, W is —C($R^g$)— or —N—, Y is direct bond, $C_{1-4}$ alkylene chain, —C(O)—, —C(O)O—, —O—, —N($R^g$)—, —S—, —C(S)—, —C(S)—O—, —O—C(O)O—, —C(O)—N($R^g$)—, or —O—C(O)—N($R^g$)—, B ring is $C_{6-12}$ aryl, 5-12 membered heteroaryl, or 4-12 membered heterocyclyl, each being optionally substituted with 1 to 3 $R^j$, each $R^j$ is independently oxo, imino, sulfoximino, halo, nitro, —CN, $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, 4-12 membered heterocyclyl, —O—$R^g$, —C(O)—$R^g$, —C(O)O—$R^g$, —C(O)—N($R^g$)($R^g$), —N($R^g$)($R^g$), —N(R)C(O)—$R^g$, —N($R^g$)C(O)O—$R^g$, —N($R^g$)C(O)N($R^g$)($R^g$), —N($R^g$)S(O)$_2$($R^g$), —N$R^g$S(O)$_2$N($R^g$)($R^g$), —N($R^g$)S(O)$_2$O($R^g$), —OC(O)$R^g$, —OC(O)—N($R^g$)($R^g$), —Si($R^g$)$_3$, —S—$R^g$, —S(O)$R^g$, —S(O)

(NH)$R^g$, —$S(O)_2R^g$ or —$S(O)_2N(R^g)(R^g)$, wherein each of $C_{1-6}$ alkyl, $C_{2-6}$ alkenyl, $C_{2-6}$ alkynyl, $C_{3-15}$ cycloalkyl, $C_{1-8}$ haloalkyl, $C_{6-12}$ aryl, 5-12 membered heteroaryl, and 4-12 membered heterocyclyl may be optionally substituted with 1 to 3 $R^k$, $R^g$ is hydrogen or $C_{1-6}$ alkyl, and each $R^k$ is independently halo, oxo, —CN, —OH, $C_{1-6}$ alkyl optionally substituted with 1 to 3 fluoro, or $C_{3-8}$ cycloalkyl, or —O—$C_{1-6}$ alkyl optionally substituted with 1 to 3 fluoro.

3. The compound of claim 1, wherein $R^2$ and $R^3$ together form ═O and the compound has a structure of Formula (Ia):

Formula (Ia)

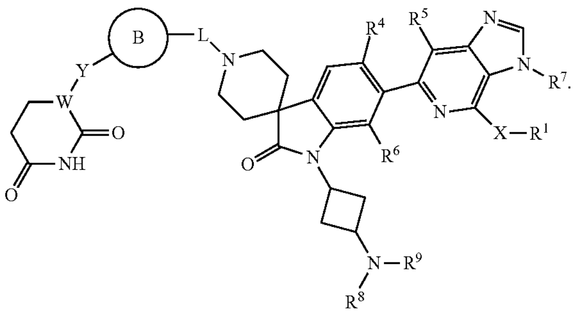

4. The compound of claim 3, wherein $R^8$ and $R^9$, together with the nitrogen to which they are attached, form piperidinyl, and the compound has a structure of Formula (Ib):

Formula (Ib)

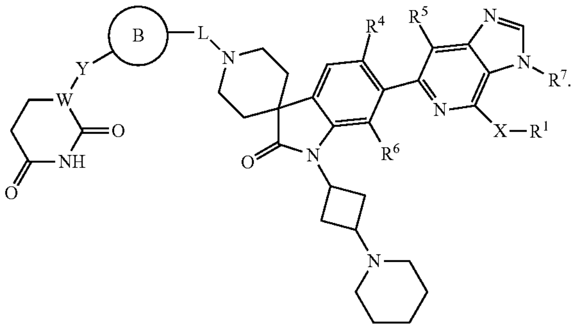

5. The compound of claim 3, wherein $R^8$ and $R^9$ are each $C_{1-3}$ alkyl.

6. The compound of claim 1, wherein X is —NH— or X is —O—.

7. The compound of claim 1, wherein $R^1$ is phenyl optionally substituted with halo, pyridinyl optionally substituted with halo, $C_{3-6}$ cycloalkyl, or 4-6 member heterocyclyl.

8. The compound of claim 7 wherein $R^1$ is 2-fluorophenyl, 3-fluoropyrini-4-yl, cyclopropyl or oxan-4-yl.

9. The compound of claim 1, wherein $R^1$ is $C_{1-6}$ alkyl,

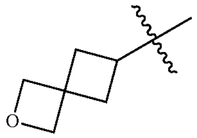

, or $C_{3-6}$ cycloalkyl optionally substituted with halo or CN.

10. The compound of claim 9, wherein $R^1$ is isopropyl, or

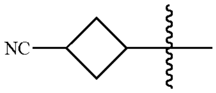

.

11. The compound of claim 1, wherein, X is —N($R^{11}$)—, and $R^{11}$ and $R^1$, together with the nitrogen atom to which they are connected, may form a 4-12 membered heterocylcle optionally substituted halo or CN.

12. The compound of claim 11 wherein —X—$R^1$ is

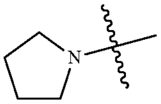

or

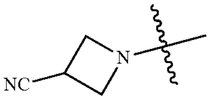

.

13. The compound of claim 1, wherein $R^2$ and $R^3$ form oxo, $R^8$ and $R^9$, together with the nitrogen to which they are attached, form one of the following heterocycle rings:

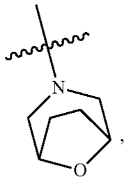

,

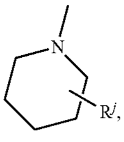

,

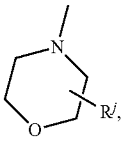

,

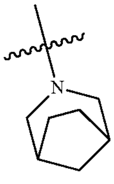

,

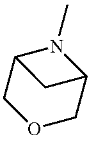

,

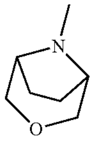

, wherein $R^j$ is H or halo.

14. The compound of claim 13, wherein $R^1$ is phenyl optionally substituted with halo, pyridinyl optionally substituted with halo, $C_{3-6}$ cycloalkyl, or 4-6 member heterocyclyl; and $R^4$, $R^5$, $R^6$ and $R^7$ are independently H or $C_{1-3}$alkyl.

15. The compound of claim 14, wherein $R^1$ is cyclopropyl, $R^4$, $R^5$, and $R^6$ are hydrogen, and $R^7$ is cyclopropyl.

16. The compound of claim 2, wherein each $L_1$, $L_2$, $L_3$, $L_4$ and $L_5$ is independently:

i)

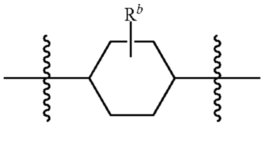

,

-continued ii)

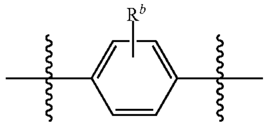

, iii)

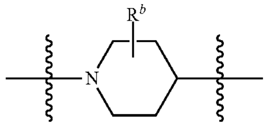

,

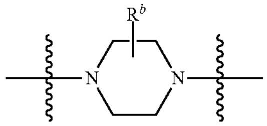

,

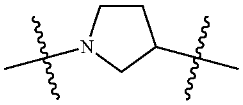

,

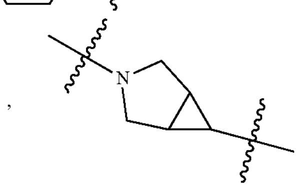

,

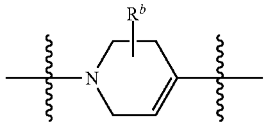

, iv)

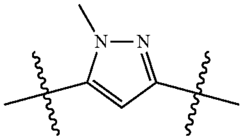

, or

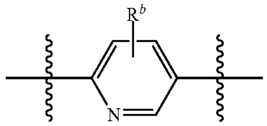

, v) direct bond, vi) $C_{1-3}$ alkylene chain, or vii) —C(O)—, —O—, —C(O)—N($R^c$)—, —$(CH_2)_m$—C(O)—, or —NH—$(CH_2)_m$—C(O)—, wherein m is 0, 1, 2 or 3, wherein $R^b$ is $C_{1-3}$ alkyl, and $R^c$ is H or $C_{1-3}$ alkyl.

17. The compound of claim 16, wherein L is connected to the B ring by $L_1$, and wherein $L_1$ is direct bond, —C(O)—, —N($R^c$)— (wherein $R^c$ is H or methyl), —O—, —$CH_2$—, or —NH—$CH_2$—C(O)—.

18. The compound of claim 17, wherein -$L_2$-$L_3$-$L_4$-$L_5$- has one of the following structures, or a stereoisomer thereof:

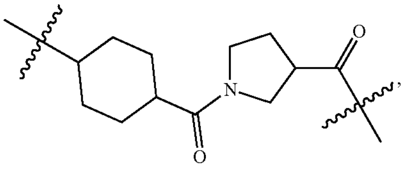

,

-continued

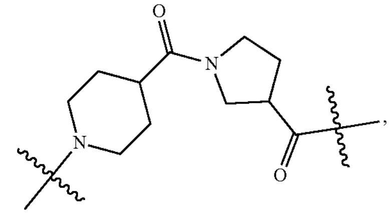

,

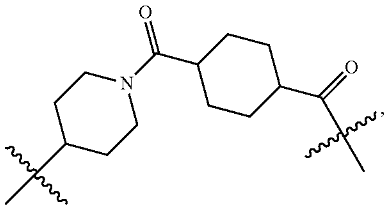

,

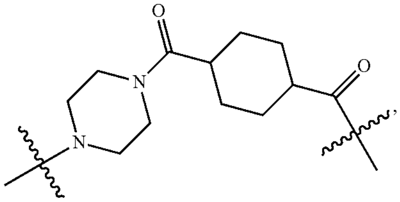

,

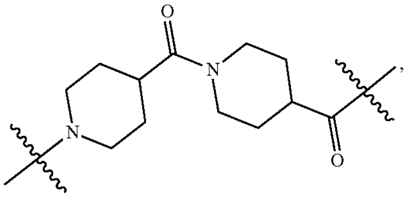

,

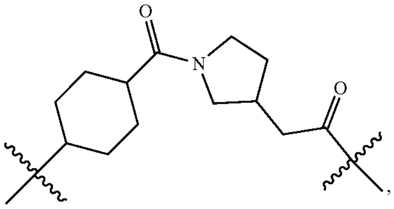

,

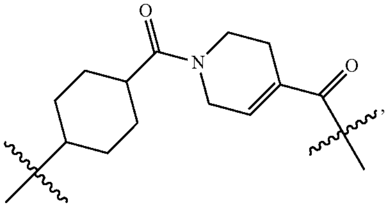

,

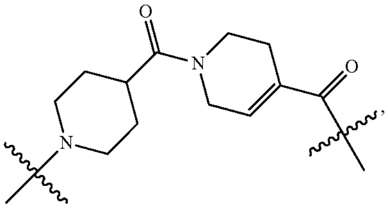

,

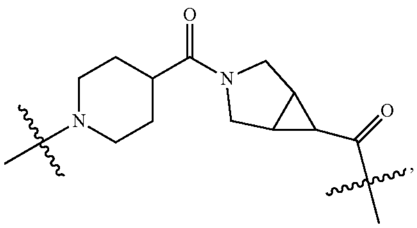

,

-continued
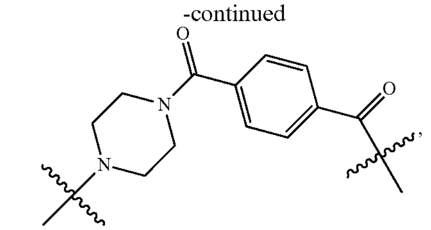
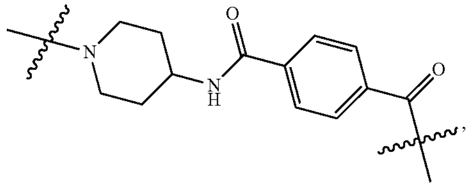
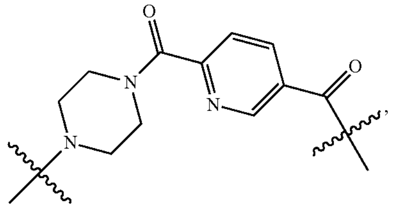
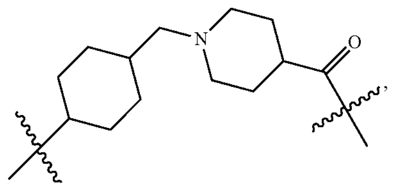
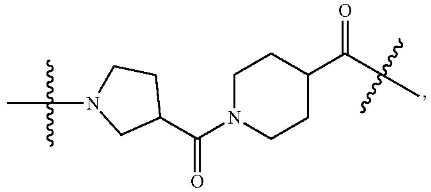
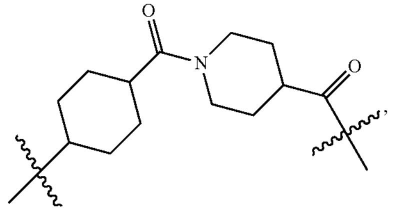
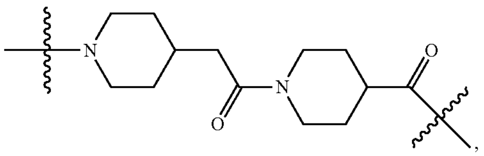
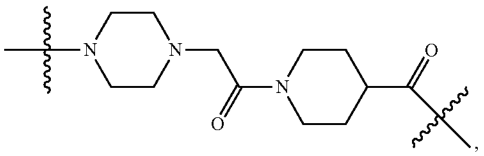
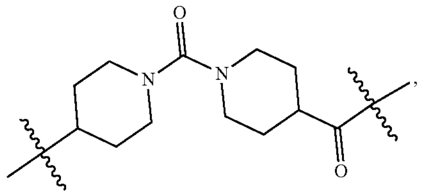
-continued
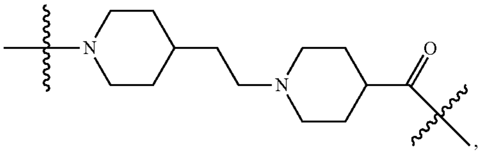
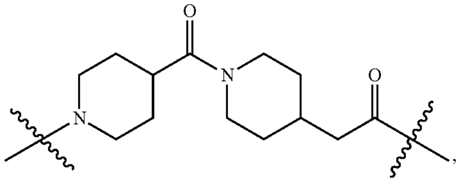
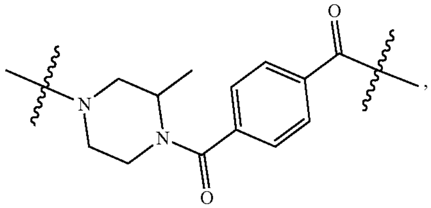
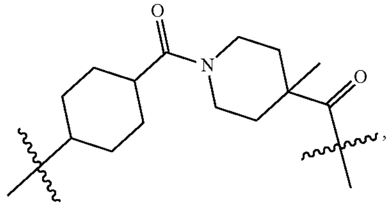
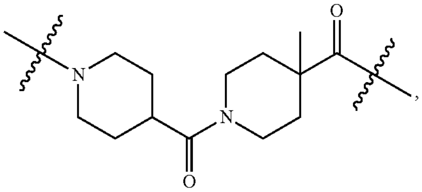
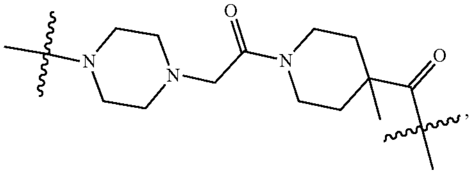
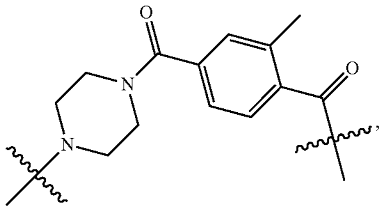
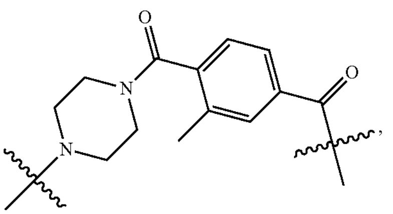

-continued
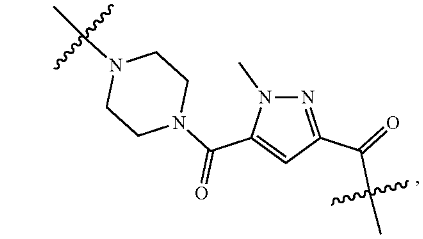
,
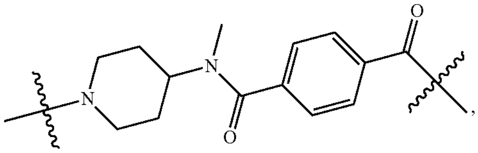
,
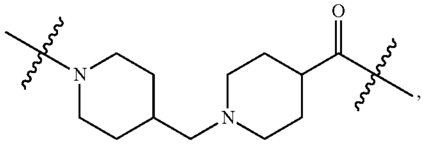
, or
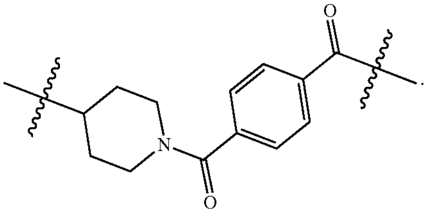
.
19. The compound of claim 16, wherein L has one of the following structures:
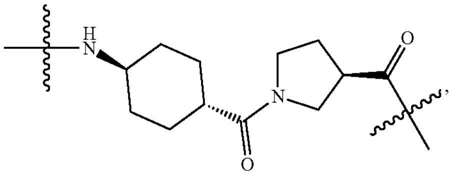
,
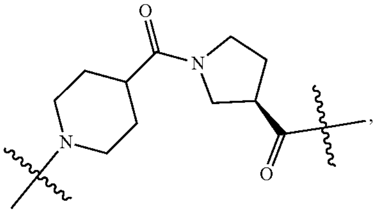
,
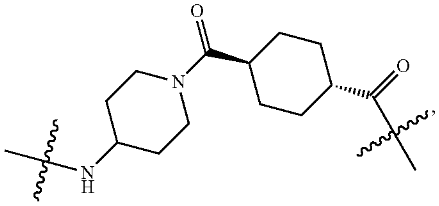
,
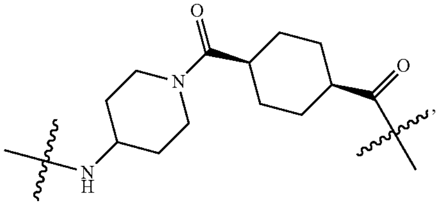
,
-continued
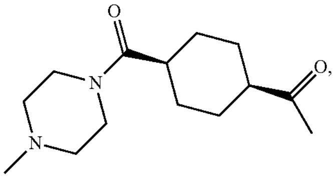
,
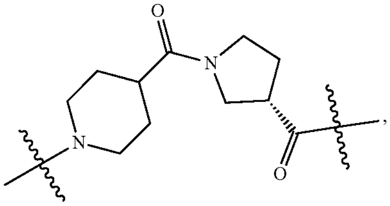
,
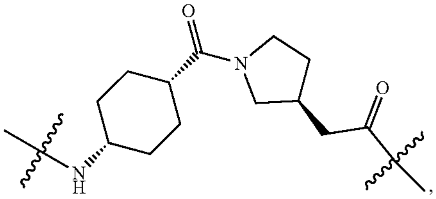
,
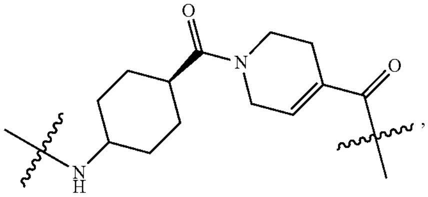
,
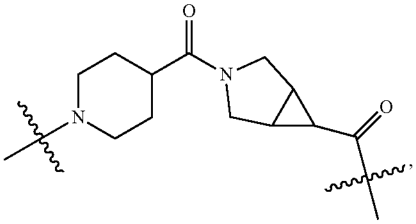
,
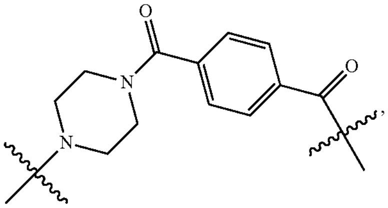
,
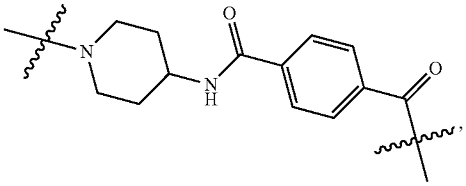
,
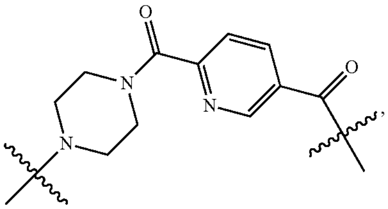
, -continued
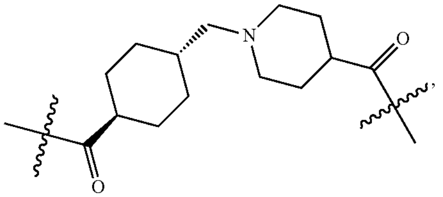
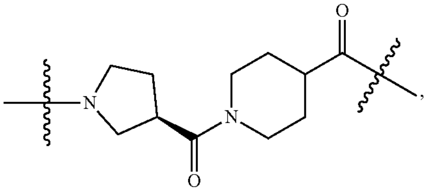
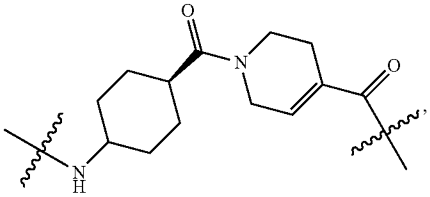
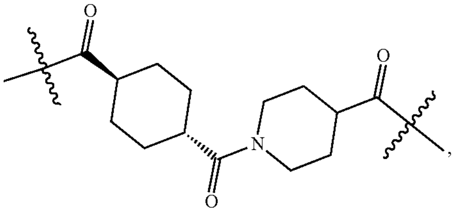
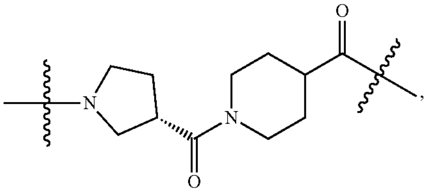
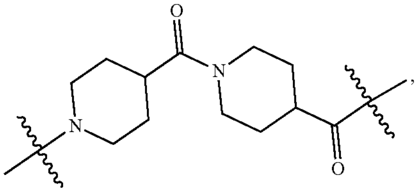
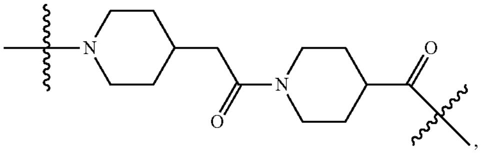
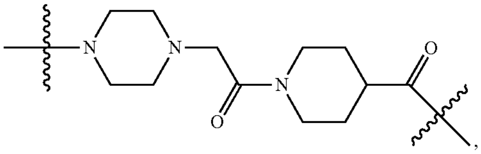
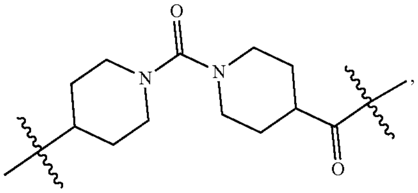
-continued
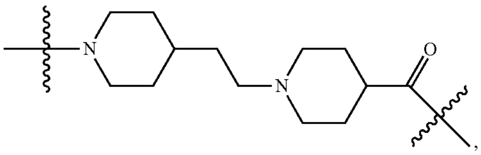
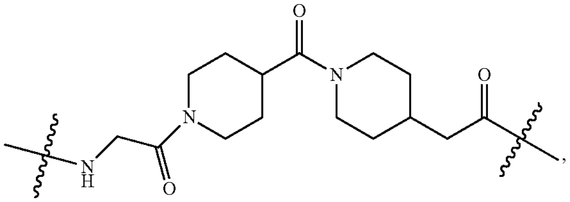
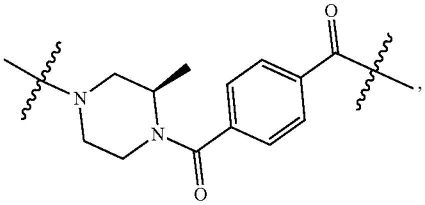
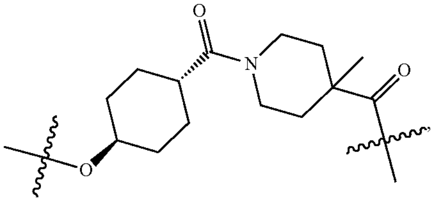
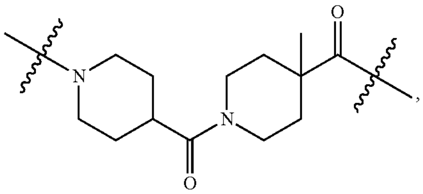
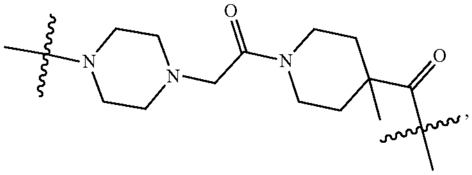
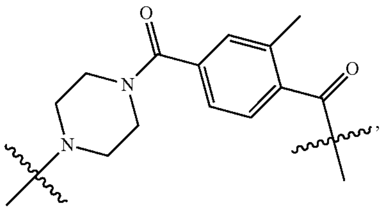
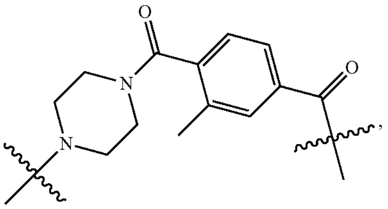

-continued
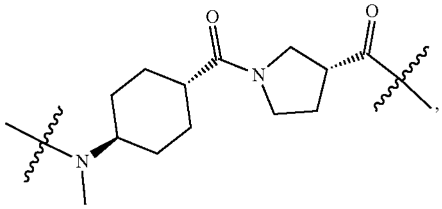,
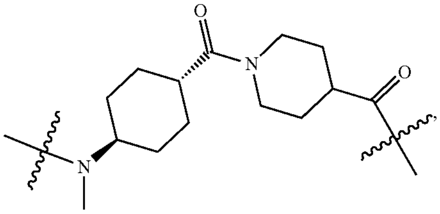,
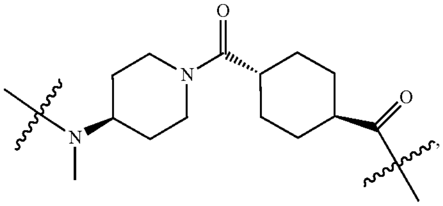,
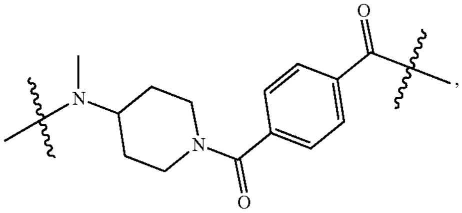,
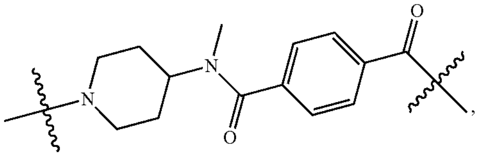,
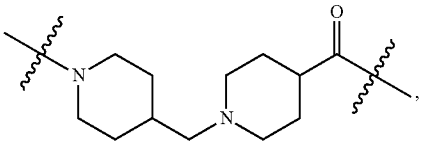,
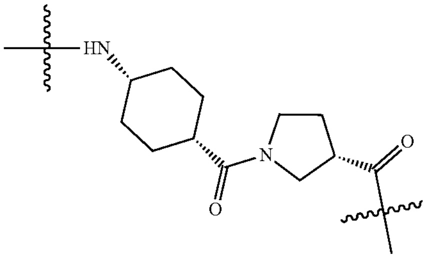,
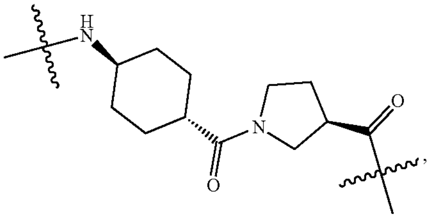,
-continued
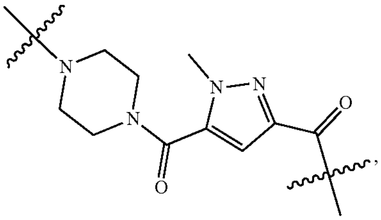,
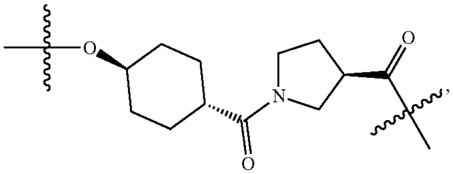,
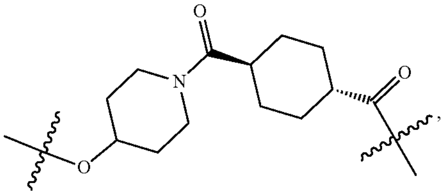,
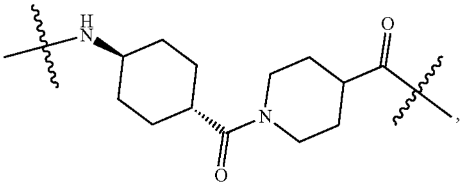,
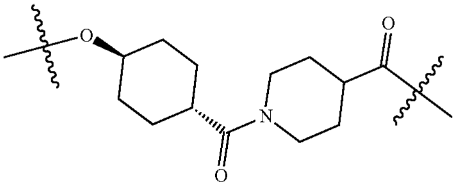
or
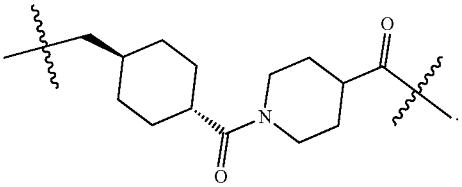.
20. The compounds of claim 1, wherein L is $-L_1-L_2-L_3-L_4-L_5-$ and each $L_1$, $L_2$, $L_3$, $L_4$ and $L_5$ is independently:
i)
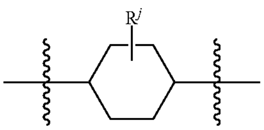
or
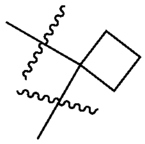, ii)
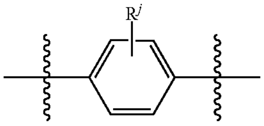
or
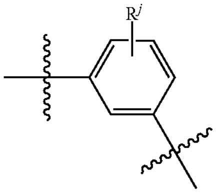
iii)
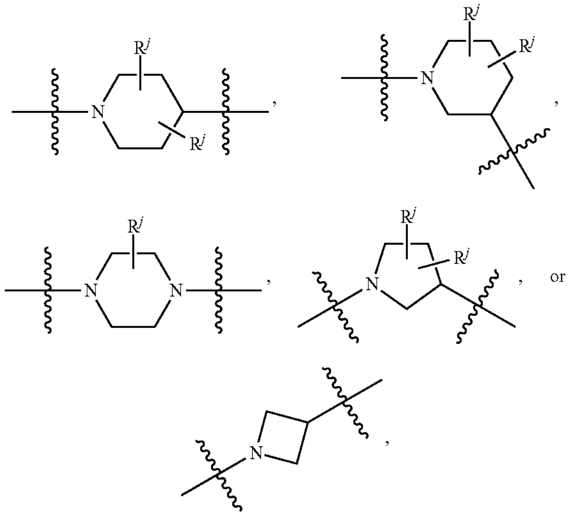
iv)
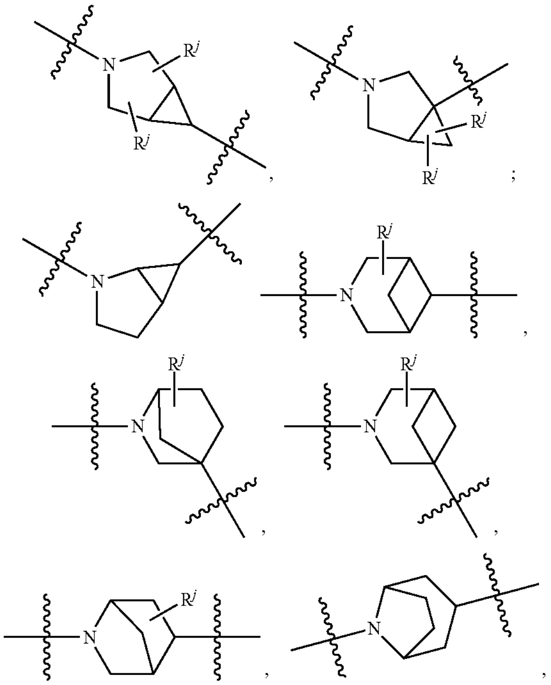
-continued
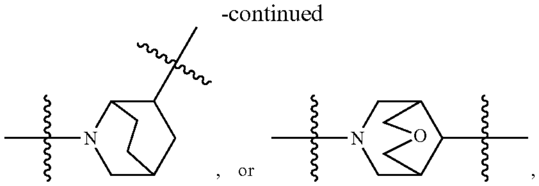
v)
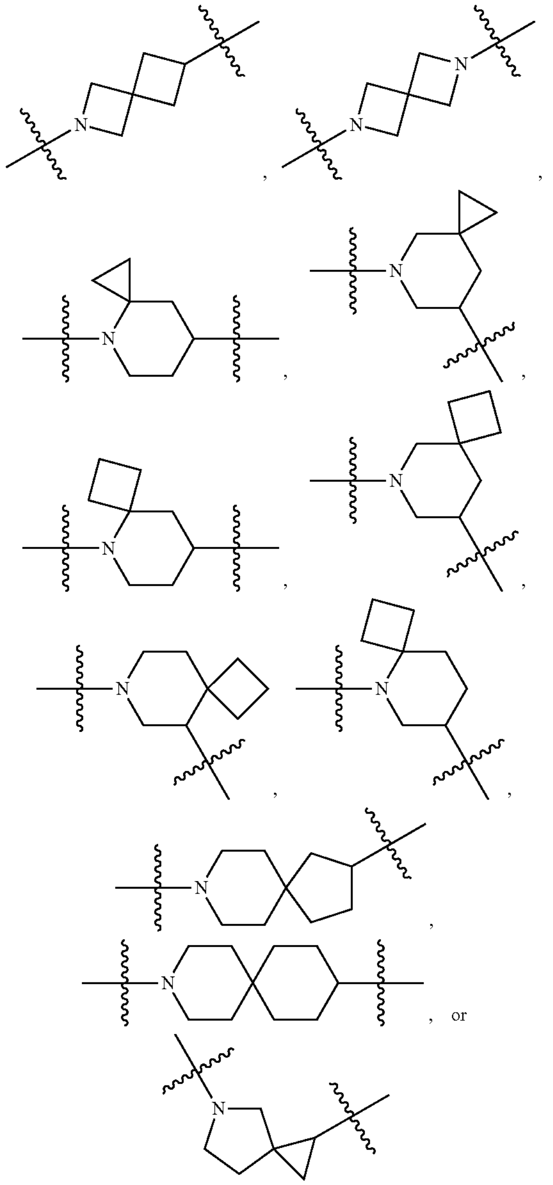
vi) direct bond;
vii) $C_{1-3}$ alkylene chain optionally substituted with 1-3 $R^d$,
viii) $C_{2-12}$ alkynylene chain optionally substituted with 1 to 3 $R^d$, or
ix) —S(O)$_2$—, —N($R^c$)—, —C(O)—, —O—, —C(O)—N($R^c$)—, —$(CH_2)_m$—C(O)—, or —NH—$(CH_2)_m$—C(O)—, wherein m is 0, 1, 2 or 3,
wherein each $R^j$ is independently H, halo, hydroxy, $C_{1-3}$ alkoxy, CN, $C_{1-6}$alkyl, or haloalkyl;

$R^d$ is halo or $C_{1-3}$alkyl; and
$R^c$ is H or $C_{1-3}$ alkyl.
21. The compound of claim 20, wherein each $L_1$, $L_2$, $L_3$, $L_4$ and $L_5$ is the same or different and independently:
i)
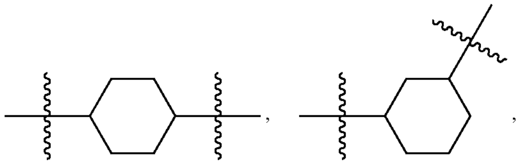
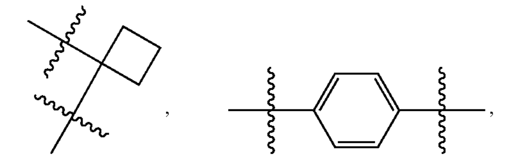
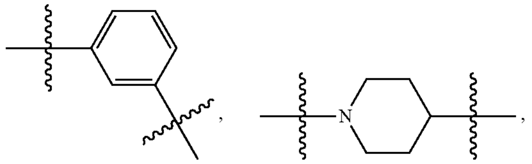
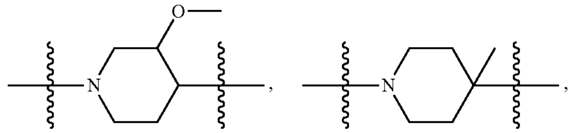
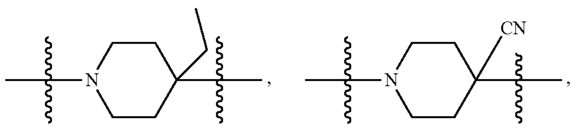
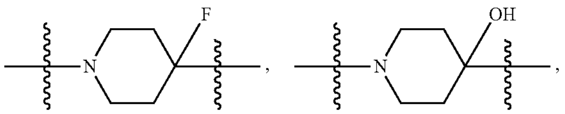
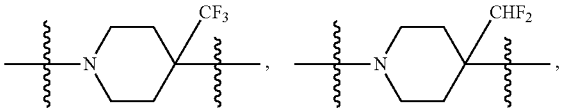
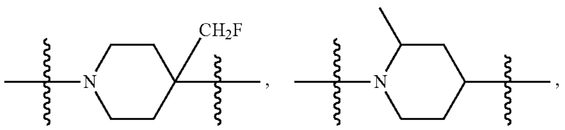
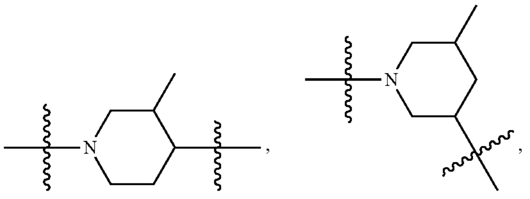
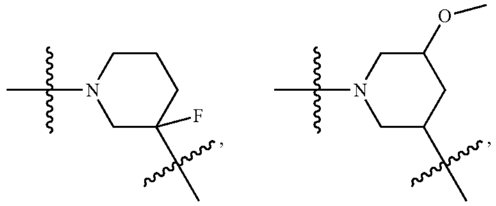
-continued
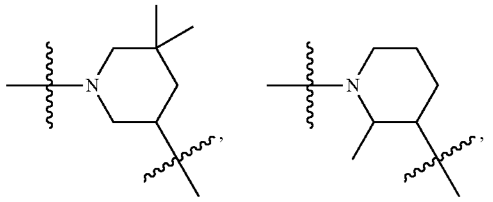
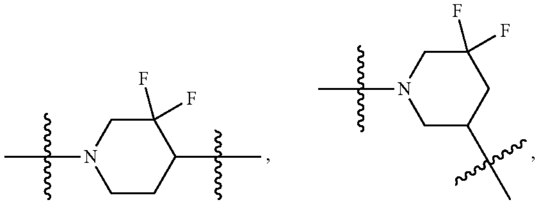
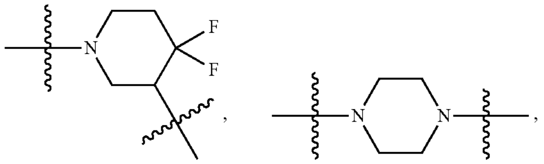
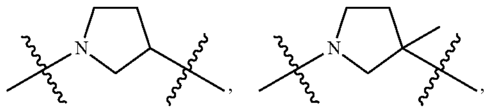
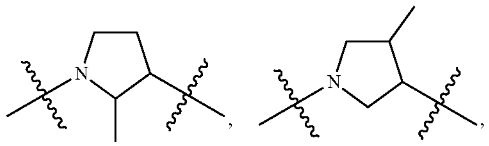
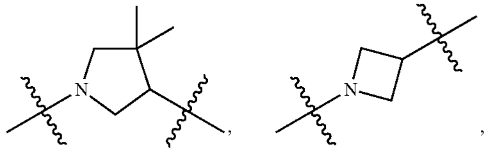
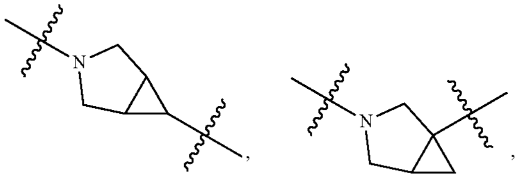
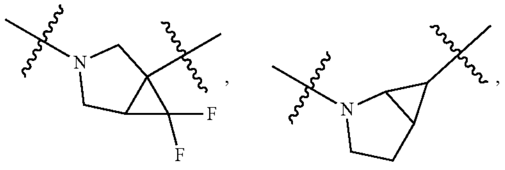
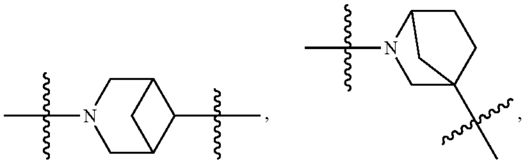
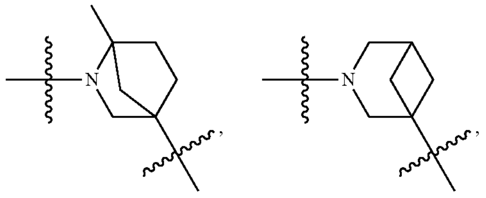

-continued
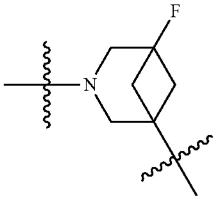,
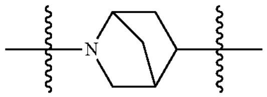,
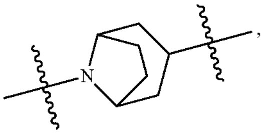,
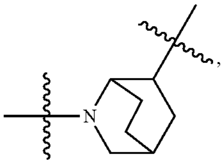,
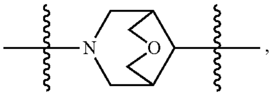,
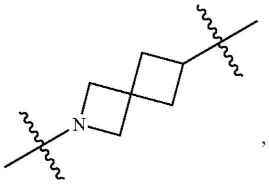,
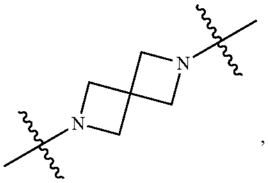,
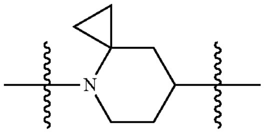,
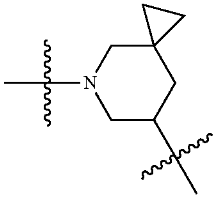,
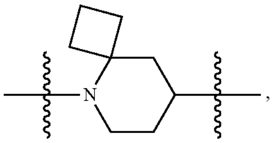,
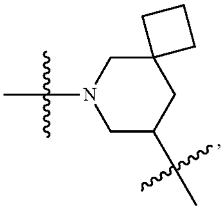,
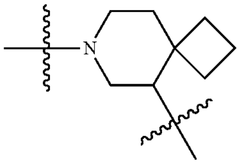,
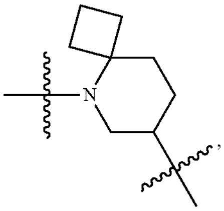,
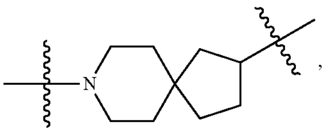,
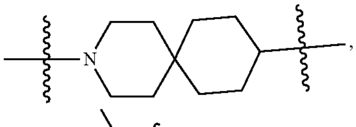, or
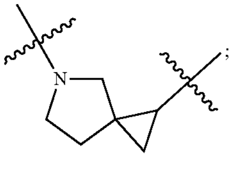;
ii) direct bond;
iii) —(CH$_2$)—, —CH(CH$_3$)—, —C(CH$_3$)$_2$—,
iv) —C≡C—; or
v) —S(O)$_2$—, —N(CH$_3$)—, —C(O)—, —O—, —C(O)—N(CH$_3$)—, —(CH$_2$)—C(O)—, or —NH—(CH$_2$)$_m$—C(O)—, wherein m is 0, 1, 2 or 3.
22. The compound of claim 21, wherein L has one of the following structures, or a stereoisomer thereof:
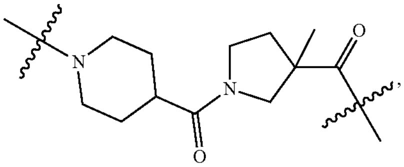,
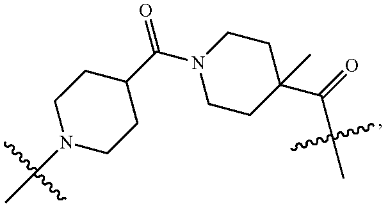,
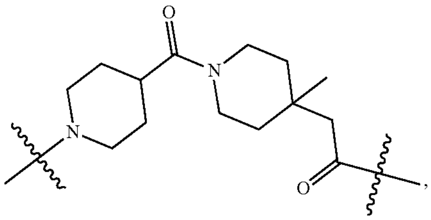,
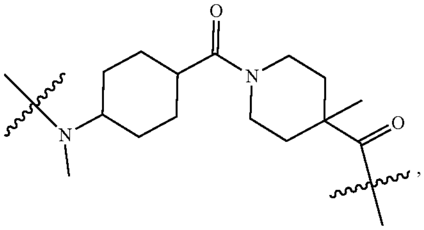,
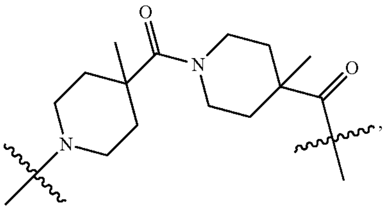,
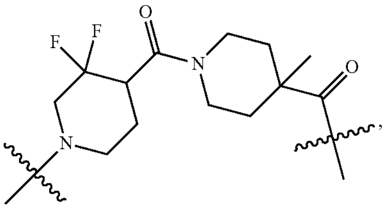,
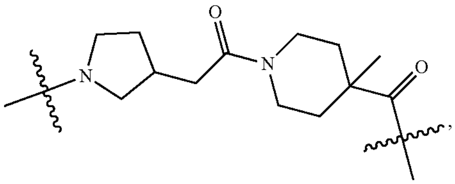, -continued
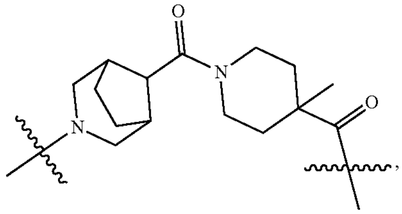
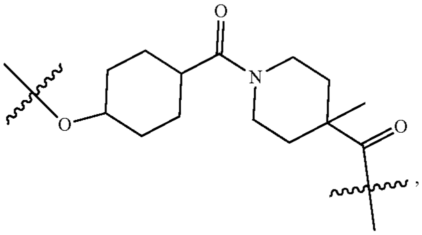
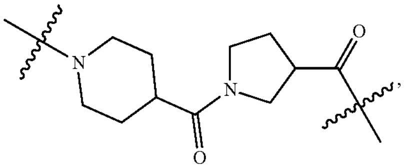
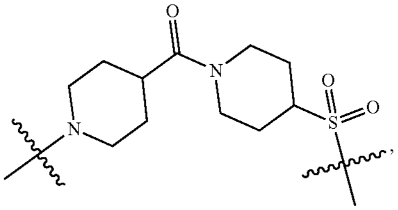
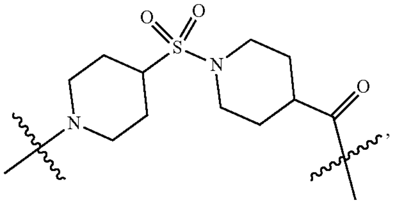
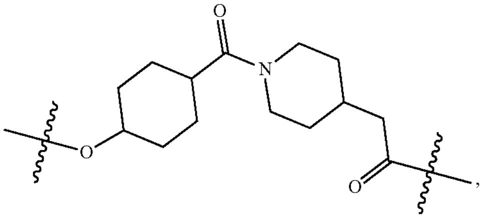
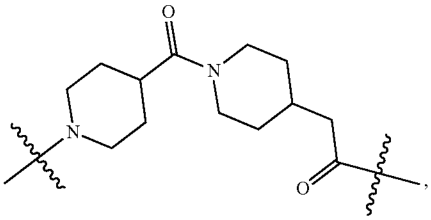
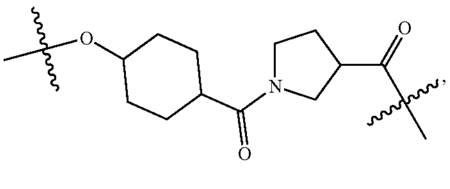
-continued
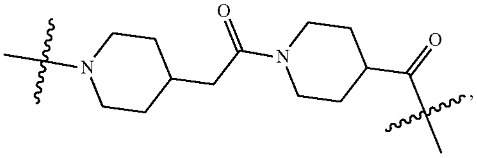
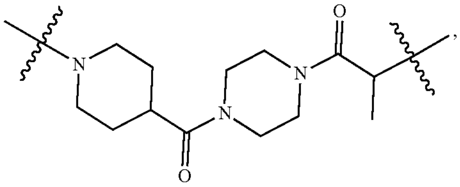
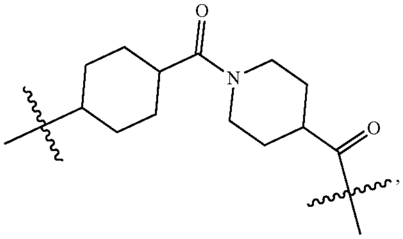
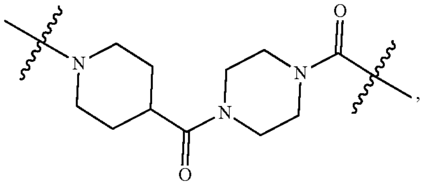
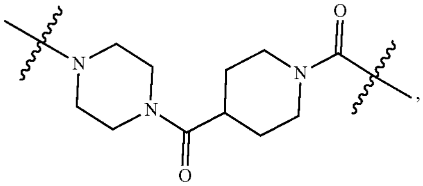
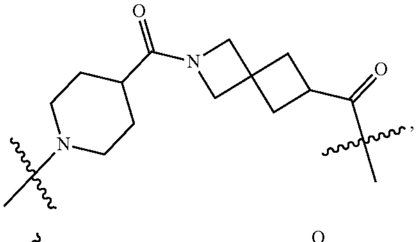
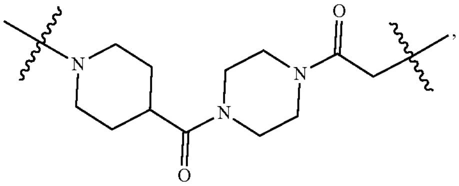
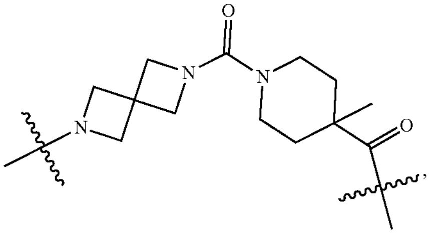

-continued
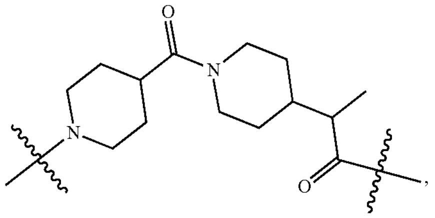
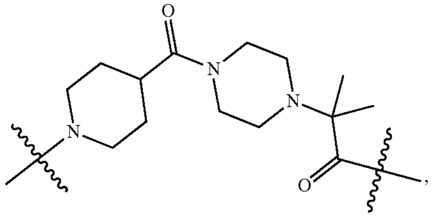
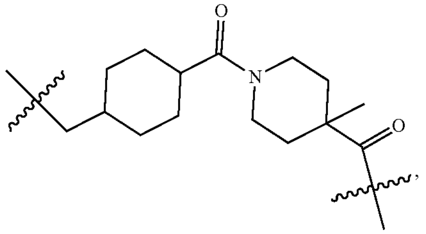
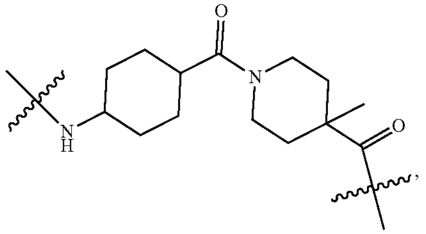
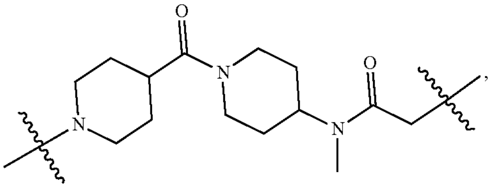
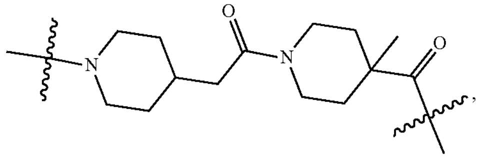
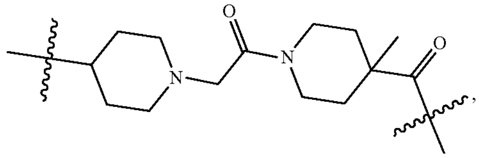
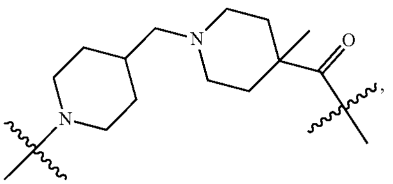
-continued
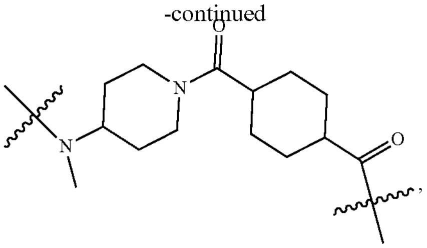
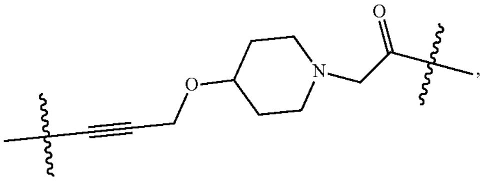
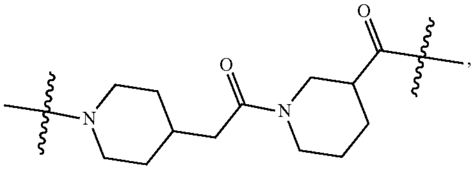
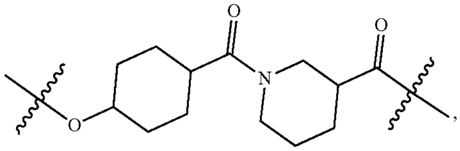
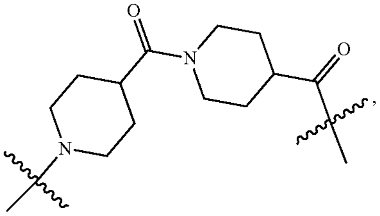
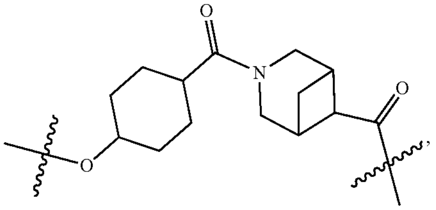
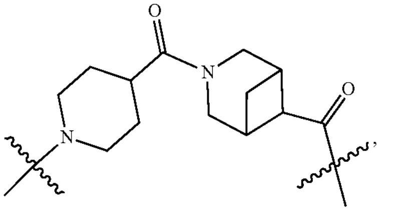
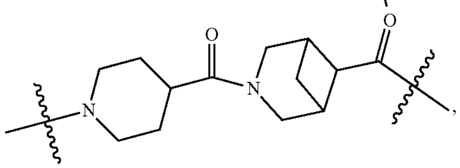
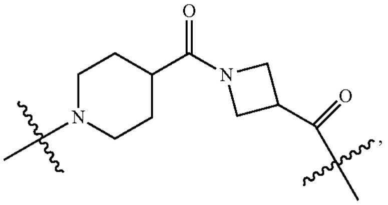

-continued
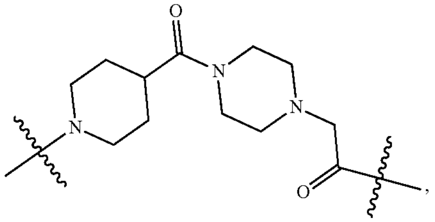
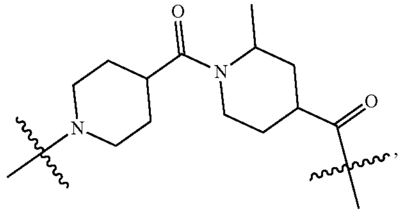
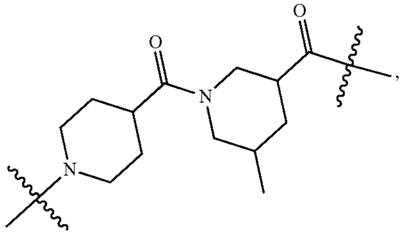
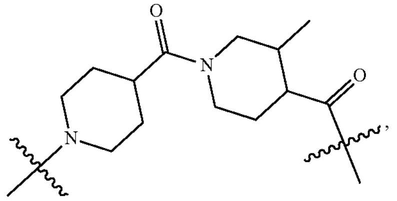
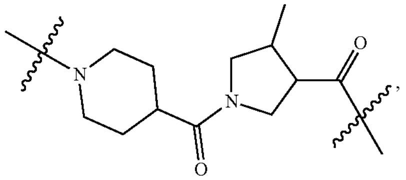
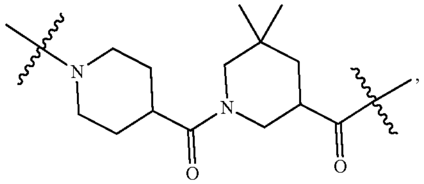
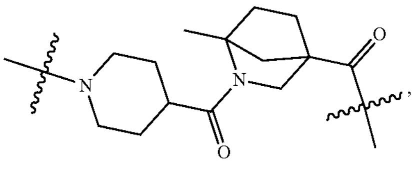
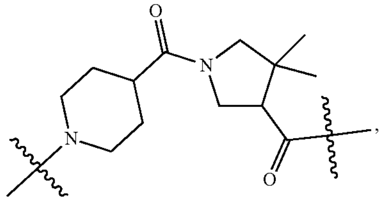
-continued
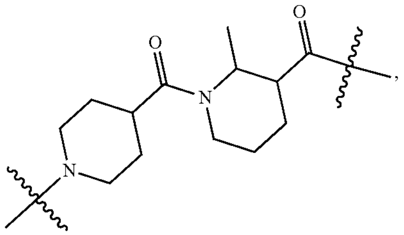
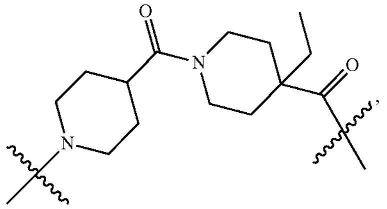
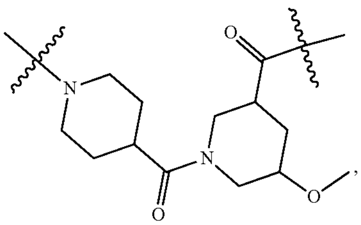
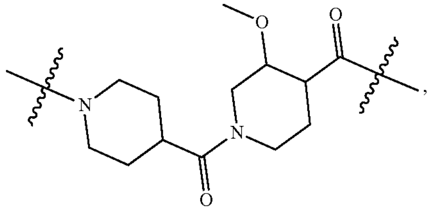
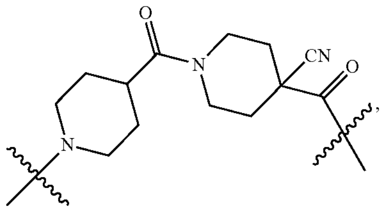
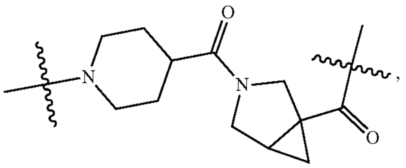
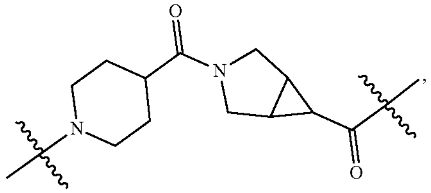
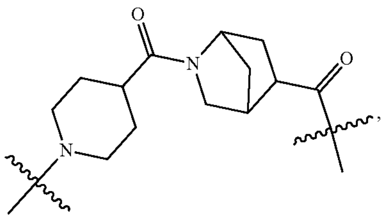

-continued
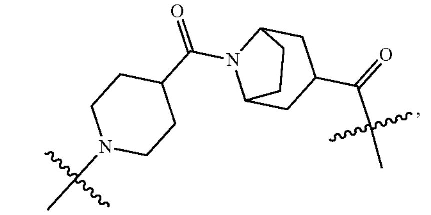
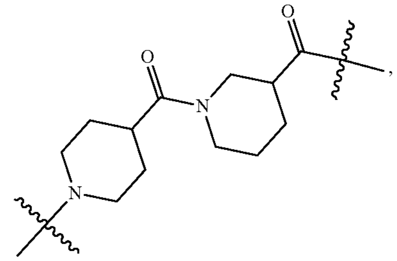
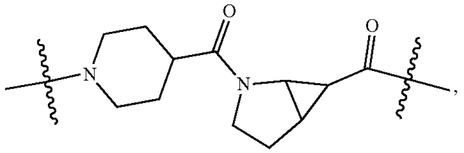
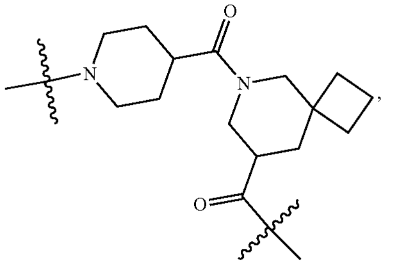
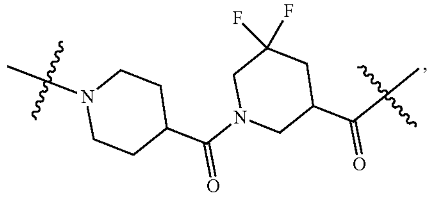
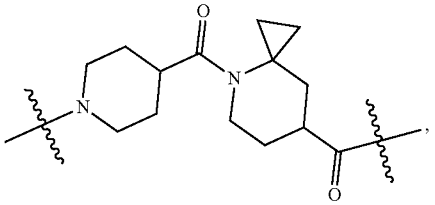
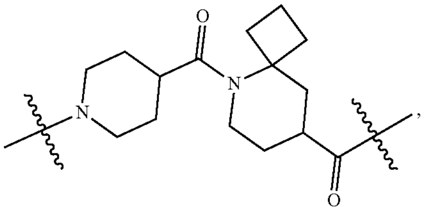
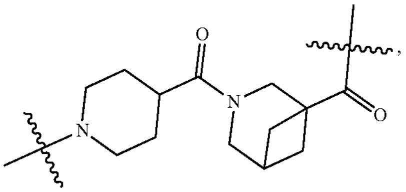
-continued
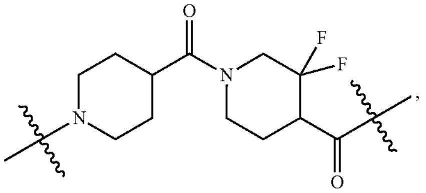
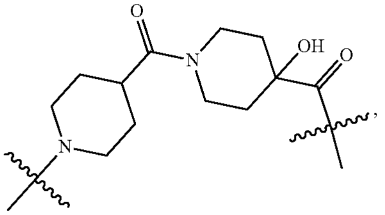
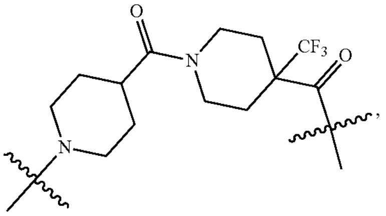
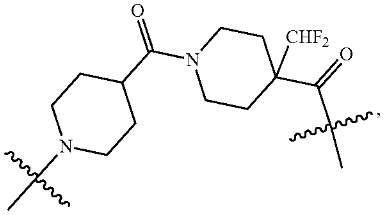
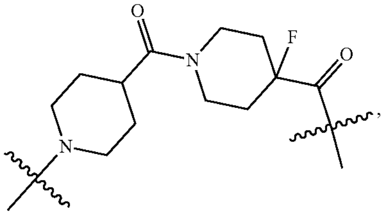
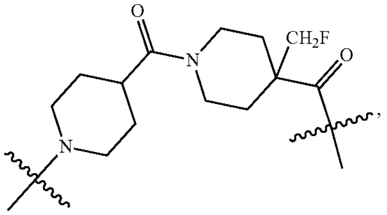
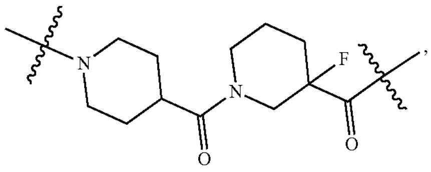
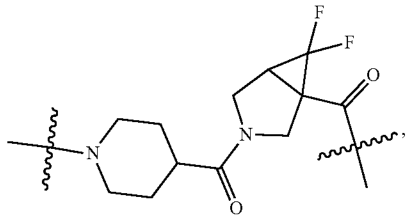

-continued
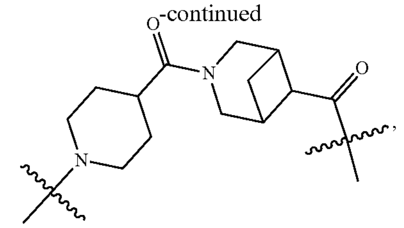
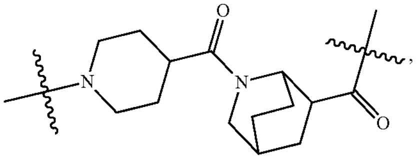
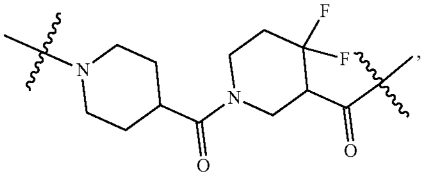
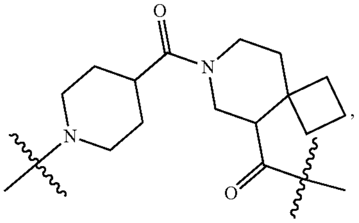
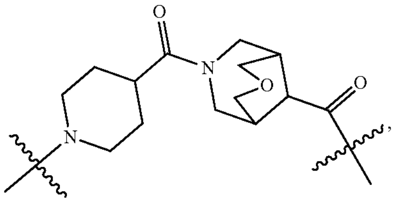
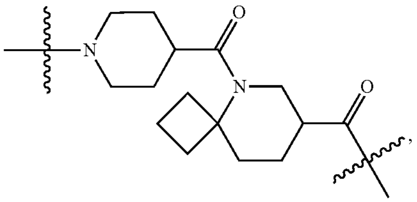
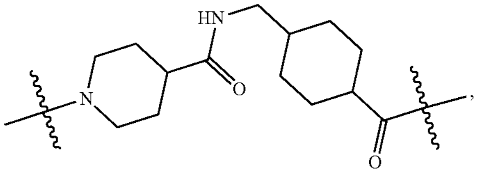
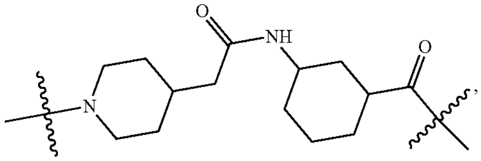
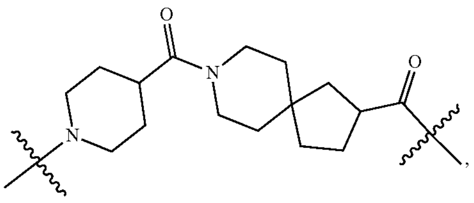
-continued
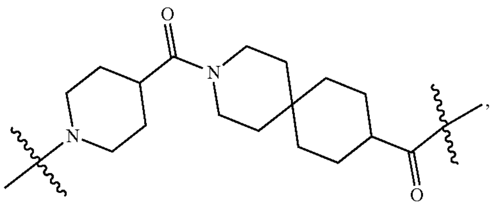
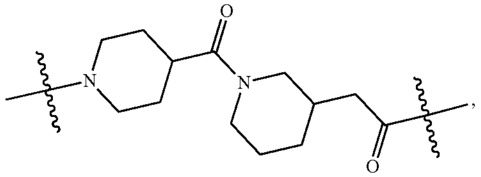
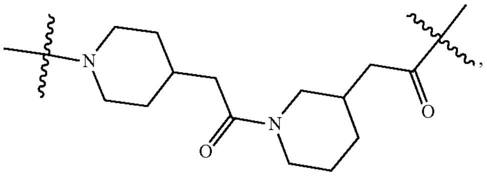
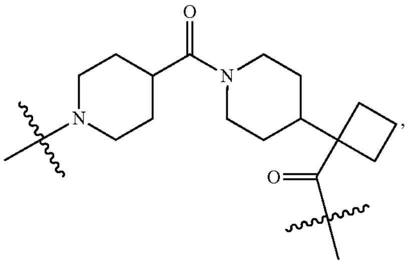
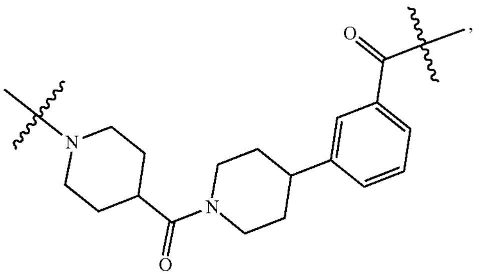
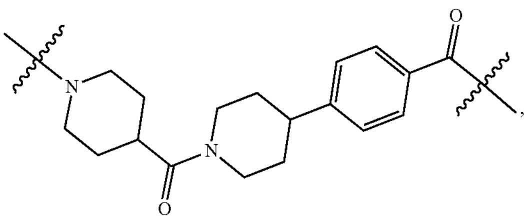
or
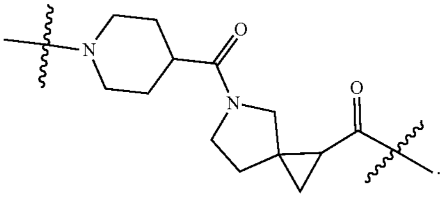

23. The compound of claim 1, wherein L is $-L_1-L_2-L_3-L_4-L_5-L_6-$ and has the following structure:
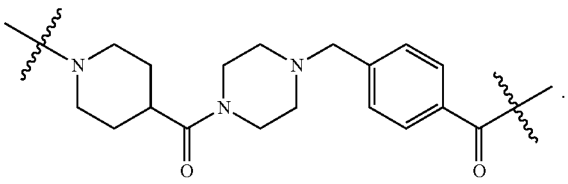 [SMILES: *C(=O)c1ccc(CN2CCN(C(=O)C3CCN(*)CC3)CC2)cc1]
24. The compound of claim 1, wherein,
W is —CH—,
Y is direct bond, and
B ring is
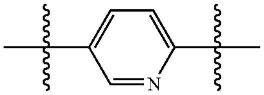 , 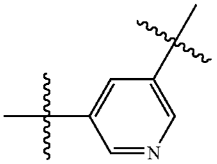 , 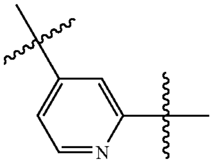 , 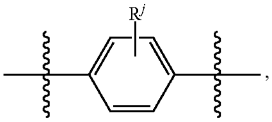 , 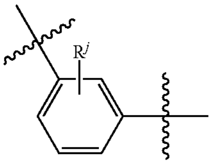 , 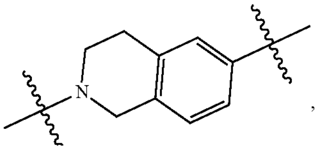 , 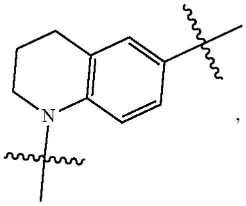 , 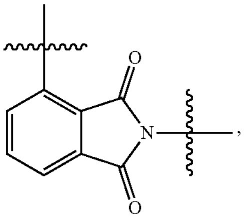 , 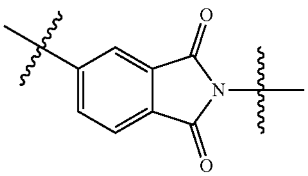 , 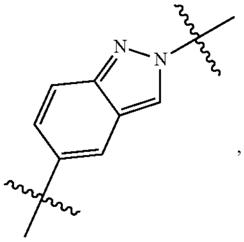 , 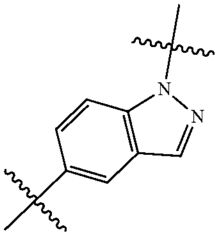 , 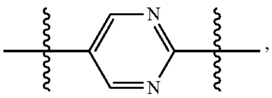 , or
-continued
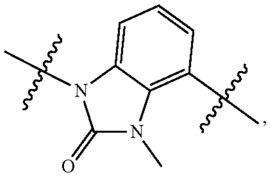 ,
wherein $R^j$ is H or $C_{1-3}$alkyl.
25. The compound of claim 1, wherein,
W is —N—,
Y is direct bond, and
B ring is
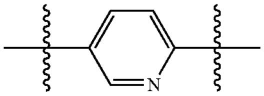 , 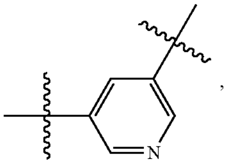 , 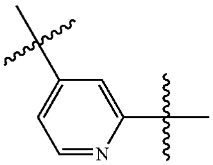 , 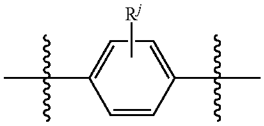 , 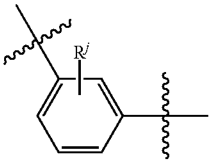 , or 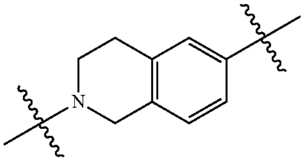 ,
wherein $R^j$ is H or $C_{1-3}$ alkyl.
26. The compound of claim 1, wherein,
W is —CH—,
Y is —NHC(O)—, and
B ring is
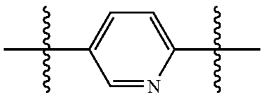 , 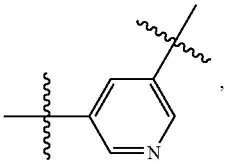 , 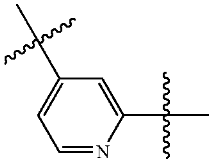 , 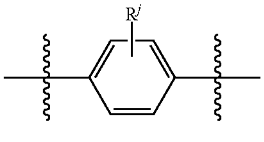 , or -continued

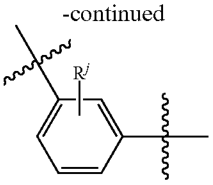
, wherein $R^j$ is H or $C_{1-3}$alkyl.

27. The compound of claim 1, wherein W is —CH—, Y is direct bond; and B ring is

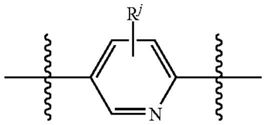
,

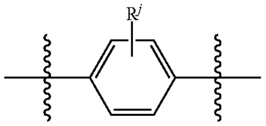
, or

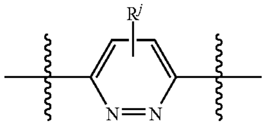
, wherein $R^j$ is H, $C_{1-3}$alkyl or halo.

28. The compound of claim 1 selected from the group consisting of the following:

(3RS)-3-(2-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-4-yl)piperidine-2,6-dione;

(3RS)-3-(4-{[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]amino}phenyl)piperidine-2,6-dione;

(3RS)-3-(4-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}phenyl)piperidine-2,6-dione;

3-(4-(((1R,4R)-4-((R)-3-(6-(4-((3-fluoropyridin-4-yl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)pyrrolidine-1-carbonyl)cyclohexyl)amino)phenyl)piperidine-2,6-dione;

(3RS)-3-(6-{[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]amino}pyridin-3-yl)piperidine-2,6-dione;

(3RS)-3-(6-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione;

N-[(3RS)-2,6-dioxopiperidin-3-yl]-5-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridine-2-carboxamide;

(3RS)-3-(6-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-2-yl)piperidine-2,6-dione;

2-[(3RS)-2,6-dioxopiperidin-3-yl]-4-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-isoindole-1,3-dione;

2-[(3RS)-2,6-dioxopiperidin-3-yl]-4-{[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]amino}-2,3-dihydro-1H-isoindole-1,3-dione;

2-[(3RS)-2,6-dioxopiperidin-3-yl]-4-{[(1r,4r)-4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-isoindole-1,3-dione;

(3RS)-3-(5-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione;

3-(4-{[(1r,4r)-4-[(3R)-3-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}phenyl)piperidine-2,6-dione;

3-(4-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}phenyl)piperidine-2,6-dione;

3-(4-{[(1r,4r)-4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}phenyl)piperidine-2,6-dione;

(3RS)-3-(6-{[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}pyridin-3-yl)piperidine-2,6-dione;

(3RS)-3-(6-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2- dihydrospiro[indole-3,4'-piperidin]-1'-yl)carbonyl]pyrrolidine-1-carbonyl]cyclohexyl]oxy}pyridin-3-yl)piperidine-2,6-dione;

(3RS)-3-(6-{[(1r,4r)-4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)piperidine-2,6-dione;

(3RS)-3-(6-{[(1r,4r)-4-[(3R)-3-[(6-{4-[(oxan-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)piperidine-2,6-dione;

1-(6-{[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]oxy}pyridin-3-yl)-1,3-diazinane-2,4-dione;

1-(6-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)-1,3-diazinane-2,4-dione;

1-(6-{[(1r,4r)-4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]oxy}pyridin-3-yl)-1,3-diazinane-2,4-dione;

(3RS)-3-(6-{4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]piperidin-1-yl}pyridin-3-yl)piperidine-2,6-dione;

3-(6-(4-((R)-3-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)pyrrolidine-1-carbonyl)piperidin-1-yl)pyridin-3-yl)piperidine-2,6-dione;

(3RS)-3-(6-{4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione;

3-(6-((1-((1R,4r)-4-(6-(4-((2-fluorophenyl)amino)-3-isopropyl-3H-imidazo[4,5-c]pyridin-6-yl)-2-oxo-1-((1s,3S)-3-(piperidin-1-yl)cyclobutyl)spiro[indoline-3,4'-piperidine]-1'-carbonyl)cyclohexane-1-carbonyl)piperidin-4-yl)amino)pyridin-3-yl)piperidine-2,6-dione;

(3RS)-3-[6-({1-[(1r,4r)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl}oxy)pyridin-3-yl]piperidine-2,6-dione;

(3RS)-3-[6-({1-[(1r,4r)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl}oxy)pyridin-3-yl]piperidine-2,6-dione;

(3RS)-3-[6-({1-[(1s,4s)-4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexanecarbonyl]piperidin-4-yl}amino)pyridin-3-yl]piperidine-2,6-dione;

(3RS)-3-[6-({1-[(1s,4s)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl}amino)pyridin-3-yl]piperidine-2,6-dione;

2-[(3RS)-2,6-dioxopiperidin-3-yl]-5-{4-[(1s,4s)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperazin-1-yl}-2,3-dihydro-1H-isoindole-1,3-dione;

(3RS)-3-(6-{4-[(3S)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]piperidin-1-yl}pyridin-3-yl)piperidine-2,6-dione;

(3RS)-3-(6-{4-[(3S)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione;

(3RS)-3-(6-{4-[(3S)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]piperidin-1-yl}pyridin-3-yl)piperidine-2,6-dione 2-[(3RS)-2,6-dioxopiperidin-3-yl]-4-{[(1r,4r)-4-[(3S)-3-(2-{6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)pyrrolidine-1-carbonyl]cyclohexyl]amino}-2,3-dihydro-1H-isoindole-1,3-dione;

4-fluoro-2-methyl-5-{[6-(2-oxo-1'-{1-[(1r,4r)-4-({2-[(3RS)-2,6-dioxopiperidin-3-yl]-1,3-dioxo-2,3-dihydro-1H-isoindol-4-yl}amino)cyclohexanecarbonyl]-1,2,3,6-tetrahydropyridine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}—N-(propan-2-yl)benzamide;

5-[(6-{1'-[1-(1-{2-[(3RS)-2,6-dioxopiperidin-3-yl]-1,3-dioxo-2,3-dihydro-1H-isoindol-5-yl}piperidine-4-carbonyl)-1,2,3,6-tetrahydropyridine-4-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

3RS)-3-(6-{4-[6-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione;

(3RS)-3-[6-(4-{6-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-3-azabicyclo[3.1.0]hexane-3-carbonyl}piperidin-1-yl)pyridin-3-yl]piperidine-2,6-dione;

(3RS)-3-[4-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]benzoyl}piperazin-1-yl)phenyl]piperidine-2,6-dione;

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]benzoyl}piperazin-1-yl)-2,3-dihydro-1H-isoindole-1,3-dione;

2-[(3RS)-2,6-dioxopiperidin-3-yl]-5-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]benzoyl}piperazin-1-yl)-2,3-dihydro-1H-isoindole-1,3-dione;

4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-N-(1-{2-[(3RS)-2,6-dioxopiperidin-3-yl]-1,3-dioxo-2,3-dihydro-1H-isoindol-5-yl}piperidin-4-yl)benzamide;

4-({6-[4-(cyclopropylamino)-3-(propan-2-yl)-3H-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-N-(1-{2-[(3RS)-2,6-dioxopiperidin-3-yl]-1,3-dioxo-2,3-dihydro-1H-isoindol-5-yl}piperidin-4-yl)benzamide;

2-[(3RS)-2,6-dioxopiperidin-3-yl]-5-(4-{5-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyridine-2-carbonyl}piperazin-1-yl)-2,3-dihydro-1H-isoindole-1,3-dione;

(3RS)-3-{2-[(1r,4r)-4-({4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidin-1-yl}methyl)cyclohexanecarbonyl]-1,2,3,4-tetrahydroisoquinolin-6-yl}piperidine-2,6-dione;

(3RS)-3-{6-[(3R)-3-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}pyrrolidin-1-yl]pyridin-3-yl}piperidine-2,6-dione;

3-(2-((1r,4r)-4-(4-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carbonyl)cyclohexane-1-carbonyl)-1,2,3,4-tetrahydroisoquinolin-6-yl)piperidine-2,6-dione;

1-{2-[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroisoquinolin-6-yl}-1,3-diazinane-2,4-dione;

(3RS)-3-{2-[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroisoquinolin-7-yl}piperidine-2,6-dione;

(3RS)-3-{1-[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexanecarbonyl]-1,2,3,4-tetrahydroquinolin-6-yl}piperidine-2,6-dione;

(3RS)-3-(2-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-4-yl)piperidine-2,6-dione;

(3RS)-3-(4-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]amino}phenyl)piperidine-2,6-dione;

(3RS)-3-(4-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}phenyl)piperidine-2,6-dione;

(3RS)-3-(4-{[(1r,4r)-4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}phenyl)piperidine-2,6-dione;

2-[(3RS)-2,6-dioxopiperidin-3-yl]-4-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]amino}-2,3-dihydro-1H-isoindole-1,3-dione;

2-[(3RS)-2,6-dioxopiperidin-3-yl]-4-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}-2,3-dihydro-1H-isoindole-1,3-dione;

(3RS)-3-(5-{[(1r,4r)-4-{4-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-3-yl)piperidine-2,6-dione;

(3RS)-3-(4-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]oxy}phenyl)piperidine-2,6-dione;

(3RS)-3-(4-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]oxy}phenyl)piperidine-2,6-dione;

(3RS)-3-(4-{[(1r,4r)-4-{4-[(6-{4-[(3-fluoropyridin-4-yl)amino]-3-(propan-2-yl)-3H-imidazo[4,5-c]pyridin-6- yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]oxy}phenyl)piperidine-2,6-dione;

(3RS)-3-(6-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]oxy}pyridin-3-yl)piperidine-2,6-dione;

(3RS)-3-(2-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]methyl}-2H-indazol-5-yl)piperidine-2,6-dione;

(3RS)-3-(1-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]methyl}-1H-indazol-5-yl)piperidine-2,6-dione;

(3RS)-3-{6-[(3S)-3-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}pyrrolidin-1-yl]pyridin-3-yl}piperidine-2,6-dione;

3-(4-(4-(4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carbonyl)piperidin-1-yl)phenyl)piperidine-2,6-dione;

(3RS)-3-[4-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]piperidine-2,6-dione;

3-(4-(4-(4-(6-(4-((3-fluoropyridin-4-yl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carbonyl)piperidin-1-yl)phenyl)piperidine-2,6-dione;

1-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}phenyl)-1,3-diazinane-2,4-dione;

1-[4-(4-{4-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]-1,3-diazinane-2,4-dione;

1-[4-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]-1,3-diazinane-2,4-dione;

5-[(6-{1'-[1-(1-{5-[(3RS)-2,6-dioxopiperidin-3-yl]pyridin-2-yl}piperidine-4-carbonyl)piperidine-4-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

3-(6-(4-(4-(6-(4-(cyclopropylamino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carbonyl)piperidin-1-yl)pyridin-3-yl)piperidine-2,6-dione;

(3RS)-3-[6-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione;

(3RS)-3-[6-(4-{4-[(6-{4-[(2-fluorophenyl)amino]-3-(propan-2-yl)-3H-imidazo[4,5-c]pyridin-6-yl}-2-oxo-1-[(1s,3s)-3-(dimethylamino)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione;

(3RS)-3-(6-{4-[4-({6-[4-(2-fluorophenoxy)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

(3RS)-3-[6-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione;

(3RS)-3-[6-(4-{4-[(6-{4-[(oxan-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione;

1-(6-{4-[4-({6-[4-(cyclopropylamino)-3-(propan-2-yl)-3h-imidazo[4,5-c]pyridin-6-yl]-2-oxo-1-[(1s, 3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)-1,3-diazinane-2,4-dione;

1-[6-(4-{4-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]-1,3-diazinane-2,4-dione;

1-[6-(4-{4-[(6-{4-[(3-fluoropyridin-4-yl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]-1,3-diazinane-2,4-dione;

(3RS)-3-[5-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-2-yl]piperidine-2,6-dione;

N-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridine-2-carboxamide;

3-(5-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3, 4'-piperidin]-1'-yl}carbonyl)piperidine-1-carbonyl]piperidin-1-yl}pyridin-2-yl)piperidine-2,6-dione;

3-[5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-2-yl]piperidine-2,6-dione;

5-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}-2-[(3RS)-2,6-dioxopiperidin-3-yl]-2,3-dihydro-1H-isoindole-1,3-dione;

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)-2,3-dihydro-1H-isoindole-1,3-dione;

2-[(3RS)-2,6-dioxopiperidin-3-yl]-5-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)-2,3-dihydro-1H-isoindole-1,3-dione;

(3RS)-3-(2-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyrimidin-5-yl)piperidine-2,6-dione;

3-(2-(4-(4-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidine-1-carbonyl)piperidin-1-yl)pyrimidin-5-yl)piperidine-2,6-dione;

(3RS)-3-[2-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyrimidin-5-yl]piperidine-2,6-dione;

3-(6-(4-(2-(4-(6-(4-((2-fluorophenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)piperidin-1-yl)-2-oxoethyl)piperidin-1-yl)pyridin-3-yl)piperidine-2,6-dione;

(3RS)-3-[6-(4-{2-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione;

(3RS)-3-[6-(4-{2-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]-2-oxoethyl}piperazin-1-yl)pyridin-3-yl]piperidine-2,6-dione;

(3RS)-3-{6-[4-(2-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidin-1-yl}-2-oxoethyl)piperazin-1-yl]pyridin-3-yl}piperidine-2,6-dione;

(3RS)-3-{6-[4-(2-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidin-1-yl}-2-oxoethyl)piperazin-1-yl]pyridin-3-yl}piperidine-2,6-dione;

(3RS)-3-[6-(1-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-4-yl)pyridin-3-yl]piperidine-2,6-dione;

(3RS)-3-{6-[4-(2-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidin-1-yl}ethyl)piperidin-1-yl]pyridin-3-yl}piperidine-2,6-dione;

5-[(6-{1'-[2-(1-{1-[2-({2-[(3RS)-2,6-dioxopiperidin-3-yl]-1,3-dioxo-2,3-dihydro-1H-isoindol-4-yl}amino)acetyl]piperidine-4-carbonyl}piperidin-4-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

(3RS)-3-{6-[(3R)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]benzoyl}-3-methylpiperazin-1-yl]pyridin-3-yl}piperidine-2,6-dione;

(3RS)-3-(4-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}phenyl)piperidine-2,6-dione;

(3RS)-3-(4-{[(1r,4r)-4-{4-[(6-{4-[(2-fluorophenyl)amino]-3-isopropylimidazo[4,5-c]pyridin-6-yl}-2-oxo-1-[(1s,3s)-3-(piperidin-1-yl)cyclobutyl]spiro[indole-3,4'-piperidin]-1'-yl)carbonyl]-4-methylpiperidine-1-carbonyl}cyclohexyl]oxy}phenyl)piperidine-2,6-dione;

(3RS)-3-(4-{[(1r,4r)-4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}phenyl)piperidine-2,6-dione;

(3RS)-3-(6-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyridin-3-yl)piperidine-2,6-dione;

(3RS)-3-(6-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)piperidine-2,6-dione;

(3RS)-3-(6-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)piperidine-2,6-dione;

1-(6-{[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyridin-3-yl)-1,3-diazinane-2,4-dione;

1-(6-{[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)-1,3-diazinane-2,4-dione;

1-(6-{[(1r,4r)-4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]oxy}pyridin-3-yl)-1,3-diazinane-2,4-dione;

(3RS)-3-[4-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)phenyl]piperidine-2,6-dione;

(3RS)-3-(4-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione;

(3RS)-3-[4-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)phenyl]piperidine-2,6-dione;

(3RS)-3-(6-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-[6-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]piperidine-2,6-dione;

1-(6-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)-1,3-diazinane-2,4-dione;

1-[6-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]-1,3-diazinane-2,4-dione;

1-[6-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]-1,3-diazinane-2,4-dione;

(3RS)-3-(5-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-2-yl)piperidine-2,6-dione;

(3RS)-3-[5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-2-yl]piperidine-2,6-dione;

(3RS)-3-[5-(4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-2-yl]piperidine-2,6-dione;

5-{4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-(2,6-dioxopiperidin-3-yl)-2,3-dihydro-1H-isoindole-1,3-dione;

2-(2,6-dioxopiperidin-3-yl)-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)-2,3-dihydro-1H-isoindole-1,3-dione;

(3RS)-3-[6-(4-{2-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperazin-1-yl)pyridin-3-yl]piperidine-2,6-dione;

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-3-methylbenzoyl}piperazin-1-yl)-2,3-dihydro-1H-isoindole-1,3-dione;

2-[(3RS)-2,6-dioxopiperidin-3-yl]-5-(4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-2-methylbenzoyl}piperazin-1-yl)-2,3-dihydro-1H-isoindole-1,3-dione;

(3RS)-3-(6-{methyl[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]amino}pyridin-3-yl)piperidine-2,6-dione;

(3RS)-3-(6-{methyl[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione;

(3RS)-3-(6-{methyl[(1r,4r)-4-[(3R)-3-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}pyridin-3-yl)piperidine-2,6-dione;

2-[(3RS)-2,6-dioxopiperidin-3-yl]-4-{methyl[(1r,4r)-4-[(3R)-3-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]cyclohexyl]amino}-2,3-dihydro-1H-isoindole-1,3-dione;

(3RS)-3-(6-{methyl[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]amino}pyridin-3-yl)piperidine-2,6-dione;

(3RS)-3-(6-{methyl[(1r,4r)-4-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-3-yl)piperidine-2,6-dione;

(3RS)-3-(6-{methyl[(1r,4r)-4-{4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}cyclohexyl]amino}pyridin-3-yl)piperidine-2,6-dione;

2-[(3RS)-2,6-dioxopiperidin-3-yl]-4-{methyl[(1r,4r)-4-[4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]amino}-2,3-dihydro-1H-isoindole-1,3-dione;

(3RS)-3-{4-[methyl({1-[(1r,4r)-4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexanecarbonyl]piperidin-4-yl})amino]phenyl}piperidine-2,6-dione;

(3RS)-3-{4-[methyl({1-[(1r,4r)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl})amino]phenyl}piperidine-2,6-dione;

(3RS)-3-{4-[methyl({1-[(1r,4r)-4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl})amino]phenyl}piperidine-2,6-dione;

(3RS)-3-{6-[methyl({1-[(1r,4r)-4-({6-[4-(cyclopropylamino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexanecarbonyl]piperidin-4-yl})amino]pyridin-3-yl}piperidine-2,6-dione;

(3RS)-3-{6-[methyl({1-[(1r,4r)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl})amino]pyridin-3-yl}piperidine-2,6-dione;

(3RS)-3-{6-[methyl({1-[(1r,4r)-4-[(6-{4-[(3-fluoropyridin-4-yl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]cyclohexanecarbonyl]piperidin-4-yl})amino]pyridin-3-yl}piperidine-2,6-dione;

(3RS)-3-{6-[(1-{4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]benzoyl}piperidin-4-yl)(methyl)amino]pyridin-3-yl}piperidine-2,6-dione;

N-(1-{5-[(3RS)-2,6-dioxopiperidin-3-yl]pyridin-2-yl}piperidin-4-yl)-4-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-N-methylbenzamide;

5-{[6-(1'-{1-[(1-{1-[(3RS)-2,6-dioxopiperidin-3-yl]-3-methyl-2-oxo-2,3-dihydro-1H-1,3-benzodiazol-4-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

(3RS)-3-(3-methyl-2-oxo-4-{[(1r,4r)-4-[(3S)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-1,3-benzodiazol-1-yl)piperidine-2,6-dione;

(3RS)-3-(3-methyl-2-oxo-4-{[(1r,4r)-4-[(3R)-3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]pyrrolidine-1-carbonyl]cyclohexyl]amino}-2,3-dihydro-1H-1,3-benzodiazol-1-yl)piperidine-2,6-dione;

5-[(6-{1'-[5-(4-{2-[(3RS)-2,6-dioxopiperidin-3-yl]-1,3-dioxo-2,3-dihydro-1H-isoindol-5-yl}piperazine-1-carbonyl)-1-methyl-1H-pyrazole-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

2-[(3RS)-2,6-dioxopiperidin-3-yl]-5-(4-{3-[(6-{4-[(2-fluorophenyl)amino]-3-(propan-2-yl)-3H-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-1-methyl-1H-pyrazole-5-carbonyl}piperazin-1-yl)-2,3-dihydro-1H-isoindole-1,3-dione;

(3RS)-3-(4-{4-[(3R)-3-({6-[4-(Cyclopropylamino)-3-(Propan-2-yl)-3H-Imidazo[4,5-C]Pyridin-6-yl]-2-Oxo-1-[(1S,3S)-3-(Piperidin-1-yl)Cyclobutyl]-1,2-Dihydrospiro[Indole-3,4'-Piperidin]-1'-yl}Carbonyl)-3-Methylpyrrolidine-1-Carbonyl]Piperidin-1-yl}-3-Fluorophenyl)Piperidine-2,6-Dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-5-methylpyridin-3-yl)piperidine-2,6-dione;

(3RS)-3-(6-{4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)-4-methylpiperidine-1-carbonyl]piperidin-1-yl}pyridin-3-yl)piperidine-2,6-dione;

(3RS)-3-(4-{methyl[(1r,4r)-4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]cyclohexyl]amino}phenyl)piperidine-2,6-dione;

(3RS)-3-(6-{4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]-4-methylpiperidin-1-yl}pyridin-3-yl)piperidine-2,6-dione;

(3RS)-3-(4-{4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]piperidin-1-yl}-3-fluorophenyl)piperidine-2,6-dione;

1-(6-{4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]-3,3-difluoropiperidin-1-yl}pyridin-3-yl)-1,3-diazinane-2,4-dione;

3-{6-[(3r)-3-{2-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidin-1-yl]-2-oxoethyl}pyrrolidin-1-yl]pyridin-3-yl}piperidine-2,6-dione;

1-(6-{8-[4-({6-[4-(cyclopropylamino)-3-(propan-2-yl)-3h-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-4-methylpiperidine-1-carbonyl]-3-azabicyclo[3.2.1]octan-3-yl}pyridin-3-yl)-1,3-diazinane-2,4-dione;

(3RS)-3-(3-methyl-4-{[(1r,4r)-4-[4-({6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}carbonyl)-4-methylpiperidine-1-carbonyl]cyclohexyl]oxy}phenyl)piperidine-2,6-dione;

(3RS)-3-[6-(4-{4-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)-2-methylpyridin-3-yl]piperidine-2,6-dione;

3-(2-(4-((r)-3-(6-(4-((2-fluorophenyl)amino)-3-isopropyl-3h-imidazo[4,5-c]pyridin-6-yl)-2-oxo-1-((1s,3s)-3-(piperidin-1-yl)cyclobutyl)spiro[indoline-3,4'-piperidine]-1'-carbonyl)pyrrolidine-1-carbonyl)piperidin-1-yl)pyrimidin-5-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}sulfonyl)piperidine-1-carbonyl]piperidin-1-yl}pyridin-3-yl)piperidine-2,6-dione;

(3RS)-3-[6-(4-{[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]sulfonyl}piperidin-1-yl)pyridin-3-yl]piperidine-2,6-dione;

3-(6-{[(1r,4r)-4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidine-1-carbonyl]cyclohexyl]oxy}pyridin-3-yl)piperidine-2,6-dione;

(3RS)-3-(6-{4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione;

3-(6-(((1r,4r)-4-((r)-3-(6-(4-(cyclopropylamino)-3-isopropyl-3h-imidazo[4,5-c]pyridin-6-yl)-2-oxo-1-((1s,3s)-3-(piperidin-1-yl)cyclobutyl)spiro[indoline-3,4'-piperidine]-1'-carbonyl)-3-methylpyrrolidine-1-carbonyl)cyclohexyl)oxy)pyridin-3-yl)piperidine-2,6-dione;

3-(6-{4-[4-({6-[4-(2-fluorophenoxy)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

3-(6-{4-[4-methyl-4-({6-[4-(oxan-4-yloxy)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-(6-{4-[4-methyl-4-({2-oxo-6-[3-(propan-2-yl)-4-[(propan-2-yl)amino]-3h-imidazo[4,5-c]pyridin-6-yl]-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-[6-(4-{2-[4-({6-[4-(2-fluorophenoxy)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione;

3-(6-{4-[4-methyl-4-({2-oxo-6-[4-phenoxy-3-(propan-2-yl)-3h-imidazo[4,5-c]pyridin-6-yl]-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-(6-{4-[4-methyl-4-({2-oxo-6-[3-(propan-2-yl)-4-(propan-2-yloxy)-3h-imidazo[4,5-c]pyridin-6-yl]-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-(6-{4-[4-methyl-4-({2-oxo-6-[3-(propan-2-yl)-4-(pyrrolidin-1-yl)-3h-imidazo[4,5-c]pyridin-6-yl]-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-[6-(4-{4-[(6-{4-[cyclopropyl(methyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}piperidin-1-yl)pyridin-3-yl]piperidine-2,6-dione;

3-(6-{4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}propanoyl)piperazine-1-carbonyl]piperidin-1-yl}pyridin-3-yl)piperidine-2,6-dione;

3-(2-{4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}propanoyl)piperazine-1-carbonyl]piperidin-1-yl}pyridin-4-yl)piperidine-2,6-dione;

(1S,3S)-3-({6-[1'-(1-{1-[5-(2,6-dioxopiperidin-3-yl)pyridin-2-yl]piperidine-4-carbonyl}-4-methylpiperidine-4-carbonyl)-2-oxo-1-[(1s,3s)-3-(piperidin-1-yl)cyclobutyl]-1,2-dihydrospiro-[indole-3,4'-piperidin]-6-yl]-3-(propan-2-yl)-3h-imidazo[4,5-c]pyridin-4-yl}amino)cyclobutane-1-carbonitrile;

1-{6-[1'-(1-{1-[5-(2,6-dioxopiperidin-3-yl)pyridin-2-yl]piperidine-4-carbonyl}-4-methylpipe-ridine-4-carbonyl)-2-oxo-1-[(1s,3s)-3-(piperidin-1-yl)cyclobutyl]-1,2-dihydrospiro[indole-3,4'-pi-peridin]-6-yl]-3-(propan-2-yl)-3h-imidazo[4,5-c]pyridin-4-yl}azetidine-3-carbonitrile;

(1R,3R)-3-({6-[1'-(1-{1-[5-(2,6-dioxopiperidin-3-yl)pyridin-2-yl]piperidine-4-carbonyl}-4-methylpiperidine-4-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3h-imidazo[4,5-c]pyridin-4-yl}amino)cyclobutane-1-carbonitrile;

3-(6-{4-[4-methyl-4-({6-[4-({2-oxaspiro[3.3]heptan-6-yl}amino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

3-(6-{4-[4-({6-[4-cyclopropoxy-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

3-{2-[(1r,4r)-4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]-2h-indazol-5-yl}piperidine-2,6-dione;

(3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperazine-1-carbonyl]piperidin-1-yl}pyridin-3-yl)piperidine-2,6-dione;

3-(6-{4-[1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-4-carbonyl]piperazin-1-yl}pyridin-3-yl)piperidine-2,6-dione;

3-(6-{4-[6-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidine]-1'-yl}carbonyl)-2-azaspiro[3.3]heptane-2-carbonyl]piperidin-1-yl}pyridin-3-yl)piperidine-2,6-dione;

3-(6-{4-[4-(2-{6-[4-(cyclopropylamino)-3-(propan-2-yl)-3h-imidazo[4,5-c]pyridin-6-yl]-2-oxo-1-[3-(piperidin-1-yl)cyclobutyl]-1,2-dihydrospiro[indole-3,4'-piperidine]-1'-yl}acetyl)piperazine-1-carbonyl]piperidin-1-yl}pyridin-3-yl)piperidine-2,6-dione;

3-(6-{6-[4-({6-[4-(cyclopropylamino)-3-(propan-2-yl)-3h-imidazo[4,5-c]pyridin-6-yl]-2-oxo-1-[(1s, 3s)-3-(piperidin-1-yl)cyclobutyl]-1,2-dihydrospiro[indole-3,4'-piperidine]-1'-yl}carbonyl)-4-methylpiperidine-1-carbonyl]-2,6-diazaspiro[3.3]heptan-2-yl}pyridin-3-yl)piperidine-2,6-dione;

(3RS)-3-(4-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}-2-fluorophenyl)piperidine-2,6-dione;

(3RS)-3-(6-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}pyridin-3-yl)piperidine-2,6-dione;

(3RS)-3-(6-{4-[4-(1-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-1-oxopropan-2-yl)piperidine-1-carbonyl]piperidin-1-yl}pyridin-3-yl)piperidine-2,6-dione;

(3RS)-3-(6-{4-[4-(1-{6-[4-(cyclopropylamino)-3-isopropylimidazo[4,5-c]pyridin-6-yl]-2-oxo-1-[(1s,3s)-3-(piperidin-1-yl)cyclobutyl]spiro[indole-3,4'-piperidin]-1'-yl}-2-methyl-1-oxopropan-2-yl)piperazine-1-carbonyl]piperidin-1-yl}pyridin-3-yl)piperidine-2,6-dione;

(3RS)-3-(6-{4-[4-({6-[4-(cyclopropylamino)-3-isopropylimidazo[4,5-c]pyridin-6-yl]-2-oxo-1-[(1S,3S)-3-(piperidin-1-yl)cyclobutyl]spiro[indole-3,4'-piperidin]-1'-yl}carbonyl)-4-methylpiperidine-1-carbonyl]piperidin-1-yl}-4-methylpyridin-3-yl)piperidine-2,6-dione;

(3RS)-3-(2-{[(1r,4r)-4-{4-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-4-methylpiperidine-1-carbonyl}cyclohexyl]methyl}-2h-indazol-5-yl)piperidine-2,6-dione;

(3RS)-3-(4-{[(1r,4r)-4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]amino}phenyl)piperidine-2,6-dione;

1-(6-{[(1r,4r)-4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]amino}pyridin-3-yl)-1,3-diazinane-2,4-dione;

(3RS)-3-(4-{[(1r,4r)-4-[4-({6-[4-(cyclopropylamino)-3-(propan-2-yl)-3h-imidazo[4,5-c]pyridin-6-yl]-2-oxo-1-[(1s,3s)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidine-1-carbonyl]cyclohexyl]oxy}phenyl)piperidine-2,6-dione;

(3RS)-3-(2-{[(1r,4r)-4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]cyclohexyl]oxy}pyrimidin-5-yl)piperidine-2,6-dione;

(3RS)-3-(4-{4-[4-{{6-[4-(cyclopropylamino)-3-(propan-2-yl)-3h-imidazo[4,5-c]pyridin-6-yl]-2-oxo-1-[(1s,3s)-3-{3-oxa-6-azabicyclo[3.1.1]heptan-6-yl}cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione;

(3RS)-3-[4-(4-{4-methyl-4-[(6-{4-[(oxan-4-yl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)phenyl]piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-{8-oxa-3-azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-[(3s)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-[(3r)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}phenyl)piperidine-2,6-dione;

2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-n-(1-{1-[5-(2,6-dioxopiperidin-3-yl)pyridin-2-yl]piperidine-4-carbonyl}piperidin-4-yl)-n-methylacetamide;

2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-n-(1-{1-[4-(2,6-dioxopiperidin-3-yl)pyridin-2-yl]piperidine-4-carbonyl}piperidin-4-yl)-n-methylacetamide;

(3RS)-3-[4-(4-{2-[4-({6-[4-(cyclopropylamino)-3-(propan-2-yl)-3h-imidazo[4,5-c]pyridin-6-yl]-2-oxo-1-[(1s,3s)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidin-1-yl]-2-oxoethyl}piperidin-1-yl)phenyl]piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-[(3s)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-{8-oxa-3-azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-[(3r)-3-fluoropiperidin-1-yl]cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-[(3s)-3-fluoropiperidin-1-yl]cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-{8-oxa-3-azabicyclo[3.2.1]octan-3-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(4-fluoropiperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridazin-3-yl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-fluorophenyl)piperidine-2,6-dione;

1-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}phenyl)-1,3-diazinane-2,4-dione;

(3R)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3R)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-[6-(4-{4-methyl-4-[(6-{4-[(oxan-4-yl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]piperidine-1-carbonyl}piperidin-1-yl)pyridin-3-yl]piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(morpholin-4-yl)cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-{3-azabicyclo[3.2.1]octan-3-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-{3-oxa-6-azabicyclo[3.1.1]heptan-6-yl}cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-[(3r)-3-fluoropiperidin-1-yl]cyclobutyl]-1,2-dihydrospiro[indole-3,4'-piperidin]-1'-yl}carbonyl)-4-methylpiperidine-1-carbonyl]piperidin-1-yl}pyridin-3-yl)piperidine-2,6-dione;

(3RS)-3-(2-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}pyrimidin-5-yl)piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-{3-oxa-8-azabicyclo[3.2.1]octan-8-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-[6-(4-{2-[4-({6-[4-(cyclopropylamino)-3-(propan-2-yl)-3h-imidazo[4,5-c]pyridin-6-yl]-2-oxo-1-[(1s,3s)-3-{3-azabicyclo[3.2.1]octan-3-yl}cyclobutyl]-1,2-dihydrospiro[indole-3,4'-piperidin]-1'-yl}carbonyl)-4-methylpiperidin-1-yl]-2-oxoethyl}piperidin-1-yl)pyridin-3-yl]piperidine-2,6-dione;

(3RS)-3-[6-(1-{2-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidin-1-yl]-2-oxoethyl}piperidin-4-yl)pyridin-3-yl]piperidine-2,6-dione;

(3RS)-3-[6-(4-{[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidin-1-yl]methyl}piperidin-1-yl)pyridin-3-yl]piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-3-methylphenyl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpiperidine-1-carbonyl]piperidin-1-yl}-2-methylphenyl)piperidine-2,6-dione;

(3RS)-3-{4-[methyl({1-[(1s,4s)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexanecarbonyl]piperidin-4-yl})amino]phenyl}piperidine-2,6-dione;

(3RS)-3-[4-(3-{[1-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidin-4-yl]oxy}prop-1-yn-1-yl)-3-methyl-2-oxo-2,3-dihydro-1h-1,3-benzodiazol-1-yl]piperidine-2,6-dione;

(3RS)-3-[4-({1-[(1r,4r)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexanecarbonyl]piperidin-4-yl}methoxy)phenyl]piperidine-2,6-dione;

(3RS)-3-[6-(4-{2-[(3s)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione;

(3RS)-3-(4-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]piperidin-1-yl}phenyl)piperidine-2,6-dione;

1-(4-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)pyrrolidine-1-carbonyl]piperidin-1-yl}phenyl)-1,3-diazinane-2,4-dione;

(3RS)-3-(4-{[(1r,4r)-4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]cyclohexyl]oxy}phenyl)piperidine-2,6-dione;

(3RS)-3-[6-(4-{2-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidin-1-yl]-2-oxoethyl}piperidin-1-yl)pyridin-3-yl]piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridazin-3-yl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}-2-fluorophenyl)piperidine-2,6-dione;

3-(4-(((1r,4r)-4-((1r,5s,6s)-6-(6-(4-(cyclopropylamino)-3-isopropyl-3h-imidazo[4,5-c]pyridin-6-yl)-2-oxo-1-((1s,3s)-3-(piperidin-1-yl)cyclobutyl)spiro[indoline-3,4'-piperidine]-1'-carbonyl)-3-azabicyclo[3.1.1]heptane-3-carbonyl)cyclohexyl)oxy)phenyl)piperidine-2,6-dione;

3-(6-(4-((1r,5s,6s)-6-(6-(4-(cyclopropylamino)-3-isopropyl-3h-imidazo[4,5-c]pyridin-6-yl)-2-oxo-1-((1s,3s)-3-(piperidin-1-yl)cyclobutyl)spiro[indoline-3,4'-piperidine]-1'-carbonyl)-3-azabicyclo[3.1.1]heptane-3-carbonyl)piperidin-1-yl)pyridin-3-yl)piperidine-2,6-dione;

3-(6-(4-(2-((1r,5s,6s)-6-(6-(4-(cyclopropylamino)-3-isopropyl-3h-imidazo[4,5-c]pyridin-6-yl)-2-oxo-1-((1s,3s)-3-(piperidin-1-yl)cyclobutyl)spiro[indoline-3,4'-piperidine]-1'-carbonyl)-3-azabicyclo[3.1.1]heptan-3-yl)-2-oxoethyl)piperidin-1-yl)pyridin-3-yl)piperidine-2,6-dione;

3-(4-{[(1r,4r)-4-[6-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]cyclohexyl]oxy}phenyl)piperidine-2,6-dione;

(3RS)-3-[6-(4-{3-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]azetidine-1-carbonyl}piperidin-1-yl)pyridin-3-yl]piperidine-2,6-dione;

(3RS)-3-(6-{4-[4-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperazine-1-carbonyl]piperidin-1-yl}pyridin-3-yl)piperidine-2,6-dione;

(3RS)-3-(4-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methylpyrrolidine-1-carbonyl]piperidin-1-yl}phenyl)piperidine-2,6-dione;

(3RS)-3-(6-{4-[(2r,4r)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-2-methylpiperidine-1-carbonyl]piperidin-1-yl}pyridin-3-yl)piperidine-2,6-dione;

(3RS)-3-(6-{4-[(3s,5r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-5-methylpiperidine-1-carbonyl]piperidin-1-yl}pyridin-3-yl)piperidine-2,6-dione;

(3RS)-3-(6-{4-[(3s,4s)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methylpiperidine-1-carbonyl]piperidin-1-yl}pyridin-3-yl)piperidine-2,6-dione;

(3RS)-3-(6-{4-[(3r,4s)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-methylpyrrolidine-1-carbonyl]piperidin-1-yl}pyridin-3-yl)piperidine-2,6-dione;

(3RS)-3-(6-{4-[(2r,3r)-3-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-2-methylpyrrolidine-1-carbonyl]piperidin-1-yl}pyridin-3-yl)piperidine-2,6-dione;

(3RS)-3-(6-{4-[5-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3,3-dimethylpiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-1-methyl-2-azabicyclo[2.2.1]heptane-2-carbonyl]piperidin-1-yl}pyridin-3-yl)piperidine-2,6-dione;

(3RS)-3-(4-{4-[(4r)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3,3-dimethylpyrrolidine-1-carbonyl]piperidin-1-yl}phenyl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methylpiperidine-1-carbonyl]piperidin-1-yl}pyridin-3-yl)piperidine-2,6-dione;

(3RS)-3-(4-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-2-methylpiperidine-1-carbonyl]piperidin-1-yl}phenyl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-ethylpiperidine-1-carbonyl]piperidin-1-yl}pyridin-3-yl)piperidine-2,6-dione;

(3RS)-3-(6-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-5-methoxypiperidine-1-carbonyl]piperidin-1-yl}pyridin-3-yl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-methoxypiperidine-1-carbonyl]piperidin-1-yl}phenyl)piperidine-2,6-dione;

4-({6-[4-(cyclopropylamino)-3-(propan-2-yl)-3h-imidazo[4,5-c]pyridin-6-yl]-2-oxo-1-[(1s, 3s)-3-(piperidin-1-yl)cyclobutyl]-1,2-dihydrospiro[indole-3,4'-piperidin]-1'-yl}carbonyl)-1-(1-{4-[(3RS)-2,6-dioxopiperidin-3-yl]phenyl}piperidine-4-carbonyl)piperidine-4-carbonitrile;

(3RS)-3-(6-{4-[(1s,5s)-1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione;

(3RS)-3-(6-{4-[(1r,5s,6s)-6-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}pyridin-3-yl)piperidine-2,6-dione;

(3RS)-3-(6-{4-[(1r,4s,5s)-5-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-2-azabicyclo[2.2.1]heptane-2-carbonyl]piperidin-1-yl}pyridin-3-yl)piperidine-2,6-dione;

(3RS)-3-(4-{4-[(1r,3r,5s)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-8- azabicyclo[3.2.1]octane-8-carbonyl]piperidin-1-yl}phenyl)piperidine-2,6-dione;

(3RS)-3-(4-{4-[(1r,5r)-1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.0]hexane-3-carbonyl]piperidin-1-yl}phenyl)piperidine-2,6-dione;

(3RS)-3-(6-{4-[(3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

(3RS)-3-(6-{4-[(1s,4r,5r)-5-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-2-azabicyclo[2.2.1]heptane-2-carbonyl]piperidin-1-yl}pyridin-3-yl)piperidine-2,6-dione;

(3RS)-3-(6-{4-[(1r,5r,6r)-6-[(6-{4-[(2-fluorophenyl)amino]-3-(propan-2-yl)-3h-imidazo[4,5-c]pyridin-6-yl}-2-oxo-1-[(1s,3s)-3-(piperidin-1-yl)cyclobutyl]-1,2-dihydrospiro[indole-3,4'-piperidin]-1'-yl)carbonyl]-2-azabicyclo[3.1.0]hexane-2-carbonyl]piperidin-1-yl}pyridin-3-yl)piperidine-2,6-dione;

(3RS)-3-(6-{4-[8-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-6-azaspiro[3.5]nonane-6-carbonyl]piperidin-1-yl}pyridin-3-yl)piperidine-2,6-dione;

(3RS)-3-(4-{4-[5-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3,3-difluoropiperidine-1-carbonyl]piperidin-1-yl}phenyl)piperidine-2,6-dione;

(3RS)-3-(6-{4-[7-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-azaspiro[2.5]octane-4-carbonyl]piperidin-1-yl}pyridin-3-yl)piperidine-2,6-dione;

(3RS)-3-(6-{4-[8-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-5-azaspiro[3.5]nonane-5-carbonyl]piperidin-1-yl}pyridin-3-yl)piperidine-2,6-dione;

(3RS)-3-(6-{4-[1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]piperidin-1-yl}pyridin-3-yl)piperidine-2,6-dione;

(3RS)-3-(6-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)piperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3,3-difluoropiperidine-1-carbonyl]piperidin-1-yl}pyridin-3-yl)piperidine-2,6-dione;

(3RS)-3-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-hydroxypiperidine-1-carbonyl]piperidin-1-yl}phenyl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-(trifluoromethyl)piperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-(difluoromethyl)piperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-fluoropiperidine-1-carbonyl]piperidin-1-yl}pyridin-3-yl)piperidine-2,6-dione;

(3RS)-3-(6-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-4-(fluoromethyl)piperidine-1-carbonyl]piperidin-1-yl}pyridin-3-yl)piperidine-2,6-dione;

(3RS)-3-(6-{4-[1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-5-fluoro-3-azabicyclo[3.1.1]heptane-3-carbonyl]piperidin-1-yl}pyridin-3-yl)piperidine-2,6-dione;

(3RS)-3-(6-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-fluoropiperidine-1-carbonyl]piperidin-1-yl}pyridin-3-yl)piperidine-2,6-dione;

(3RS)-3-(6-{4-[1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-6,6-difluoro-3-azabicyclo[3.1.0]hexane-3-carbonyl]piperidin-1-yl}pyridin-3-yl)piperidine-2,6-dione;

(3RS)-3-(6-{4-[6-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.1.1]heptane-3-carbonyl]piperidin-1-yl}pyridin-3-yl)piperidine-2,6-dione;

(3RS)-3-(6-{4-[6-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-2-azabicyclo[2.2.2]octane-2-carbonyl]piperidin-1-yl}pyridin-3-yl)piperidine-2,6-dione;

(3RS)-3-(6-{4-[8-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azabicyclo[3.2.1]octane-3-carbonyl]piperidin-1-yl}pyridin-3-yl)piperidine-2,6-dione;

(3RS)-3-(6-{4-[3-({6-[4-(cyclopropylamino)-3-(propan-2-yl)-3h-imidazo[4,5-c]pyridin-6-yl]-2-oxo-1-[(1s,3s)-

3-(piperidin-1-yl)cyclobutyl]-1,2-dihydrospiro[indole-3,4'-piperidin]-1'-yl}carbonyl)-4,4-difluoropiperidine-1-carbonyl]piperidin-1-yl}pyridin-3-yl)piperidine-2,6-dione;

(3sr)-3-(6-{4-[(1s,3r,5rs)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-8-azabicyclo[3.2.1]octane-8-carbonyl]piperidin-1-yl}pyridin-3-yl)piperidine-2,6-dione;

(3RS)-3-(6-{4-[5-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-7-azaspiro[3.5]nonane-7-carbonyl]piperidin-1-yl}pyridin-3-yl)piperidine-2,6-dione;

(3RS)-3-(6-{4-[9-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-oxa-7-azabicyclo[3.3.1]nonane-7-carbonyl]piperidin-1-yl}pyridin-3-yl)piperidine-2,6-dione;

(3RS)-3-(4-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-8-azabicyclo[3.2.1]octane-8-carbonyl]piperidin-1-yl}phenyl)piperidine-2,6-dione;

(3RS)-3-(6-{4-[7-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-5-azaspiro[3.5]nonane-5-carbonyl]piperidin-1-yl}pyridin-3-yl)piperidine-2,6-dione;

1-{5-[(3RS)-2,6-dioxopiperidin-3-yl]pyridin-2-yl}-n-{[(1r,4r)-4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexyl]methyl}piperidine-4-carboxamide;

N-[(1s, 3r)-3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclohexyl]-2-(1-{5-[(3RS)-2,6-dioxopiperidin-3-yl]pyridin-2-yl}piperidin-4-yl)acetamide;

(3RS)-3-{6-[4-(4-{[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)phenyl methyl}piperazine-1-carbonyl)piperidin-1-yl]pyridin-3-yl}piperidine-2,6-dione;

(3RS)-3-(6-{4-[2-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-8-azaspiro[4.5]decane-8-carbonyl]piperidin-1-yl}pyridin-3-yl)piperidine-2,6-dione;

(3RS)-3-(6-{4-[9-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)-3-azaspiro[5.5]undecane-3-carbonyl]piperidin-1-yl}pyridin-3-yl)piperidine-2,6-dione;

(3RS)-3-(6-{4-[(3r)-3-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione;

(3RS)-3-[6-(4-{2-[(3r)-3-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidin-1-yl]-2-oxoethyl}piperidin-1-yl)pyridin-3-yl]piperidine-2,6-dione;

(3RS)-3-(6-{4-[(3s)-3-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidine-1-carbonyl]piperidin-1-yl}pyridin-3-yl)piperidine-2,6-dione;

(3RS)-3-[6-(4-{2-[(3s)-3-(2-{6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)piperidin-1-yl]-2-oxoethyl}piperidin-1-yl)pyridin-3-yl]piperidine-2,6-dione;

(3RS)-3-[6-(4-{4-[1-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)cyclobutyl]piperidine-1-carbonyl}piperidin-1-yl)pyridin-3-yl]piperidine-2,6-dione;

(3RS)-3-[6-(4-{4-[3-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)phenyl]piperidine-1-carbonyl}piperidin-1-yl)pyridin-3-yl]piperidine-2,6-dione;

(3RS)-3-[6-(4-{4-[4-({6-[4-(cyclopropylamino)-3-(propan-2-yl)-3h-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}carbonyl)phenyl]piperidine-1-carbonyl}piperidin-1-yl)pyridin-3-yl]piperidine-2,6-dione; and (3RS)-3-(6-{4-[1-({6-[4-(cyclopropylamino)-3-(propan-2-yl)-3h-imidazo[4,5-c]pyridin-6-yl]-2-oxo-1-[(1S,3S)-3-(piperidin-1-yl)cyclobutyl]-1,2-dihydrospiro[indole-3,4'-piperidin]-1'-yl}carbonyl)-5-azaspiro[2.4]heptane-5-carbonyl]piperidin-1-yl}pyridin-3-yl)piperidine-2,6-dione.

29. A pharmaceutical composition comprising the compound of claim 1, or a pharmaceutically acceptable salt thereof, and a pharmaceutically acceptable excipient or carrier.

* * * * *

UNITED STATES PATENT AND TRADEMARK OFFICE

CERTIFICATE OF CORRECTION

PATENT NO. : 12,091,426 B2
APPLICATION NO. : 18/054118
DATED : September 17, 2024
INVENTOR(S) : John Buell et al.

It is certified that error appears in the above-identified patent and that said Letters Patent is hereby corrected as shown below:

In the Claims

Column 794, Claim 1, Line 23:
"heterocylcle" should read: --heterocyclyl--.

Column 794, Claim 1, Line 24:
"1-3 $R^b$," should read: --1-3 $R^b$;--.

Column 794, Claim 1, Line 28:
"$R^b$," should read: --$R^b$;--.

Column 794, Claim 1, Line 31:
"1-3 $R^b$," should read: --1-3 $R^b$;--.

Column 794, Claim 1, Line 33:
"1-3 $R^b$," should read: --1-3 $R^b$;--.

Column 794, Claim 1, Line 36:
"1-3 $R^d$," should read: --1-3 $R^d$;--.

Column 794, Claim 1, Line 39:
"1-3 $R^d$," should read: --1-3 $R^d$;--.

Column 794, Claim 1, Line 41:
"1-3 $R^d$," should read: --1-3 $R^d$;--.

Column 800, Claim 11, Line 21:
"heterocylcle" should read: --heterocyclyl--.

Signed and Sealed this
Nineteenth Day of November, 2024

Katherine Kelly Vidal

Katherine Kelly Vidal
*Director of the United States Patent and Trademark Office*